United States Patent
Jeon et al.

(10) Patent No.: US 12,120,953 B2
(45) Date of Patent: Oct. 15, 2024

(54) HETEROCYCLIC COMPOUND, ORGANIC LIGHT-EMITTING DEVICE INCLUDING HETEROCYCLIC COMPOUND, AND ELECTRONIC APPARATUS INCLUDING ORGANIC LIGHT-EMITTING DEVICE

(71) Applicant: Samsung Electronics Co., Ltd., Suwon-si (KR)

(72) Inventors: Soonok Jeon, Suwon-si (KR); Dmitry Androsov, Suwon-si (KR); Juhyun Kim, Seoul (KR); Jong Soo Kim, Hanam-si (KR); Sooghang Ihn, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 787 days.

(21) Appl. No.: 17/197,235

(22) Filed: Mar. 10, 2021

(65) Prior Publication Data
US 2022/0115600 A1   Apr. 14, 2022

(30) Foreign Application Priority Data
Sep. 10, 2020   (KR) .................. 10-2020-0116215

(51) Int. Cl.
| | | |
|---|---|---|
| H01L 51/00 | (2006.01) | |
| C07D 495/04 | (2006.01) | |
| C07D 519/00 | (2006.01) | |
| C09K 11/06 | (2006.01) | |
| H10K 85/60 | (2023.01) | |
| H10K 50/11 | (2023.01) | |
| H10K 101/10 | (2023.01) | |

(52) U.S. Cl.
CPC ....... H10K 85/6572 (2023.02); C07D 495/04 (2013.01); C07D 519/00 (2013.01); C09K 11/06 (2013.01); C09K 2211/1007 (2013.01); C09K 2211/1018 (2013.01); H10K 50/11 (2023.02); H10K 2101/10 (2023.02)

(58) Field of Classification Search
CPC ............ H01L 51/0072; H01L 51/5016; C07D 519/00; C07D 495/04; C09K 11/06; C09K 2211/1018; C09K 2211/1007
See application file for complete search history.

(56) References Cited

U.S. PATENT DOCUMENTS

| | | | |
|---|---|---|---|
| 9,502,656 B2 | 11/2016 | Scott et al. | |
| 10,361,377 B2 | 7/2019 | Kim et al. | |
| 10,586,931 B2 | 3/2020 | Kanamoto et al. | |
| 10,790,453 B2 | 9/2020 | Park et al. | |
| 2015/0053939 A1 | 2/2015 | Adamovich et al. | |
| 2020/0028091 A1 | 1/2020 | Parham et al. | |
| 2020/0199135 A1 | 6/2020 | Kurihara et al. | |

FOREIGN PATENT DOCUMENTS

| | | | | |
|---|---|---|---|---|
| EP | 2910555 A1 | * | 8/2015 | ........... C07D 491/04 |
| KR | 1020160126792 A | | 11/2016 | |
| WO | 2014084612 A1 | | 6/2014 | |
| WO | 2015108301 A8 | | 7/2015 | |
| WO | 2017043908 A1 | | 3/2017 | |
| WO | WO-2017109637 A1 | * | 6/2017 | ......... C07D 491/048 |
| WO | 2018060218 A1 | | 4/2018 | |
| WO | 2018123924 A1 | | 7/2018 | |
| WO | 2018234926 A1 | | 12/2018 | |
| WO | 2019172623 A1 | | 9/2019 | |

OTHER PUBLICATIONS

English Abstract of KR 10-2016-0126792.
English Abstract of WO 2017-043908.
English Abstract of WO 2018-123924.
English Abstract of WO 2019-172623.

* cited by examiner

Primary Examiner — Robert D Harlan
(74) Attorney, Agent, or Firm — CANTOR COLBURN LLP

(57) ABSTRACT

Provided are a heterocyclic compound represented by Formula 1, an organic light-emitting device including the heterocyclic compound, and an electronic apparatus including the organic light-emitting device:

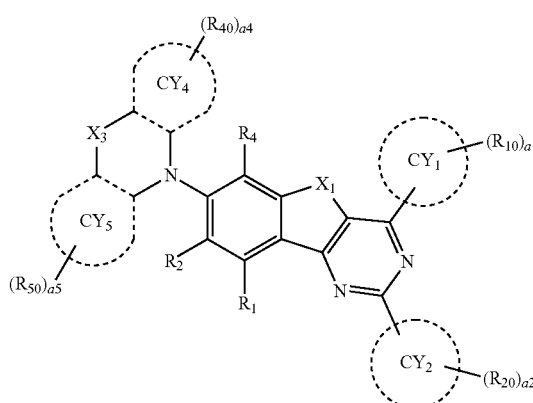

Formula 1 wherein Formula 1 may be understood by referring to the description of Formula 1 provided herein.

19 Claims, 1 Drawing Sheet

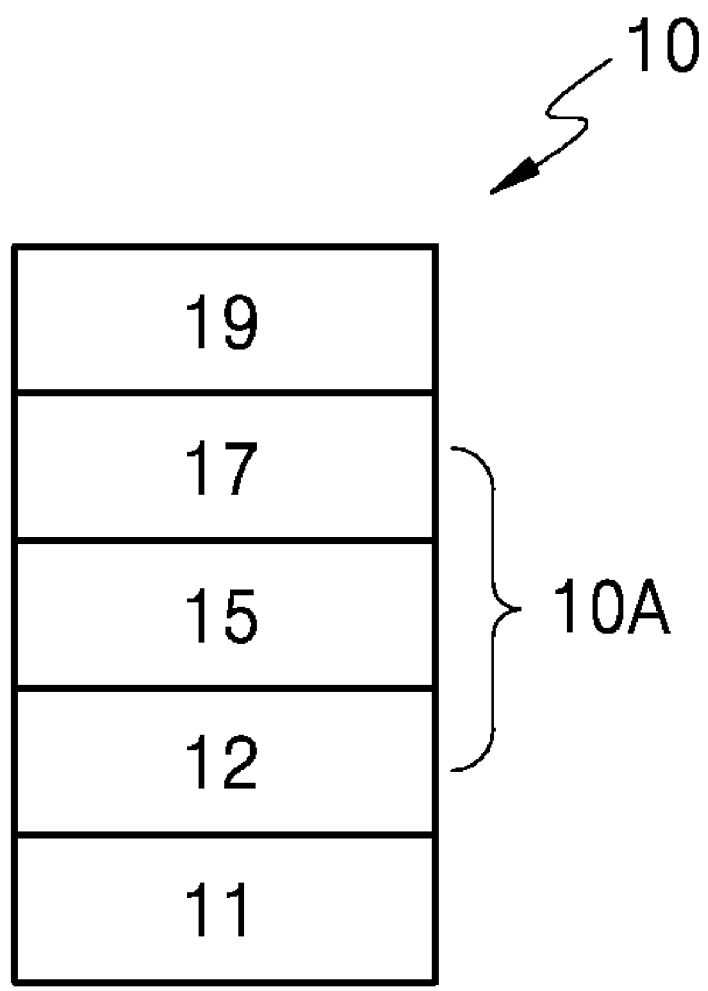

HETEROCYCLIC COMPOUND, ORGANIC LIGHT-EMITTING DEVICE INCLUDING HETEROCYCLIC COMPOUND, AND ELECTRONIC APPARATUS INCLUDING ORGANIC LIGHT-EMITTING DEVICE

CROSS-REFERENCE TO RELATED APPLICATION

This application claims priority under 35 U.S.C. § 119 to Korean Patent Application No. 10-2020-0116215, filed on Sep. 10, 2020, in the Korean Intellectual Property Office, the content of which is incorporated by reference herein in its entirety.

BACKGROUND

1. Field

The present disclosure relates to a heterocyclic compound, an organic light-emitting device including the heterocyclic compound, and an electronic apparatus including the organic light-emitting device.

2. Description of Related Art

Organic light-emitting devices (OLEDs) are self-emissive devices which produce full-color images. In addition, OLEDs have wide viewing angles and exhibit excellent driving voltage and response speed characteristics.

OLEDs include an anode, a cathode, and an organic layer between the anode and the cathode and including an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transit from an excited state to a ground state to thereby generate light.

SUMMARY

Provided are a novel heterocyclic compound, an organic light-emitting device including the heterocyclic compound, and an electronic apparatus including the organic light-emitting device.

Additional aspects will be set forth in part in the description which follows and, in part, will be apparent from the description, or may be learned by practice of the presented embodiments of the disclosure.

According to one or more embodiments, a heterocyclic compound is represented by Formula 1:

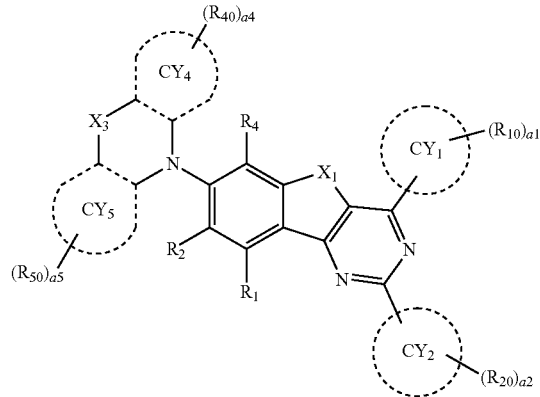

Formula 1 wherein, in Formula 1, ring $CY_1$ ring $CY_2$, ring $CY_4$, and ring $CY_5$ are each independently a π electron-rich $C_3$-$C_{60}$ cyclic group, $X_1$ is O, S, $Si(R_5)(R_6)$, $Ge(R_5)(R_6)$, or $P(=O)(R_5)$, $X_3$ is a single bond, O, S, $N(R_{31})$, $C(R_{31})(R_{32})$, $Si(R_{31})(R_{32})$, or $Ge(R_{31})(R_{32})$, $R_1$, $R_2$, $R_4$ to $R_6$, $R_{10}$, and $R_{20}$ are each independently hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$Ge(Q_3)(Q_4)(Q_5)$, —$B(Q_6)(Q_7)$, —$P(=O)(Q_8)(Q_9)$, or —$P(Q_8)(Q_9)$, $R_{31}$, $R_{32}$, $R_{40}$, and $R_{50}$ are each independently:

hydrogen, deuterium, —F, or a cyano group; or a $C_1$-$C_{60}$ alkyl group, a $C_1$-$C_{60}$ alkoxy group, a π electron-rich $C_3$-$C_{60}$ cyclic group, or a pyridinyl group, each unsubstituted or substituted with deuterium, —F, a cyano group, a $C_1$-$C_{60}$ alkyl group, a $C_1$-$C_{60}$ alkoxy group, a π electron-rich $C_3$-$C_{60}$ cyclic group, a pyridinyl group, a biphenyl group, a terphenyl group, or any combination thereof, a1, a2, a4, and a5 may each independently be an integer from 0 to 20, and a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$Ge(Q_{13})(Q_{14})(Q_{15})$, —$B(Q_{16})(Q_{17})$, —$P(=O)(Q_{18})(Q_{19})$, —$P(Q_{18})(Q_{19})$, or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_8$-$C_{80}$ aryl group, a $C_8$-$C_{80}$ aryloxy group, a $C_8$-$C_{80}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$Ge(Q_{23})(Q_{24})(Q_{25})$, —$B(Q_{26})(Q_{27})$, —$P(=O)(Q_{28})(Q_{29})$, —$P(Q_{28})(Q_{29})$, or any combination thereof;

—$N(Q_{31})(Q_{32})$, —$Si(Q_{33})(Q_{34})(Q_{35})$, —$Ge(Q_{33})(Q_{34})(Q_{35})$, —$B(Q_{36})(Q_{37})$, —$P(=O)(Q_{38})(Q_{39})$, or —$P(Q_{38})(Q_{39})$; or any combination thereof,
wherein $Q_1$ to $Q_9$, $Q_{11}$ to $Q_{19}$, $Q_{21}$ to $Q_{29}$, and $Q_{31}$ to $Q_{39}$ are each independently be: hydrogen; deuterium; —F; —Cl; —Br; —I; a hydroxyl group; a cyano group; a nitro group; an amidino group; a hydrazine group; a hydrazone group; a carboxylic acid group or a salt thereof; a sulfonic acid group or a salt thereof; a phosphoric acid group or a salt thereof; a $C_1$-$C_{60}$ alkyl group unsubstituted or substituted with deuterium, a $C_1$-$C_{60}$ alkyl group, a $C_6$-$C_{60}$ aryl group, or any combination thereof; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group unsubstituted or substituted with deuterium, a $C_1$-$C_{60}$ alkyl group, a $C_6$-$C_{60}$ aryl group, or any combination thereof; a $C_6$-$C_{60}$ aryloxy group; a $C_6$-$C_{60}$ arylthio group; a $C_1$-$C_{60}$ heteroaryl group; a monovalent non-aromatic condensed polycyclic group; or a monovalent non-aromatic condensed heteropolycyclic group.

According to an aspect of another embodiment, an organic light-emitting device may include: a first electrode; a second electrode; and an organic layer located between the first electrode and the second electrode and including an emission layer and at least one heterocyclic compound.

According to an aspect of another embodiment, an electronic apparatus may include the organic light-emitting device.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 1 illustrates a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween In contrast, when an element is referred to as being "directly on" another element, there are no intervening elements present It will be understood that, although the terms "first," "second," "third" etc. may be used herein to describe various elements, components, regions, layers and/or sections, these elements, components, regions, layers and/or sections should not be limited by these terms These terms are only used to distinguish one element, component, region, layer or section from another element, component, region, layer or section Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity and are intended to cover both the singular and plural, unless the context clearly indicates otherwise. For example, "an element" has the same meaning as "at least one element," unless the context clearly indicates otherwise.

"Or" means "and/or." As used herein, the term "and/or" includes any and all combinations of one or more of the associated listed items It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the FIGURES It will be understood that relative terms are intended to encompass different orientations of the device in addition to the orientation depicted in the FIGURES For example, if the device in one of the FIGURES is turned over, elements described as being on the "lower" side of other elements would then be oriented on "upper" sides of the other elements The exemplary term "lower," can therefore, encompasses both an orientation of "lower" and "upper," depending on the particular orientation of the FIGURE Similarly, if the device in one of the FIGURES is turned over, elements described as "below" or "beneath" other elements would then be oriented "above" the other elements The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments As such, variations from the shapes of the illustrations as a result, for example, of manufacturing techniques and/or tolerances, are to be expected Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features Moreover, sharp angles that are illustrated may be rounded Thus, the regions illustrated in the figures are schematic in nature and their shapes are not intended to illustrate the precise shape of a region and are not intended to limit the scope of the present claims.

A heterocyclic compound may be represented by Formula 1:

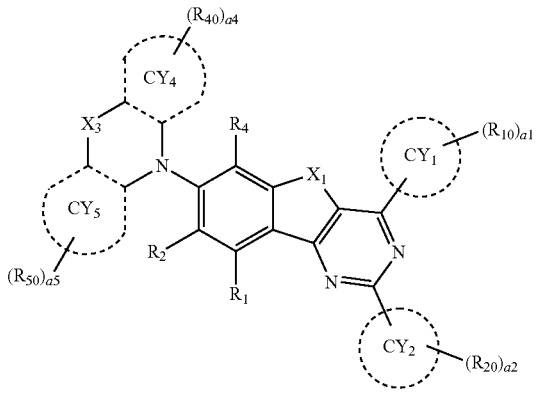

Formula 1 wherein, in Formula 1, ring $CY_1$ ring $CY_2$, ring $CY_4$, and ring $CY_5$ may each independently be a π electron-rich $C_3$-$C_{60}$ cyclic group.

In some embodiments, ring $CY_1$ ring $CY_2$, ring $CY_4$, and ring $CY_5$ in Formula 1 may each independently be a benzene group, a naphthalene group, a phenanthrene group, a furan group, a thiophene group, a pyrrole group, a cyclopentene group, a silole group, a germole group, a benzofuran group, a benzothiophene group, an indole group, an indene group, a benzosilole group, a benzogermole group, a dibenzofuran group, a dibenzothiophene group, a carbazole group, a fluorene group, a dibenzosilole group, a dibenzogermole group, an indolodibenzofuran group, an indolodibenzothiophene group, an indolocarbazole group, an indolofluorene group, an indolodibenzosilole group, an indolodibenzogermole group, or a 9,10-dihydroacridine group.

In some embodiments, in Formula 1, ring $CY_1$ ring $CY_2$, and ring $CY_4$ may each independently be a benzene group or a naphthalene group.

In one or more embodiments, in Formula 1, ring $CY_5$ may be a benzene group, a naphthalene group, a dibenzofuran group, a dibenzothiophene group, a carbazole group, a fluorene group, a dibenzosilole group, a dibenzogermole group, an indolodibenzofuran group, an indolodibenzothiophene group, an indolocarbazole group, an indolofluorene group, an indolodibenzosilole group, an indolodibenzogermole group, or a 9,10-dihydroacridine group.

In Formula 1, $X_1$ may be O, S, $Si(R_5)(R_6)$, $Ge(R_5)(R_6)$, or $P(=O)(R_5)$.

In some embodiments, in Formula 1, $X_1$ may be O or S.

In Formula 1, $X_3$ may be a single bond, O, S, $N(R_{31})$, $C(R_{31})(R_{32})$, $Si(R_{31})(R_{32})$, or $Ge(R_{31})(R_{32})$.

In an embodiment, in Formula 1, $X_3$ may be a single bond.

In Formula 1, $R_1$, $R_2$, $R_4$ to $R_6$, $R_{10}$, and $R_{20}$ may each independently be hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —Ge($Q_3$)($Q_4$)($Q_5$), —B($Q_6$)($Q_7$), —P(=O)($Q_8$)($Q_9$), or —P($Q_8$)($Q_9$). $Q_1$ to $Q_9$ may respectively be understood by referring to the descriptions of $Q_1$ to $Q_3$ provided herein.

In some embodiments, in Formula 1, $R_1$, $R_2$, $R_4$ to $R_6$, $R_{10}$, and $R_{20}$ may each independently be:

hydrogen, deuterium, —F, or a cyano group; or a $C_1$-$C_{60}$ alkyl group, a $C_1$-$C_{60}$ alkoxy group, a π electron-rich $C_3$-$C_{60}$ cyclic group, or a pyridinyl group, each unsubstituted or substituted with deuterium, —F, a cyano group, a $C_1$-$C_{60}$ alkyl group, a $C_1$-$C_{60}$ alkoxy group, a π electron-rich $C_3$-$C_{60}$ cyclic group, a pyridinyl group, a biphenyl group, a terphenyl group, or any combination thereof.

In Formula 1, $R_{31}$, $R_{32}$, $R_{40}$, and $R_{50}$ may each independently be:

hydrogen, deuterium, —F, or a cyano group; or a $C_1$-$C_{60}$ alkyl group, a $C_1$-$C_{60}$ alkoxy group, a π electron-rich $C_3$-$C_{60}$ cyclic group, or a pyridinyl group, each unsubstituted or substituted with deuterium, —F, a cyano group, a $C_1$-$C_{60}$ alkyl group, a $C_1$-$C_{60}$ alkoxy group, a π electron-rich $C_3$-$C_{60}$ cyclic group, a pyridinyl group, a biphenyl group, a terphenyl group, or any combination thereof.

In an embodiment, in Formula 1, $R_2$, $R_4$ to $R_6$, $R_{10}$, $R_{20}$, $R_{31}$, $R_{32}$, $R_{40}$, and $R_{50}$ may each independently be:

hydrogen, deuterium, —F, or a cyano group; or a $C_1$-$C_{20}$ alkyl group, a phenyl group, a naphthyl group, a phenanthrenyl group, a furanyl group, a thiophenyl group, a pyrrolyl group, a cyclopentenyl group, a silolyl group, a germolyl group, a benzofuranyl group, a benzothiophenyl group, an indolyl group, an indenyl group, a benzosilolyl group, a benzogermolyl group, a dibenzofuranyl group, a dibenzothiophenyl group, a carbazolyl group, a fluorenyl group, a dibenzosilolyl group, a dibenzogermolyl group, a benzonaphthofuranyl group, a benzonaphthothiophenyl group, a benzocarbazolyl group, a benzofluorenyl group, a benzonaphthosilolyl group, a benzonaphthogermolyl group, a dinaphthofuranyl group, a dinaphthothiophenyl group, a dibenzocarbazolyl group, a dibenzofluorenyl group, a dinaphthosilolyl group, a dinaphthogermolyl group, a pyridinyl group, a biphenyl group, or a terphenyl group, each unsubstituted or substituted with deuterium, —F, a cyano group, a $C_1$-$C_{20}$ alkyl group, a phenyl group, a naphthyl group, a phenanthrenyl group, a furanyl group, a thiophenyl group, a pyrrolyl group, a cyclopentenyl group, a silolyl group, a germolyl group, a benzofuranyl group, a benzothiophenyl group, an indolyl group, an indenyl group, a benzosilolyl group, a benzogermolyl group, a dibenzofuranyl group, a dibenzothiophenyl group, a carbazolyl group, a fluorenyl group, a dibenzosilolyl group, a dibenzogermolyl group, a benzonaphthofuranyl group, a benzonaphthothiophenyl group, a benzocarbazolyl group, a benzofluorenyl group, a benzonaphthosilolyl group, a benzonaphthogermolyl group, a dinaphthofuranyl group, a dinaphthothiophenyl group, a dibenzocarbazolyl group, a dibenzofluorenyl group, a dinaphthosilolyl group, a dinaphthogermolyl group, a pyridinyl group, a biphenyl group, a terphenyl group, or any combination thereof.

In one or more embodiments, Formula 1 may each satisfy at least one of Conditions (1) to (9):

Condition (1)
wherein, $R_1$ may include at least one carbon atom, and $R_1$ may be bound to a benzene group (see Formula 1' provided herein) of an "acceptor" in Formula 1 via a carbon-carbon bond;

Condition (2)
wherein, $R_2$ may include at least one carbon atom, and $R_2$ may be bound to a benzene group (see Formula 1' provided herein) of an "acceptor" in Formula 1 via a carbon-carbon bond;

Condition (3)
wherein, $R_4$ may include at least one carbon atom, and $R_4$ may be bound to a benzene group (see Formula 1' provided herein) of an "acceptor" in Formula 1 via a carbon-carbon bond;

Condition (4)
wherein, ring $CY_1$ may include at least one carbon atom, and ring $CY_1$ may be bound to a pyrimidine group in Formula 1 via a carbon-carbon bond;

Condition (5)
wherein, $R_{10}$ may include at least one carbon atom, and $R_{10}$ may be bound to ring $CY_1$ in Formula 1 via a carbon-carbon bond;

Condition (6)
wherein, ring $CY_2$ may include at least one carbon atom, and ring $CY_2$ may be bound to a pyrimidine group in Formula 1 via a carbon-carbon bond;

Condition (7)
wherein, $R_{20}$ may include at least one carbon atom, and $R_{20}$ may be bound to ring $CY_2$ in Formula 1 via a carbon-carbon bond;

Condition (8)
wherein, $R_{40}$ may include at least one carbon atom, and $R_{40}$ may be bound to ring $CY_4$ in Formula 1 via a carbon-carbon bond; and Condition (9)
wherein, $R_{50}$ may include at least one carbon atom, and $R_{50}$ may be bound to ring $CY_5$ in Formula 1 via a carbon-carbon bond.

In one or more embodiments, in Formula 3, $R_{50}$ may include at least one nitrogen atom, and the nitrogen atom in $R_{50}$ may be bound to a carbon atom in ring $CY_5$ in Formula 1 via a nitrogen-carbon bond.

In Formula 1, a1, a2, a4, and a5 may respectively indicate the number of $R_{10}$(s), $R_{20}$(s), $R_{40}$(s), and $R_{50}$(s), and a1, a2, a4, and a5 may each independently be an integer from 0 to 20. When a1 is 2 or greater, at least two $R_{10}$(s) may be identical to or different from each other, when a2 is 2 or greater, at least two $R_{20}$(s) may be identical to or different from each other, when a4 is 2 is or greater, at least two $R_{40}$(s) may be identical to or different from each other, and when a5 is 20 is or greater, at least two $R_{50}$(s) may be identical to or different from each other. For example, in Formula 1, a1 and a2 may each independently be an integer from 0 to 5, and in Formula 3, a4 and a5 may each independently be an integer from 0 to 4.

In one or more embodiments, a group represented by

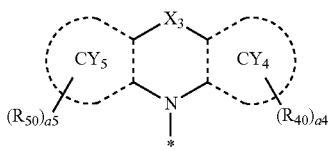

in Formula 1 may be represented by one of Formulae 3-1 to 3-7:

3-1

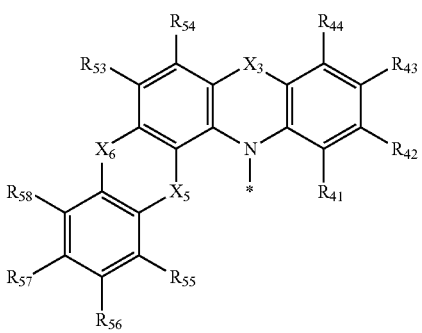

3-2

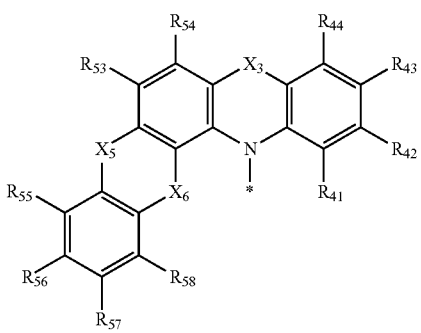

3-3

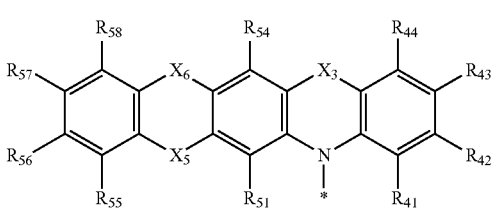

3-4

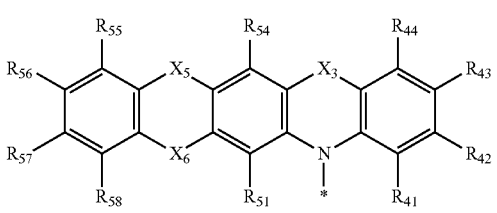

3-5

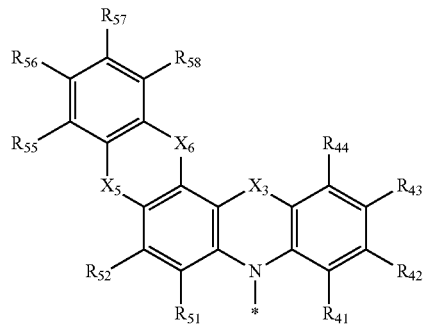

3-6

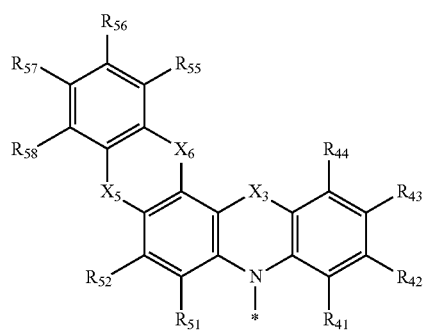

3-7

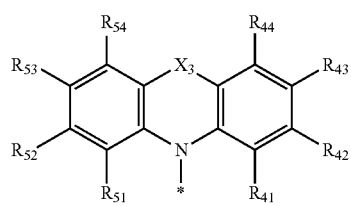

wherein, in Formulae 3-1 to 3-7, $X_3$ may be understood by referring to the description of $X_3$ provided herein, $X_5$ may be O, S, $N(R_{59})$, $C(R_{59a})(R_{59b})$, $Si(R_{59a})(R_{59b})$, or $Ge(R_{59a})(R_{59b})$, $X_6$ may be a single bond, O, S, $N(R_{59c})$, $C(R_{59d})(R_{59e})$, $Si(R_{59d})(R_{59e})$, or $Ge(R_{59a})(R_{59b})$, $R_{41}$ to $R_{44}$ may each be understood by referring to the description of $R_{40}$ provided herein, $R_{51}$ to $R_{59}$ and $R_{59a}$ to $R_{59e}$ may each be understood by referring to the description of $R_{50}$ provided herein,

* indicates a binding site to an adjacent atom.

For example, $X_6$ may be a single bond or $C(R_{59d})(R_{59e})$.

For example, a group represented by

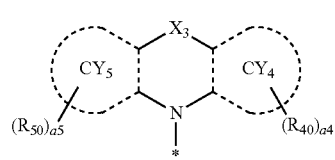

in Formula 1 may be represented by Formula 3-7, and at least one of $R_{43}$ and $R_{53}$ in Formula 3-7 may not be hydrogen.

In one or more embodiments, the heterocyclic compound represented by Formula 1 may be any one of Compounds 1 to 196:
1
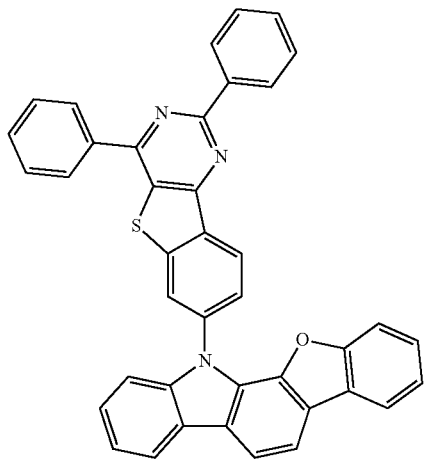
2
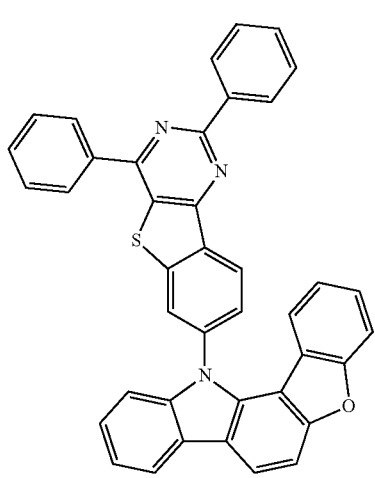
3
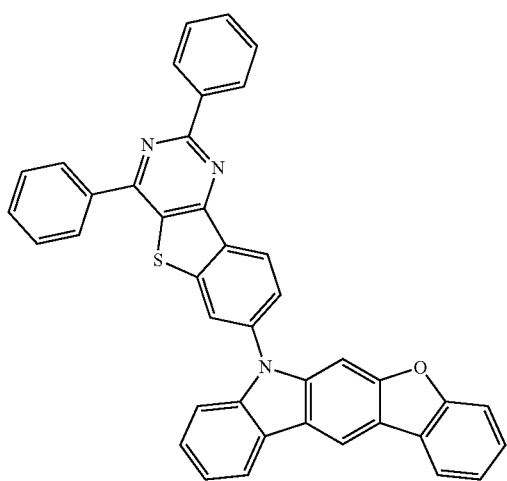
-continued
4
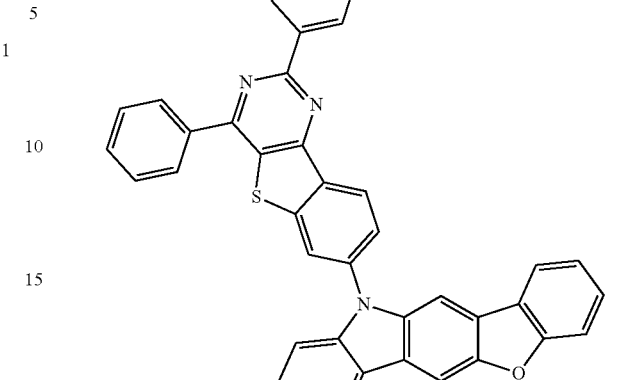
5
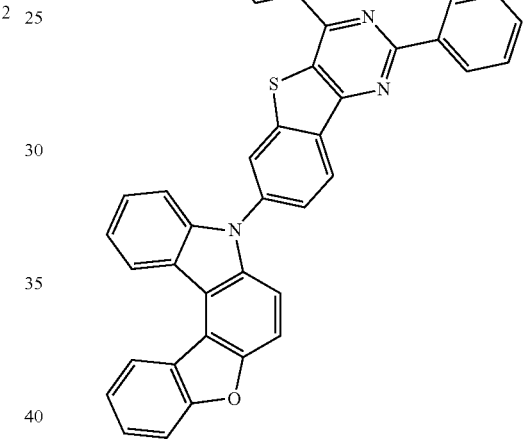
6
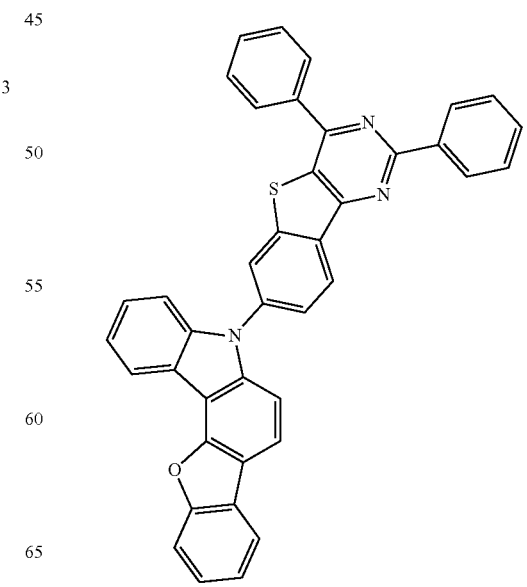

7
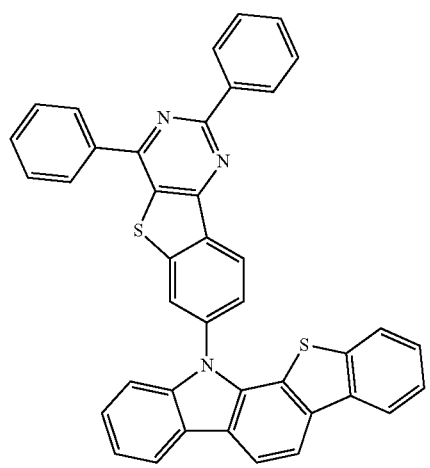
8
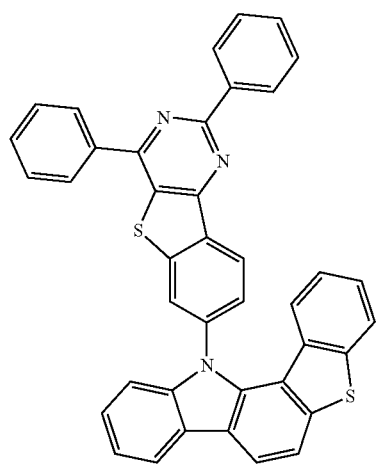
9
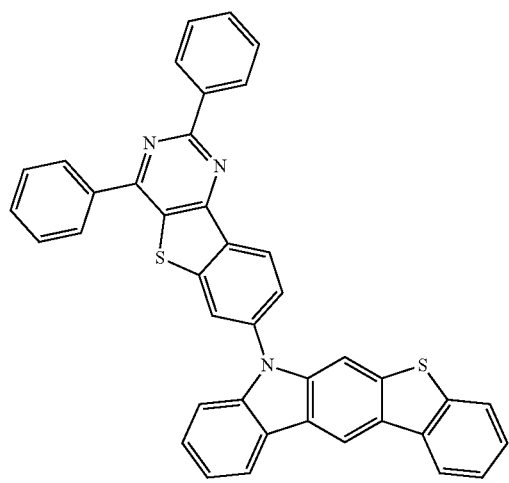
10
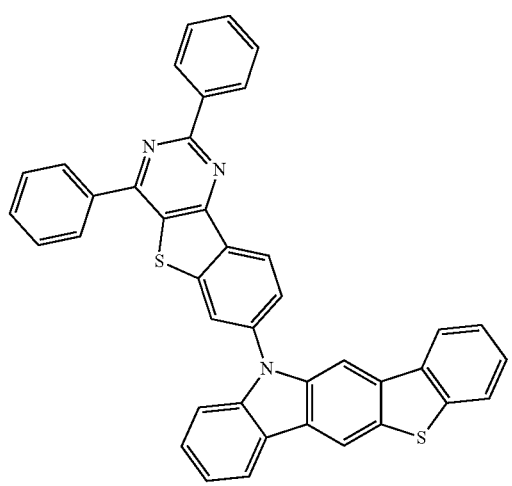
11
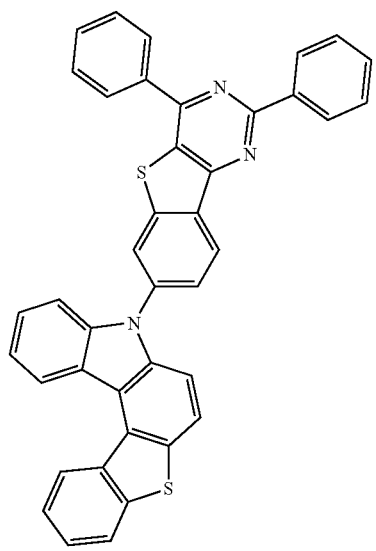
12
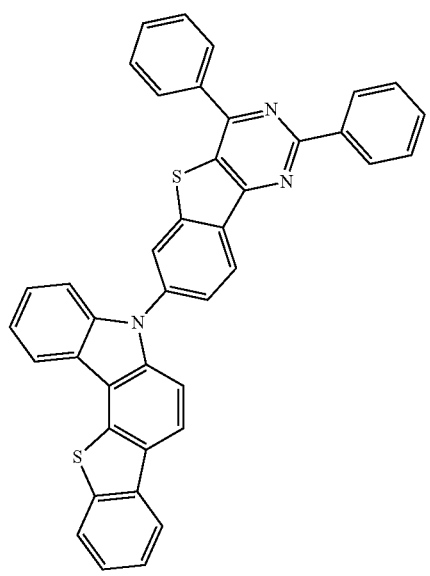

13
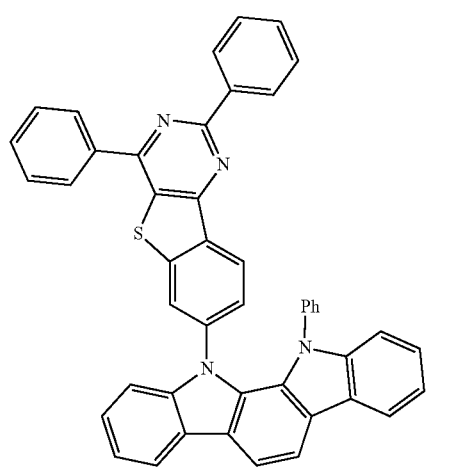
14
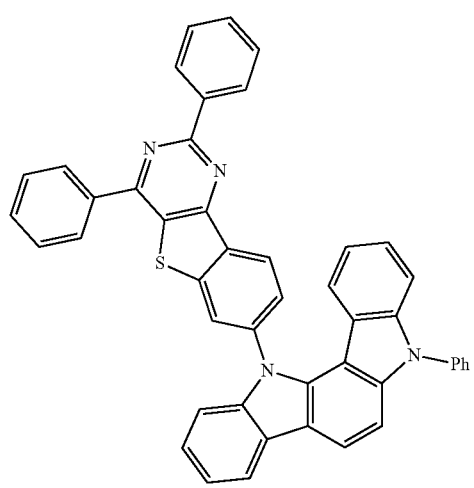
15
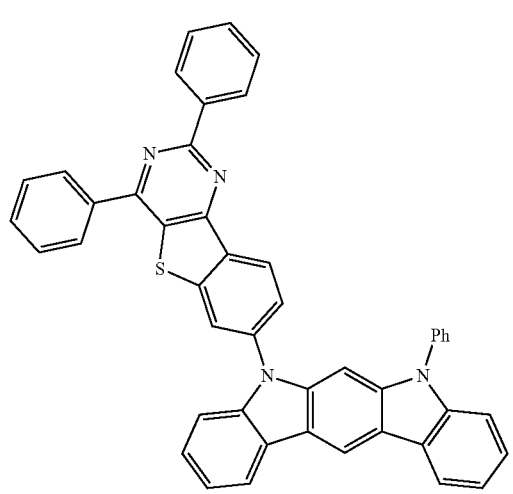
16
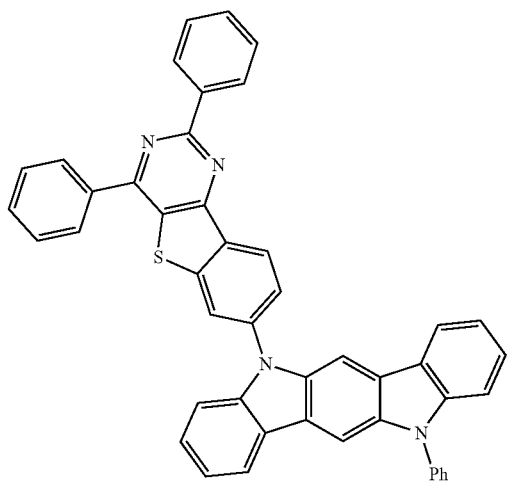
17
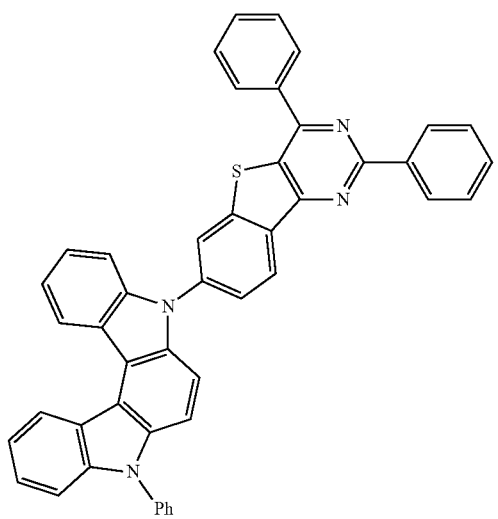
18
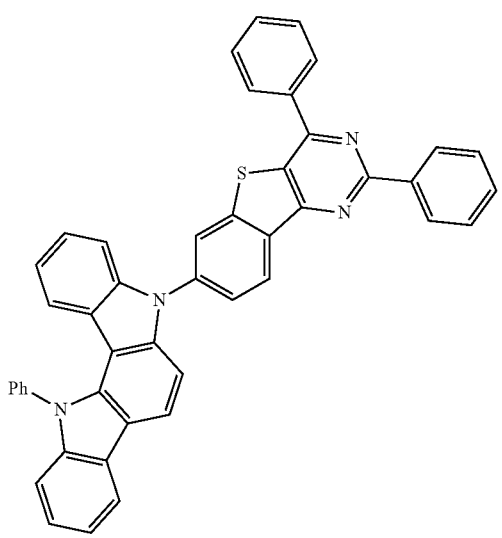

-continued
19
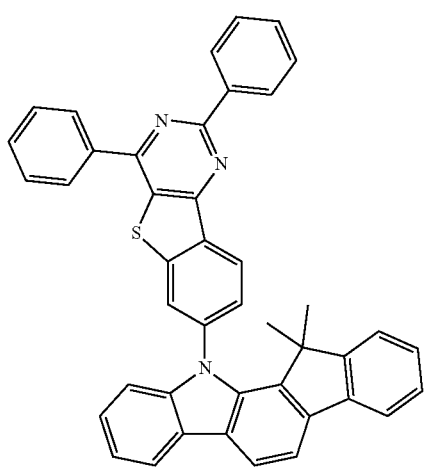
20
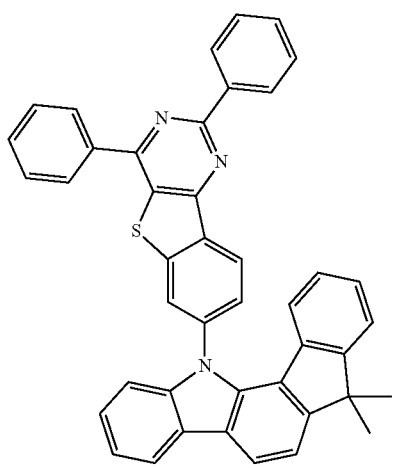
21
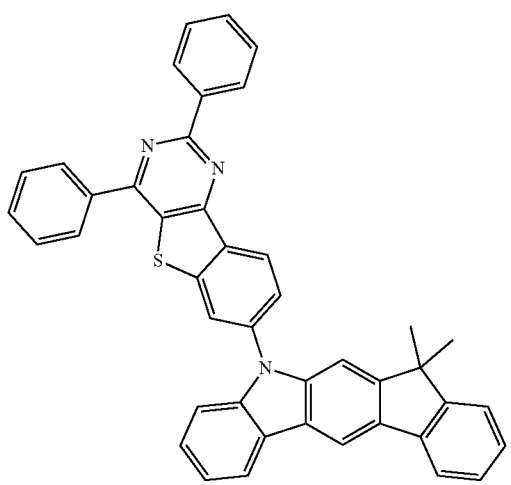
-continued
22
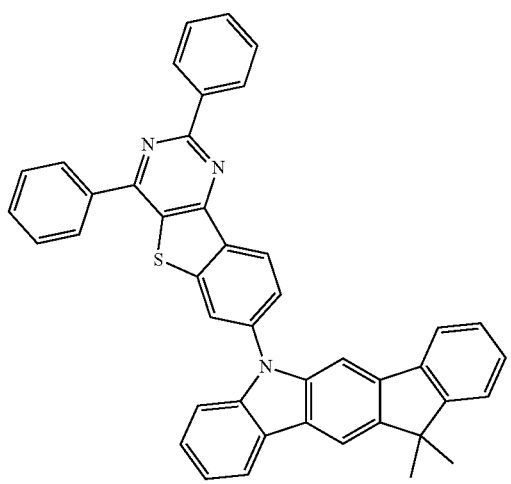
23
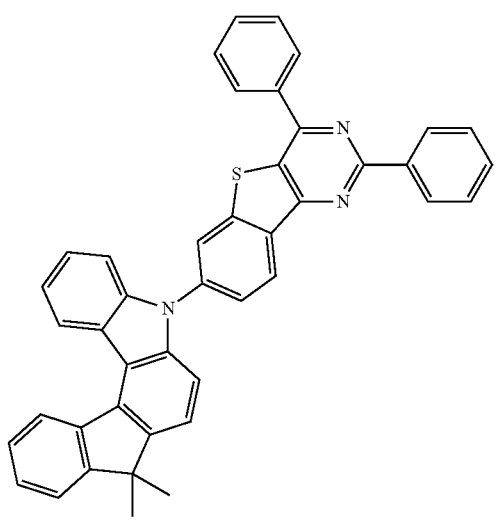
24
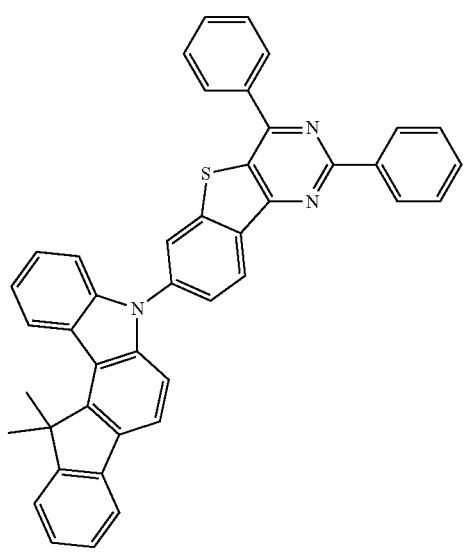

25
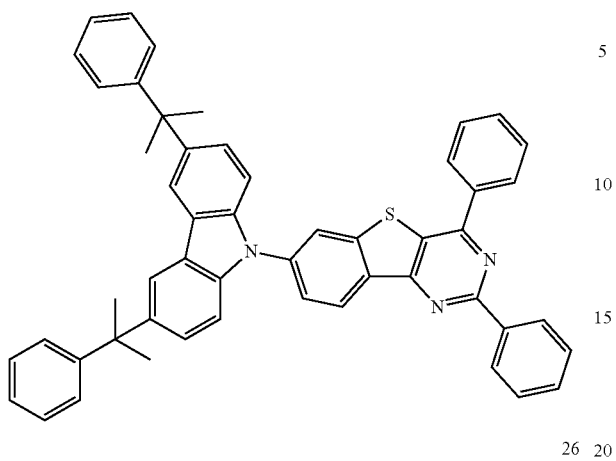
26
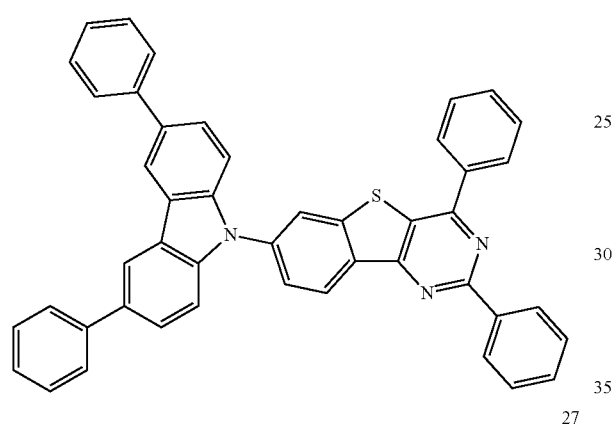
27
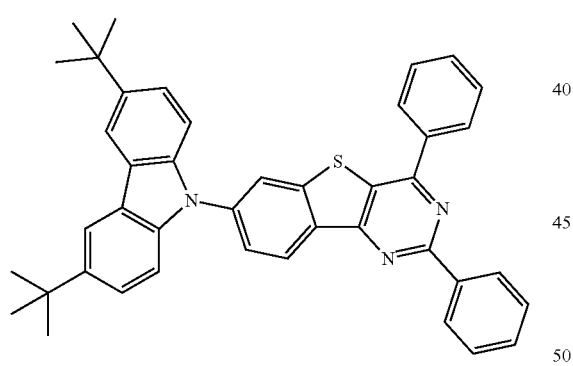
28
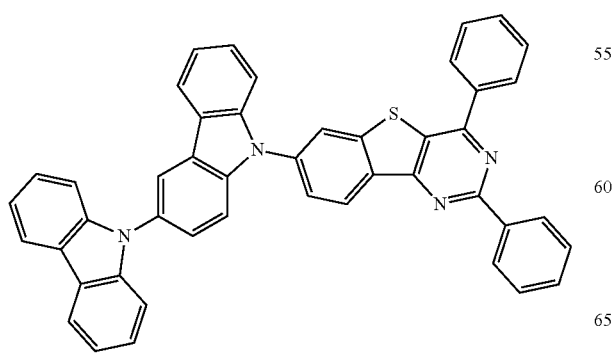
29
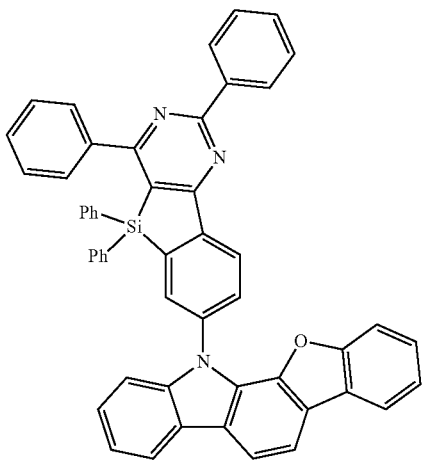
30
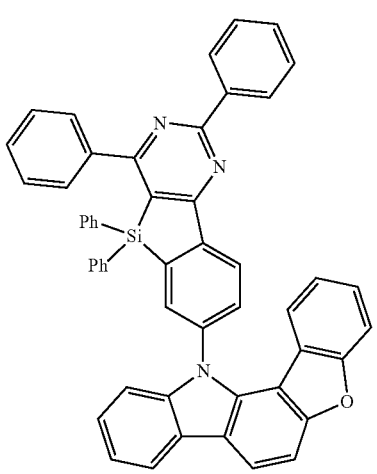
31
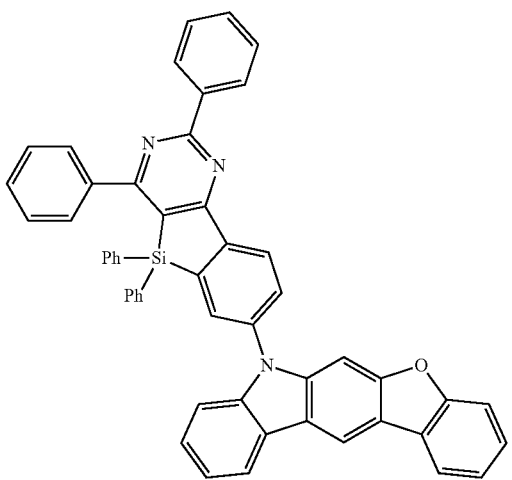

32
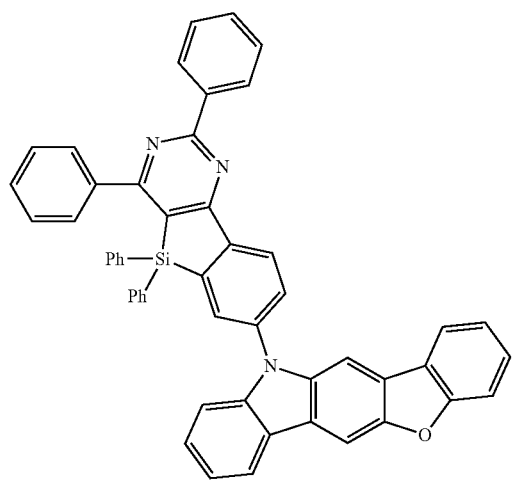
33
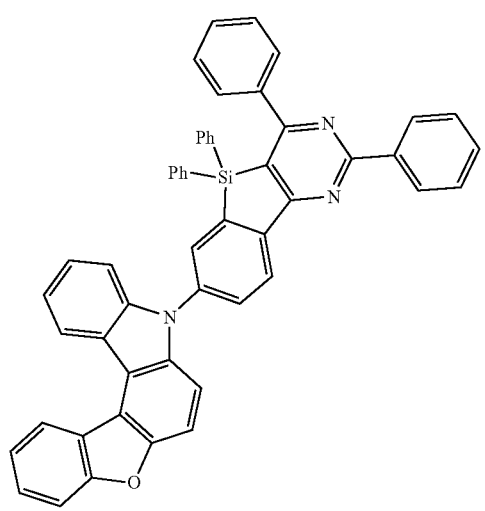
34
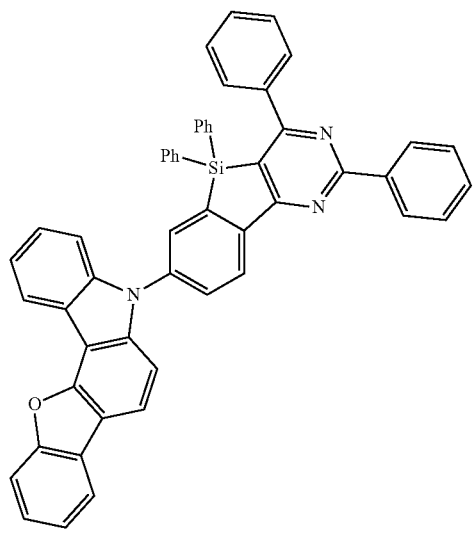
35
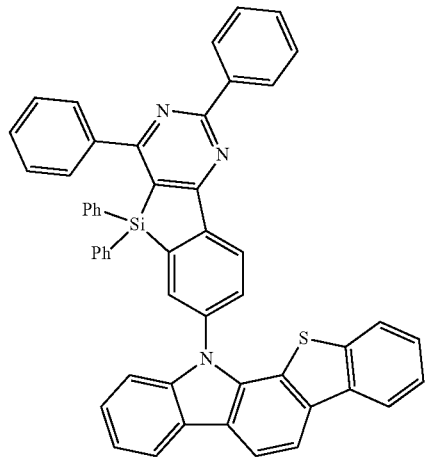
36
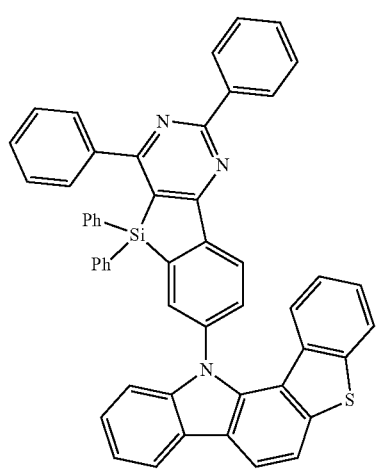
37
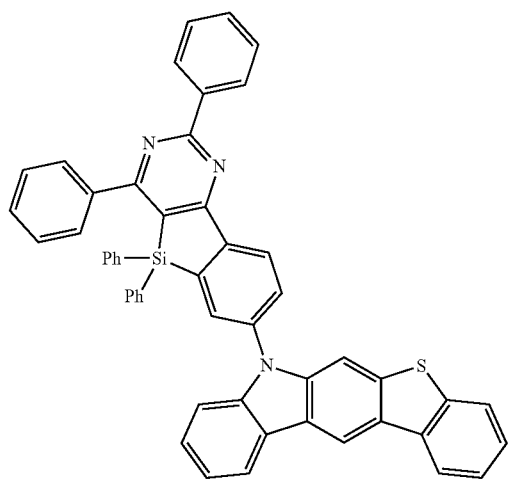

38
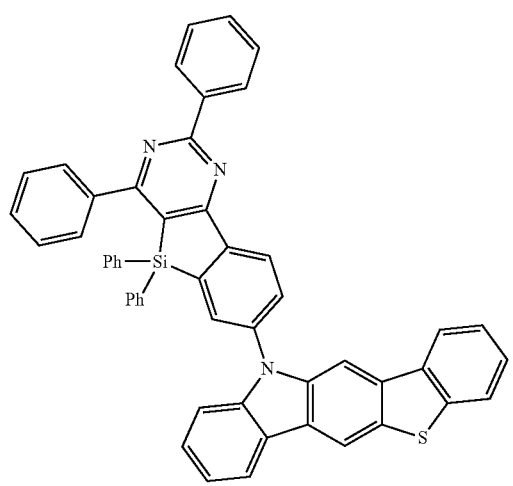
39
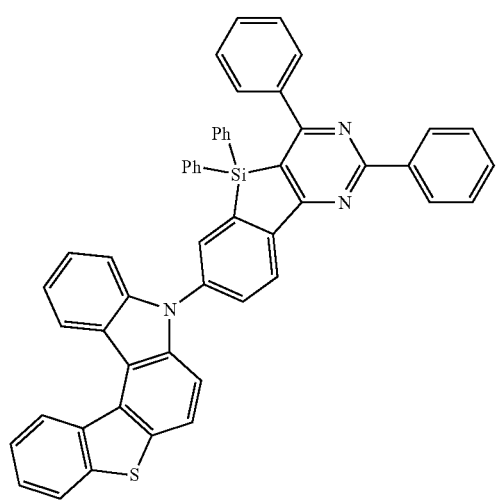
40
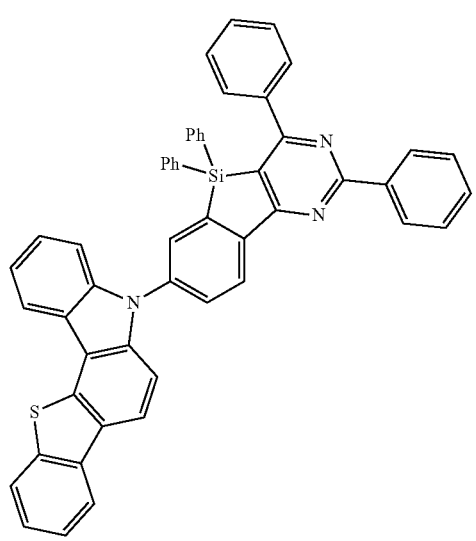
41
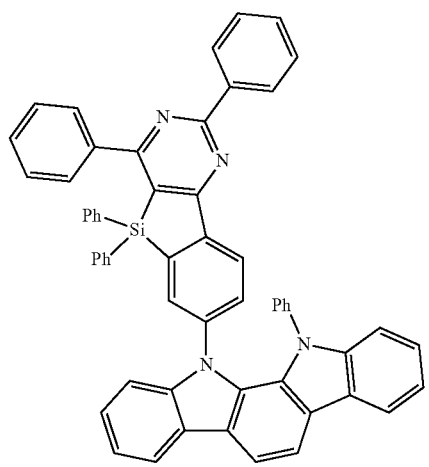
42
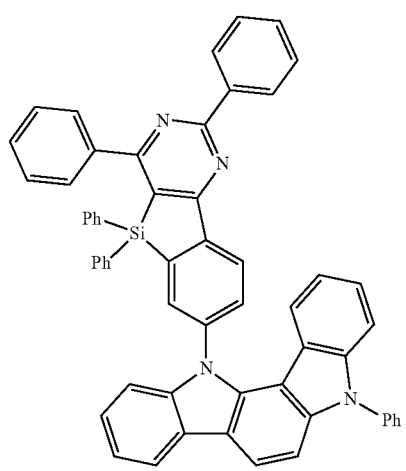
43
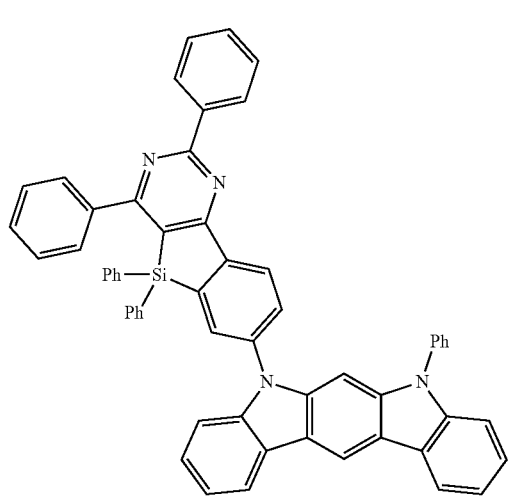

44
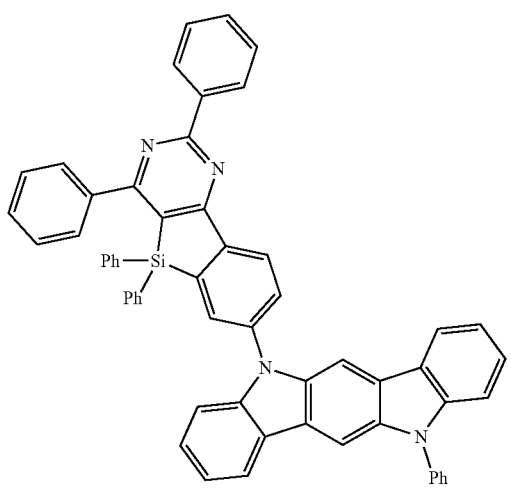
45
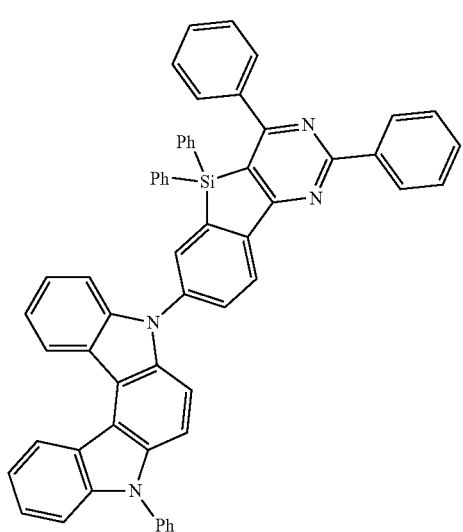
46
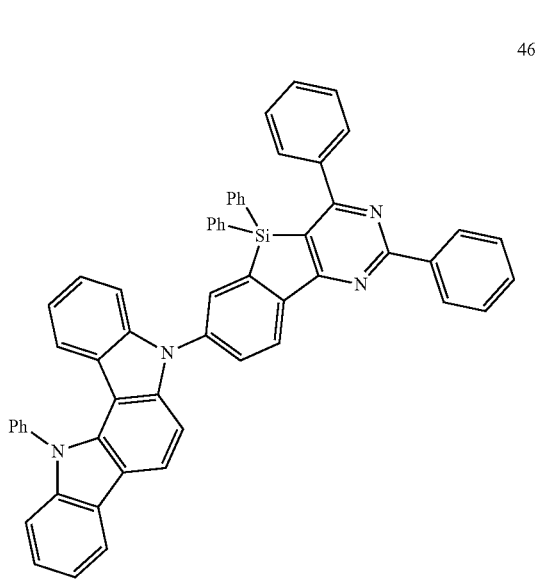
47
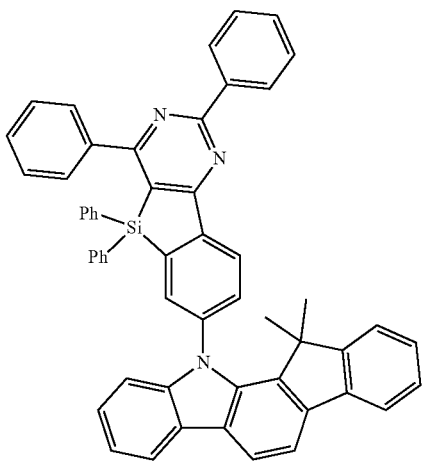
48
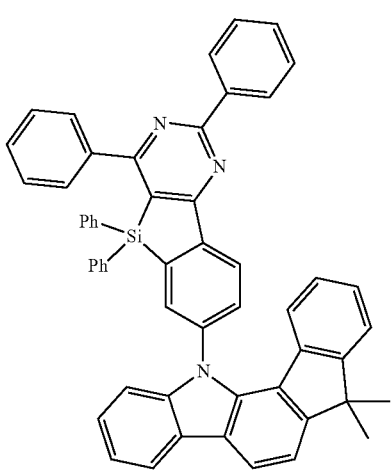
49
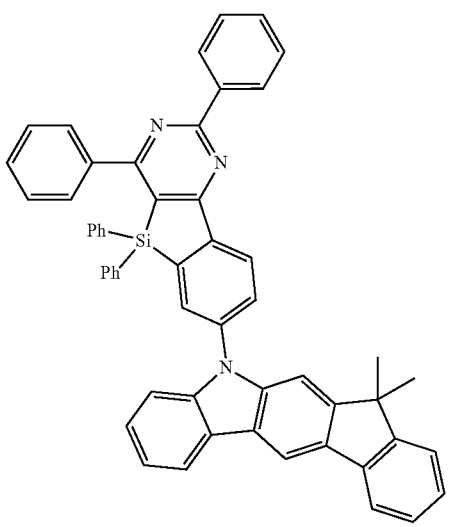

-continued
50
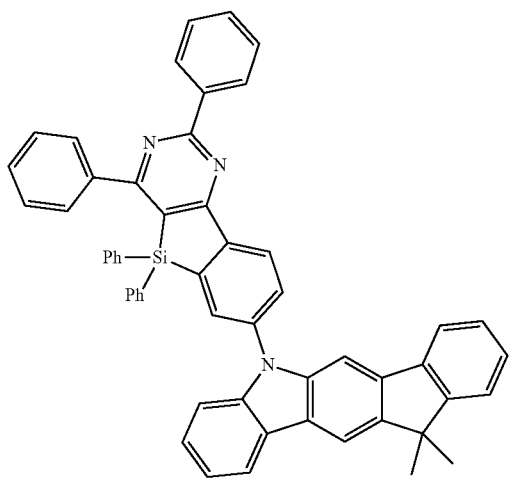
51
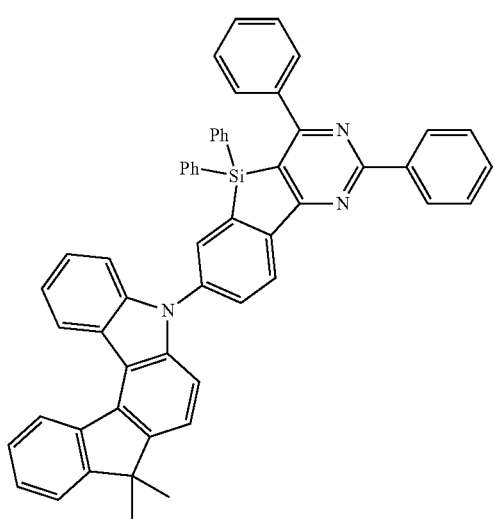
52
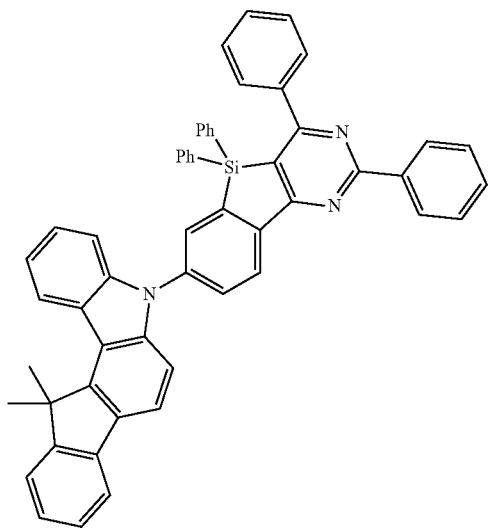
-continued
53
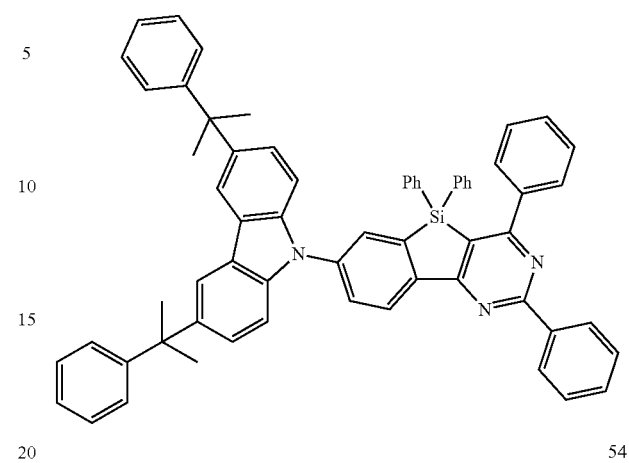
54
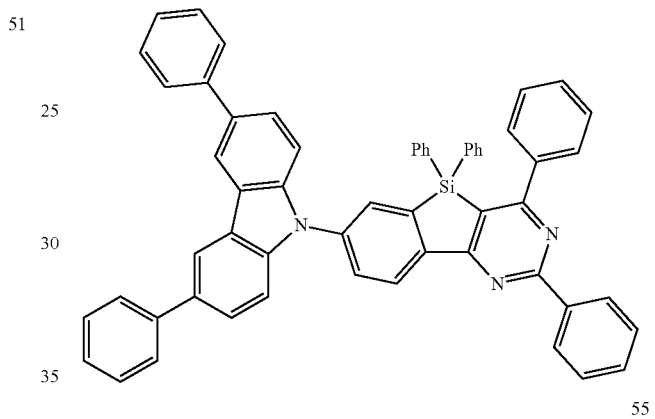
55
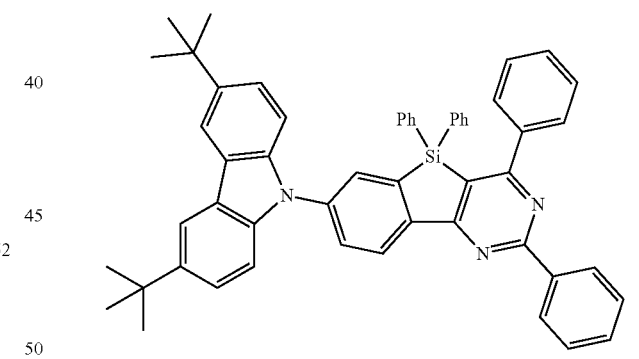
56
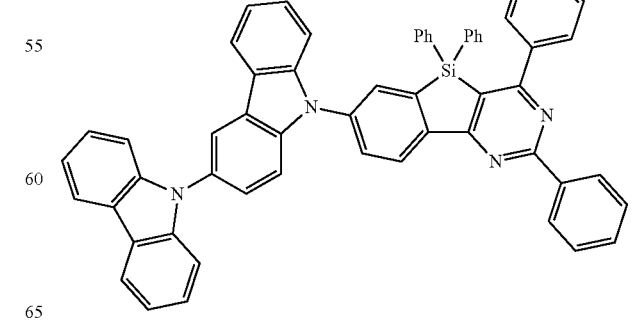

57
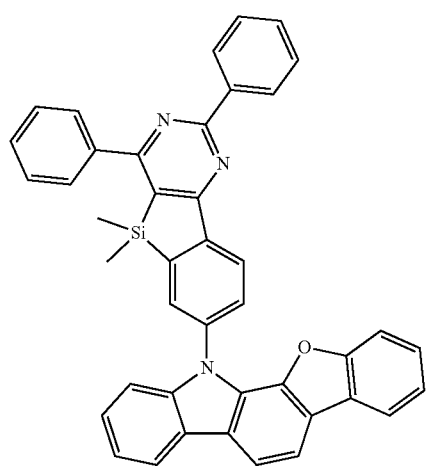
58
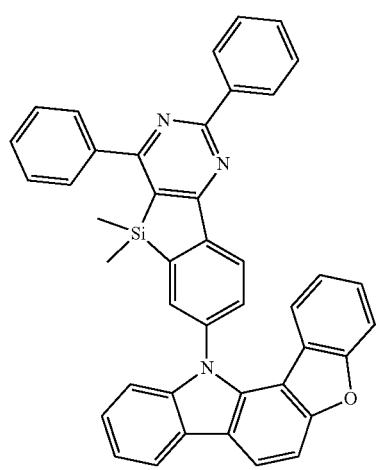
59
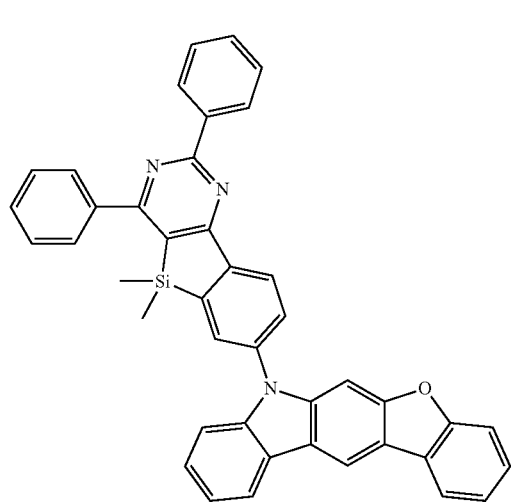
60
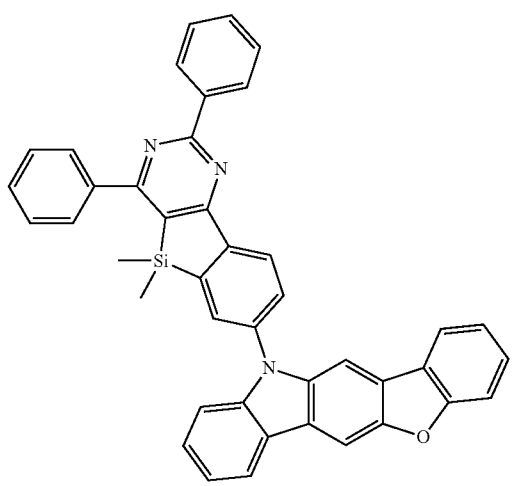
61
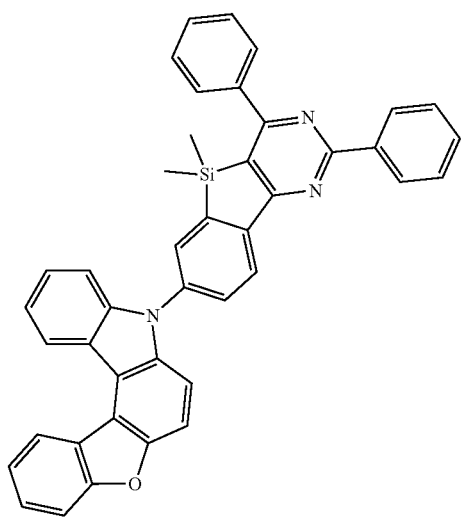
62
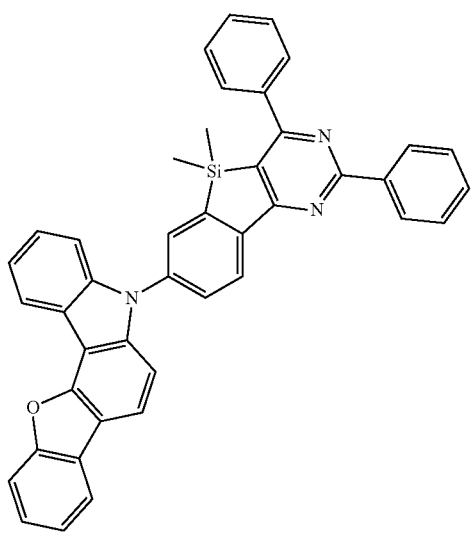

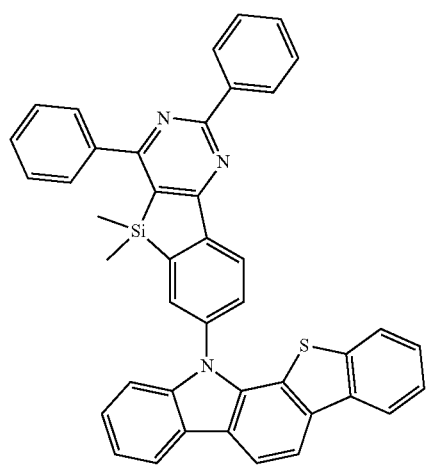
63
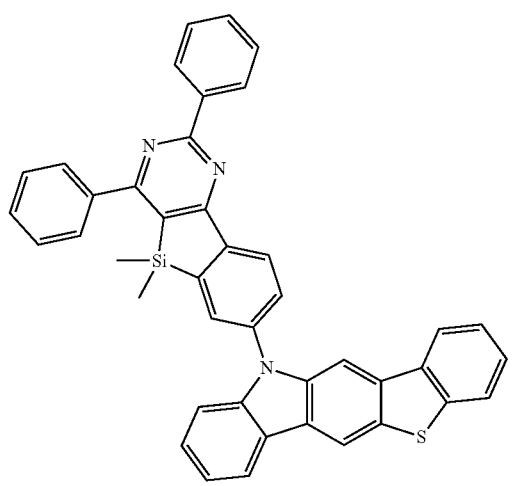
66
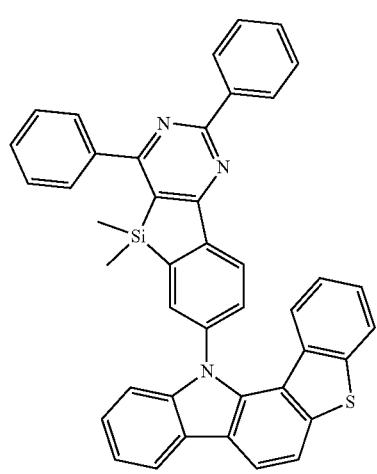
64
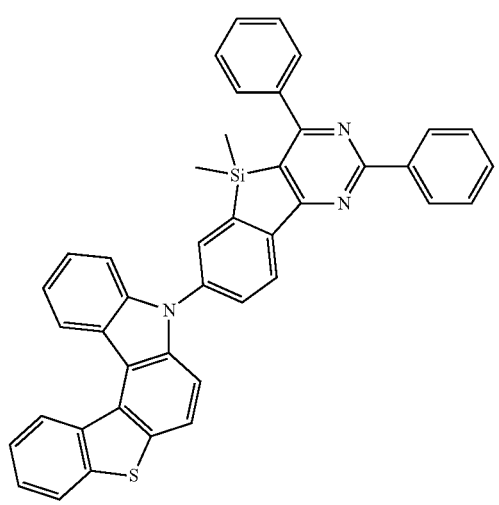
67
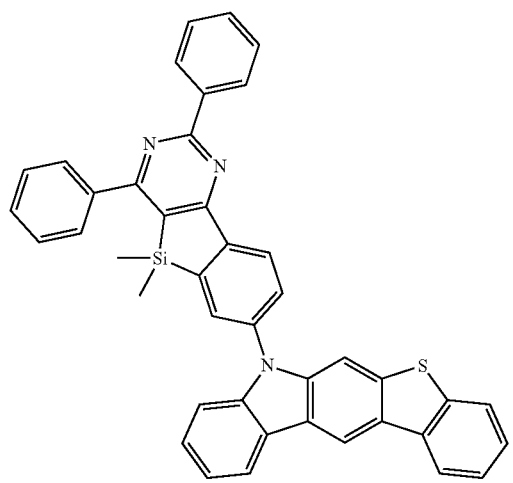
65
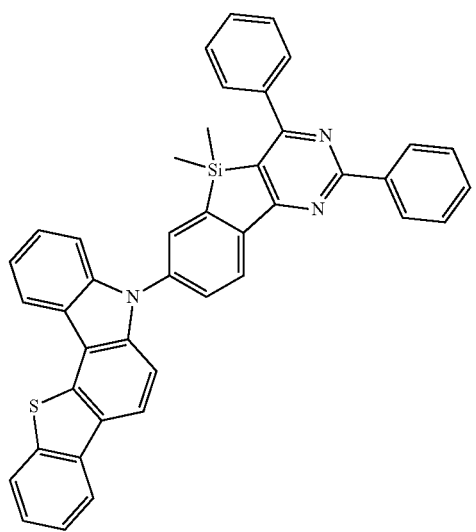
68

-continued
69
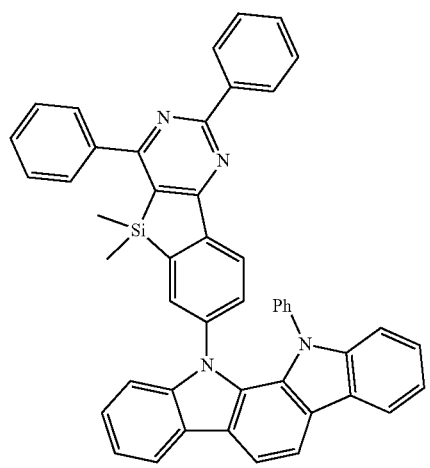
70
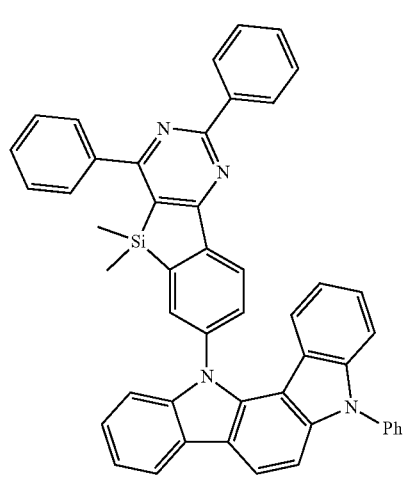
71
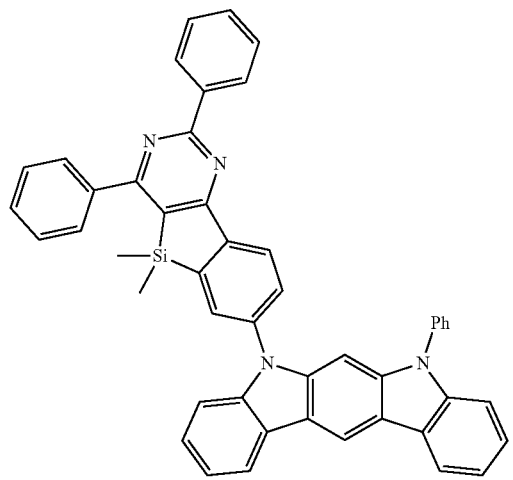
-continued
72
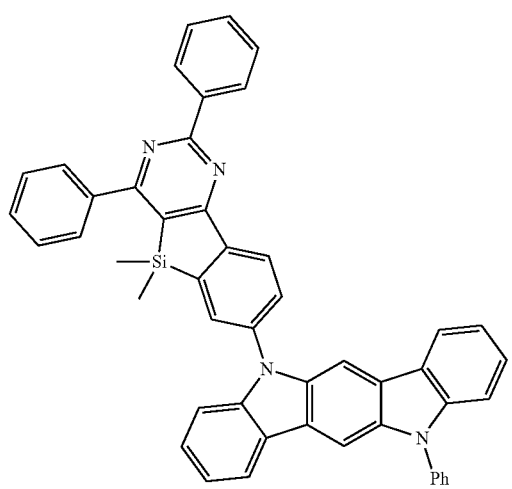
73
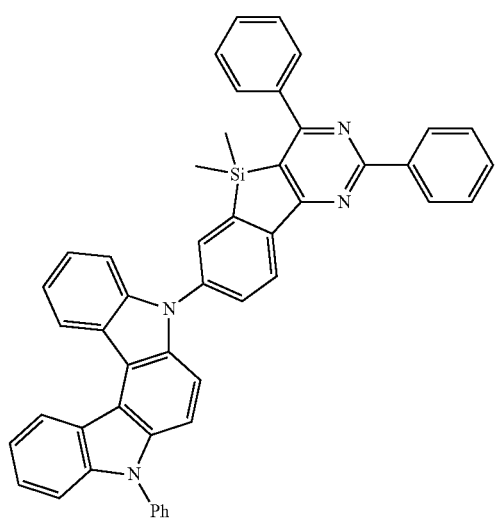
74
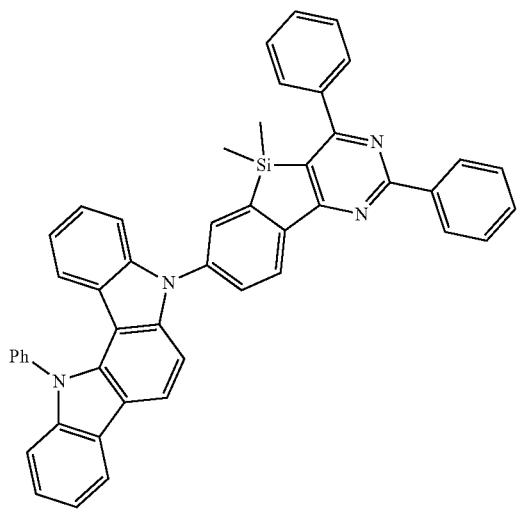

75
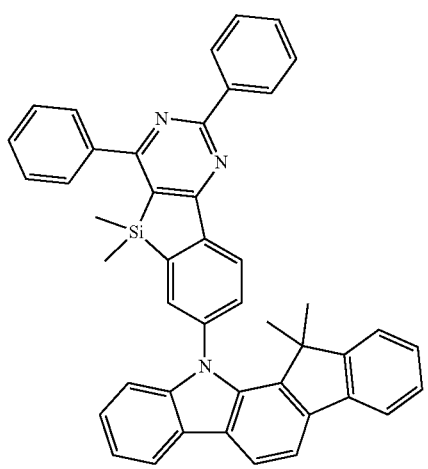
76
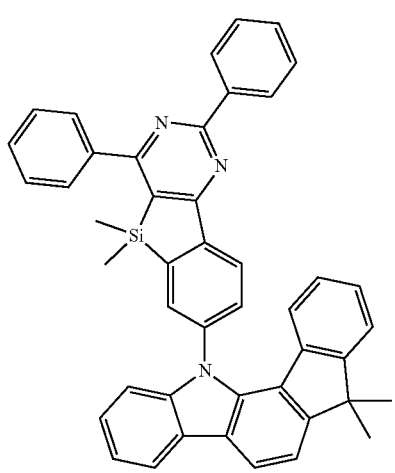
77
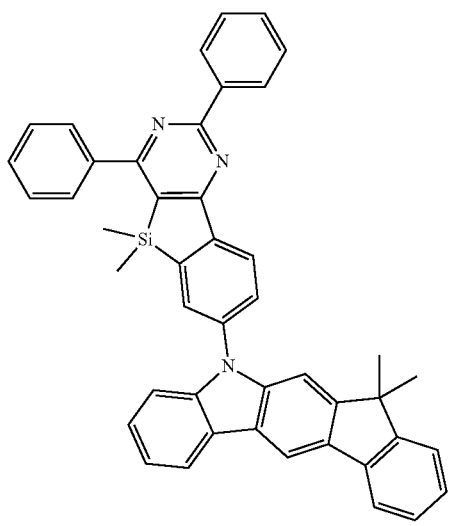
78
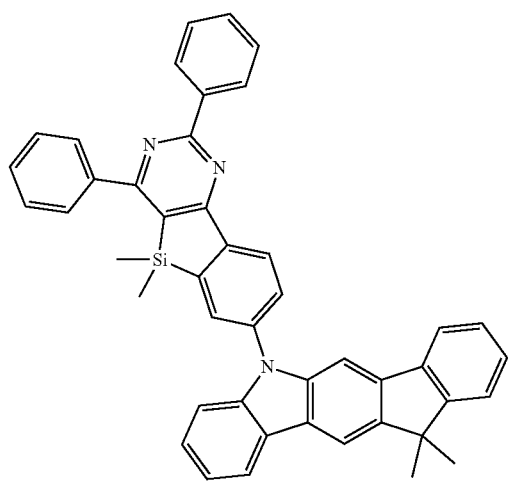
79
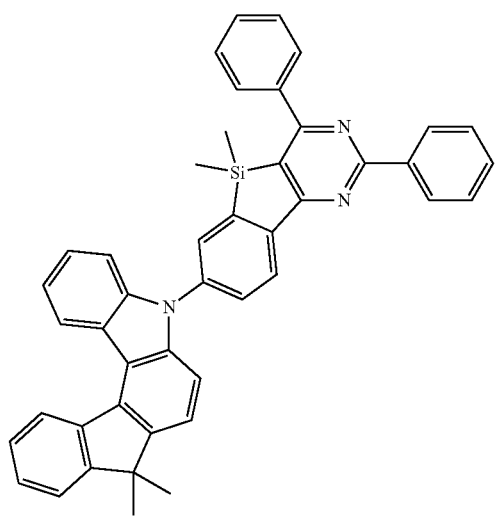
80
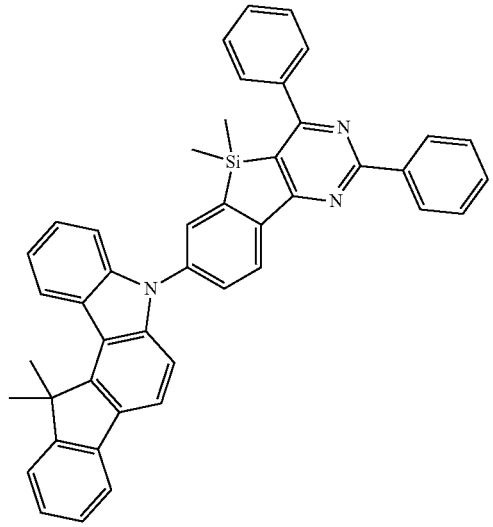

81
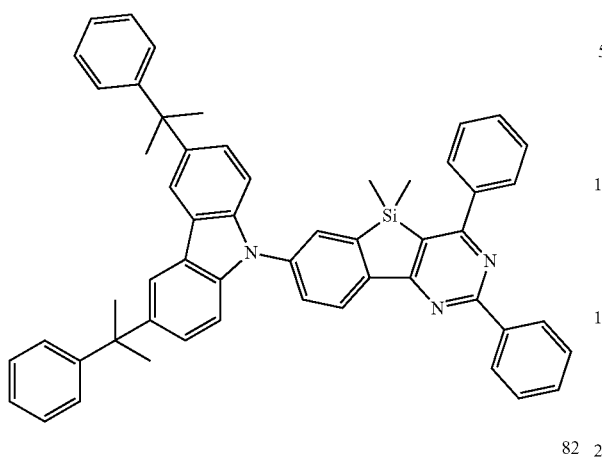
82
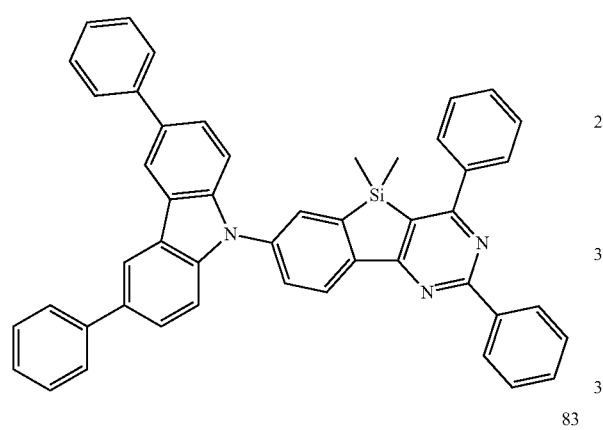
83
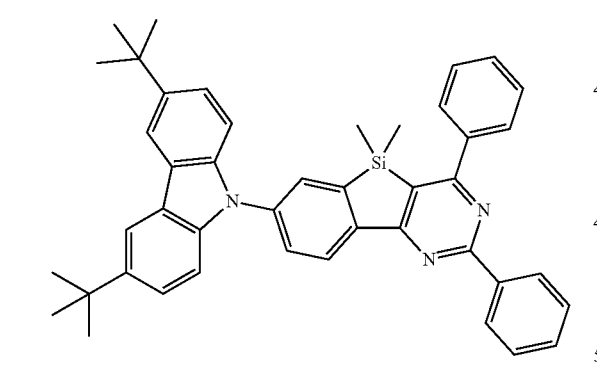
84
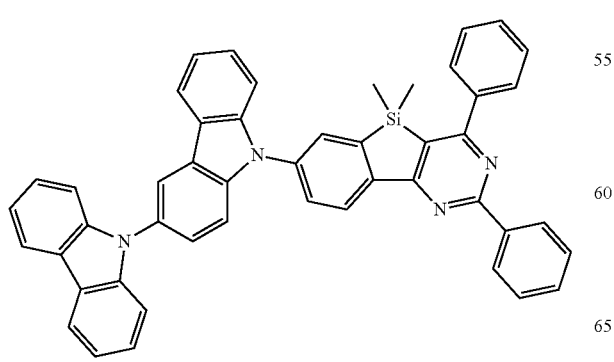
85
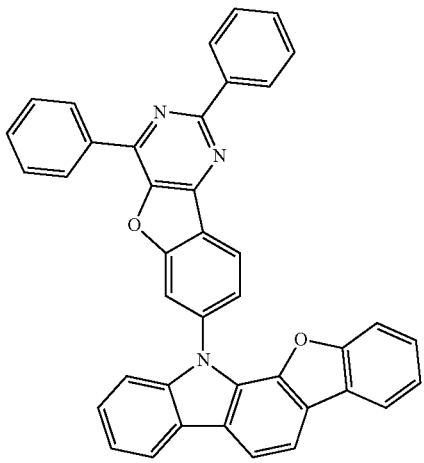
86
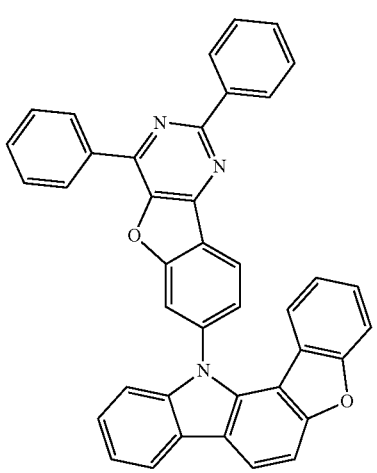
87
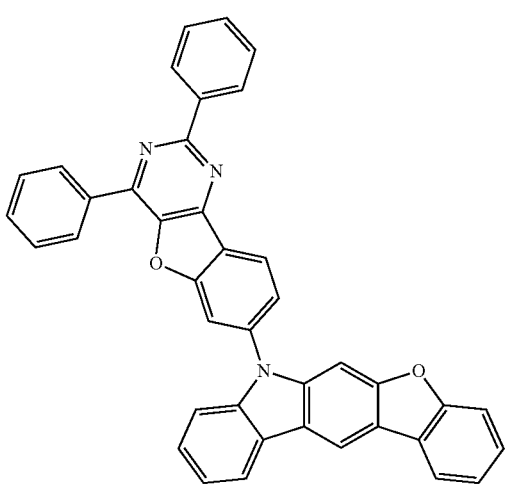

88
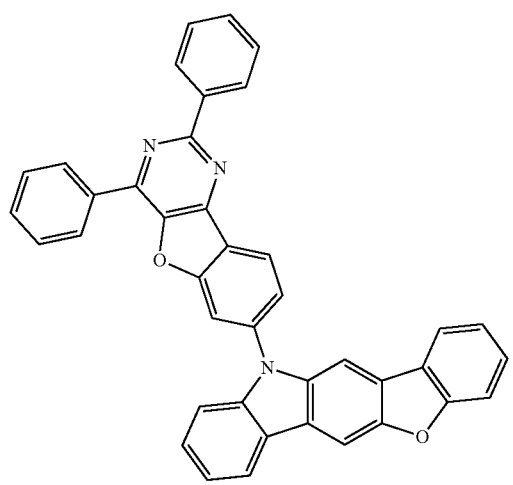
89
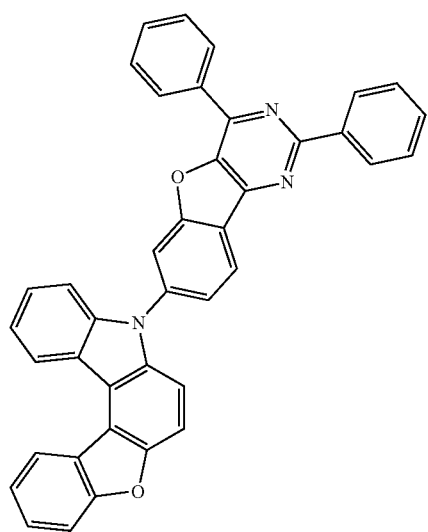
90
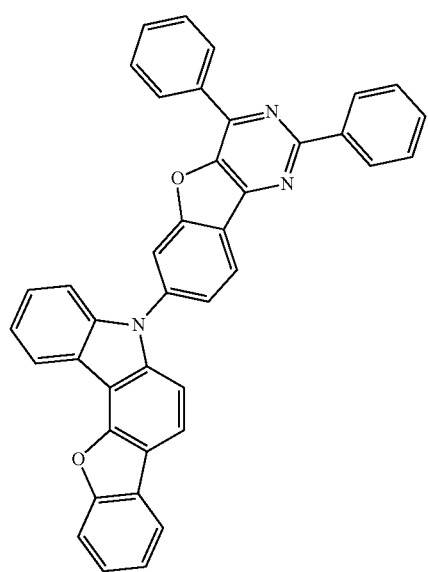
91
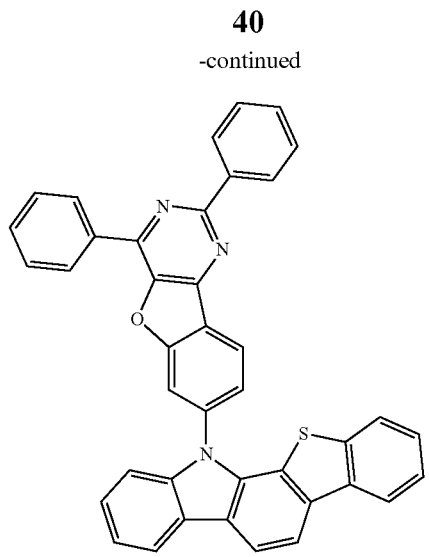
92
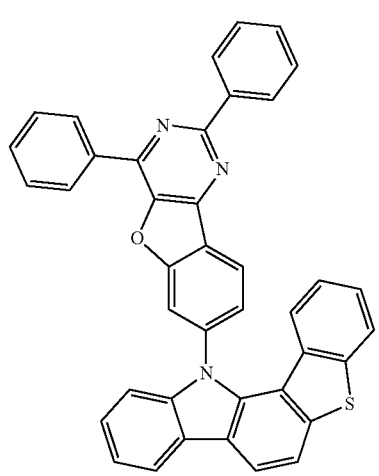
93
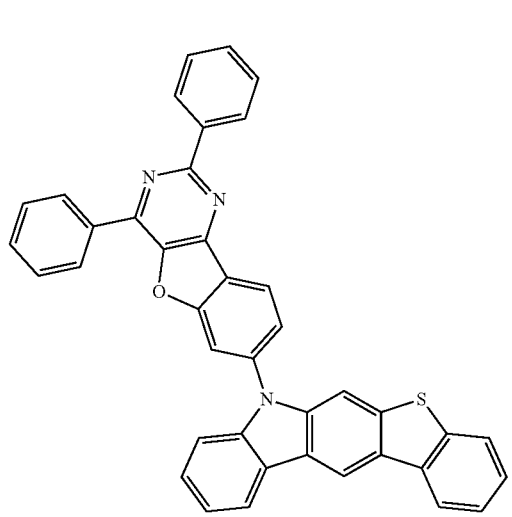

94
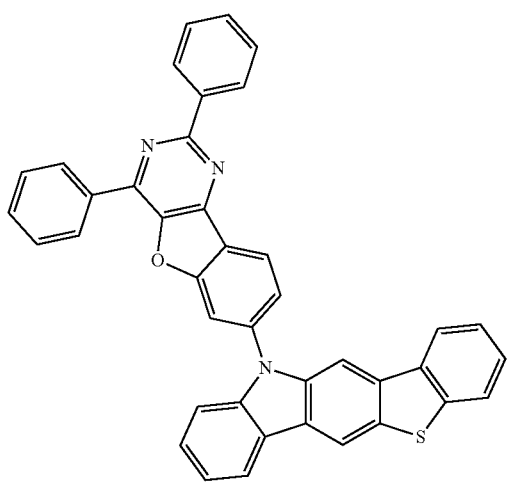
95
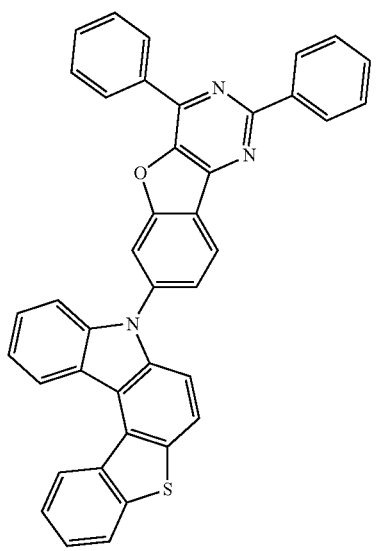
96
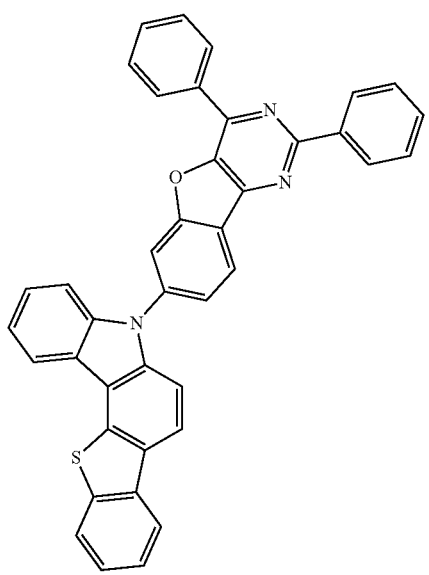
97
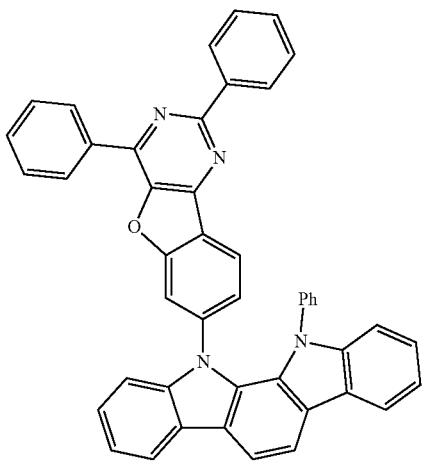
98
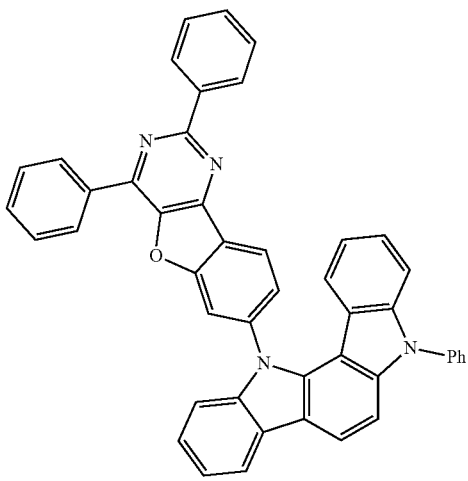
99
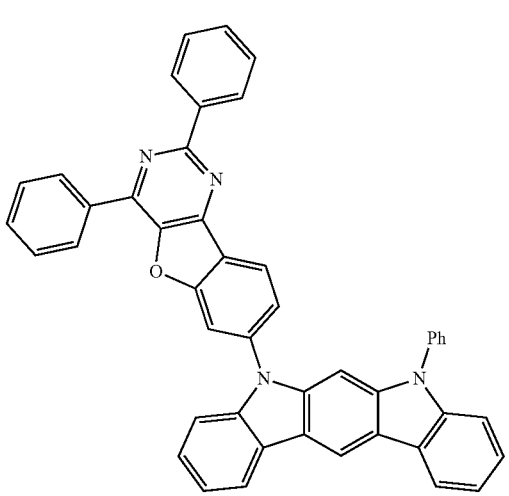

100
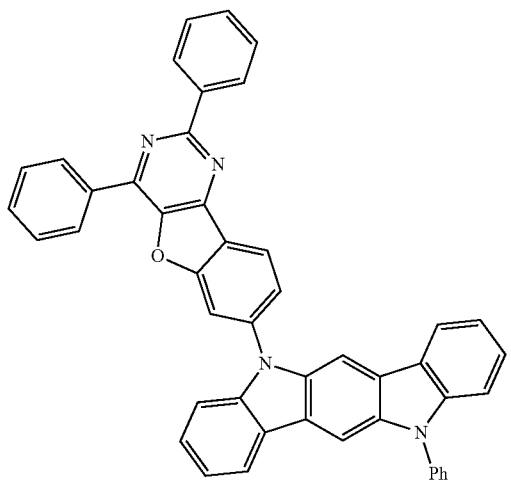
101
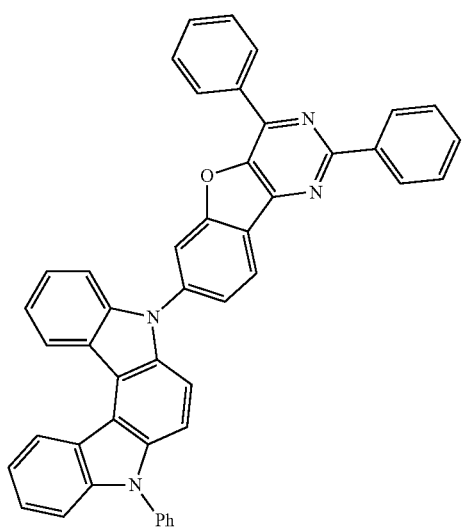
102
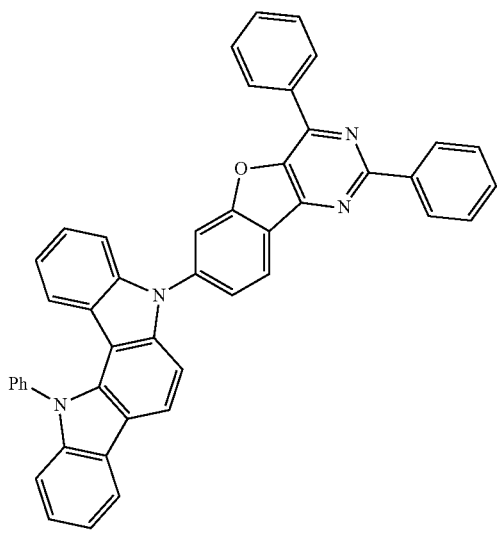
103
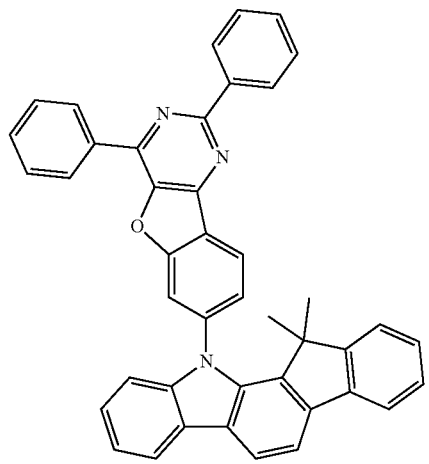
104
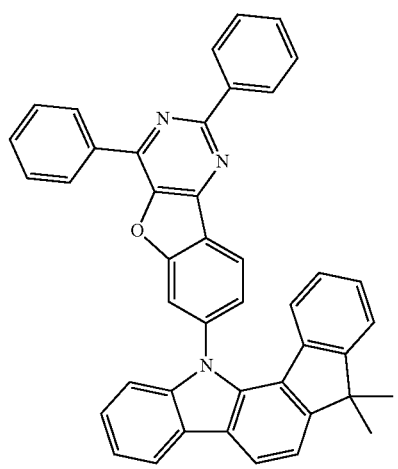
105
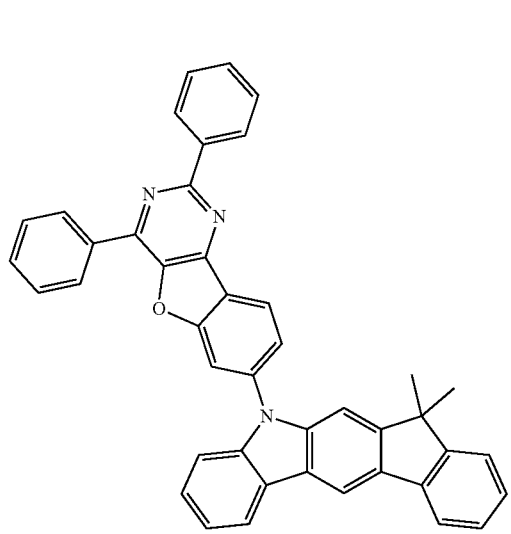

106
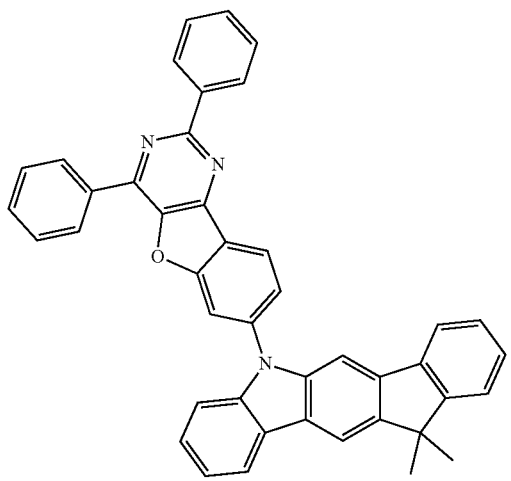
107
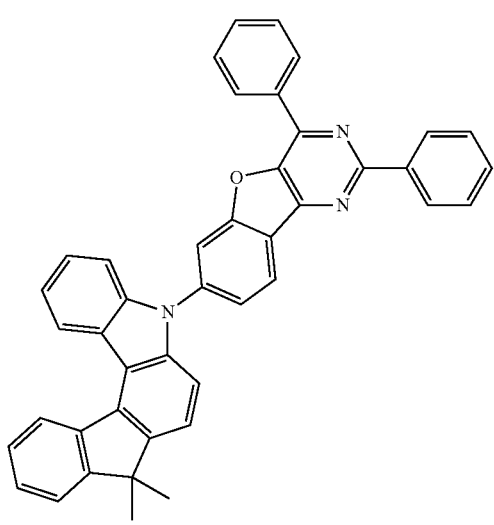
108
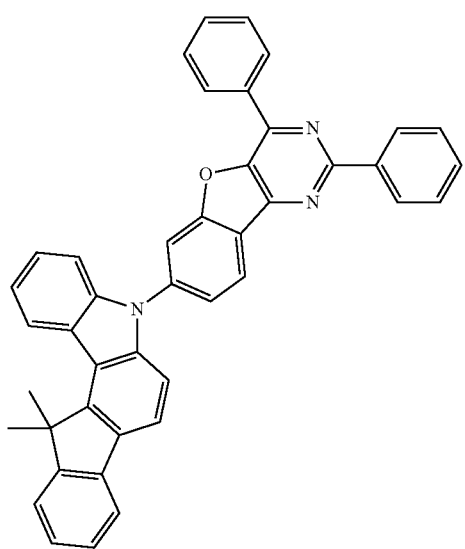
109
110
111
112
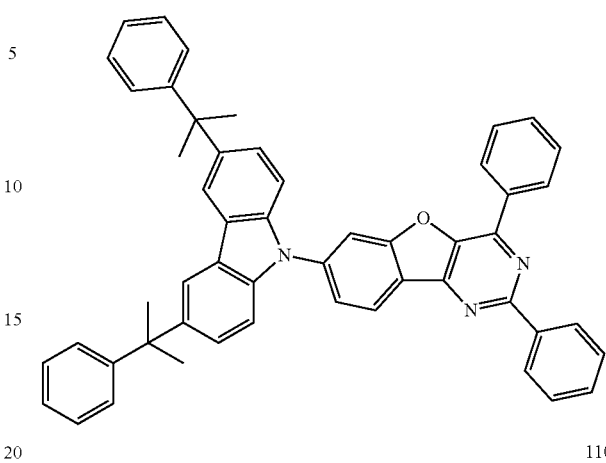

113
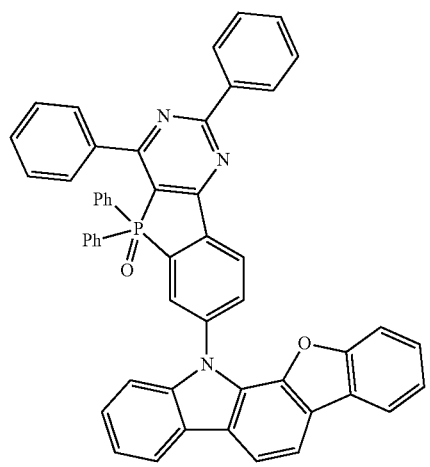
114
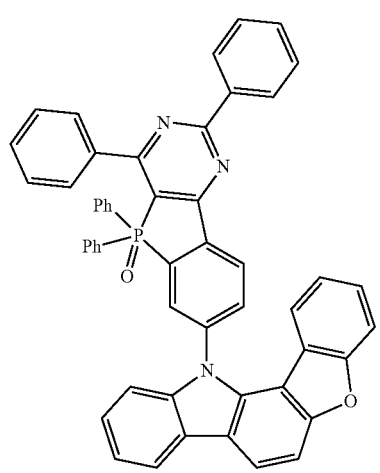
115
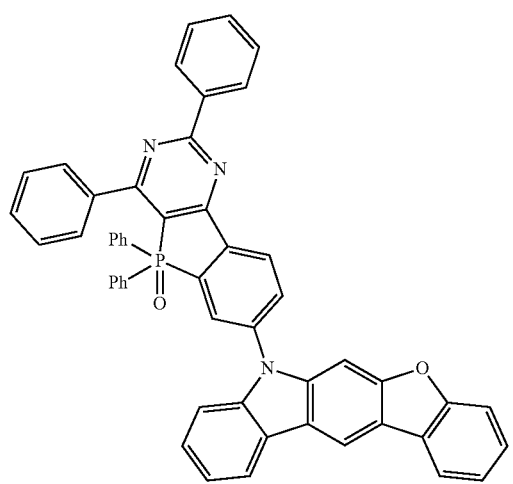
116
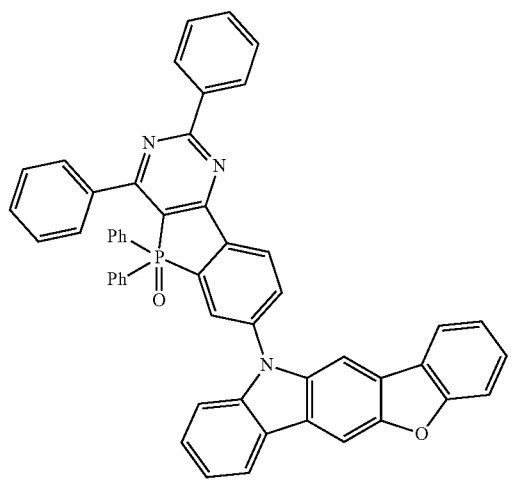
117
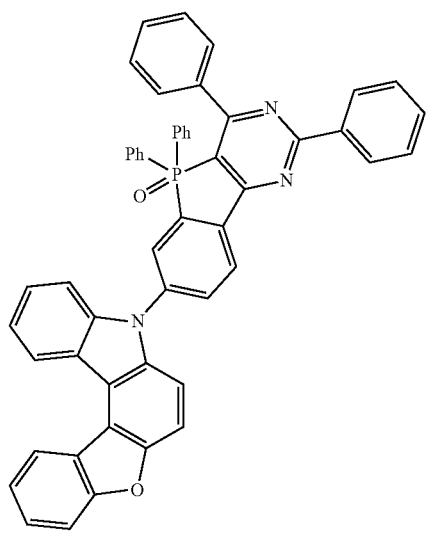
118
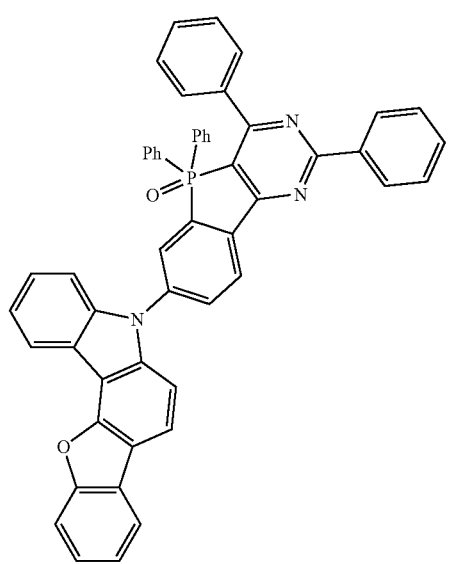

119
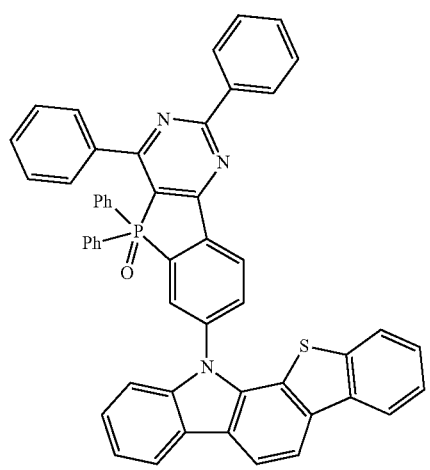
120
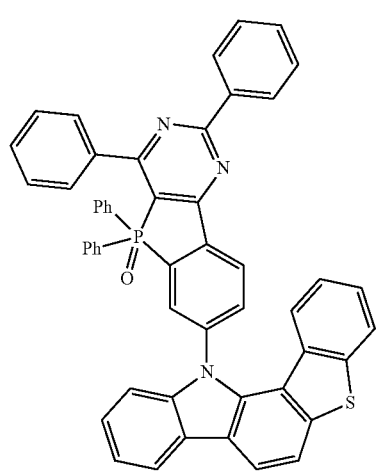
121
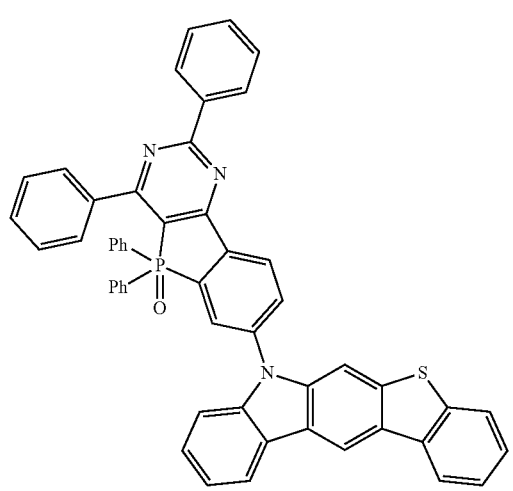
122
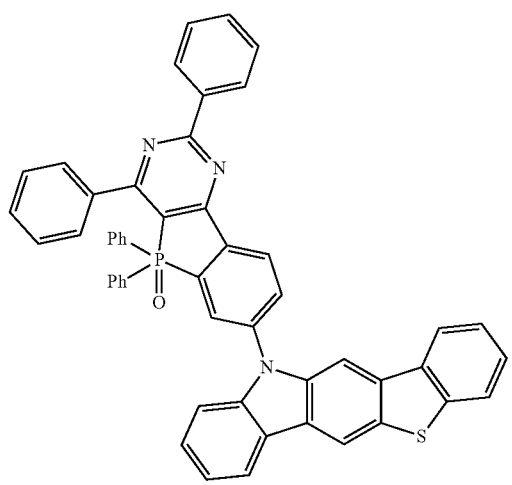
123
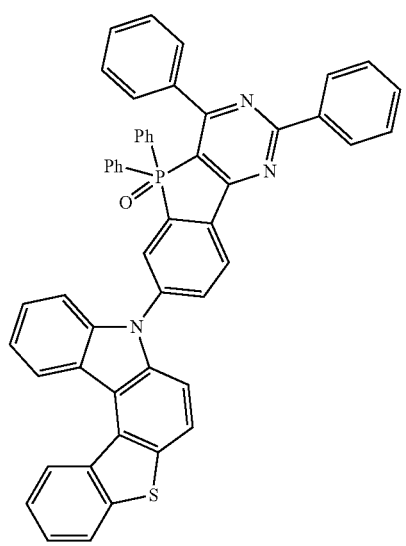
124
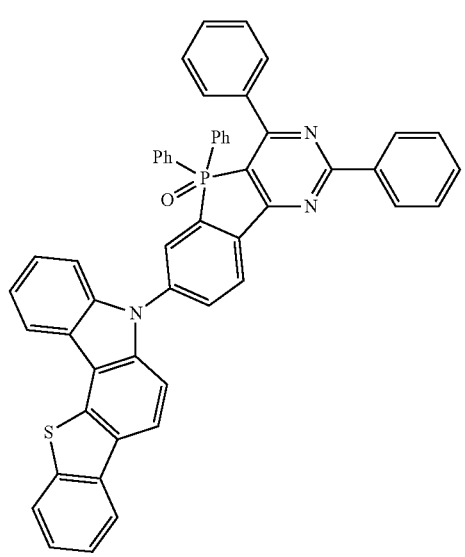

125
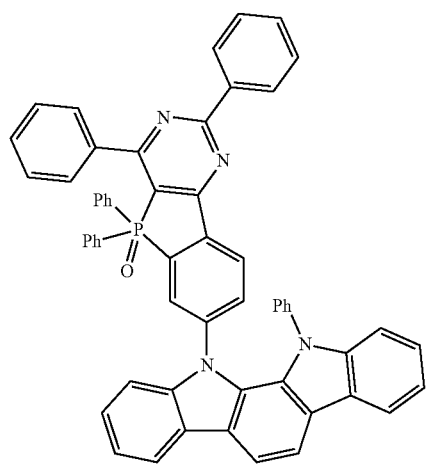
126
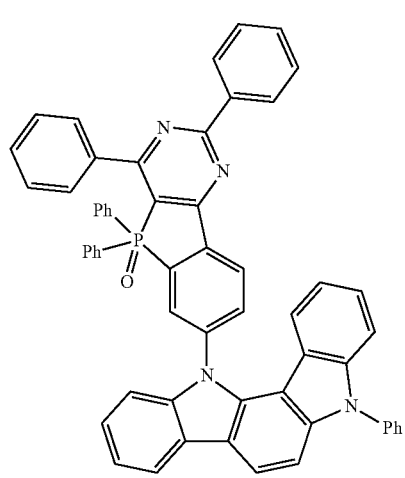
127
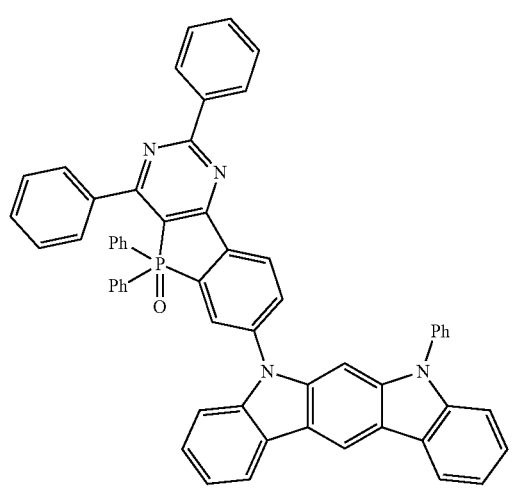
128
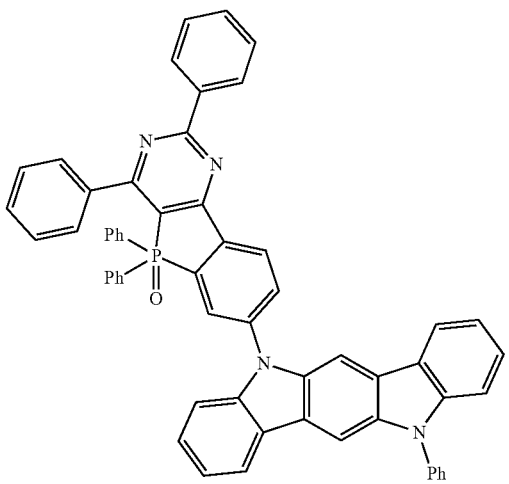
129
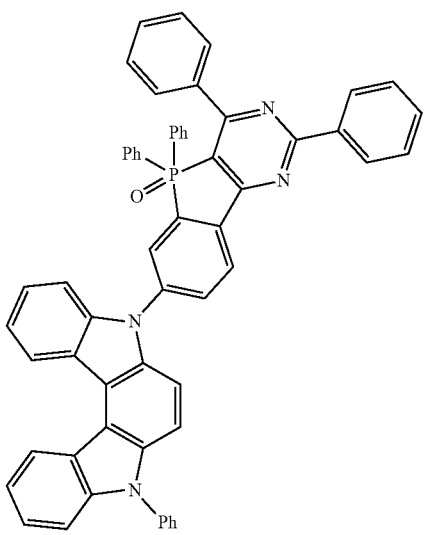
130
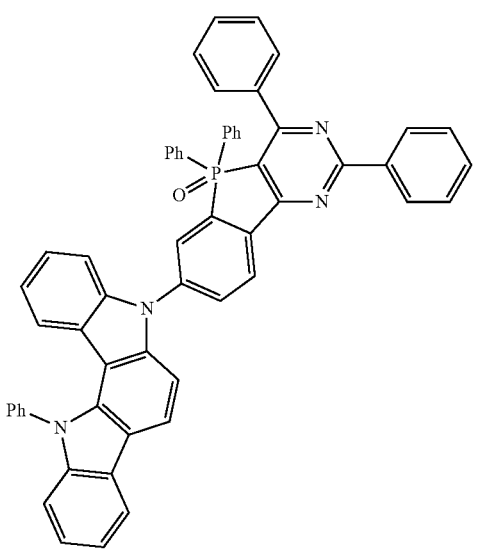

131
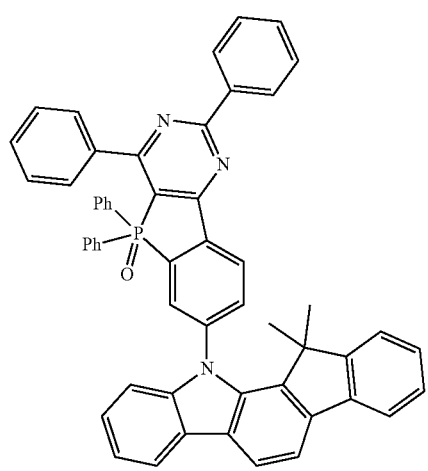
132
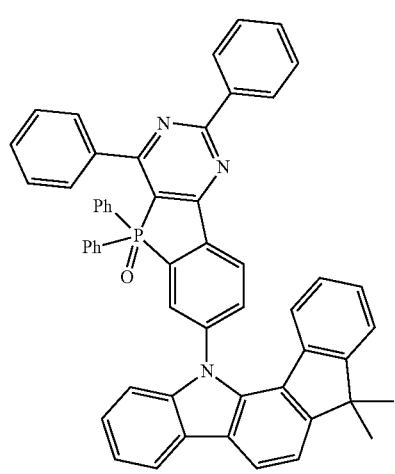
133
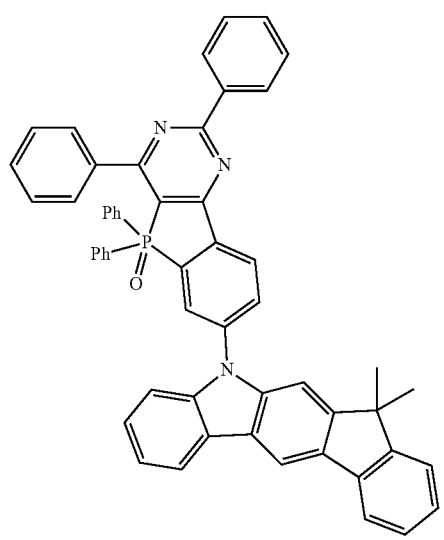
134
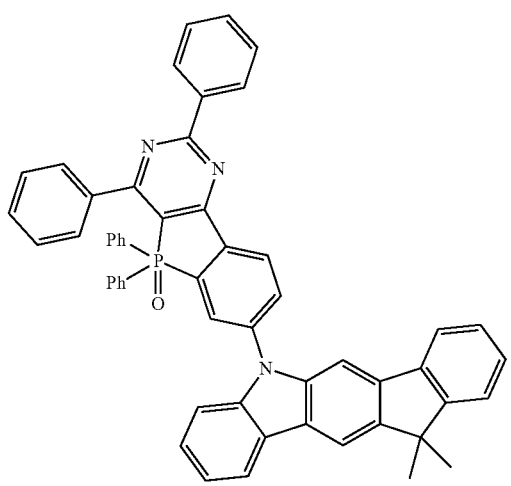
135
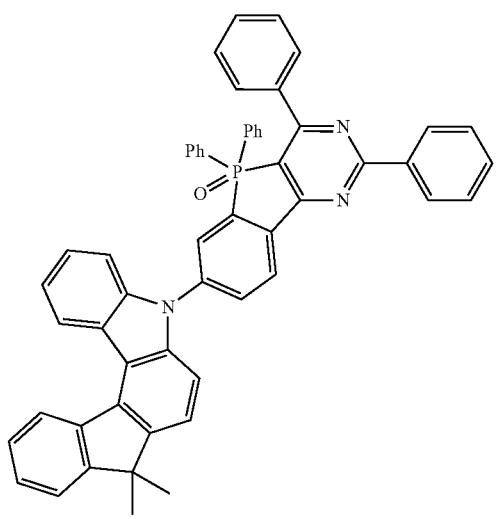
136
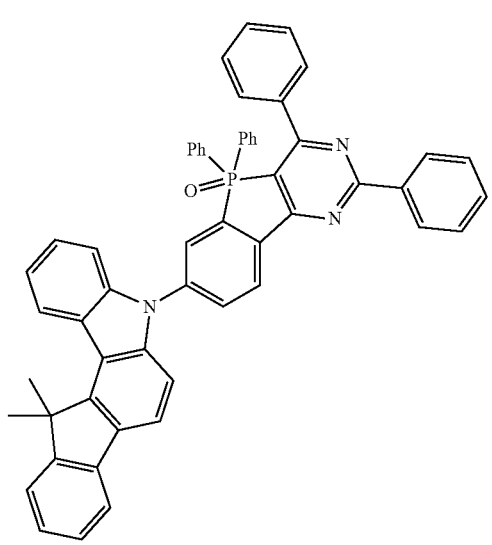

137
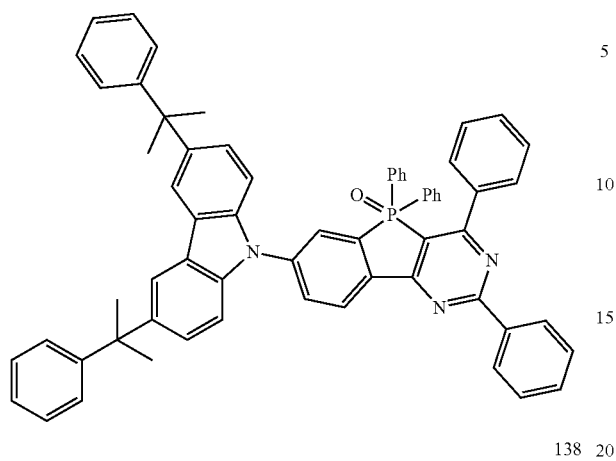
138
139
140
141
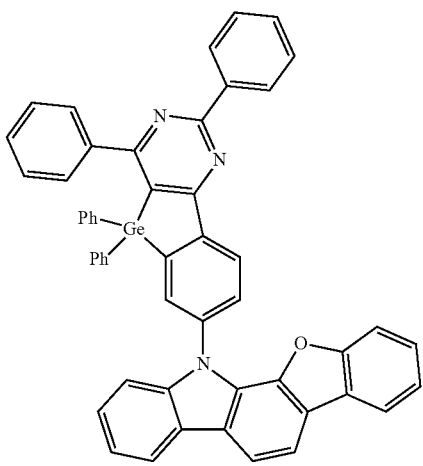
142
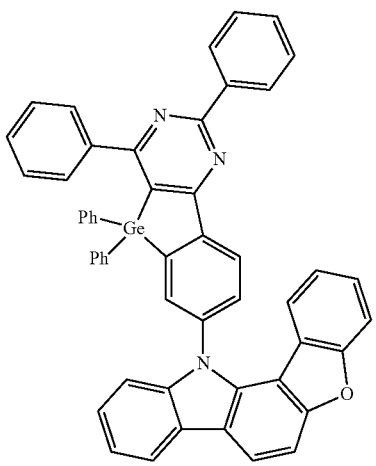
143
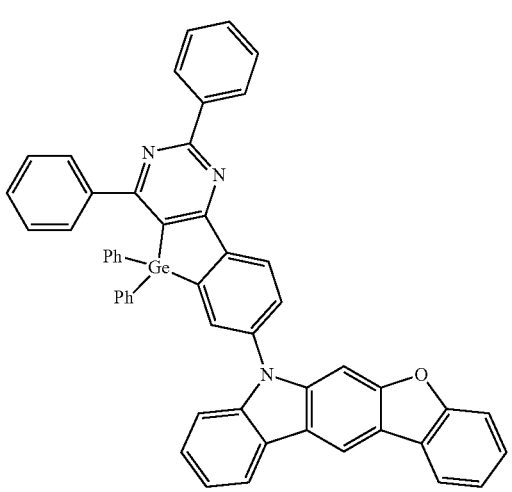

144
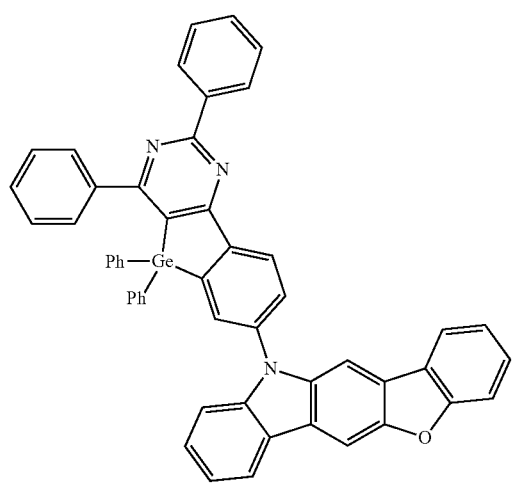
145
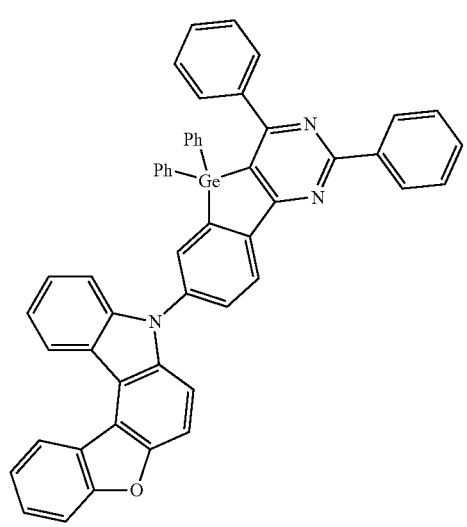
146
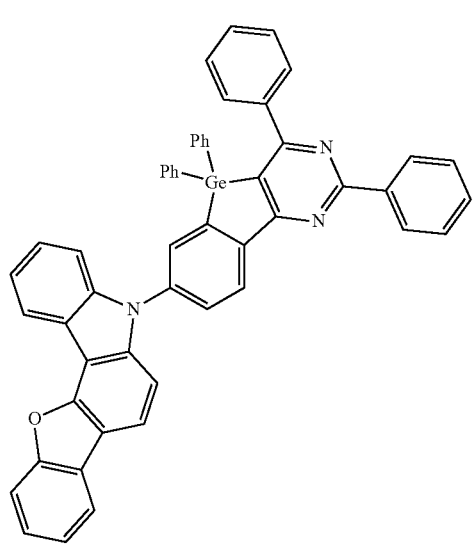
147
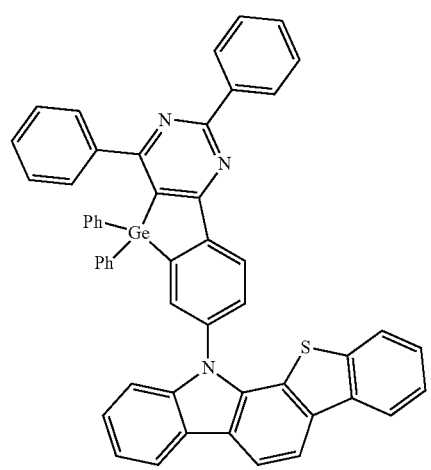
148
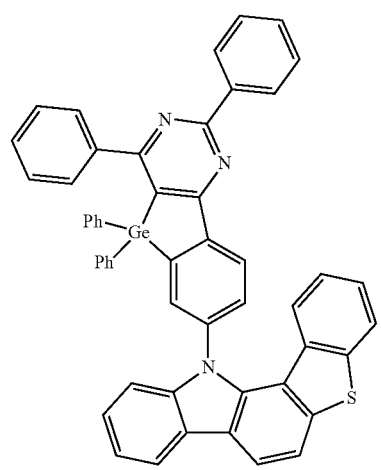
149
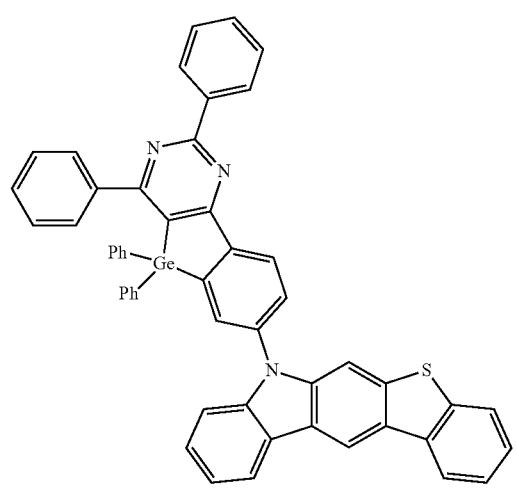

150
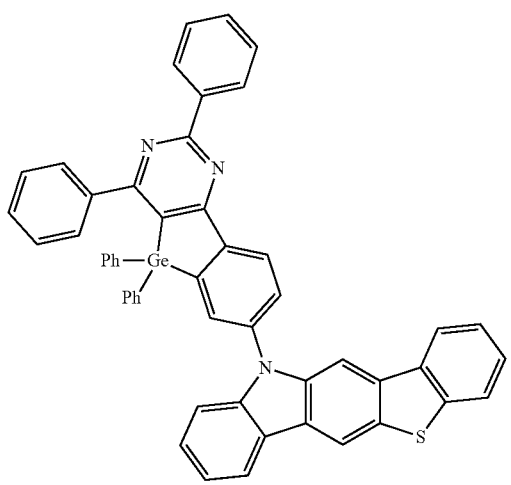
151
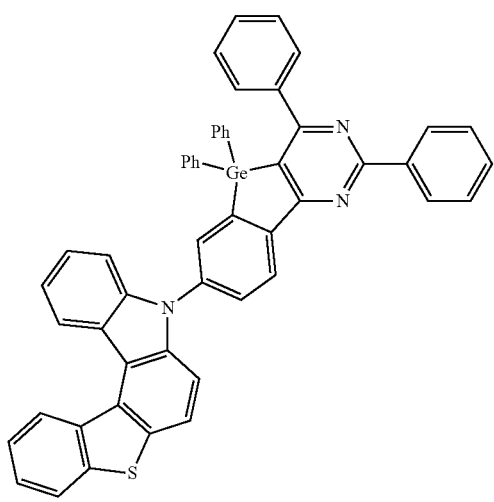
152
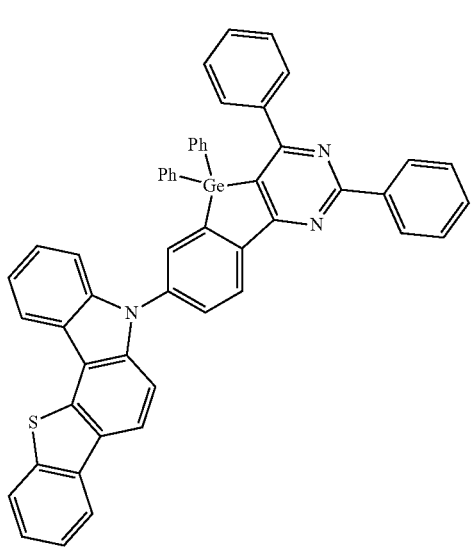
153
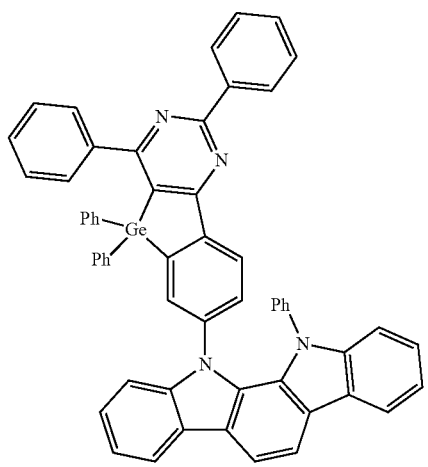
154
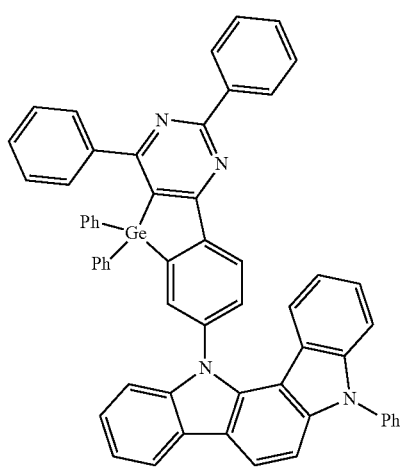
155
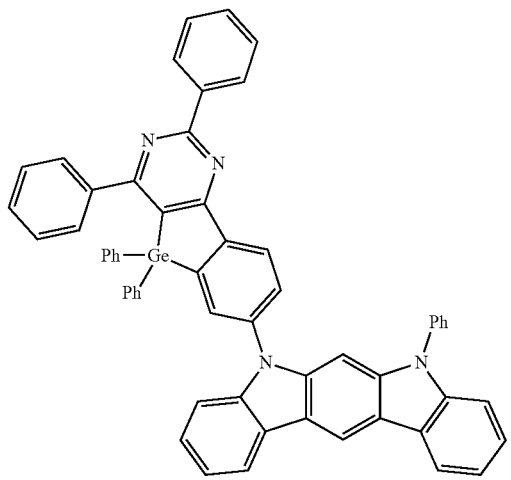

156
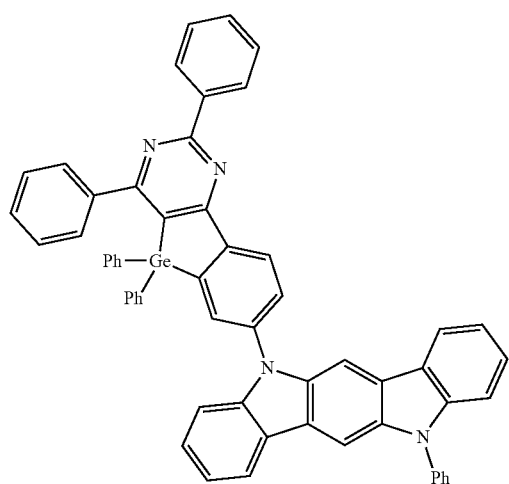
157
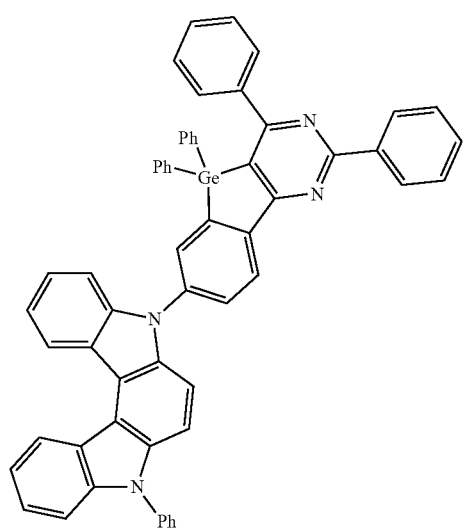
159
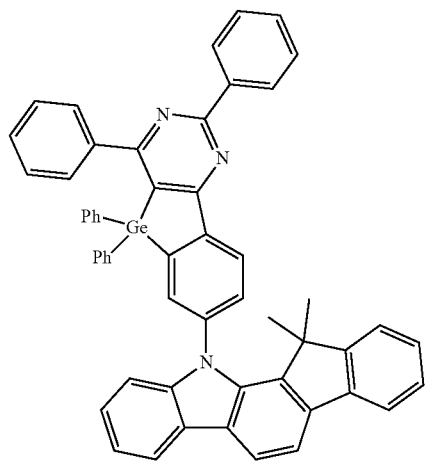
160
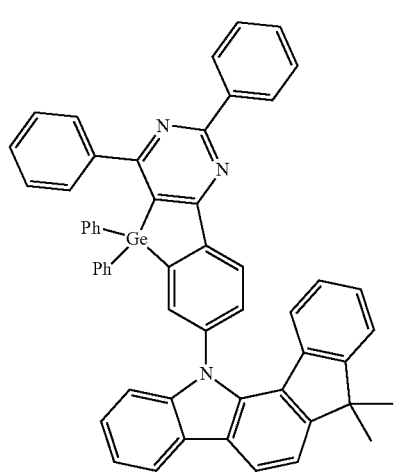
158
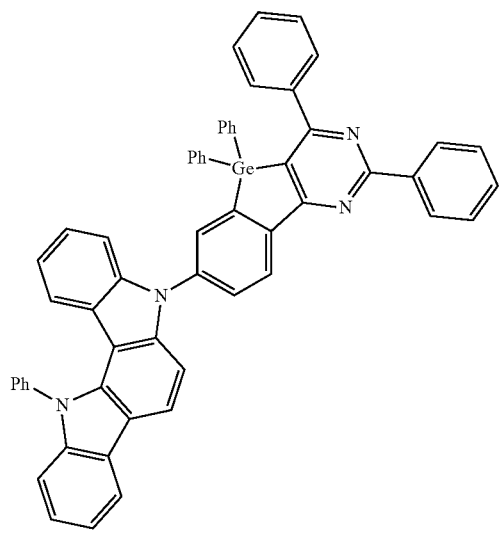
161
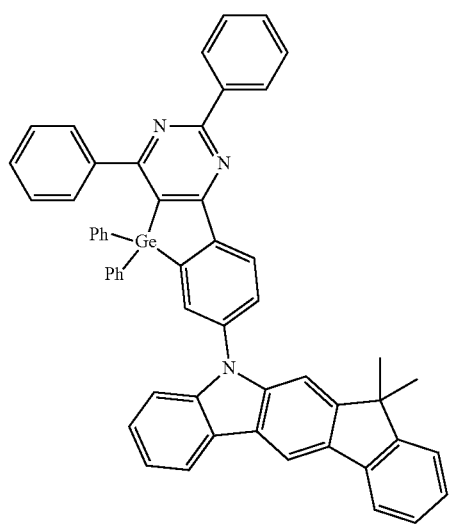

162
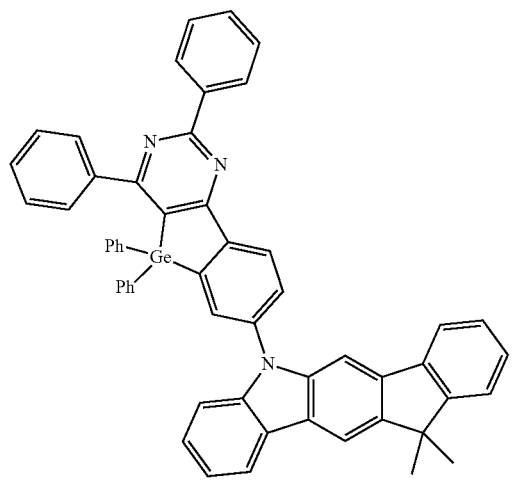
163
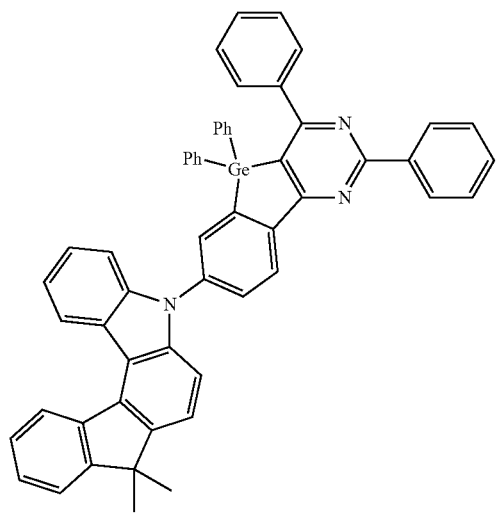
164
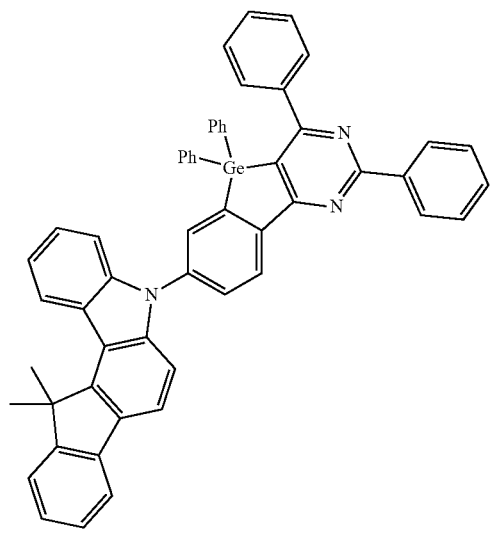
165
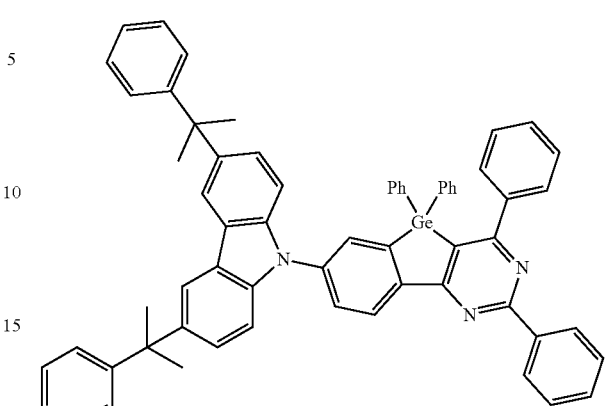
166
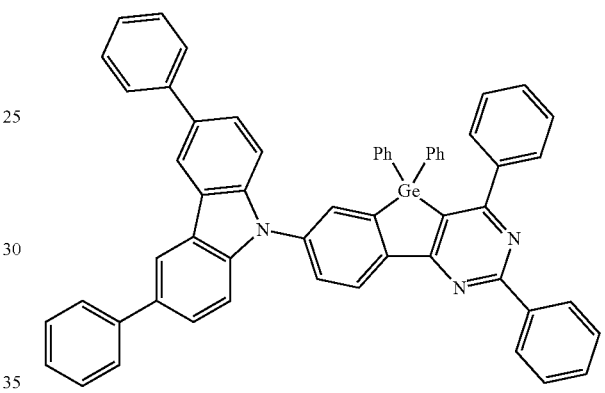
167

168
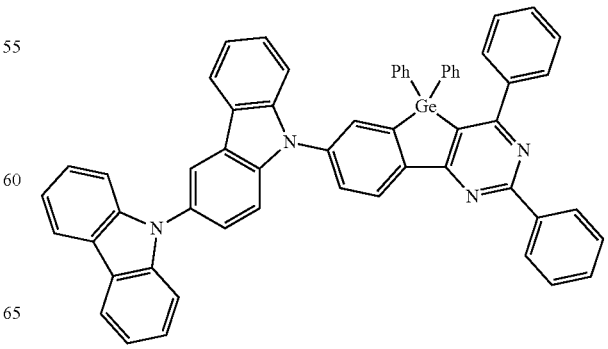

65
-continued
169
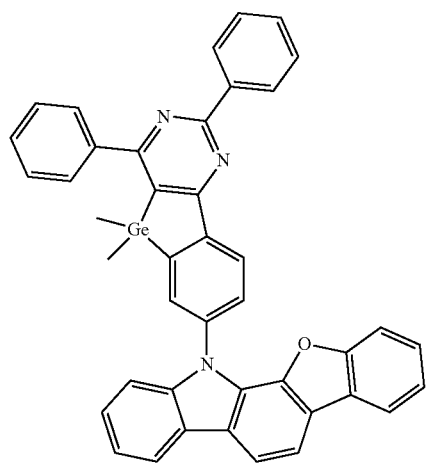
170
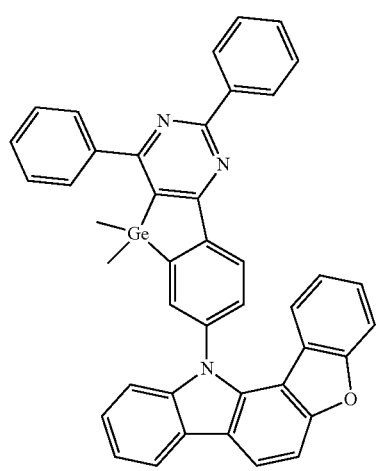
171
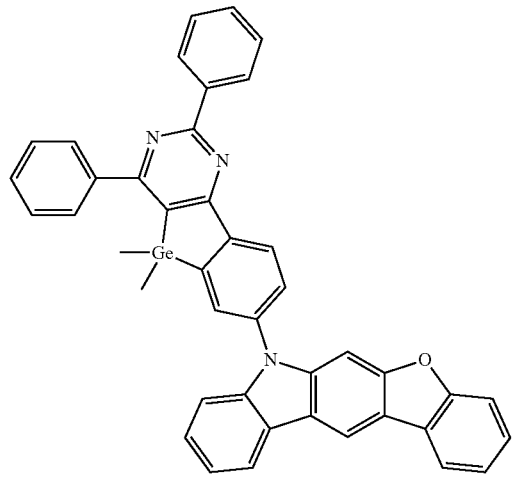
66
-continued
172
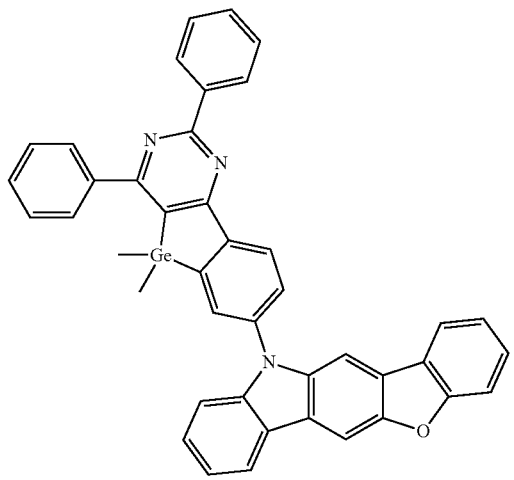
173
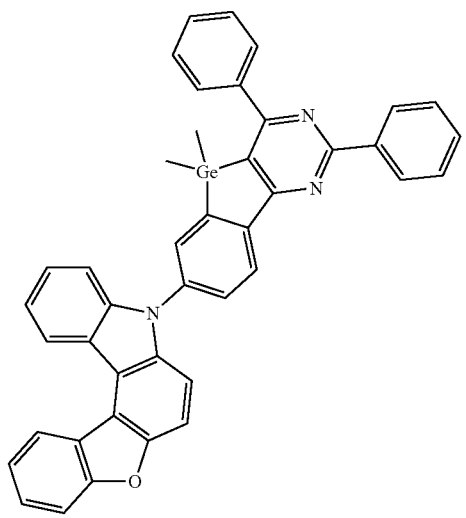
174
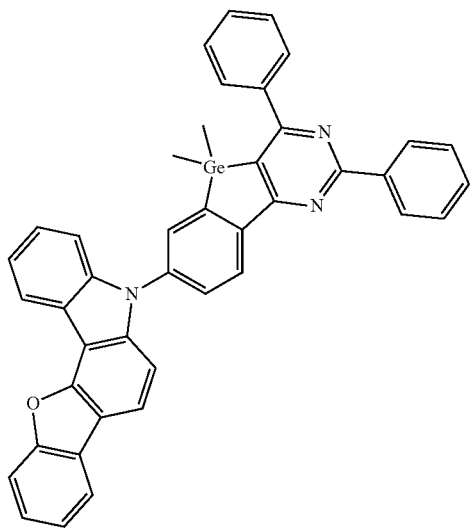

175
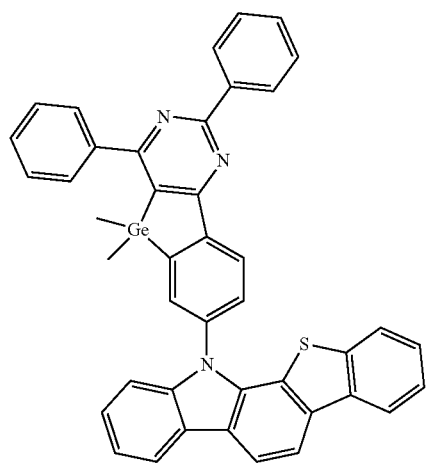
176
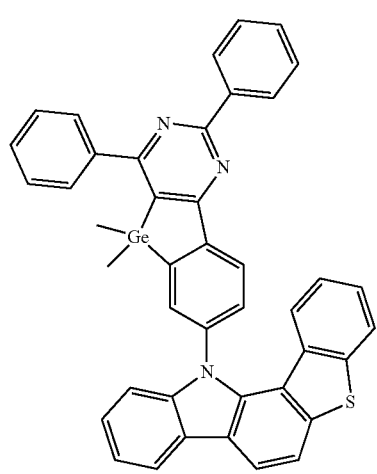
177
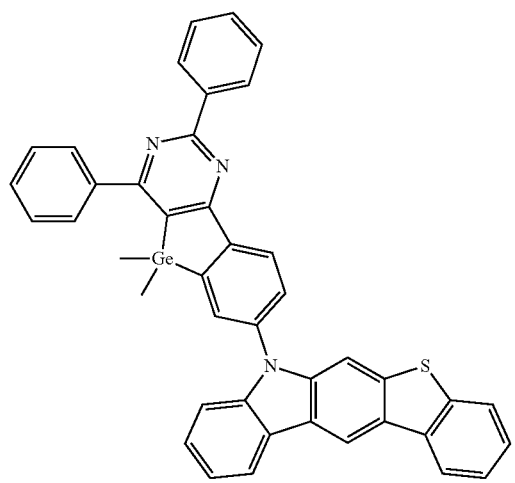
178
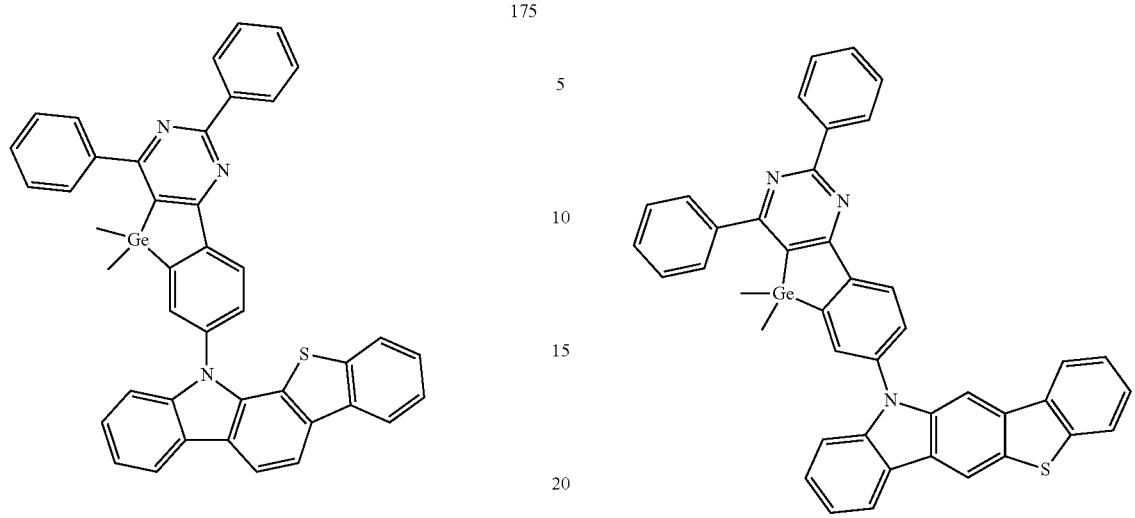
179
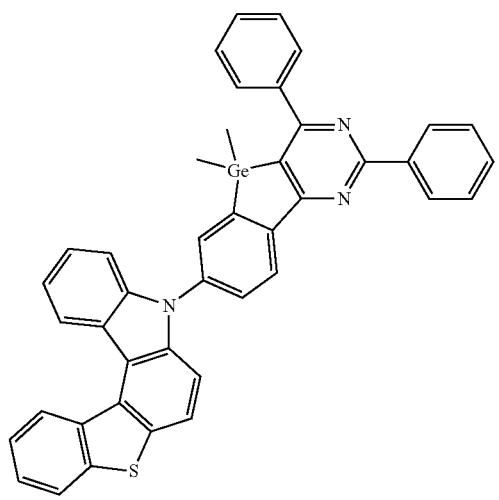
180
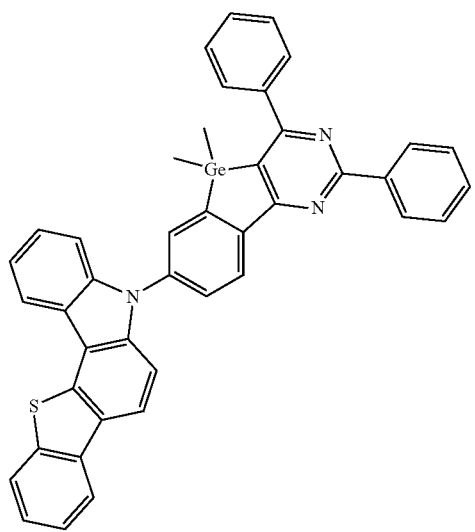

181
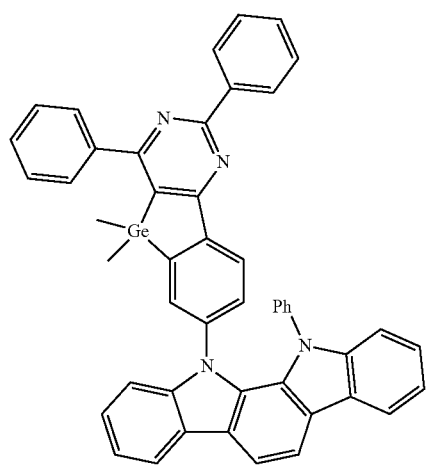
182
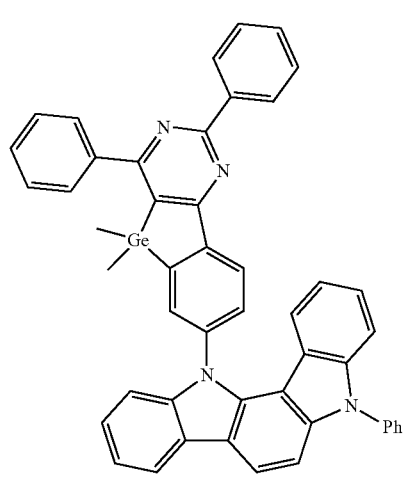
183
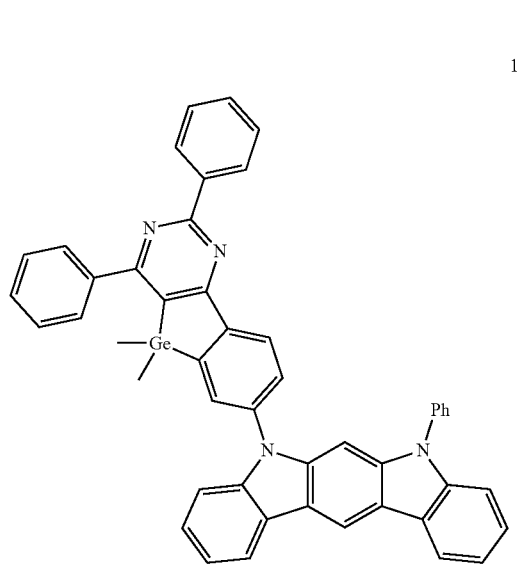
184
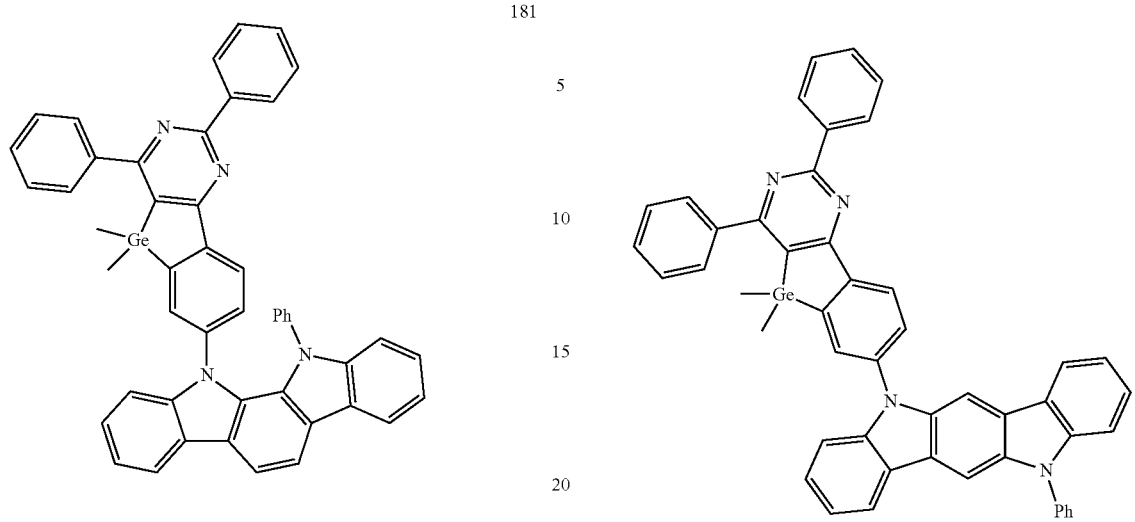
185
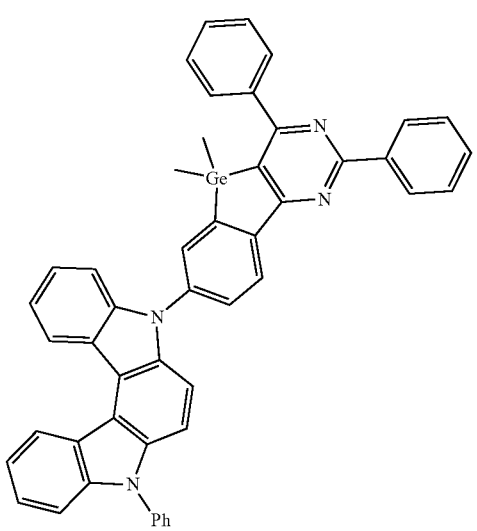
186
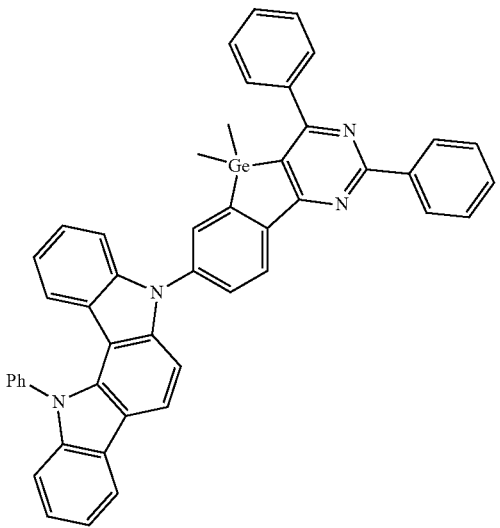

187
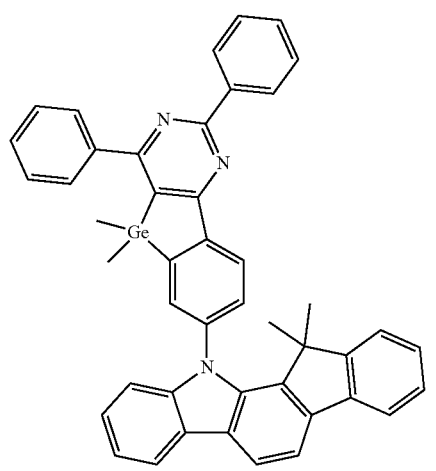
188
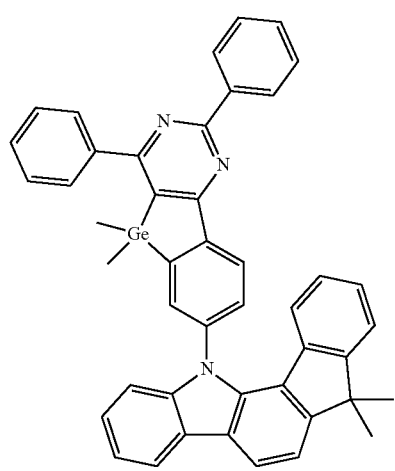
189
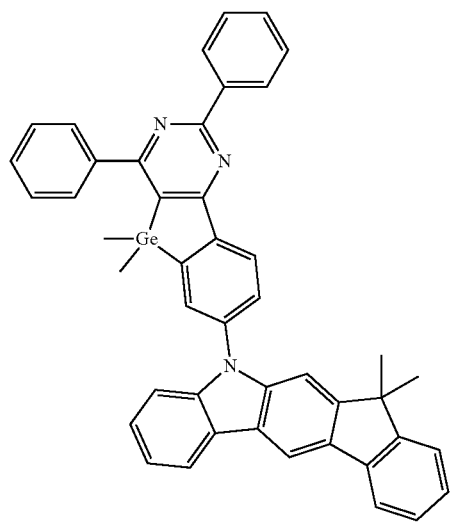
190
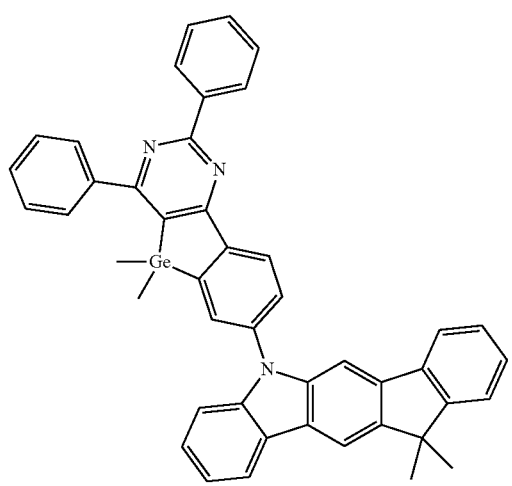
191
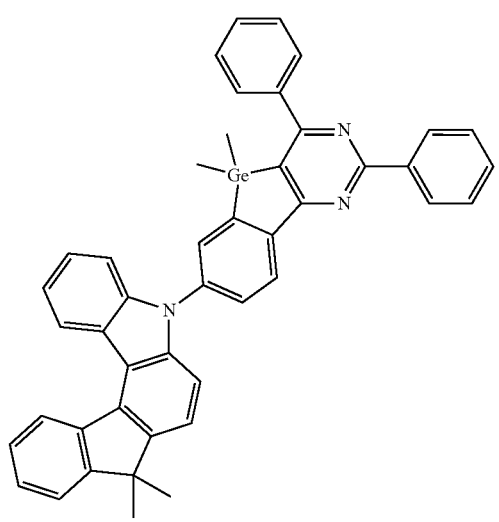
192
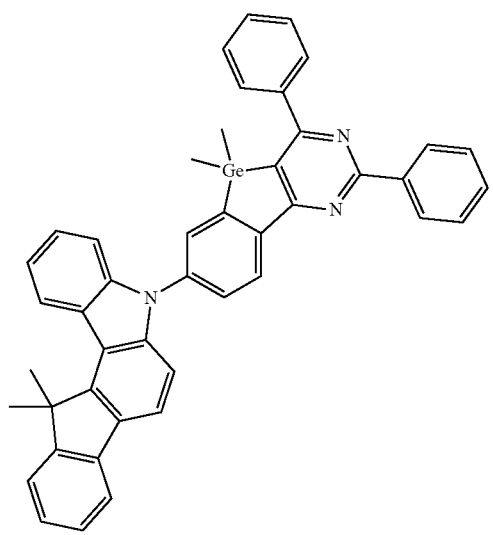

193

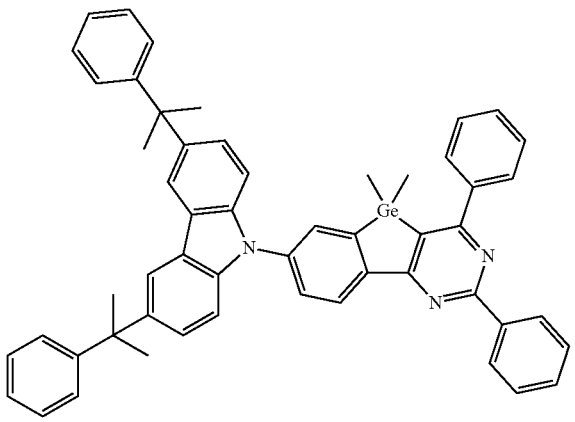

194

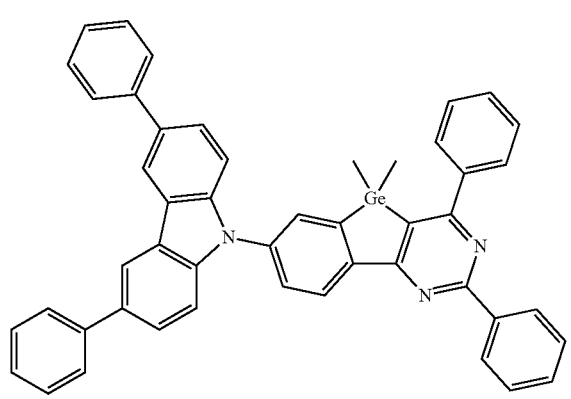

195

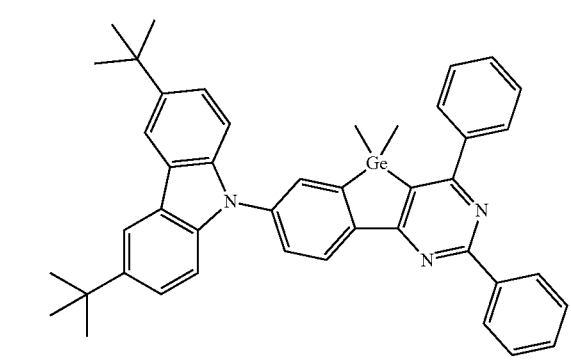

196

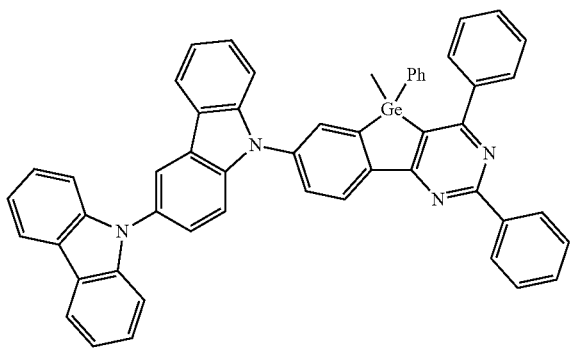

A "donor" in the heterocyclic compound represented by Formula 1 may be bound to a benzene group, not a pyrimidine group, of an "acceptor" (see Formula 1'). Accordingly, the heterocyclic compound represented by Formula 1 may have a high triplet energy and a short decay time.

In addition, the "donor" in the heterocyclic compound represented by Formula 1 may be bound to 3'-carbon in a benzene group of the "acceptor" (see Formula 1'). Accordingly, an overlap density of the highest occupied molecular orbital (HOMO) orbital and the lowest unoccupied molecular orbital (LUMO) orbital in the heterocyclic compound represented by Formula 1 may be a relatively high value, for example, 0.25 or greater. Thus, an electronic device, e.g., an organic light-emitting device, including the heterocyclic compound represented by Formula 1 may have a high emission efficiency.

Further, the "donor" and the "acceptor" in the heterocyclic compound represented by Formula 1 may be bound via a single bond (see Formula 1'). Accordingly, the HOMO orbital and the LUMO orbital in the heterocyclic compound represented by Formula 1 may be effectively separated, and thus, a gap between the triplet energy level ($T_1$) and the singlet energy level ($S_1$) and the decay time of the heterocyclic compound may be reduced. Therefore, the heterocyclic compound may have excellent emission efficiency and excellent lifespan at the same time.

The "donor" and the "acceptor" in the heterocyclic compound represented by Formula 1 may be bound via a carbon-carbon bond (see Formula 1'). Accordingly, the "donor" and the "acceptor" may be effectively separated in the heterocyclic compound, and thus, the heterocyclic compound may effectively emit delayed fluorescence. While not wishing to be bound by theory, a "donor" and an "acceptor" in Compound D of Comparative Example D are not effectively separated, and thus, Compound D substantially may not emit delayed fluorescence.

$X_1$ in the "acceptor" in the heterocyclic compound represented by Formula 1 may be O, S, Si($R_5$)($R_6$), Ge($R_5$)($R_6$), or P(=O)($R_5$) (see Formula 1' and descriptions of $X_1$ provided herein). Accordingly, the heterocyclic compound represented by Formula 1 may have excellent thermal stability and excellent delayed fluorescence emitting characteristics. While not wishing to be bound by theory, as Compound E of Comparative Example E may not have a twisted structure, and a gap between the triplet energy level ($T_1$) and a singlet energy level ($S_1$) may be relatively big, Compound E may not substantially emit delayed fluorescence.

Formula 1

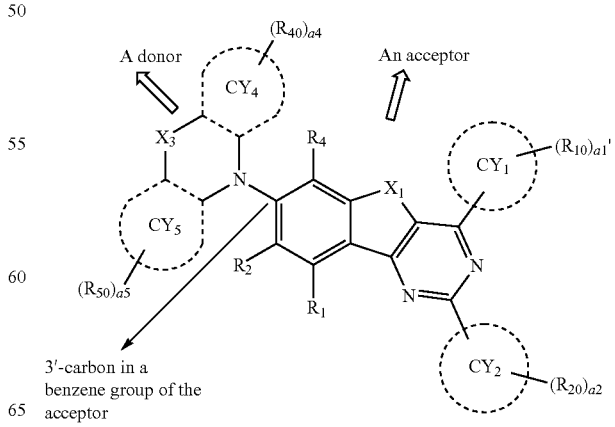

In some embodiments, the heterocyclic compound represented by Formula 1 may emit fluorescent light (fluorescence). For example, the heterocyclic compound may emit delayed fluorescence.

In one or more embodiments, the heterocyclic compound represented by Formula 1 may emit blue light. In some embodiments, the blue light may have a maximum emission wavelength in a range of about 400 nanometers (nm) to about 550 nm.

In one or more embodiments, a singlet energy level (eV) of the heterocyclic compound represented by Formula 1 may be about 2.5 electron volts (eV) or greater and about 3.0 eV or lower.

In one or more embodiments, a difference between a triplet energy level (eV) of the heterocyclic compound represented by Formula 1 and a singlet energy level (eV) of the heterocyclic compound may be about 0 eV or greater and 0.5 eV or lower. Accordingly, the heterocyclic compound represented by Formula 1 may emit delayed fluorescence of high emission efficiency and/or high luminance. For example, the heterocyclic compound may emit thermal activated delayed fluorescence (TADF).

When a difference between a triplet energy level (eV) of the heterocyclic compound represented by Formula 1 and a singlet energy level (eV) of the TADF emitter is within this range, up-conversion from a triplet state to a singlet state may occur effectively, and thus, the heterocyclic compound may emit delayed fluorescence.

Here, the triplet energy level and the singlet energy level may be evaluated according to density functional theory (DFT) method, wherein structure optimization is performed at a degree of B3LYP, and 6-31G(d,p), for example, according to Gaussian according to the DFT method.

A method of synthesizing the heterocyclic compound represented by Formula 1 may be apparent to one of ordinary skill in the art by referring to Synthesis Examples provided herein.

According to an aspect of another embodiment, an organic light-emitting device may include: a first electrode; a second electrode; and an organic layer located between the first electrode and the second electrode and including an emission layer and at least one heterocyclic compound represented by Formula 1.

For example, the heterocyclic compound represented by Formula 1 may be included in the emission layer. The emission layer including the heterocyclic compound may be an emission layer according to one of First to Third Embodiments:

First Embodiment

The emission layer may consist of the heterocyclic compound represented by Formula 1. The emission layer consisting of the heterocyclic compound represented by Formula 1 may emit fluorescence from the heterocyclic compound, e.g., delayed fluorescence.

Second Embodiment

The emission layer may include a host and an emitter, the host may be different from the emitter, and the heterocyclic compound may be included in the emitter. That is, the heterocyclic compound represented by Formula 1 may serve as an emitter. Accordingly, a ratio of emission components emitted from the heterocyclic compound may be in a range of about 70 percent (%) to about 100%, about 75% to about 100%, about 80% to about 100%, about 85% to about 100%, about 90% to about 100%, or about 95% to about 100%, based on total emission components emitted from the emission layer. In some embodiments, a content of the host may be greater than a content of the emitter. For example, light emitted from the emission layer may be fluorescence, e.g., delayed fluorescence (for example, TADF). In some embodiments, blue light emitted from the emission layer, e.g., blue light having a maximum emission wavelength of about 400 nm or greater and about 550 nm or lower may be obtained. As the heterocyclic compound represented by Formula 1 has excellent electrical characteristics and stability, an organic light-emitting device including an emission layer according to the Second Embodiment may have excellent emission efficiency and lifespan characteristics.

The emission layer according to the Second Embodiment may not include a phosphorescence emitter. In some embodiments, the emission layer according to the Second Embodiment may not include a transition metal. That is, the emission layer may not include a compound that may emit light according to a phosphorescence luminescence mechanism. Thus, the emission layer may not include a phosphorescence emitter and substantially may not emit phosphorescence. Instead, the emission layer may be, for example, a "delayed fluorescence" emission layer that may emit delayed fluorescence by transition to the ground state of triplet excitons of the heterocyclic compound represented by Formula 1 after reverse intersystem crossing (RISC) of the triplet excitons from a triplet state to a singlet state.

As described above, the "delayed fluorescence" emission layer described herein is different from a "phosphorescence" emission layer including a phosphorescence emitter (e.g., an iridium complex or a platinum complex) as an emitter, in which energy transfer to the phosphorescence emitter from a host may occur without delayed fluorescence emission by transition to the ground state of triplet excitons of the host after RISC to a singlet state.

The content of the emitter in the emission layer in the Second Embodiment may be in a range of about 0.01 parts to about 30 parts by weight, about 0.5 parts to about 20 parts by weight, or about 1 part to about 10 parts by weight, based on 100 parts by weight of the emission layer. When the content of the emitter is within any of these ranges, an organic light-emitting device having high emission efficiency and long lifespan without concentration quenching may be realized.

Third Embodiment

The emission layer may include a host, an emitter, and a sensitizer, the host, the emitter, and the sensitizer may be different from each other, and the heterocyclic compound may be included in the sensitizer. That is, the emission layer may include three different types of compounds, and the heterocyclic compound represented by Formula 1 may serve as a sensitizer that transfers energy to the emitter, and not as an emitter.

In the Third Embodiment, the emitter in the emission layer may be a fluorescence emitter. For example, 25% of the energy of the singlet excitons generated from the host may be transferred to a sensitizer by Forster energy transfer, and 75% of energy of triplet excitons generated from the host may be transferred to a singlet excited state and a triplet excited state of the sensitizer. In this embodiment, after triplet excitons transferred to a triplet excited state undergo RISC to a singlet excited state, singlet excitons of the sensitizer may be transferred to a singlet excited state of the fluorescence emitter by Forster energy transfer. Accordingly, as both singlet excitons and triplet excitons generated from the emission layer may be transferred to a singlet excited state of the fluorescent emitter, an organic light-emitting device including the emission layer according to the Third Embodiment may have excellent emission efficiency and lifespan characteristics.

Accordingly, a ratio of emission components emitted from the emitter may be in a range of about 70% to about 100%, about 75% to about 100%, about 80% to about 100%, about 85% to about 100%, about 90% to about 100%, or about 95% to about 100%, based on total emission components emitted from the emission layer according to the Third Embodiment. For example, light emitted from the emission layer may be red light, green light, or blue light. In some embodiments, blue light emitted from the emission layer, e.g., blue light having a maximum emission wavelength of about 400 nm or greater and about 550 nm or lower may be obtained.

The content of the emitter and the sensitizer in the emission layer in the Third Embodiment may be in a range of about 0.5 parts to about 50 parts by weight, about 1 part to about 30 parts by weight, or about 5 part to about 20 parts by weight, based on 100 parts by weight of the emission layer. The content ratio of the emitter to the sensitizer may be in a range of about 10:90 to about 90:10, for example, about 30:70 to about 70:30. When the content of the emitter and the sensitizer is within any of these ranges, and/or when the content ratio of the emitter to the sensitizer is within any of these ranges, an organic light-emitting device having high emission efficiency and long lifespan without concentration quenching may be realized.

The host that may be used in the Second Embodiment and the Third Embodiment and the emitter that may be used in the Third Embodiment may be understood by referring to the descriptions thereof provided herein.

DESCRIPTION OF FIGURE

FIG. 1 illustrates a schematic cross-sectional view of an organic light-emitting device 10 according to an embodiment. Hereinafter, a structure of an organic light-emitting device according to one or more embodiments and a method of manufacturing the organic light-emitting device will be described with reference to FIGURE.

In FIGURE, an organic light-emitting device 10 includes a first electrode 11, a second electrode 19 facing the first electrode 11, and an organic layer 10A between the first electrode 11 and the second electrode 19.

In FIGURE, the organic layer 10A includes an emission layer 15, a hole transport region 12 is between the first electrode 11 and an emission layer 15, and an electron transport region 17 is between the emission layer 15 and the second electrode 19.

A substrate may be additionally disposed under the first electrode 11 or on the second electrode 19. The substrate may be a conventional substrate used in organic light-emitting devices, e.g., a glass substrate or a transparent plastic substrate, each having excellent mechanical strength, thermal stability, transparency, surface smoothness, ease of handling, and water repellency.

First Electrode 11

The first electrode 11 may be formed by depositing or sputtering, onto the substrate, a material for forming the first electrode 11. The first electrode 11 may be an anode. The material for forming the first electrode 11 may include a material with a high work function for easy hole injection.

The first electrode 11 may be a reflective electrode, a semi-transmissive electrode, or a transmissive electrode. When the first electrode 11 is a transmissive electrode, a material for forming the first electrode 110 may include indium tin oxide (ITO), indium zinc oxide (IZO), tin oxide (SnO$_2$), zinc oxide (ZnO), or any combinations thereof. In some embodiments, when the first electrode 110 is a semi-transmissive electrode or a reflective electrode, a material for forming the first electrode 110 may include magnesium (Mg), silver (Ag), aluminum (Al), aluminum-lithium (Al—Li), calcium (Ca), magnesium-indium (Mg-ln), magnesium-silver (Mg—Ag), or any combination thereof.

The first electrode 11 may have a single-layered structure or a multi-layered structure including a plurality of layers.

Emission Layer 15

The emission layer 15 may include the heterocyclic compound represented by Formula 1. The emission layer 15 may further include a host in addition to the heterocyclic compound represented by Formula 1.

The thickness of the emission layer may be in a range of about 100 Å to about 1,000 Å, and in some embodiments, about 200 Å to about 600 Å. When the thickness of the emission layer is within any of these ranges, improved luminescence characteristics may be obtained without a substantial increase in driving voltage.

For example, the emission layer 15 may be an emission layer according to any one of the First Embodiment, the Second Embodiment, and the Third Embodiment. The host that may be used in the Second Embodiment and the Third Embodiment and the emitter that may be used in the Third Embodiment will be described hereinafter.

Host in Emission Layer 15

The host may not include a transition metal.

The host may consist of one type of compound or a mixture of two different types of compounds.

The host may be any suitable host.

In some embodiments, the host may be a bipolar host, an electron transporting host, a hole transporting host, or any combination thereof. The bipolar host, the electron transporting host, and the hole transporting host may be identical to each other.

The electron transporting host may include at least one electron transporting group.

The hole transporting host may not include an electron transporting group.

The term "electron transporting group" as used herein may include a cyano group, a π electron-depleted nitrogen-containing C$_1$-C$_{60}$ cyclic group, a group represented by one of the following Formulae, or any combination thereof:

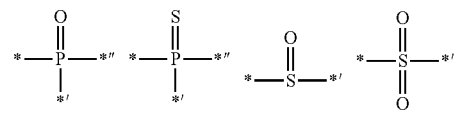

wherein, in the Formulae above, *, *' and *" may each indicate a binding site to an adjacent atom.

In some embodiments, the electron transporting host in the emission layer 15 may include a cyano group, a π electron-depleted nitrogen-containing C$_1$-C$_{60}$ cyclic group, or any combination thereof.

In one or more embodiments, the electron transporting host in the emission layer 15 may include at least one cyano group.

In one or more embodiments, the electron transporting host in the emission layer 15 may include at least one cyano group and a π electron-depleted nitrogen-containing $C_1$-$C_{60}$ cyclic group.

In one or more embodiments, the host may include a bipolar host.

In one or more embodiments, the host may include an electron transporting host.

In one or more embodiments, the host may include a hole transporting host.

In one or more embodiments, the hole transporting host may not be 1,3-bis(9-carbazolyl)benzene (mCP), tris(4-carbazoyl-9-ylphenyl)amine (TCTA), 4,4'-bis(N-carbazolyl)-1,1'-biphenyl (CBP), 3,3-bis(carbazol-9-yl)biphenyl (mCBP), N,N'-di(1-naphthyl)-N,N'-diphenyl-(1,1'-biphenyl)-4,4'-diamine (NPB), 4,4',4''-tris[phenyl(m-tolyl)amino]triphenylamine (m-MTDATA), or N,N'-bis(3-methylphenyl)-N,N-diphenylbenzidine (TPD).

In one or more embodiments,
the host may include an electron transporting host and a hole transporting host,
the electron transporting host may include at least one π electron-rich $C_3$-$C_{60}$ cyclic group, at least one electron transporting group, or any combination thereof,
the hole transporting host may include at least one π electron-rich $C_3$-$C_{60}$ cyclic group and not include an electron transporting group, and
the electron transporting group may include a cyano group, a π electron-depleted nitrogen-containing $C_1$-$C_{60}$ cyclic group, or any combination thereof.

In one or more embodiments, the electron transporting host may include i) a cyano group, a pyrimidine group, a pyrazine group, a triazine group, or any combination thereof and ii) a triphenylene group, a carbazole group, or any combination thereof.

In one or more embodiments, the hole transporting host may include at least one carbazole group.

In one or more embodiments, the electron transporting host may include a compound represented by Formula E-1:

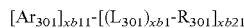   Formula E-1 wherein, in Formula E-1,
$Ar_{301}$ may be a $C_5$-$C_{60}$ carbocyclic group unsubstituted or substituted with at least one $R_{301a}$ or a $C_1$-$C_{60}$ heterocyclic group unsubstituted or substituted with at least one $R_{301a}$,
xb11 may be 1, 2, or 3,
$L_{301}$ may each independently be a single bond, a group represented by one of the following Formulae, a $C_5$-$C_{60}$ carbocyclic group unsubstituted or substituted with at least one $R_{301a}$ or a $C_1$-$C_{60}$ heterocyclic group unsubstituted or substituted with at least one $R_{301a}$, wherein in Formulae, *, *', and *'' each indicate a binding site to an adjacent atom,

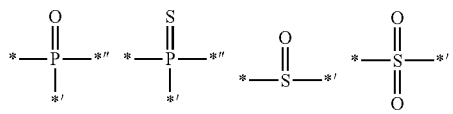

xb1 may be an integer from 1 to 5,
$R_{301a}$ and $R_{301}$ may each independently be hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), —S(=O)($Q_{301}$), —P(=O)($Q_{301}$)($Q_{302}$), or —P(=S)($Q_{301}$)($Q_{302}$),
xb21 may be an integer from 1 to 5,
wherein $Q_{301}$ to $Q_{303}$ may each independently be a $C_1$-$C_{10}$ alkyl group, a $C_1$-$C_{10}$ alkoxy group, a phenyl group, a biphenyl group, a terphenyl group, or a naphthyl group, and
at least one of Conditions 1 to 3 may be satisfied:
Condition 1
wherein, at least one of $Ar_{301}$, $L_{301}$, and $R_{301}$ in Formula E-1 may each independently include a π electron-depleted nitrogen-containing $C_1$-$C_{60}$ cyclic group,
Condition 2
wherein, $L_{301}$ in Formula E-1 may be a group represented by one of the following Formulae, and

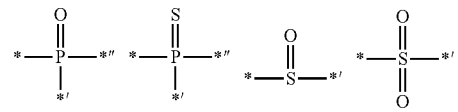

Condition 3
wherein, $R_{301}$ in Formula E-1 may be a cyano group, —S(=O)$_2$($Q_{301}$), —S(=O)($Q_{301}$), P(=O)($Q_{301}$)($Q_{302}$), or —P(=S)($Q_{301}$)($Q_{302}$).

In one or more embodiments, the hole transporting host may include a compound represented by Formula H-1:

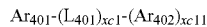

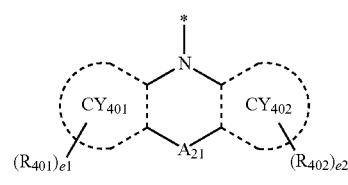

11

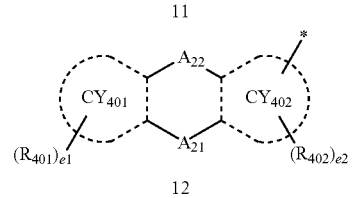

12 wherein, in Formulae H-1, 11 and 12,
$L_{401}$ may be:
a single bond; or
a π electron-rich $C_3$-$C_{60}$ cyclic group unsubstituted or substituted with deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, —Si($Q_{401}$)($Q_{402}$)($Q_{403}$), or any combination thereof, xc1 may be an integer from 1 to 10, and when xc1 is 2 or greater, at least two $L_{401}$(s) may be identical to or different from each other, $Ar_{401}$ may be a group represented by Formula 11 or Formula 12, $Ar_{402}$ may be:
a group represented by Formula 11 or Formula 12; or
a π electron-rich $C_3$-$C_{60}$ cyclic group (e.g., a phenyl group, a naphthyl group, a fluorenyl group, a carbazolyl group, a dibenzofuranyl group, a dibenzothiophenyl group, a biphenyl group, a terphenyl group, or a triphenylenyl group), unsubstituted or substituted with deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, or any combination thereof, xc11 may be an integer from 1 to 10, and when xc11 is 2 or greater, at least two $Ar_{402}$(s) may be identical to or different from each other, $CY_{401}$ and $CY_{402}$ may each independently be a π electron-rich $C_3$-$C_{60}$ cyclic group (a benzene group, a naphthalene group, a fluorene group, a carbazole group, a benzocarbazole group, an indolocarbazole group, a dibenzofuran group, a dibenzothiophene group, a dibenzosilole group, a benzonaphthofuran group, a benzonapthothiophene group, or a benzonaphthosilole group), $A_{21}$ may be a single bond, O, S, N($R_{411}$), C($R_{411}$)($R_{412}$), or Si($R_{411}$)($R_{412}$), $A_{22}$ may be a single bond, O, S, N($R_{411}$), C($R_{411}$)($R_{412}$), or Si($R_{411}$)($R_{412}$), at least one of $A_{21}$ and $A_{22}$ in Formula 12 may not be a single bond, $R_{401}$, $R_{402}$, $R_{411}$, and $R_{412}$ may each independently be:
hydrogen, deuterium, a $C_1$-$C_{20}$ alkyl group, or a $C_1$-$C_{20}$ alkoxy group;
a $C_1$-$C_{20}$ alkyl group or a $C_1$-$C_{20}$ alkoxy group, each substituted with deuterium, a phenyl group, a naphthyl group, a fluorenyl group, a carbazolyl group, a dibenzofuranyl group, a dibenzothiophenyl group, or any combination thereof;
a π electron-rich $C_3$-$C_{60}$ cyclic group unsubstituted or substituted with deuterium, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a biphenyl group, or any combination thereof; or —Si($Q_{404}$)($Q_{405}$)($Q_{406}$), e1 and e2 may each independently be an integer from 0 to 10,
wherein $Q_{401}$ to $Q_{406}$ may each independently be hydrogen, deuterium, a $C_1$-$C_{20}$ alkyl group, a phenyl group, a naphthyl group, a fluorenyl group, a carbazolyl group, a dibenzofuranyl group, a dibenzothiophenyl group, a biphenyl group, a terphenyl group, or a triphenylenyl group, and

* indicates a binding site to an adjacent atom.

In some embodiments, in Formula E-1, $Ar_{301}$ and $L_{301}$ may each independently be a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl)triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), —P(=O)($Q_{31}$)($Q_{32}$), or any combination thereof, at least one of $L_{301}$(s) in the number of xb1 may each independently be an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl)triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), —P(=O)($Q_{31}$)($Q_{32}$), or any combination thereof, and $R_{301}$ may be hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a tetraphenyl group, a naphthyl group, a cyano group-containing phenyl group, a cyano group-containing biphenyl group, a cyano group-containing terphenyl group, a cyano group-containing tetraphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl)triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group.

In some embodiments, $Ar_{301}$ may be: a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, or a dibenzothiophene group, each unsubstituted or substituted with deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl)triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), —P(=O)($Q_{31}$)($Q_{32}$), or any combination thereof; or a group represented by one of Formulae 5-1 to 5-3 and Formulae 6-1 to 6-33, and $L_{301}$ may be a group represented by one of Formulae 5-1 to 5-3 and Formulae 6-1 to 6-33:

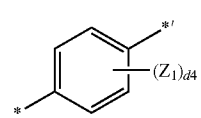

5-1

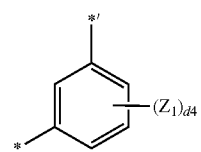

5-2

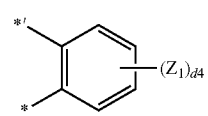

5-3

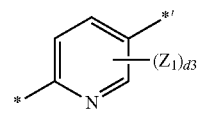

6-1

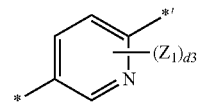

6-2

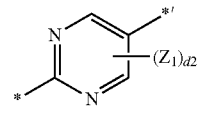

6-3

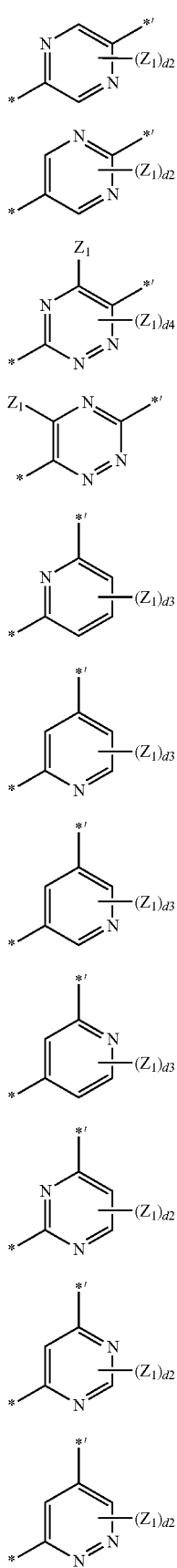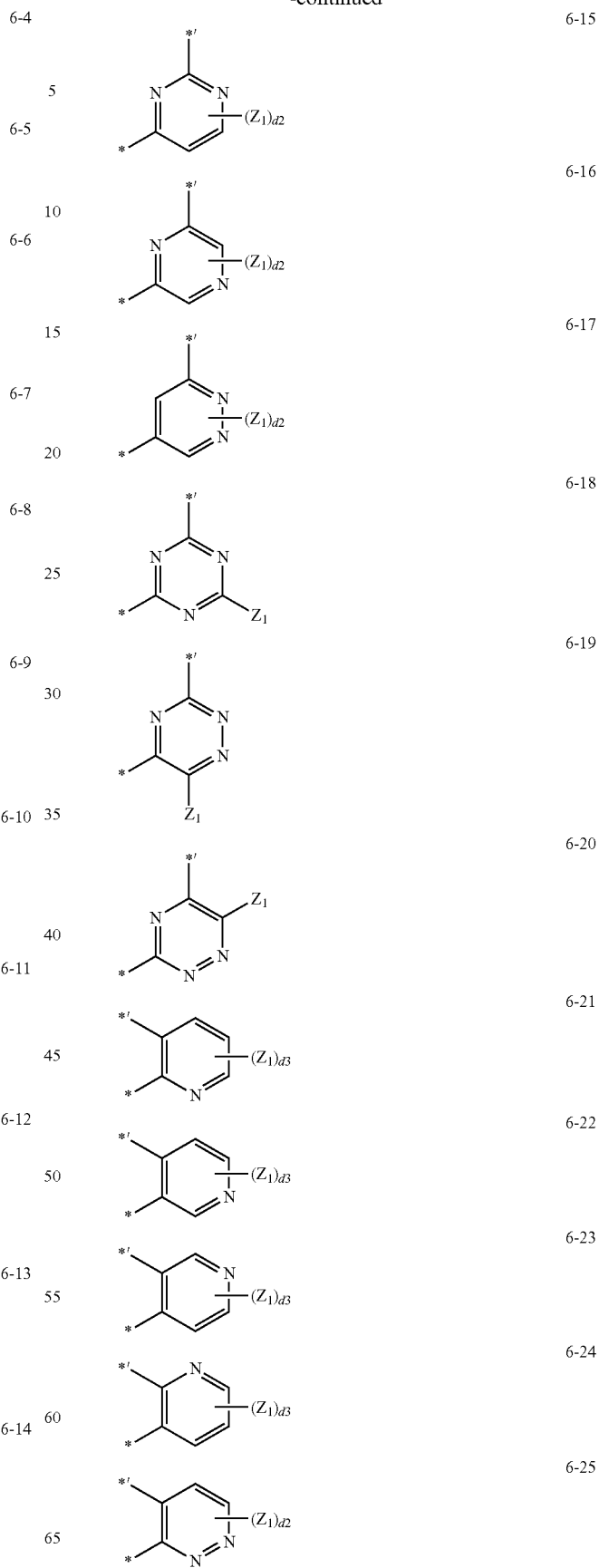

-continued

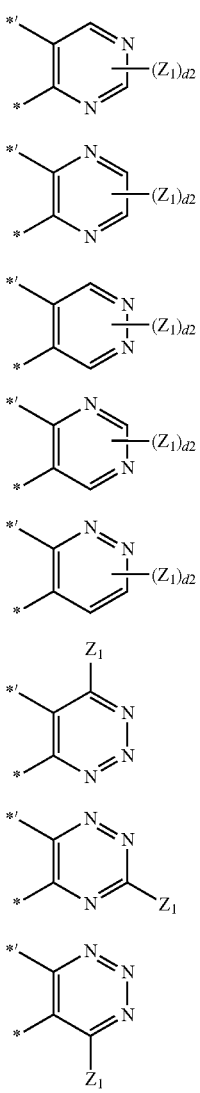

wherein, in Formulae 5-1 to 5-3 and 6-1 to 6-33, $Z_1$ may be hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl)triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), d4 may be 0, 1, 2, 3, or 4, d3 may be 0, 1, 2, or 3, d2 may be 0, 1, or 2, and

* and *' each indicate a binding site to an adjacent atom.

$Q_{31}$ to $Q_{33}$ may respectively be understood by referring to the descriptions of to $Q_{33}$ provided herein.

In one or more embodiments, $L_{301}$ may be a group represented by one of Formulae 5-2, 5-3, and 6-8 to 6-33.

In one or more embodiments, $R_{301}$ may be a cyano group or a group represented by one of Formulae 7-1 to 7-18, and at least one of $Ar_{402}$(s) in the number of xc11 may be represented by one of Formulae 7-1 to 7-18:

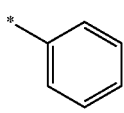

7-1

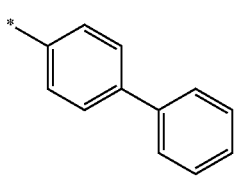

7-2

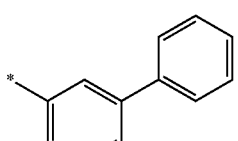

7-3

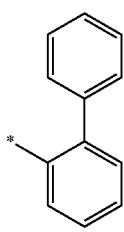

7-4

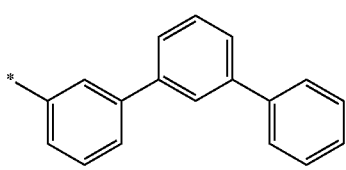

7-5

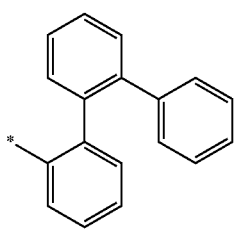

7-6

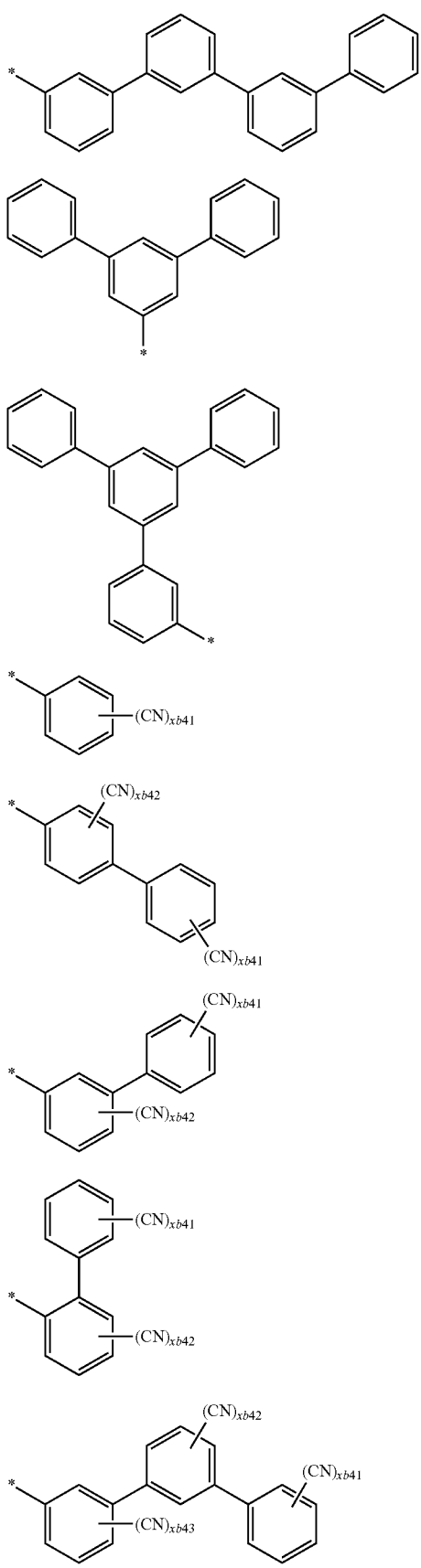
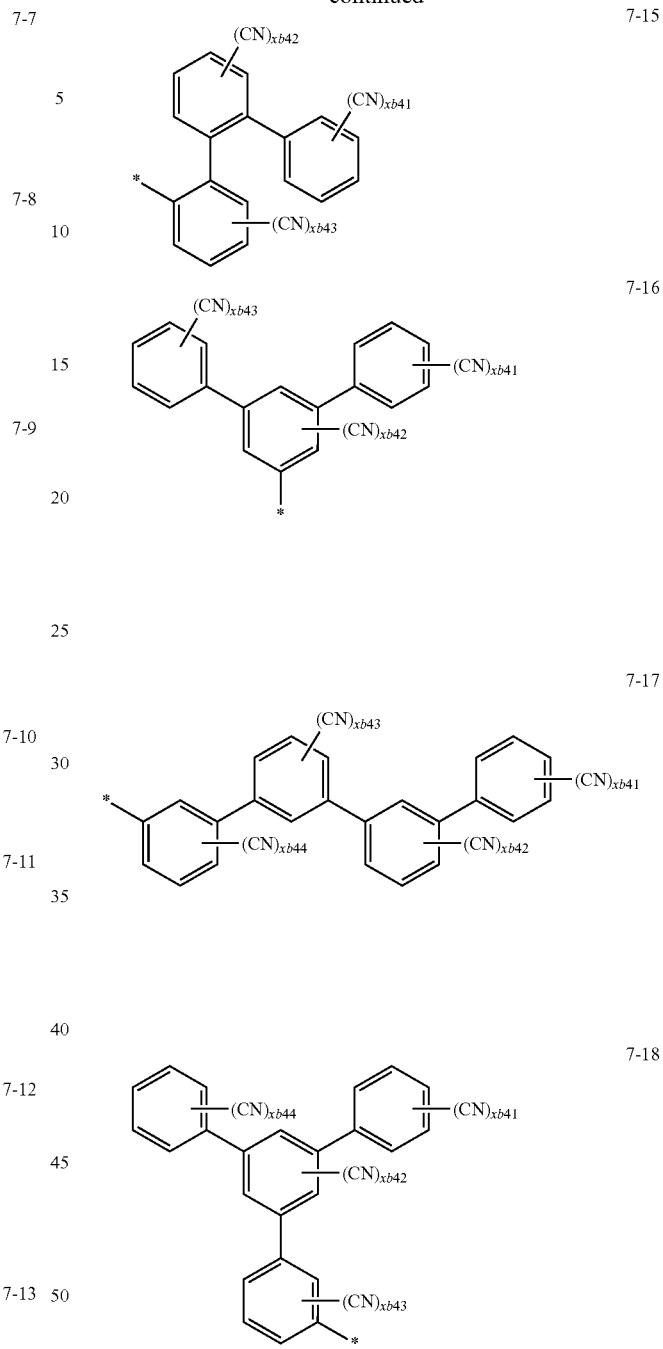

wherein, in Formulae 7-1 to 7-18, xb41 to xb44 may each be 0, 1, or 2, provided that xb41 in Formula 7-10 may not be 0, xb41+xb42 in Formulae 7-11 to 7-13 may not be 0, xb41+xb42+xb43 in Formulae 7-14 to 7-16 may not be 0, xb41+xb42+xb43+xb44 in Formulae 7-17 and 7-18 may not be 0, and * indicates a binding site to an adjacent atom.

In Formula E-1, at least two $Ar_{301}$(s) may be identical to or different from each other, and at least two $L_{301}$(s) may be identical to or different from each other. In Formula H-1, at least two $L_{401}$(s) may be identical to or different from each other, and at least two $Ar_{402}$(s) may be identical to or different from each other.

Examples of the electron transporting host may include a compound of Groups HE1 to HE7:
Group HE1
H-E1
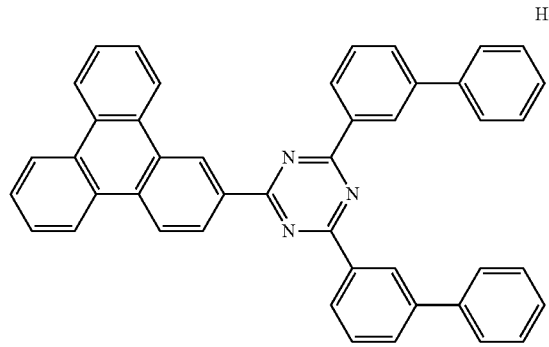
H-E2
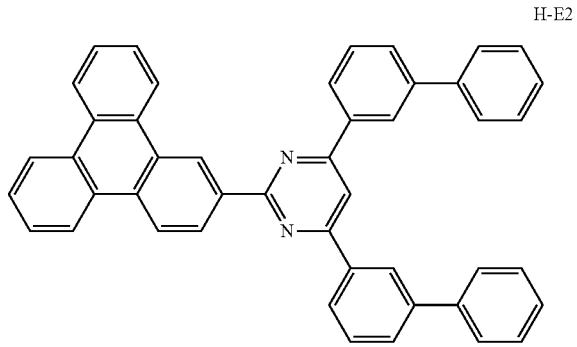
H-E3
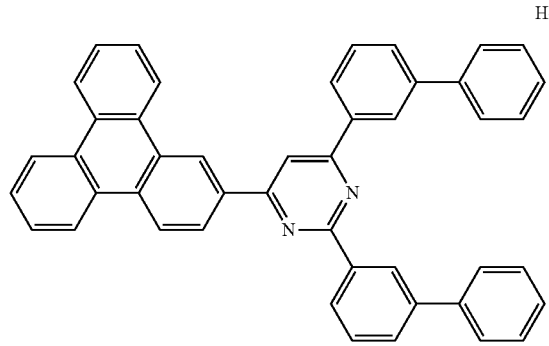
H-E4
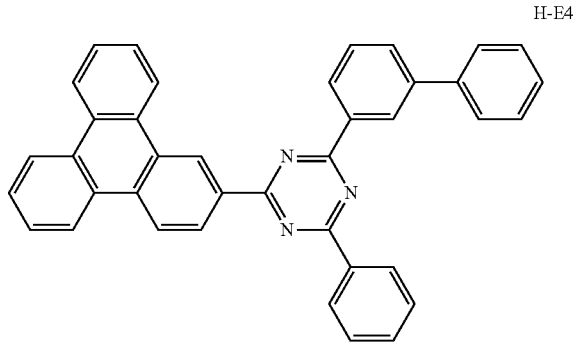
H-E5
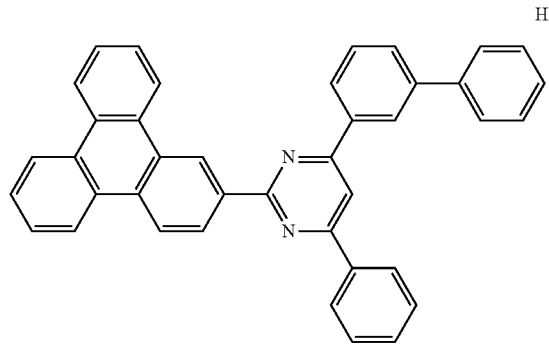
H-E6
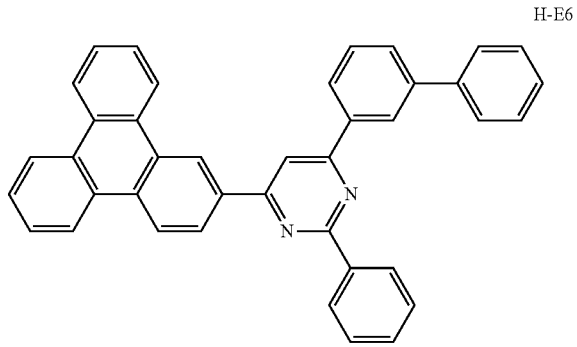
H-E7
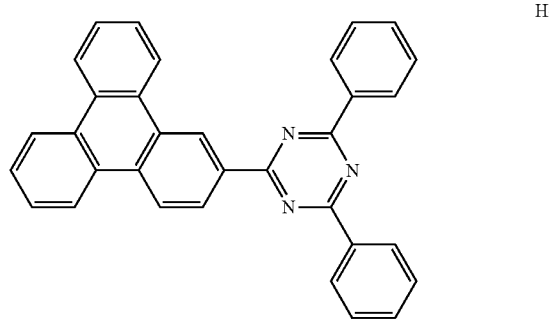
H-E8
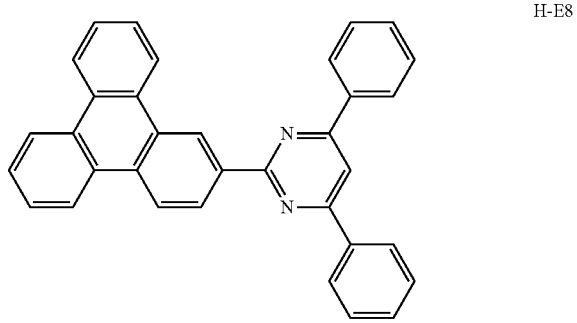

-continued
H-E9
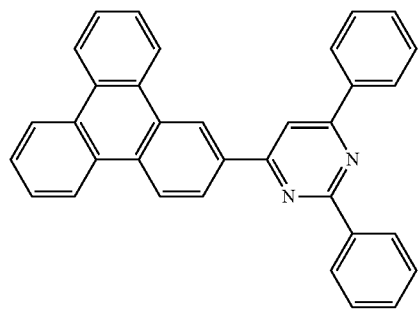
H-E10
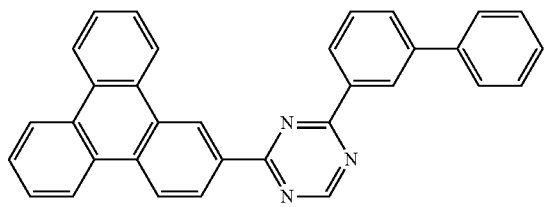
H-E11
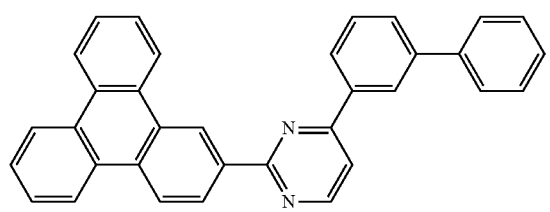
H-E12
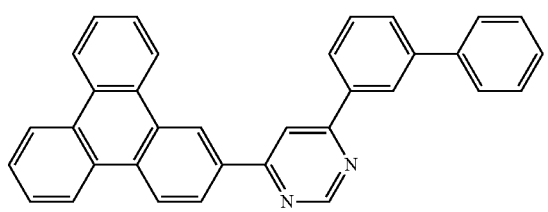
H-E13
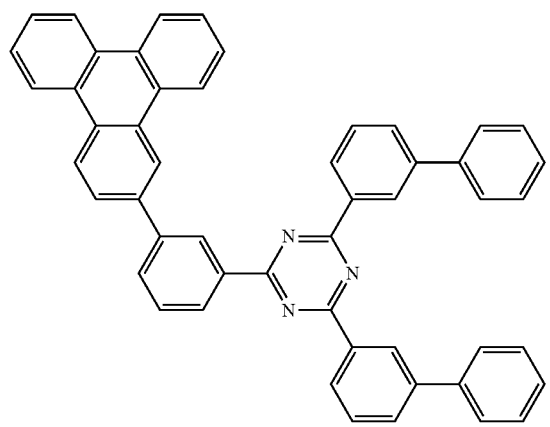
H-E14
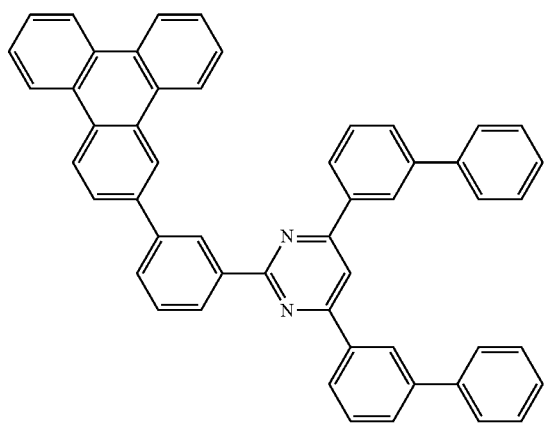
H-E15
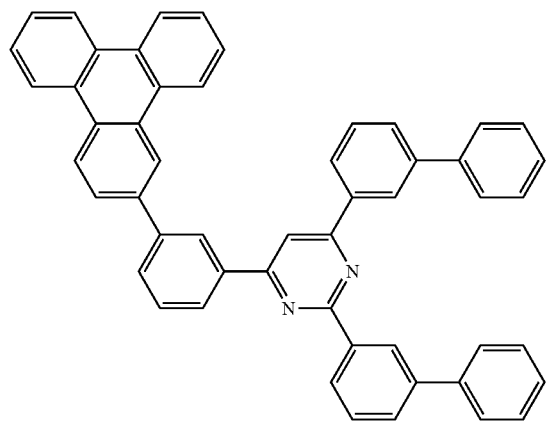
H-E16
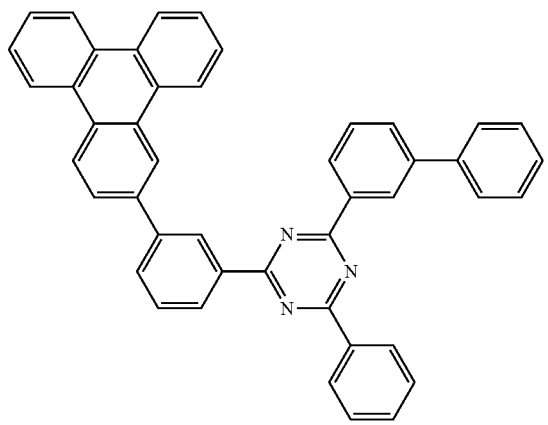

-continued
H-E17
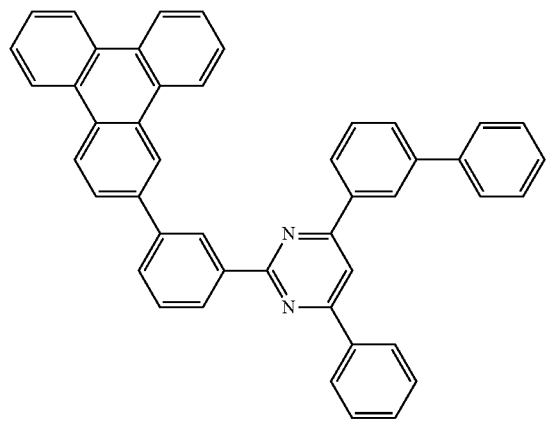
H-E18
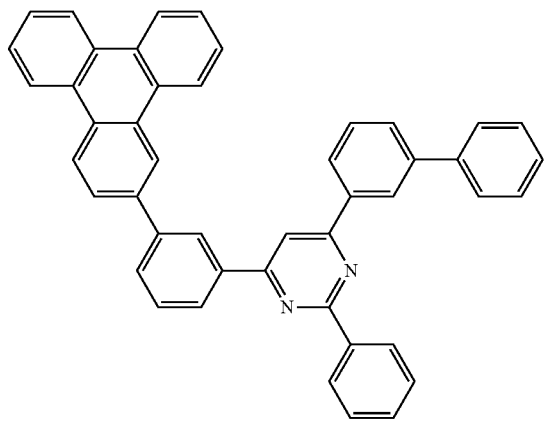
H-E19
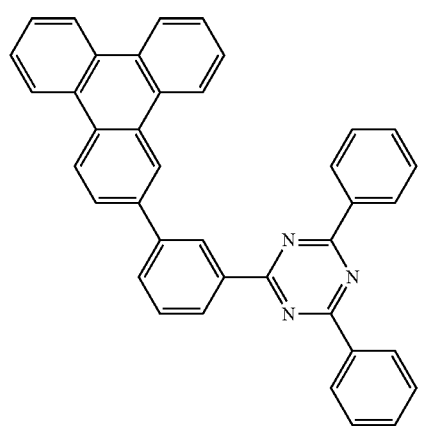
H-E20
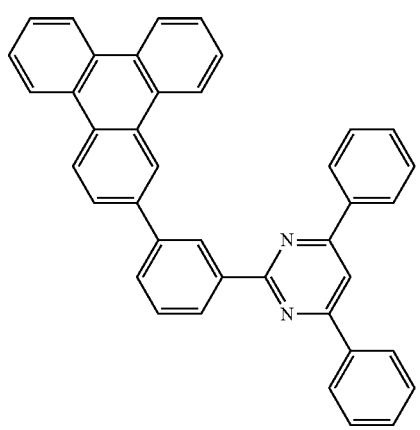
H-E21
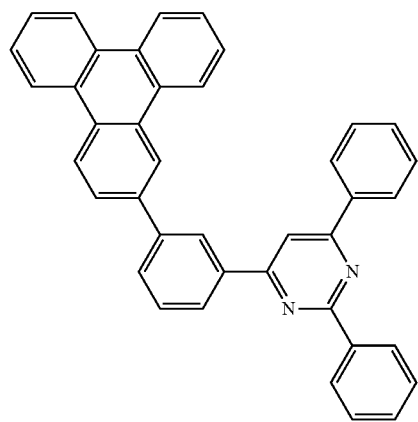
H-E22
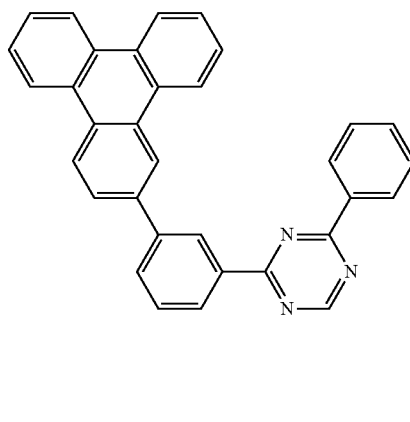
H-E23
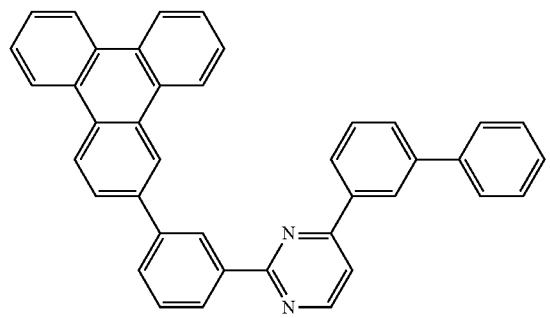
H-E24
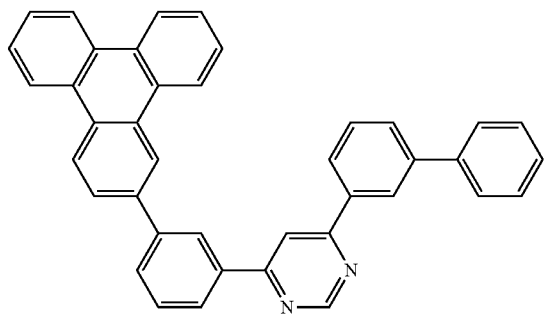

-continued
H-E25
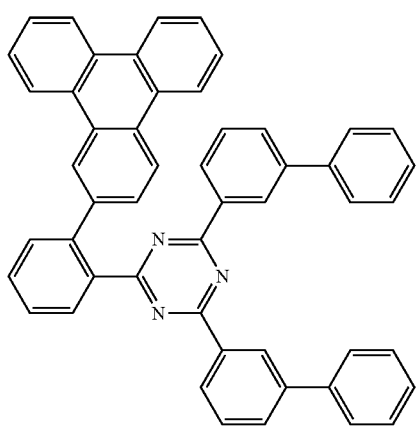
H-E26
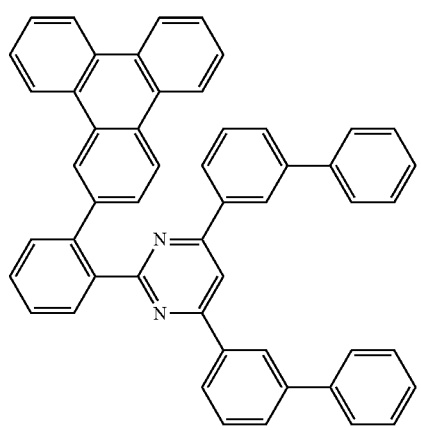
H-E27
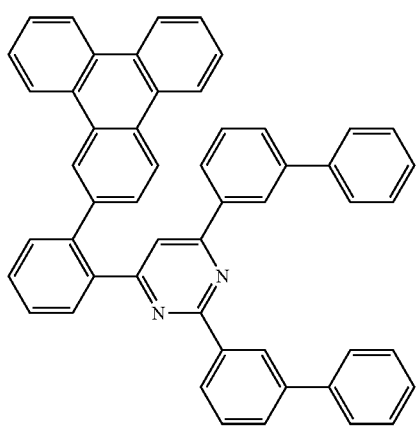
H-E28
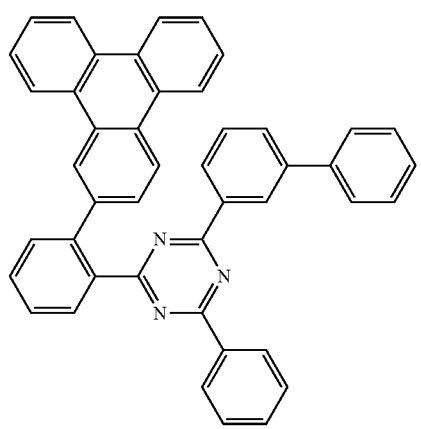
H-E29
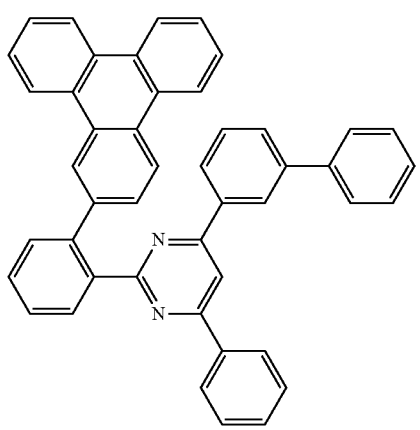
H-E30
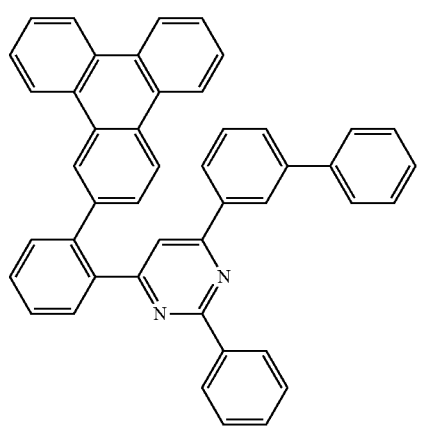

-continued
H-E31
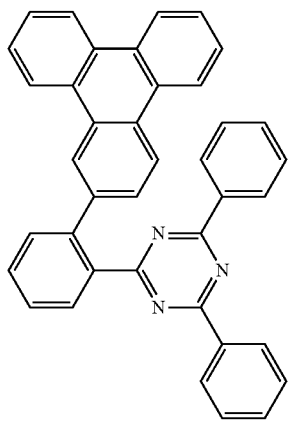
H-E32
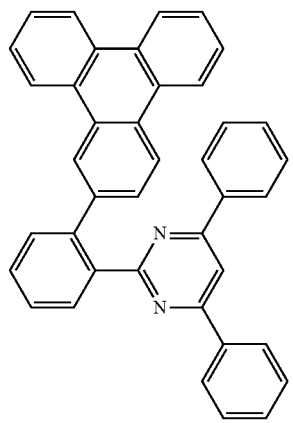
H-E33
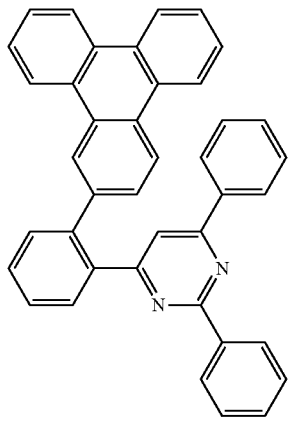
H-E34
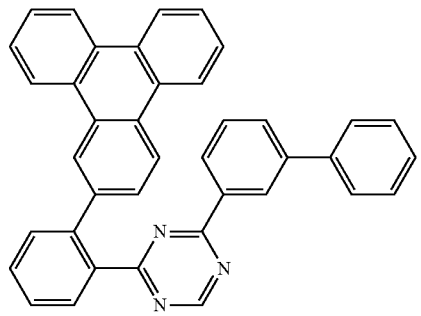
H-E35
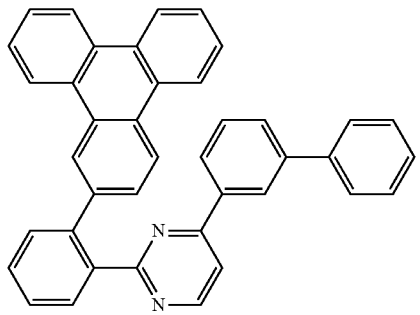
H-E36
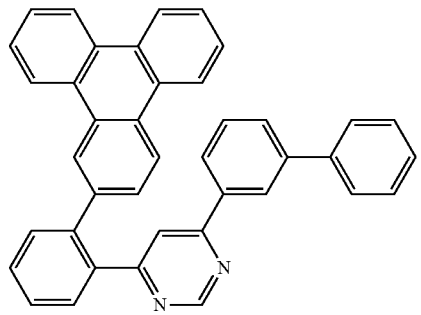

-continued
H-E37
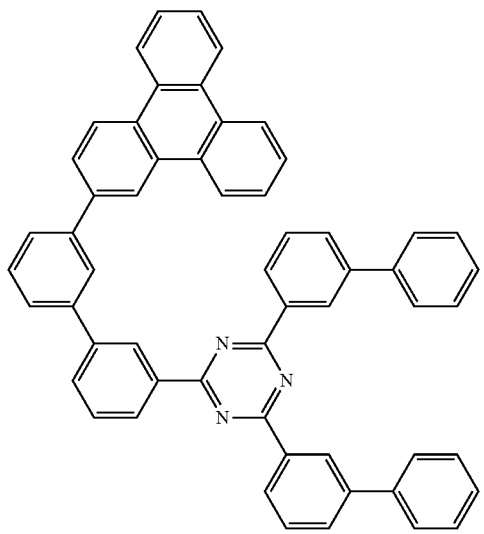
H-E38
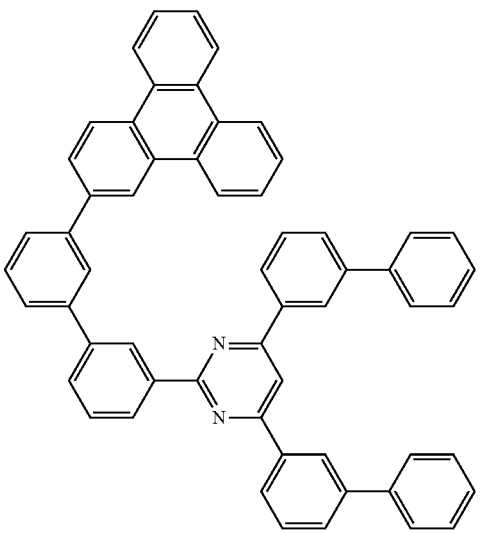
H-E39
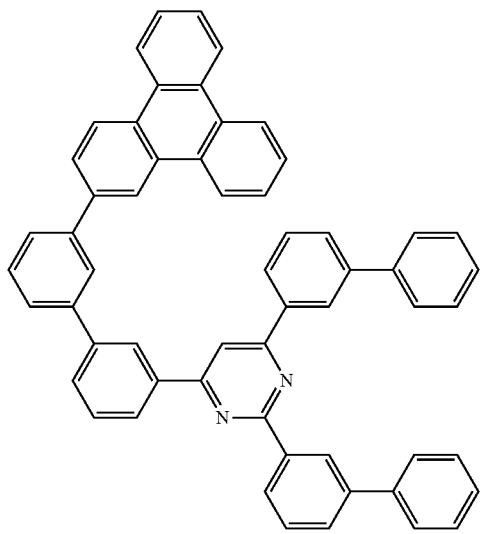
H-E40
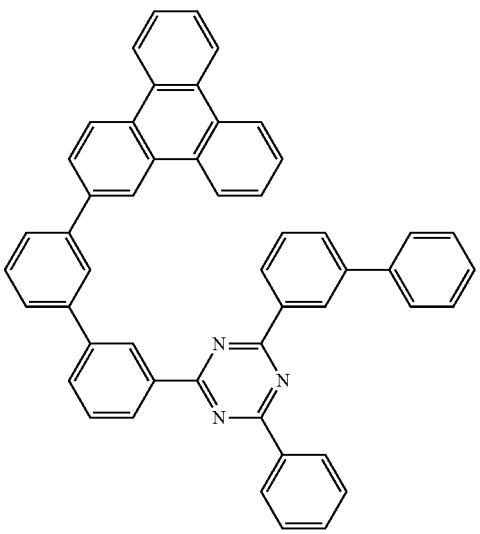
H-E41
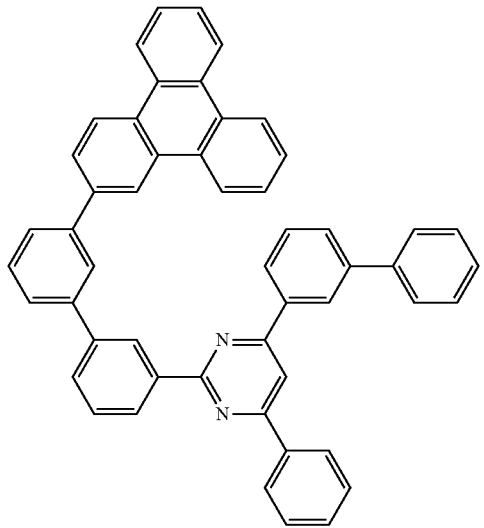
H-E42
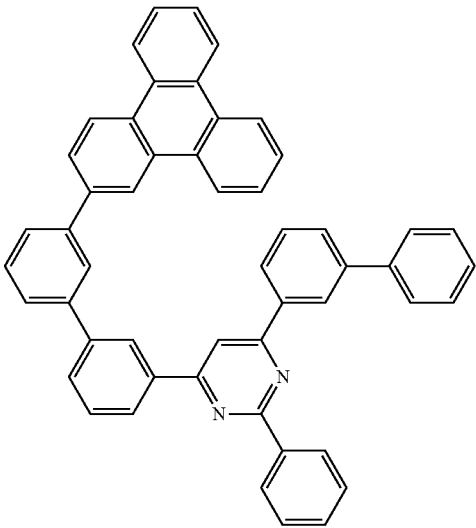

-continued
H-E43
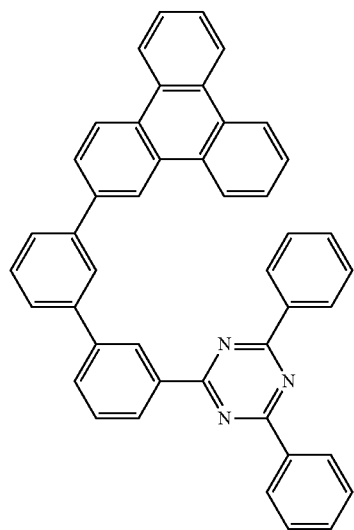
H-E44
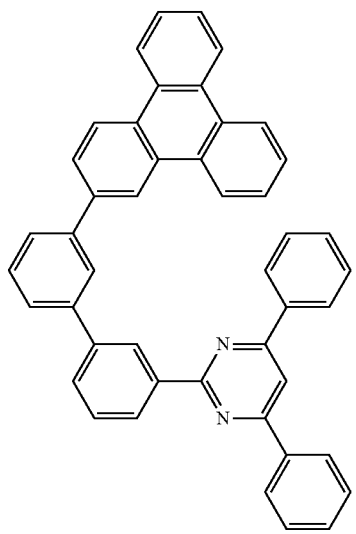
H-E45
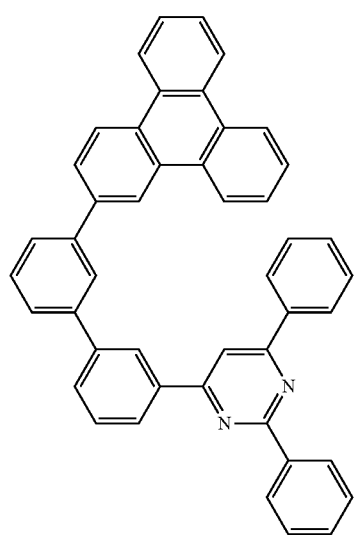
H-E46
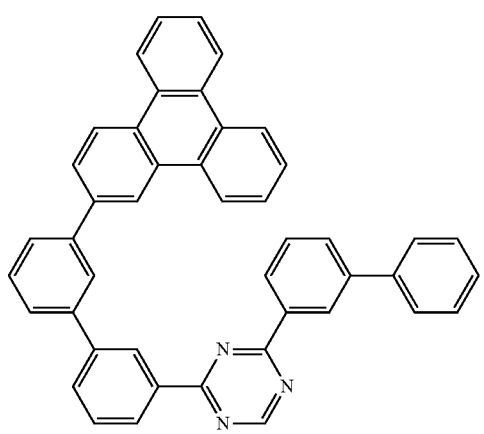
H-E47
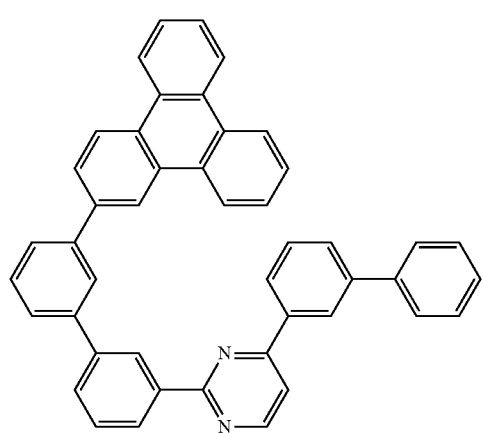
H-E48
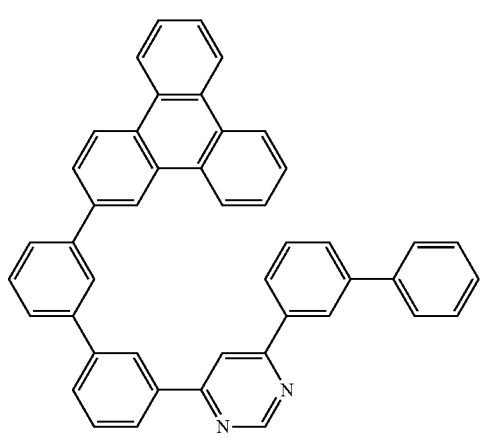

-continued
H-E49
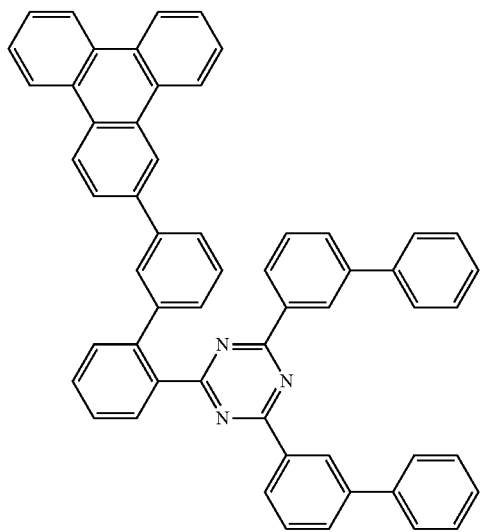
H-E50
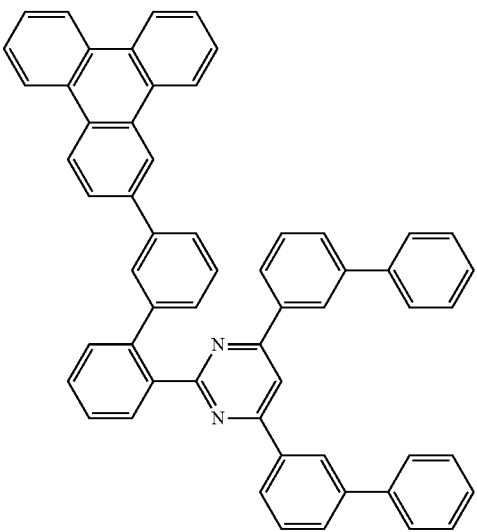
H-E51
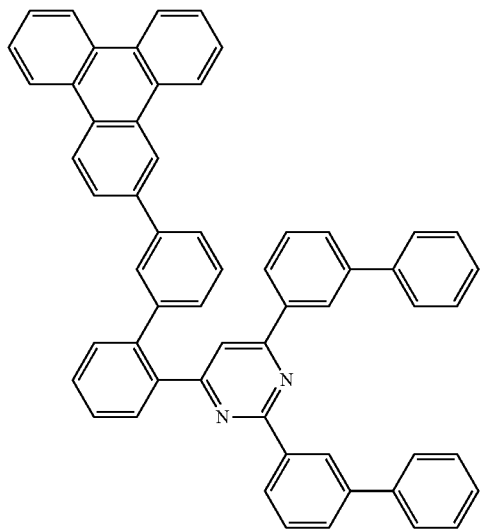
H-E52
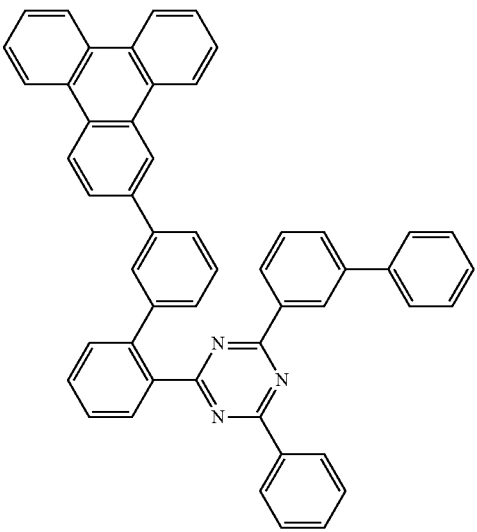
H-E53
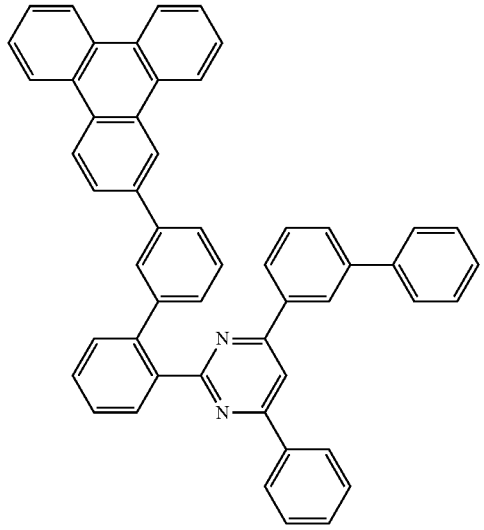
H-E54
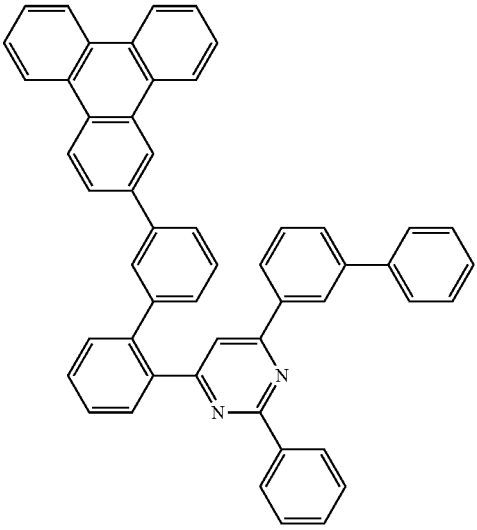

-continued
H-E55
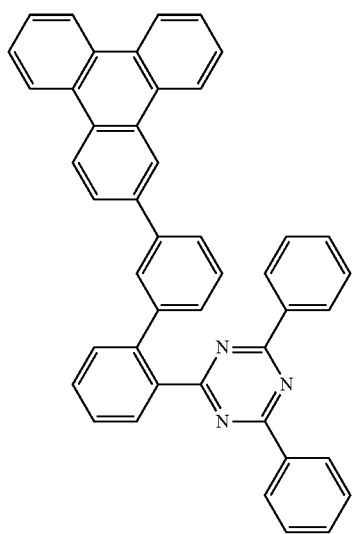
H-E56
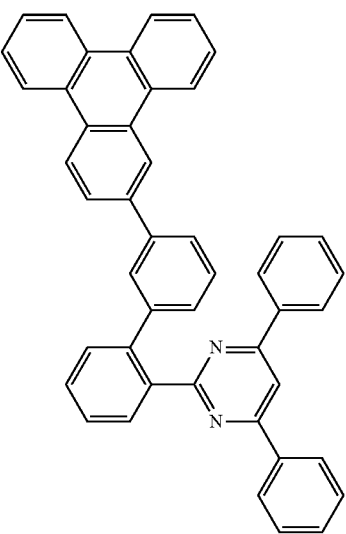
H-E57
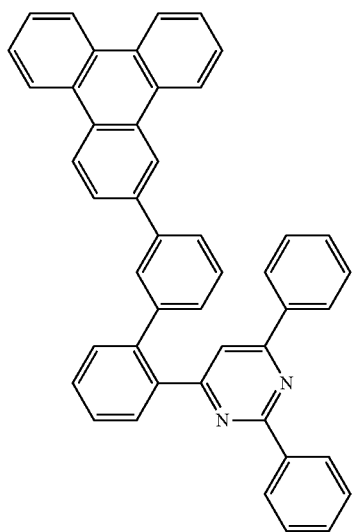
H-E58
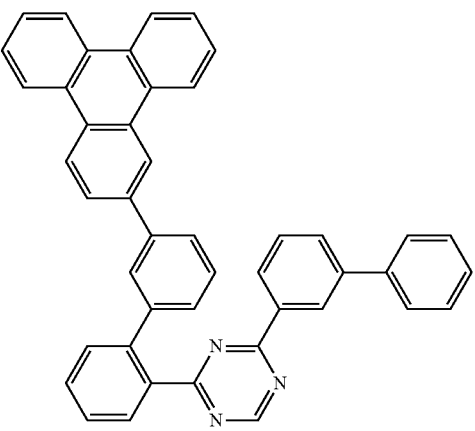
H-E59
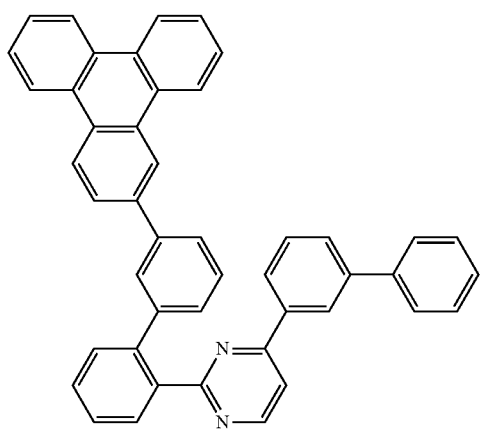
H-E60
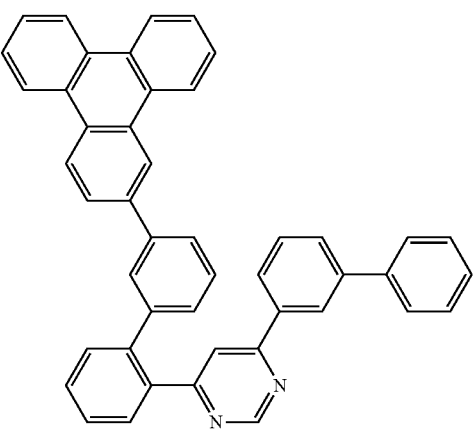

-continued
H-E61
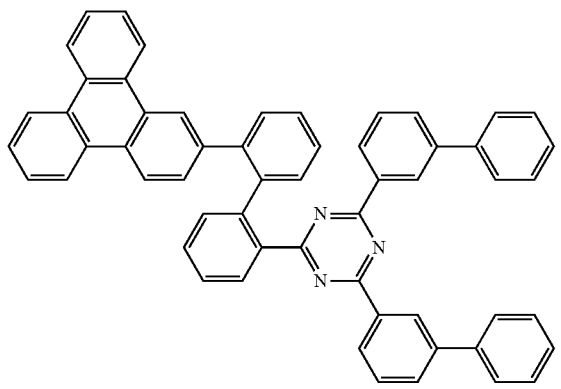
H-E62
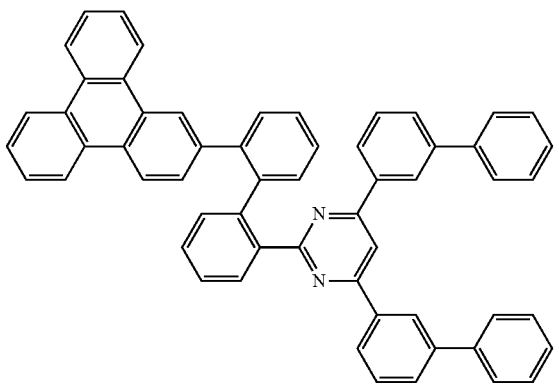
H-E63
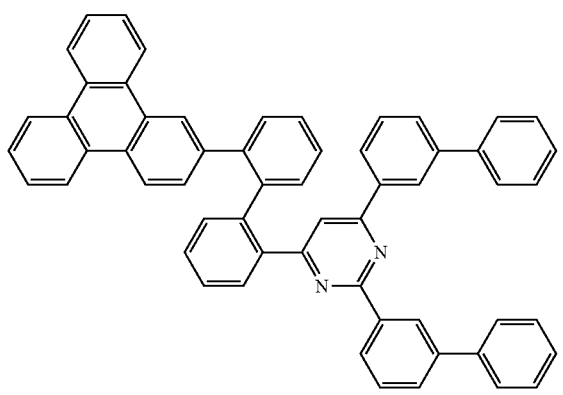
H-E64
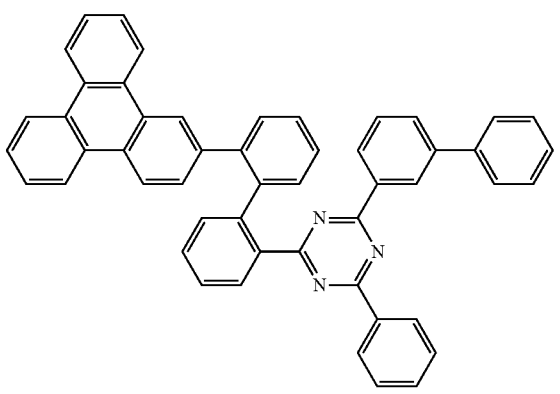
H-E65
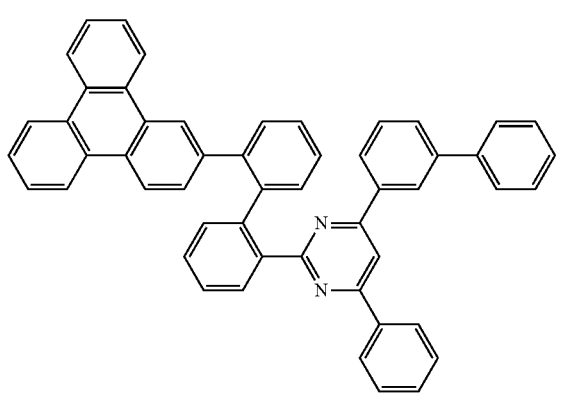
H-E66
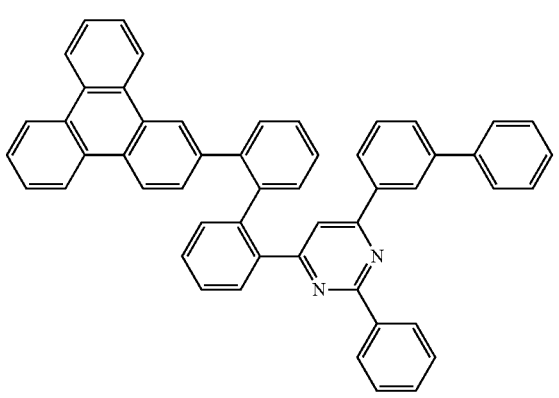
H-E67
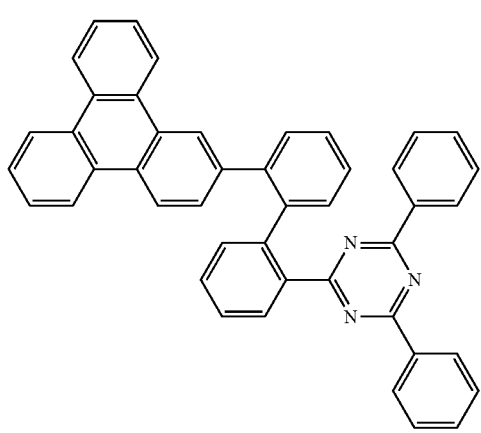
H-E68

-continued
H-E69
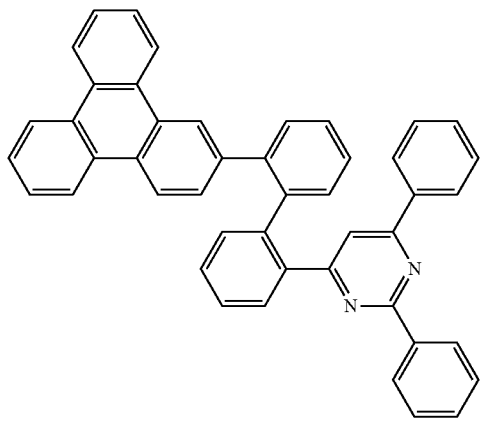
H-E70
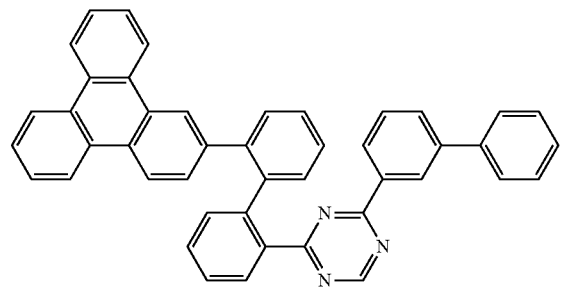
H-E71
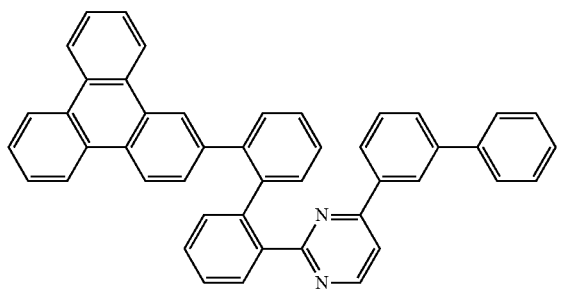
H-E72
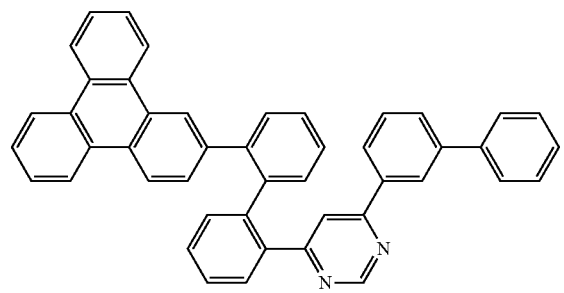
H-E73
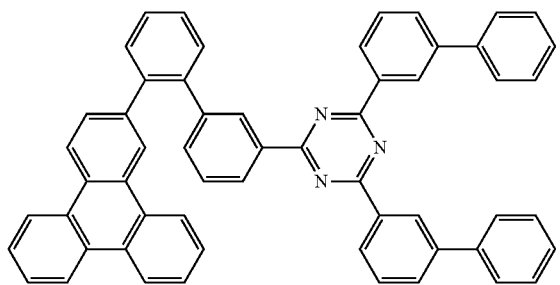
H-E74
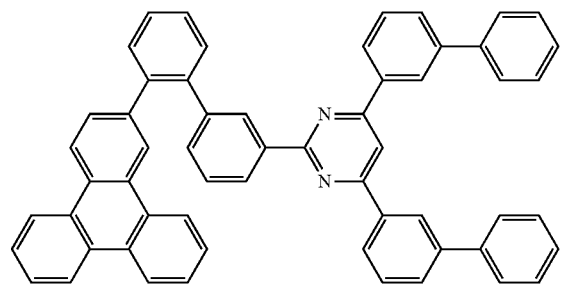
H-E75
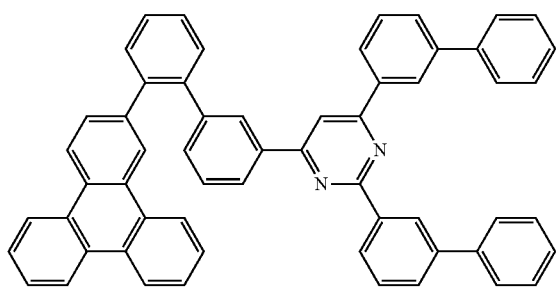
H-E76
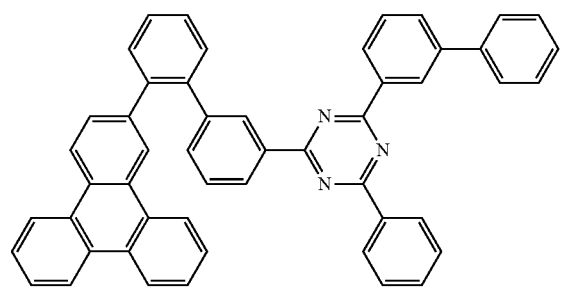

-continued
H-E77
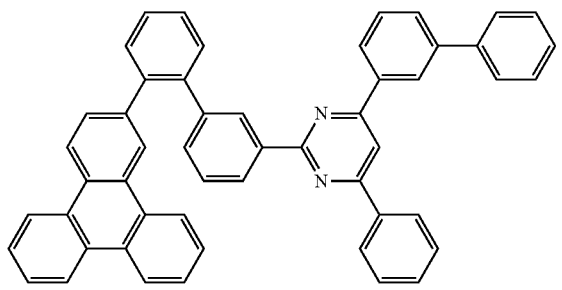
H-E78
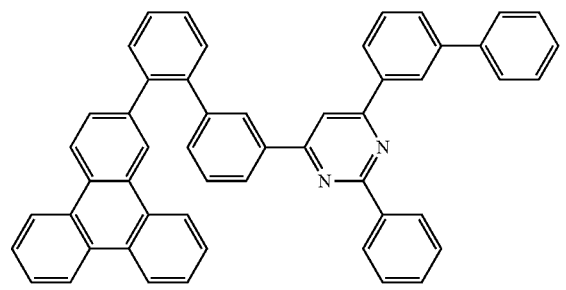
H-E79
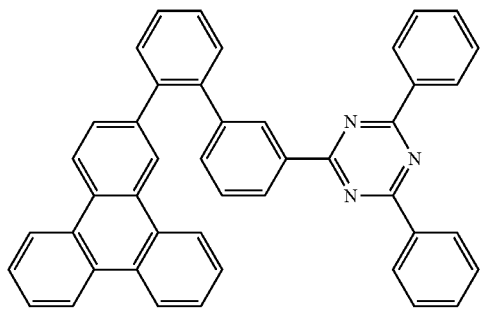
H-E80
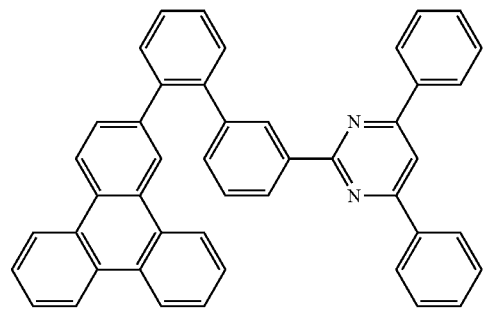
H-E81
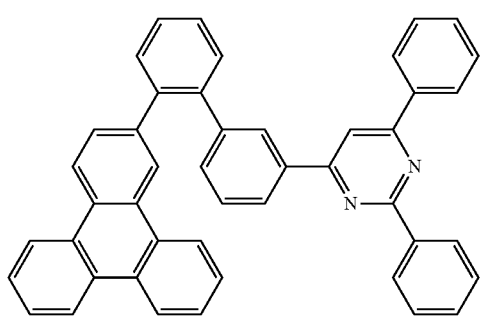
H-E82
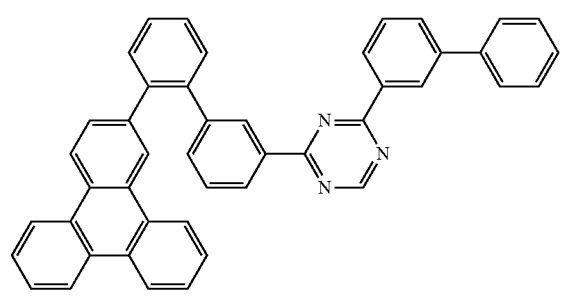
H-E83

H-E84
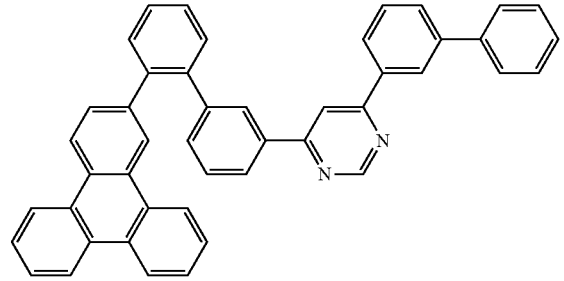
H-E(1)
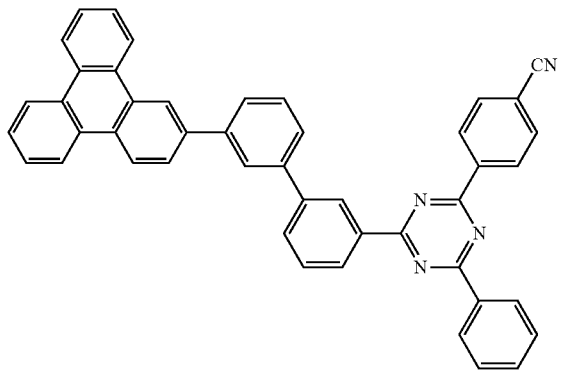
H-E(2)
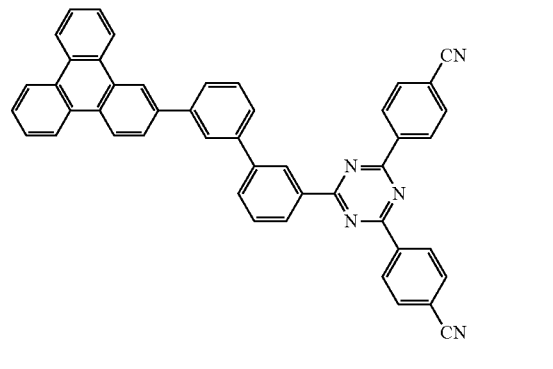

-continued
H-E(3)
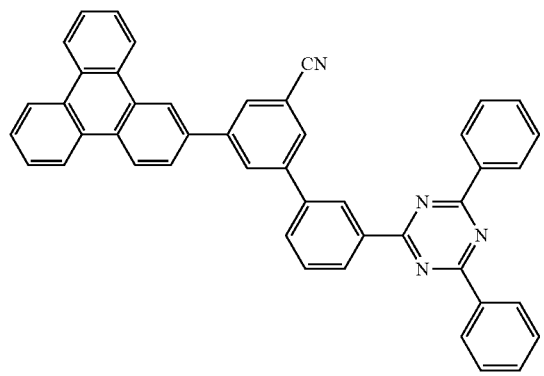
H-E(4)
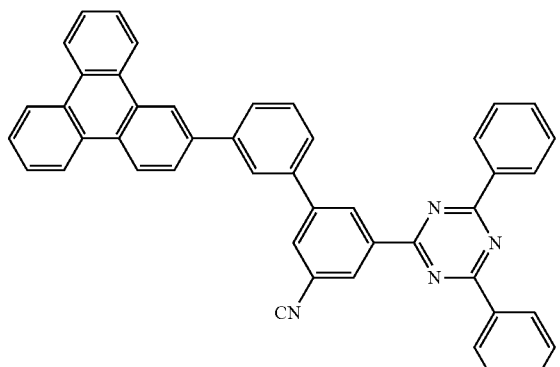
A-1
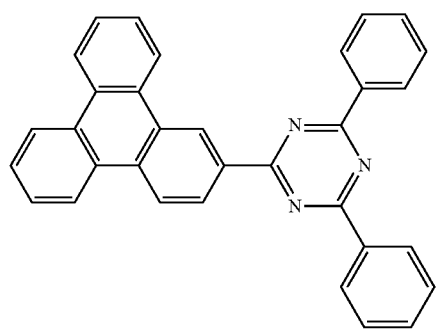
A-2
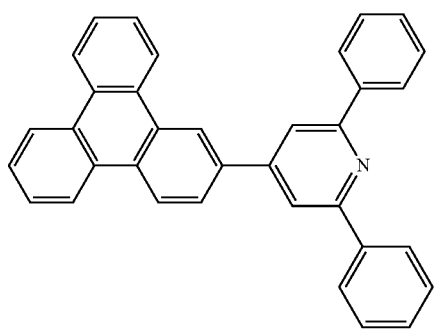
A-3
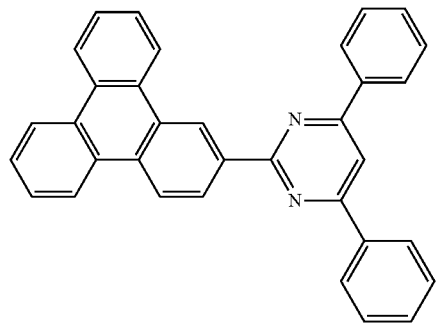
A-4
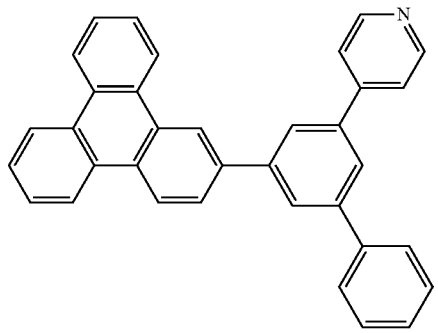
A-5
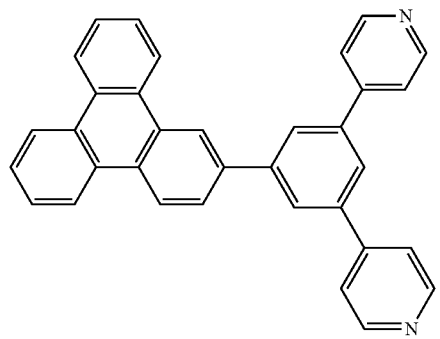
A-6
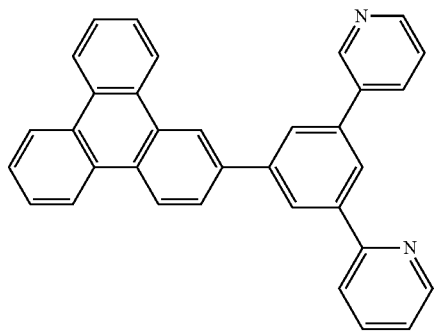

-continued
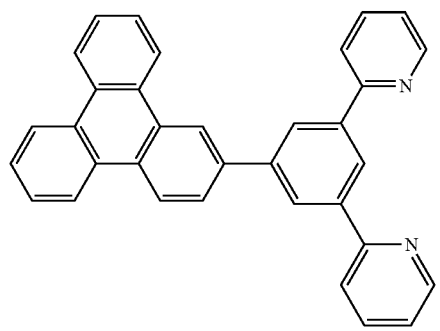
A-7
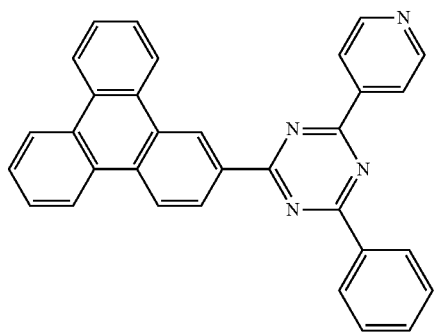
A-8
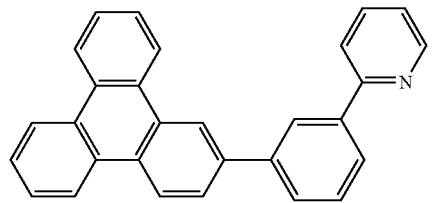
A-9
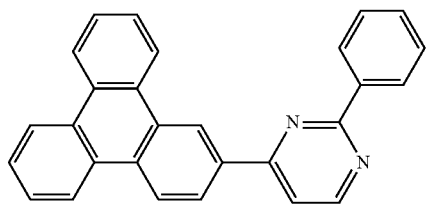
A-10
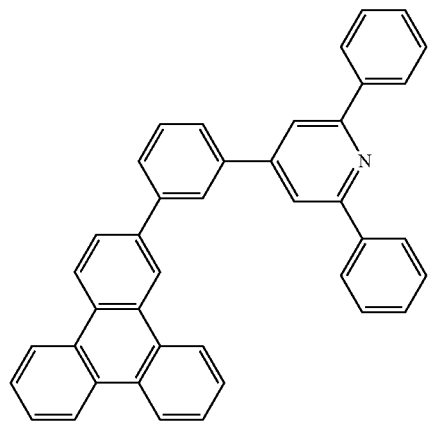
A-11
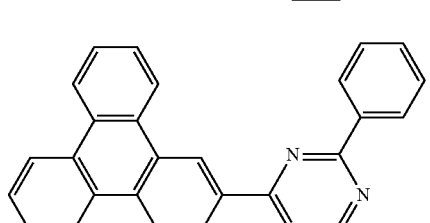
A-12
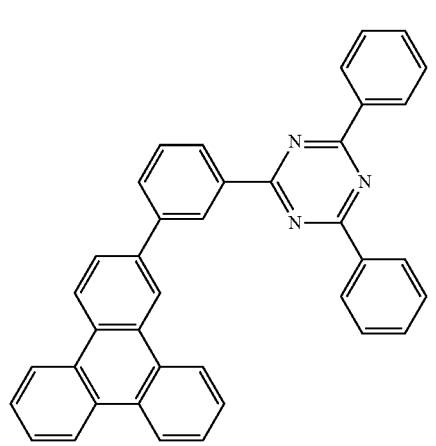
A-13
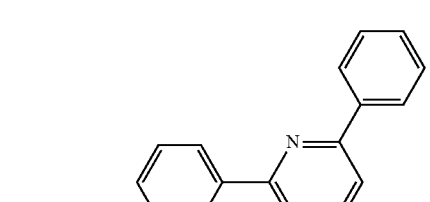
A-14
A-15
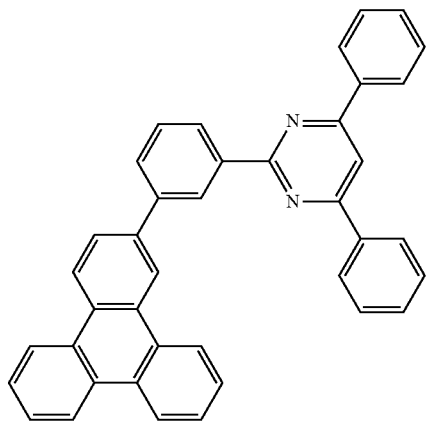
A-16
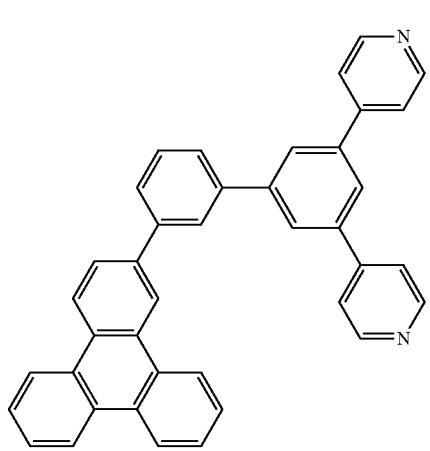

-continued
A-17
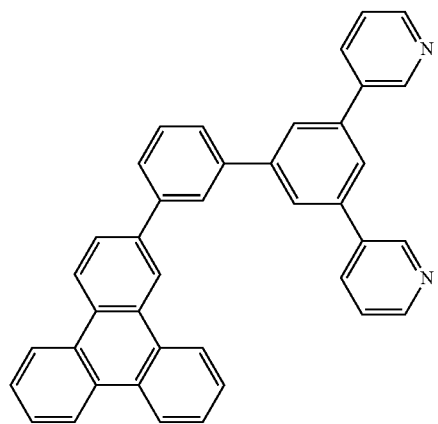
A-18
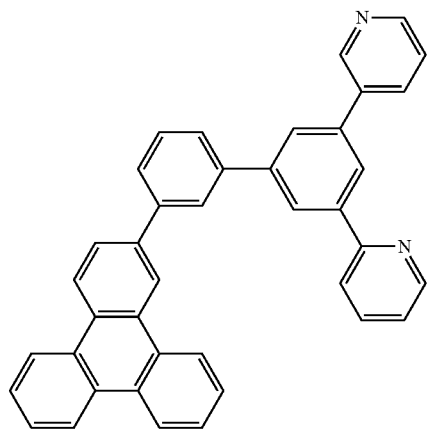
A-19
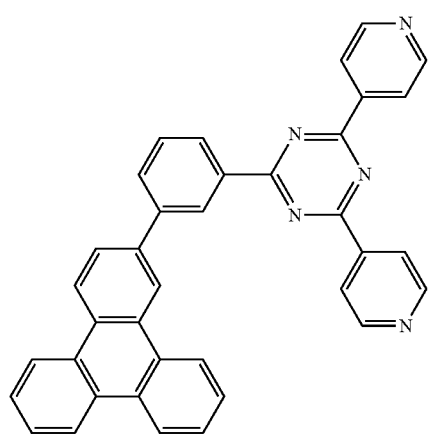
A-20
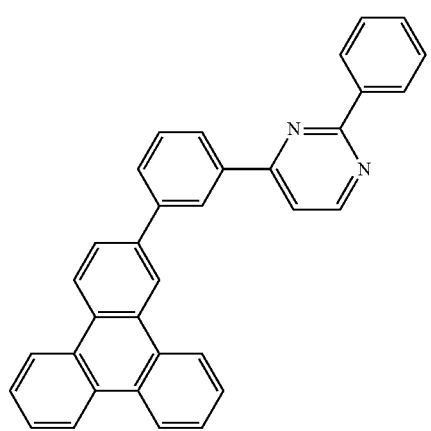
A-21
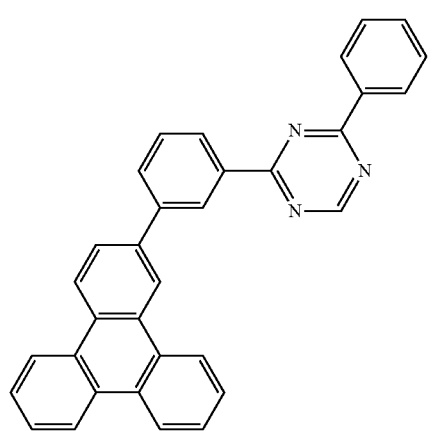
A-22
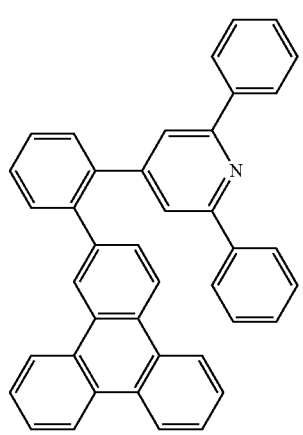

-continued
A-23
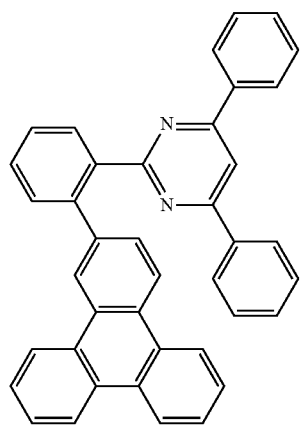
A-24
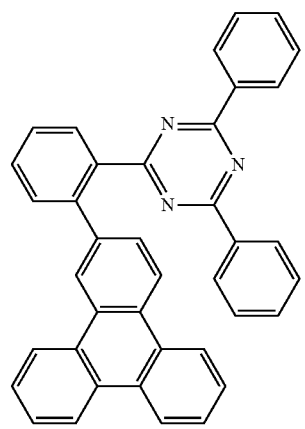
A-25
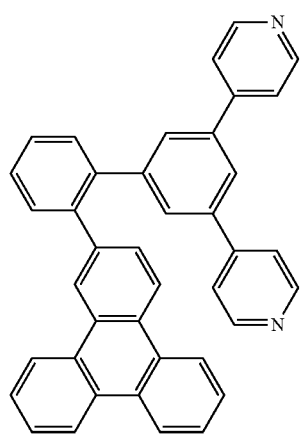
A-26
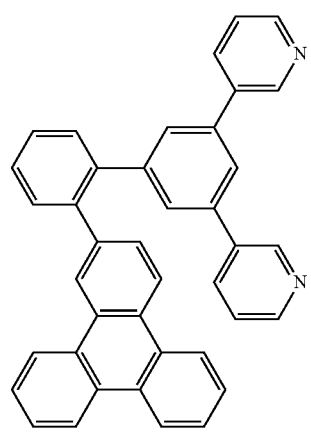
A-27
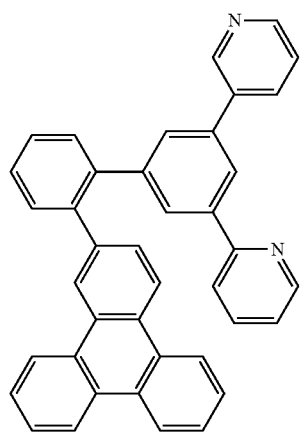
A-28
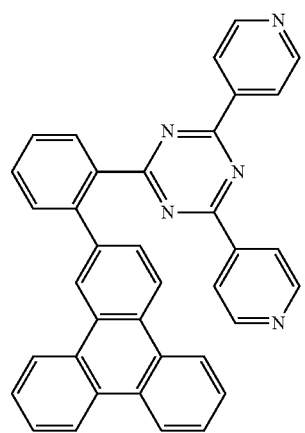

-continued
A-29
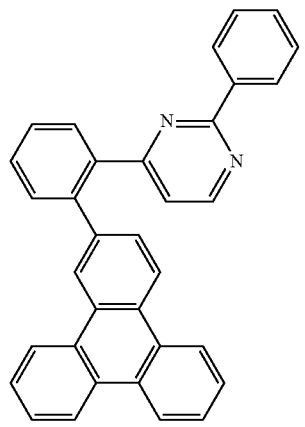
A-30
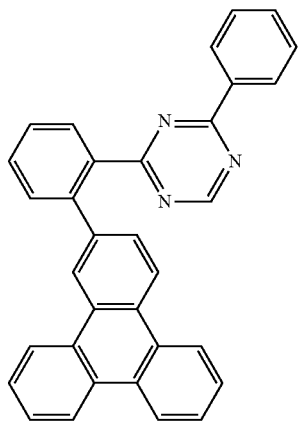
A-31
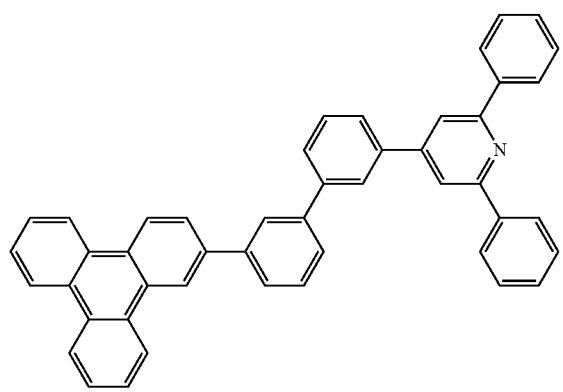
A-32
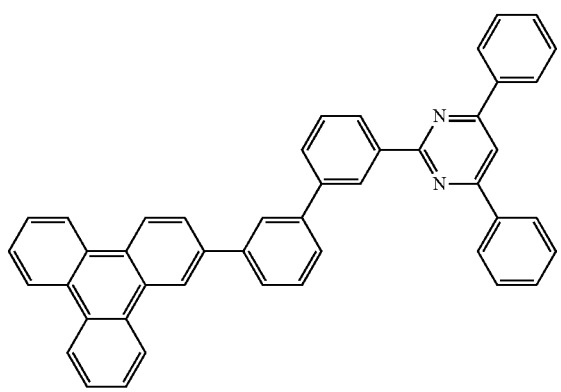
A-33
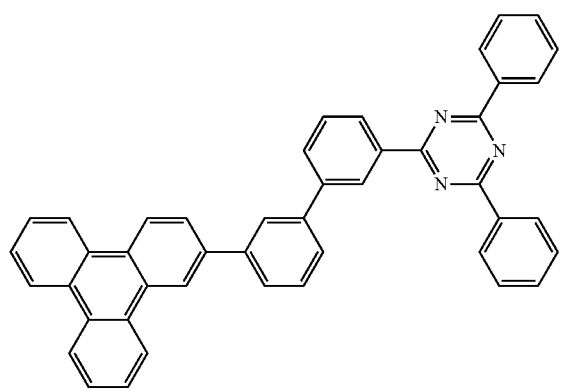
A-34
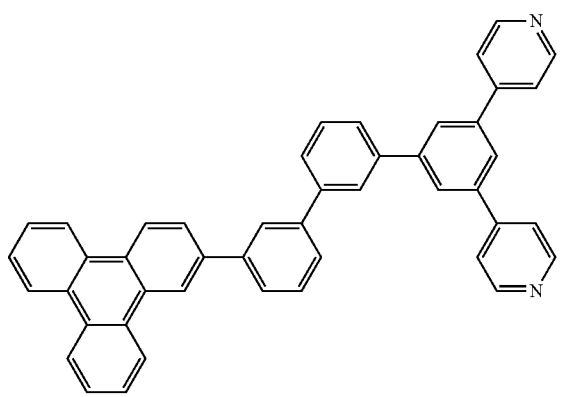
A-35
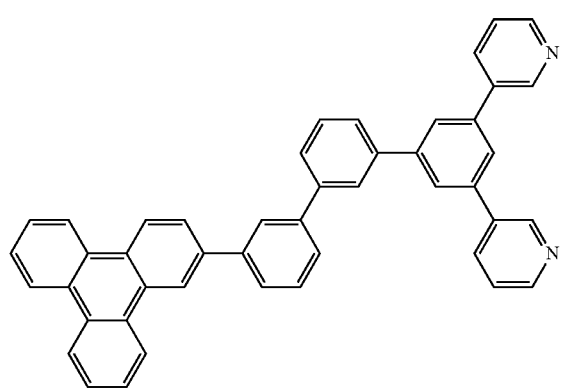
A-36
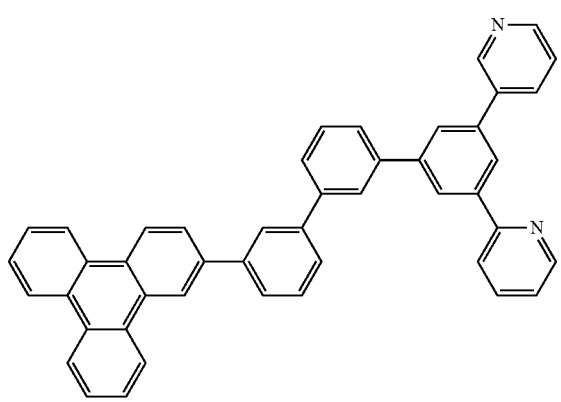

-continued
A-37
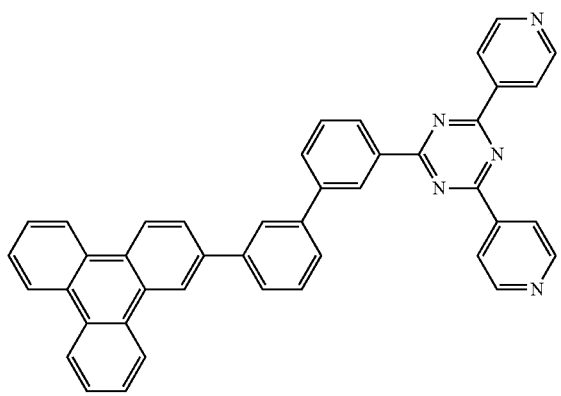
A-38
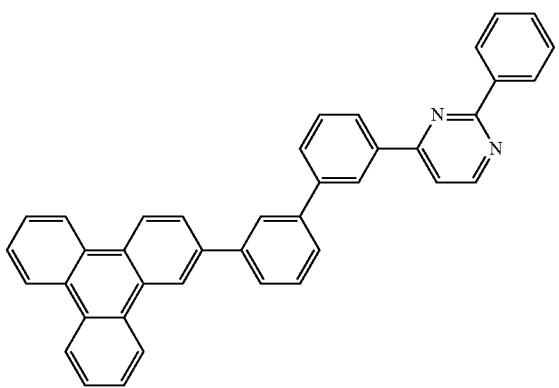
A-39
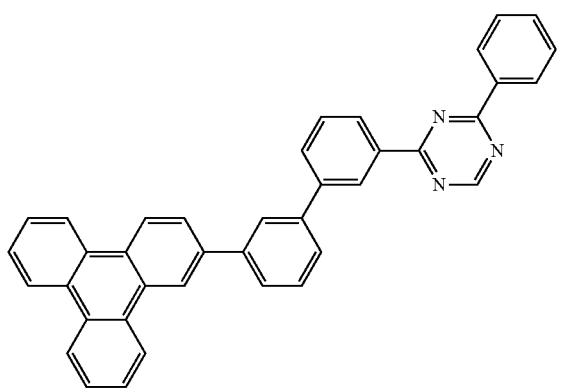
A-40
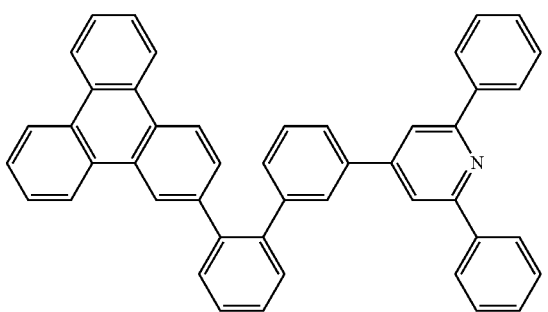
A-41
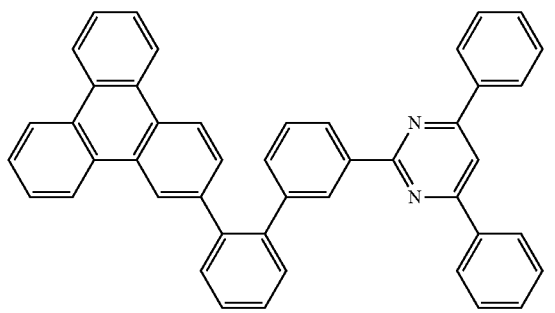
A-42
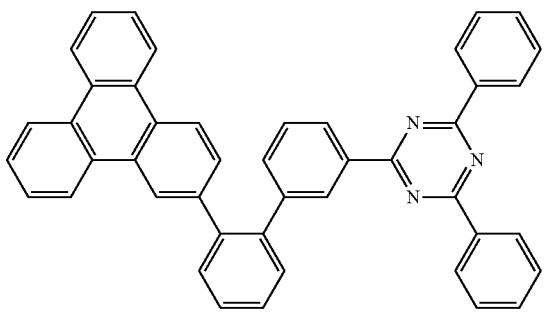
A-43
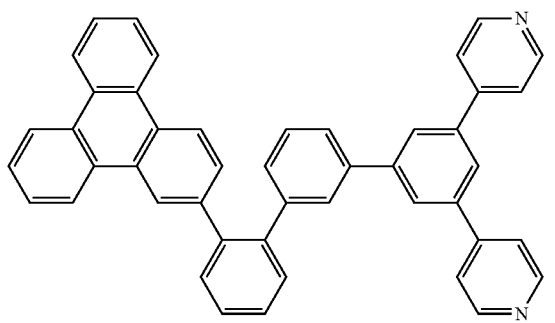
A-44
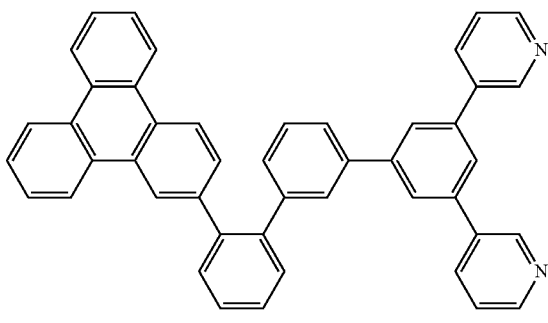

A-45
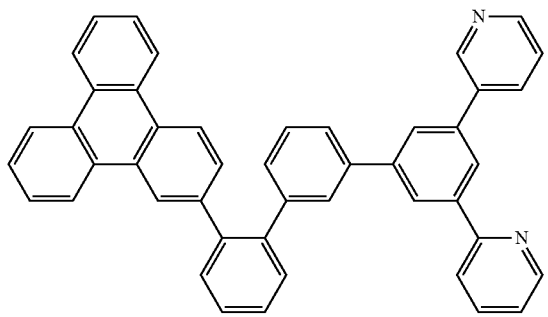
A-46
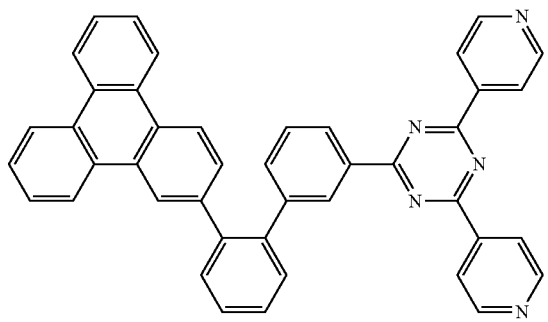
A-47
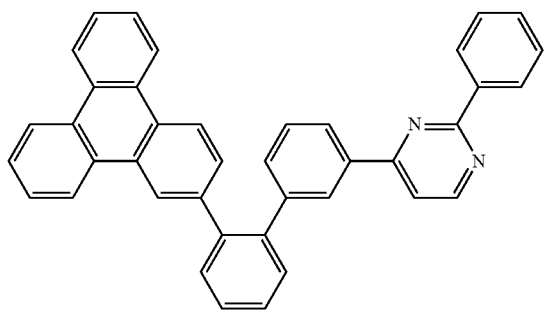
A-48
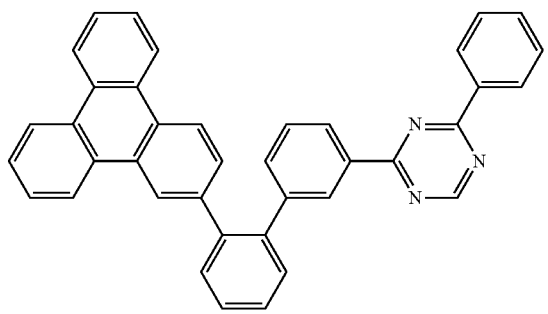
A-49
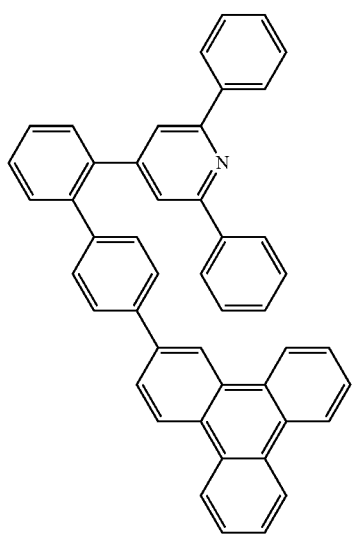
A-50
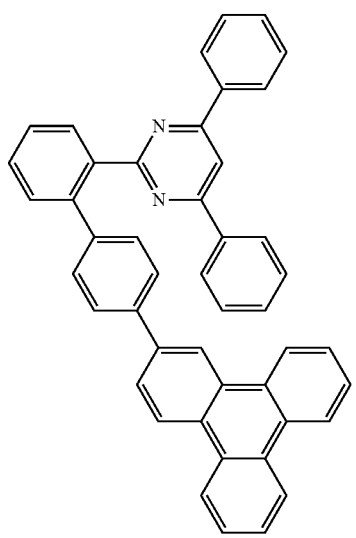

-continued
A-51
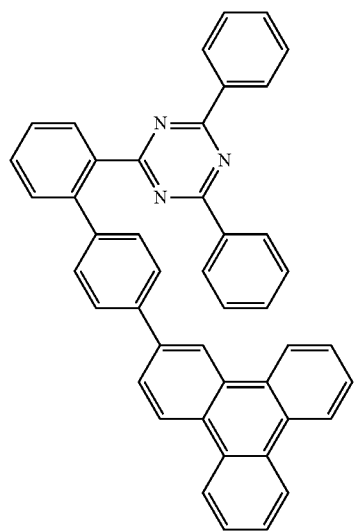
A-52
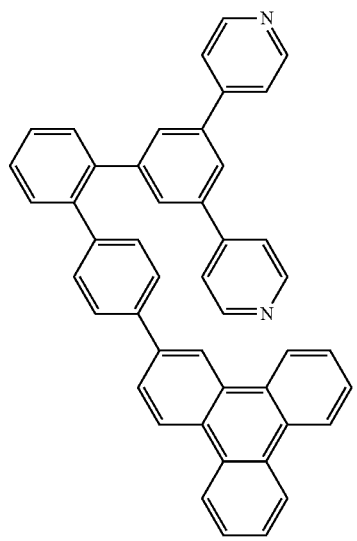
A-53
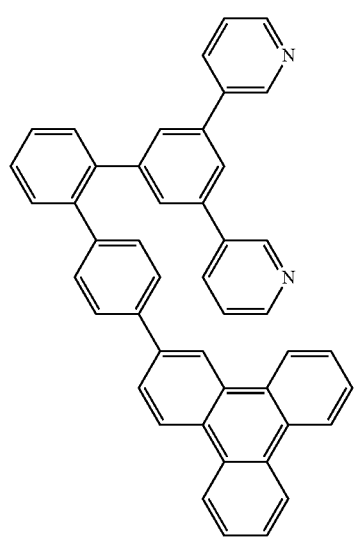
A-54
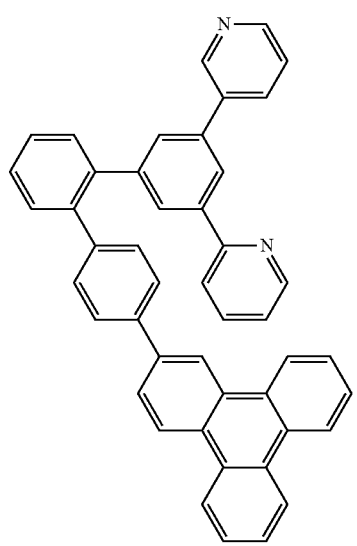
A-55
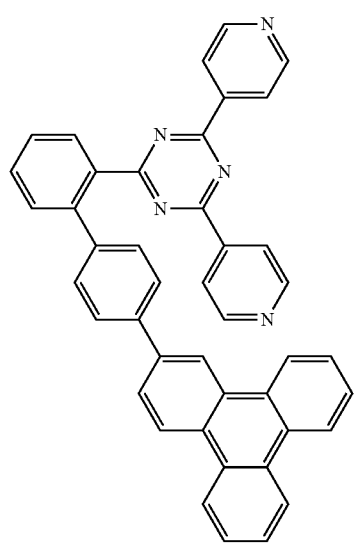
A-56
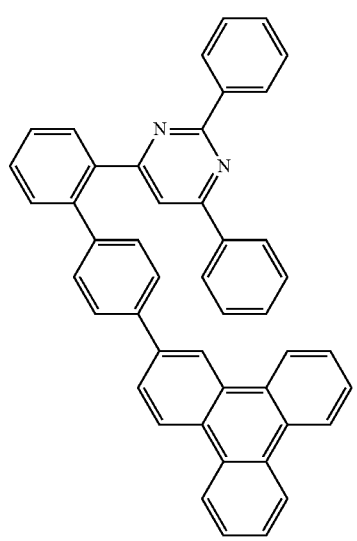

-continued
A-57
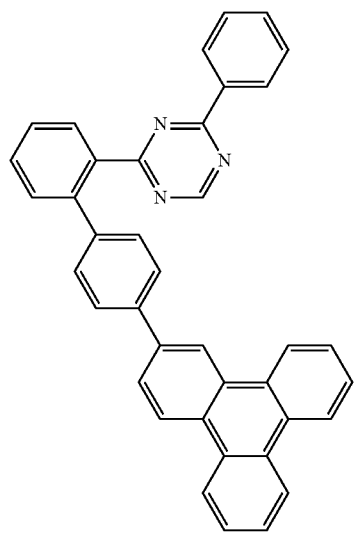
A-58
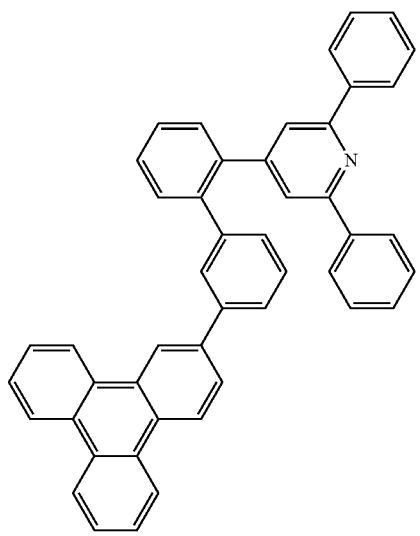
A-59
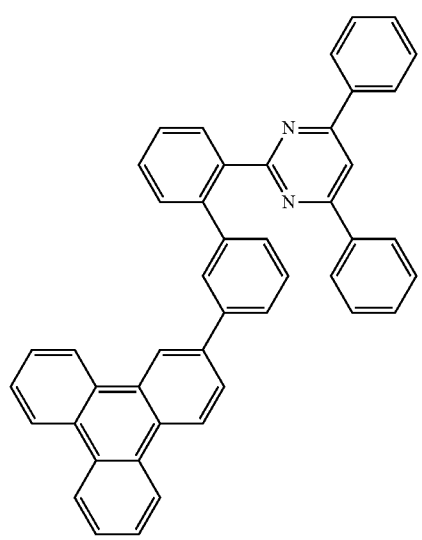
A-60
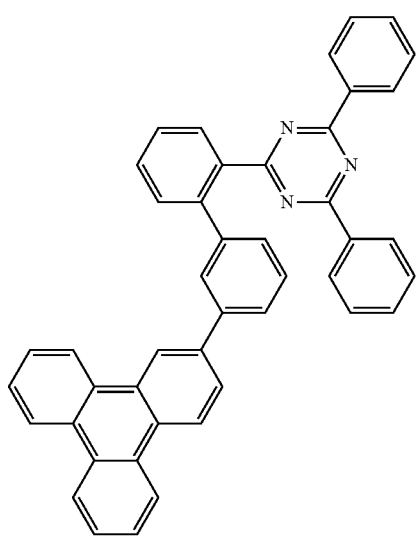
A-61
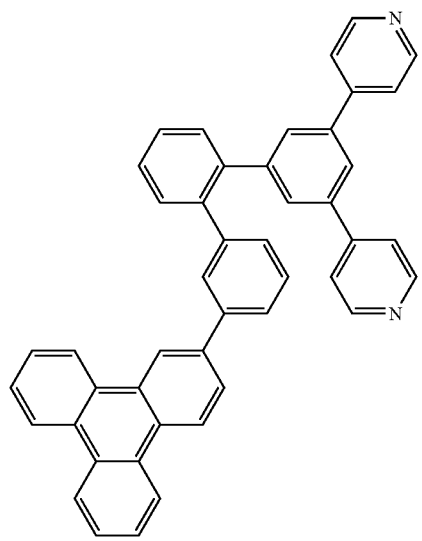
A-62
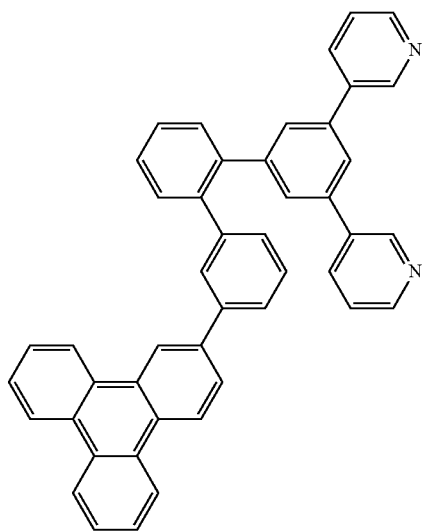

-continued
A-63
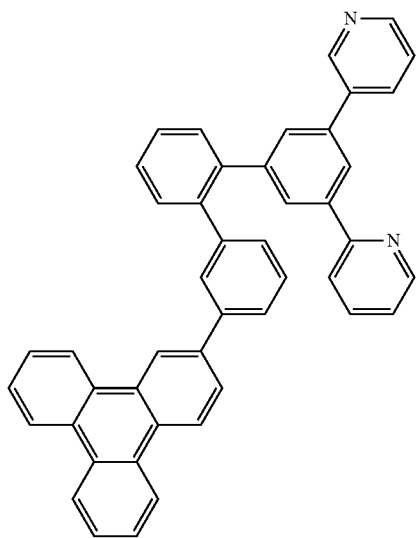
A-64
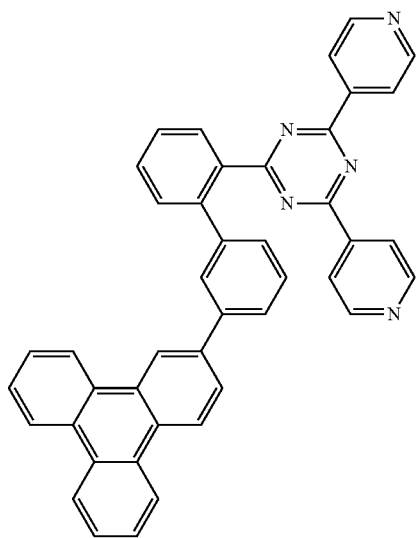
A-65
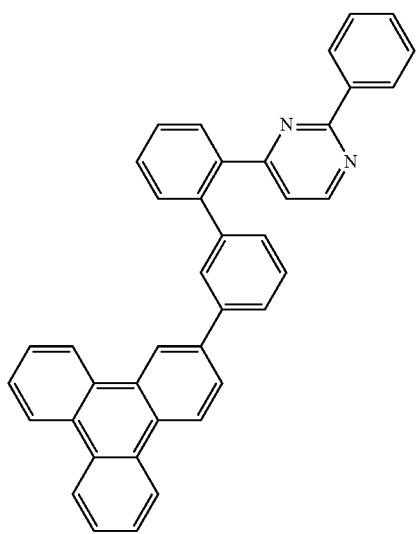
A-66
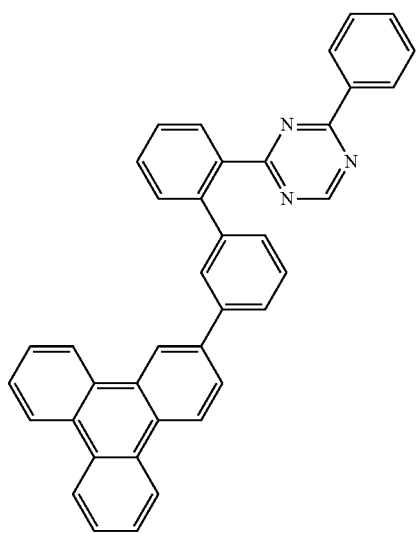
A-67
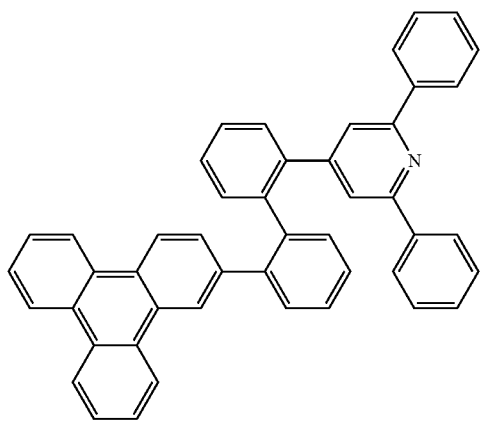
A-68
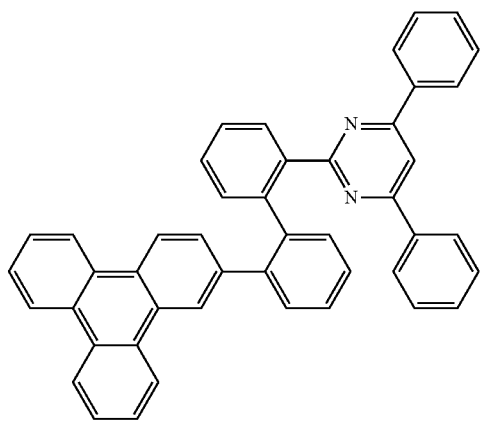

-continued
A-69
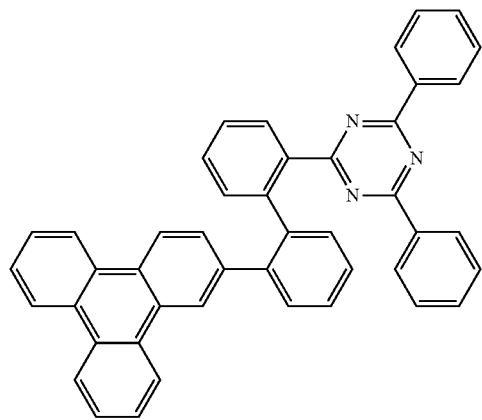
A-70
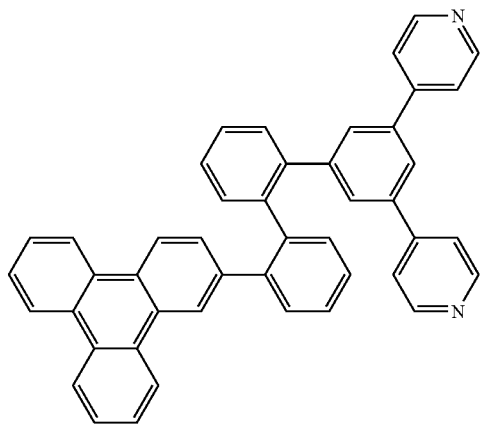
A-71
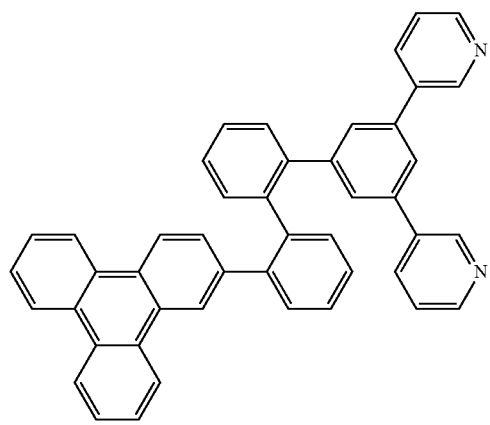
A-72
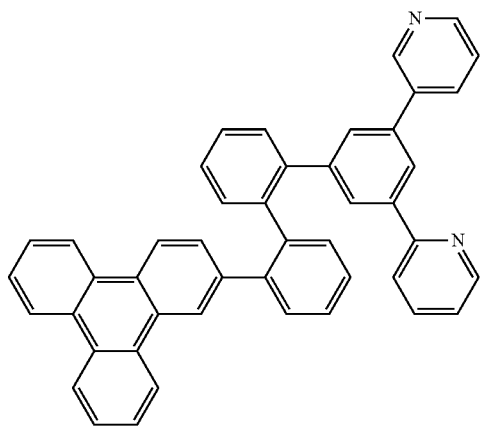
A-73
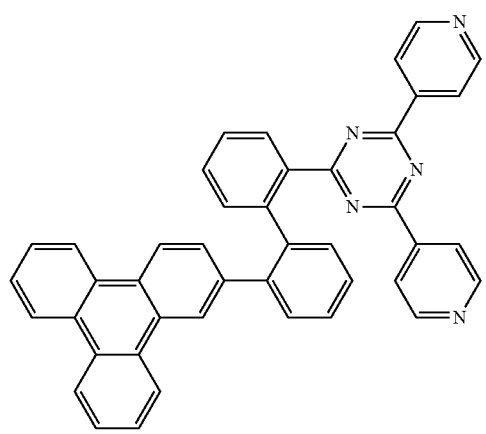
A-74
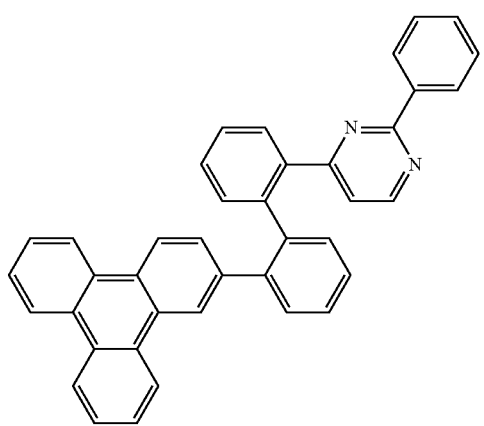

-continued
A-75
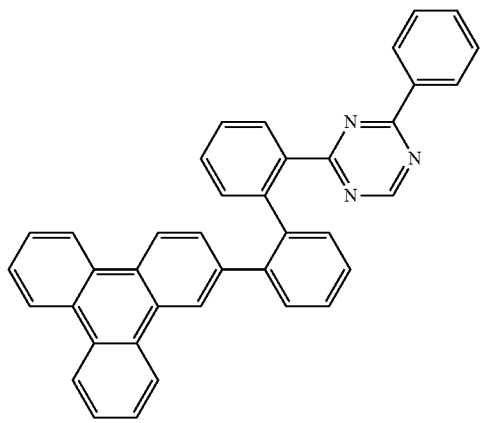
A-76
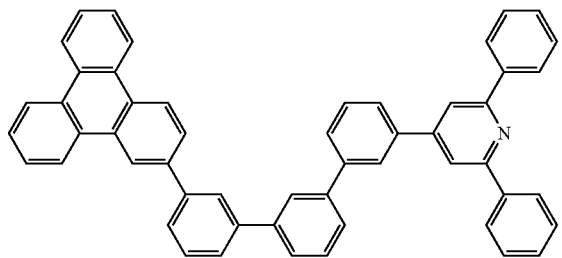
A-77
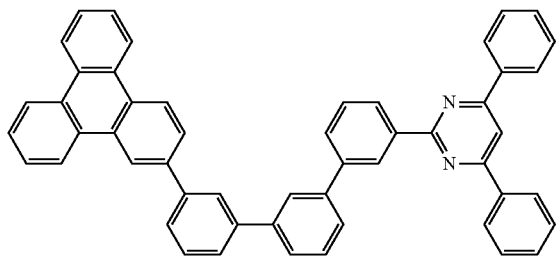
A-78
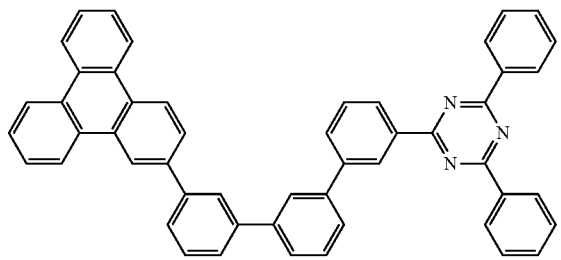
A-79
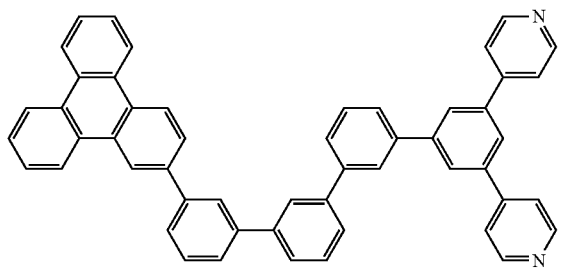
A-80
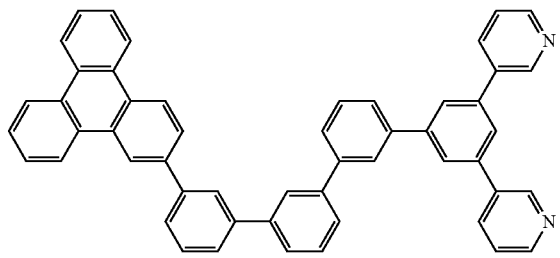
A-81
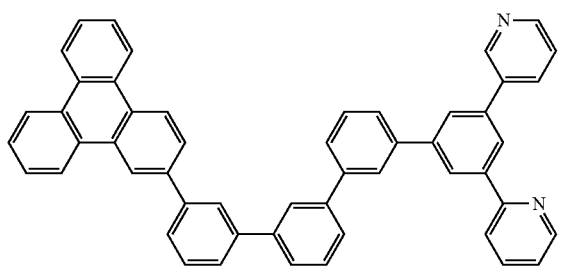
A-82
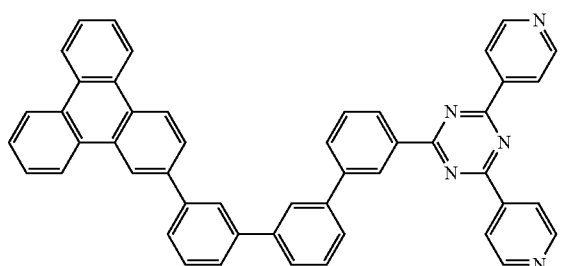
A-83
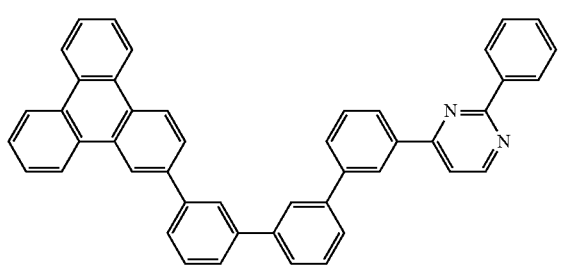
A-84
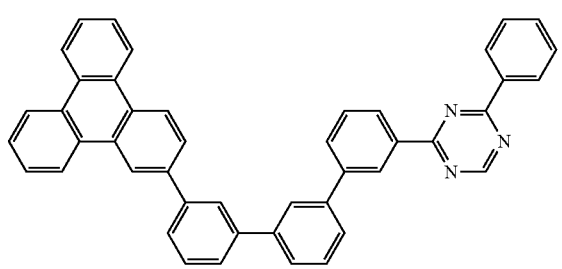

-continued
A-85
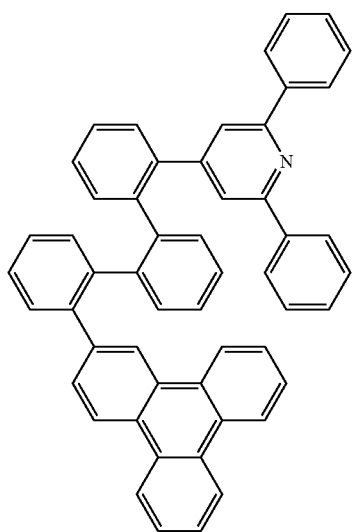
A-86
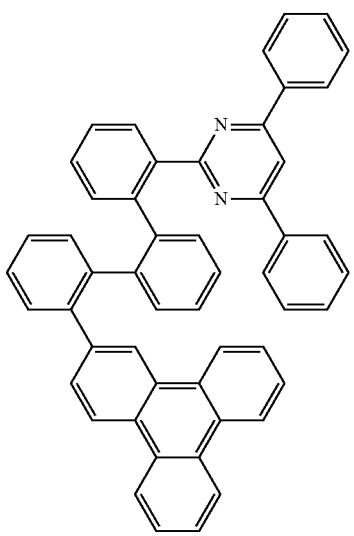
A-87
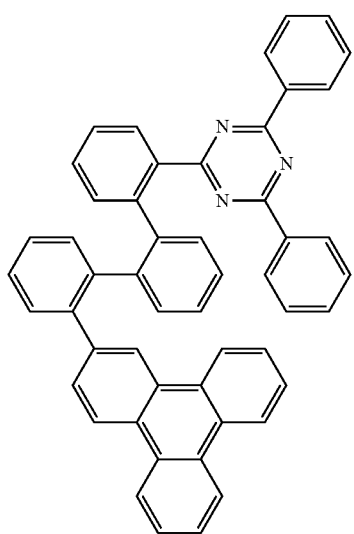
A-88
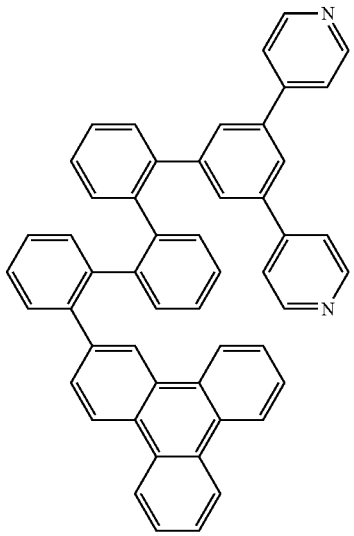
A-89
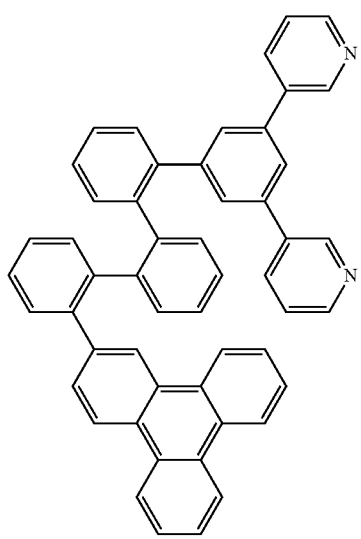
A-90
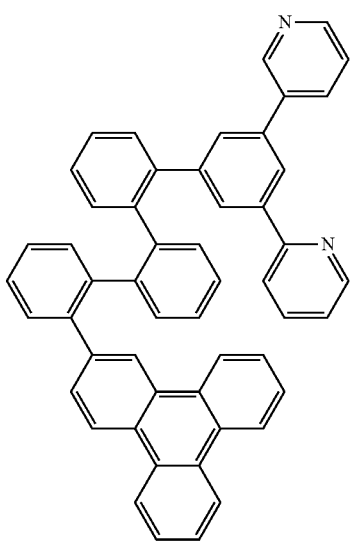

-continued
A-91
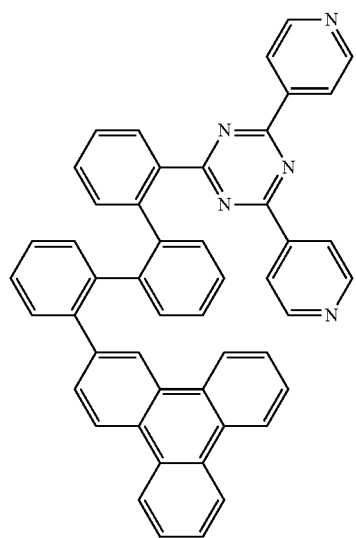
A-92
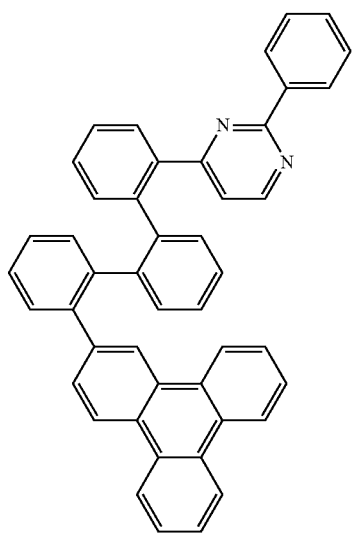
A-93
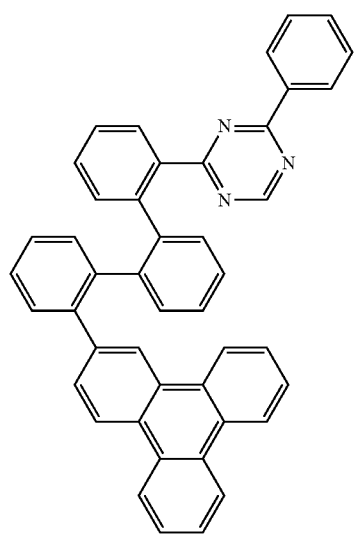
A-94
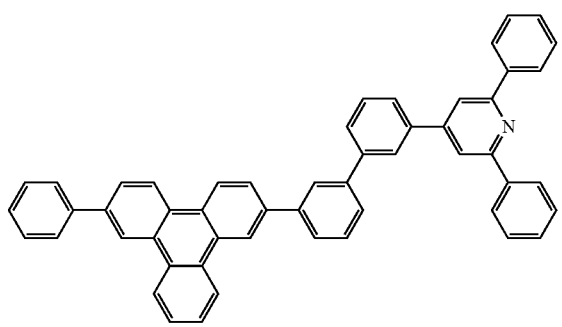
A-95
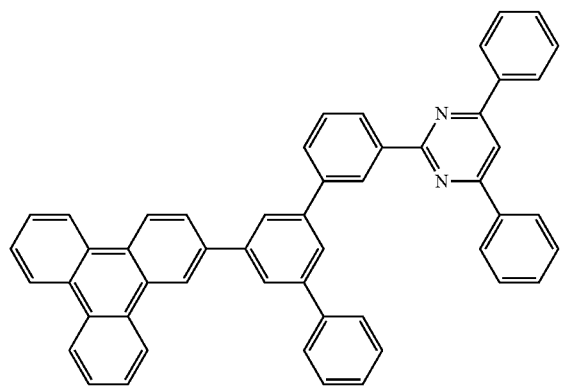
A-96
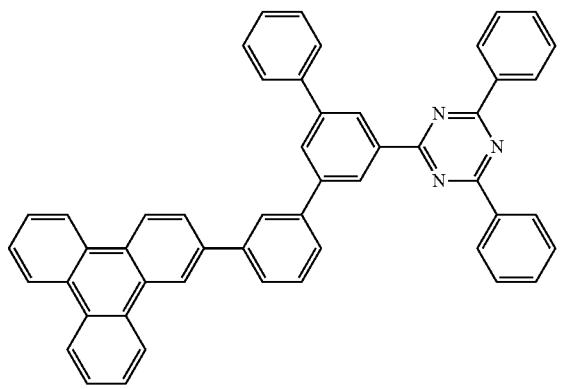

-continued
A-97
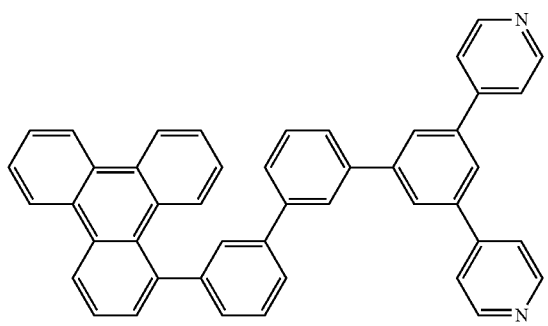
A-98
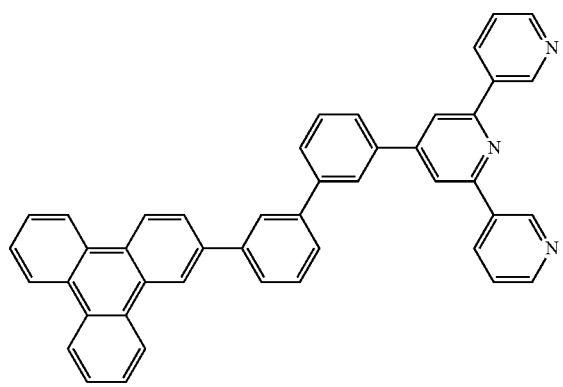
A-99
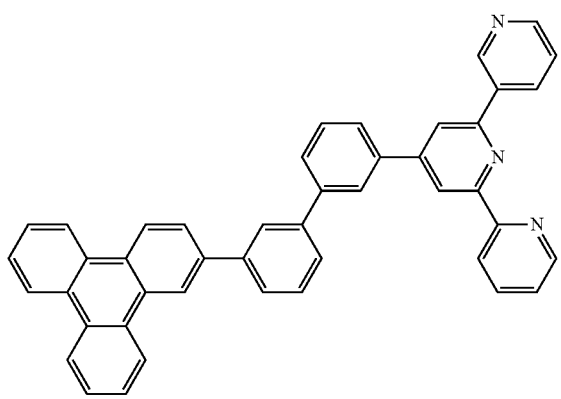
A-100
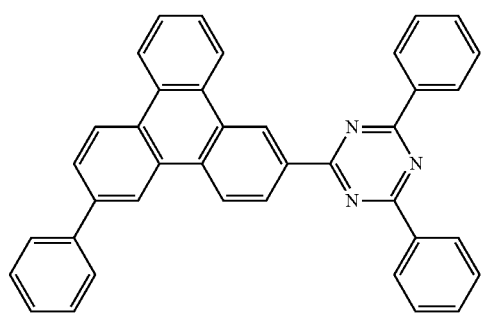
A-101
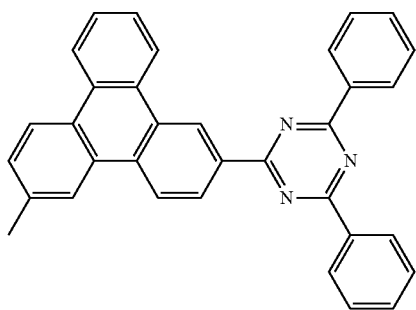
A-102
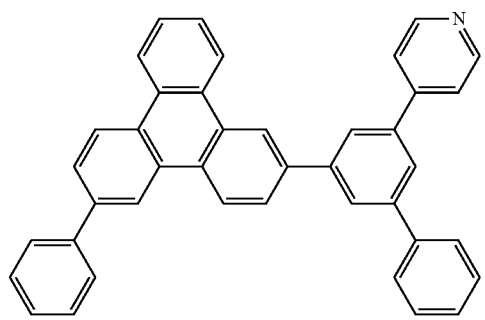
A-103
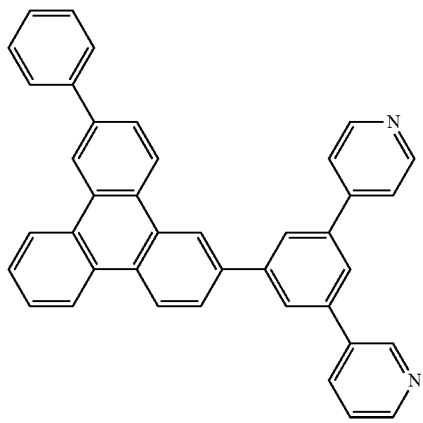
A-104
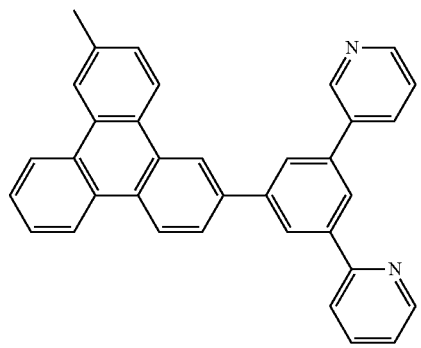

-continued
A-105
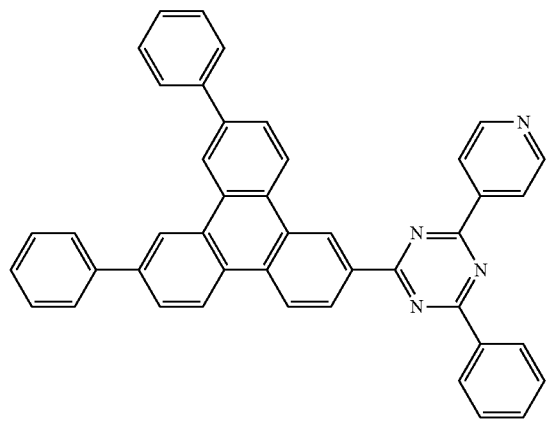
A-106
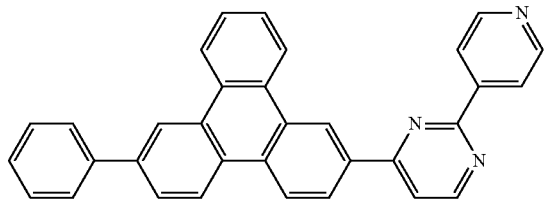
A-107
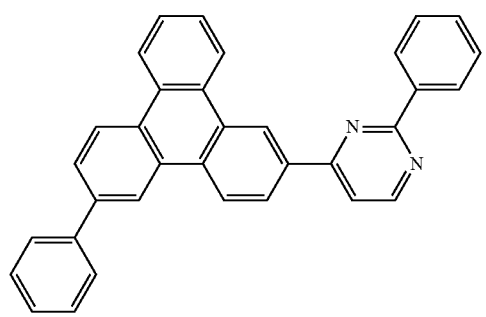
A-108
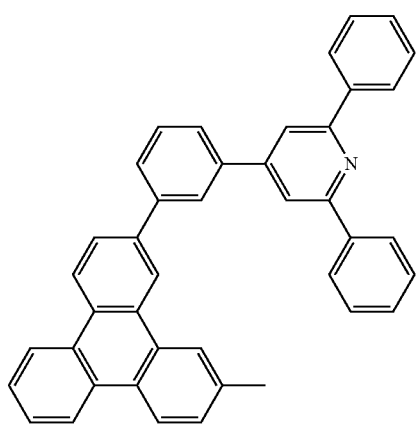
A-109
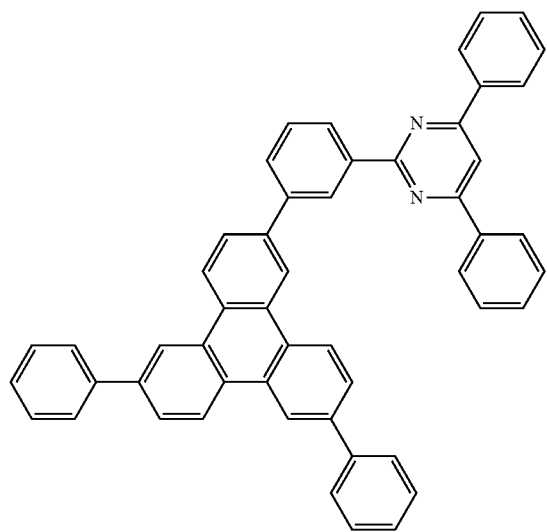
A-110
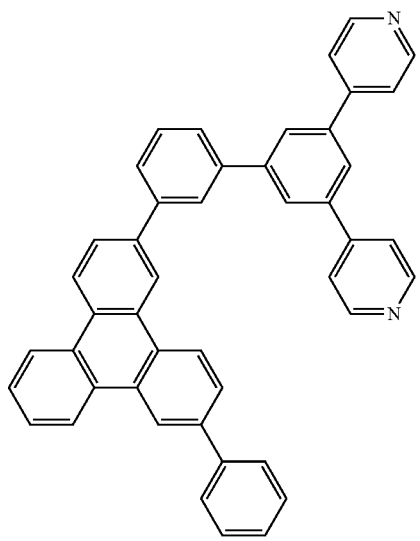

-continued
A-111
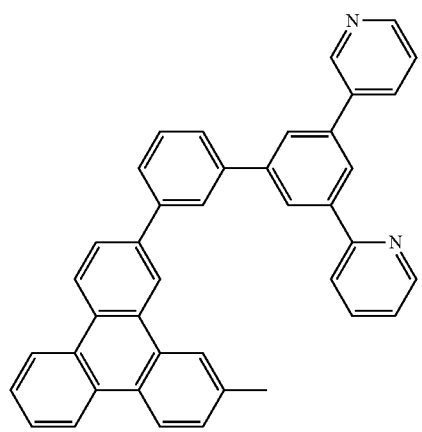
A-112
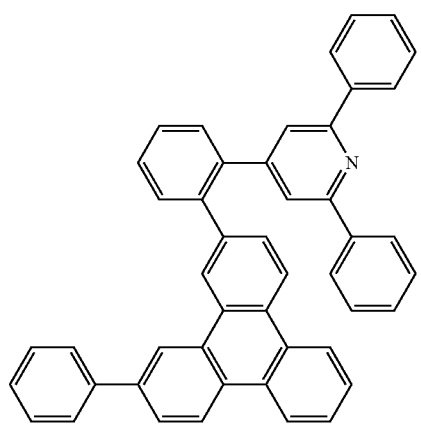
A-113
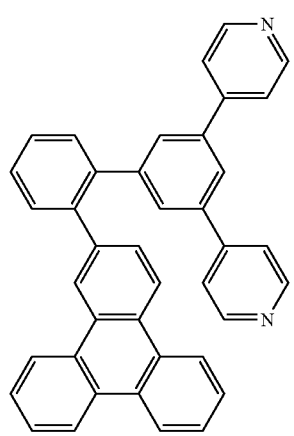
A-114
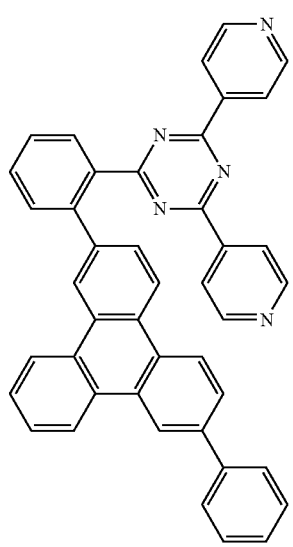
A-115
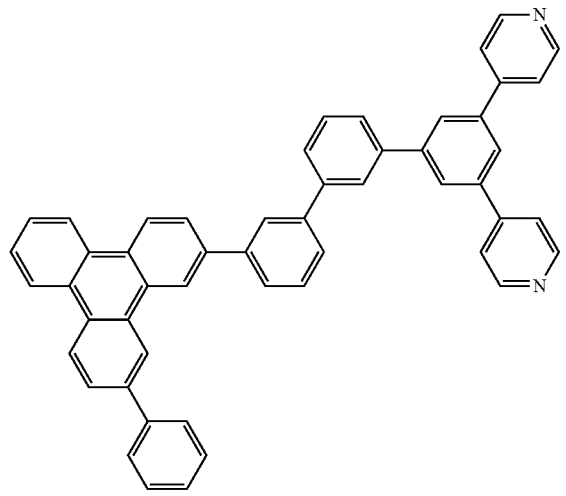
A-116
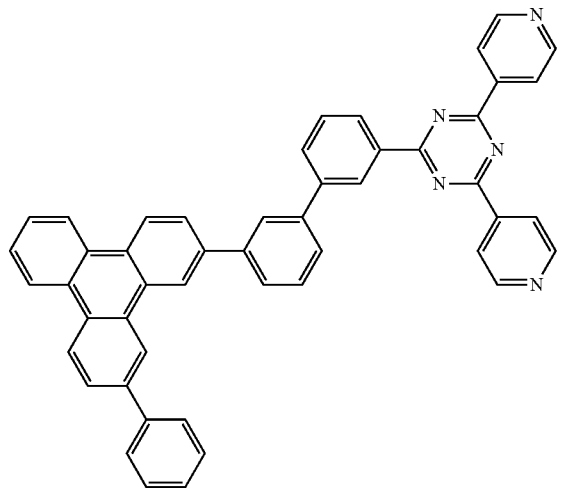

A-117
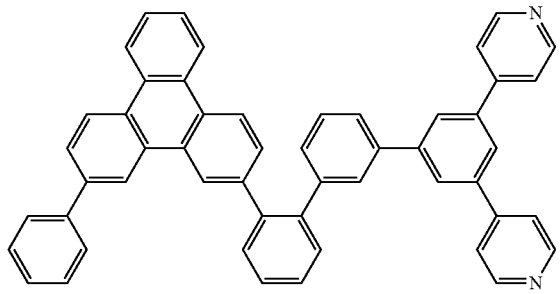
A-118
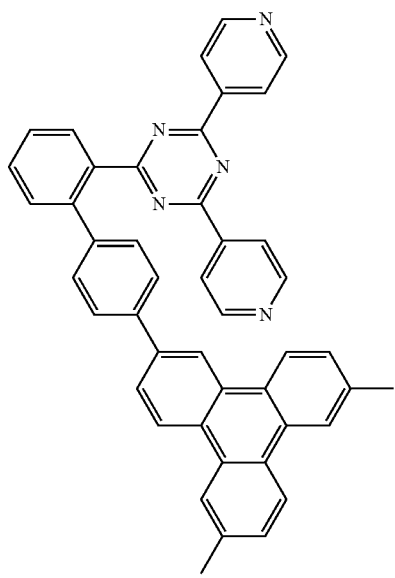
A-119
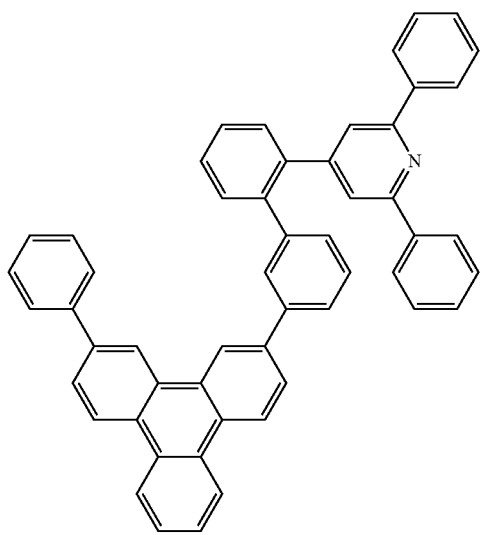
A-120
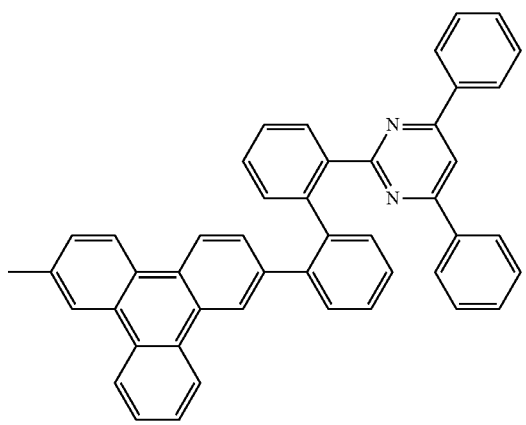

-continued
A-121
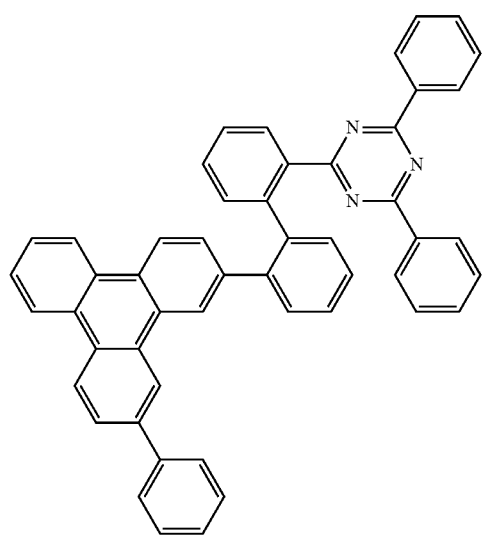
A-122
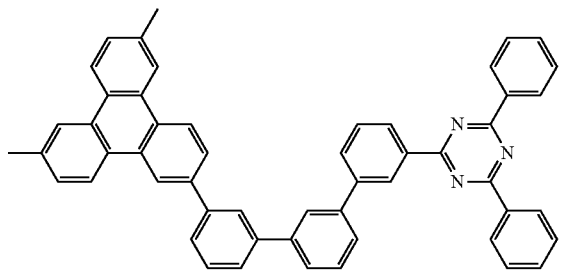
A-123
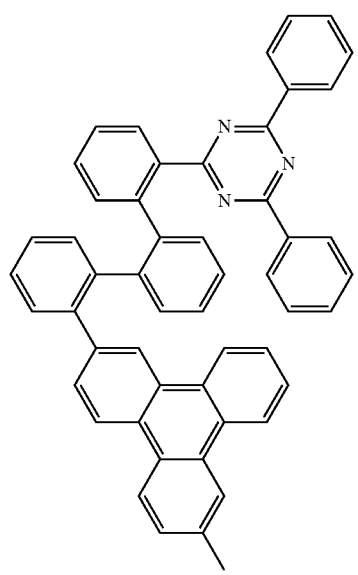
A-124
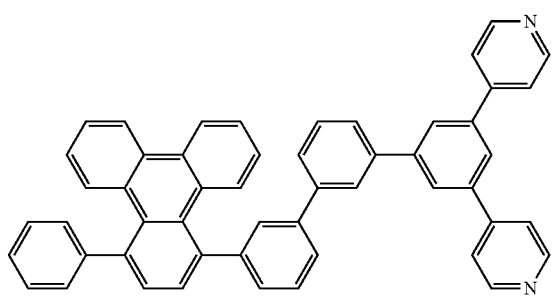
A-125 A(1)
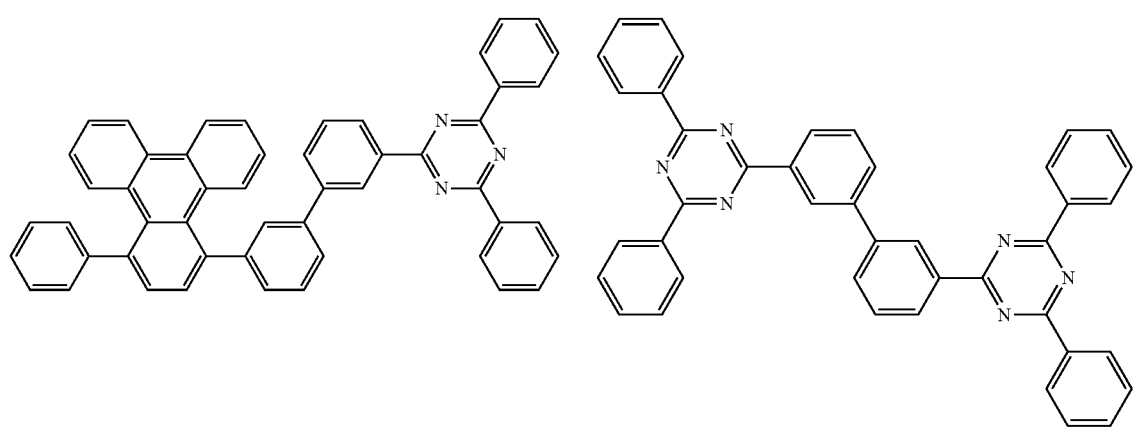

-continued
A(2)
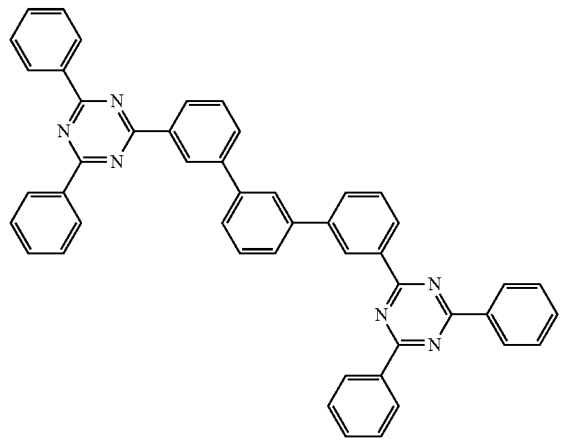
A(3)
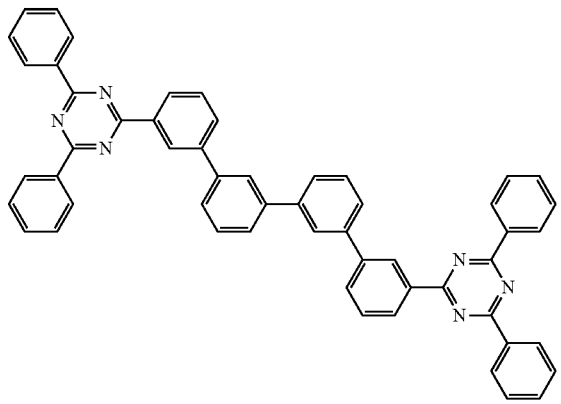
A(4)
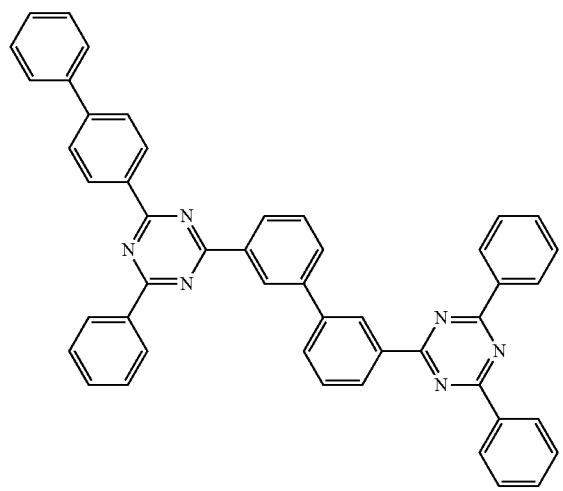
A(5)
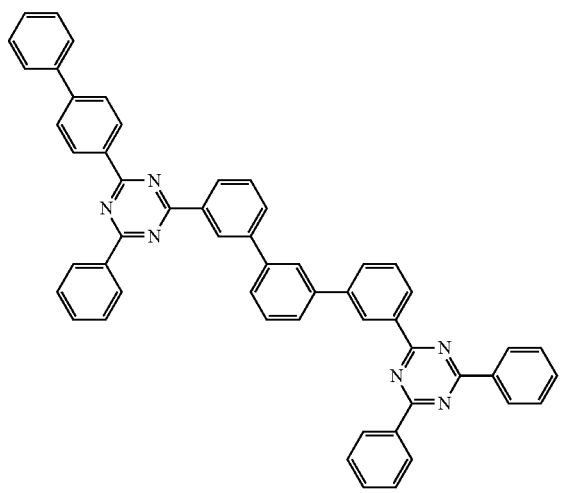
A(6)
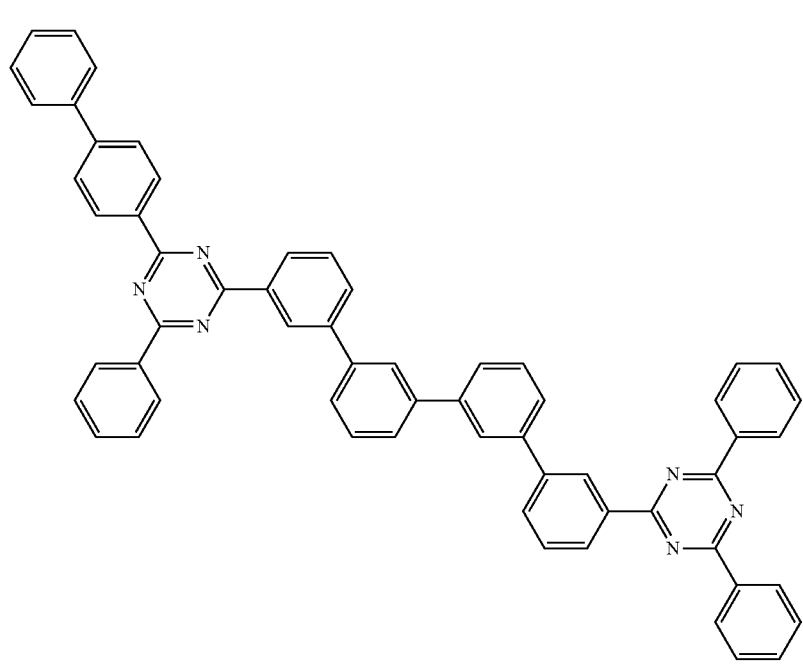

-continued
A(7)
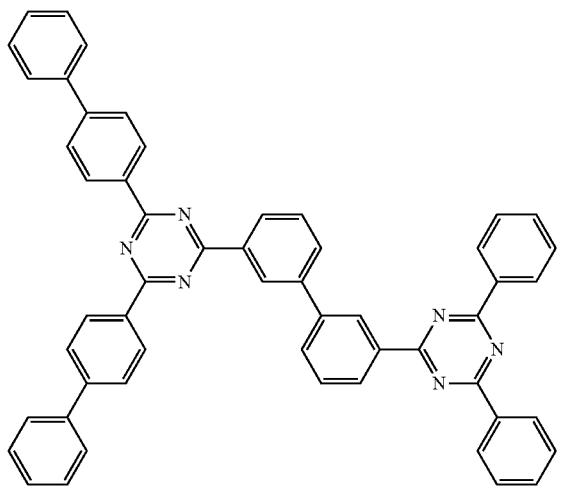
A(8)
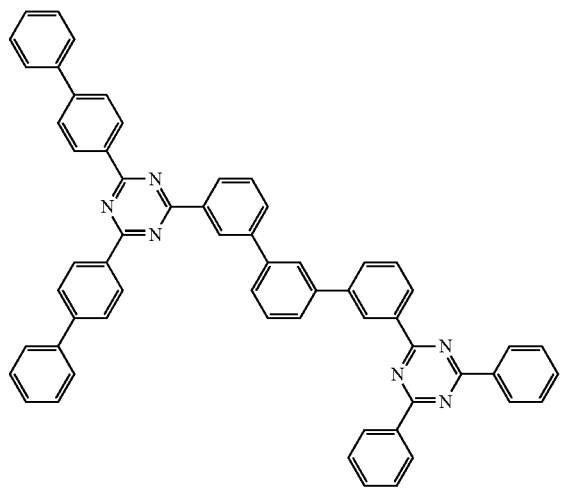
A(9)
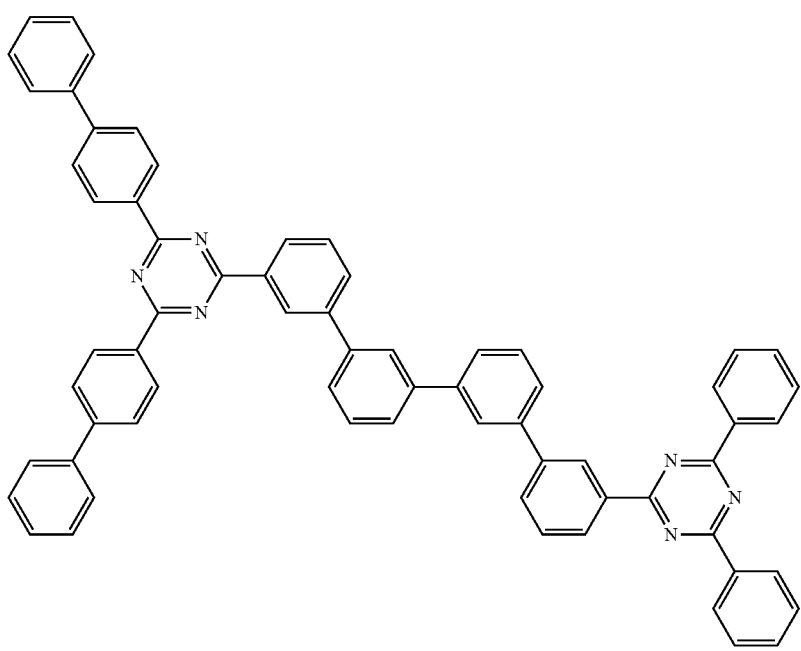

-continued
A(10)
A(11)
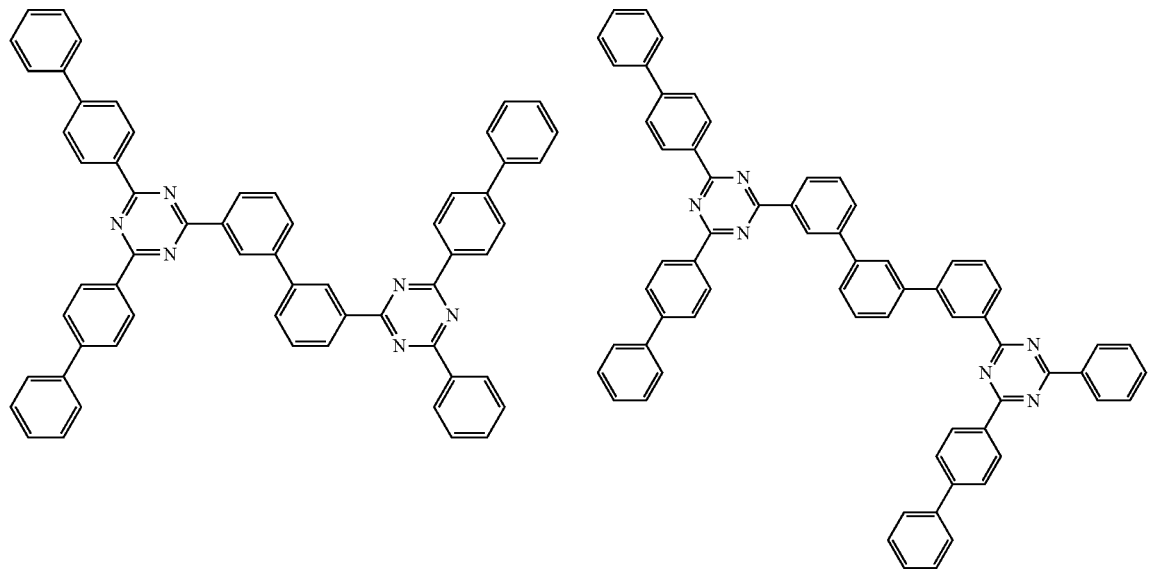
A(12)
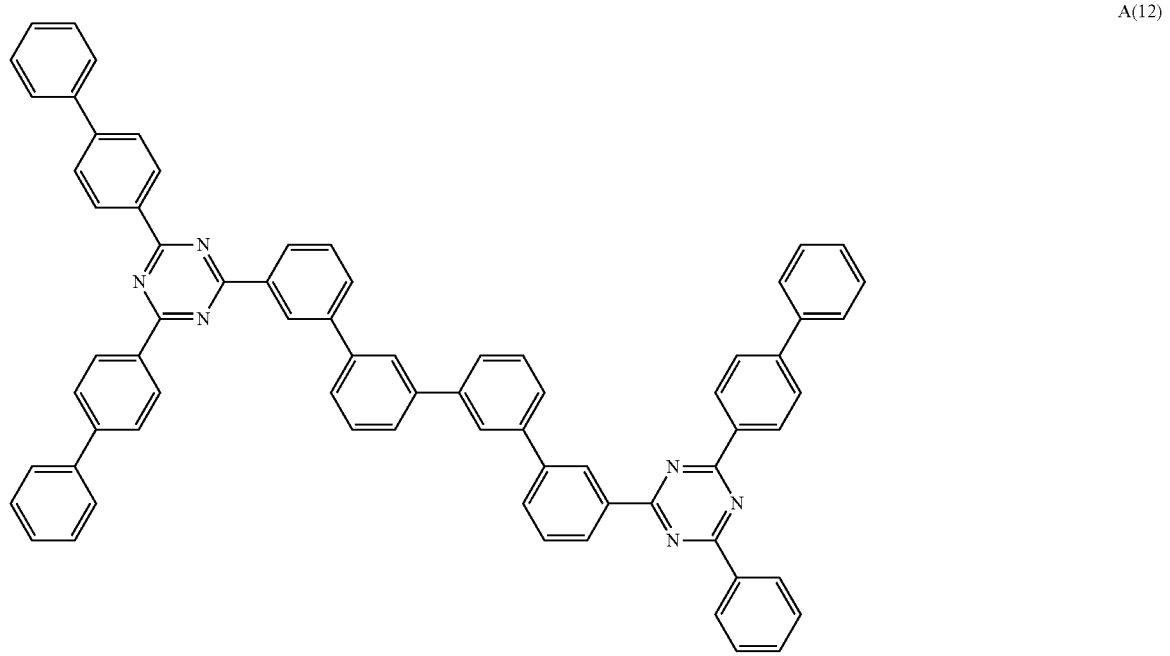

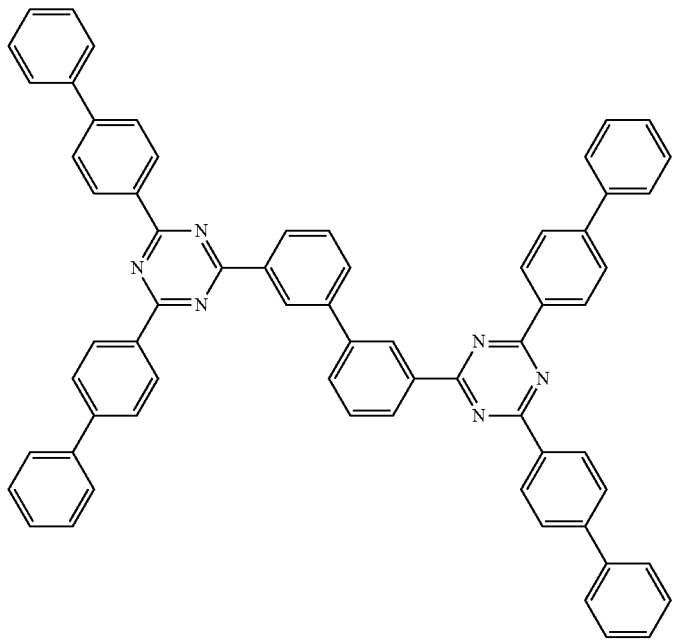
A(13)
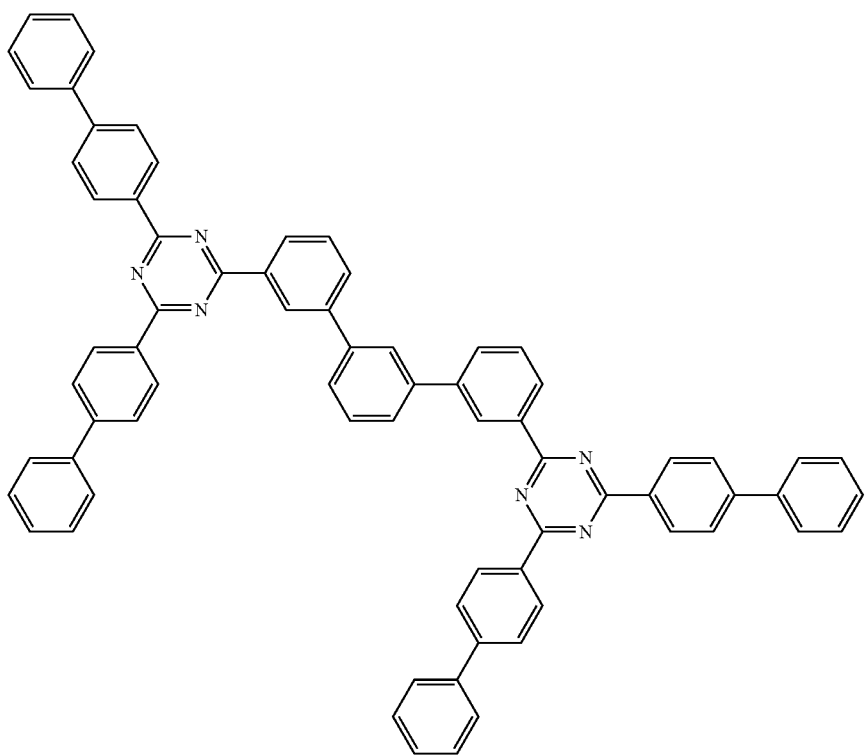
A(14)

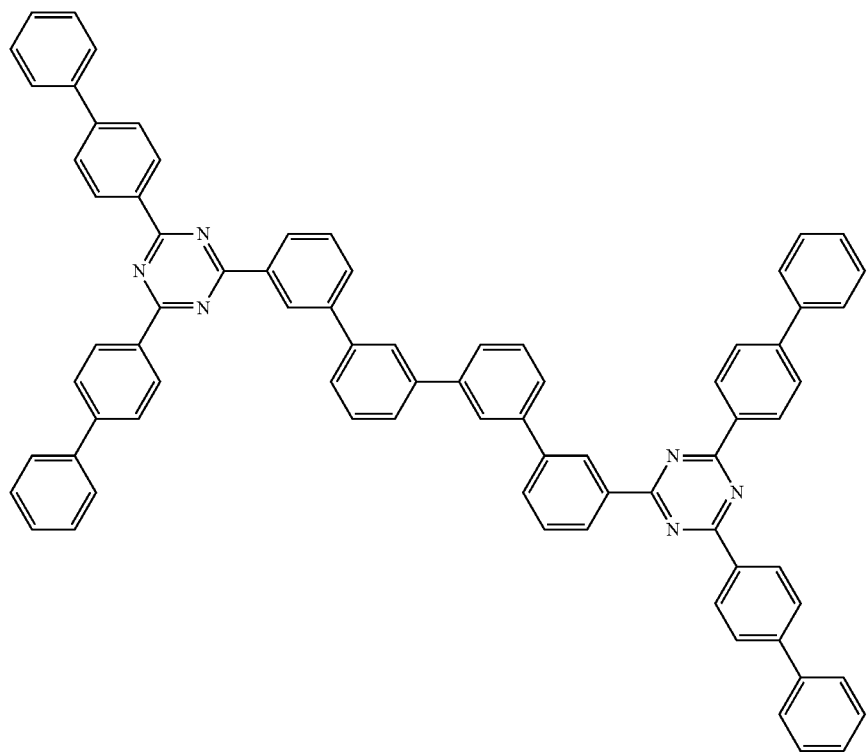
A(15)
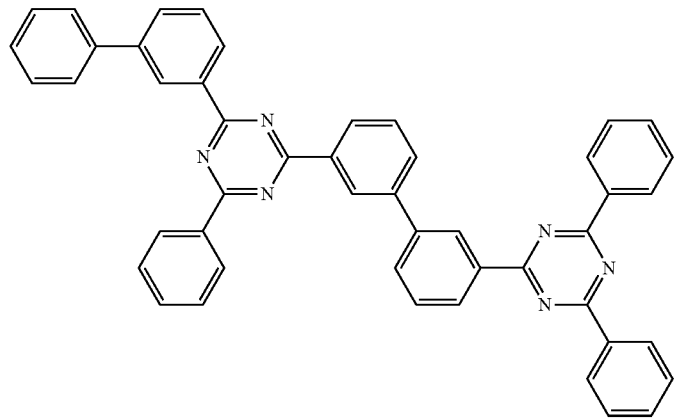
A(16)

-continued
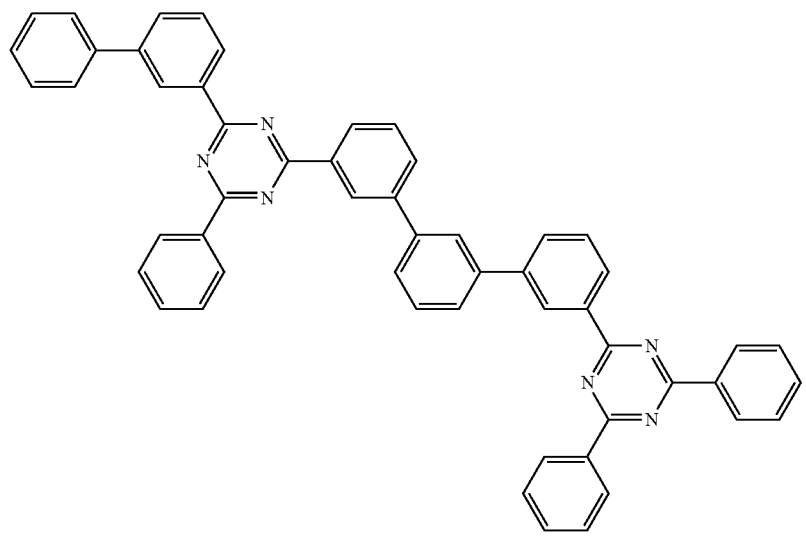
A(17)
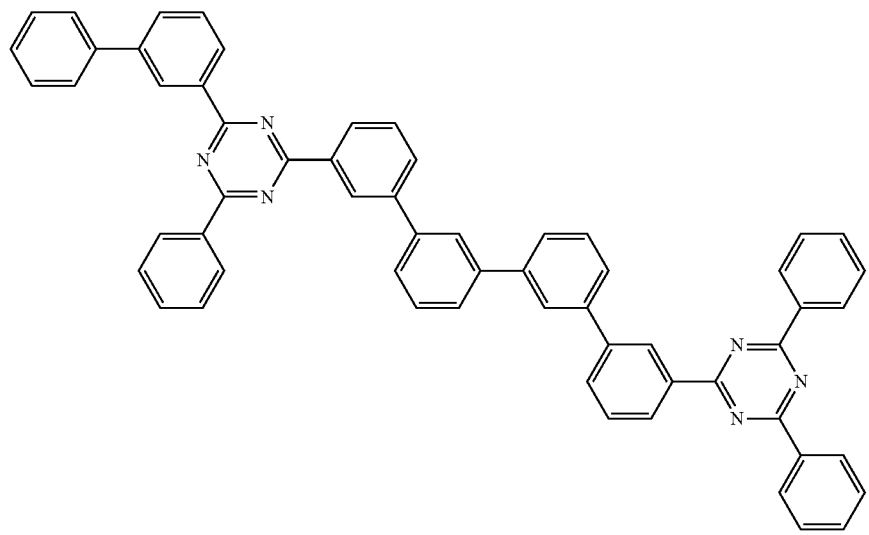
A(18)
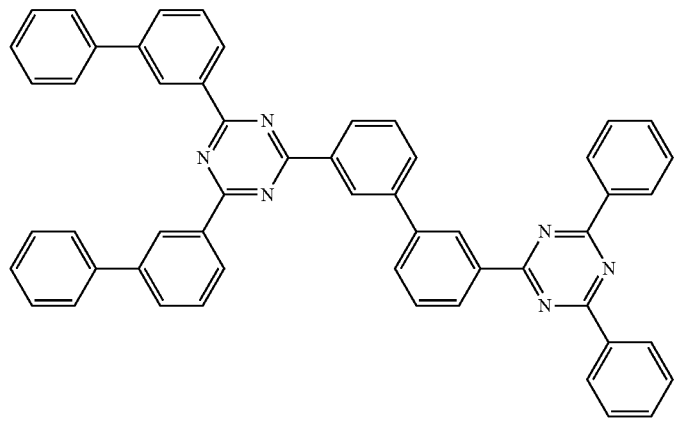
A(19)

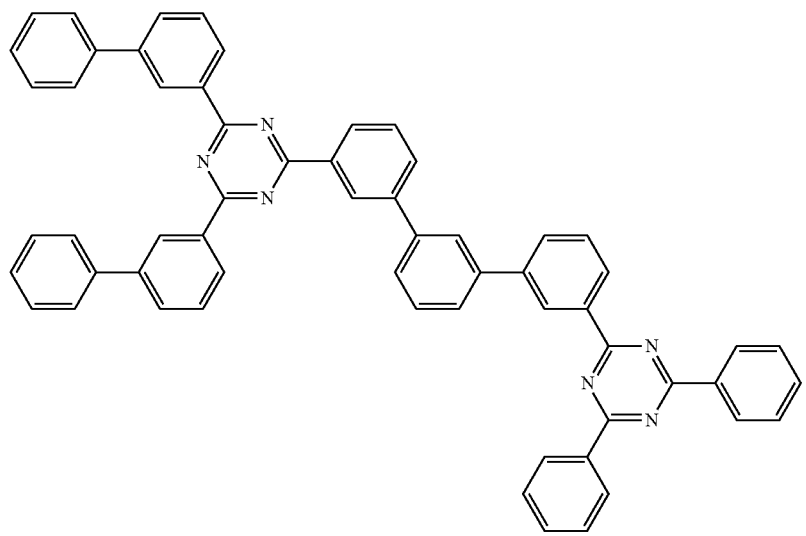
A(20)
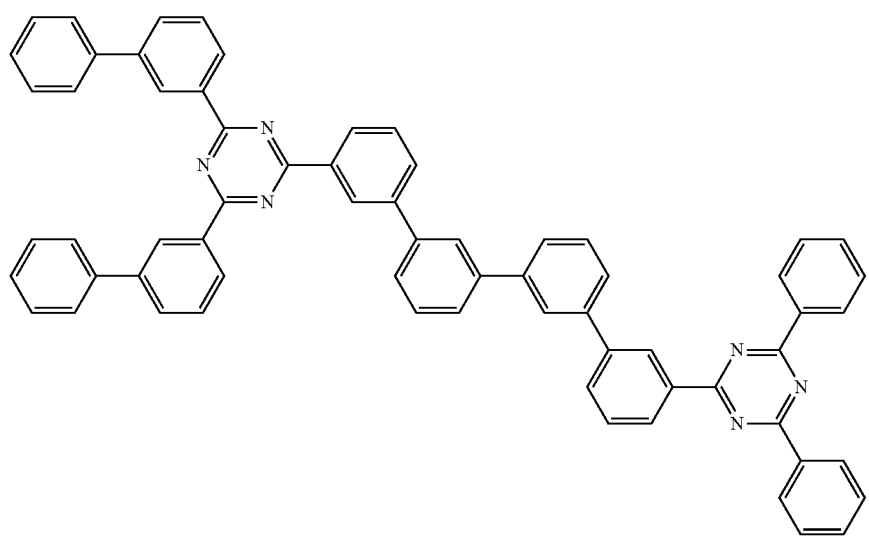
A(21)
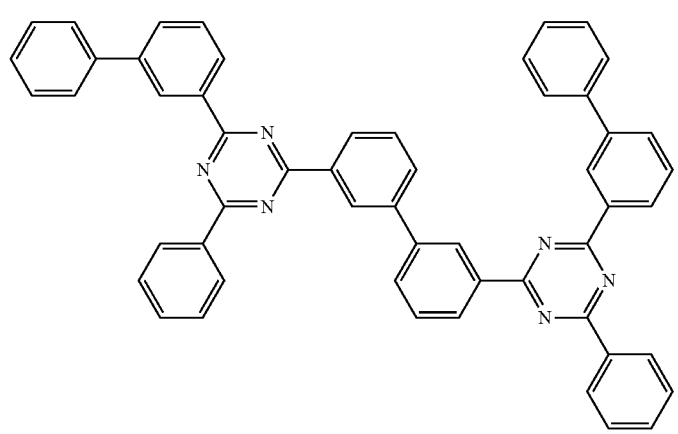
A(22)

-continued
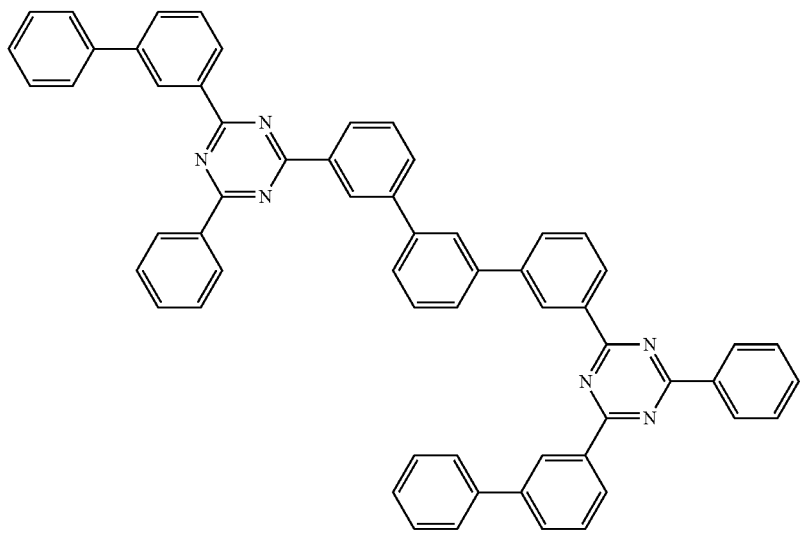
A(23)
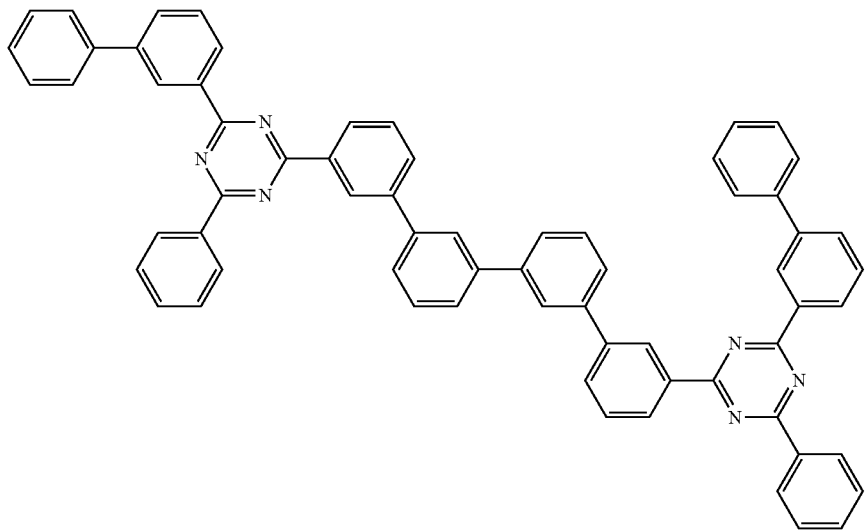
A(24)
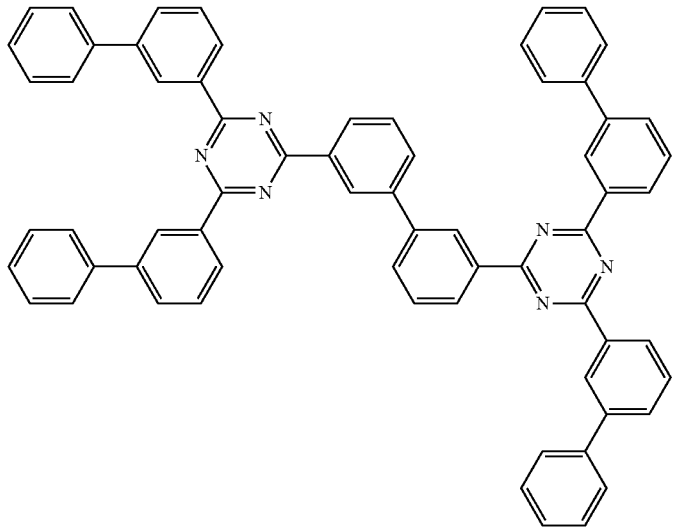
A(25)

-continued
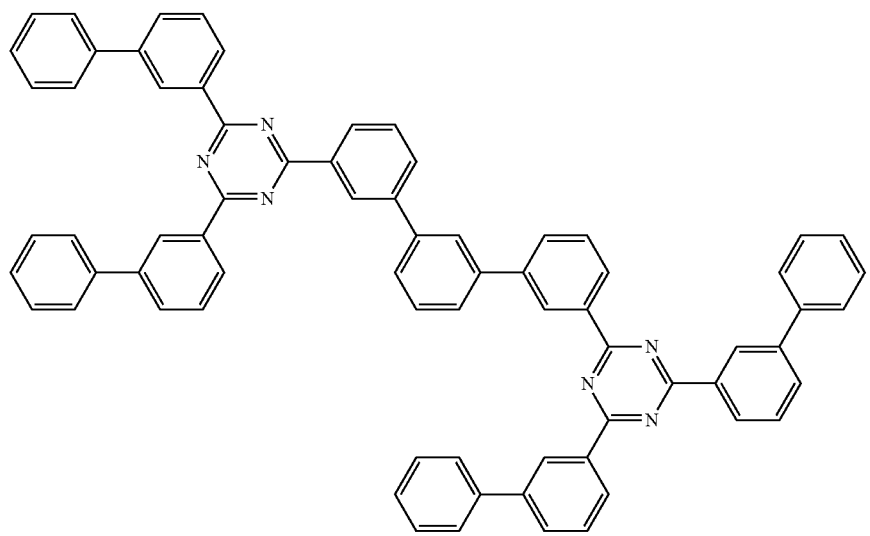
A(26)
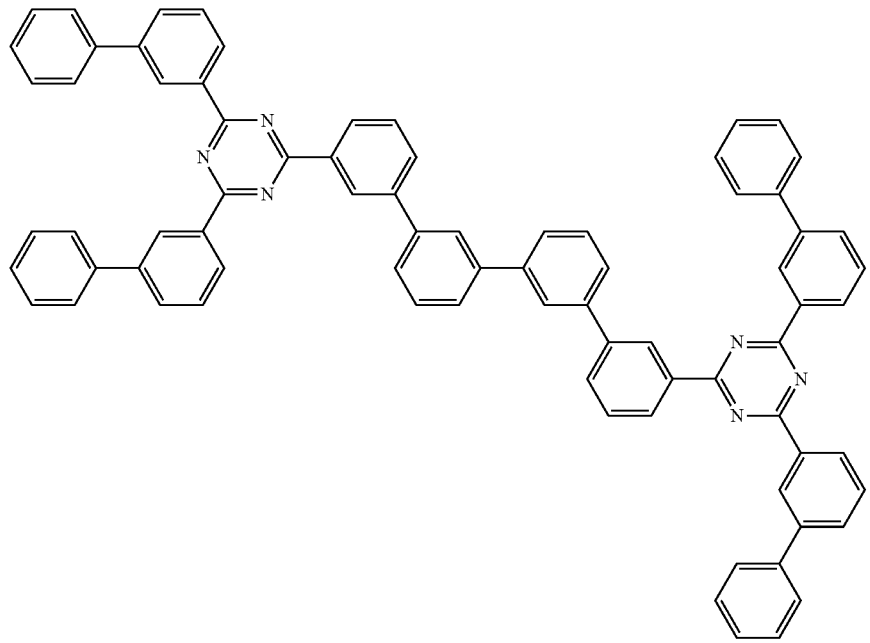
A(27)
A(28) A(29)
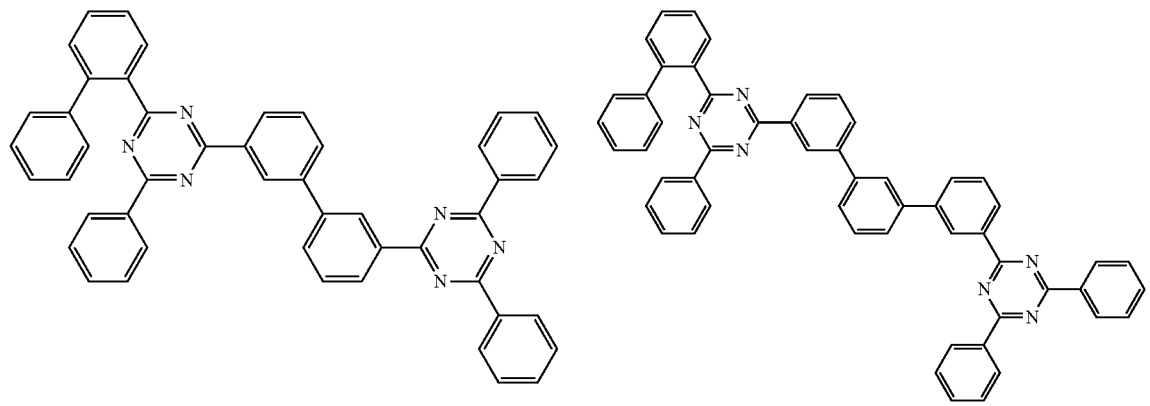

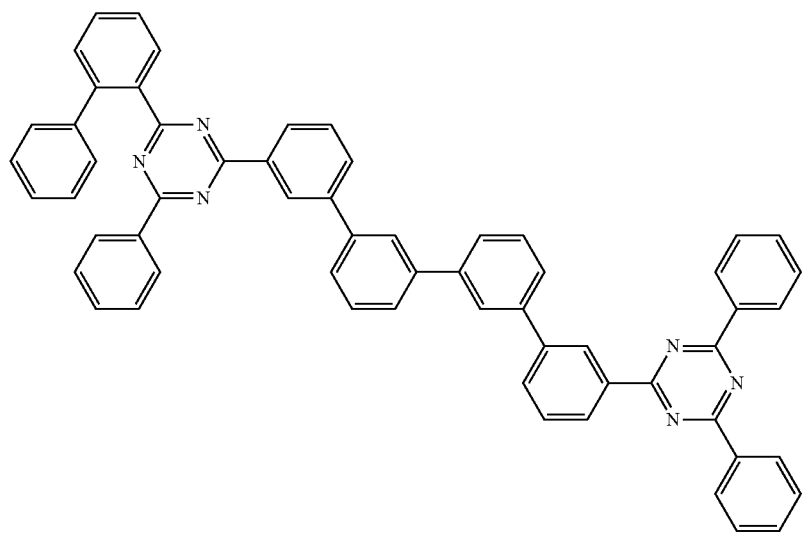
A(30)
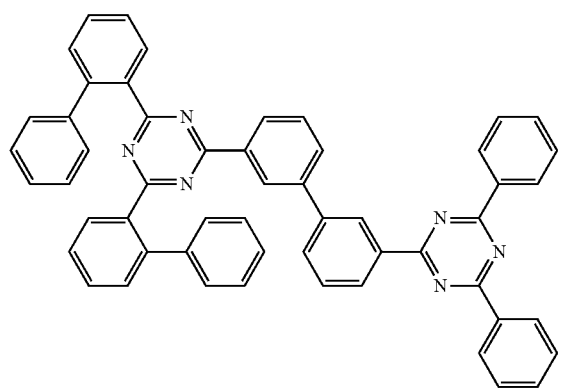
A(31)
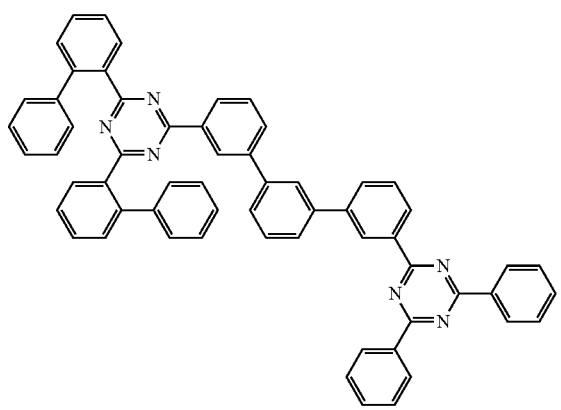
A(32)
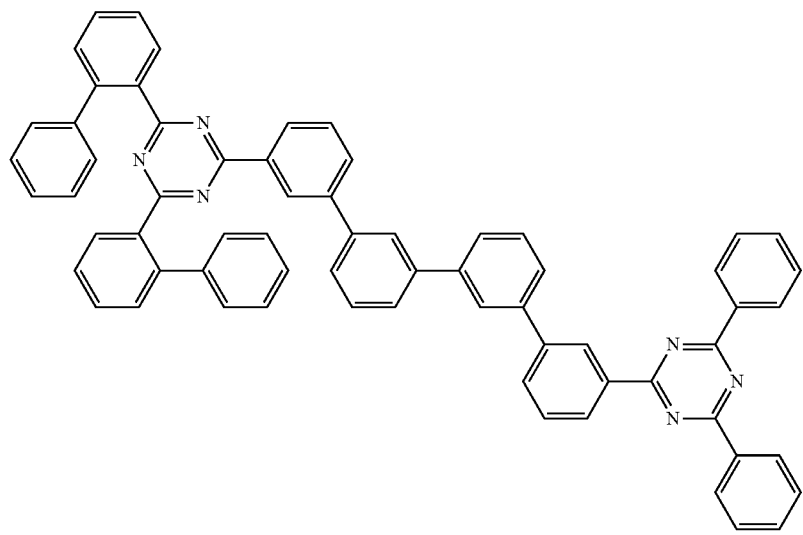
A(33)

-continued
A(34)
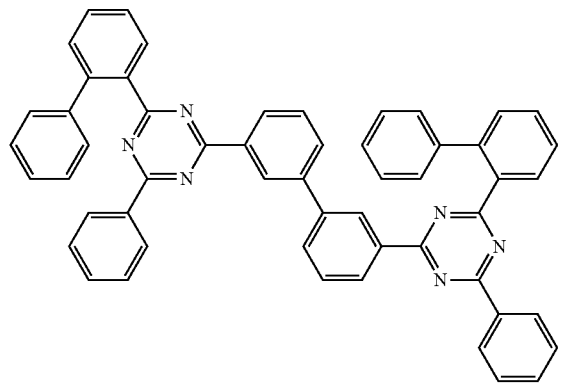
A(35)
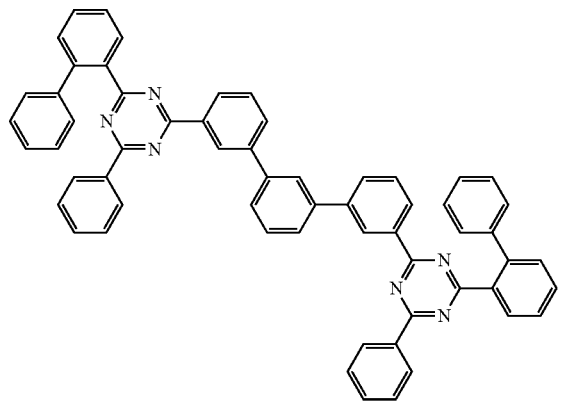
A(36)
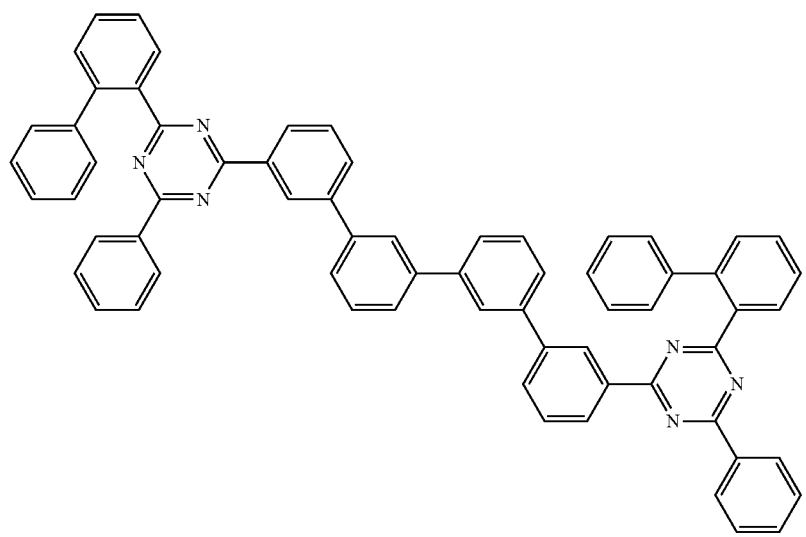
A(37)
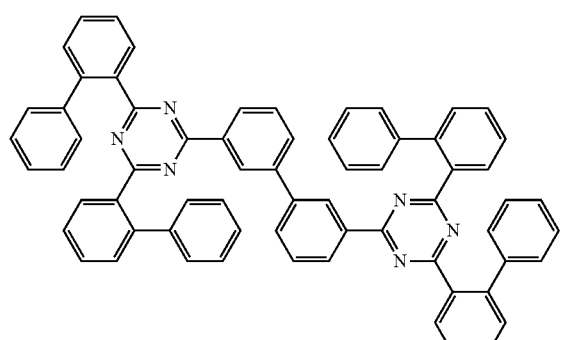
A(38)
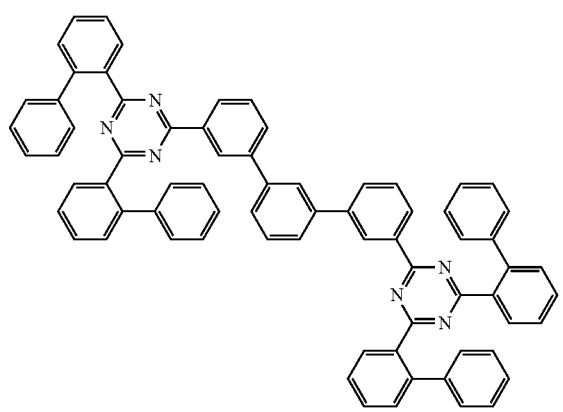

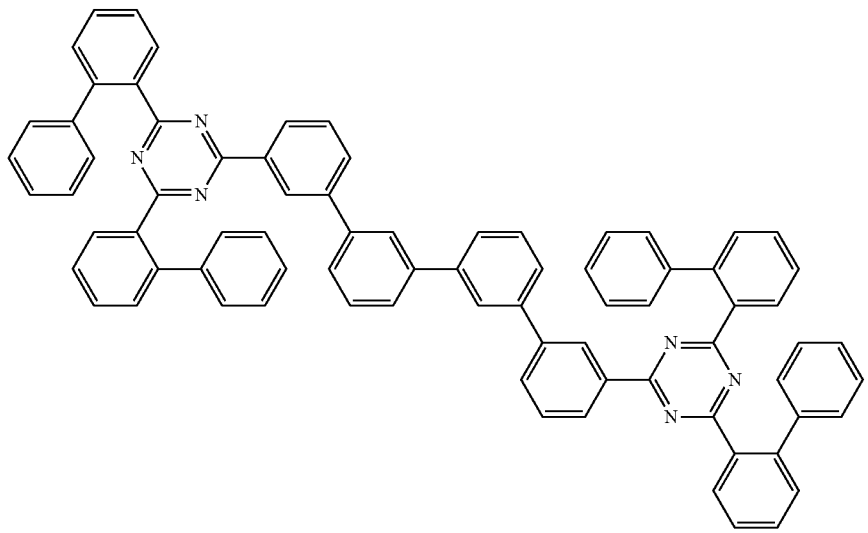
A(39)
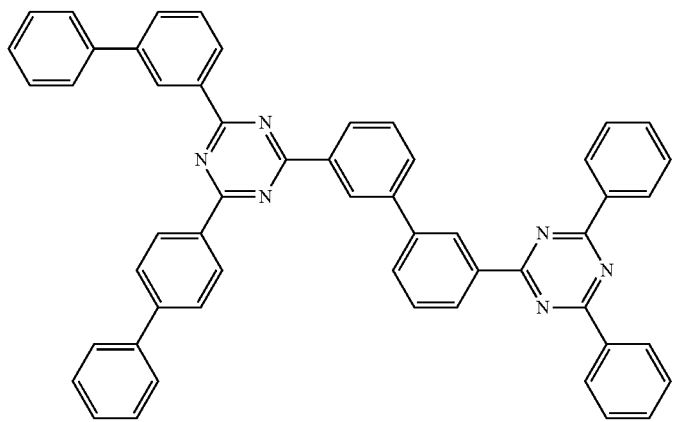
A(40)
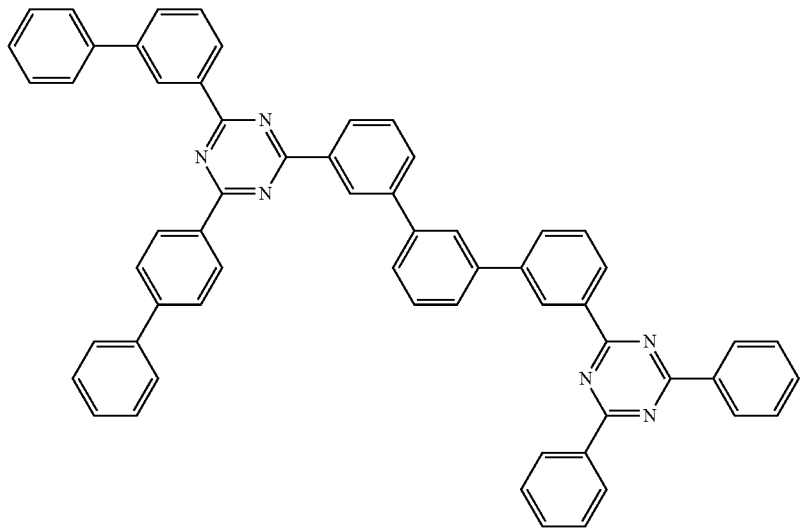
A(41)

-continued
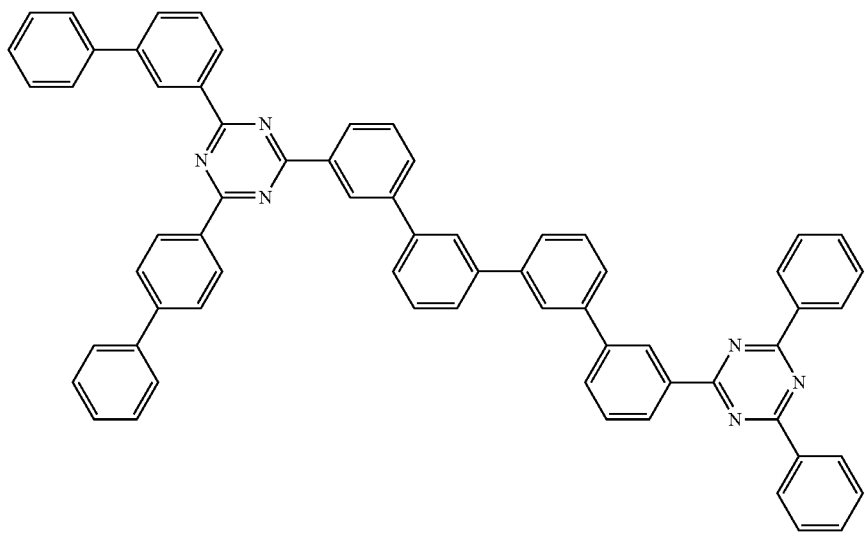
A(42)
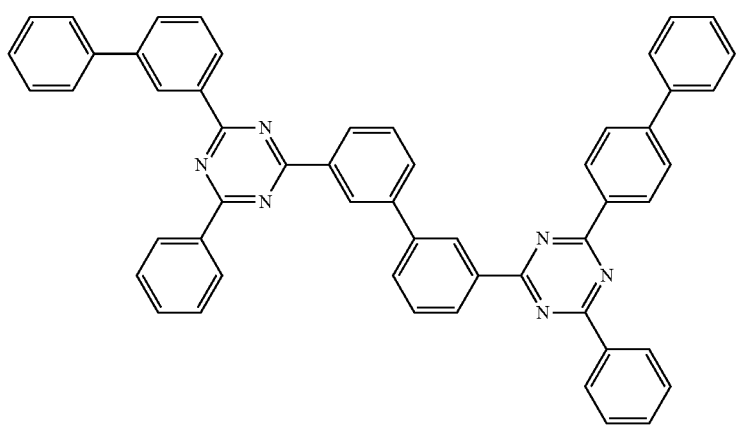
A(43)
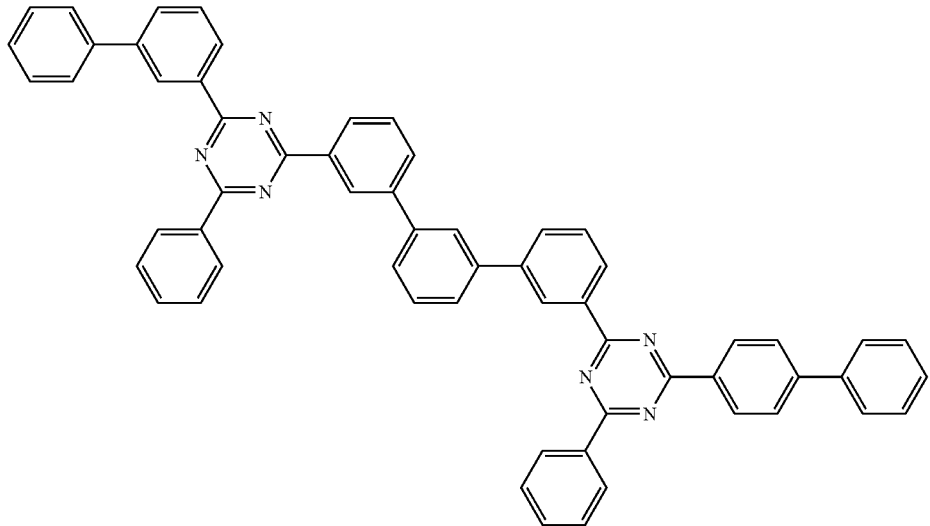
A(44)

-continued
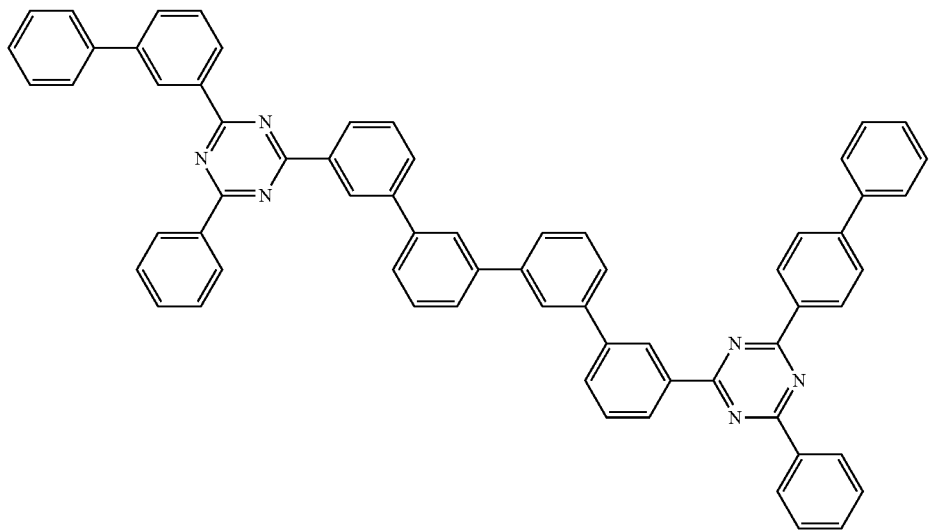
A(45)
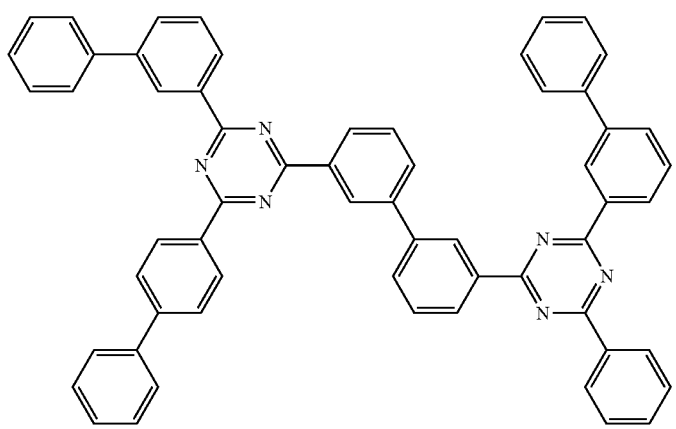
A(46)
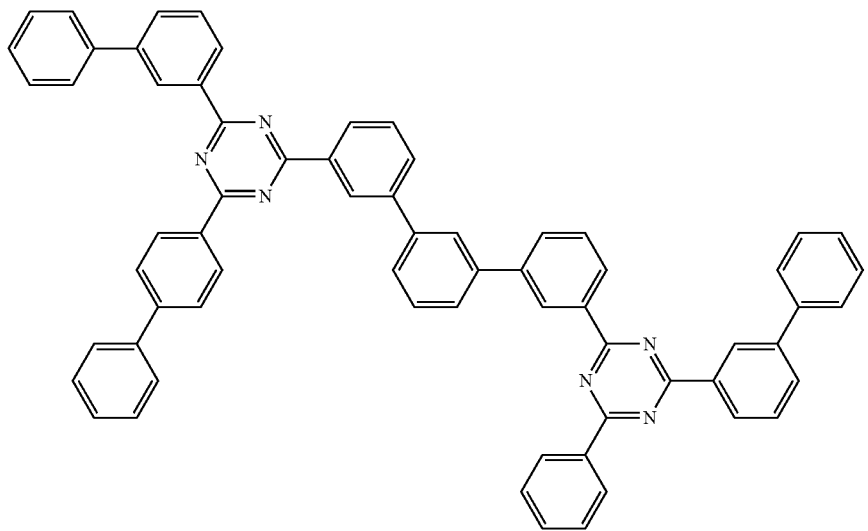
A(47)

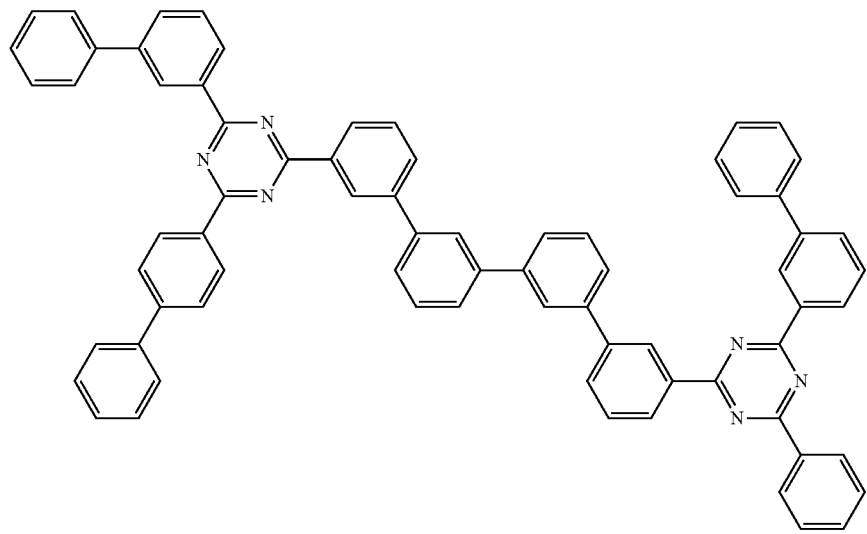
A(48)
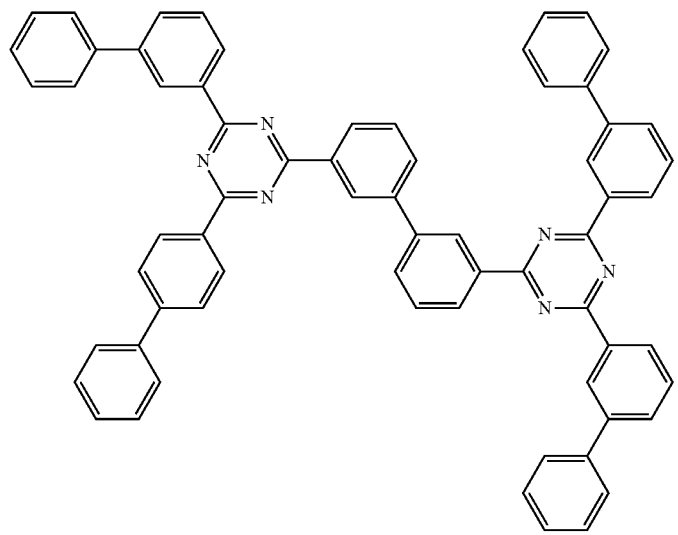
A(49)
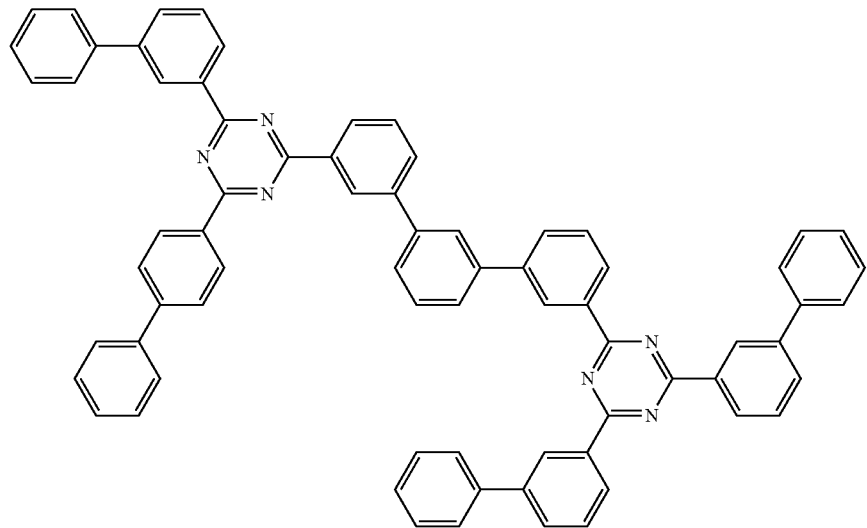
A(50)

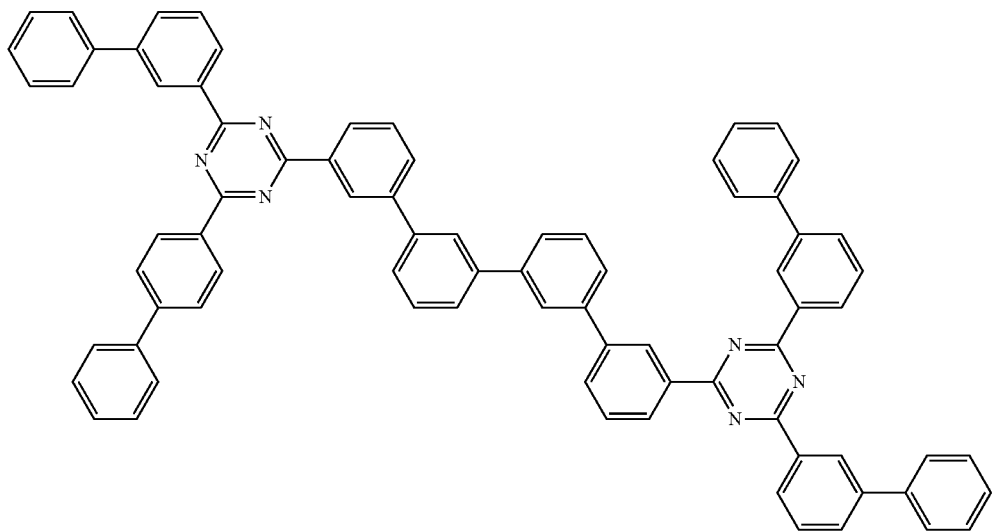
A(51)
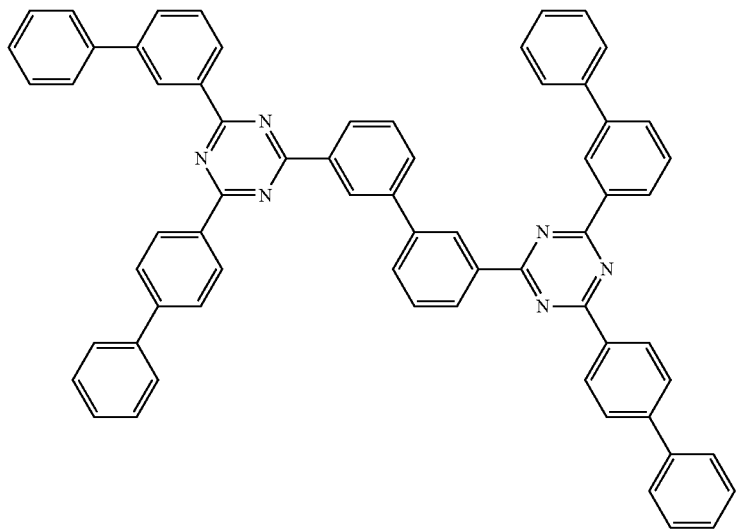
A(52)

-continued
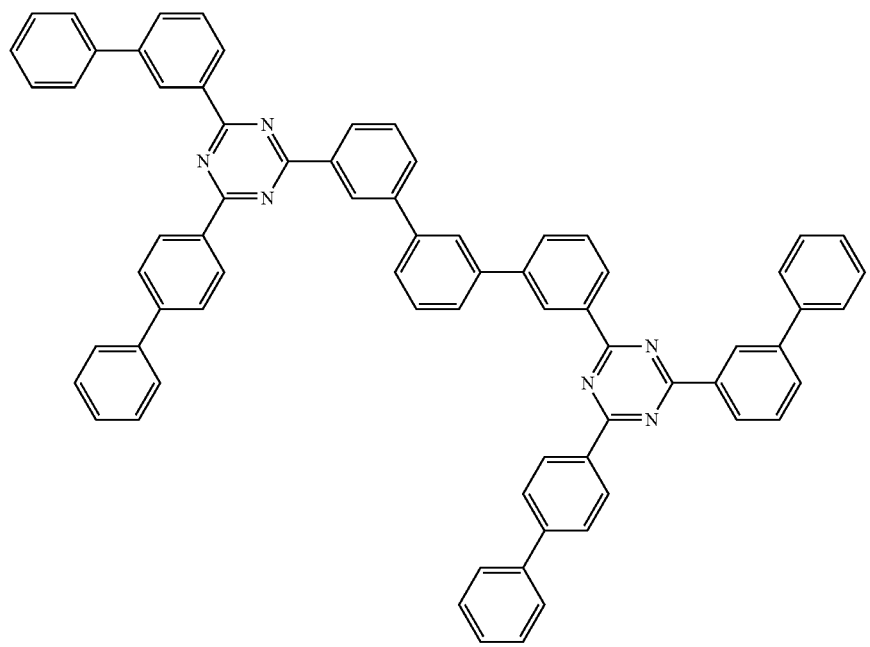
A(53)
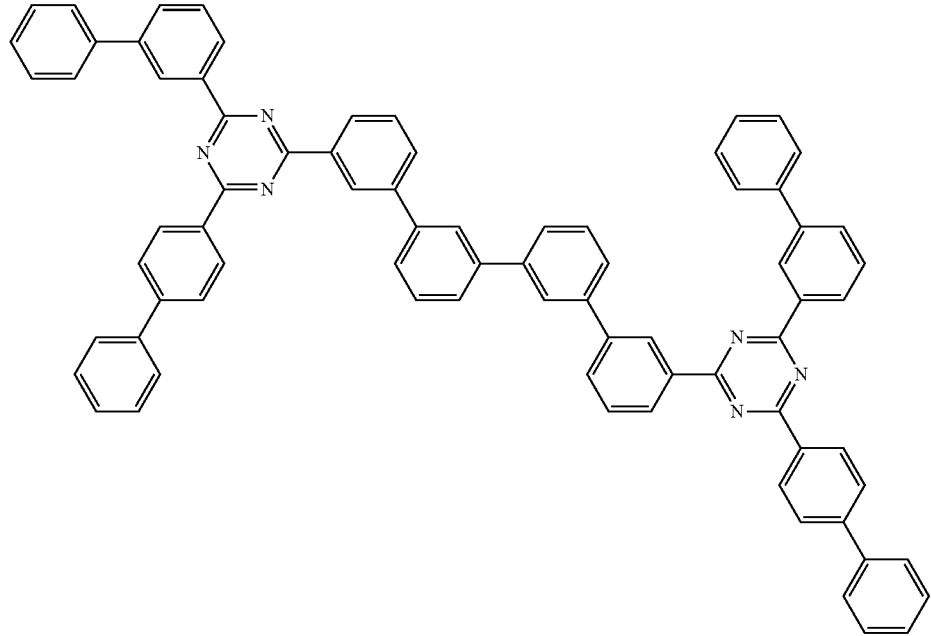
A(54)

-continued
A(55)
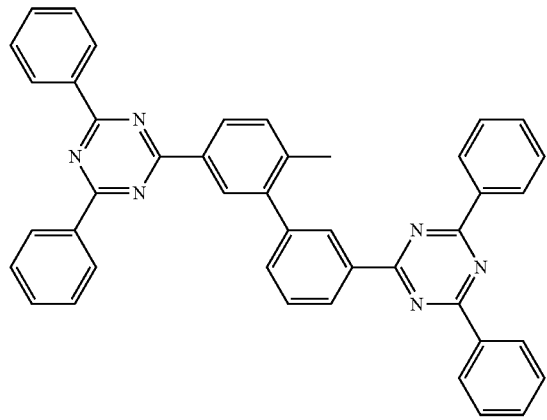
A(56)
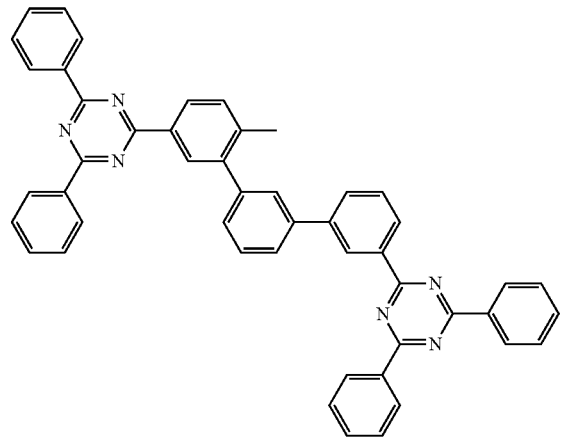
A(57)
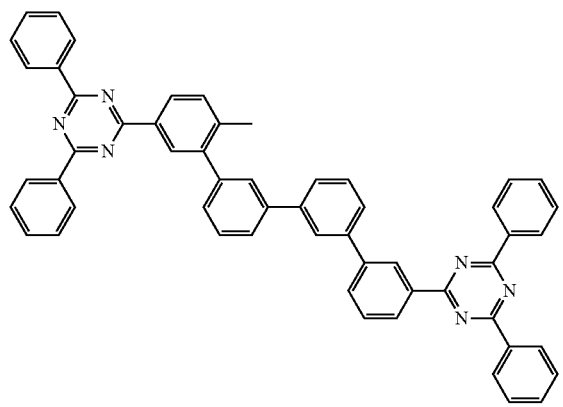
A(58)
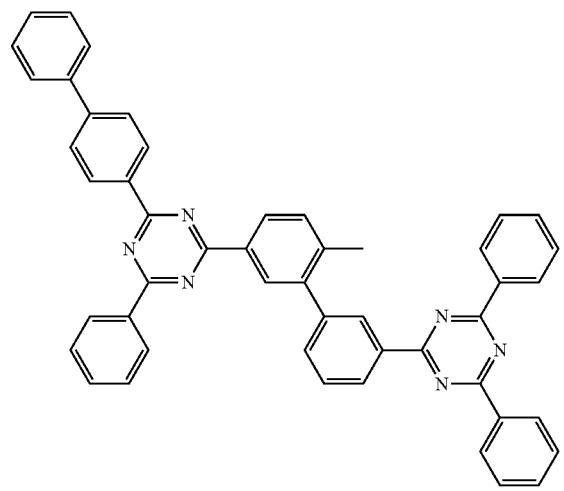
A(59)
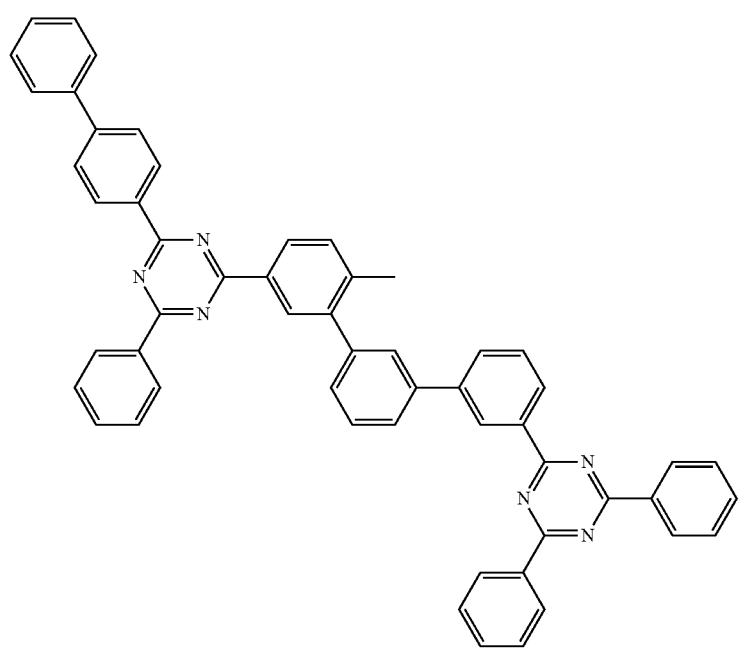

-continued
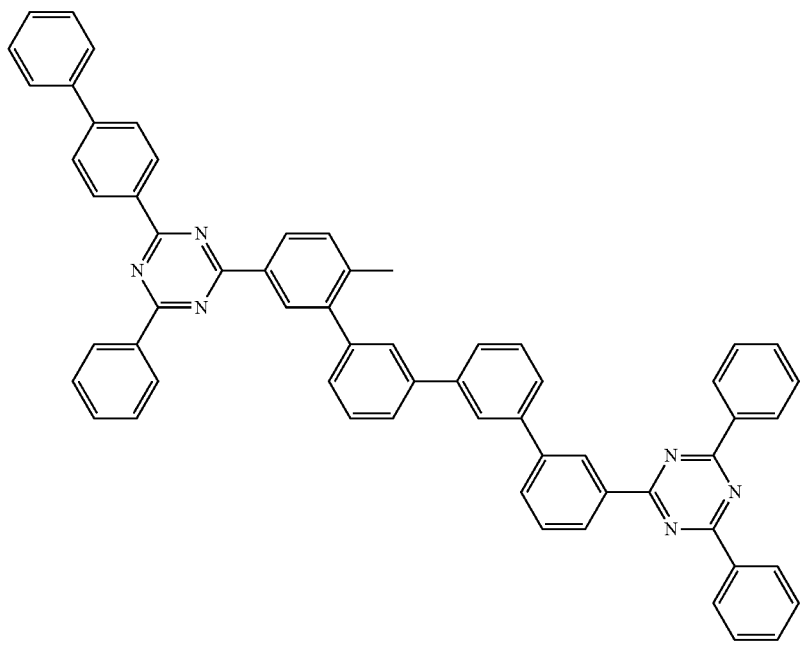
A(60)
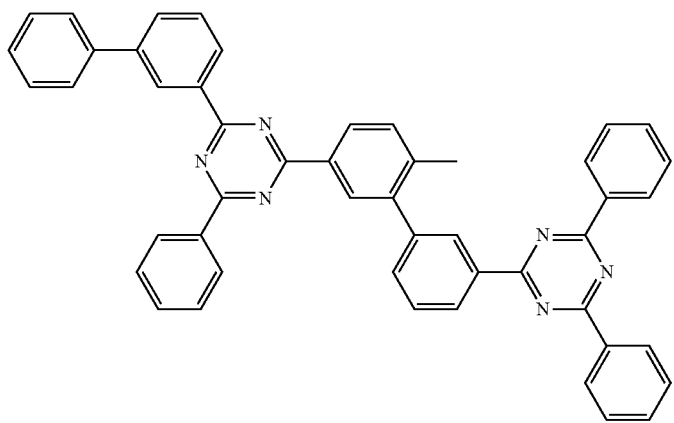
A(61)
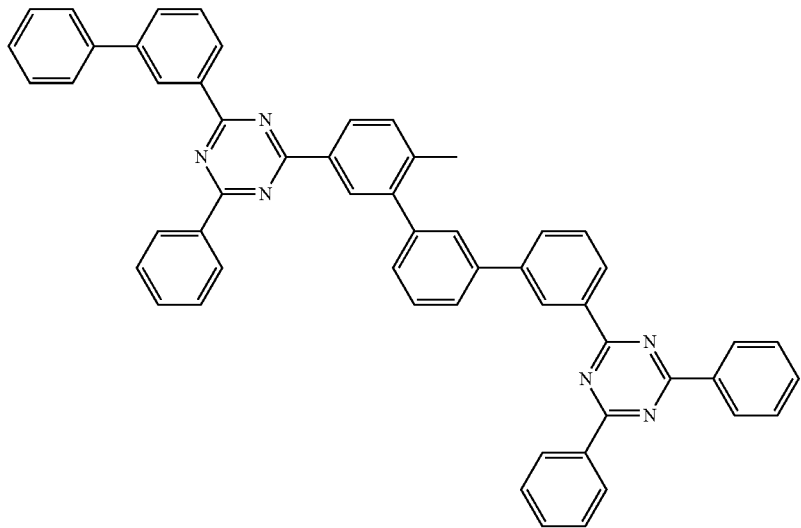
A(62)

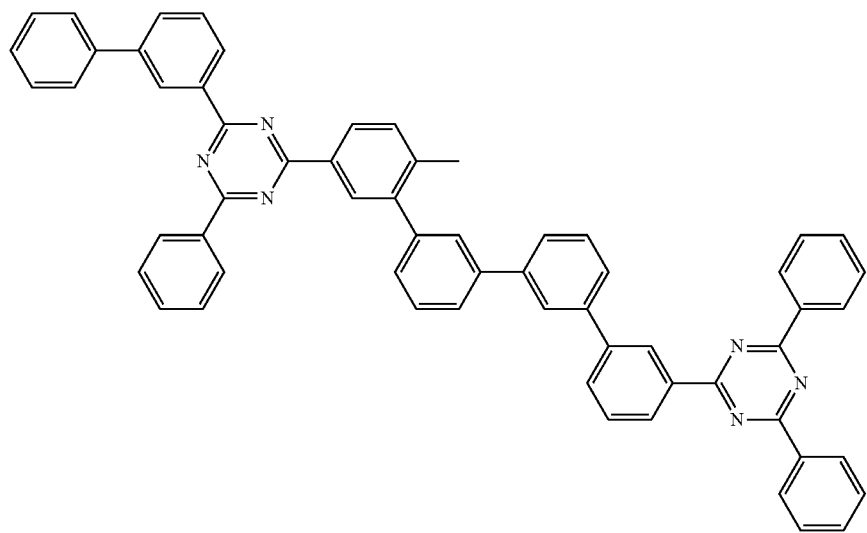
A(63)
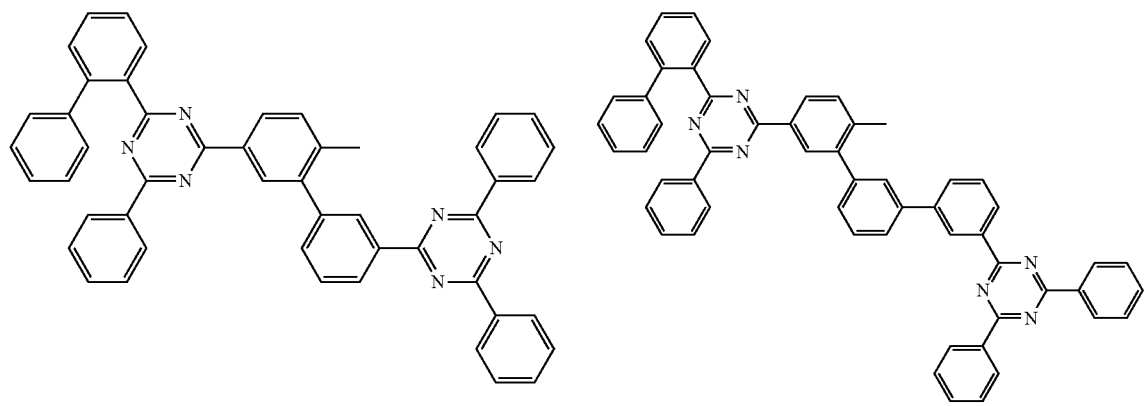
A(64) A(65)
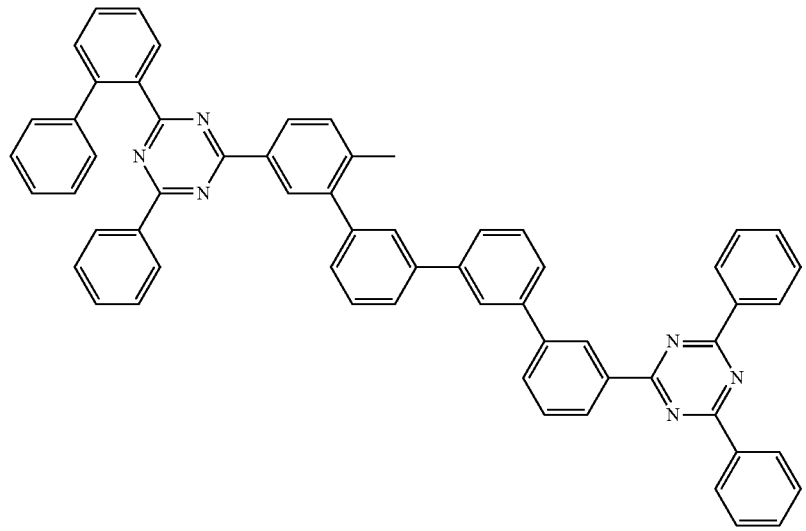
A(66)

-continued
A(67)
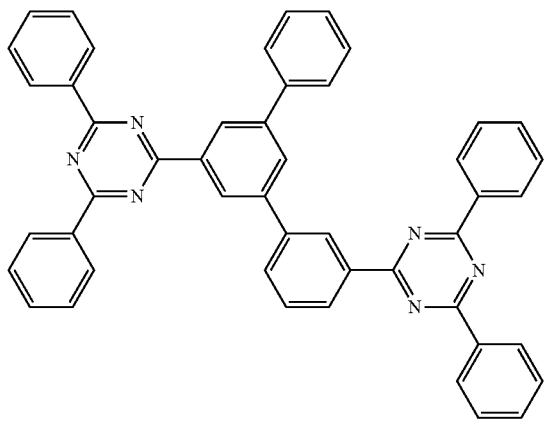
A(68)
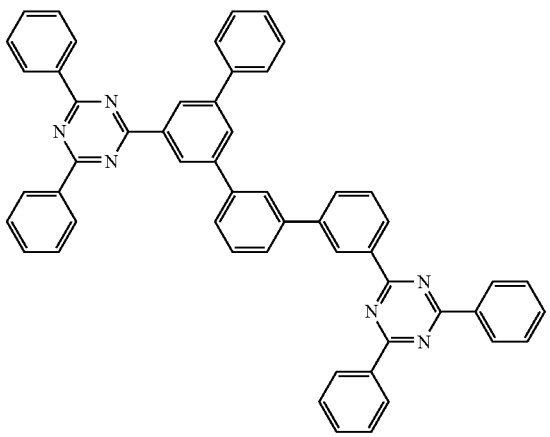
A(69)
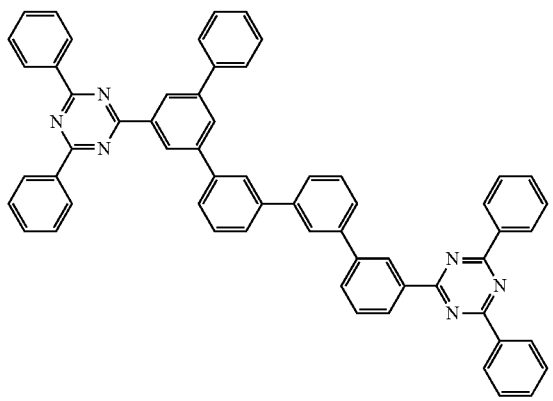
A(70)
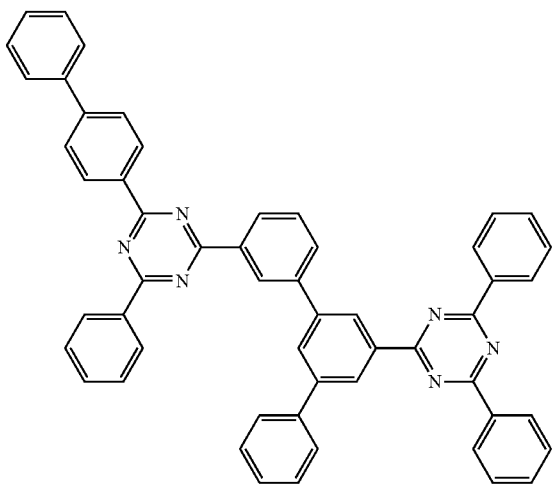
A(71)
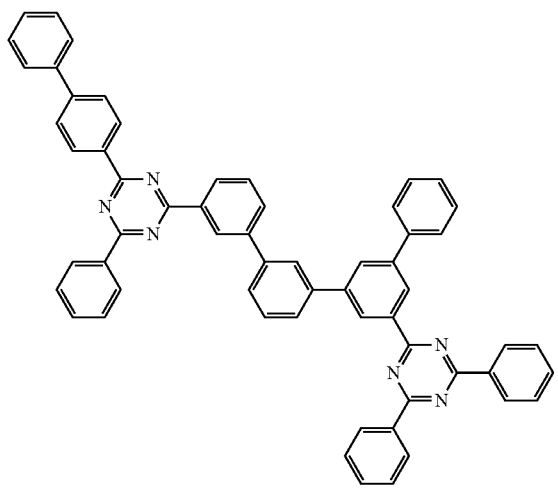

A(72)
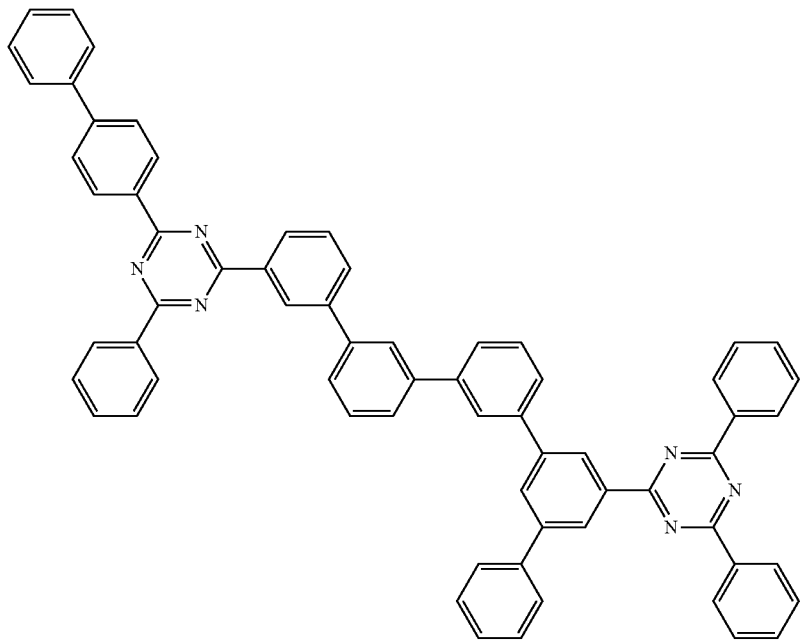
A(73)
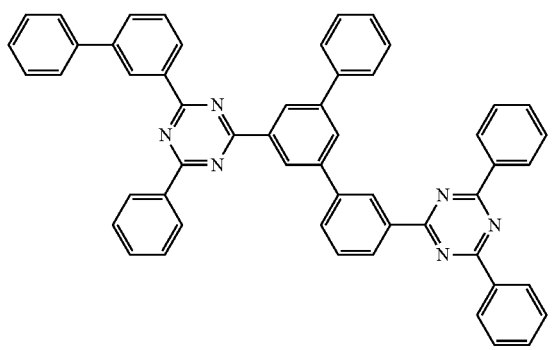
A(74)
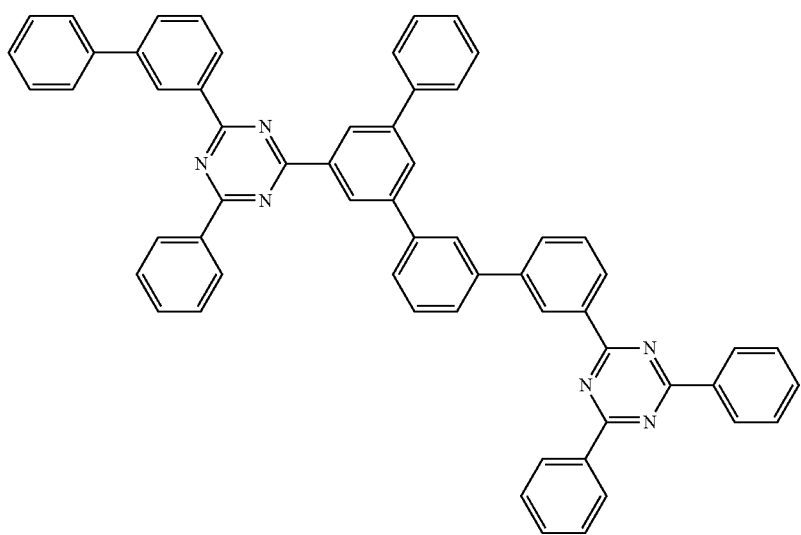

-continued
A(75)
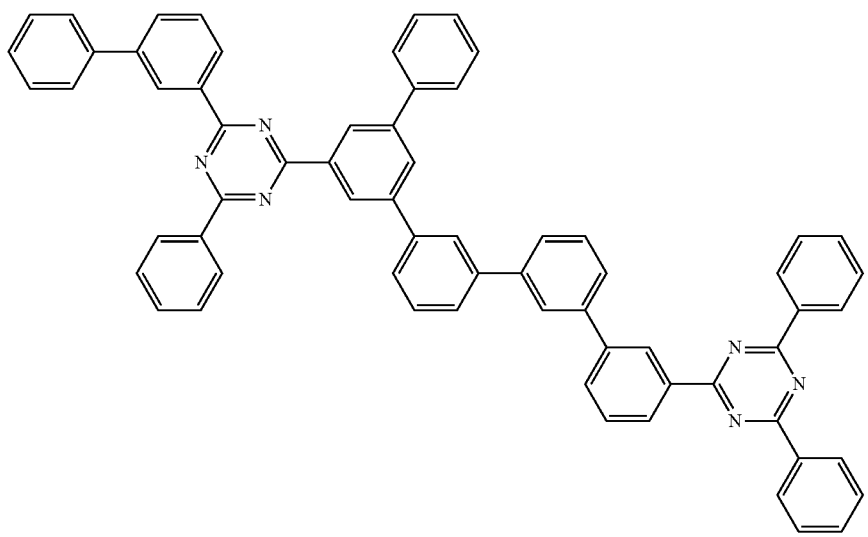
A(76)
A(77)
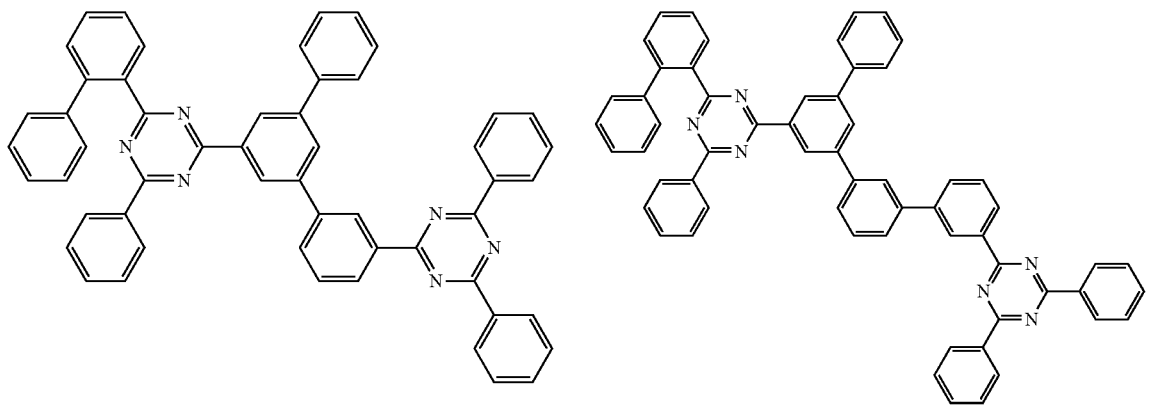
A(78)
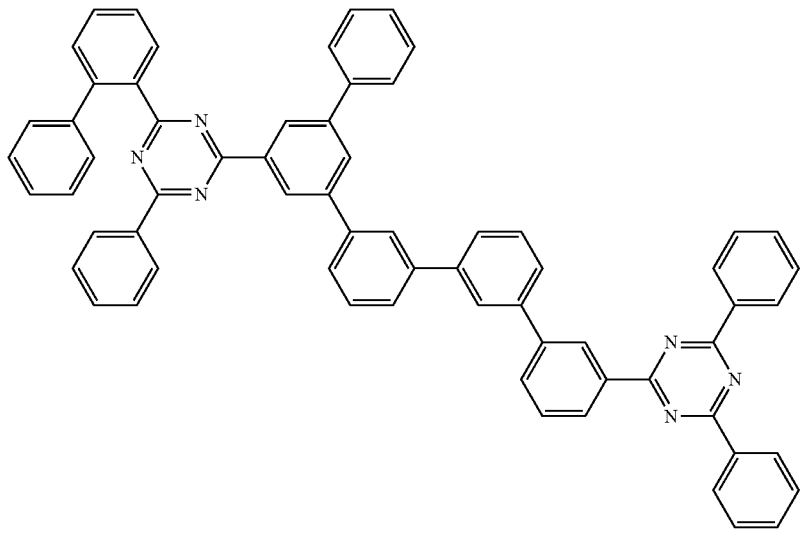

-continued
A(79)
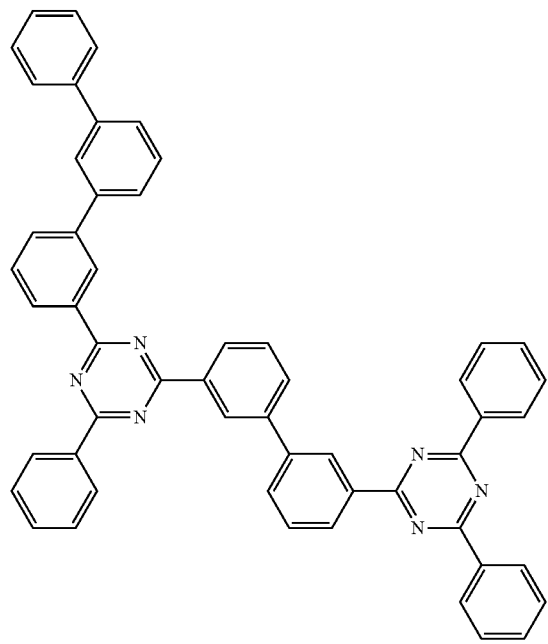
A(80)
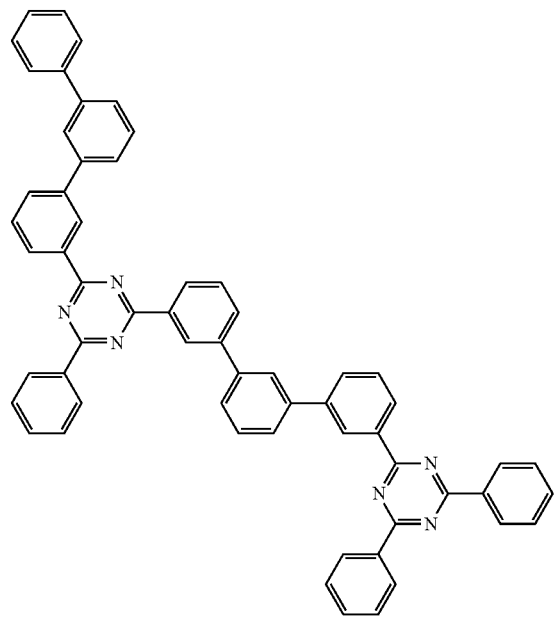
A(81)
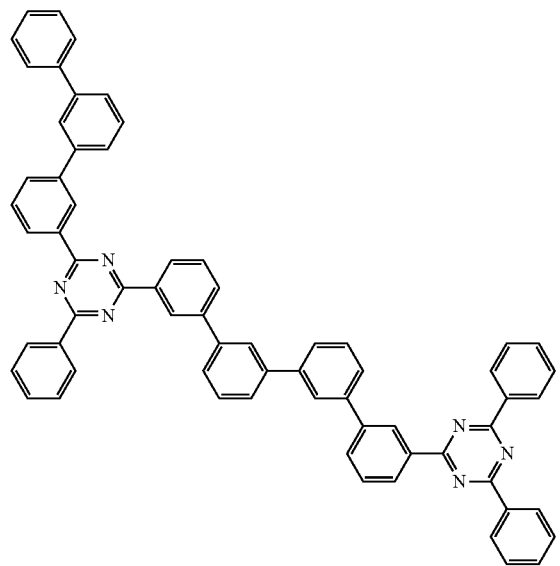
A(82)
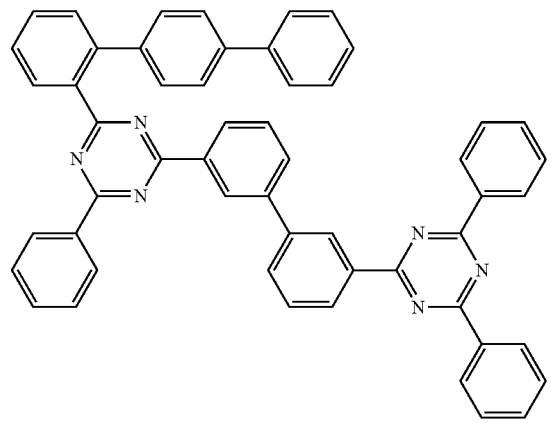

-continued
A(83)
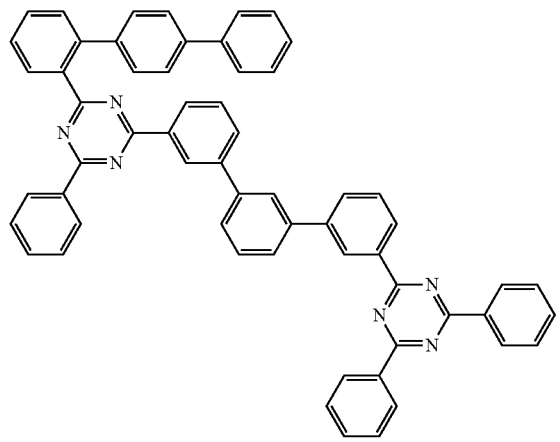
A(84)
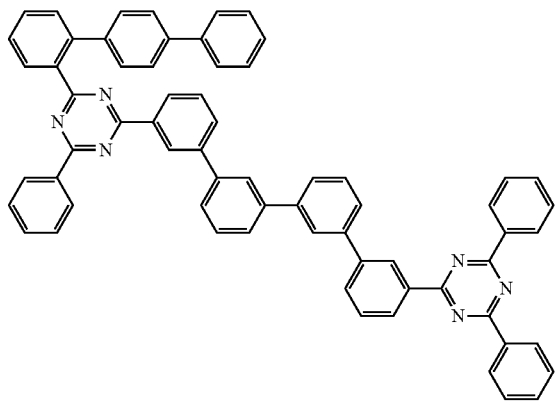
A(85)
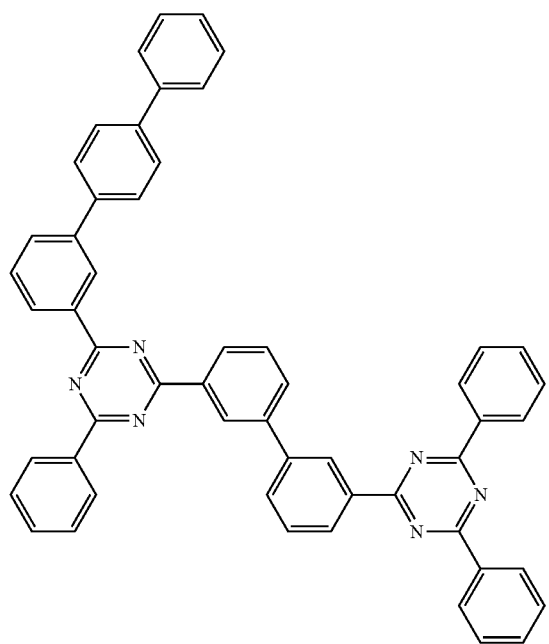
A(86)
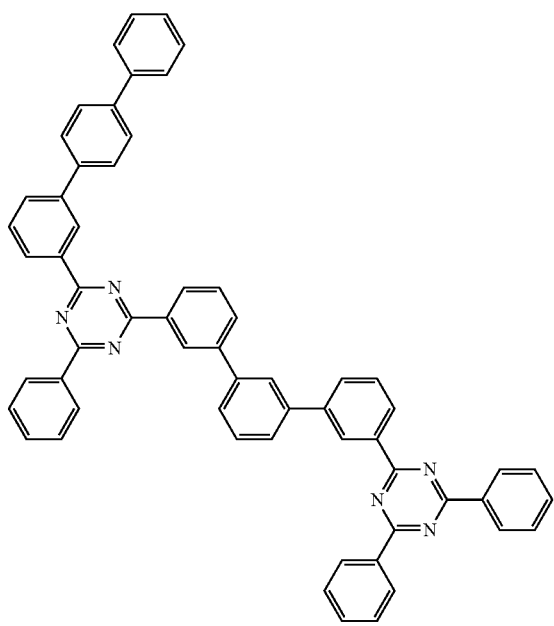

-continued
A(87)
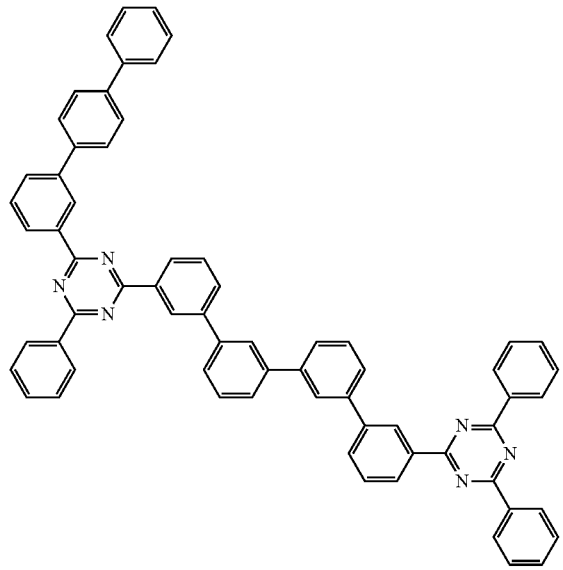
A(89)
A(88)
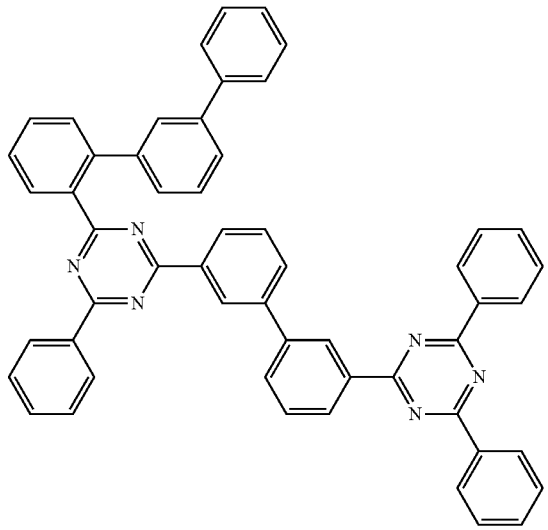
A(90)
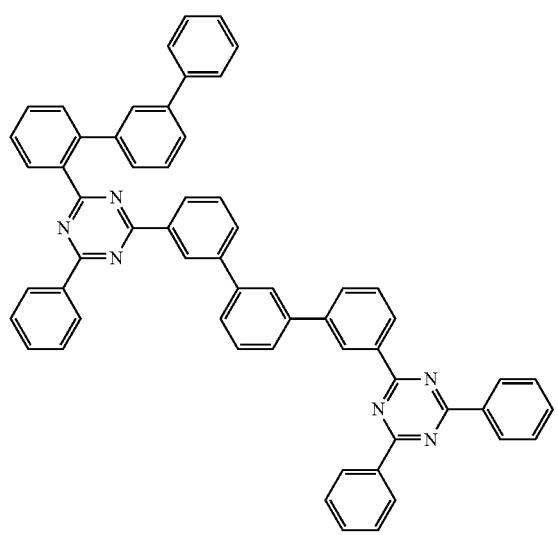
A(91)
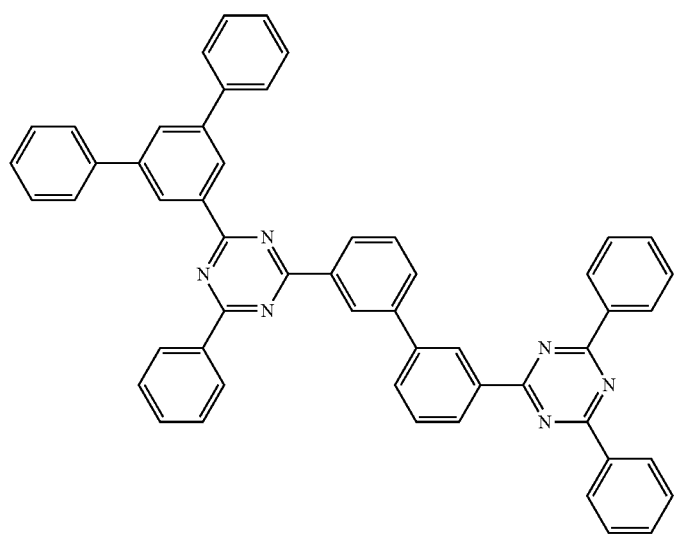

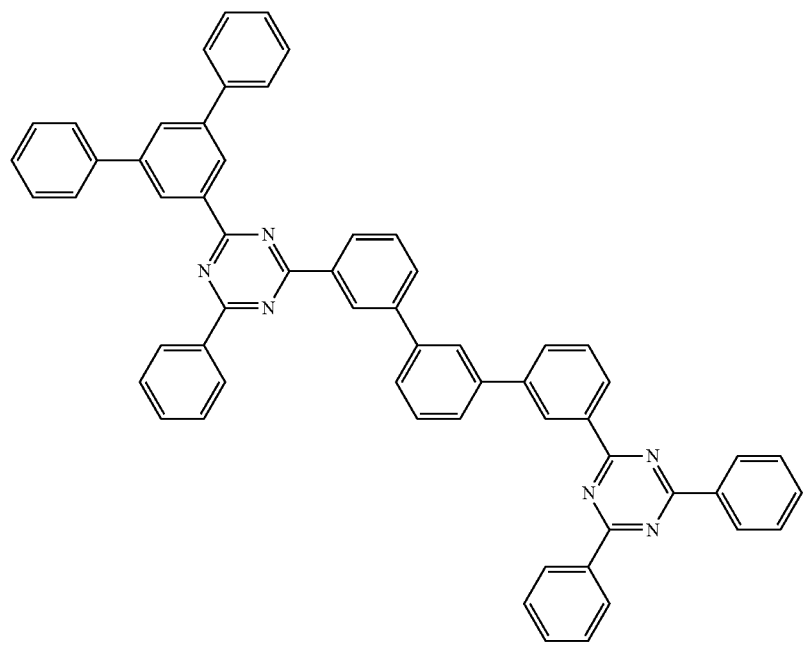
A(92)
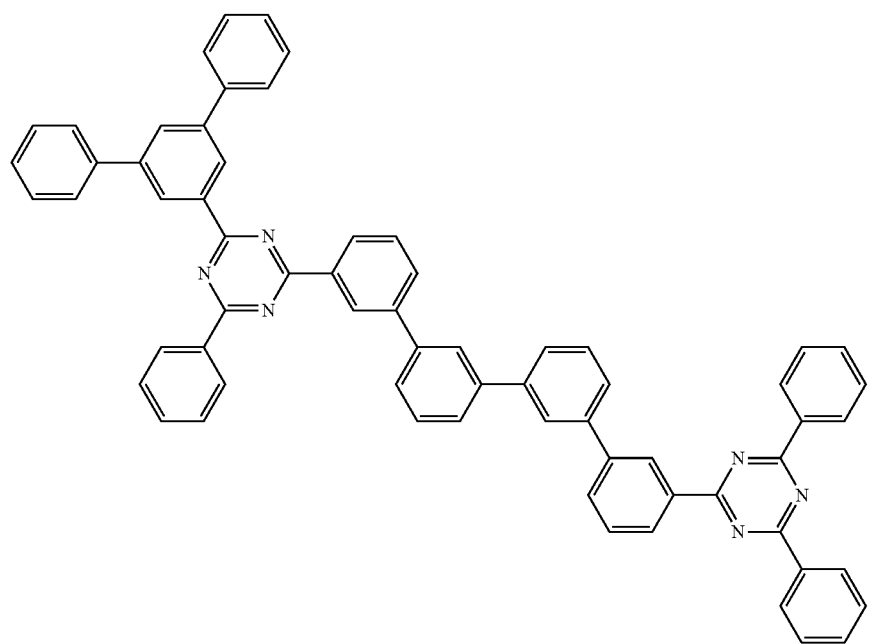
A(93)

-continued
A(94)
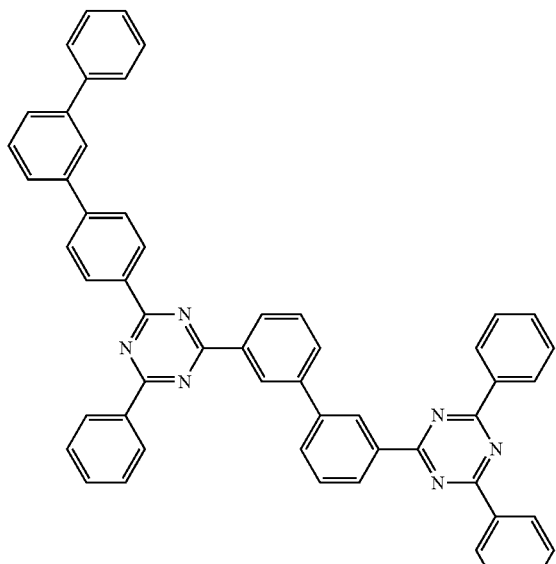
A(95)
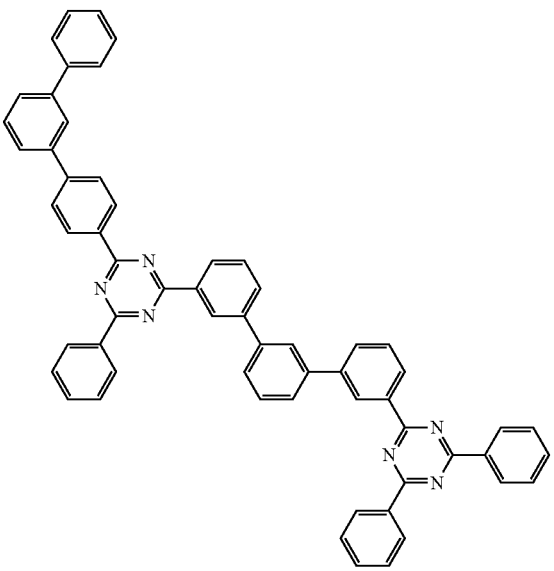
A(96)
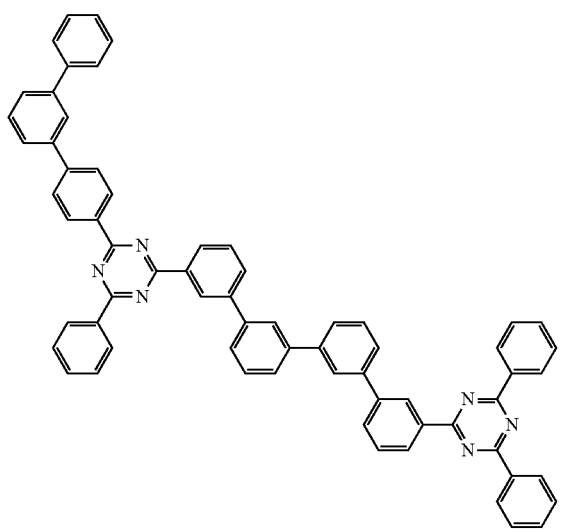
A(97)
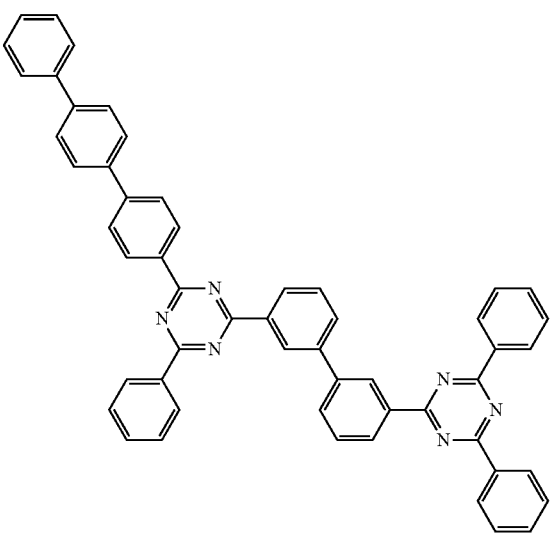
A(98)
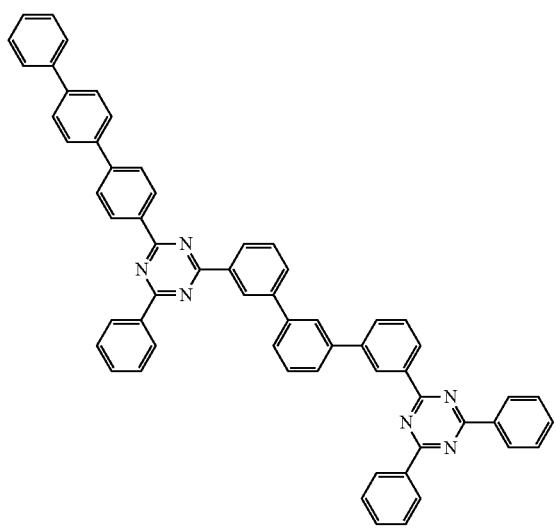

-continued
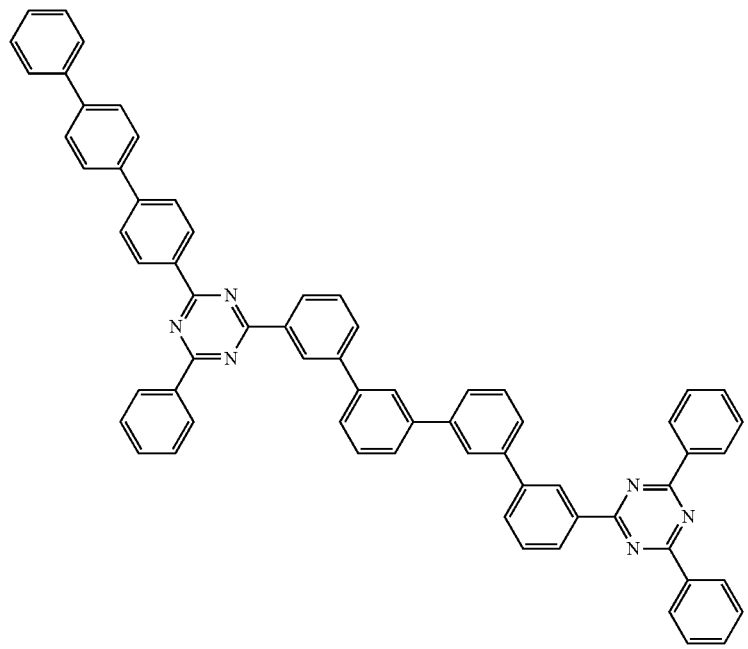
A(99)
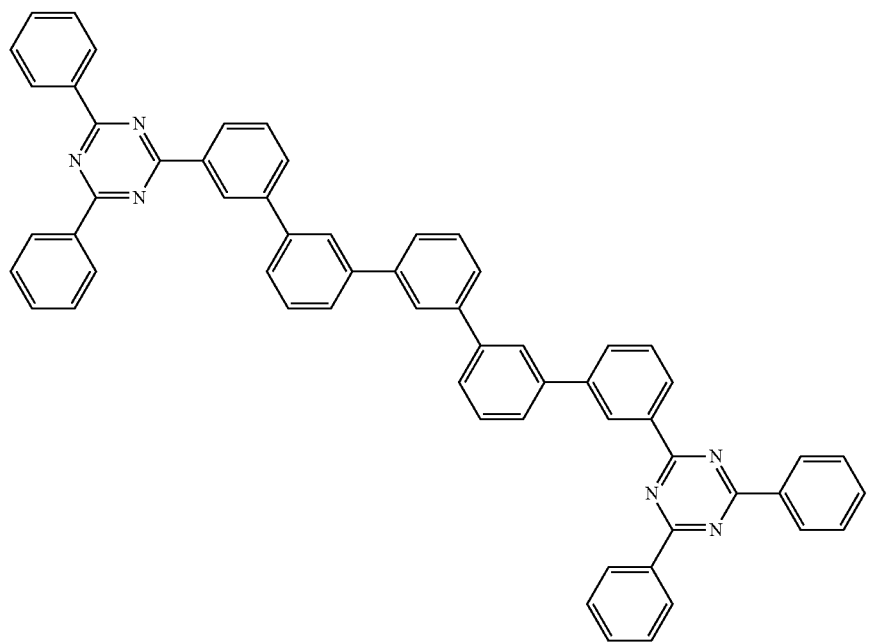
A(100)

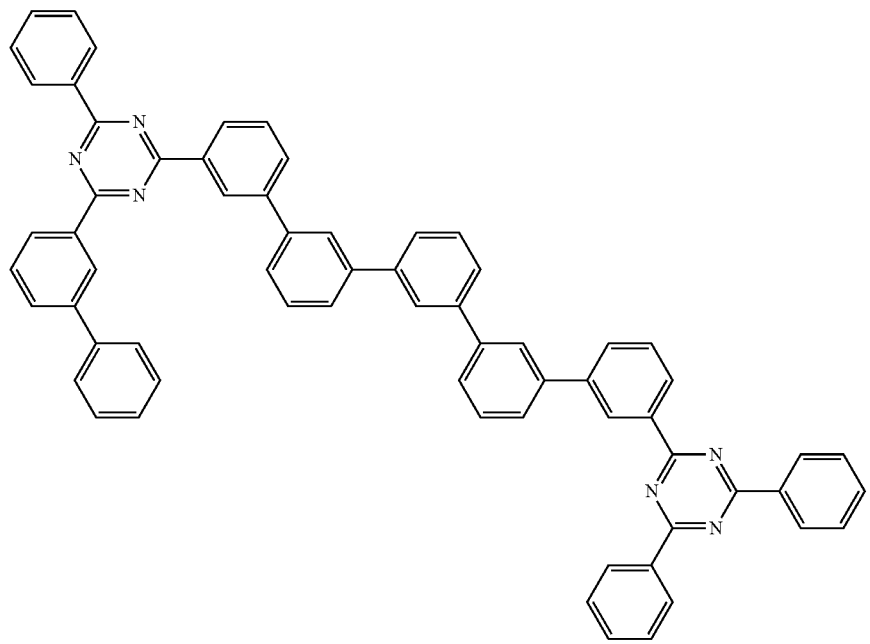
A(101)
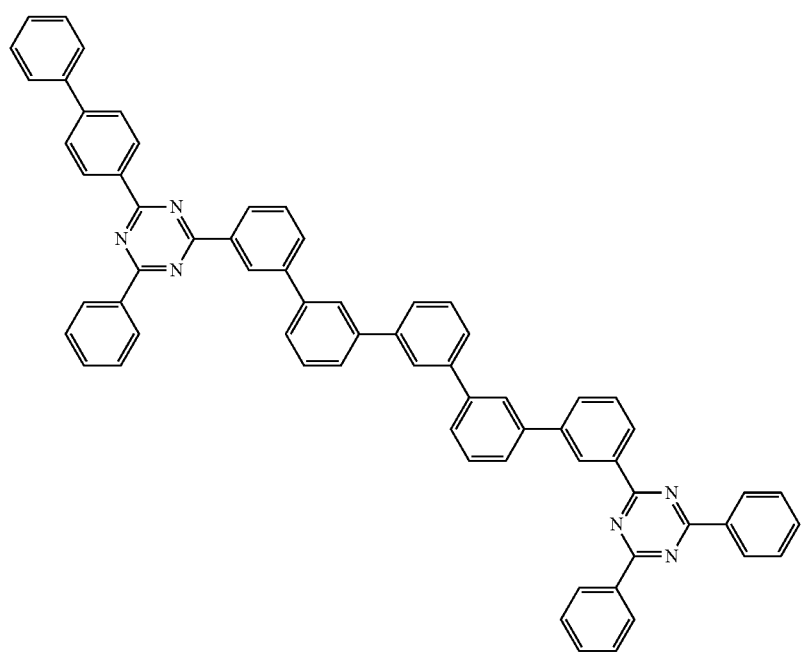
A(102)

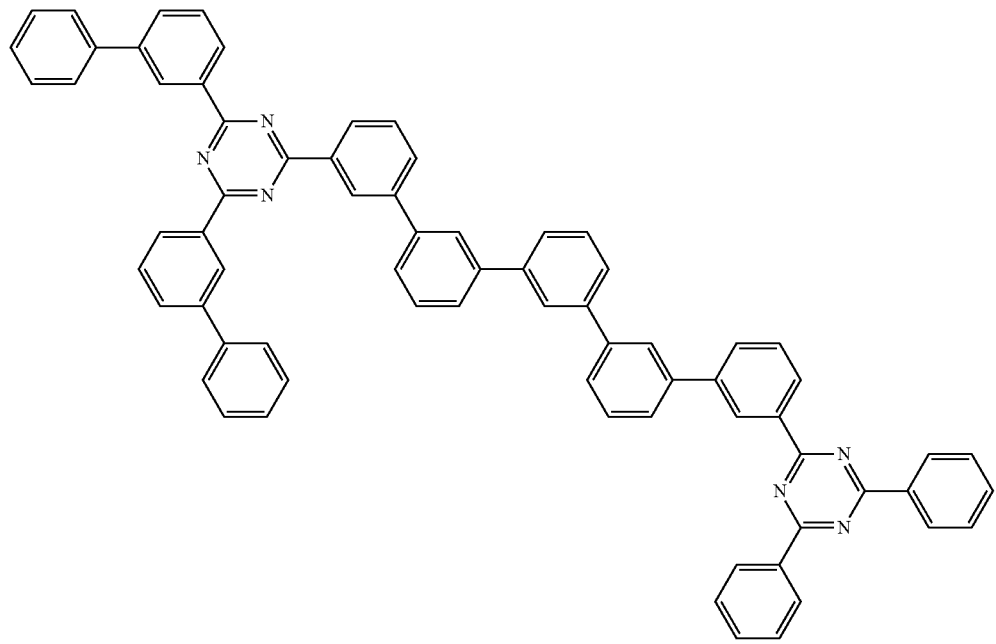
A(103)
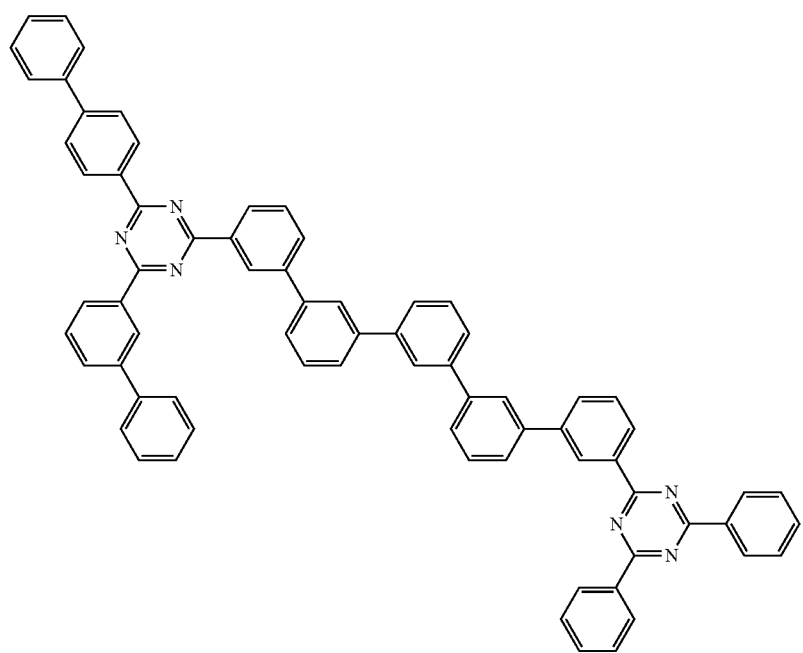
A(104)

-continued
A(105)
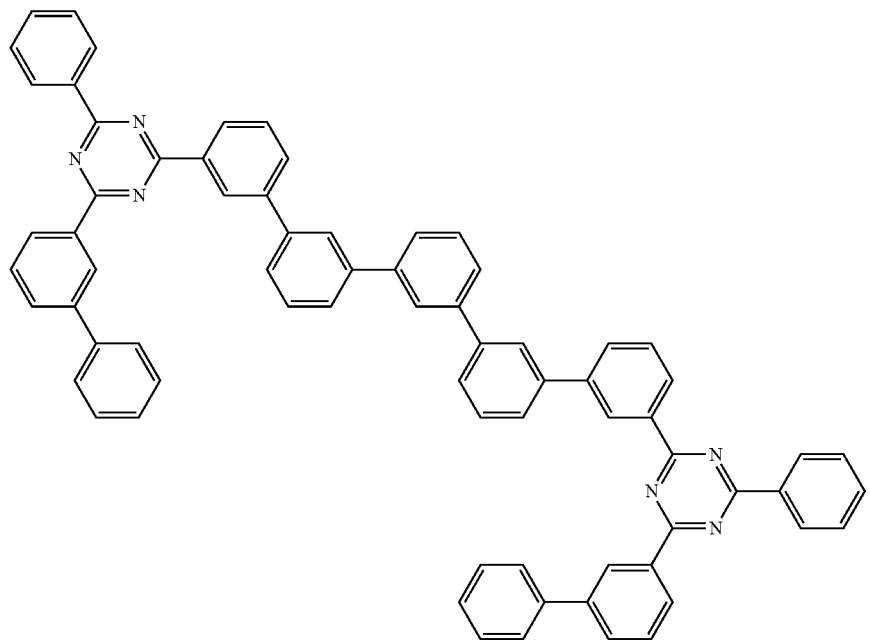
A(106)
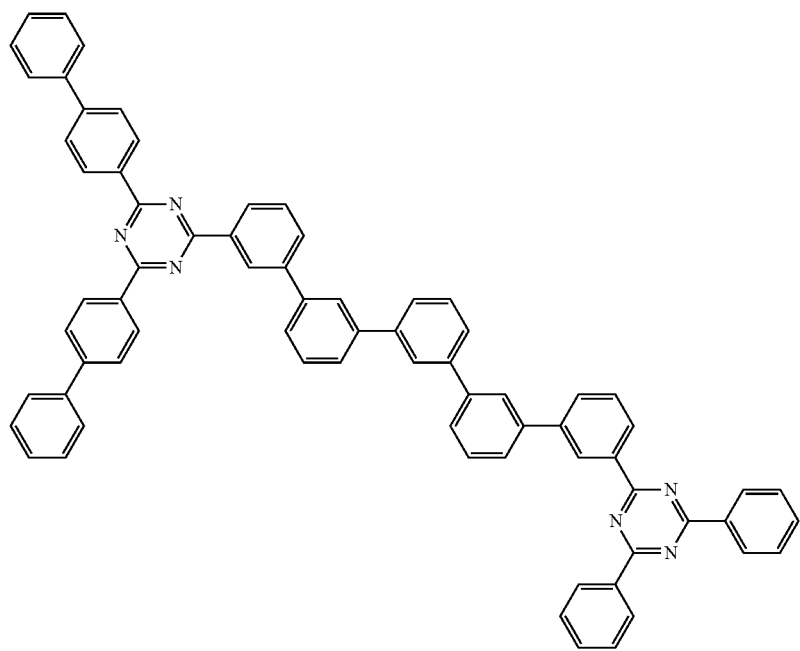

A(107)
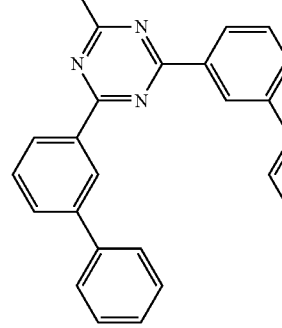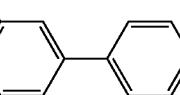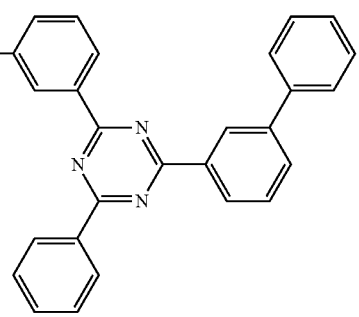
A(108)
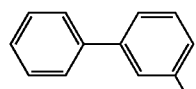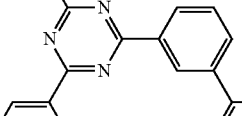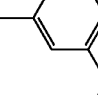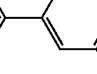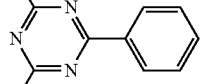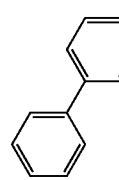

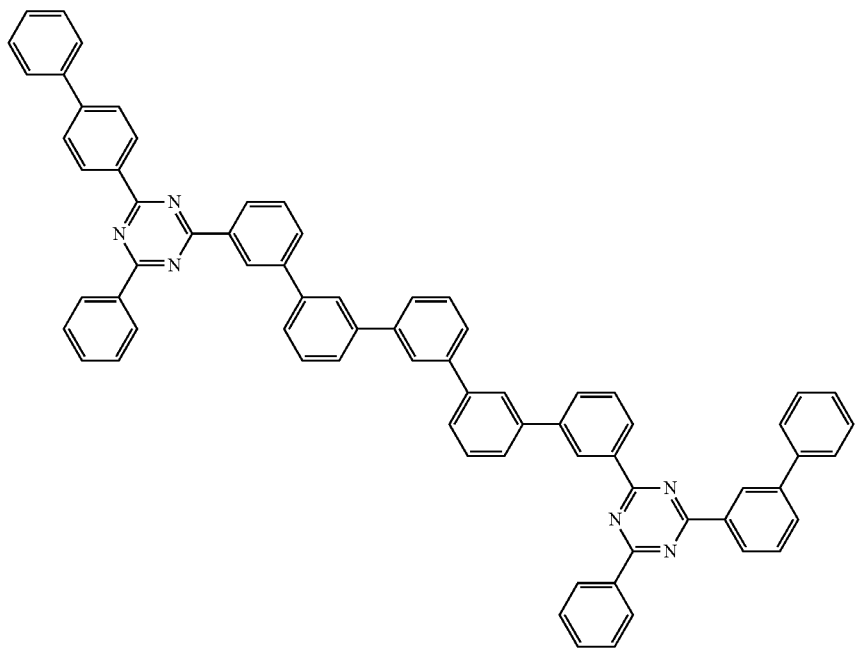
A(109)
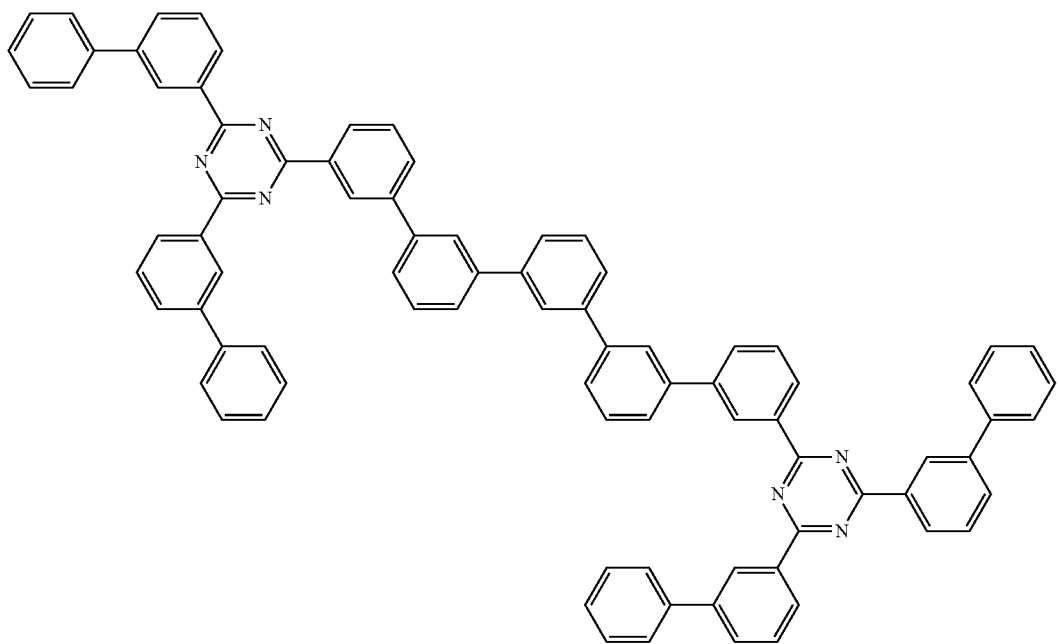
A(110)

-continued
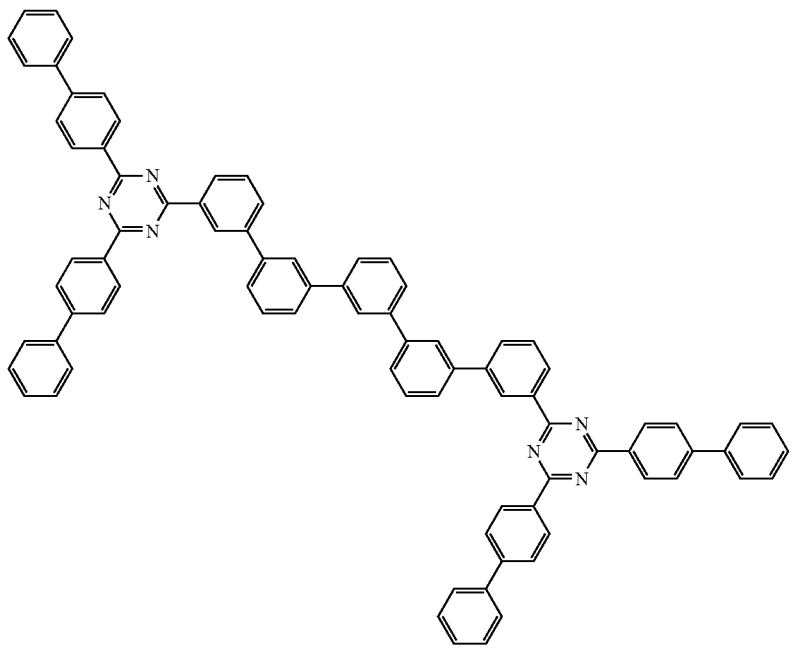
A(111)
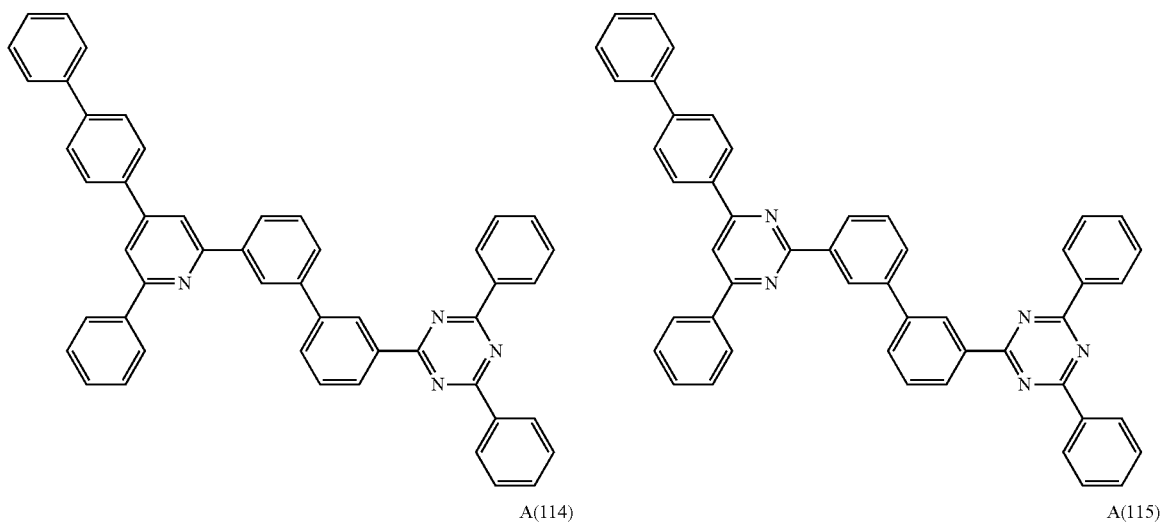
A(112)　　　　A(113)
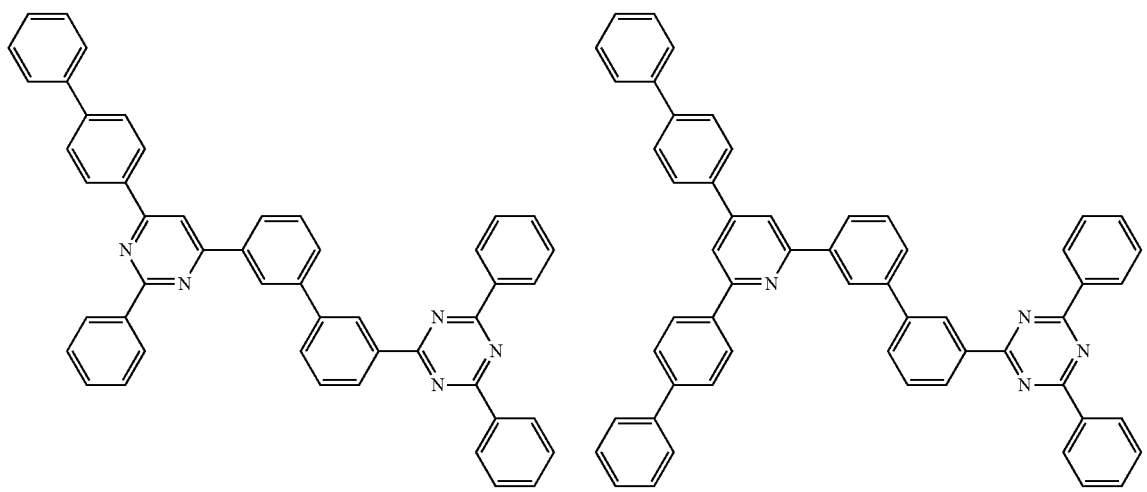
A(114)　　　　A(115)

A(116)
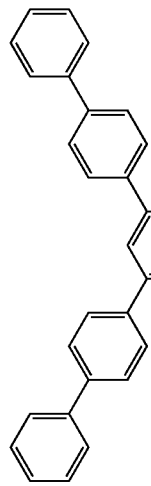
A(117)
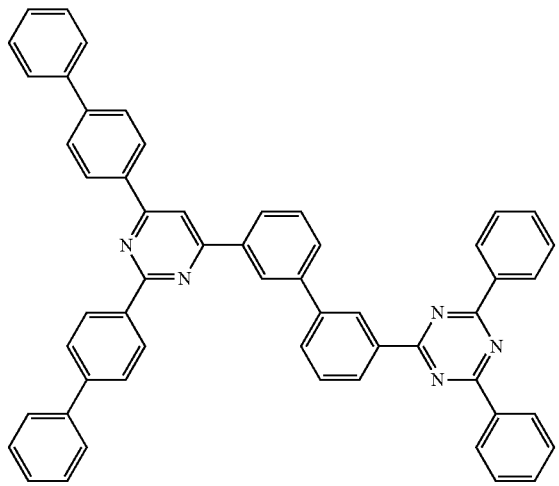
A(118) A(119)
A(120)
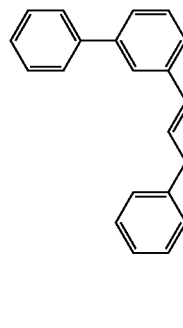
A(121)
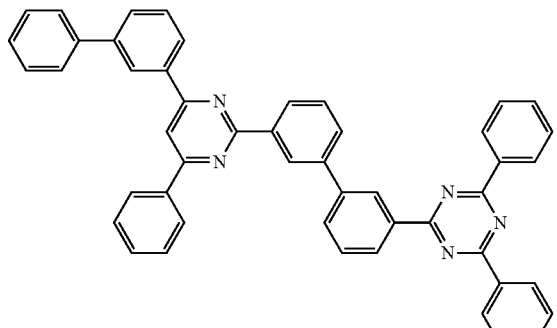
A(122)
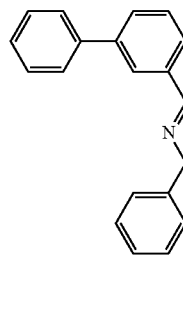
A(123)
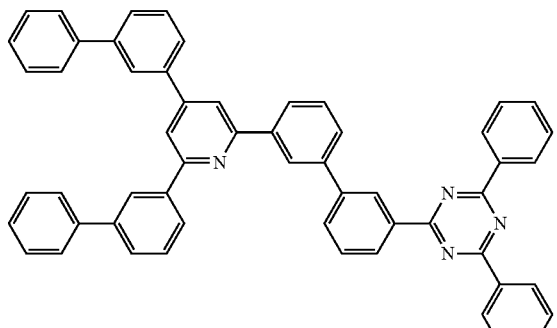
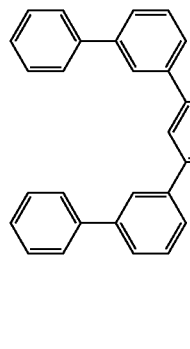
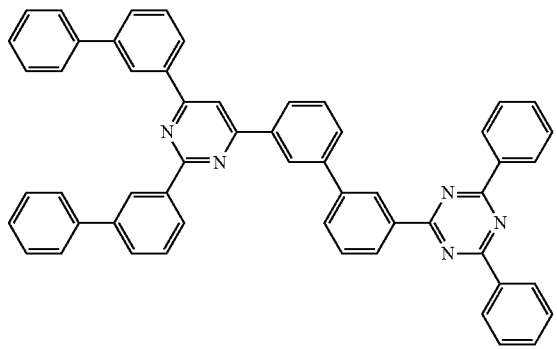

-continued
A(124)
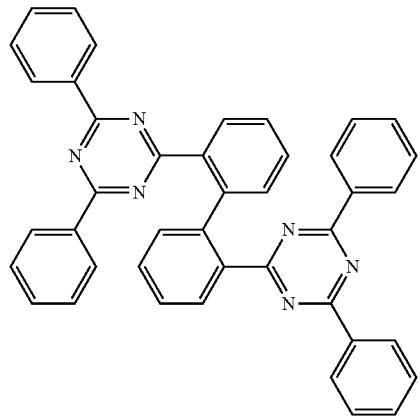
A(125)
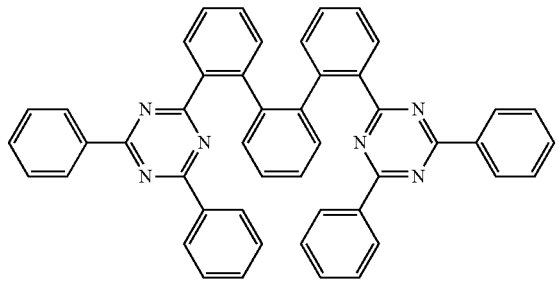
A(126)
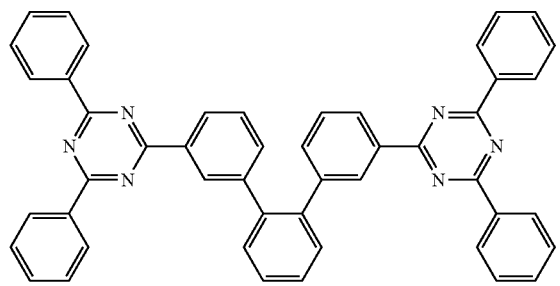
A(127)
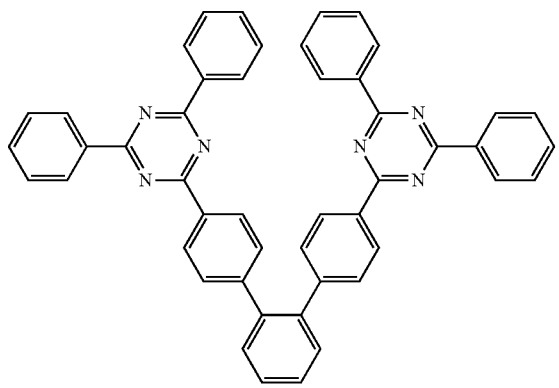
A(128)
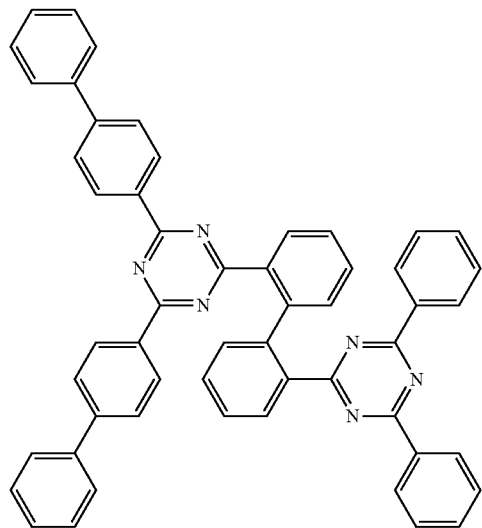
A(129)
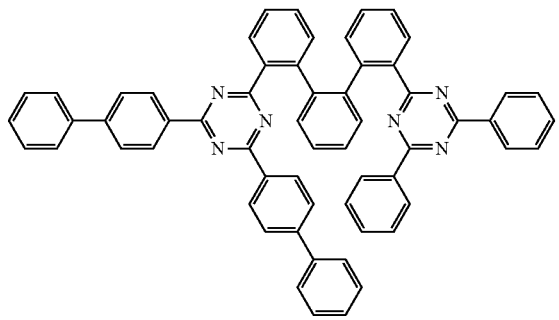

-continued

A(130)

A(131)

A(132)

A(133)

A(134)
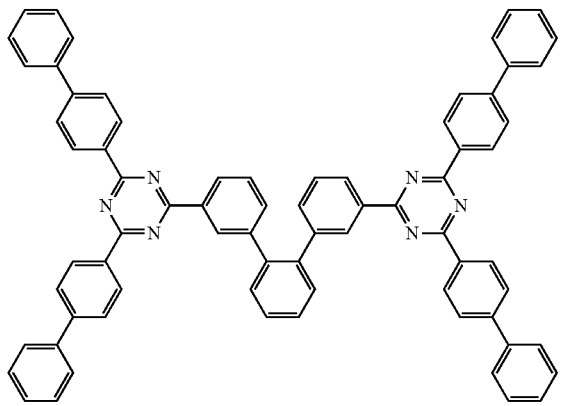
A(135)
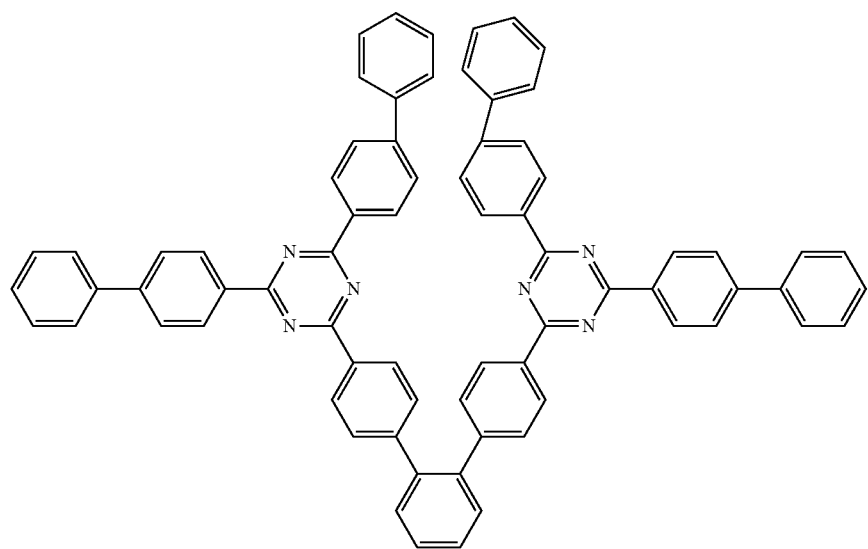
A(136)
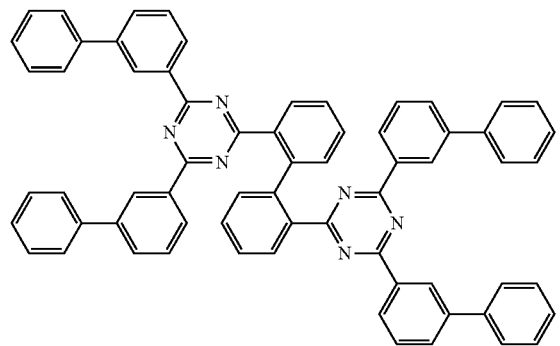
A(137)
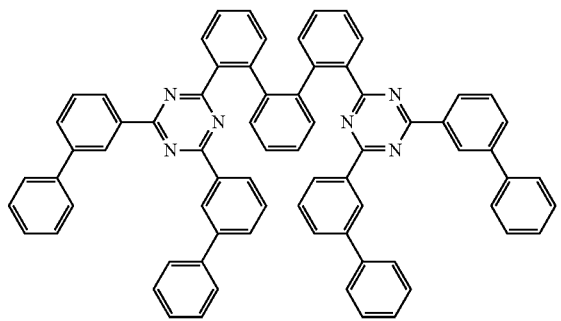

A(138)
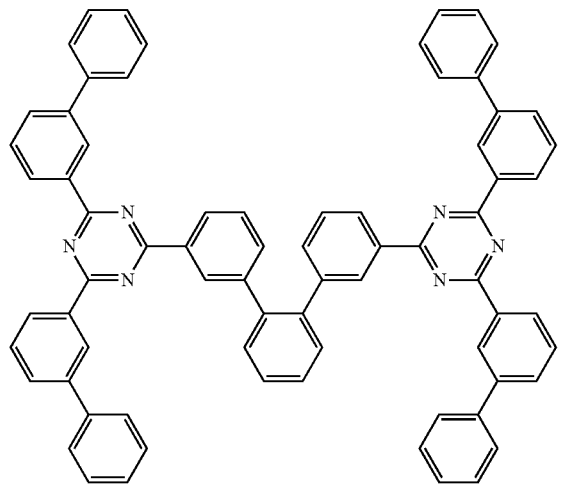
A(139)
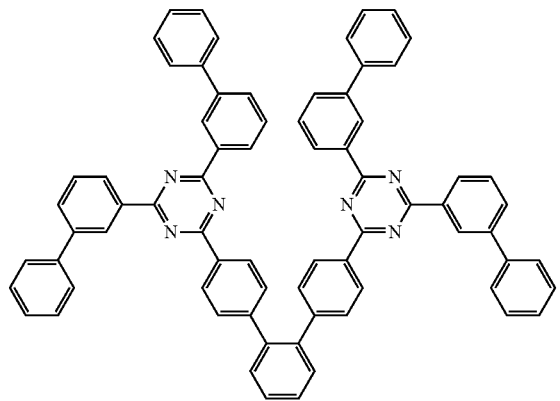
A(140)
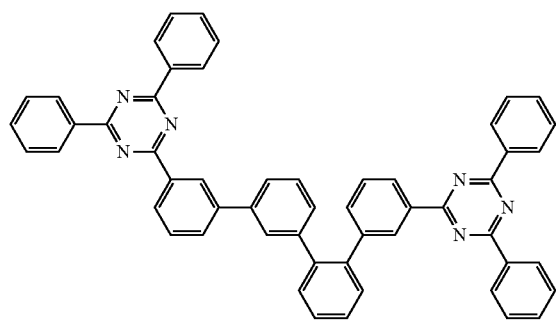
A(141)
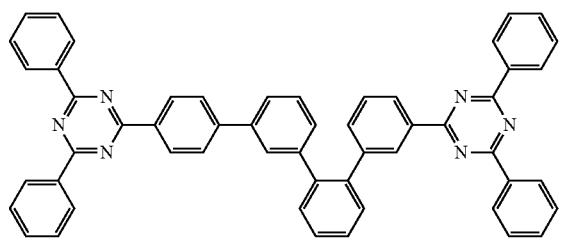
A(142)
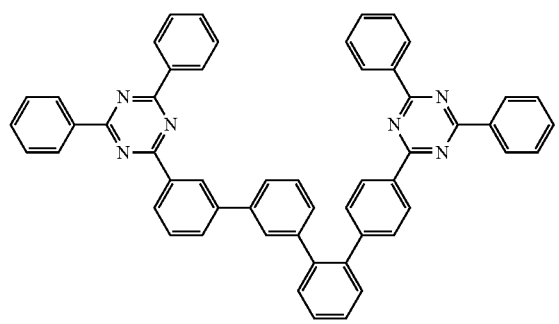
A(143)
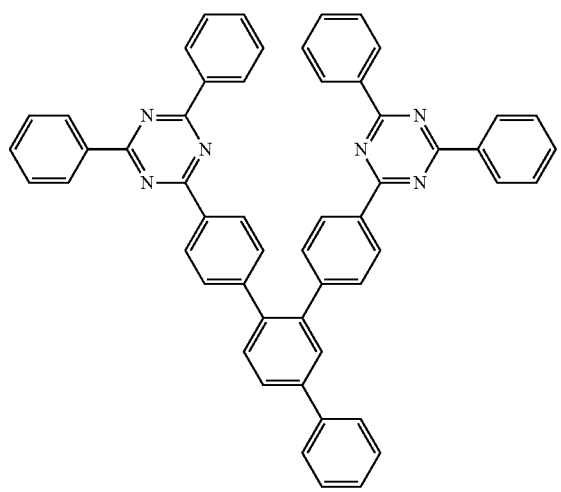

-continued
A(144)
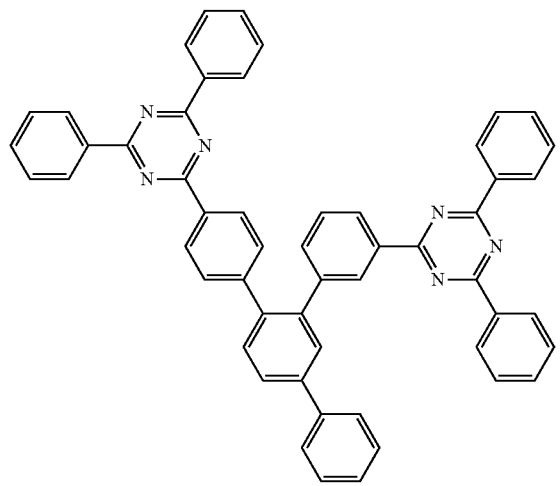
A(145)
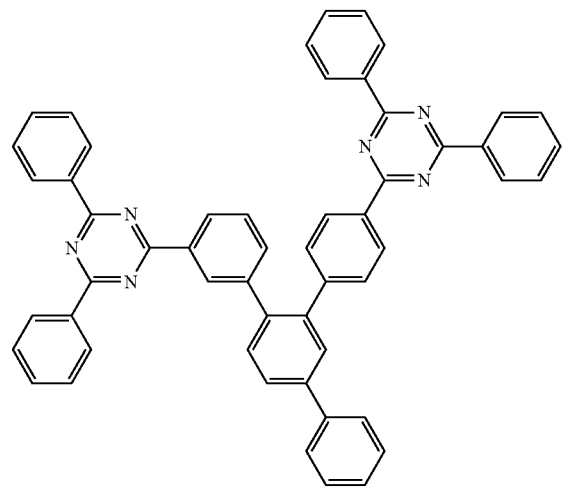
A(146)
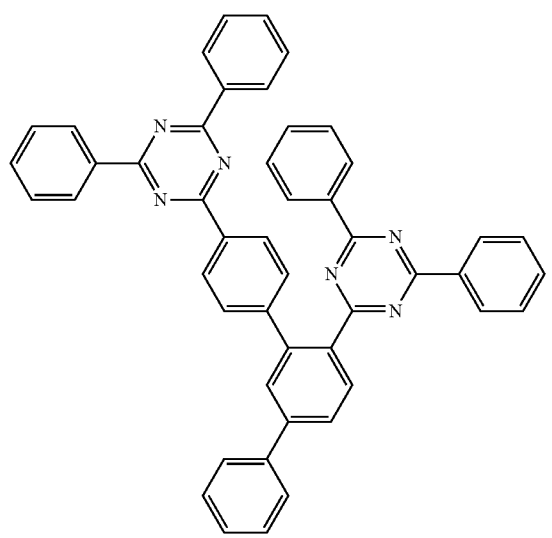
A(147)
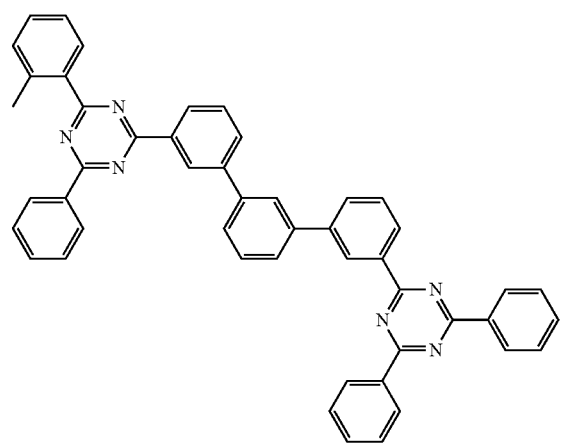
A(148)
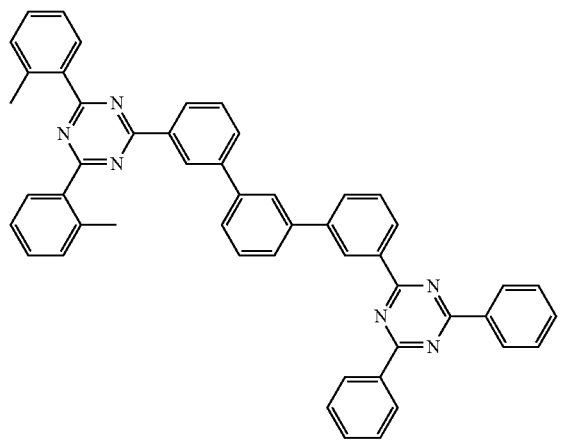
A(149)
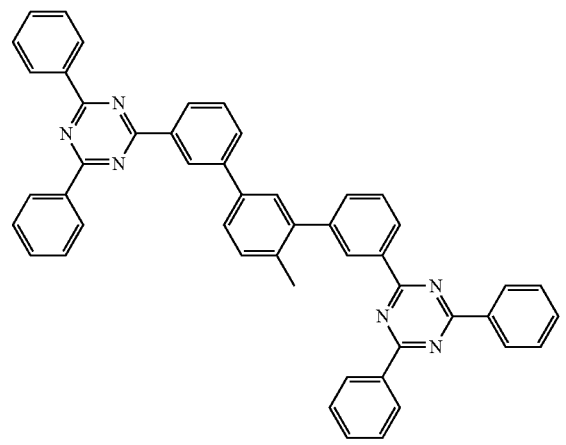

-continued
A(150)
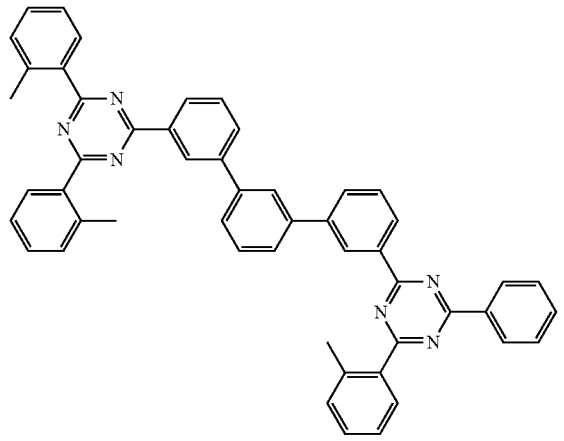
A(151)
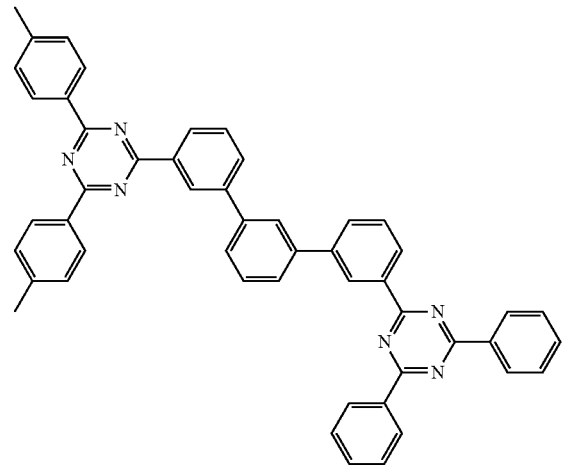
A(152)
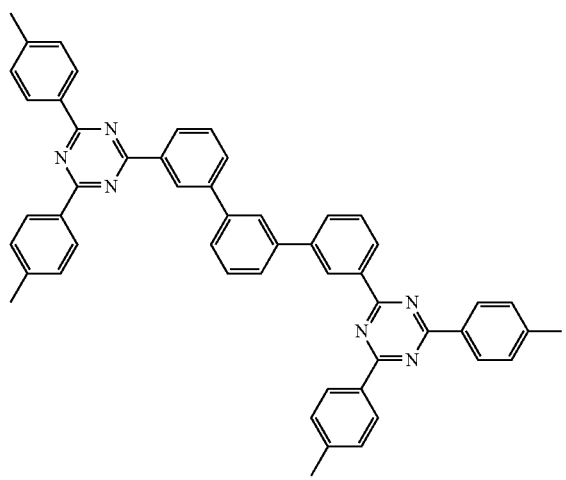
A(153)
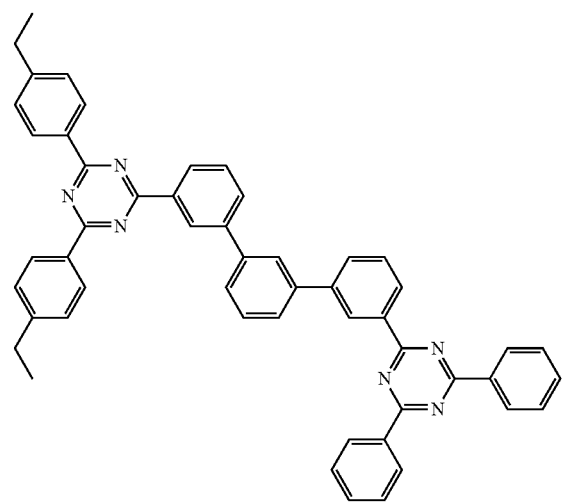
A(154)
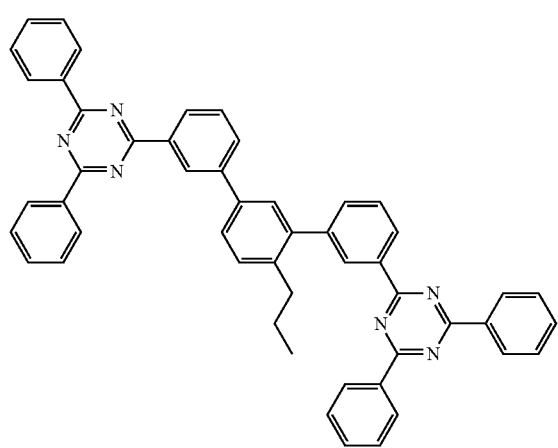

Group HE2
1
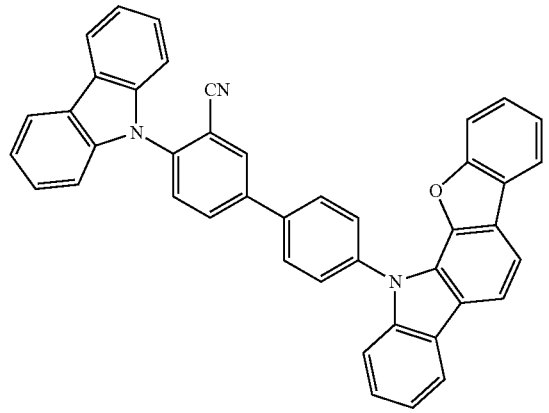
2
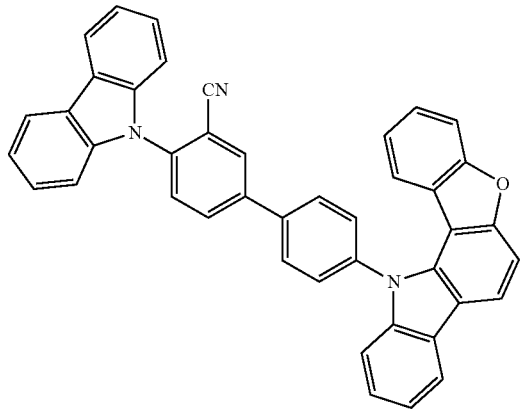
3
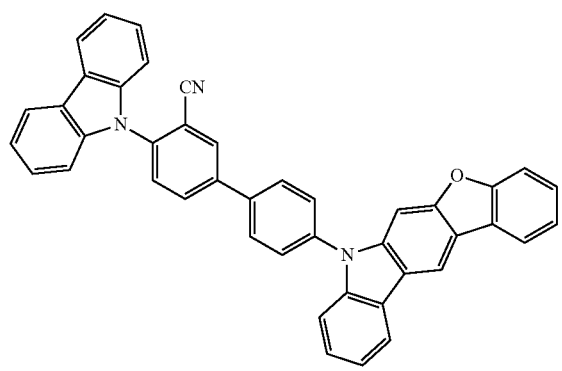
4
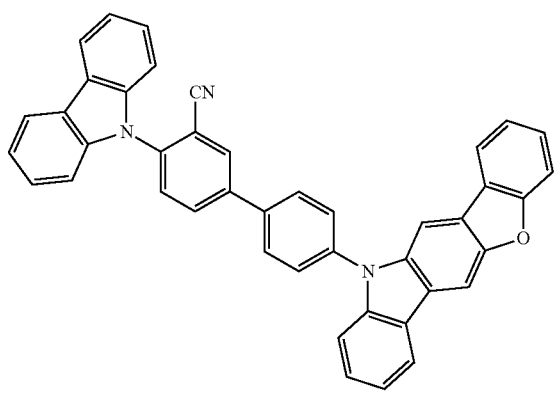
5
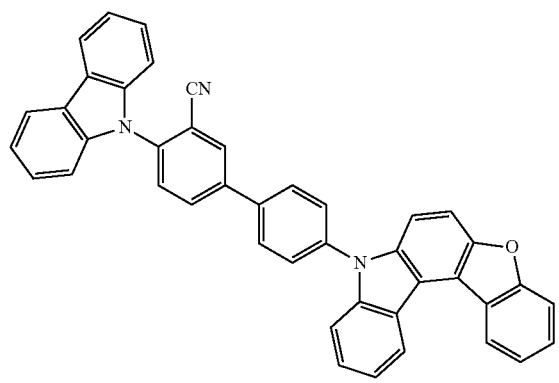
6
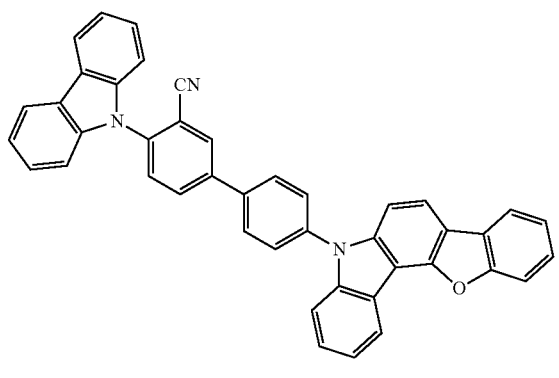

7
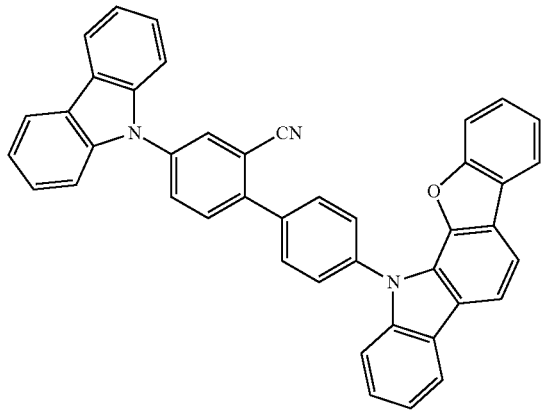
8
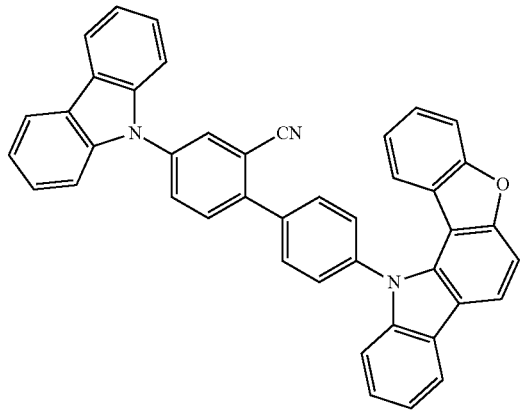
9
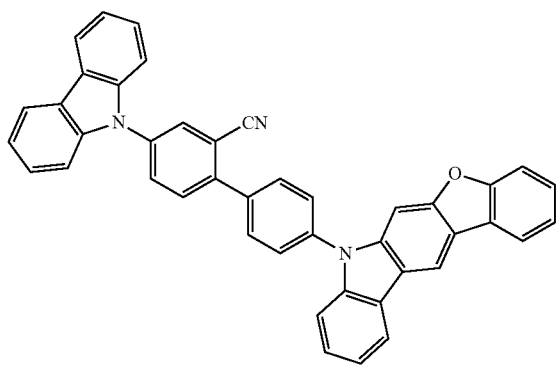
10
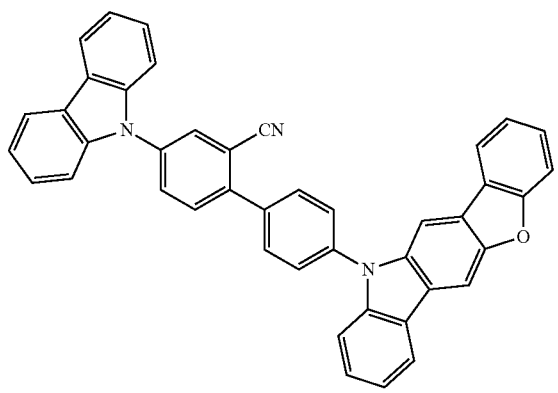
11
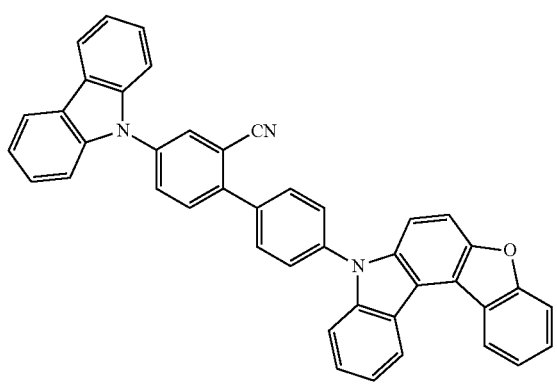
12
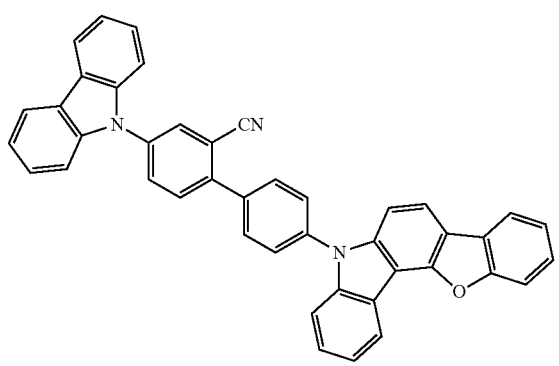

13
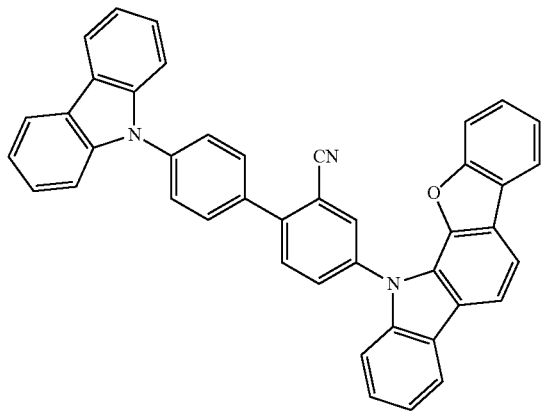
14
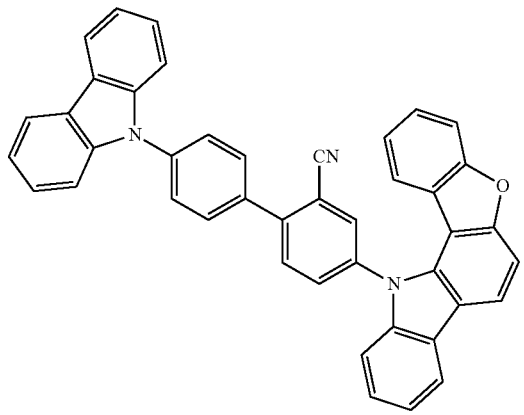
15
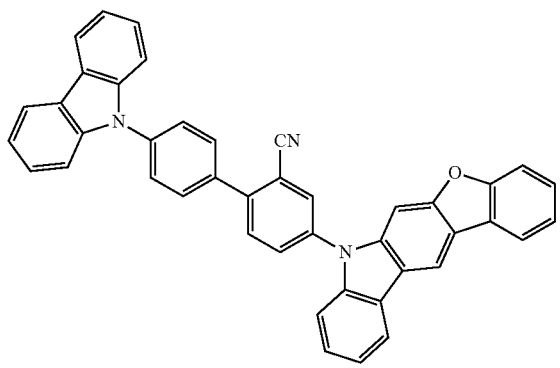
16
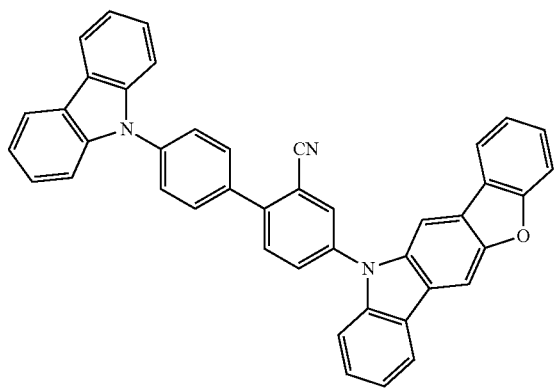
17
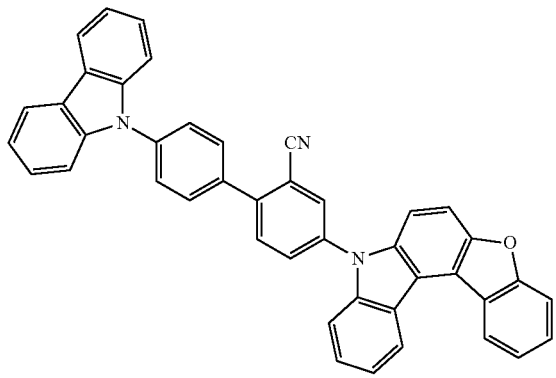
18
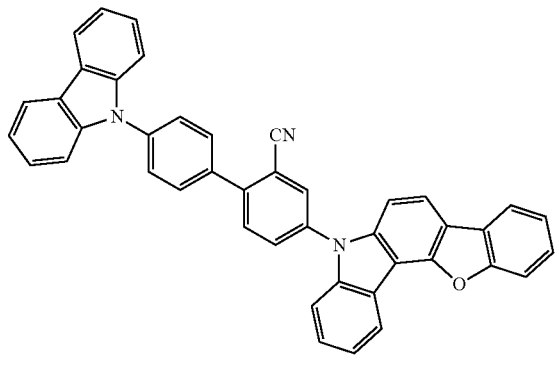

-continued
19
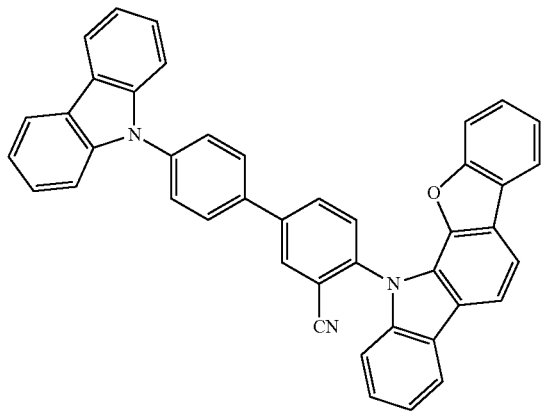
20
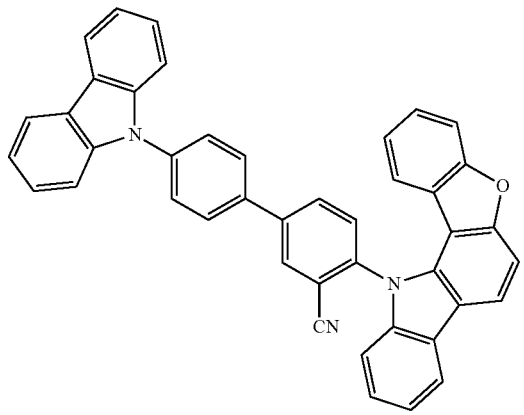
21
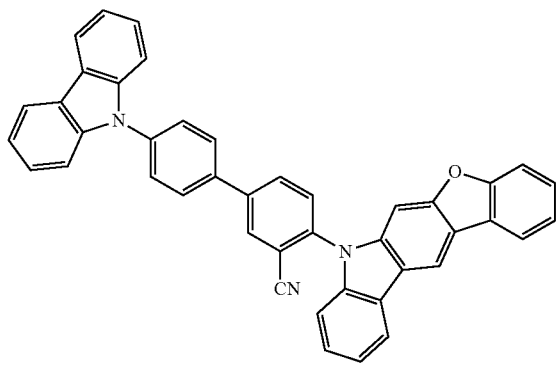
22
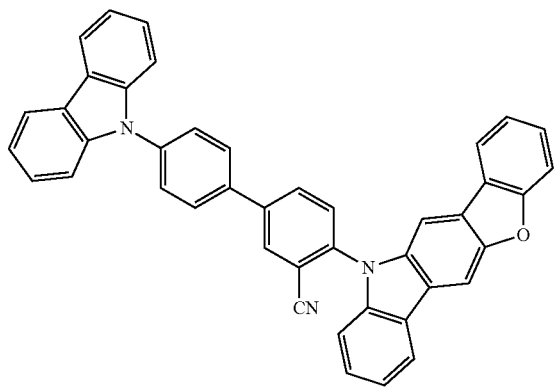
23
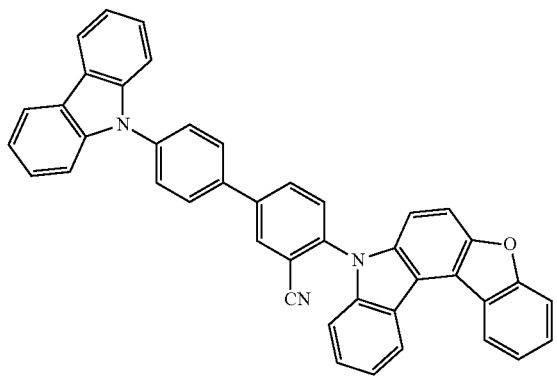
24
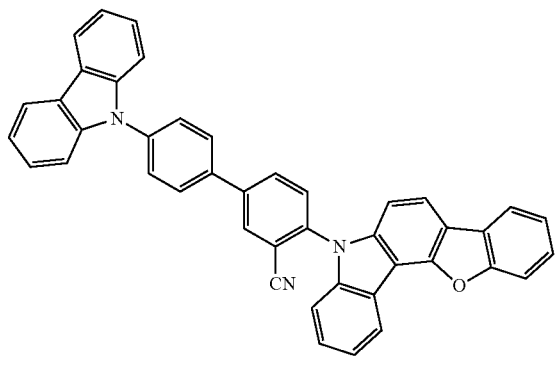

25
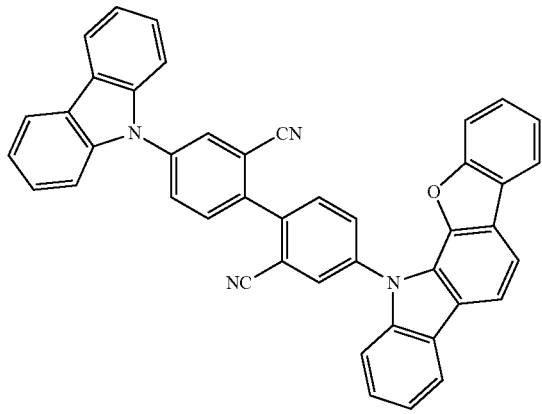
26
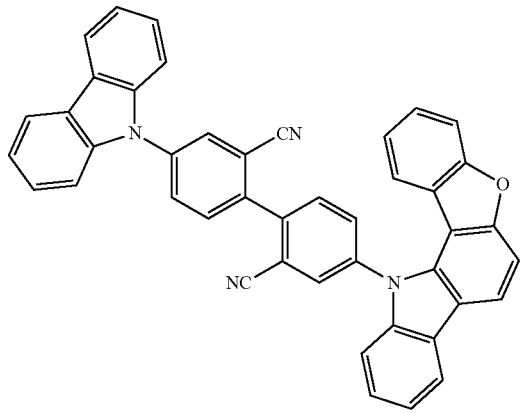
27
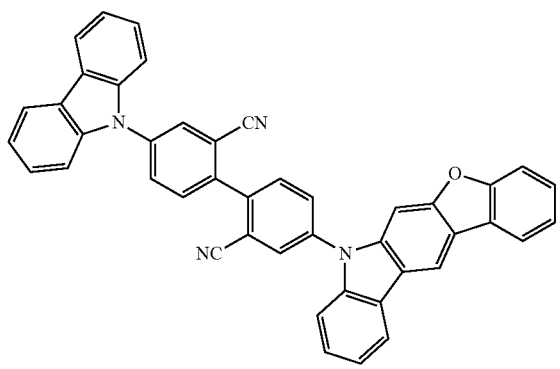
28
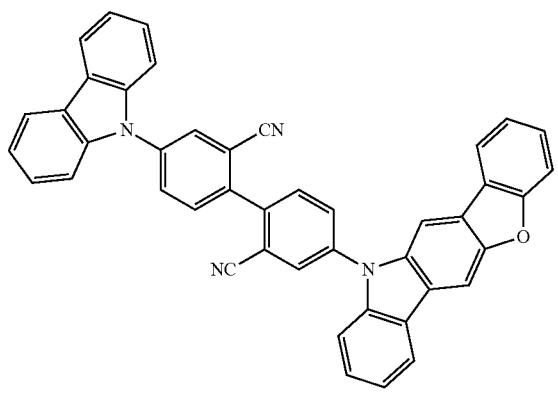
29
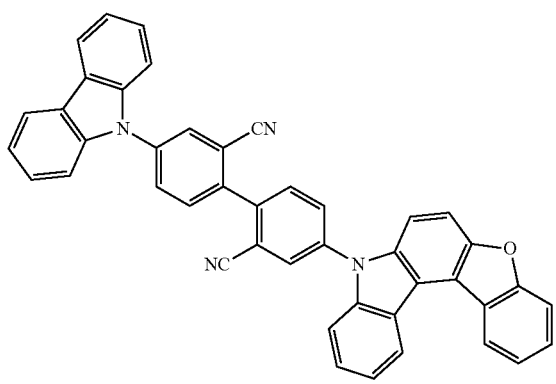
30
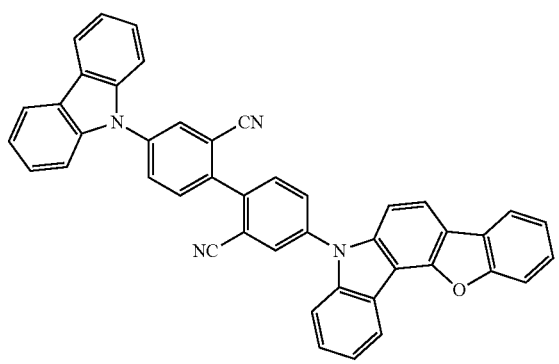

31
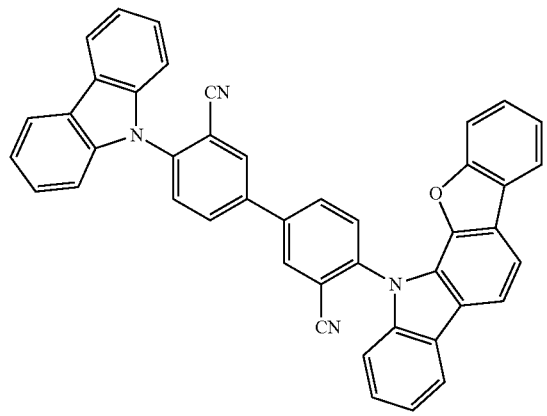
32
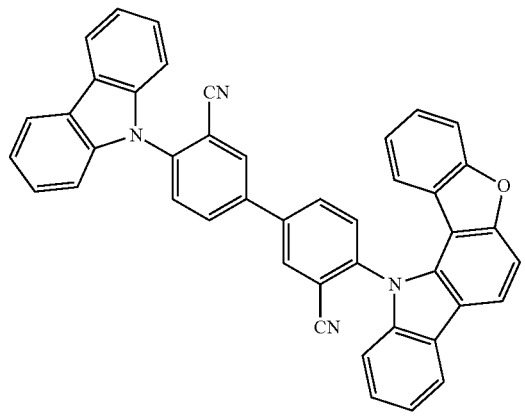
33
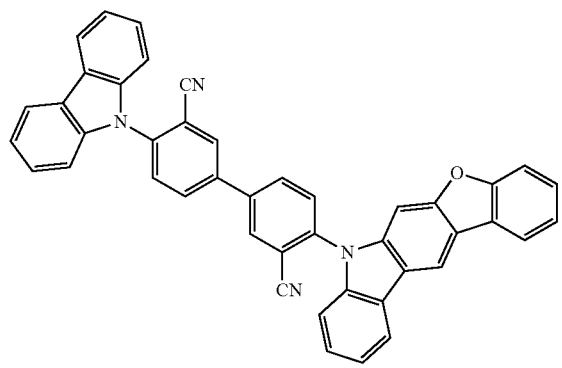
34
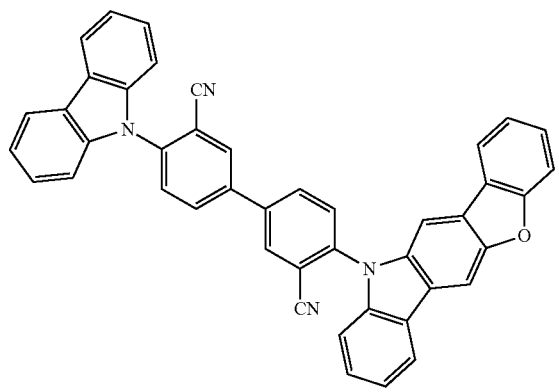
35
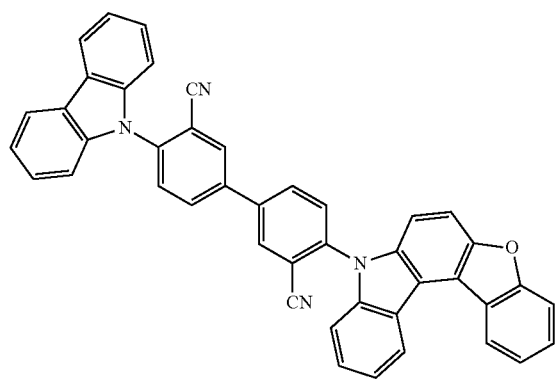
36
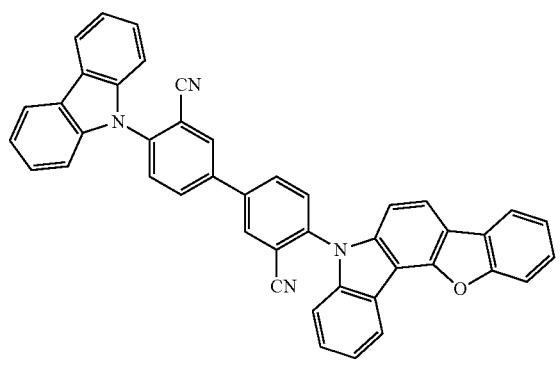

-continued
37
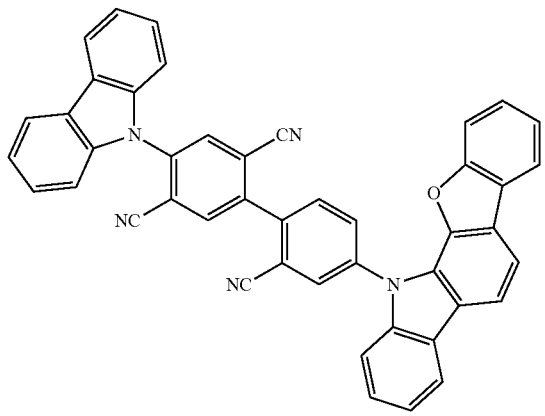
38
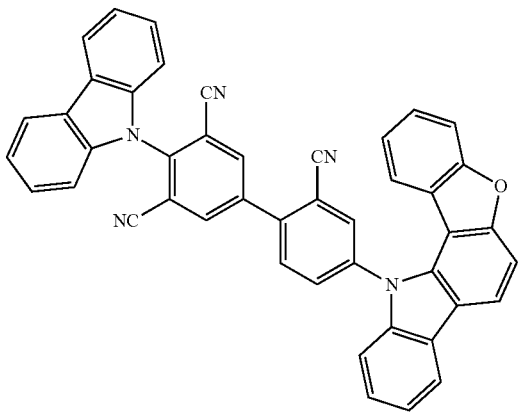
39
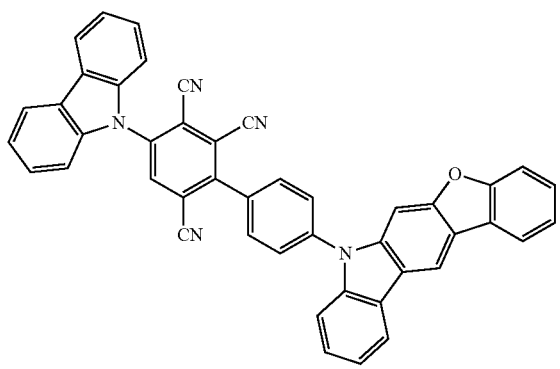
40
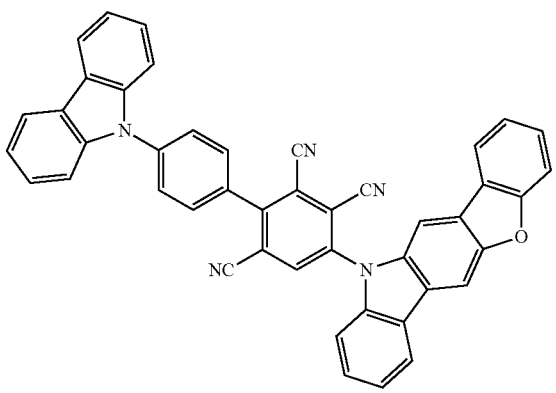
41
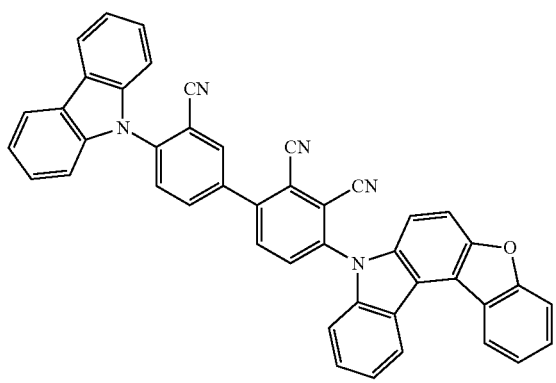
42
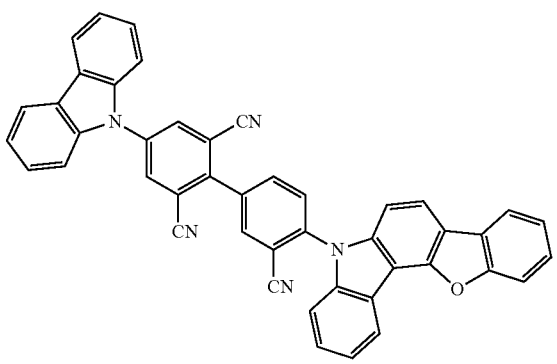

43
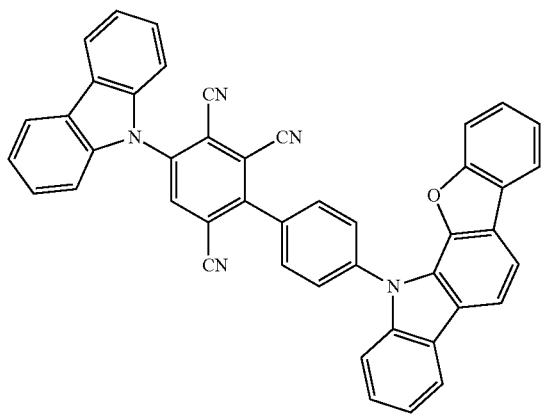
44
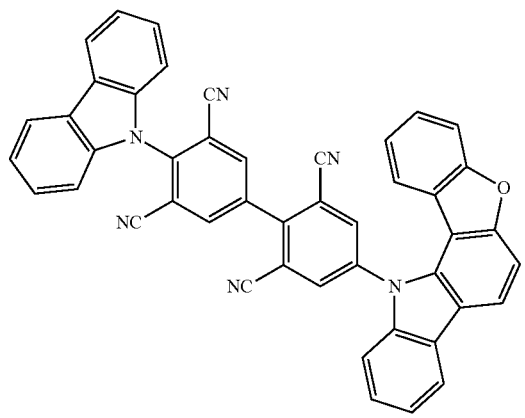
45
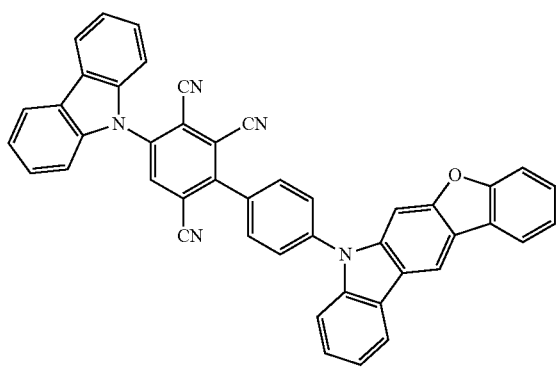
46
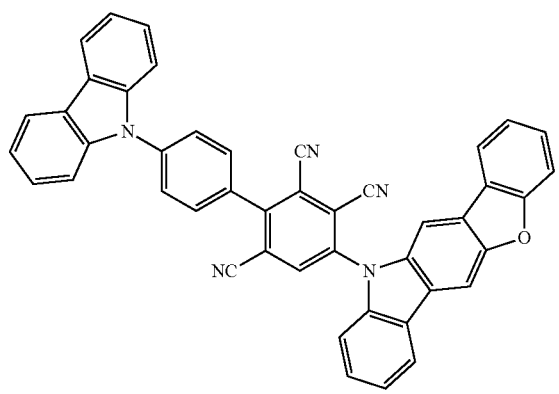
47
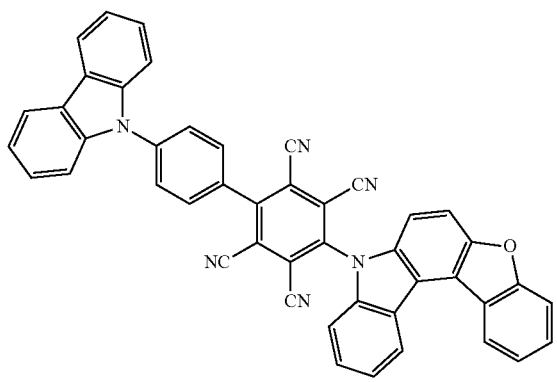
48
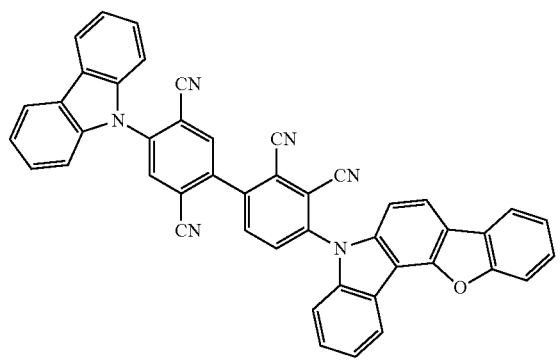

49
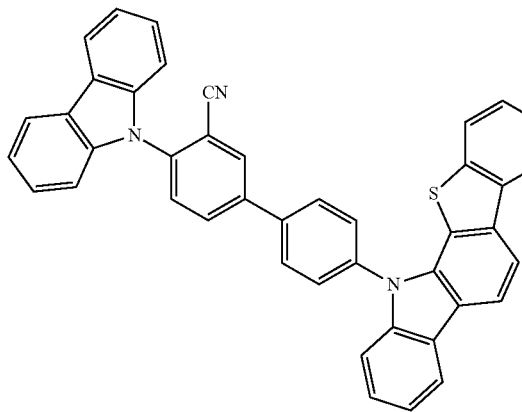
50
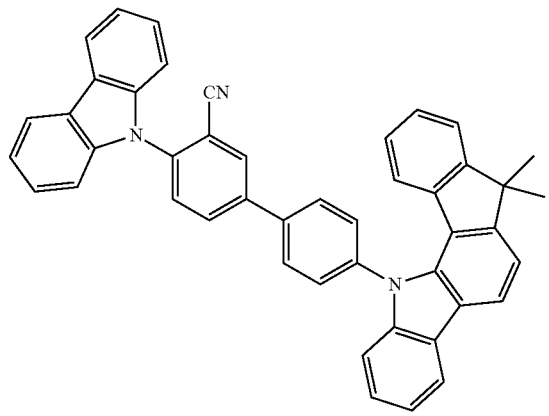
51
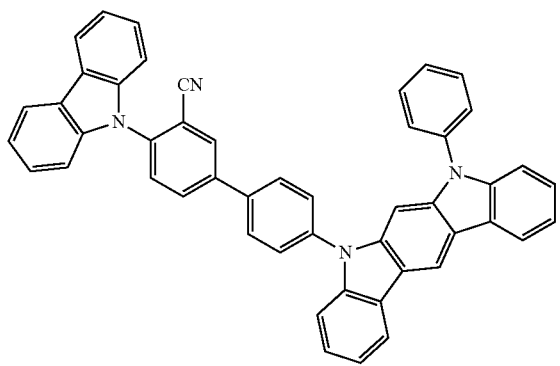
52
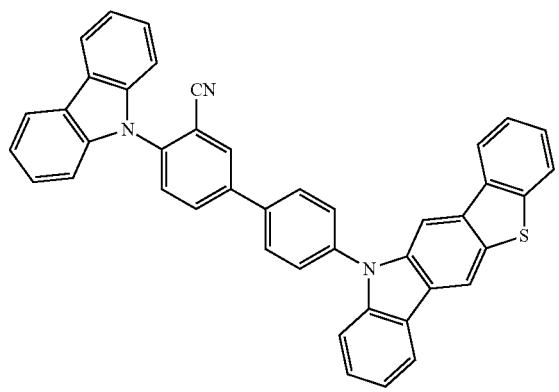
53
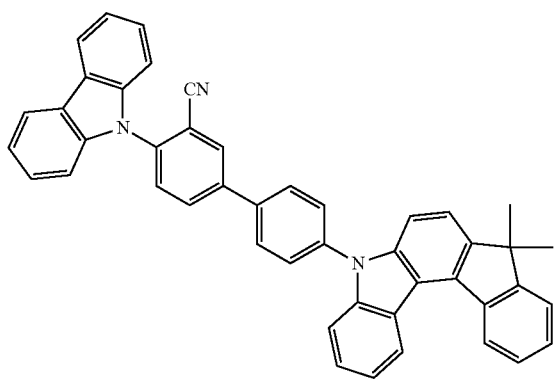
54
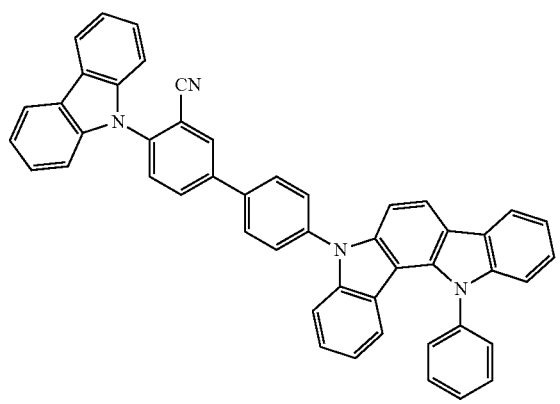

-continued
55
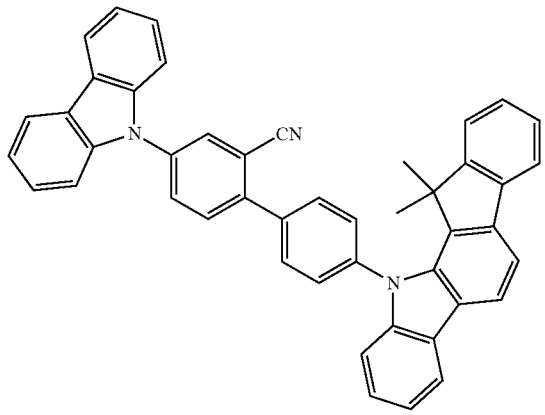
56
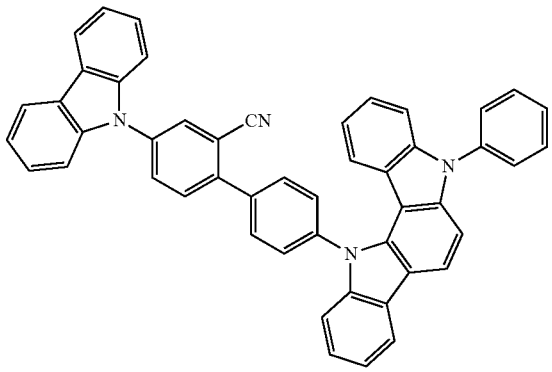
57
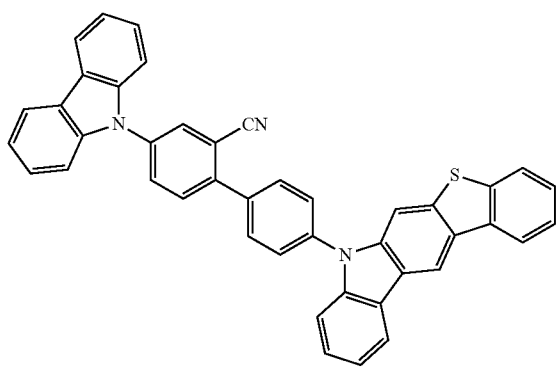
58
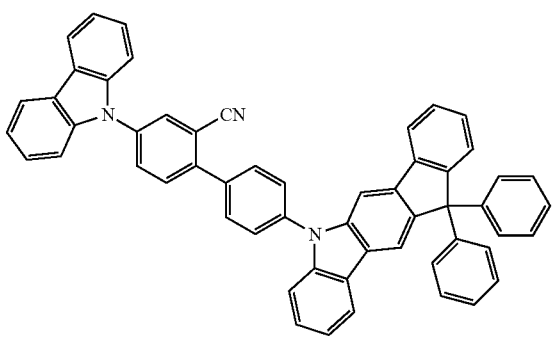
59
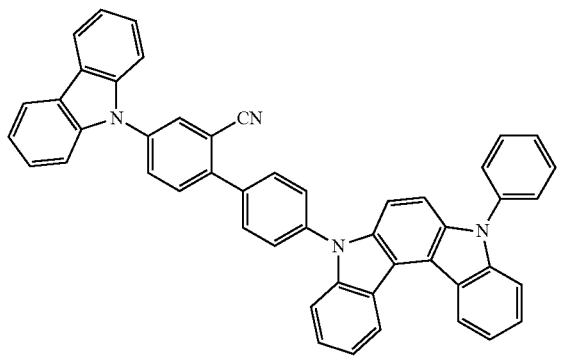
60
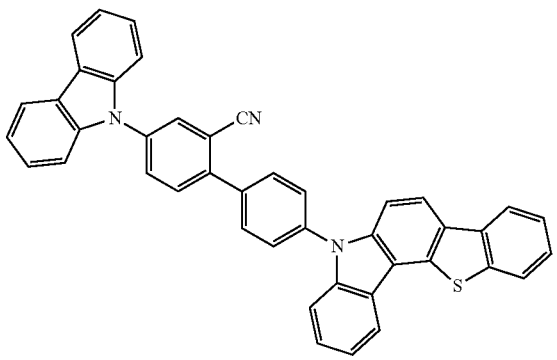
61
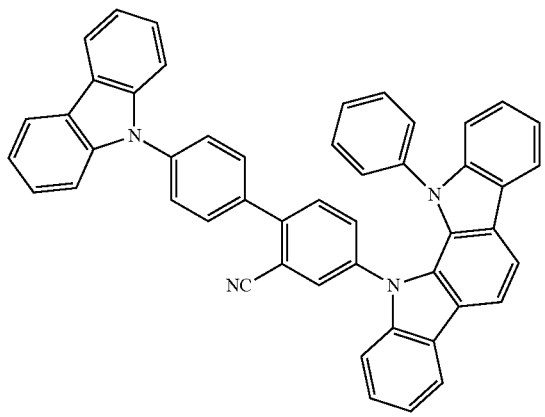
62
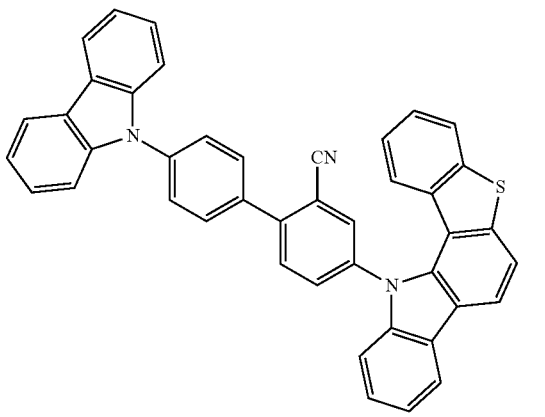

-continued
63
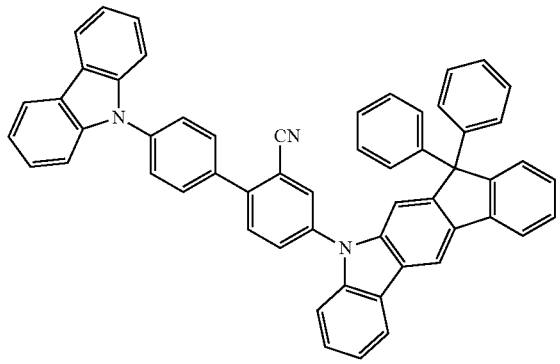
64
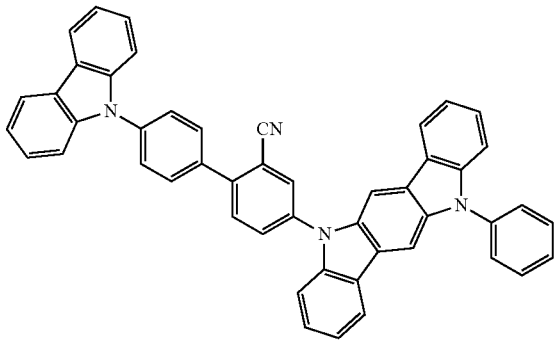
65
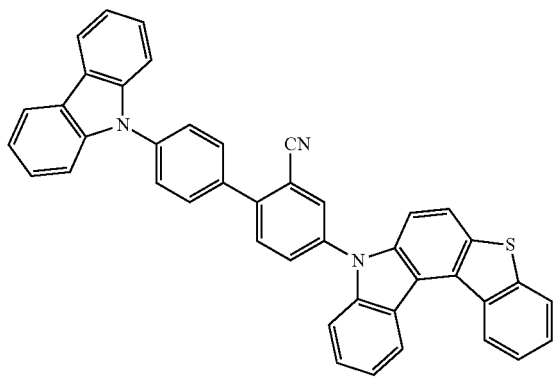
66
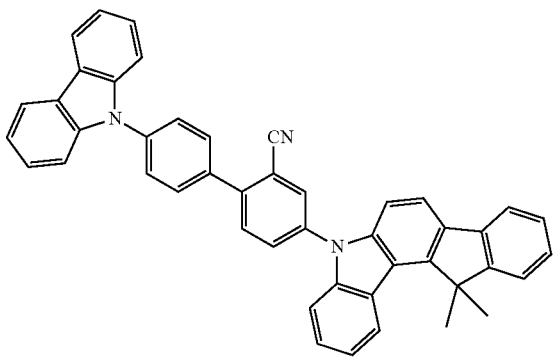
67
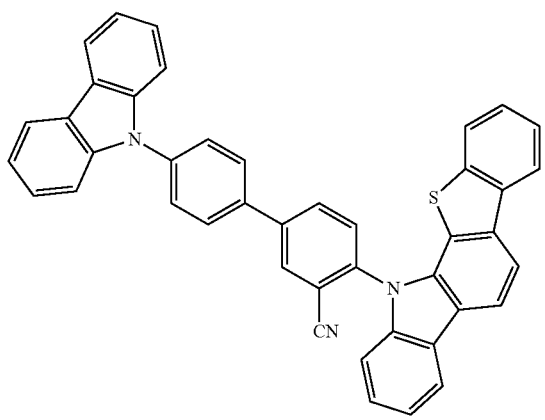
68
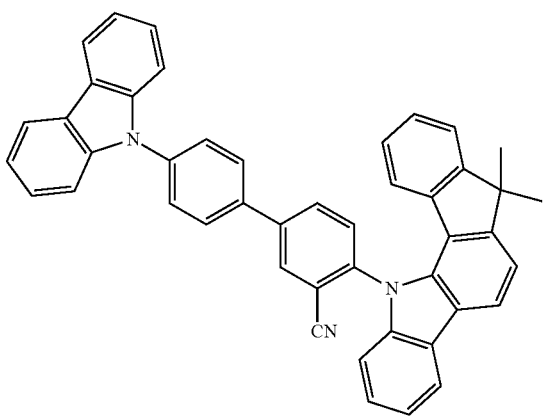
69
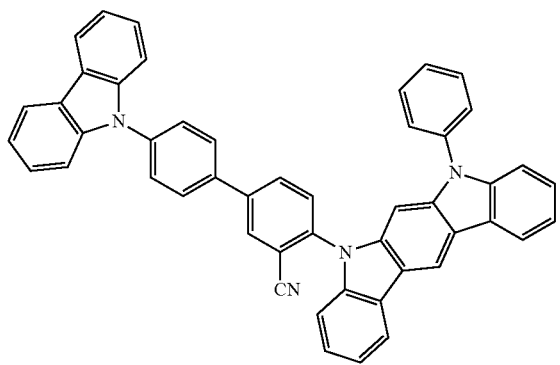
70
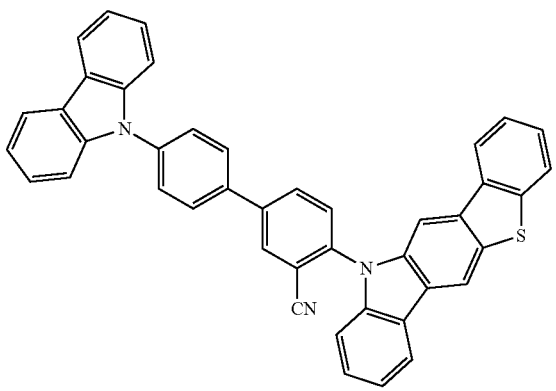

-continued
71
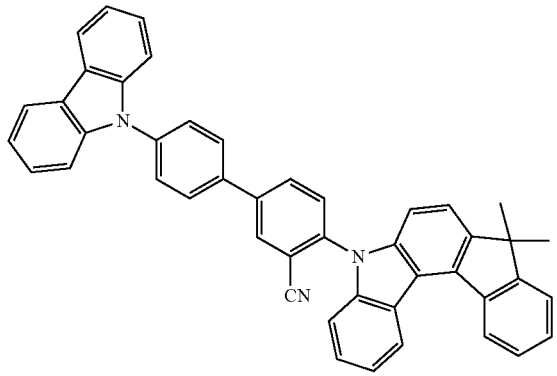
72
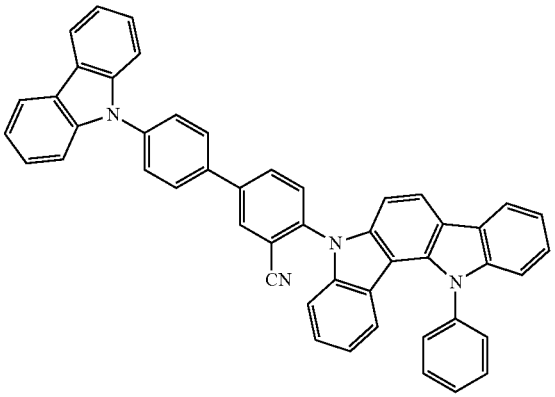
73
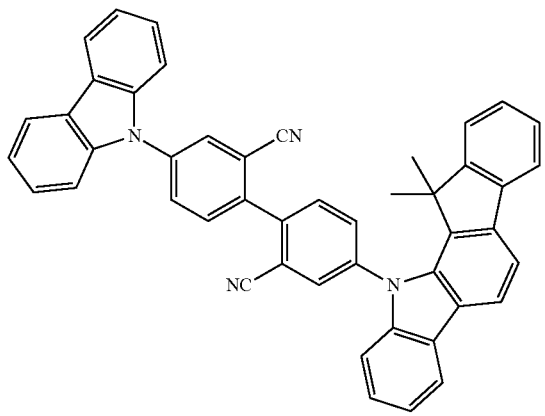
74
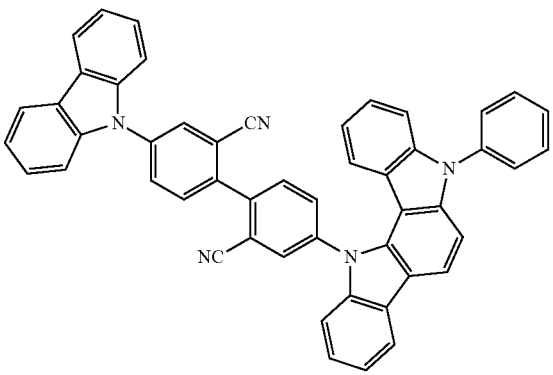
75
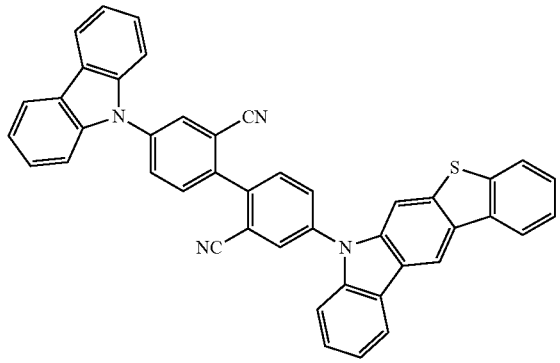
76
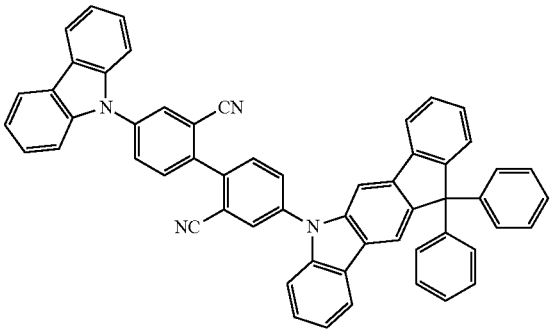
77
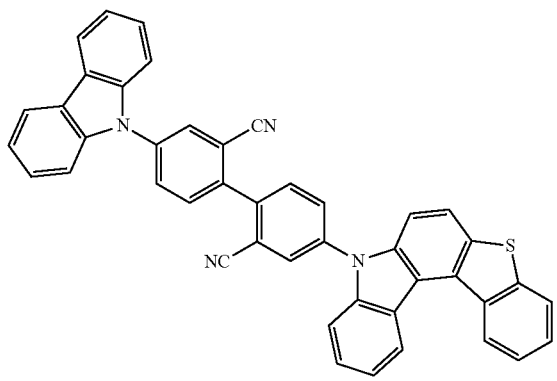
78
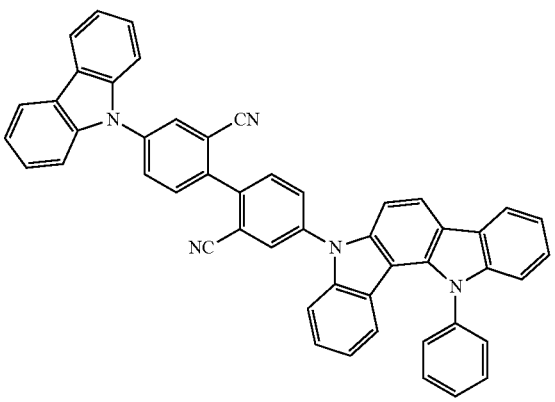

79
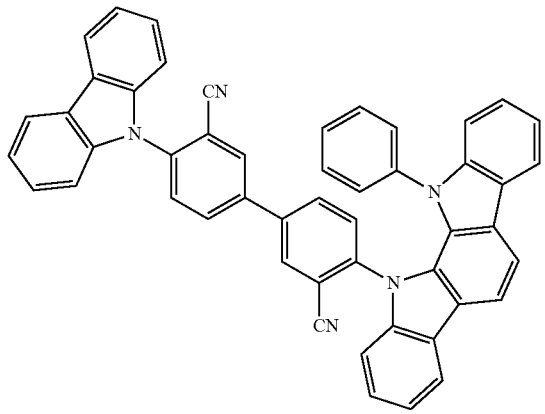
80
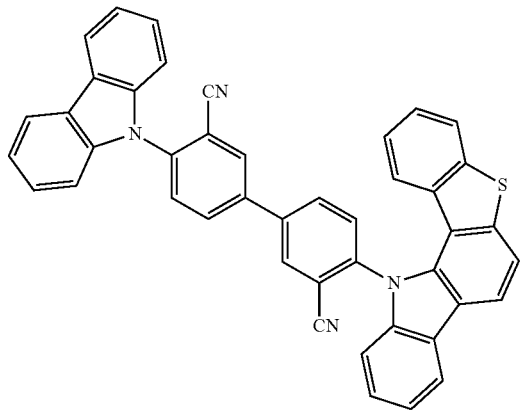
81
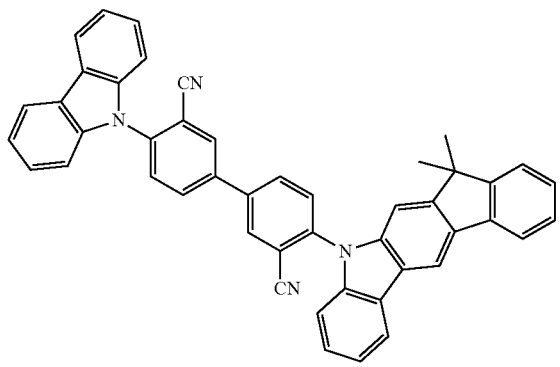
82
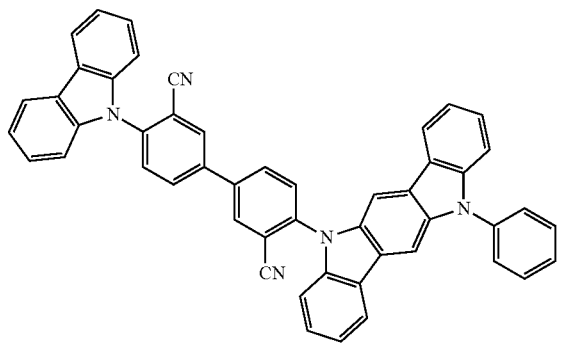
83
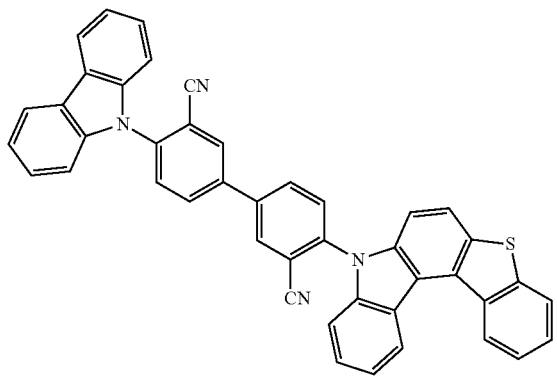
84
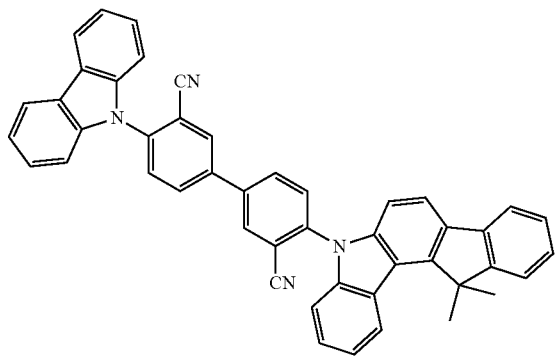
85
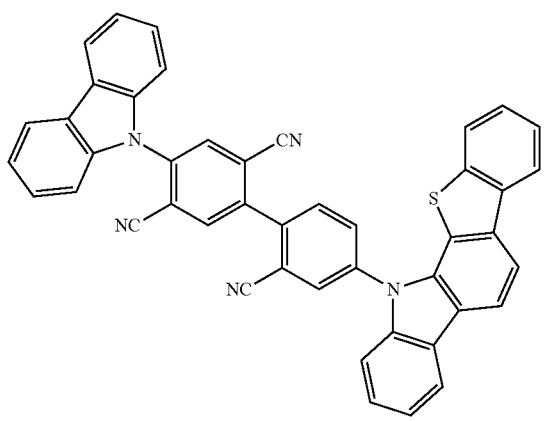
86
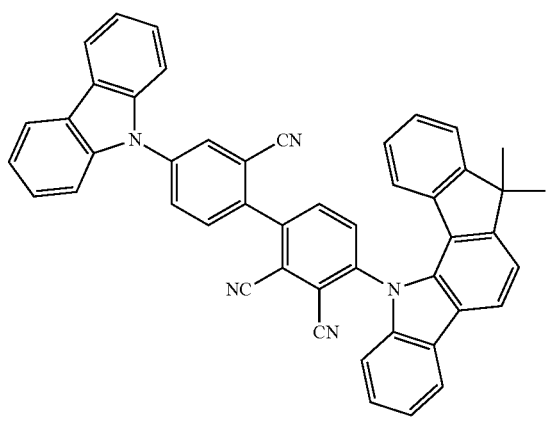

-continued
87
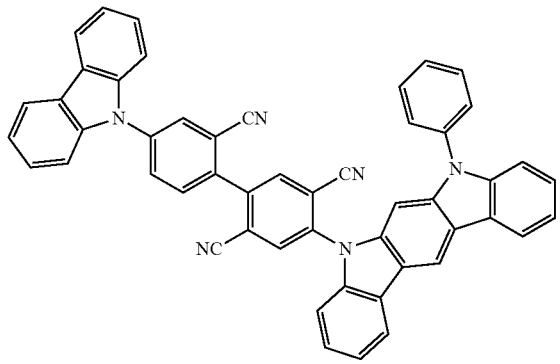
88
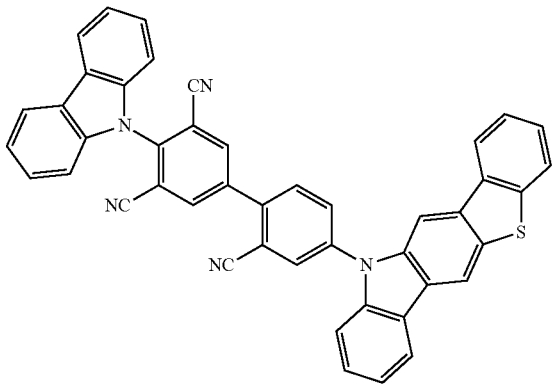
89
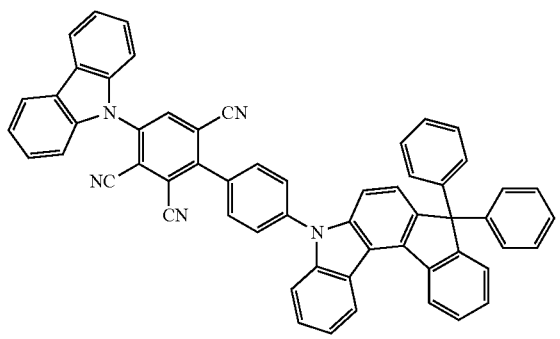
90
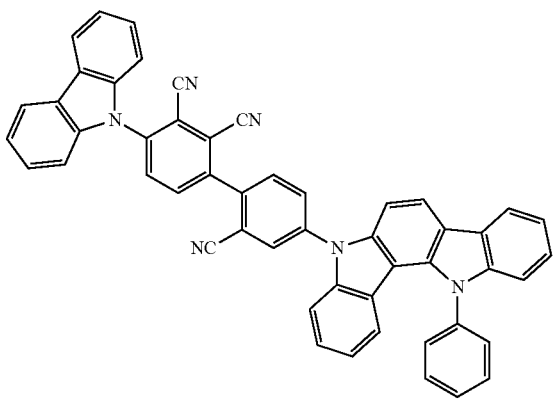
91
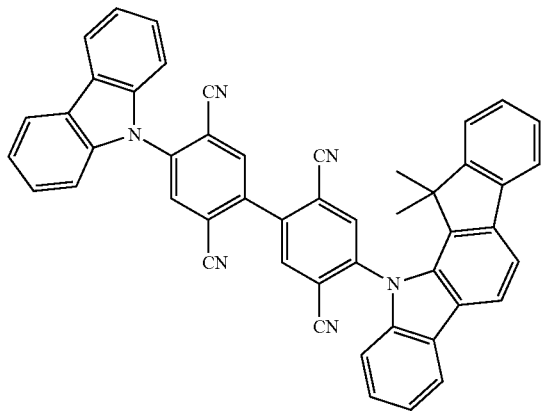
92
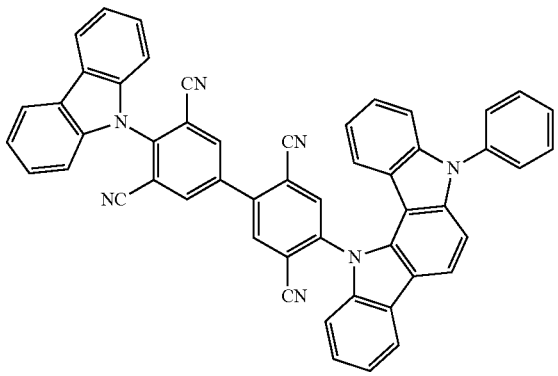
93
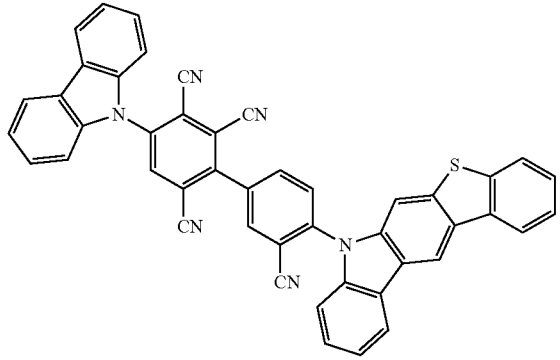
94
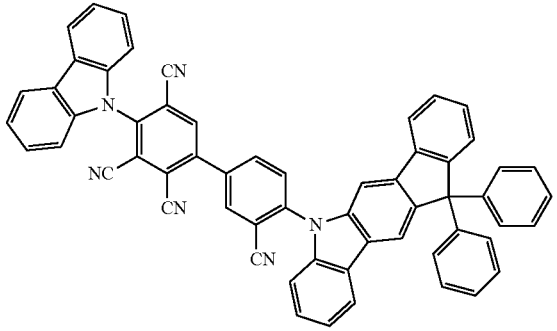

-continued
95
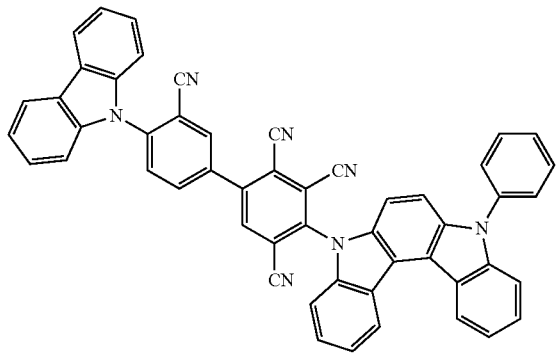
96
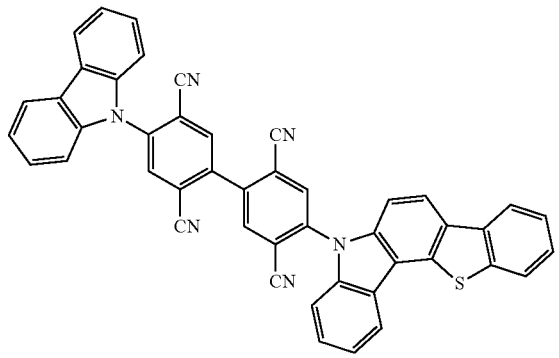
97
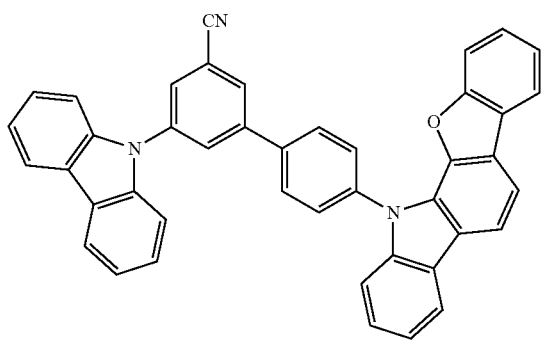
98
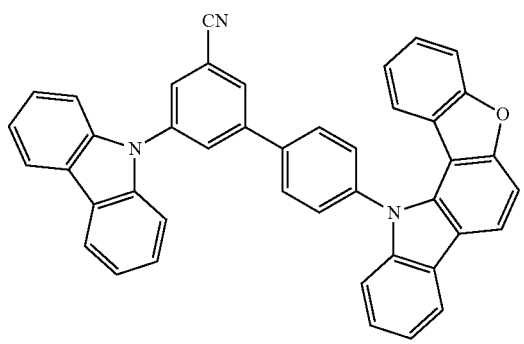
99
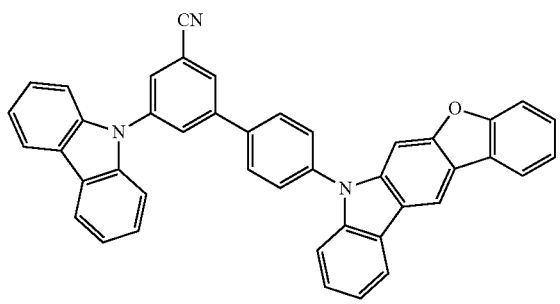
100
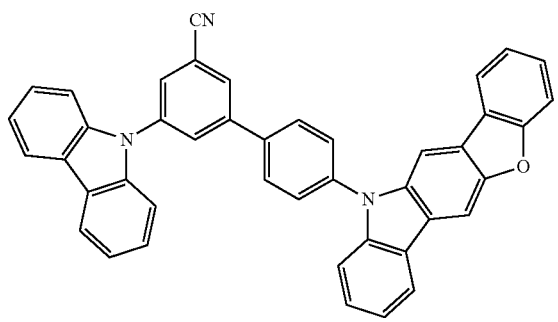
101
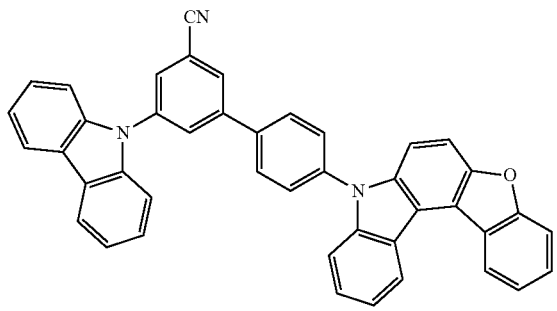
102
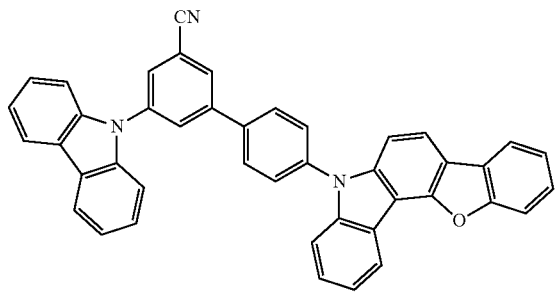

-continued
103
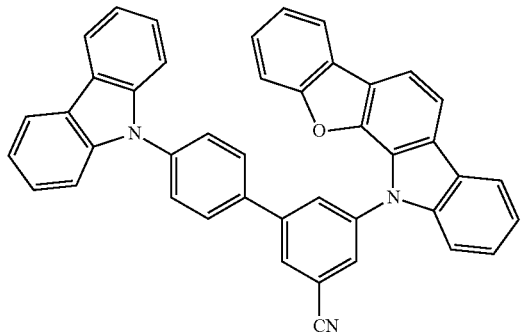
104
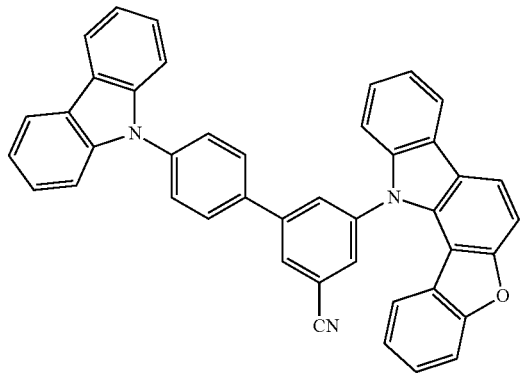
105
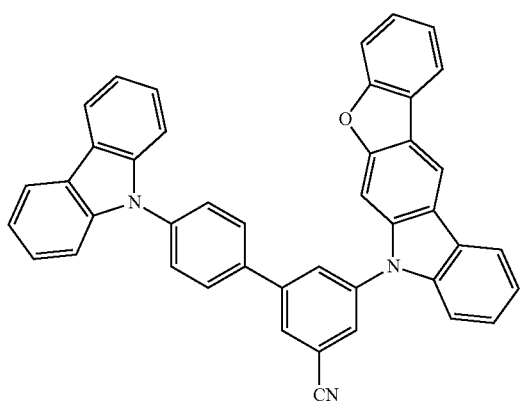
106
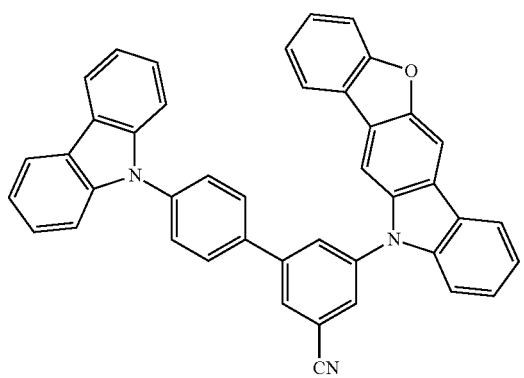
107
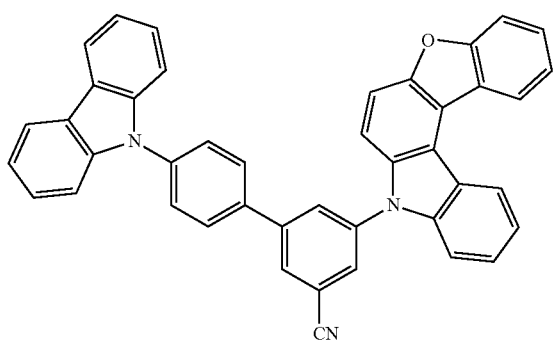
108
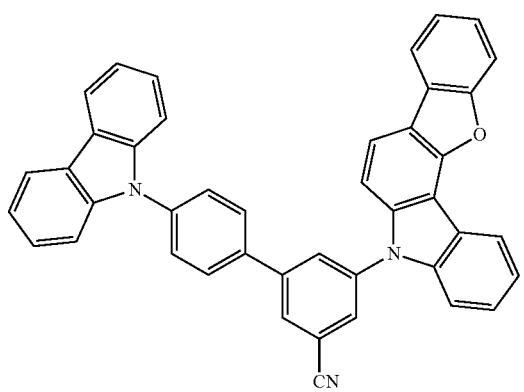
109
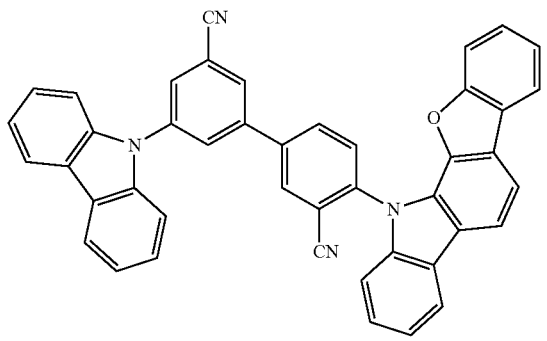
110
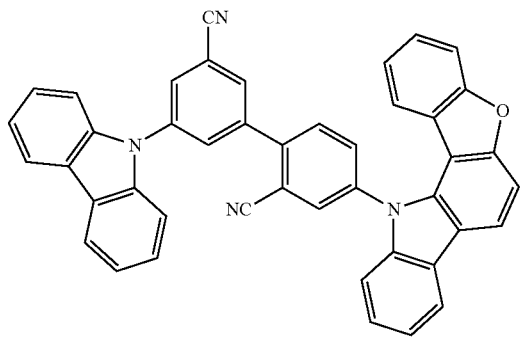

111
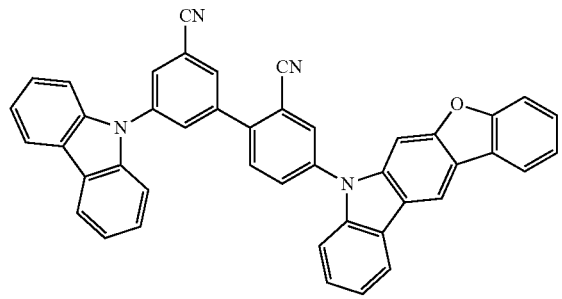
112
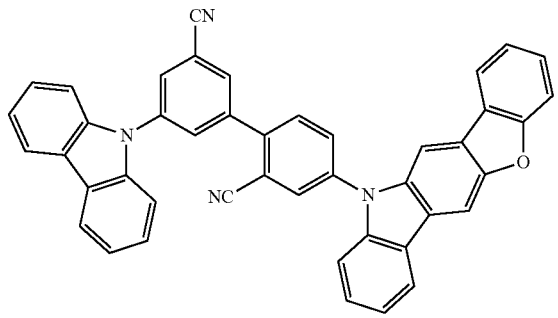
113
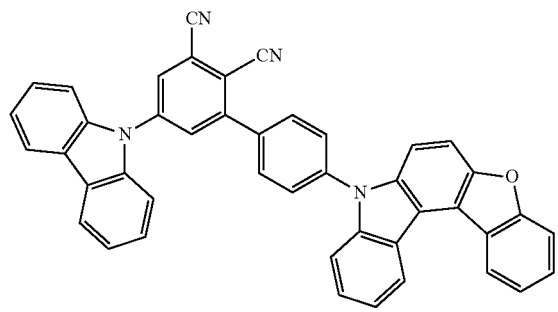
114
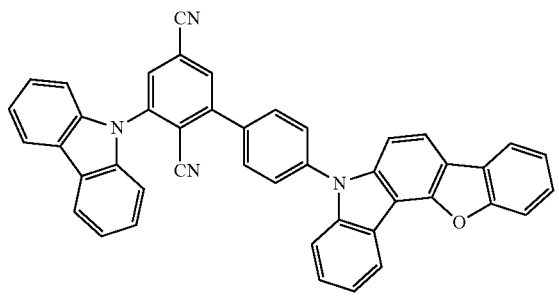
115
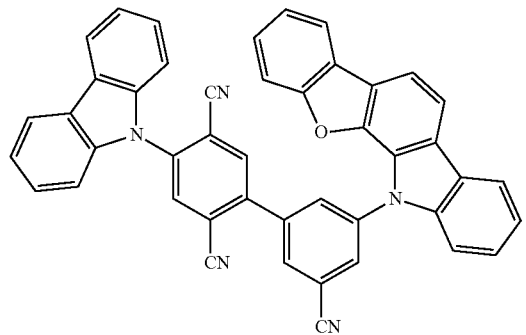
116
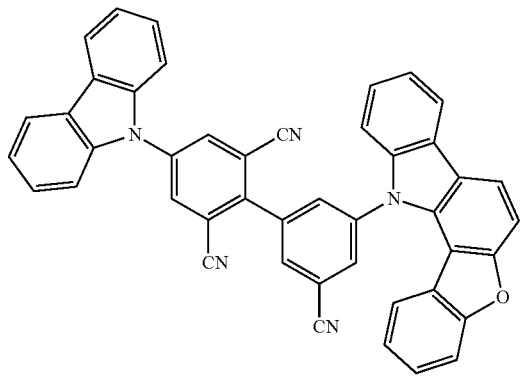
117
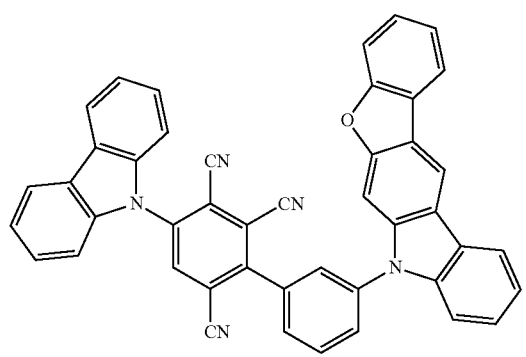
118
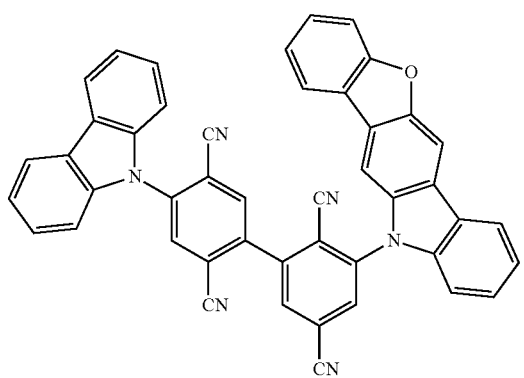

119
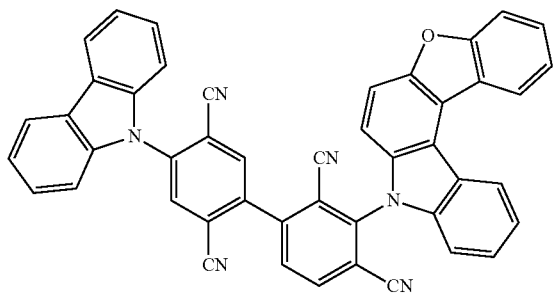
120
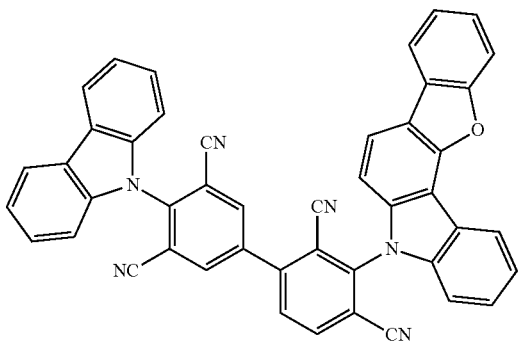
121
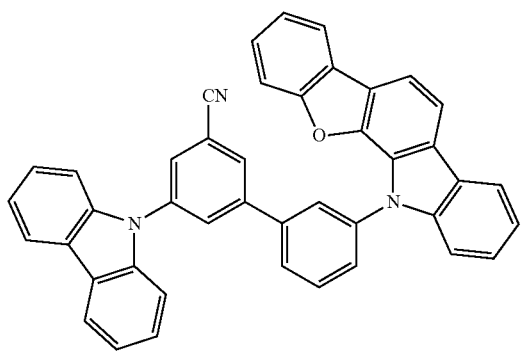
122
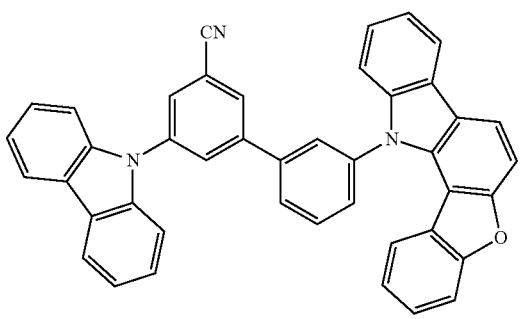
123
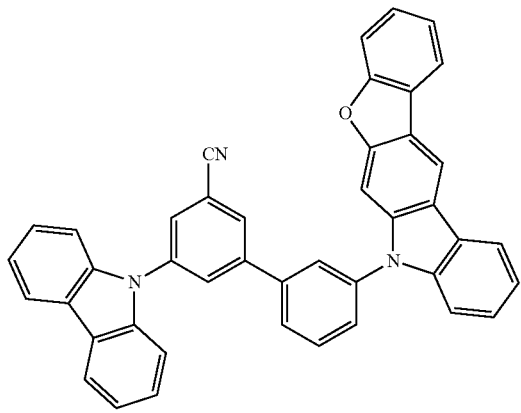
124
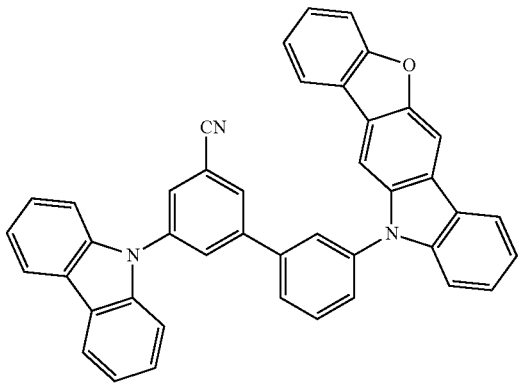
125
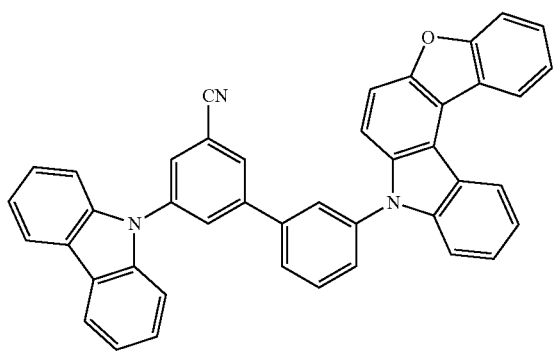
126
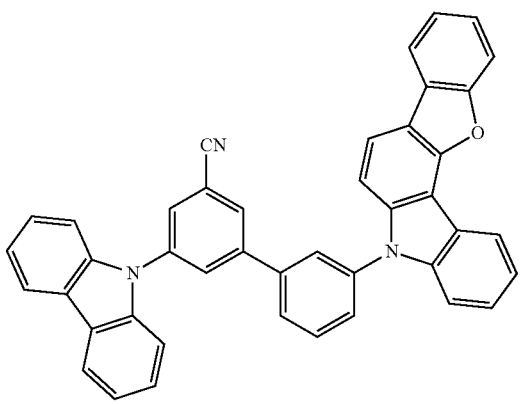

-continued
127
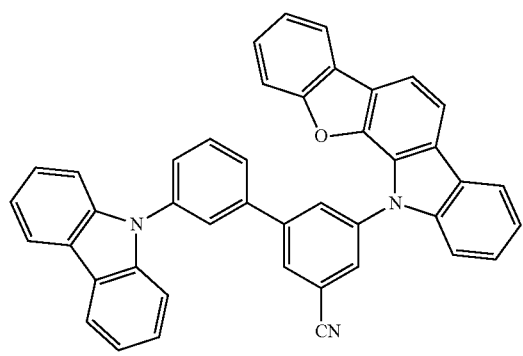
128
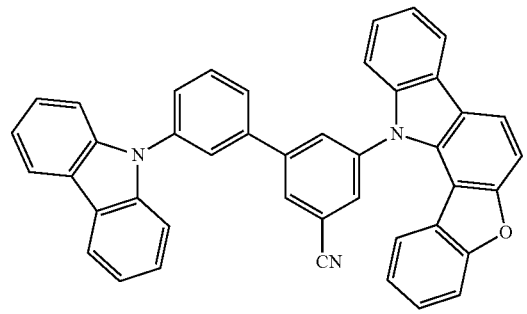
129
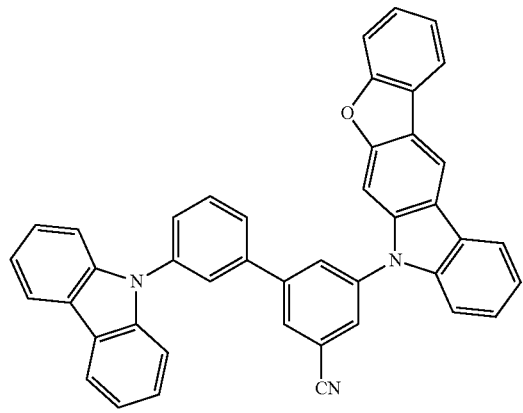
130
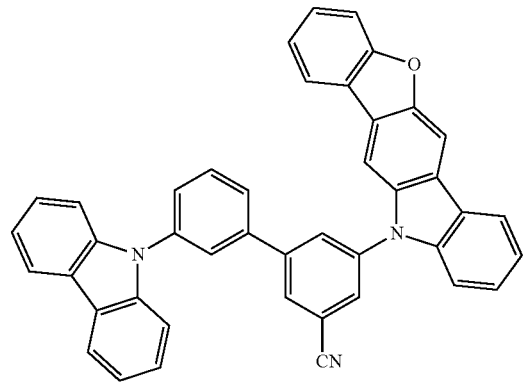
131
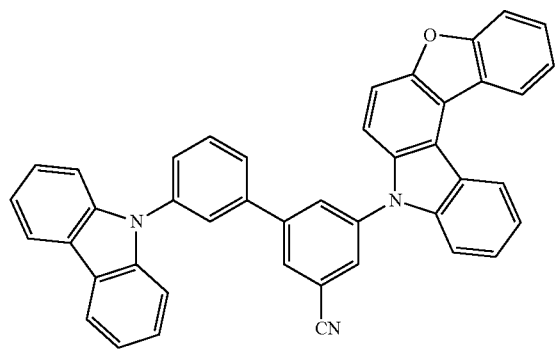
132
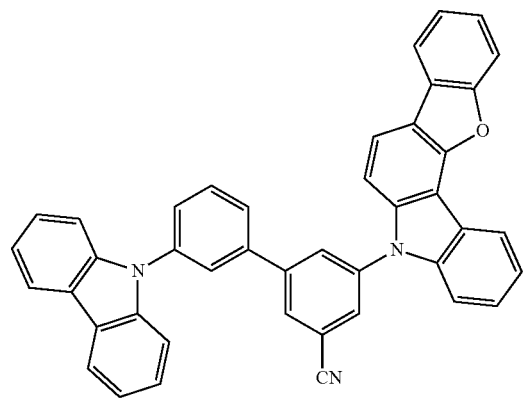
133
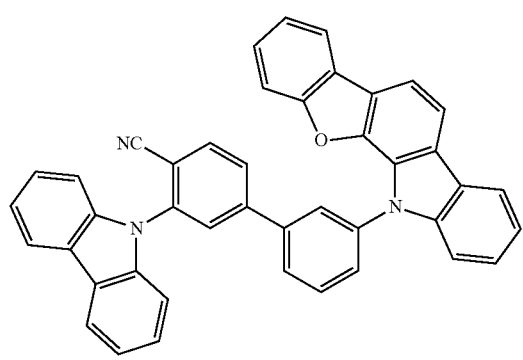
134
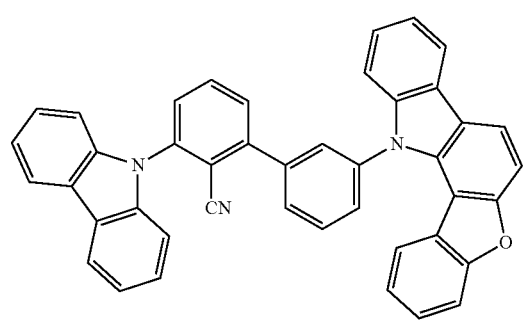

-continued
135
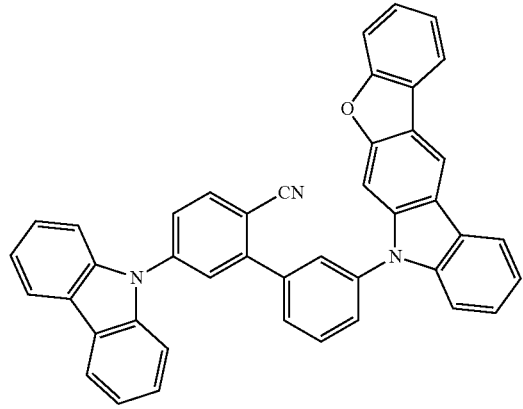
136
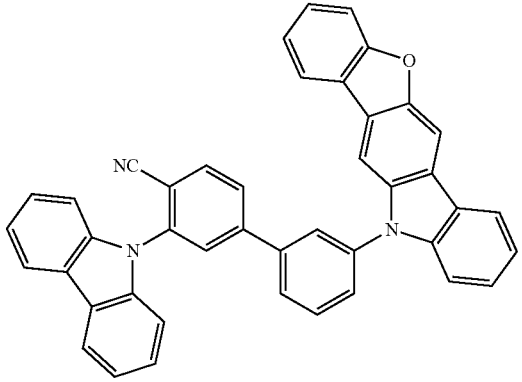
137
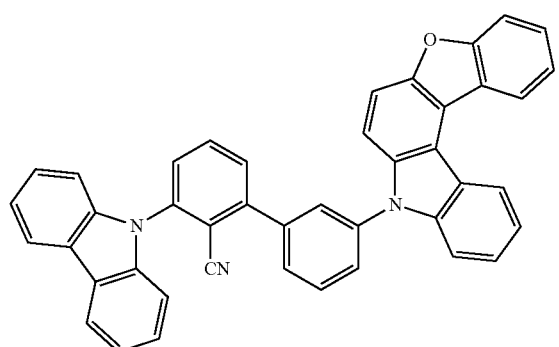
138
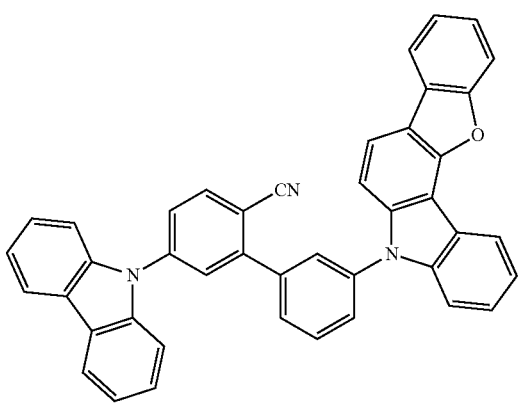
139
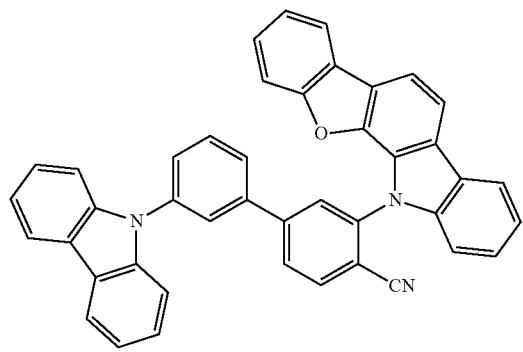
140
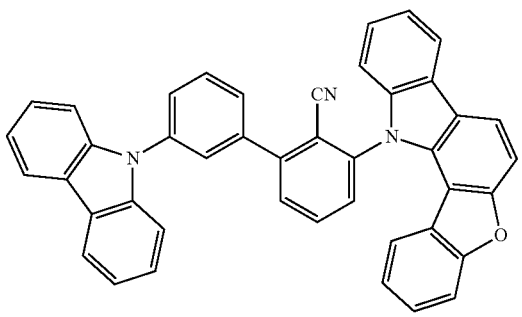
141
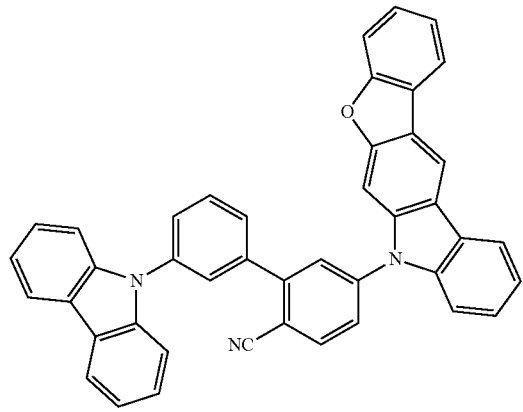
142
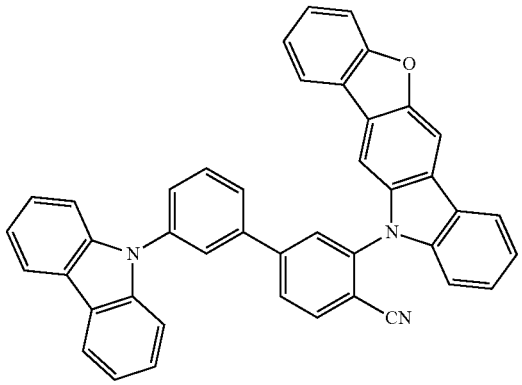

143
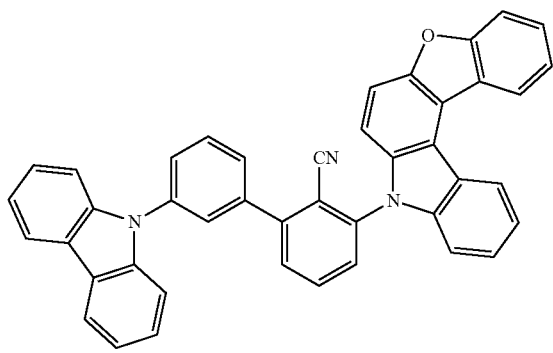
144
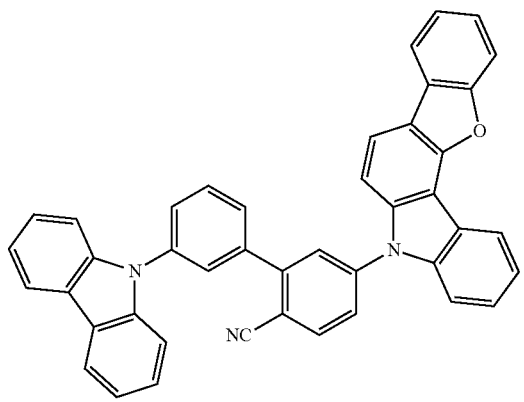
145
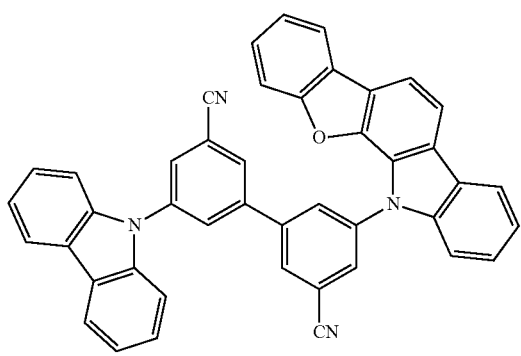
146
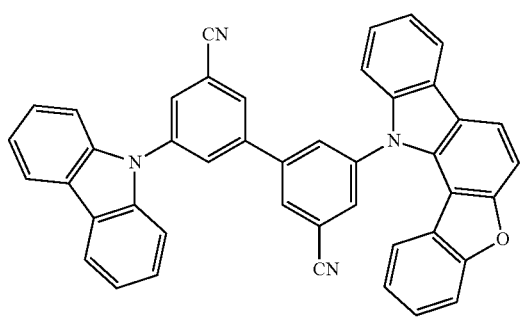
147
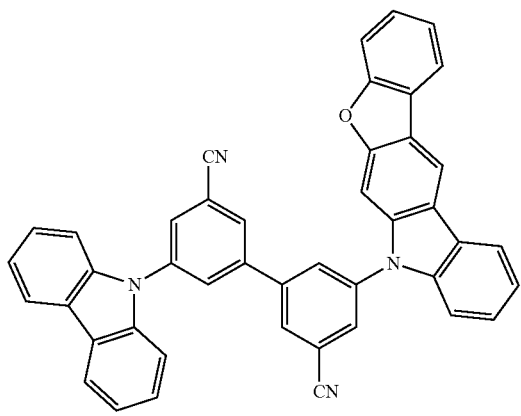
148
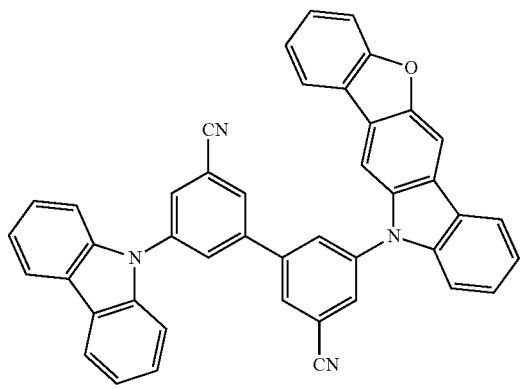
149
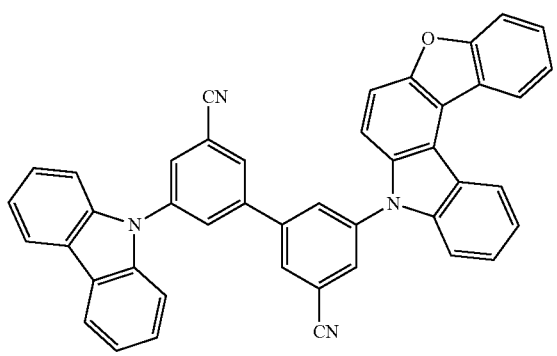
150
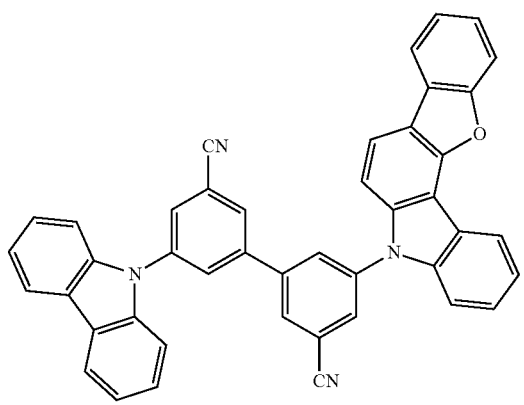

-continued
150
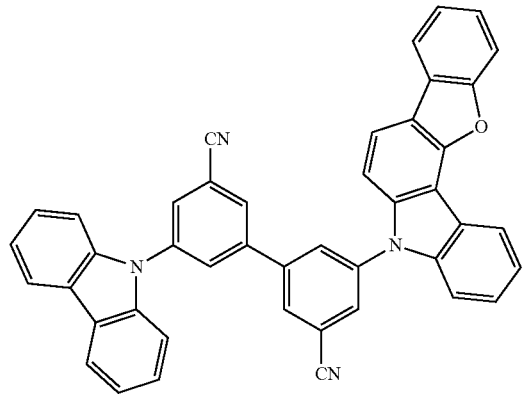
151
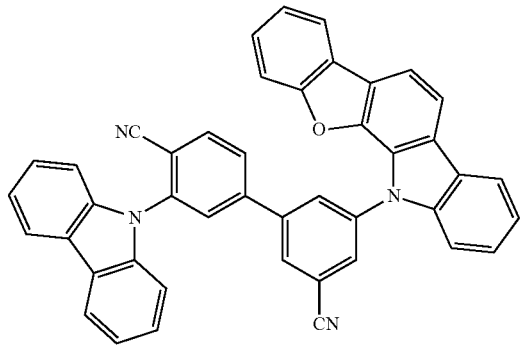
152
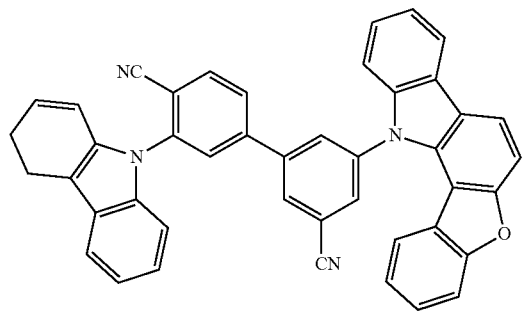
153
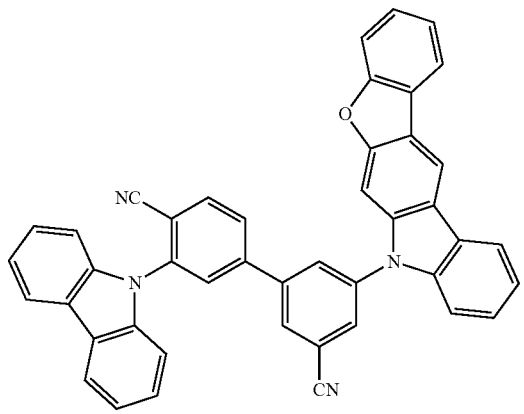
154
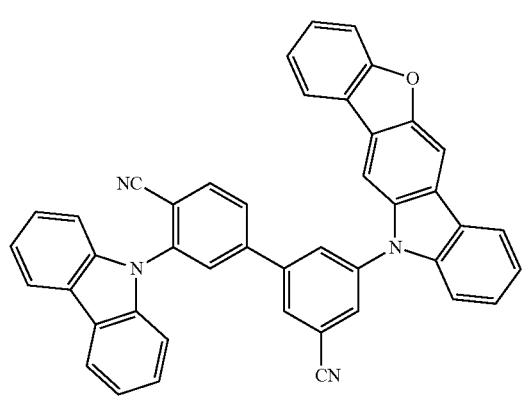
155
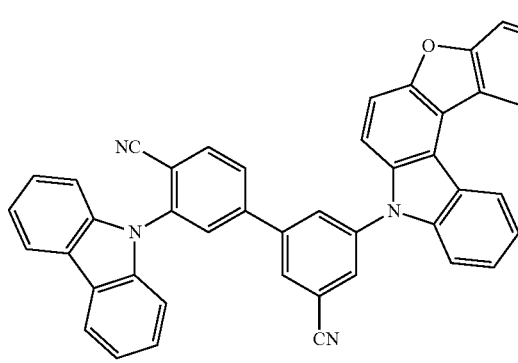
156
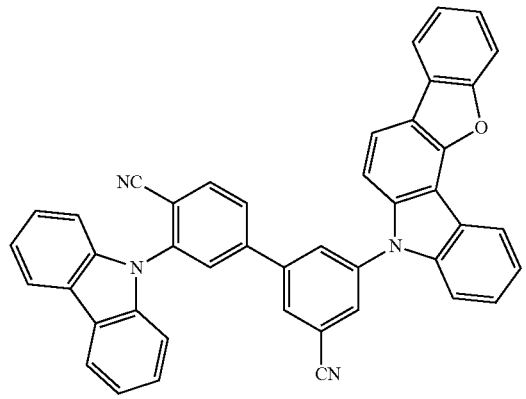
157
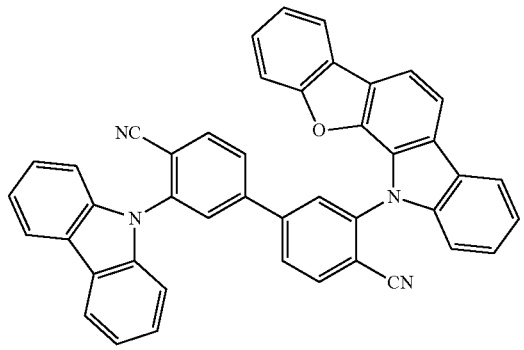

-continued
158
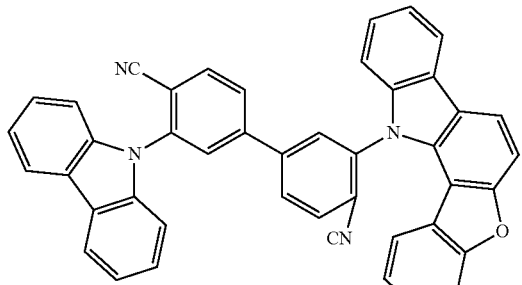
159
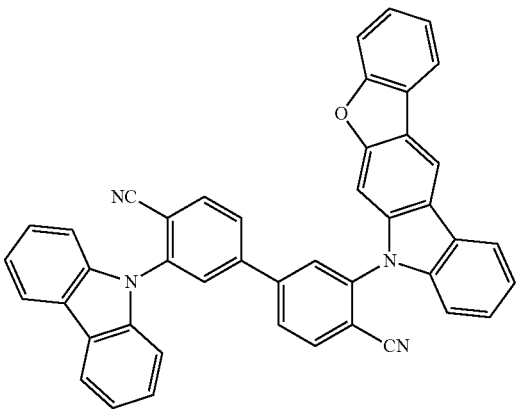
160
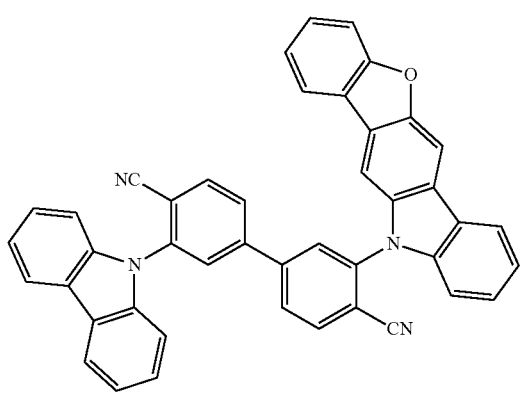
161
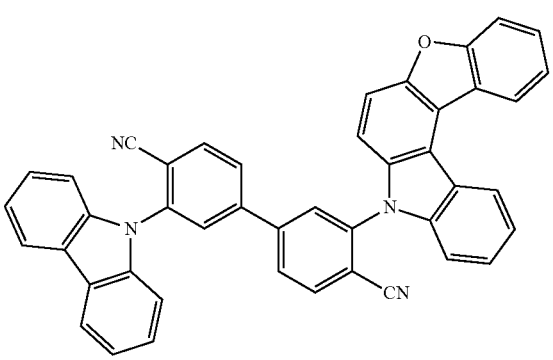
162
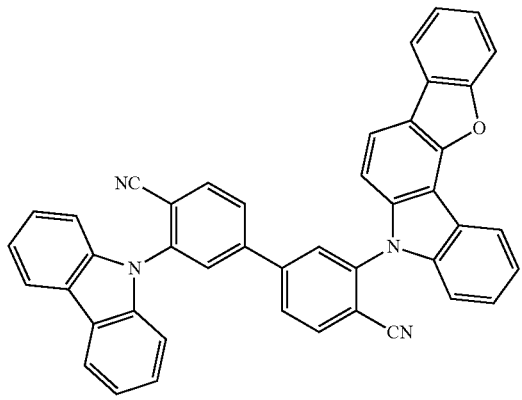
163
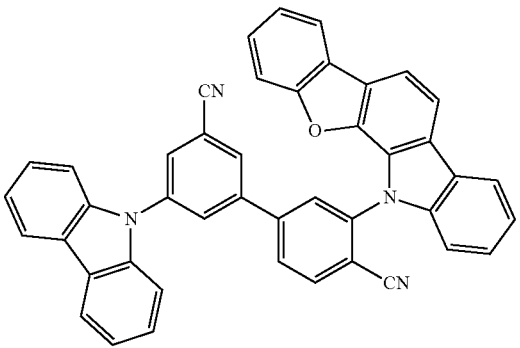
164
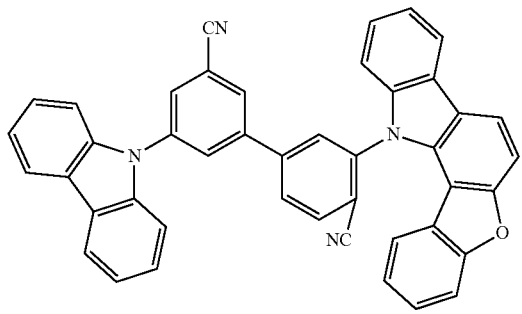
165
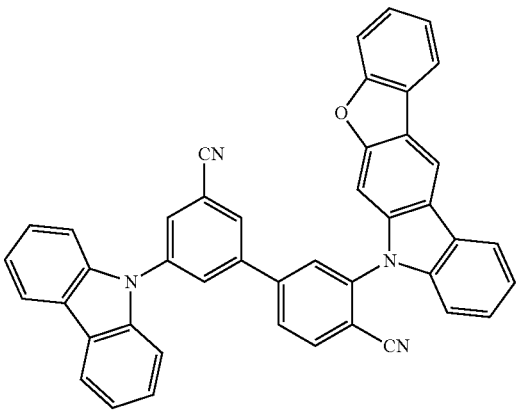

-continued
166
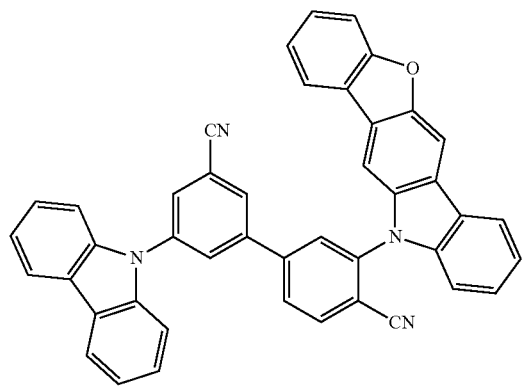
167
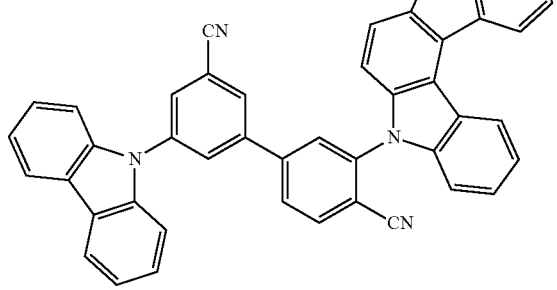
168
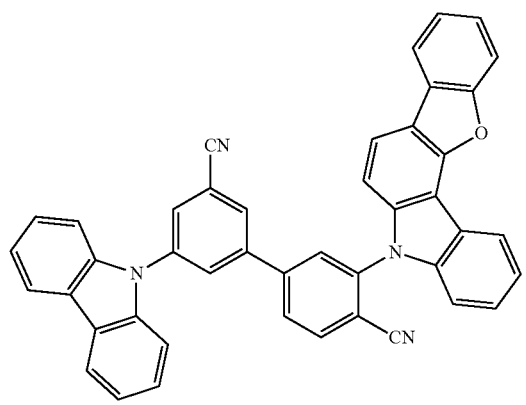
169
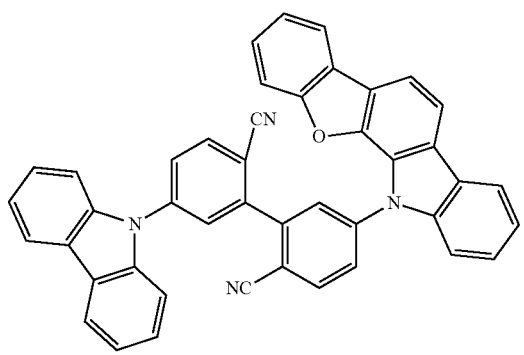
170
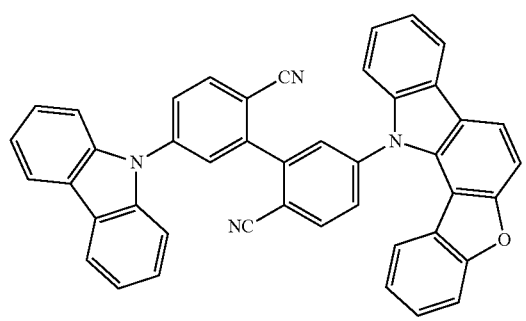
171
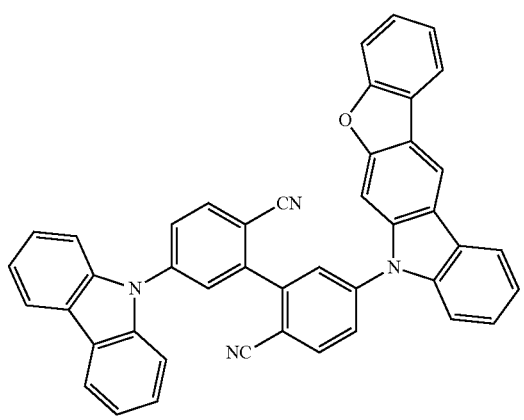
172
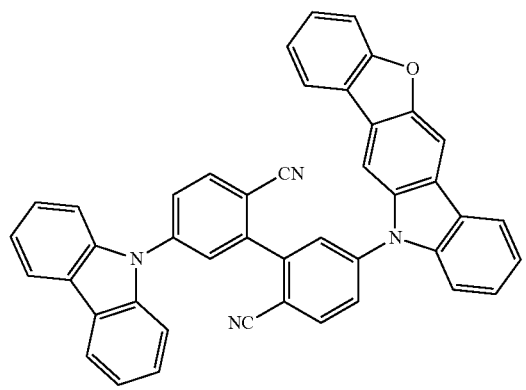
173
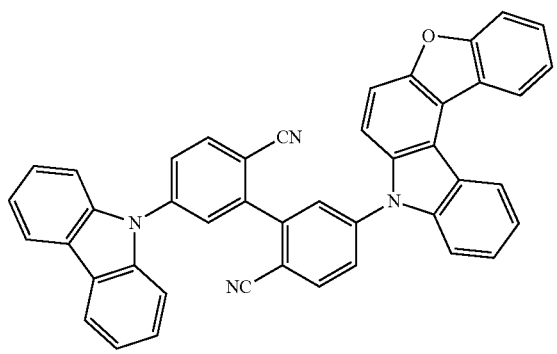

-continued
174
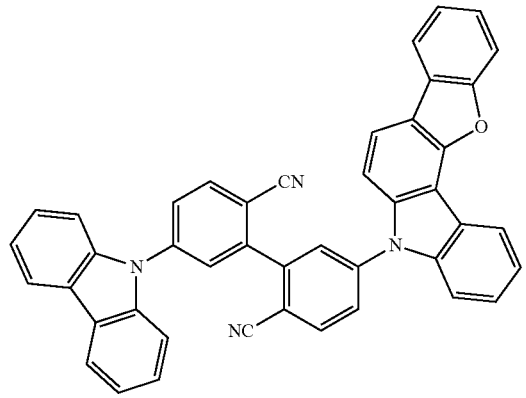
175
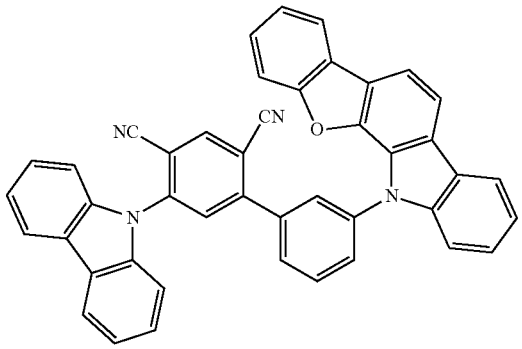
176
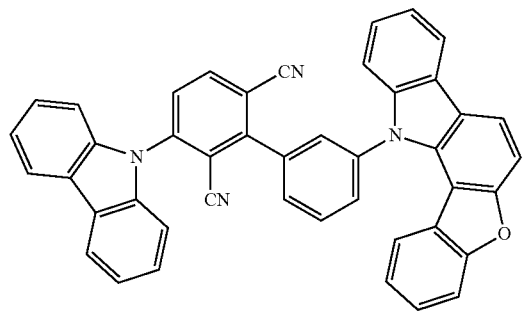
177
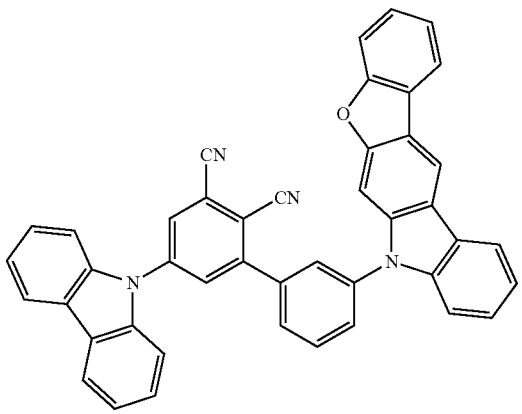
178
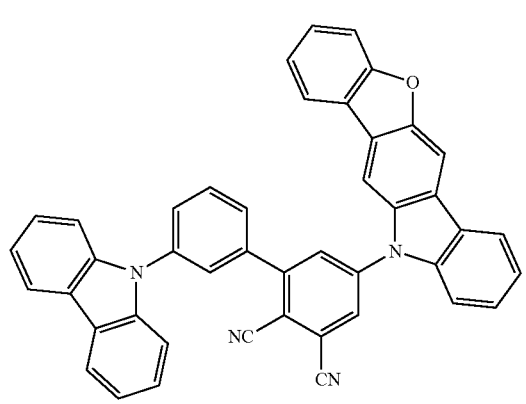
179
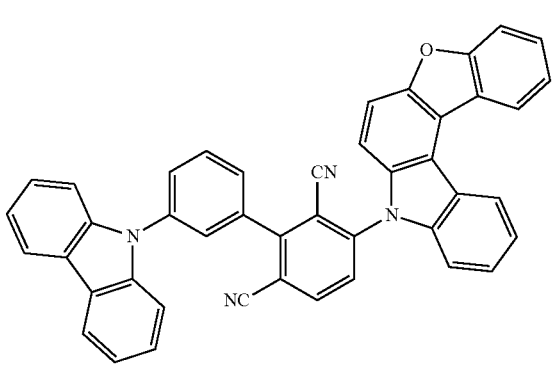
180
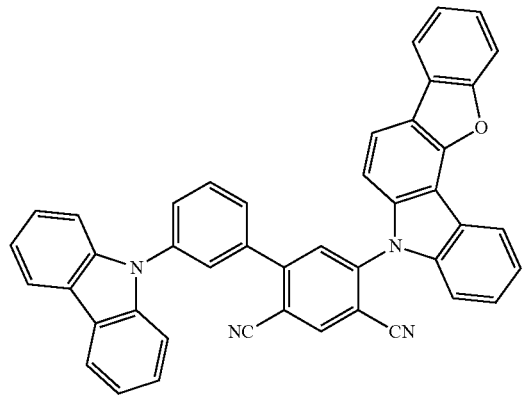
181
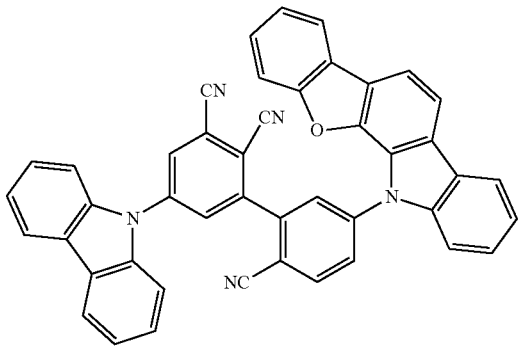

-continued
182
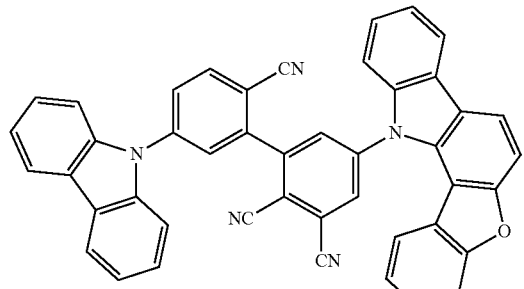
183
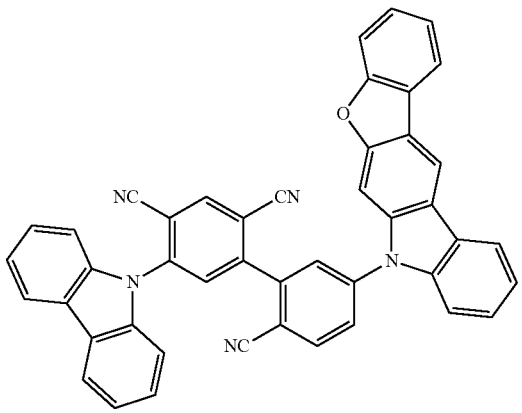
184
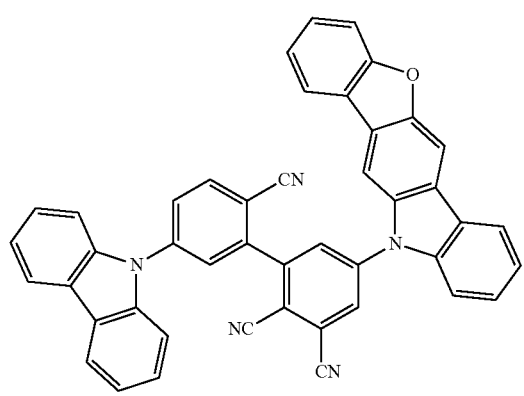
185
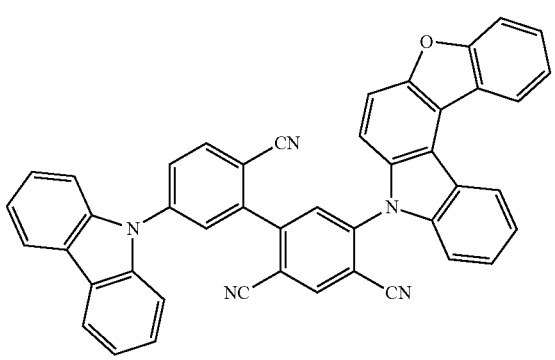
186
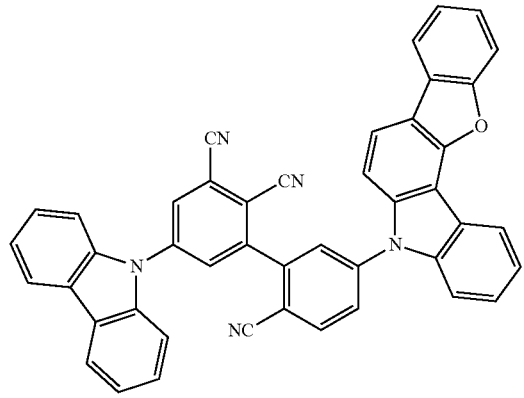
187
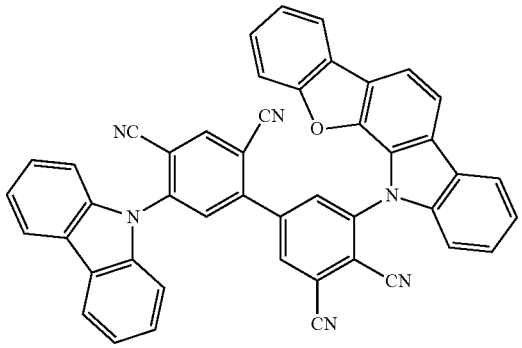
188
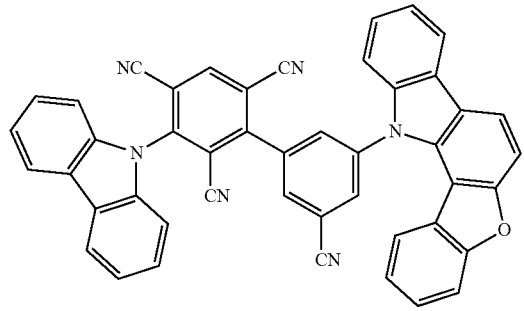
189
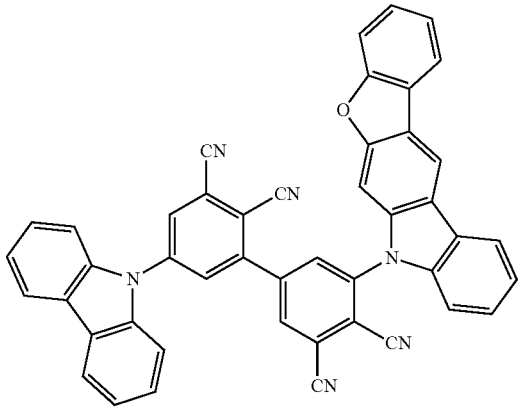

-continued
190
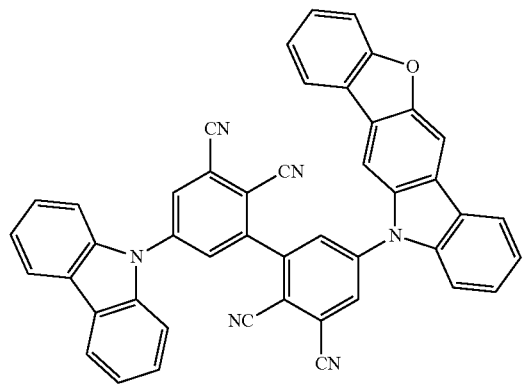
191
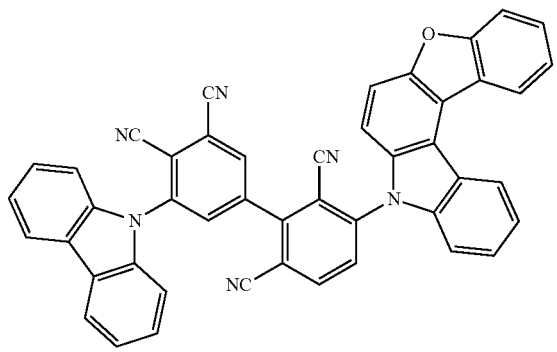
192
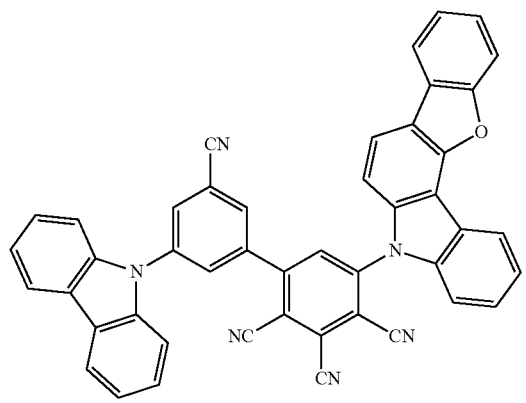
193
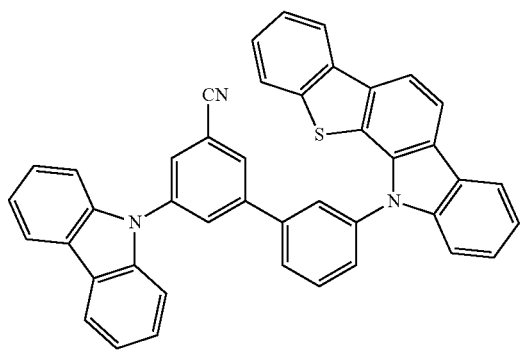
194
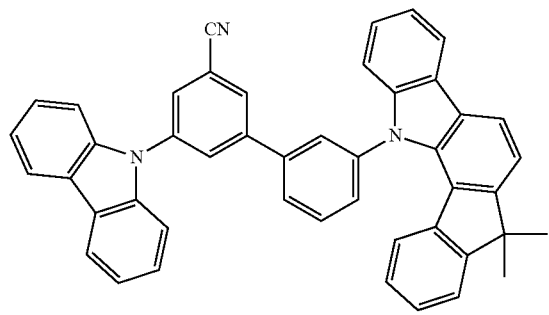
195
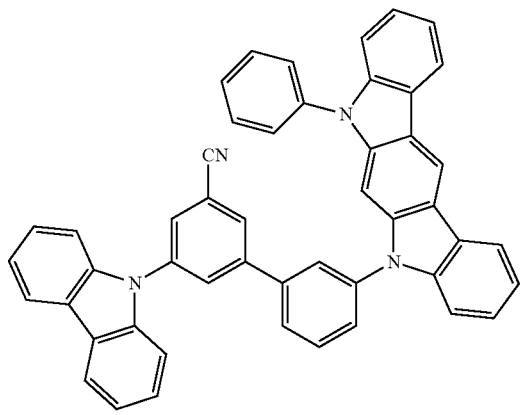
196
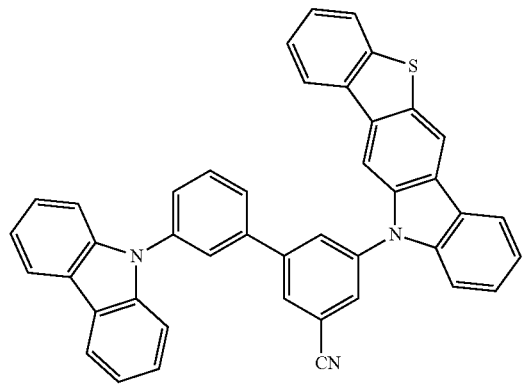
197
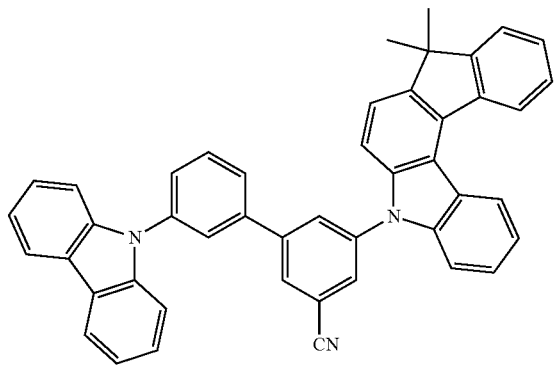

-continued
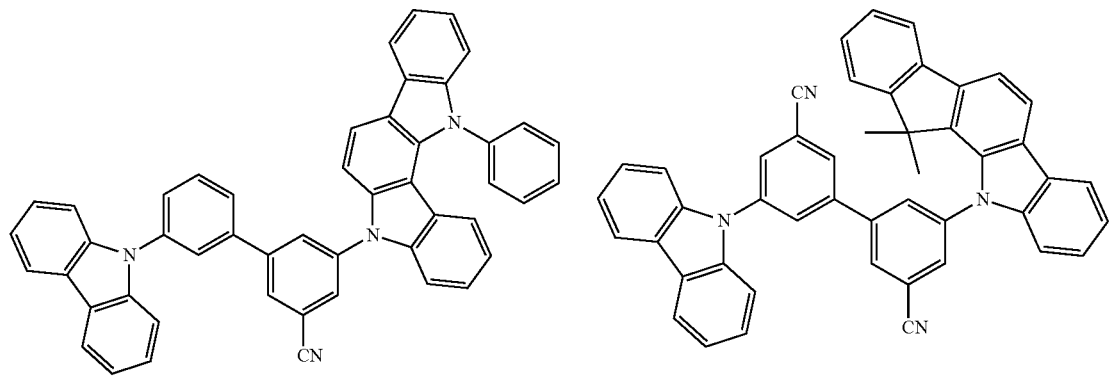
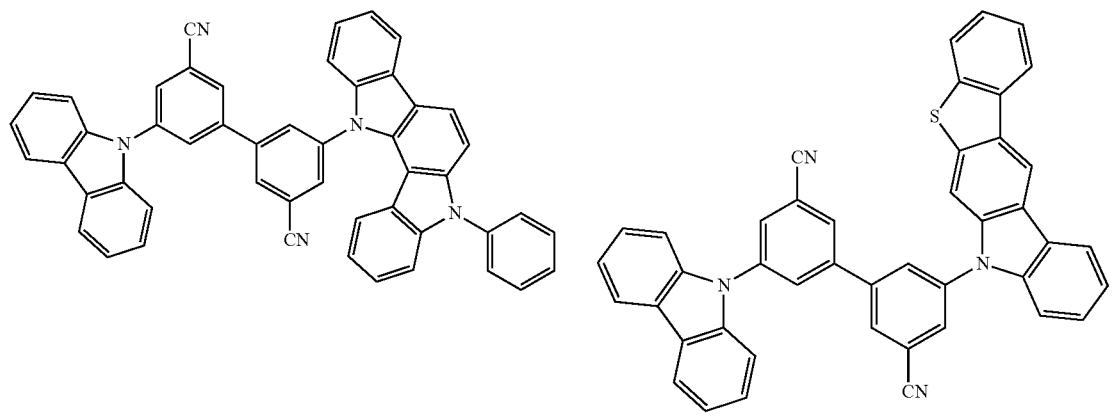
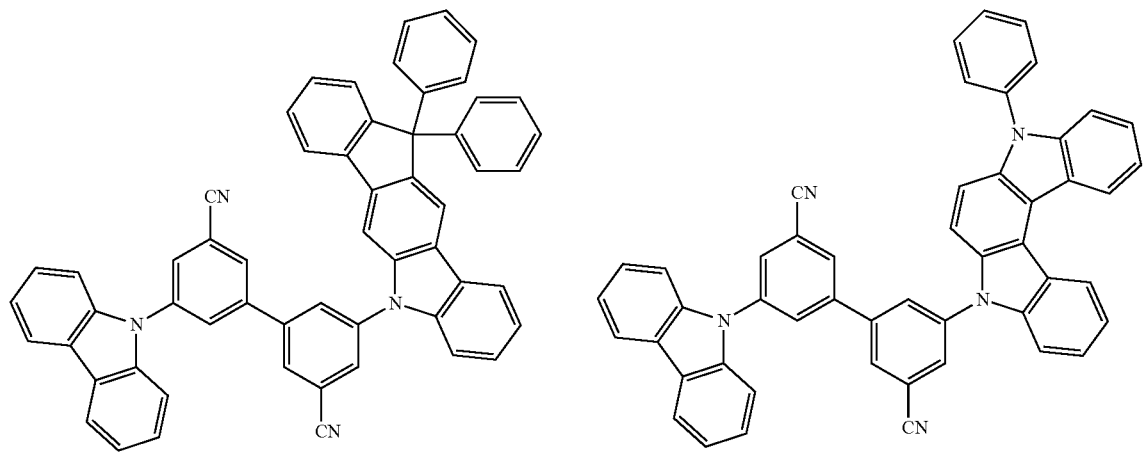

-continued
204
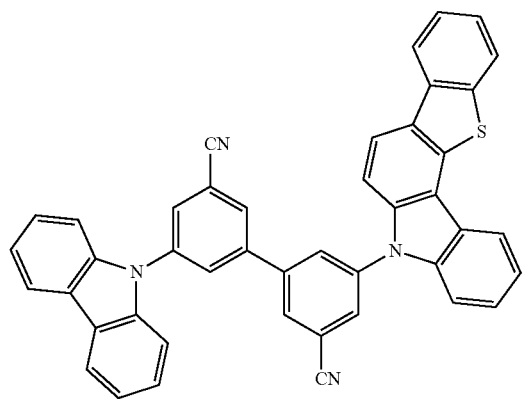
205
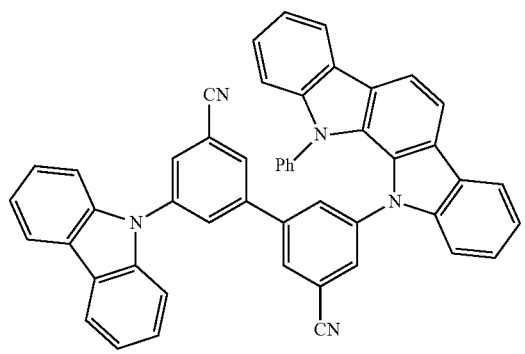
206
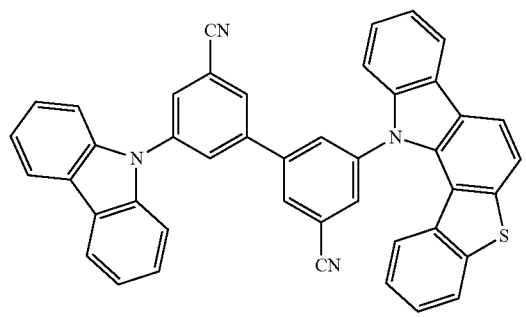
207
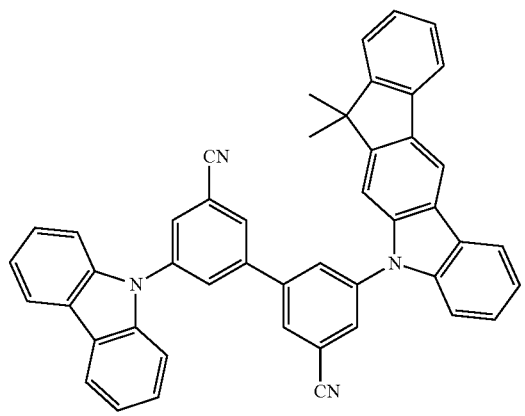
208
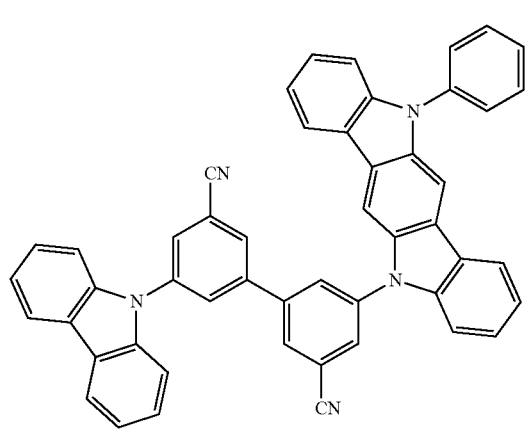
209
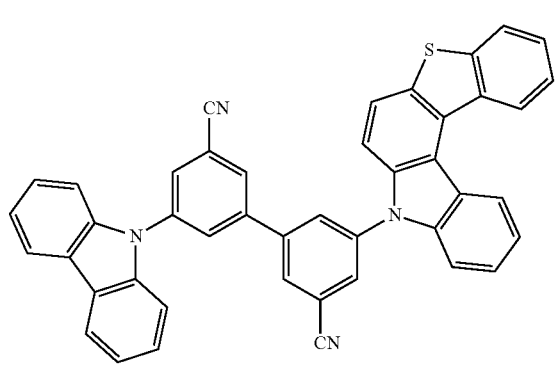
210
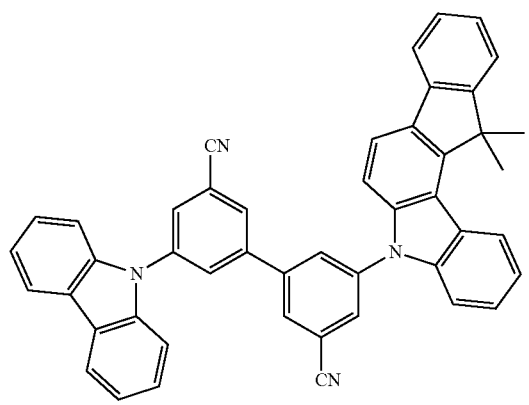
211
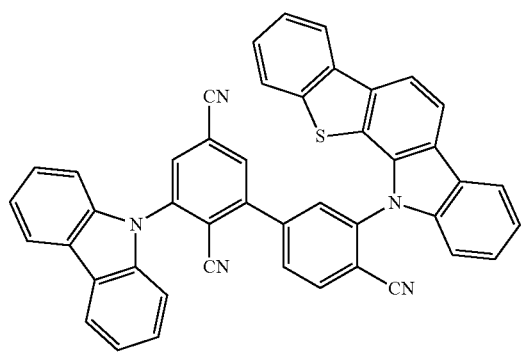

-continued
212
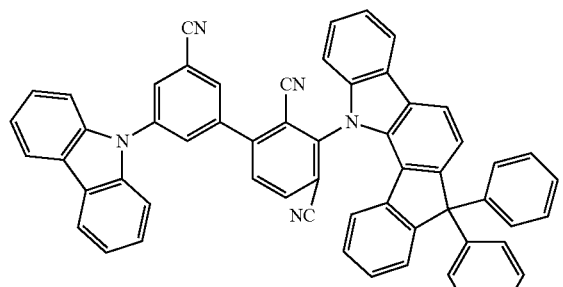
213
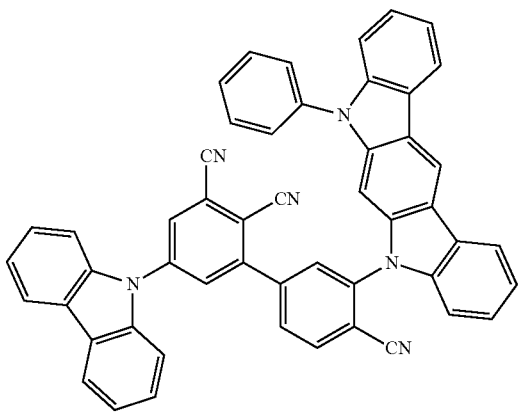
214
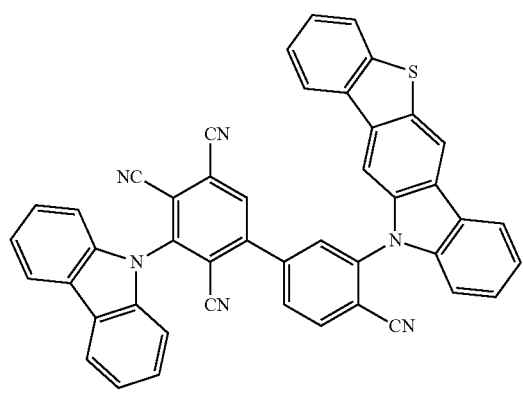
215
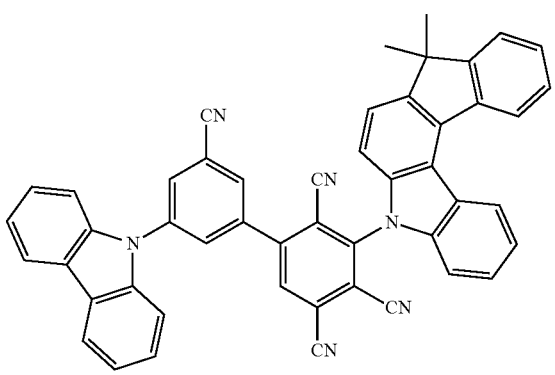
216
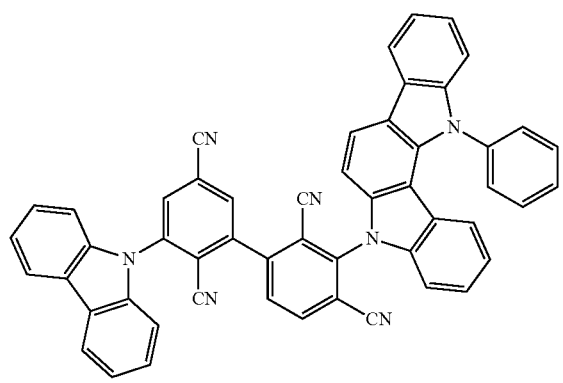
217
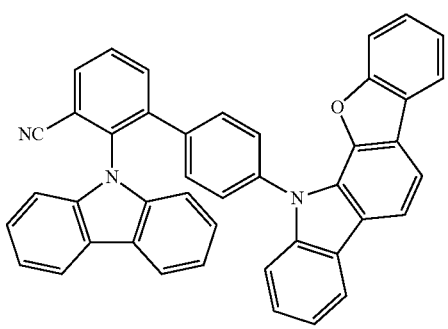
218
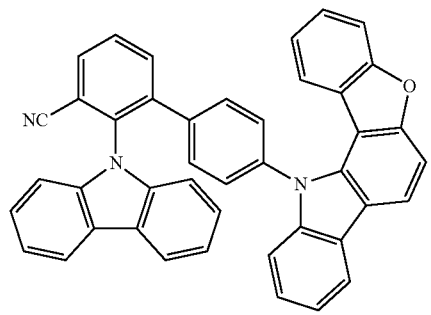
219
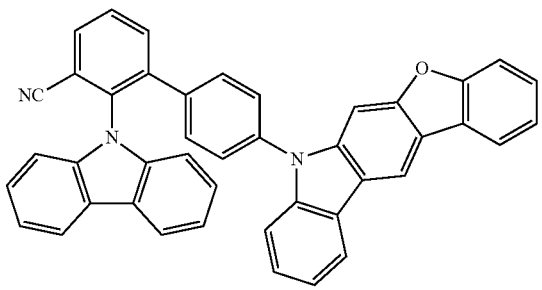

-continued
220
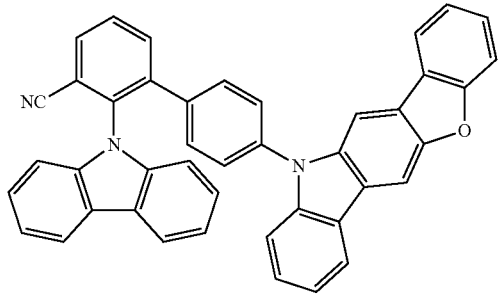
221
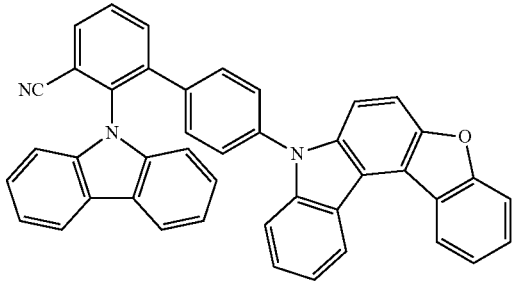
222
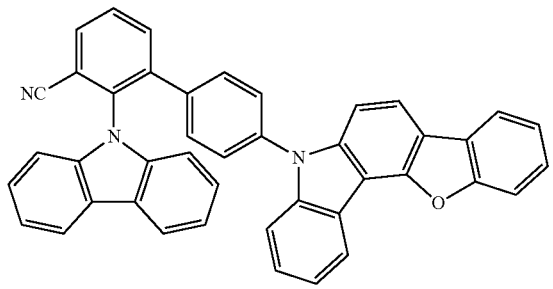
223
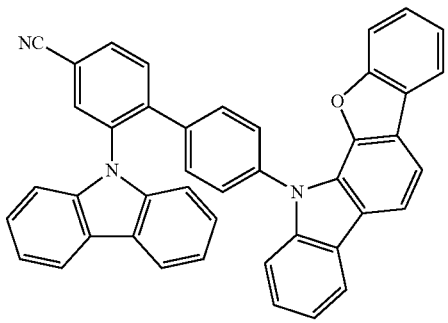
224
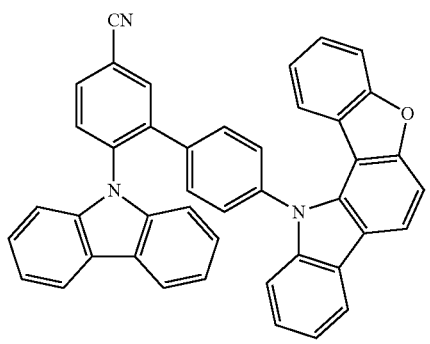
225
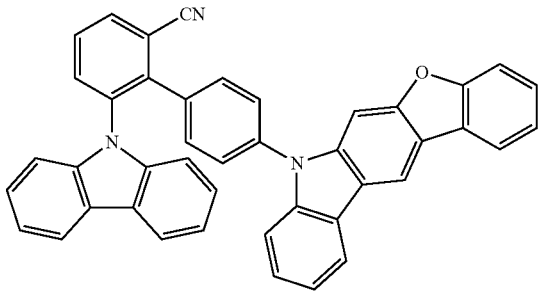
226
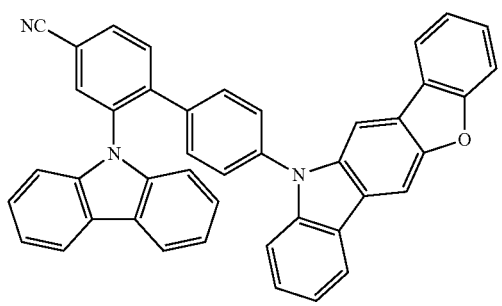
227
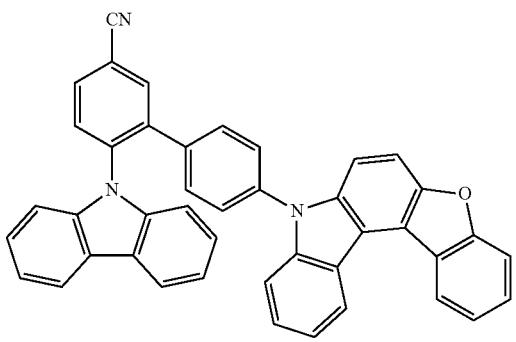

-continued
228
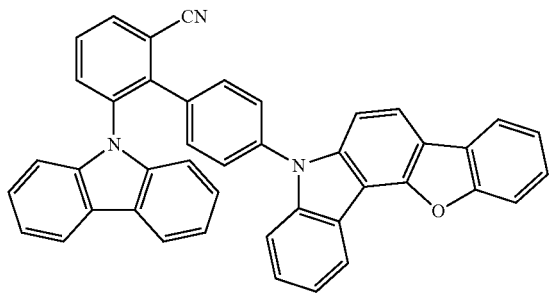
-continued
229
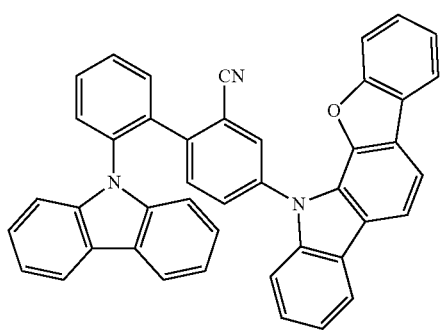
232
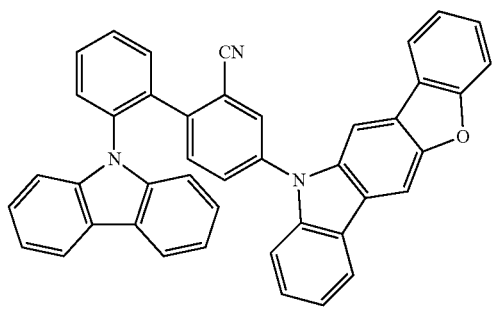
233
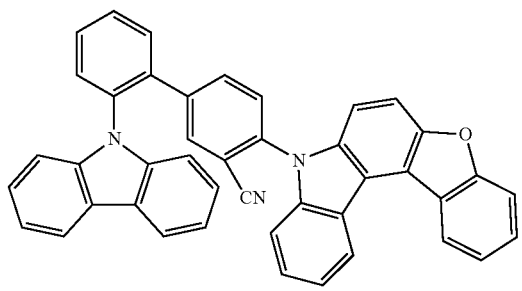
230
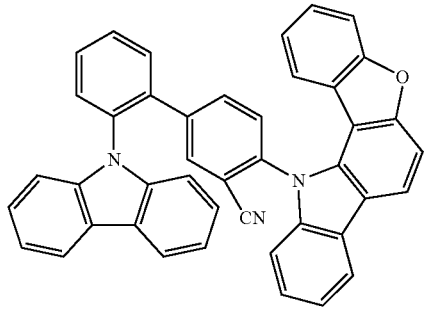
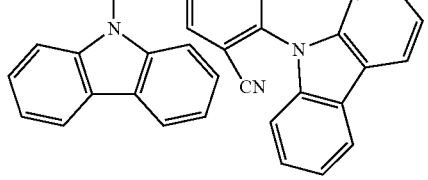
234
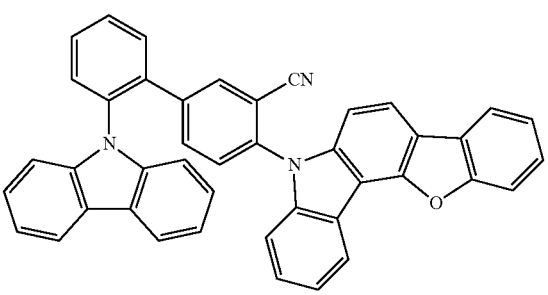
231
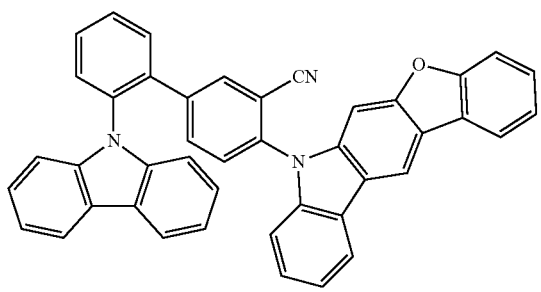
235
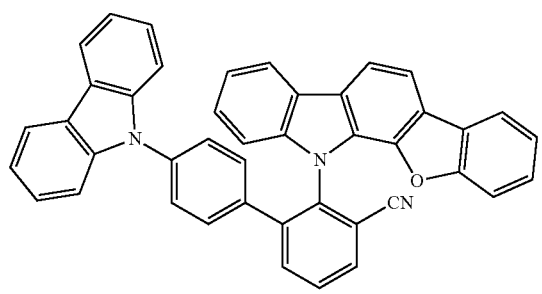

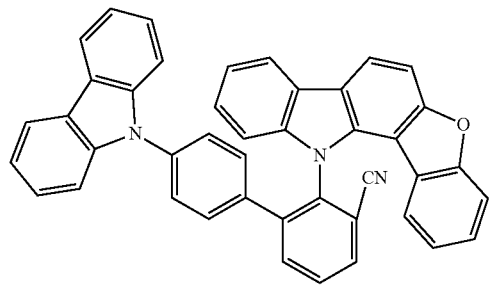
236
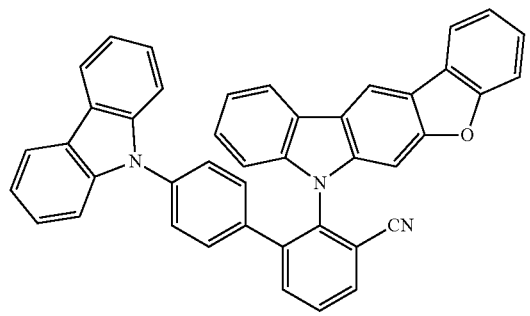
237
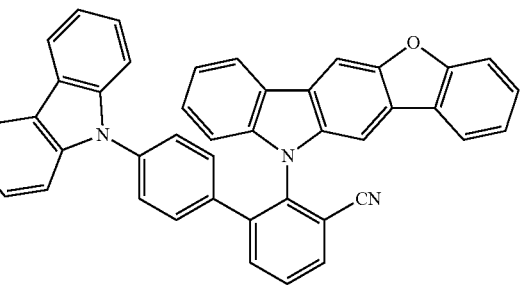
238
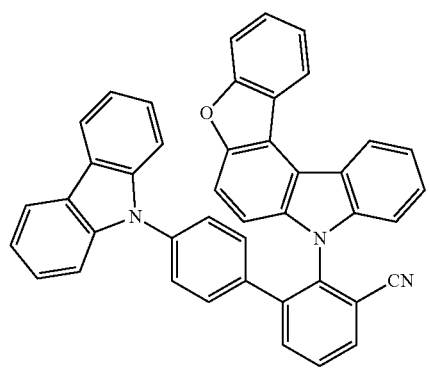
239
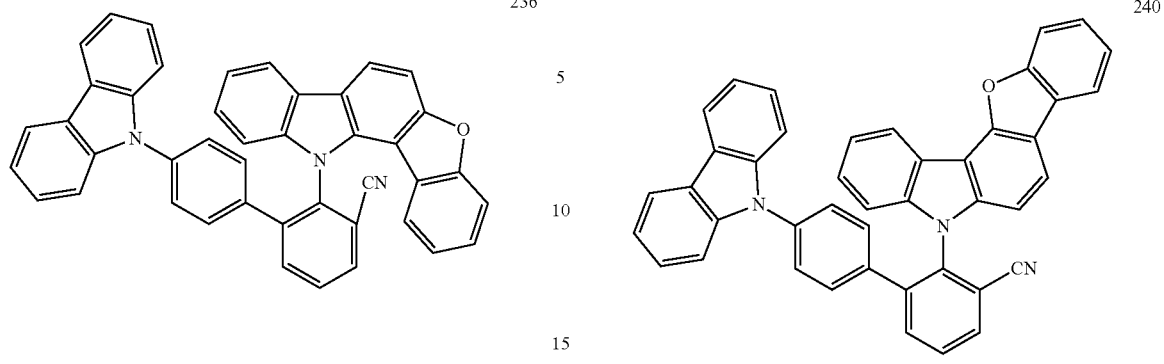

-continued
244
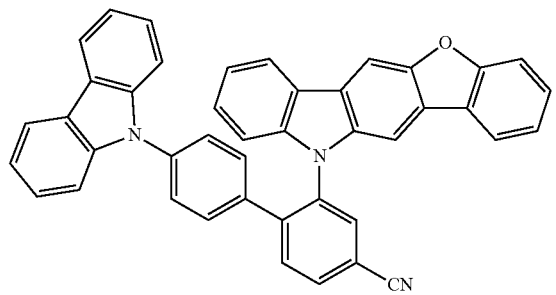
245
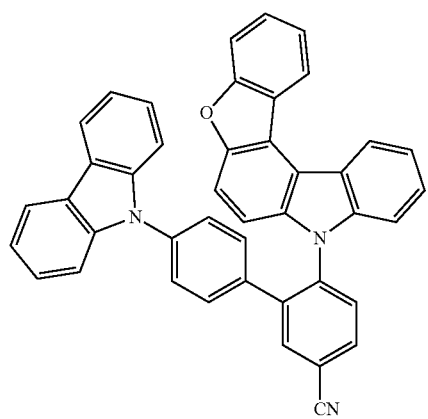
246
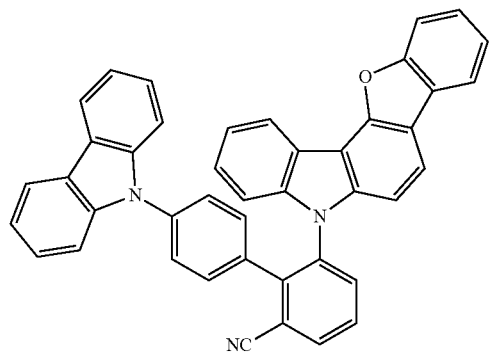
247
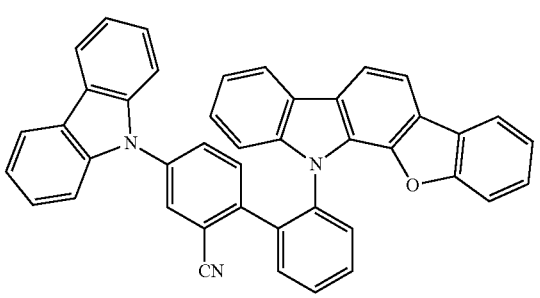
-continued
248
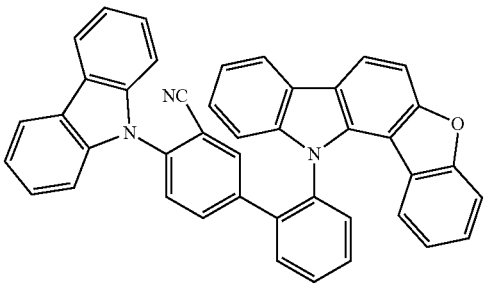
249
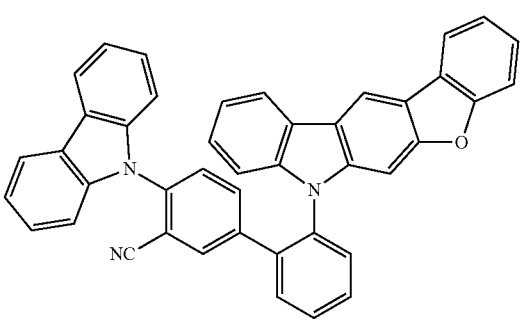
250
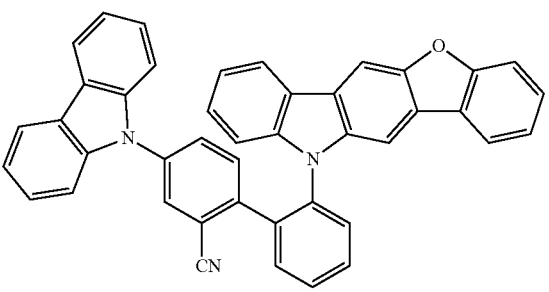
251
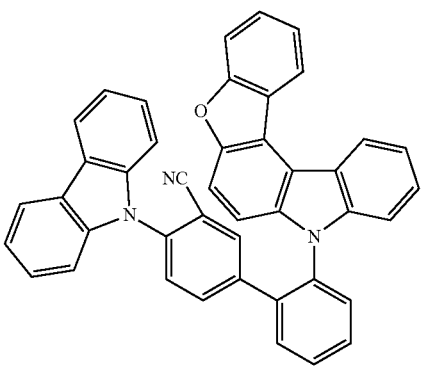

252
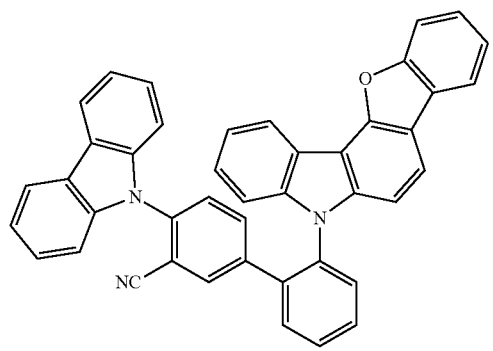
253
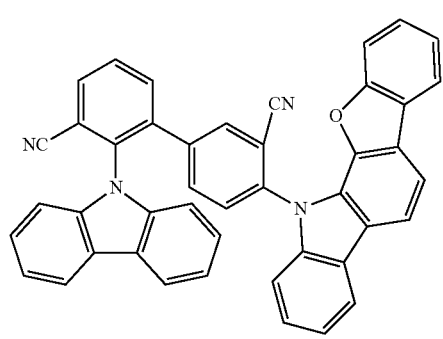
254
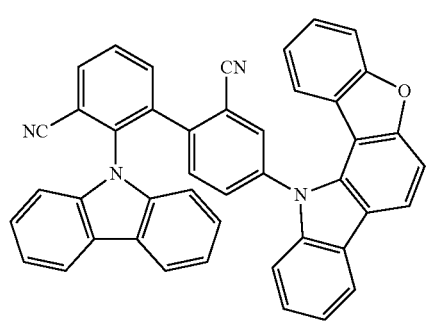
255
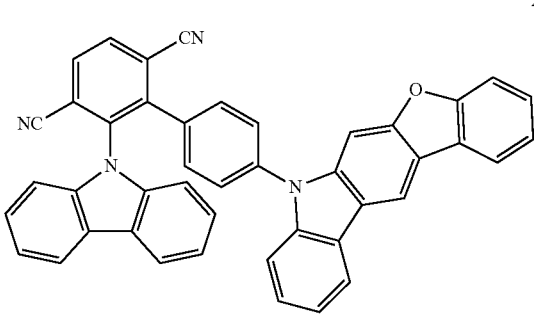
256
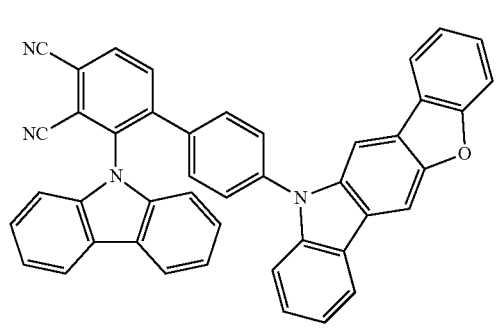
257
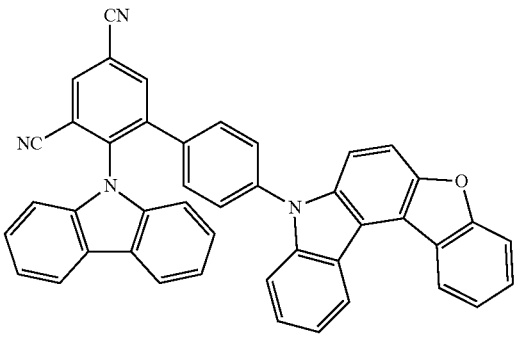
258
259
260
261

262
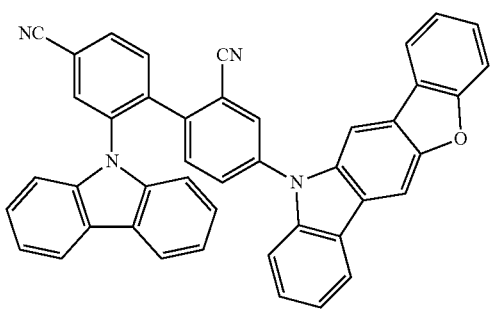
263
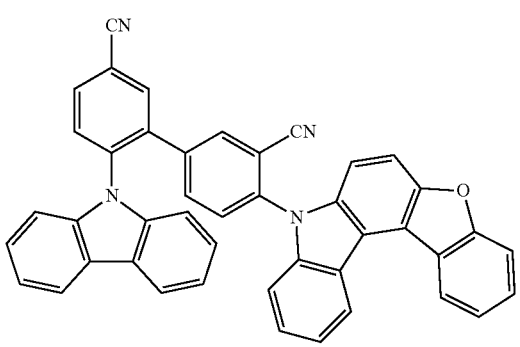
264
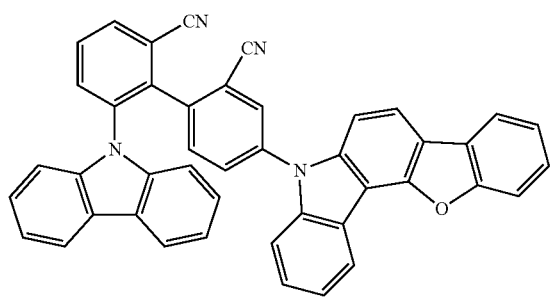
265
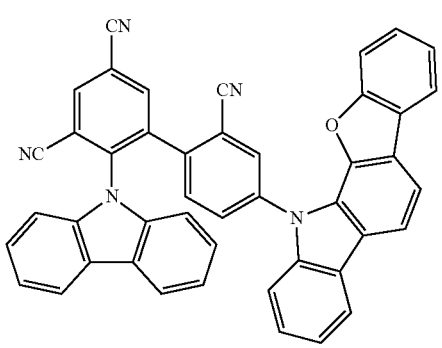
266
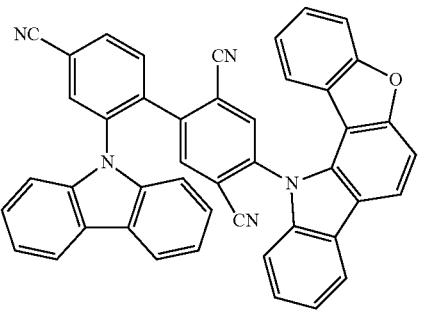
267
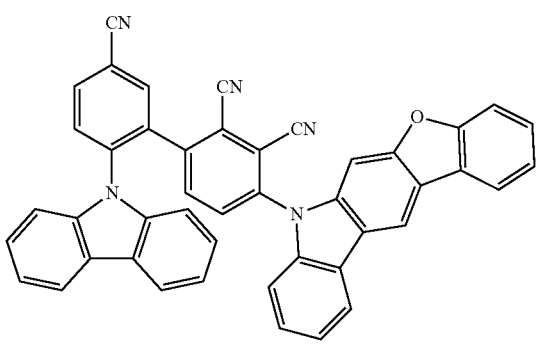
268
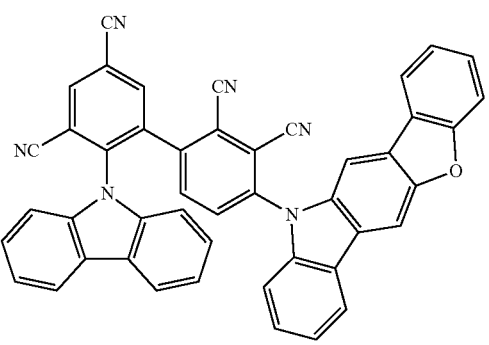
269
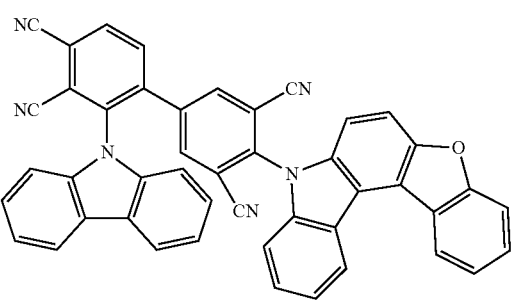

309
-continued
270
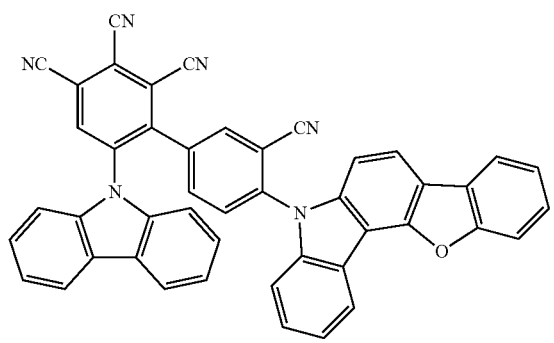
271
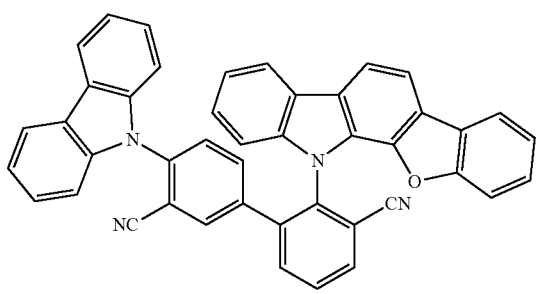
272
273
274
310
-continued
275
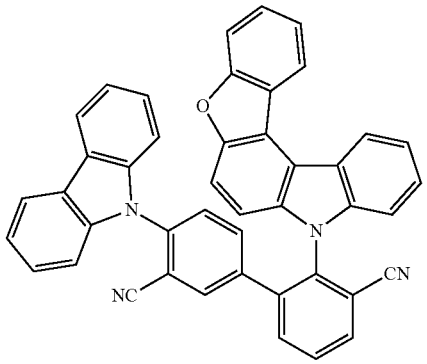
276
277
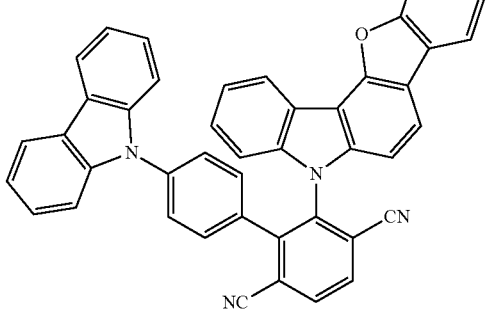
278

-continued
279
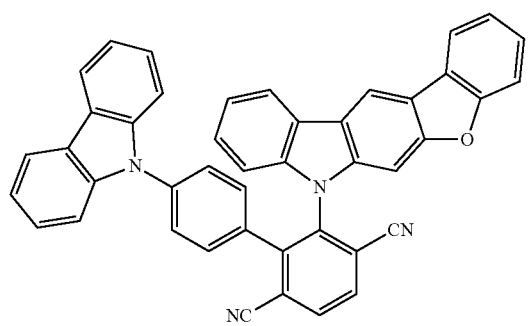
280
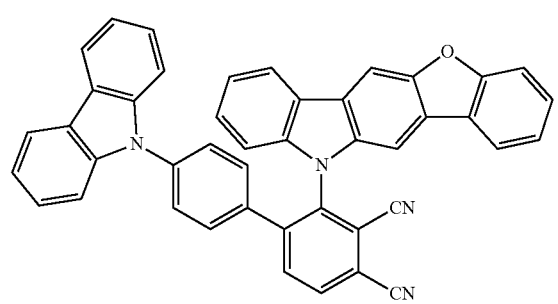
281
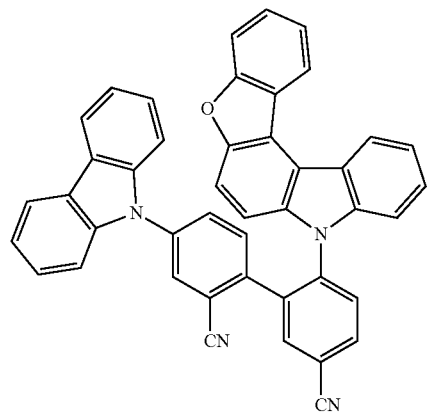
282
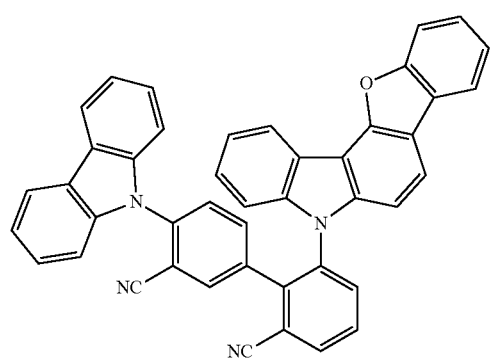
-continued
283
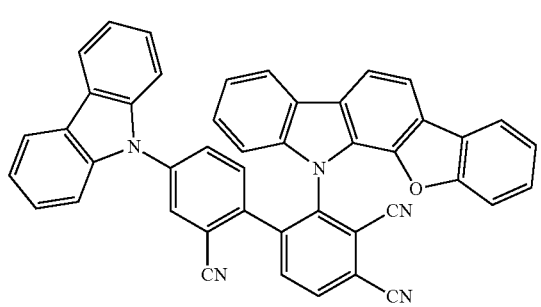
284
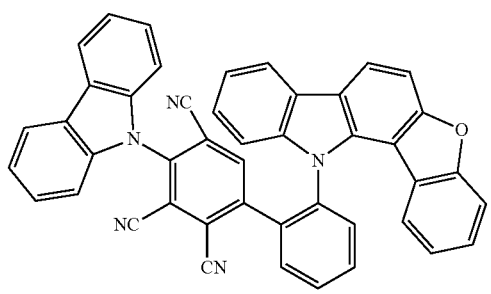
285
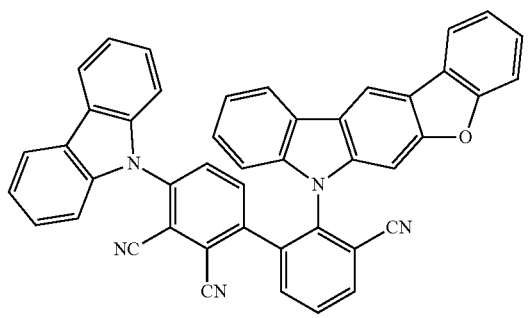
286
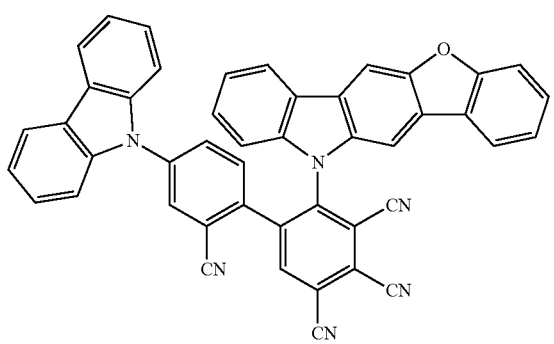

287
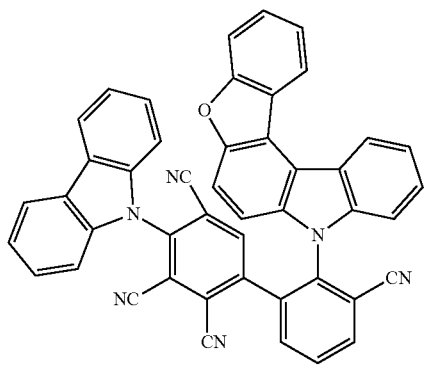
288
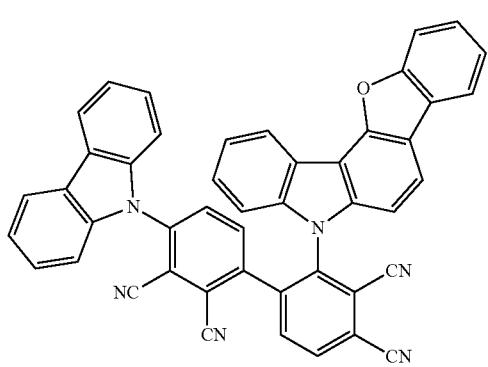
289
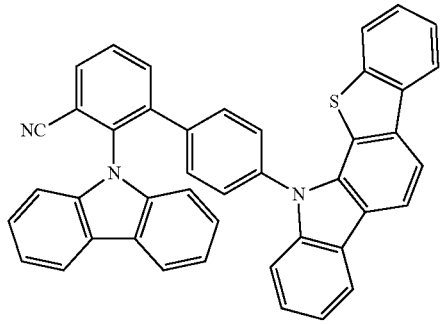
290
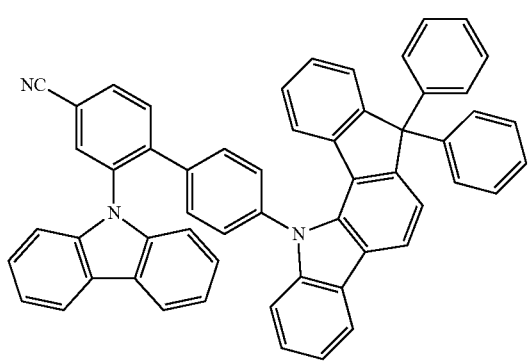
291
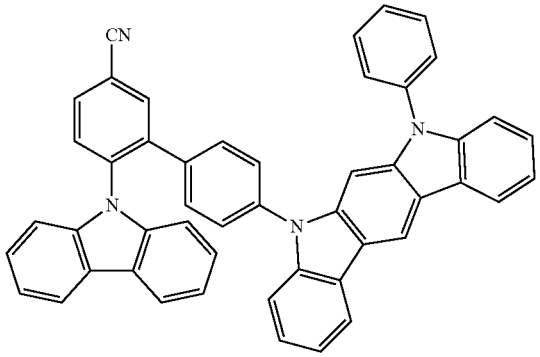
292
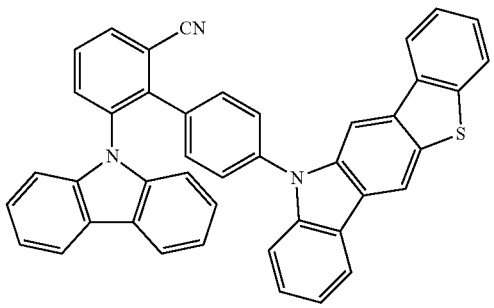
293
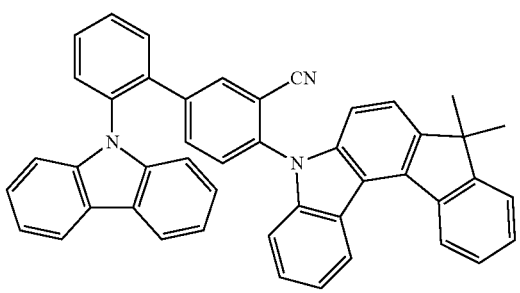
294
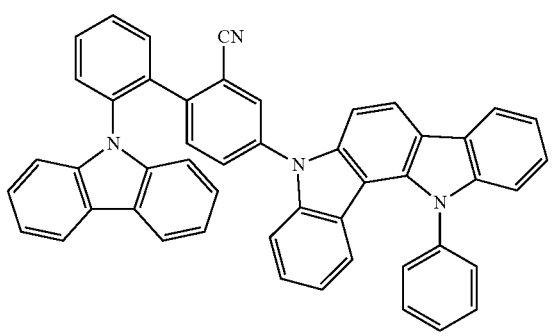

-continued
295
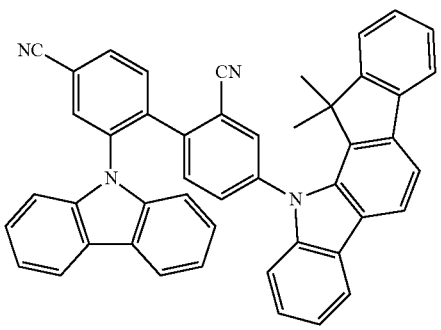
296
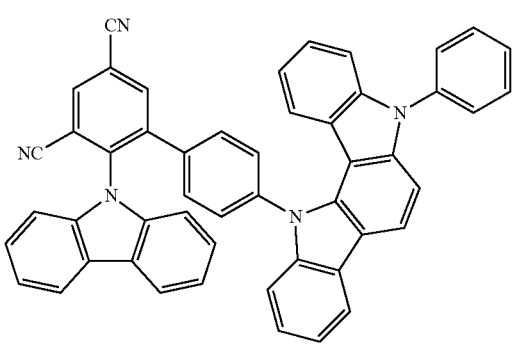
297
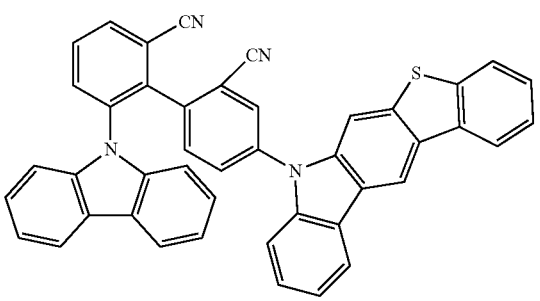
298
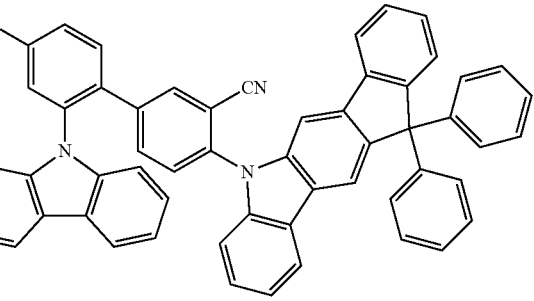
-continued
299
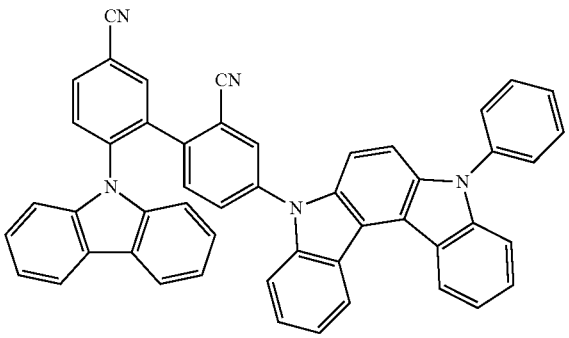
300
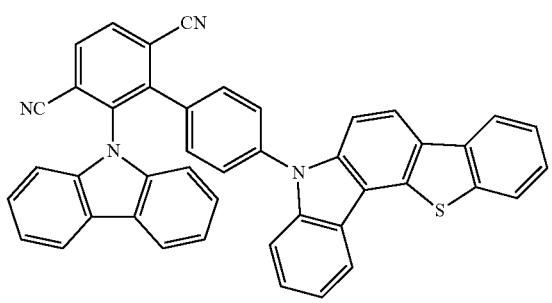
301
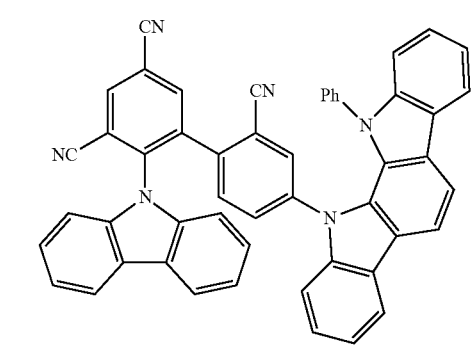
302
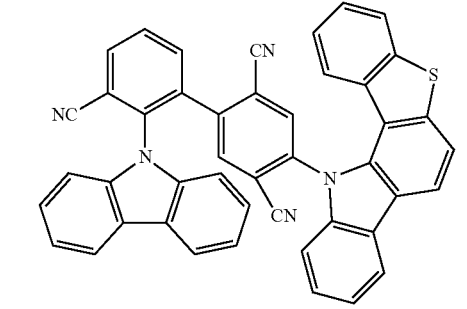
303
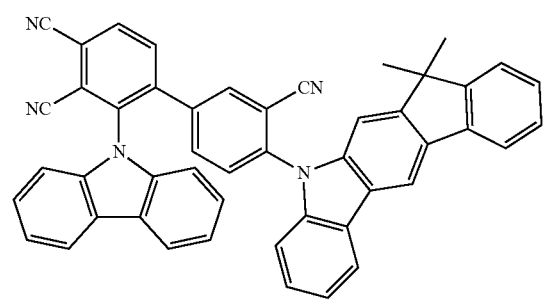

-continued
304
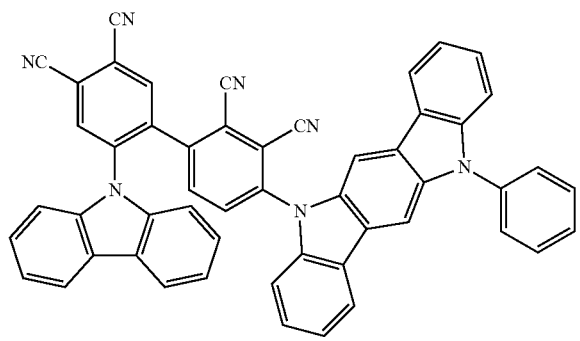
305
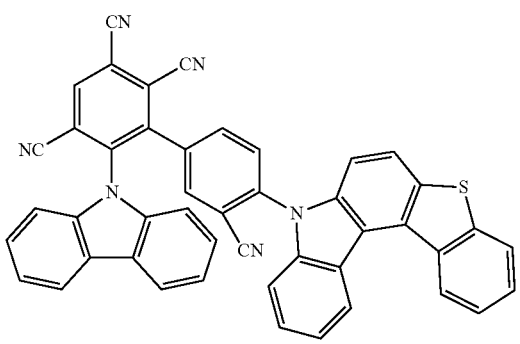
306
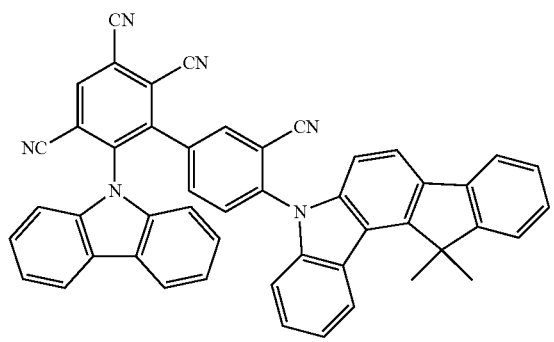
307
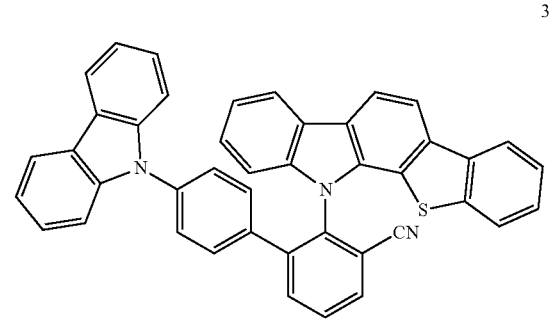
-continued
308
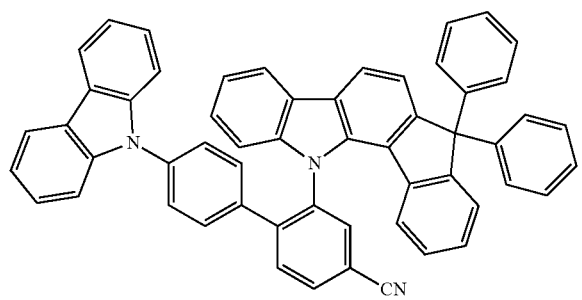
309
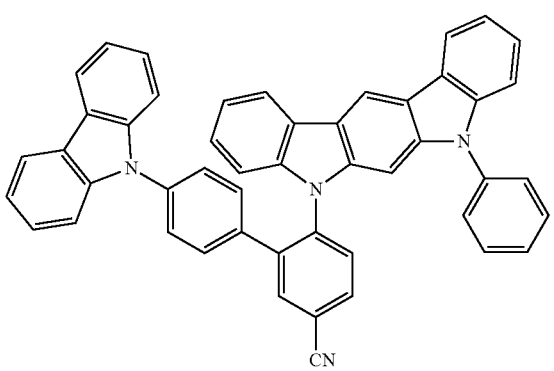
310
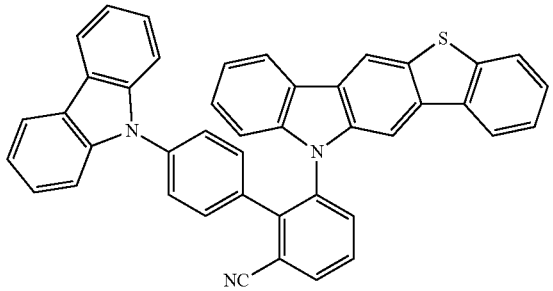
311
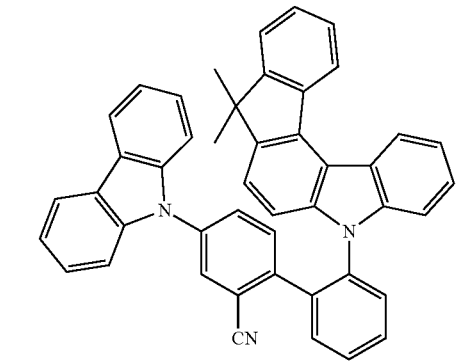

-continued
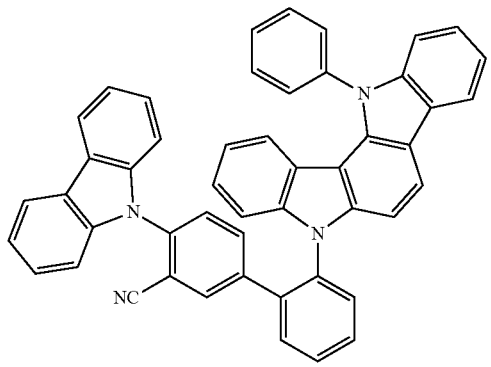
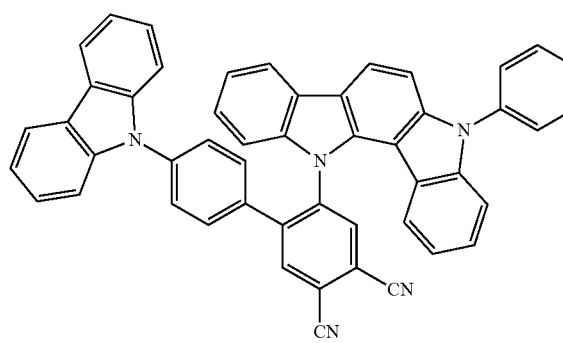
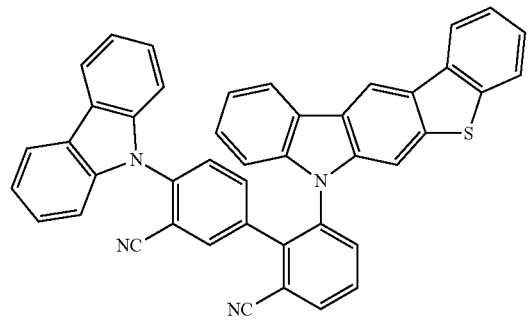
-continued
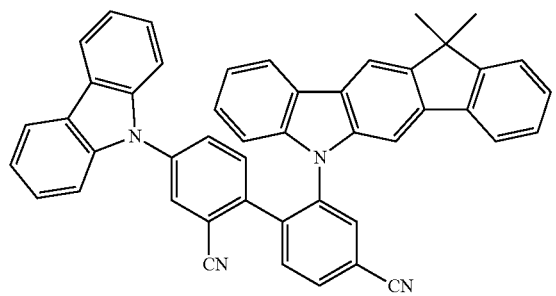
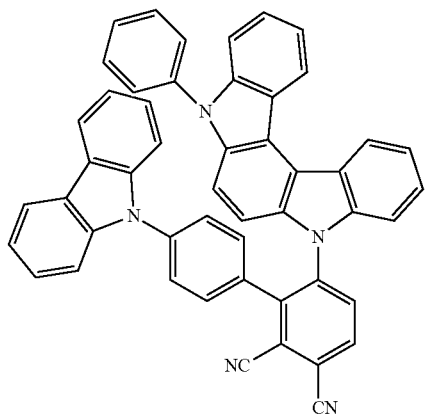
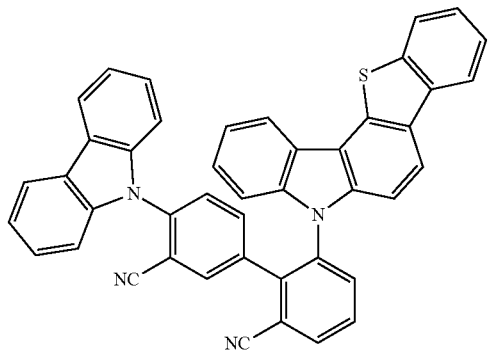
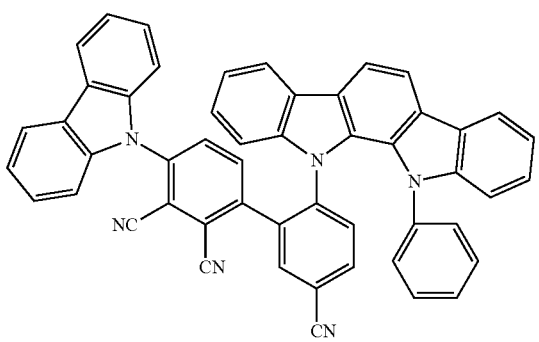

321
-continued
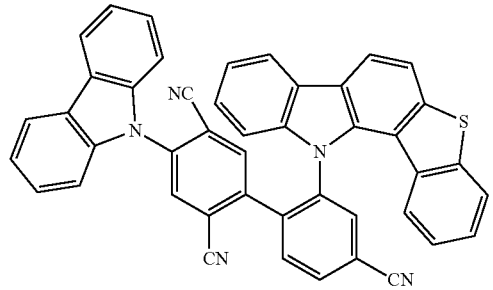
320
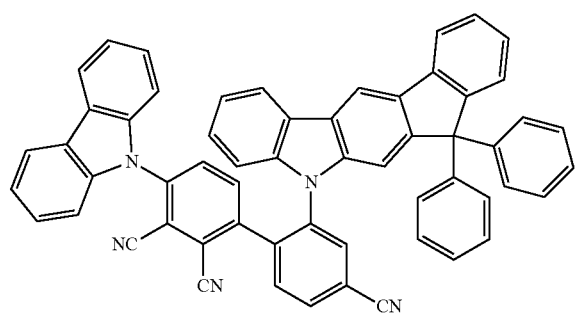
321
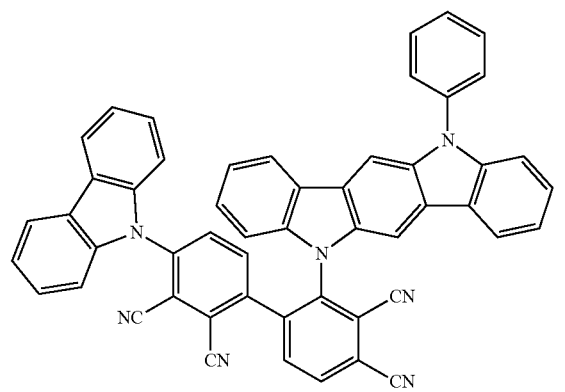
322
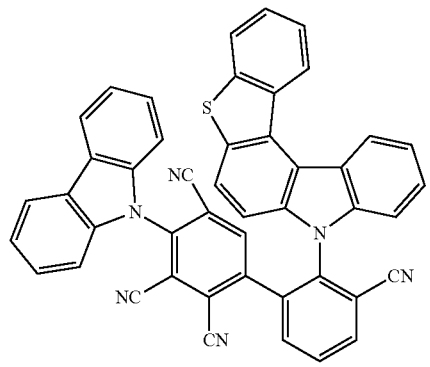
323
322
-continued
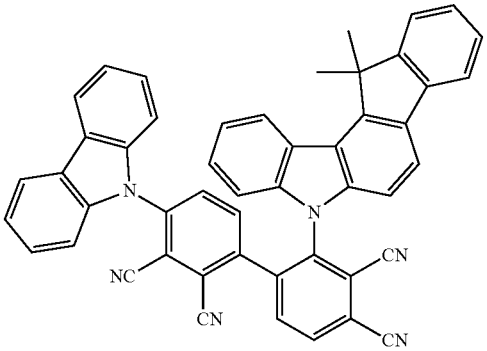
324
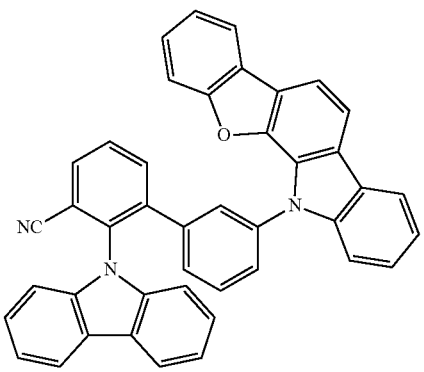
325
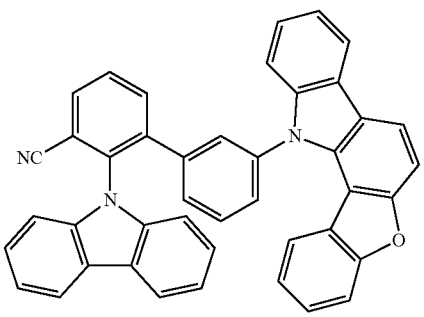
326
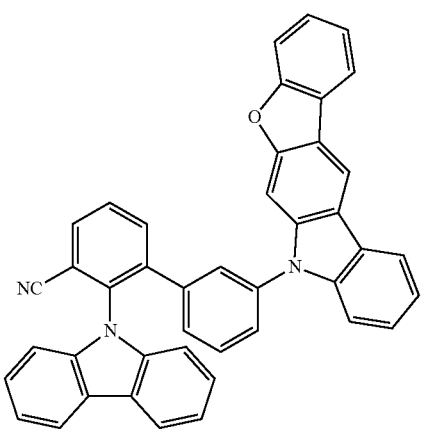
327

328 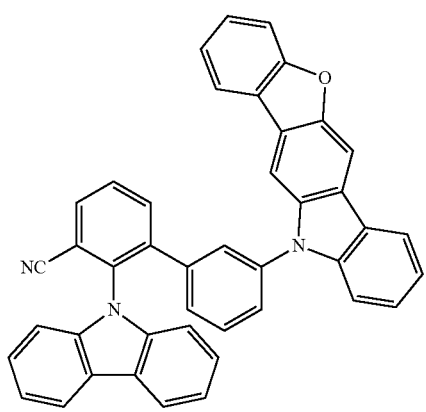
329 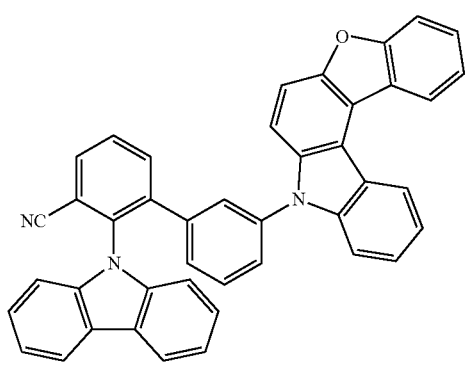
330 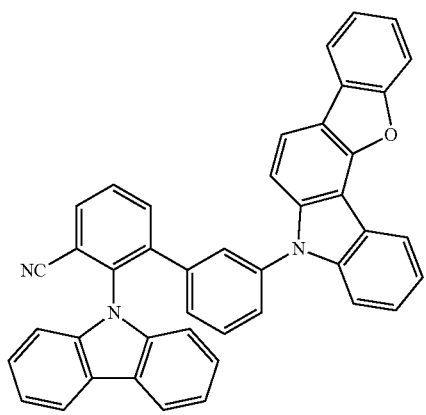
331 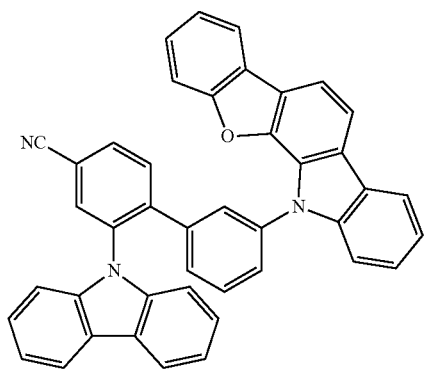
332 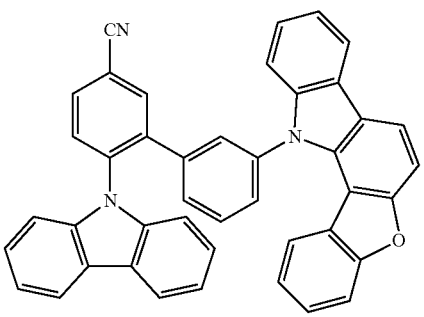
333 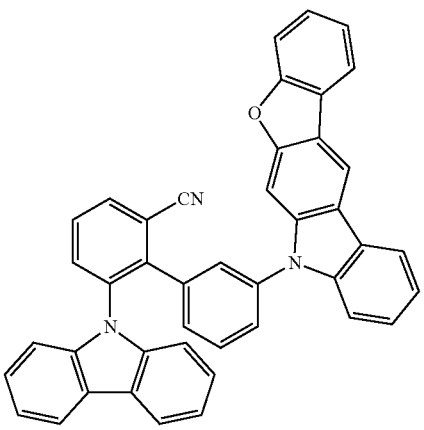
334 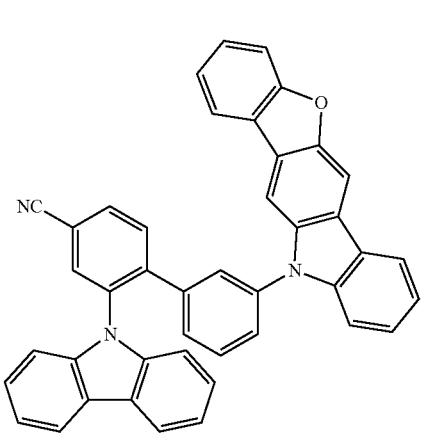
335 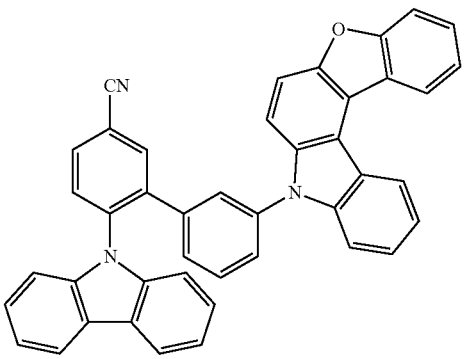

336
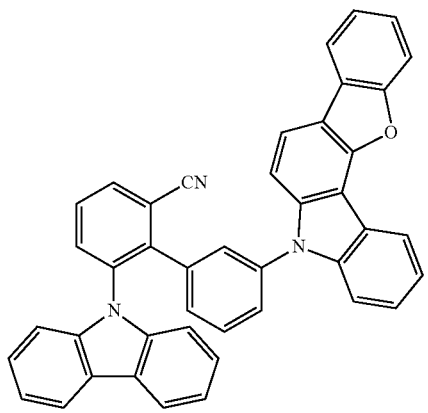
337
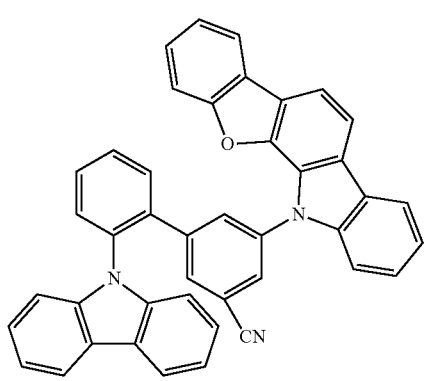
338
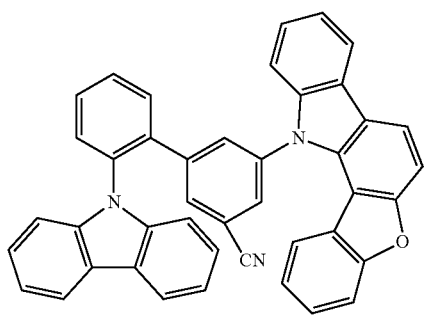
339
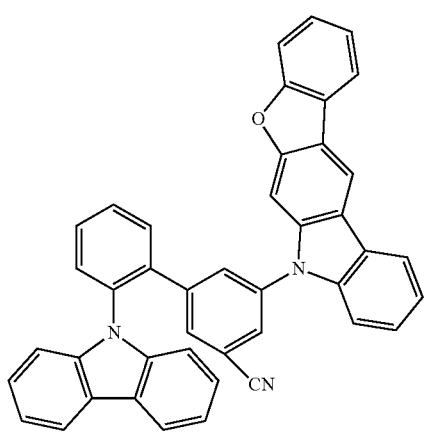
340
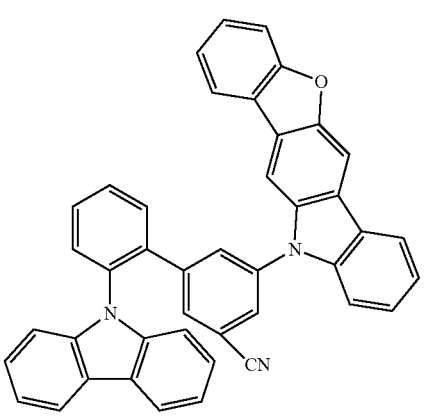
341
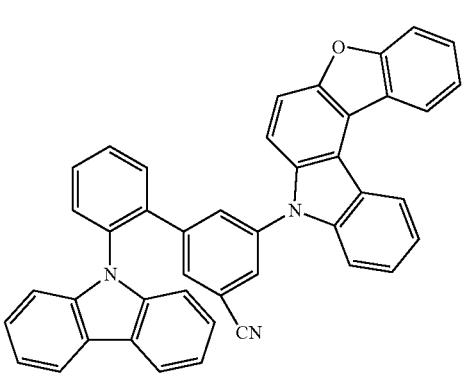
342
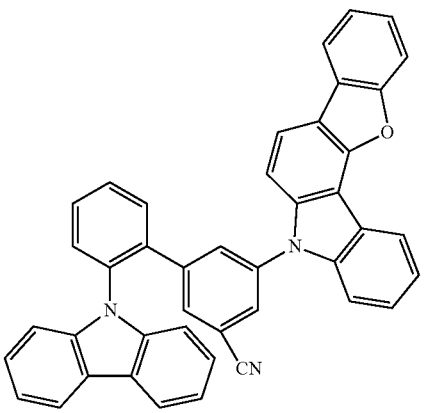
343
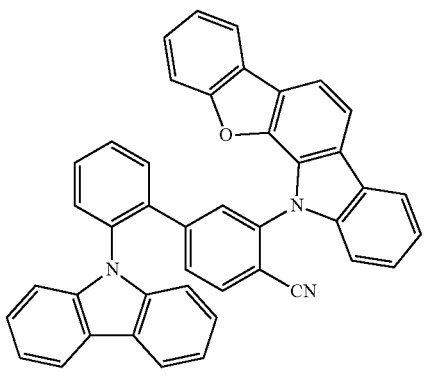

327
-continued
344

345

346

349
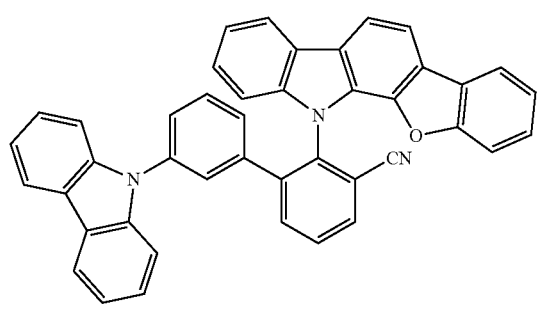
328
-continued
347
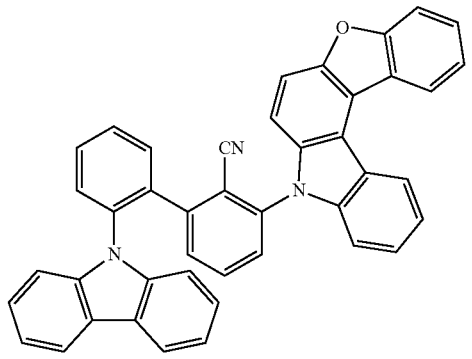
348
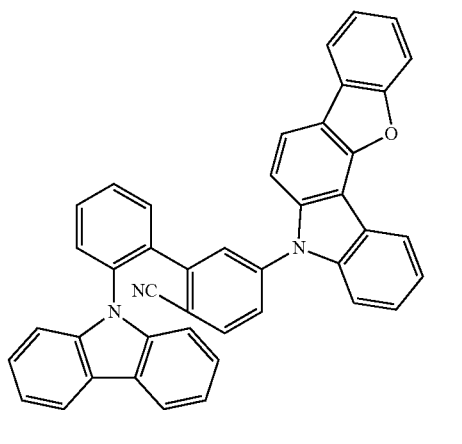
350
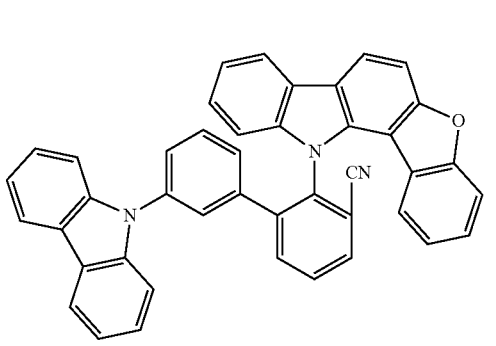

-continued
351
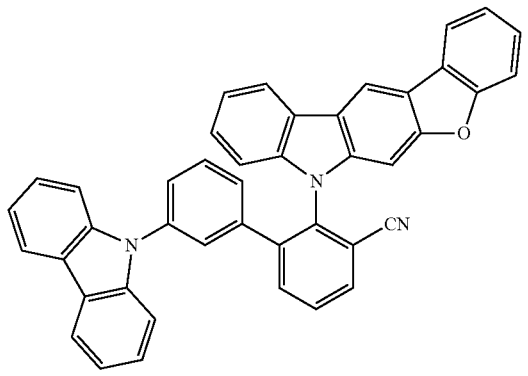
352
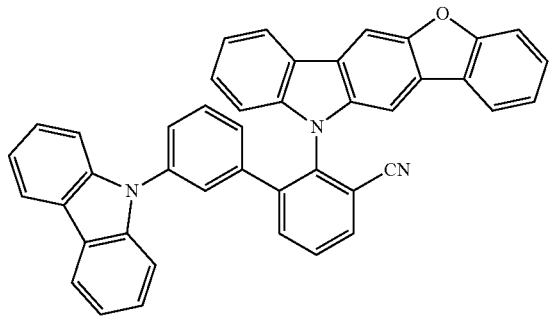
353
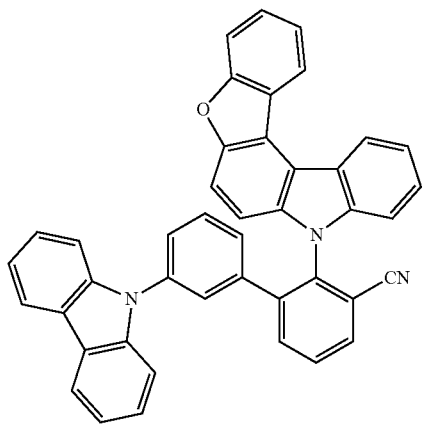
354
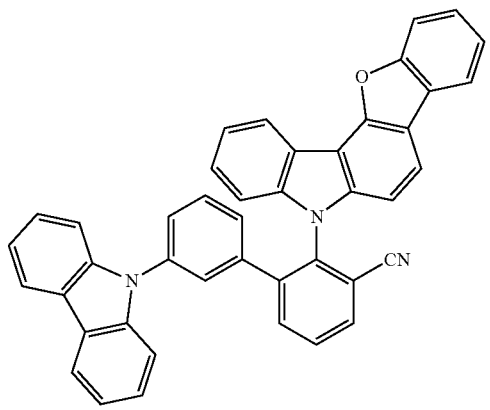
355
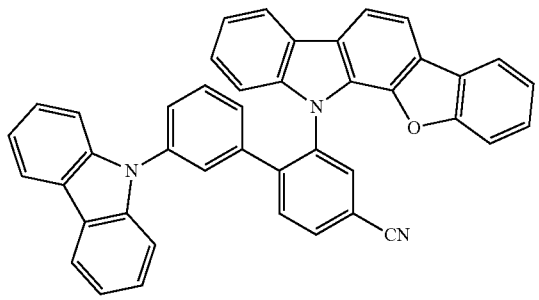
356
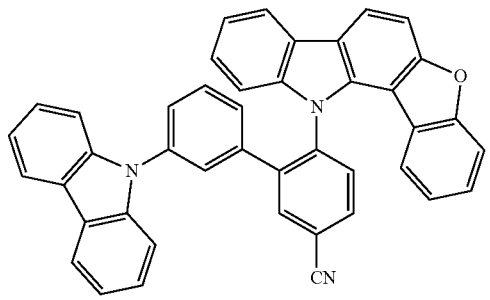
357
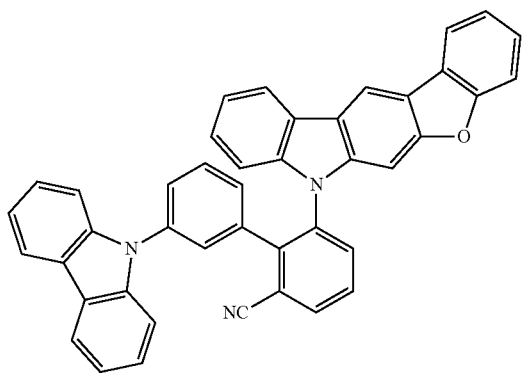
358
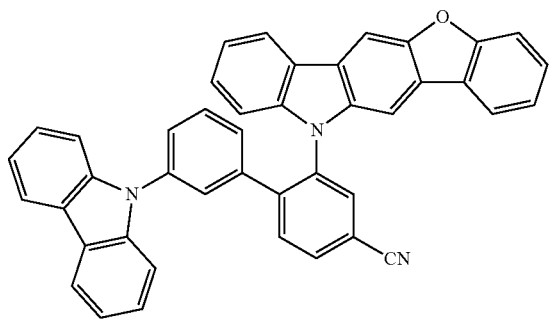

-continued
359
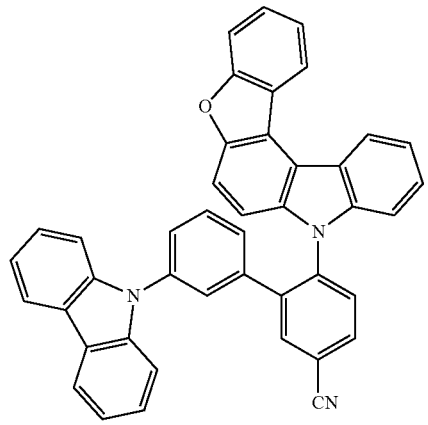
360
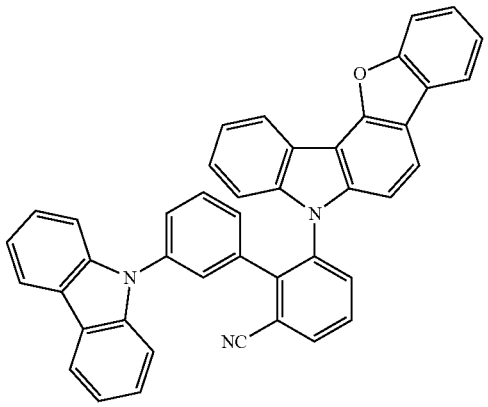
361
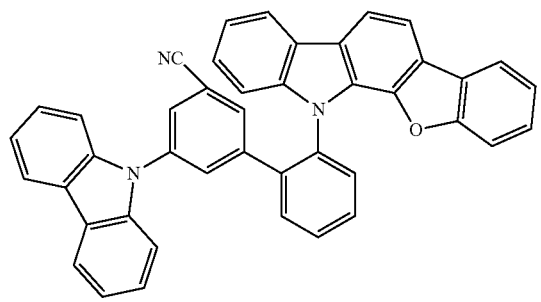
362
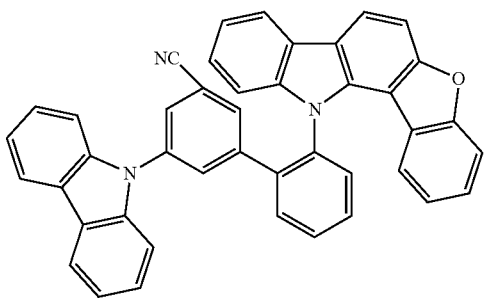
363
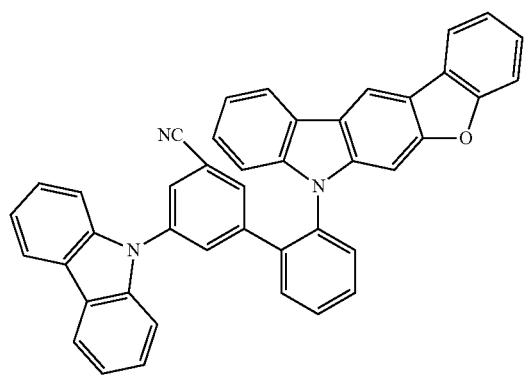
364
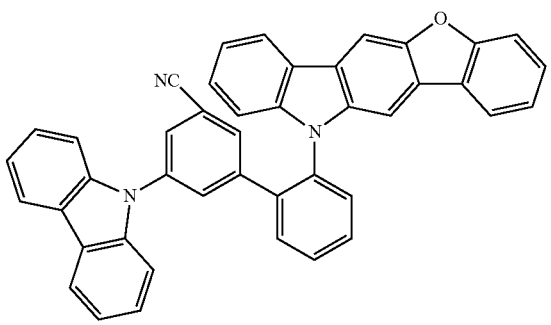
365
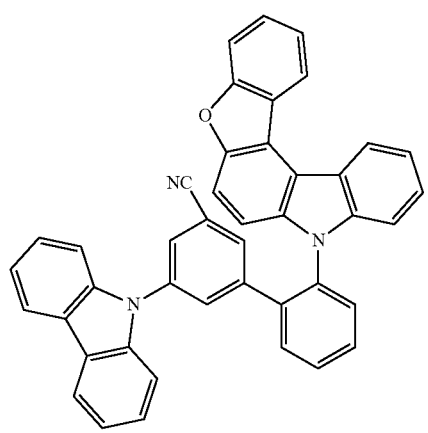
366
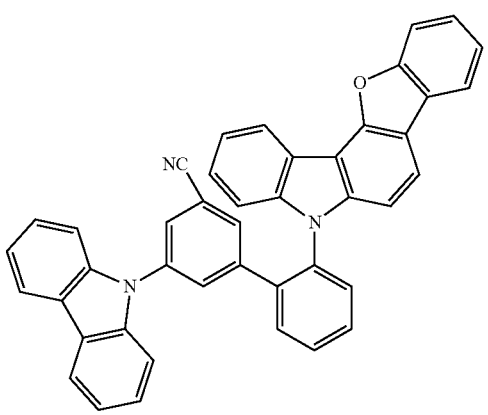

333 334
-continued
367
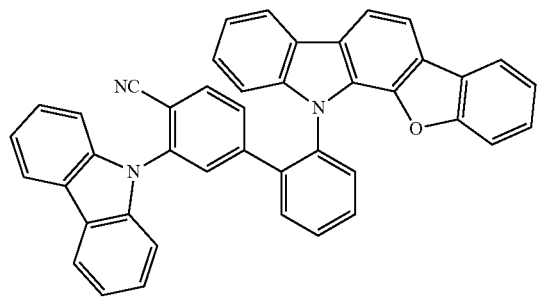
368
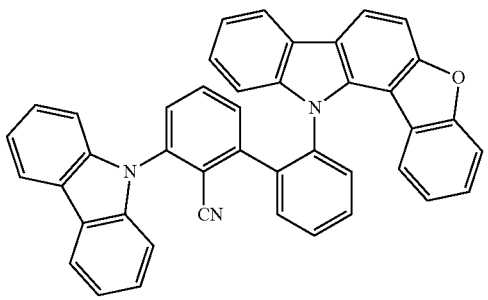
369
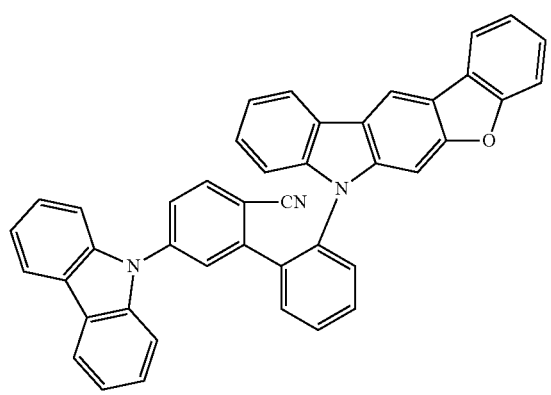
370
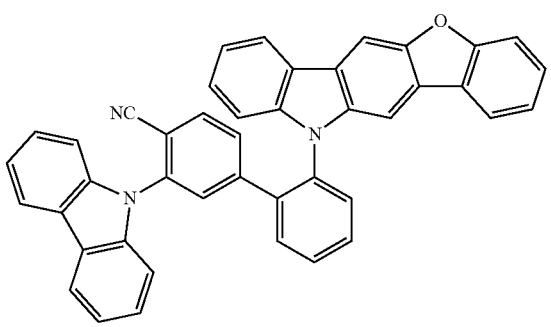
371
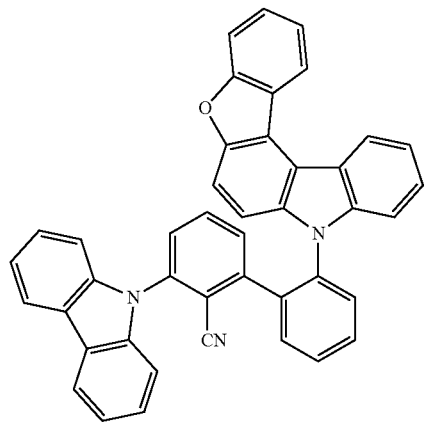
372
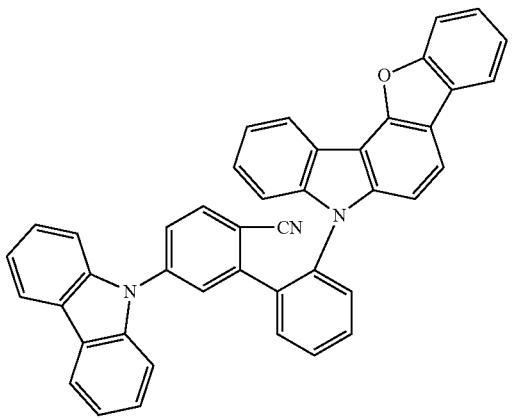
373
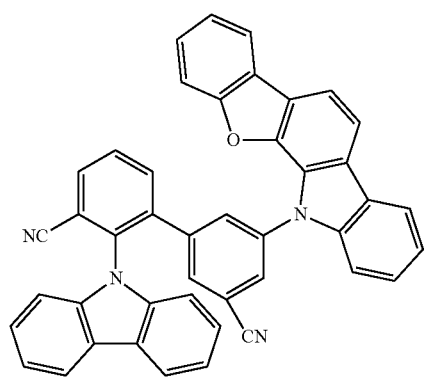
374
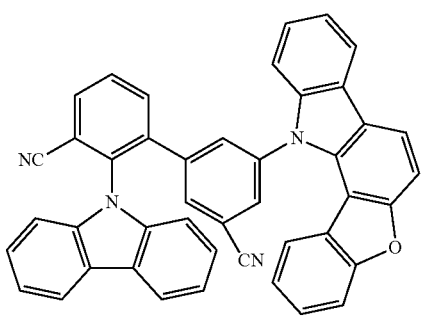

-continued
375
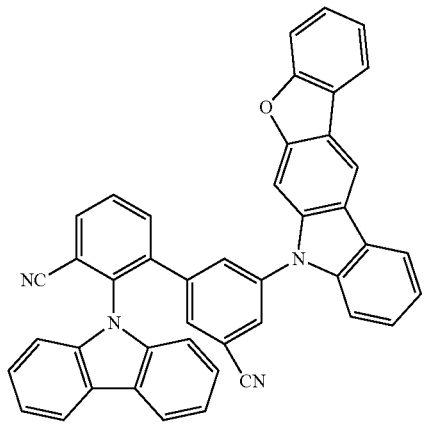
376
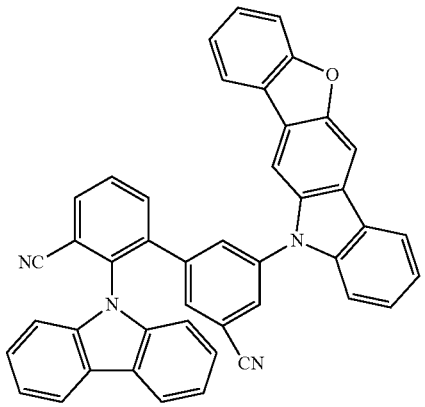
377
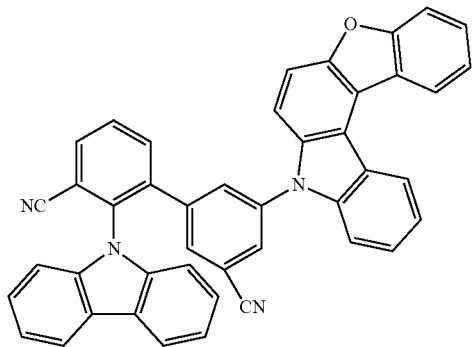
378
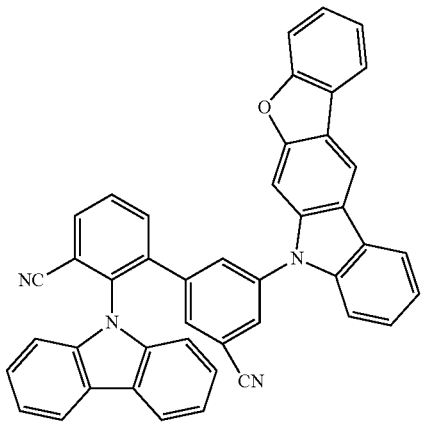
379
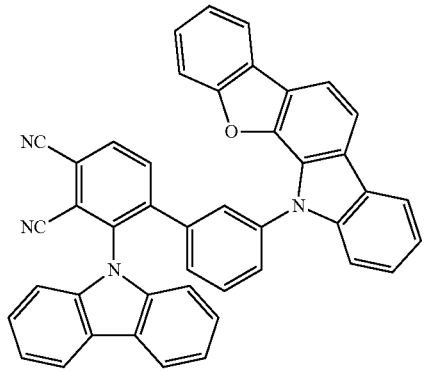
380
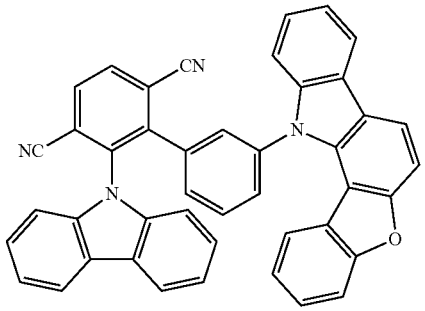
381
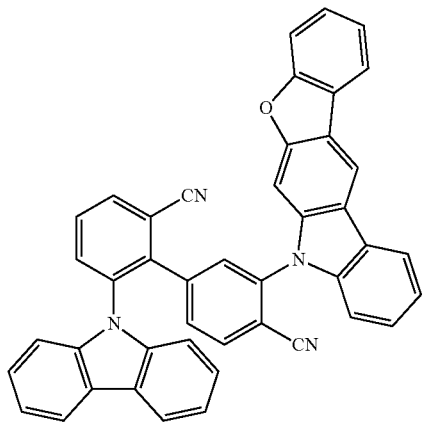
382
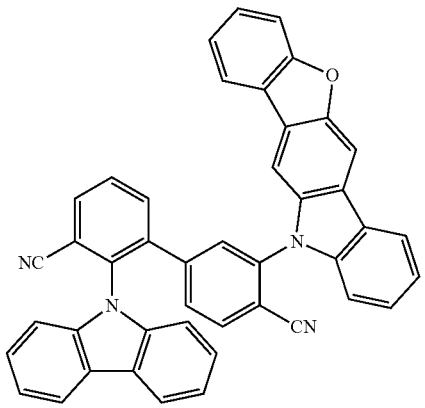

-continued
383
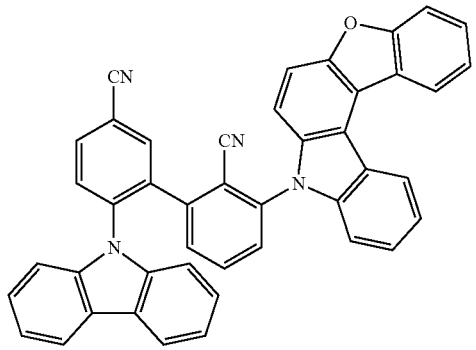
384
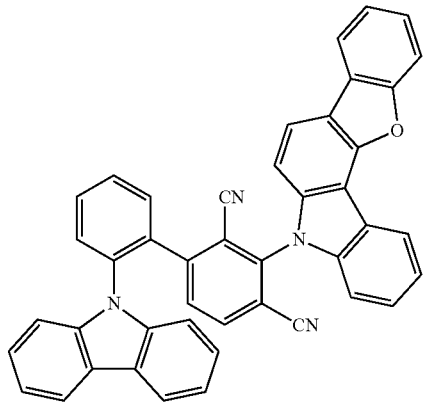
385
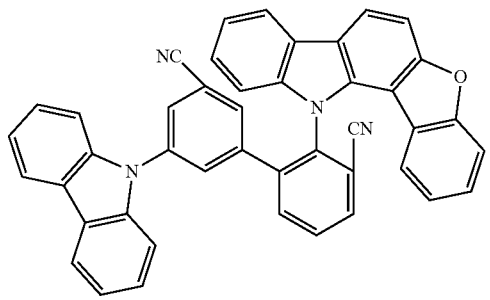
386
387
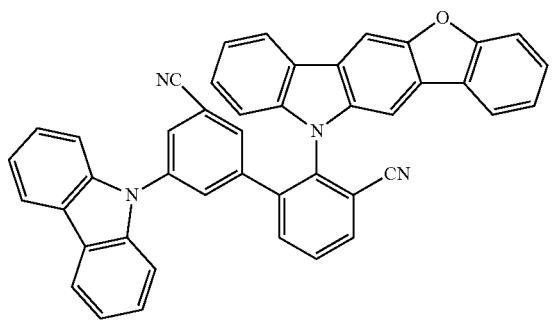
388
389
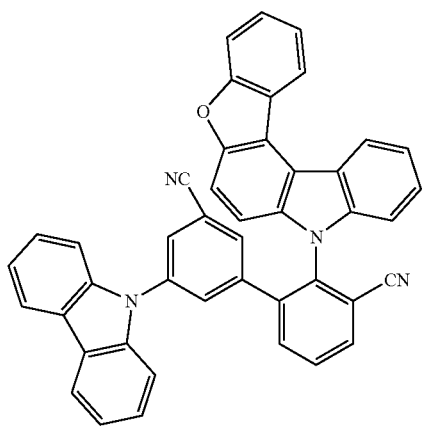
390
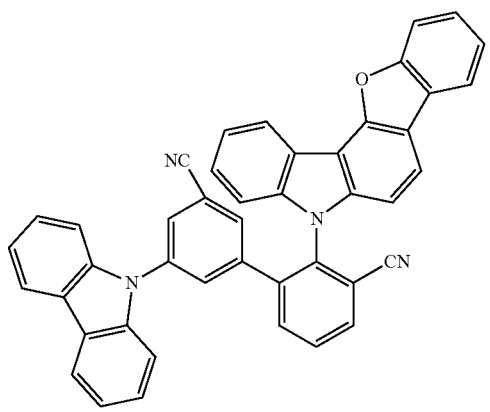

-continued
391 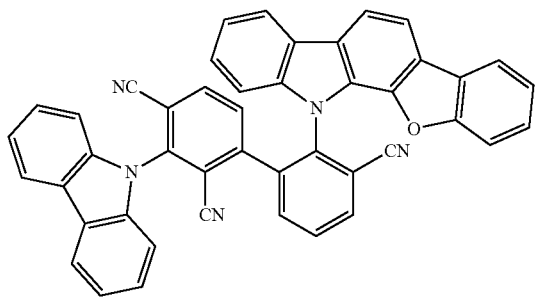
392 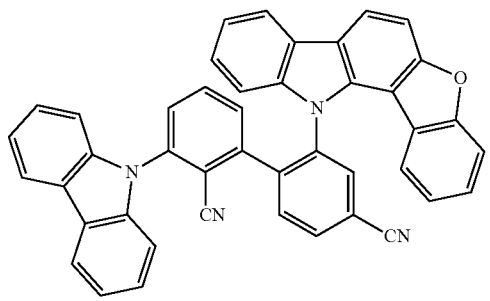
393 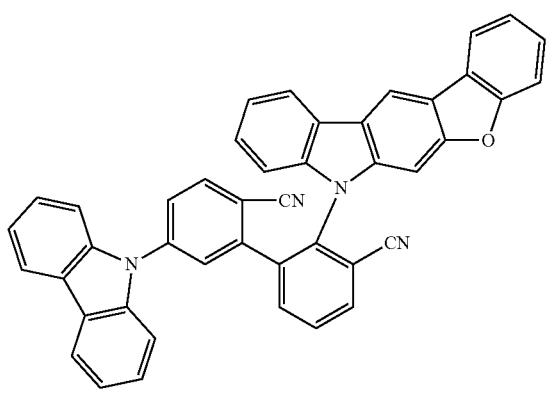
394 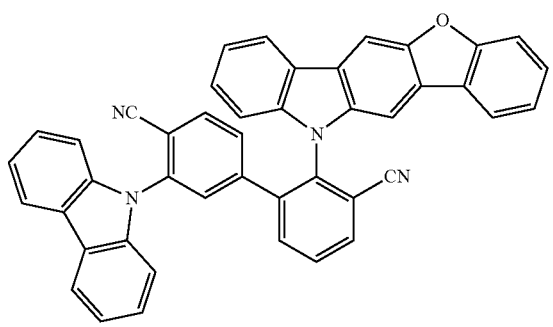
395 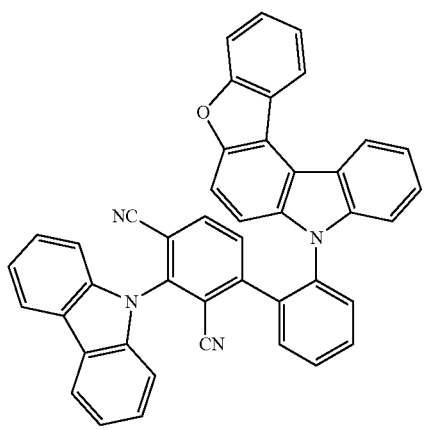
396 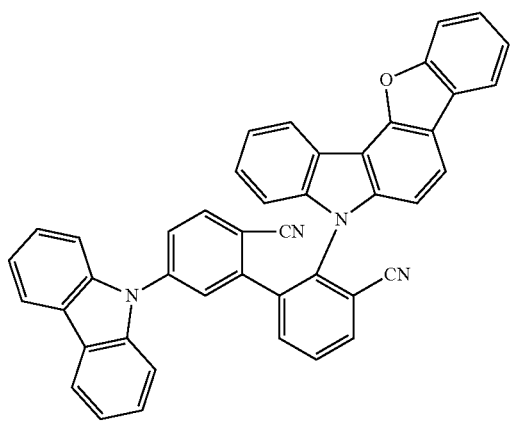
397 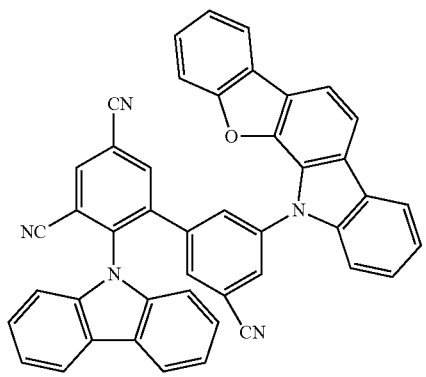
398 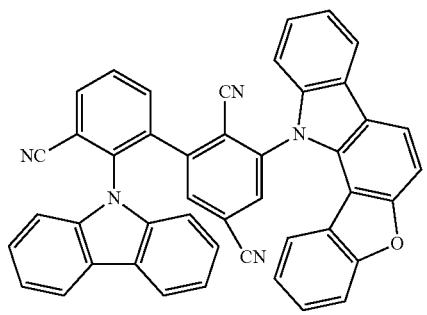

-continued
399
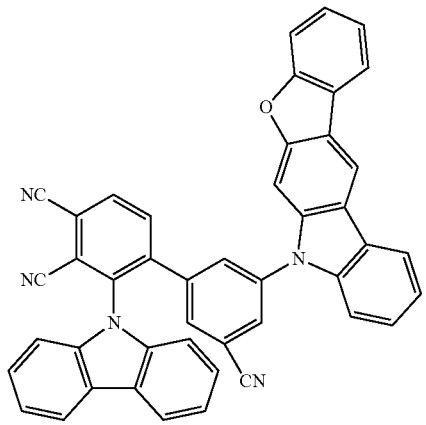
400
401
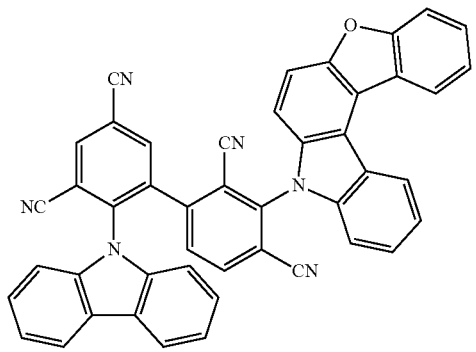
402
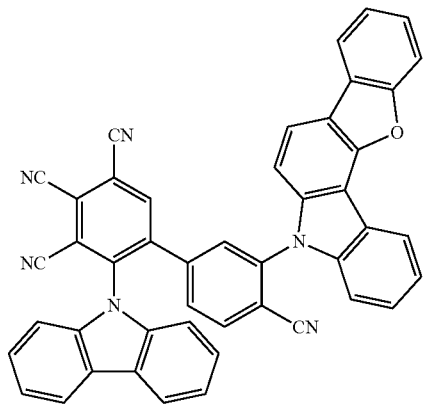
403
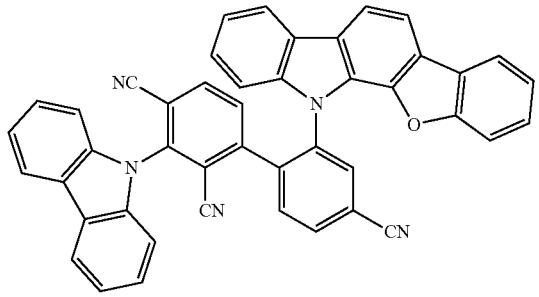
404
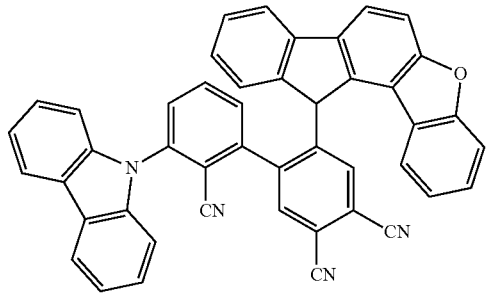
405
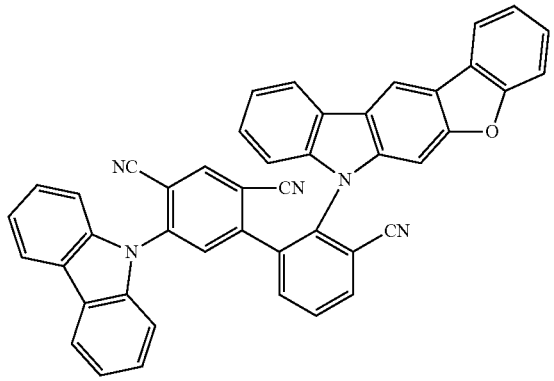
406
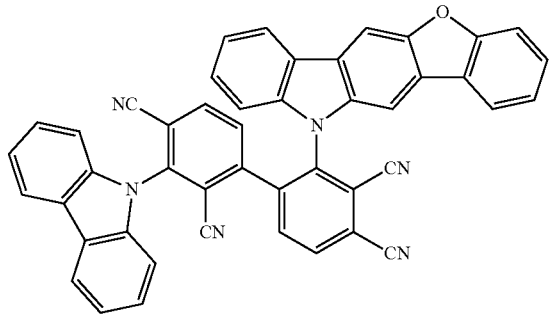

-continued
407
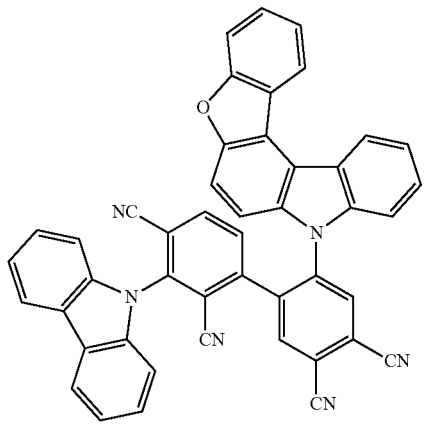
408
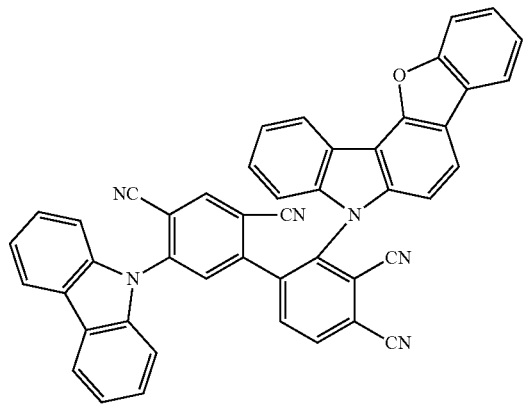
409
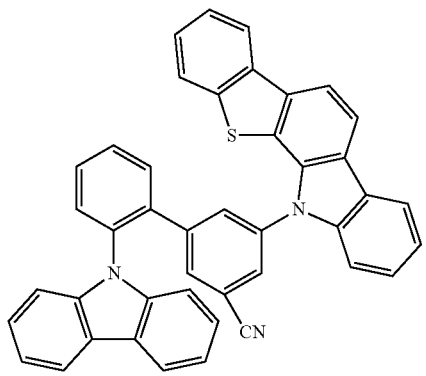
410
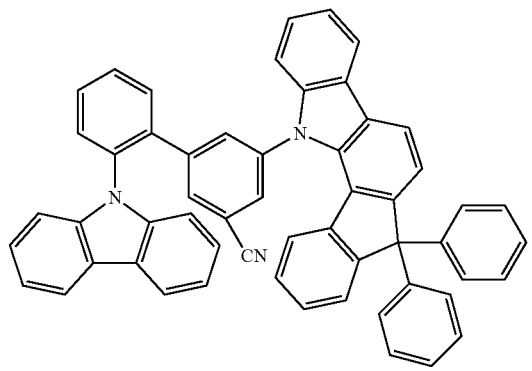
411
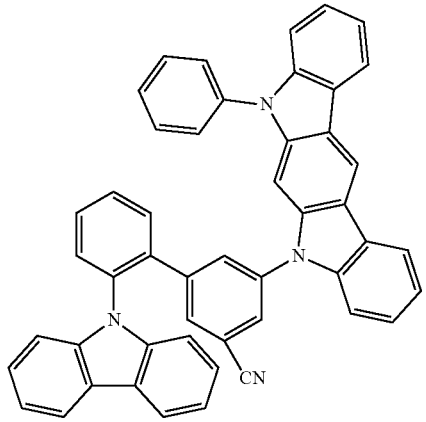
412
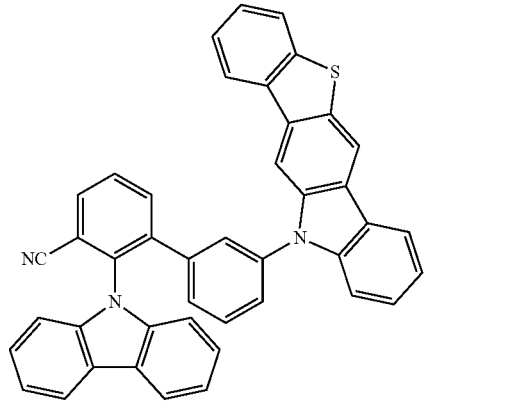
413
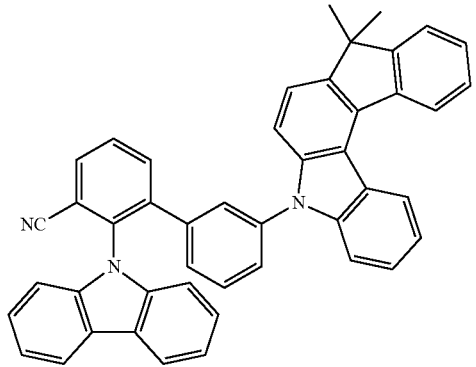
414
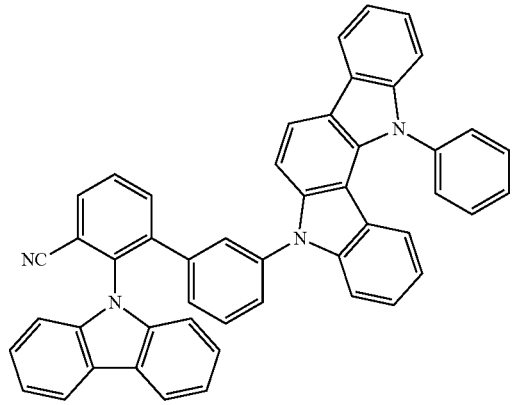

-continued
415
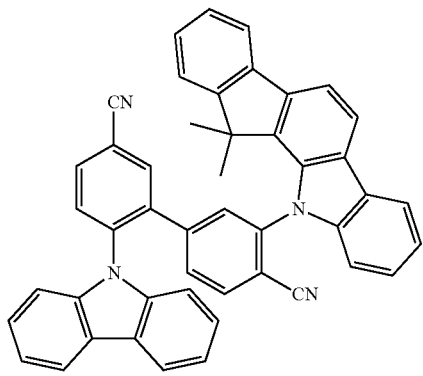
416
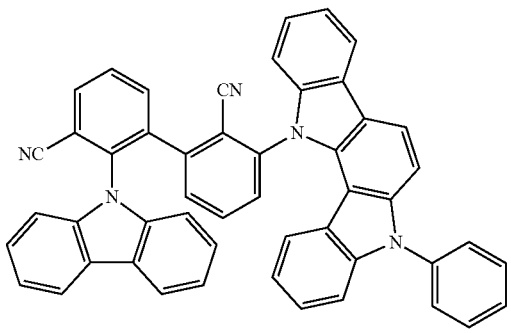
417
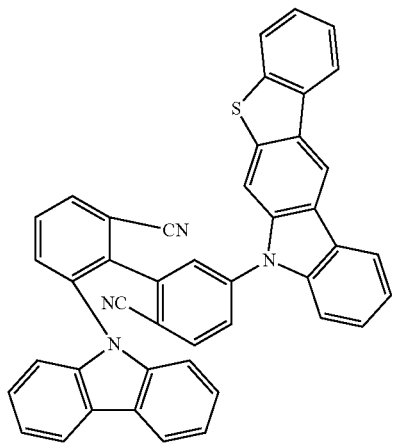
418
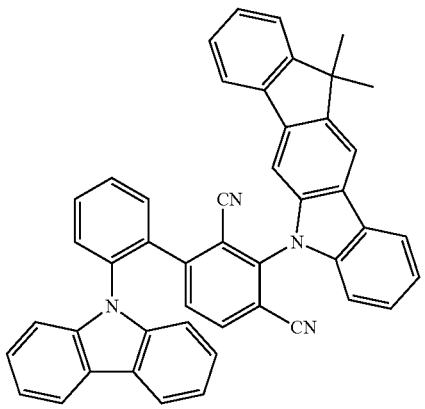
419
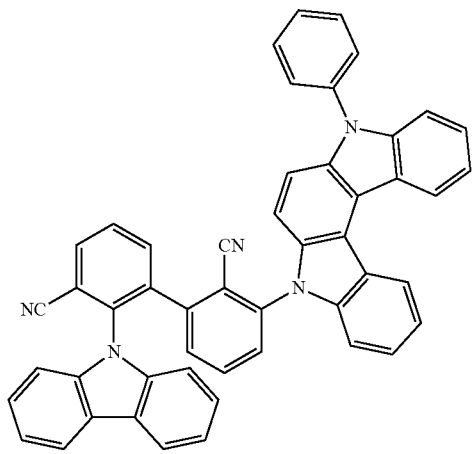
420
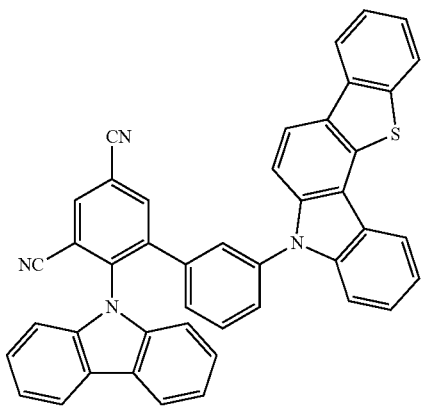
421
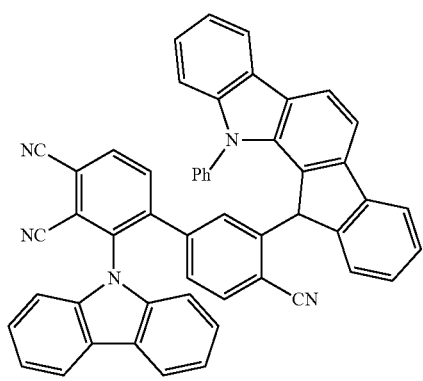
422
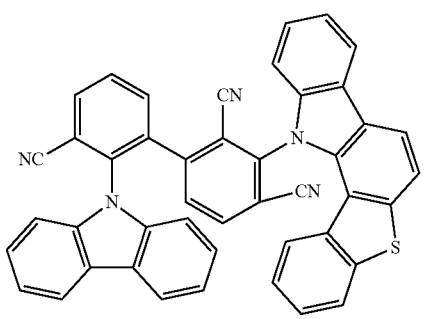

-continued
423
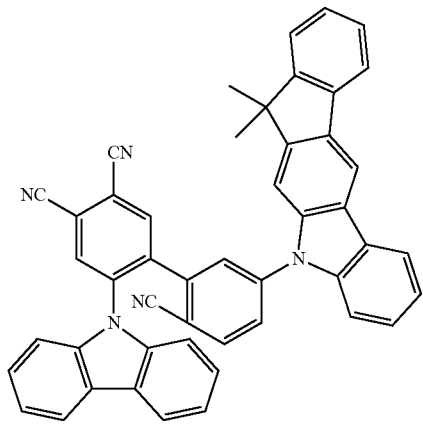
424
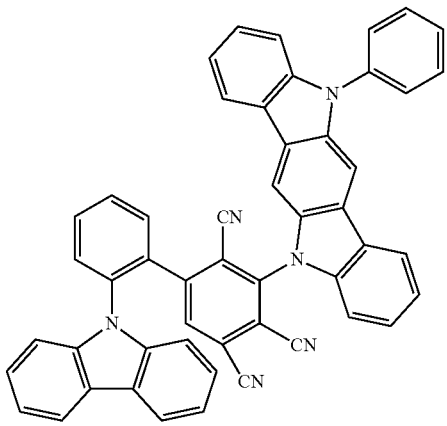
425
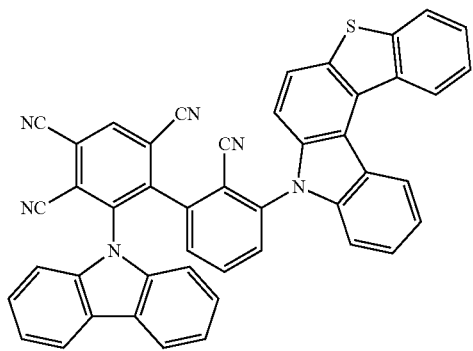
426
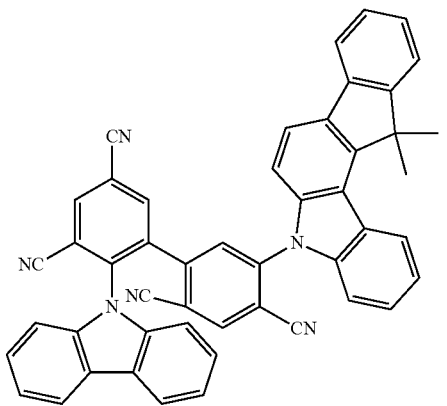
427
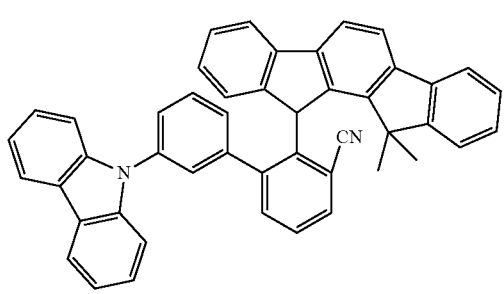
428
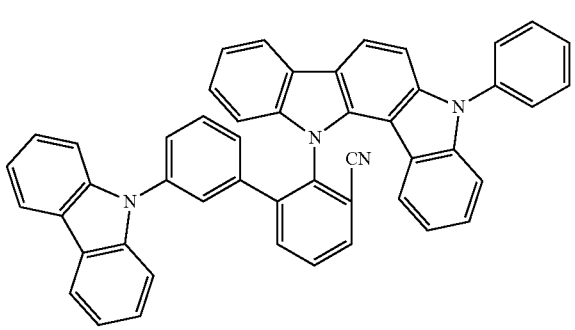
429
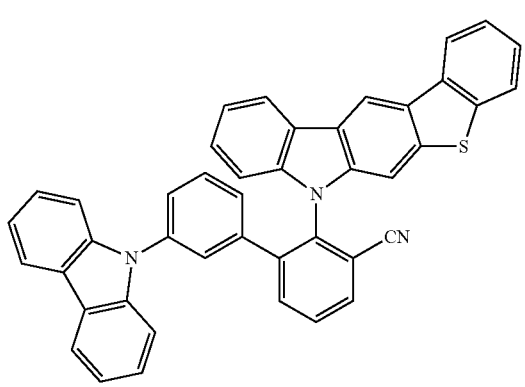
430
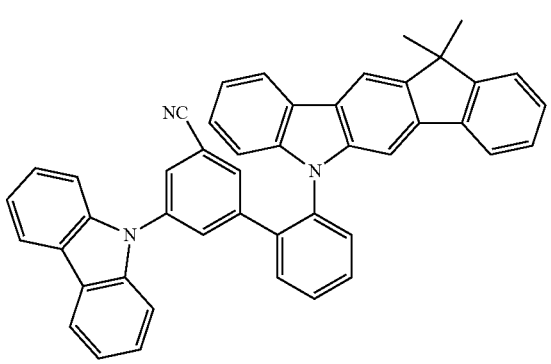

-continued
| 431 | 432 |
|---|---|
| 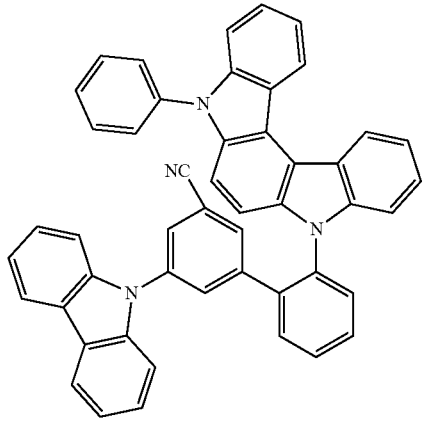 | 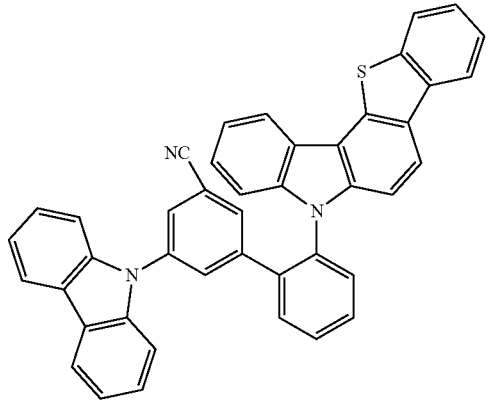 |
| 433 | 434 |
| 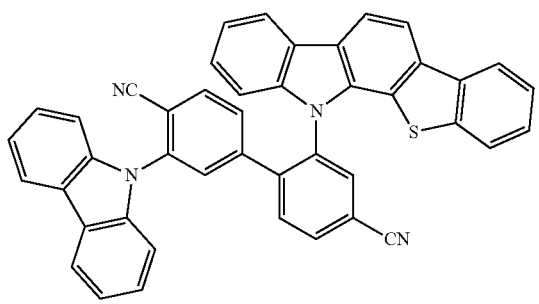 | 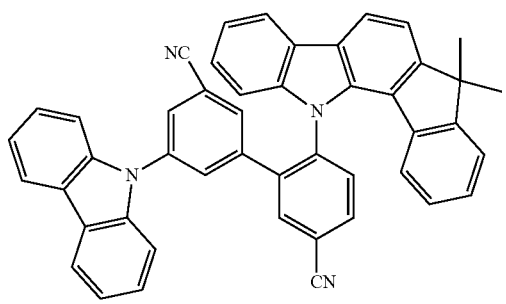 |
| 435 | 436 |
| 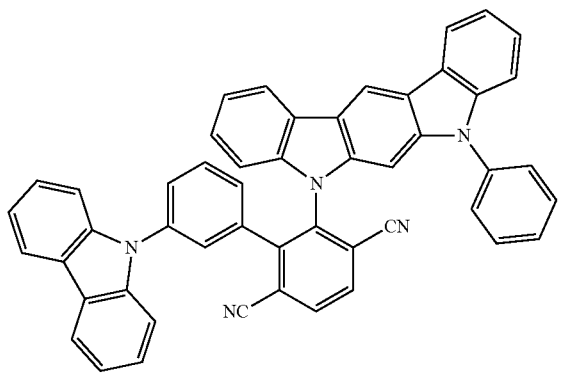 | 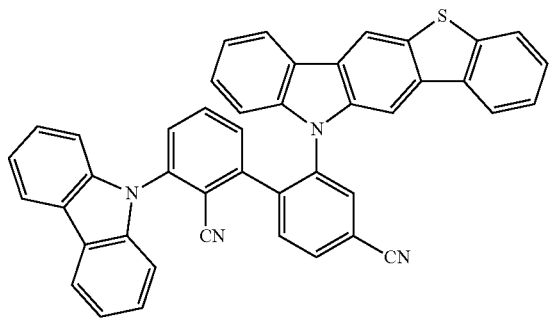 |
| 437 | 438 |
| 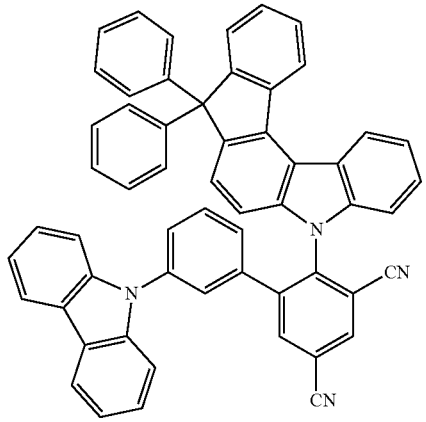 | 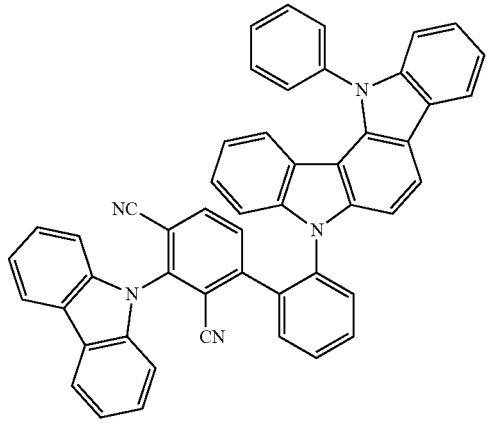 |

-continued
439
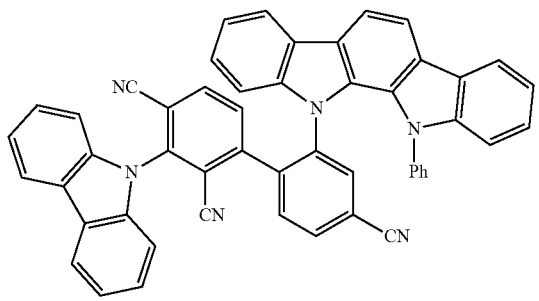
440
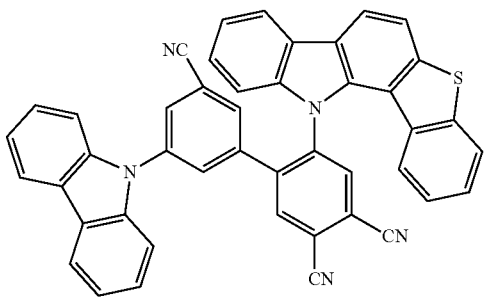
441
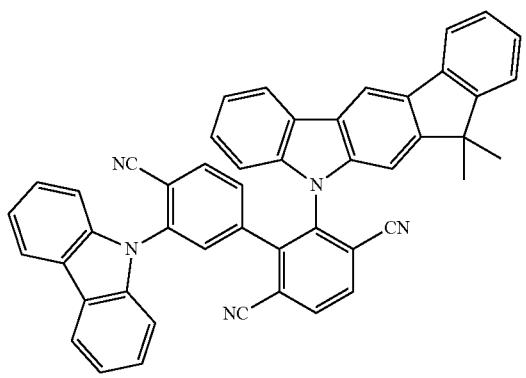
442
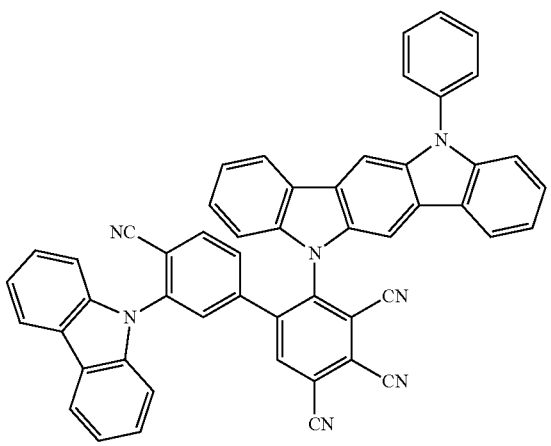
443
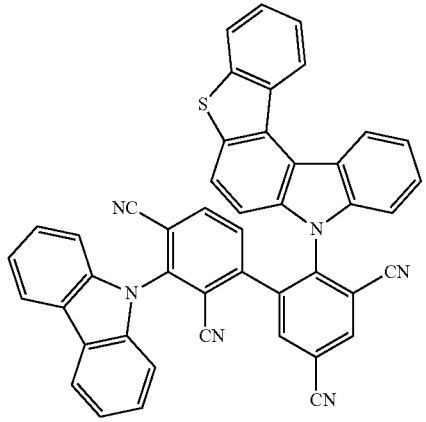
444
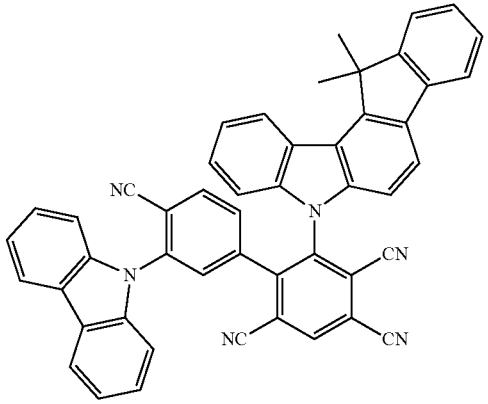
445
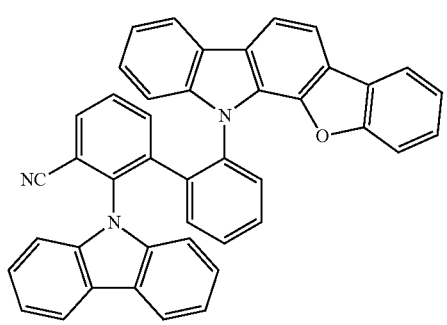
446
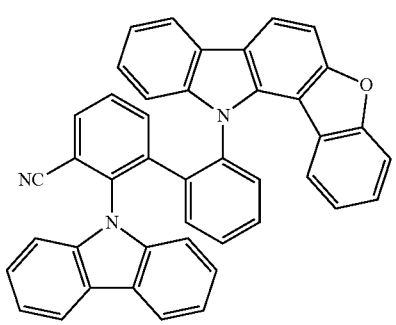

-continued
447
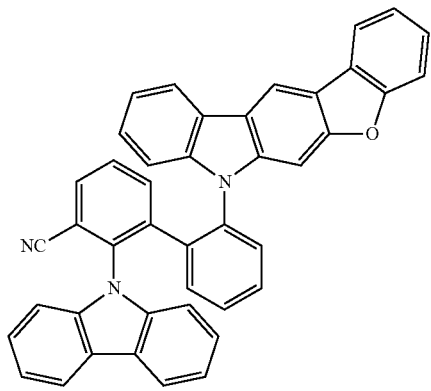
4148
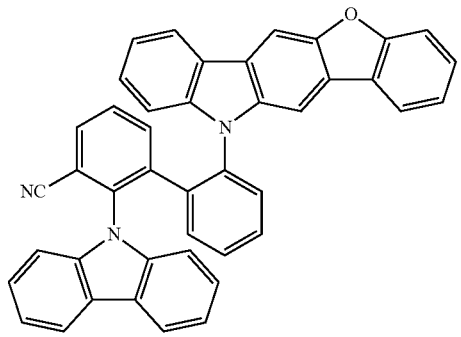
449
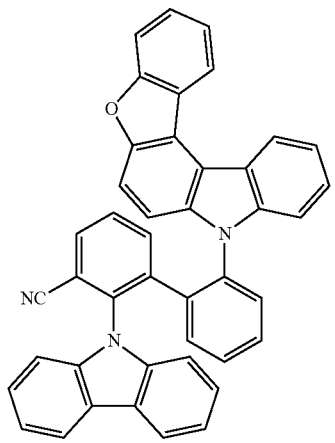
450
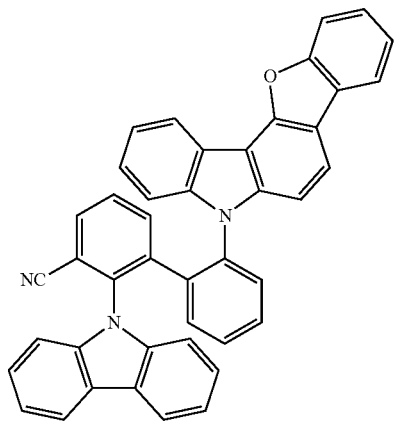
451
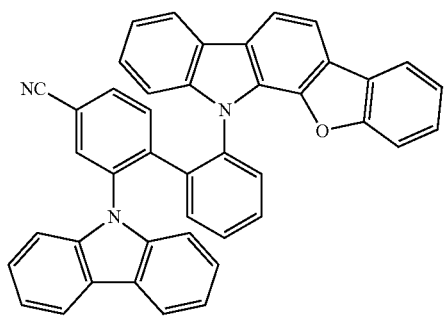
452
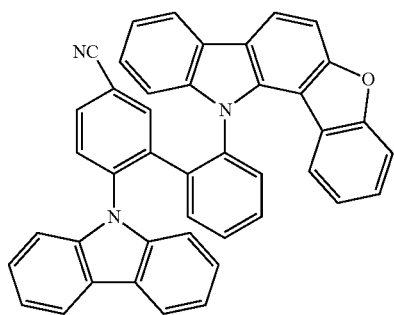
453
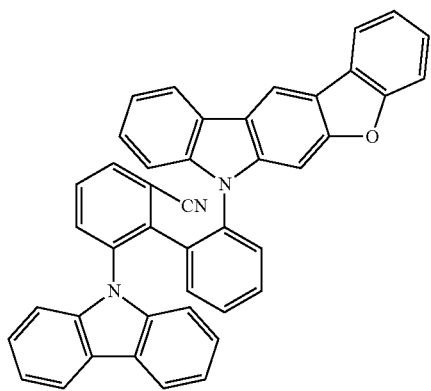
454
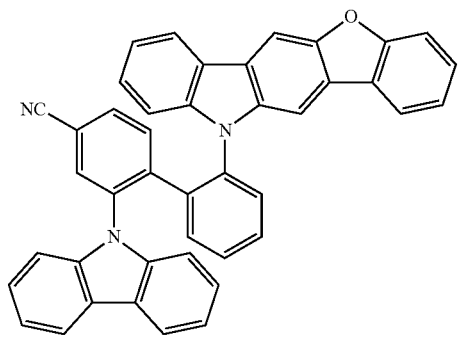

-continued
455
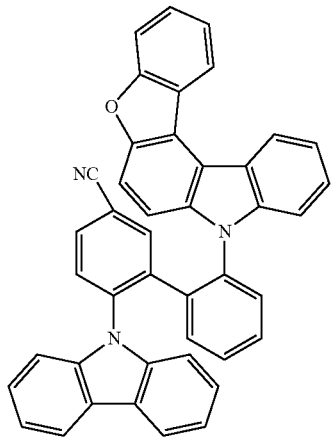
456
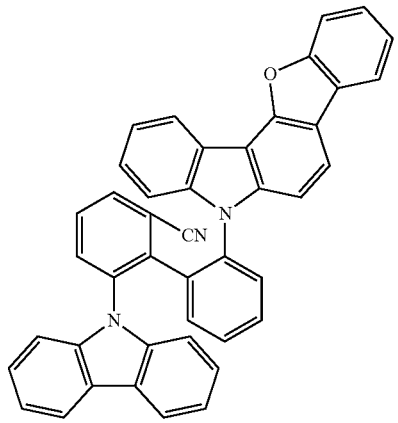
457
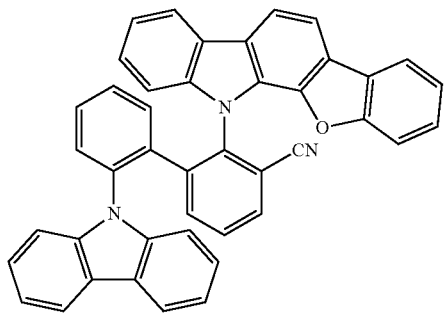
458
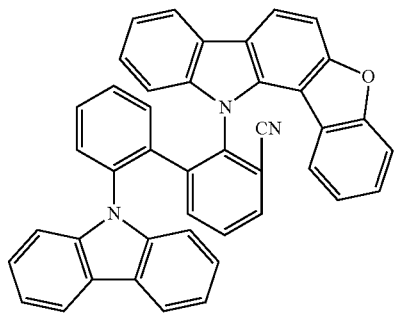
459
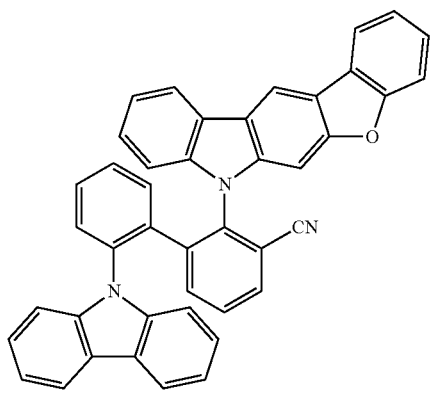
460
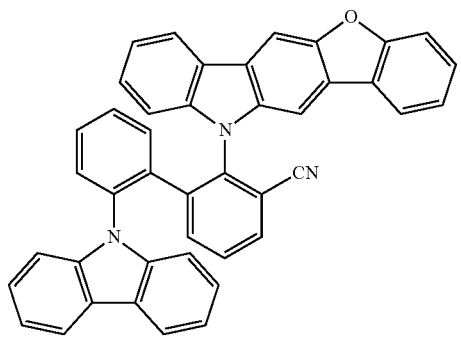
461
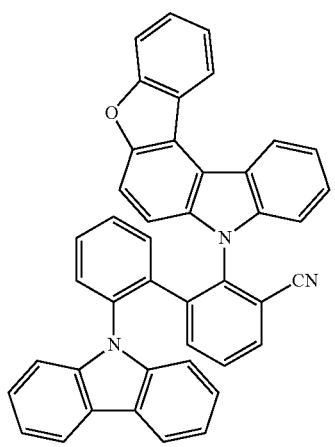
462
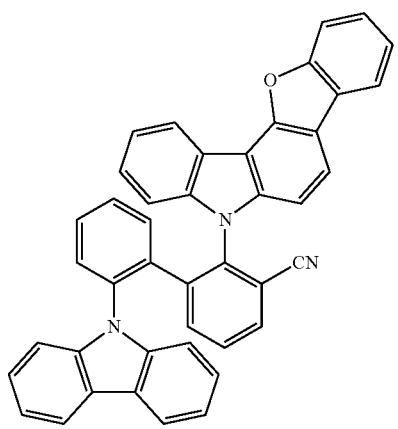

-continued
463
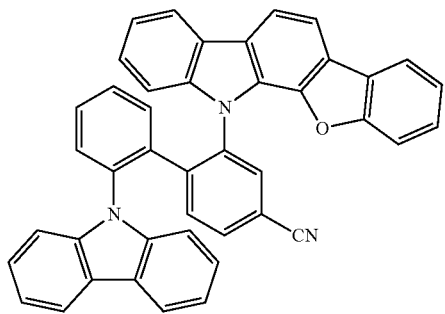
464
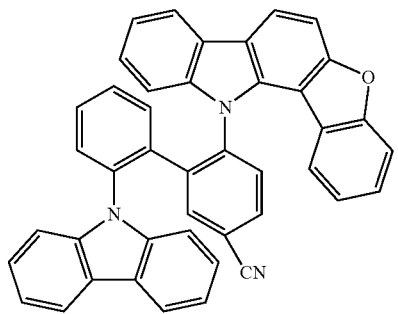
465
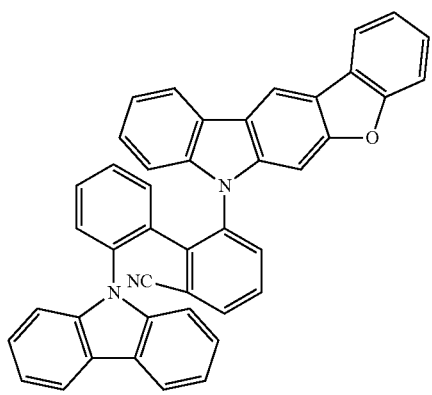
466
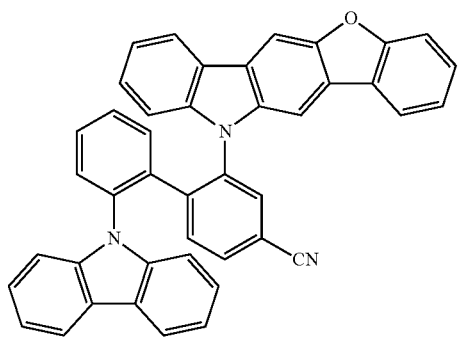
467
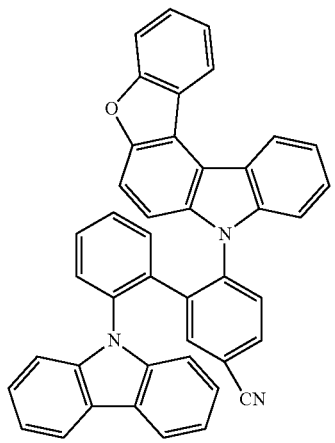
468
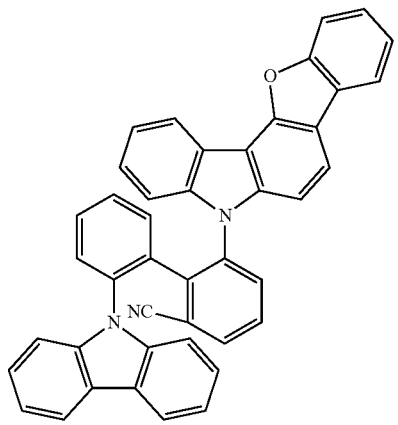
469
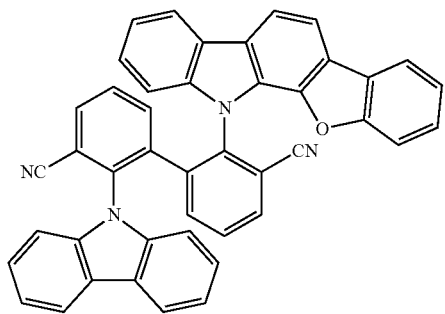
470
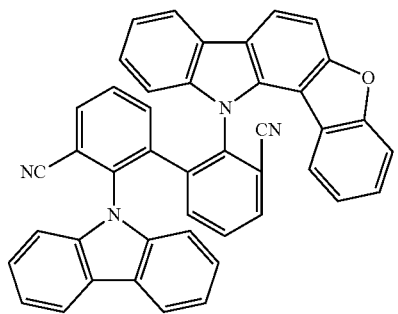

-continued
471 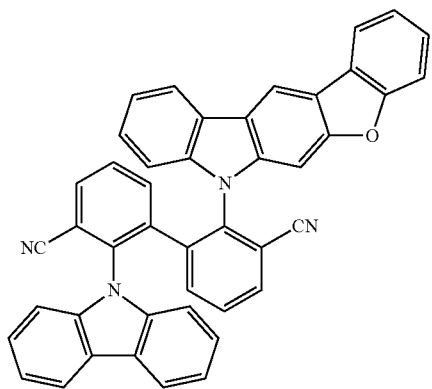
472 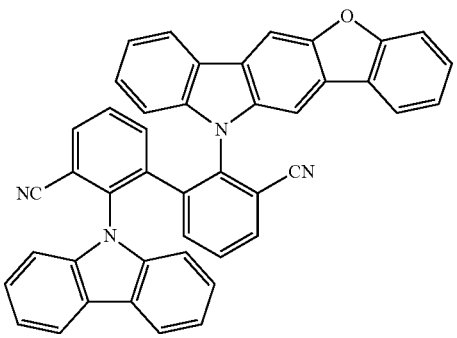
473 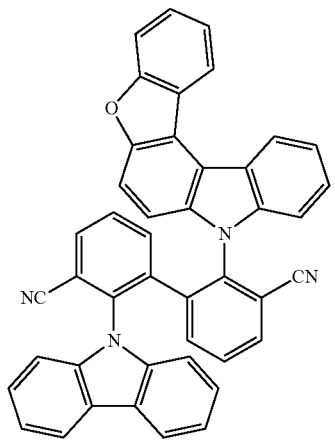
474 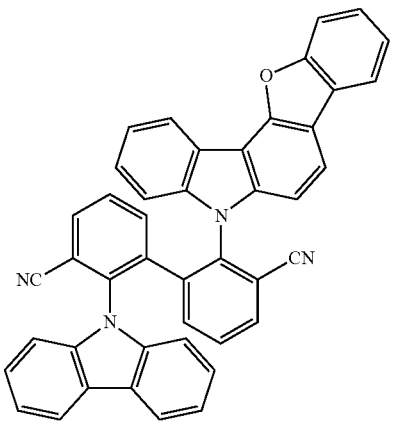
475 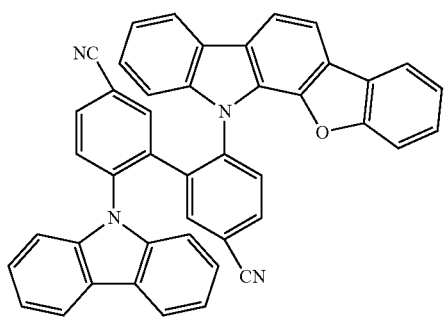
476 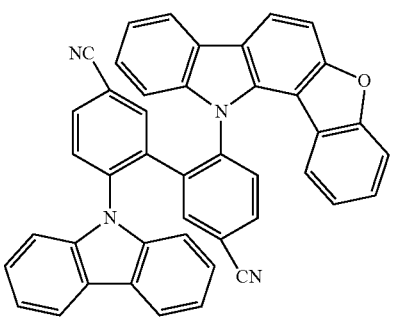
477 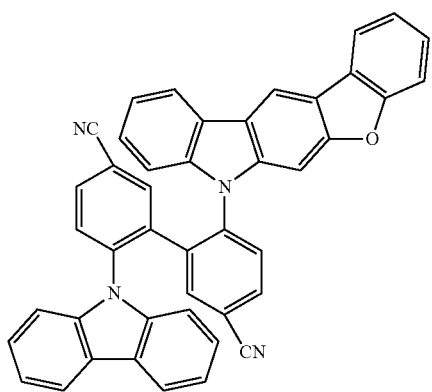
478 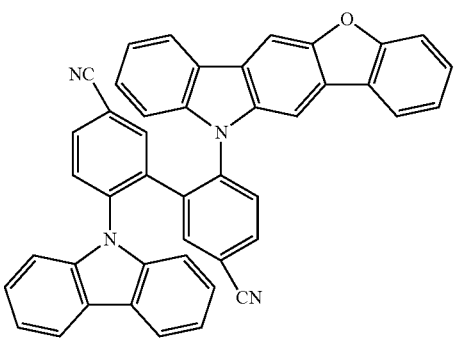

-continued
| 479 | 480 |
|---|---|
| 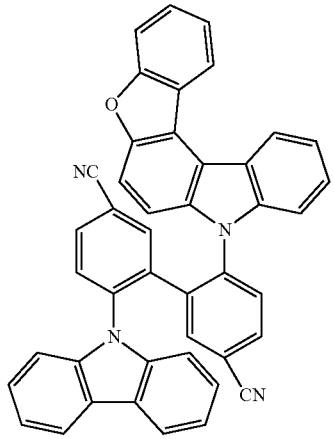 | 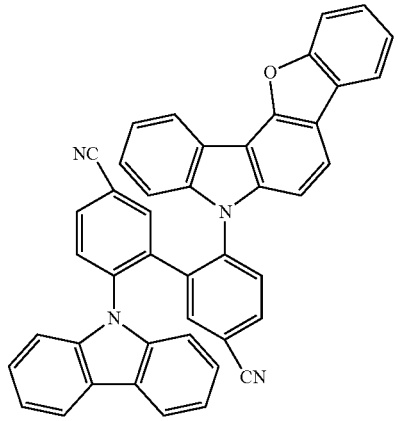 |
| 481 | 482 |
| 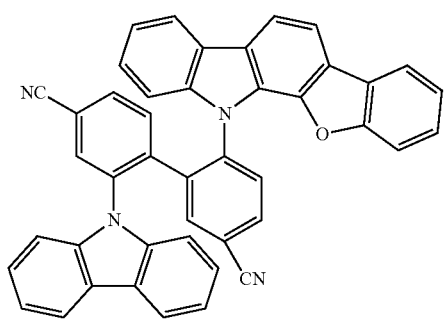 | 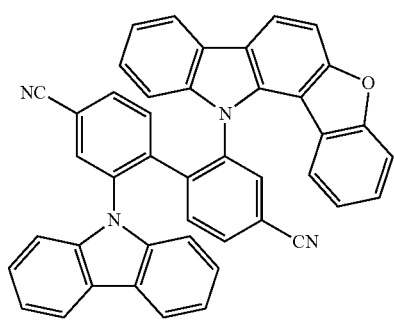 |
| 483 | 484 |
| 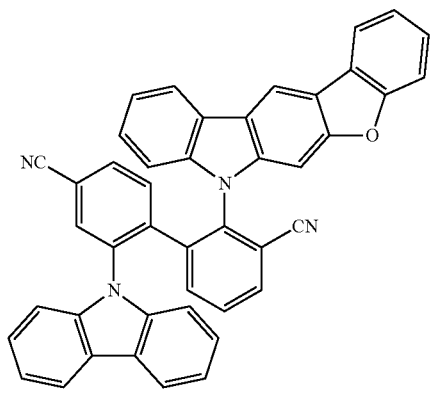 | 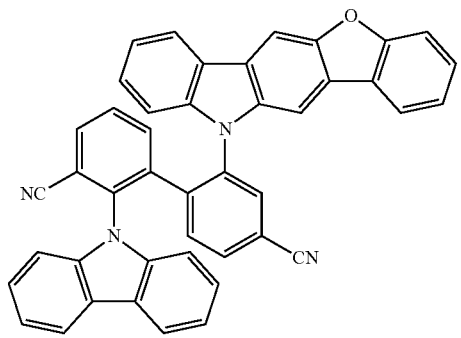 |
| 485 | 486 |
| 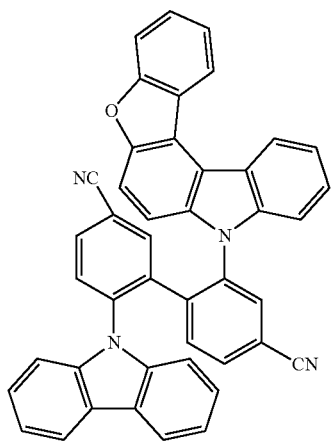 | 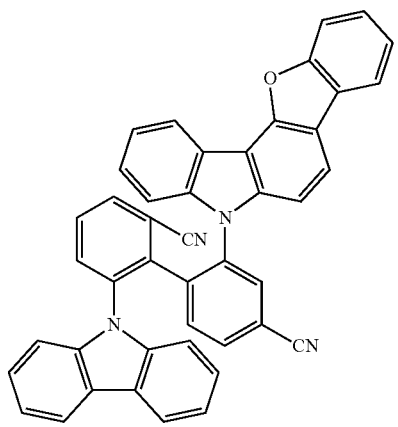 |

-continued
| 487 | 488 |
|---|---|
| 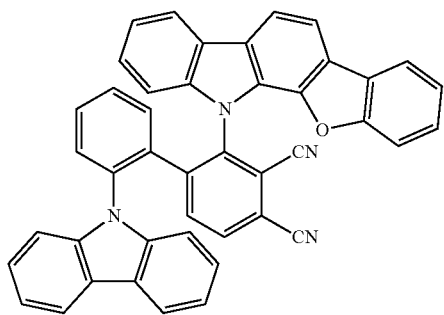 | 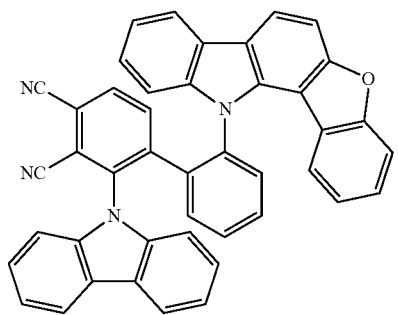 |
| 490 | 489 |
| 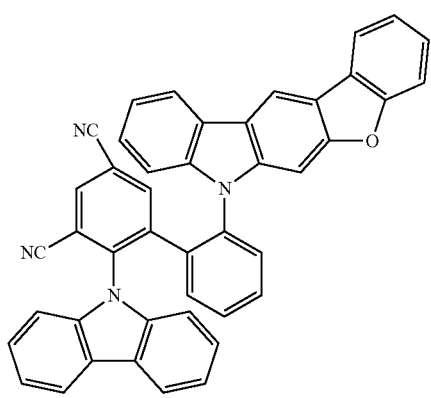 | 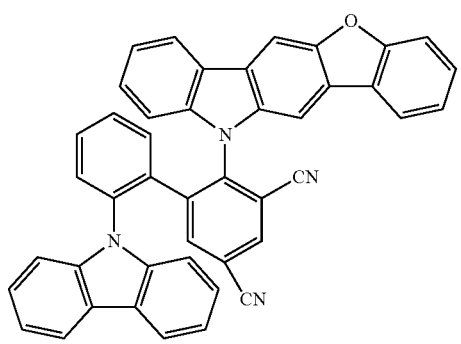 |
| 491 | 492 |
| 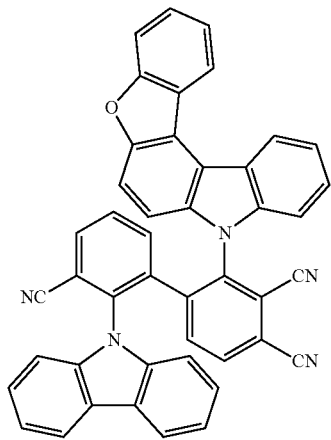 | 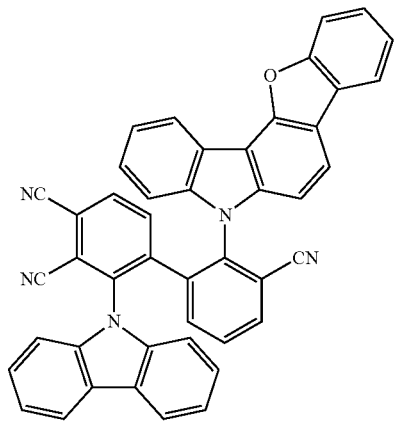 |
| 493 | 494 |
| 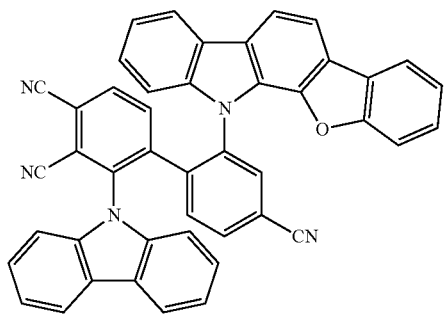 | 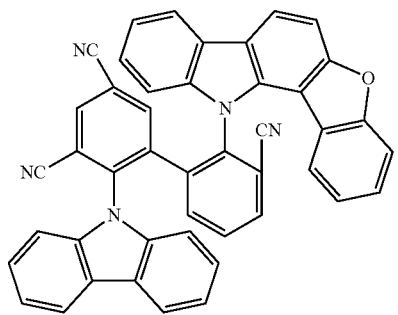 |

-continued
495
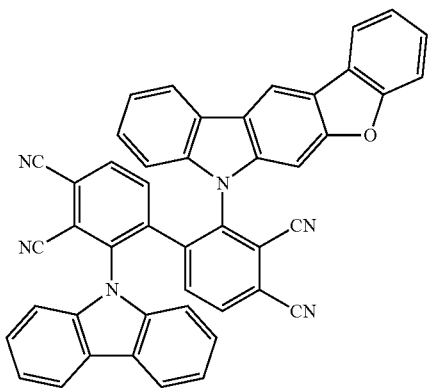
496
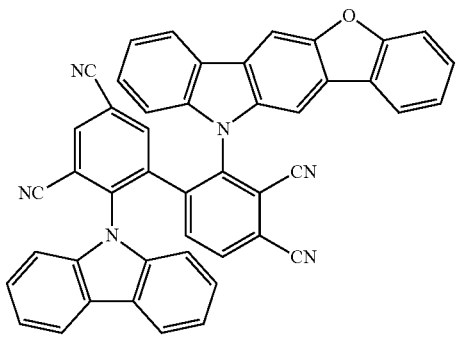
497
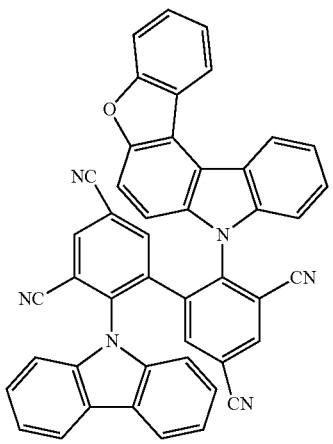
498
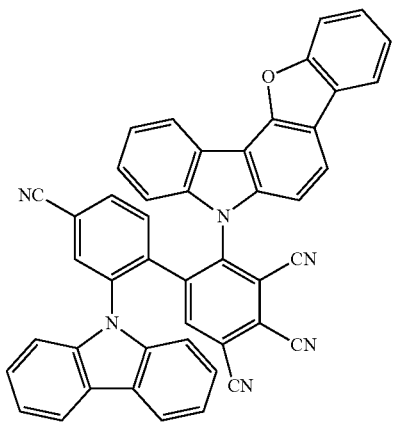
499
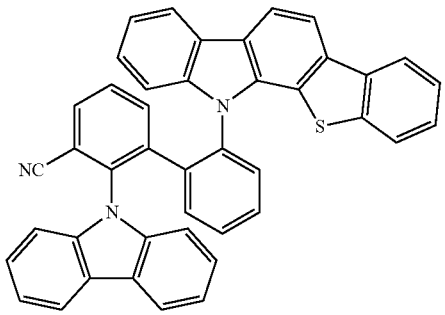
500
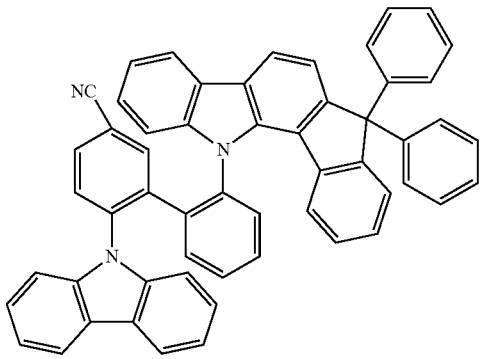
501
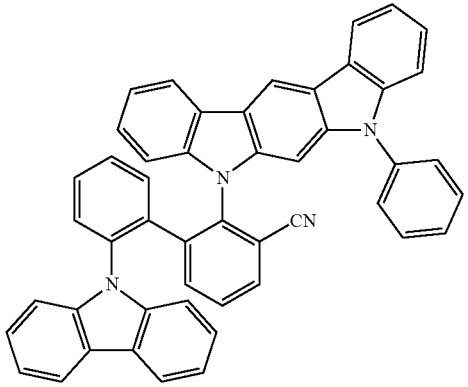
502
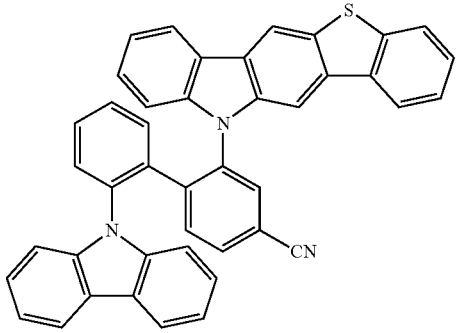

-continued
| 503 | 504 |
|---|---|
| 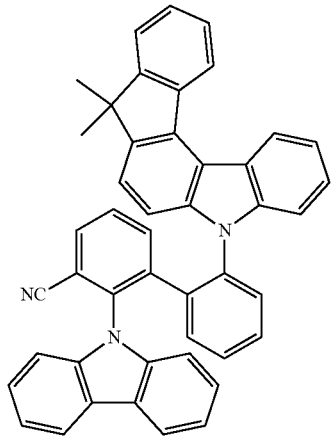 | 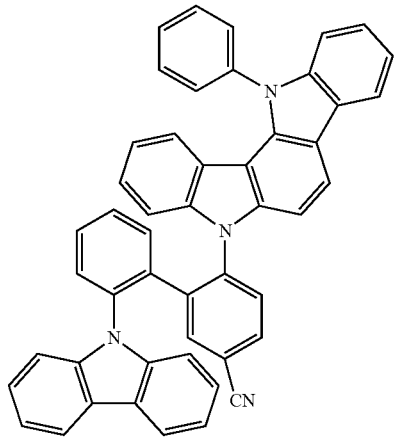 |
| 505 | 506 |
| 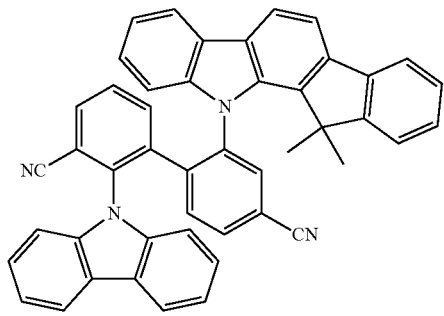 | 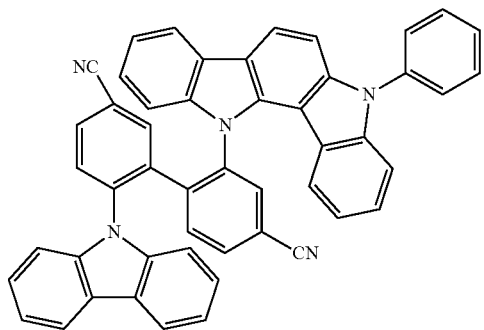 |
| 507 | 508 |
| 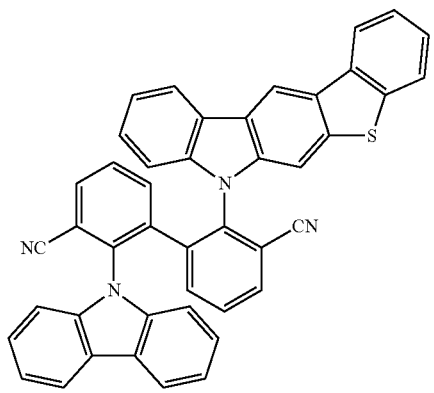 | 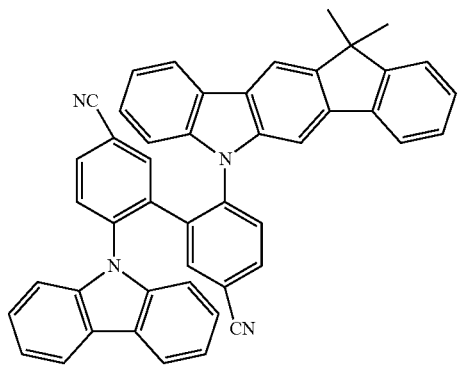 |
| 509 | 510 |
| 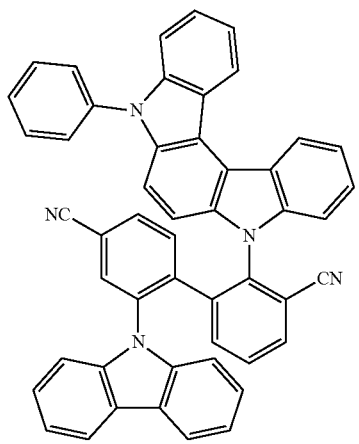 | 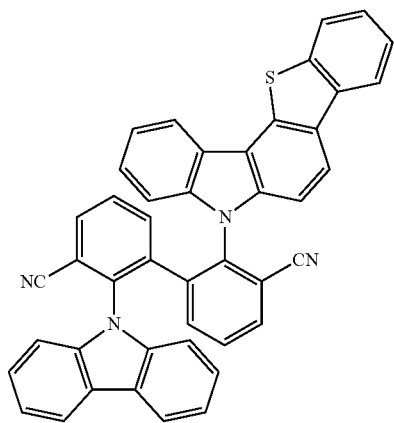 |

-continued
511
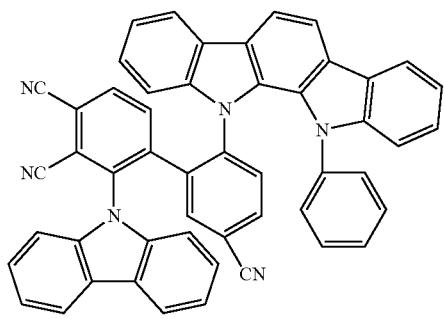
512
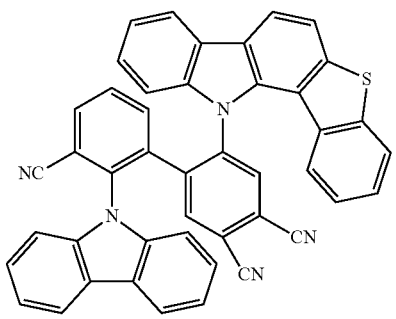
513
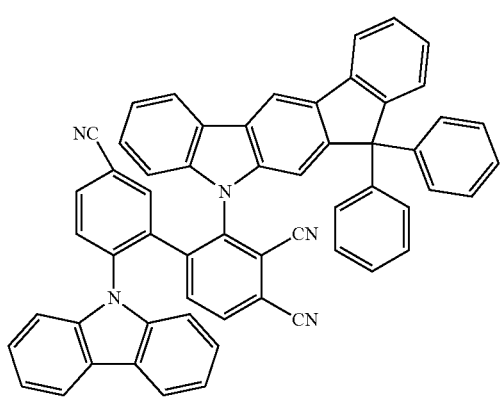
514
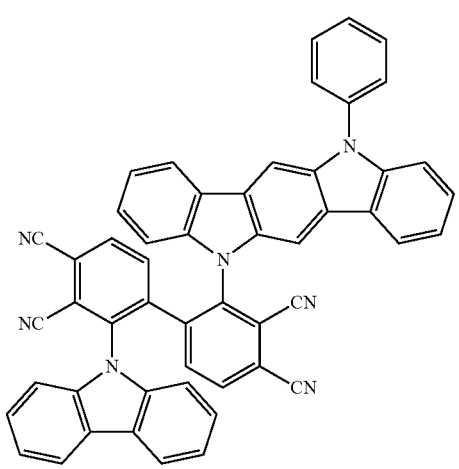
515
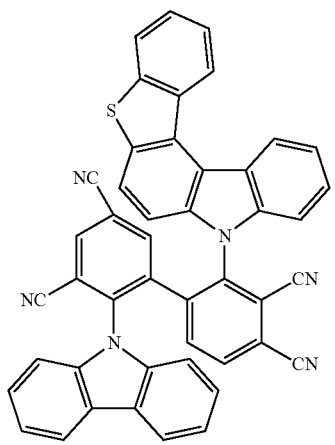
516
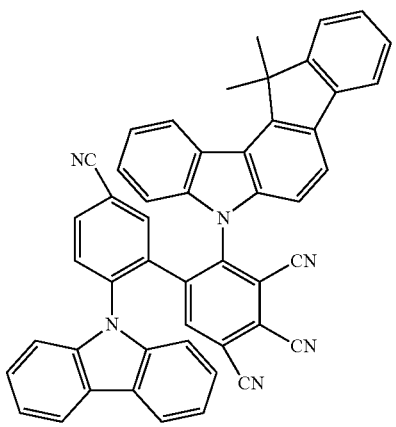
517
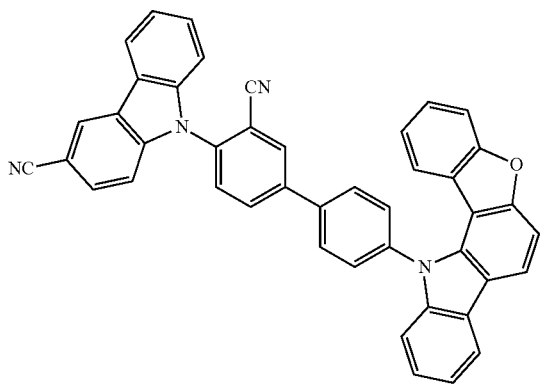
518
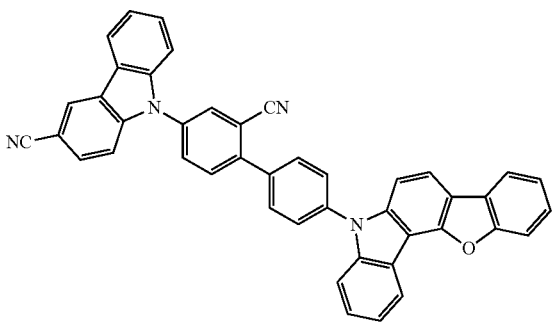

-continued
519
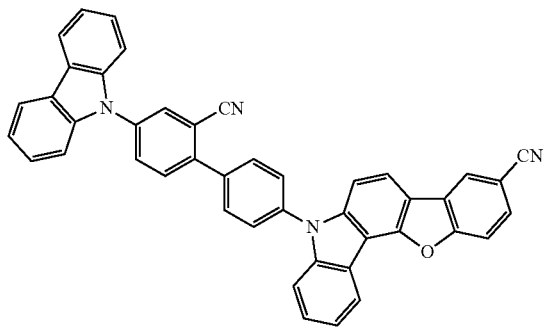
520
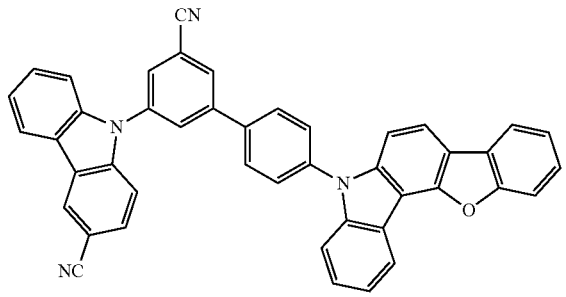
521
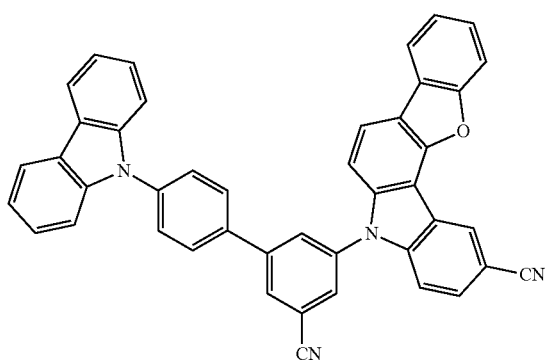
522
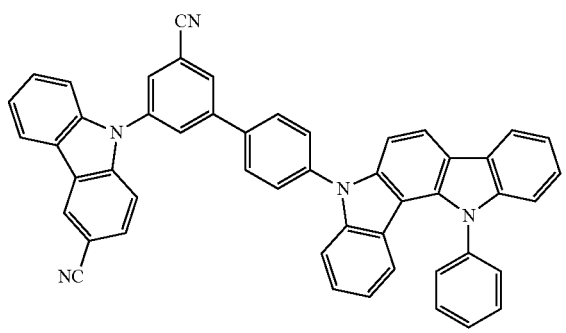
523
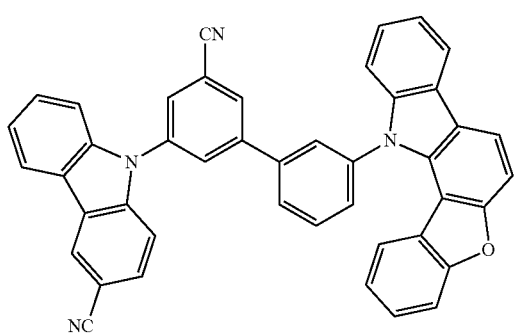
524
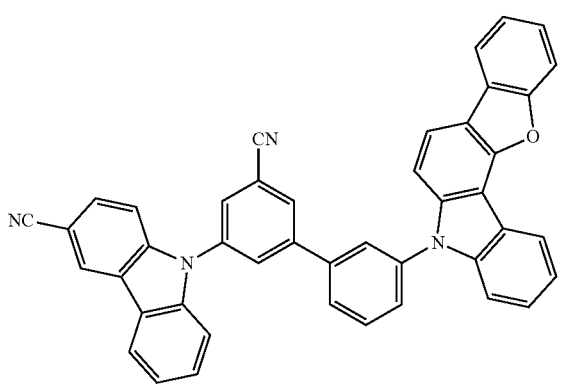
525
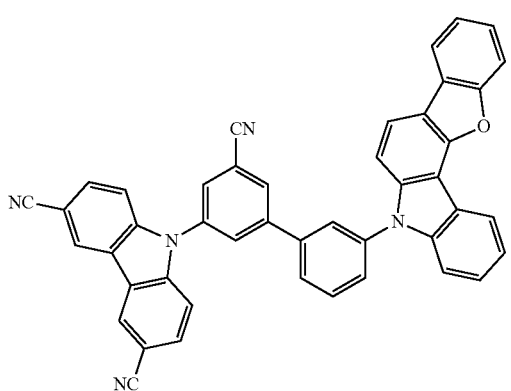
526
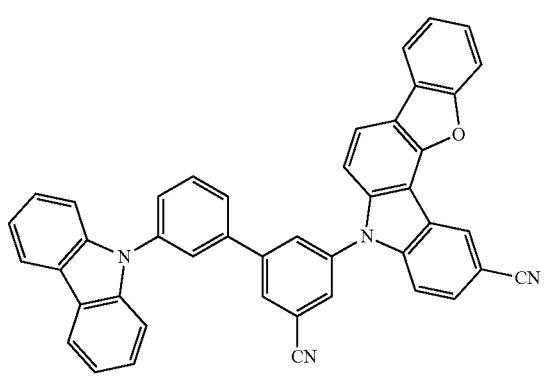

527 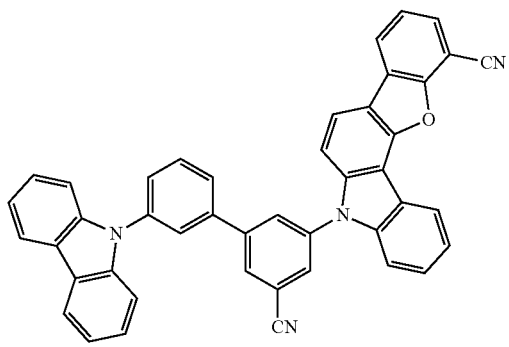
528 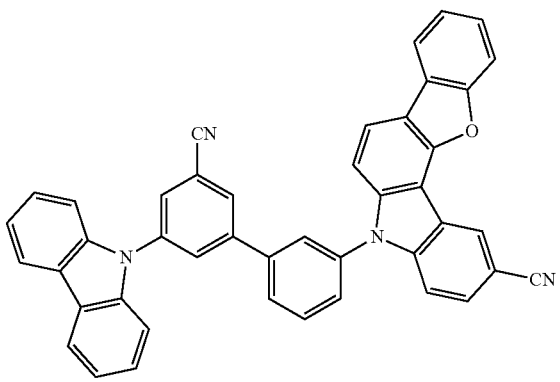
529 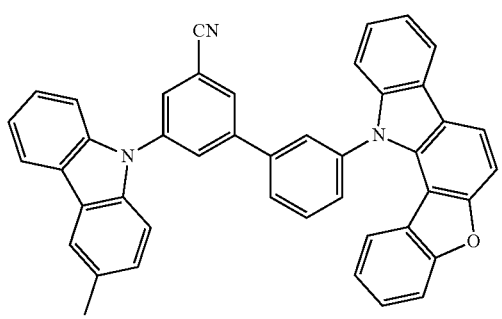
530 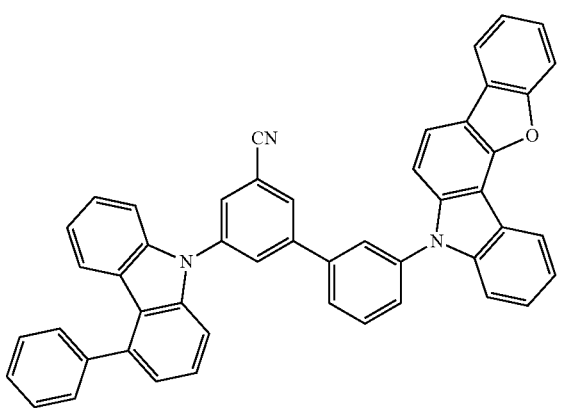
531 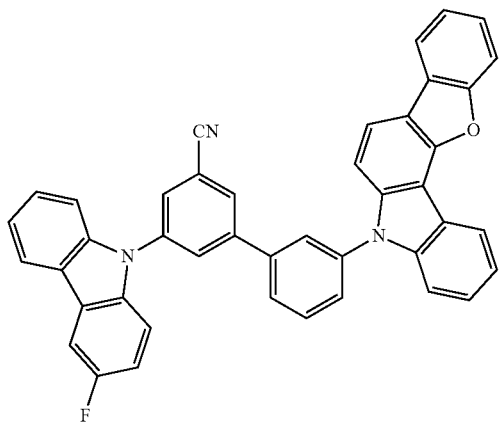
532 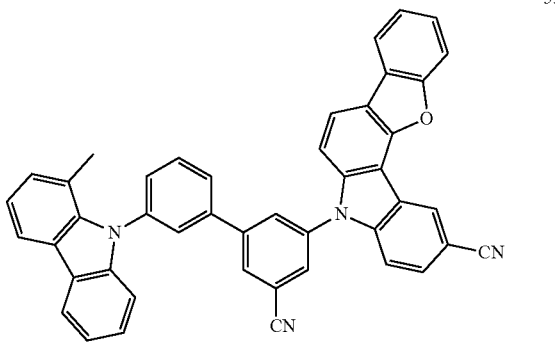
533 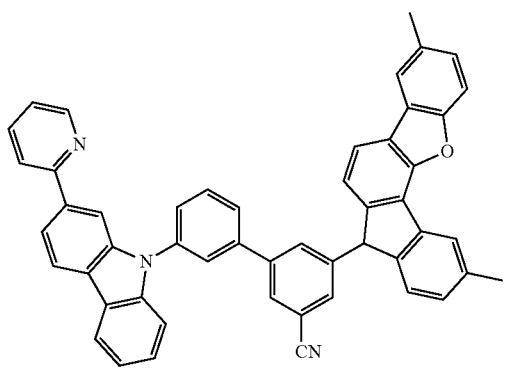
534 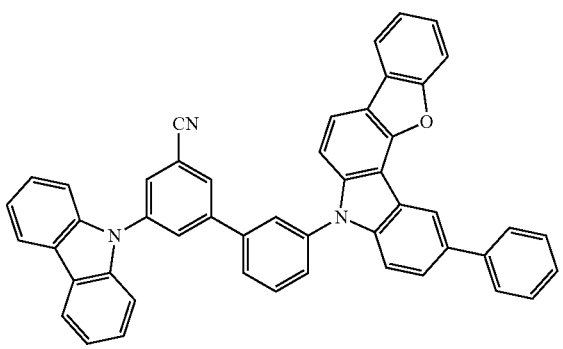

-continued
535
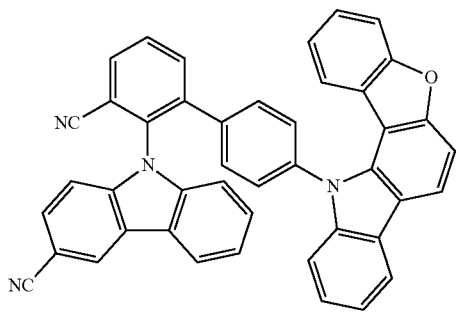
536
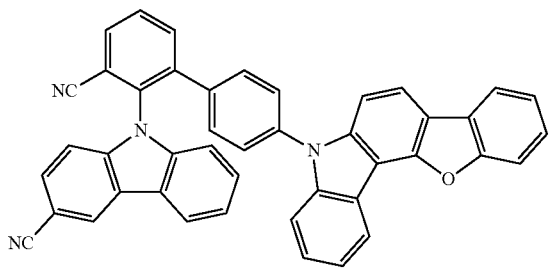
537
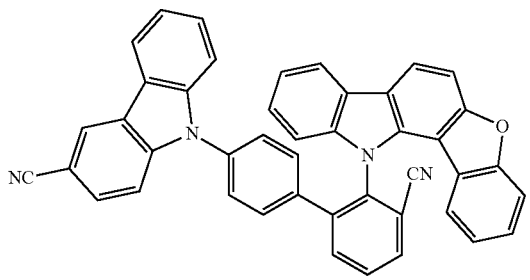
538
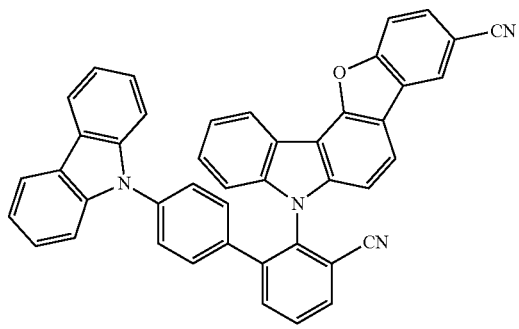
539
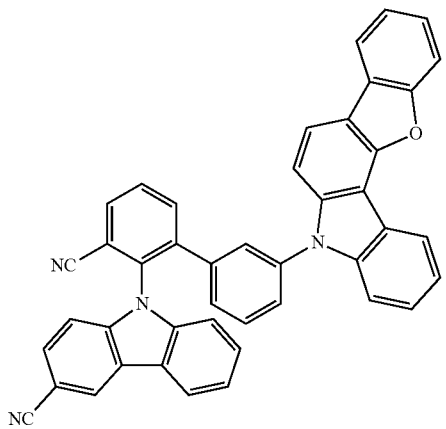
540
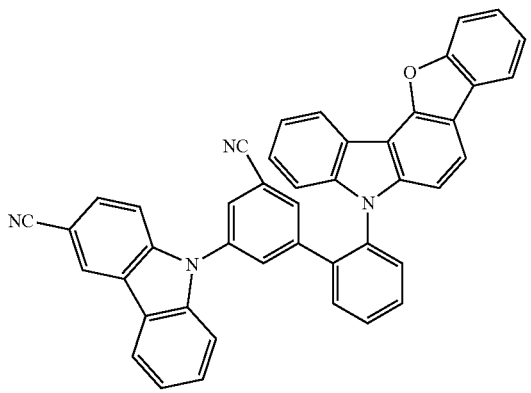
541
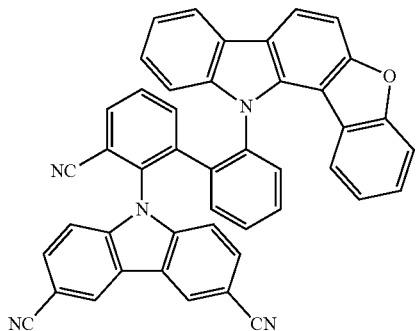
542
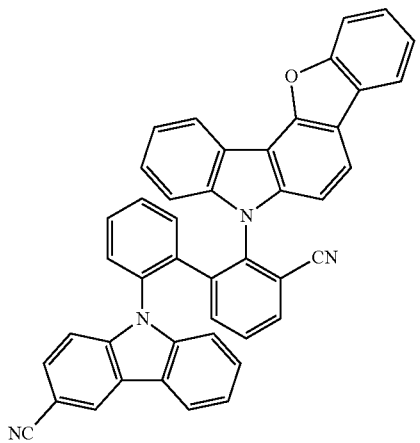

-continued
543
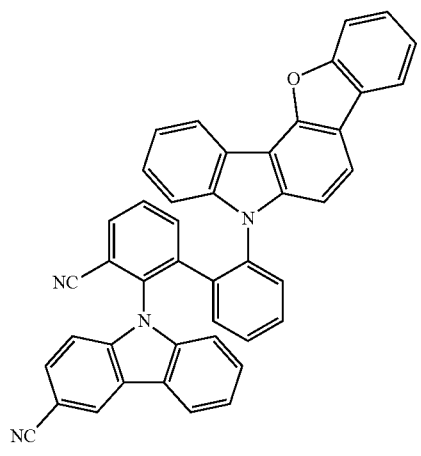
544
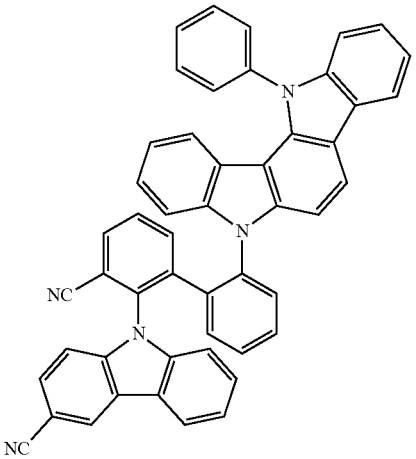
545
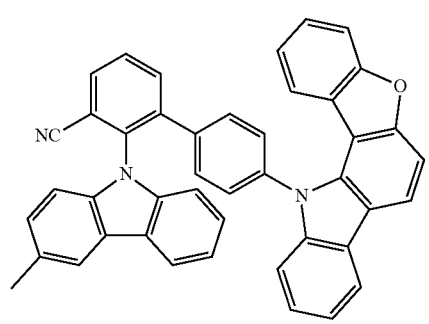
546
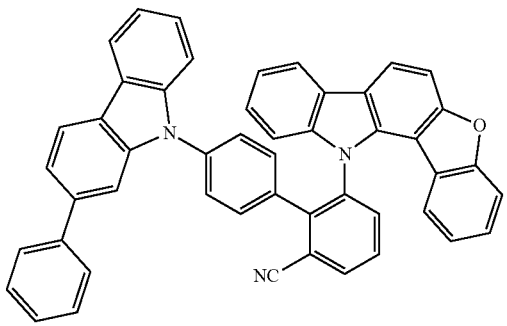
547
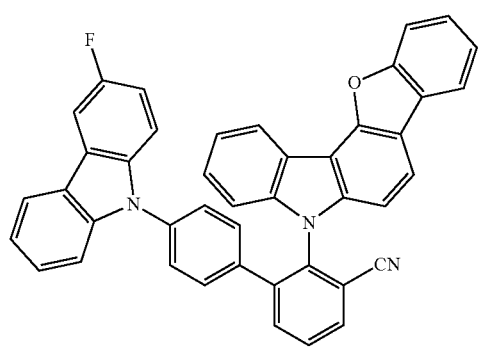
548
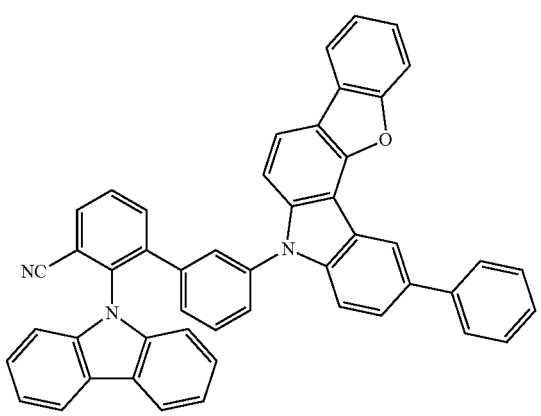

-continued
549
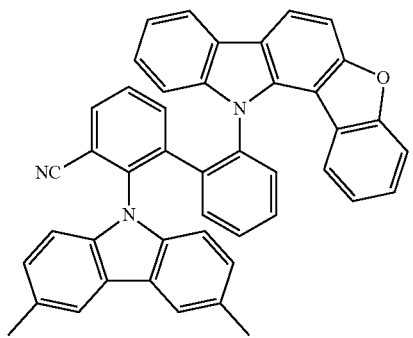
550
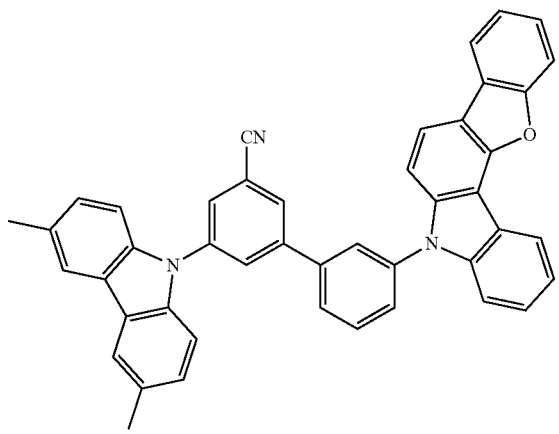
551
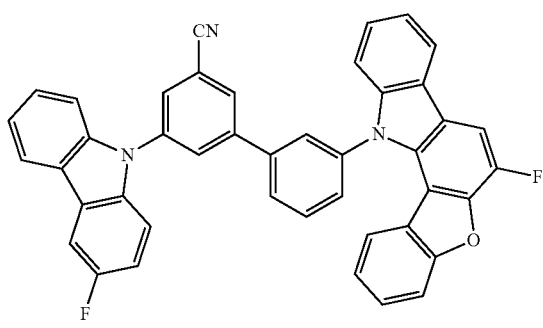
552
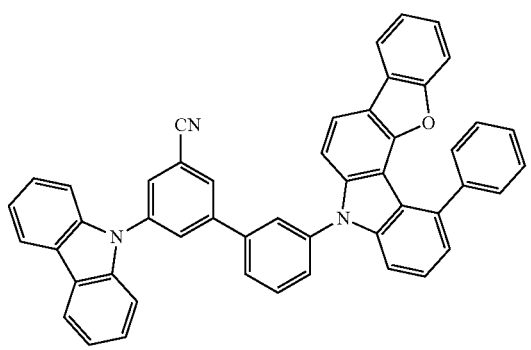
553
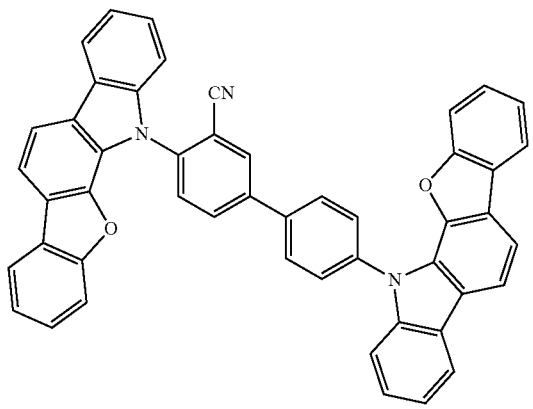
554
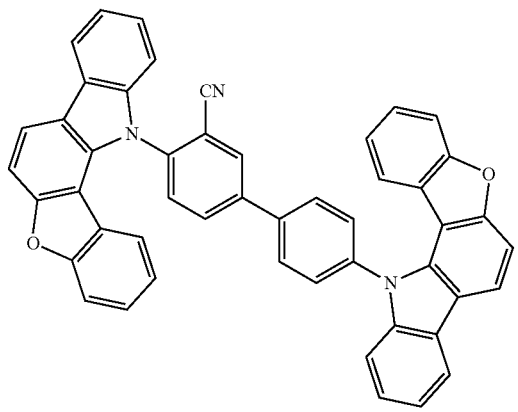
555
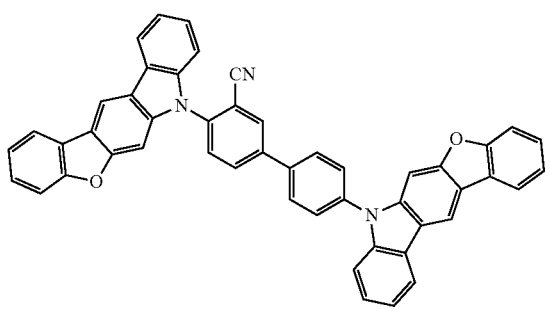
556
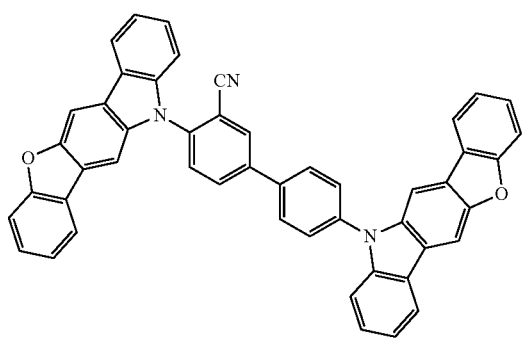

557
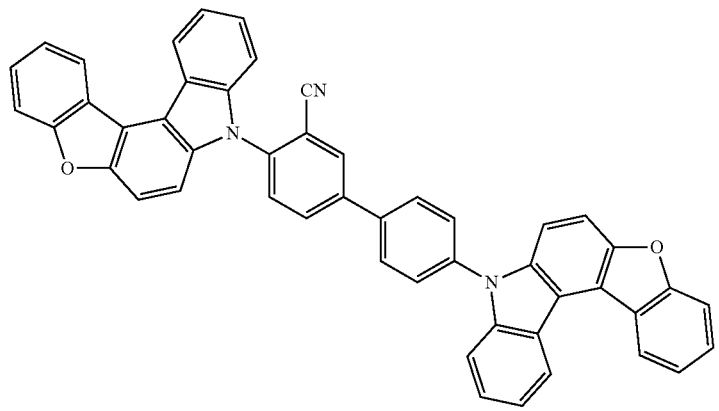
558
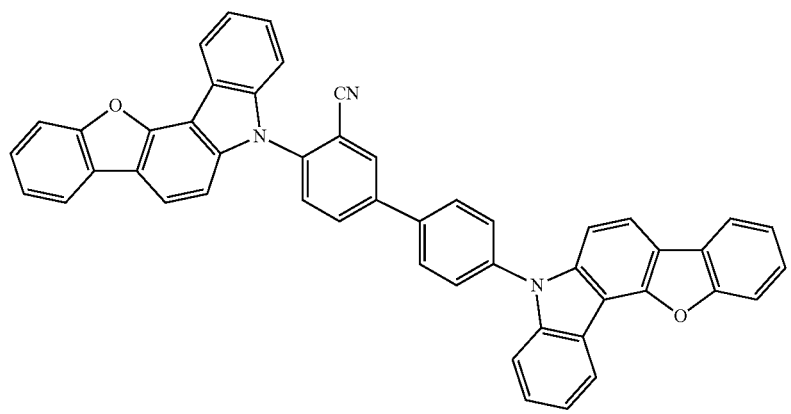
559 560
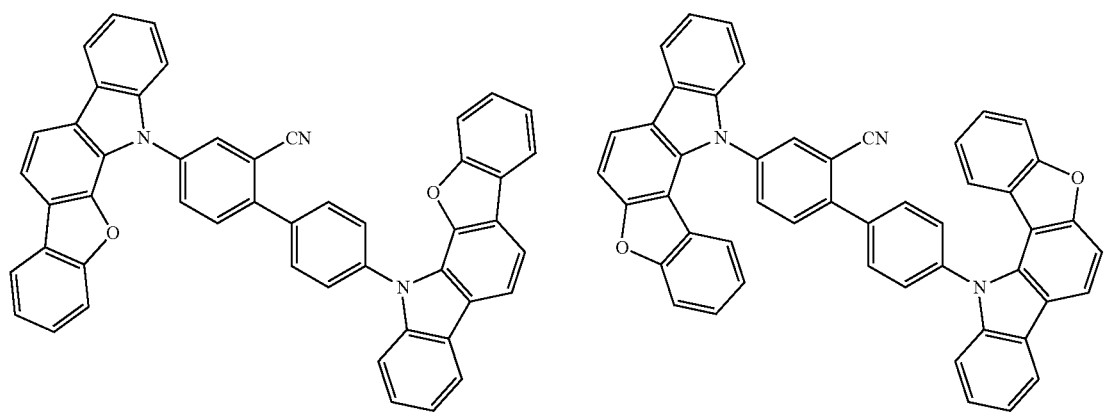

-continued
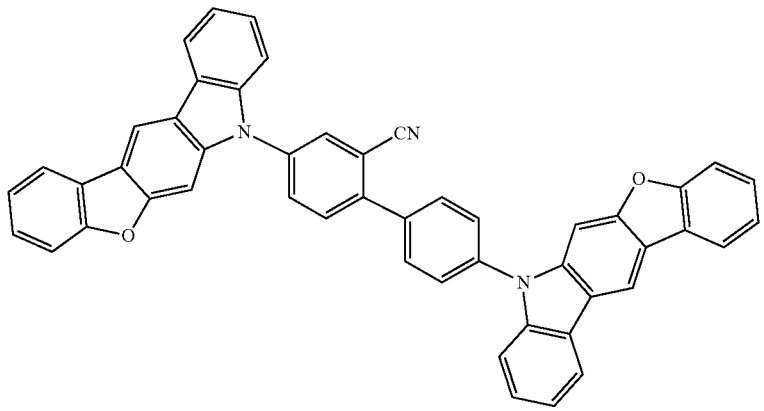
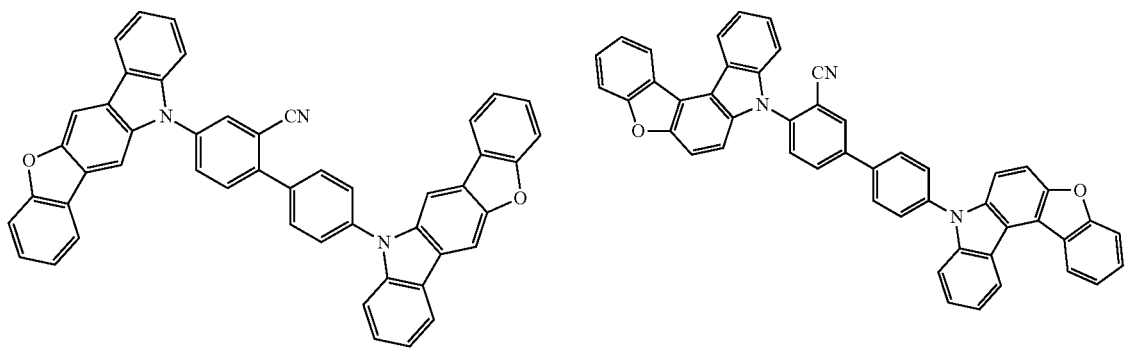
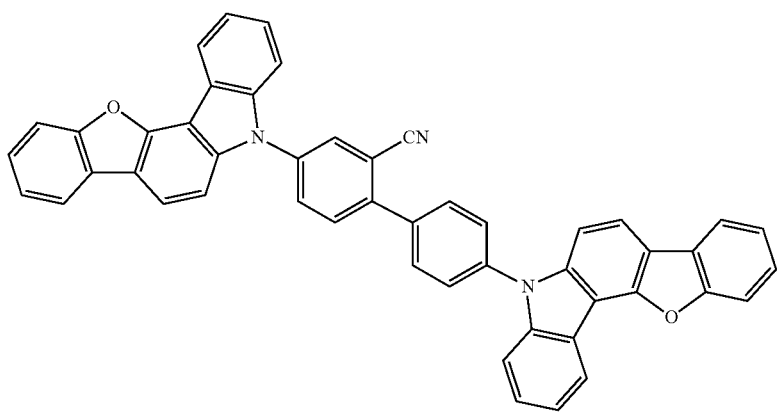
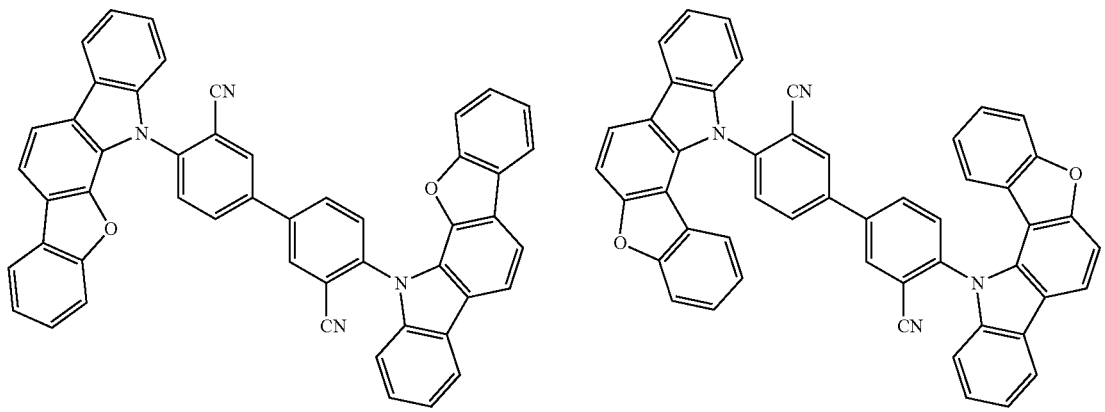

-continued
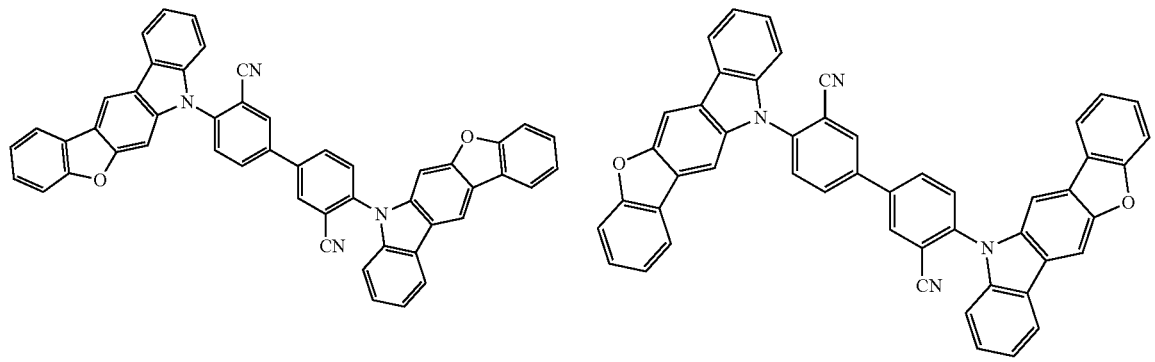
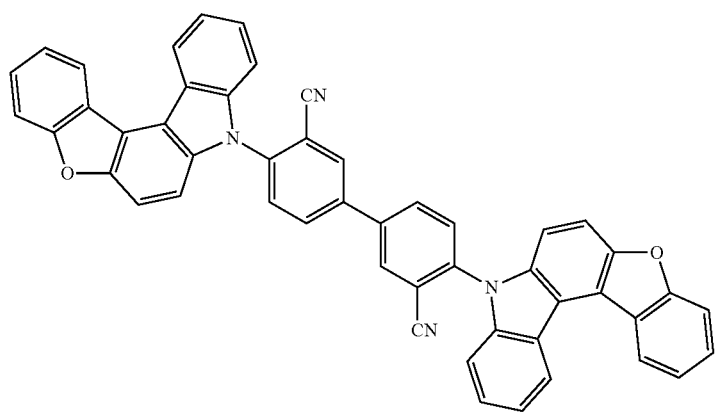
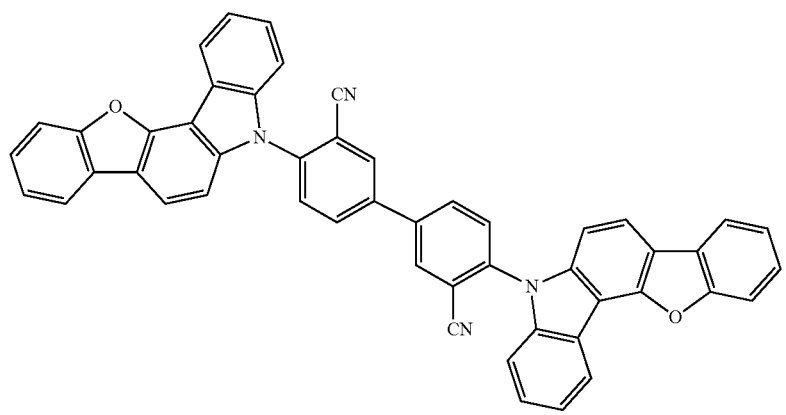
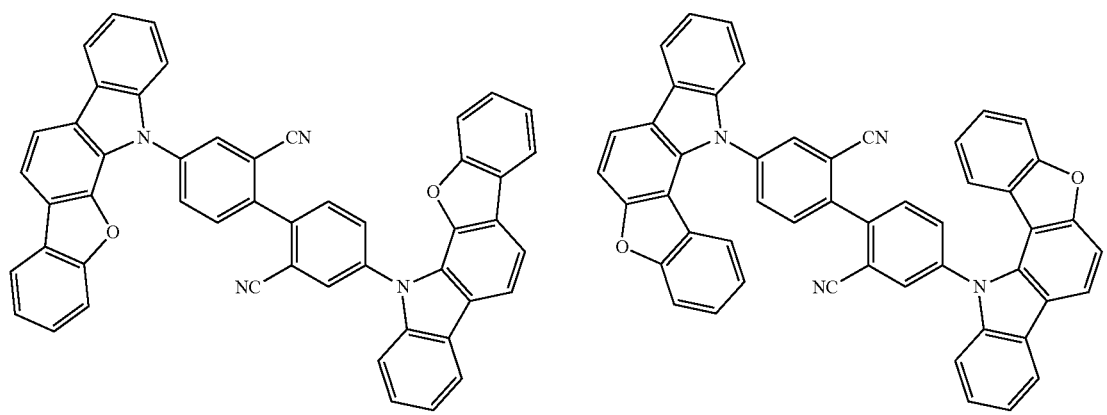

-continued
573
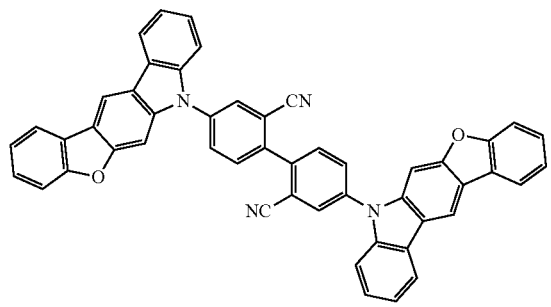
574
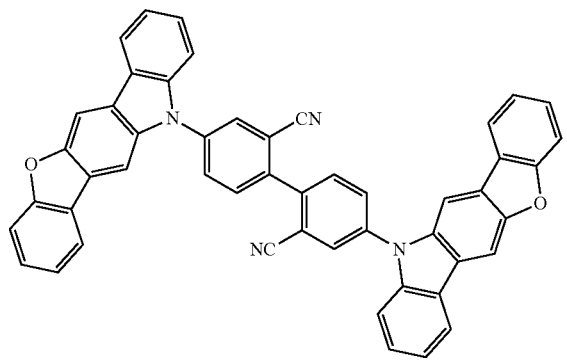
575
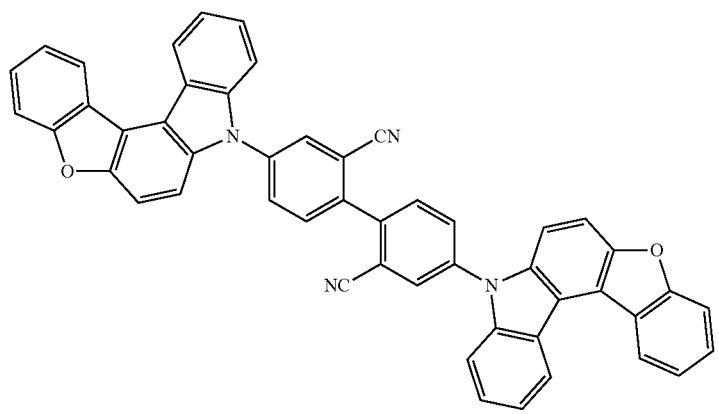
576
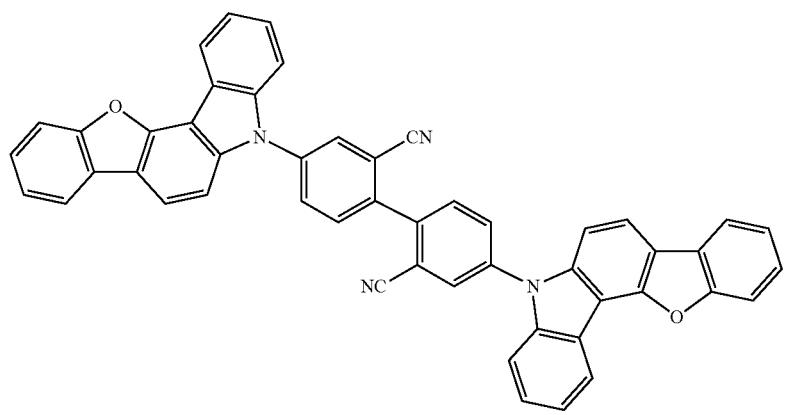
577 578
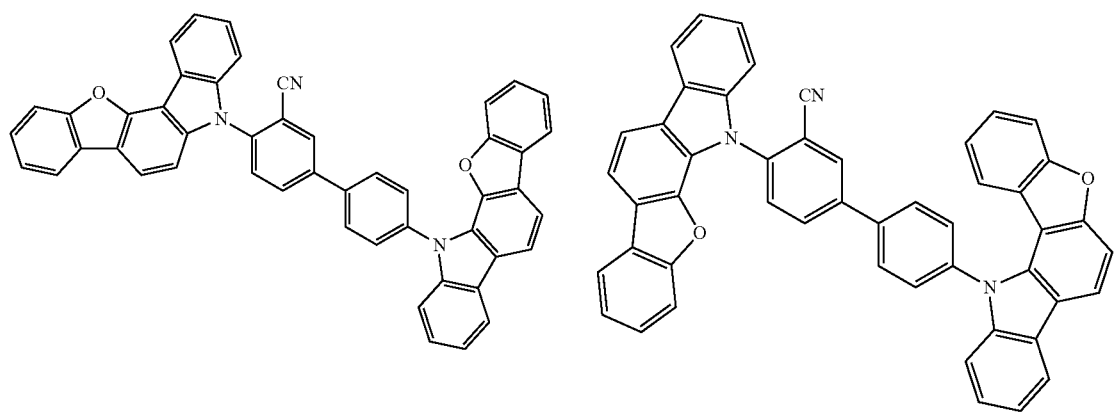

579
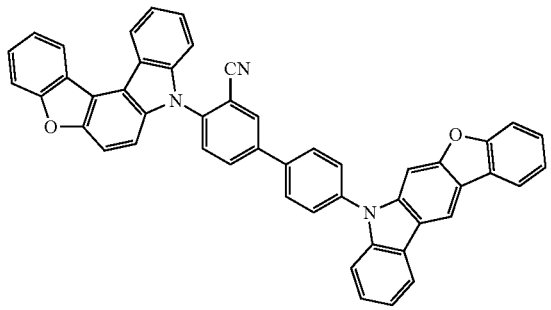
580
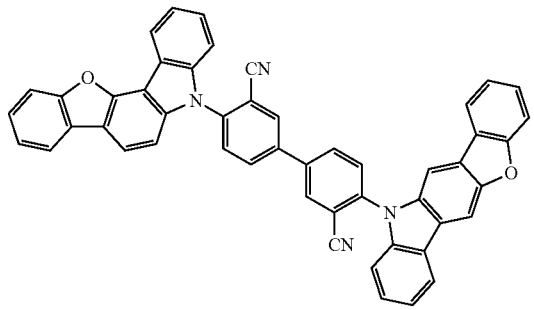
581
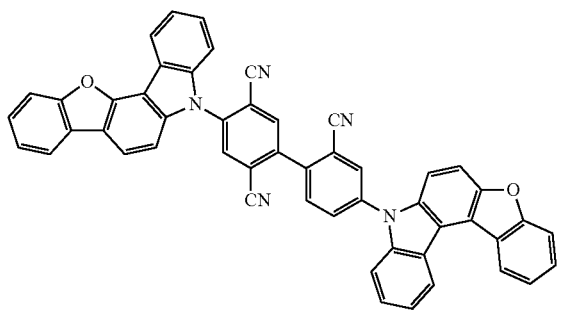
582
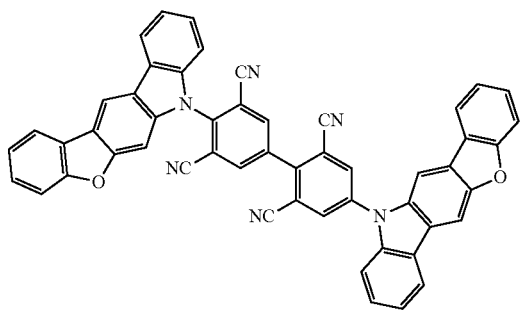
583
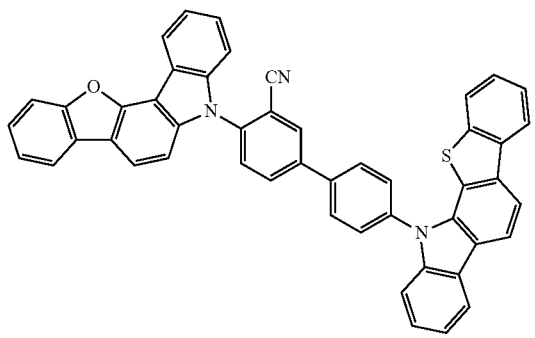
584
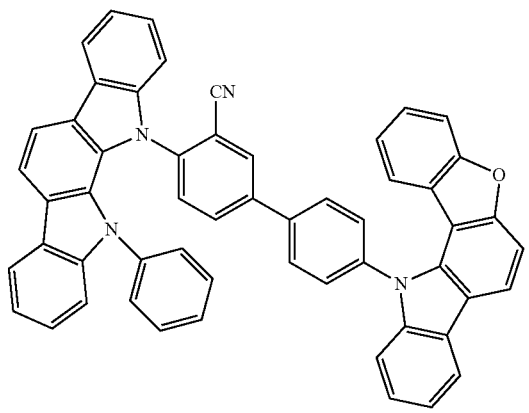
585
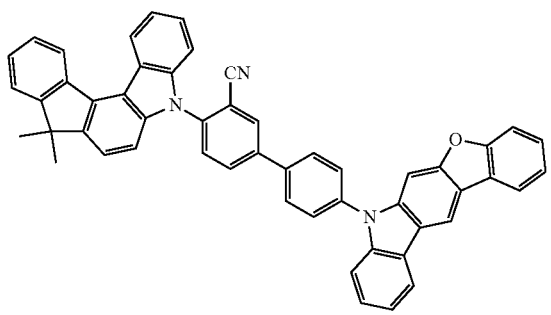
586
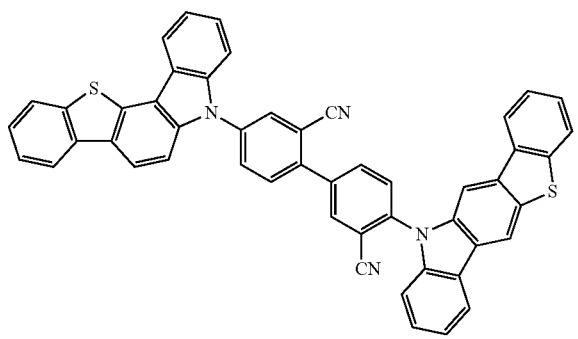

-continued
587
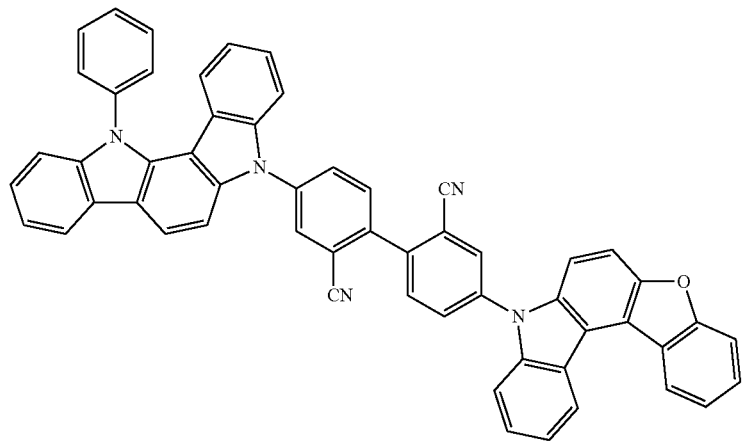
588
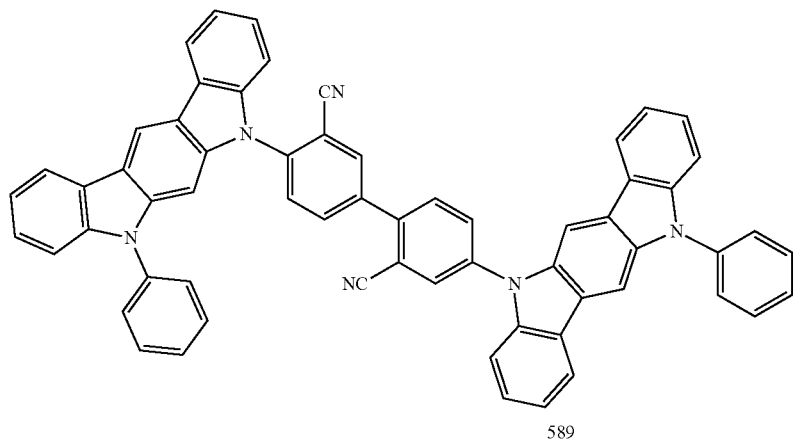
589
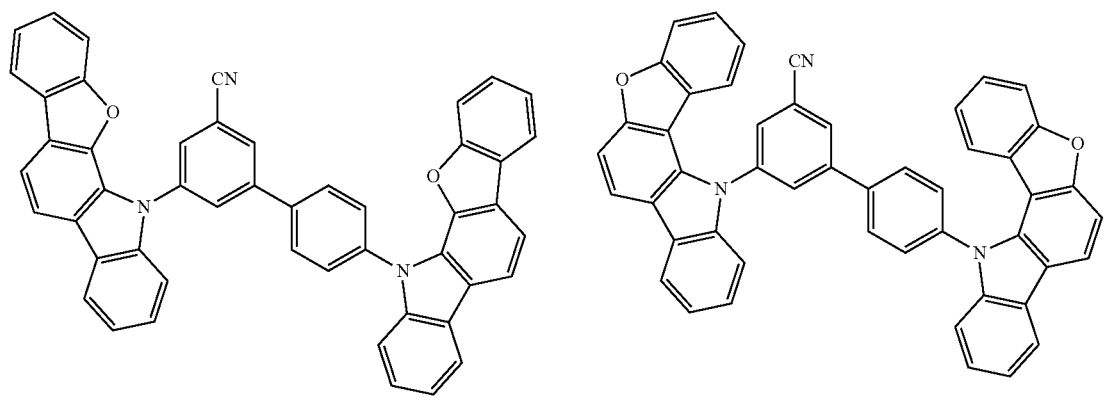
590
591
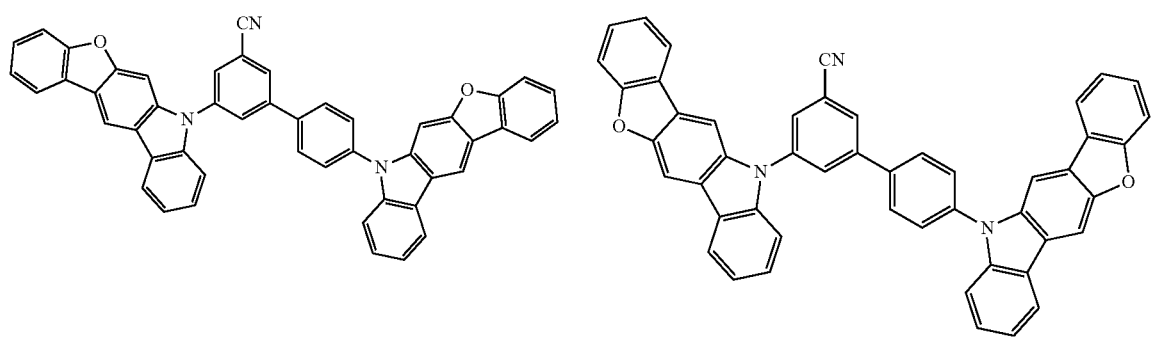
592

593
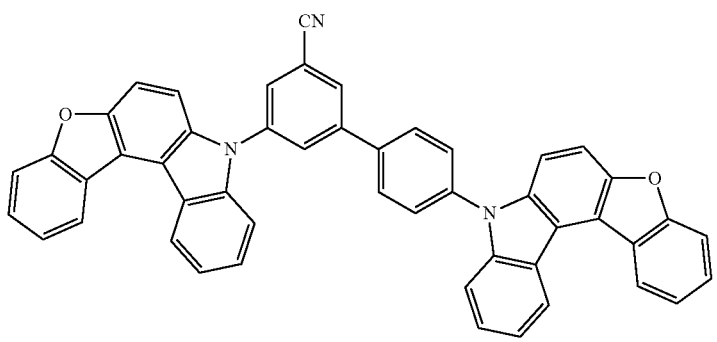
594
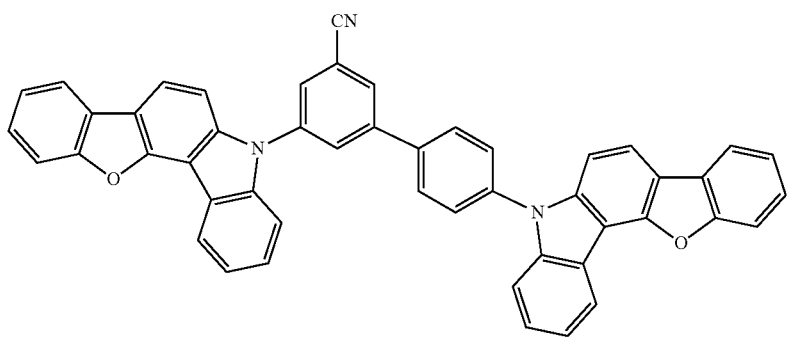
595
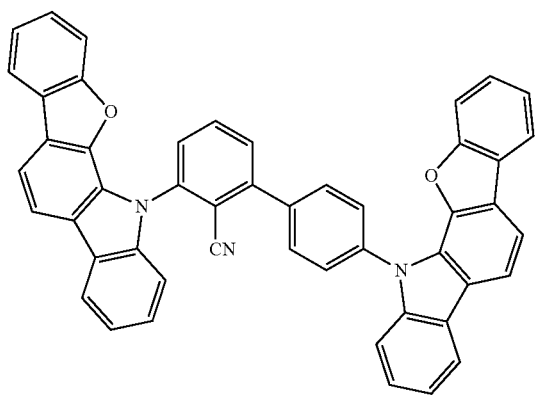
596
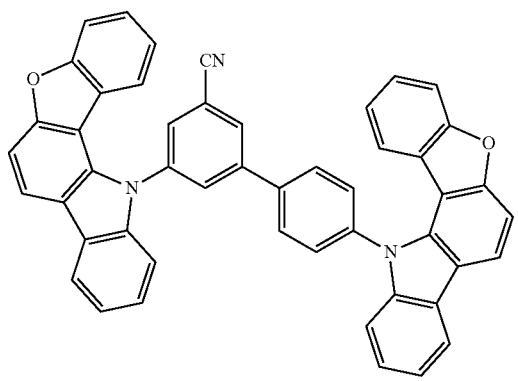
597
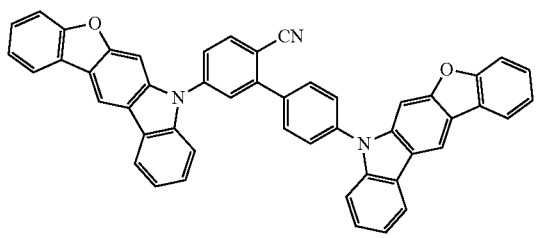
598
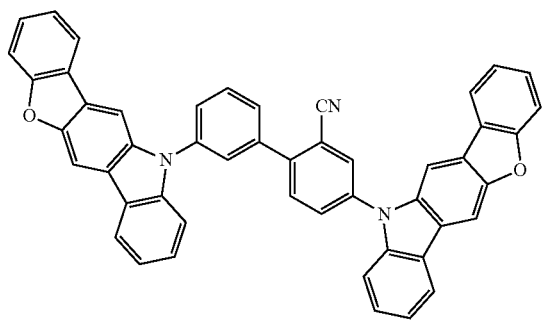

599
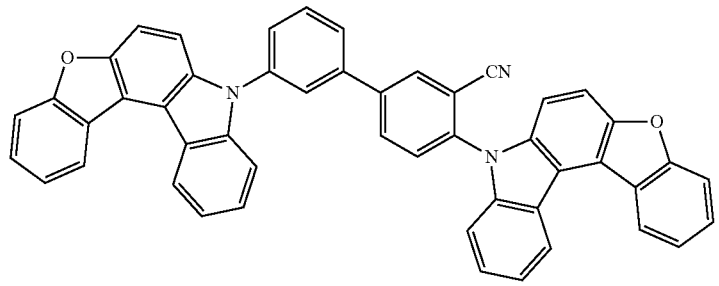
600
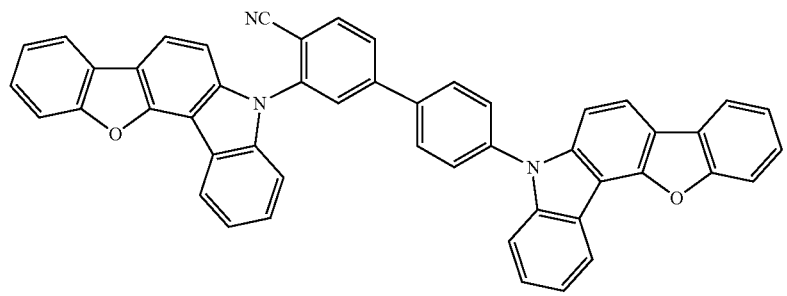
601 602
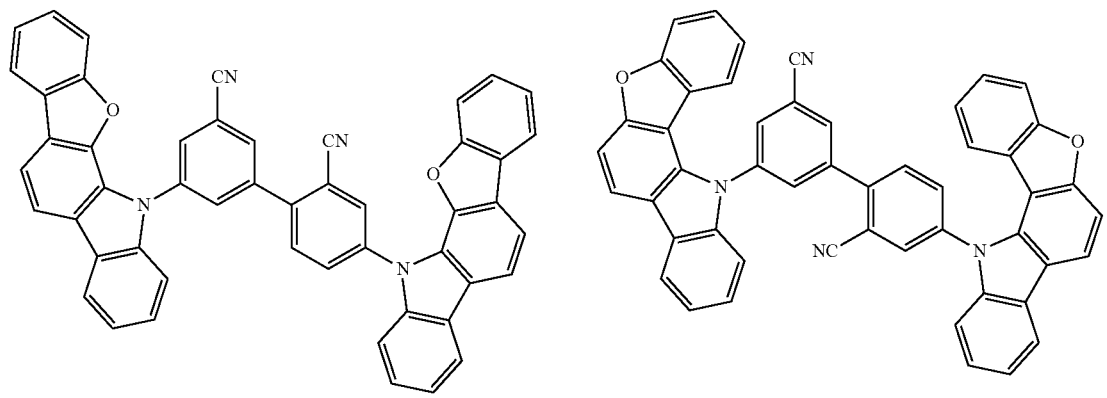
603
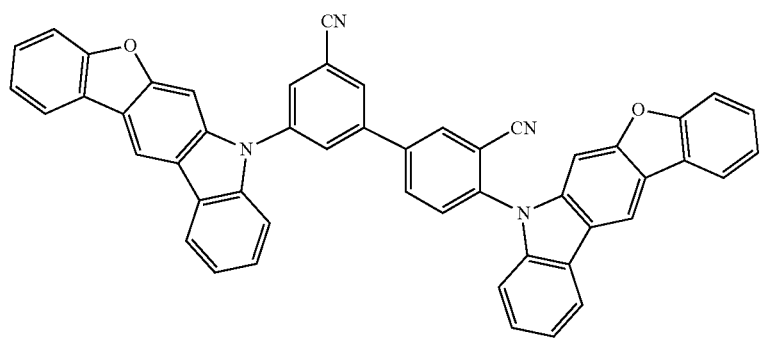

-continued
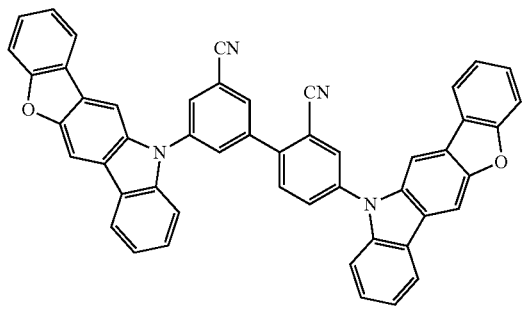
604
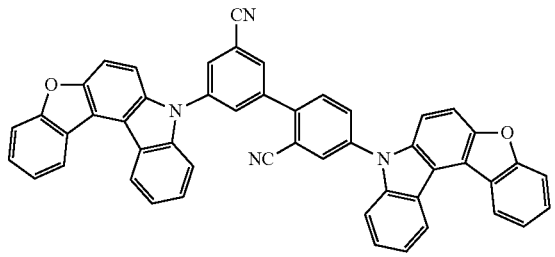
605
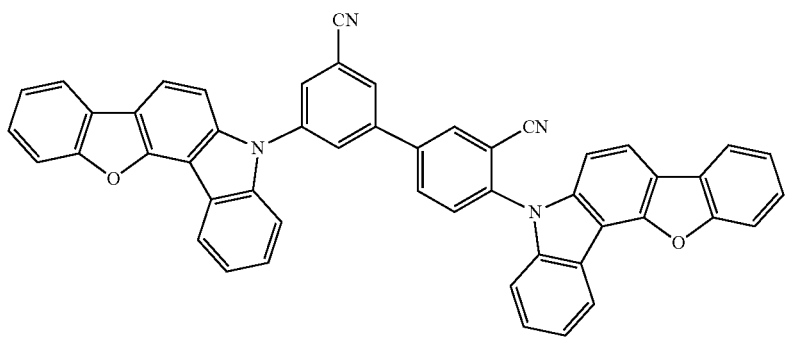
606
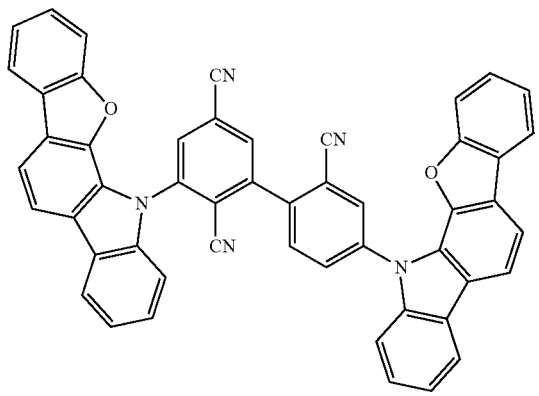
607
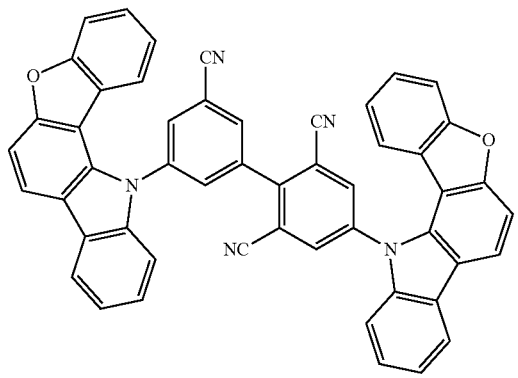
608
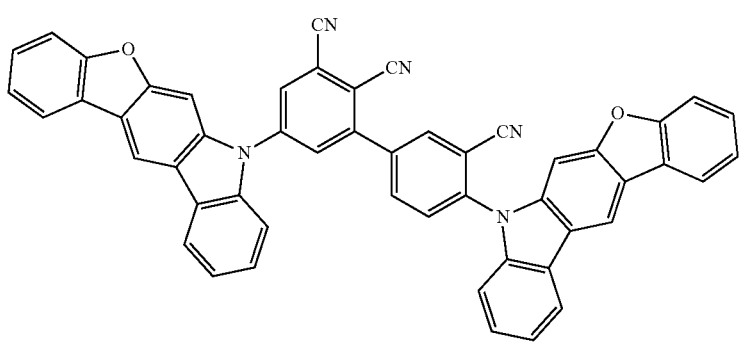
609

-continued
610
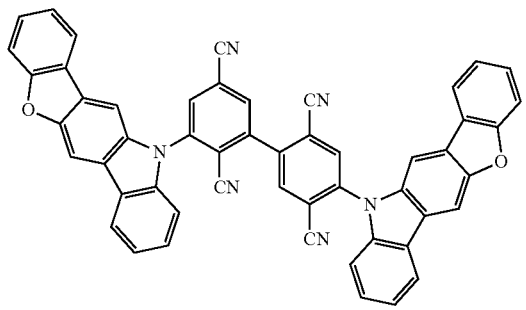
611
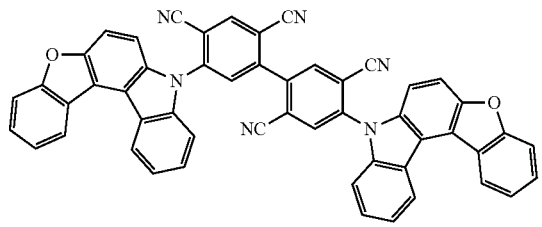
612
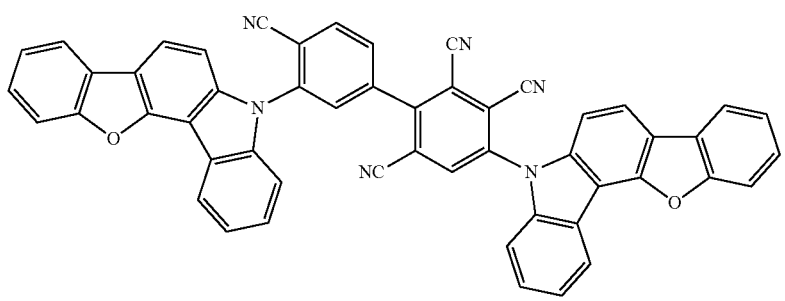
613
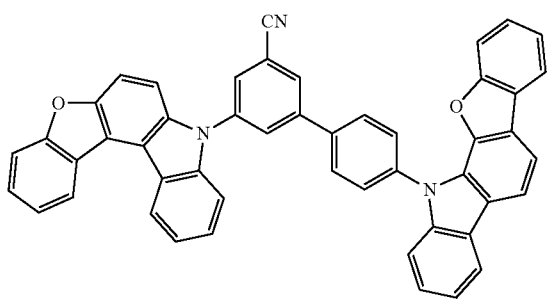
614
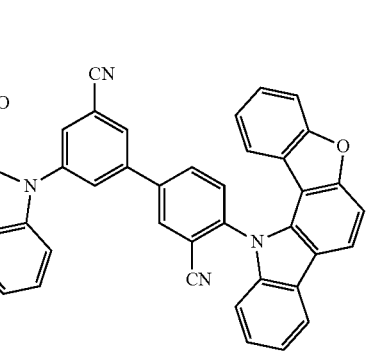
615
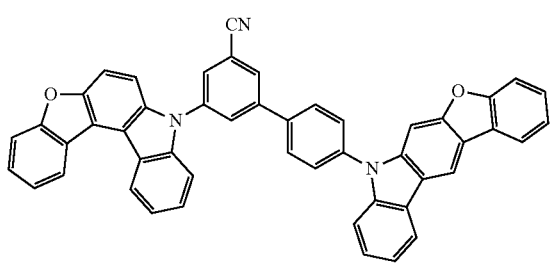
616
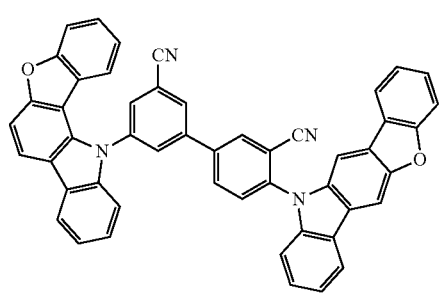
617
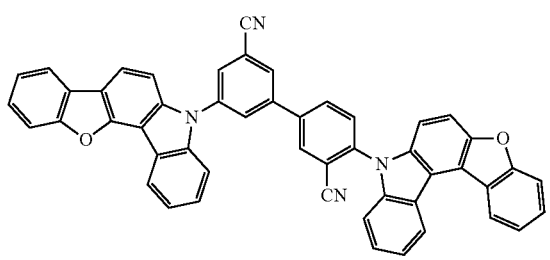
618
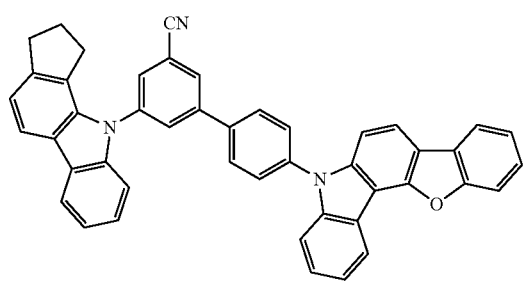

-continued
619
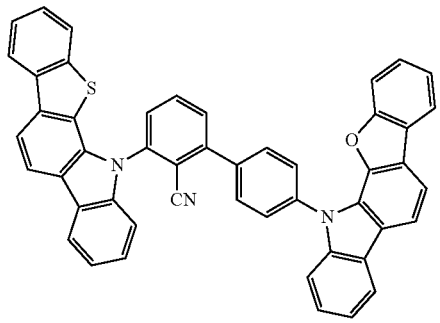
620
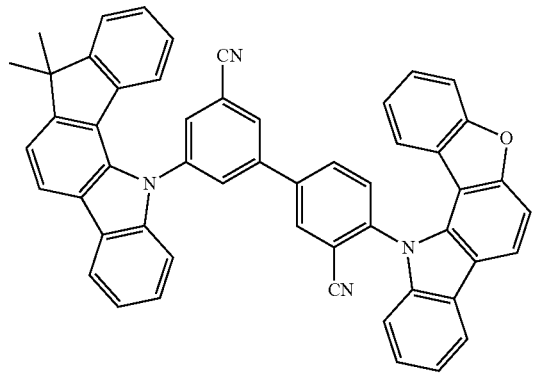
621
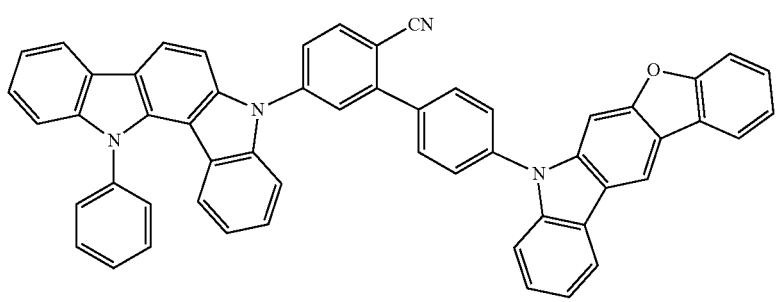
622
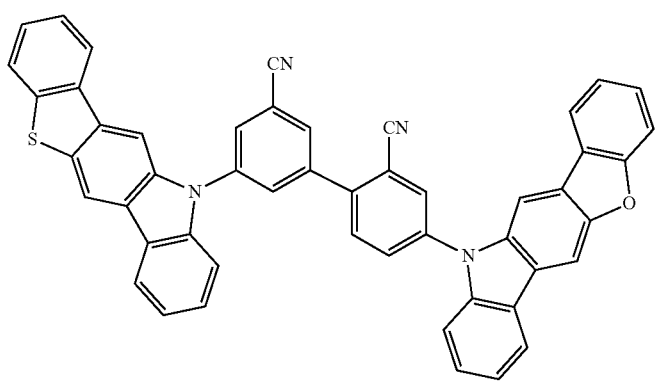
623
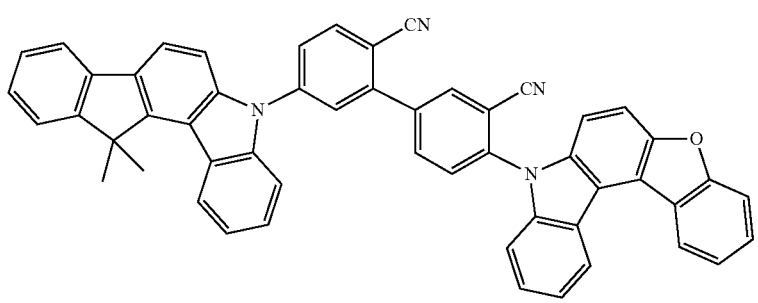

-continued
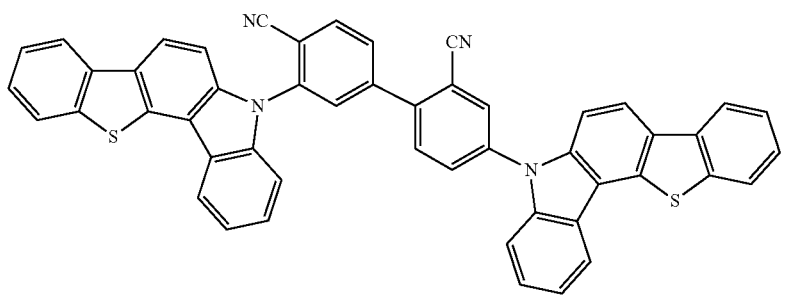
624
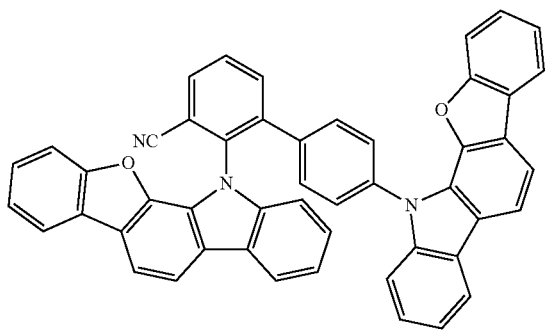
625
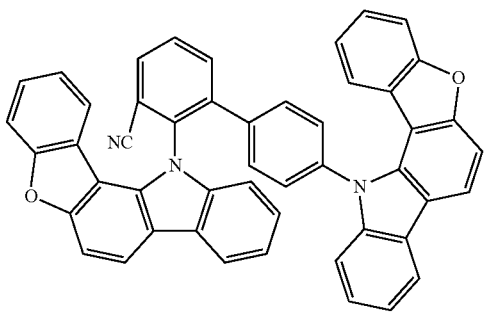
626
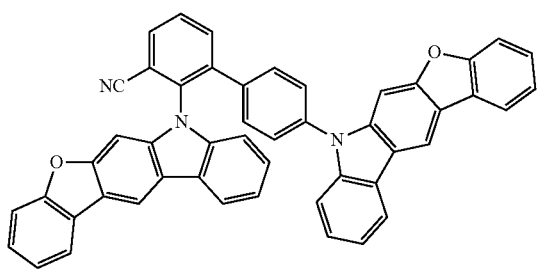
627
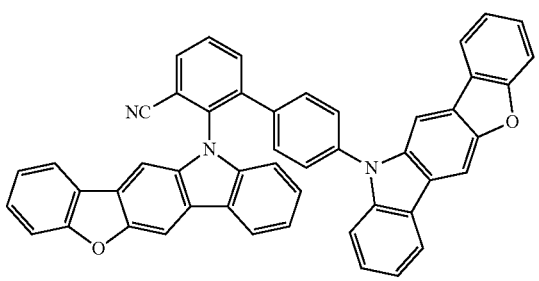
628
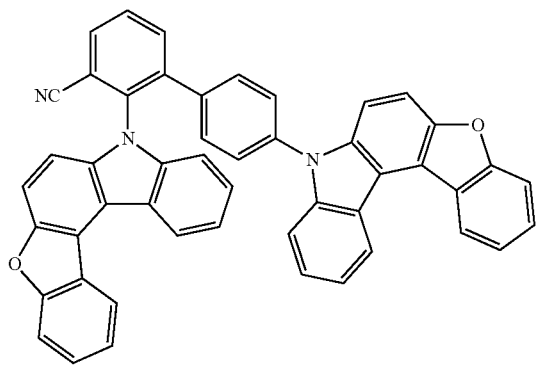
629
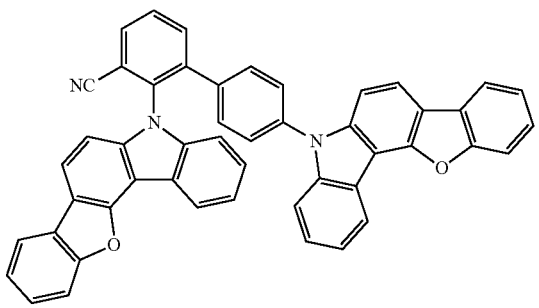
630

-continued
631
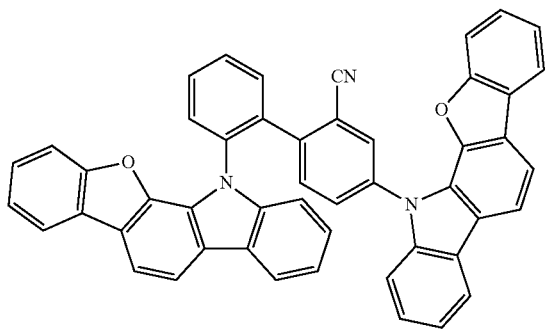
632
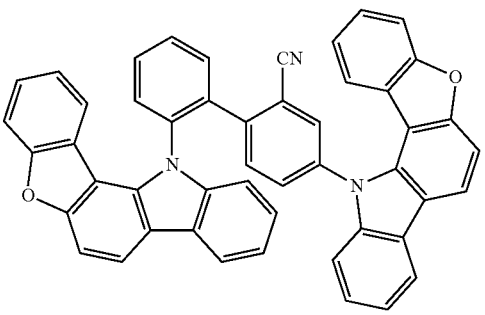
633
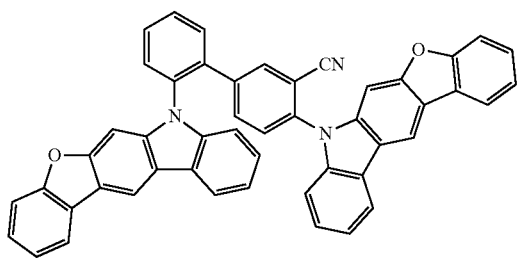
634
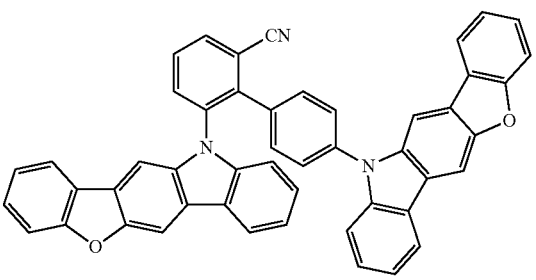
635
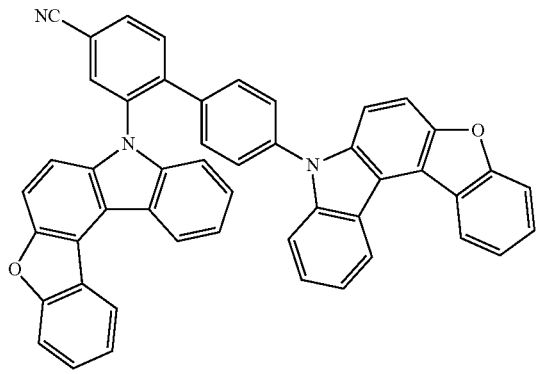
636
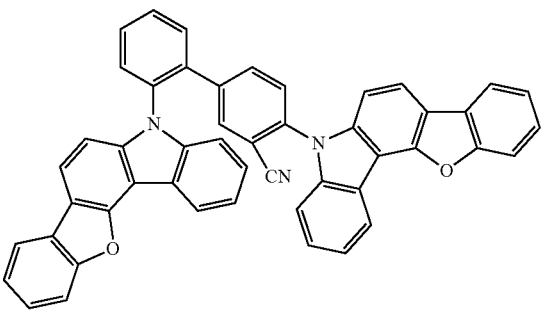
637
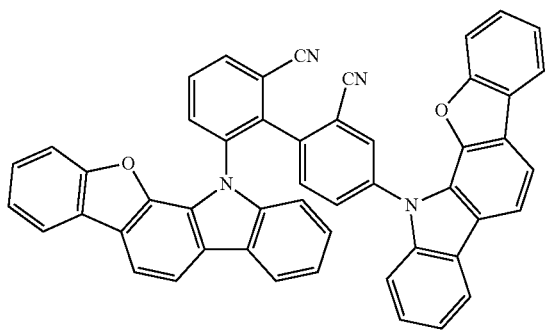
638
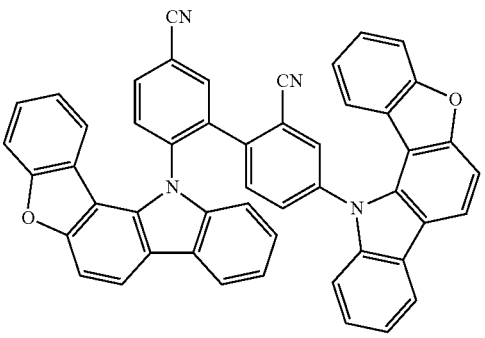

-continued
639
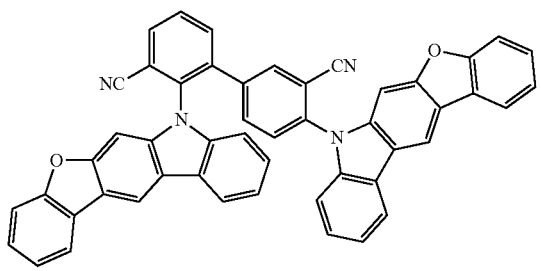
640
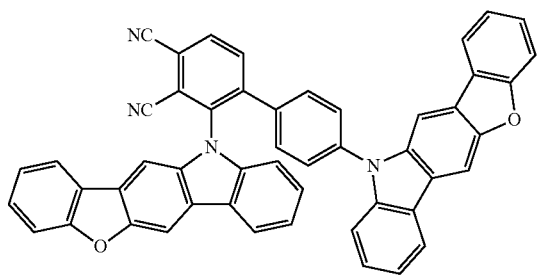
641
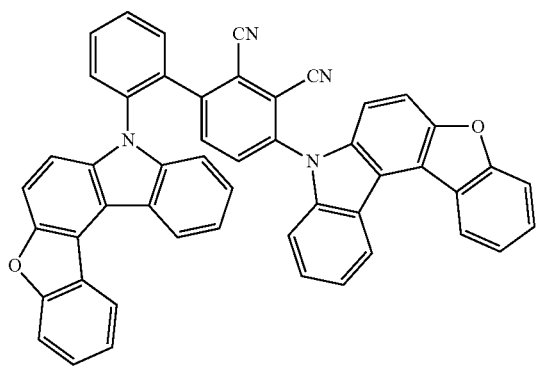
642
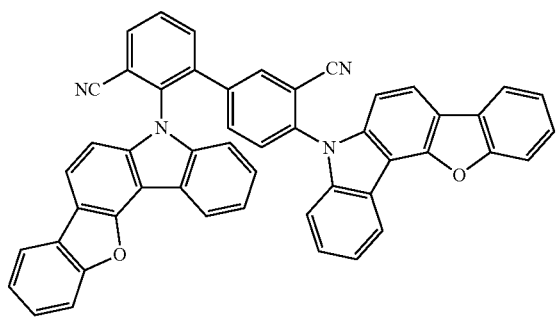
643
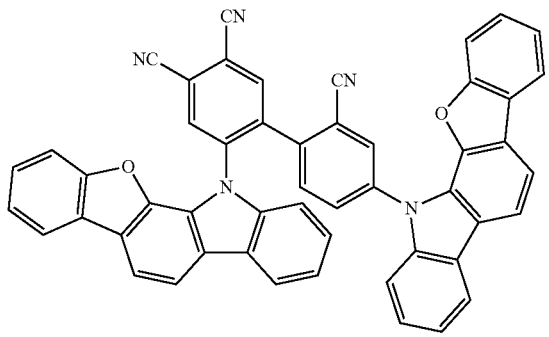
644
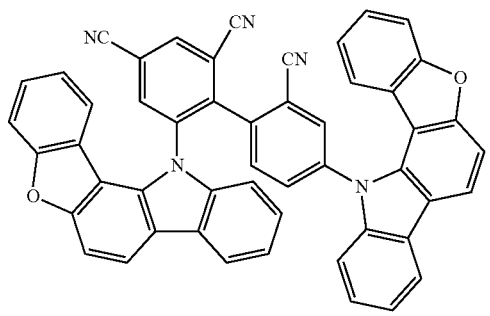
645
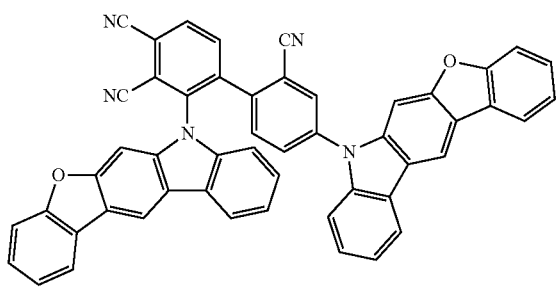
646
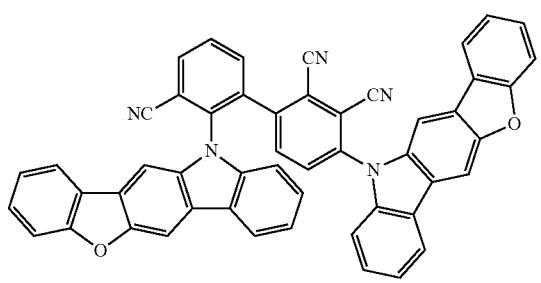

-continued
647
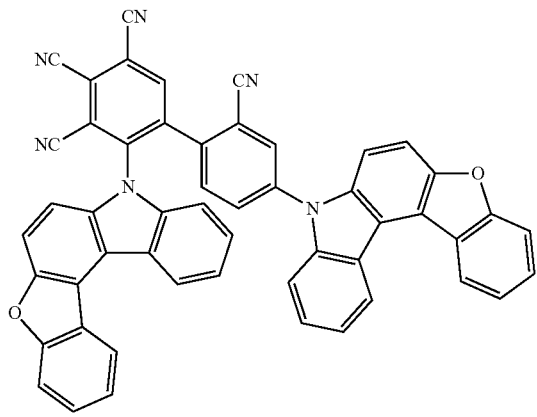
648
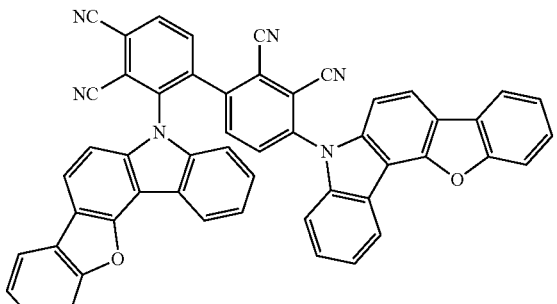
649
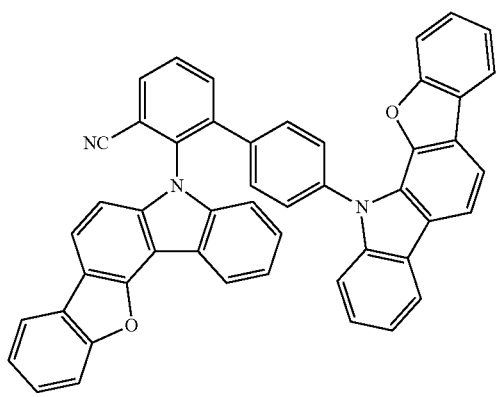
650
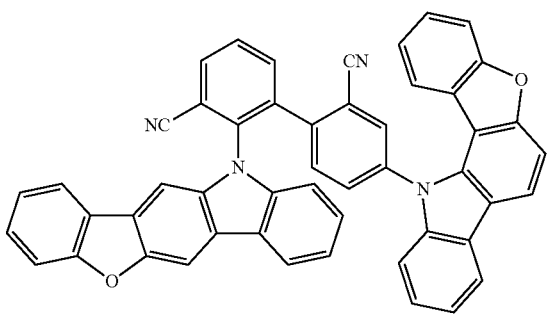
651
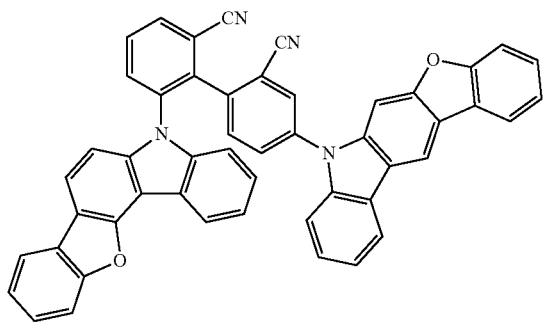
652
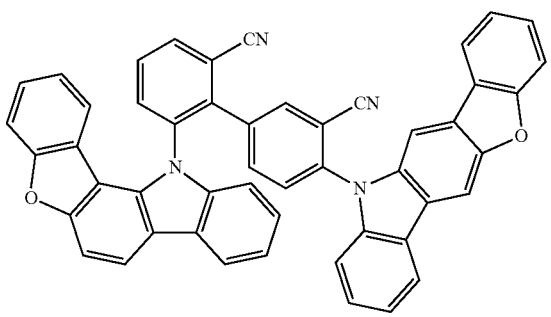
653
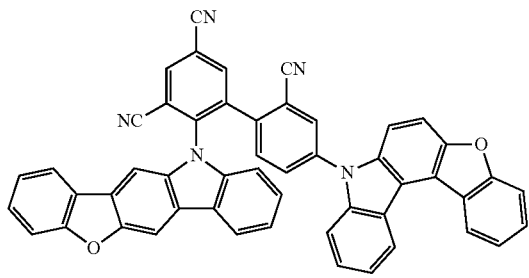
654
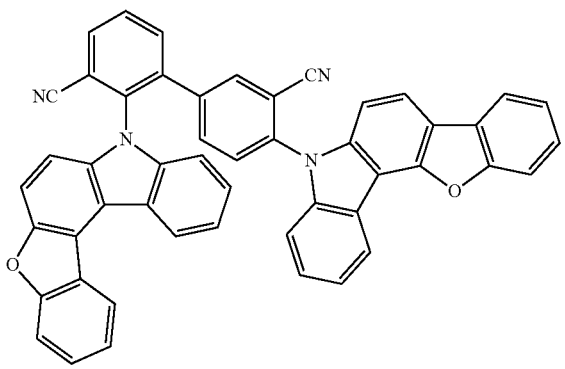

-continued
| 411 | 412 |
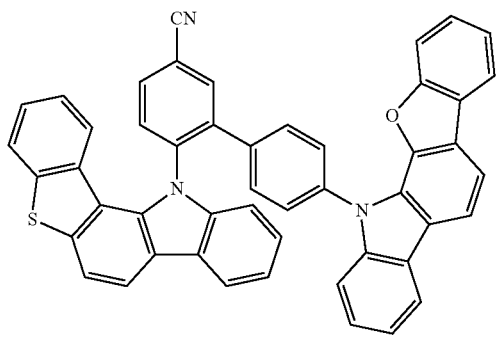
655
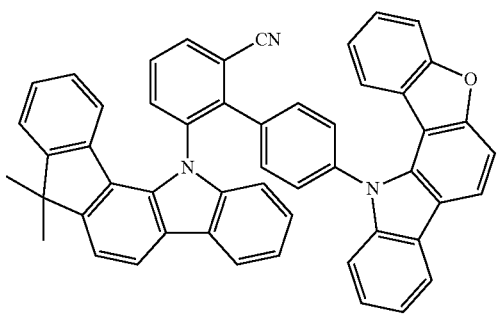
656
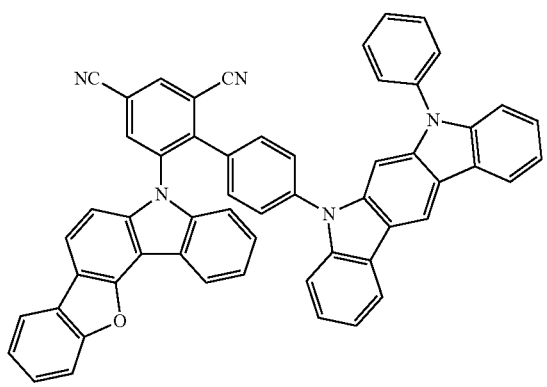
657
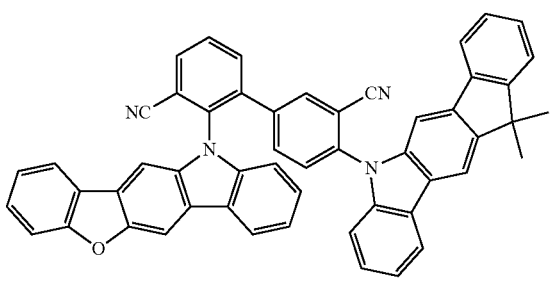
658
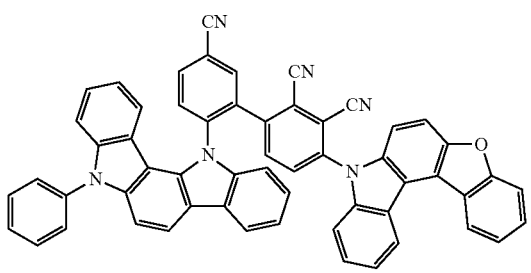
659
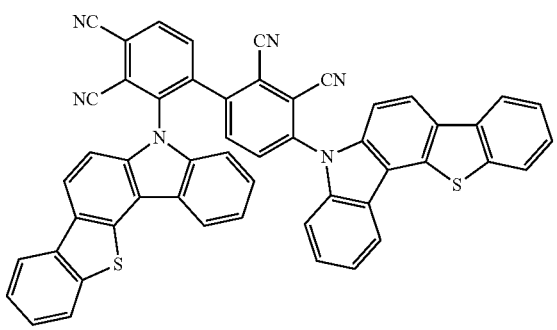
660
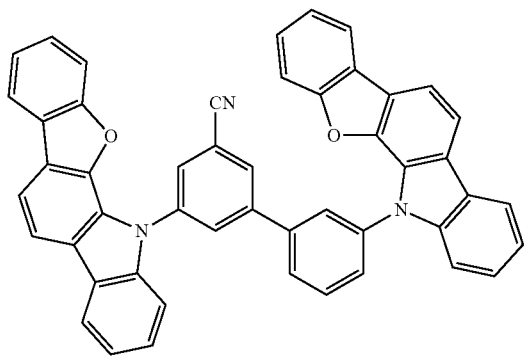
661
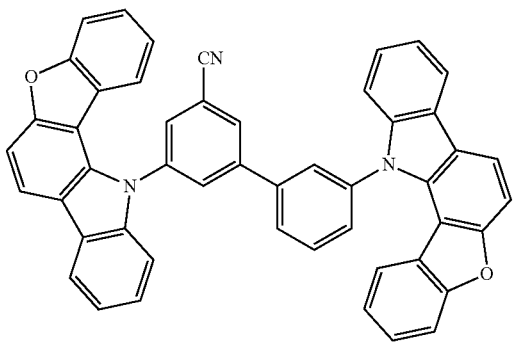
662

-continued
663
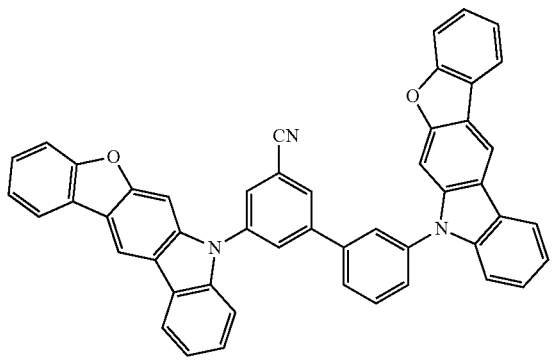
664
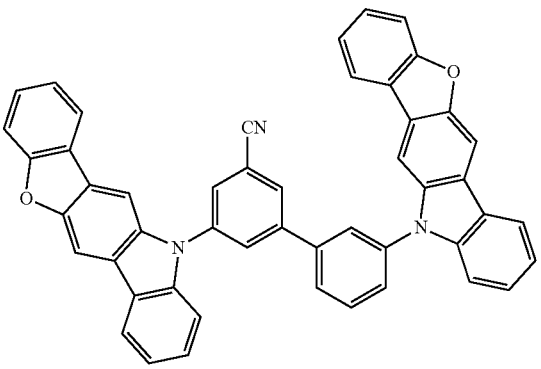
665
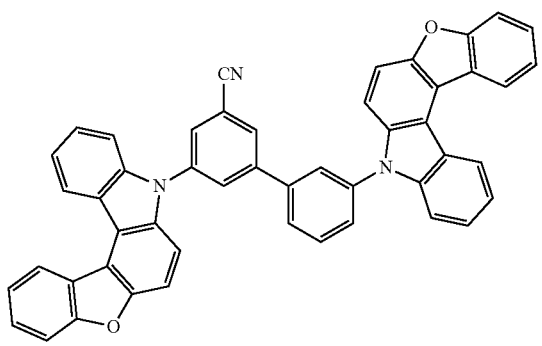
666
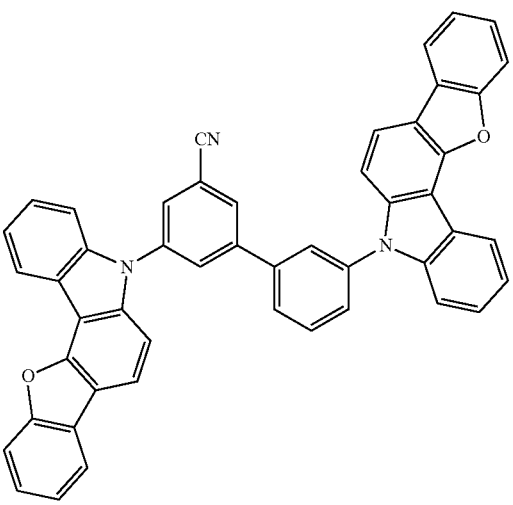
667
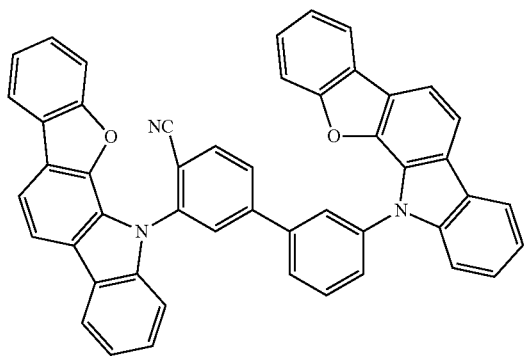
668
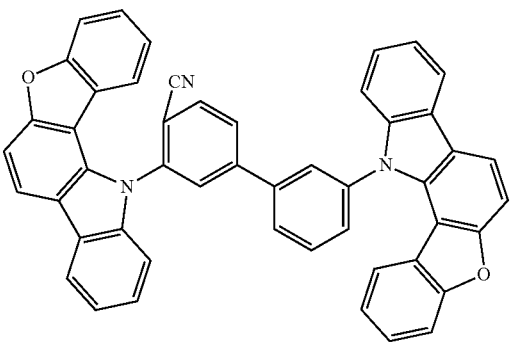
669
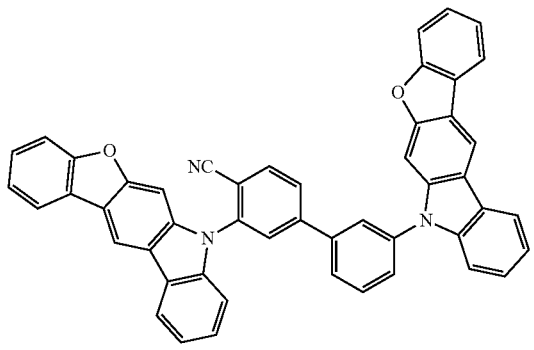
670
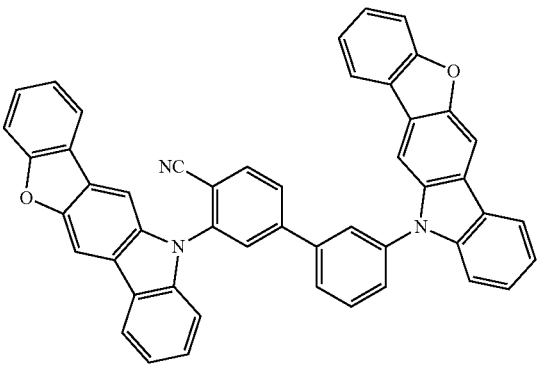

-continued
671
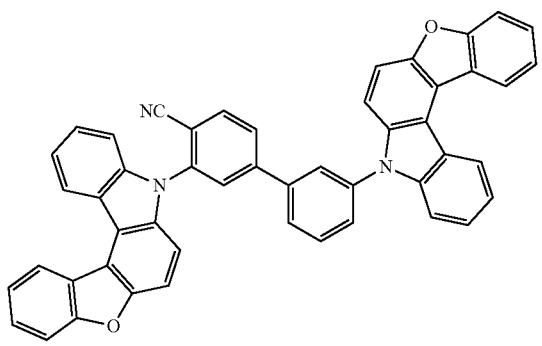
672
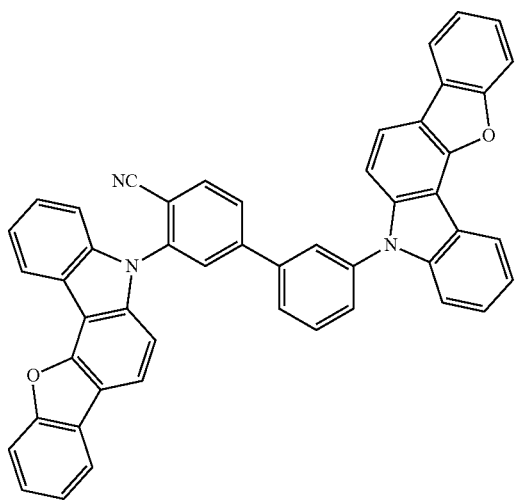
673
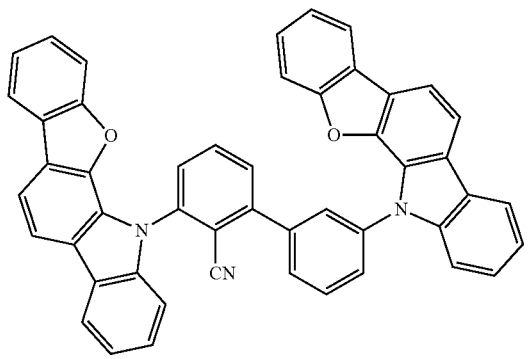
674
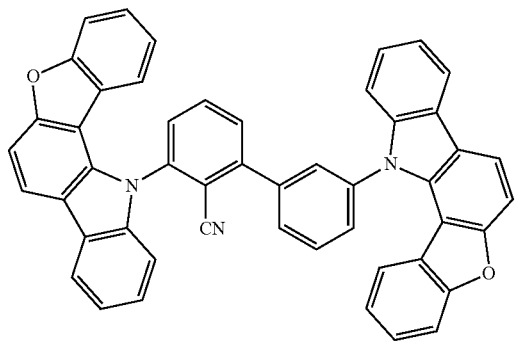
675
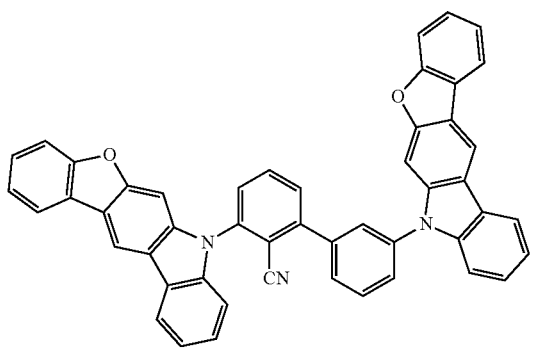
676
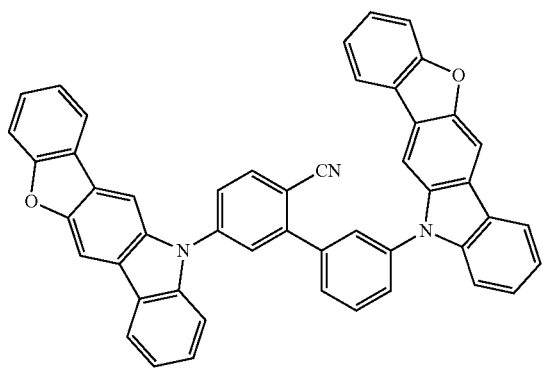

-continued
677
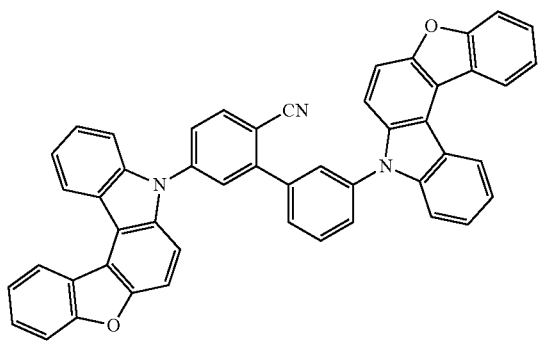
678
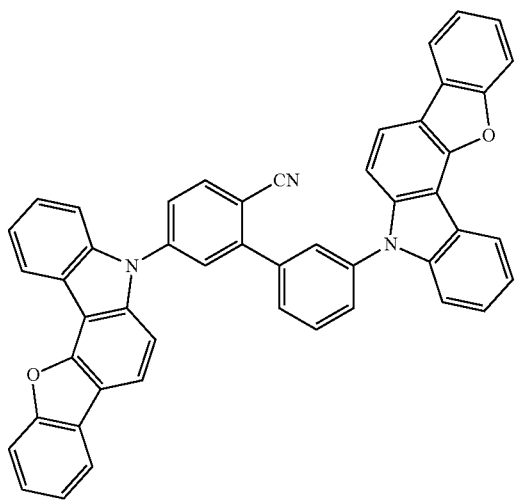
679
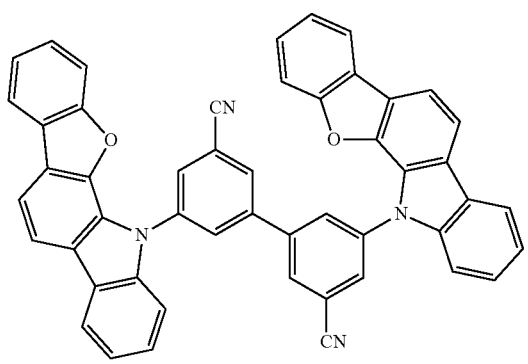
680
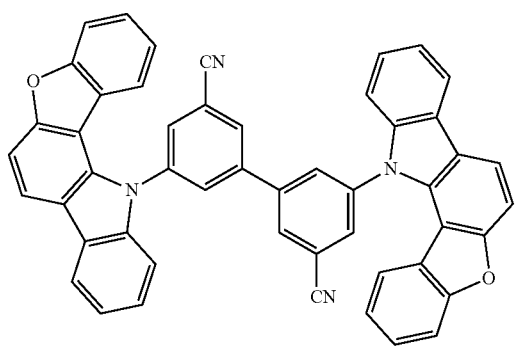
681
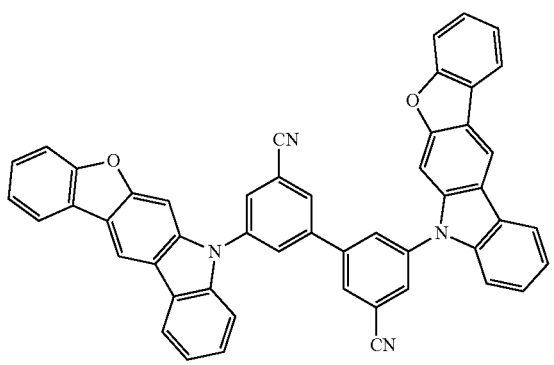
682
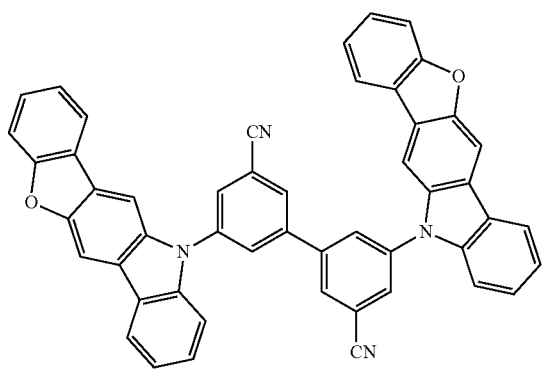

-continued
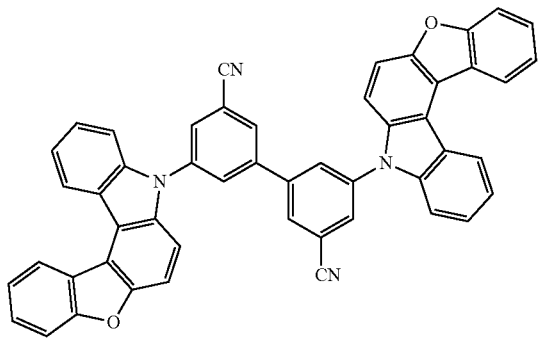
683
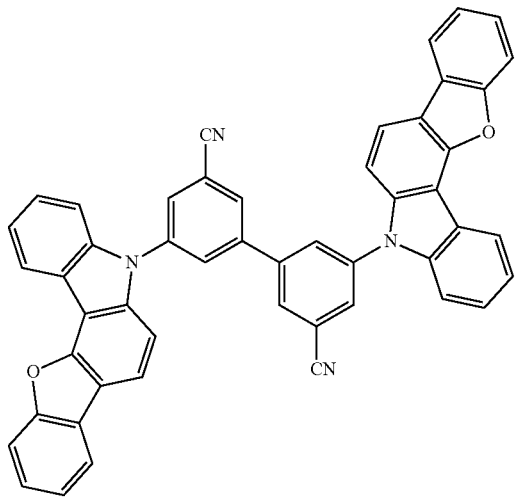
684
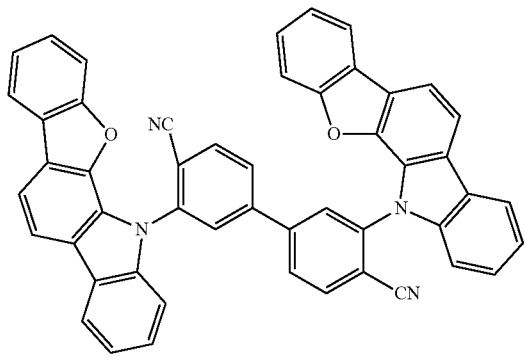
685
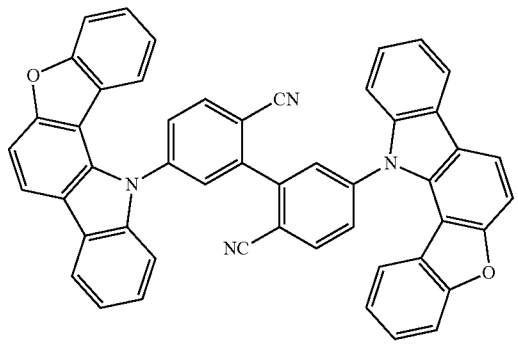
686
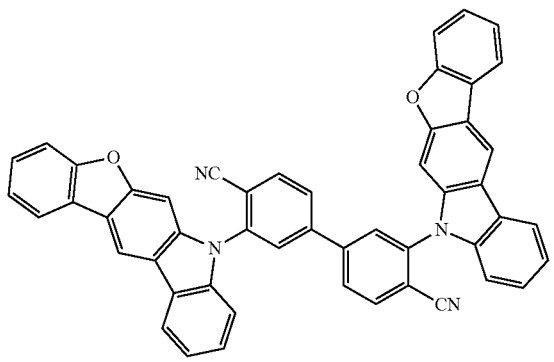
687
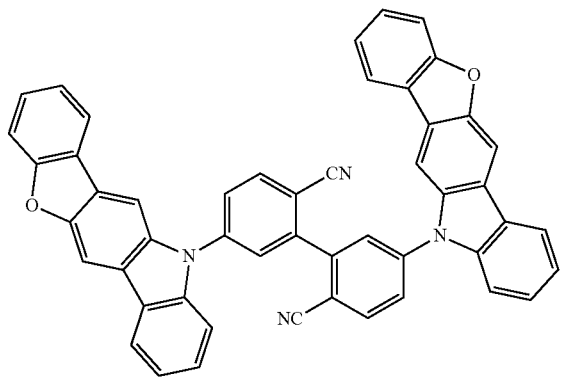
688

-continued
689
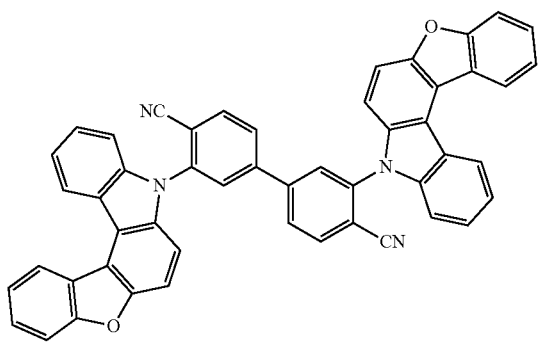
690
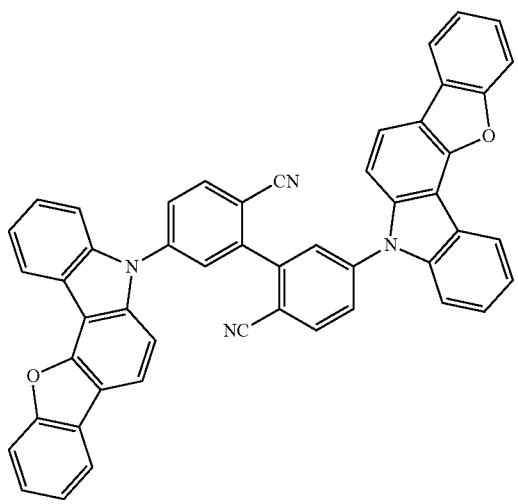
691
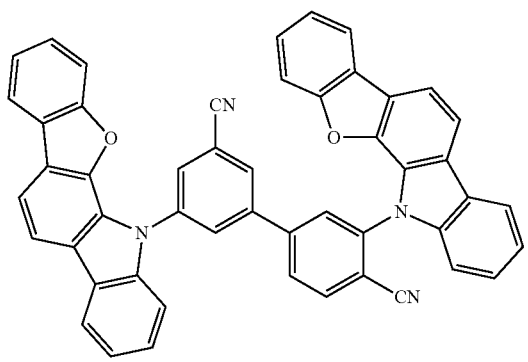
692
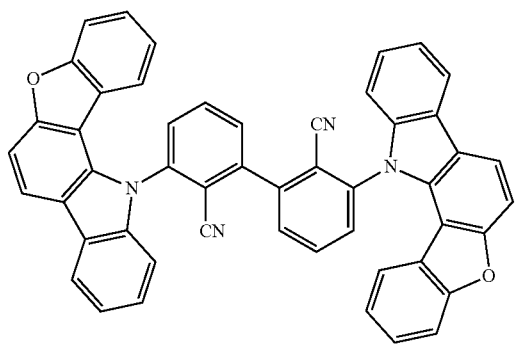
693
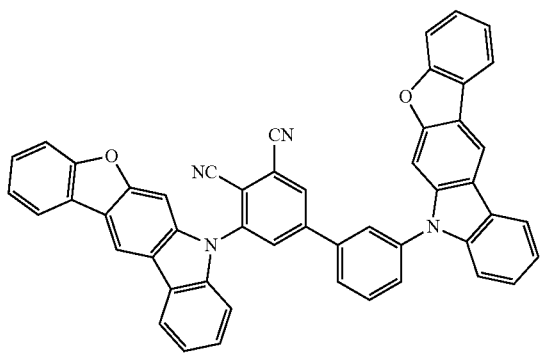
694
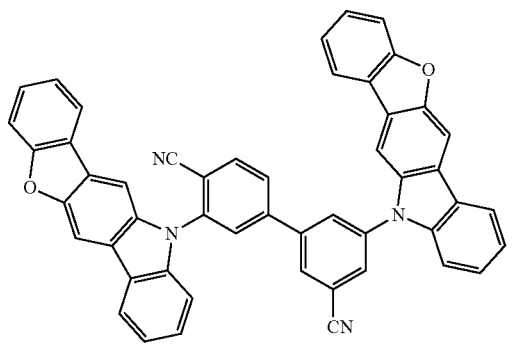

-continued
695
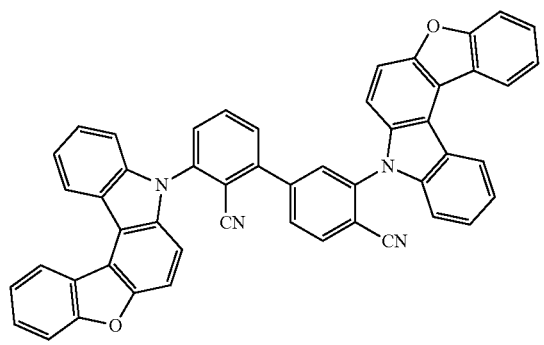
696
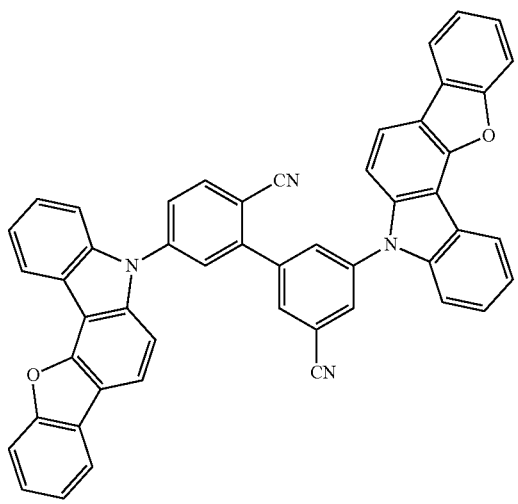
697
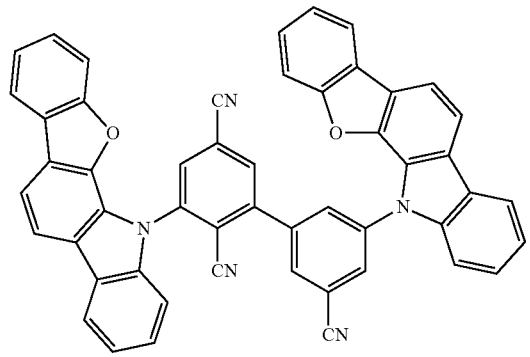
698
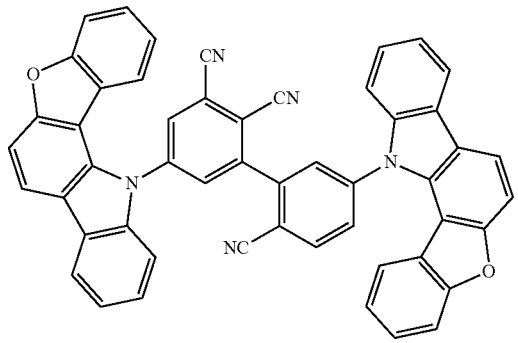
699
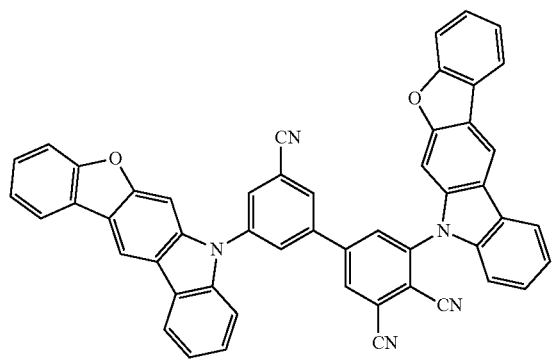
700
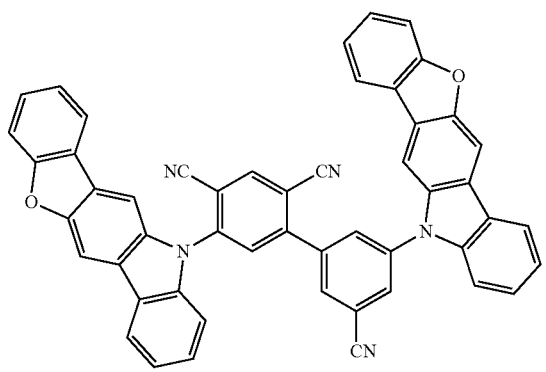

-continued
701
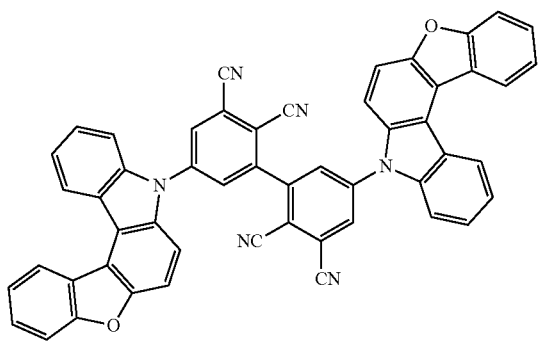
702
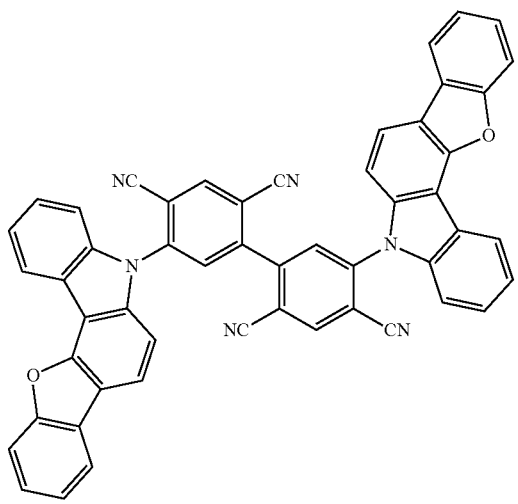
703
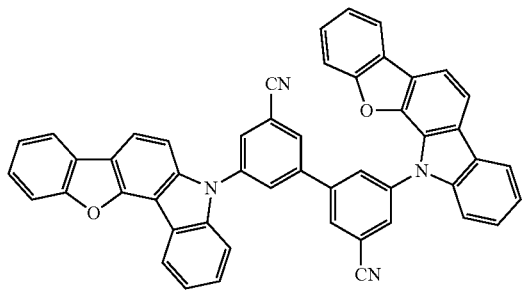
704
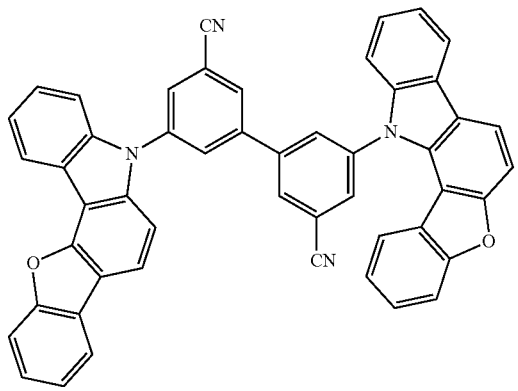
705
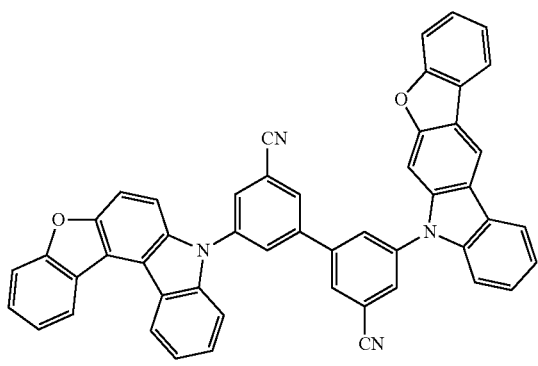
706
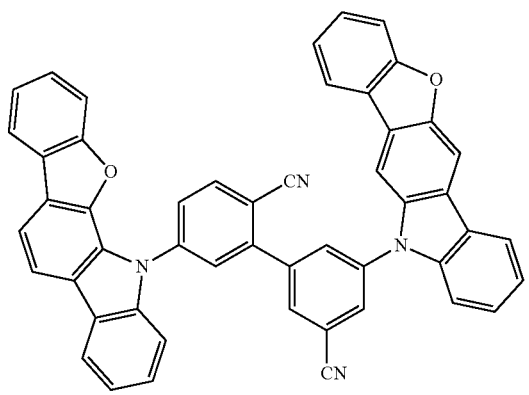

-continued
707
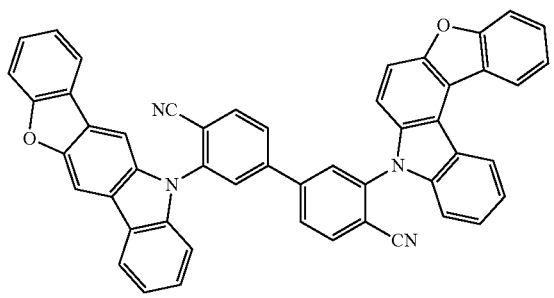
708
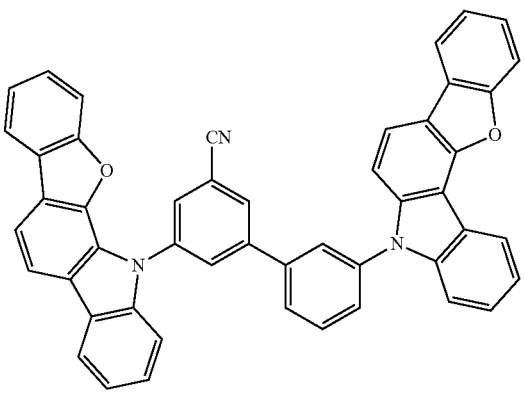
709
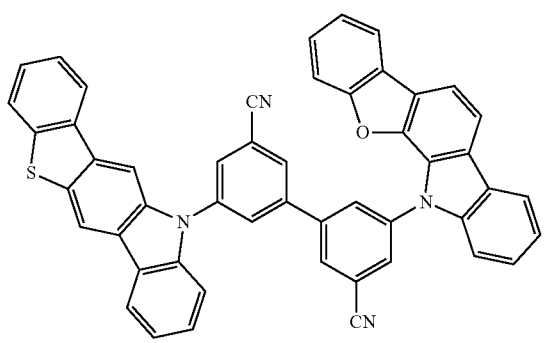
710
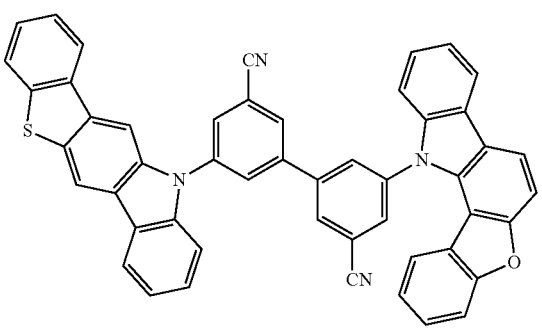
711
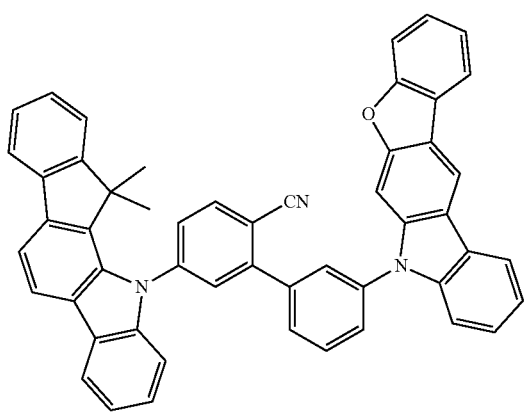
712
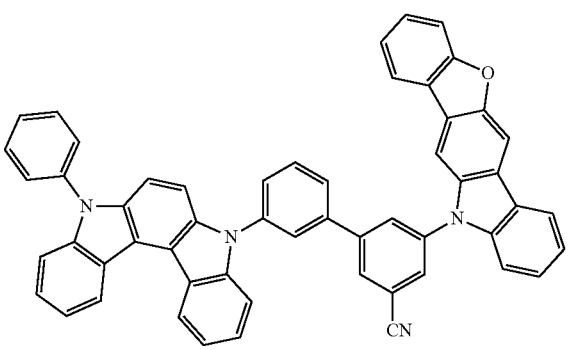
713
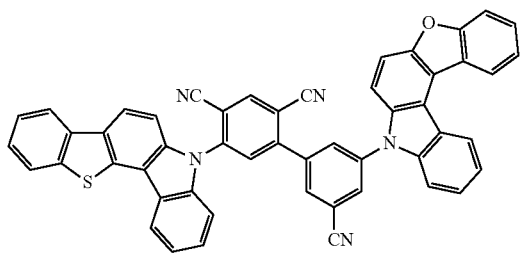
714
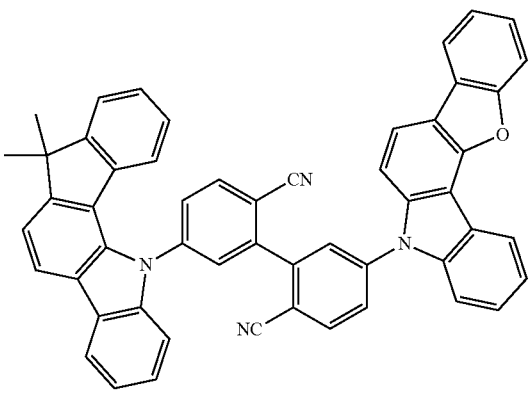

-continued
715
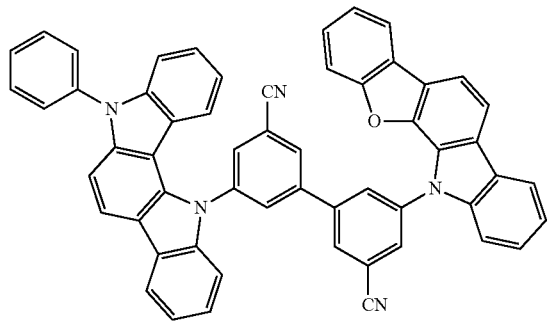
716
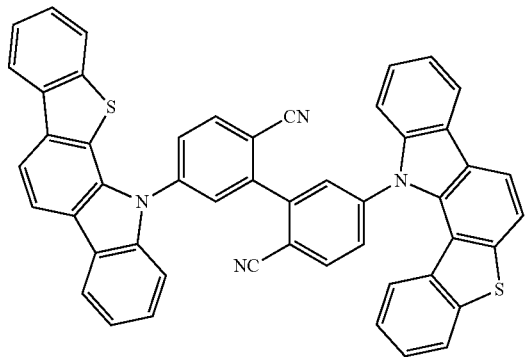
717
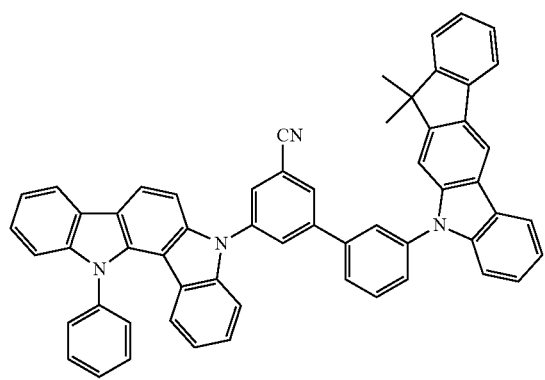
718
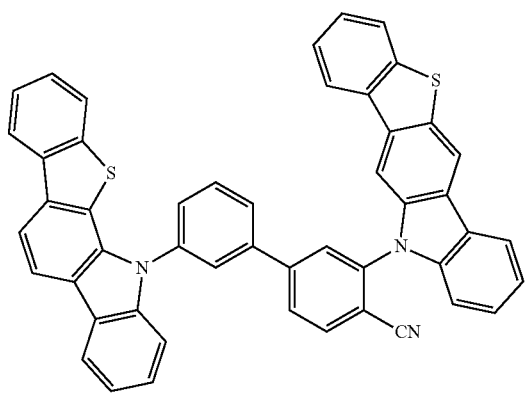
719
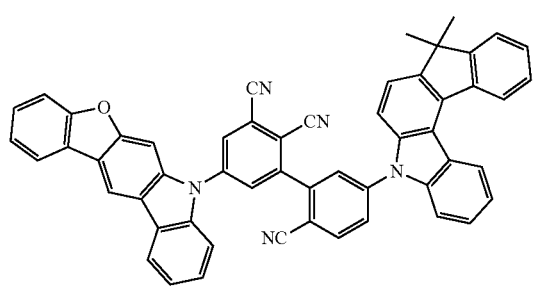
720
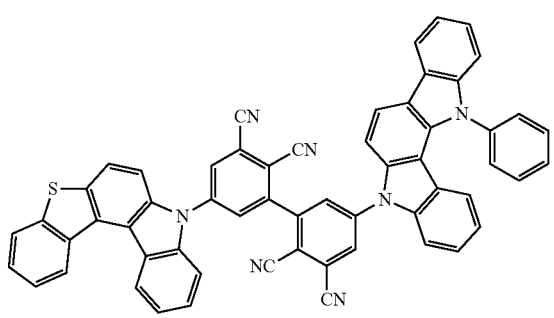
721
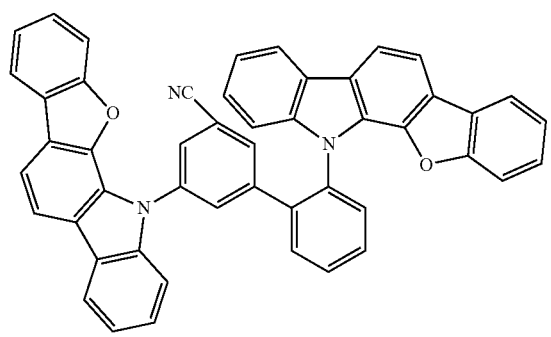
722
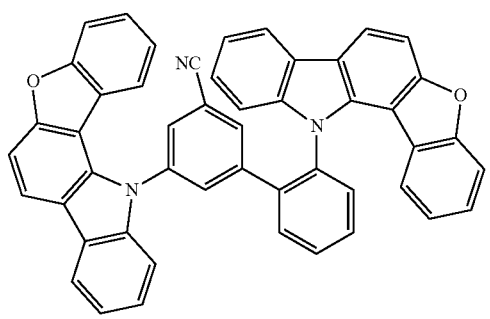

-continued
723
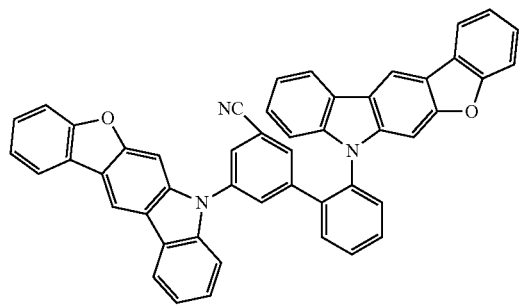
724
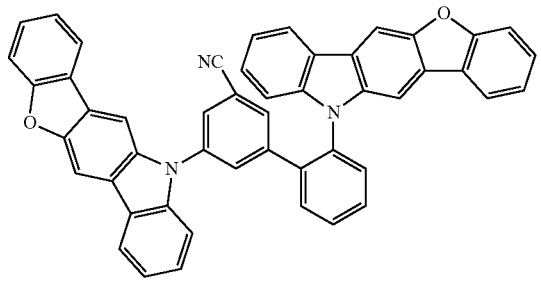
725
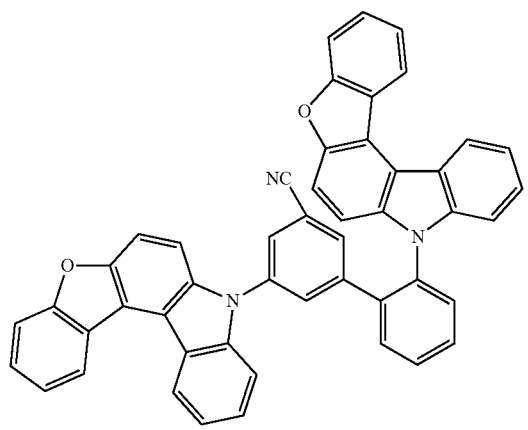
726
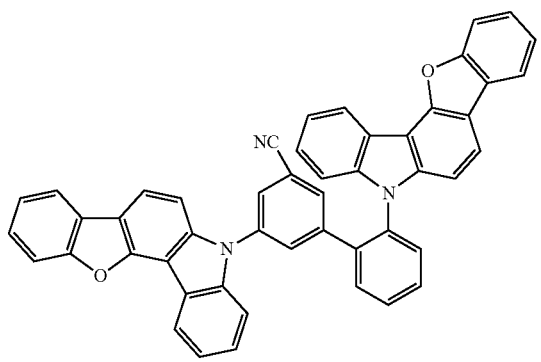
727
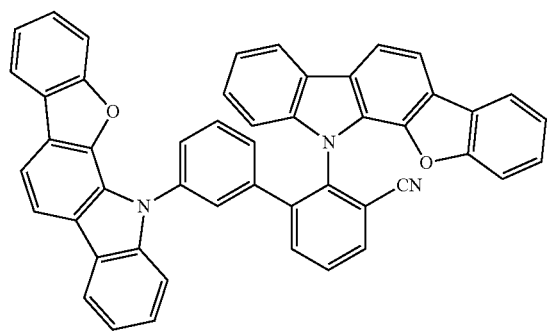
728
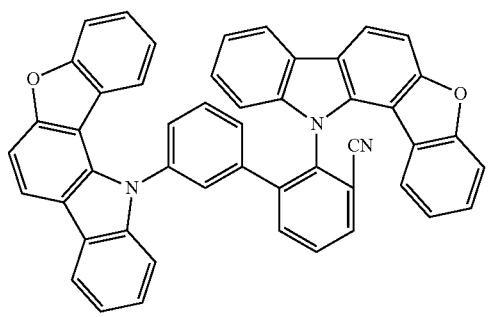
730
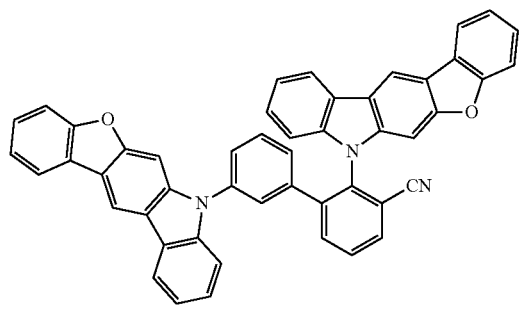
729
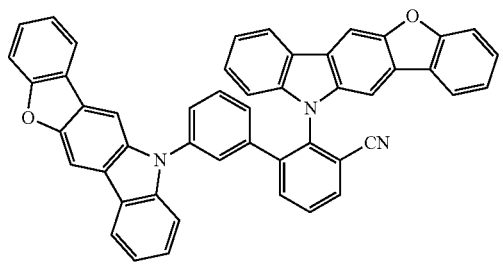

731
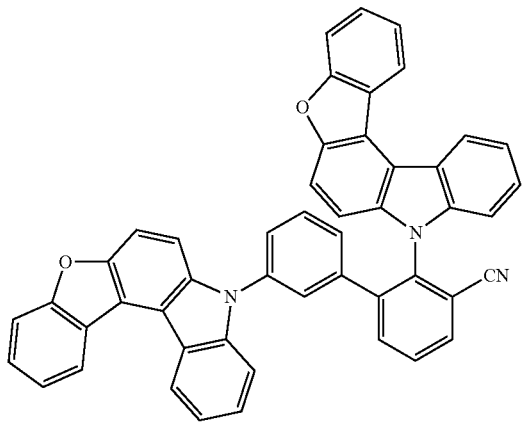
732
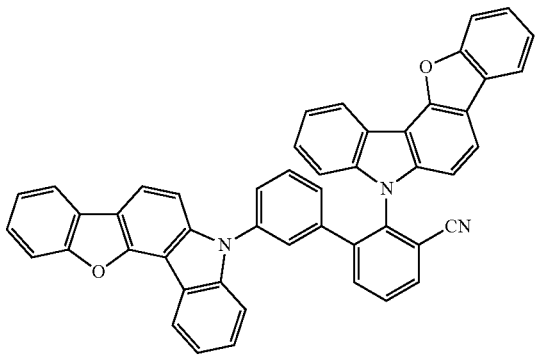
733
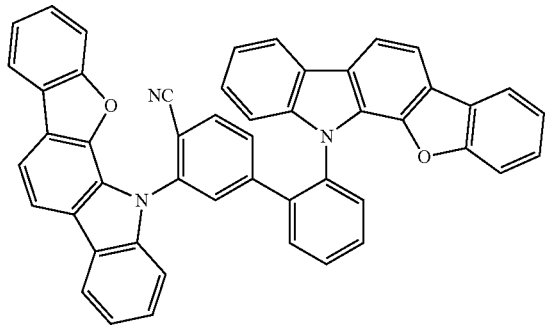
734
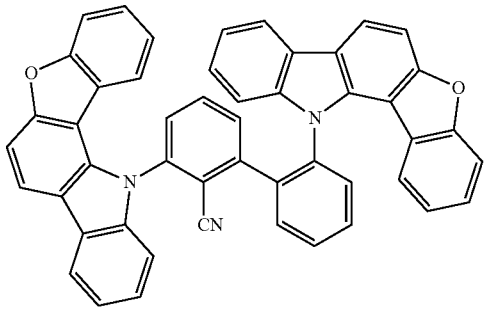
735
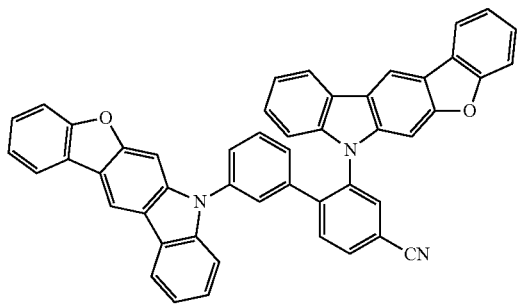
736
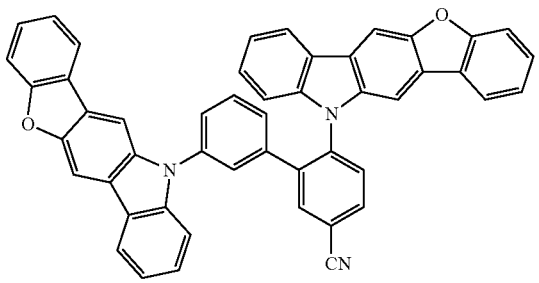
737
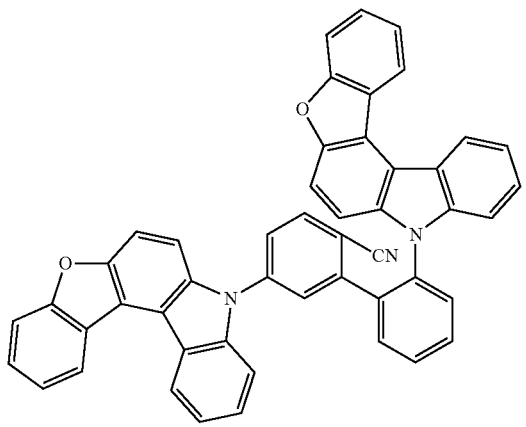
738
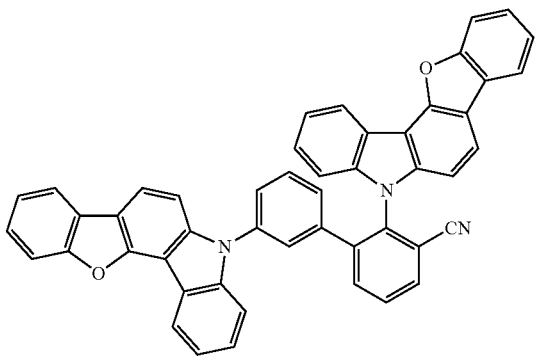

739
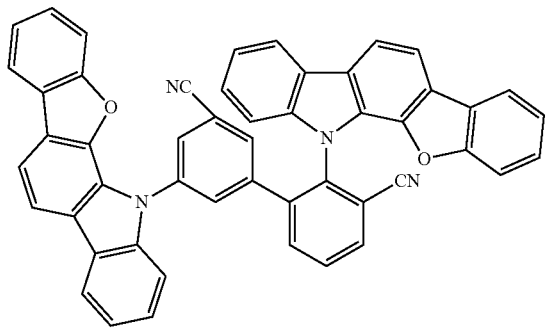
740
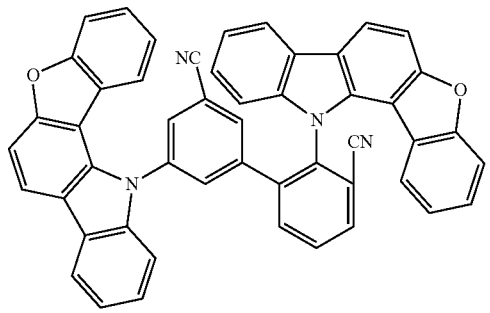
741
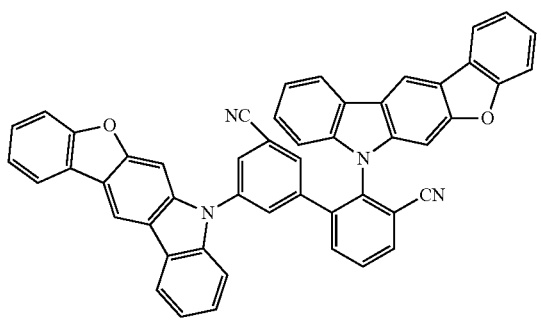
742
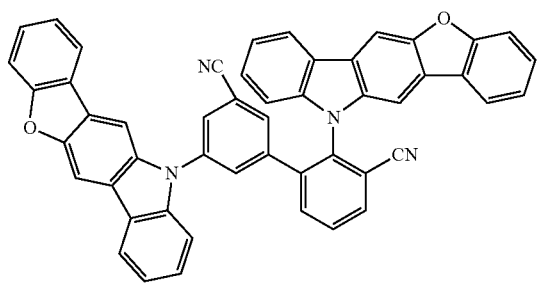
743
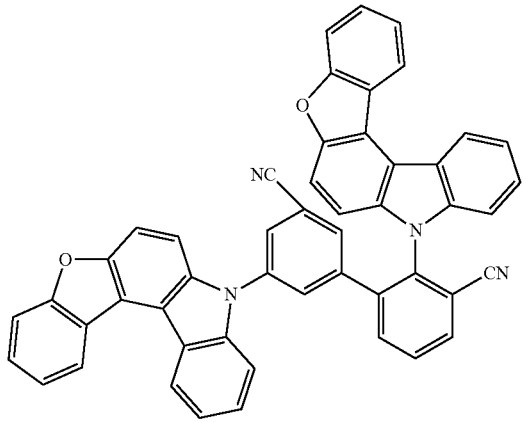
744
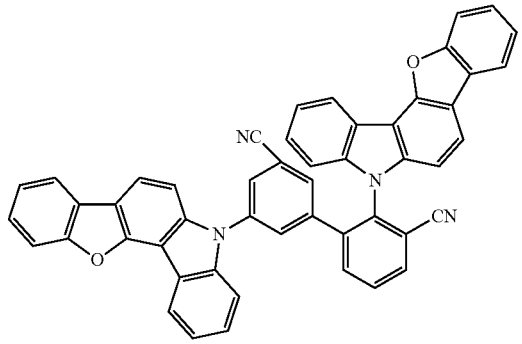
745
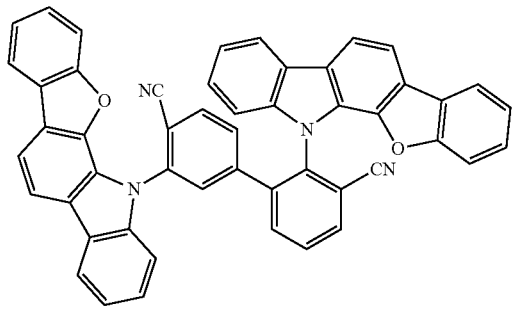
746
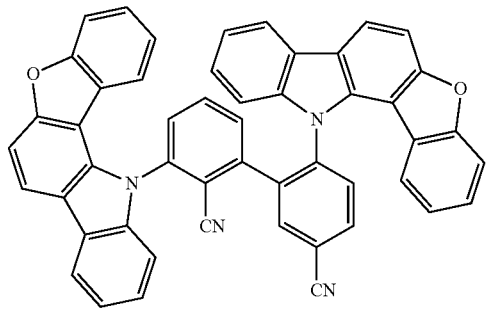

-continued
747 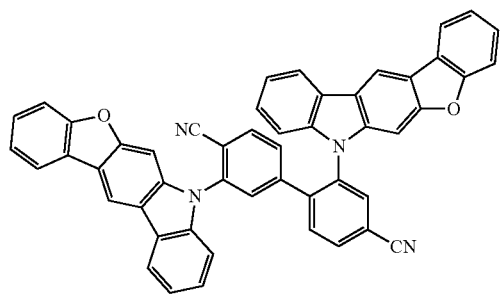
748 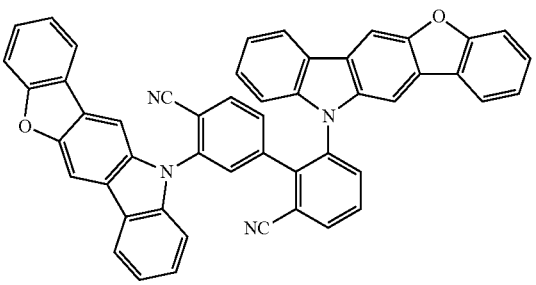
749 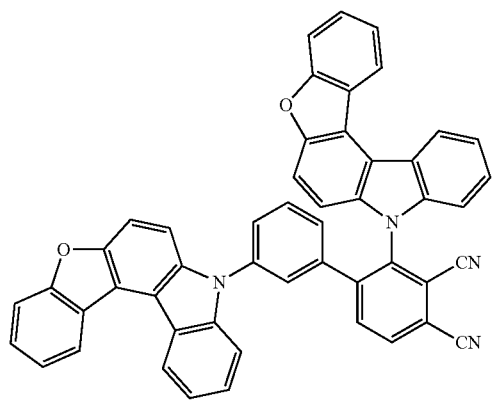
750 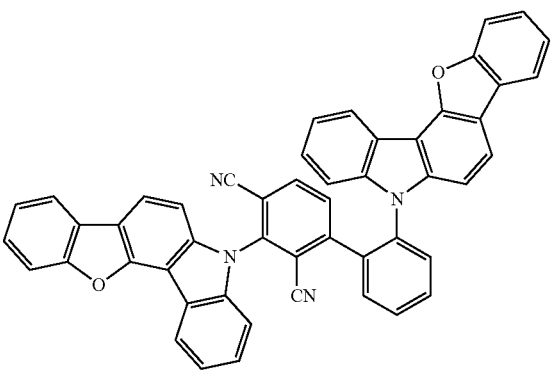
751 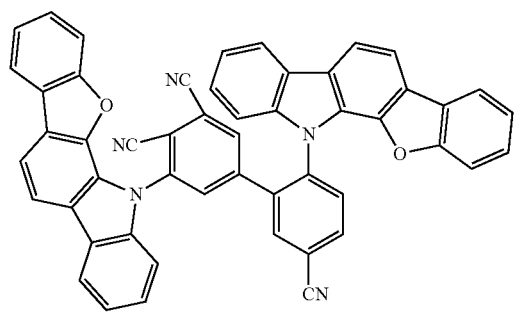
752 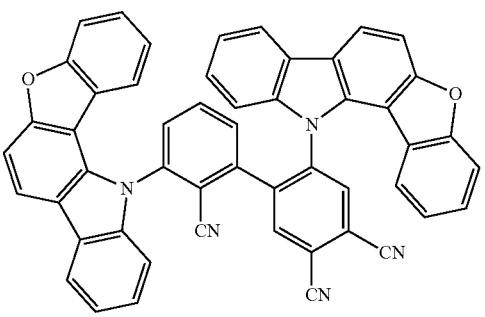
753 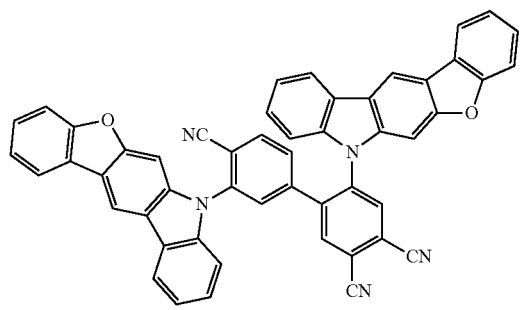
754 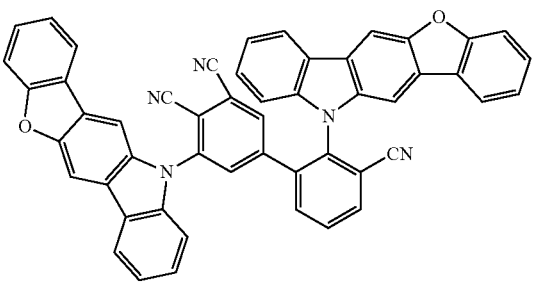

755
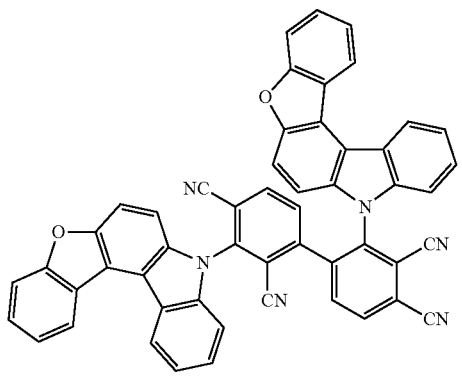
756
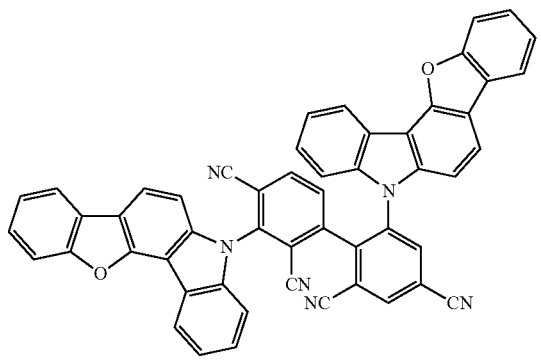
757
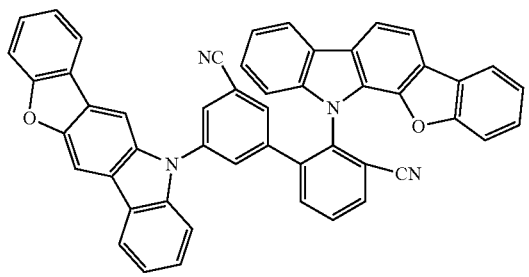
758
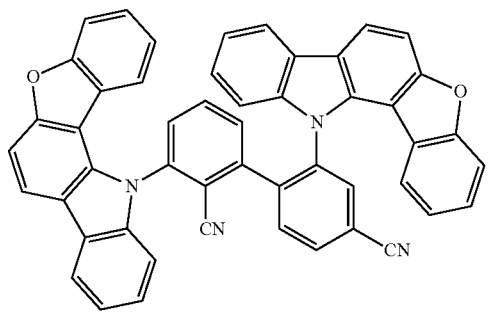
759
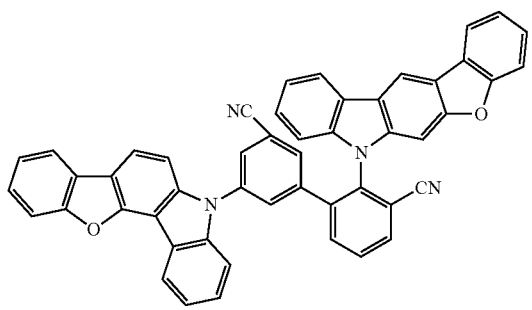
760
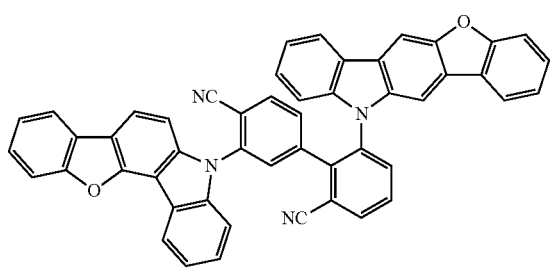
761
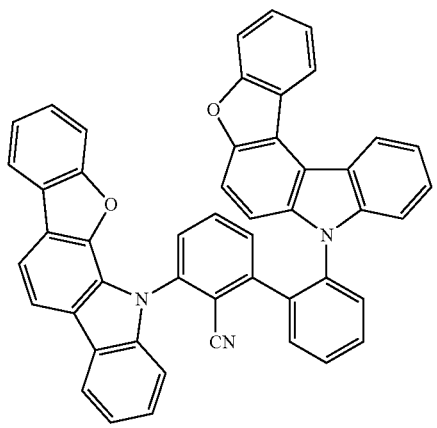
762
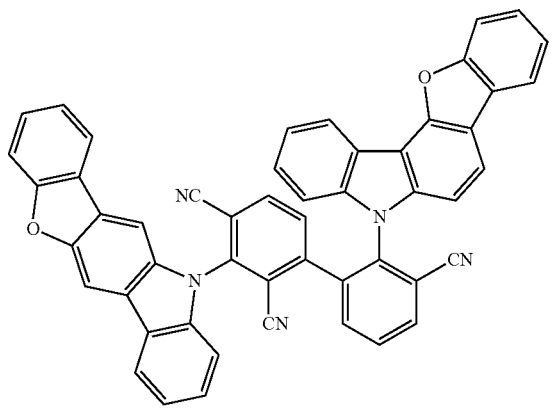

-continued
763
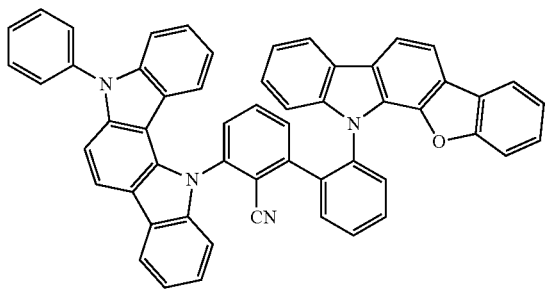
764
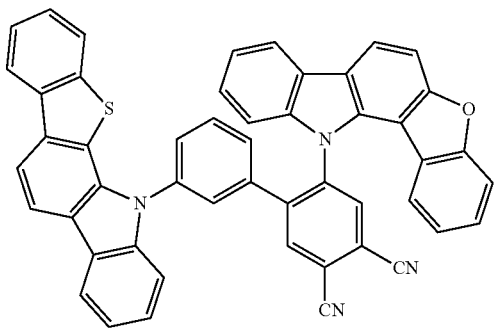
765
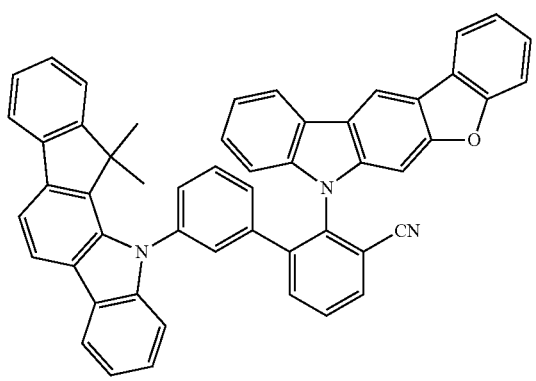
766
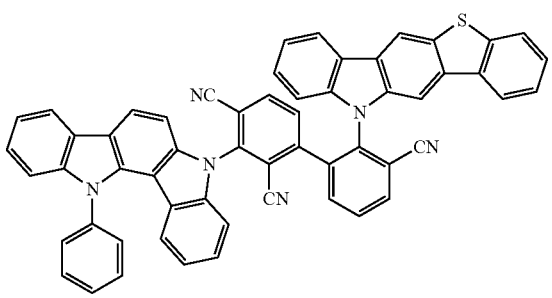
767
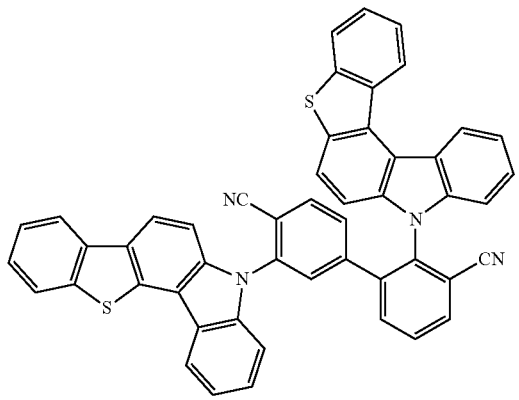
768
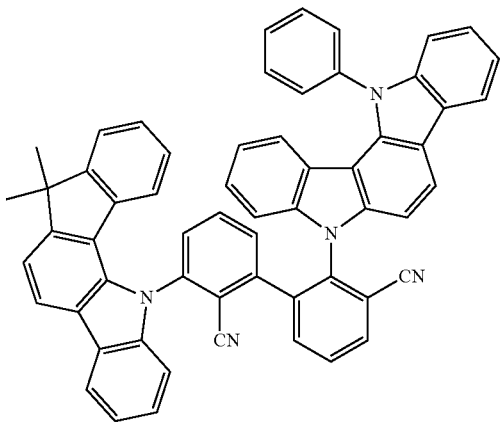
769
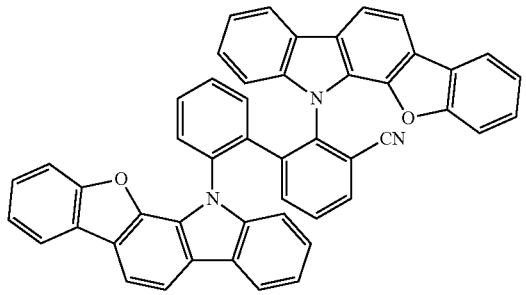
770
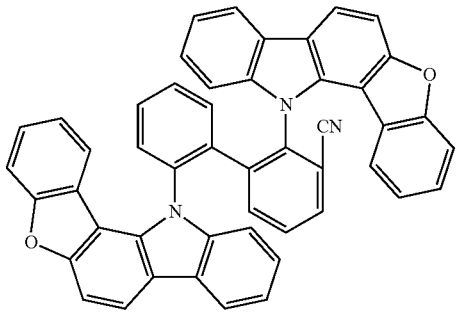

-continued
| 771 | 772 |
|---|---|
| 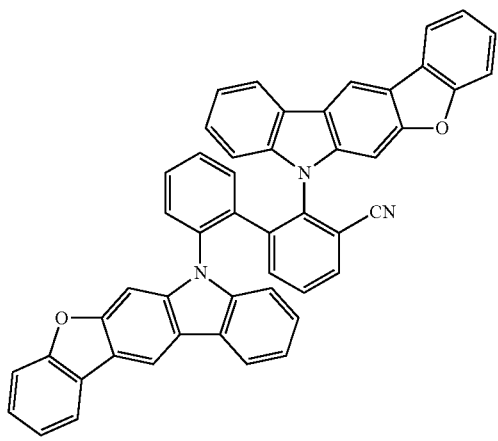 | 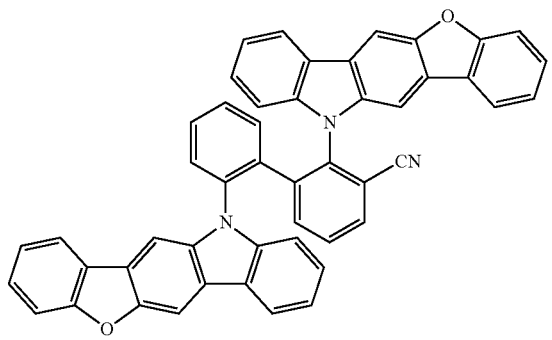 |
| 773 | 774 |
| 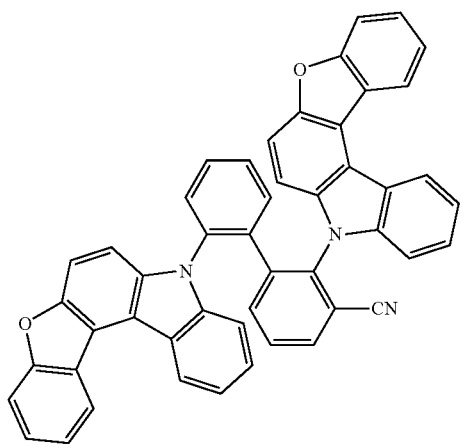 | 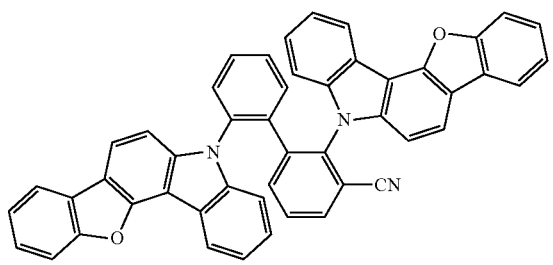 |
| 775 | 776 |
| 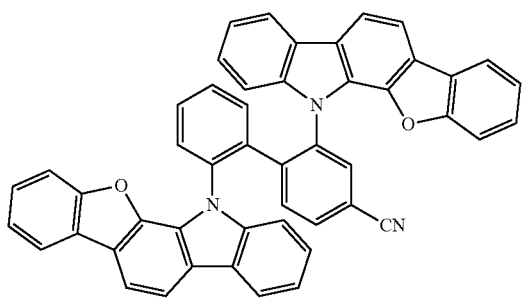 | 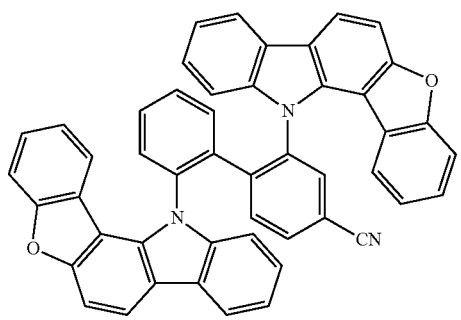 |

-continued
445
777
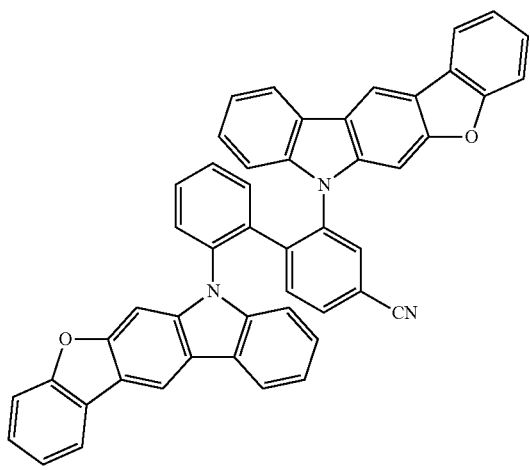
446
778
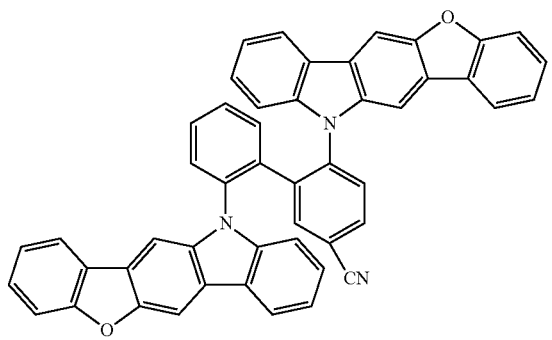
779
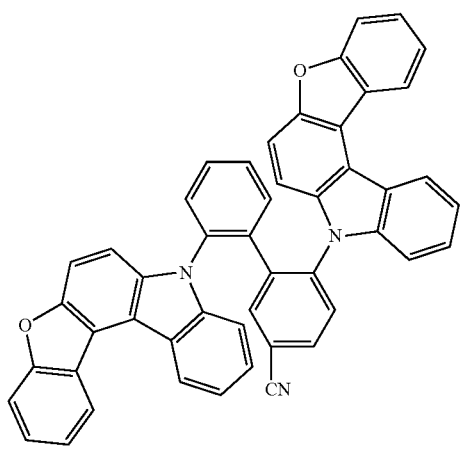
780
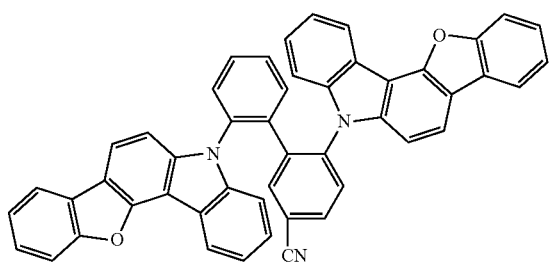
781
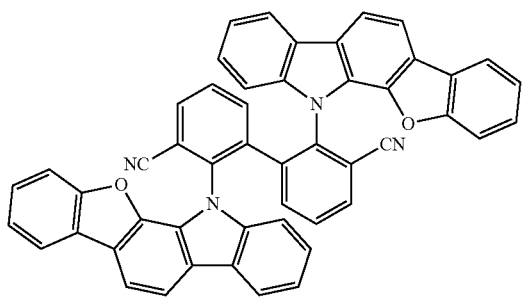
782
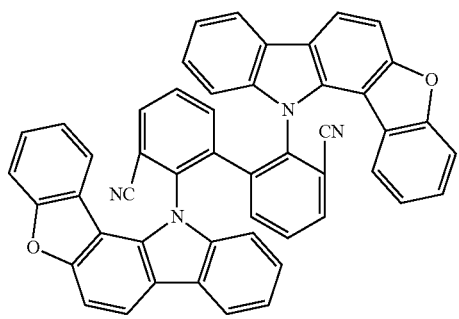

783
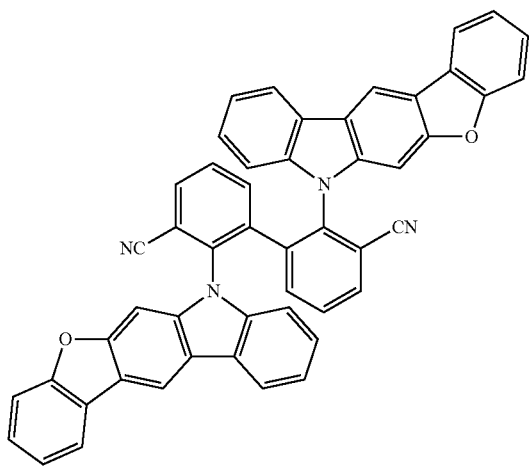
784
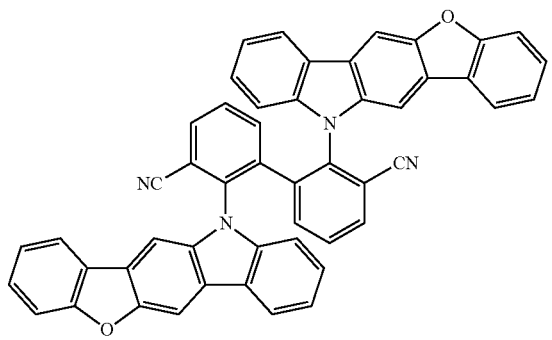
785
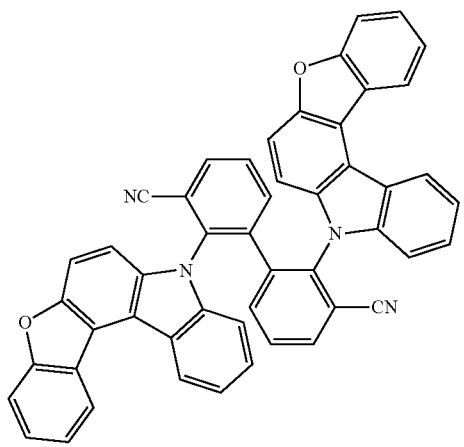
786
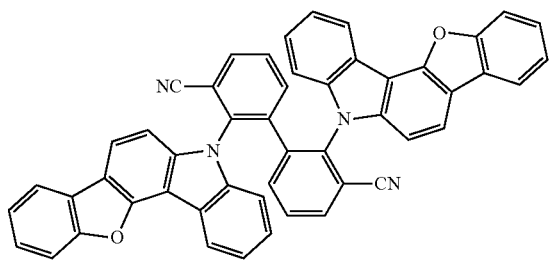
787
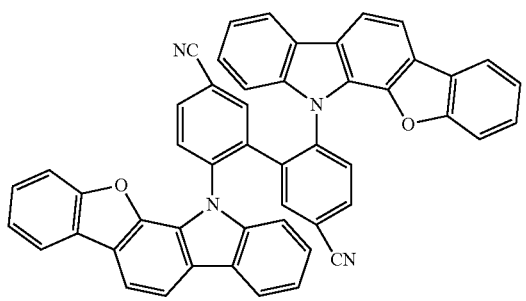
788
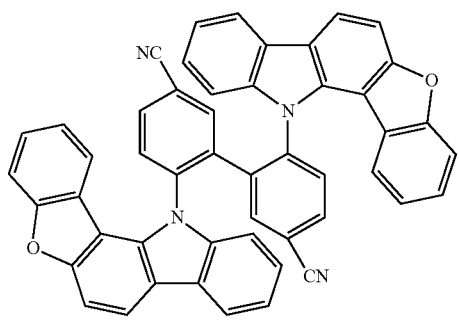

-continued
789
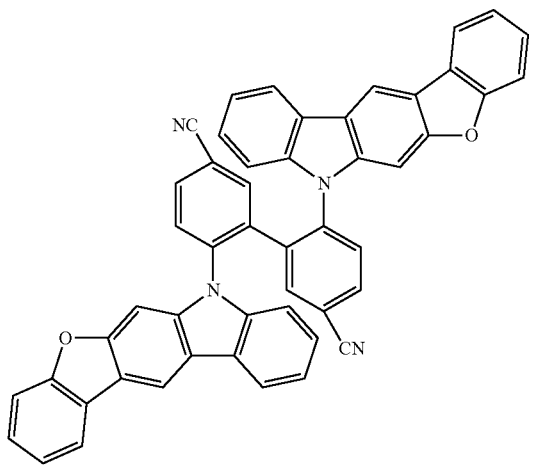
790
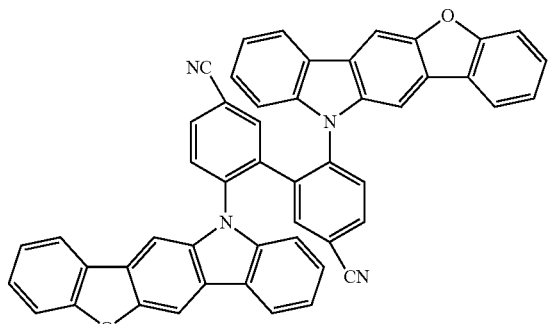
791
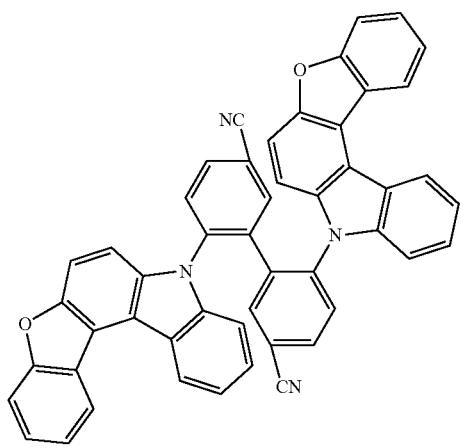
792
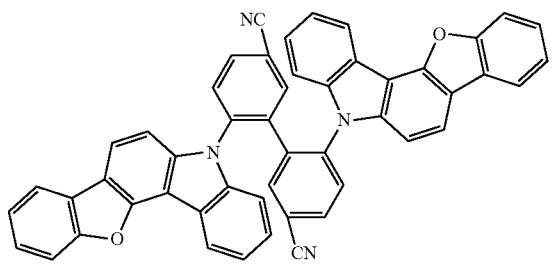
793
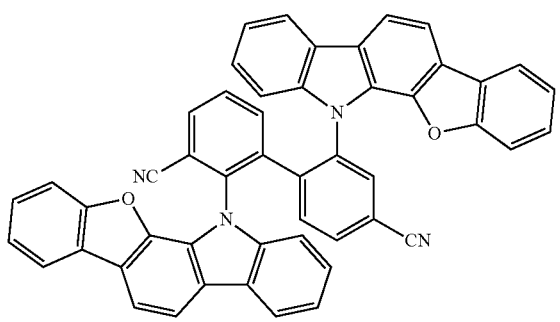
794
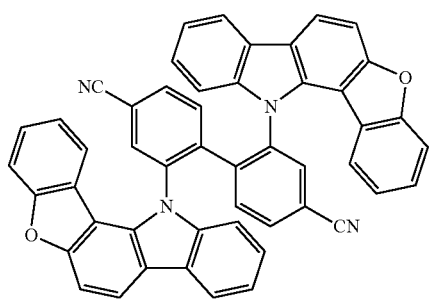

-continued
795
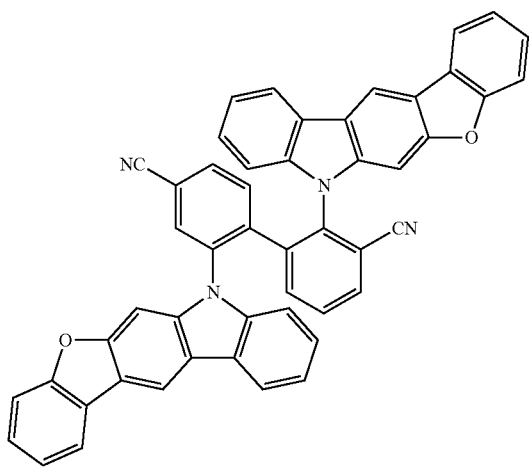
796
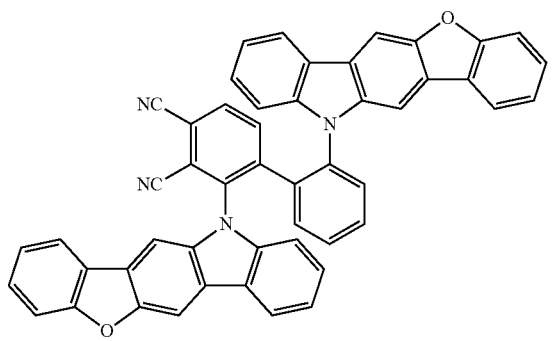
797
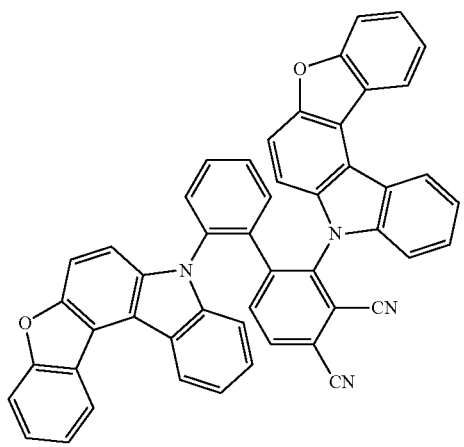
798
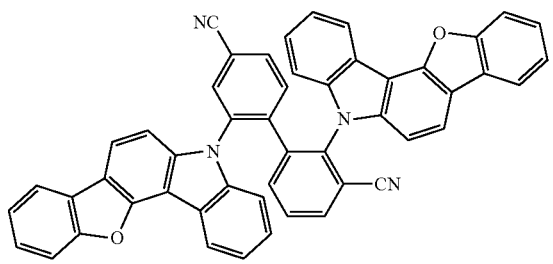
799
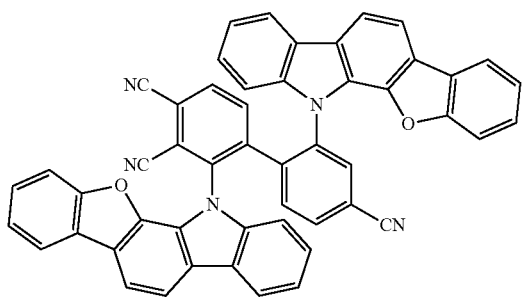
800
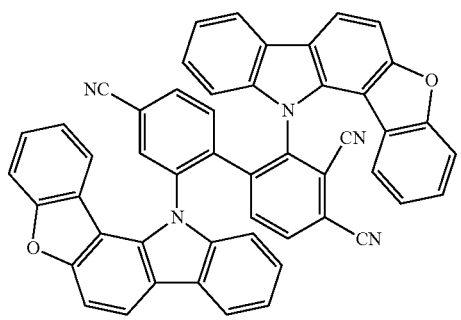

-continued
453
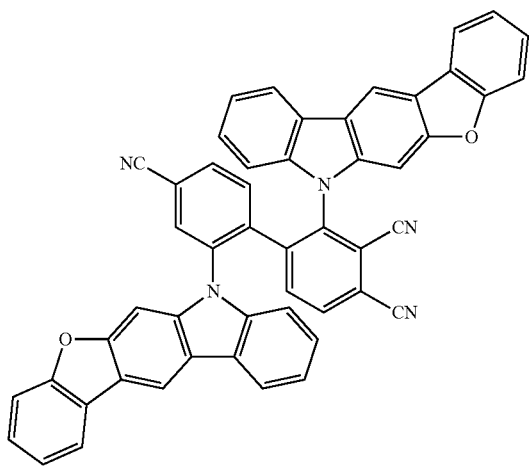
801
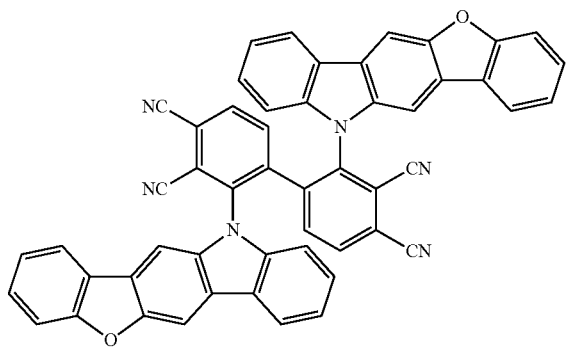
802
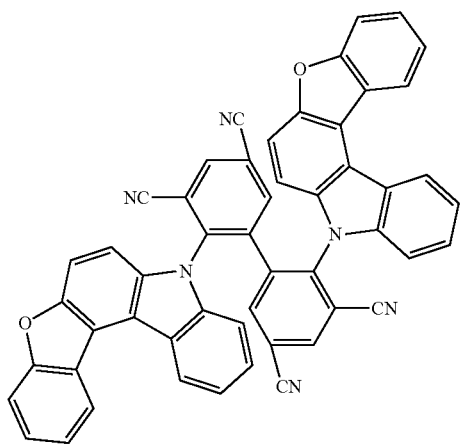
803
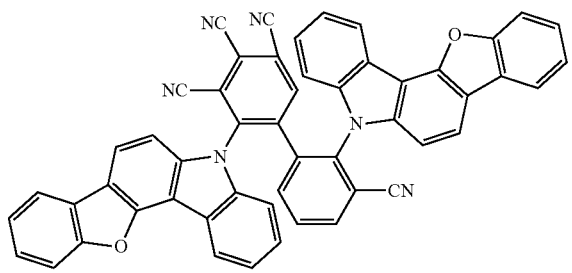
804
454
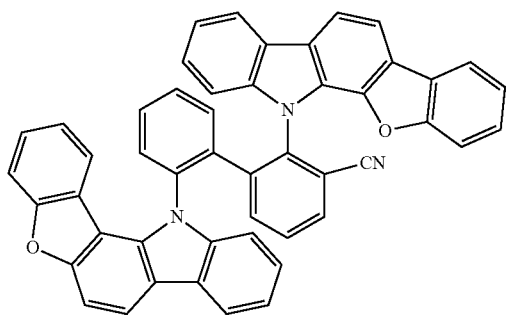
805
-continued
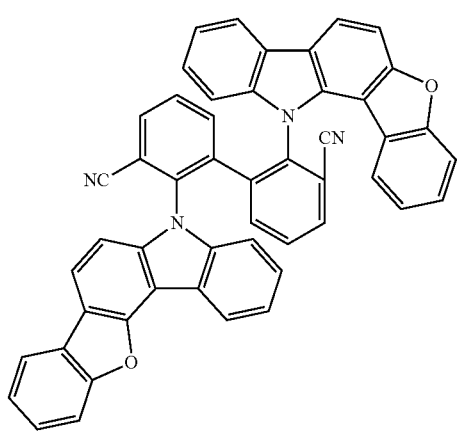
806

455
-continued
807
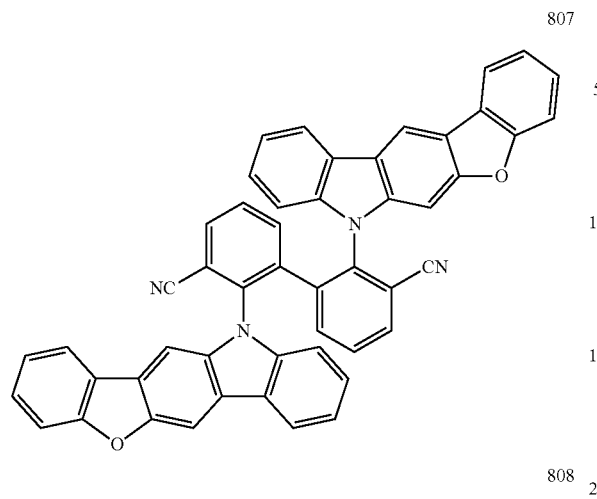
808
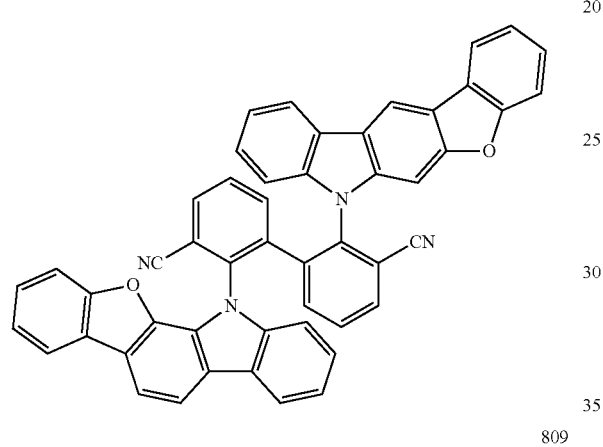
809
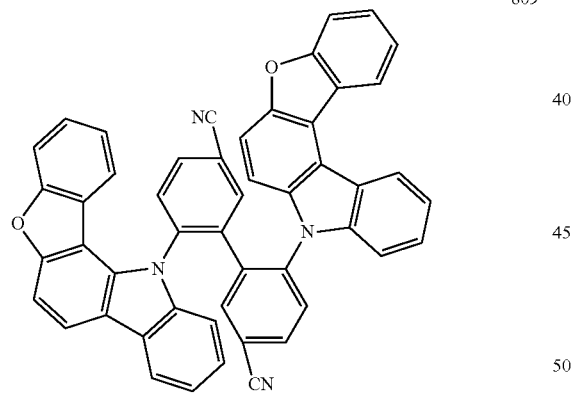
810
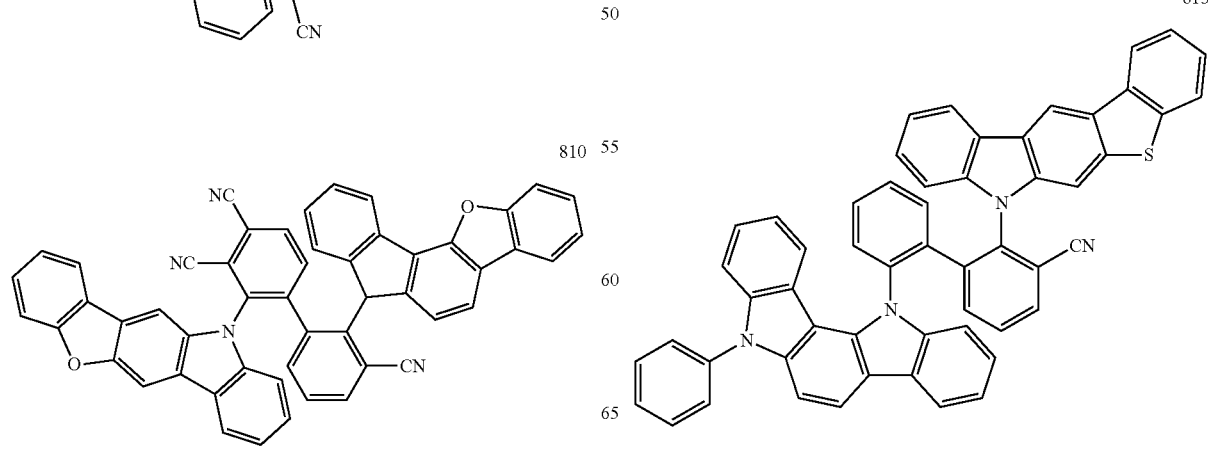
456
-continued
811
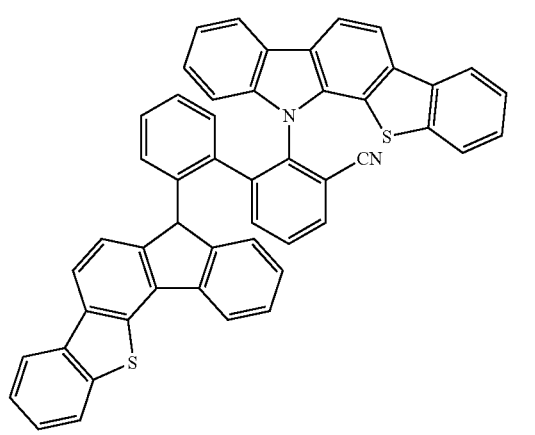
812
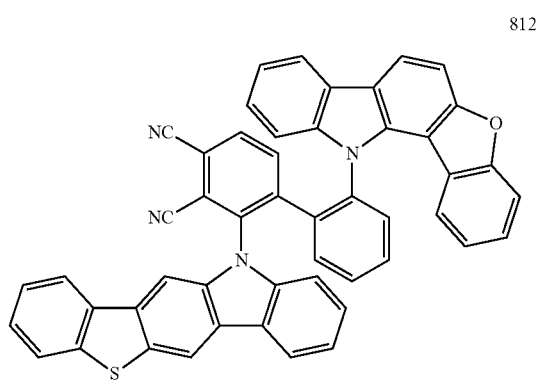
813

814
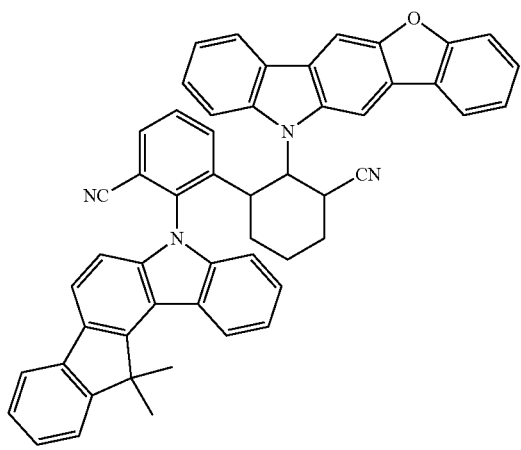
815
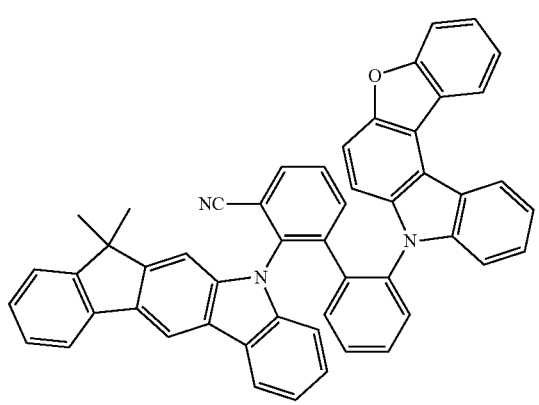
816
817
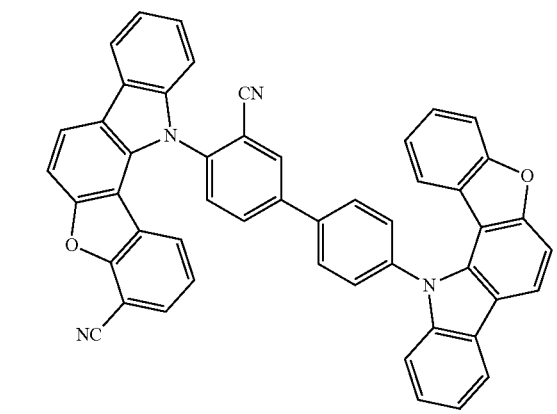
818
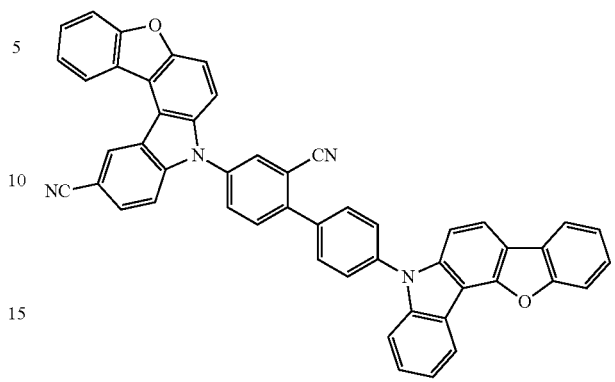
819
820
821
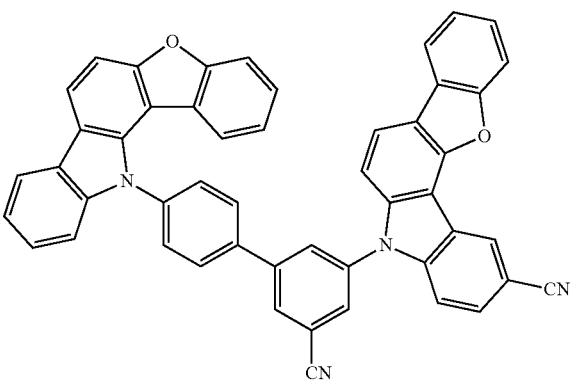

822
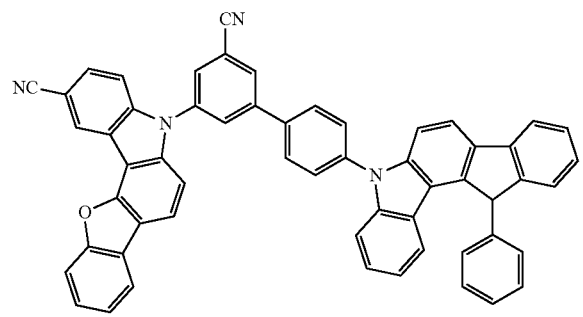
823
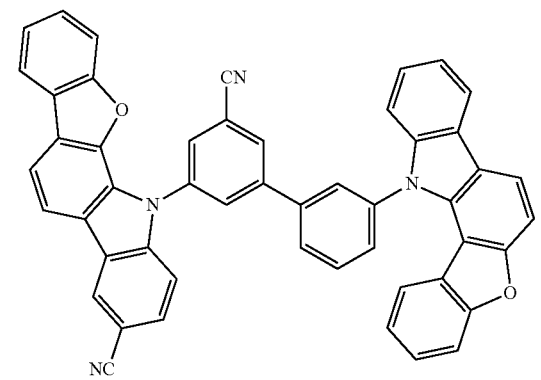
824
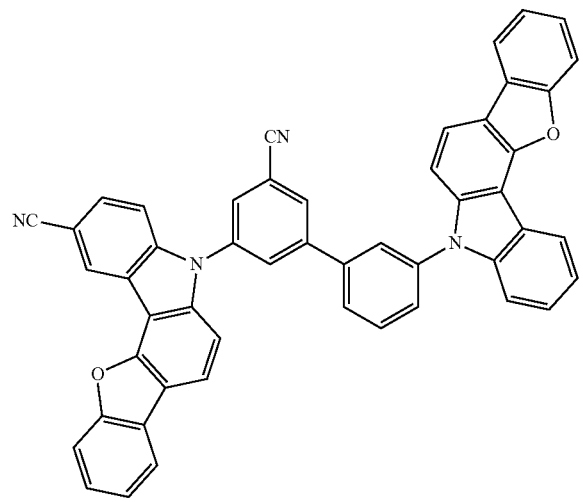
825
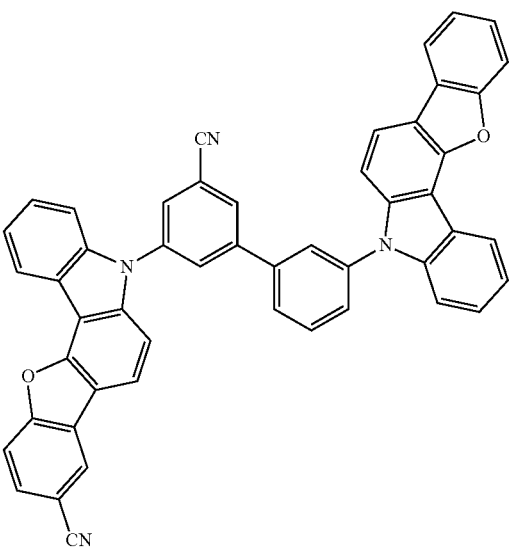
826
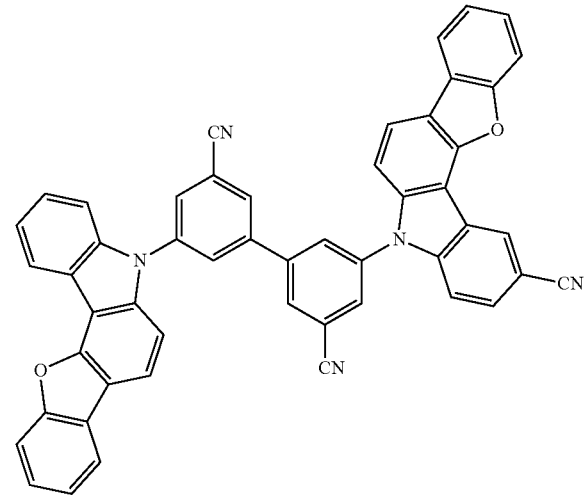
827
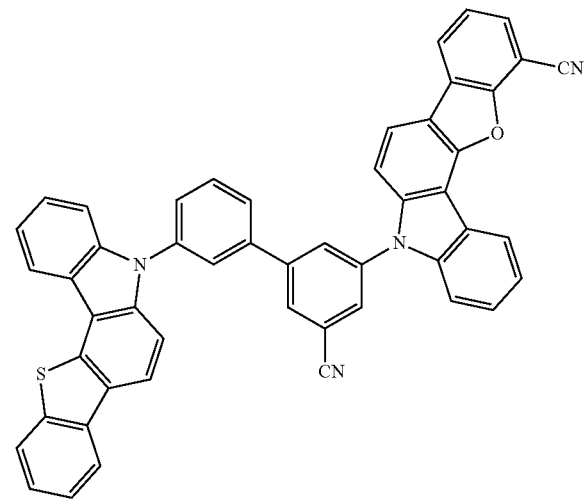

828
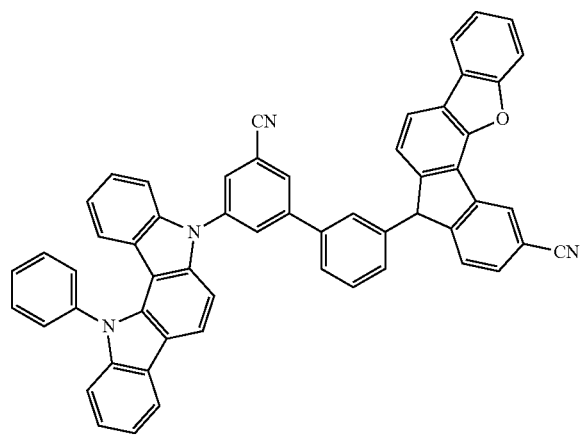
831
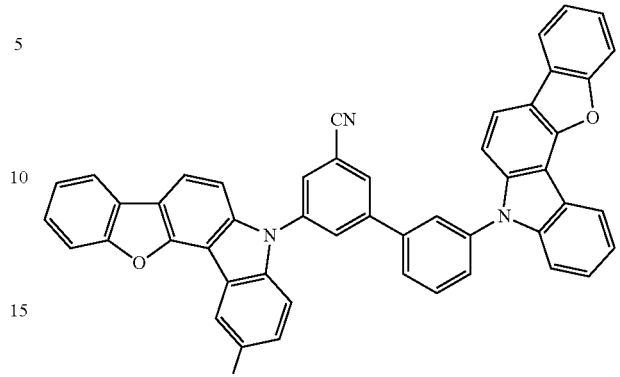
829
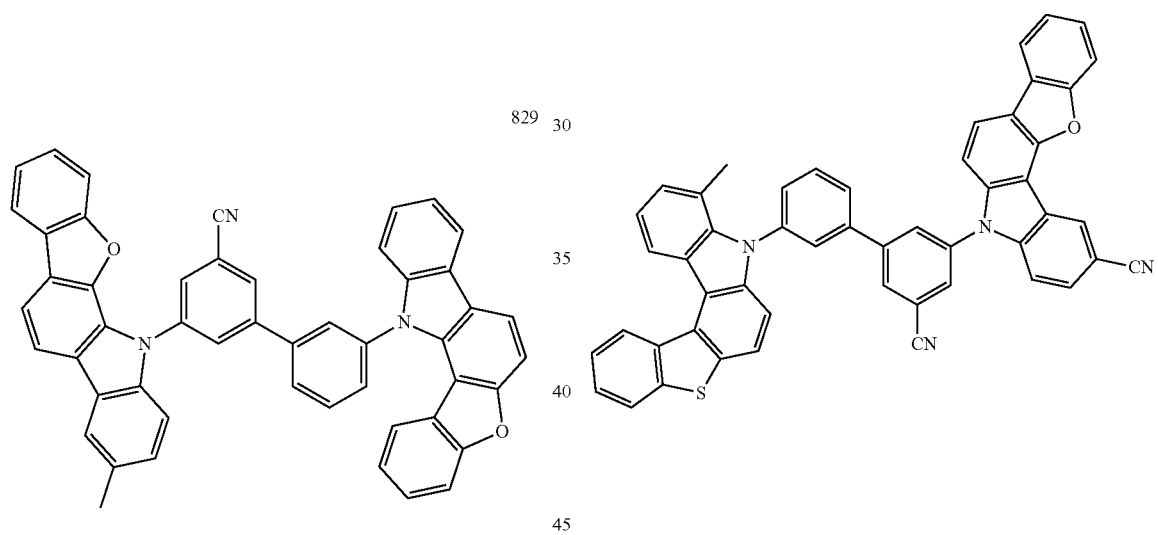
832
833

| 834 | 838 |
| 835 | 839 |
| 836 | |
| 837 | 840 |

465
-continued
841
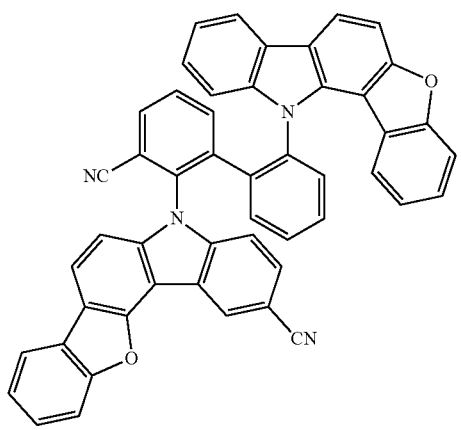
842
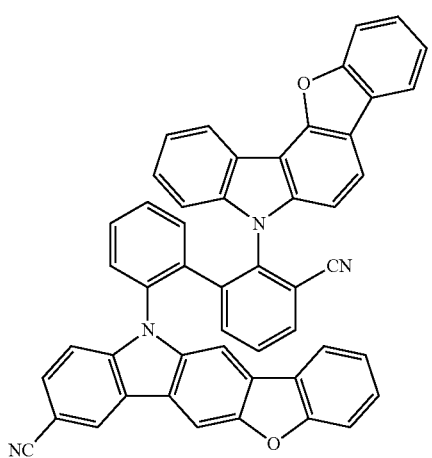
843
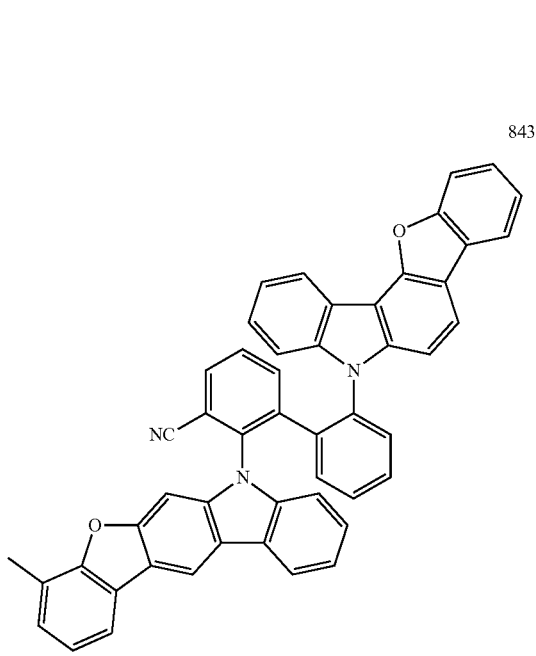
466
-continued
844
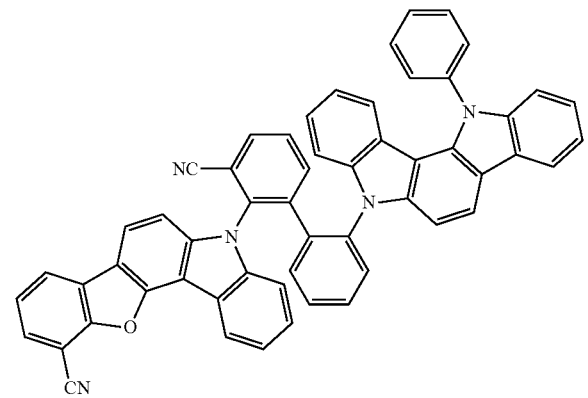
845
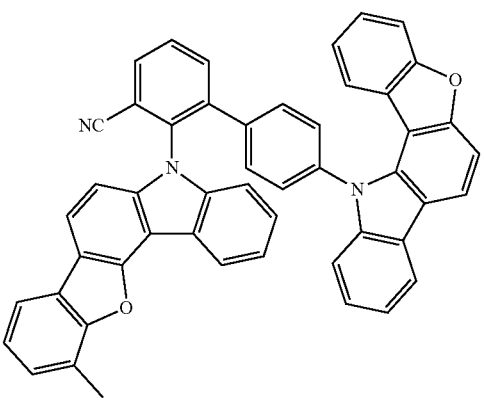
846
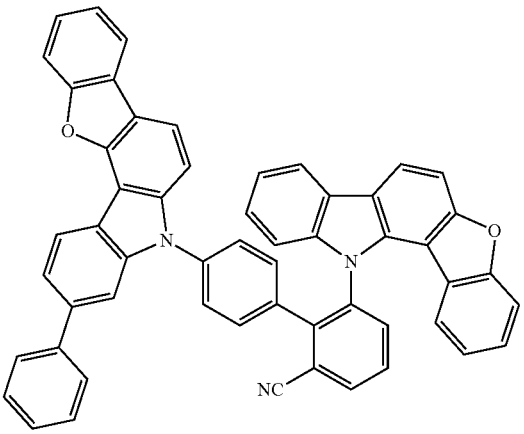
847
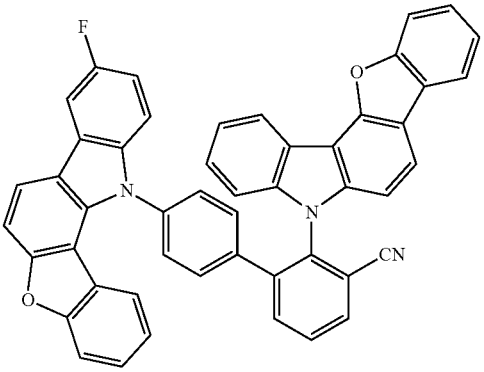

-continued
848
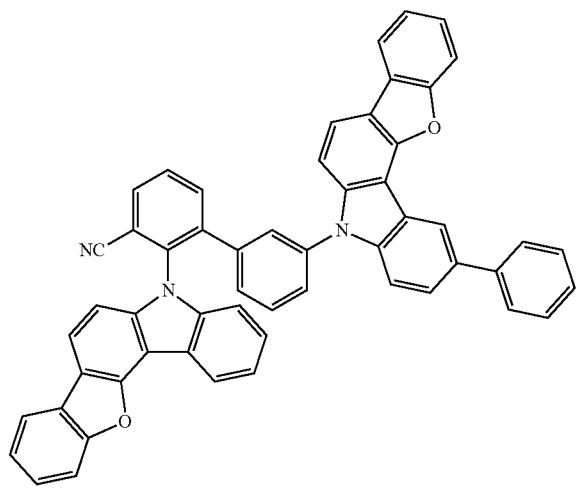
849
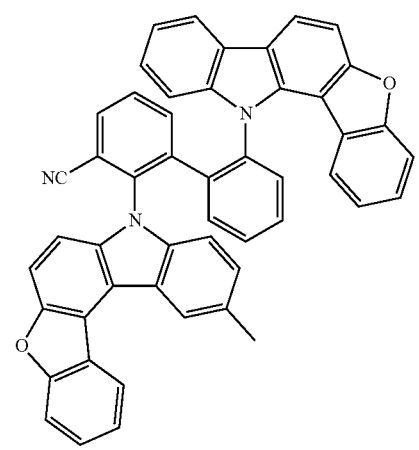
850
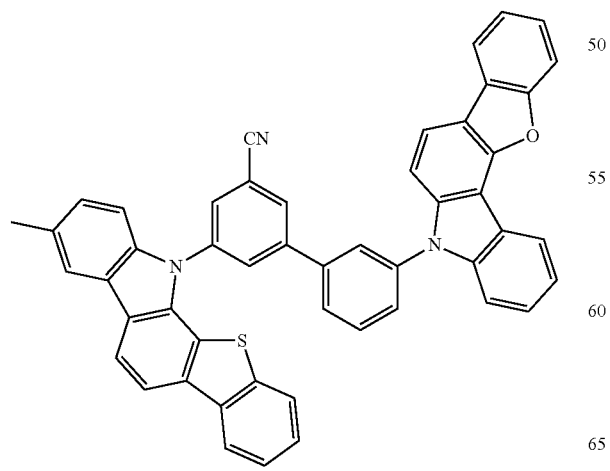
-continued
851
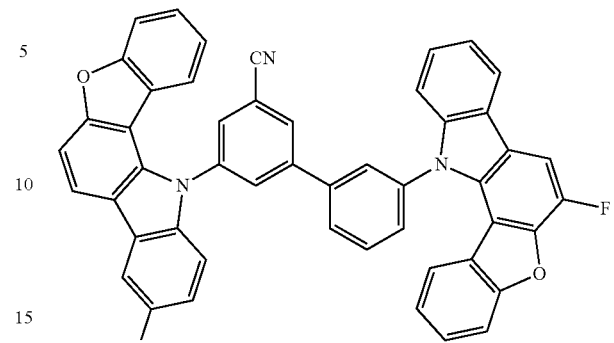
852
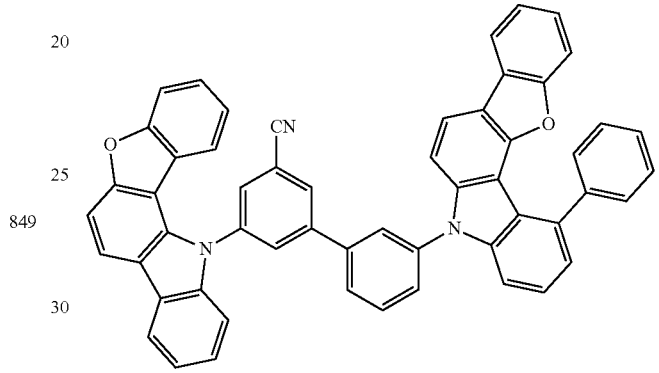
1
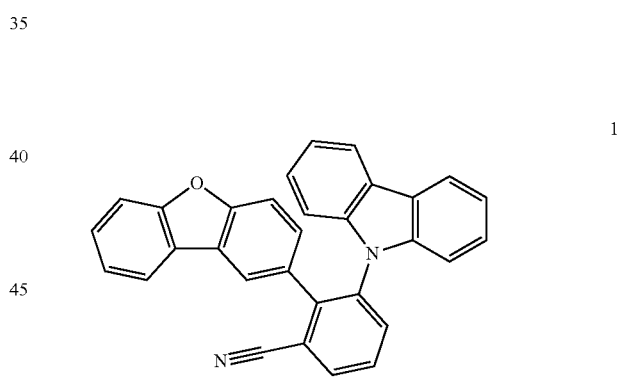
2
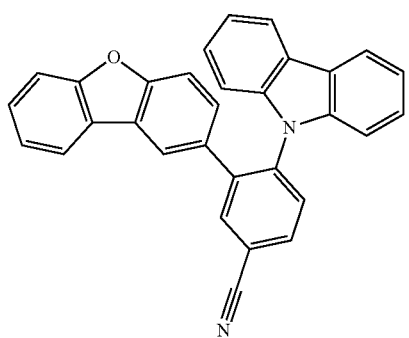

469
-continued
3
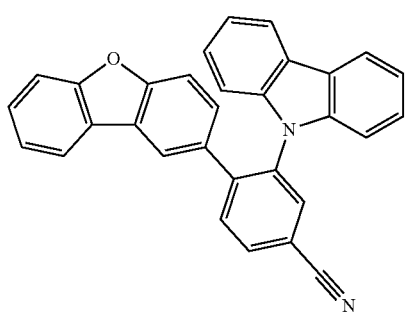
4
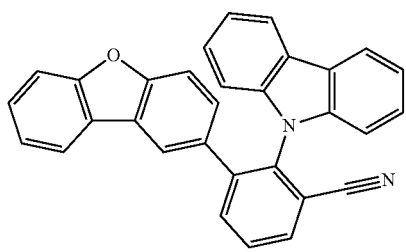
5
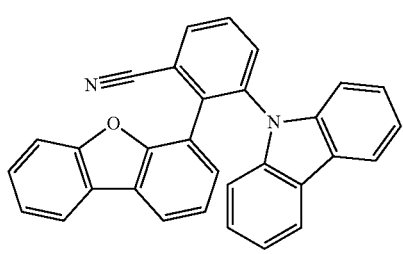
6
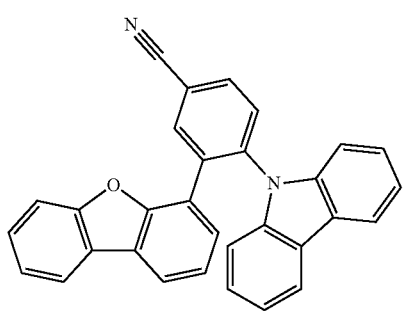
7
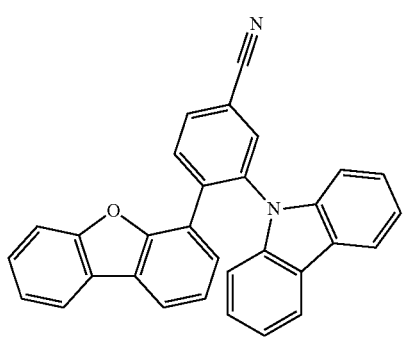
470
-continued
8
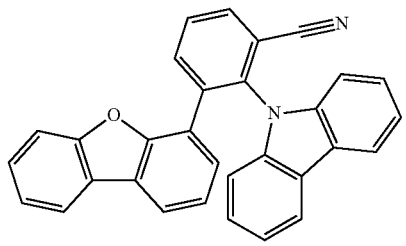
9

10
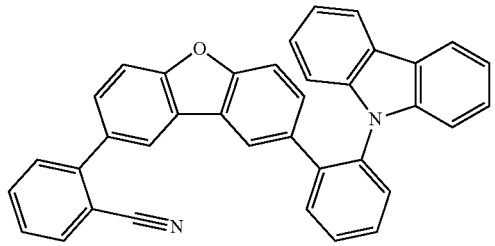
11
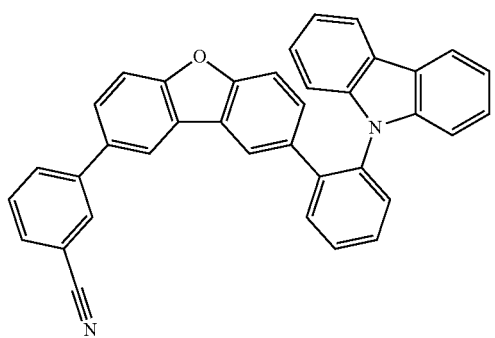
12
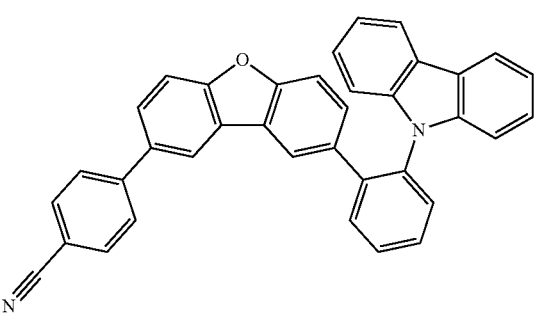

13
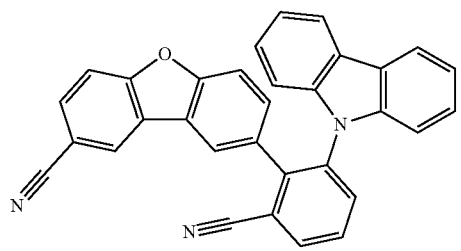
14
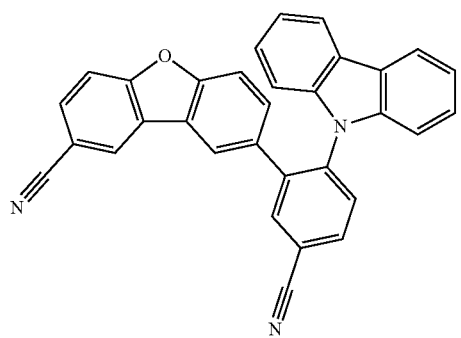
15
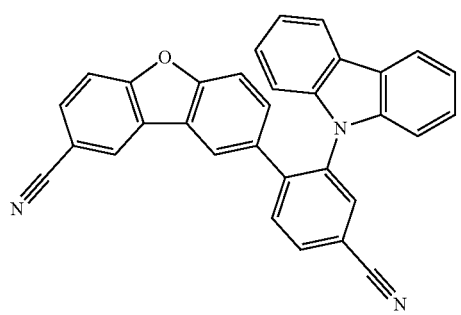
16
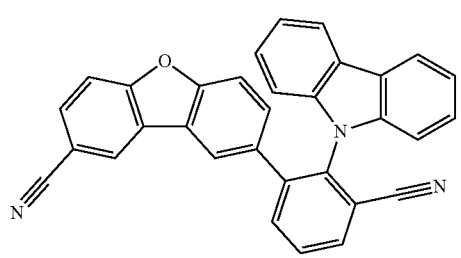
17
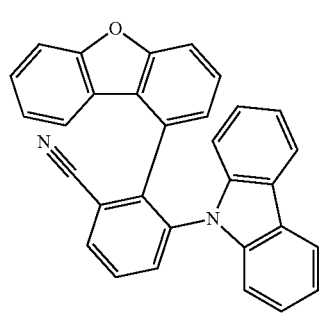
18
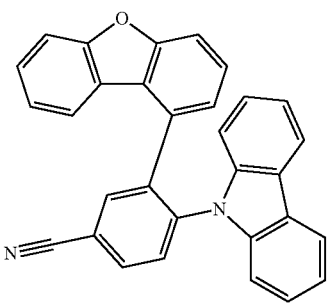
19
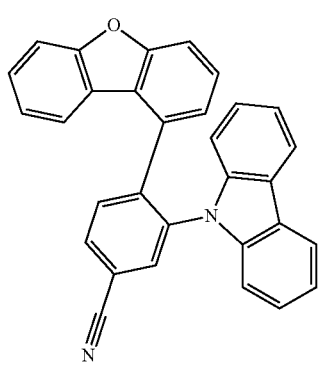
20
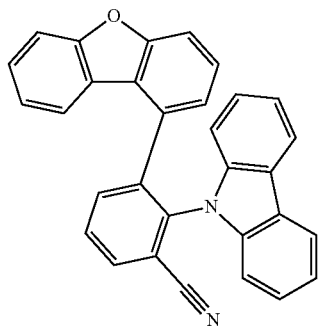
21
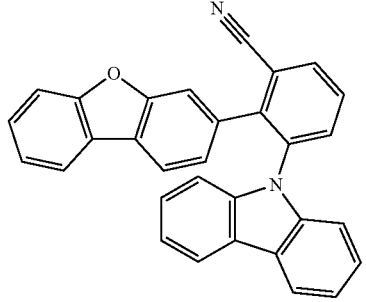
22
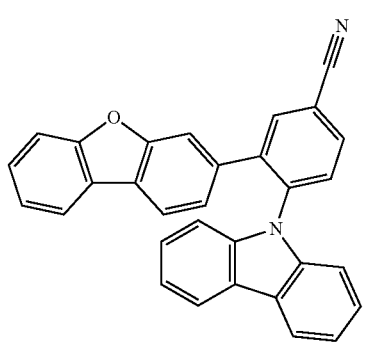

| 473 | 474 |
|---|---|
| -continued | -continued |
23
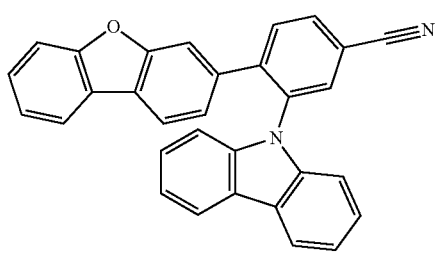
28
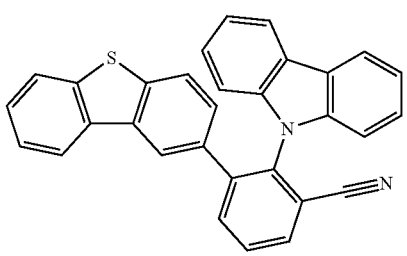
24
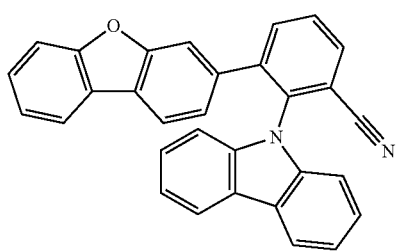
29
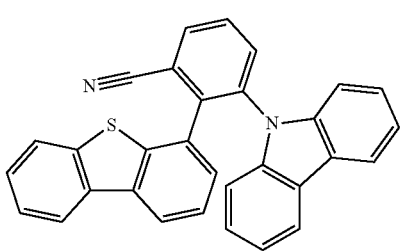
25
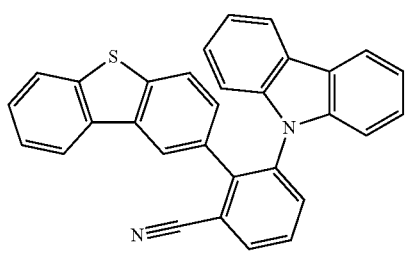
30
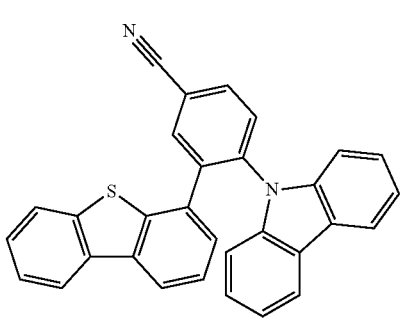
26
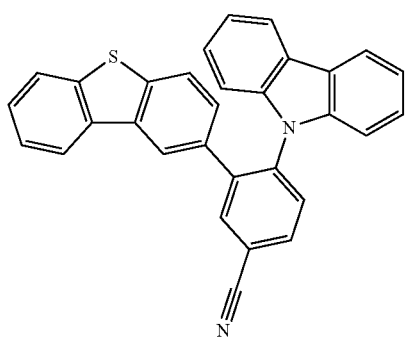
31
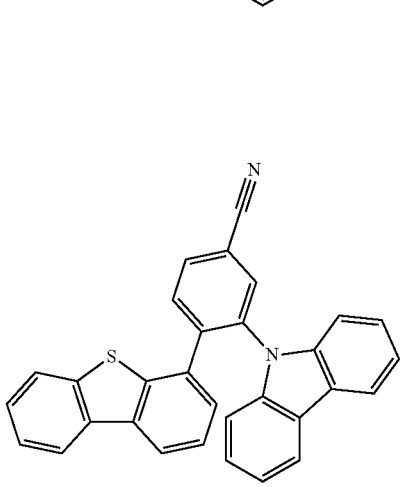
27
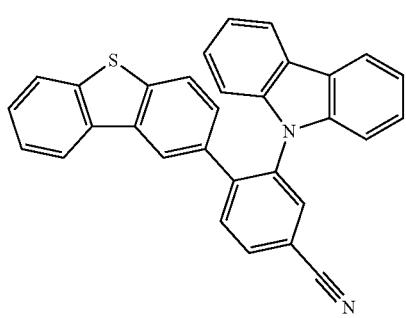
32
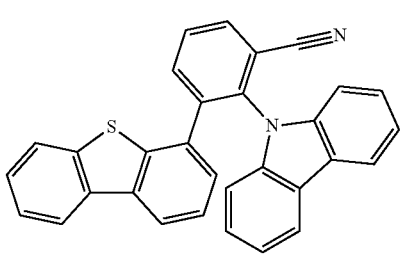

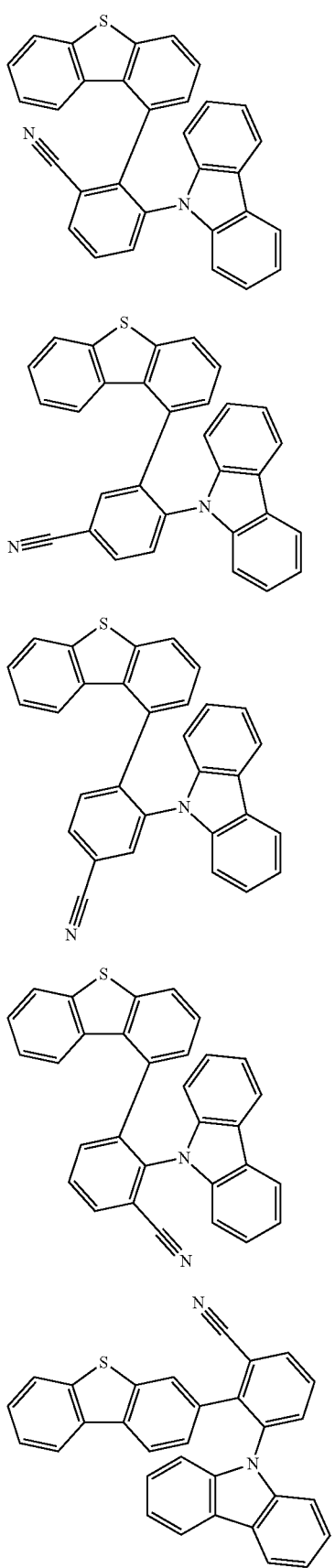
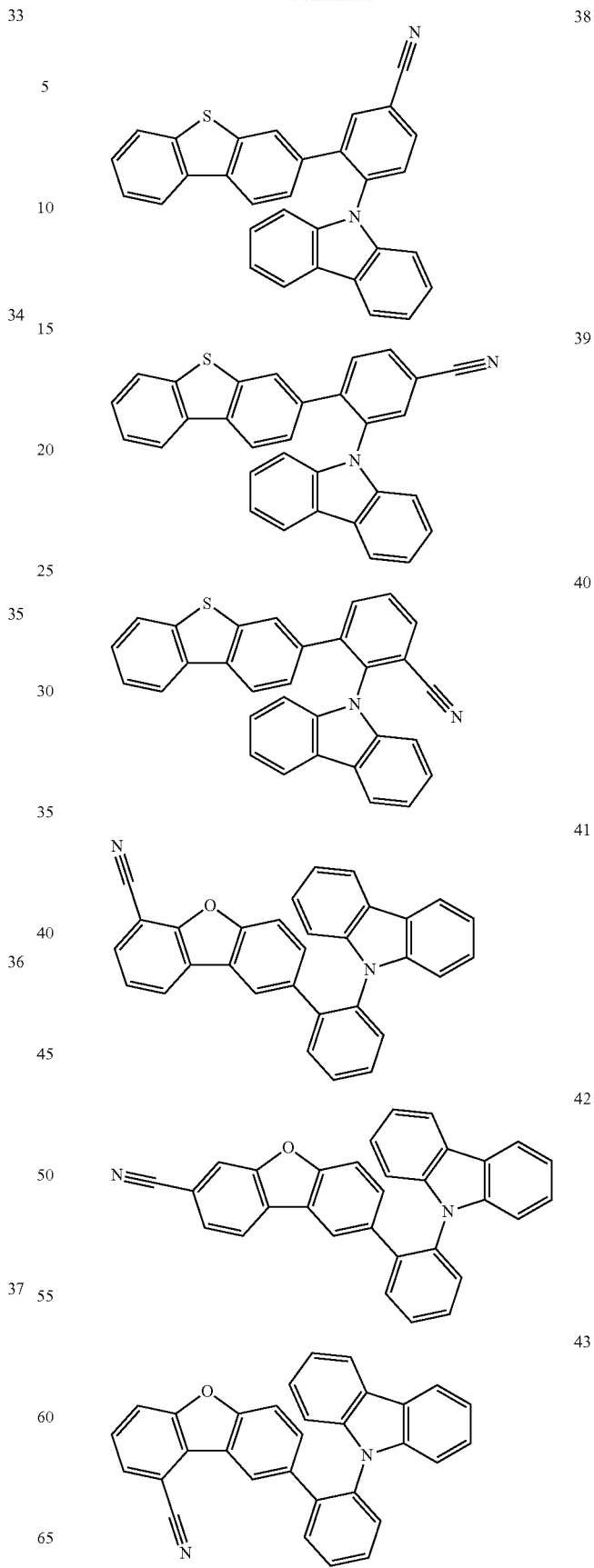

477
-continued
44
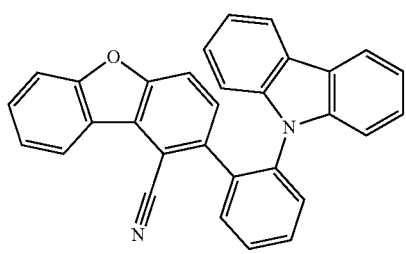
45
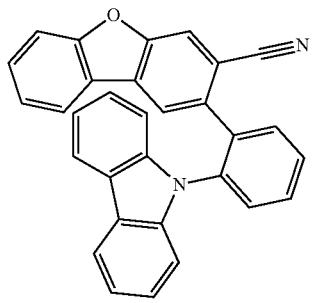
46
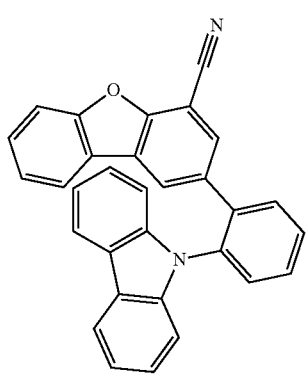
47
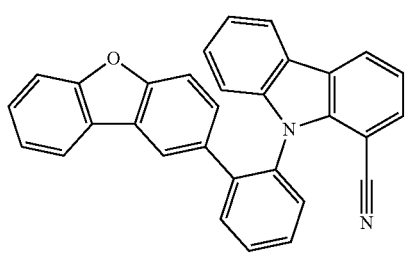
48
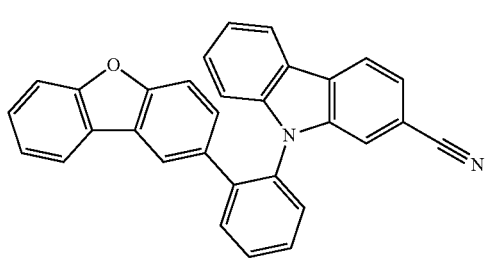
478
-continued
49
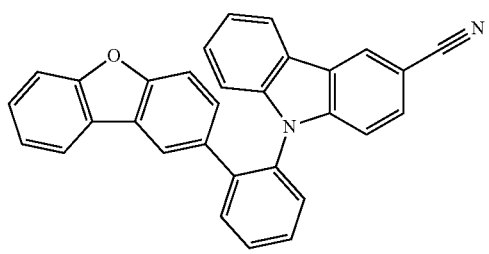
50
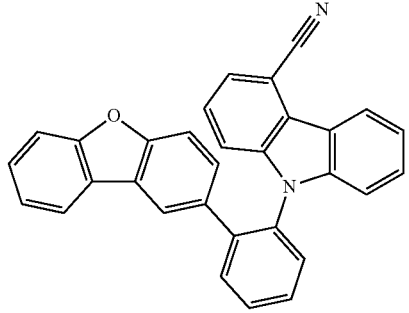
51
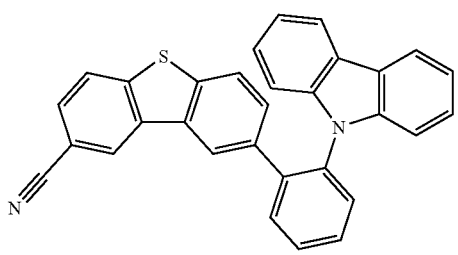
52
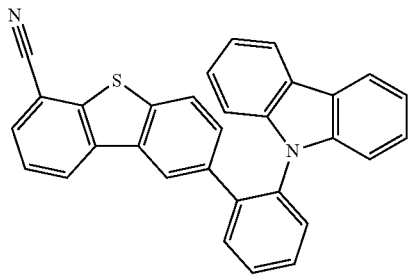
53
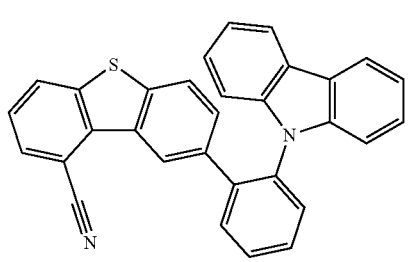
54

55
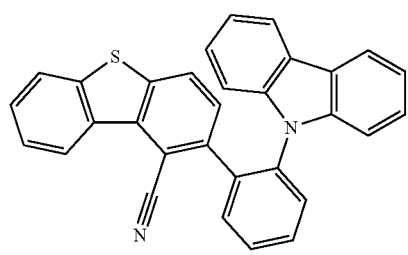
56
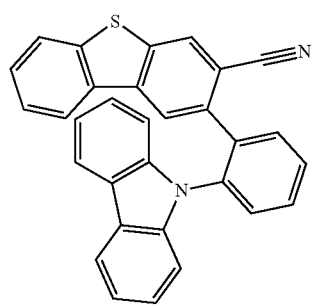
57
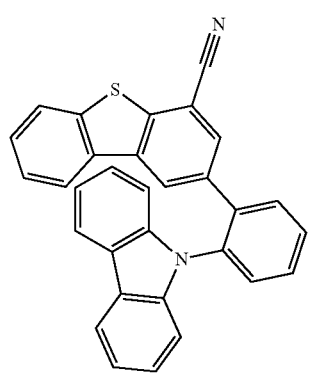
58
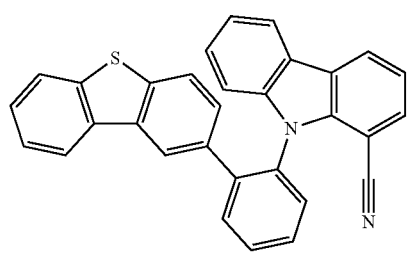
59
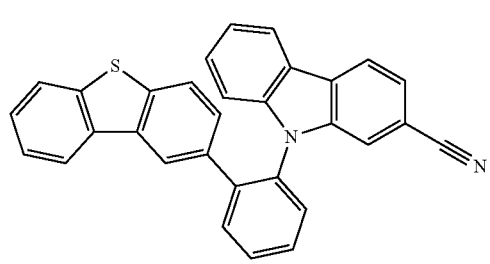
60
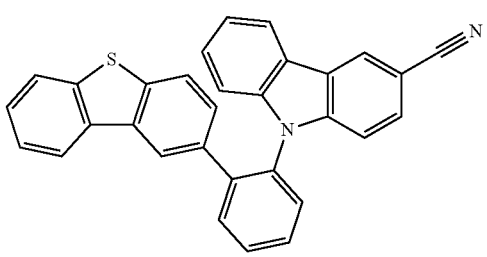
61

62
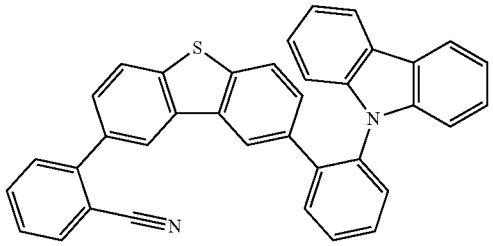
63
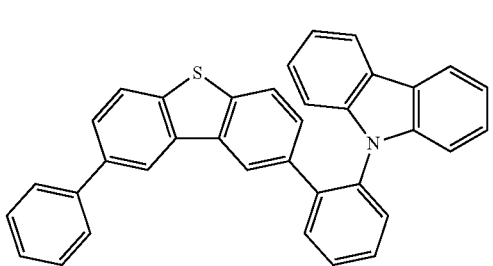
64
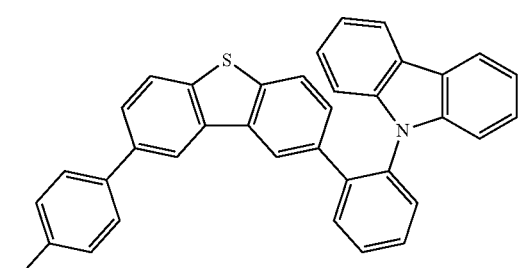

65
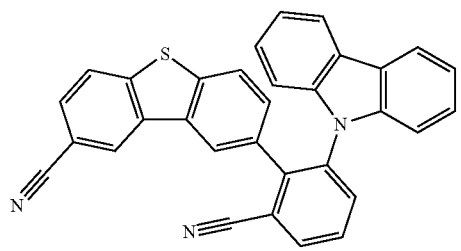
66
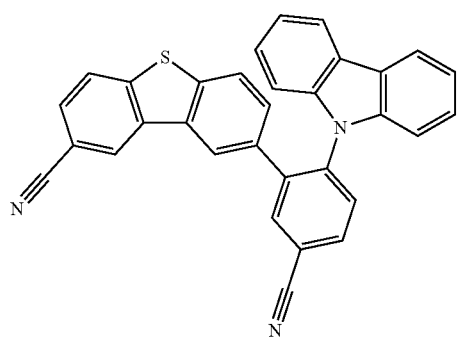
67
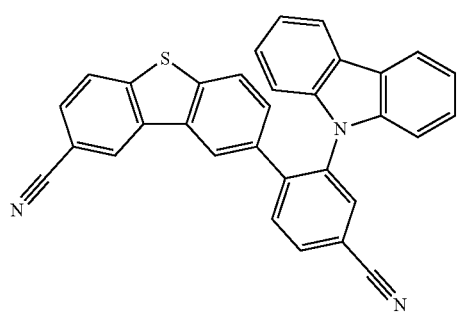
68
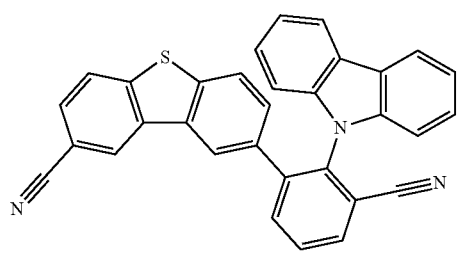
69
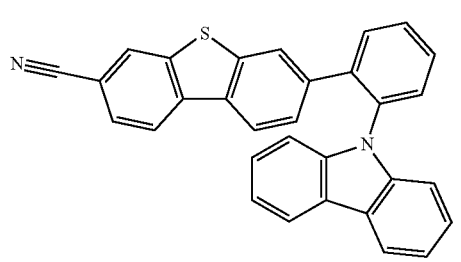
70
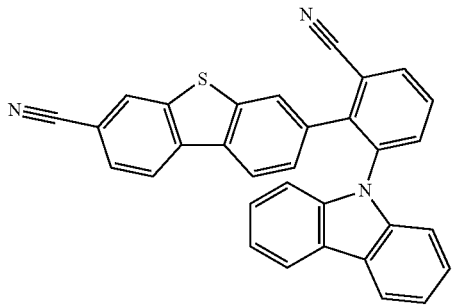
71

72
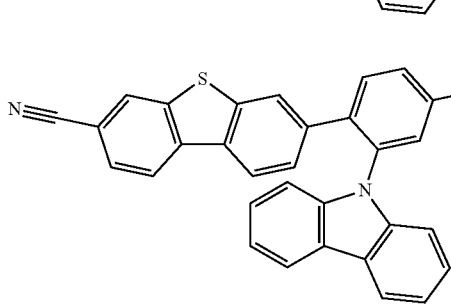
73
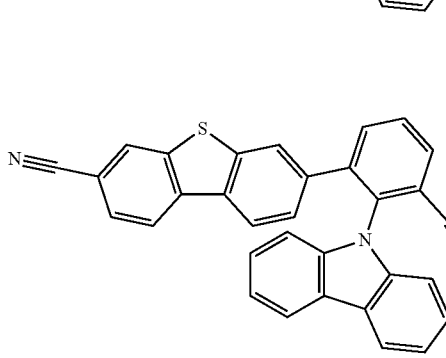
74
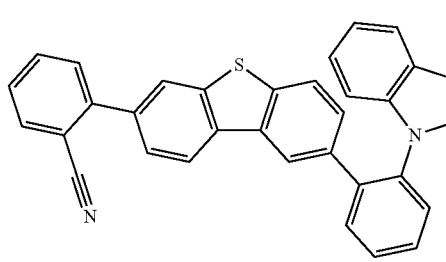

75
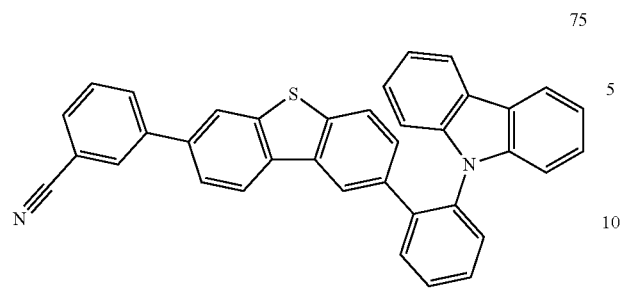
76
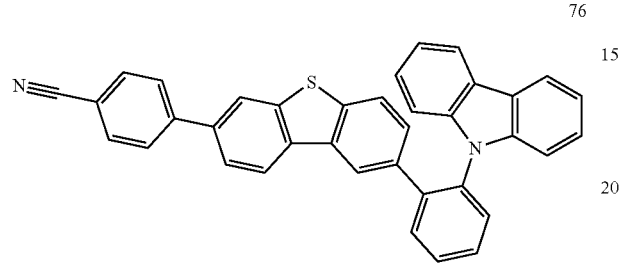
77
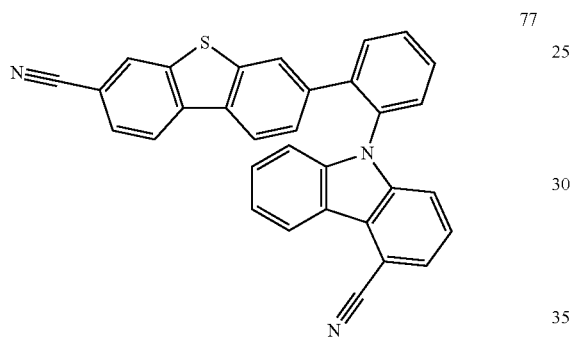
78

79
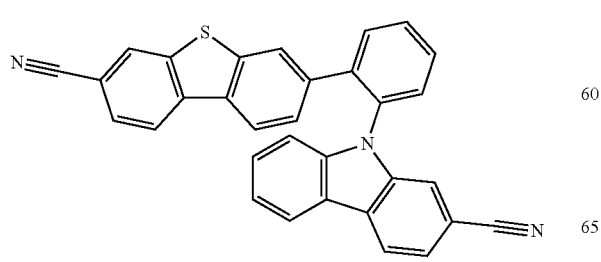
80
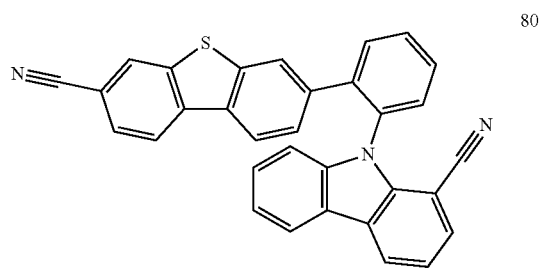
81
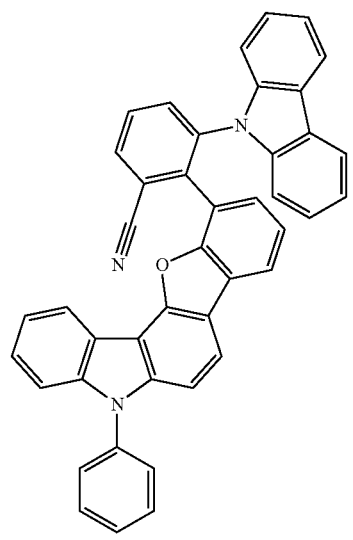
82
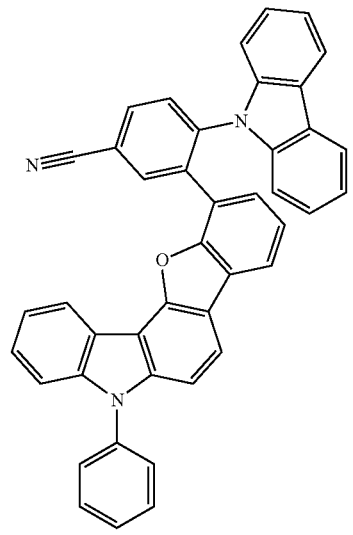

485
-continued
83
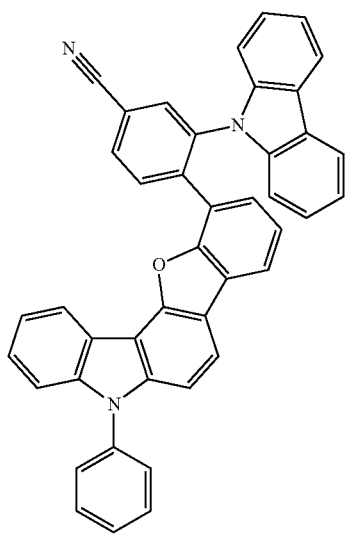
84
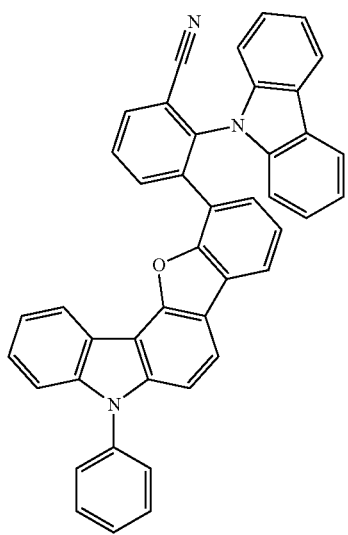
85
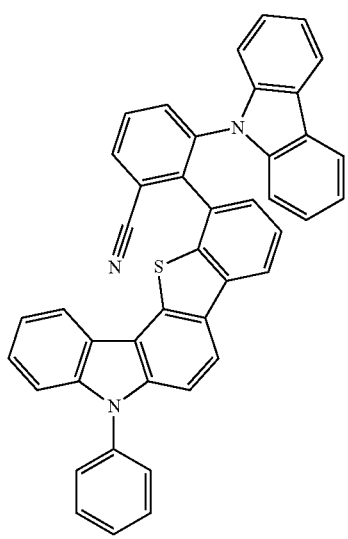
486
-continued
86
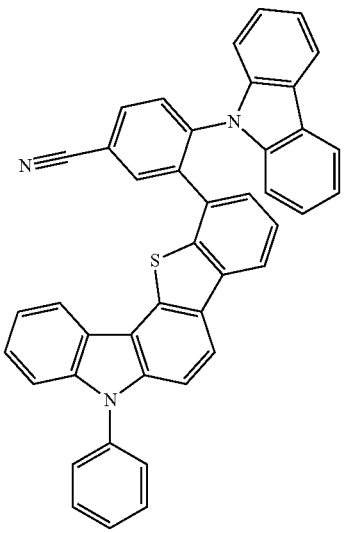
87
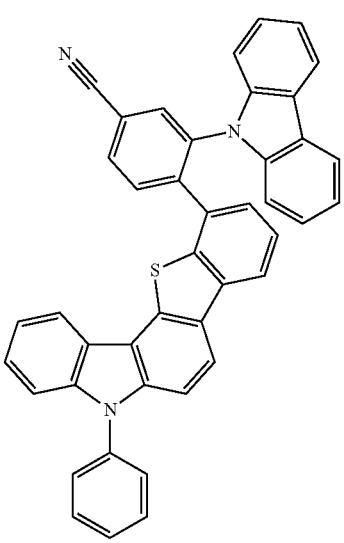
88
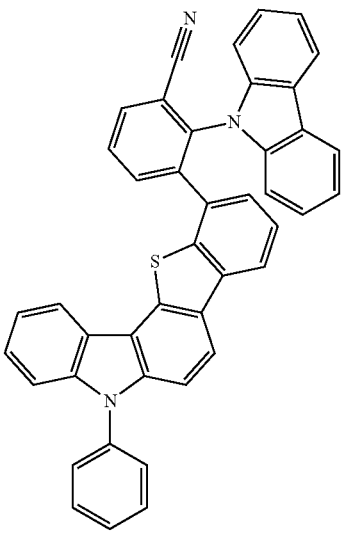

89
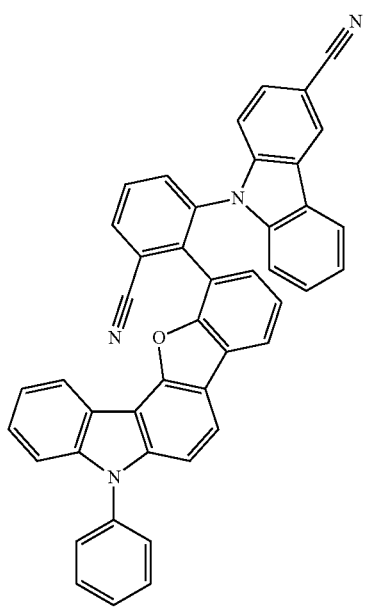
90
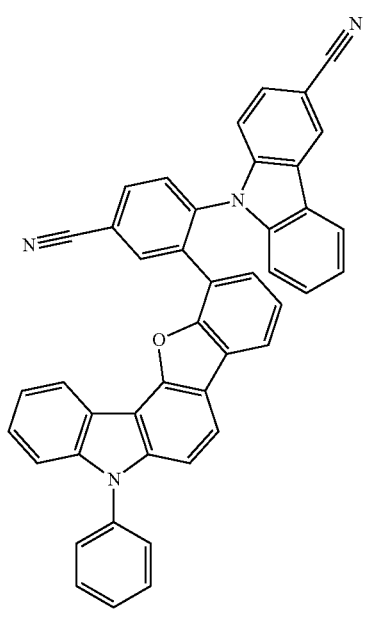
91
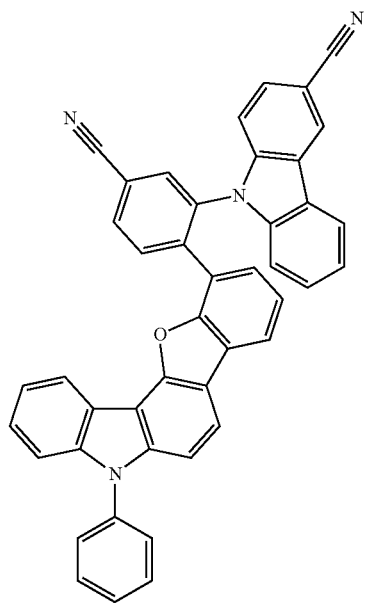
92
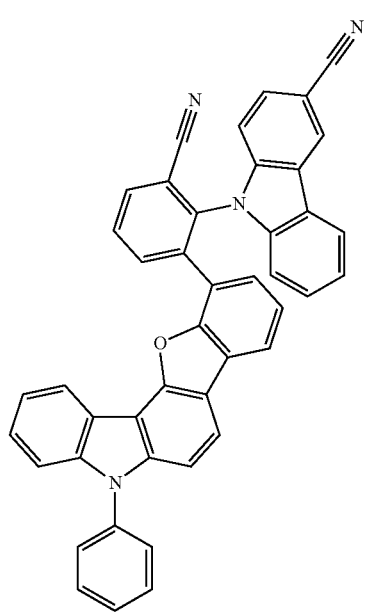

-continued
93
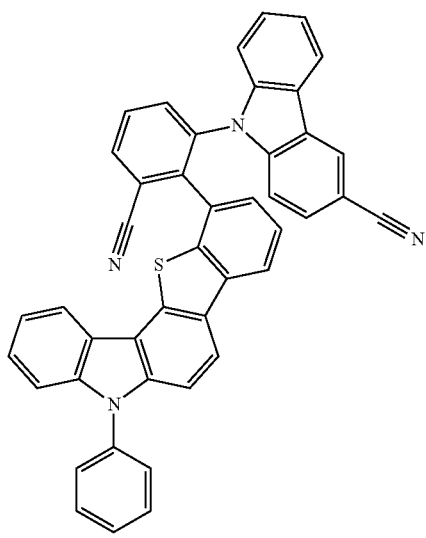
94
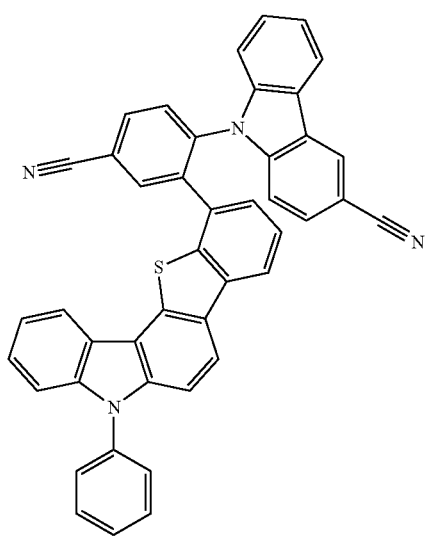
95
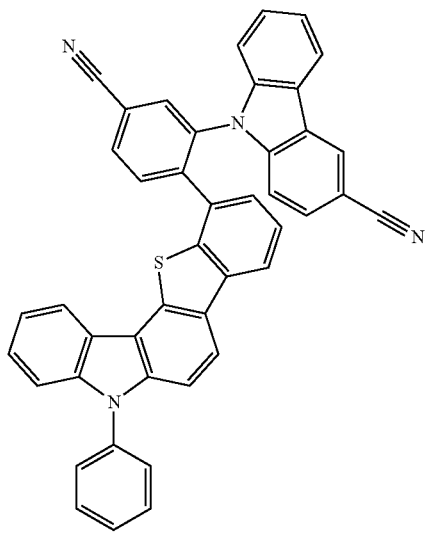
-continued
96
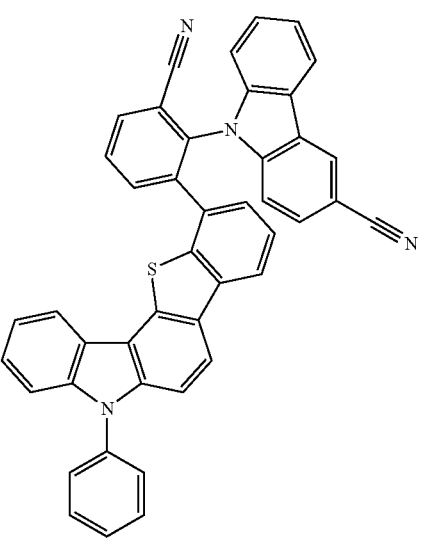
97
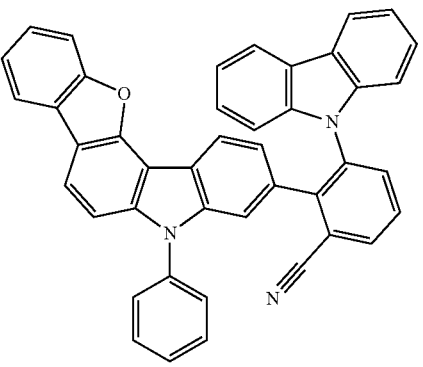
98
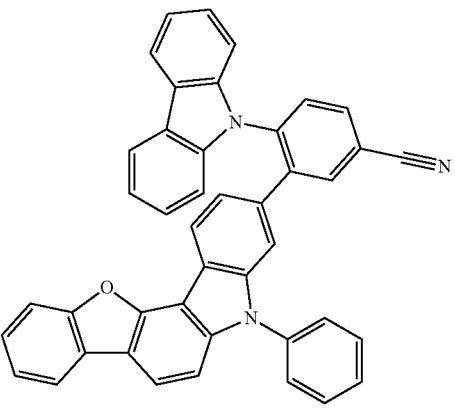

-continued
99
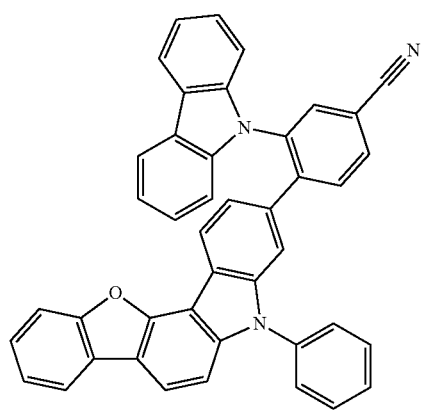
100
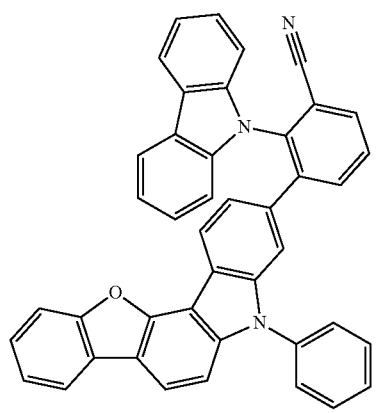
101
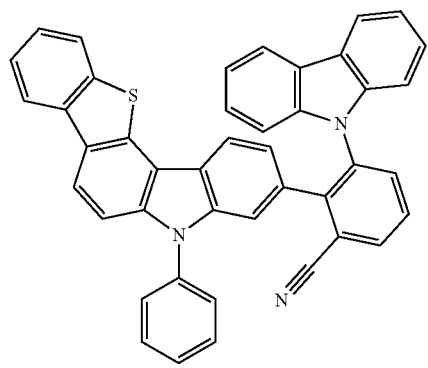
102
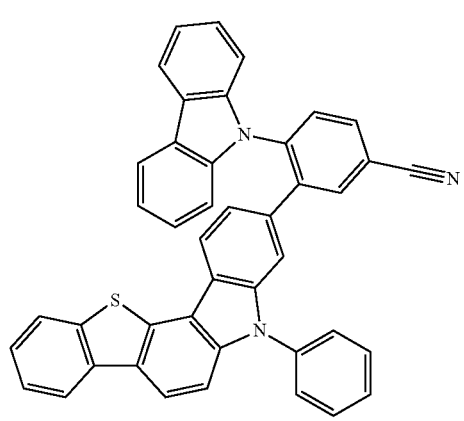
-continued
103
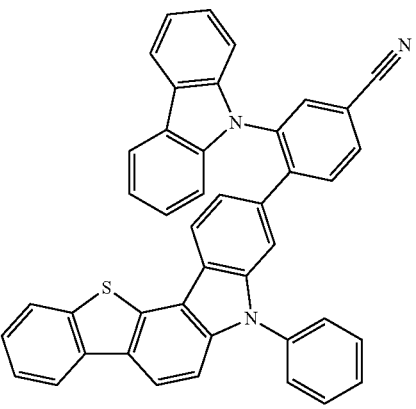
104
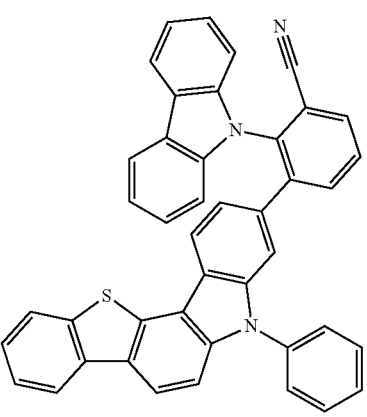
105
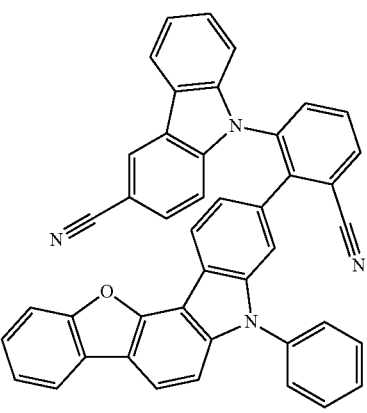
106
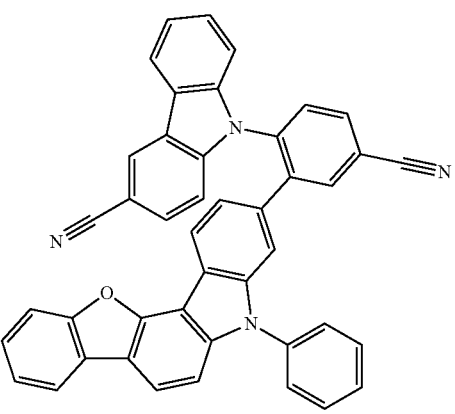

107
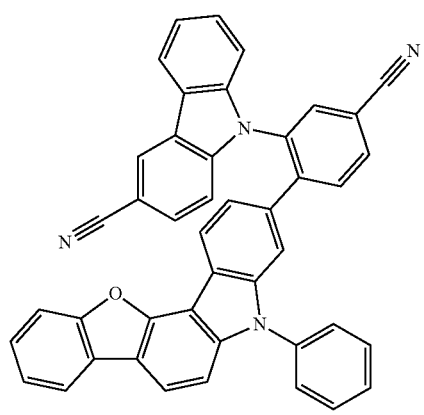
108
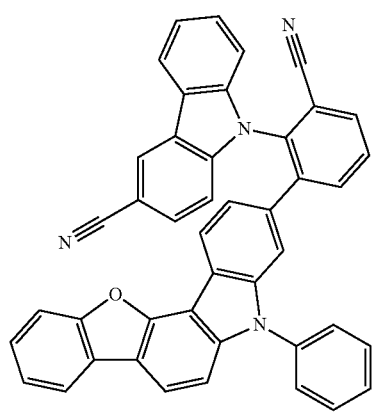
109
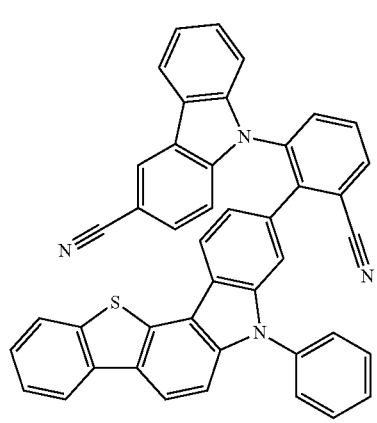
110
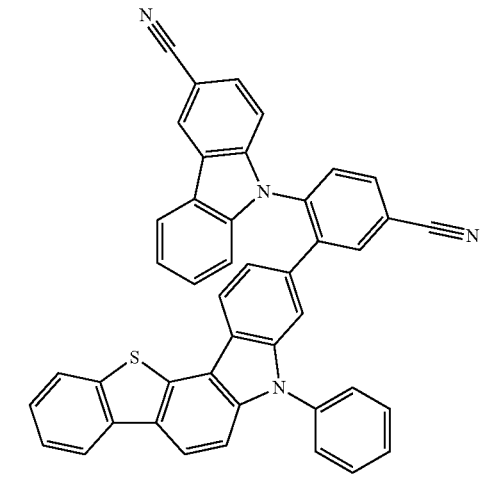
111
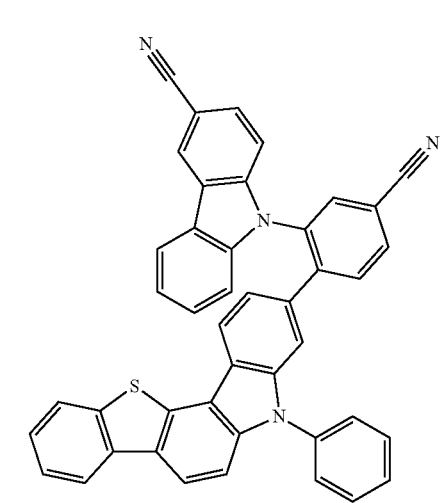
112
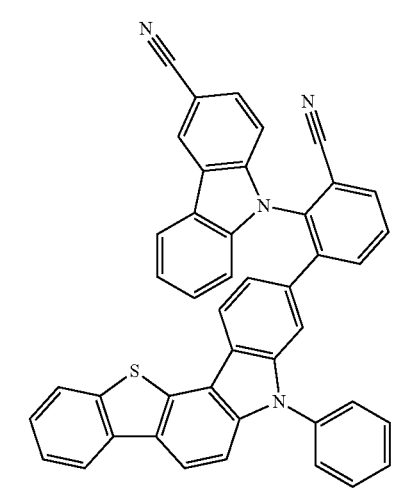

-continued
113
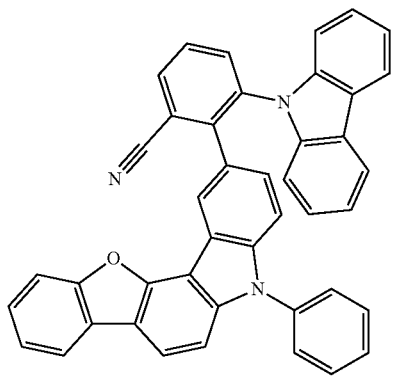
114
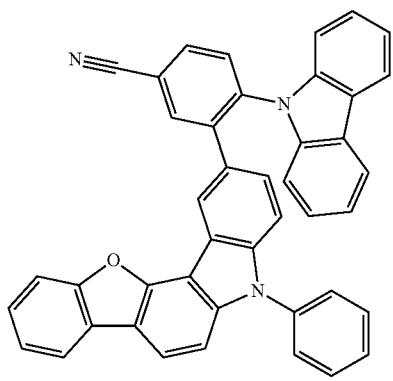
115
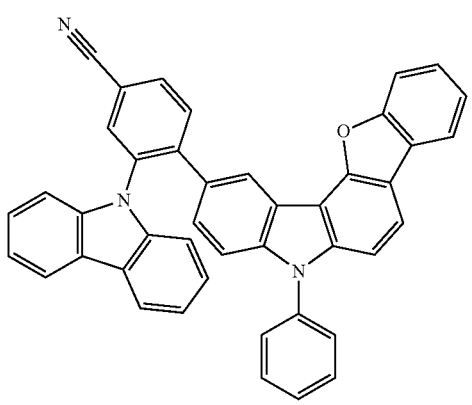
116
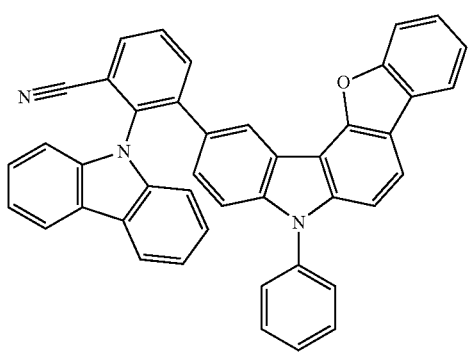
-continued
117
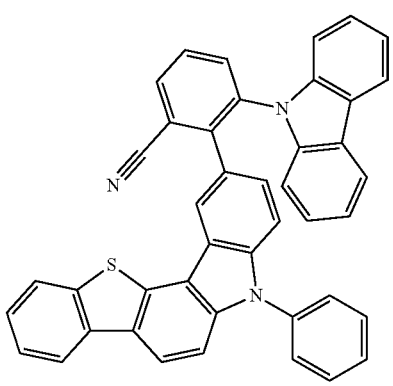
118

119
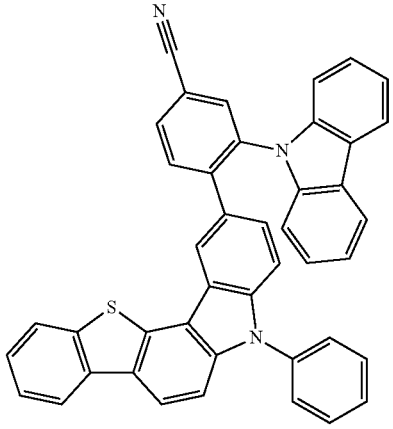
120
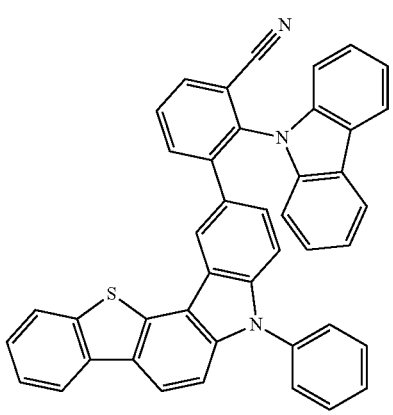

497
-continued
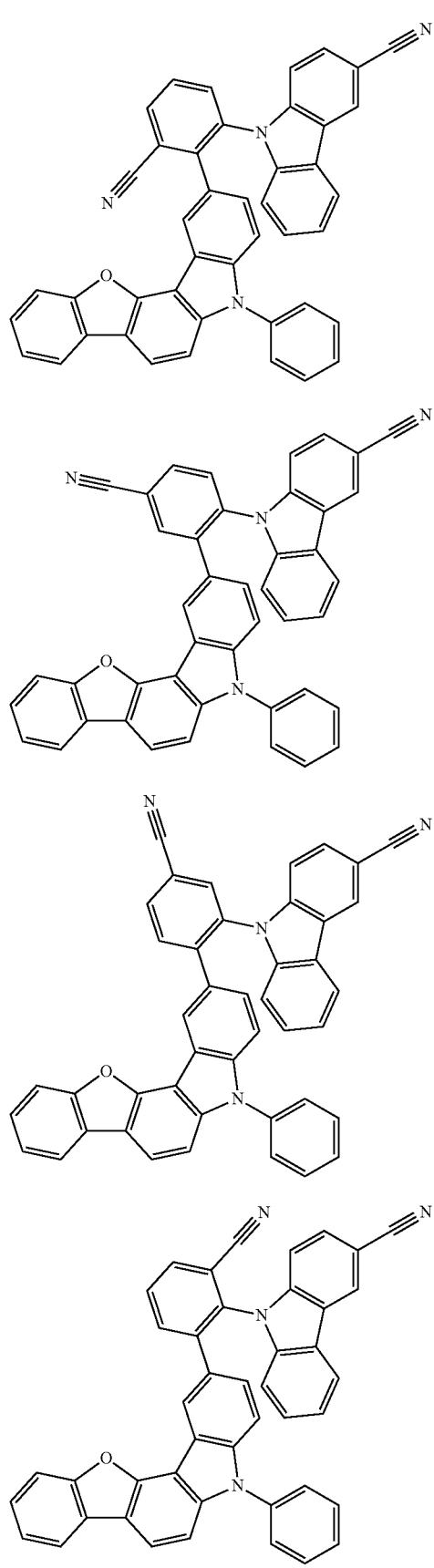
498
-continued
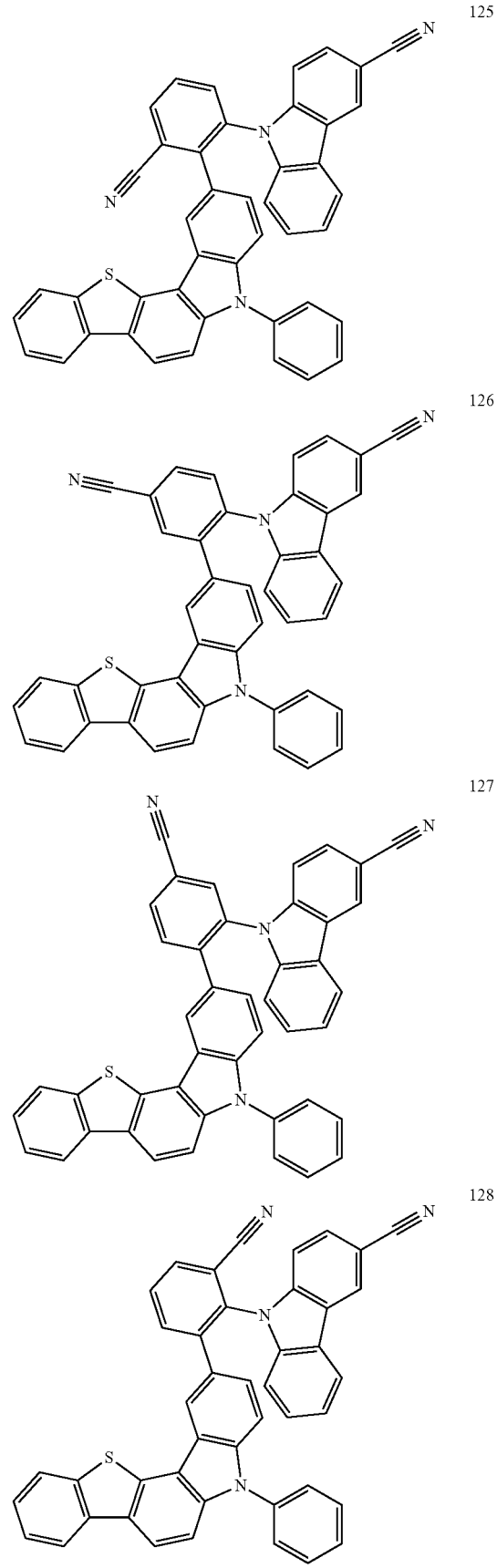

-continued
129
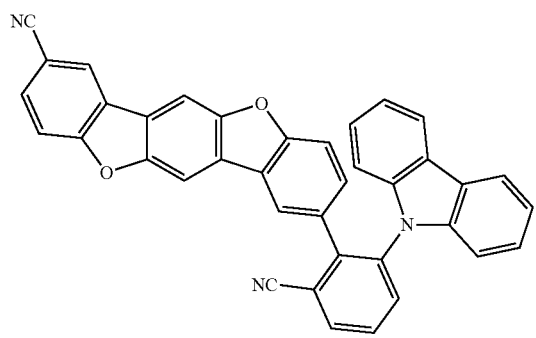
130
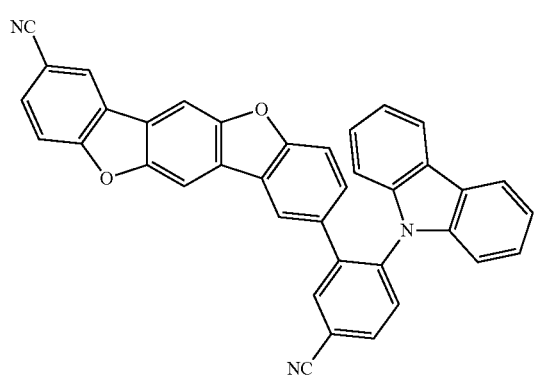
131
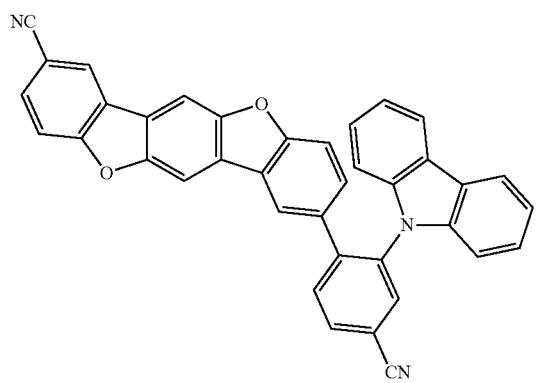
132
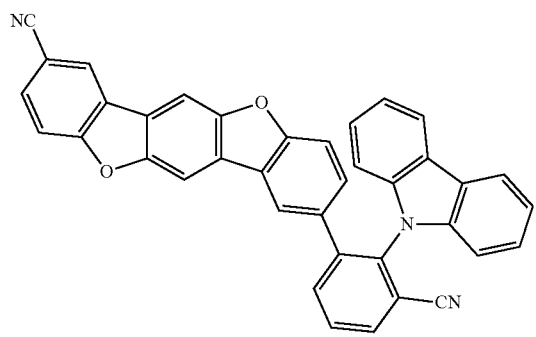
-continued
133
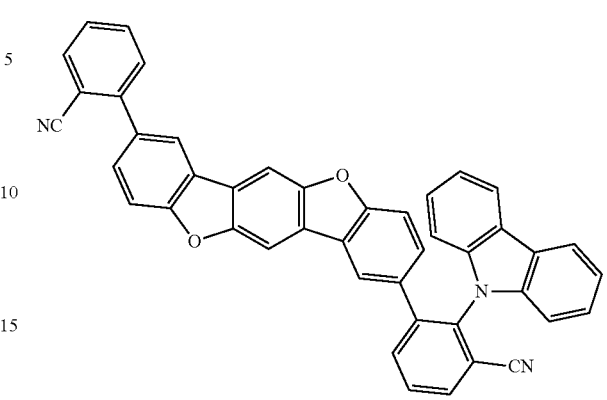
134
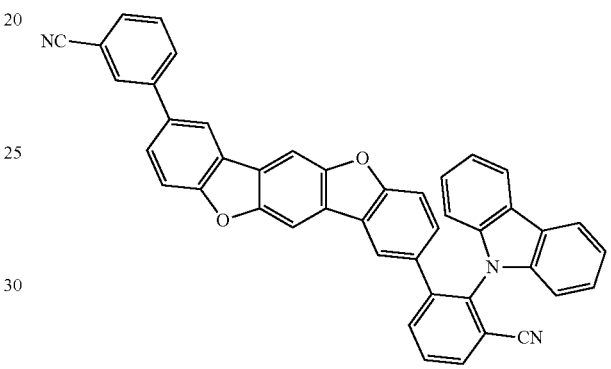
135
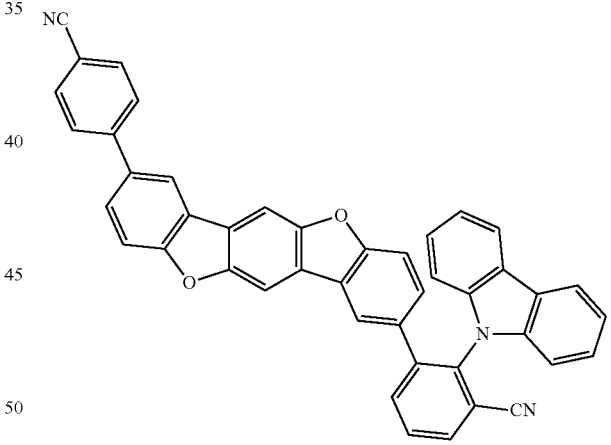
136
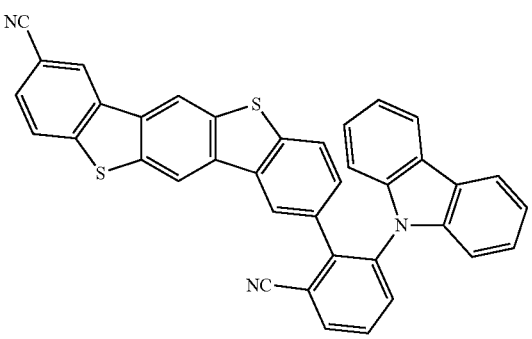

-continued
137
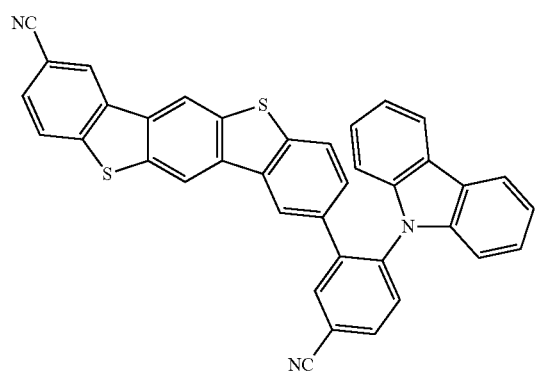
138
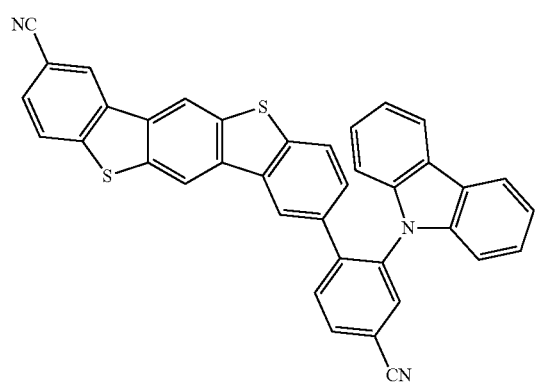
139
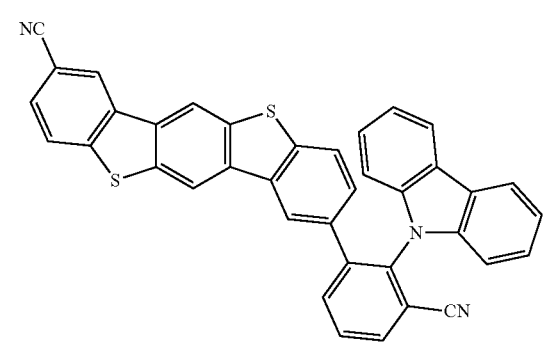
140
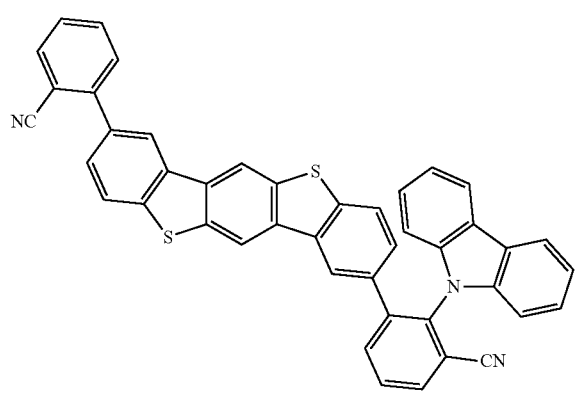
-continued
141
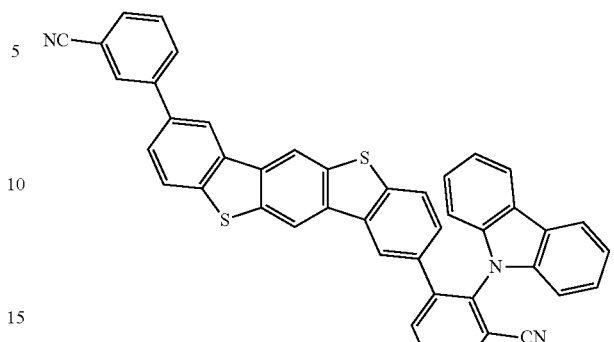
142
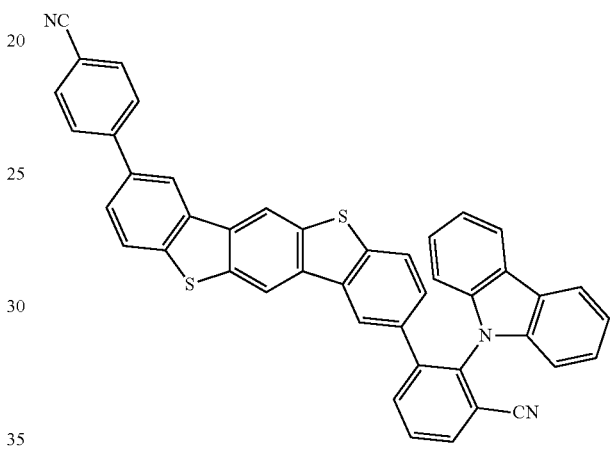
143
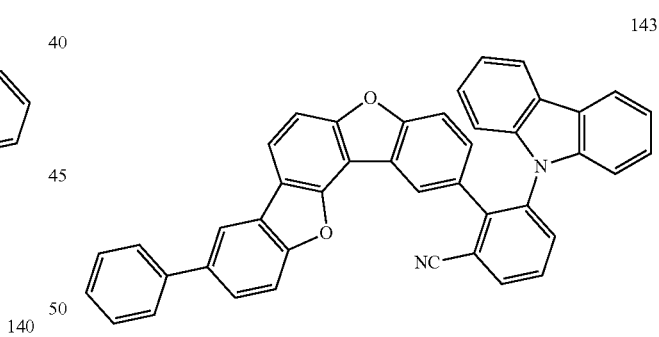
144
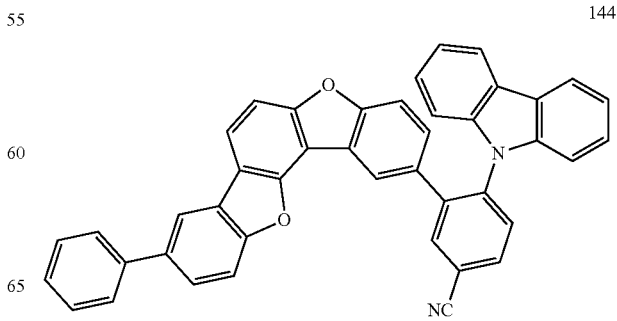

503
-continued
145
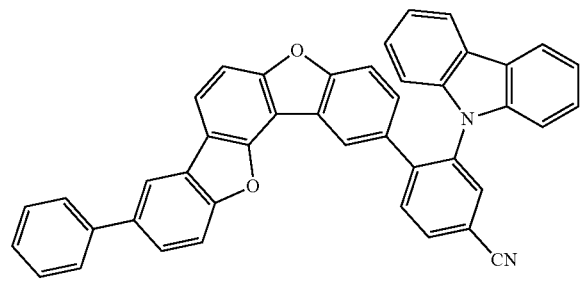
146
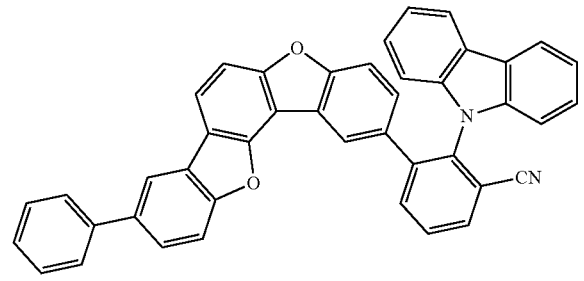
147
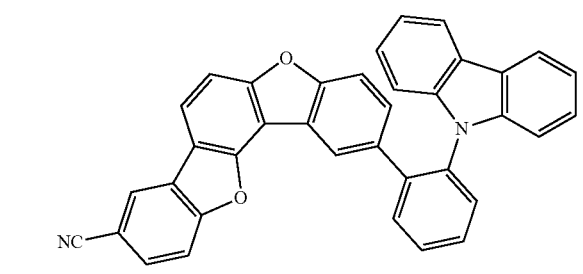
148
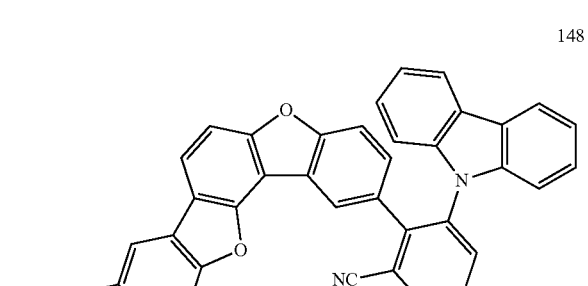
149
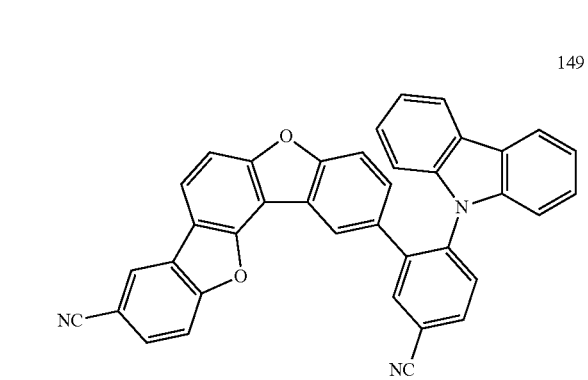
504
-continued
150
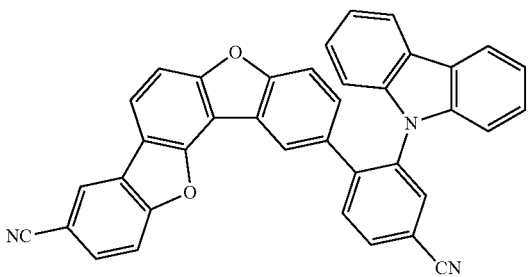
151
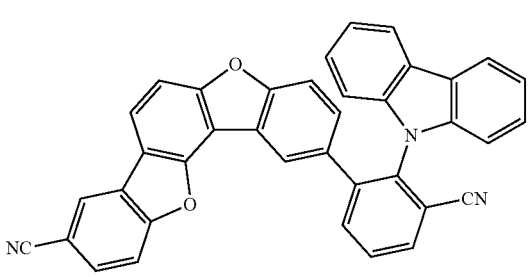
152
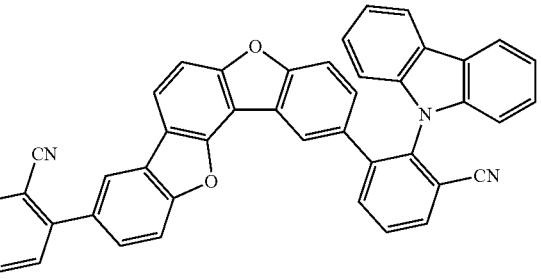
153
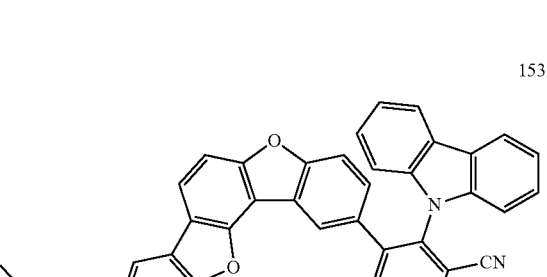
154
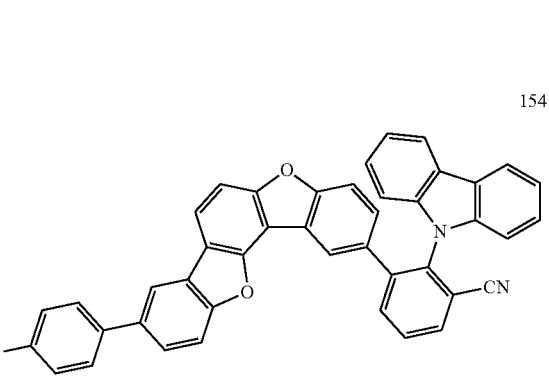

505
-continued
| | |
|---|---|
| 155 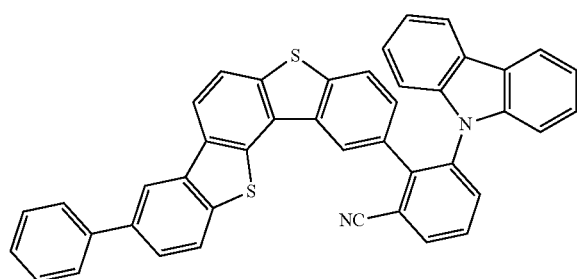 | 160 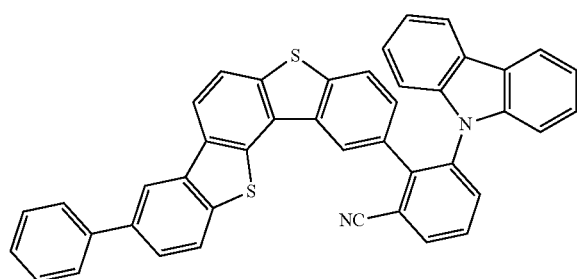 |
| 156 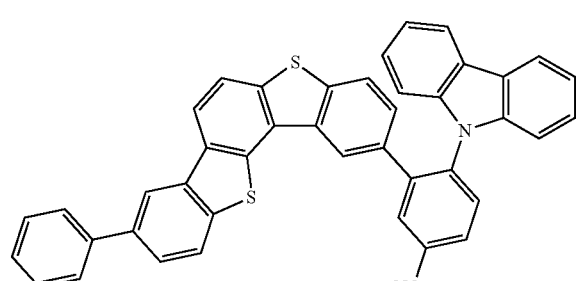 | 161 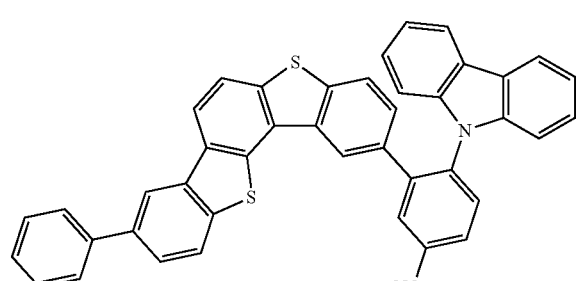 |
| 157  | 162  |
| 158  | 163  |
| 159 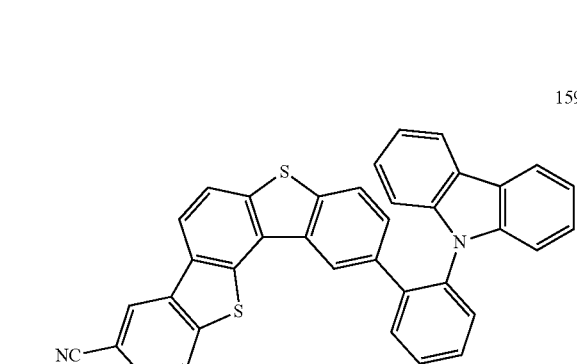 | 164 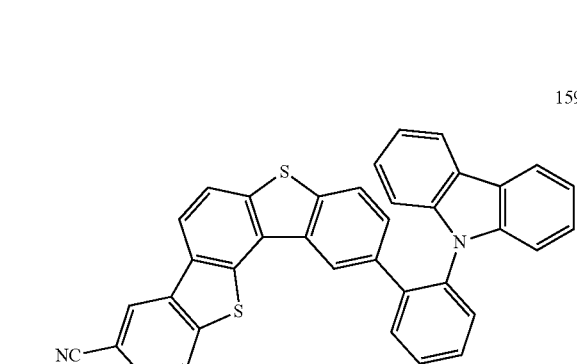 |
506
-continued 165
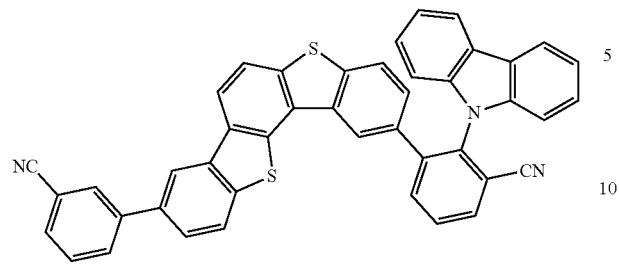
166
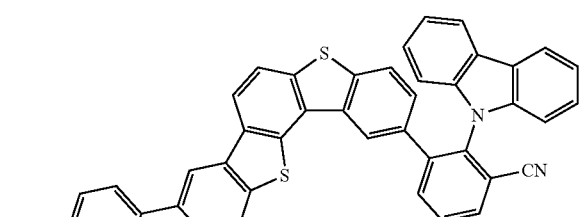
167
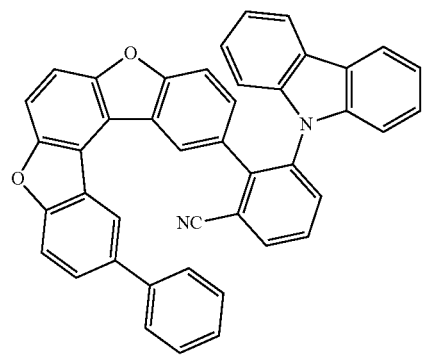
168
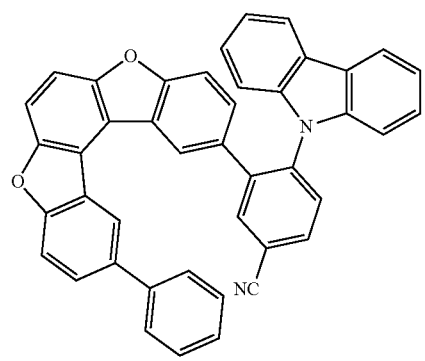
169
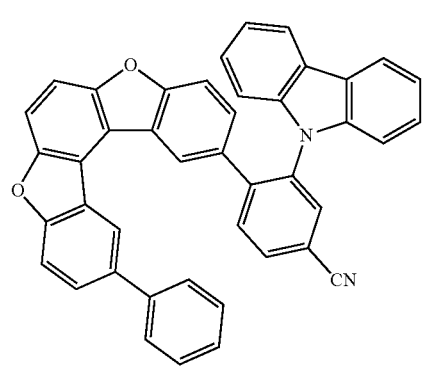
170
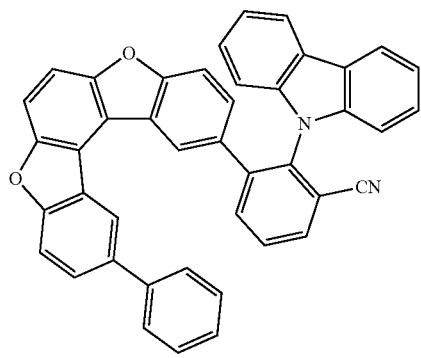
171
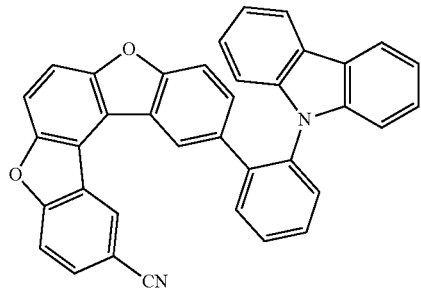
172
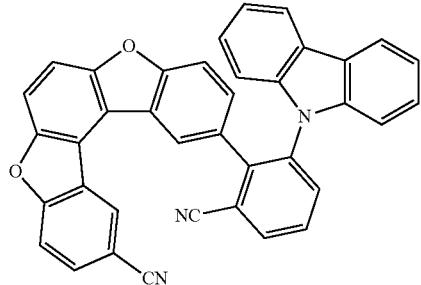
173
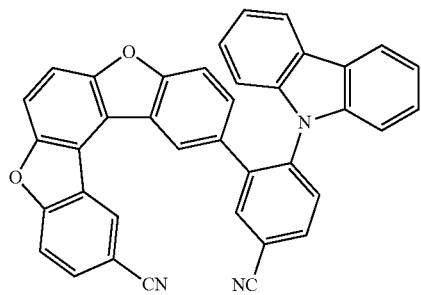
174
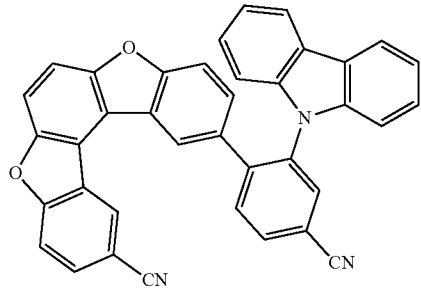

509
-continued
175
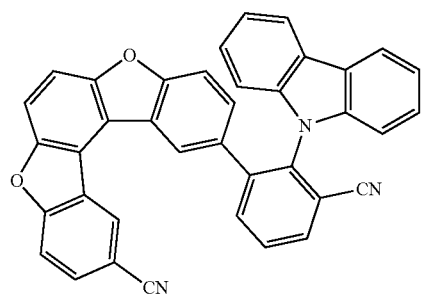
176
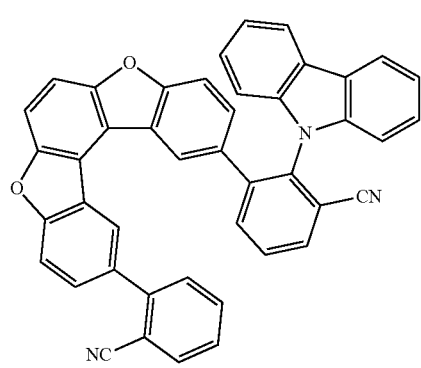
177
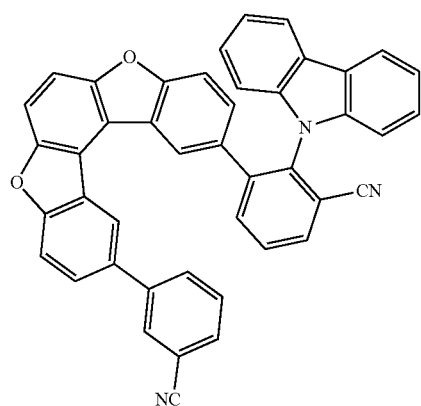
178
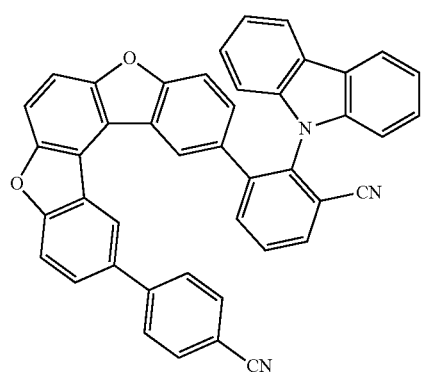
510
-continued
179
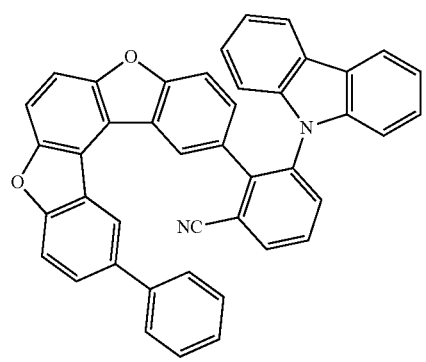
180
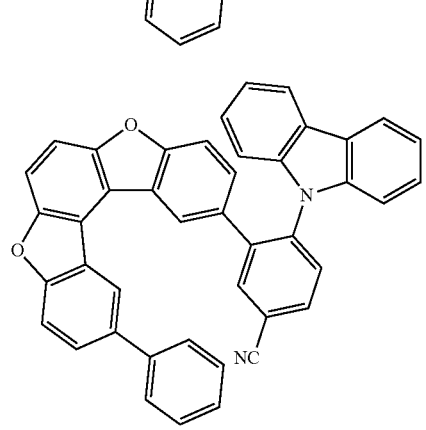
181
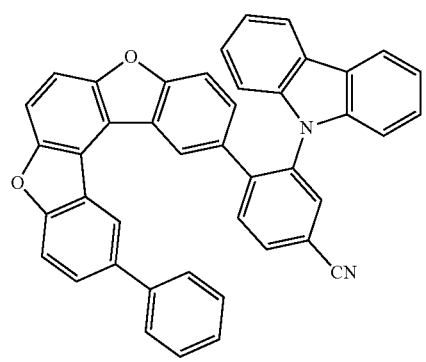
182
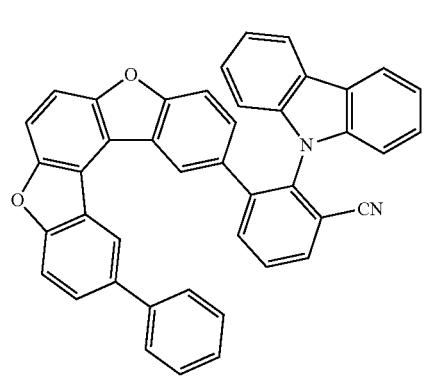

183
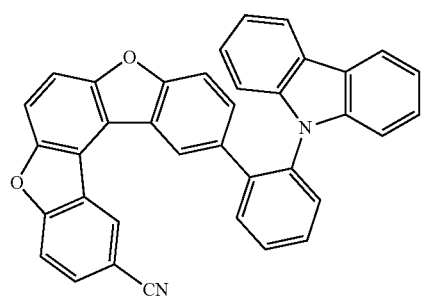
184
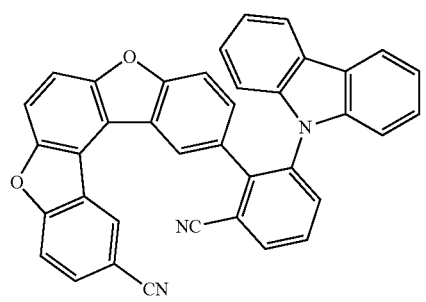
185
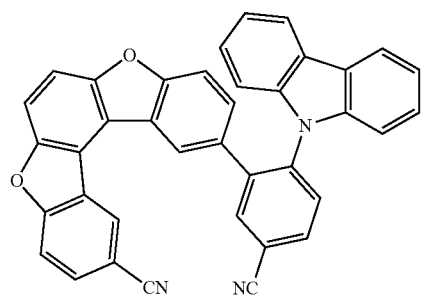
186
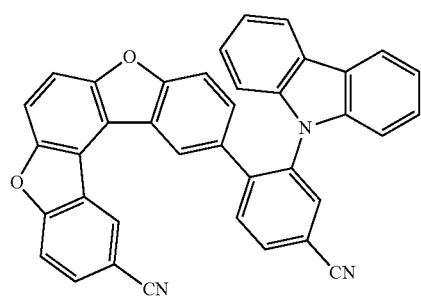
187
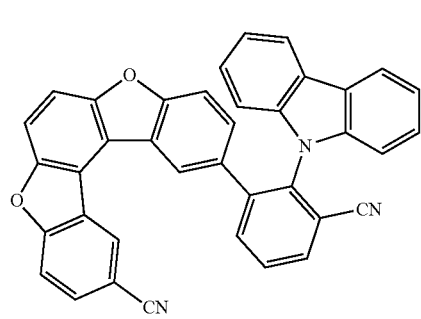
188
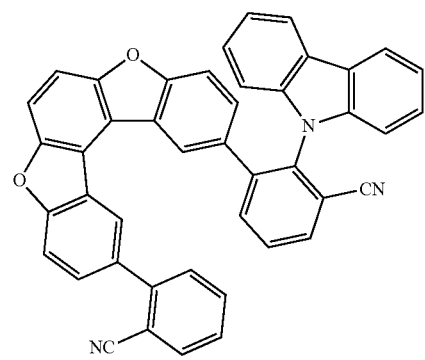
189
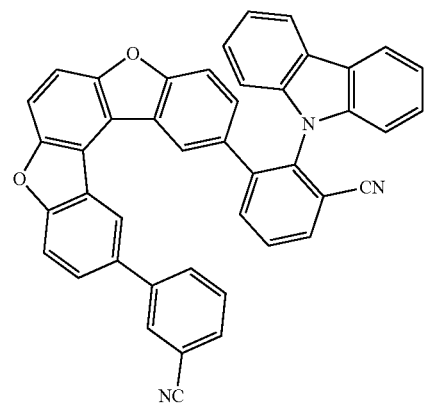
190
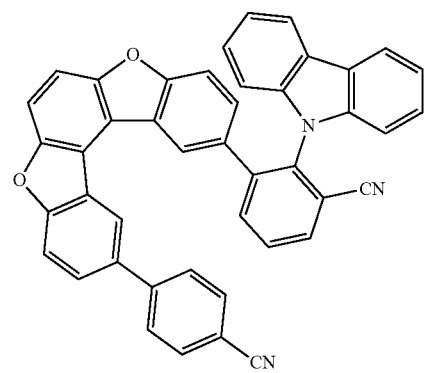
191
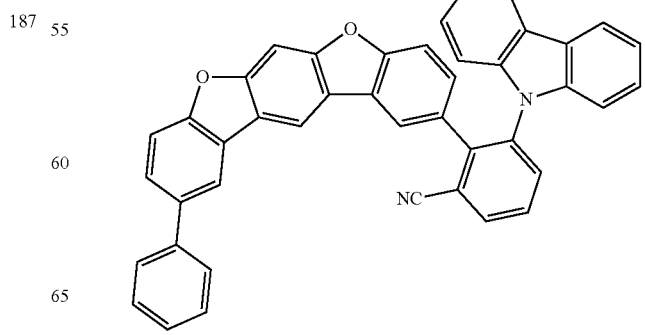

192
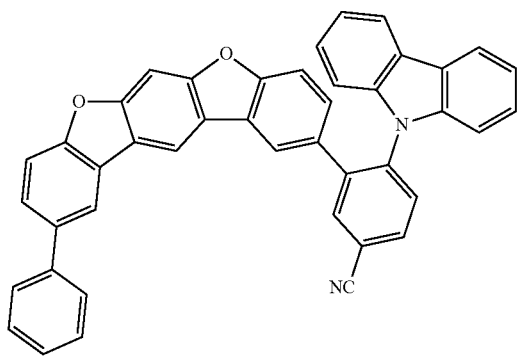
193
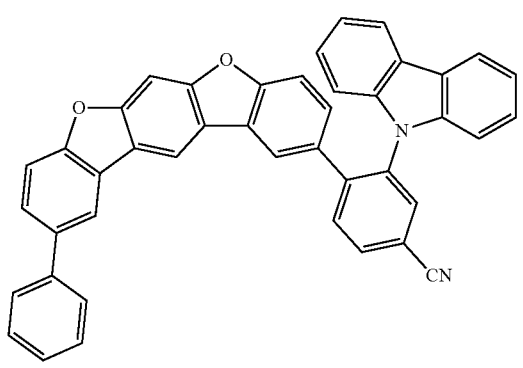
194
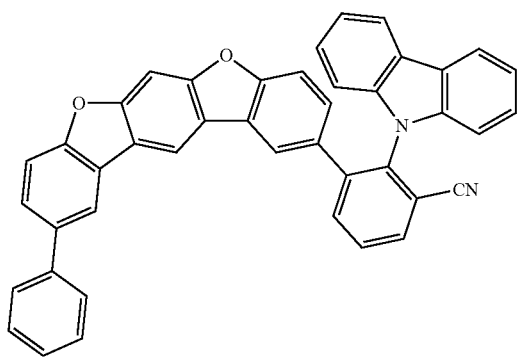
195
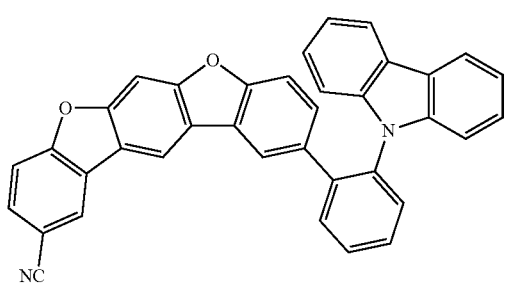
196
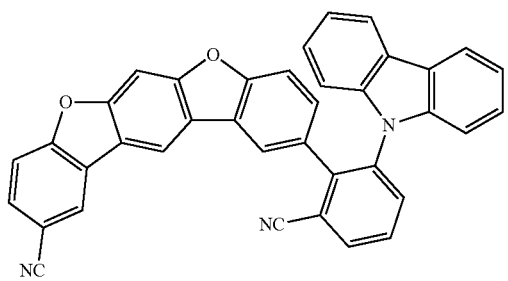
197
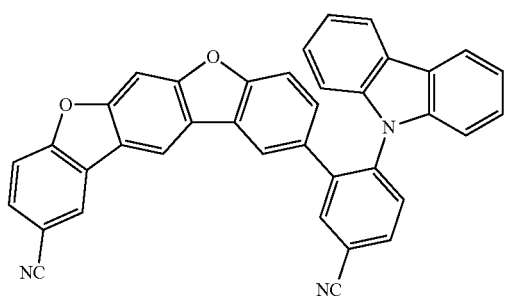
198
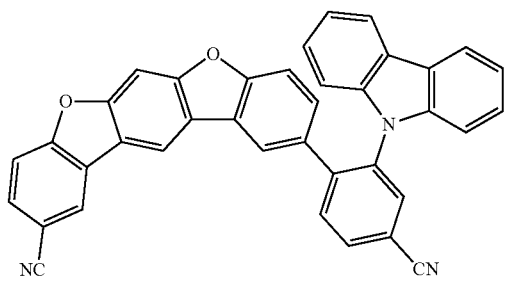
199
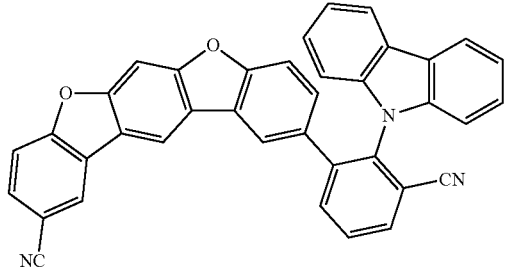
200
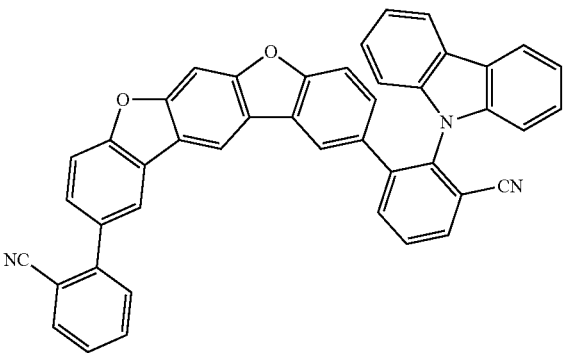

515
-continued
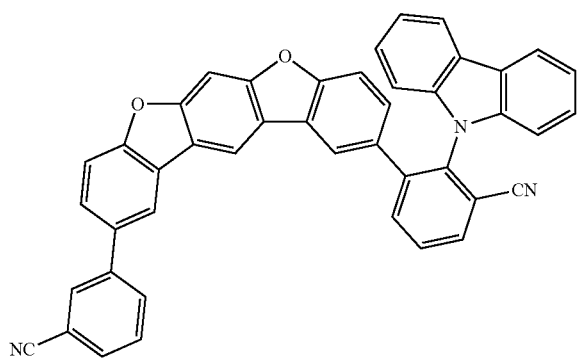
201
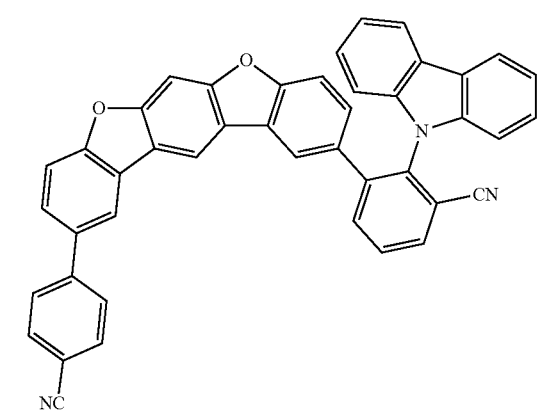
202
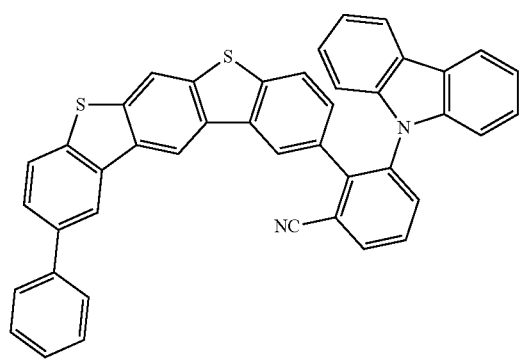
203
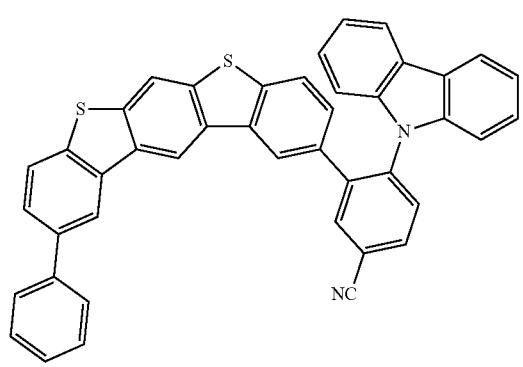
204
516
-continued
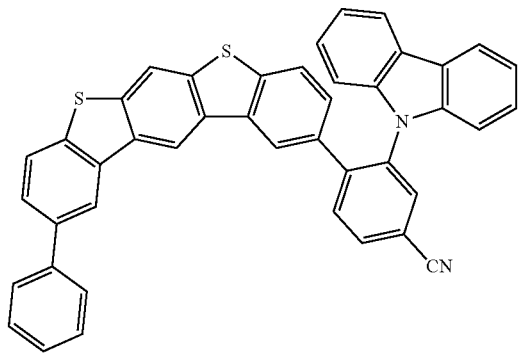
205
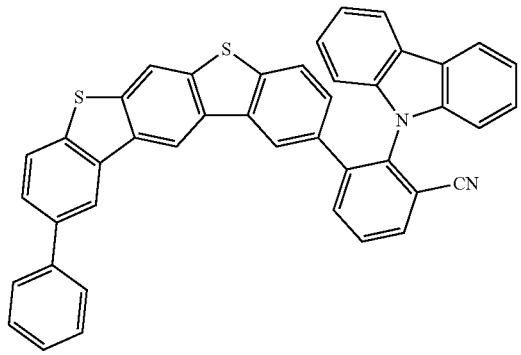
206
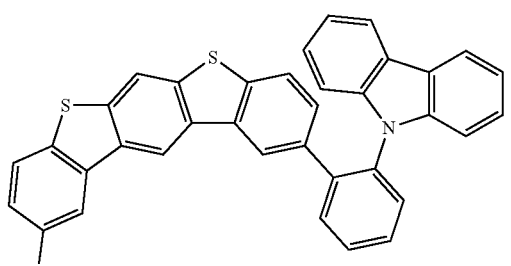
207
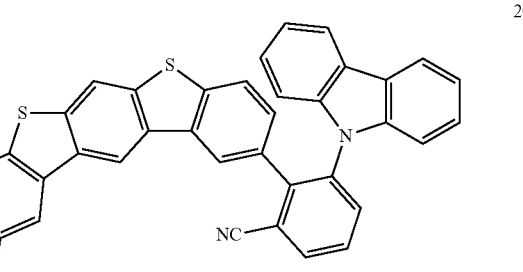
208
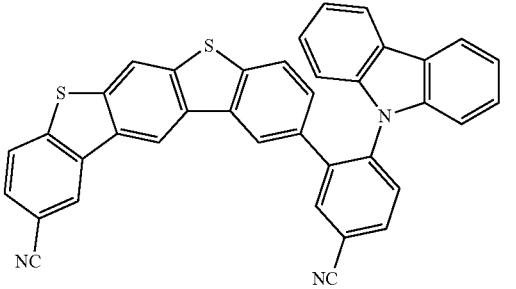
209

517 -continued
210
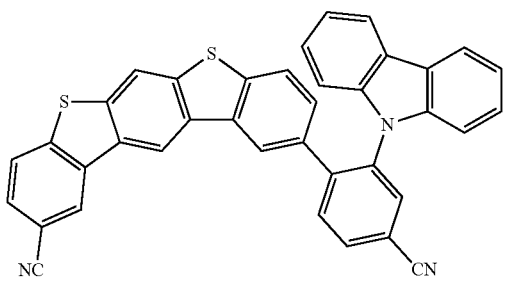
211
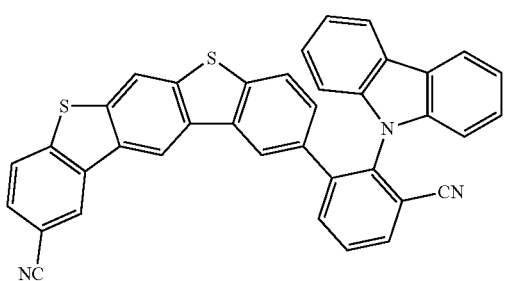
212
213
518 -continued
214
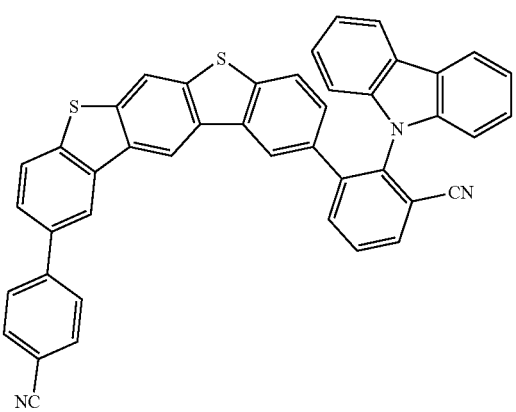
215
216
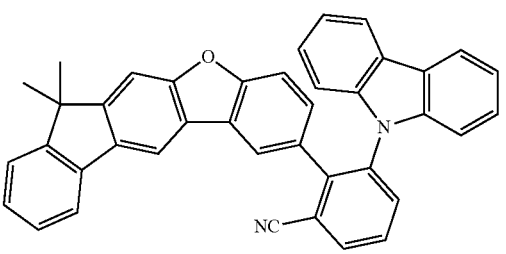
217
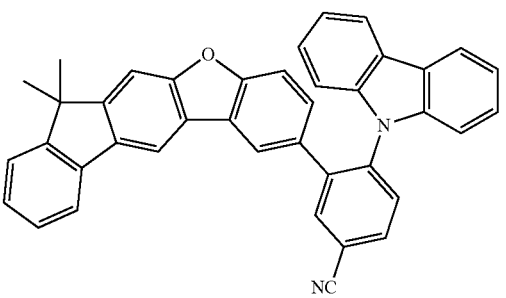
218
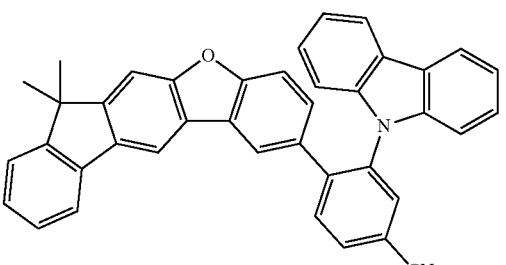
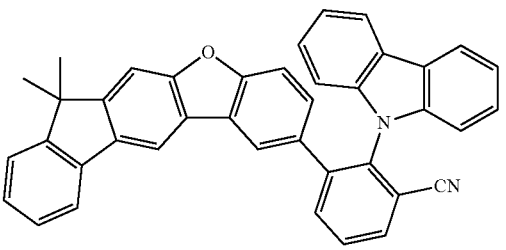

519                                    520
-continued                             -continued
219
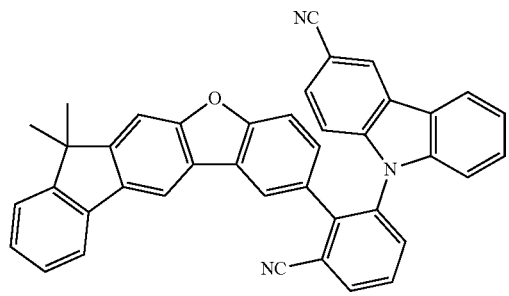
220
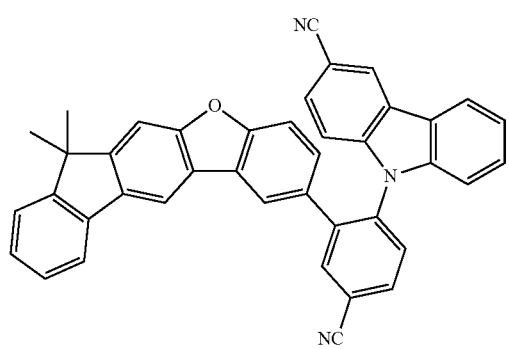
221
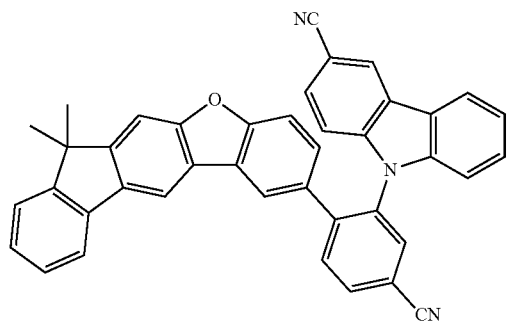
222
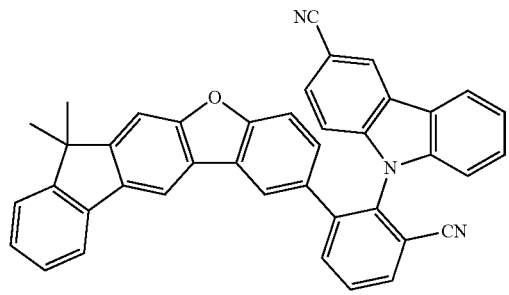
223
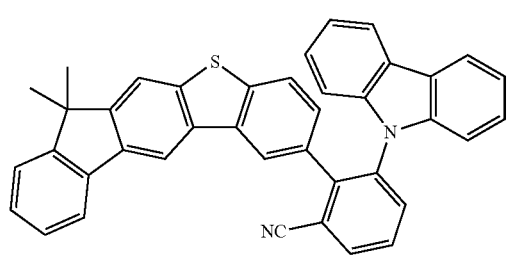
224
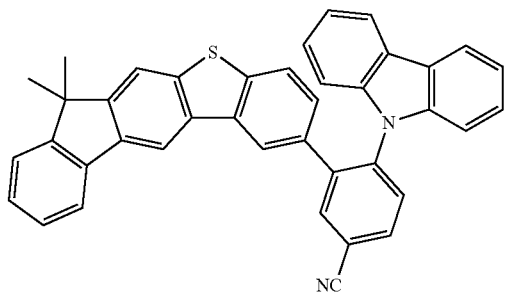
225
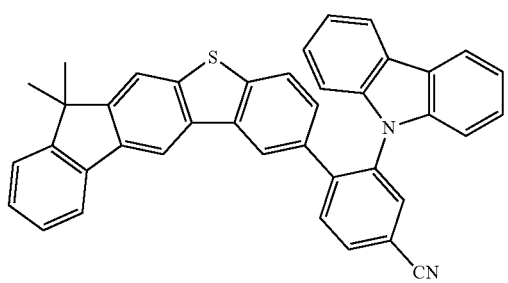
226
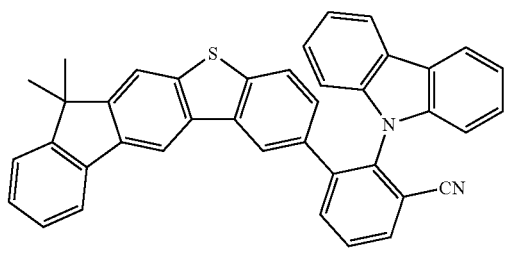
227
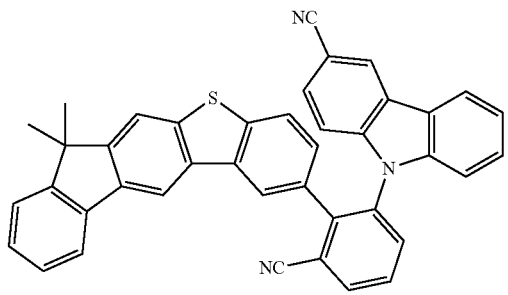
228
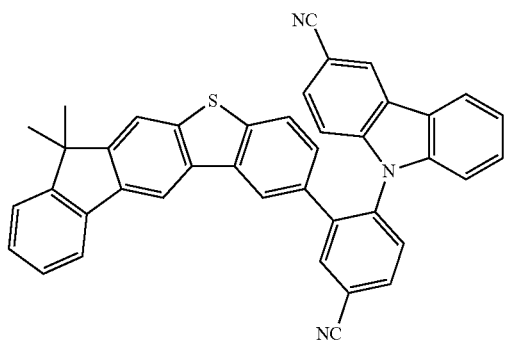

521
-continued
229
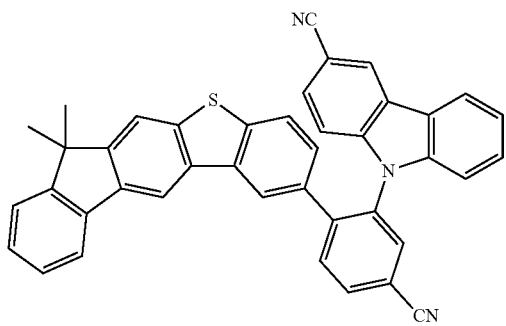
230
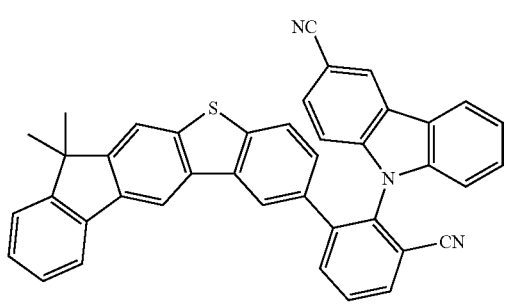
231
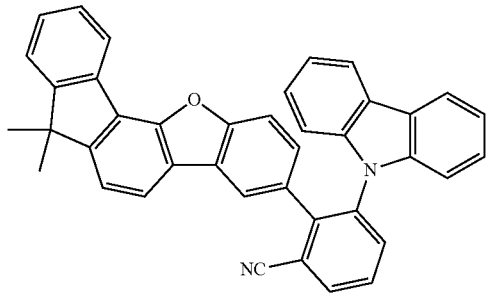
232
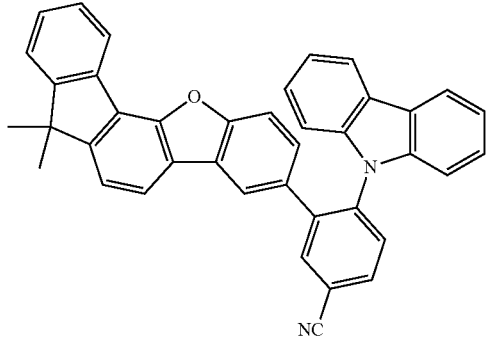
233
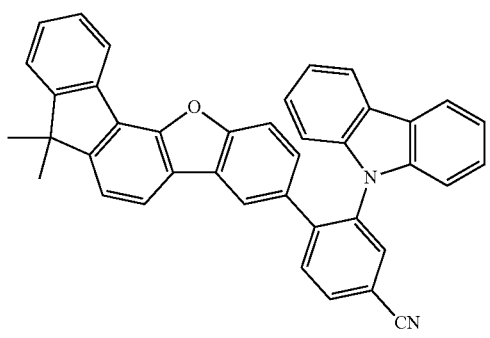
522
-continued
234
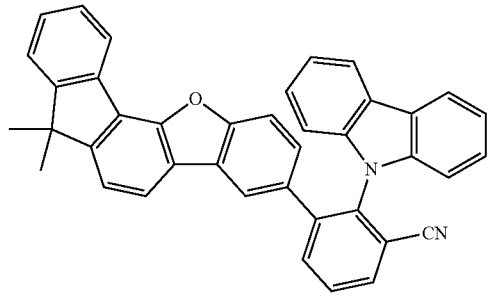
235
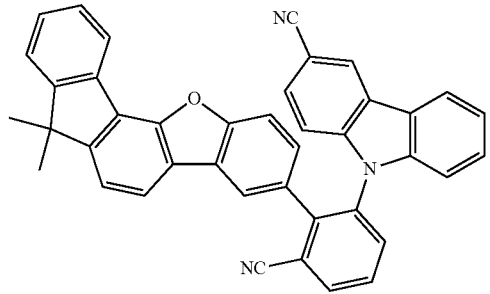
236
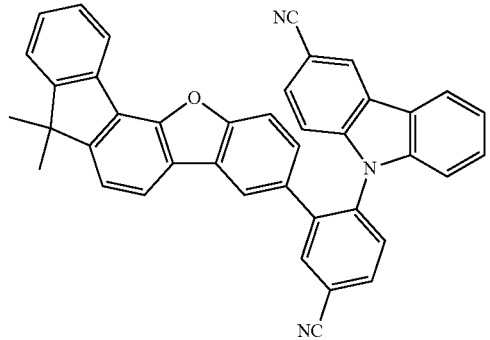
237
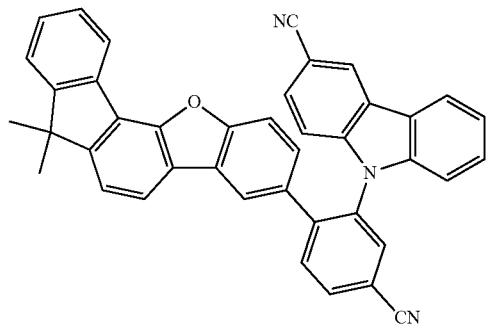

523
-continued
238
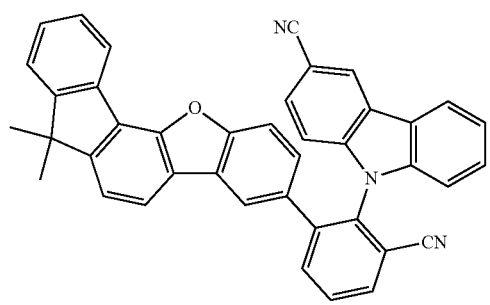
239
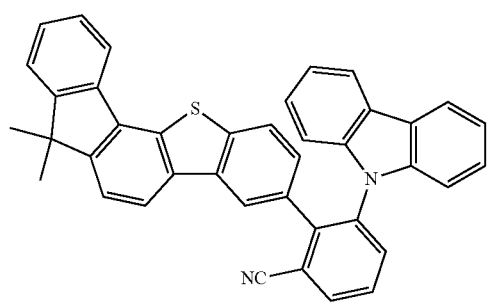
240
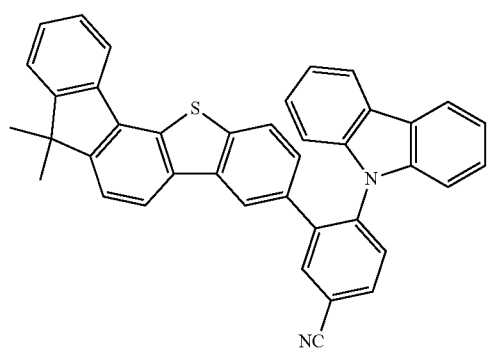
241
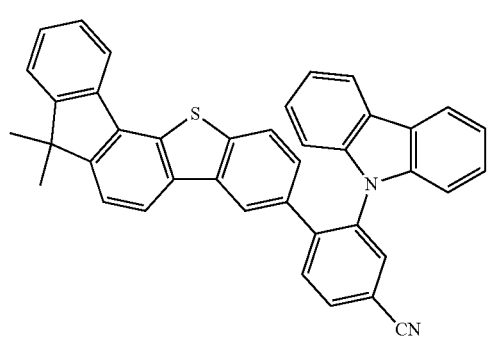
242
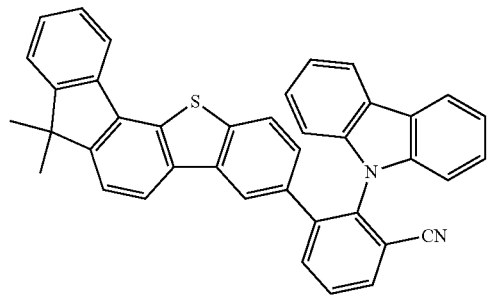
524
-continued
243
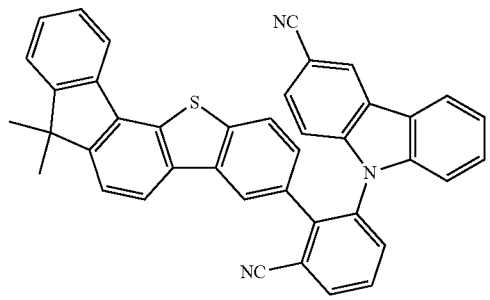
244
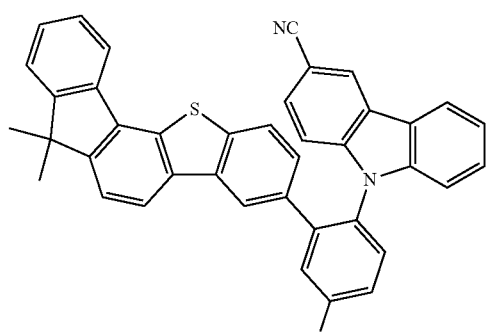
245
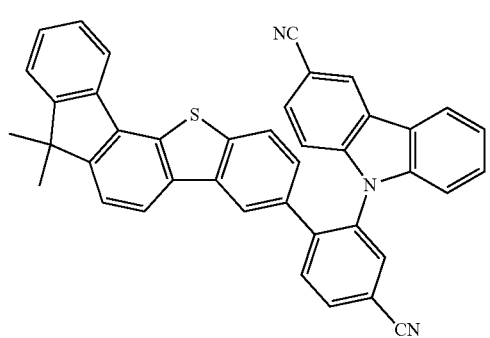
246
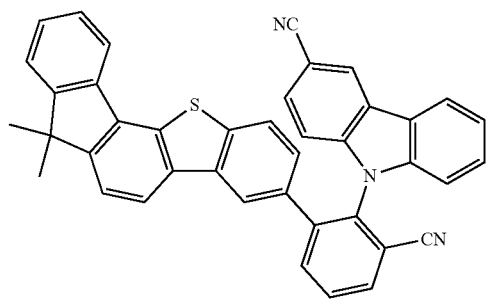
247
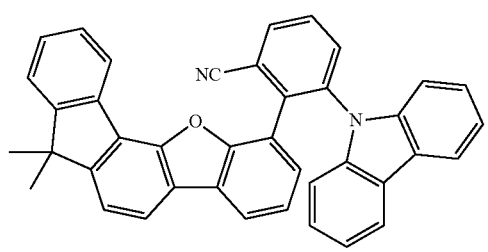

-continued
| 525 | 526 |
|---|---|
| 248 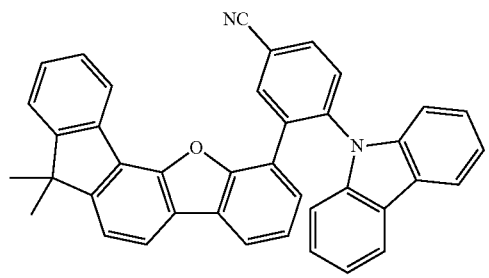 | 253 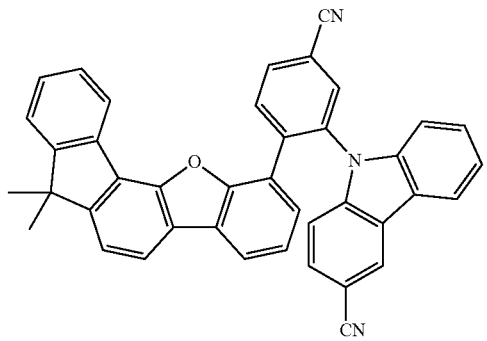 |
| 249 | 254 |
| 250 | 255 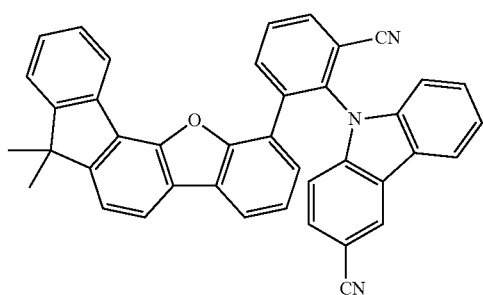 |
| 251 | 256 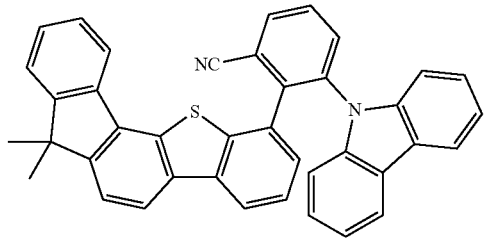 |
| 252 | 257 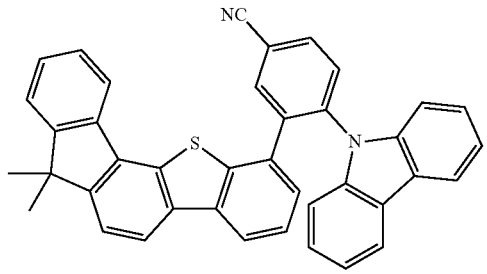 |
|  | 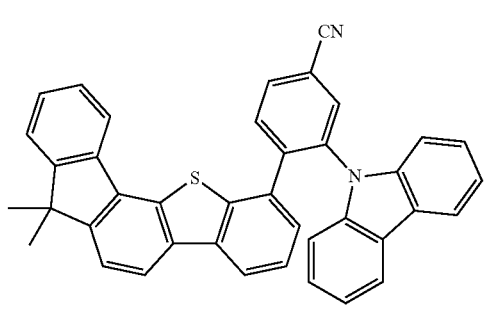 |

527
-continued
258
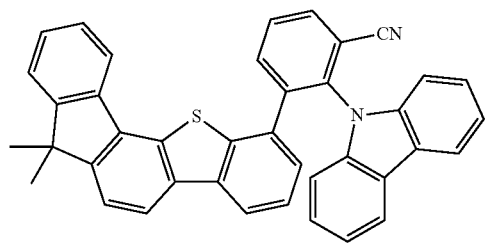
259
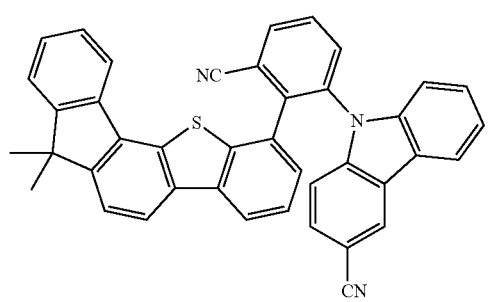
260
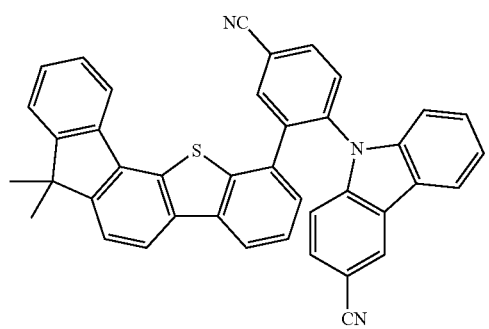
261
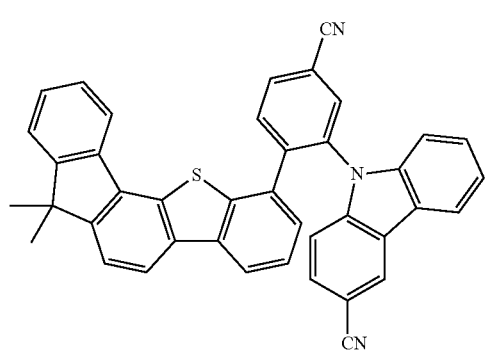
262
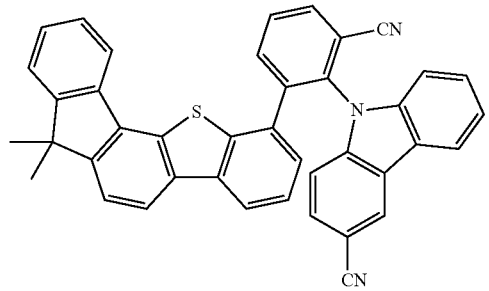
528
-continued
263
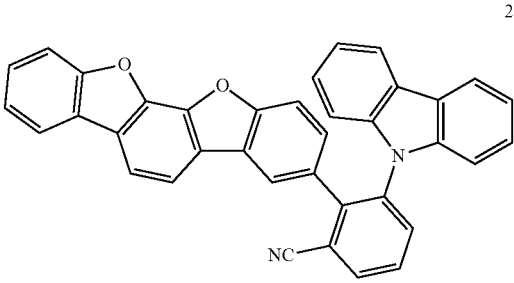
264
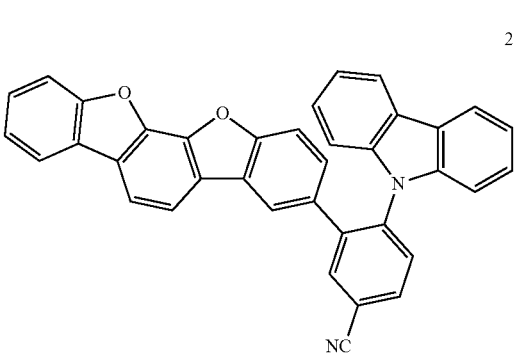
265
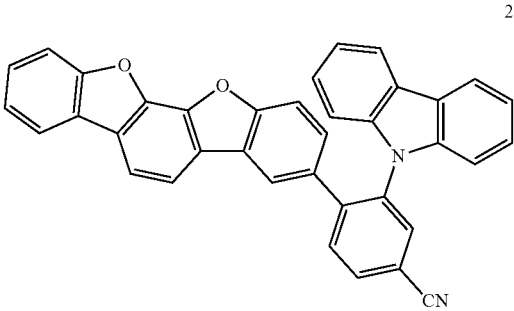
266
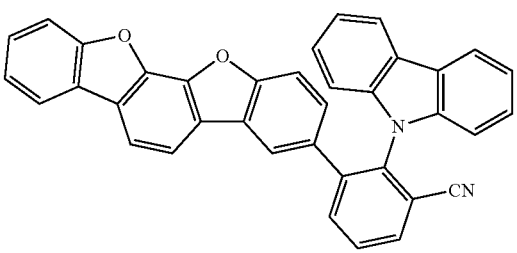
267
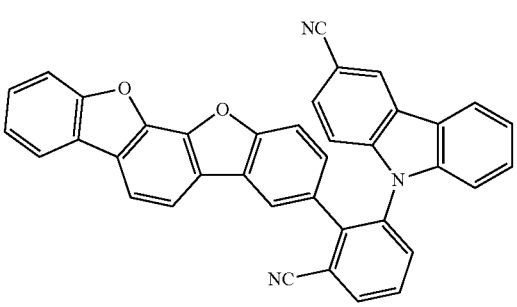

268
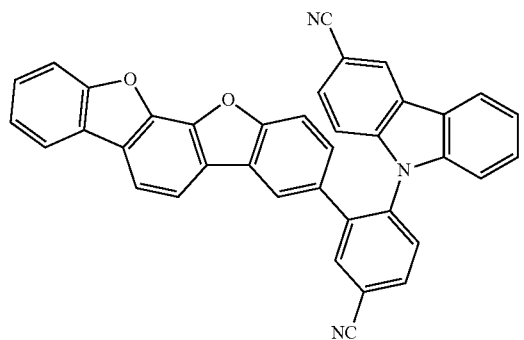
269
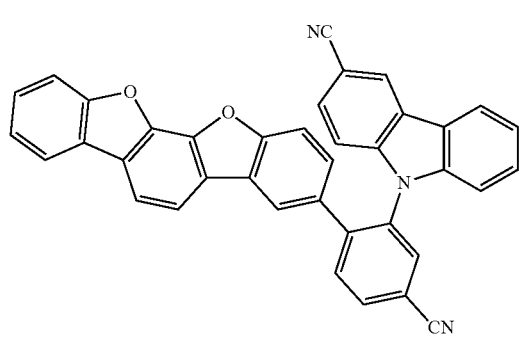
270
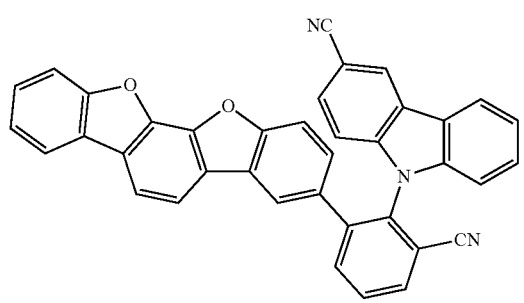
271
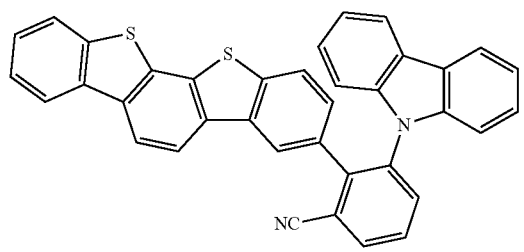
272
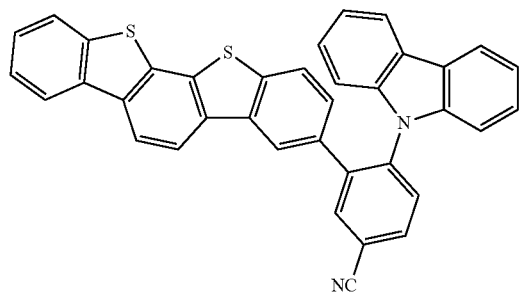
273
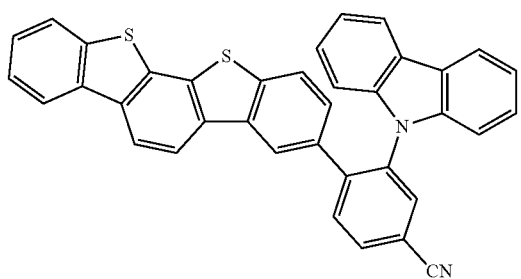
274
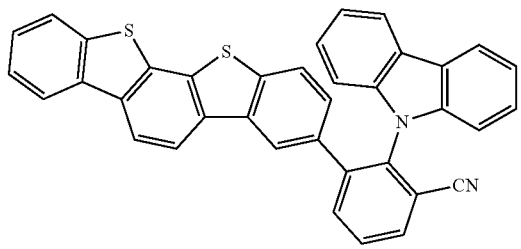
275
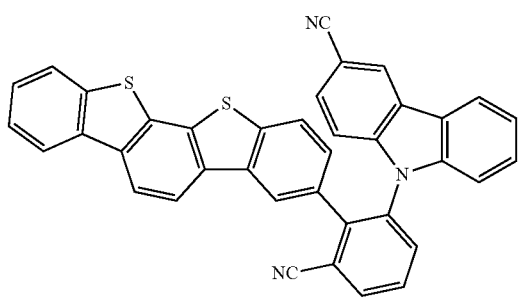
276
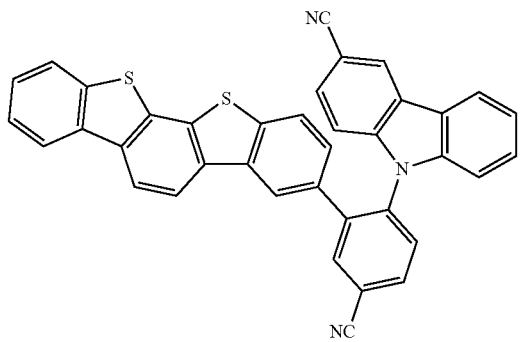
277
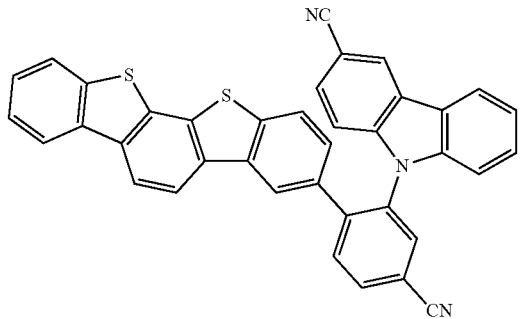

278
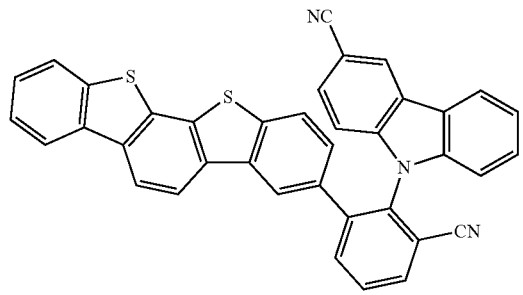
283
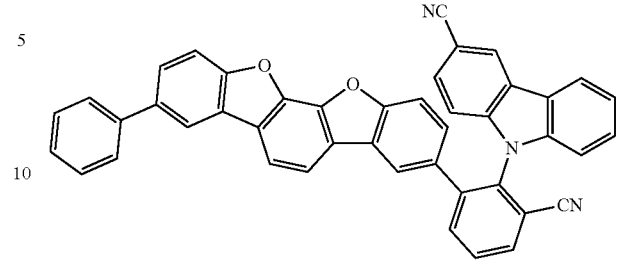
279
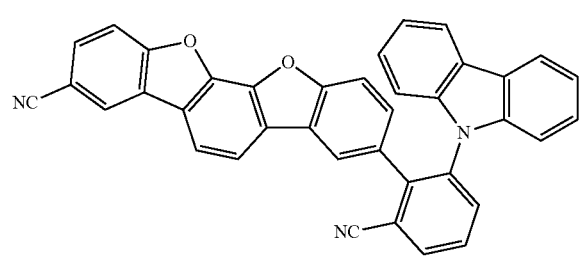
284
284
285
280
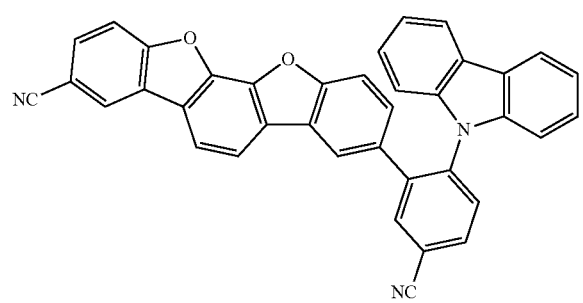
285
281
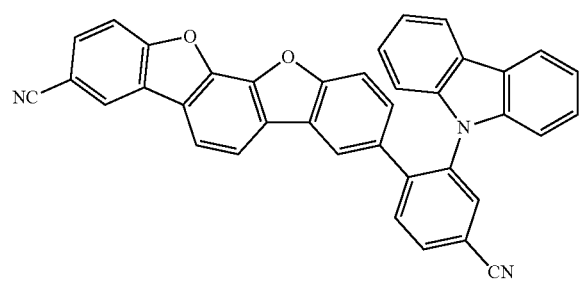
286
282
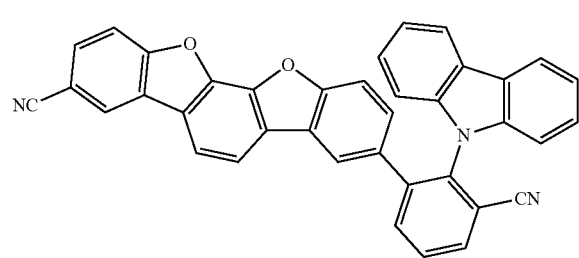
287
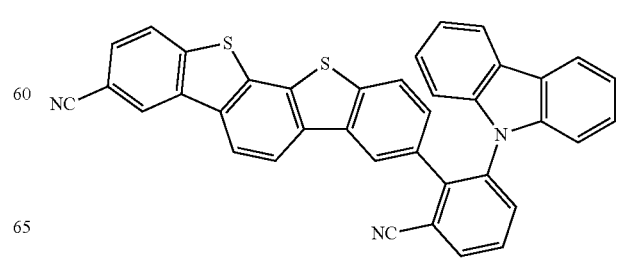

-continued
288
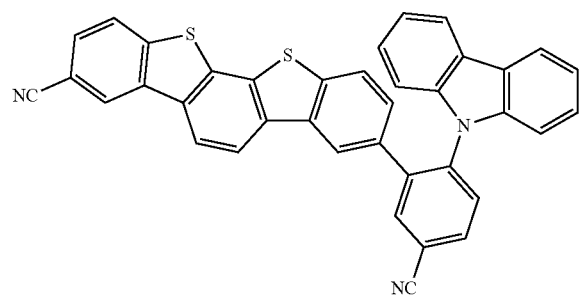
289
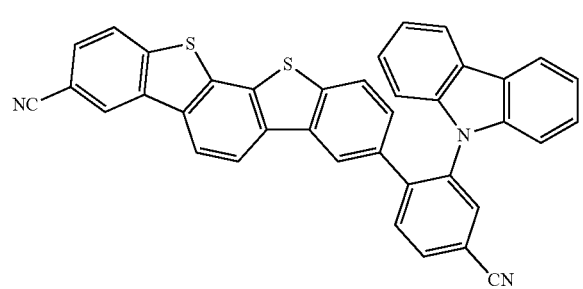
290
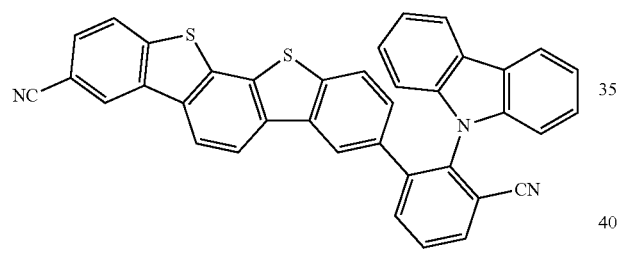
291
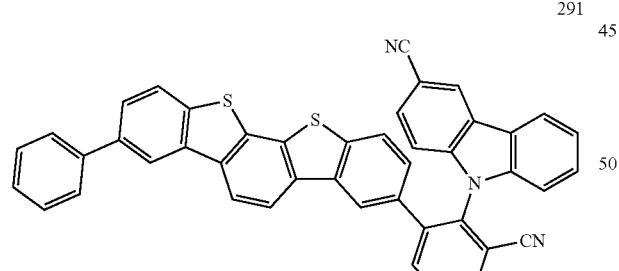
292
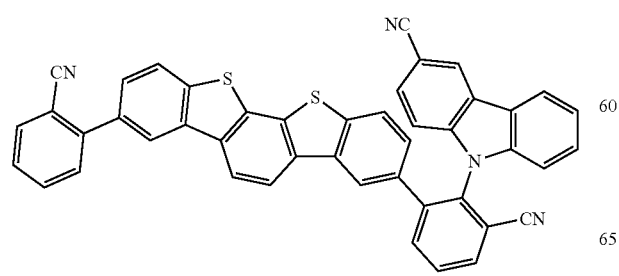
-continued
293
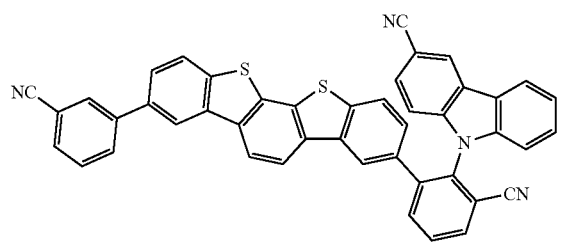
294
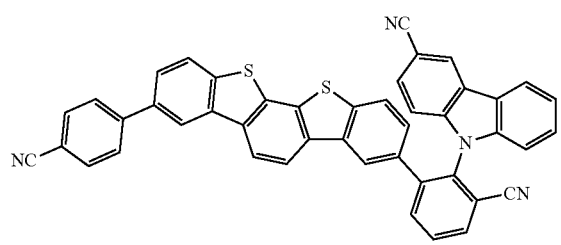
295
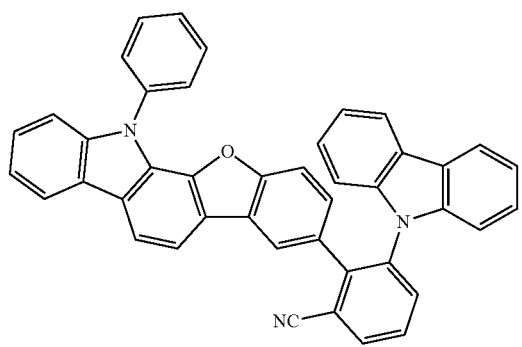
296
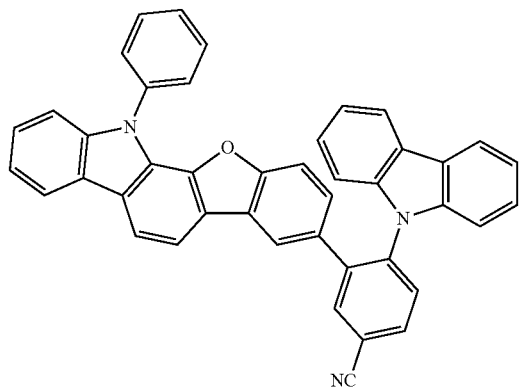

297
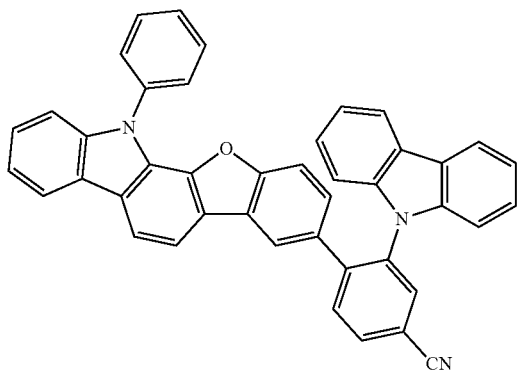
298
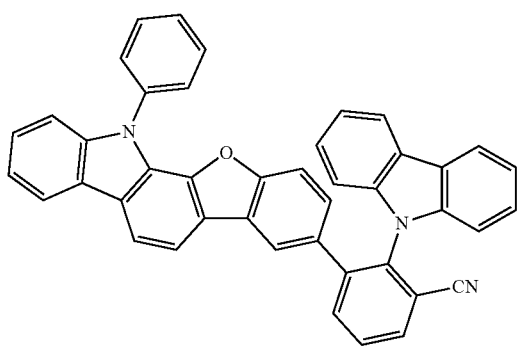
299
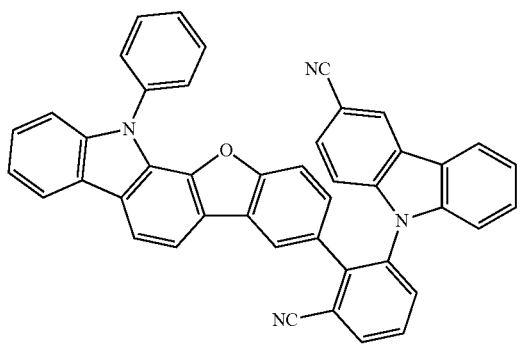
300
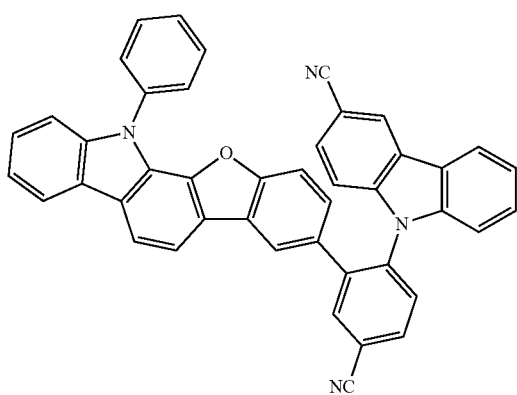
301
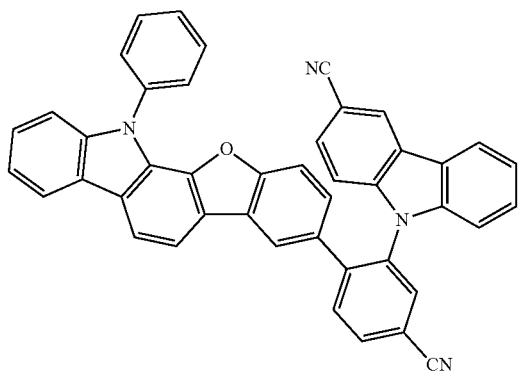
302
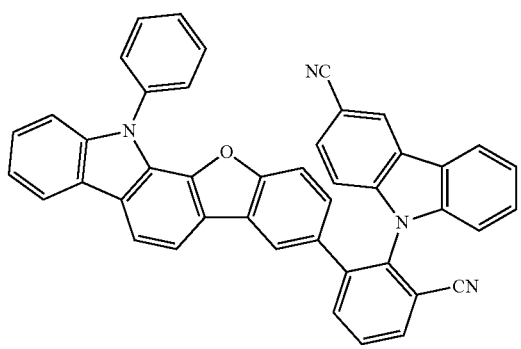
303
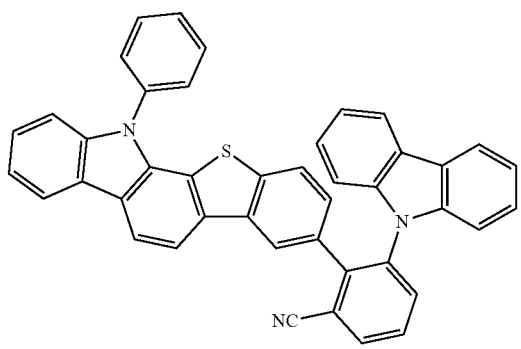
304
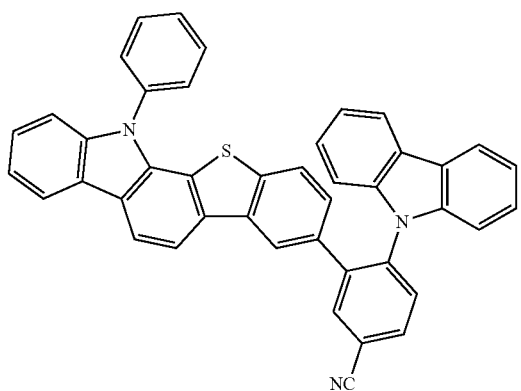

537
-continued
305
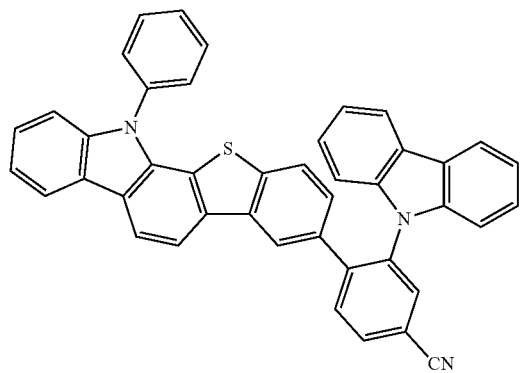
306
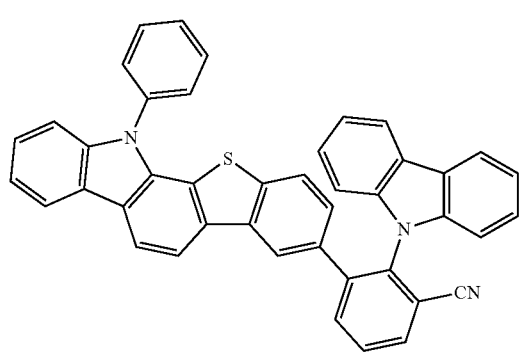
307
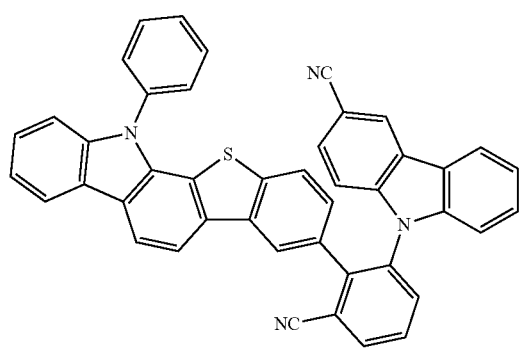
308
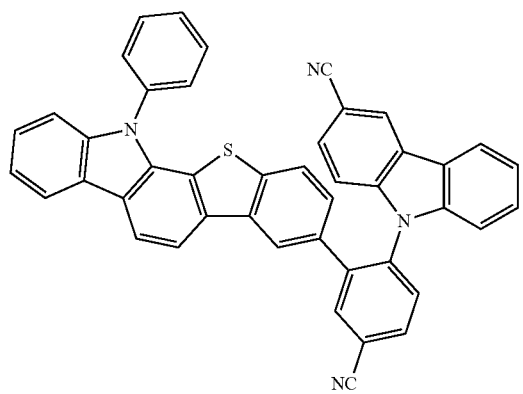
538
-continued
309
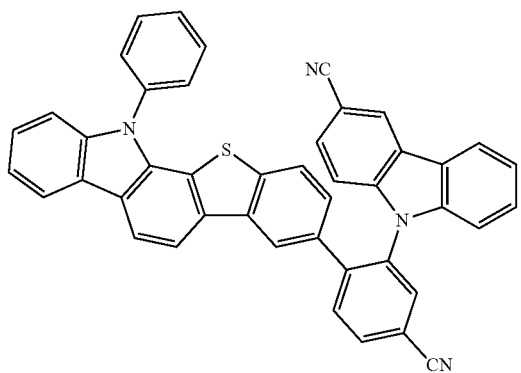
310
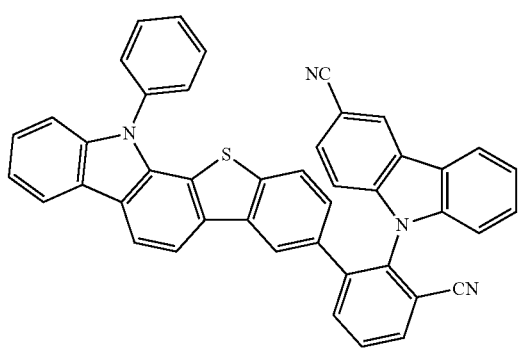
311
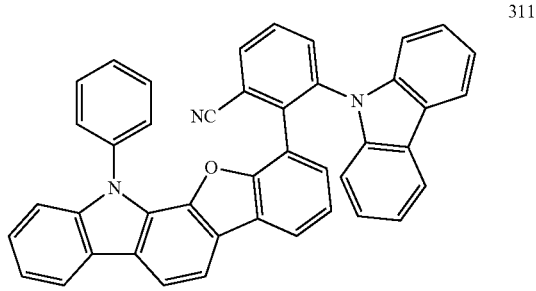
312
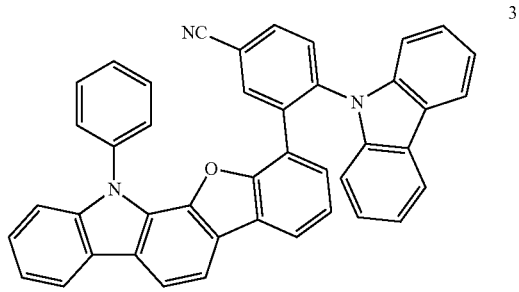
313
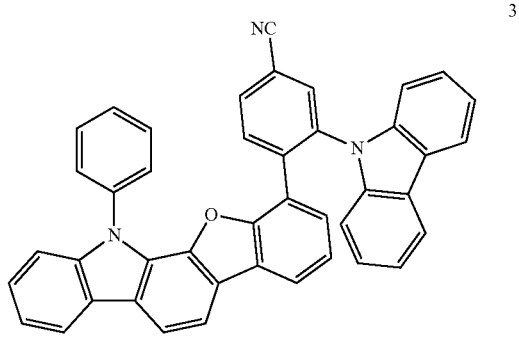

314
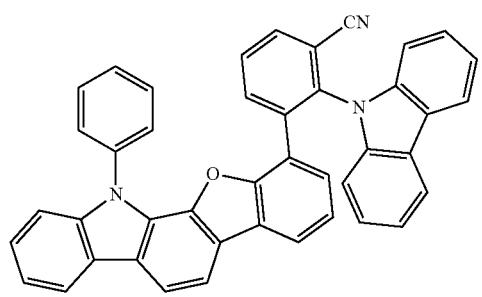
315
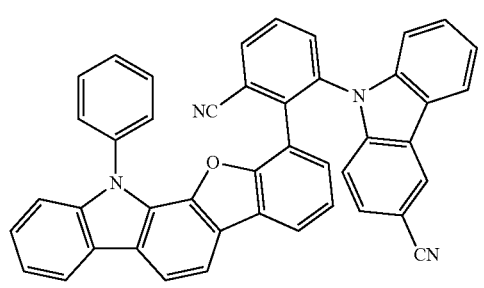
316
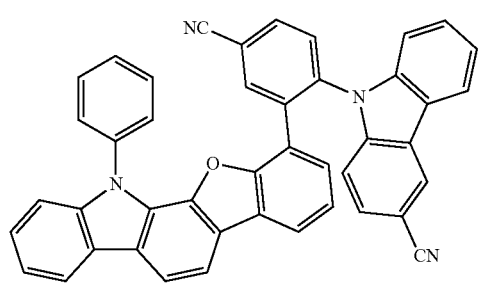
317
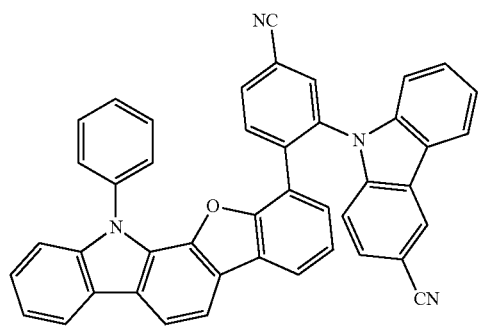
318
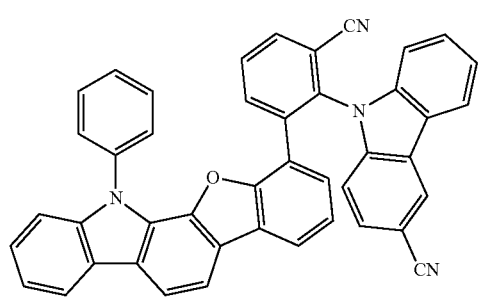
319
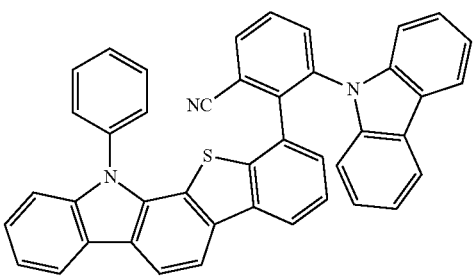
320
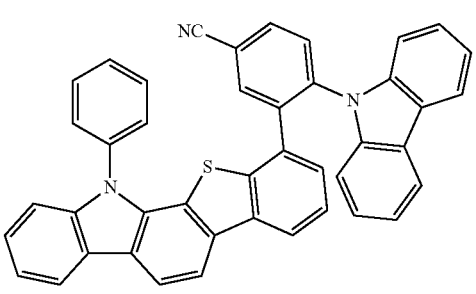
321
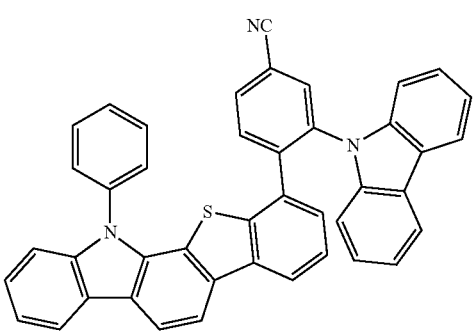
322
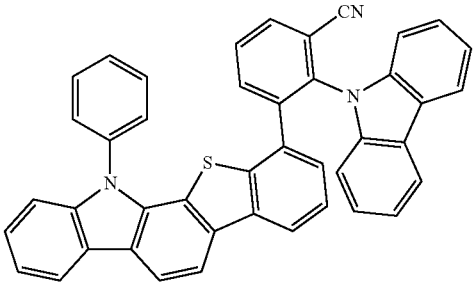
323
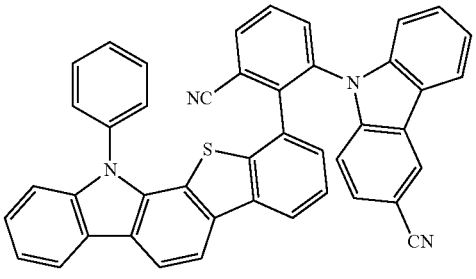

324
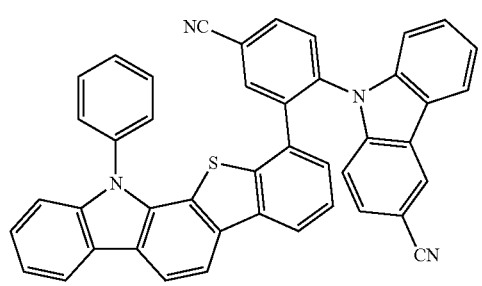
325
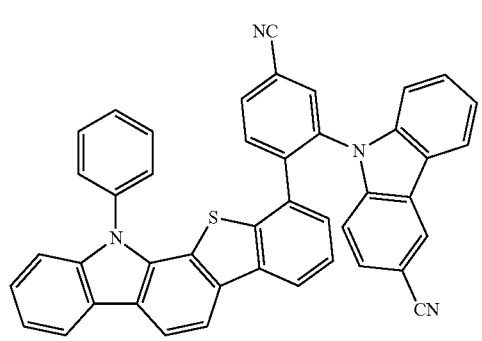
326
327
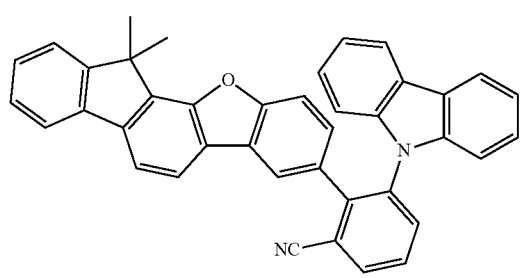
328
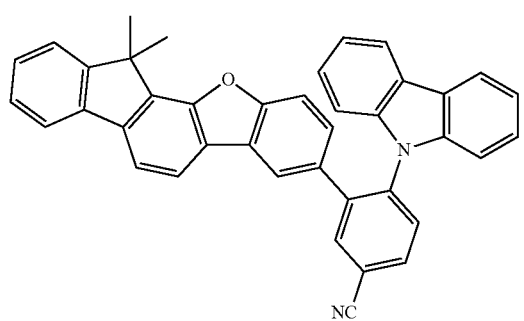
329
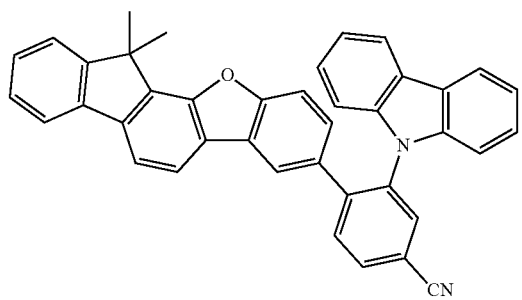
330
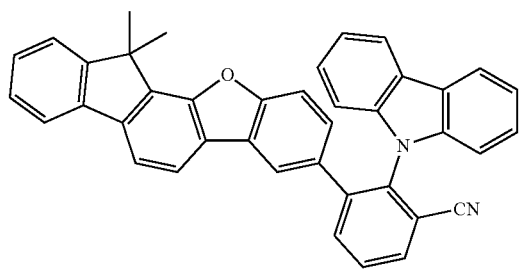
331
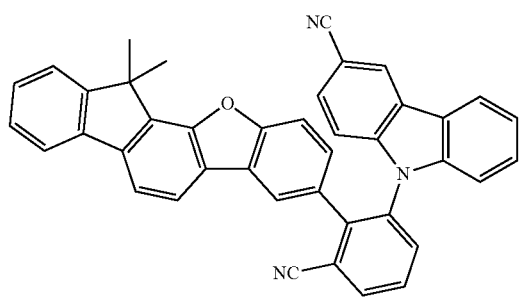
332
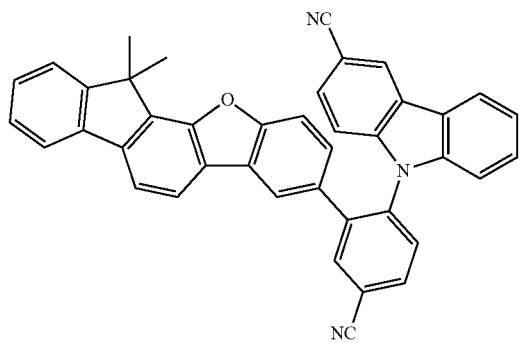
333
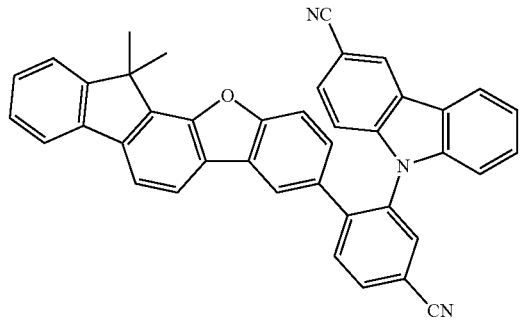

334
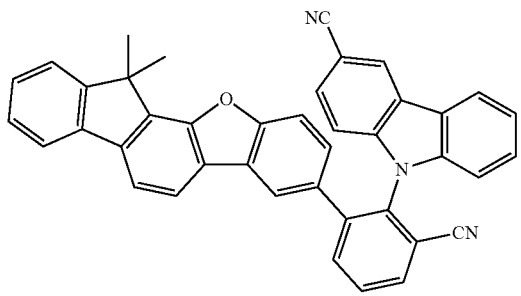
335
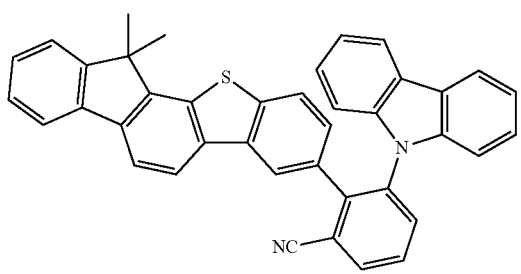
336
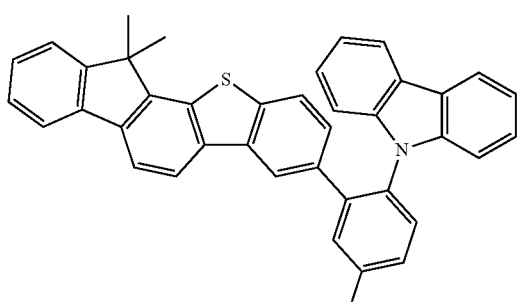
337
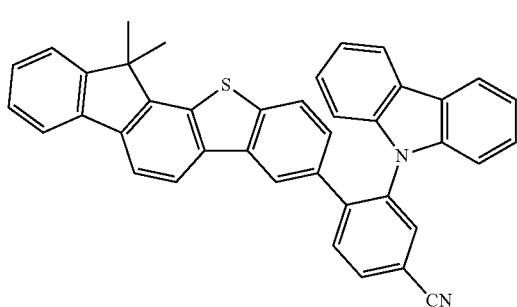
338
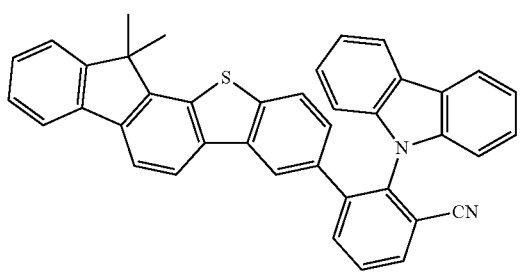
339
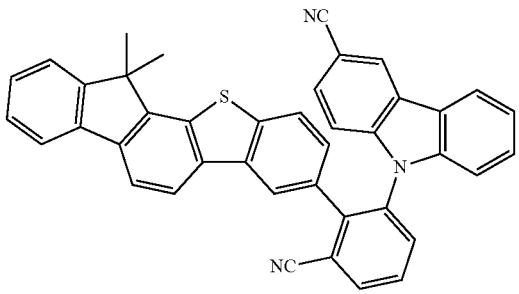
340
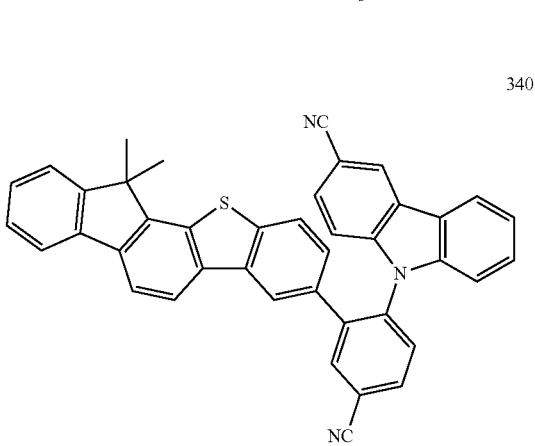
341
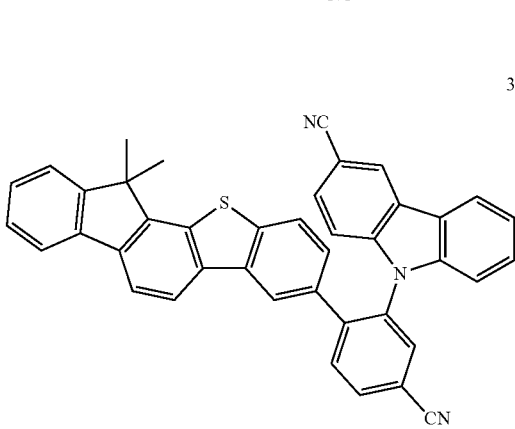
342
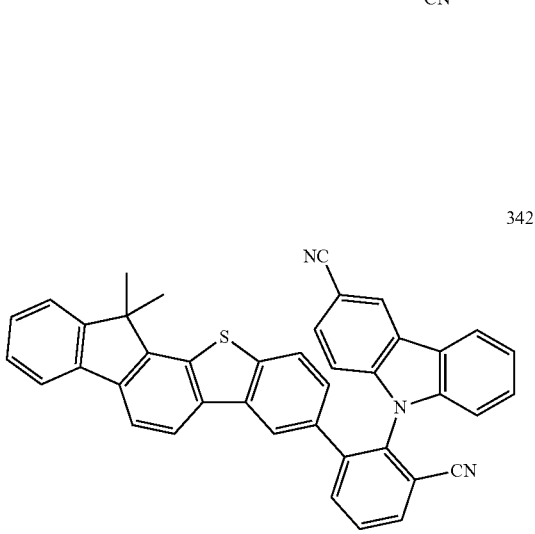

343
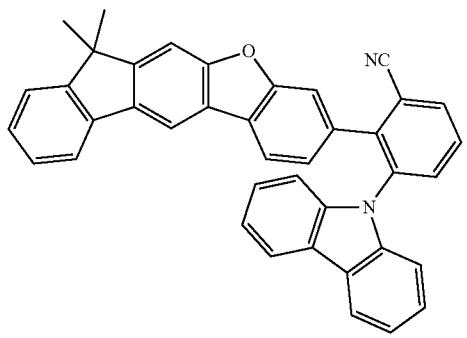
347
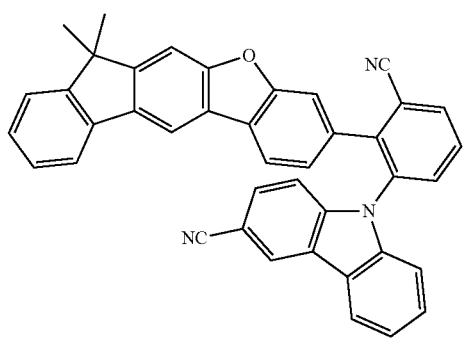
344
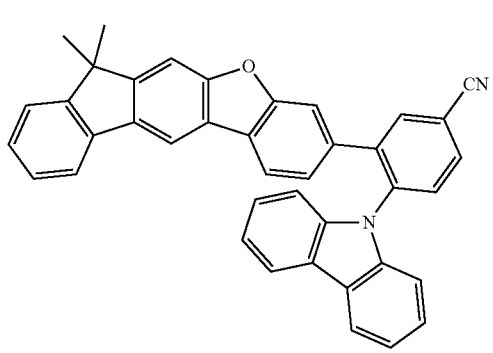
348
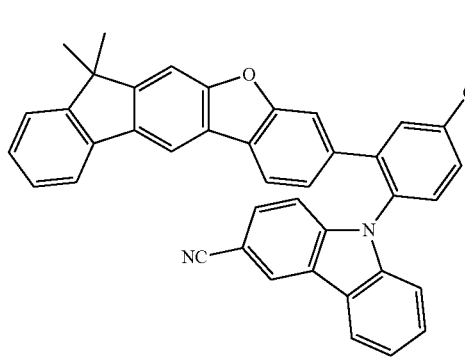
345
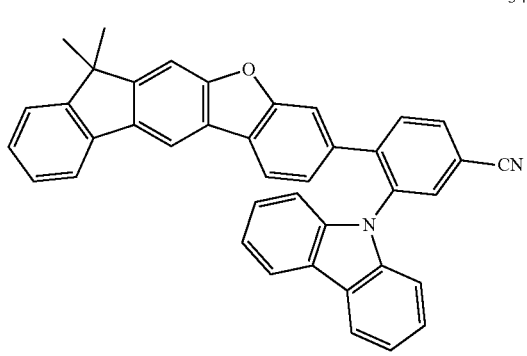
349
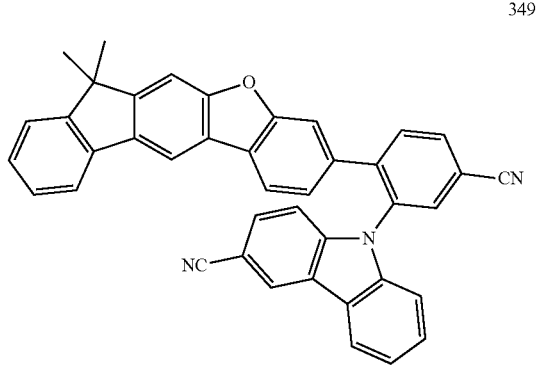
346
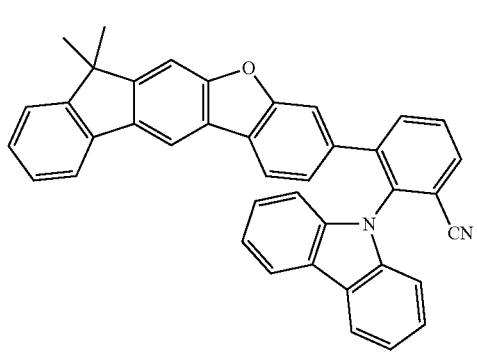
350
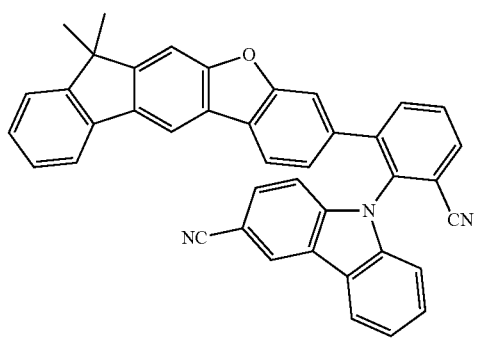

547
-continued
351
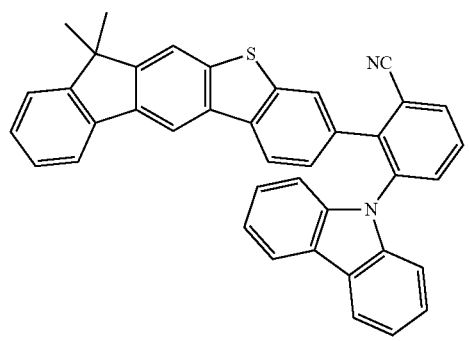
352
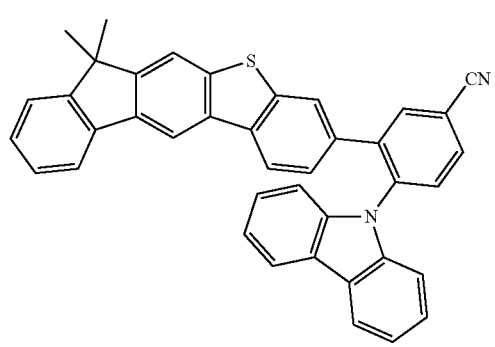
353
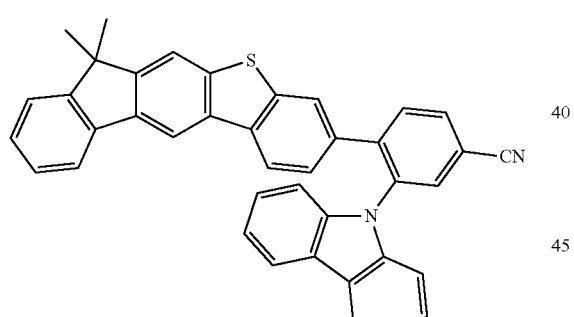
354
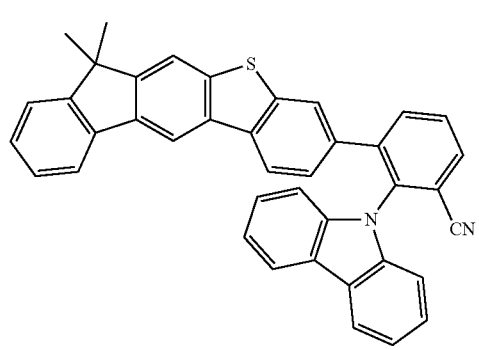
548
-continued
355
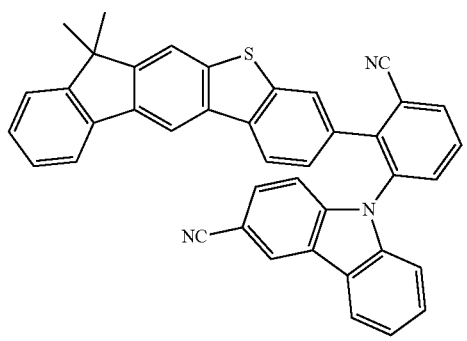
356
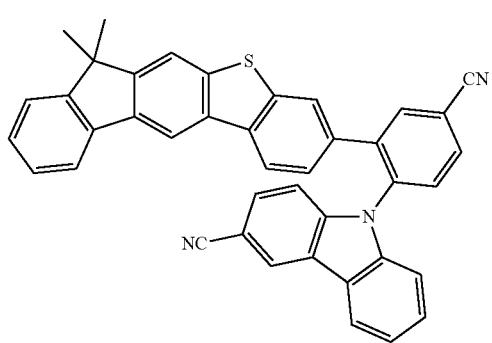
357
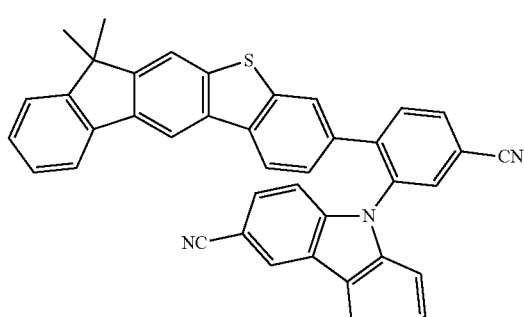
358
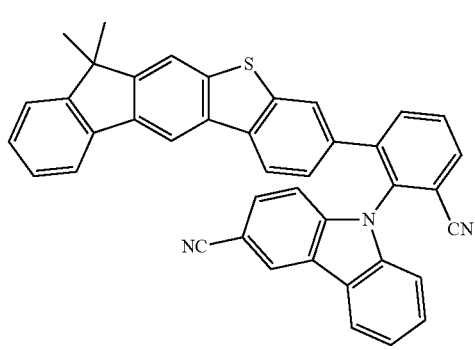

359
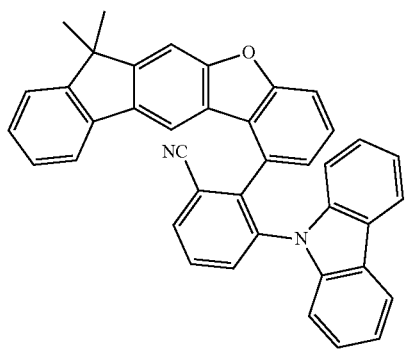
360
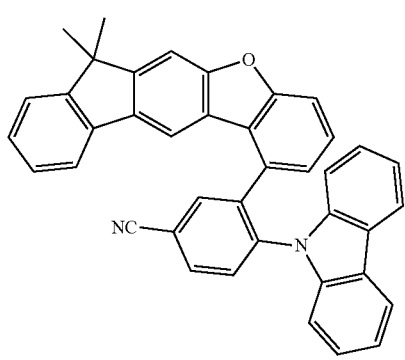
361
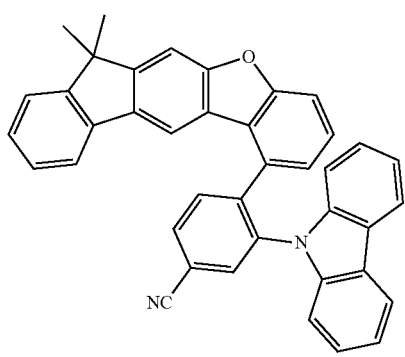
362
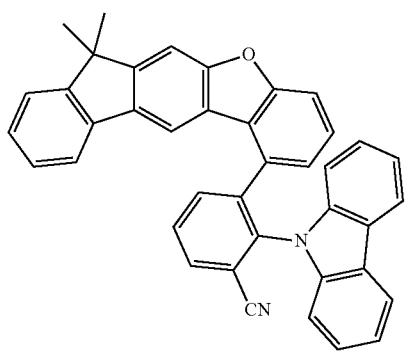
363
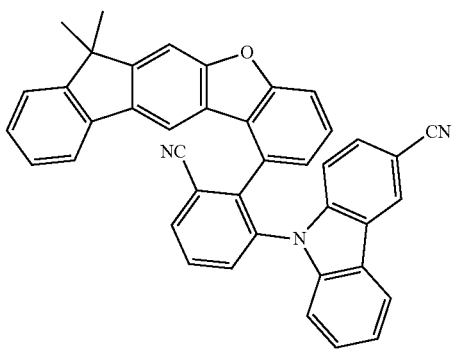
364
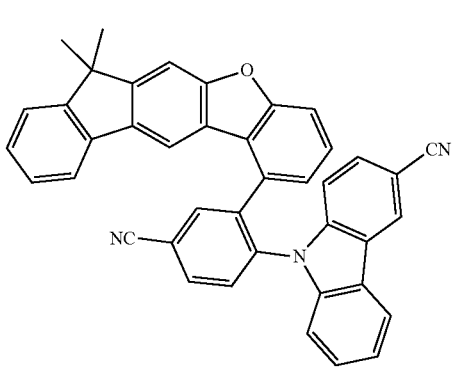
365
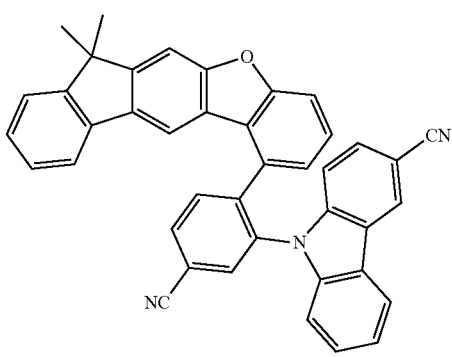
366
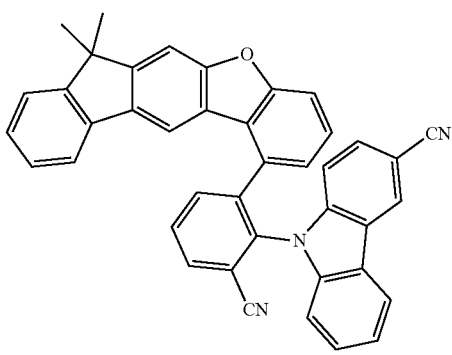

| 551 -continued | 552 -continued |
|---|---|
| 367 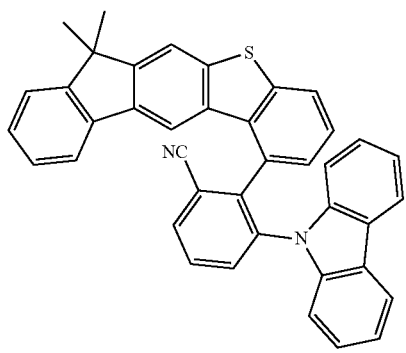 | 371 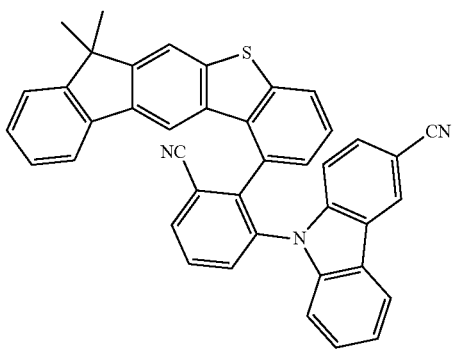 |
| 368 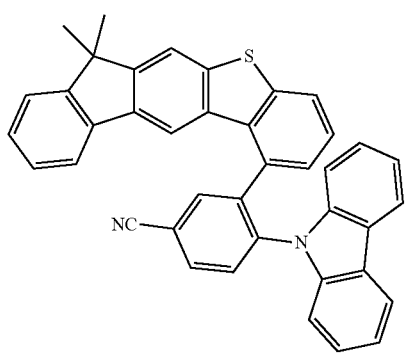 | 372 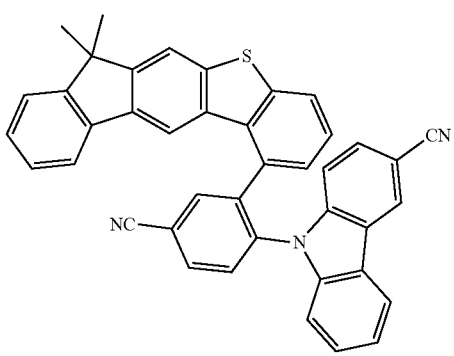 |
| 369 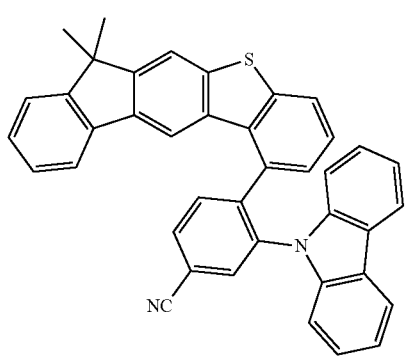 | 373 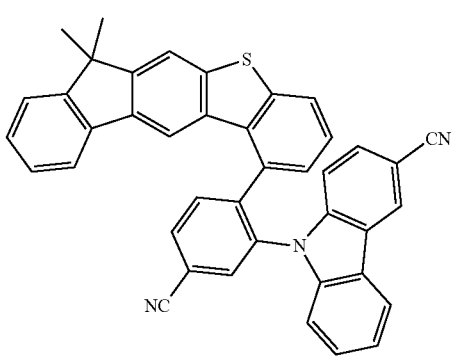 |
| 370 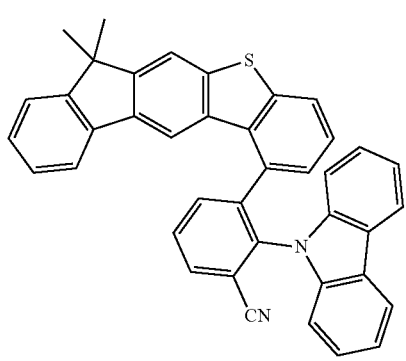 | 374 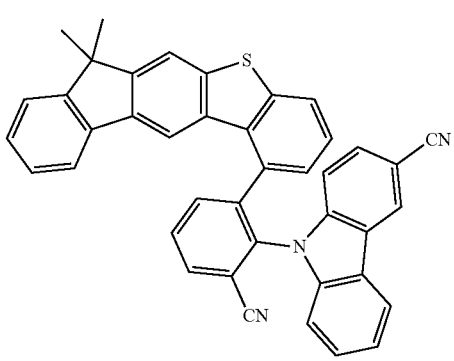 |

375 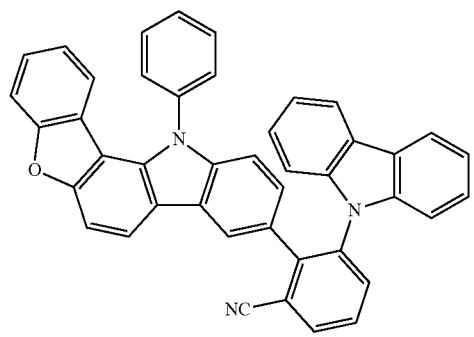
376 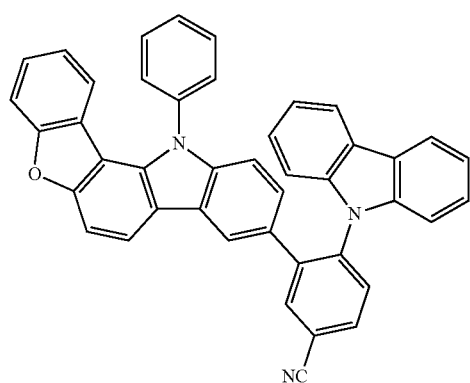
377 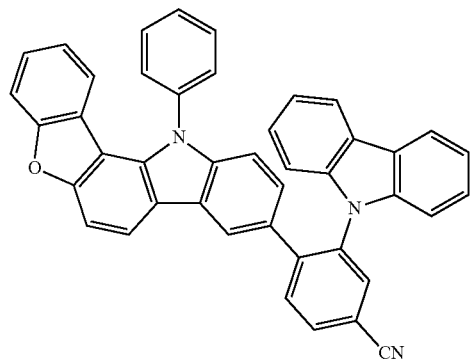
378 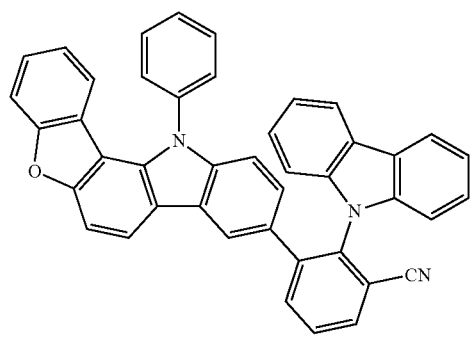
379 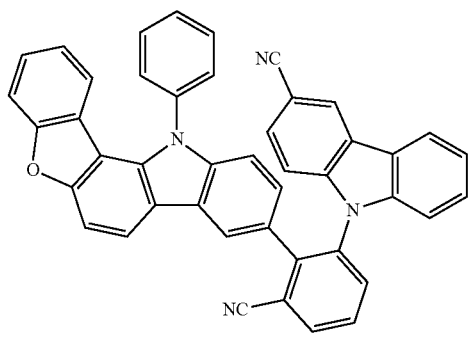
380 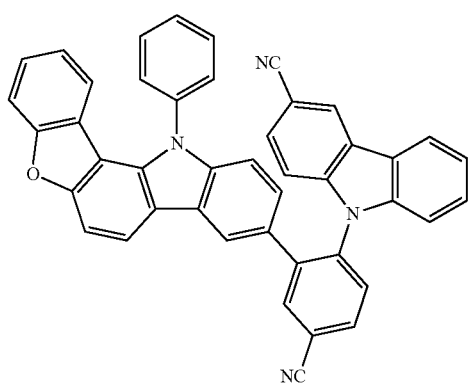
381 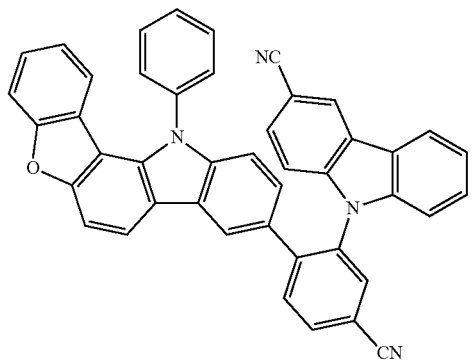
382 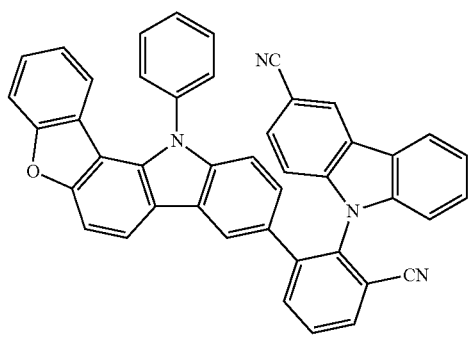

555
-continued
383
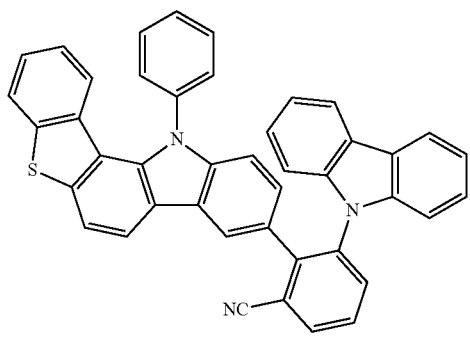
384
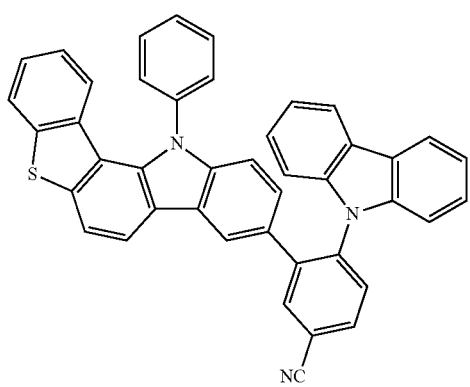
385
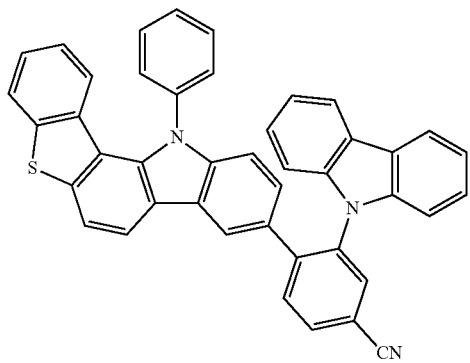
386
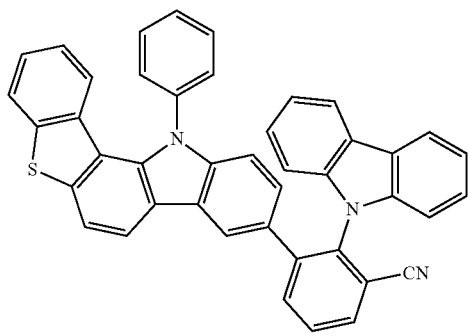
556
-continued
387
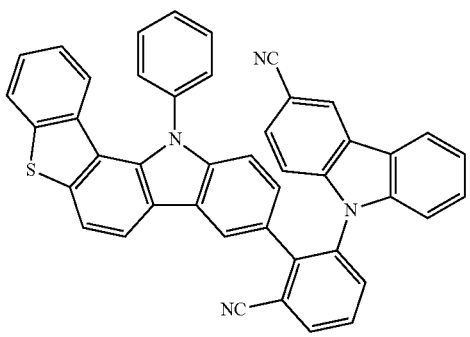
388
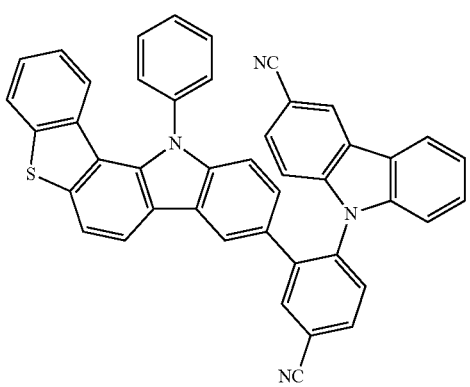
389
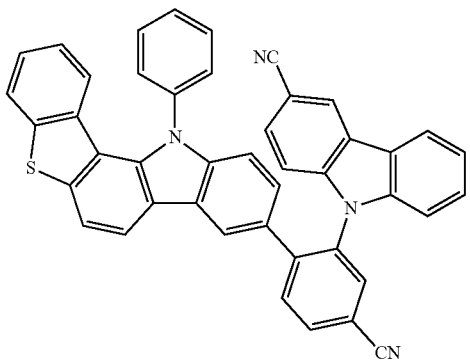
390
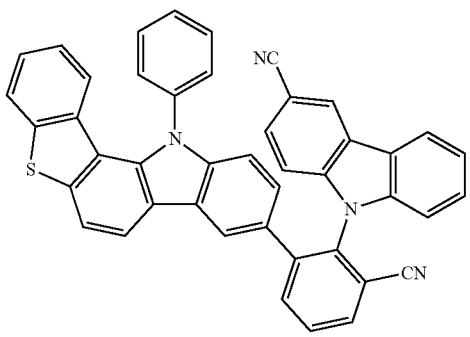

-continued
391
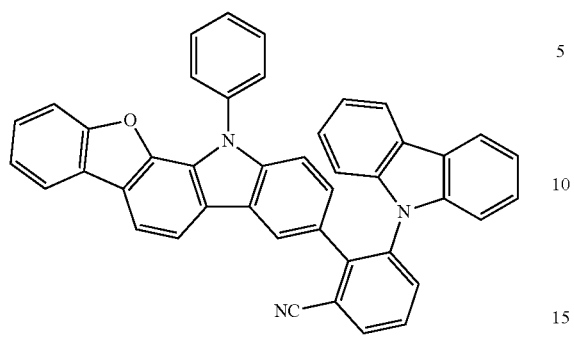
392
393
394
-continued
395
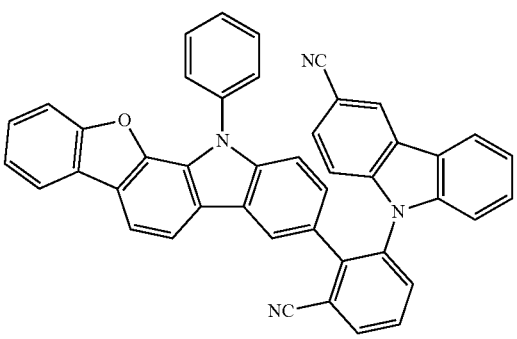
396
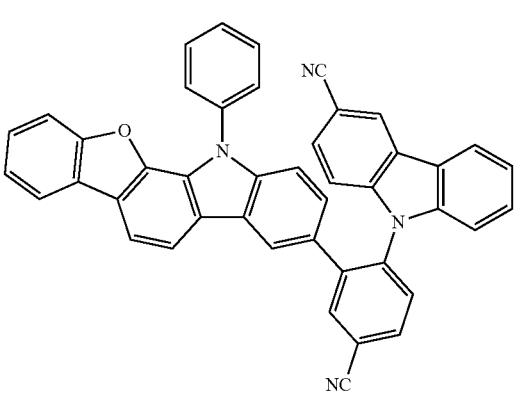
397
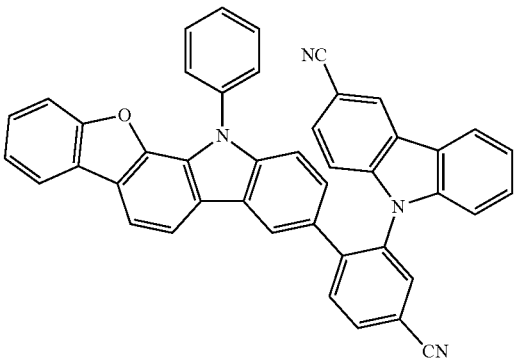
398
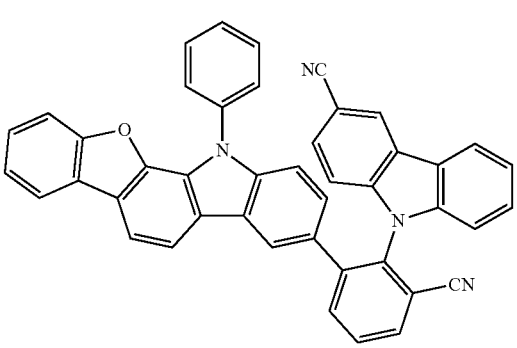

399
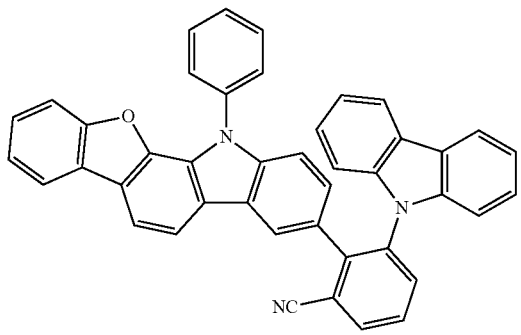
403
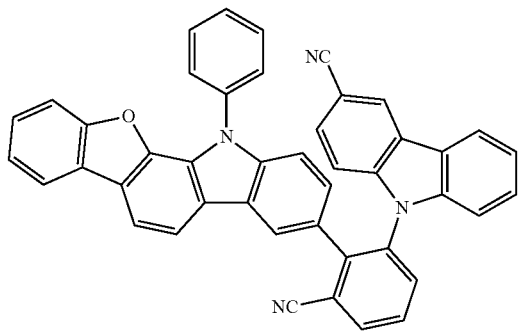
400
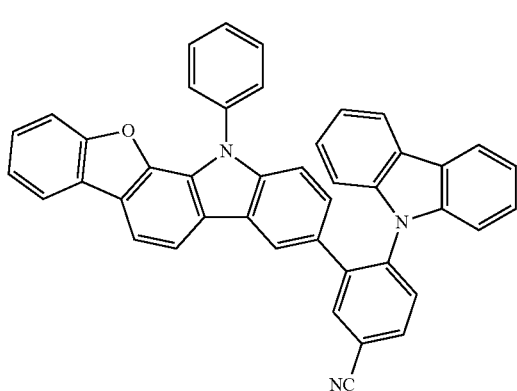
404
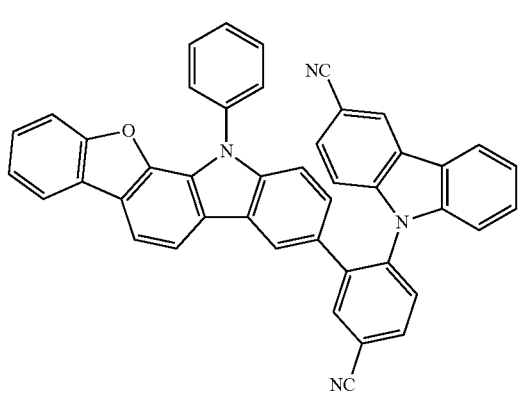
401
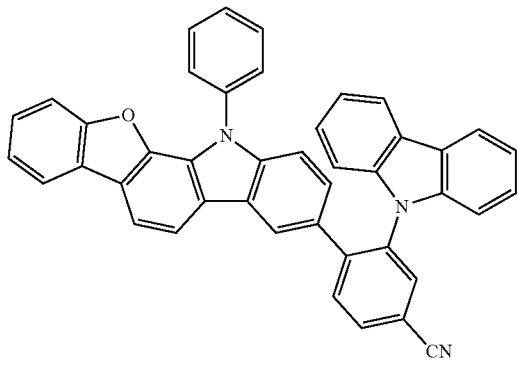
405
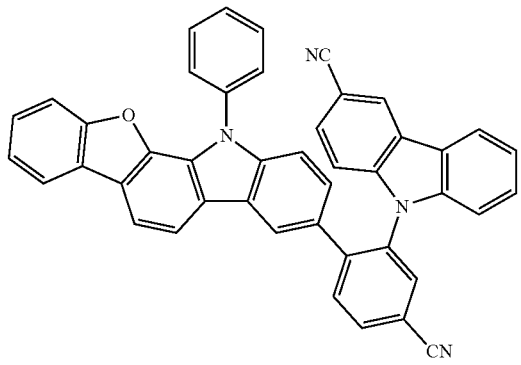
402
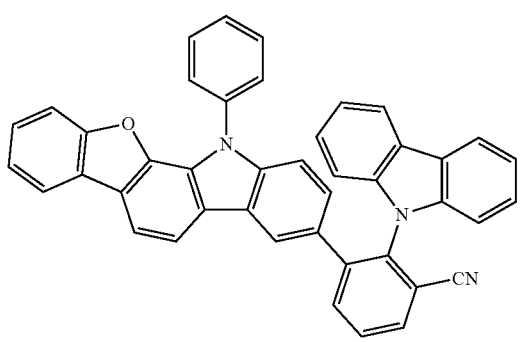
406
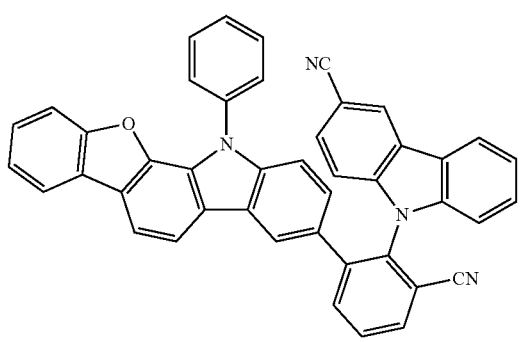

407
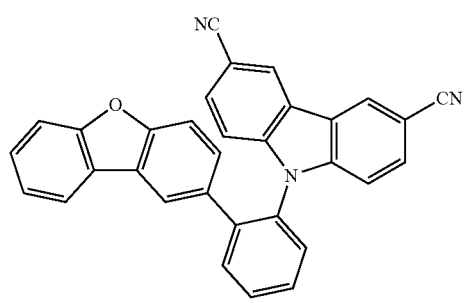
408
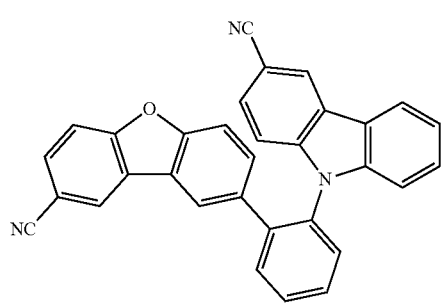
409
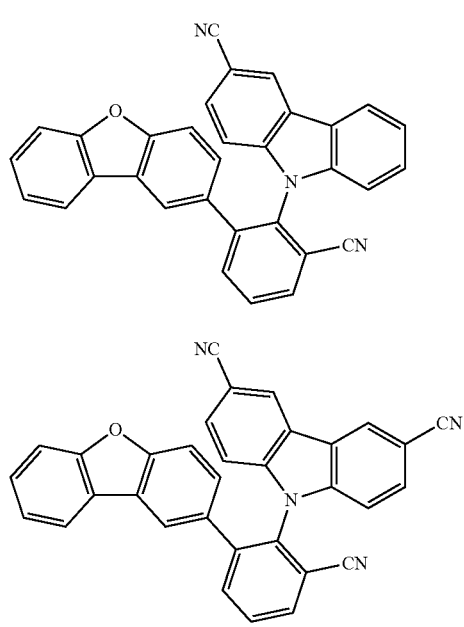
410
411
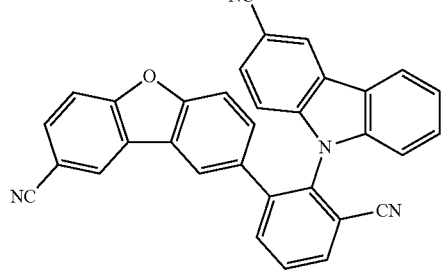
412
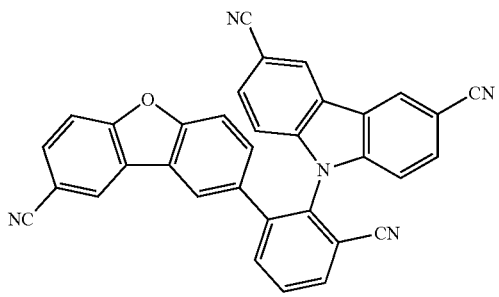
413
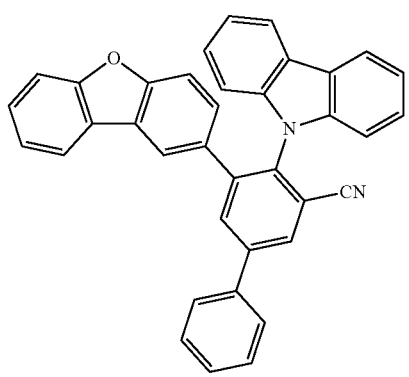
414
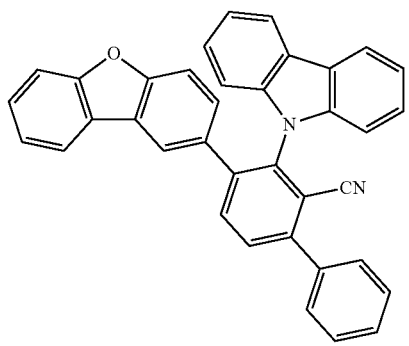
415
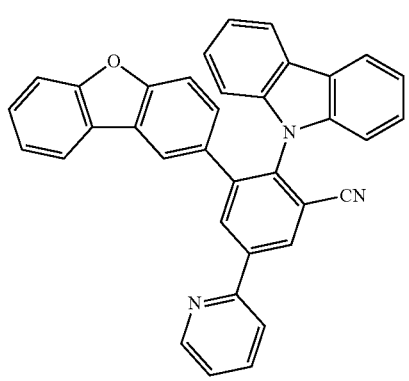

563
-continued
416
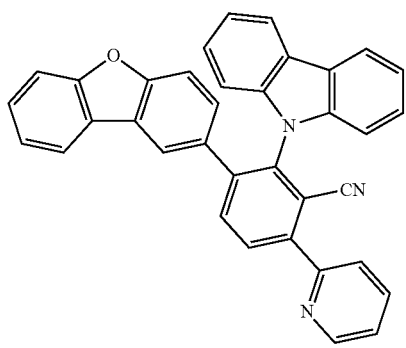
417
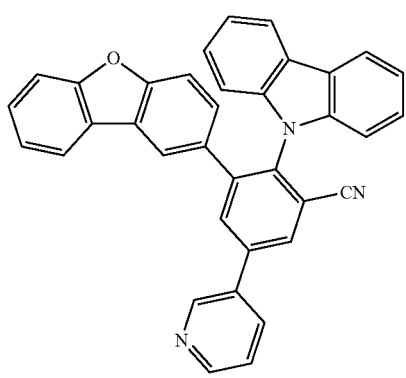
418
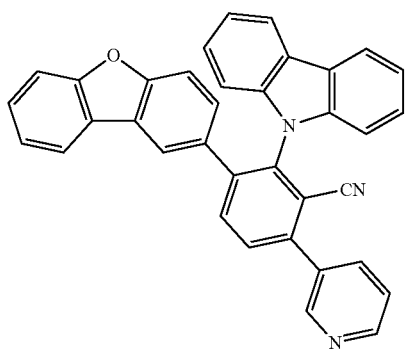
419
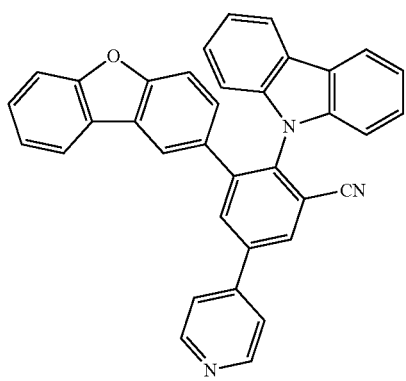
564
-continued
420

421
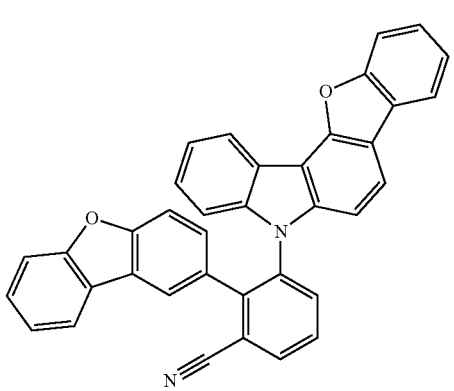
422
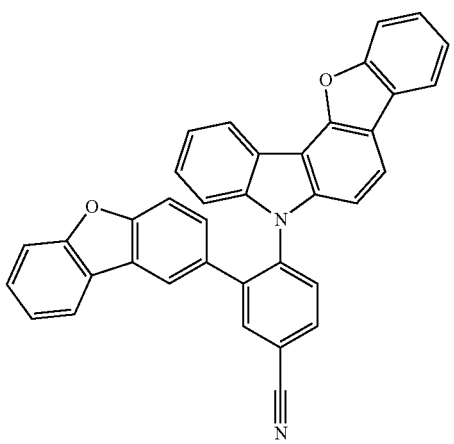
423
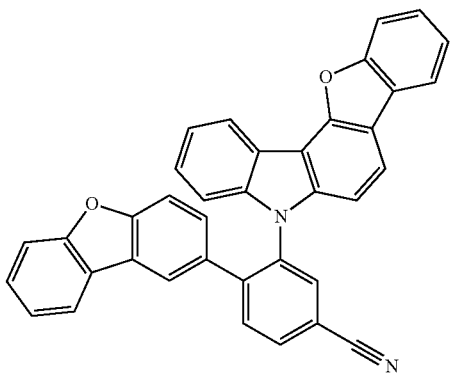

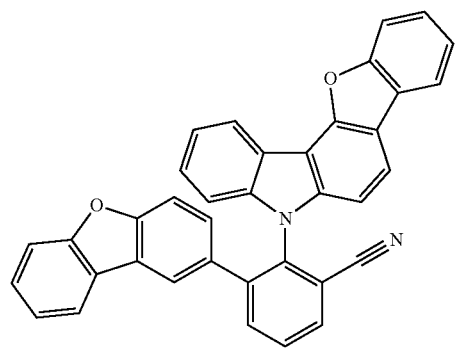
424
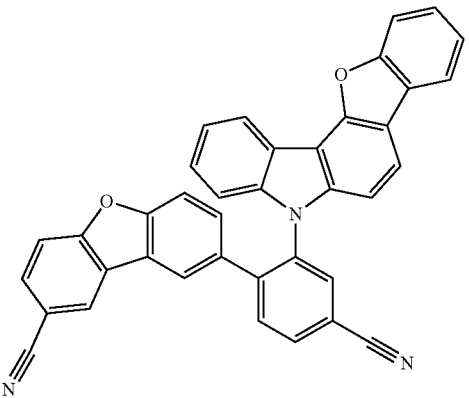
428
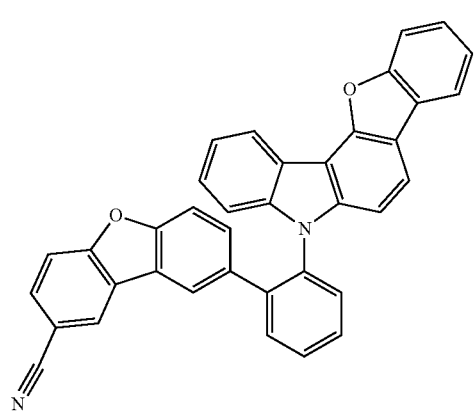
425
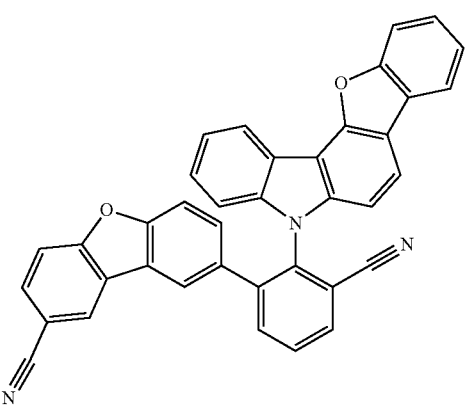
429
426
427
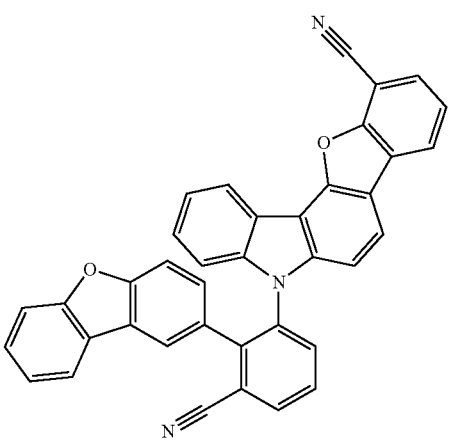
430

431
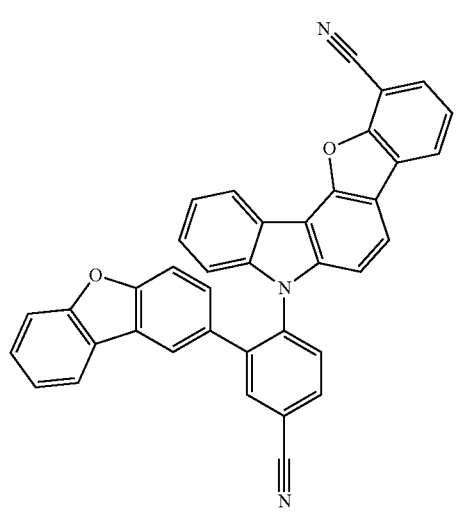
432
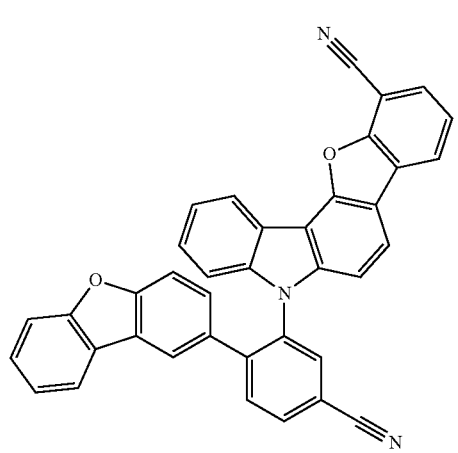
433
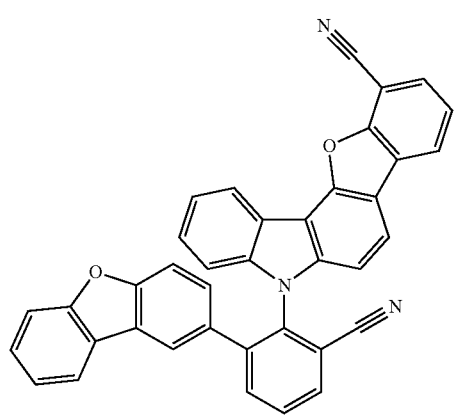
434
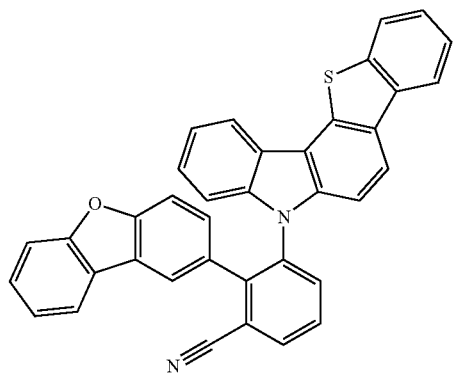
435
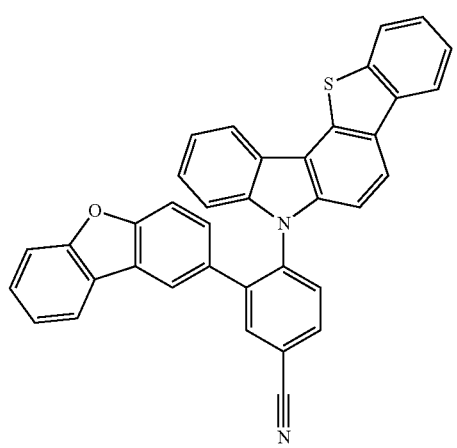
436
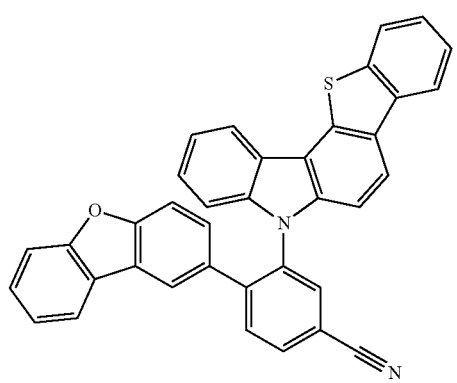
437
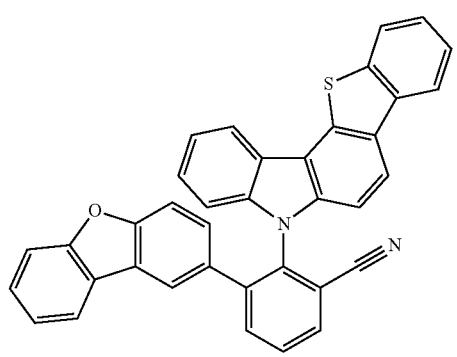

569 -continued
438
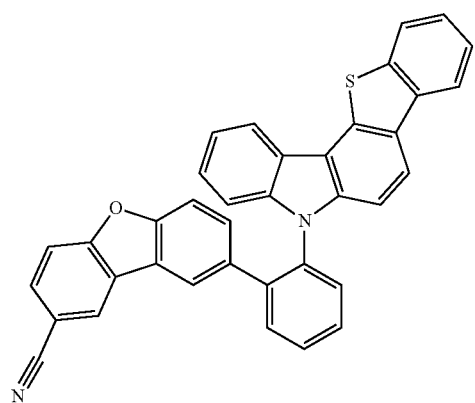
439
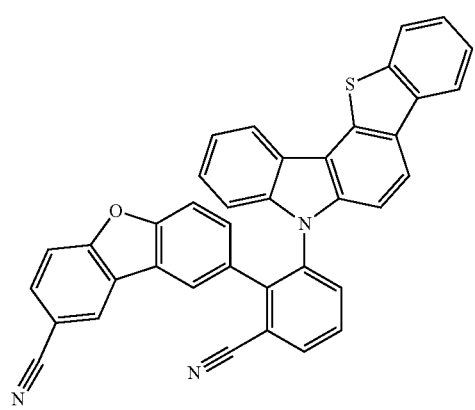
440
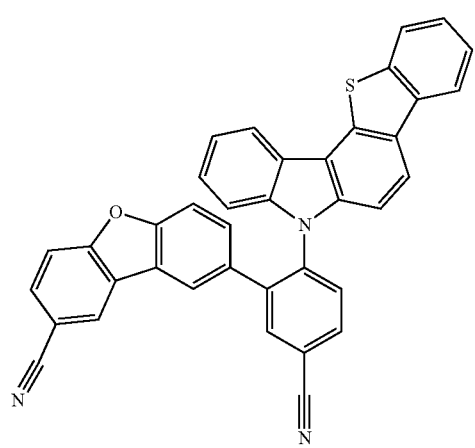
441
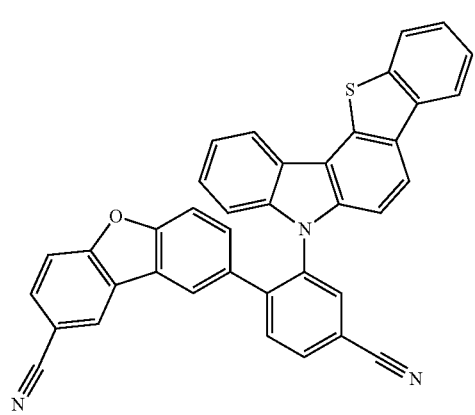
570 -continued
442
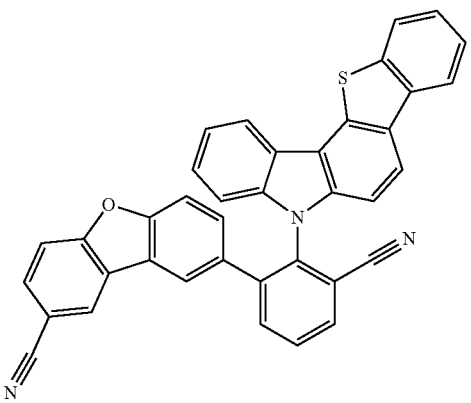
443
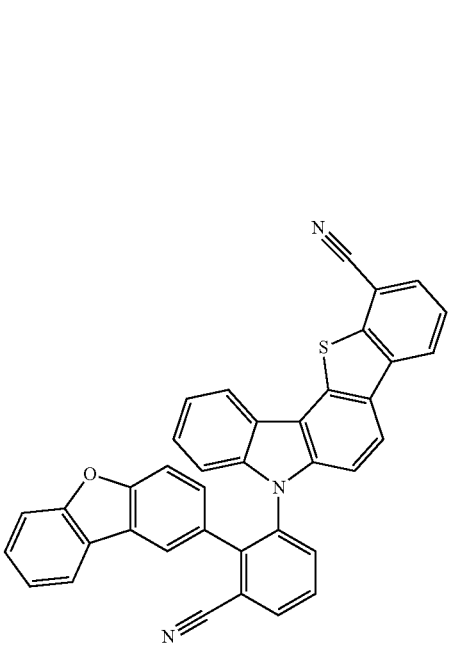
444
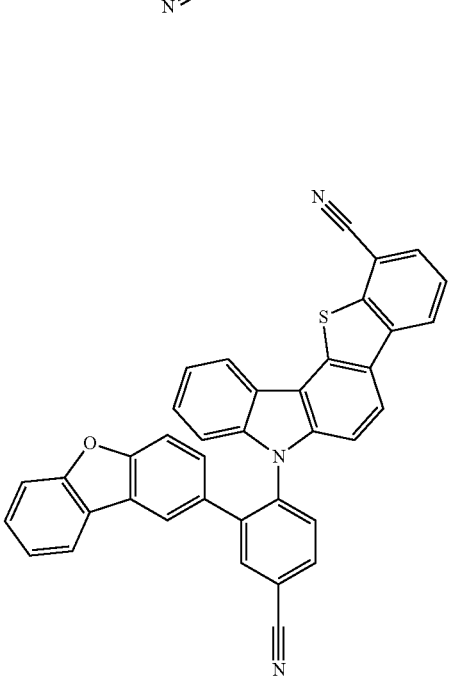

445
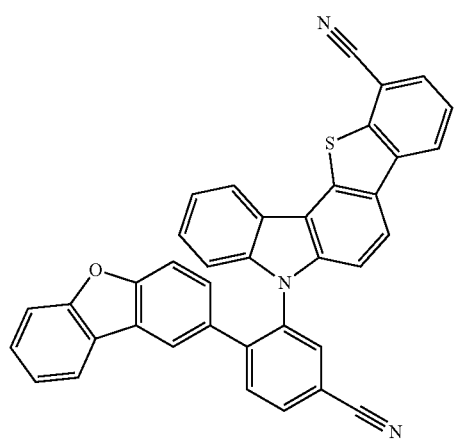
446
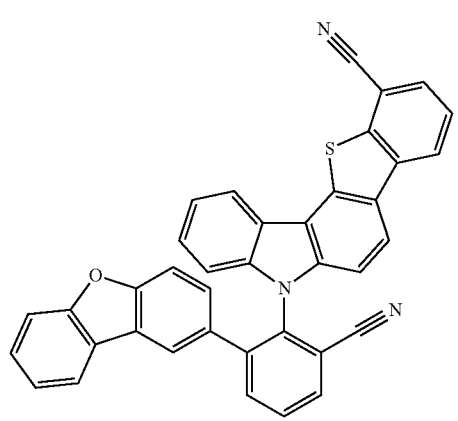
447
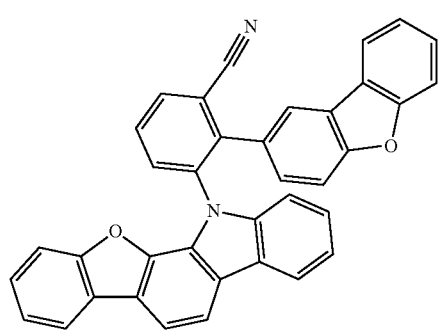
448
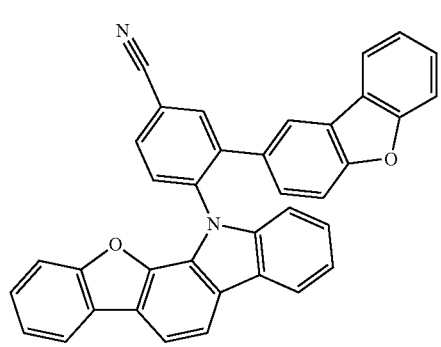
449
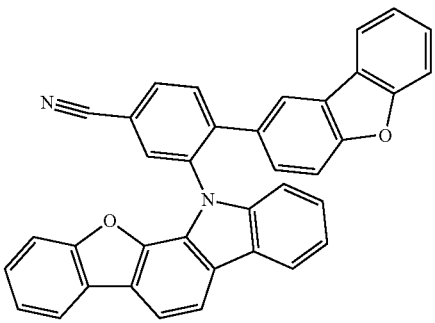
450
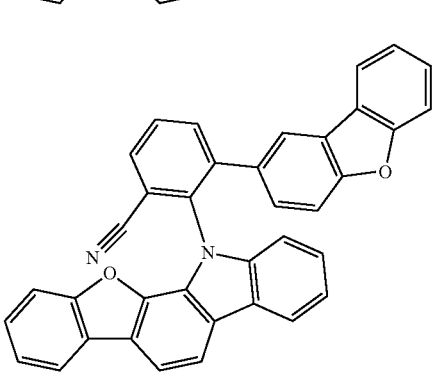
451
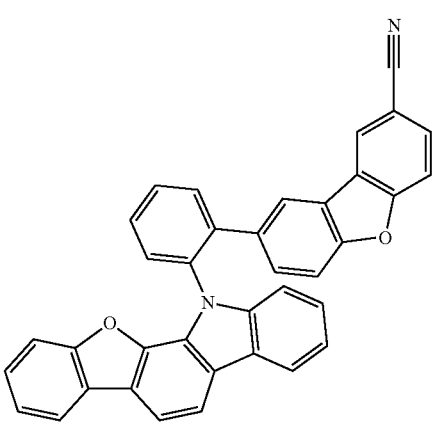
452
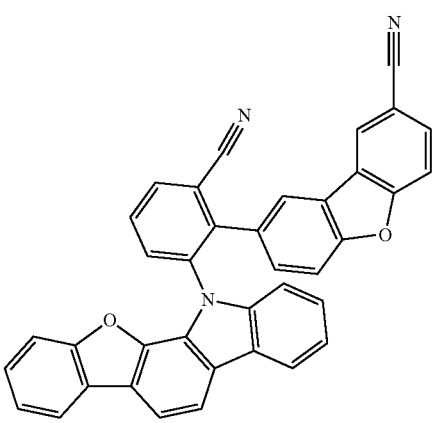

573
-continued
453
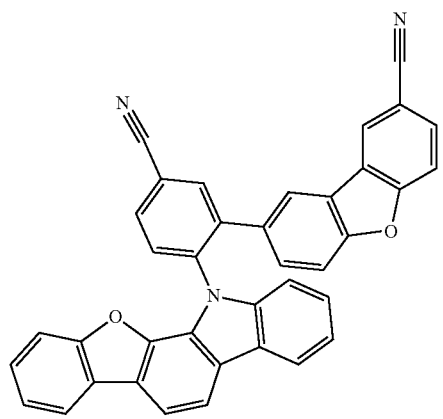
454
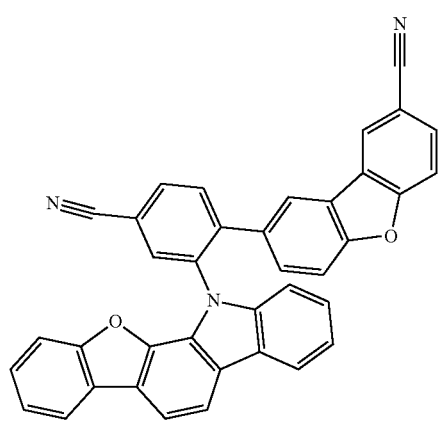
455
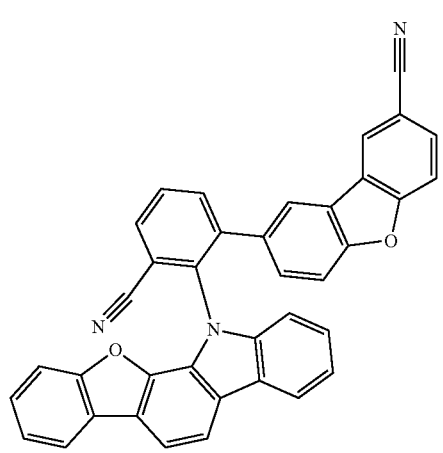
546
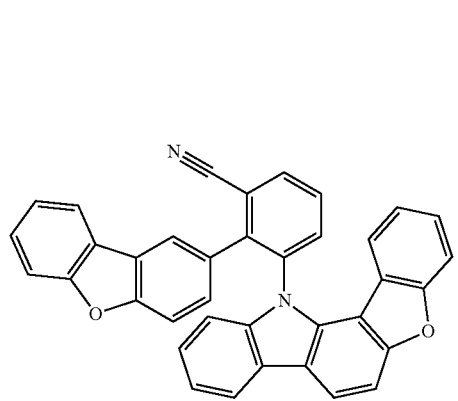
574
-continued
547
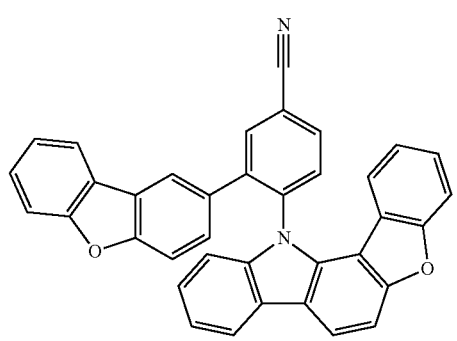
458
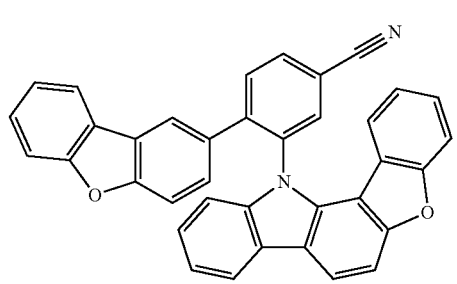
459
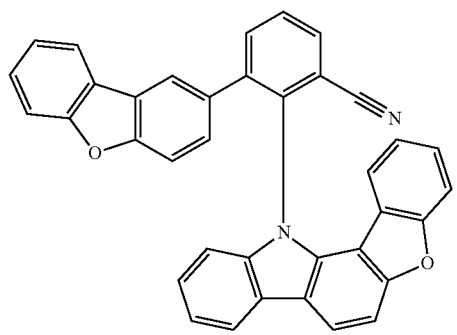
460
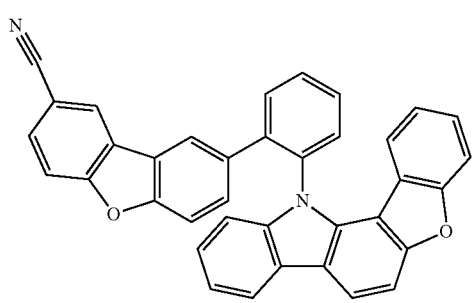
461
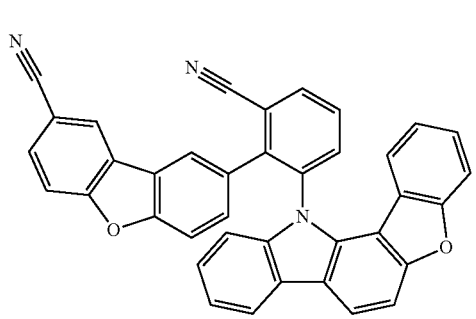

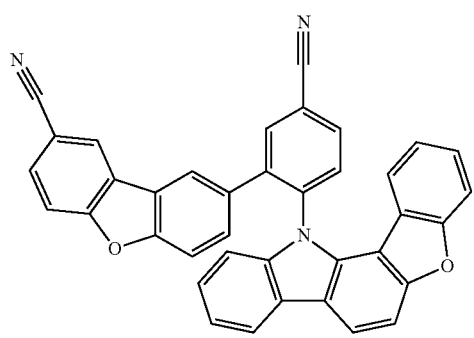
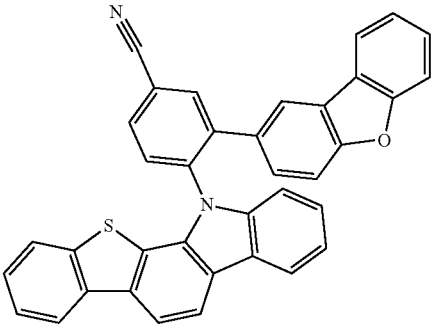
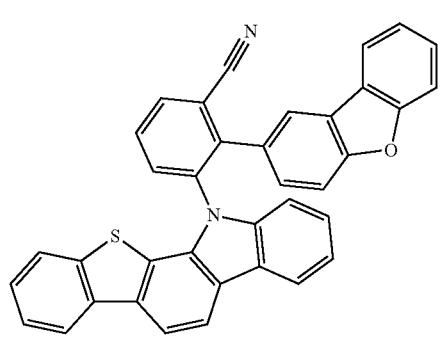
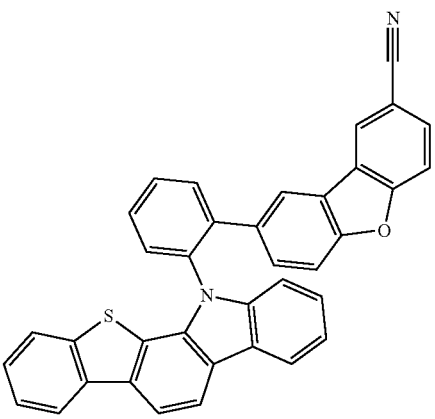

-continued
470
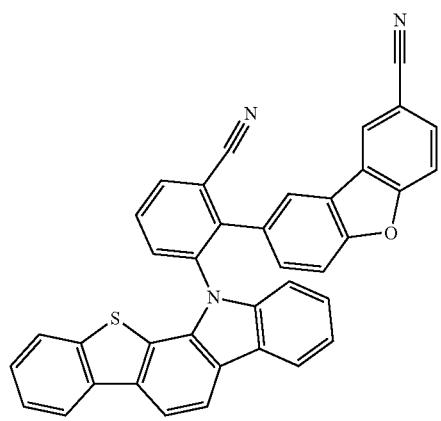
471
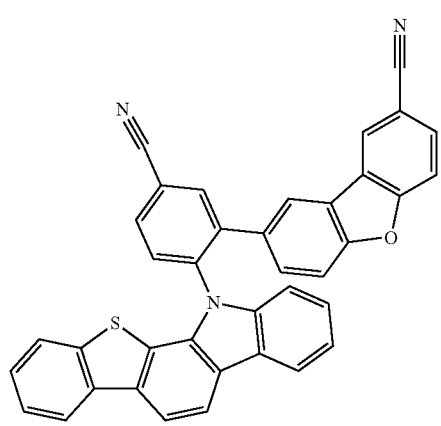
472
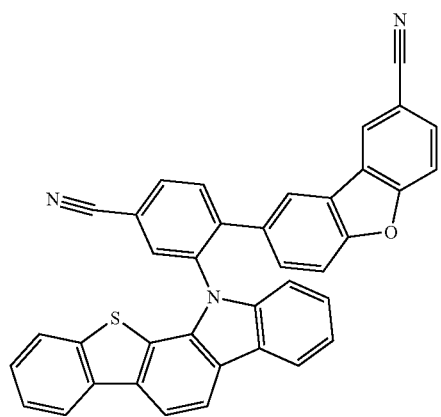
-continued
473
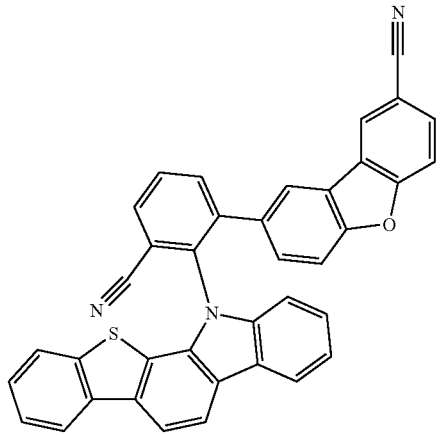
474
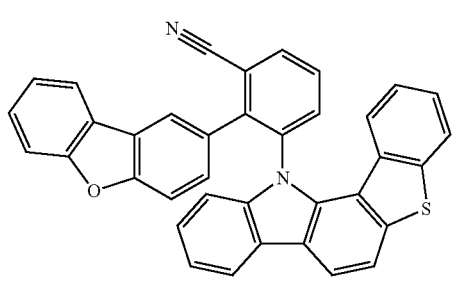
475
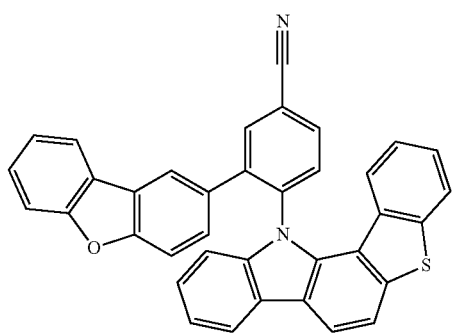
476
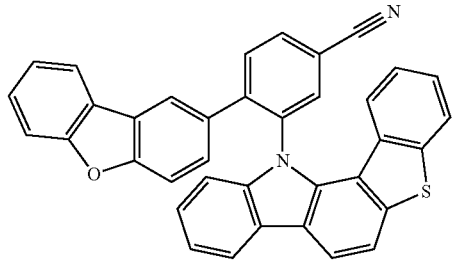
477
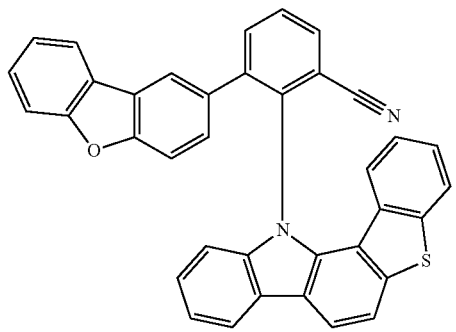

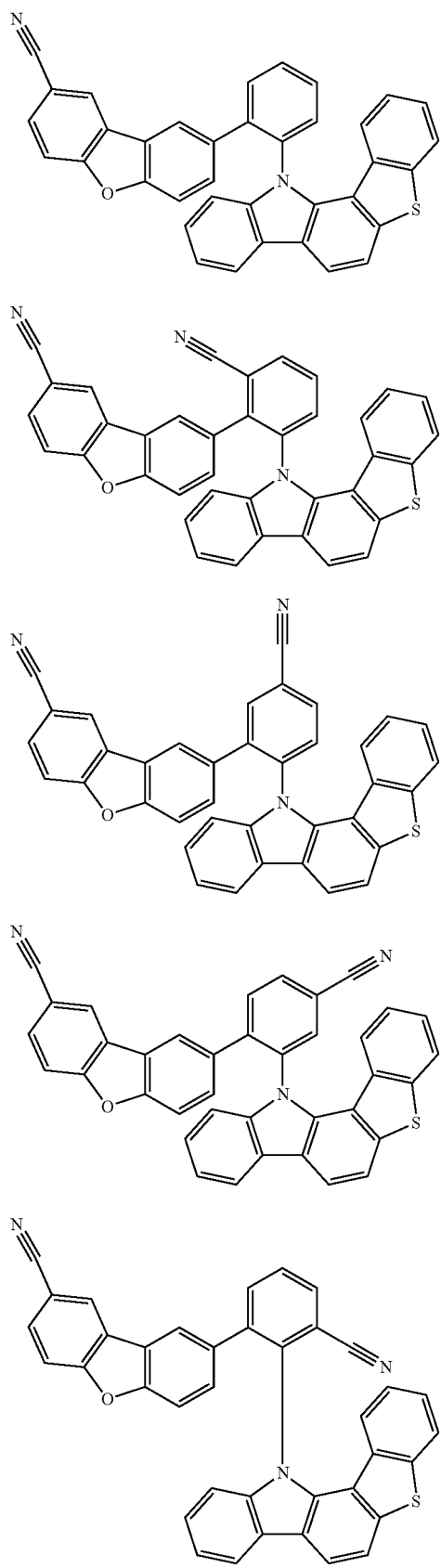
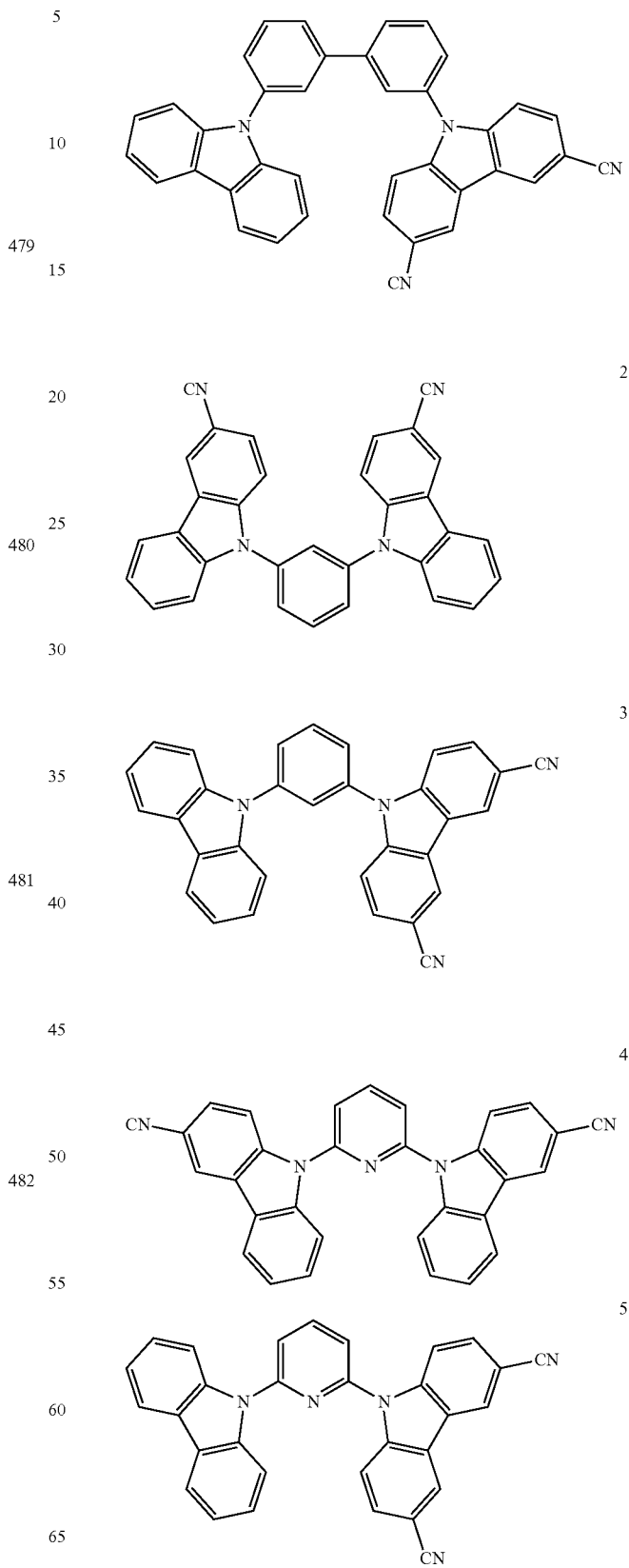
Group HE4

-continued
6
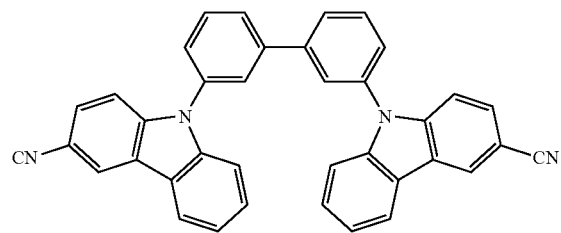
7
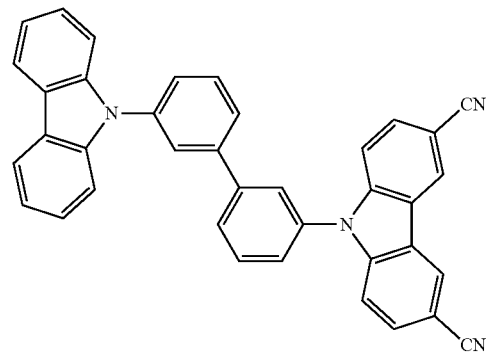
8
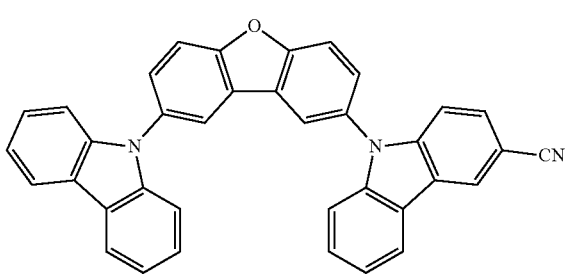
9
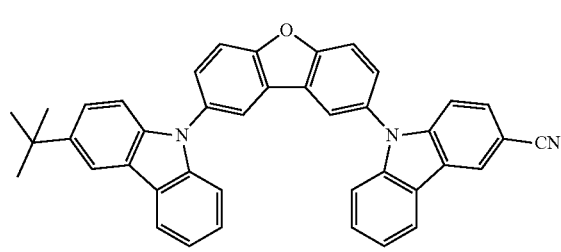
10
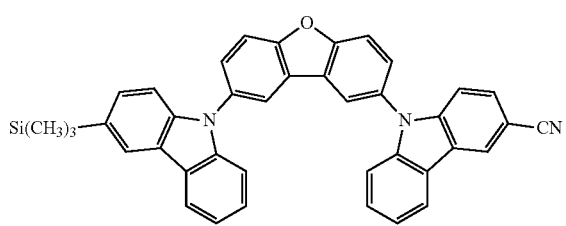
-continued
11
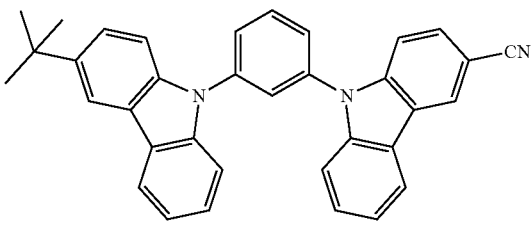
12
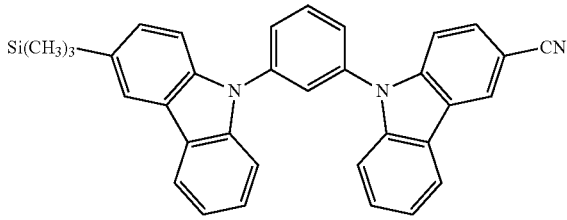
13
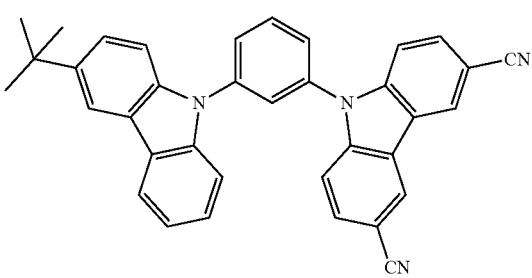
14
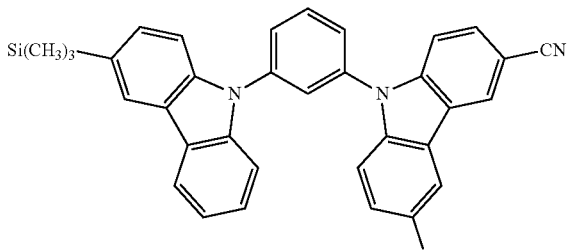
15
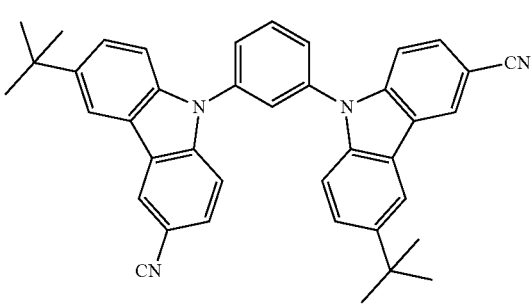

16
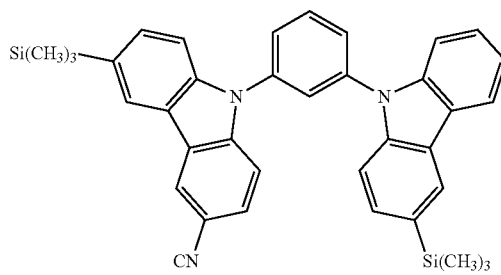
17
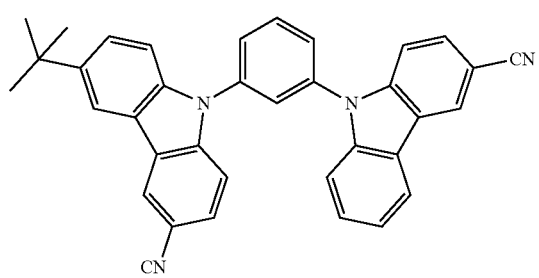
18
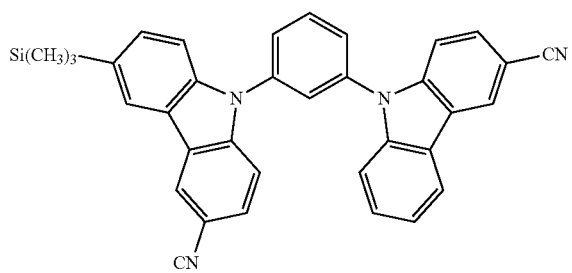
19
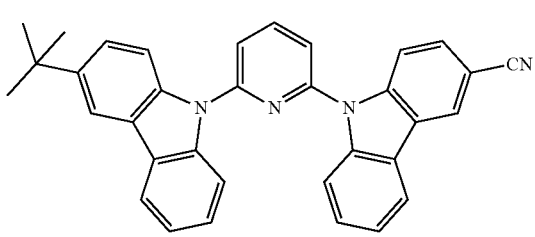
20
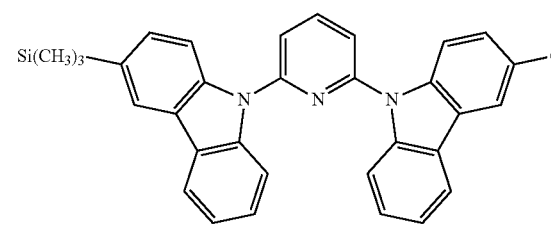
21
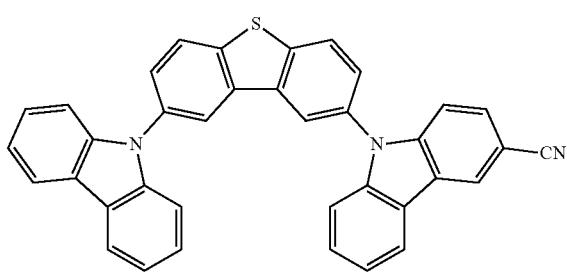
22
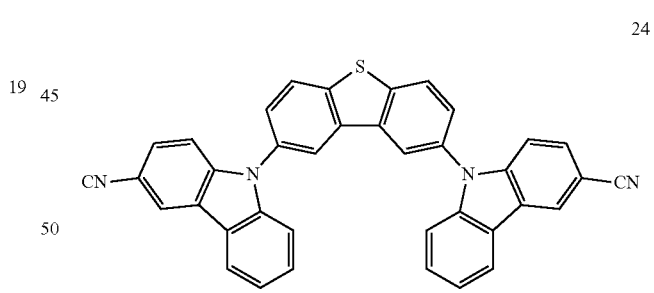
23
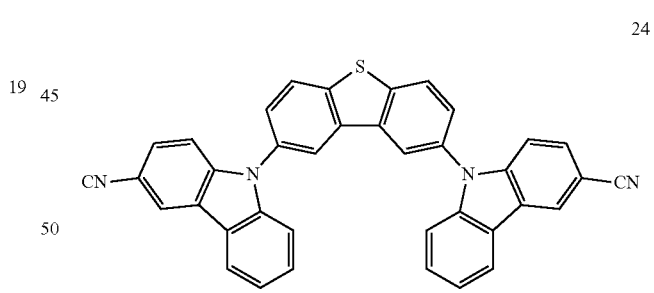
24
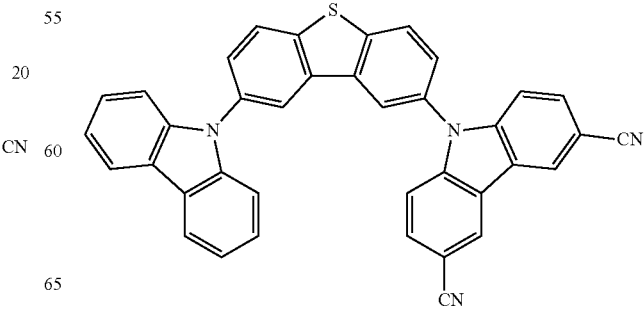
25

26
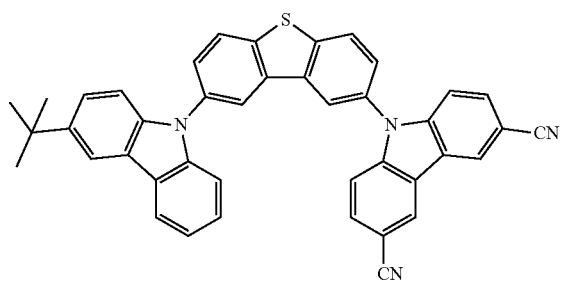
27
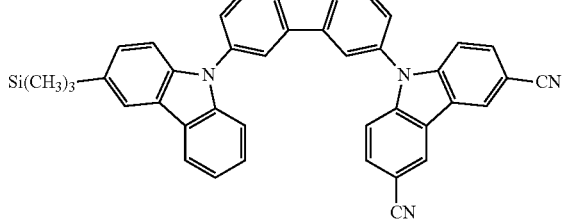
28
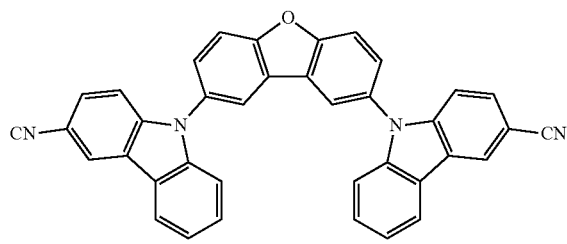
29
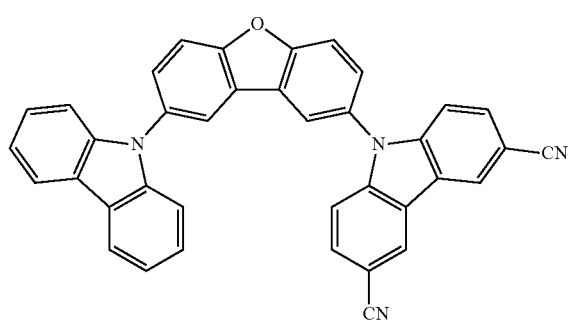
30
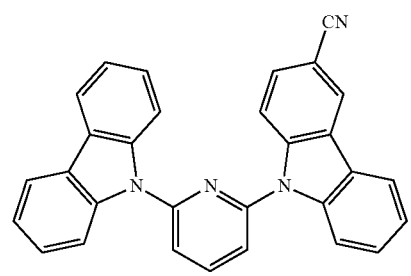
31
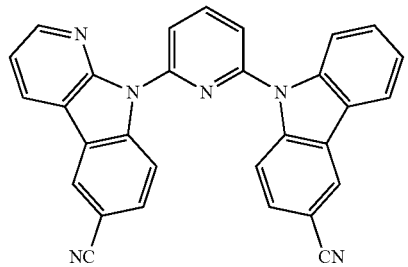
32
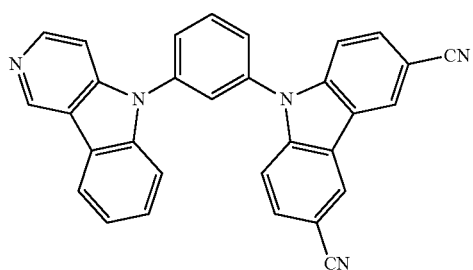
33
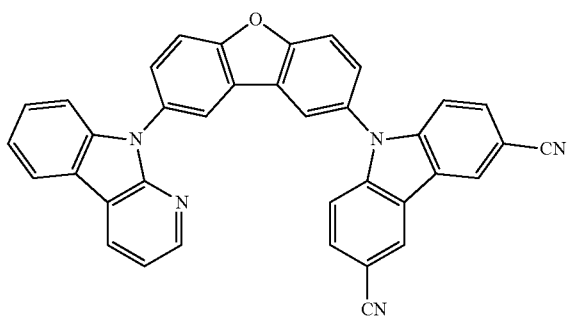
34
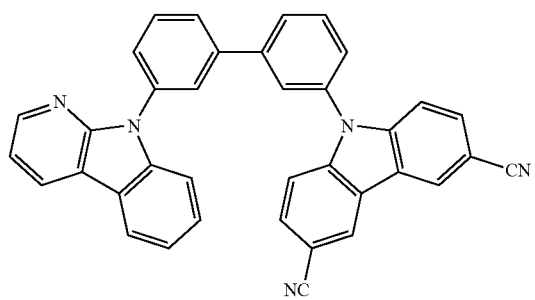
35
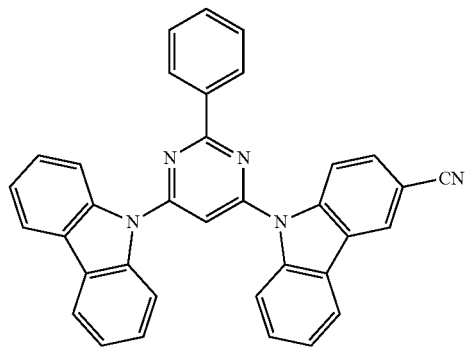

36
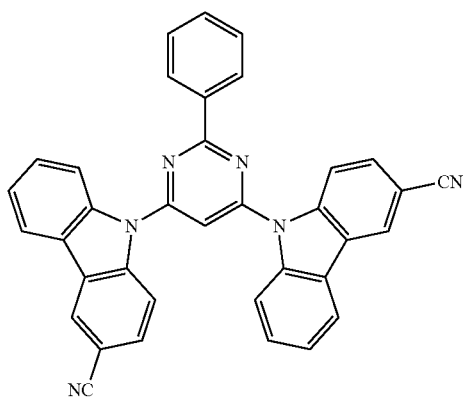
40
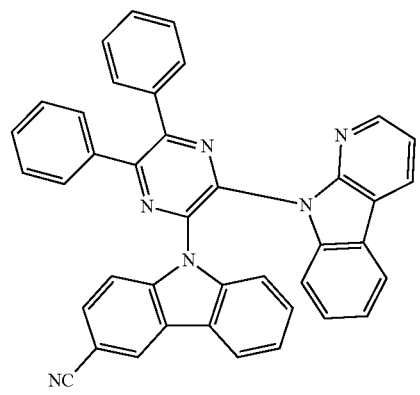
37
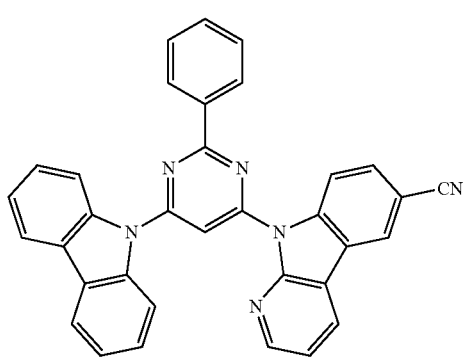
41
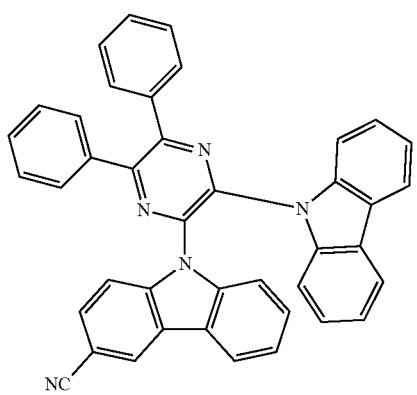
38
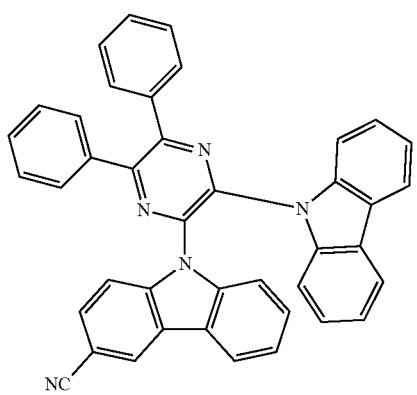
42
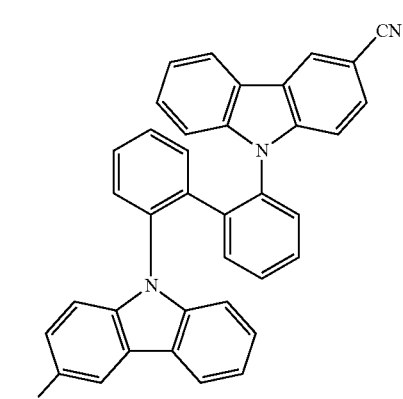
39
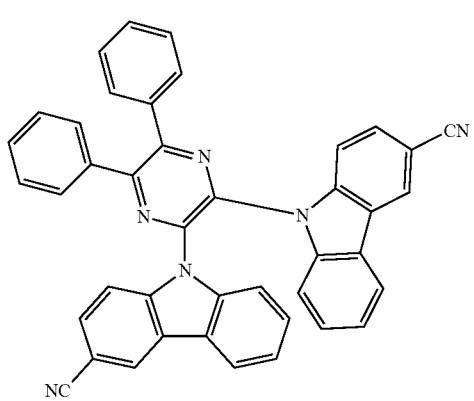
43
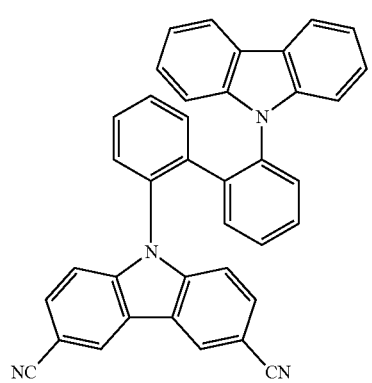

-continued
44
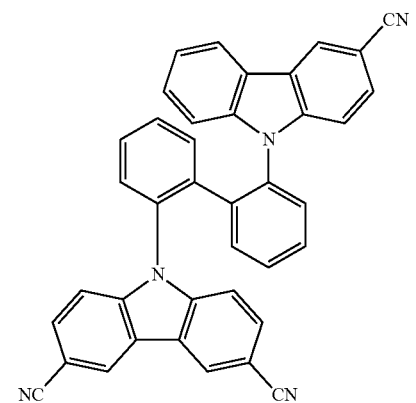
45
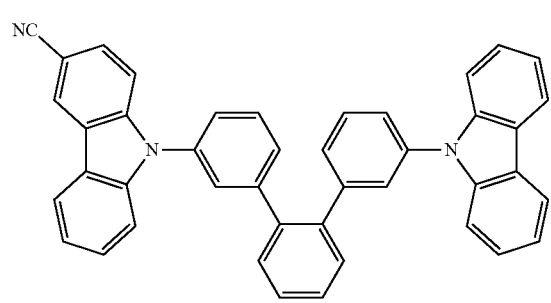
46
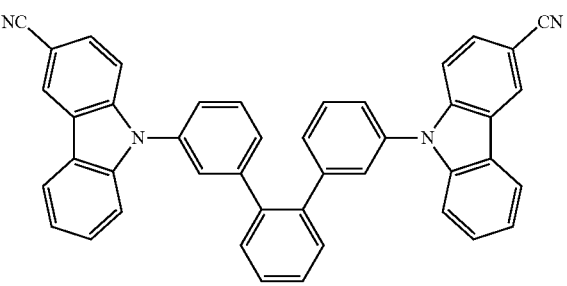
47
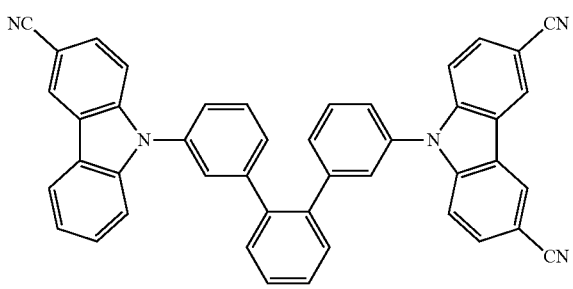
48
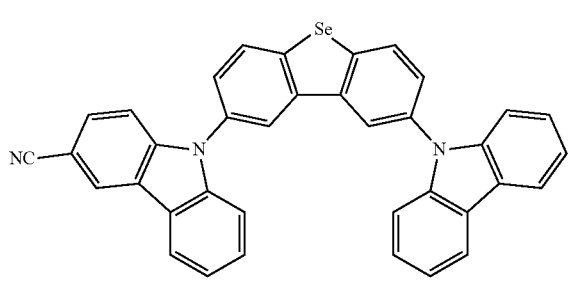
-continued
49
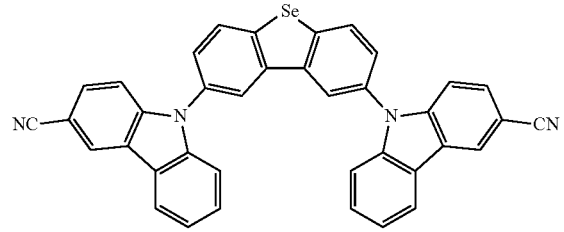
50
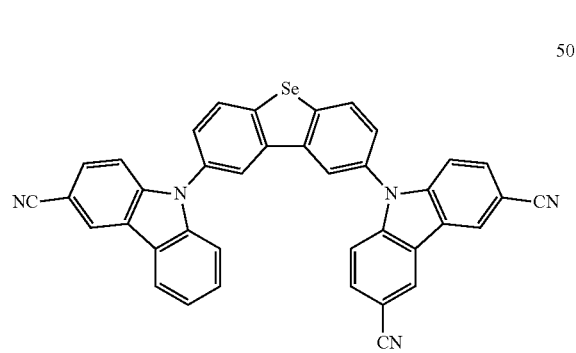
51
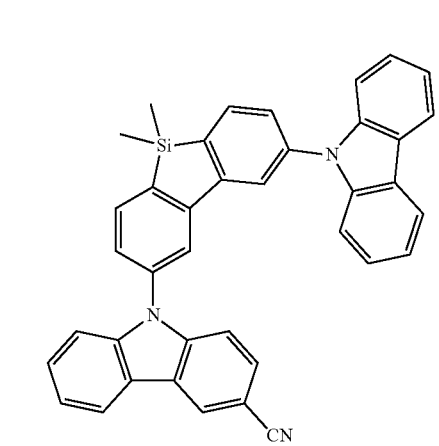
52
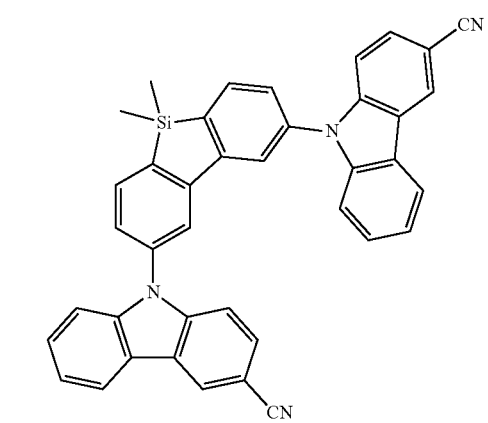

53
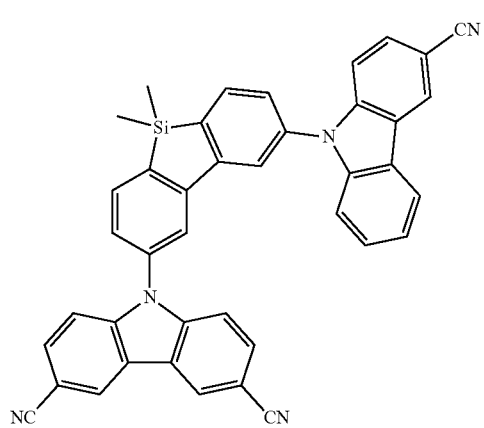
54
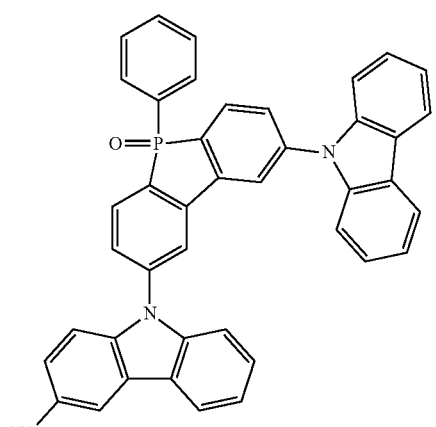
55
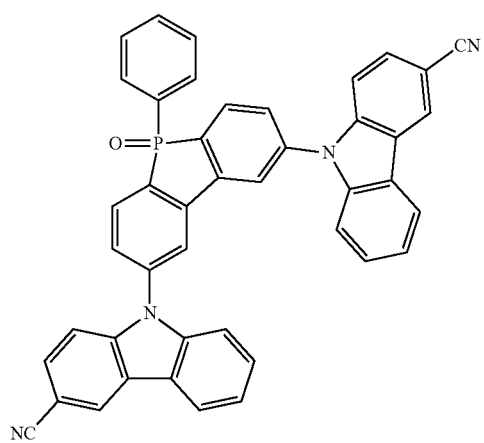
56
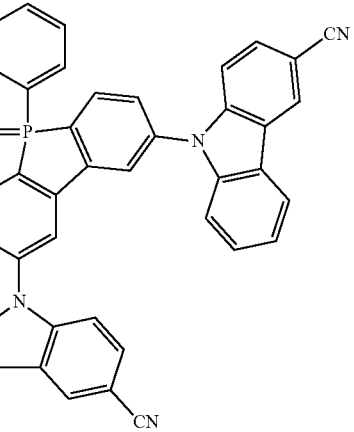
Group HE5
1
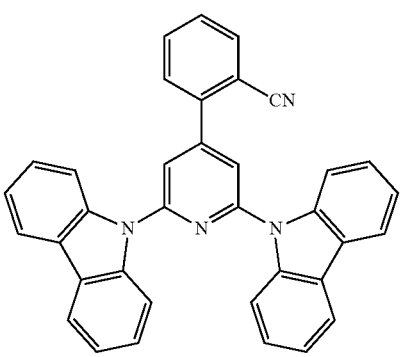
2
3
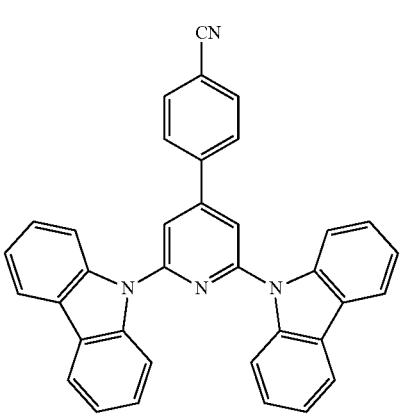

593
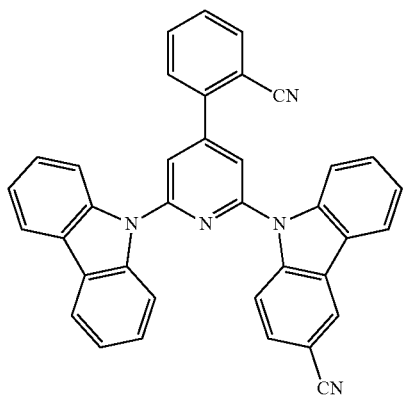
4
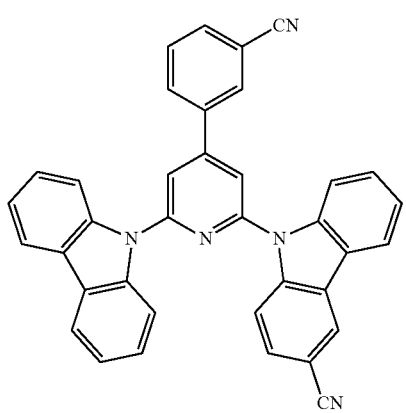
5
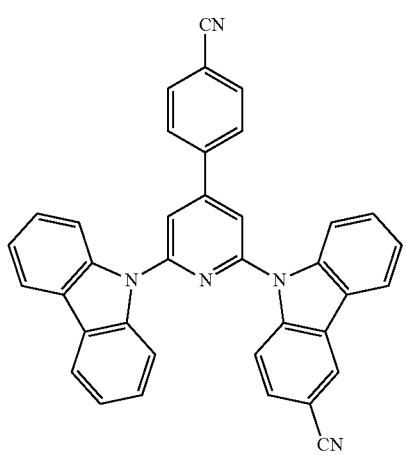
6
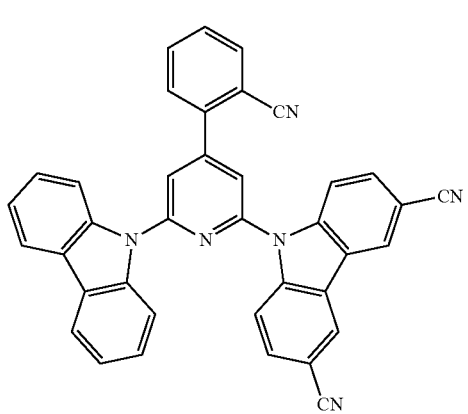
7
594
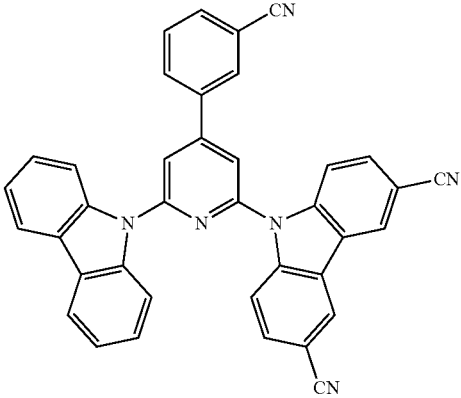
8
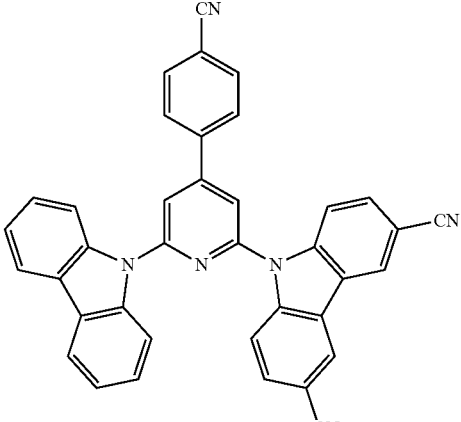
9
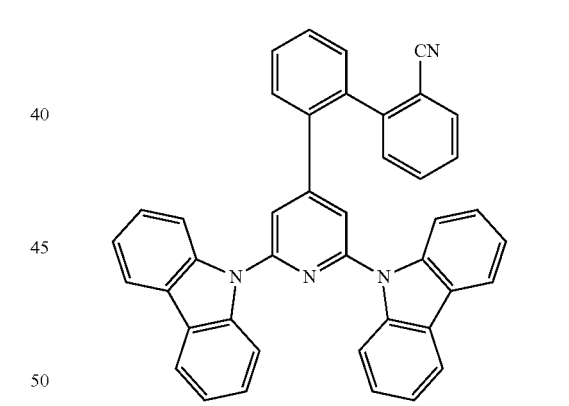
10
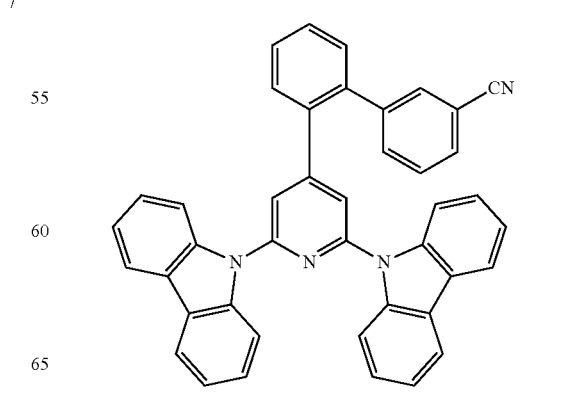
11

12
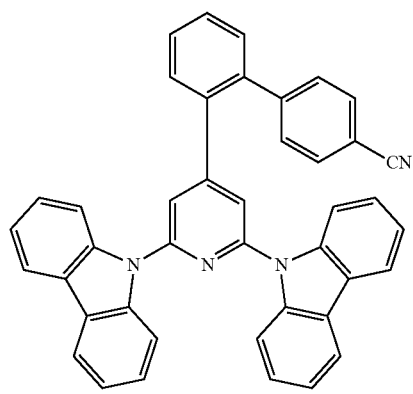
13
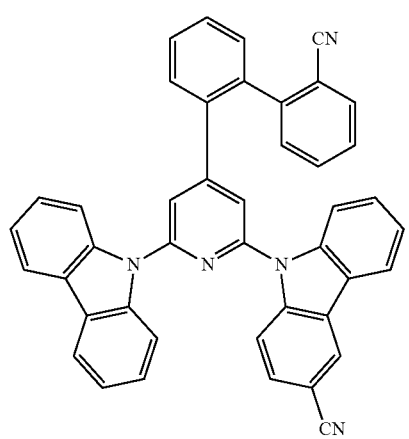
14
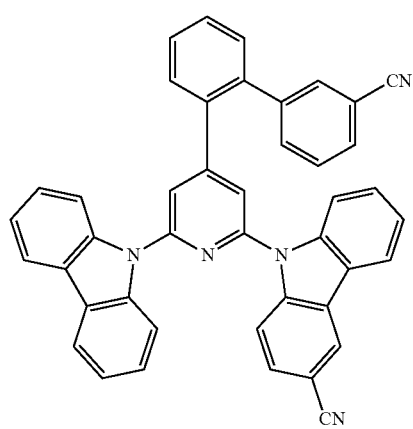
15
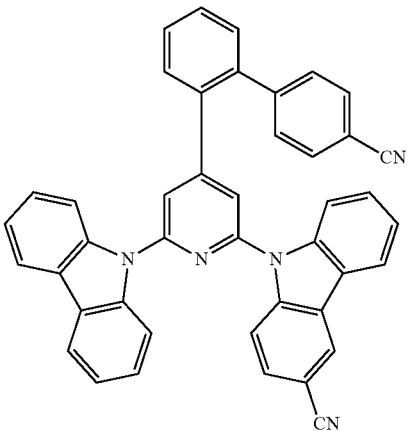
16
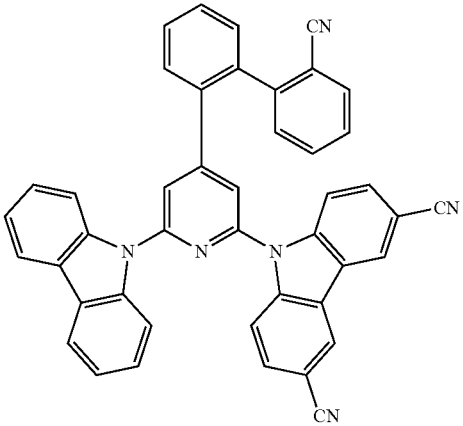
17
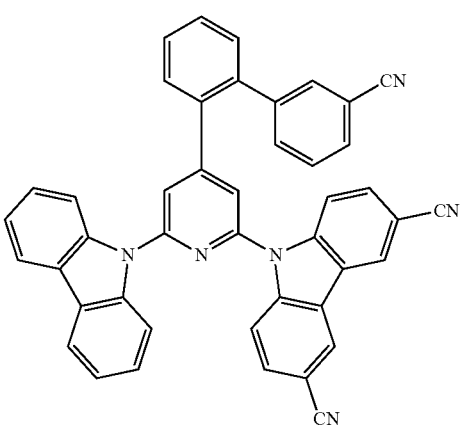

-continued
18
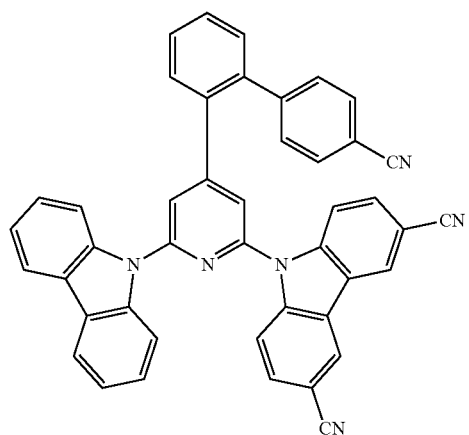
19
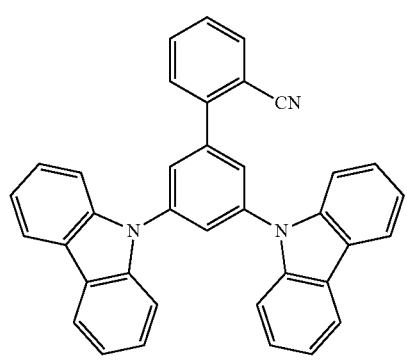
20
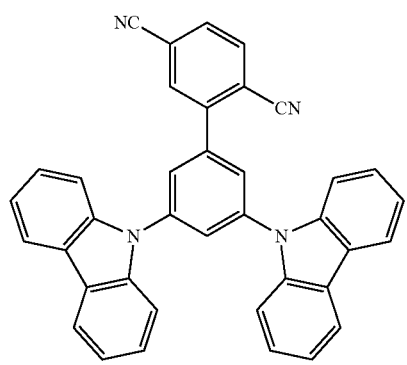
21
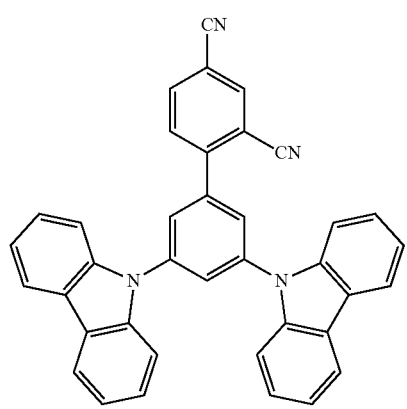
-continued
22
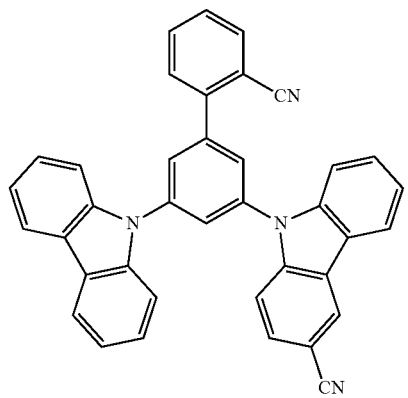
23

24
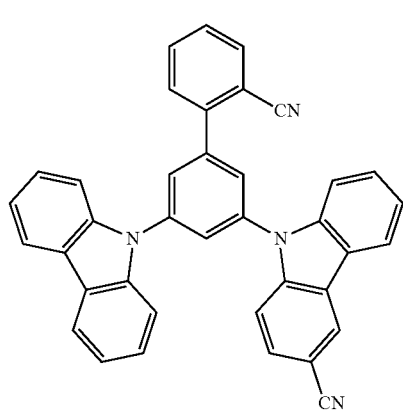
25
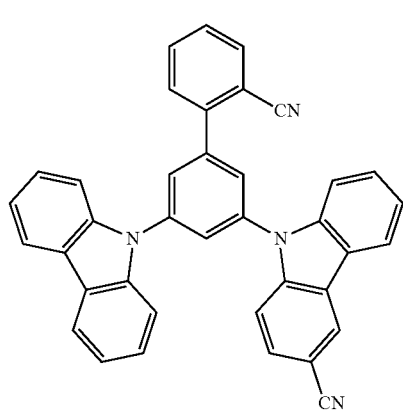

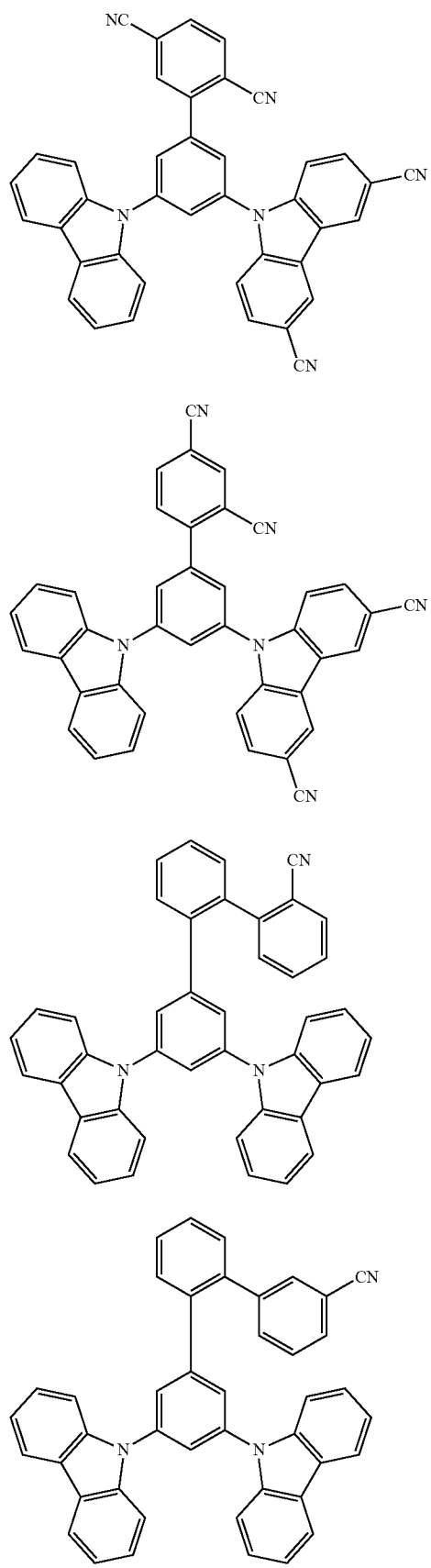
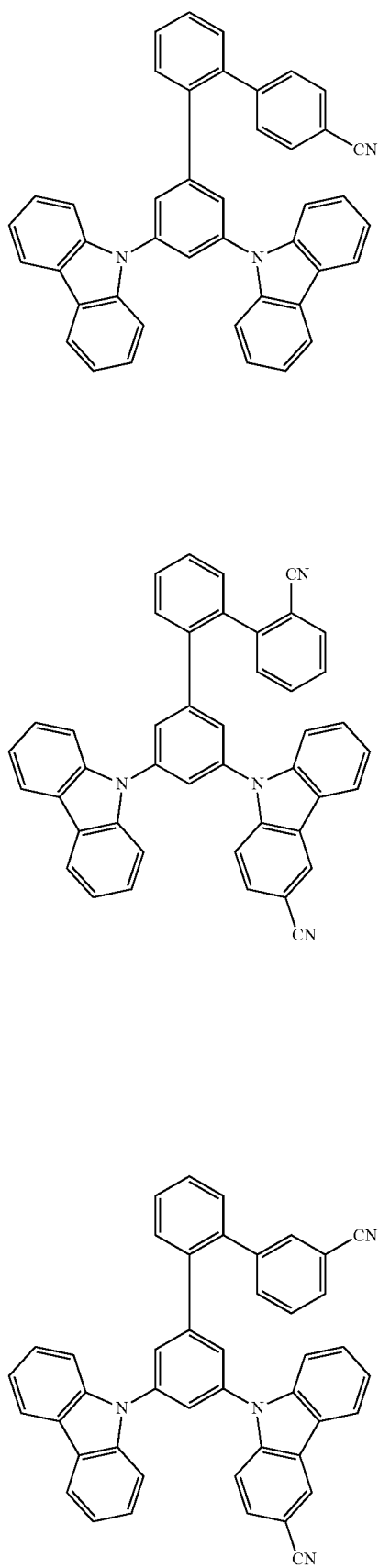

33
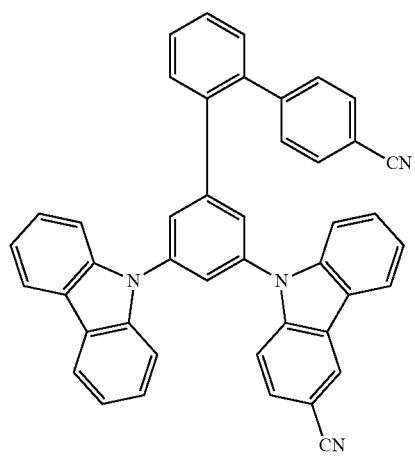
34
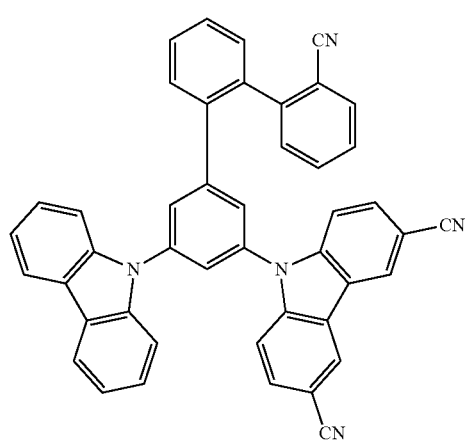
35
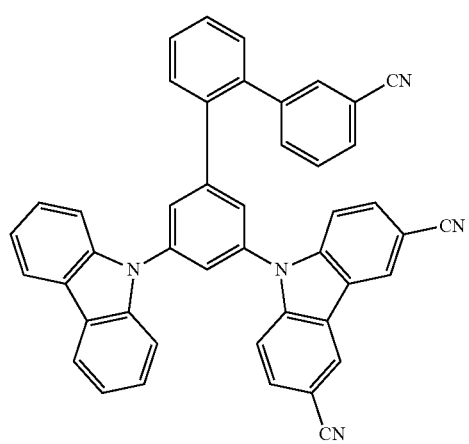
36
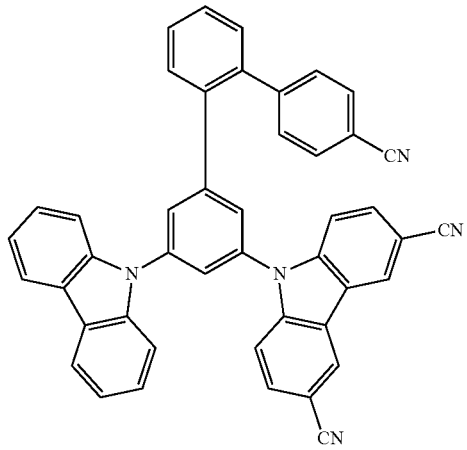
37
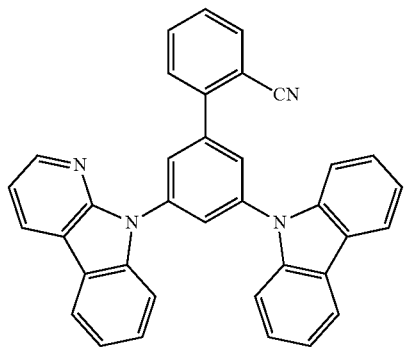
38
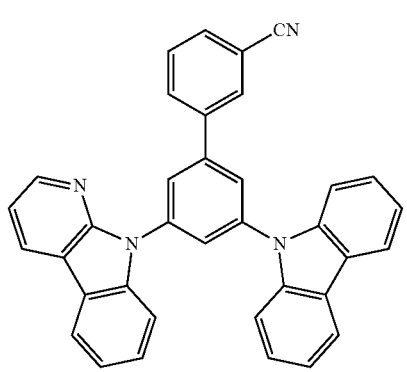
39
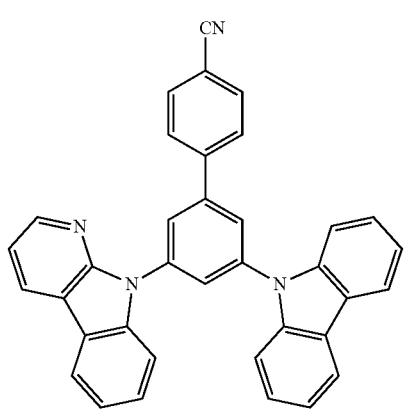

40
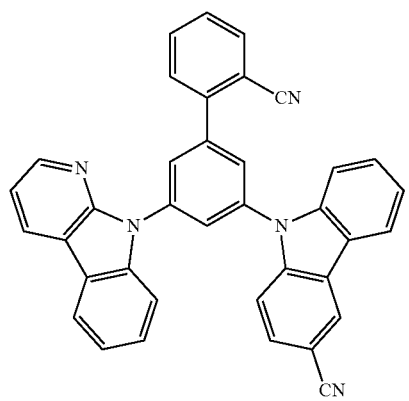
41
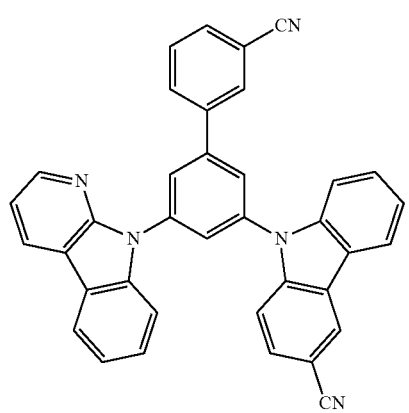
42
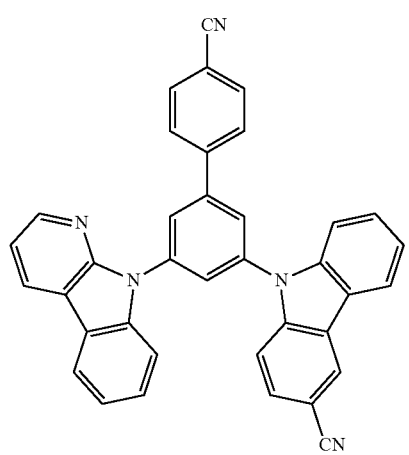
43
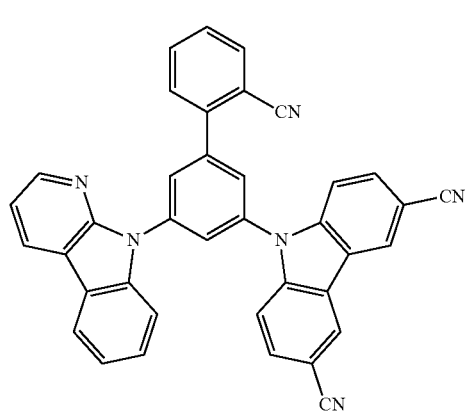
44
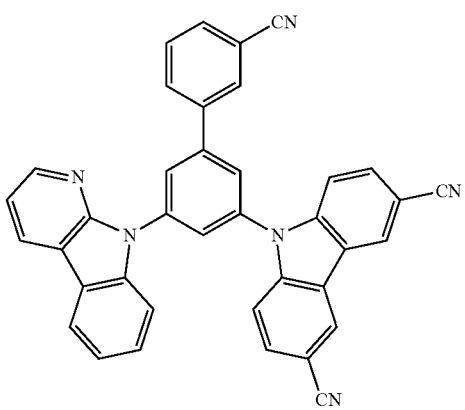
45
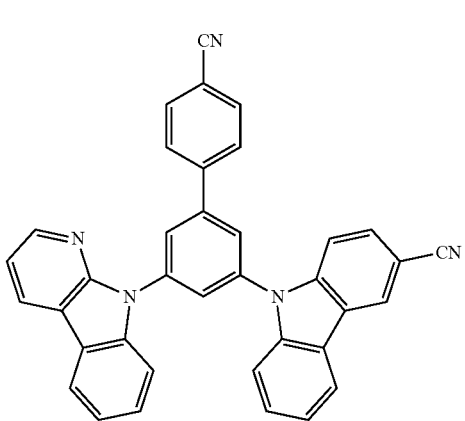
46
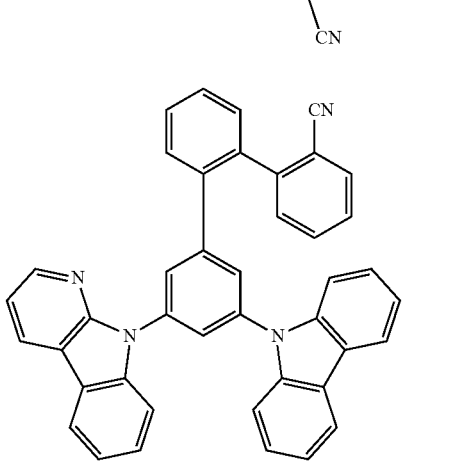
47
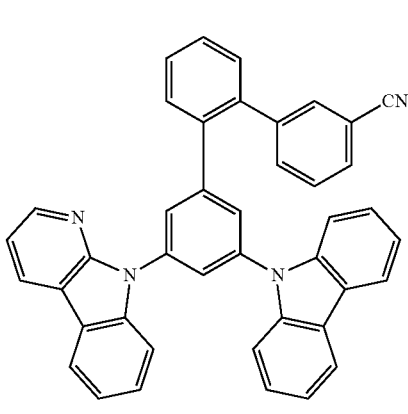

-continued
48
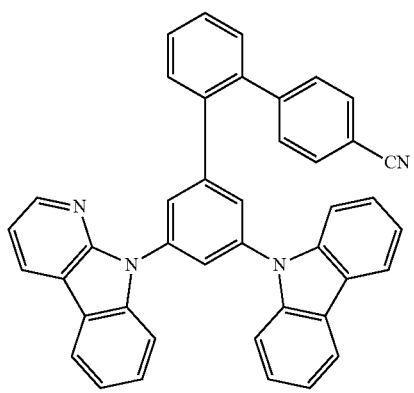
49
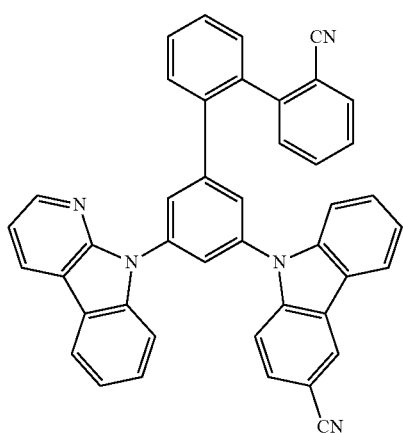
50
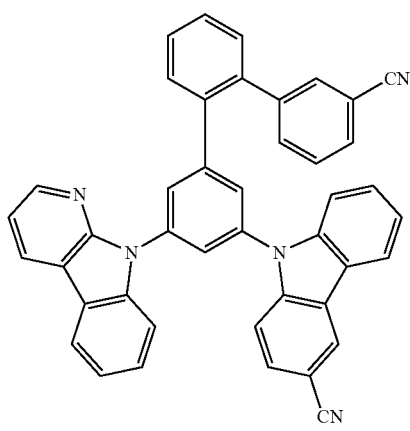
-continued
51
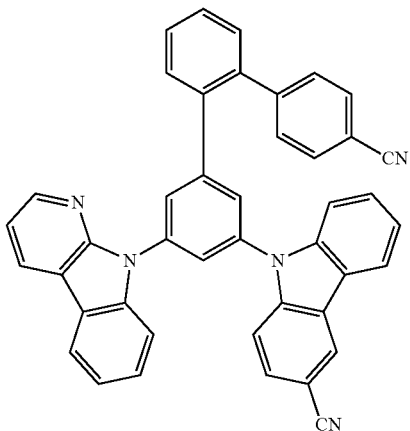
52
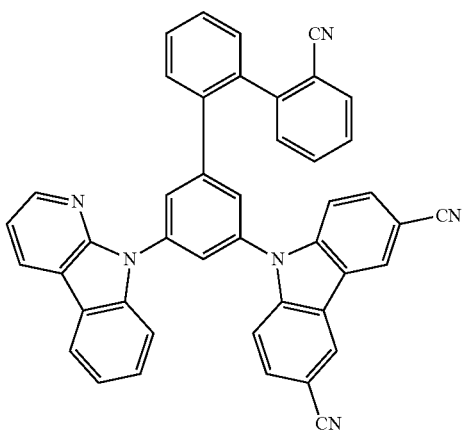
53
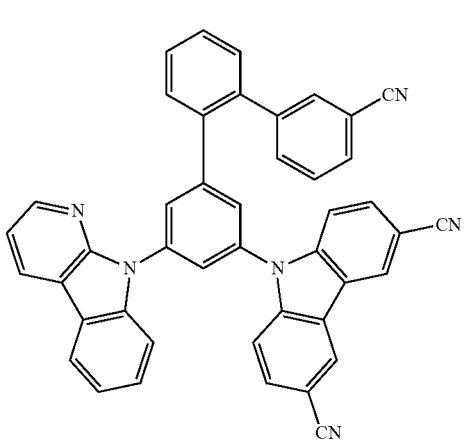

54
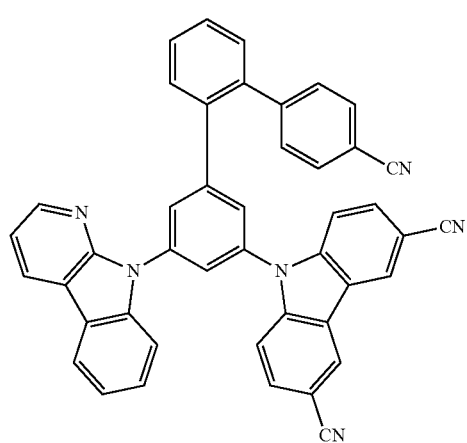
55
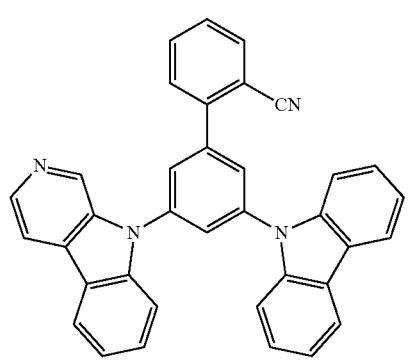
56
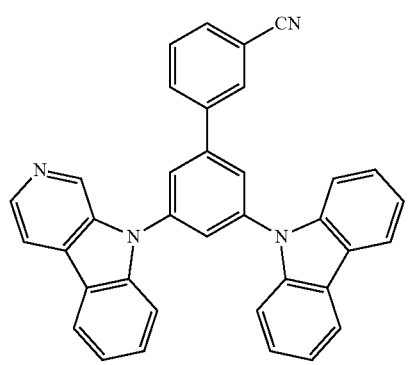
57
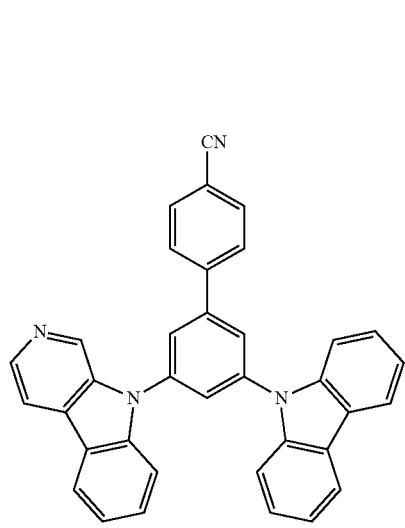
58
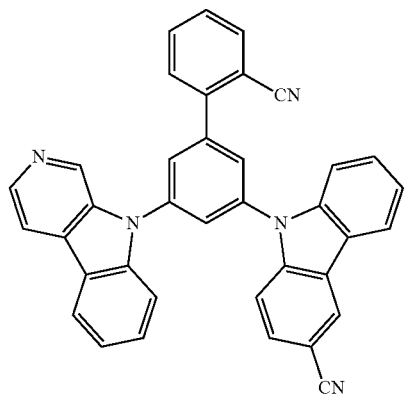
59
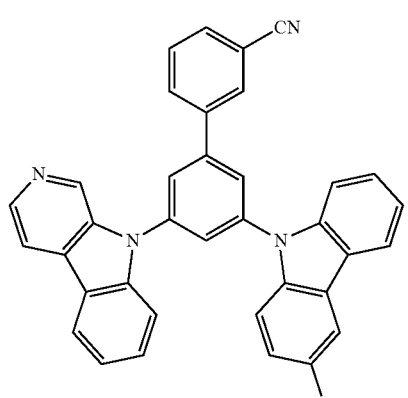
60
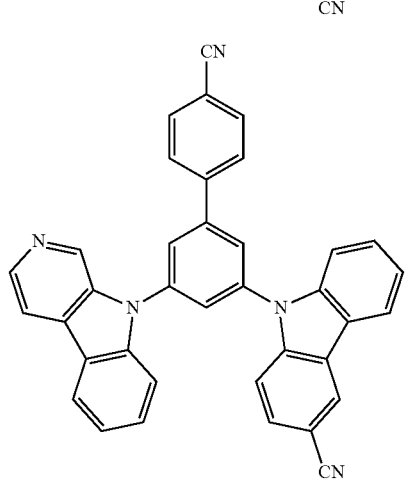
61
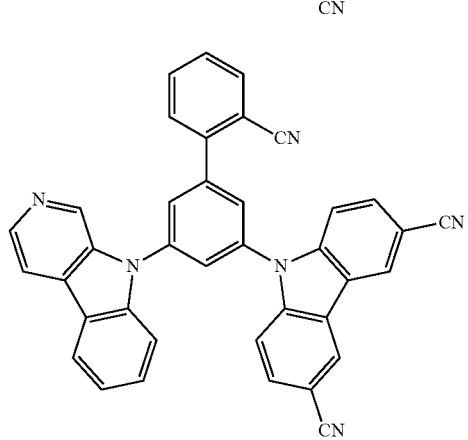

609
-continued
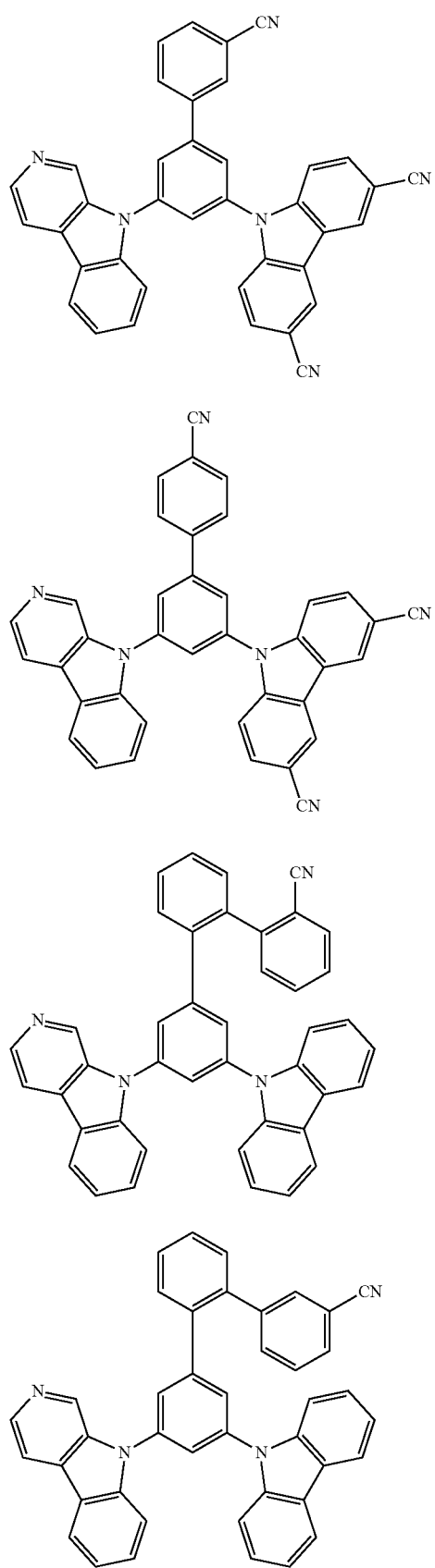
610
-continued
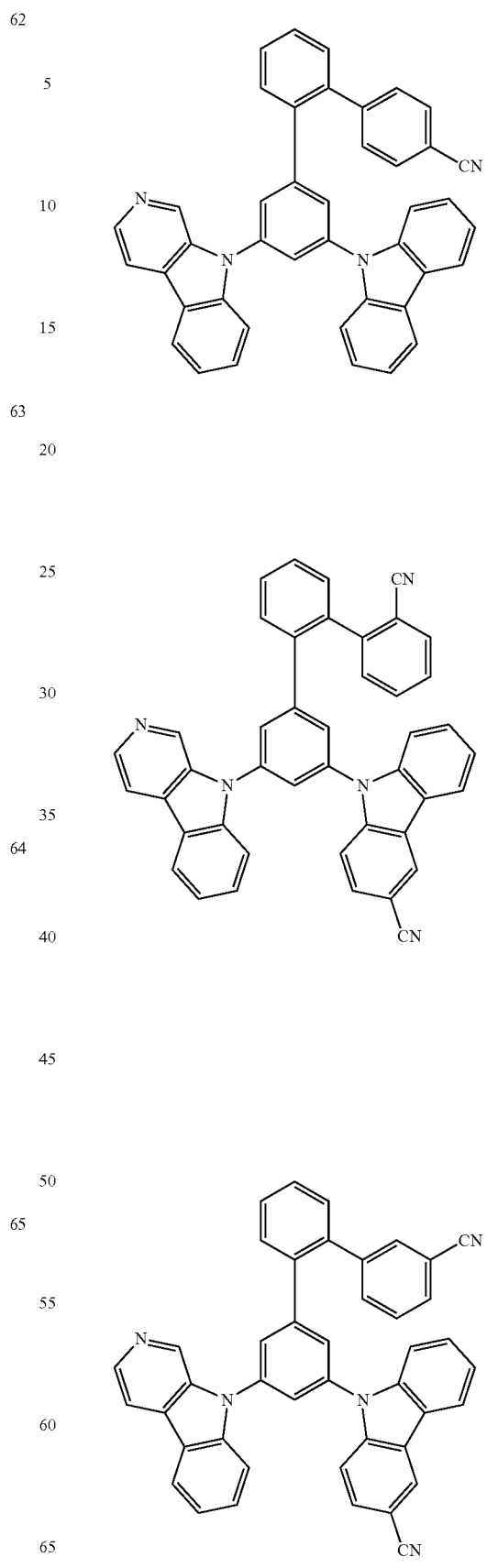

-continued
69
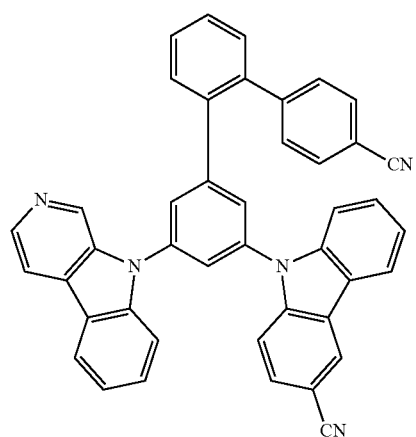
70
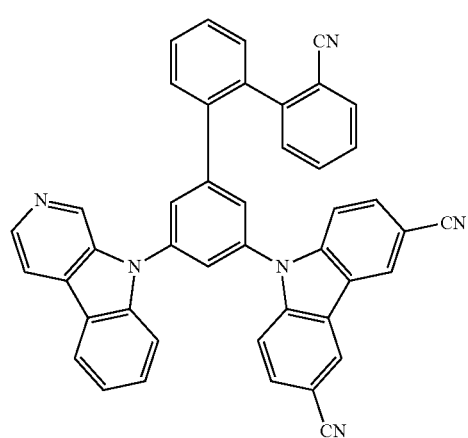
71
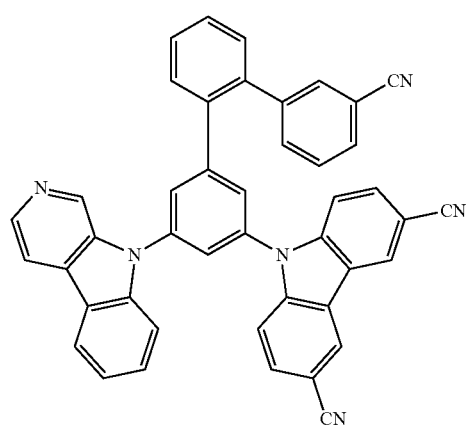
-continued
72
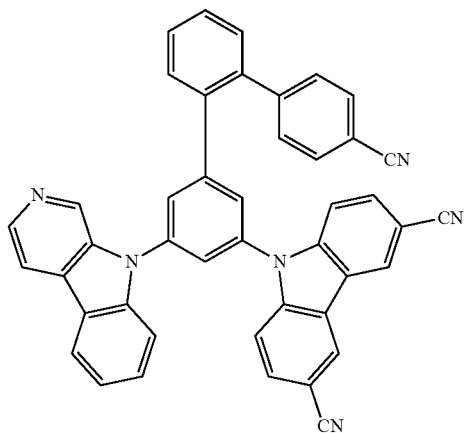
73
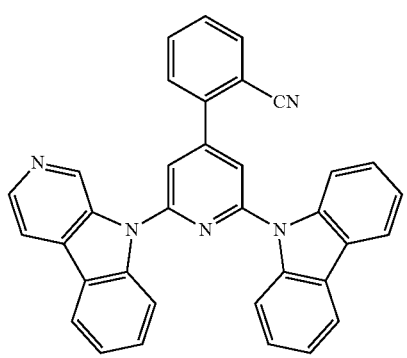
74
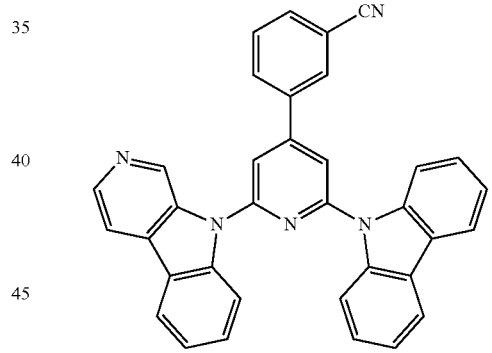
75
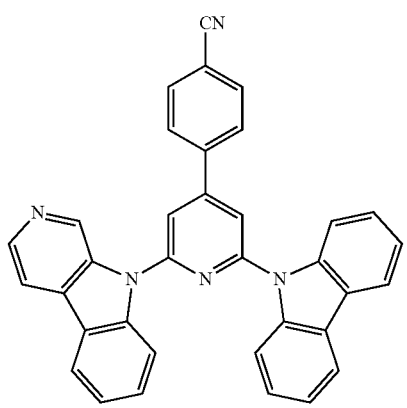

76
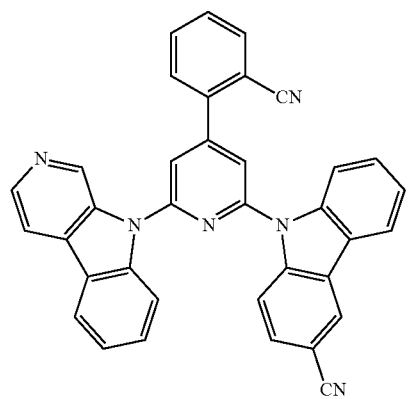
77
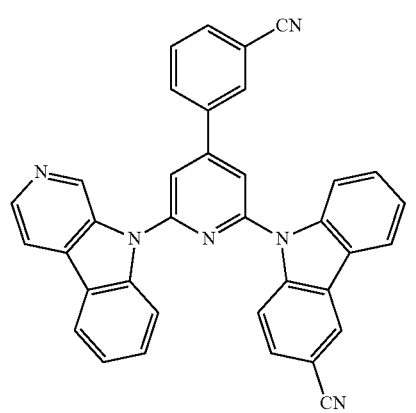
78
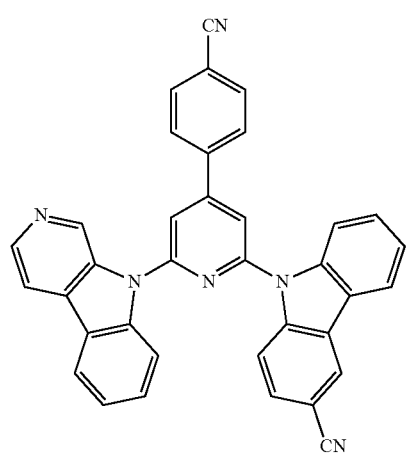
79
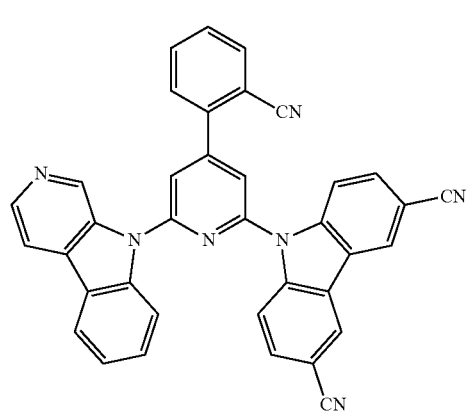
80
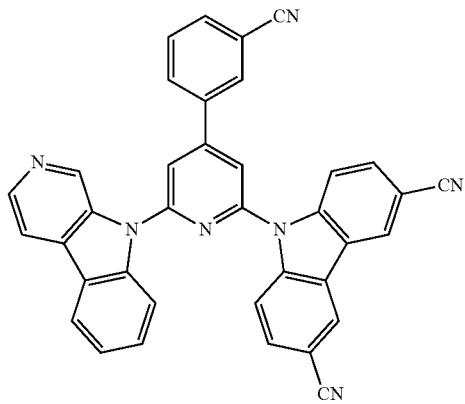
81
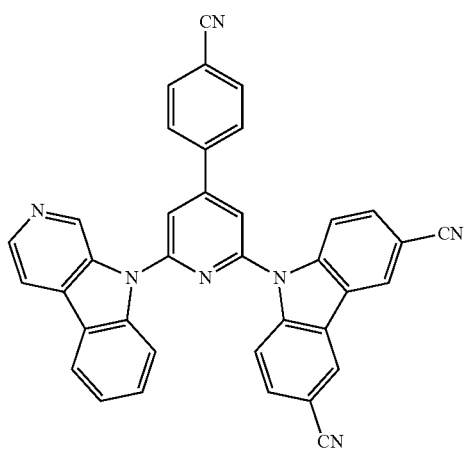
82
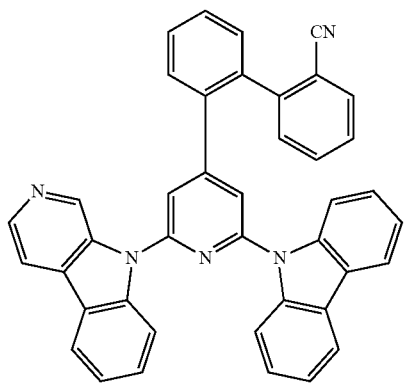
83
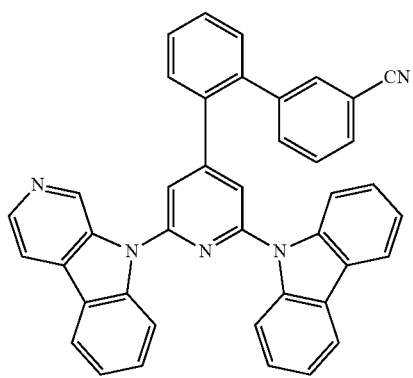

615
-continued
84
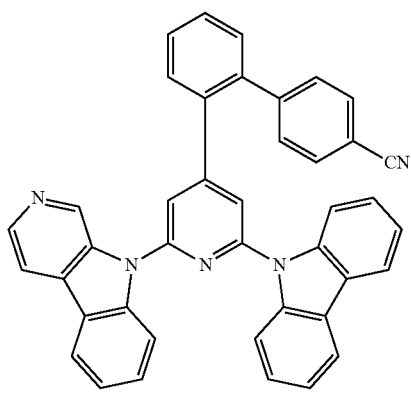
85
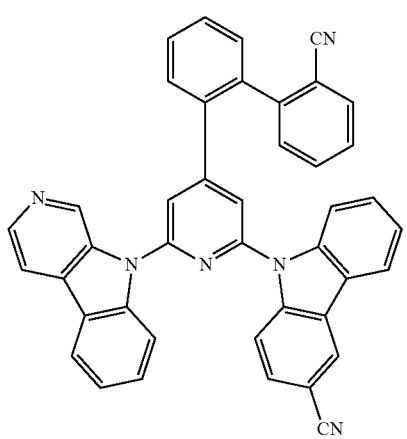
86
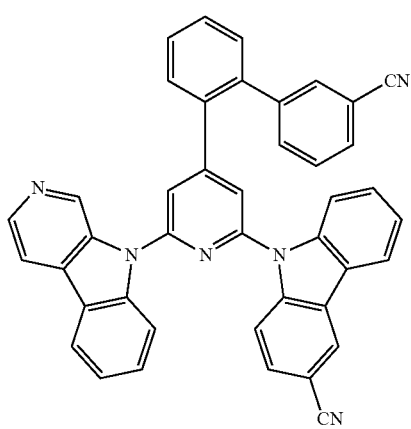
616
-continued
87
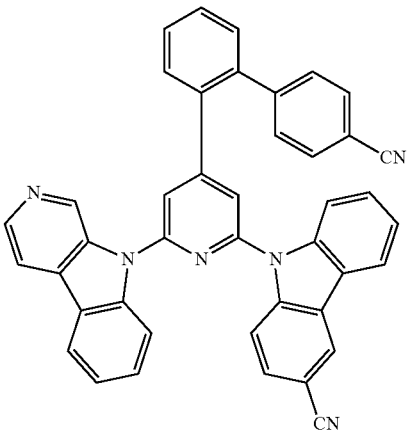
88
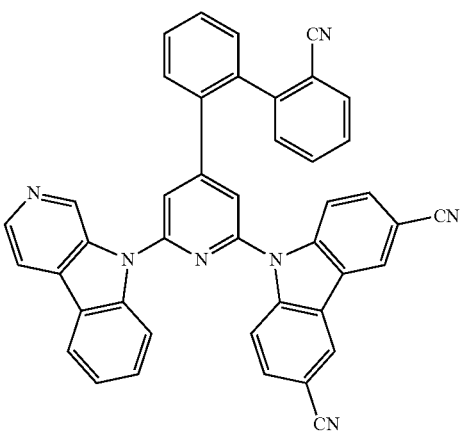
89
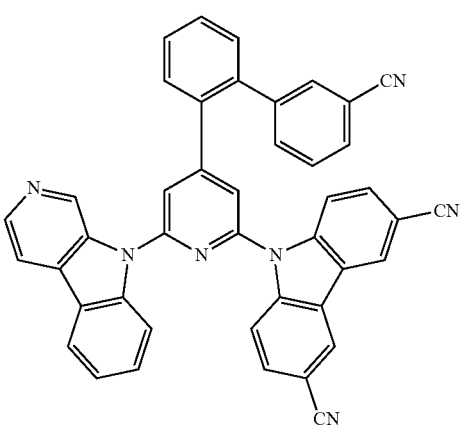

-continued
90
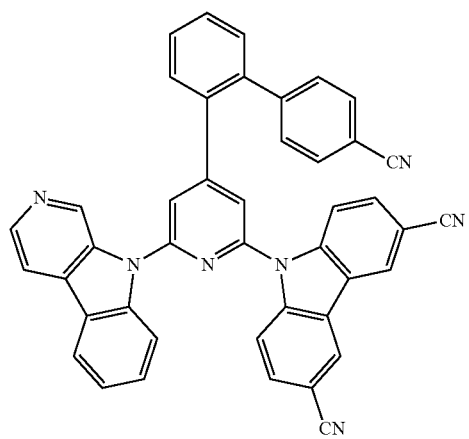
91
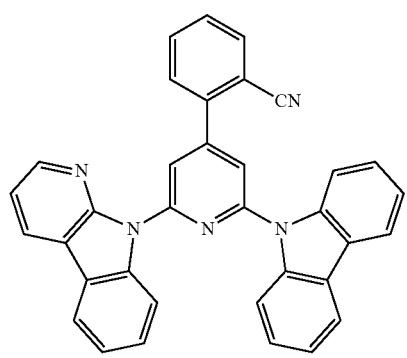
92
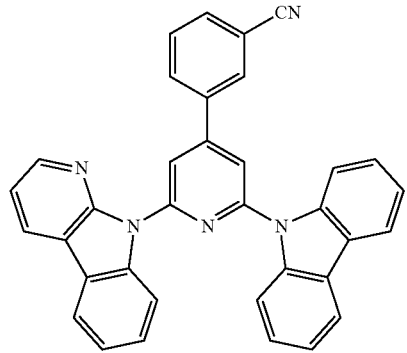
93
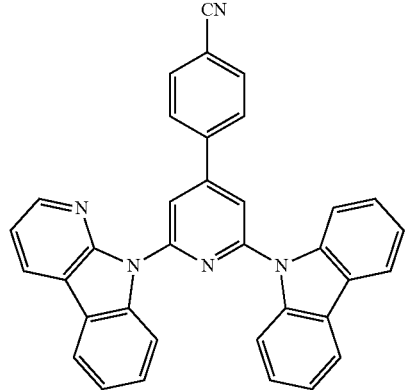
-continued
94
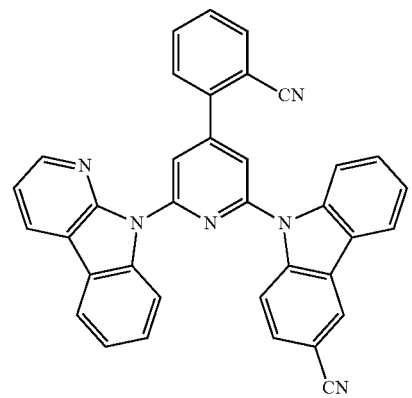
95
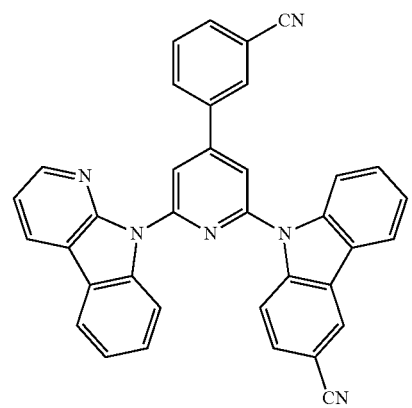
96
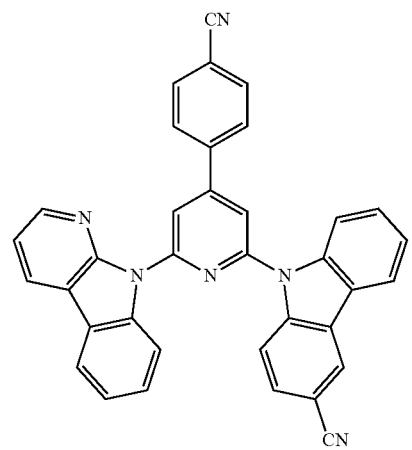
97
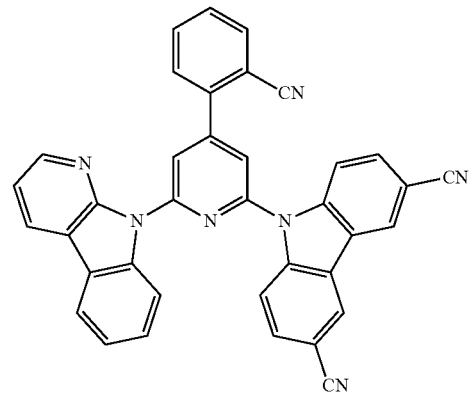

98
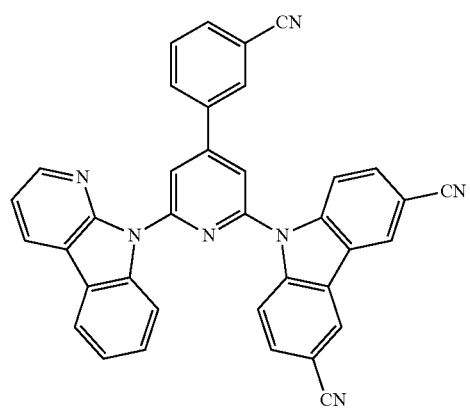
99
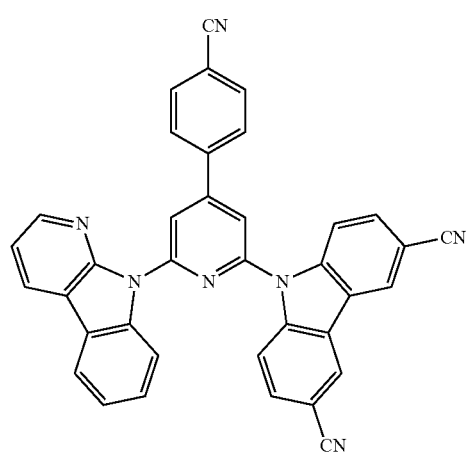
100

101
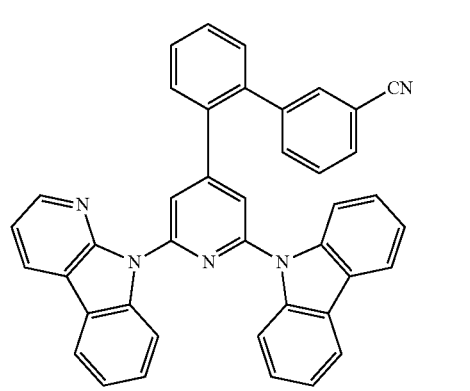
102
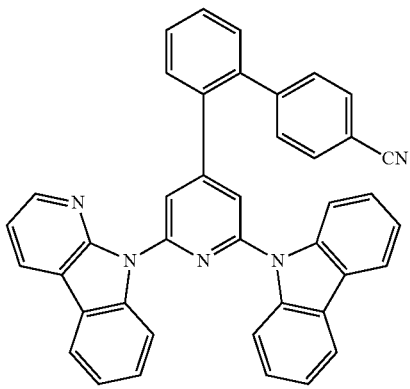
103
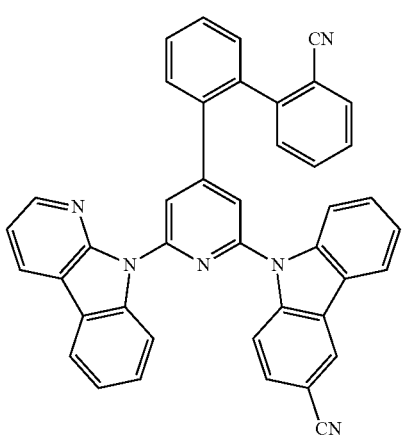
104
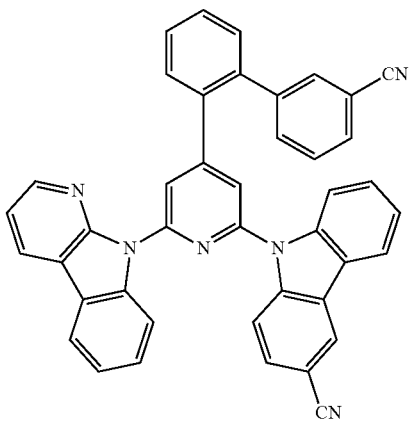

621
-continued
105
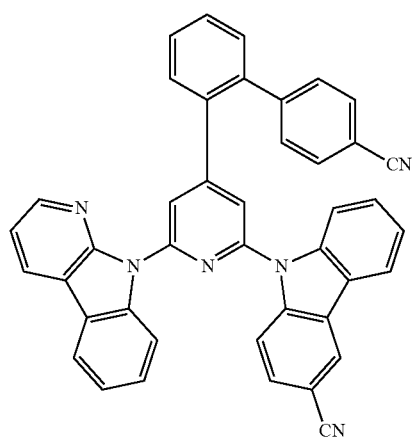
106
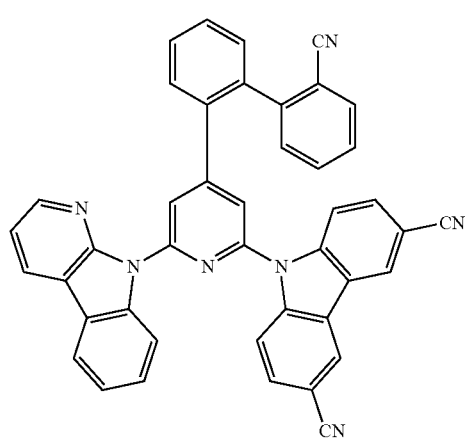
107
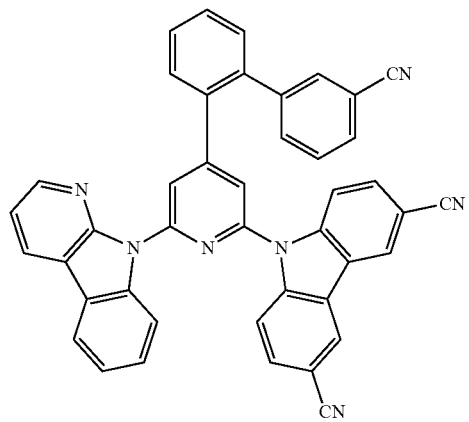
622
-continued
108
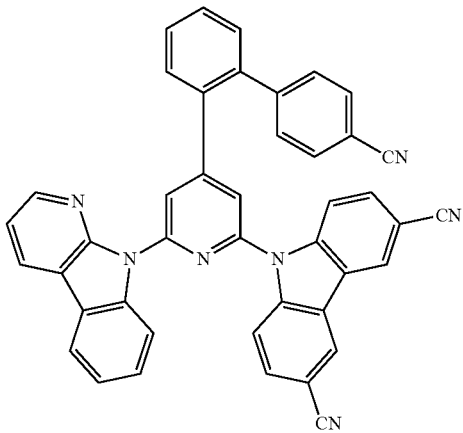
109
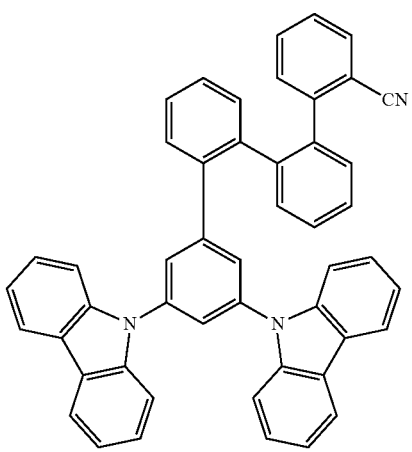
110
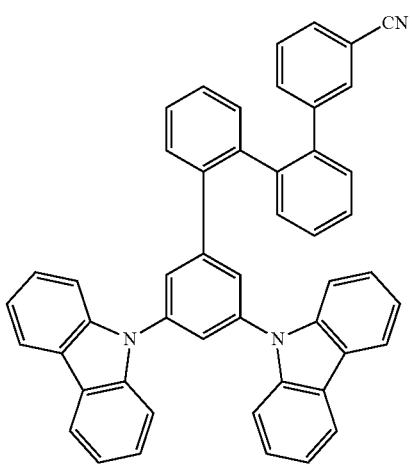

623
-continued
111
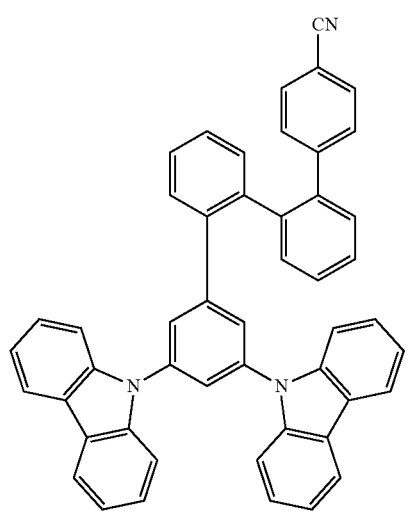
112
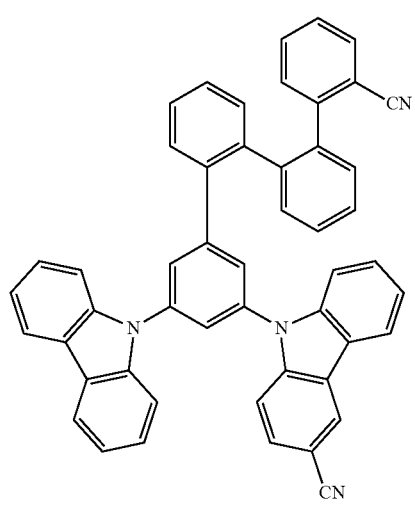
113
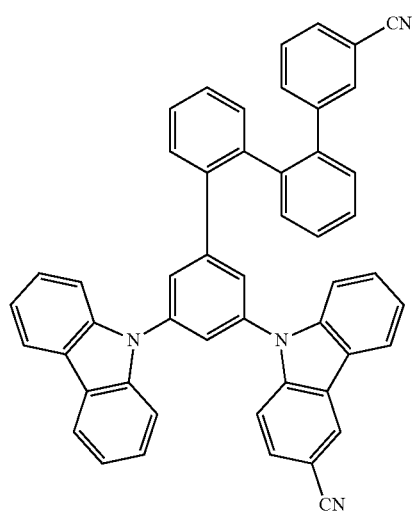
624
-continued
114
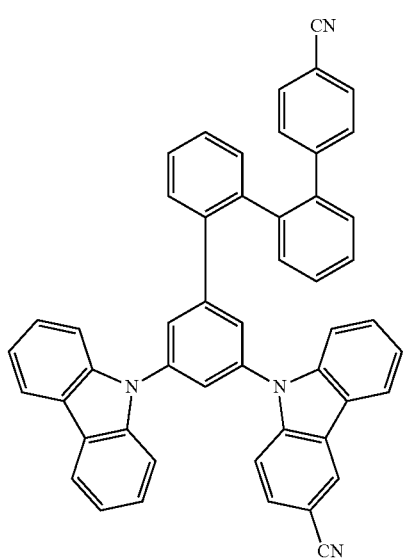
115
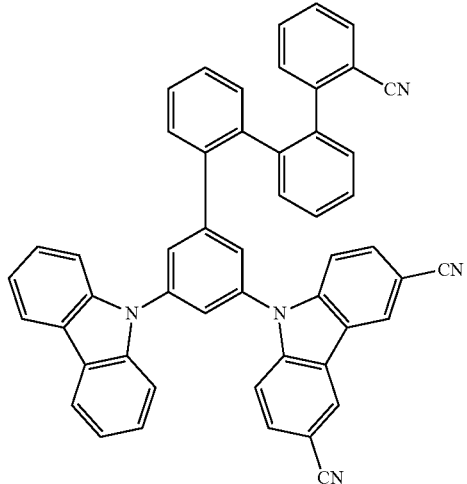
116
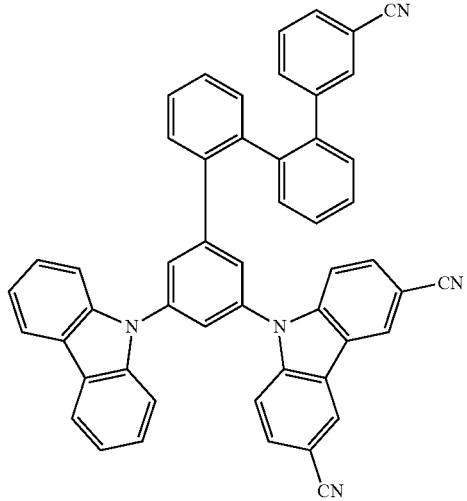

-continued
117
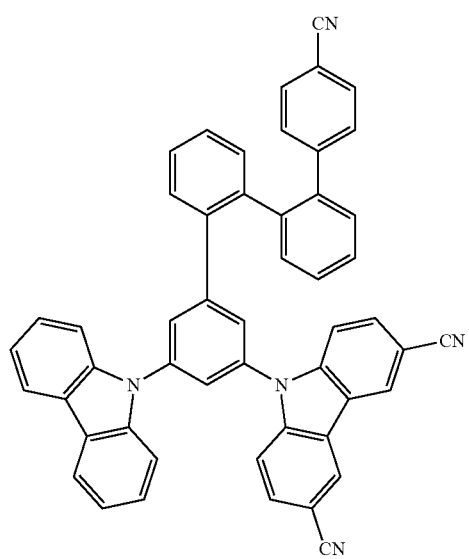
118
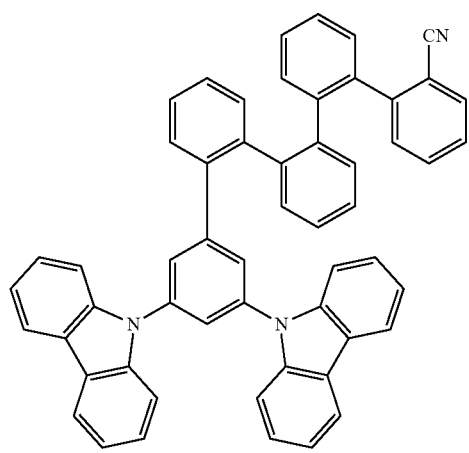
119
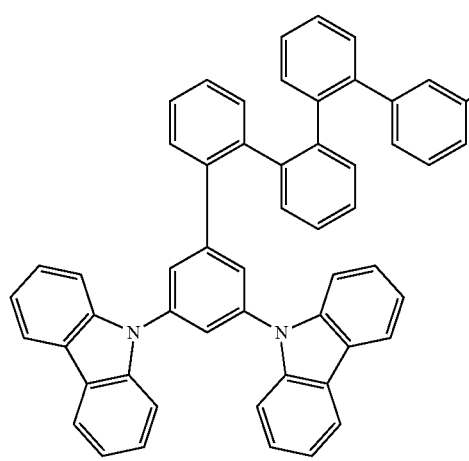
-continued
120
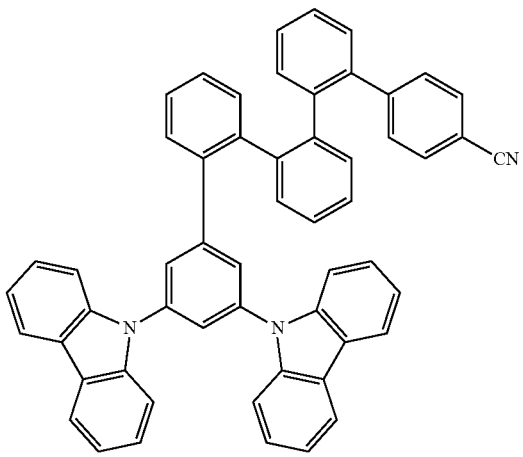
121
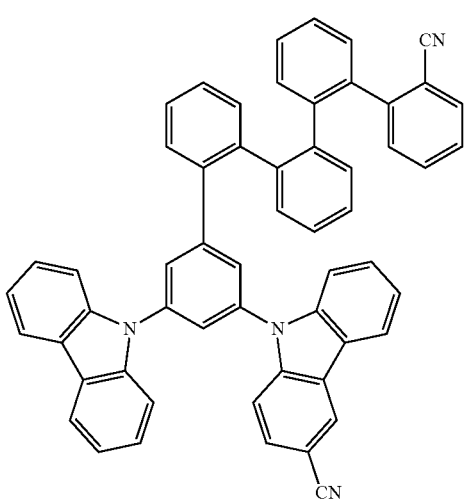
122
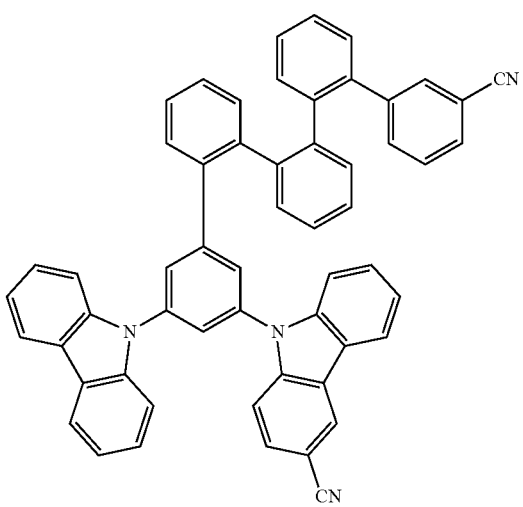

627
-continued
123
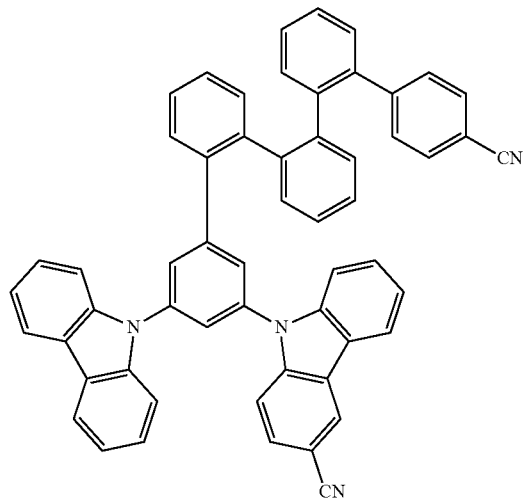
124
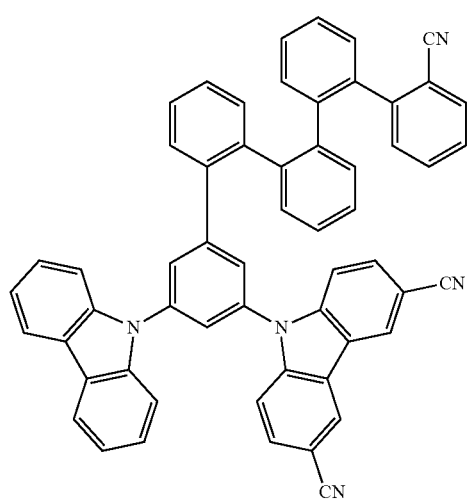
125
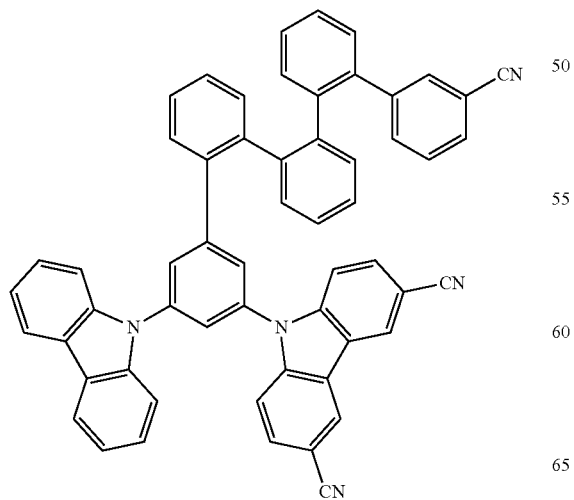
628
-continued
126
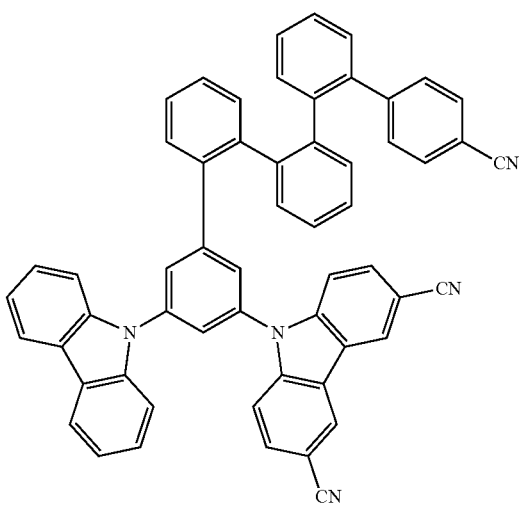
127
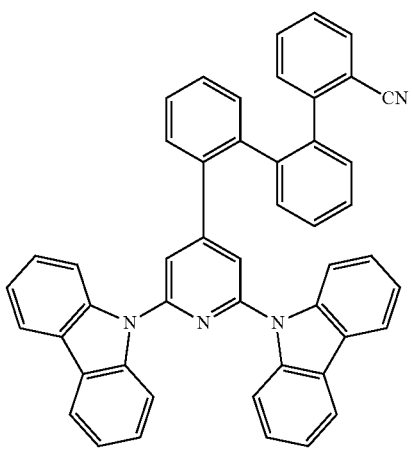
128
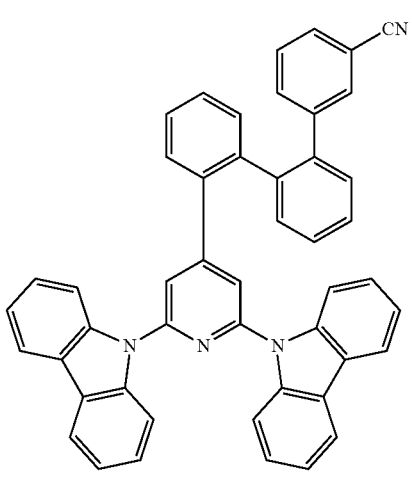

-continued
129
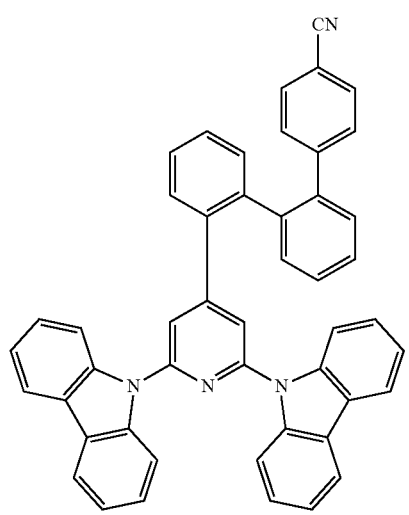
130
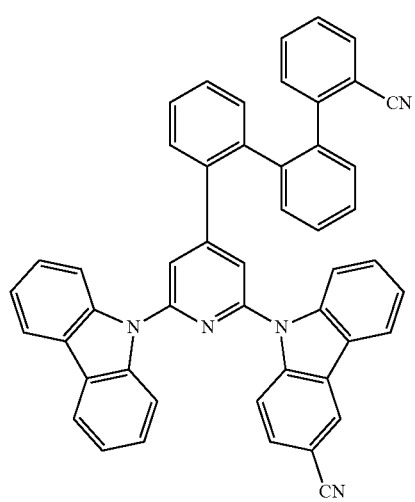
131
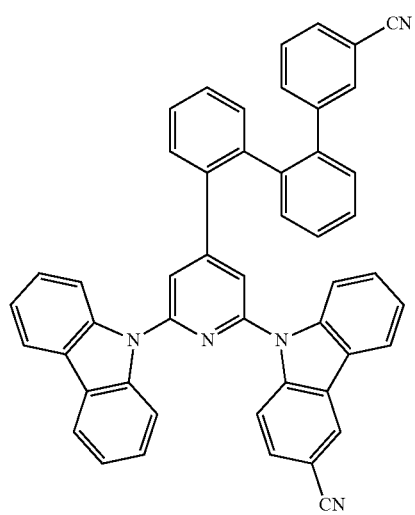
-continued
132
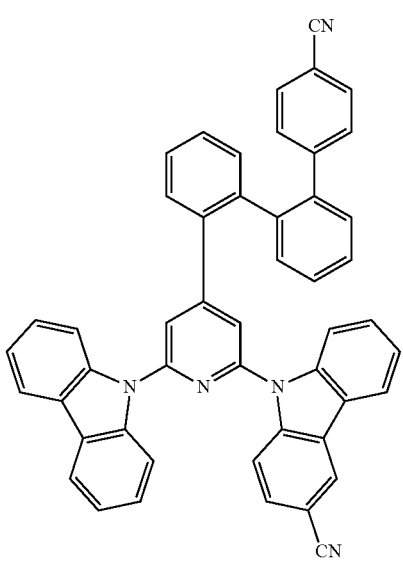
133
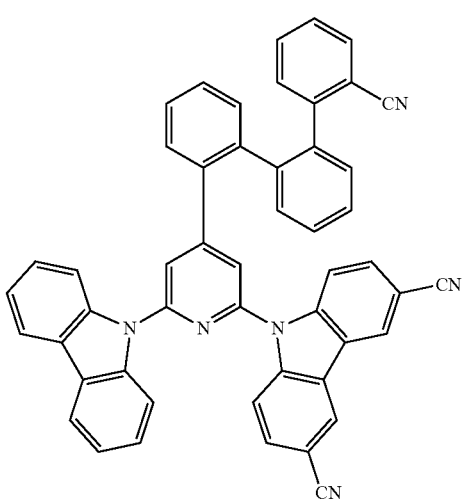
134
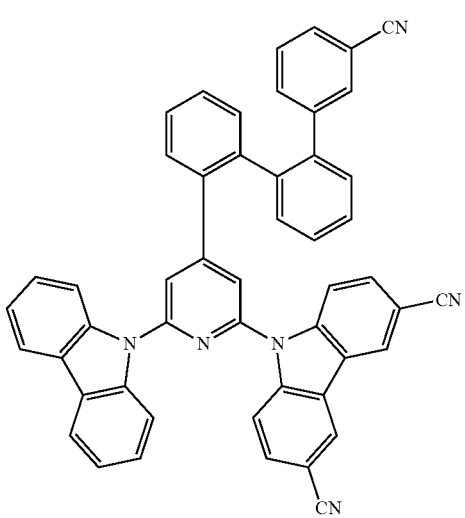

631
-continued
135
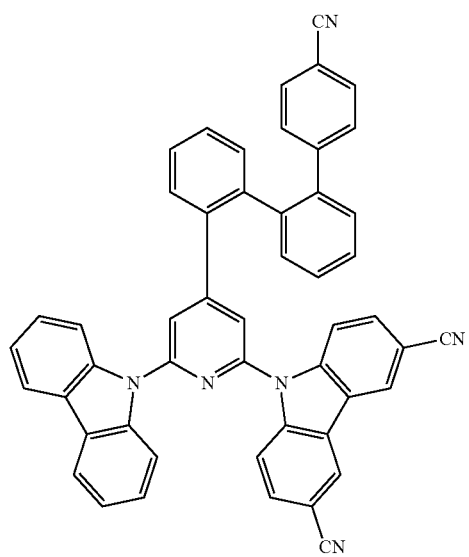
136
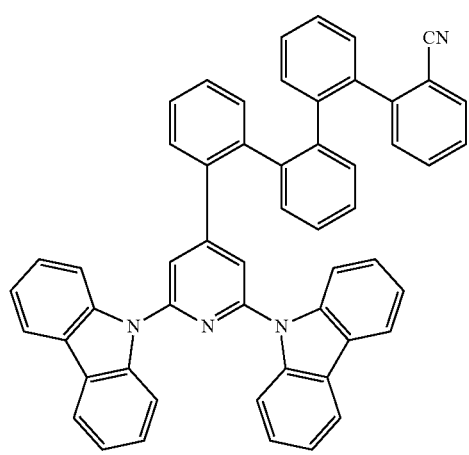
137
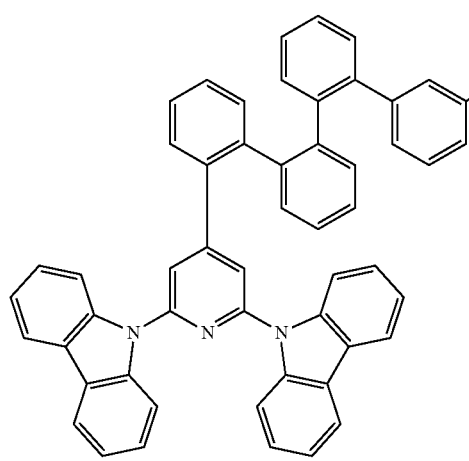
632
-continued
138
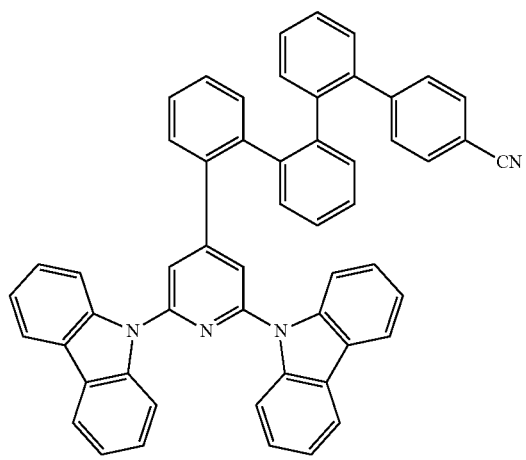
139
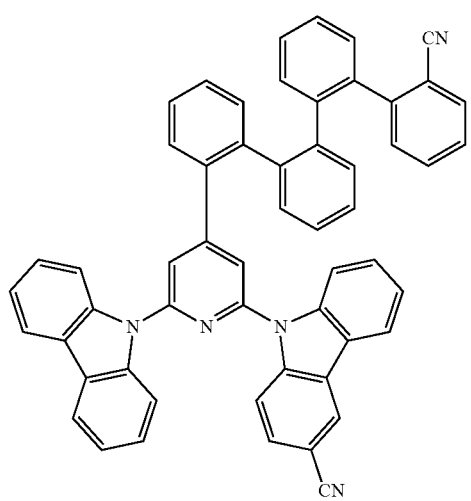
140
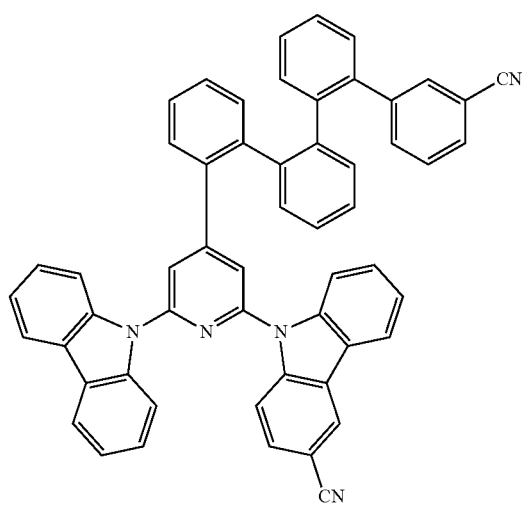

141
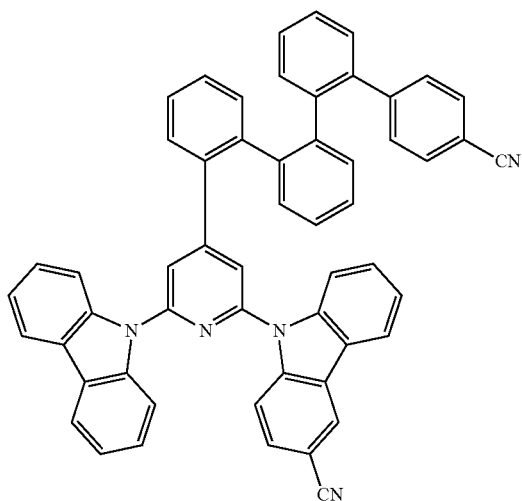
142
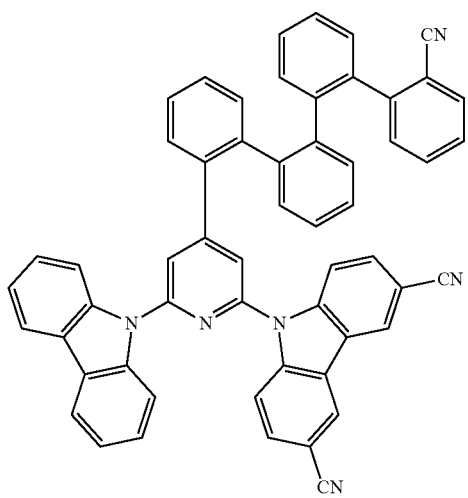
143
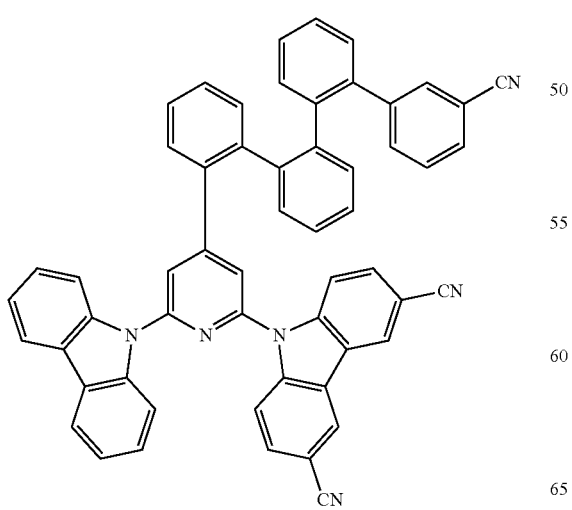
144
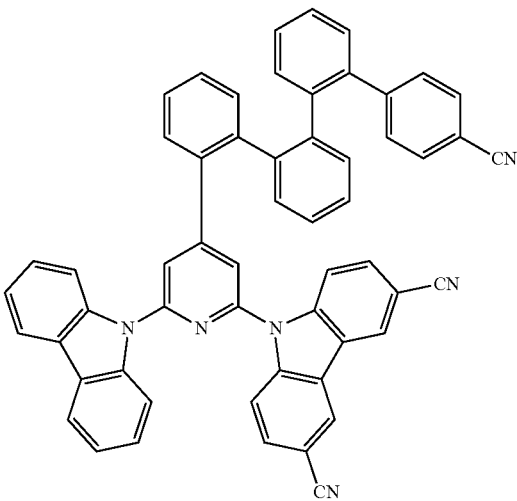
145
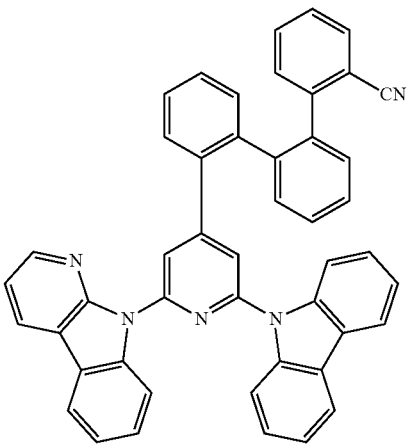
146
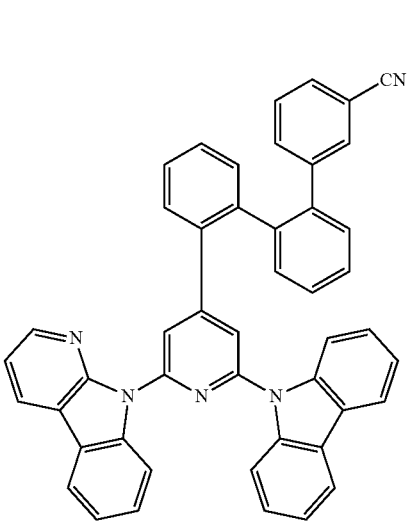

147
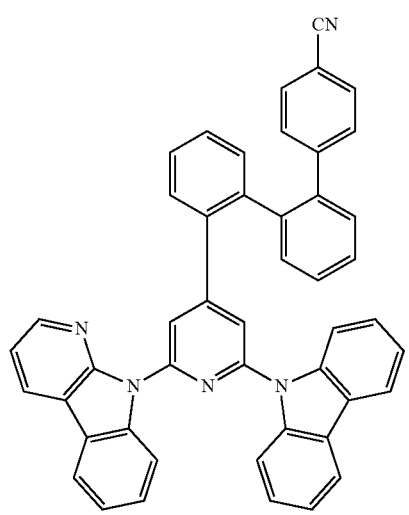
148
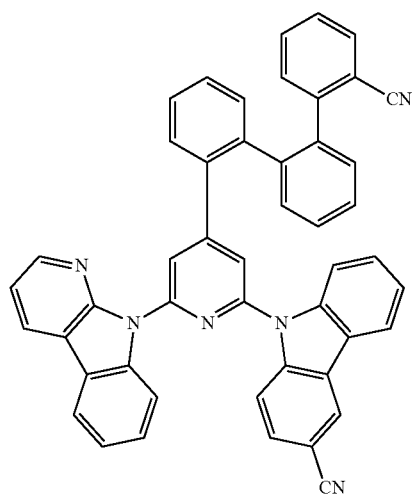
149
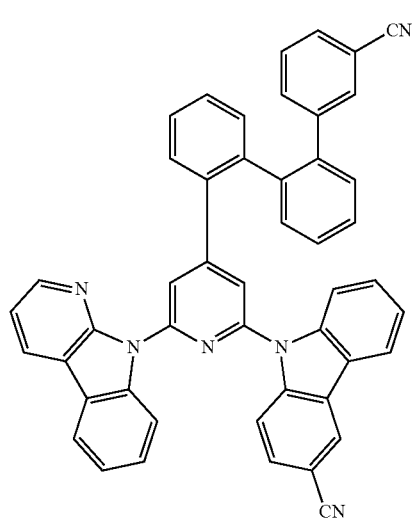
150
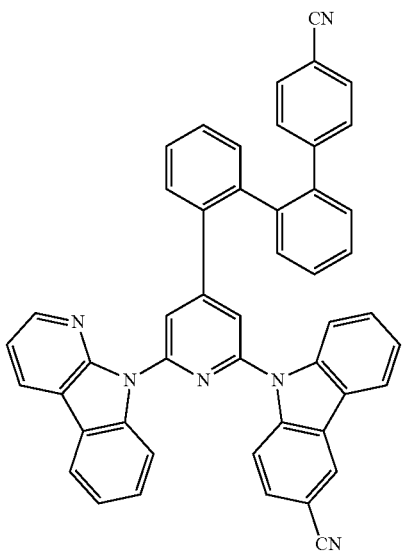
151
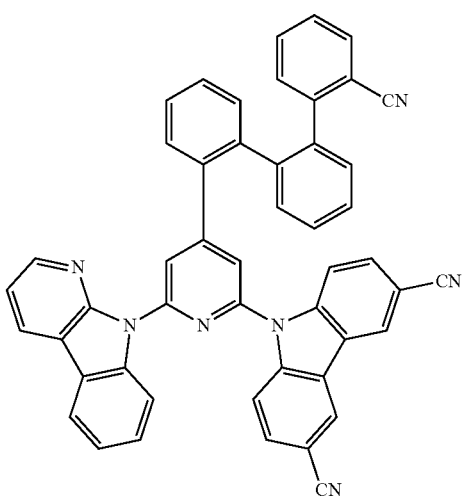
152
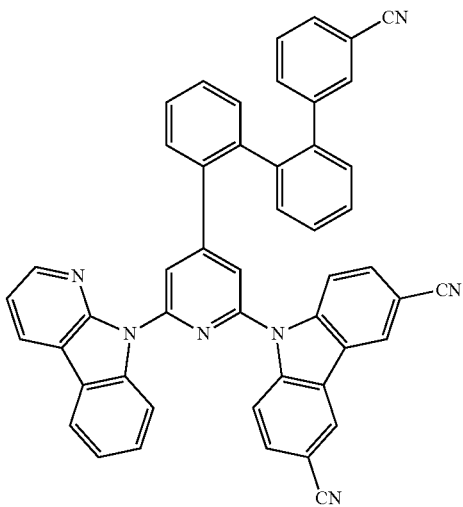

153
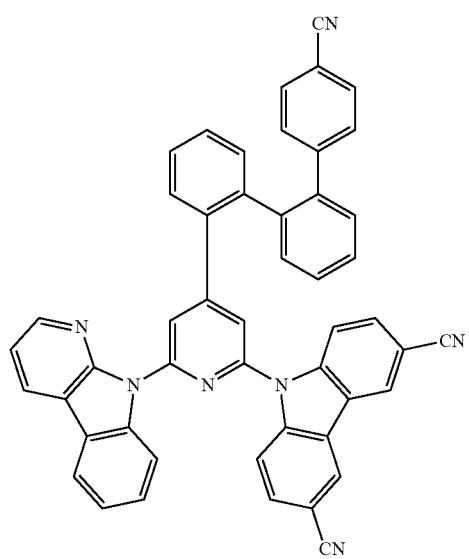
154
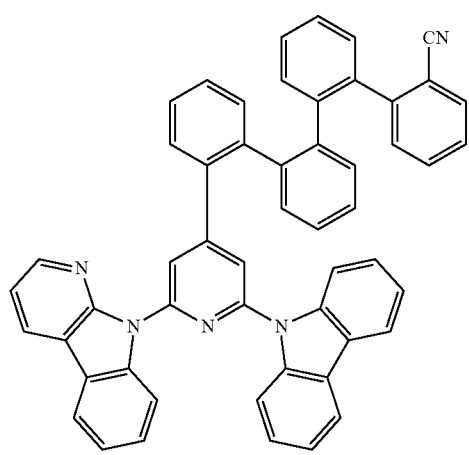
155
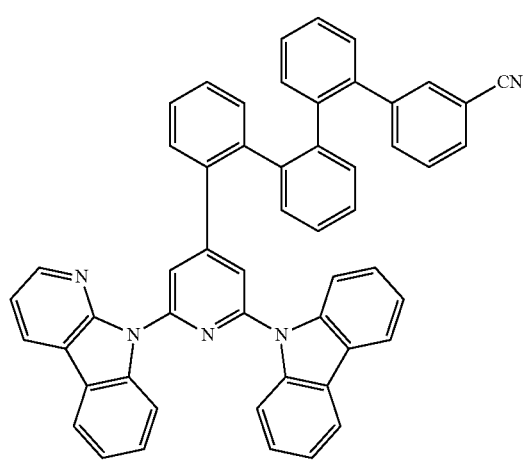
156
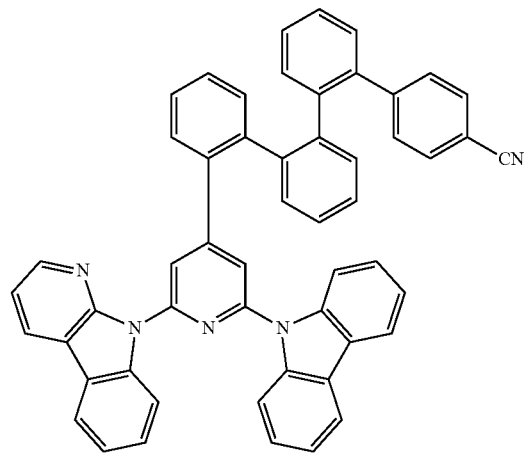
157
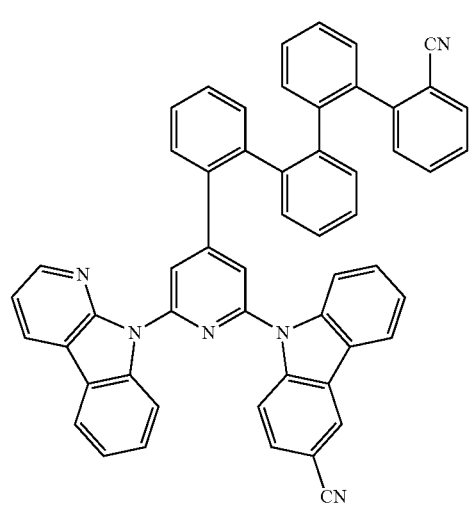
158
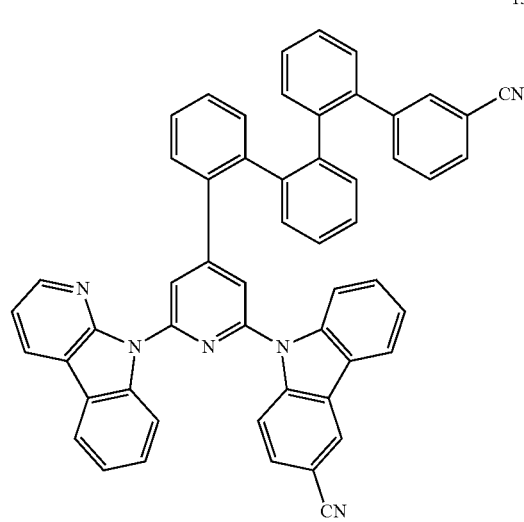

159
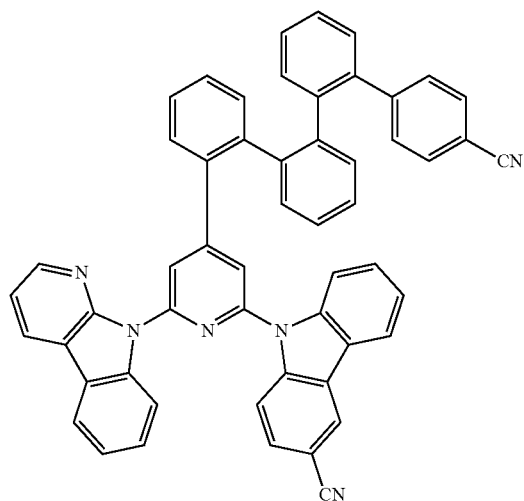
162
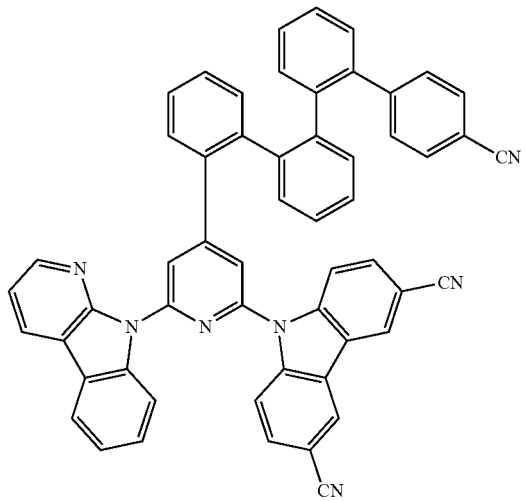
160
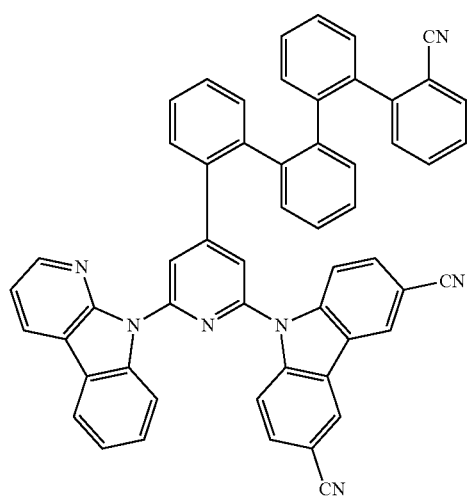
163
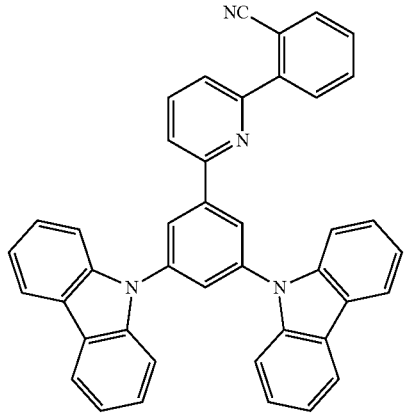
161
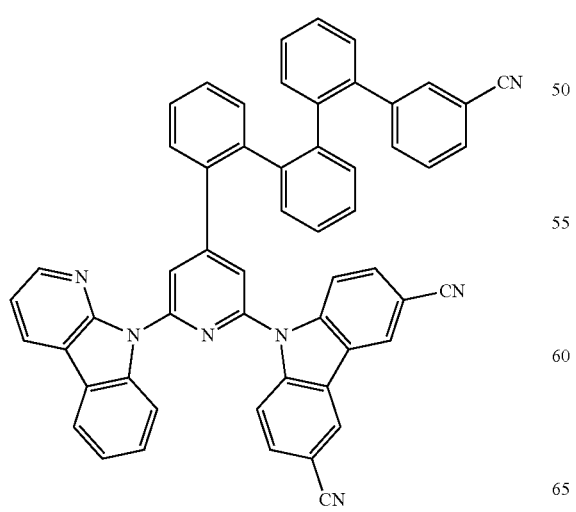
164
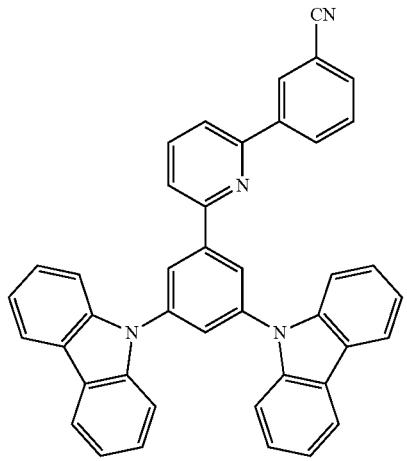

-continued
165
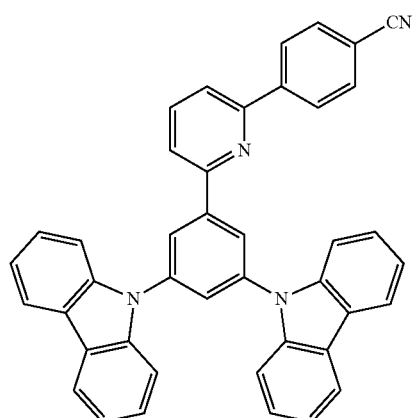
166
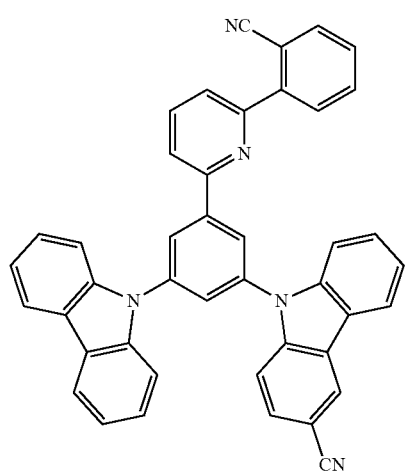
167
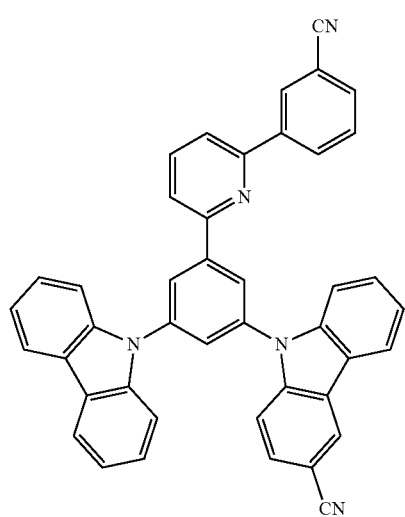
-continued
168
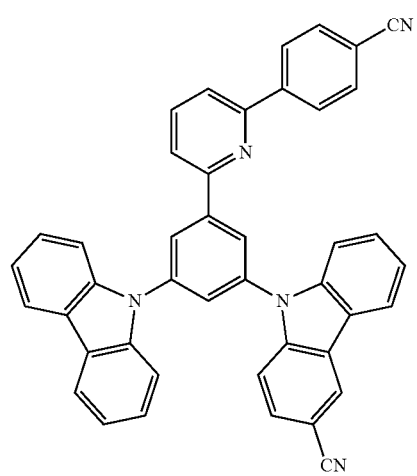
169
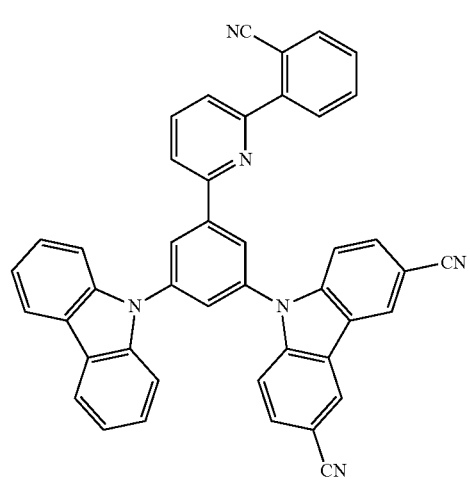
170
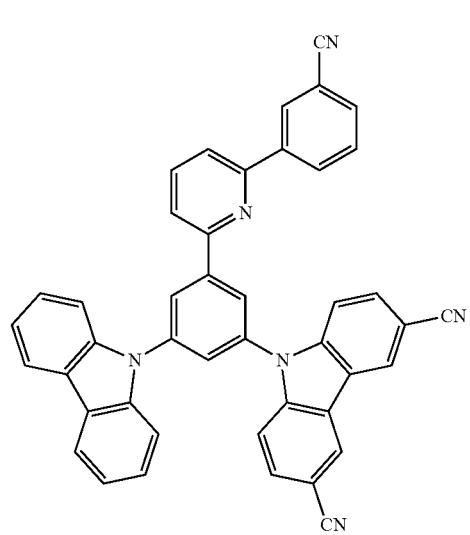

171
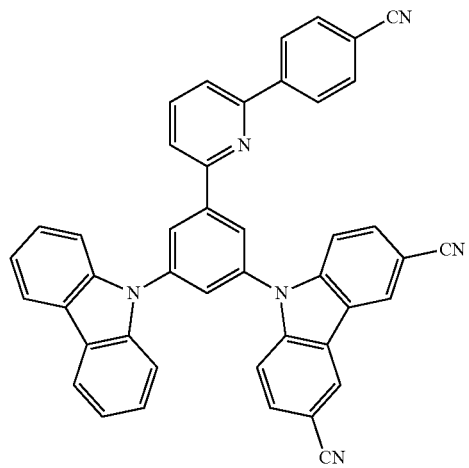
172
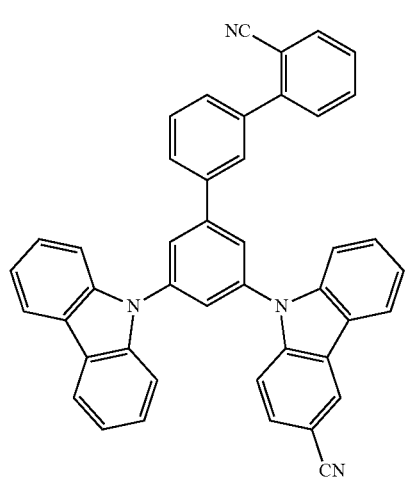
173
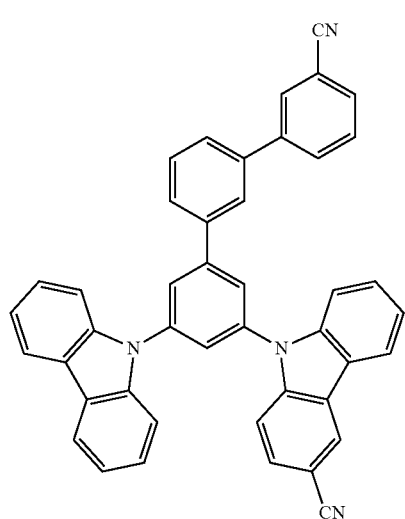
174
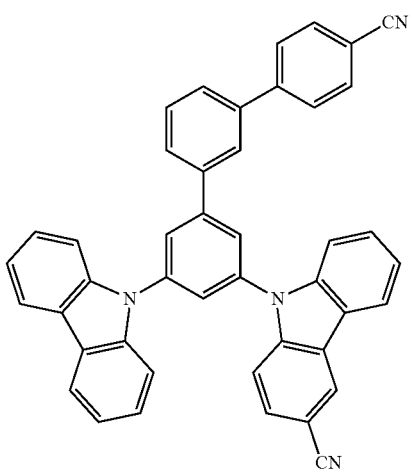
175
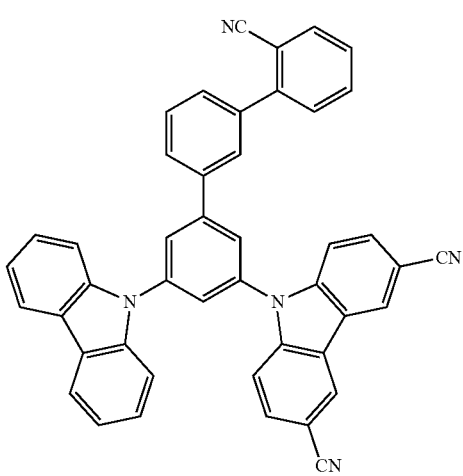
176
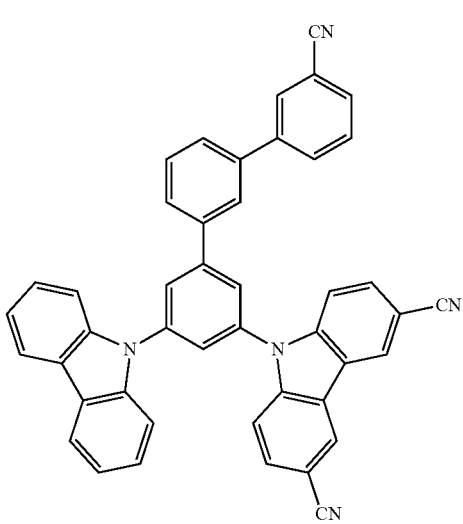

177
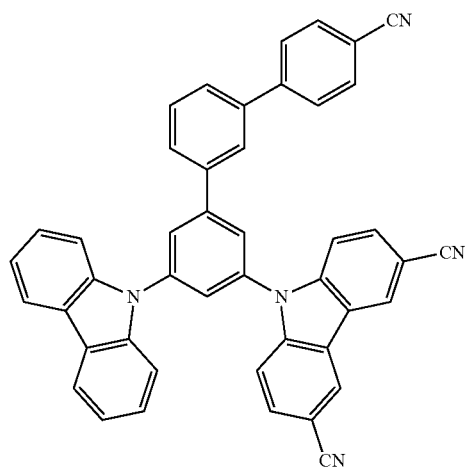
180
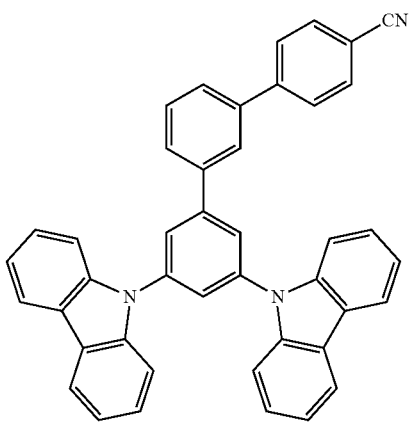
178
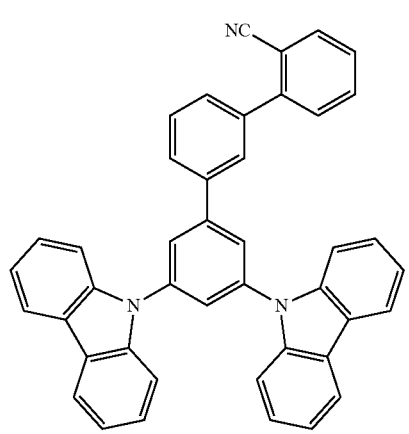
181
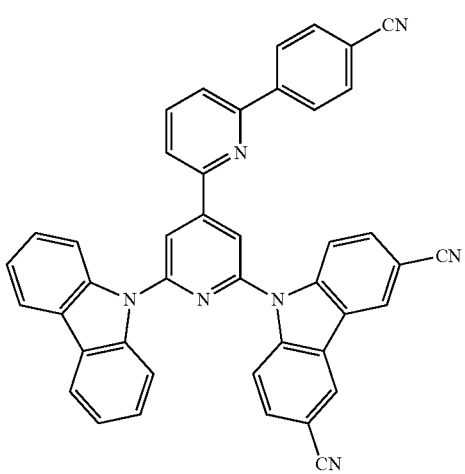
179
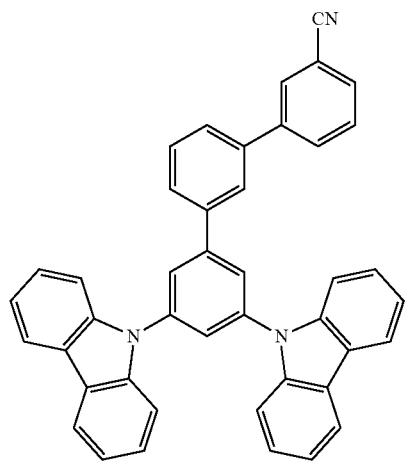
182
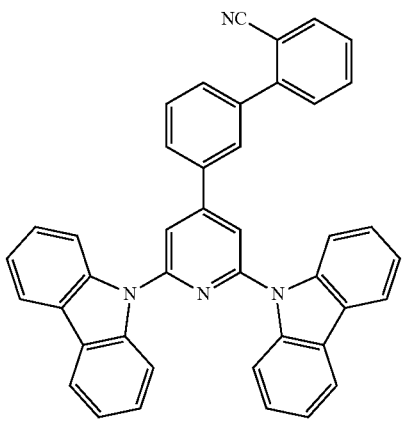

-continued
183
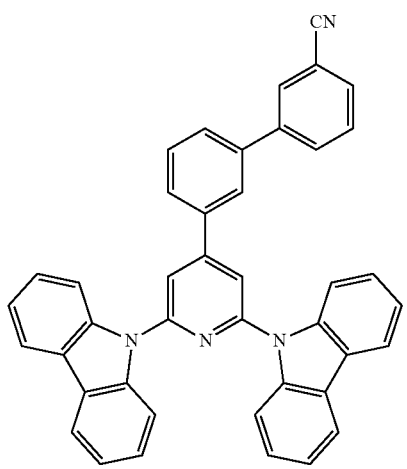
184
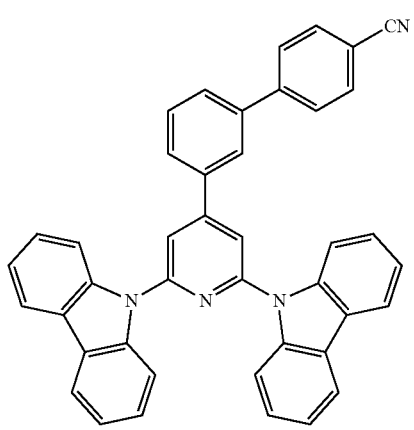
185
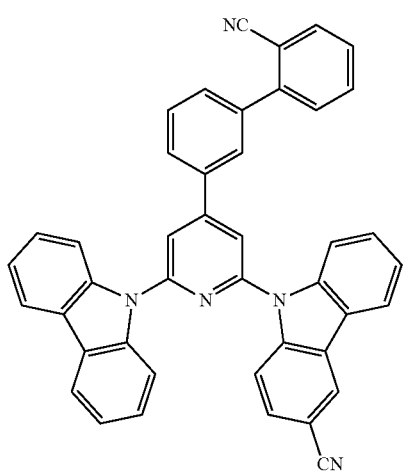
-continued
186
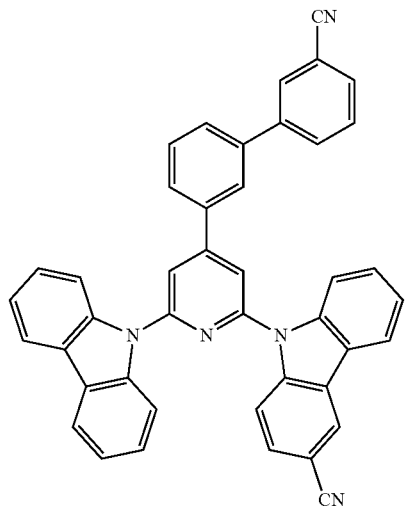
187
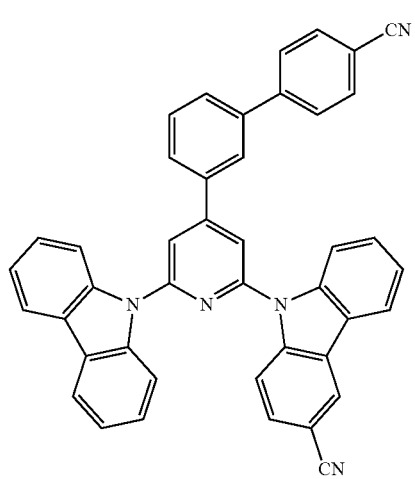
188
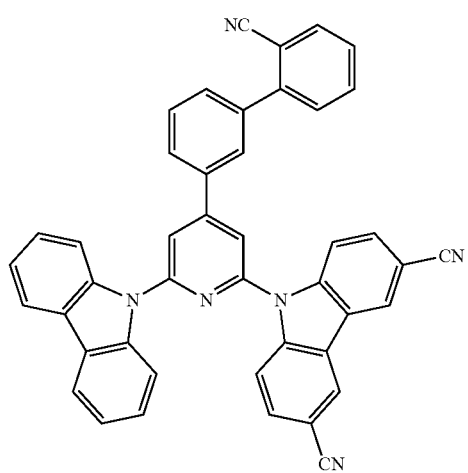

649
-continued
189
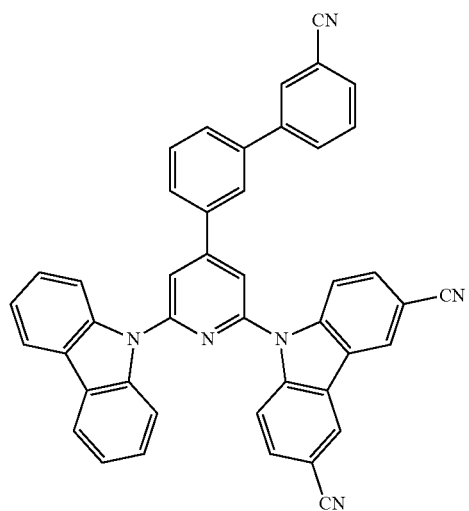
190
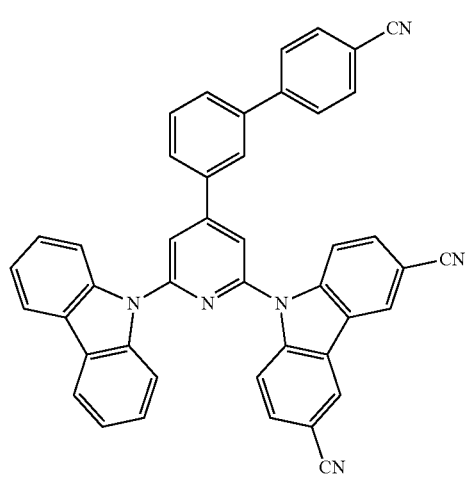
191
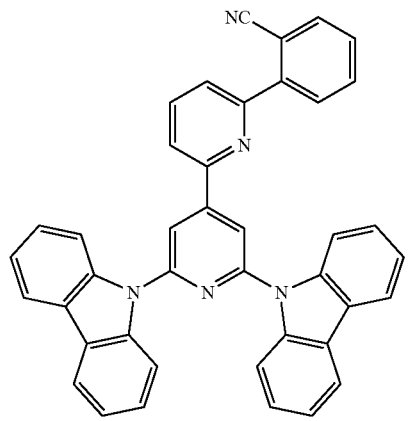
650
-continued
192
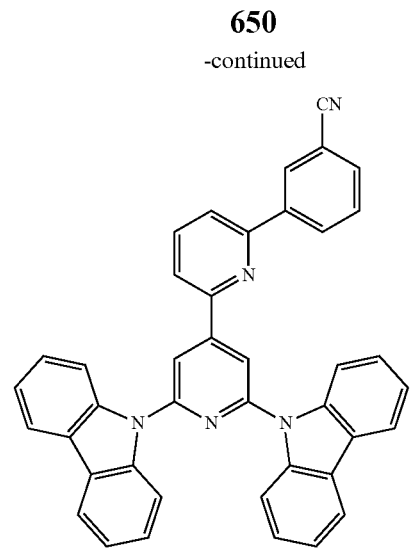
193
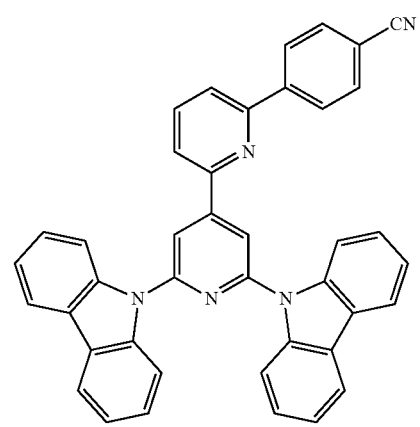
194
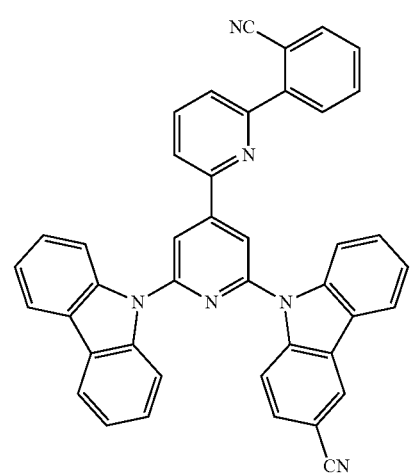

195
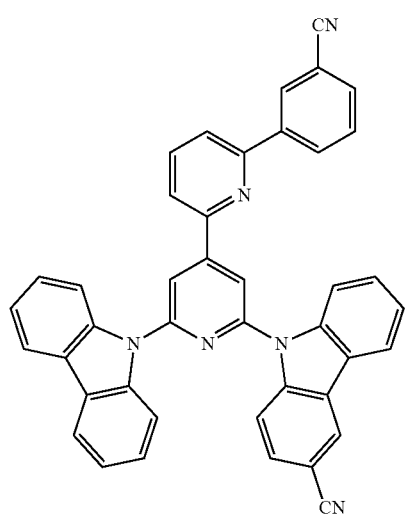
196
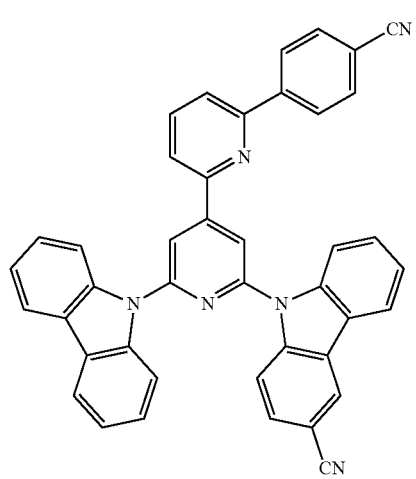
197
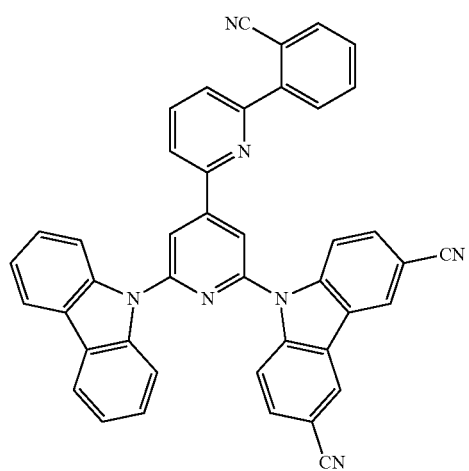
198
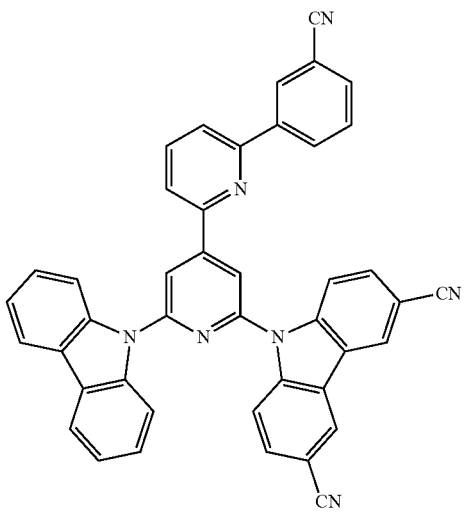
199
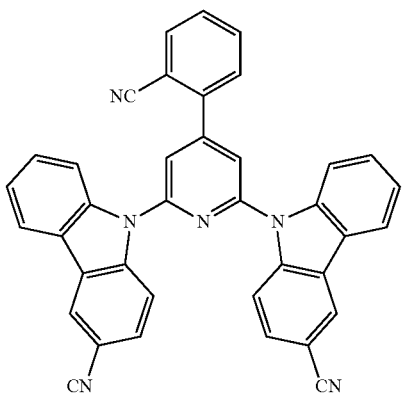
200
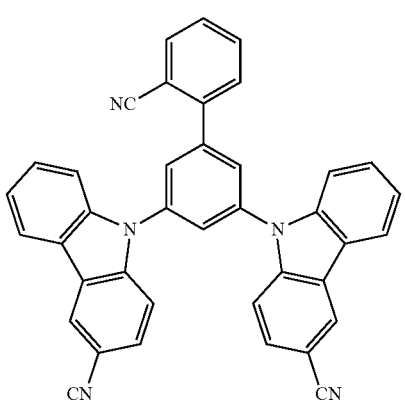

201
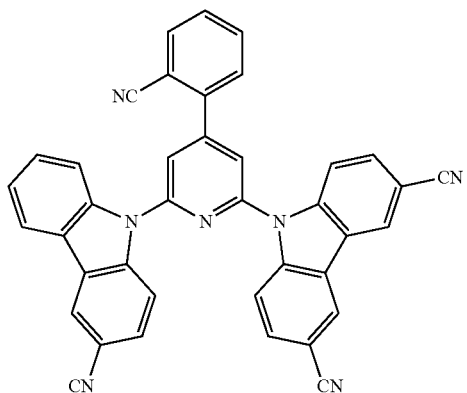
202
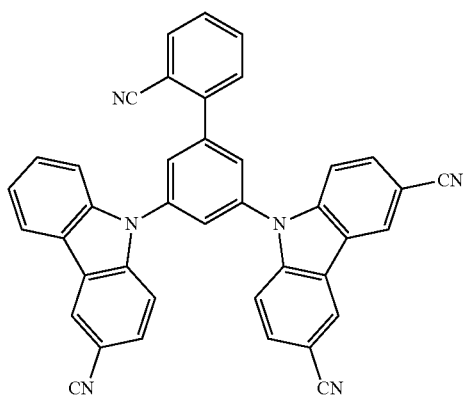
Group HE6
1
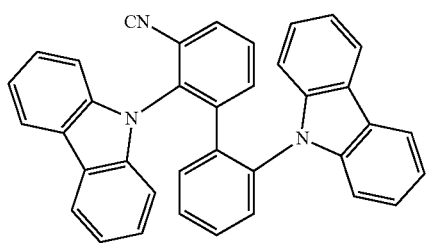
2
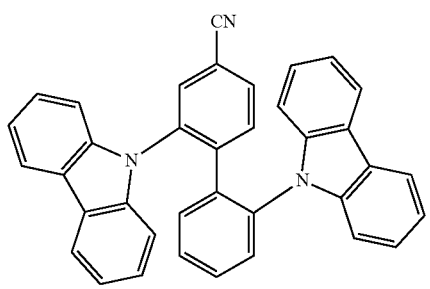
3
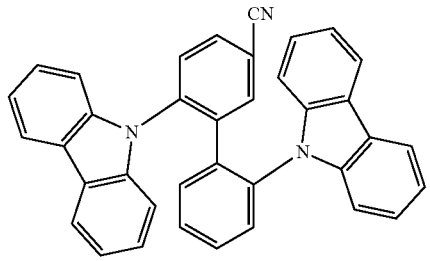
4
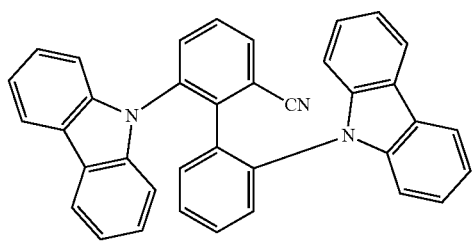
5
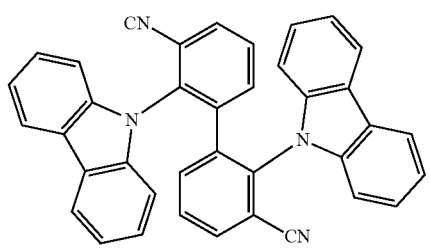
6
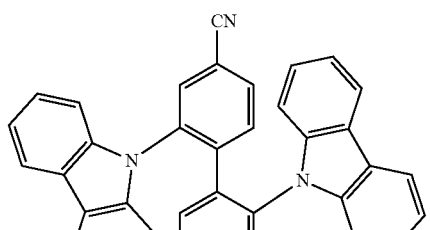
7

8
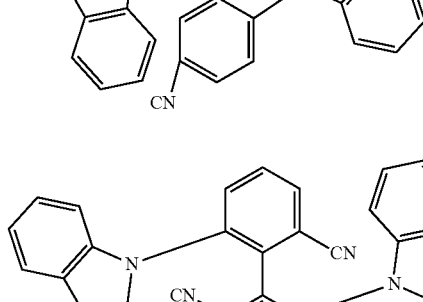

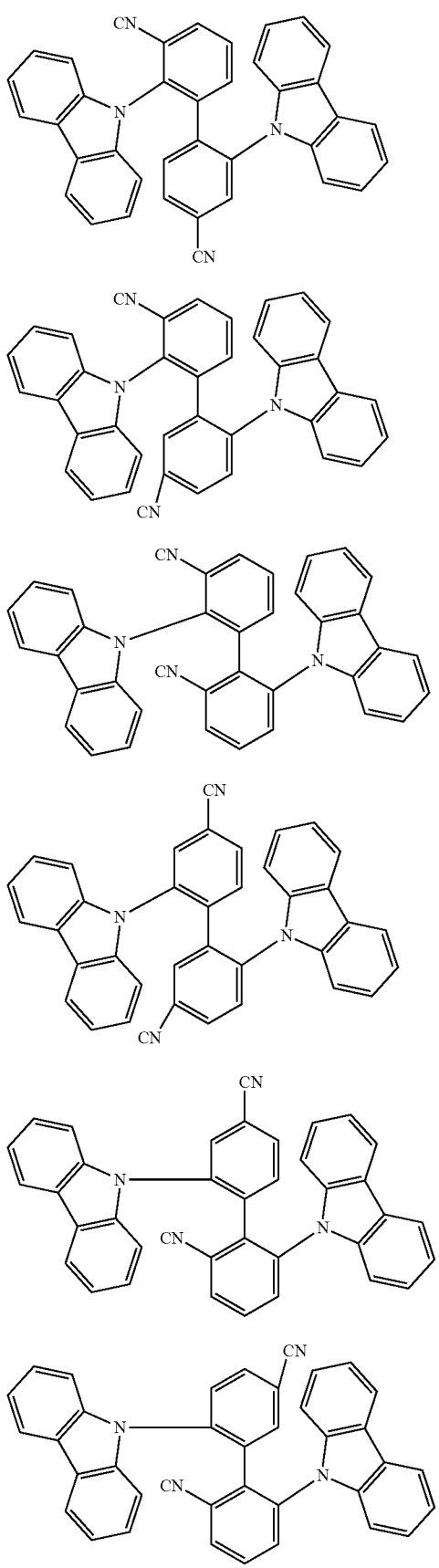
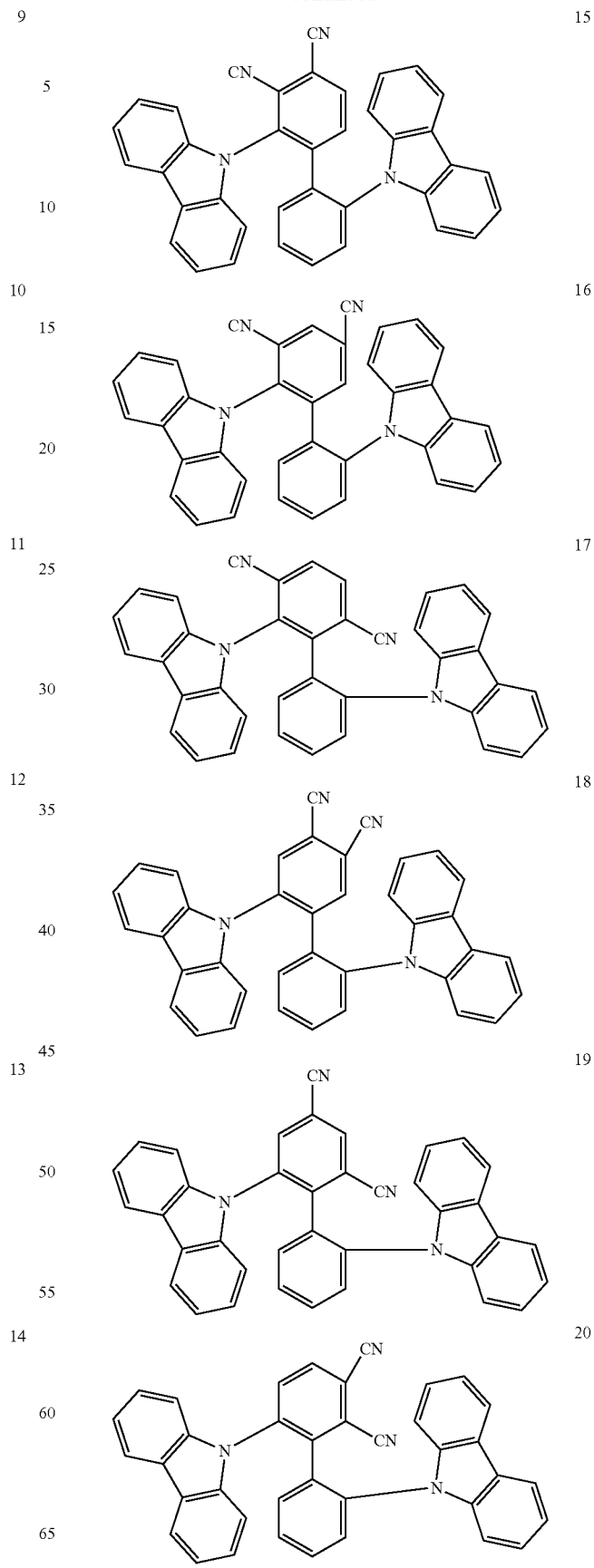

21
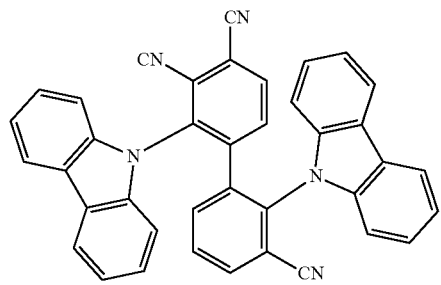
22
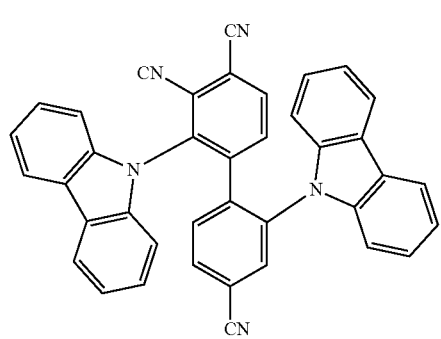
23
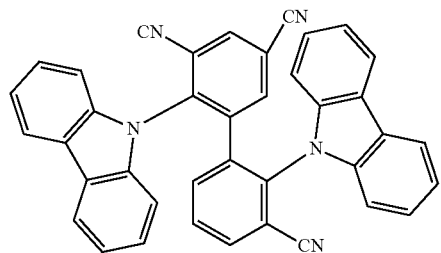
24
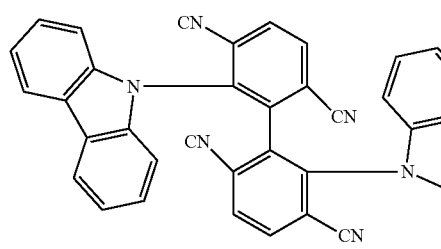
25
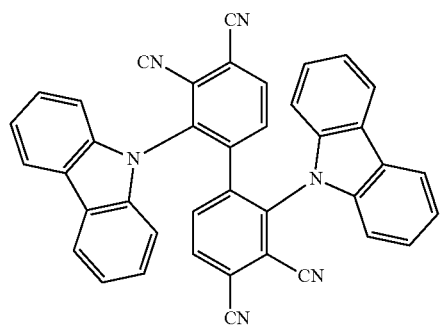
26
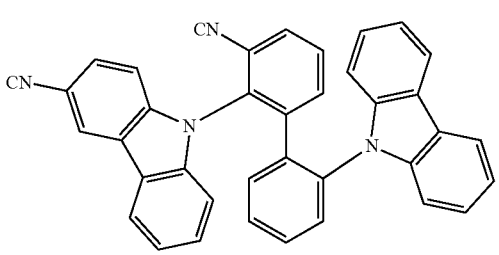
27
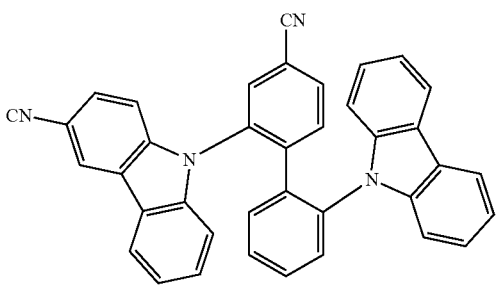
28
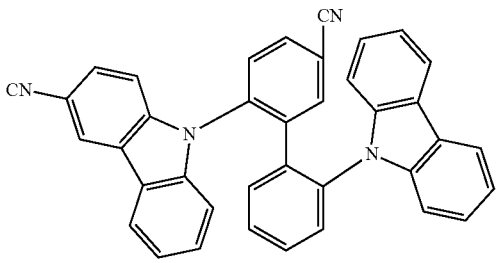
29
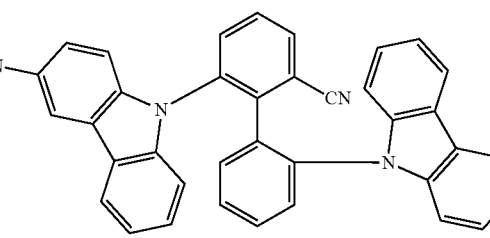
30
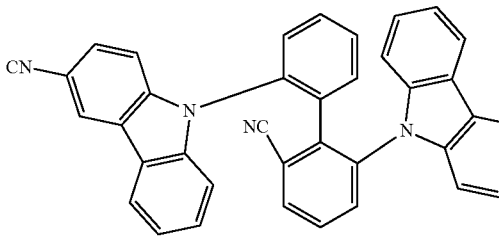
31
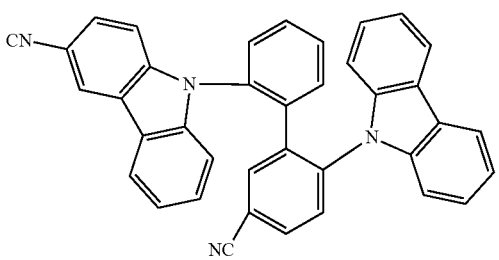

-continued
32
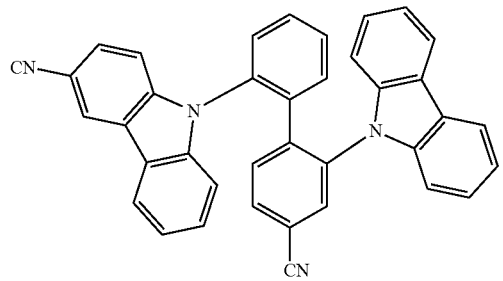
33
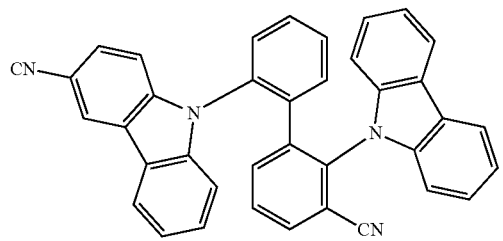
34
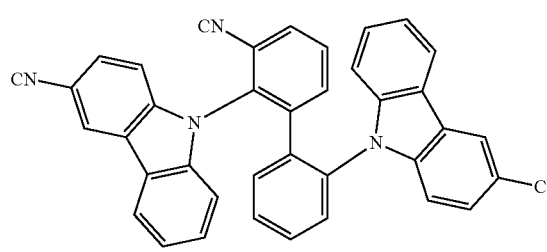
35
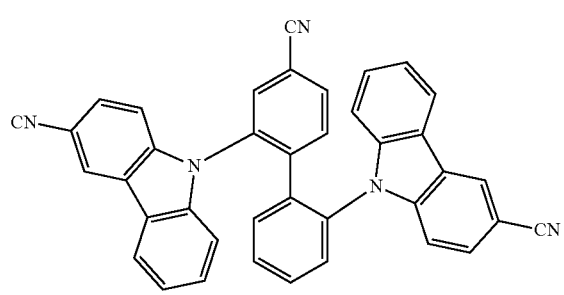
36
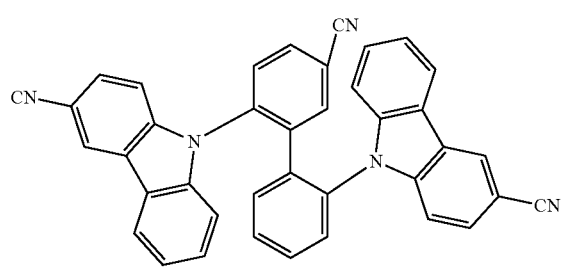
37
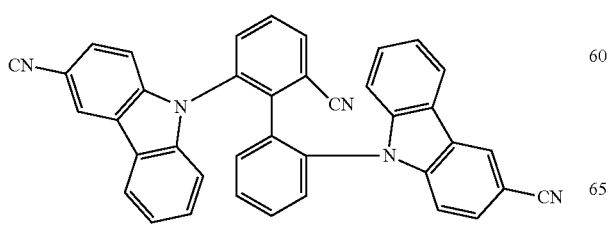
-continued
38
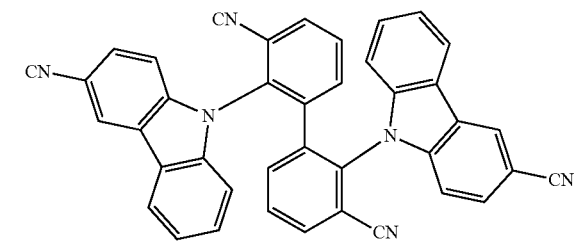
39
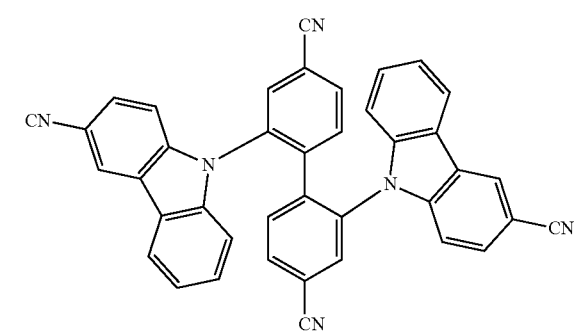
40
41
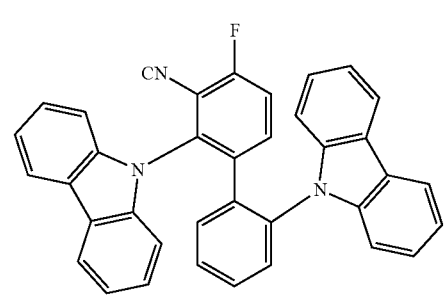
42
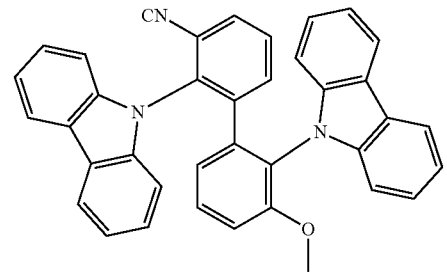

43
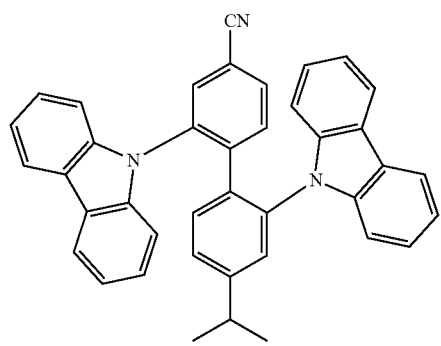
44
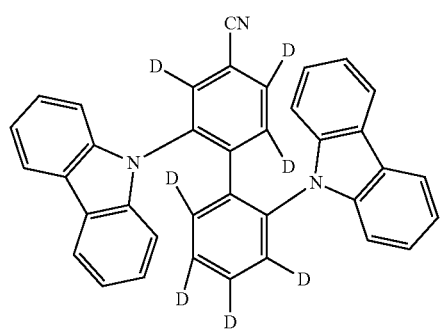
45
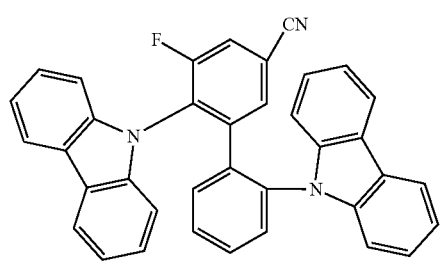
46
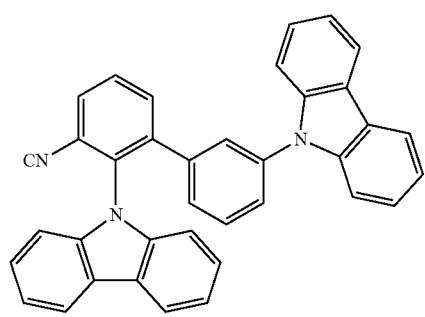
47
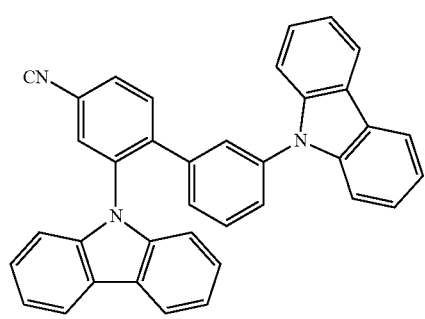
48
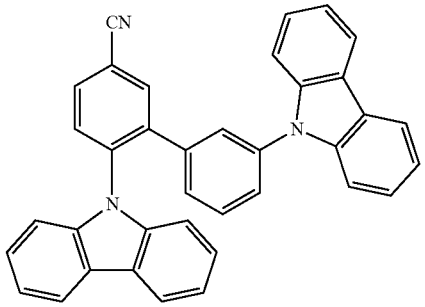
49
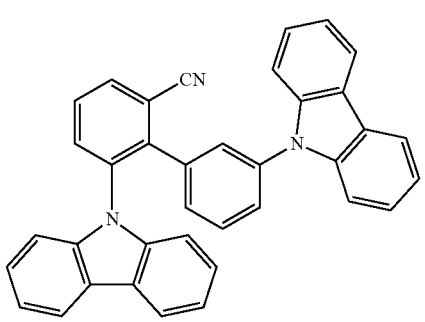
50
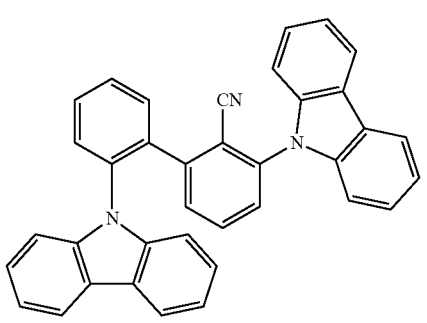
51
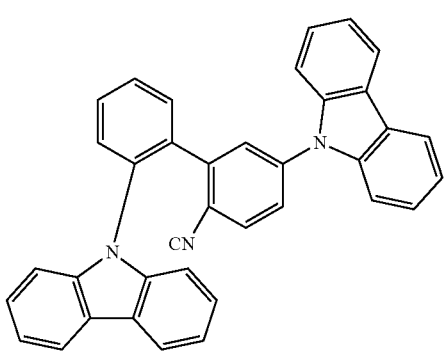
52
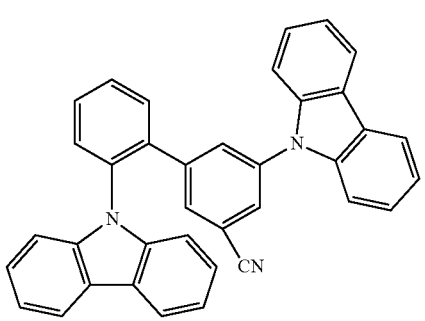

| | |
|---|---|
| 53 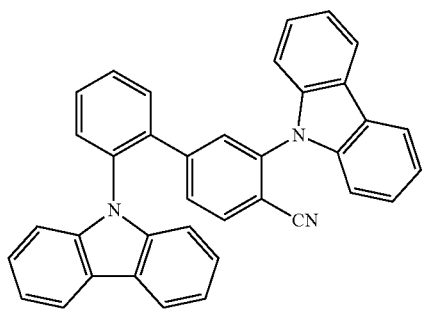 | 58 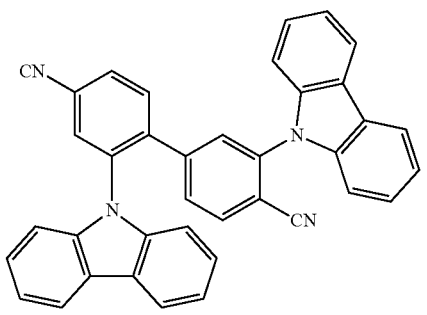 |
| 54 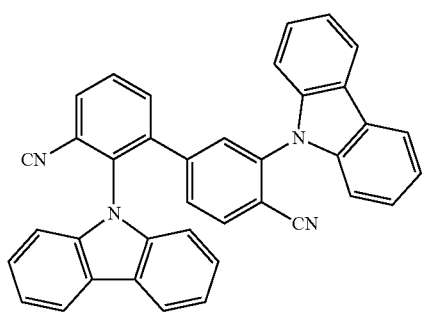 | 59 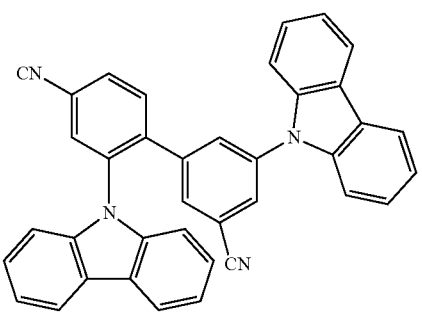 |
| 55 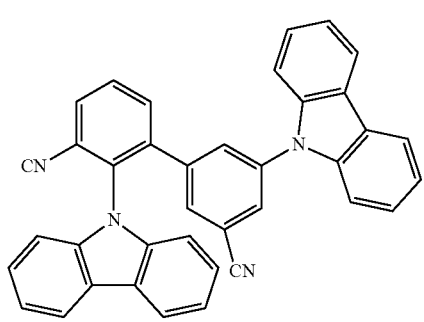 | 60 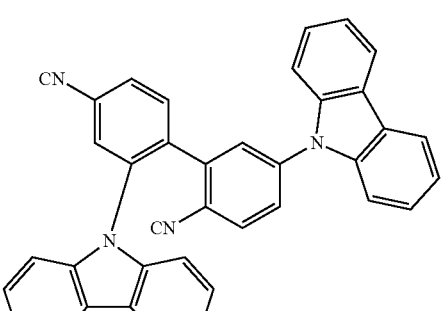 |
| 56 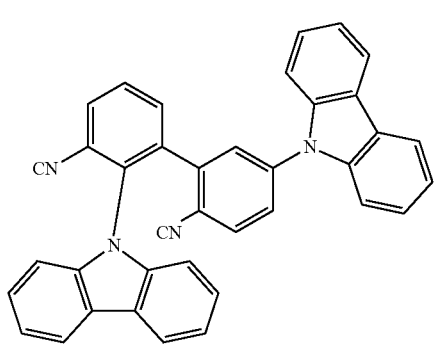 | 61 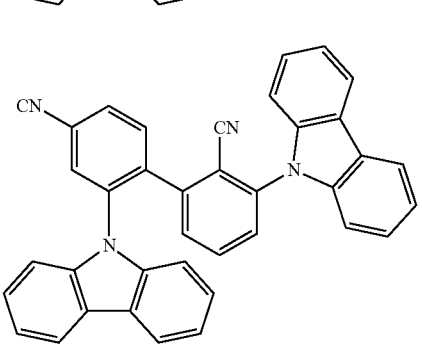 |
| 57 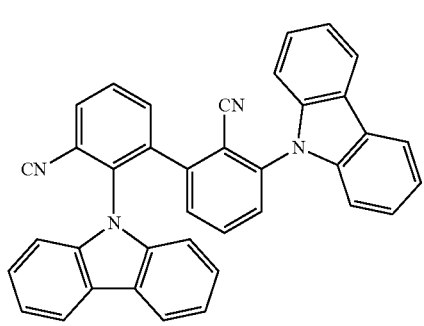 | 62 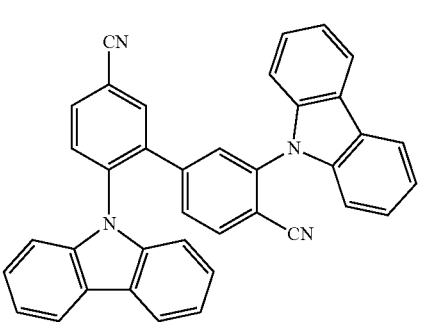 |

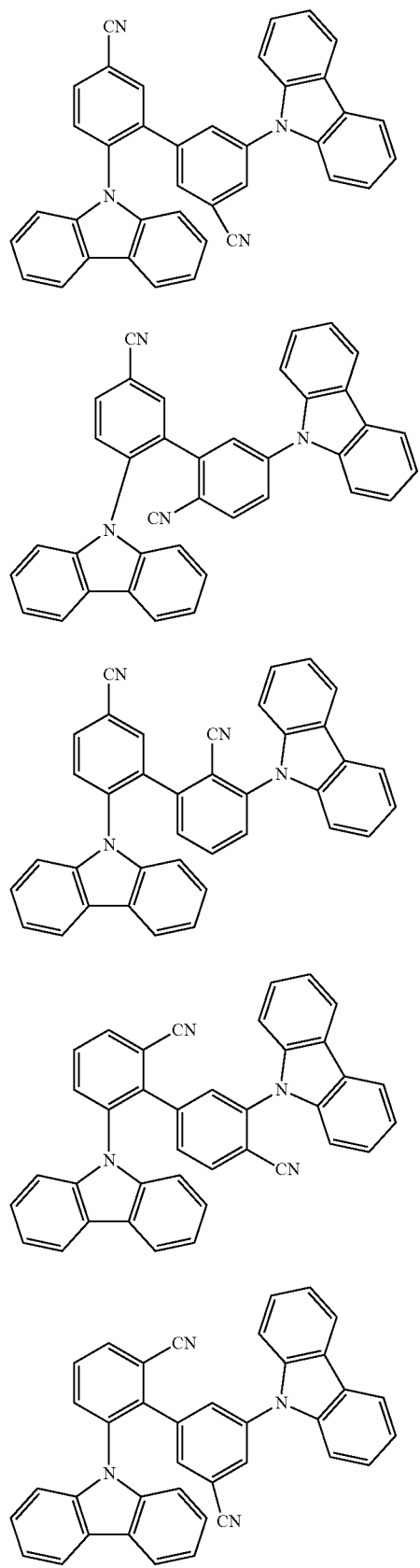
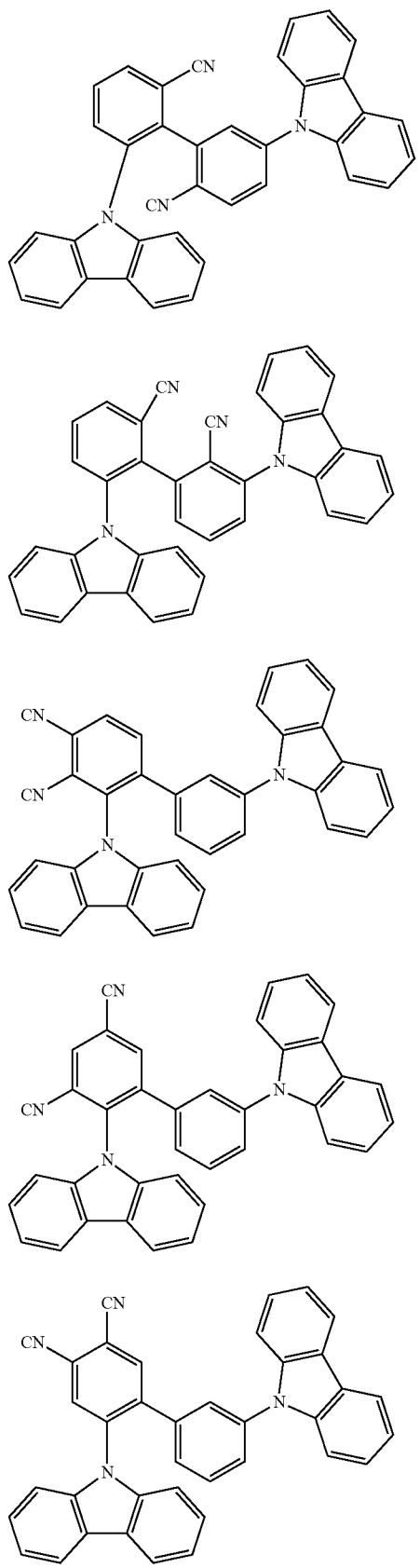

| 73 | 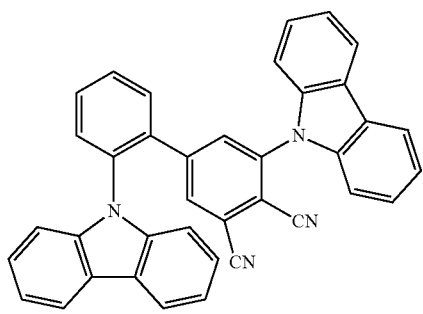 | 78 | 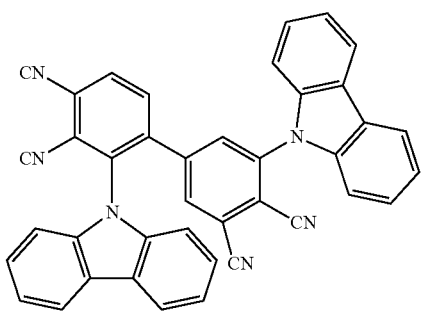 |
| 74 | 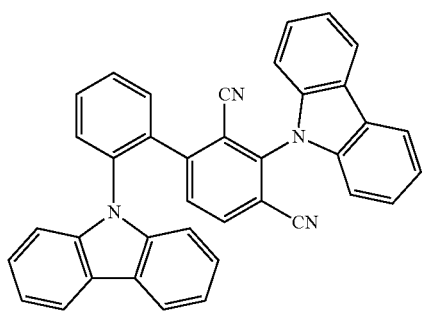 | 79 | 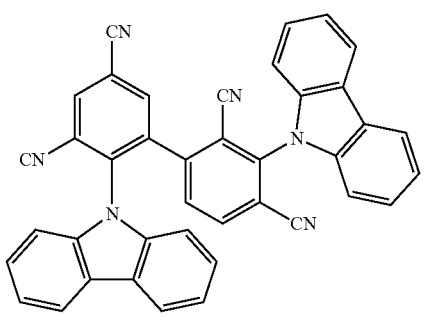 |
| 75 | 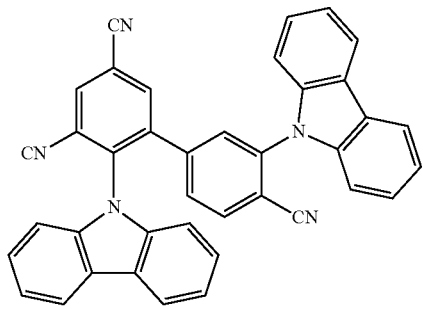 | 80 | 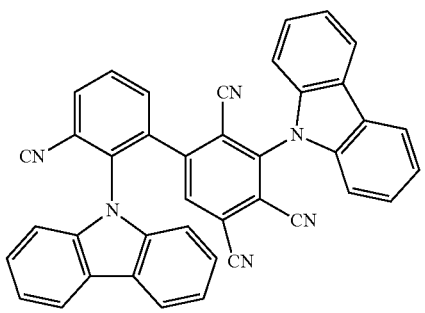 |
| 76 | 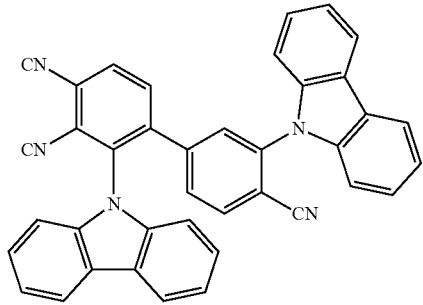 | 81 | 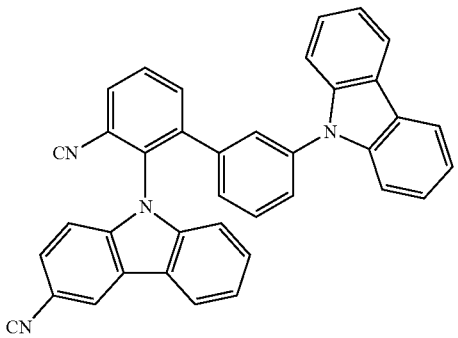 |
| 77 | 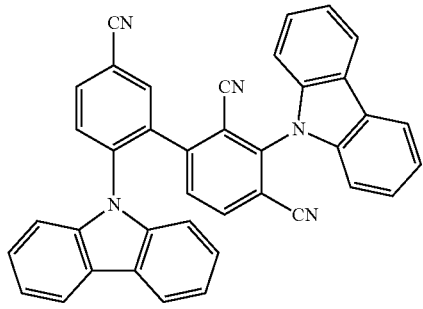 | 82 | 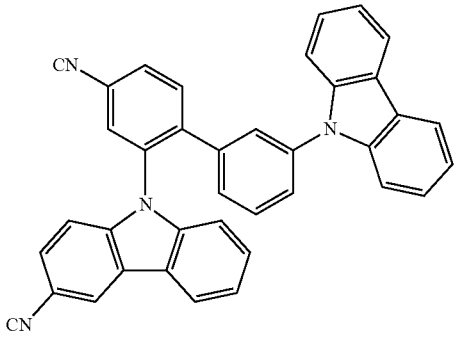 |

| 83 | 87 |
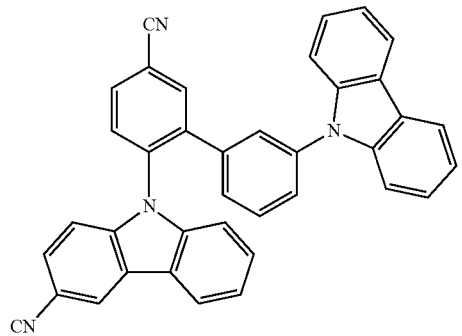
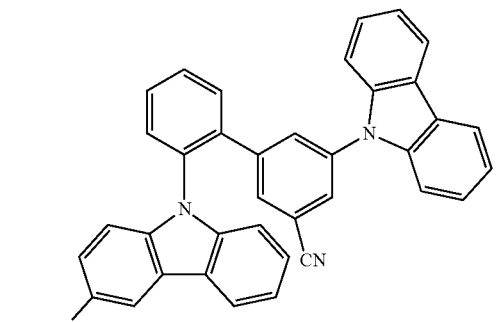
| 84 | 88 |
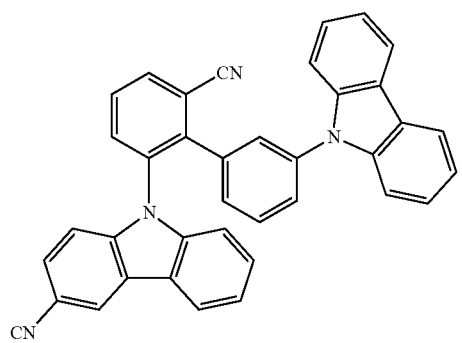
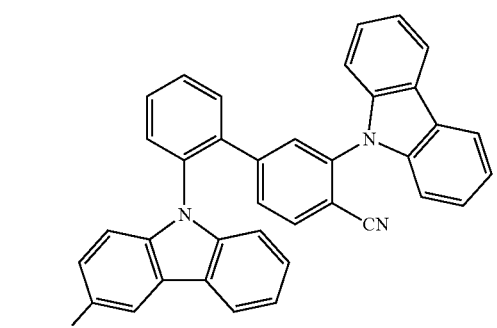
| 85 | 89 |
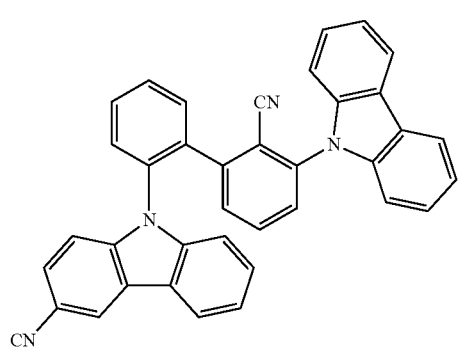
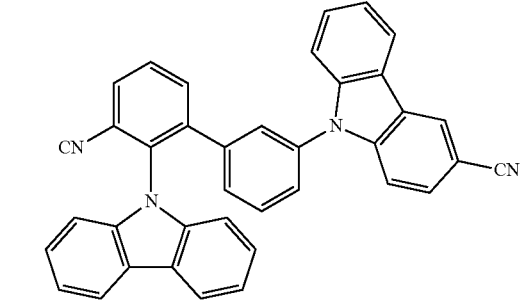
| | 90 |
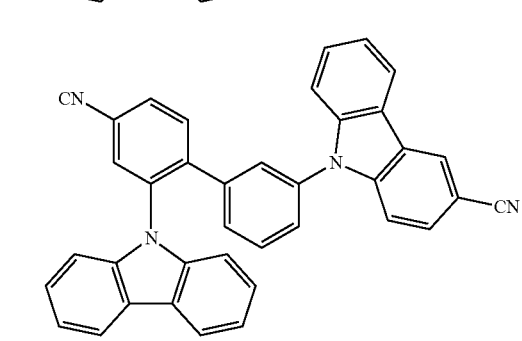
| 86 | 91 |
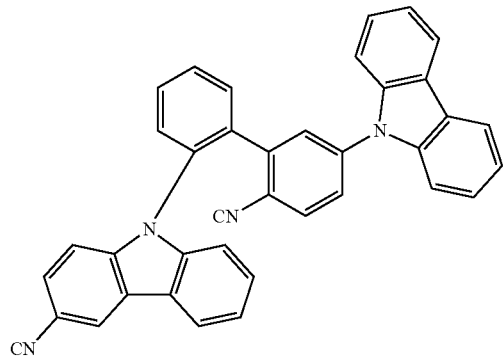
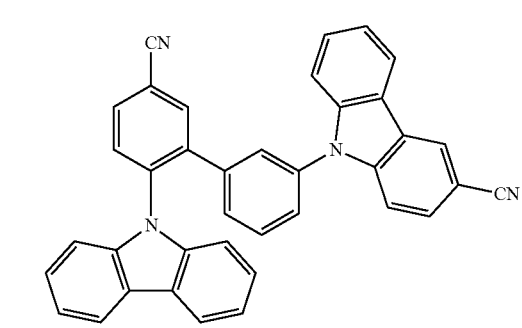

-continued
92
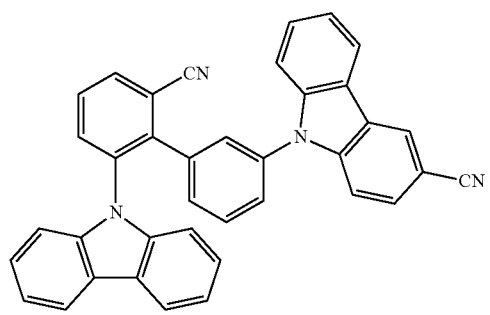
93
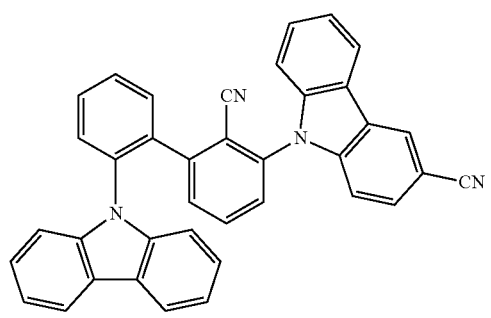
94
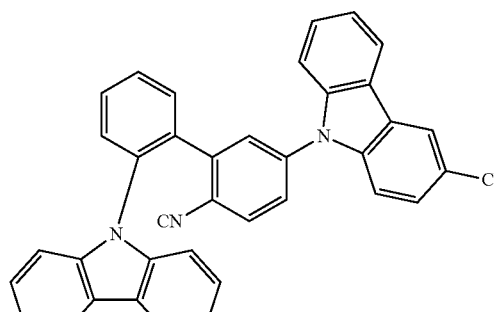
95
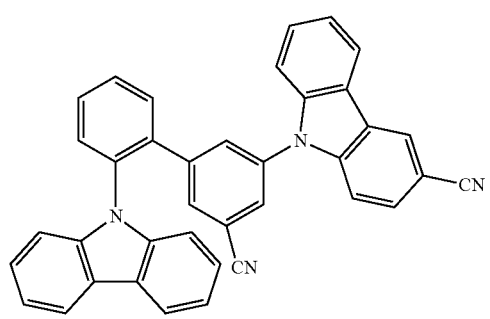
96
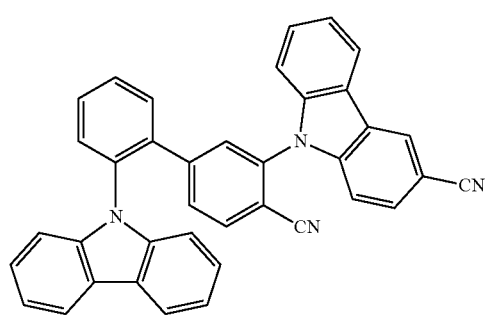
-continued
97
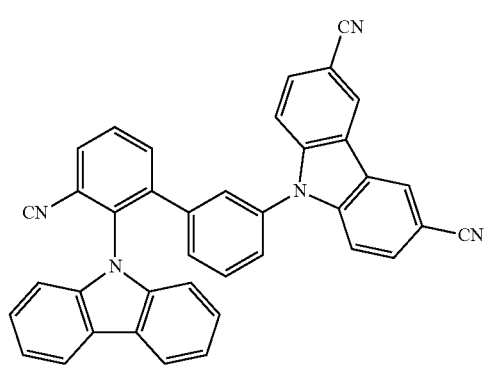
98
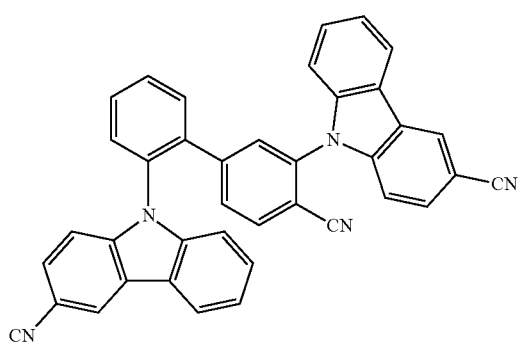
99
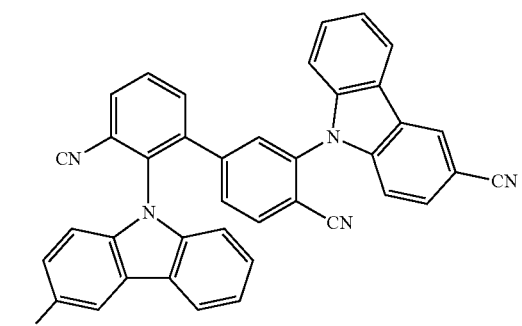
100
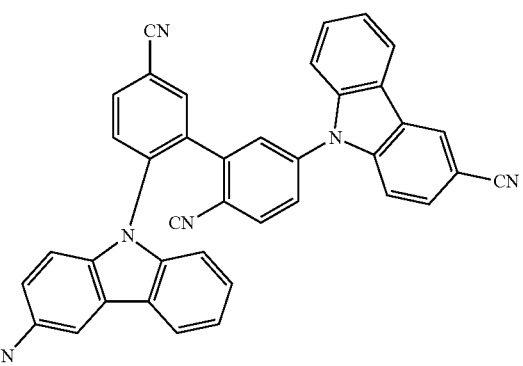

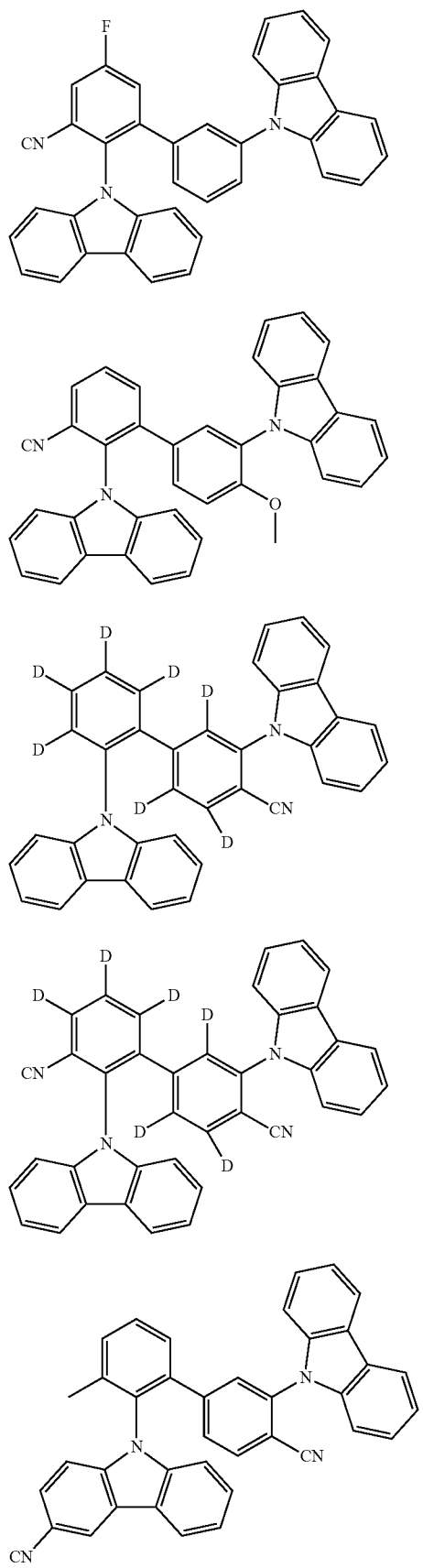
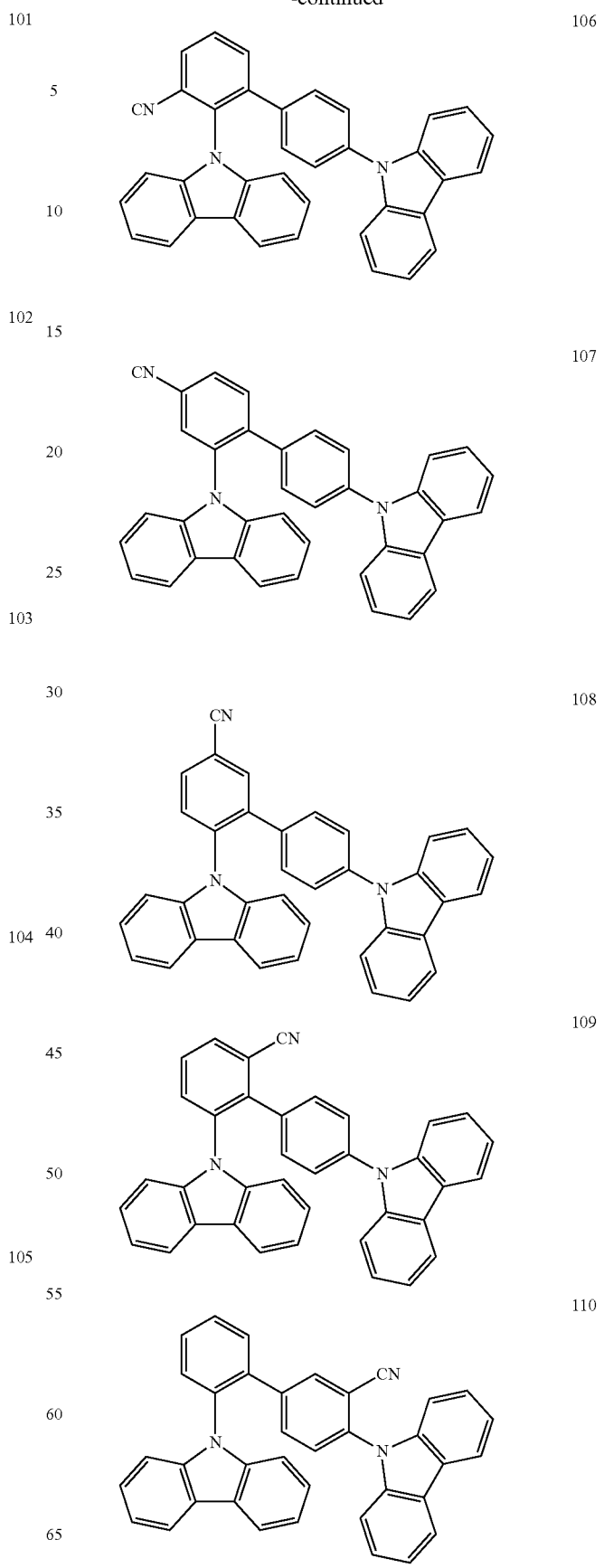

111
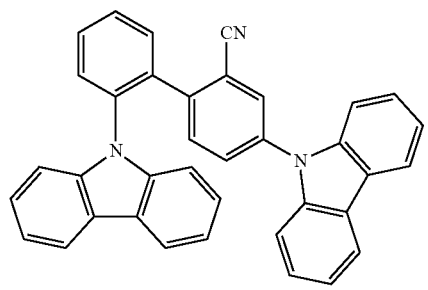
112
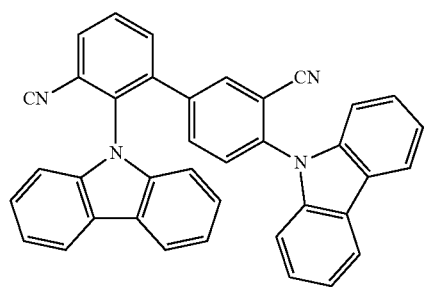
113
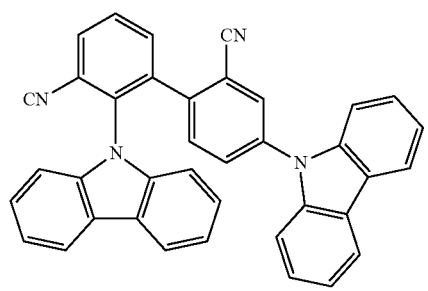
114
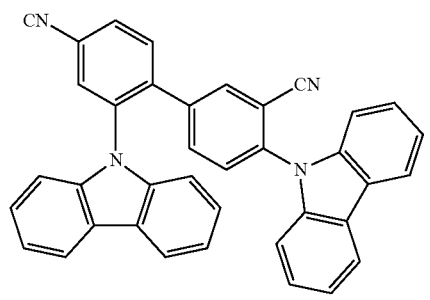
115
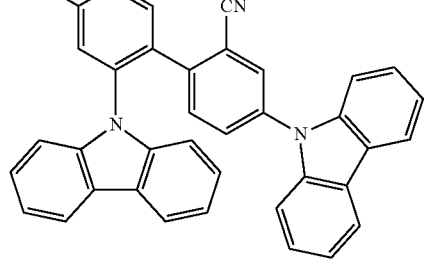
116
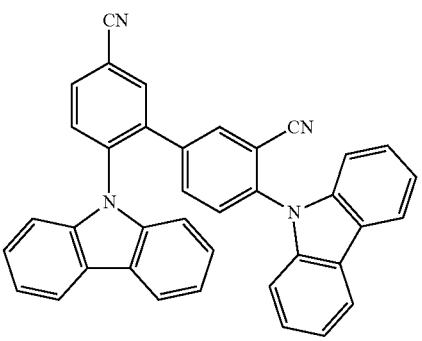
117
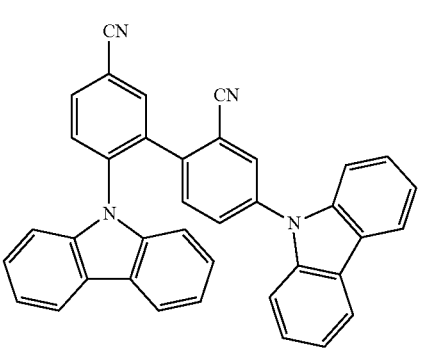
118
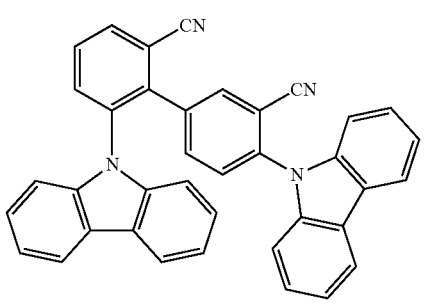
119
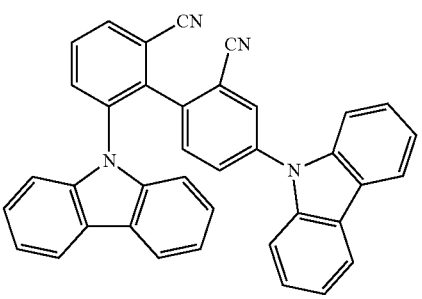
120
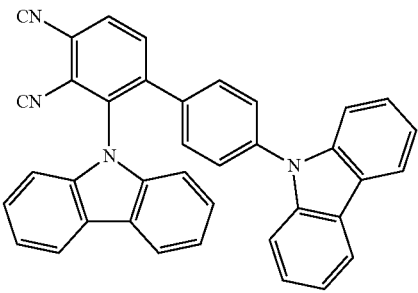

121
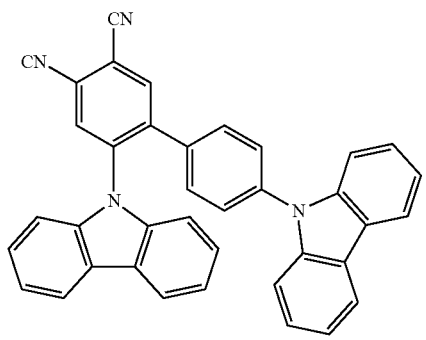
122
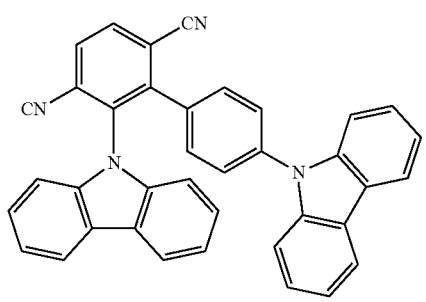
123
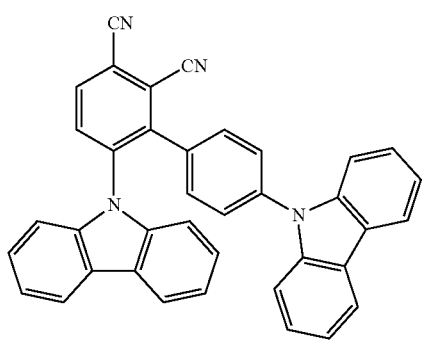
124
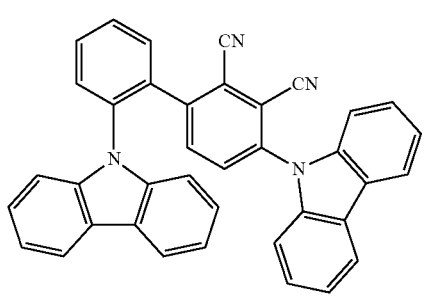
125
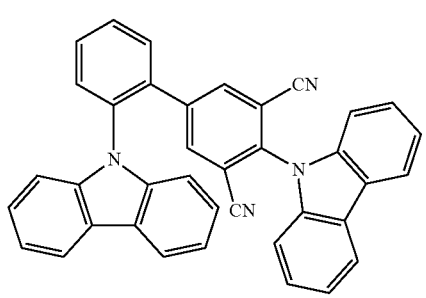
126
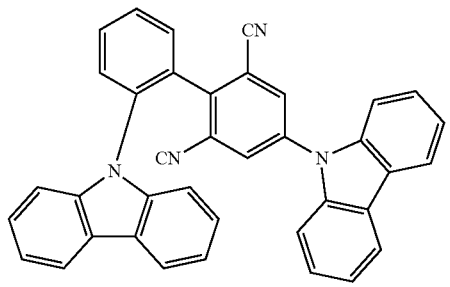
127
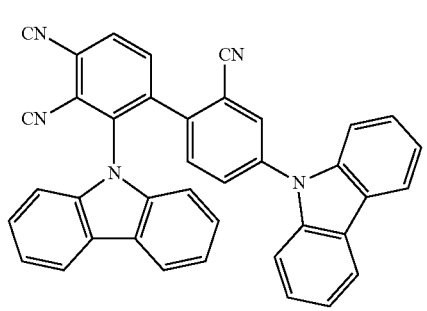
128
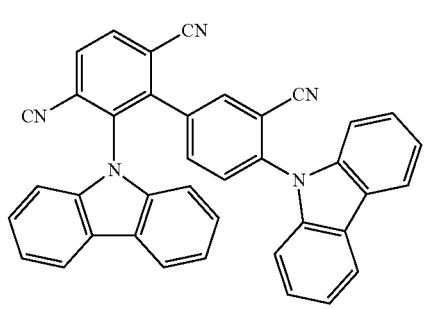
129
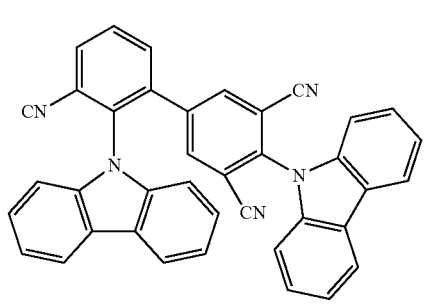
130
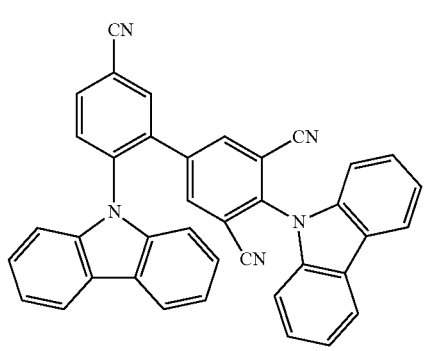

| | |
|---|---|
| 131 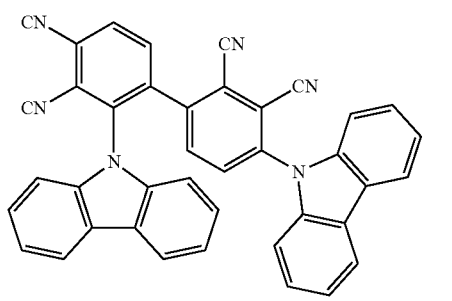 | 136 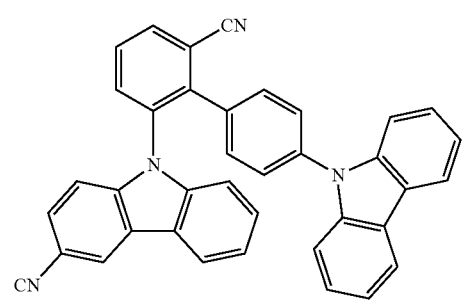 |
| 132 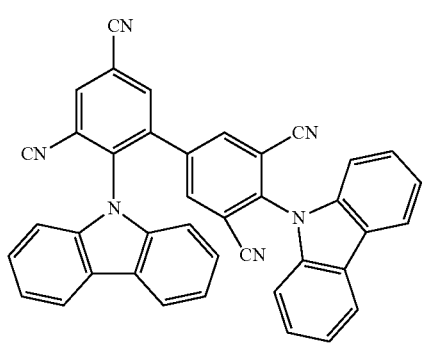 | 137 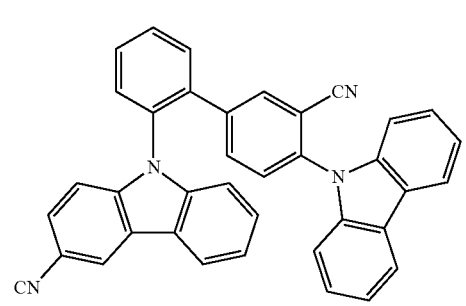 |
| 133 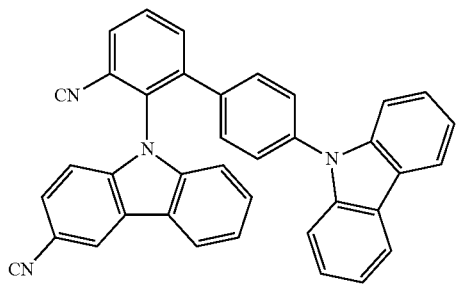 | 138 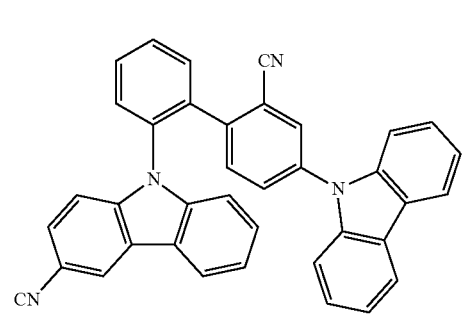 |
| 134 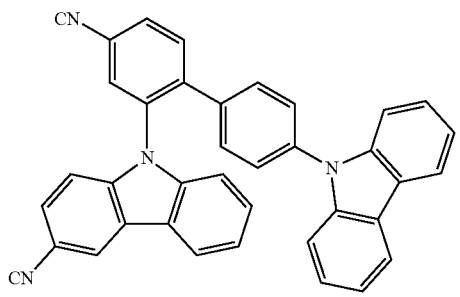 | 139 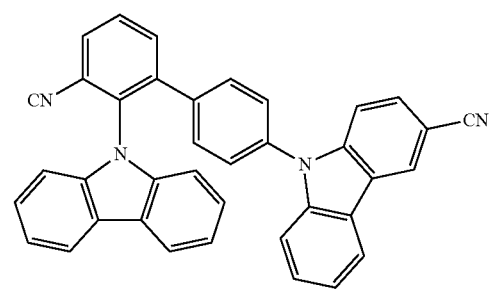 |
| 135 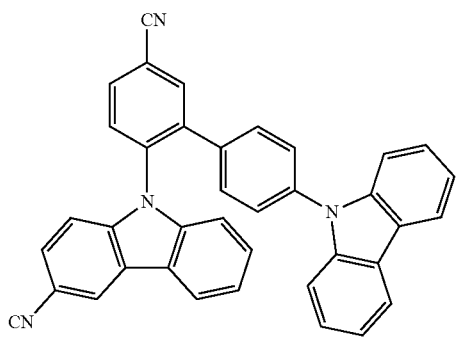 | 140 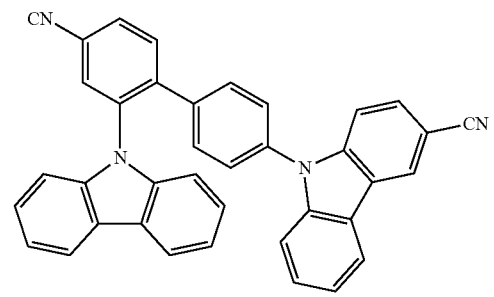 |

141
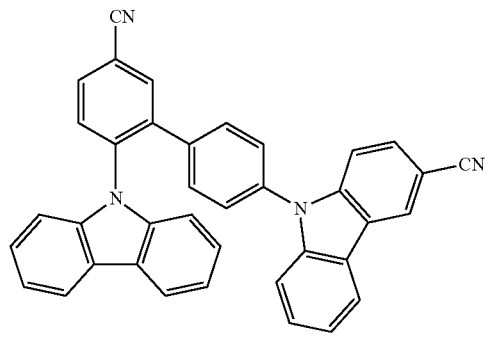
142
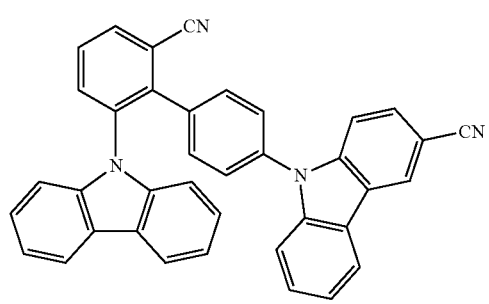
143
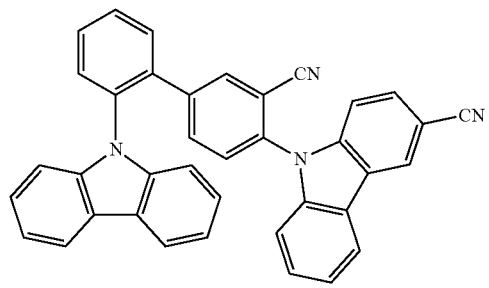
144
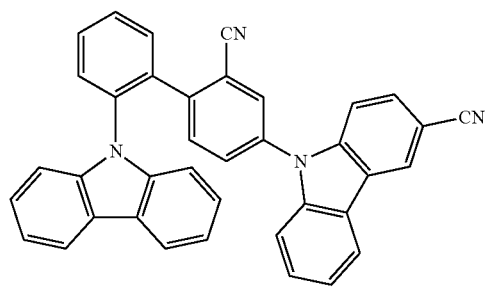
145
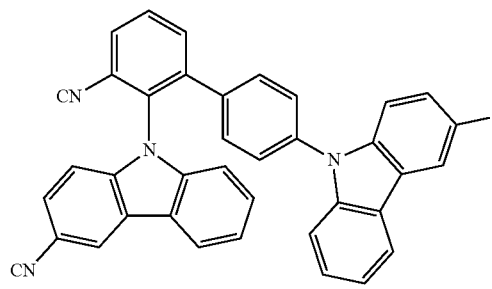
146
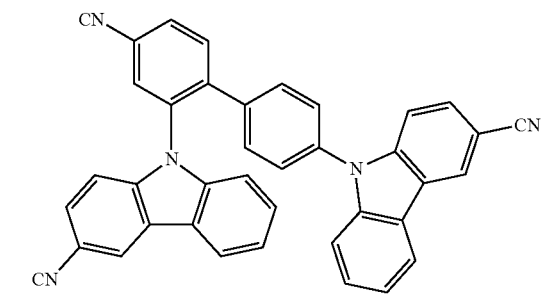
147
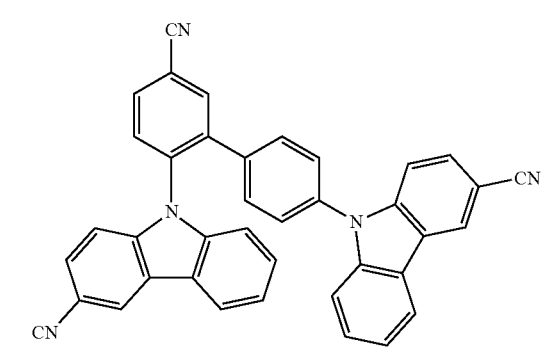
148
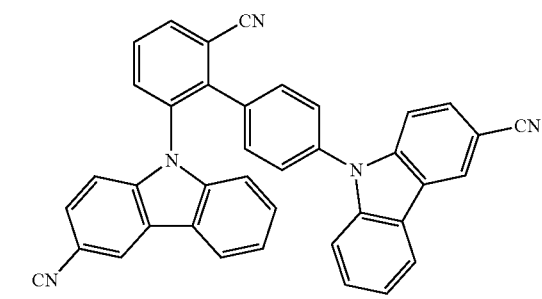
149
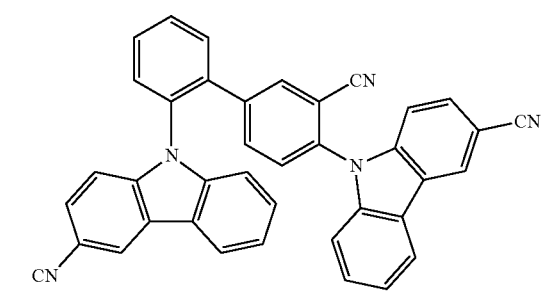
150
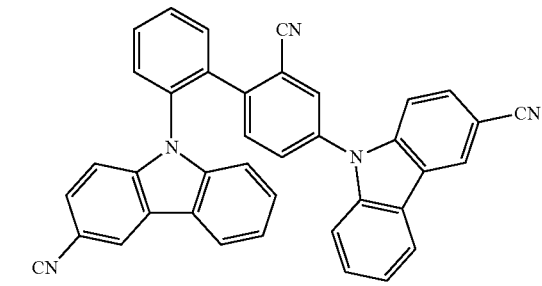

-continued
151
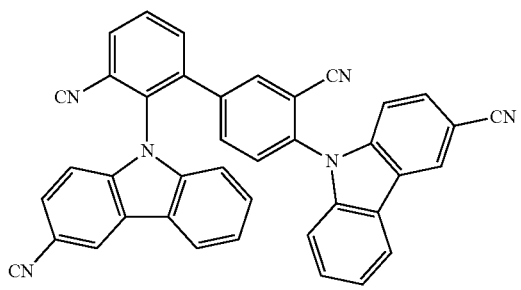
152
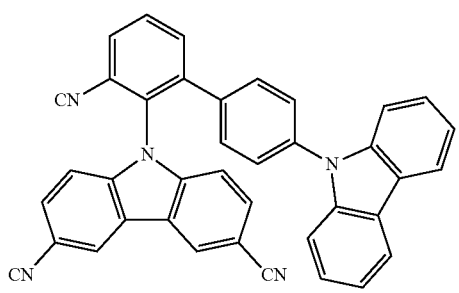
153
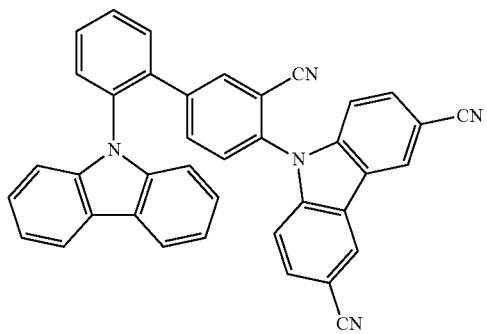
154
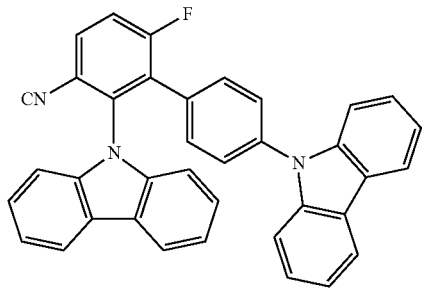
155
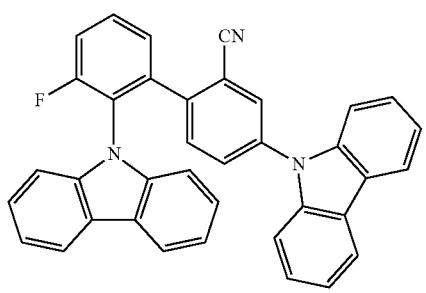
-continued
156
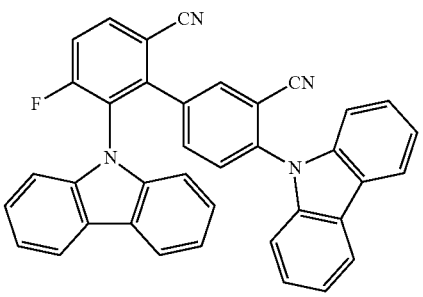
157
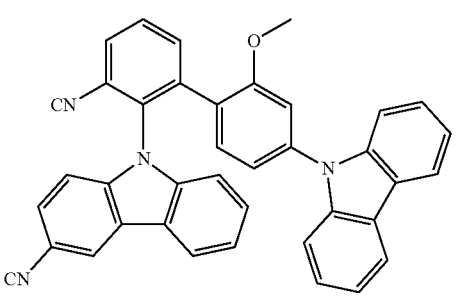
158
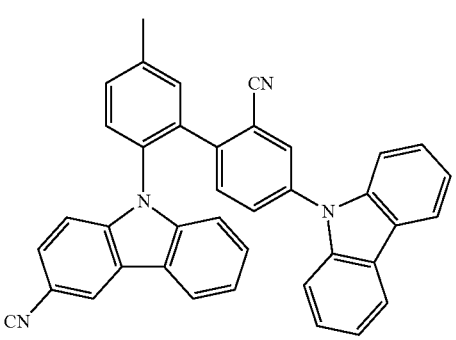
159
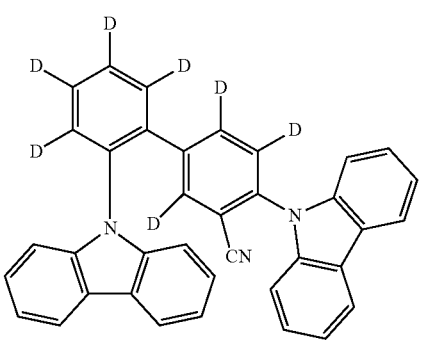
160
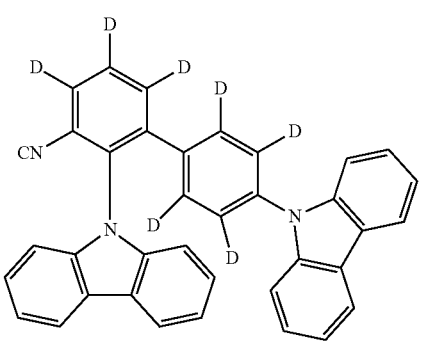

161
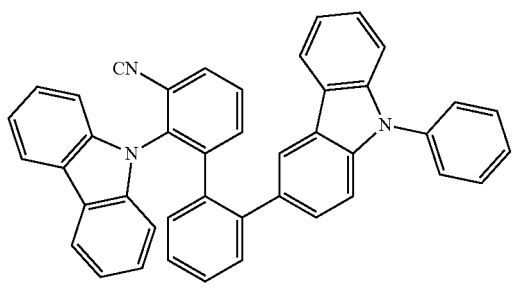
162
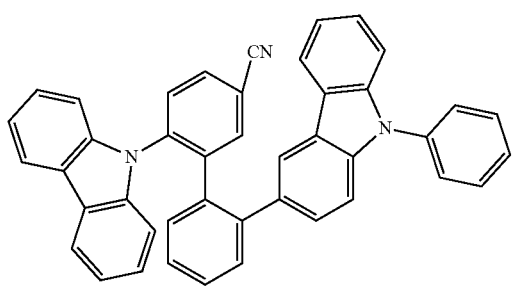
163
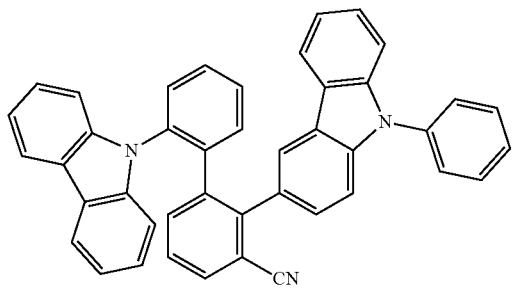
164
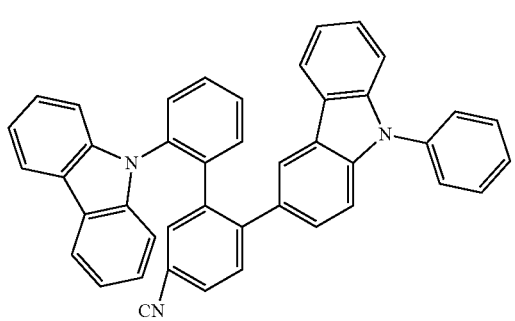
165
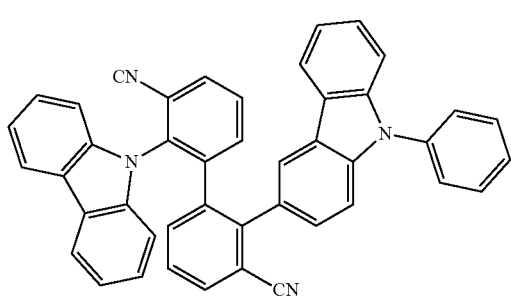
166
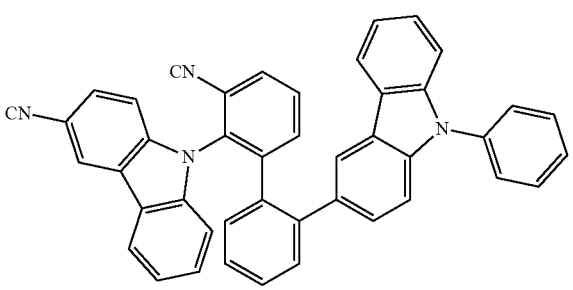
167
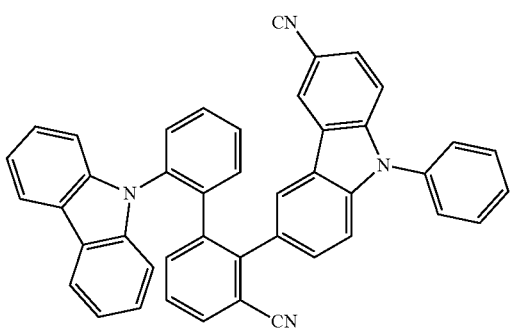
168
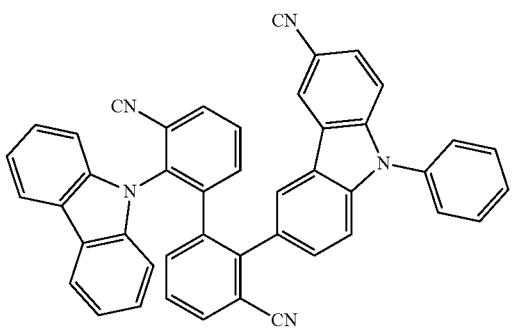
169
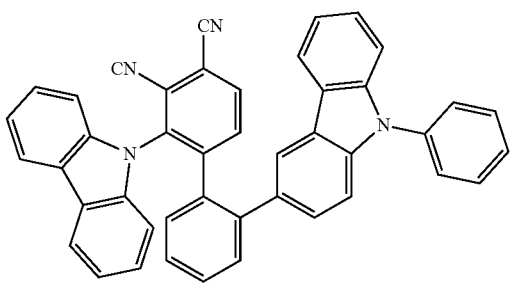
170
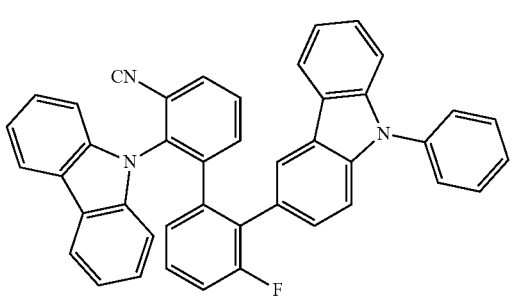

171
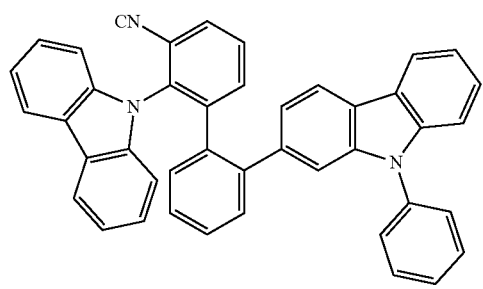
172
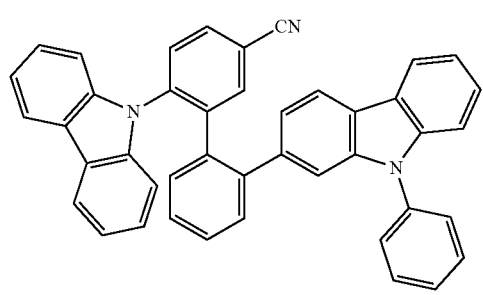
173
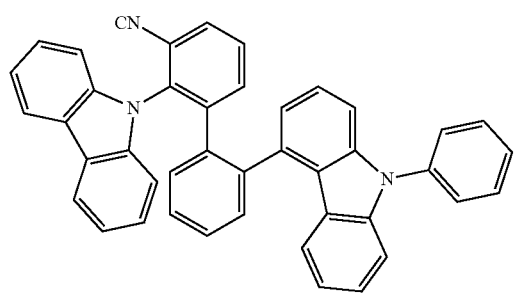
174
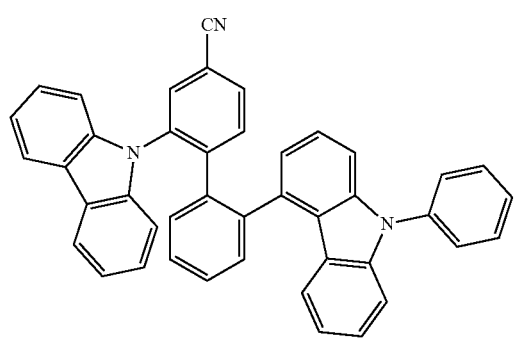
175
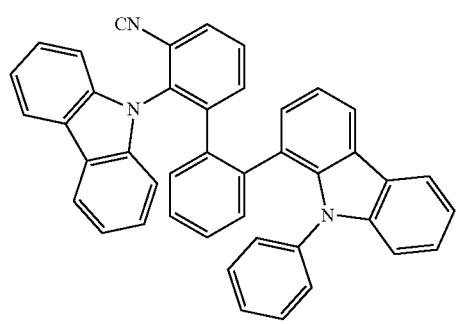
176
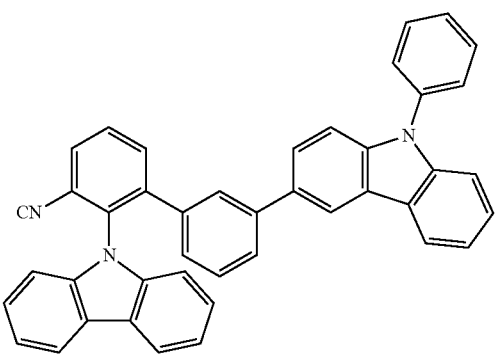
177
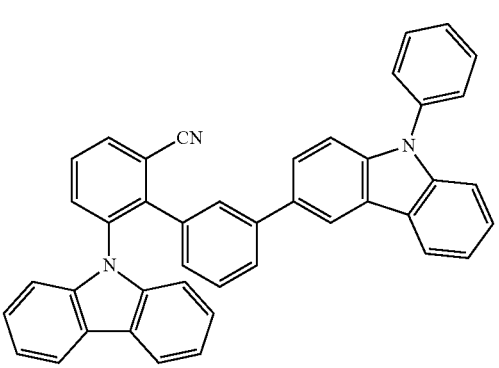
178
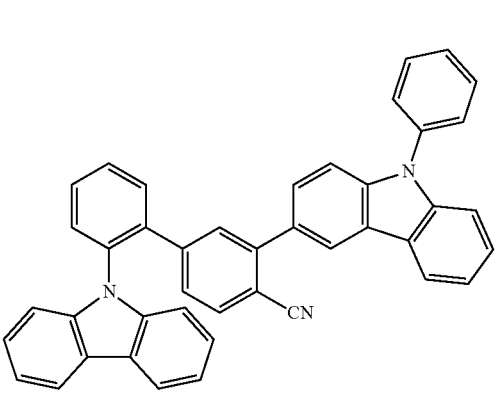
179
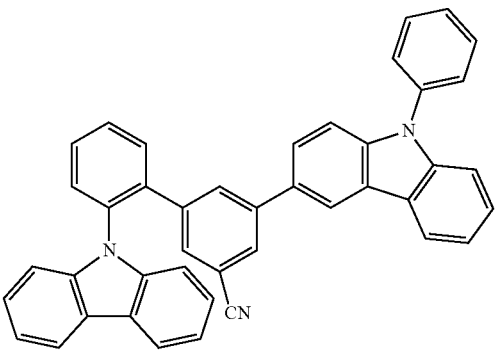

180 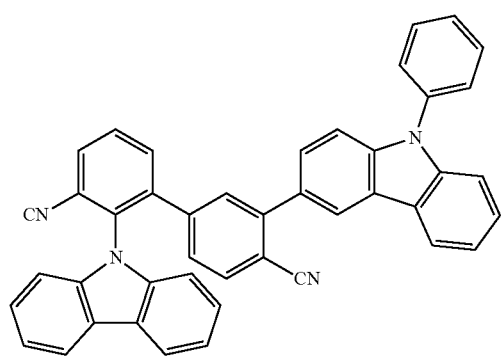
181 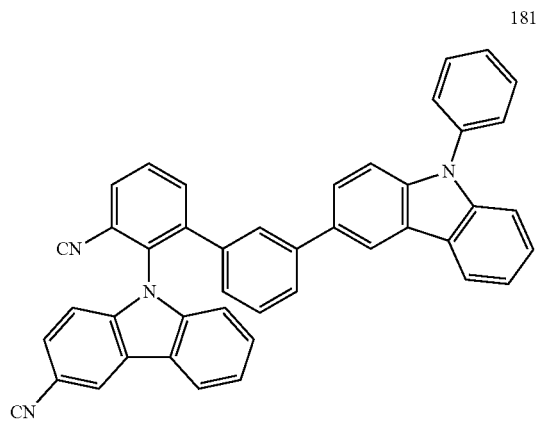
182 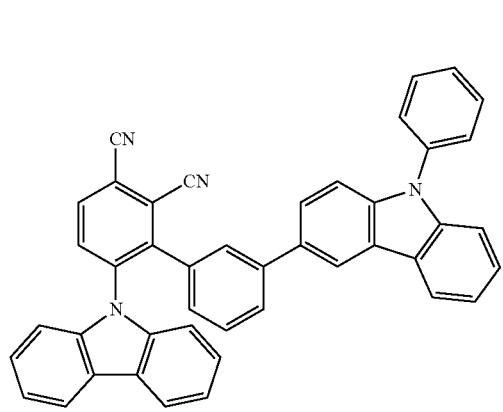
183 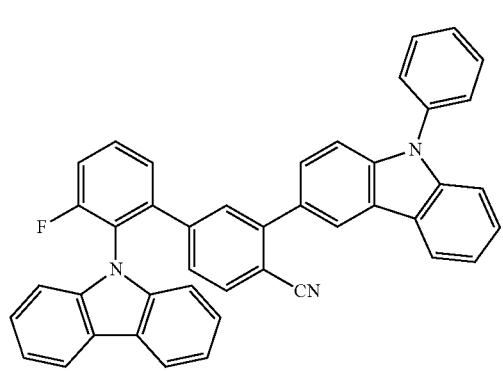
184 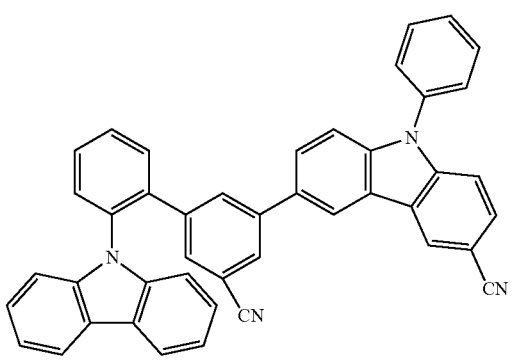
185 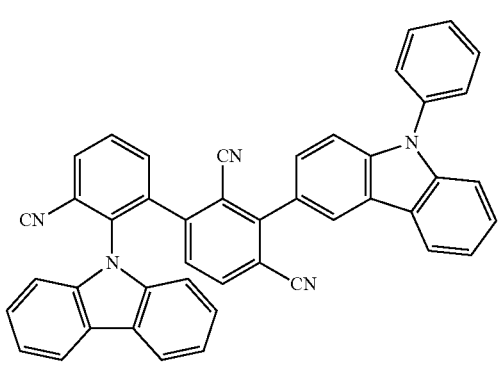
186 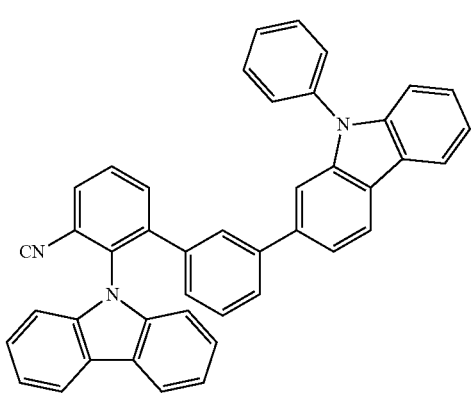
187 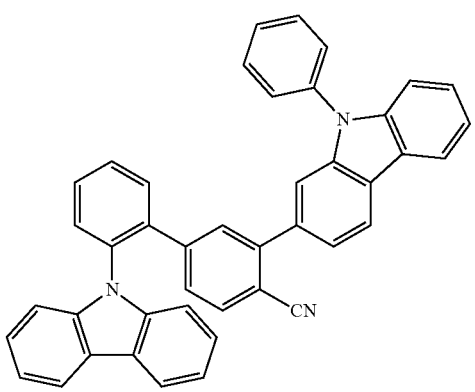

188
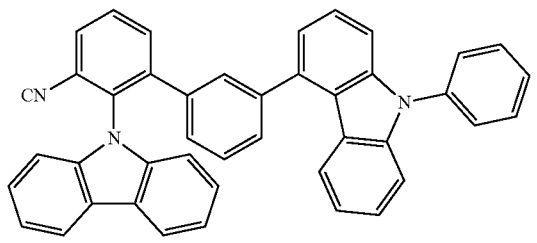
189
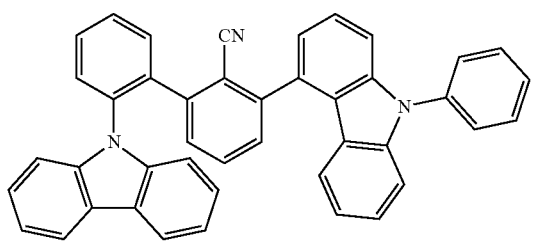
190
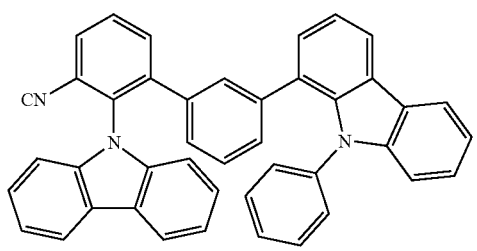
191
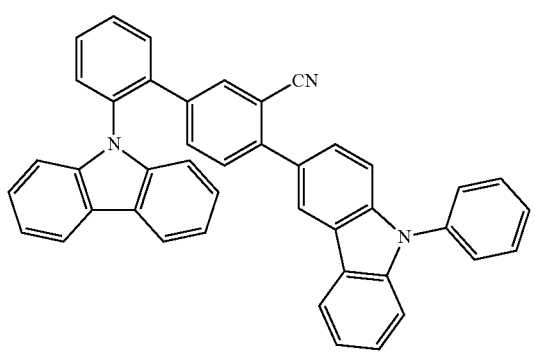
192
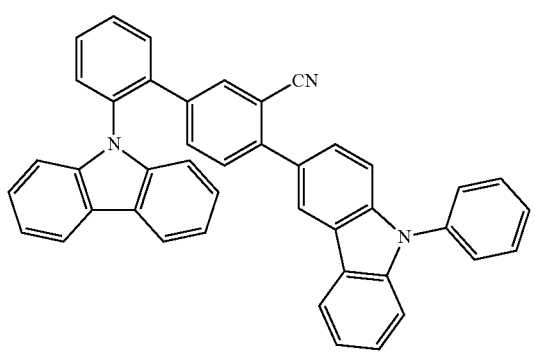
193
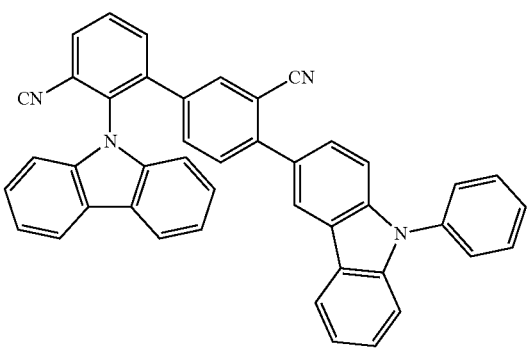
194
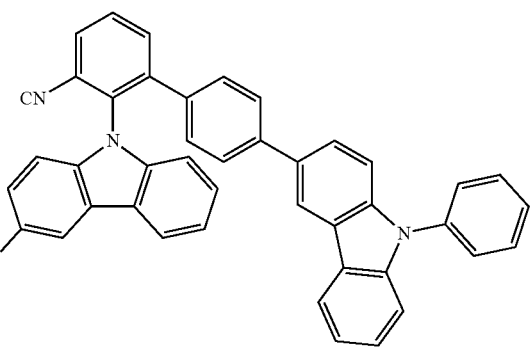
195
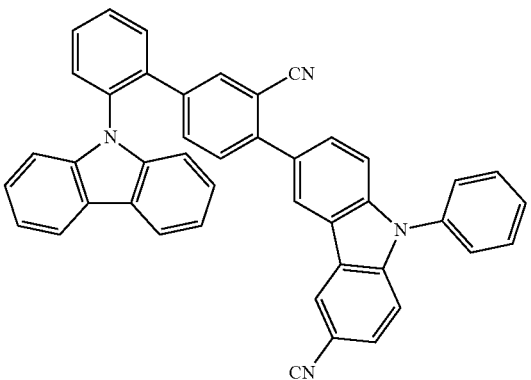
196
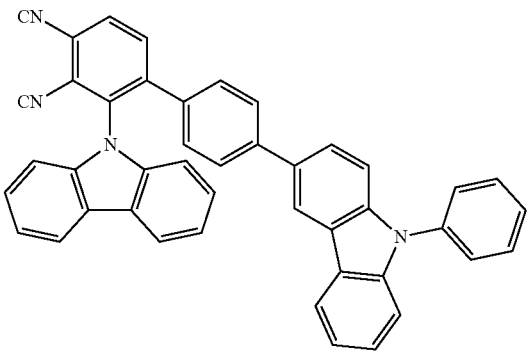

693
-continued
197
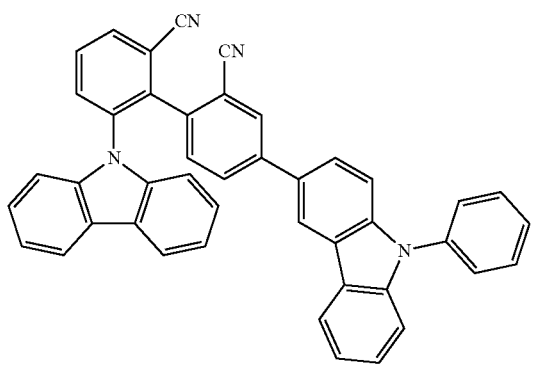
198
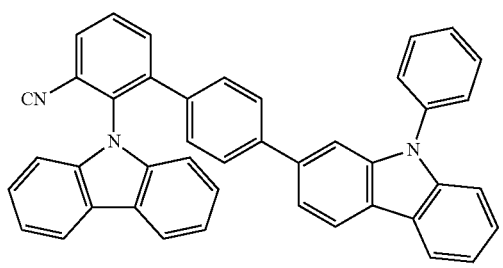
199
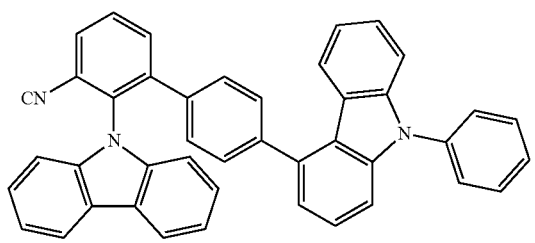
200
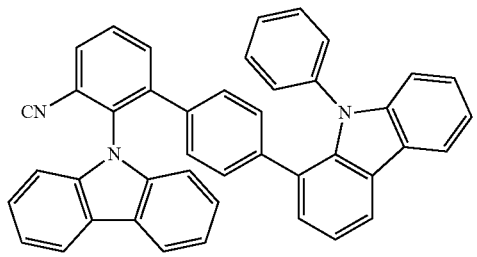
201
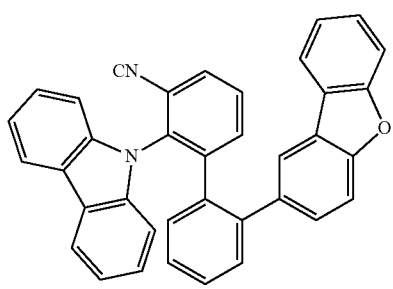
694
-continued
202
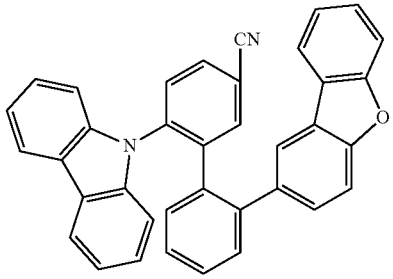
203
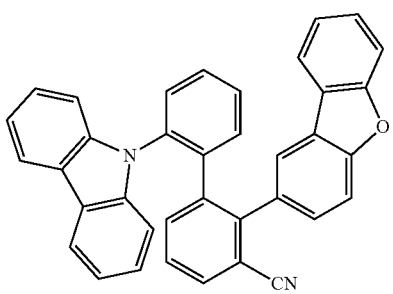
204
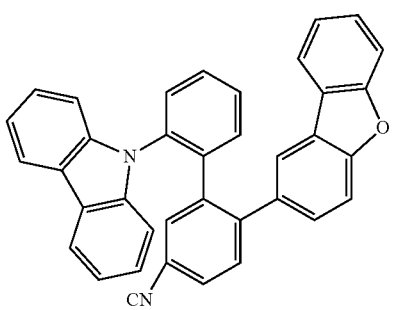
205
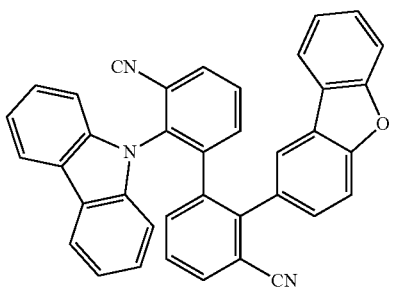
206
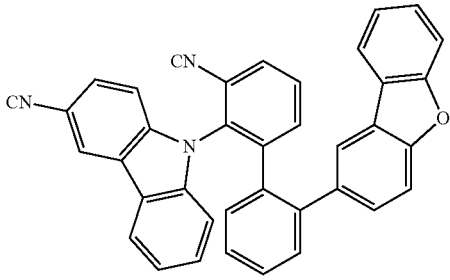

207
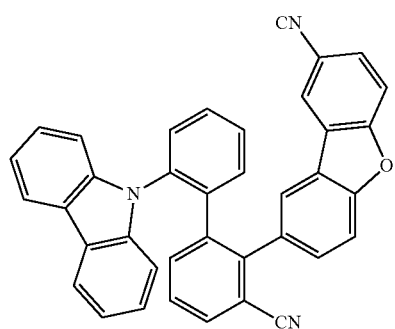
208
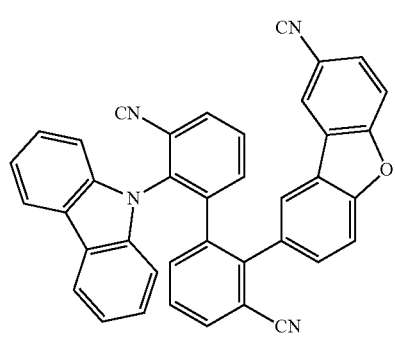
209
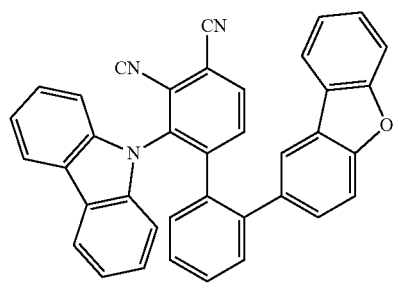
210
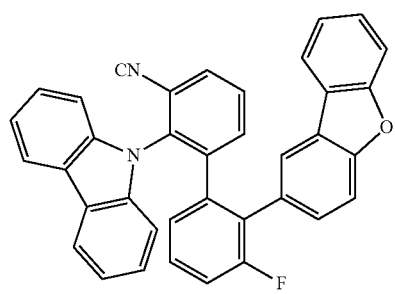
211
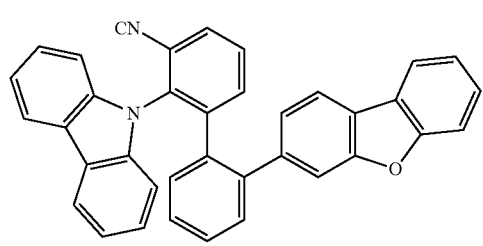
212
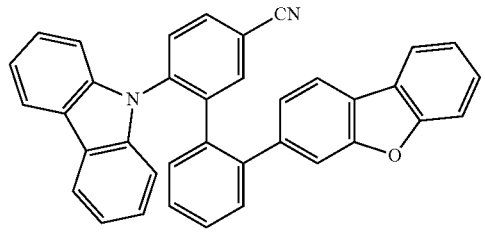
213
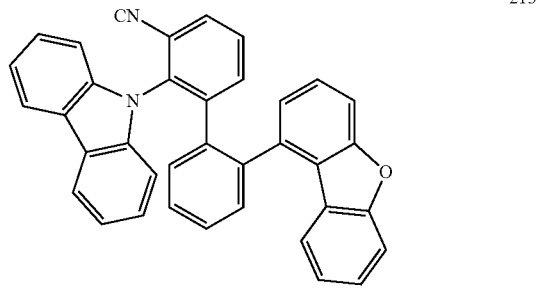
214
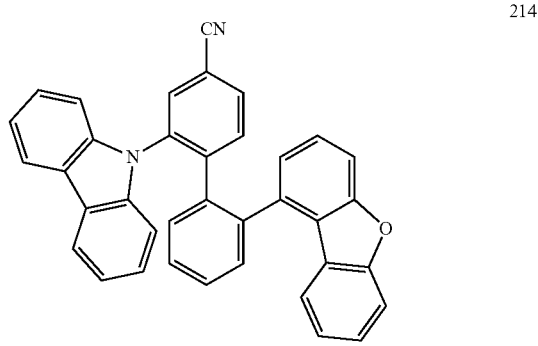
215
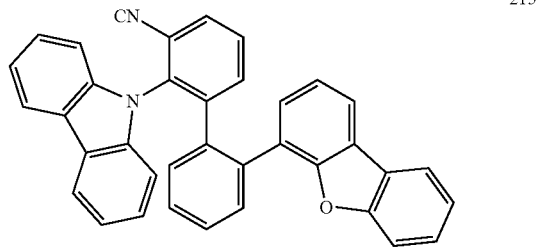
216
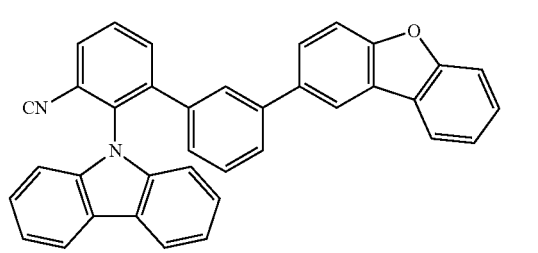
217
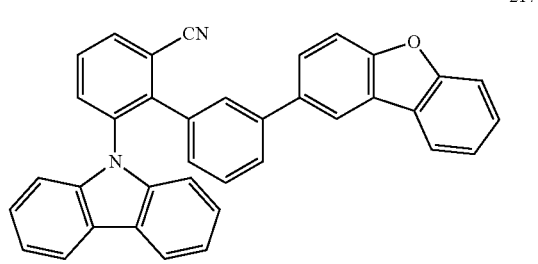

-continued
218
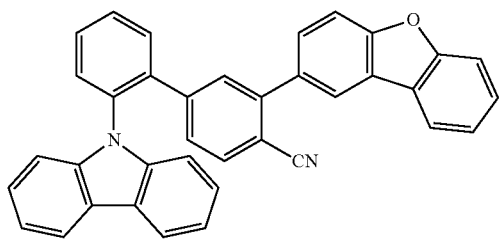
219
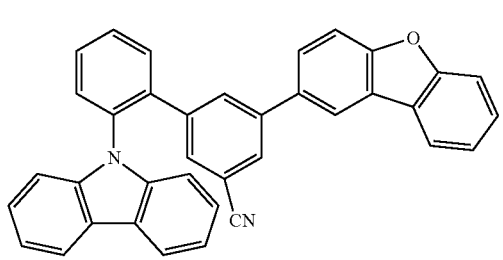
220
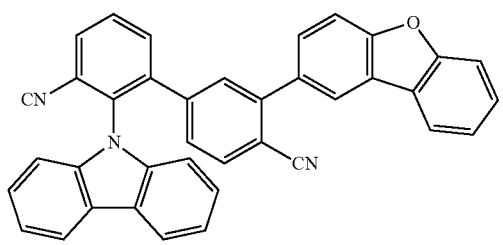
221
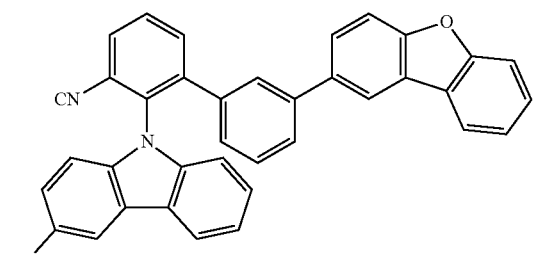
222
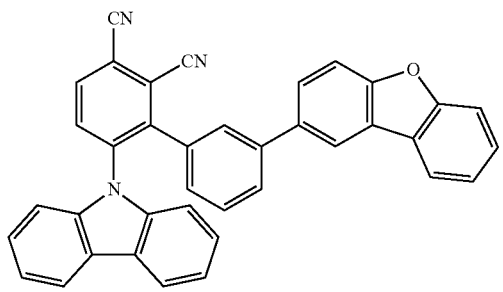
-continued
223
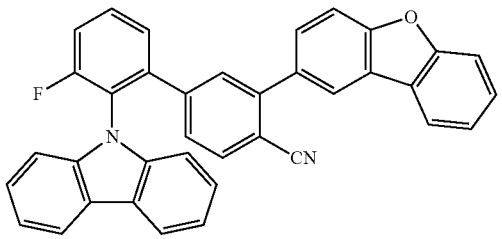
224
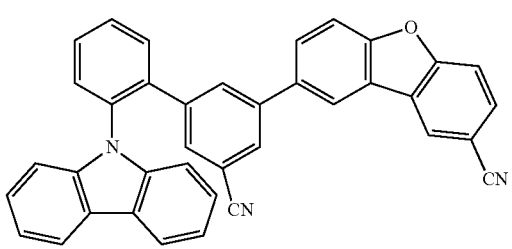
225
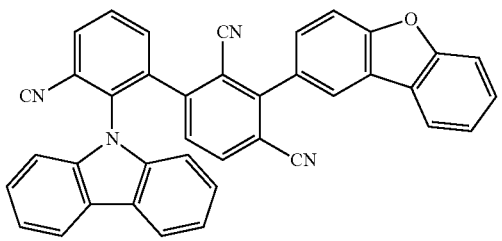
226
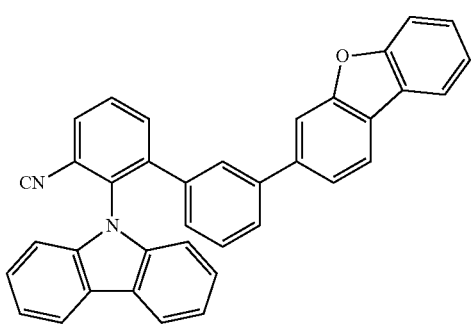
227
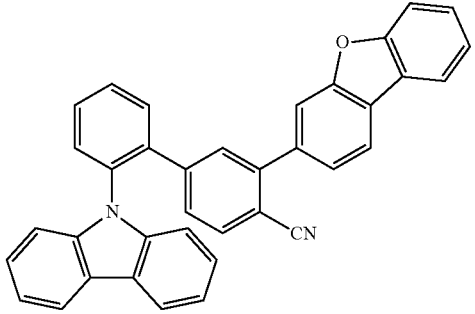

699
-continued
228
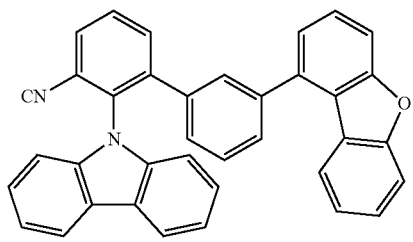
229
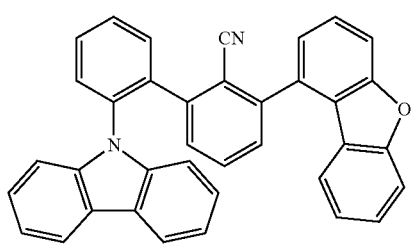
230
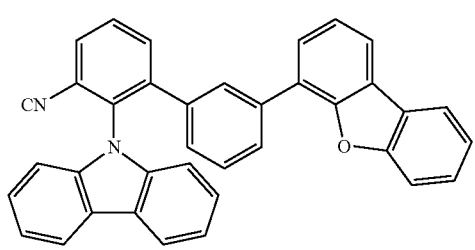
231
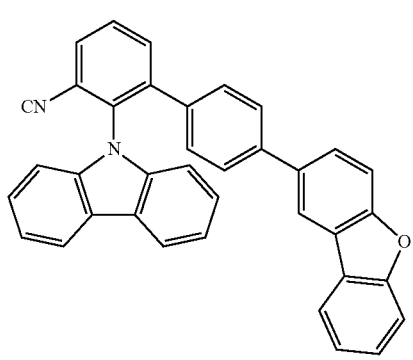
232
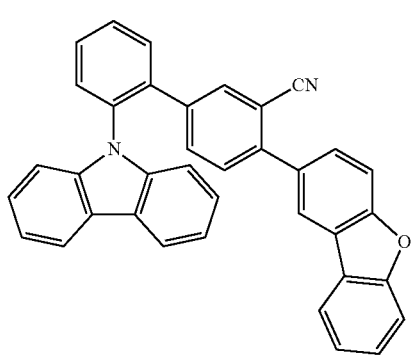
700
-continued
233
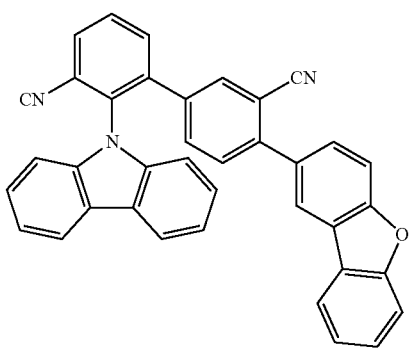
234
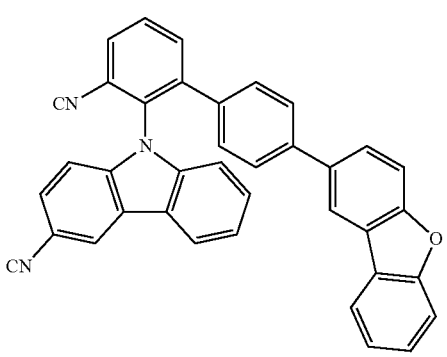
235

236
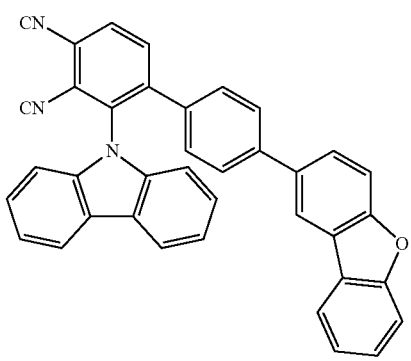

701
-continued
237
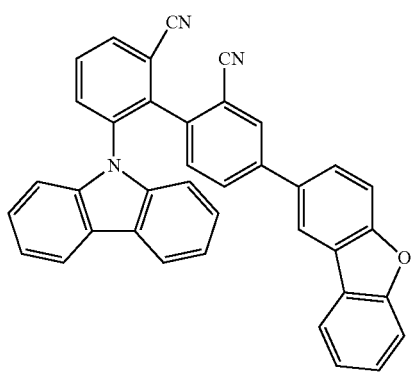
238
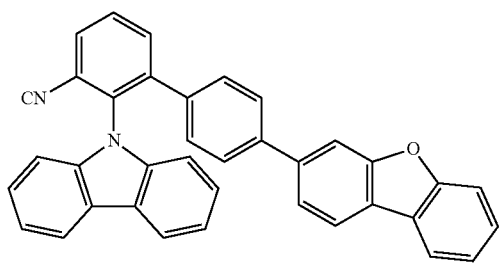
239
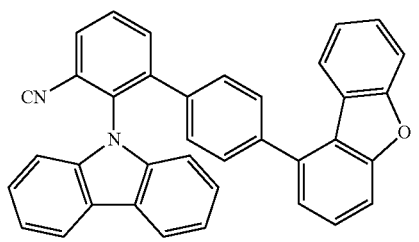
240
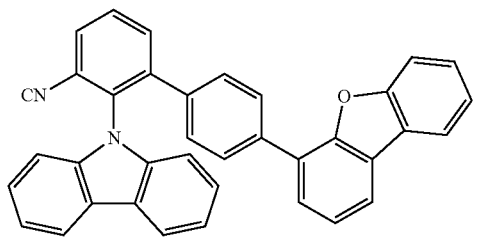
241
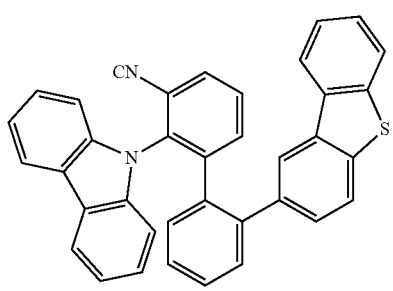
702
-continued
242
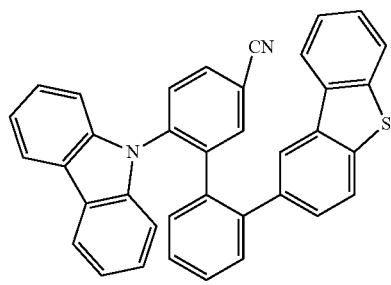
243
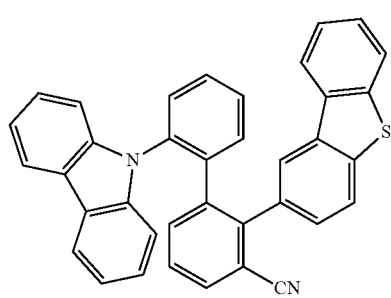
244
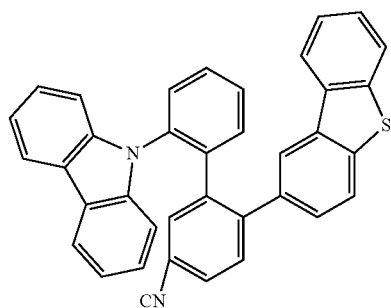
245
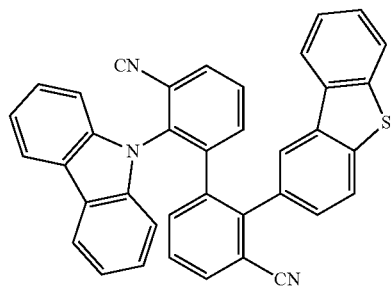
246
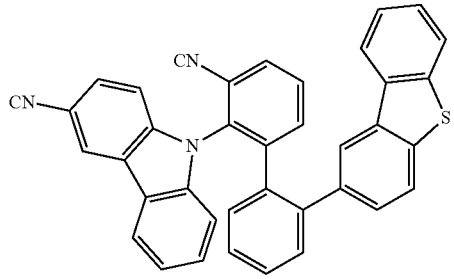

247
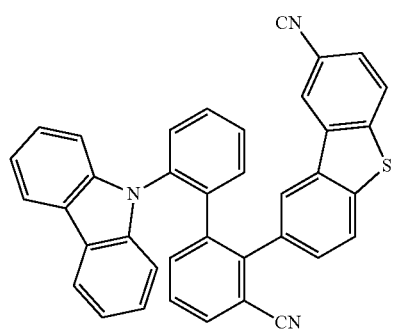
248
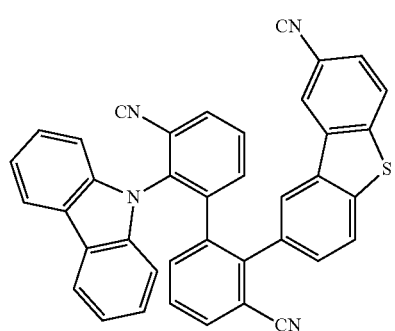
249
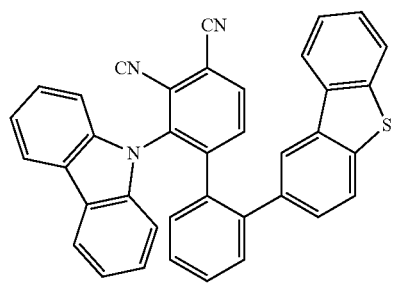
250
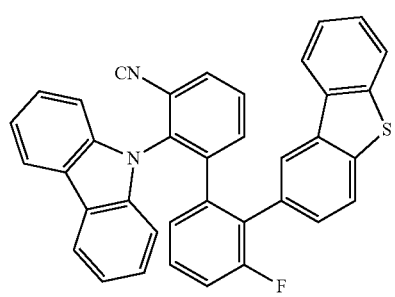
251
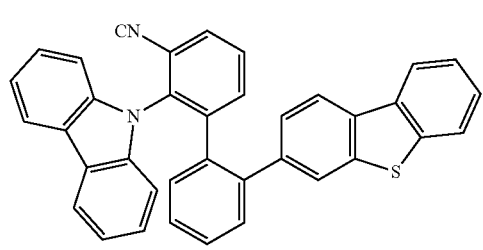
252
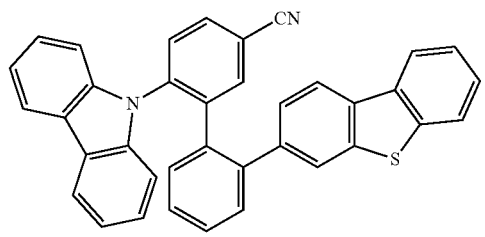
253
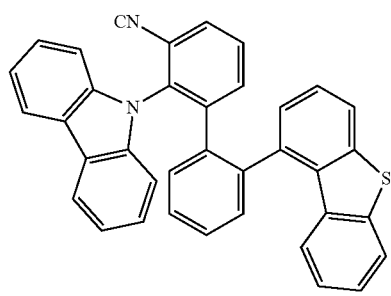
254
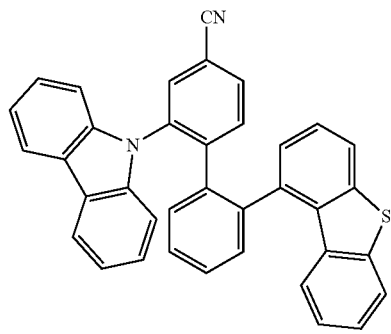
255
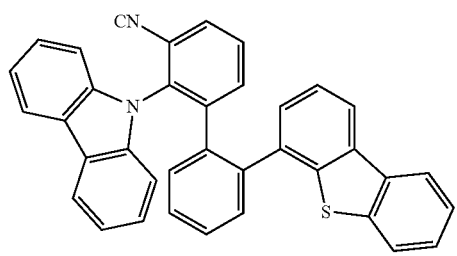
256
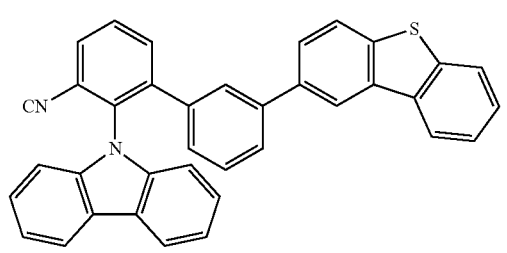
257
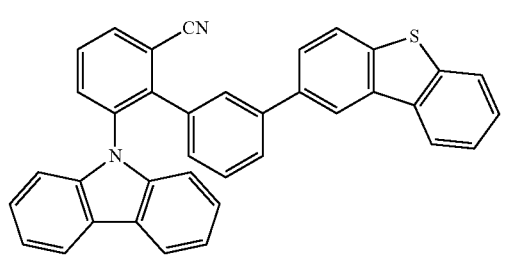

258
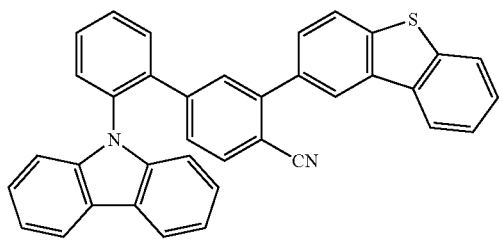
259
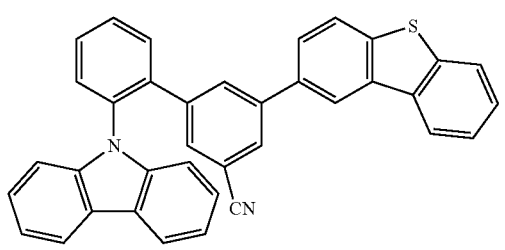
260
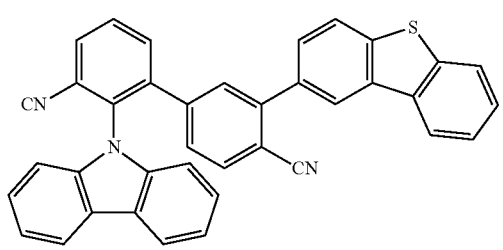
261
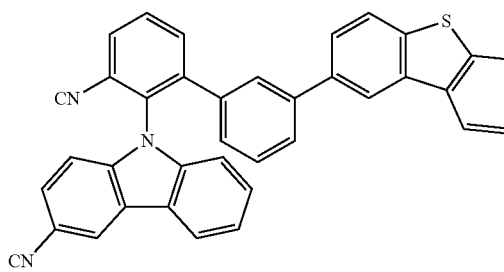
262
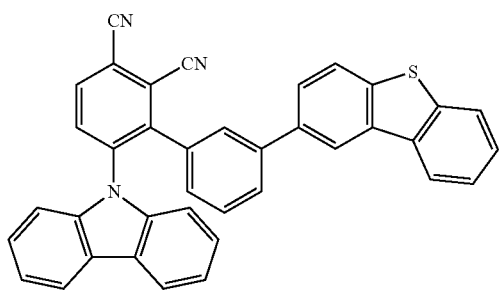
263
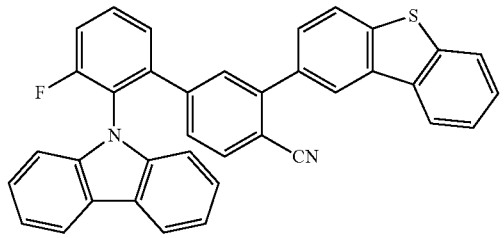
264
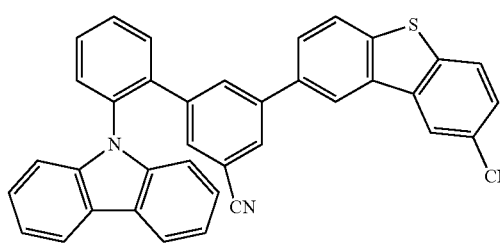
265
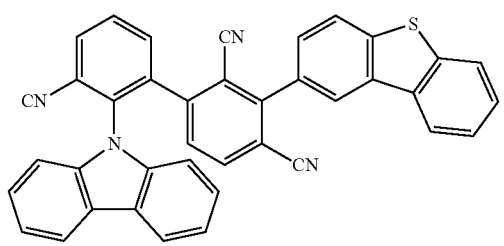
266
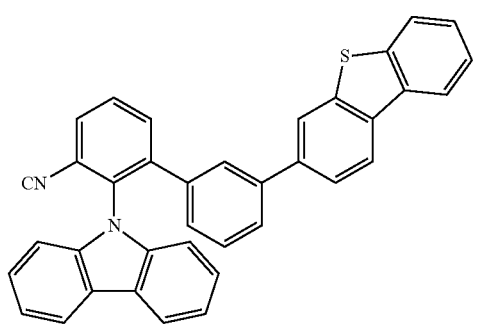
267
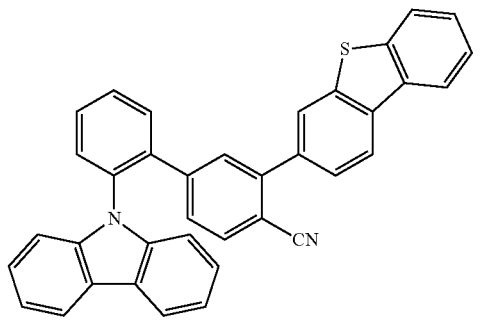

268
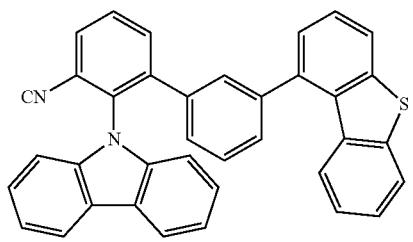
269
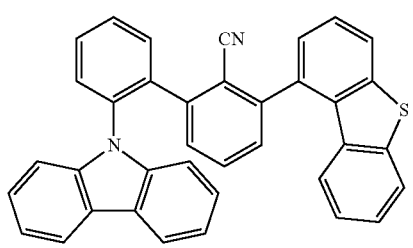
270
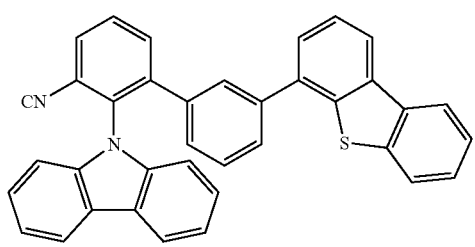
271
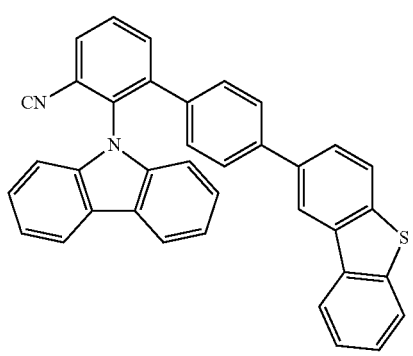
272
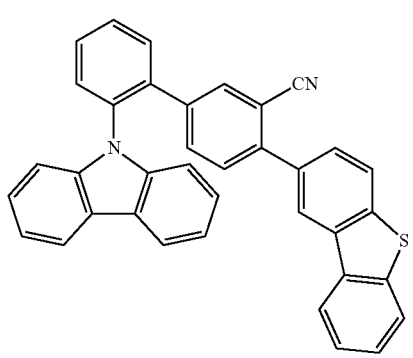
273
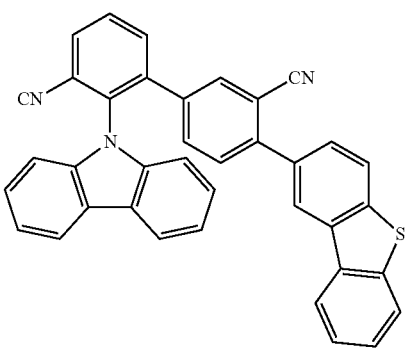
274
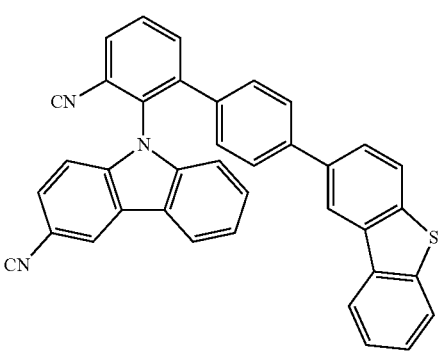
275
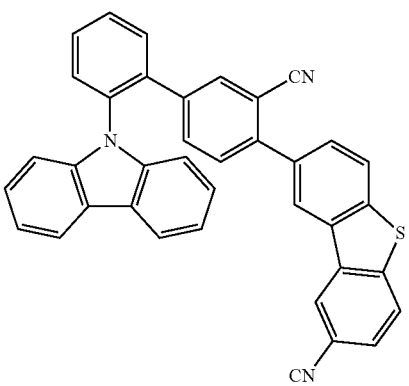
276
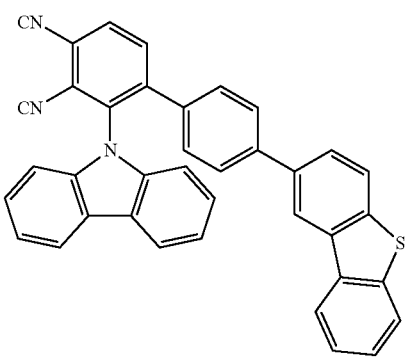

709
-continued
277
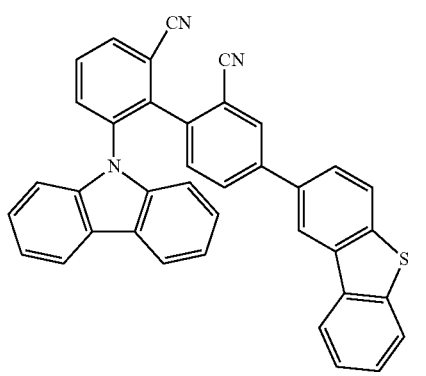
278
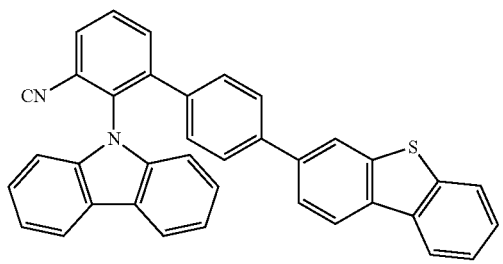
279
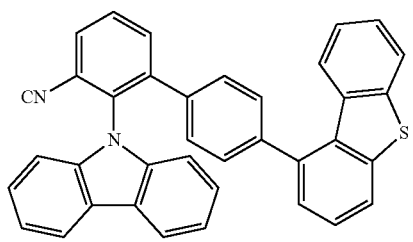
280
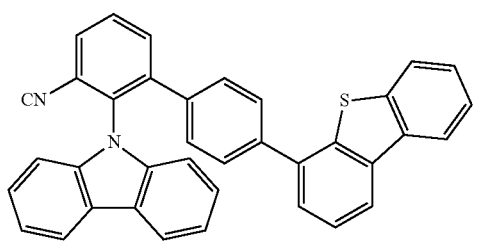
281
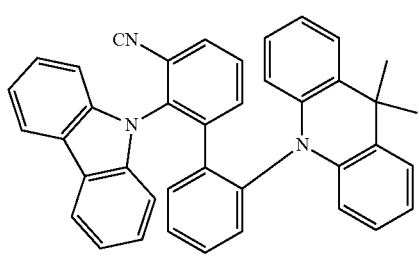
710
-continued
282
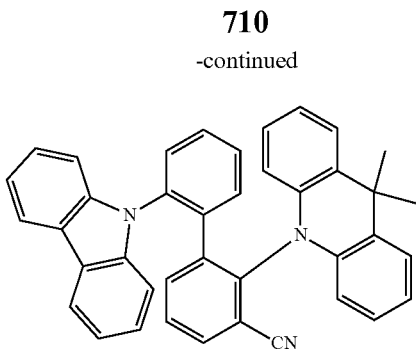
283
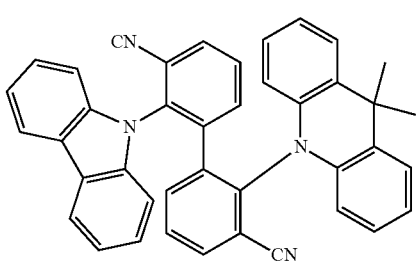
284
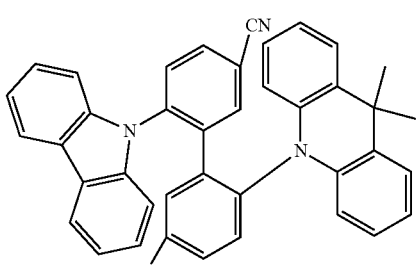
285
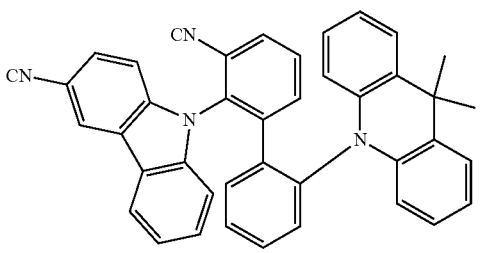
286
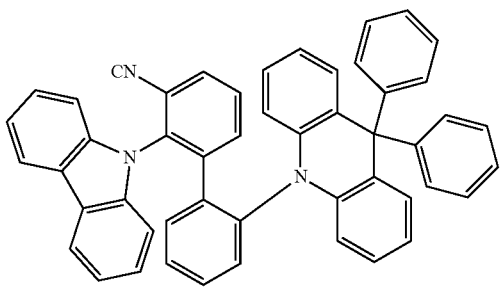

-continued
287
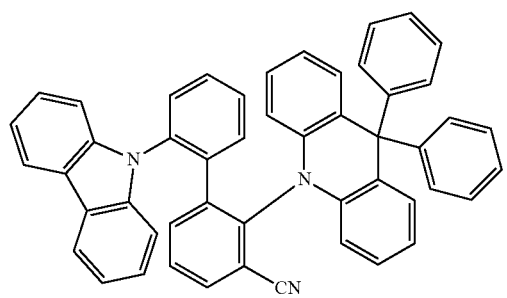
288
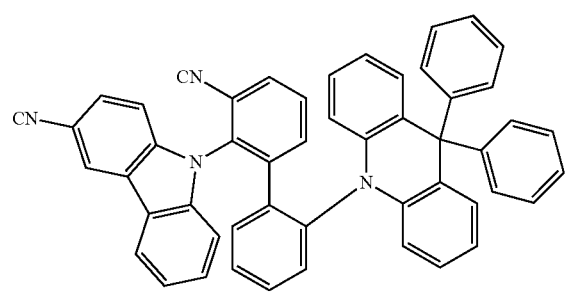
289
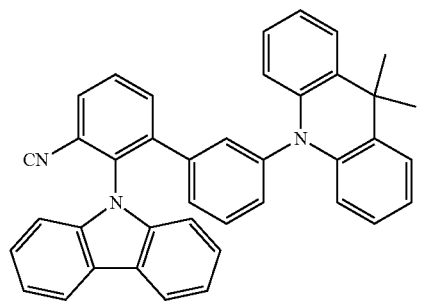
290
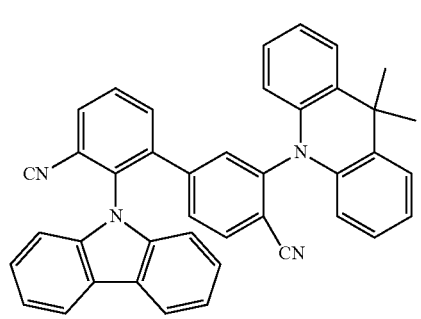
291
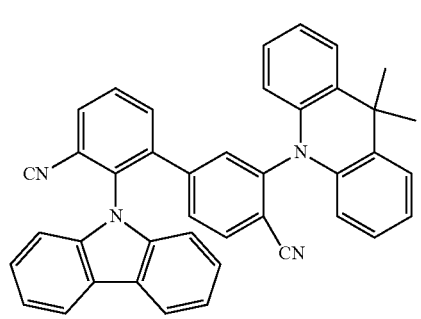
-continued
292
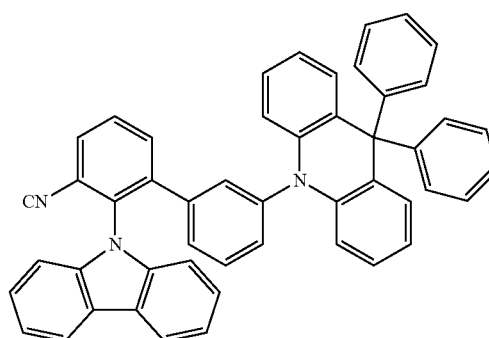
293
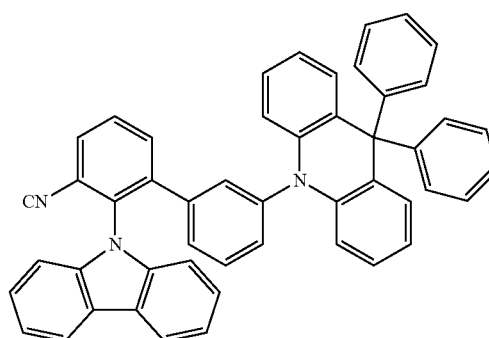
294
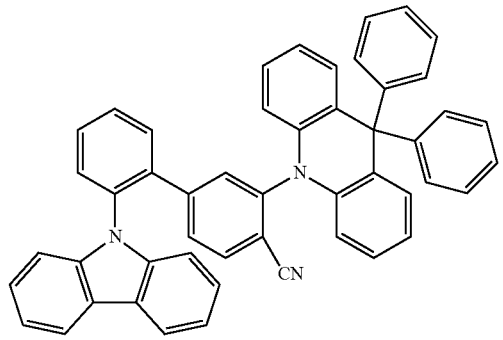
295
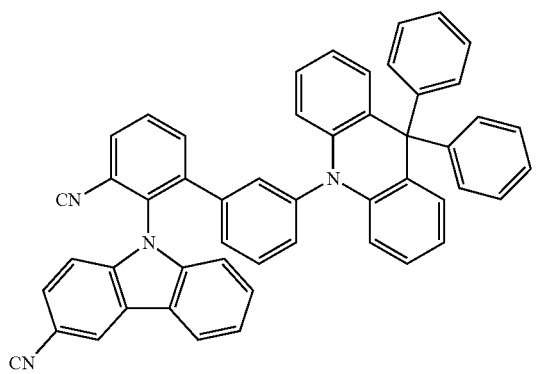

296
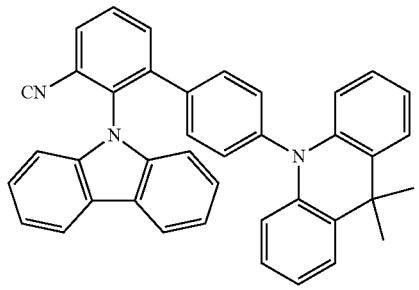
297
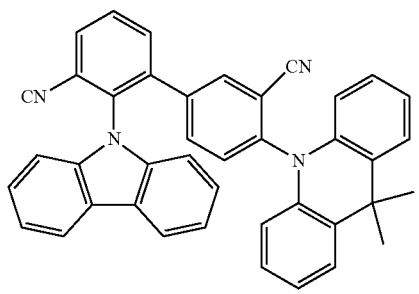
298
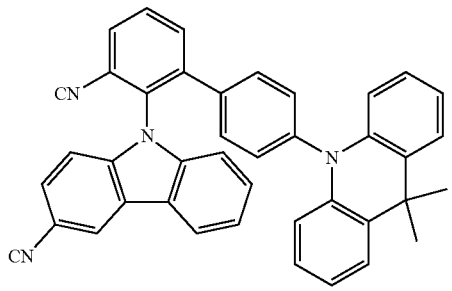
299
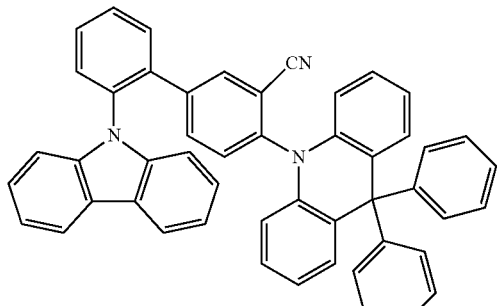
300
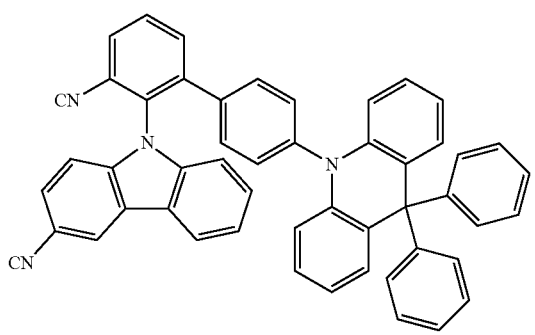
301
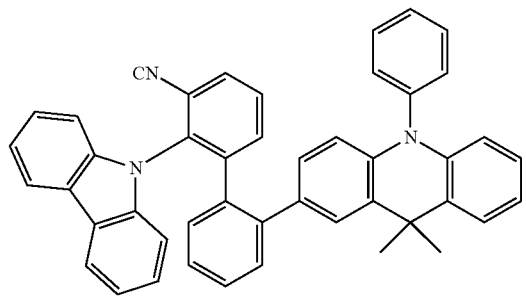
302
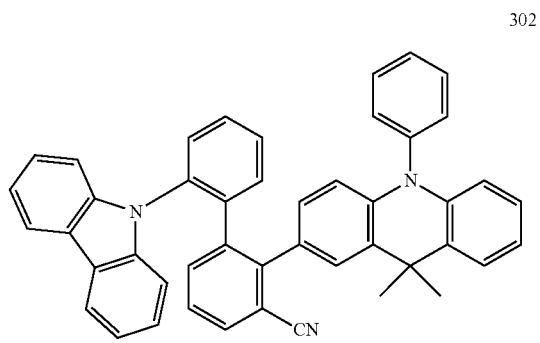
303
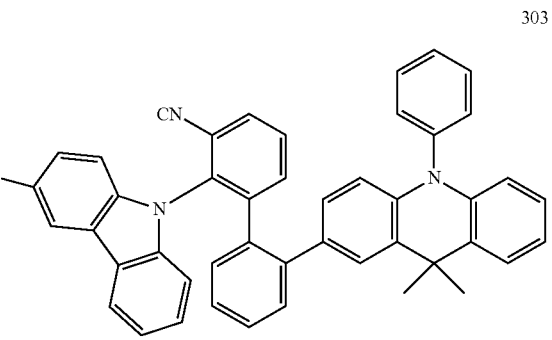
304
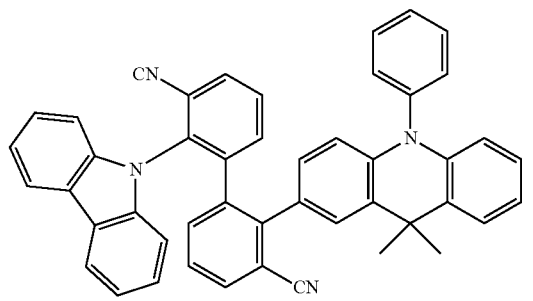
305
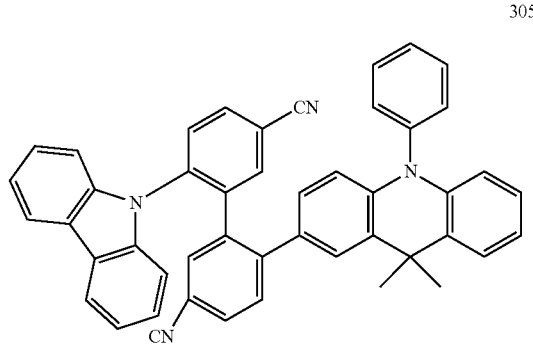

306
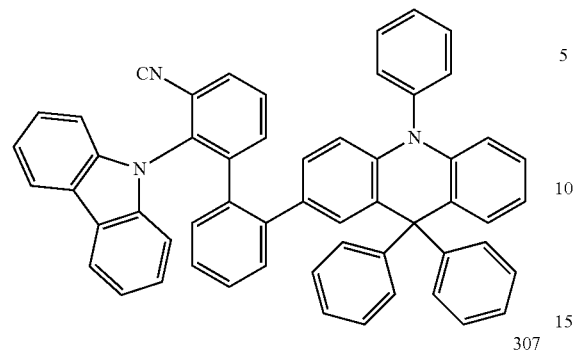
307
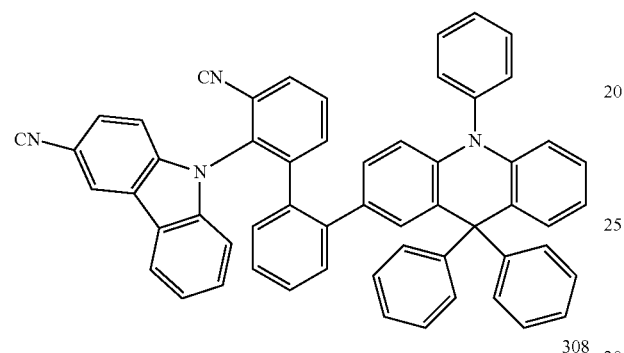
308
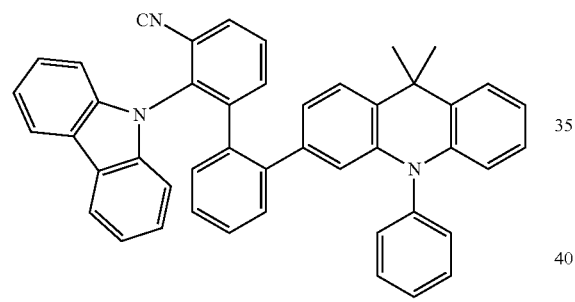
309
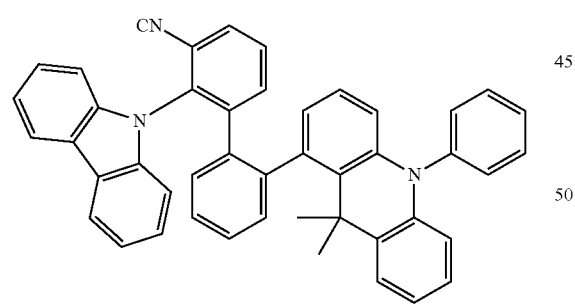
310
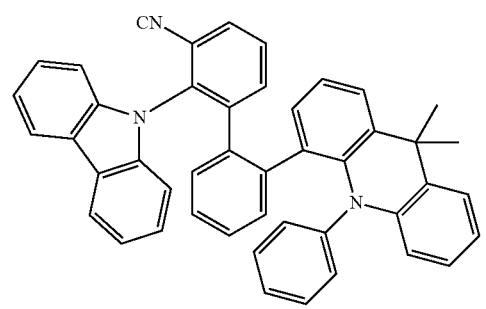
311
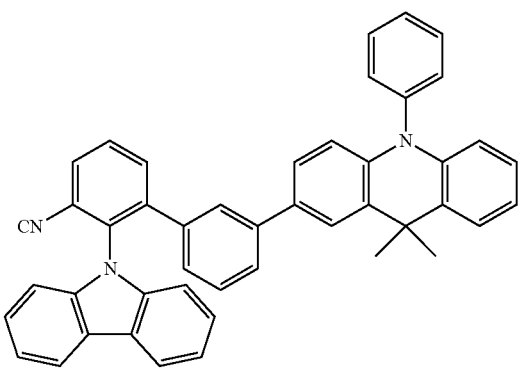
312
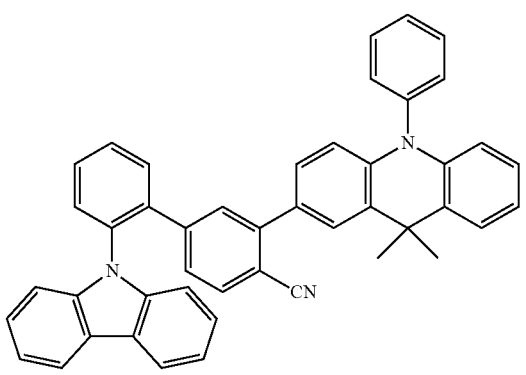
313
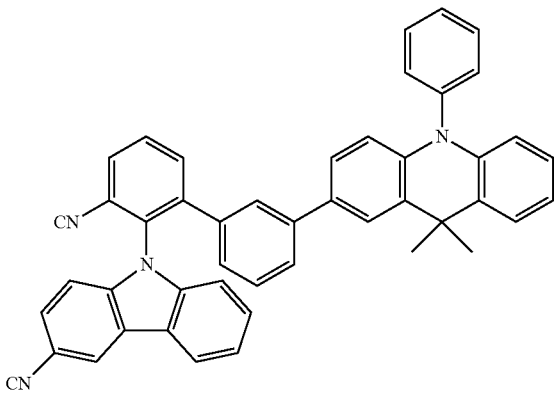
314
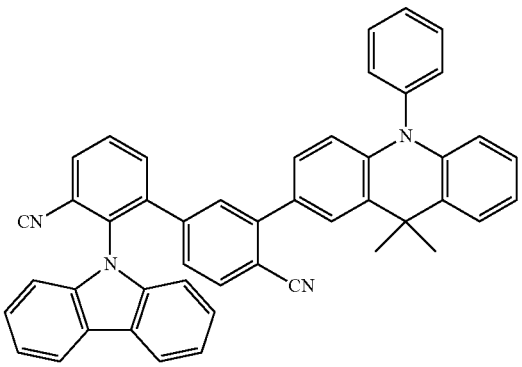

-continued
315
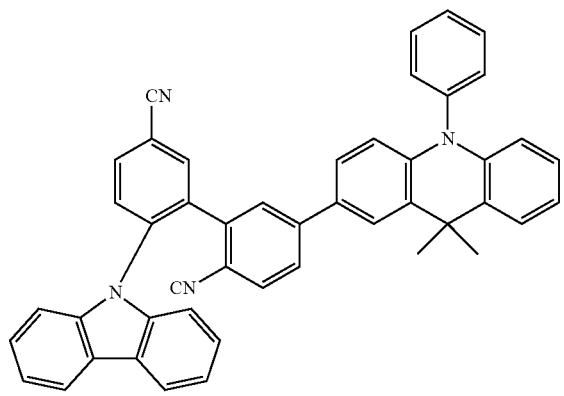
316
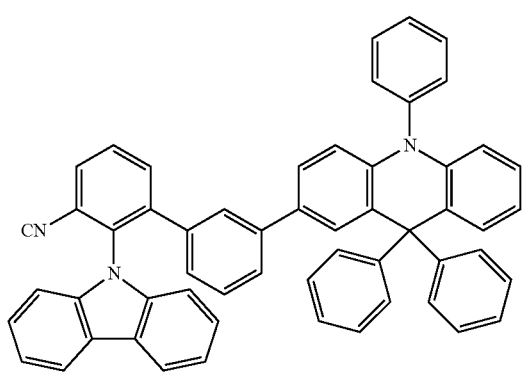
317
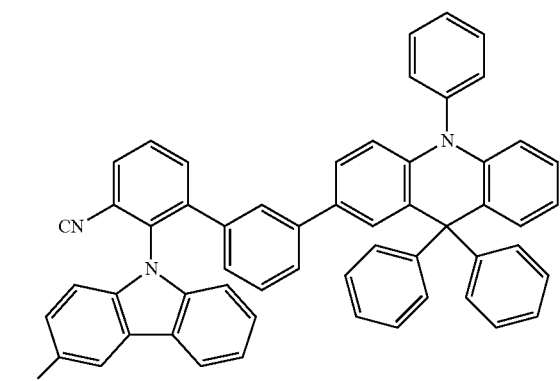
318
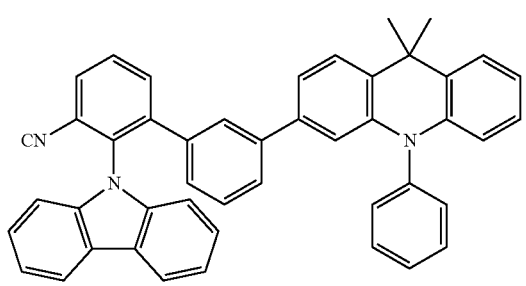
-continued
319
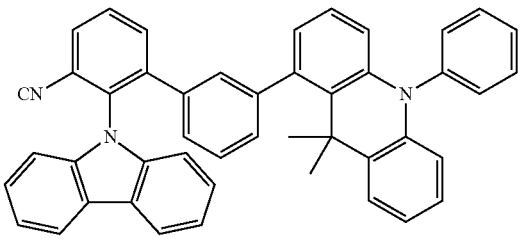
320
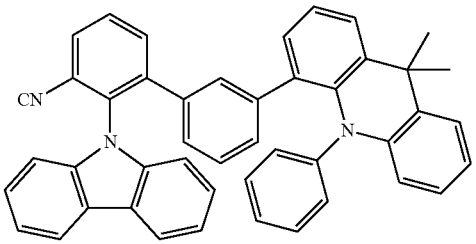
321
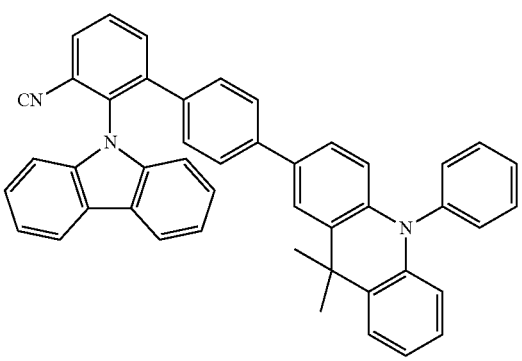
322
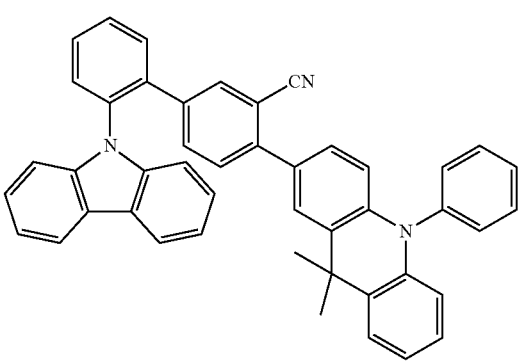
323
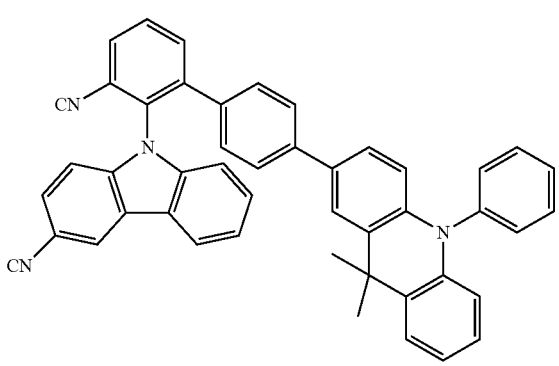

324
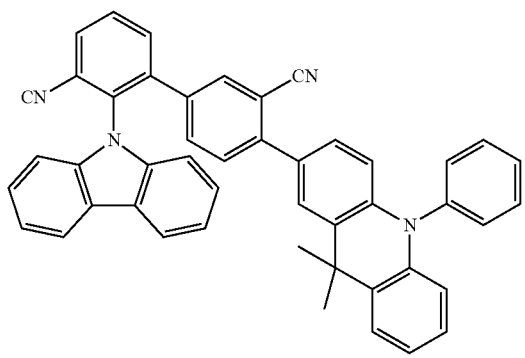
325
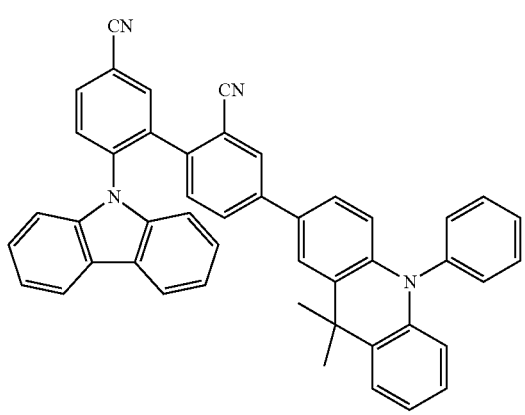
326
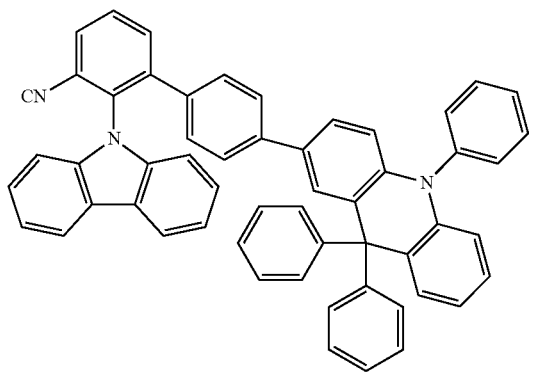
327
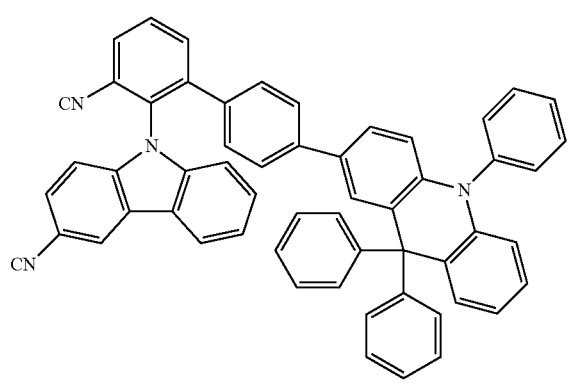
328
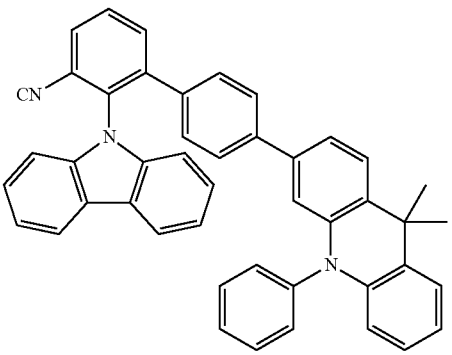
329
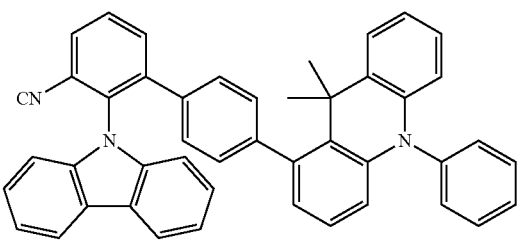
330
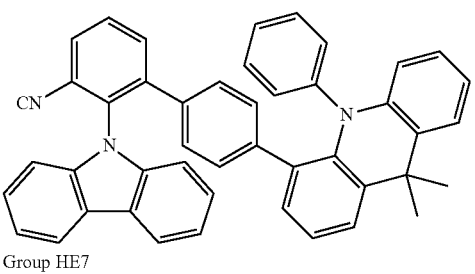
Group HE7
1
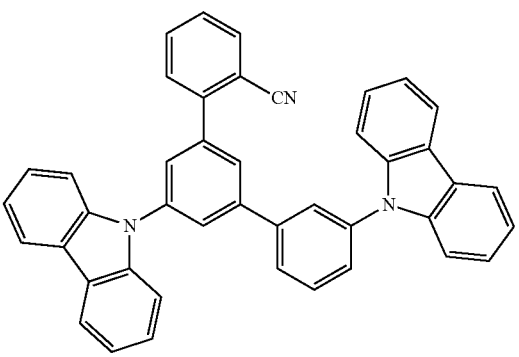

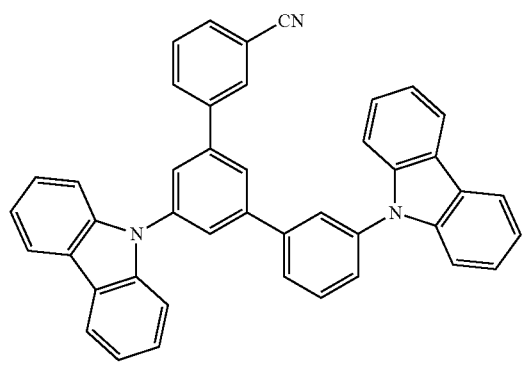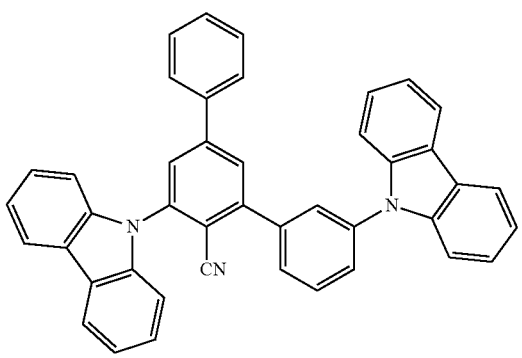

723
-continued
10
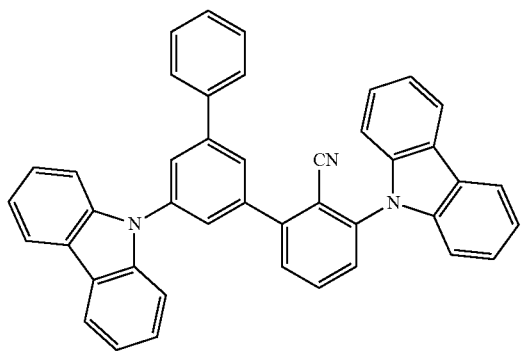
11
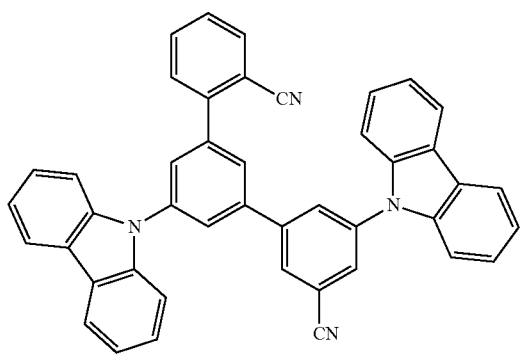
12
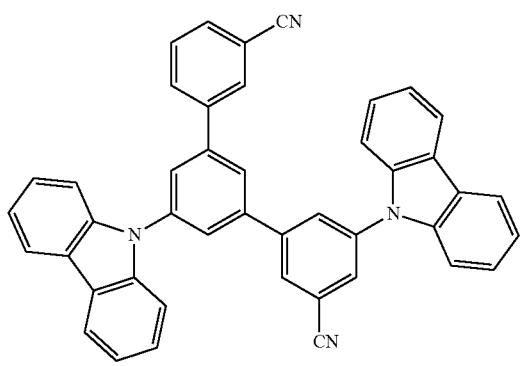
13
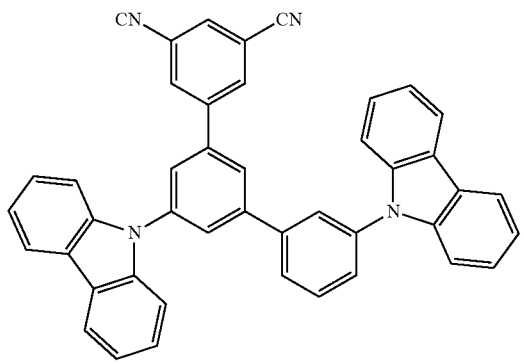
724
-continued
14
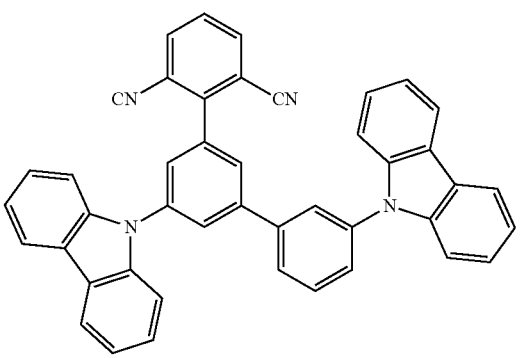
15
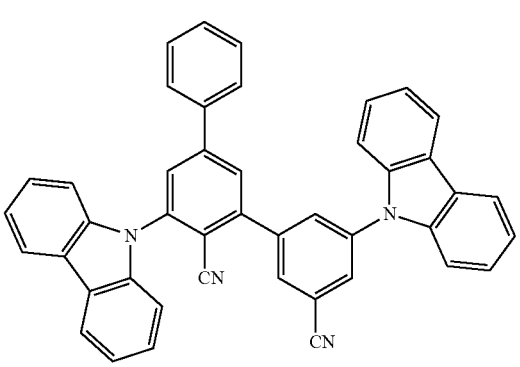
16
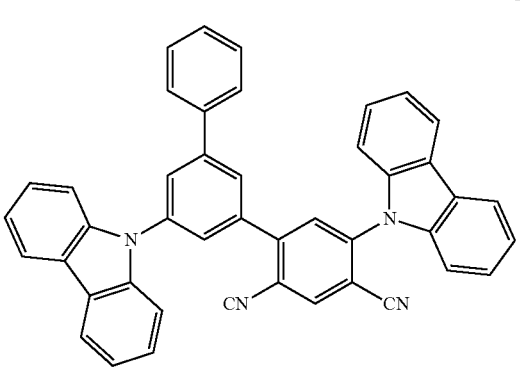
17
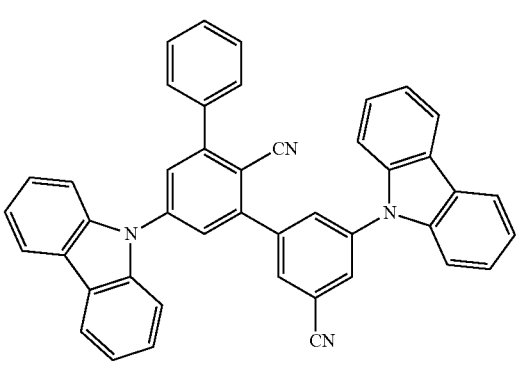

18
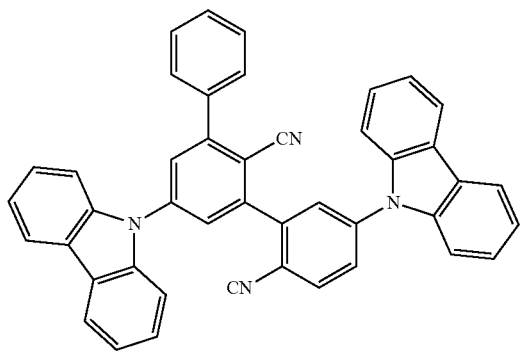
19
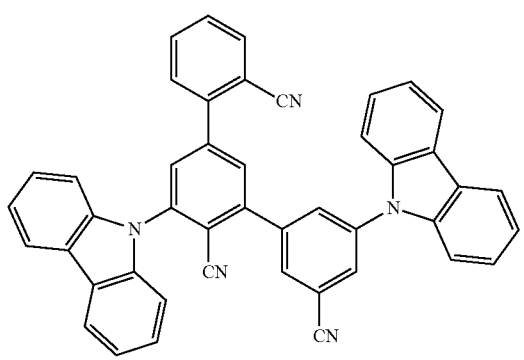
20
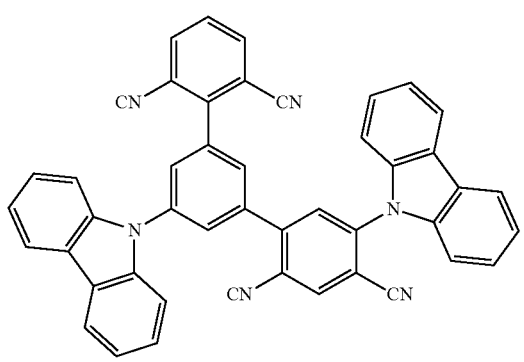
21
22
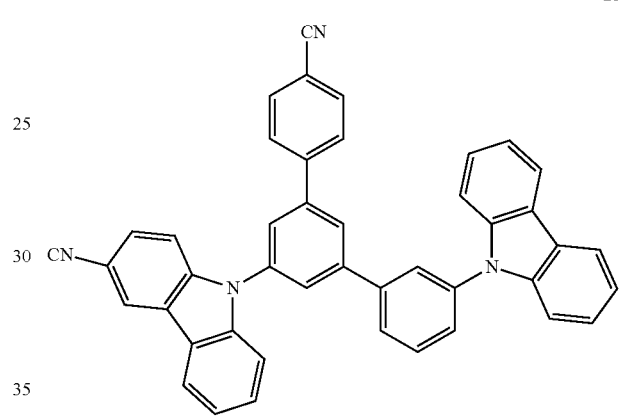
23
24
25
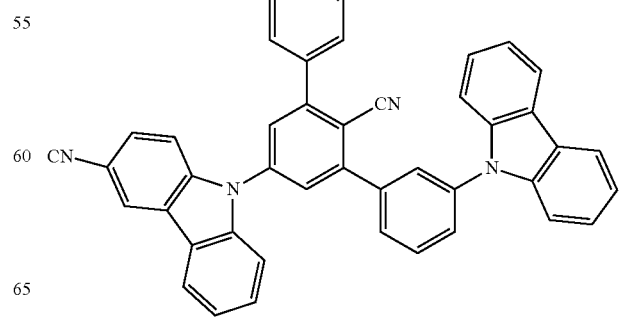

-continued
26
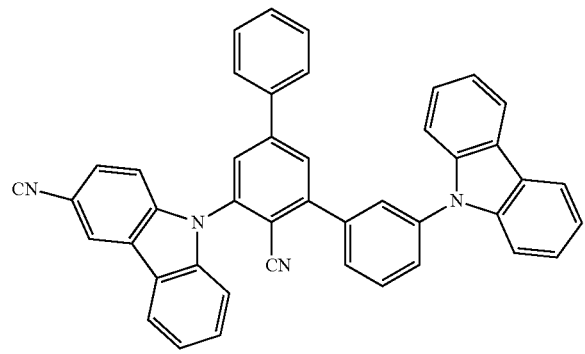
27
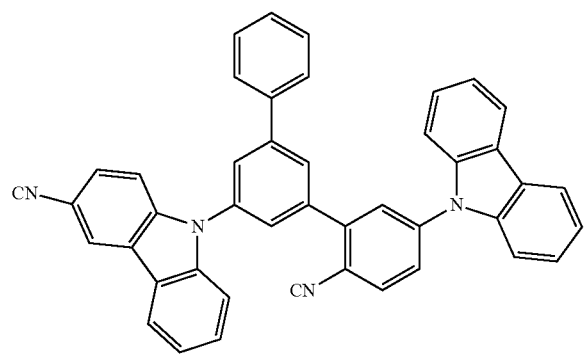
28
29
-continued
30
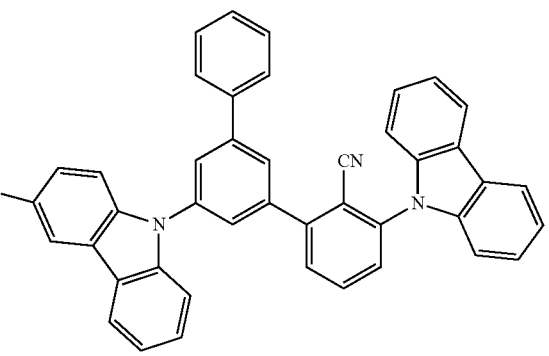
31
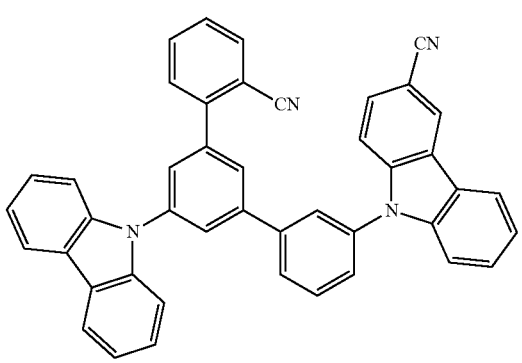
32
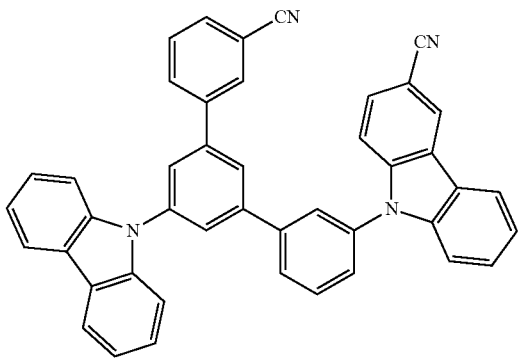
33
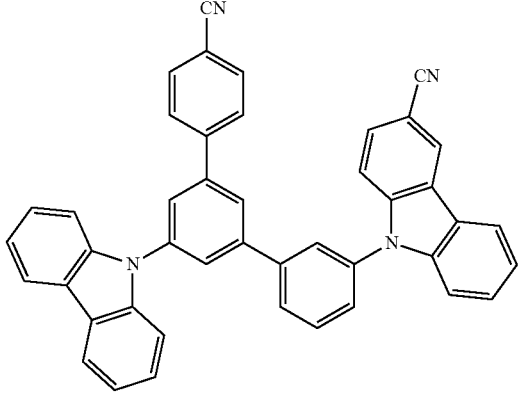

34
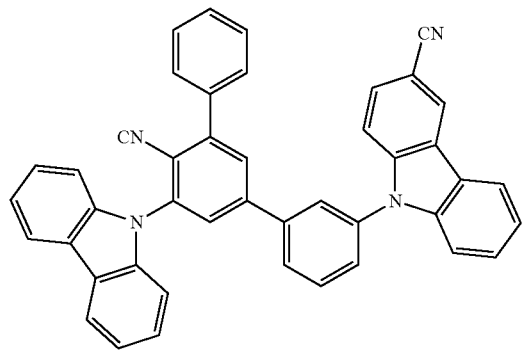
35
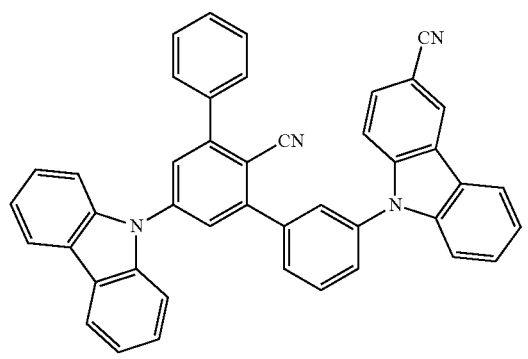
36
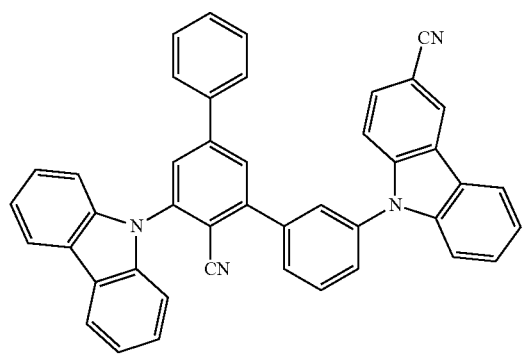
37
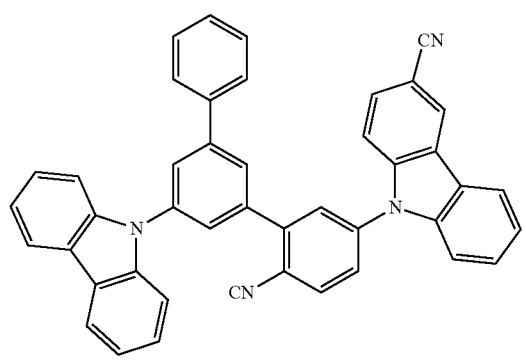
38
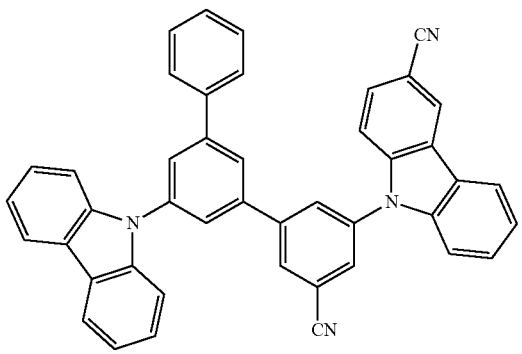
39
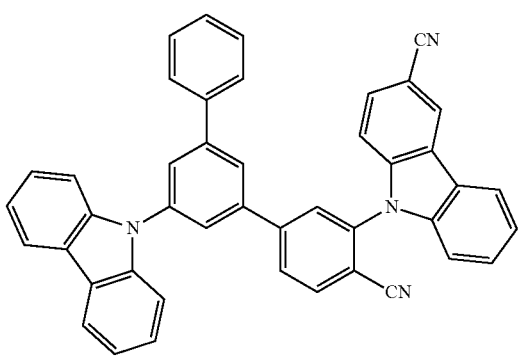
40
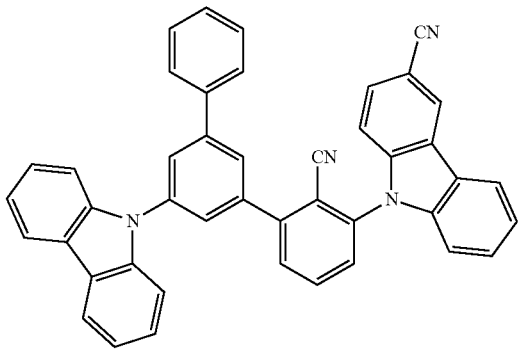
41
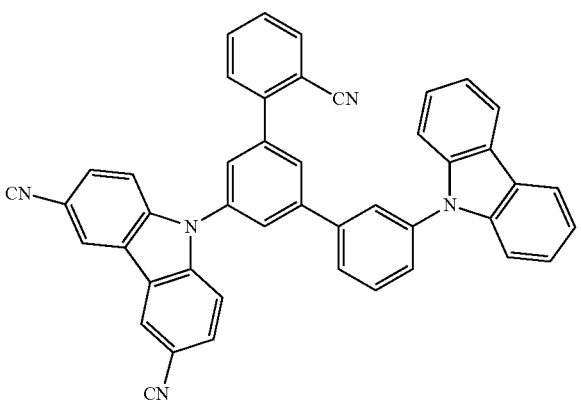

731
-continued
732
-continued
42
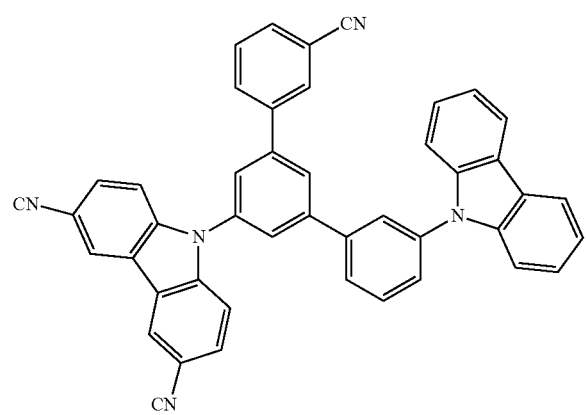
45
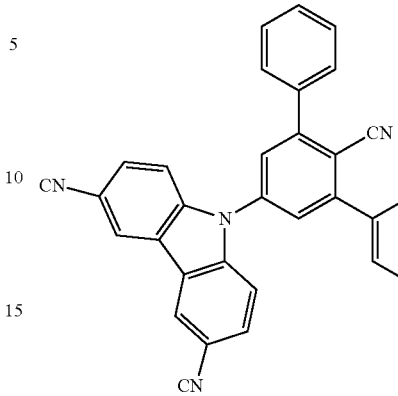
43
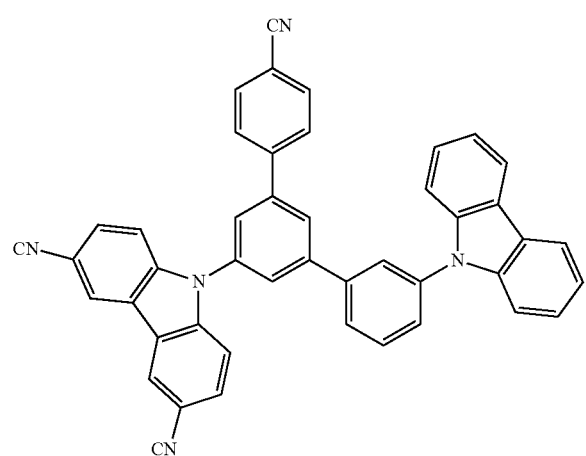
46
44
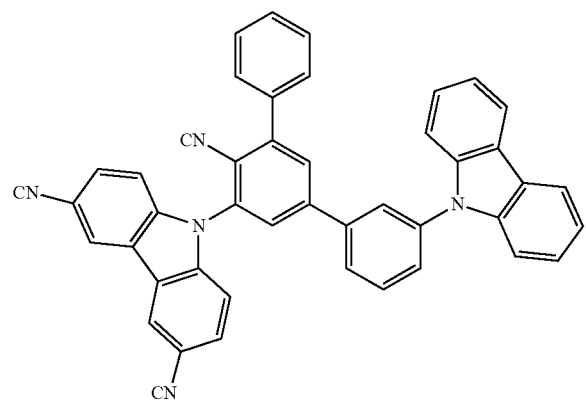
47
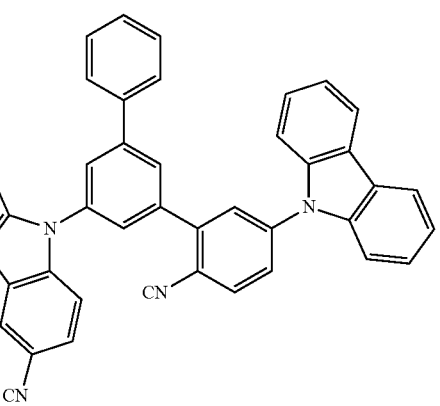

48
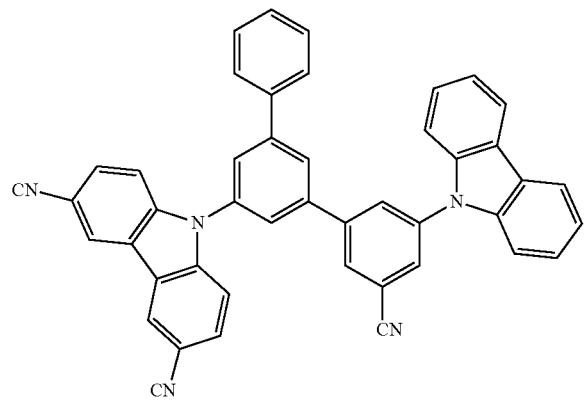
49
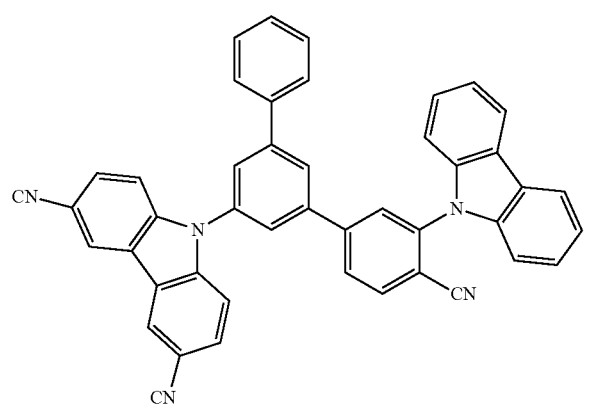
50
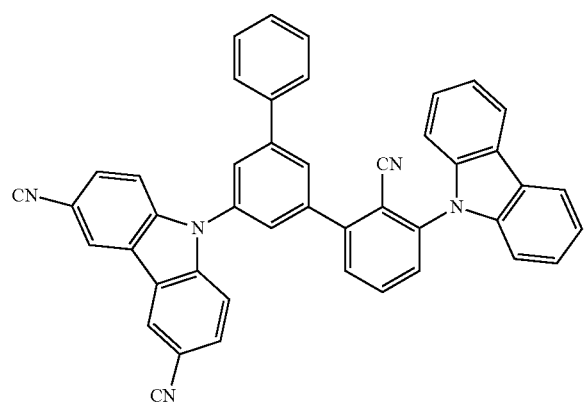
51
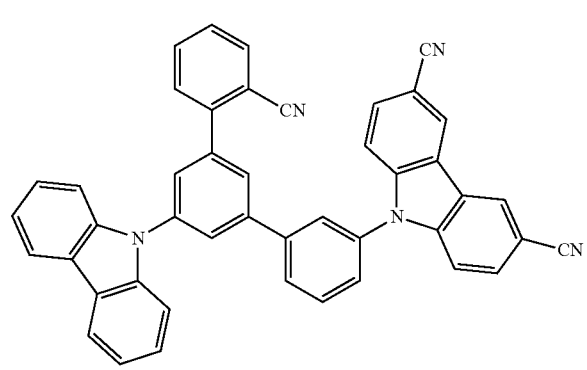
52
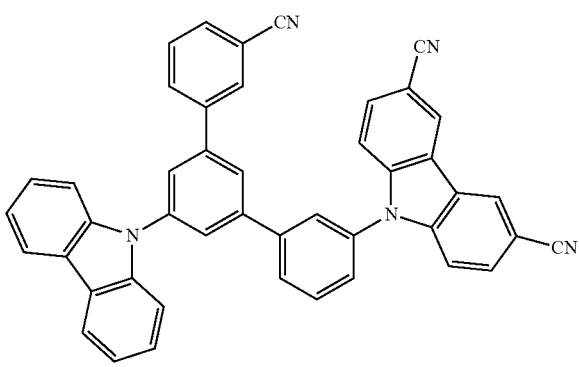
53
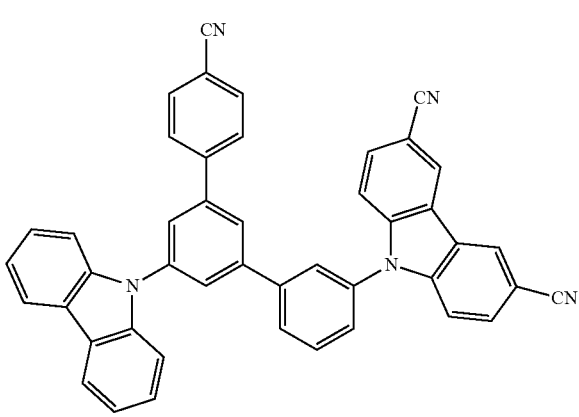
54
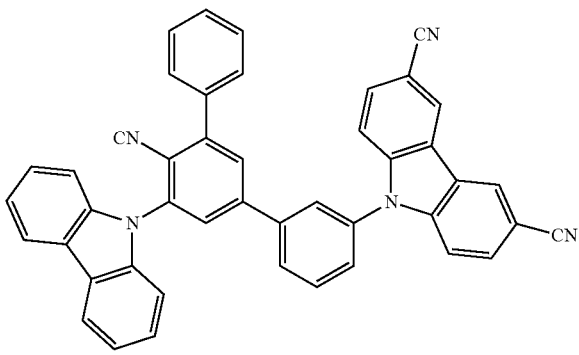
55

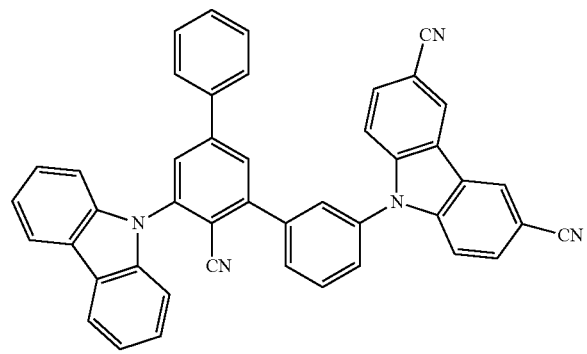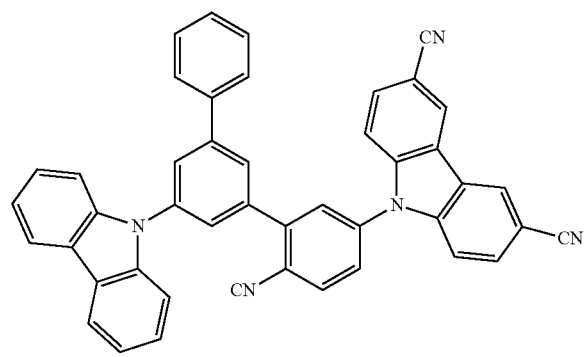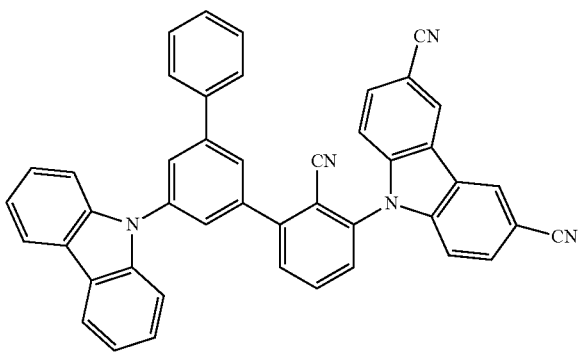

64
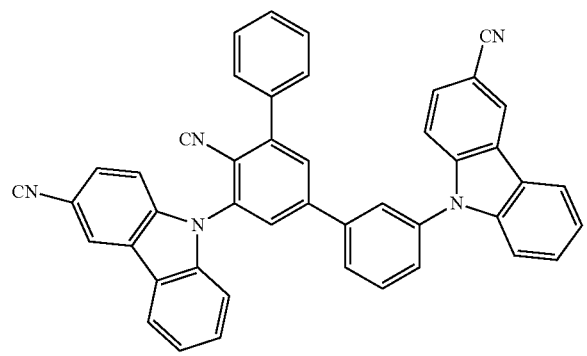
65
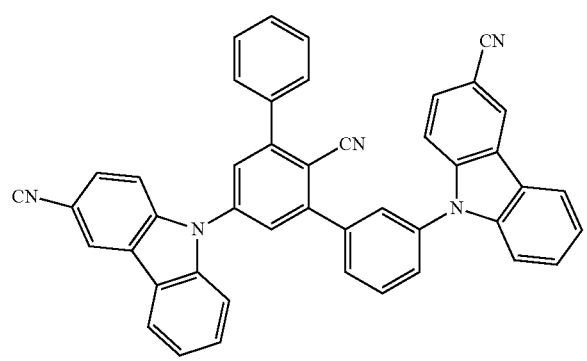
66
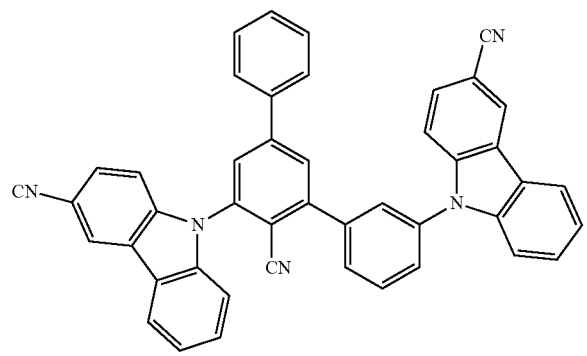
67
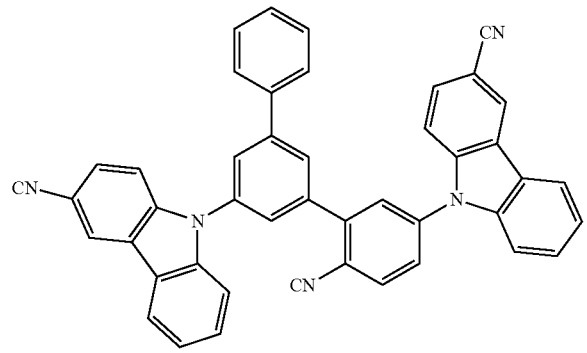
68
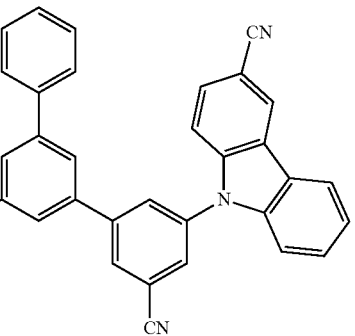
69
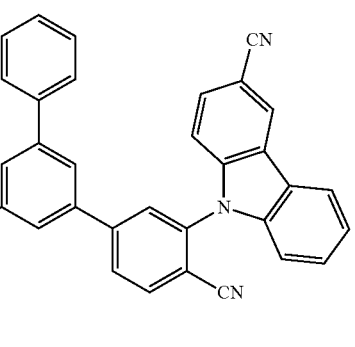
70
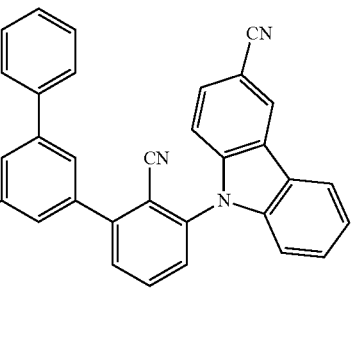
71
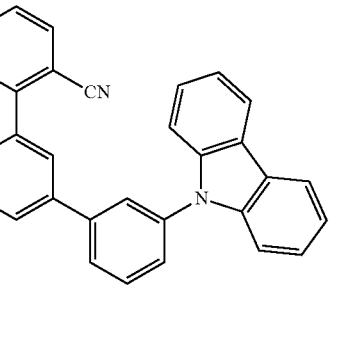

| 739 -continued | 740 -continued |
|---|---|
| 72 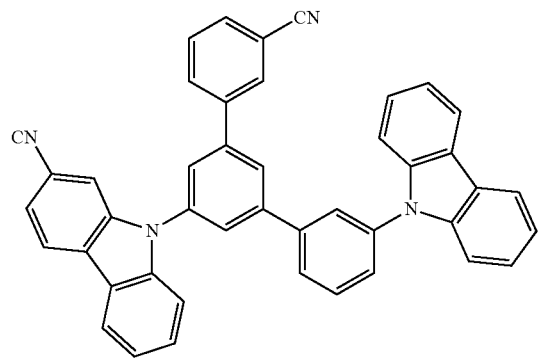 | 76 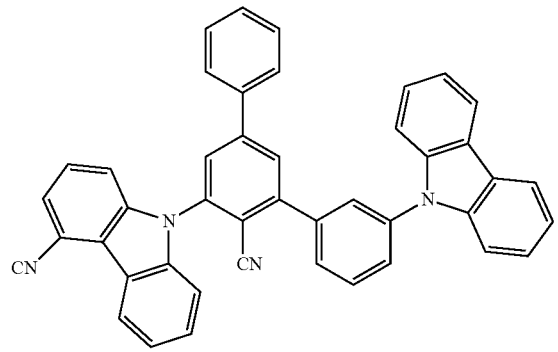 |
| 73 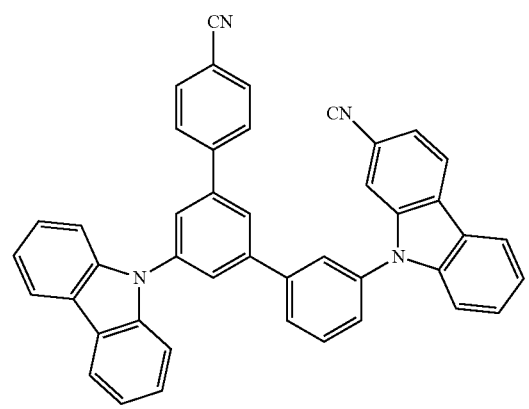 | 77 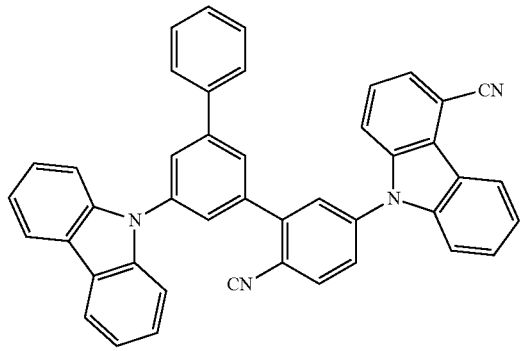 |
| 74 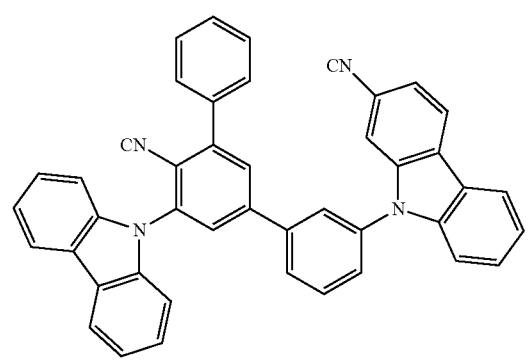 | 78 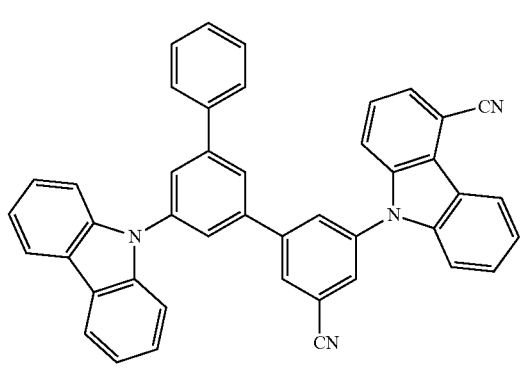 |
| 75 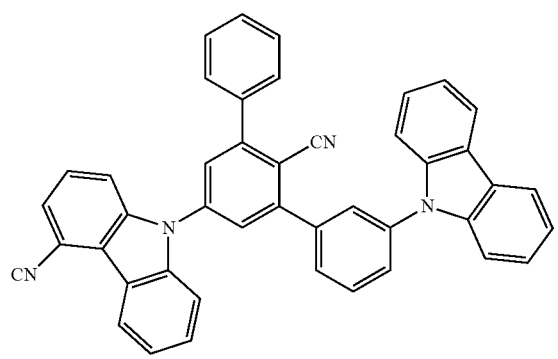 | 79 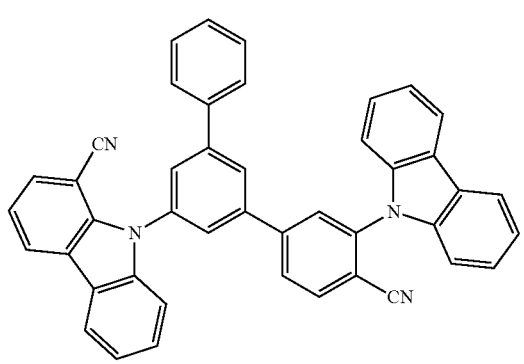 |

-continued
80
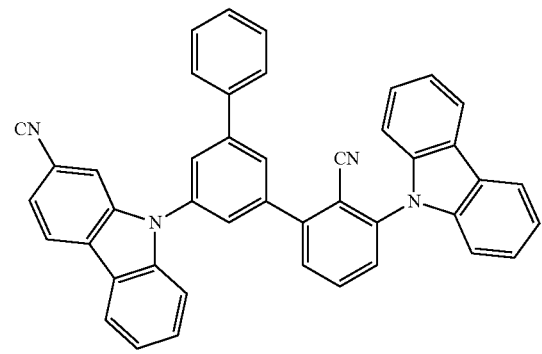
81
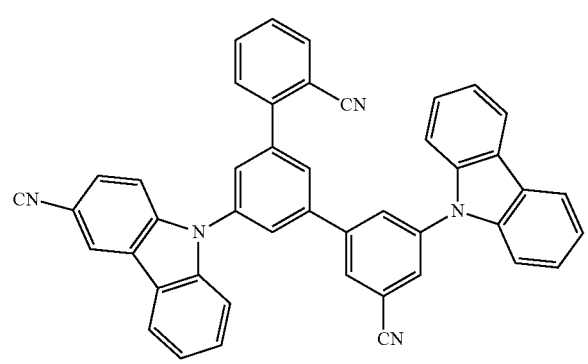
82
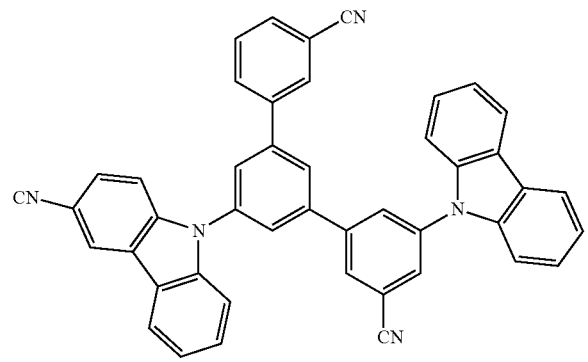
83
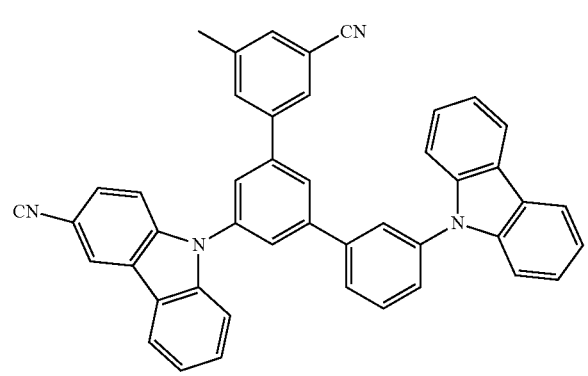
-continued
84
85
86
87
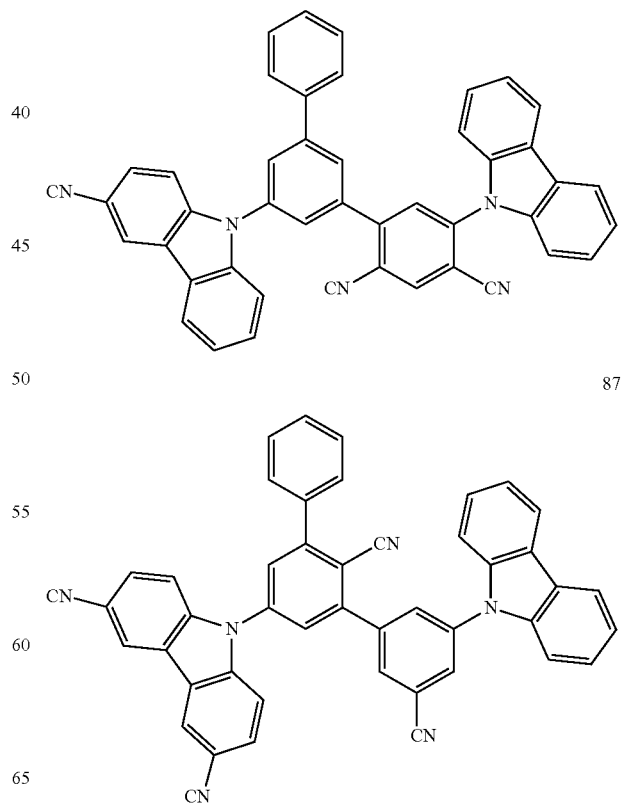

-continued
88
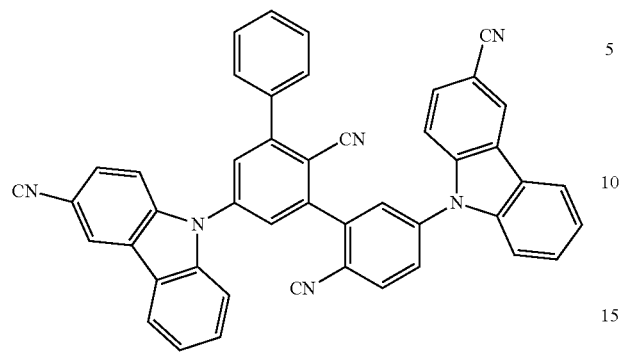
89
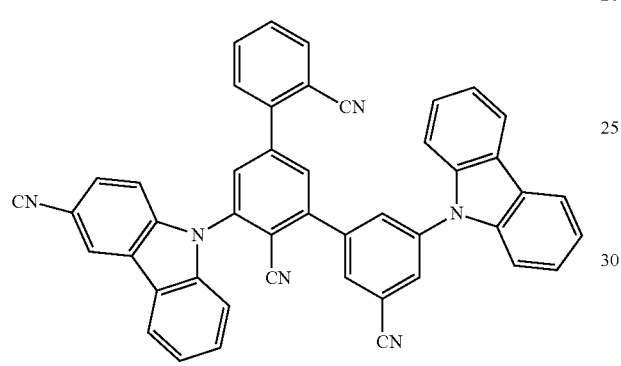
90
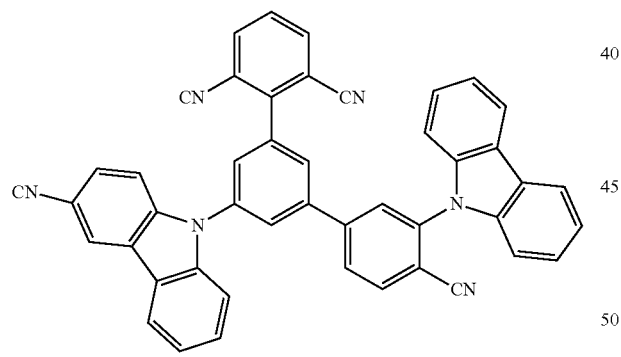
91
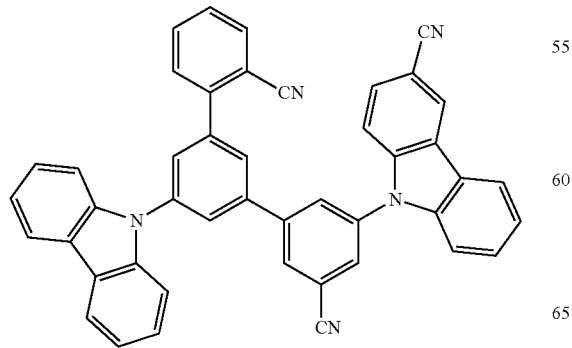
-continued
92
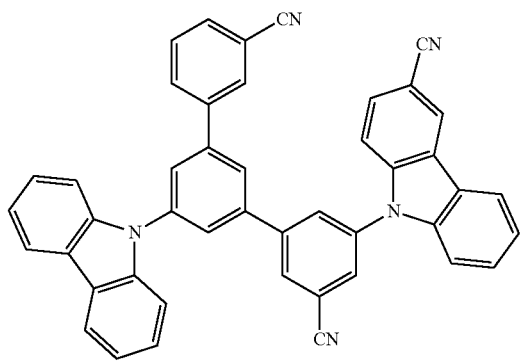
93
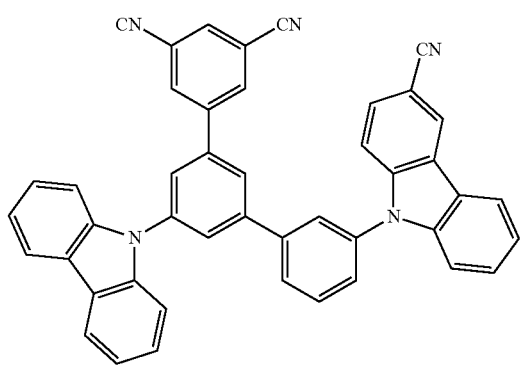
94
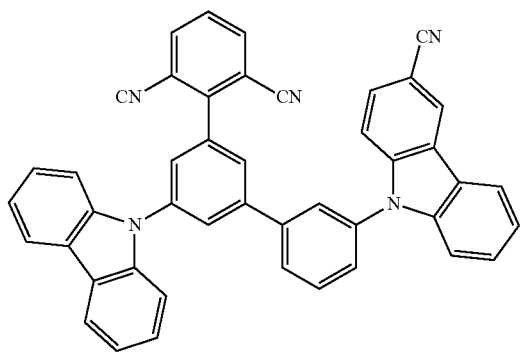
95
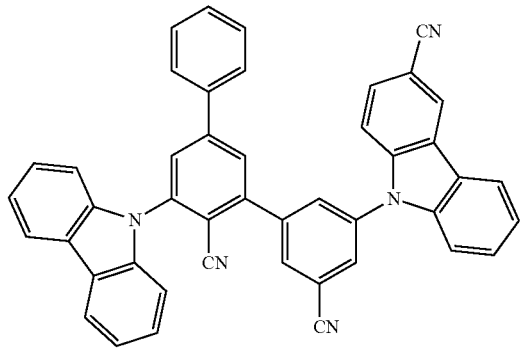

96
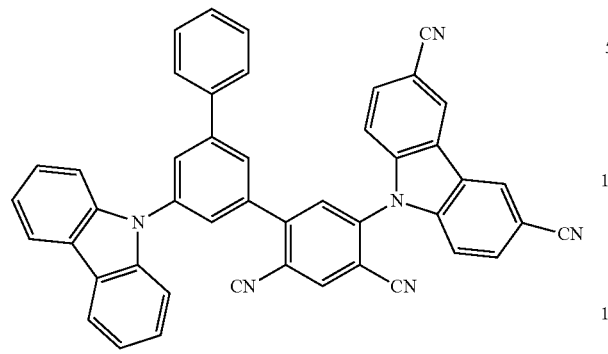
97
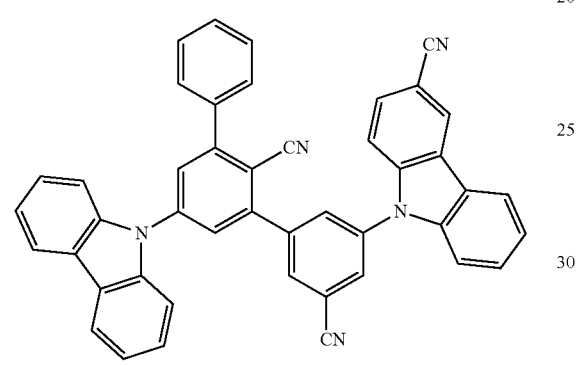
98
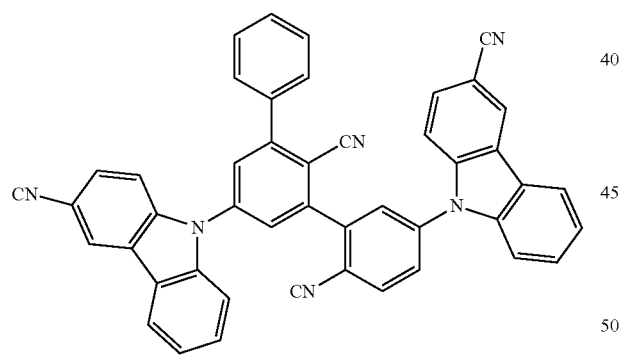
99
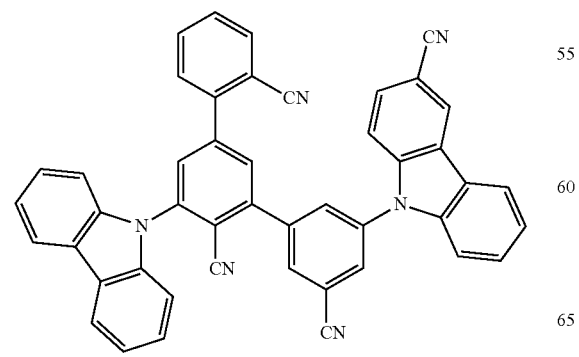
100
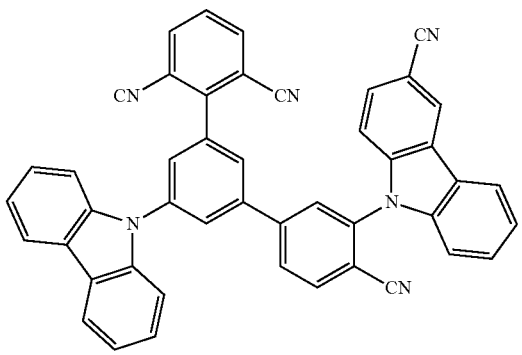
101
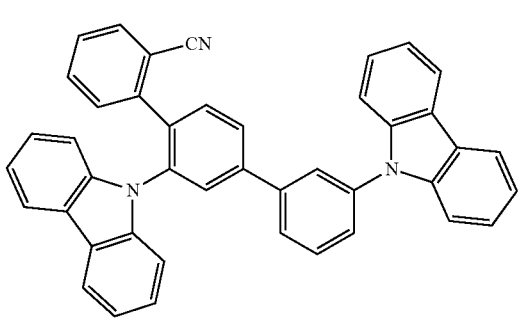
102
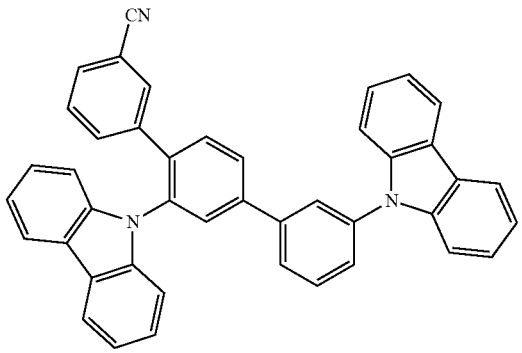
103
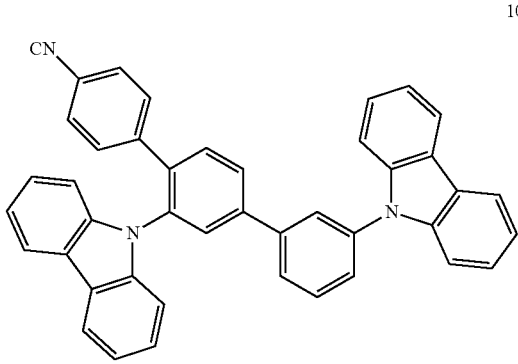

104
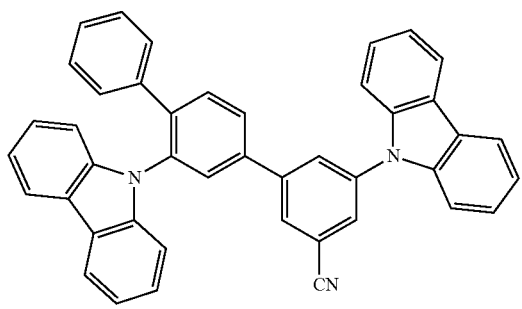
105
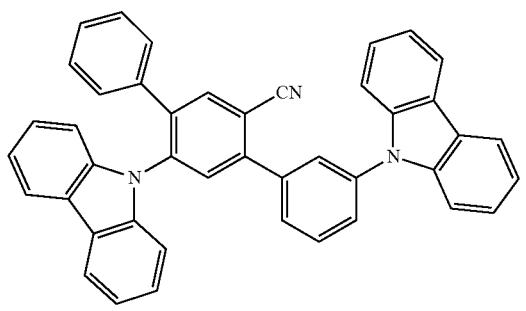
106
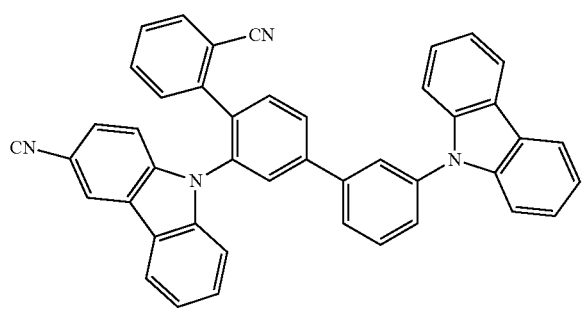
107
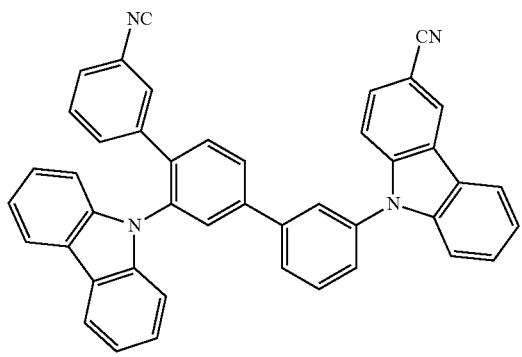
108
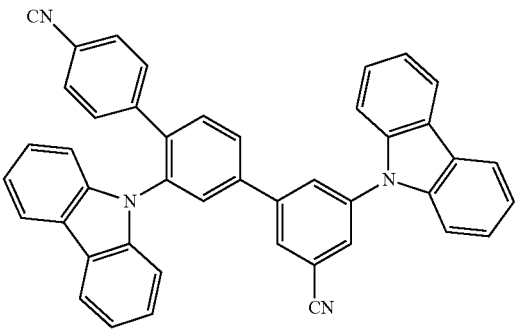
109
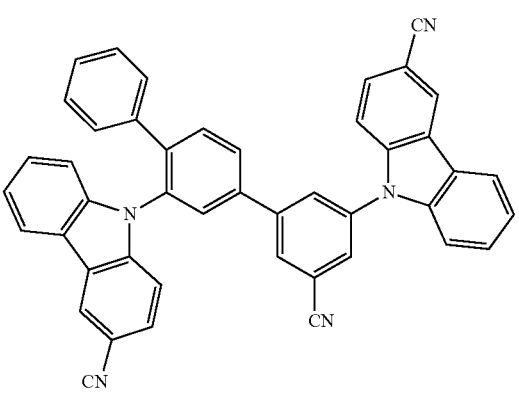
110
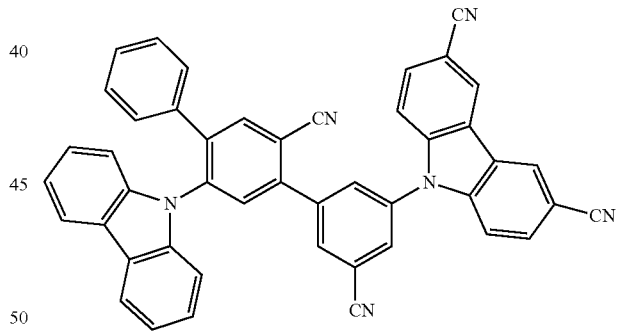
111
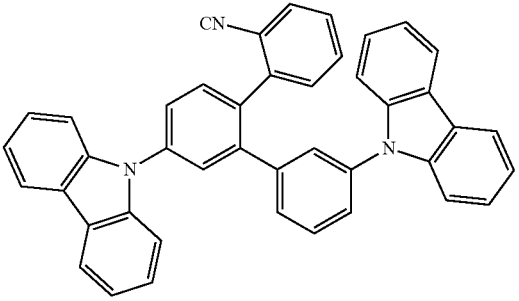

-continued
112
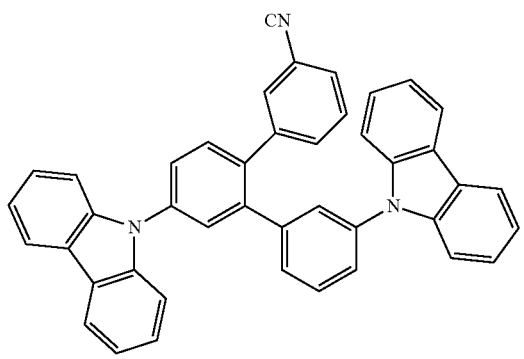
113
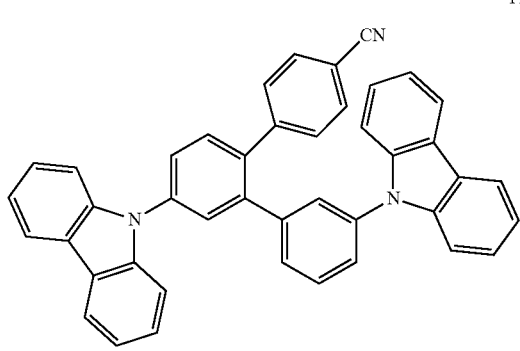
114
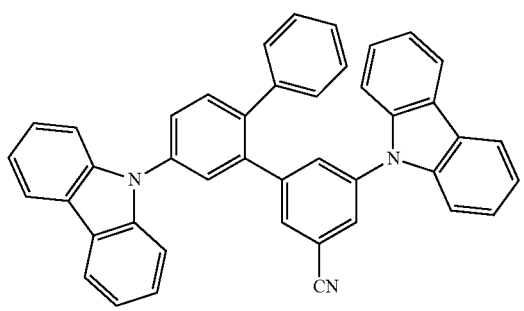
115
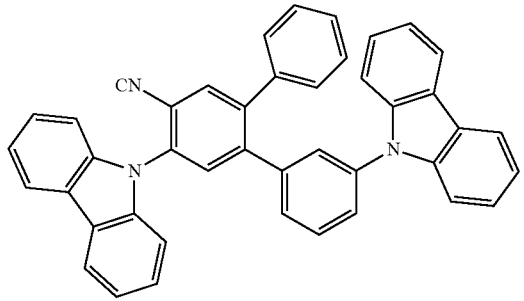
-continued
116
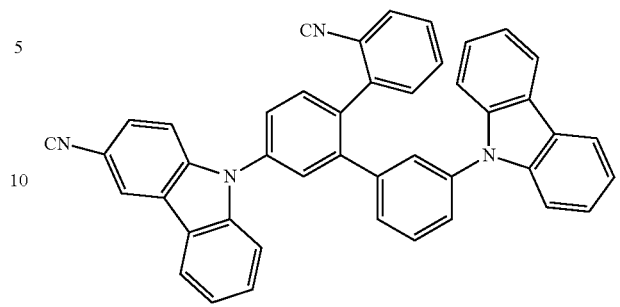
117
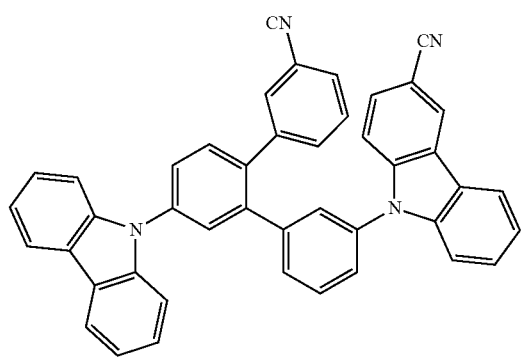
118
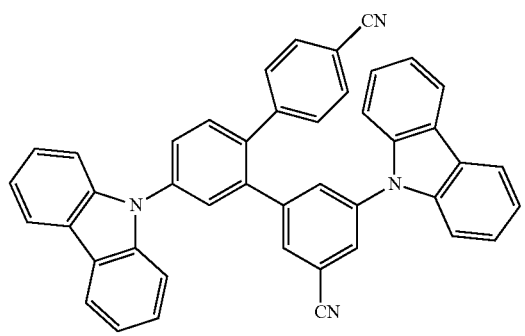
119
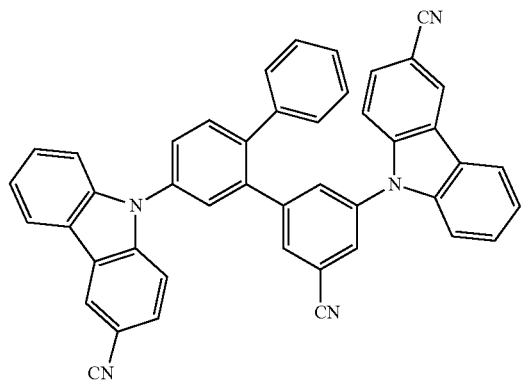

751
-continued
120
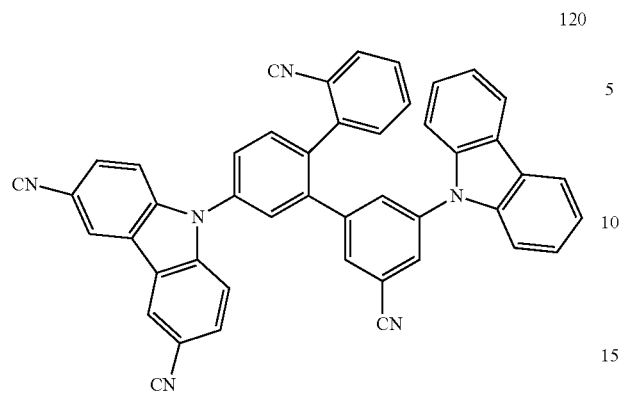
121
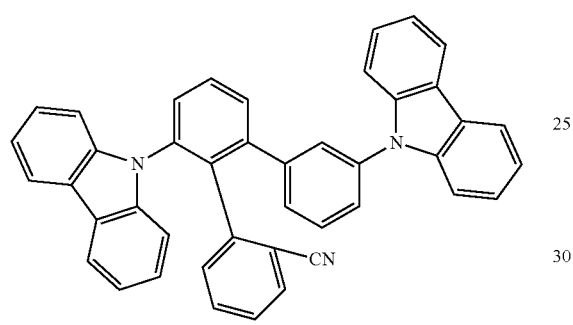
122
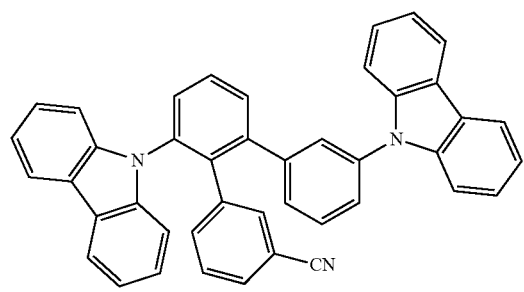
123
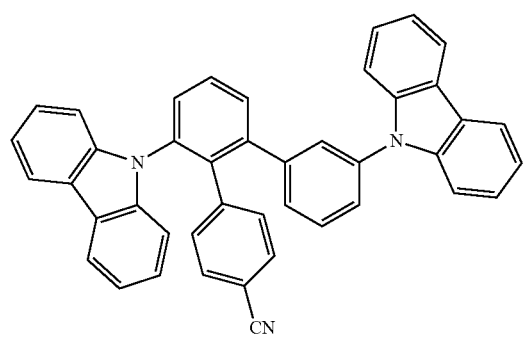
752
-continued
124
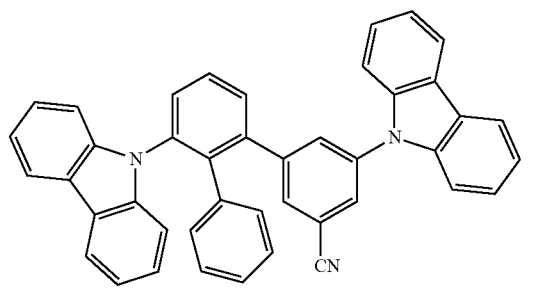
125
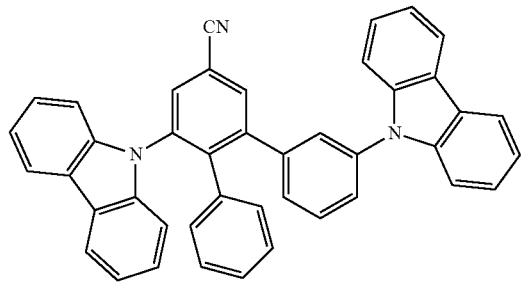
126
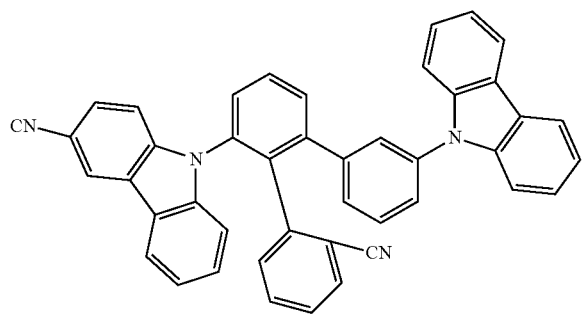
127
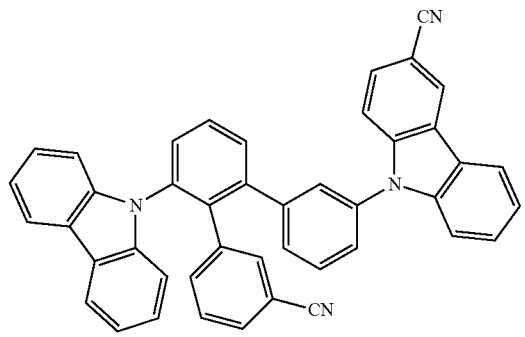

128
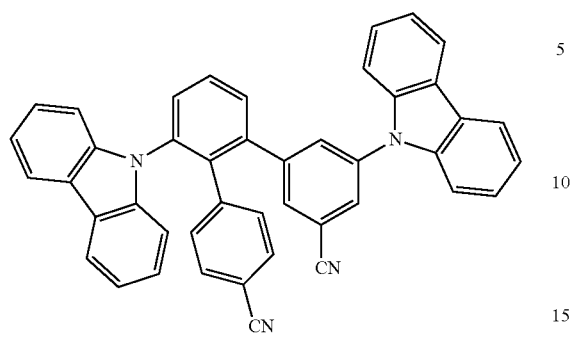
129
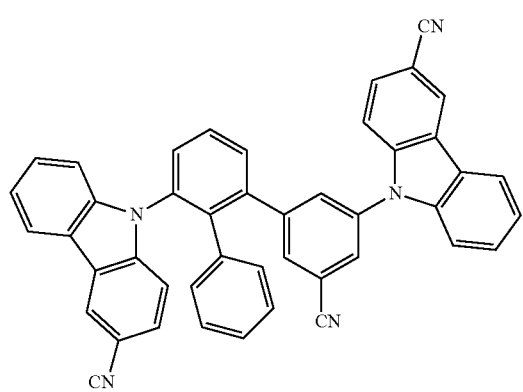
130
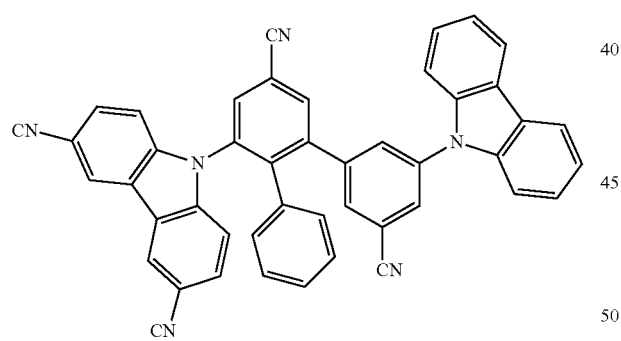
131
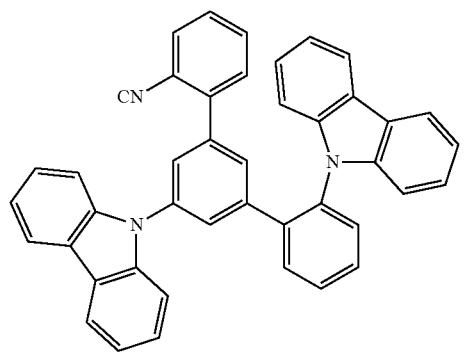
132
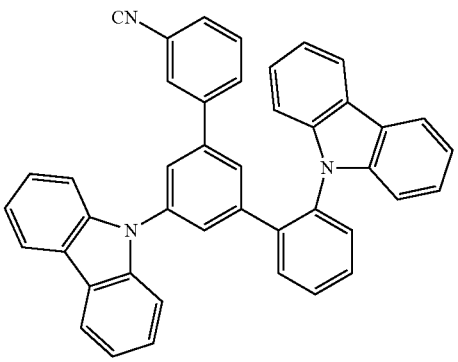
133
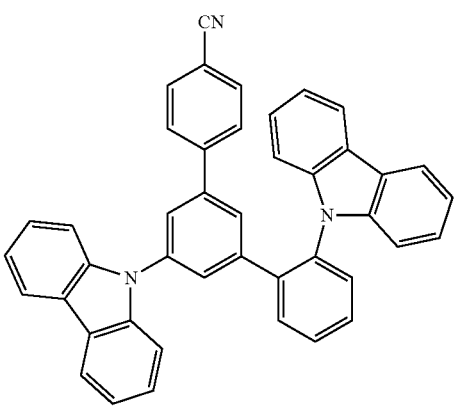
134
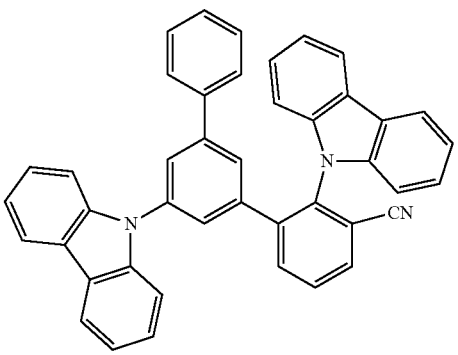
135
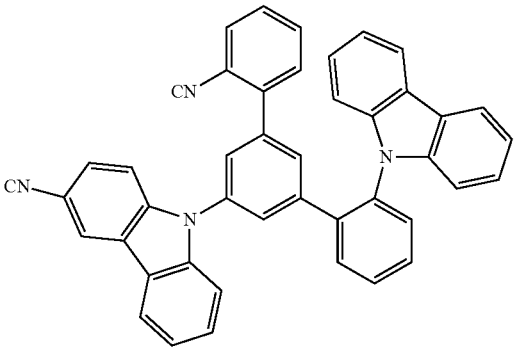

755
-continued
136
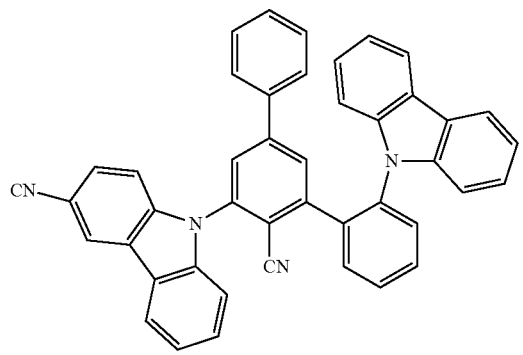
137
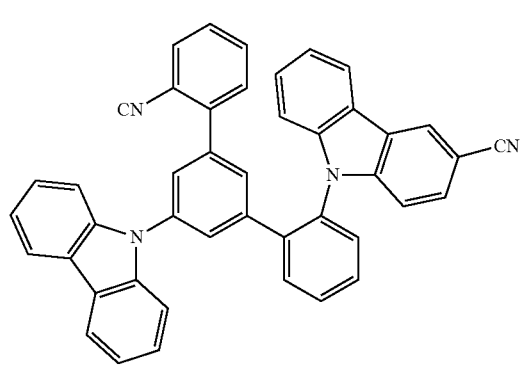
138
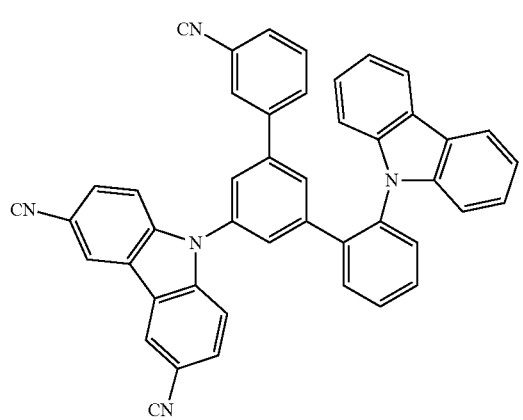
139
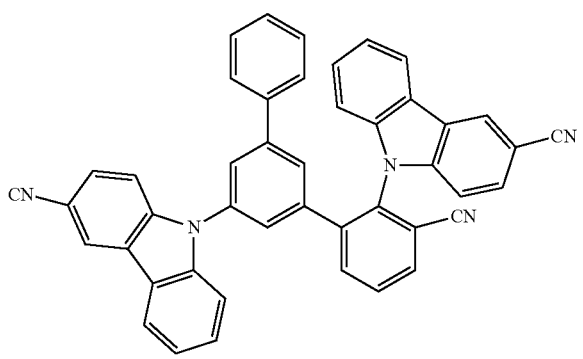
756
-continued
140
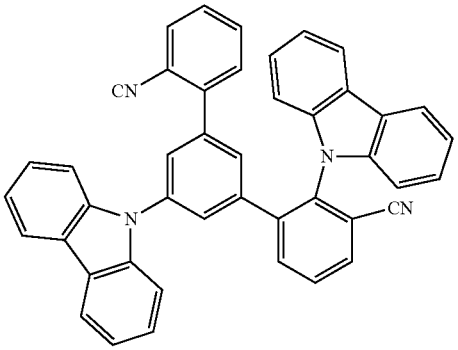
141
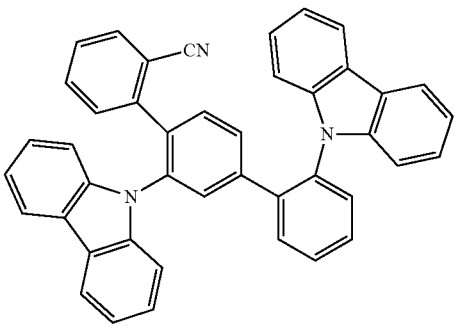
142
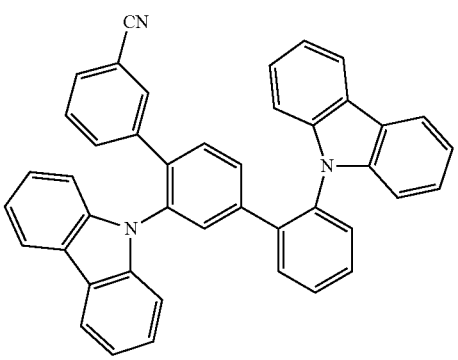
143
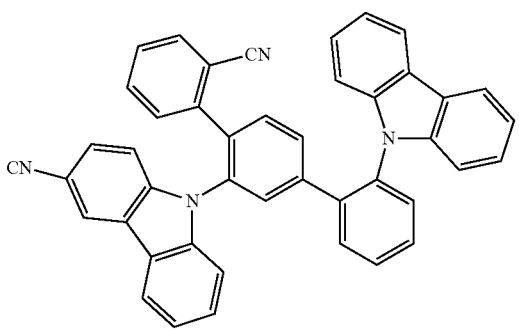

144
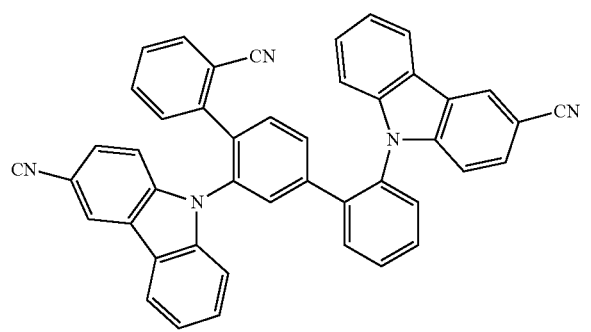
145
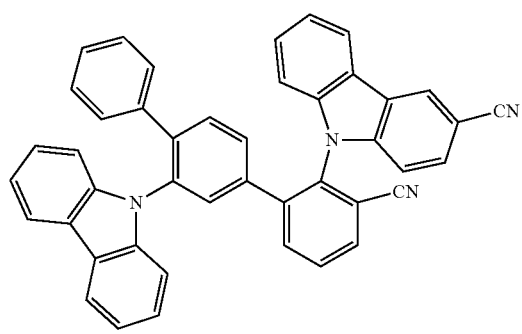
146
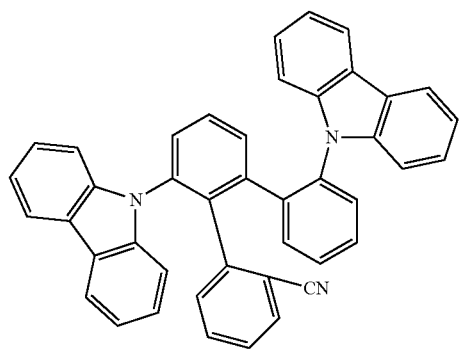
147
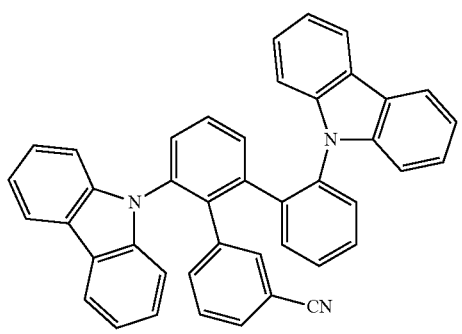
148
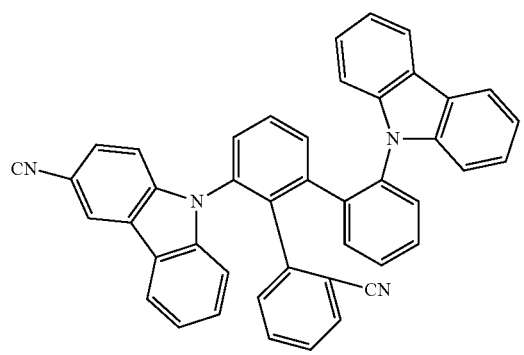
149
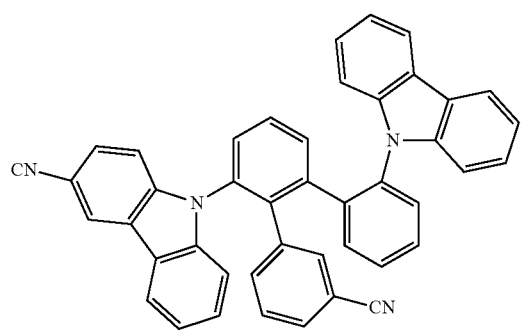
150
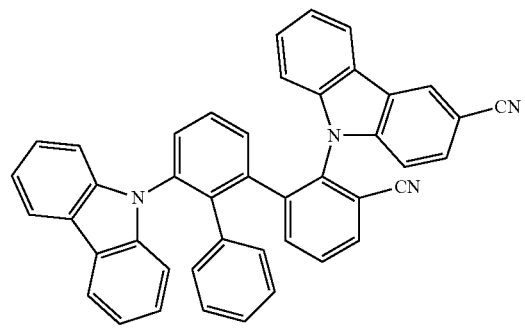
151
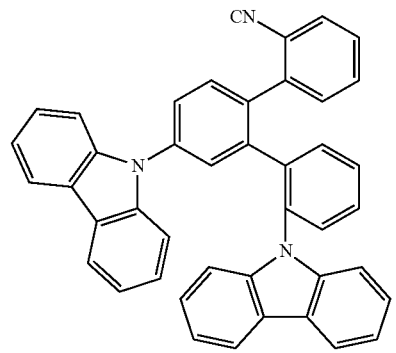

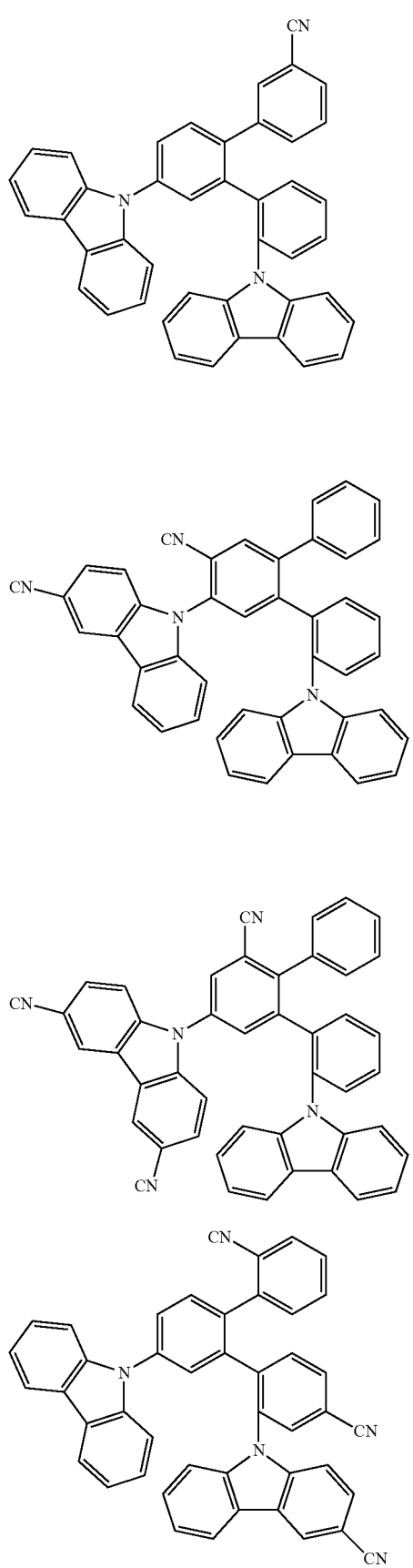
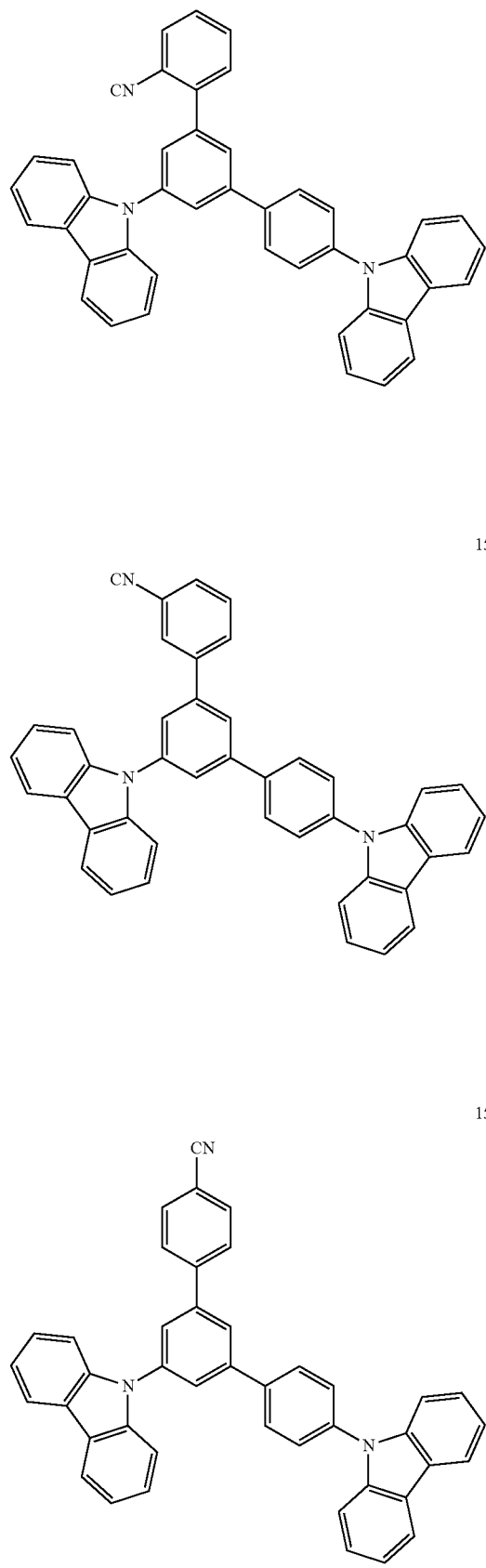

159
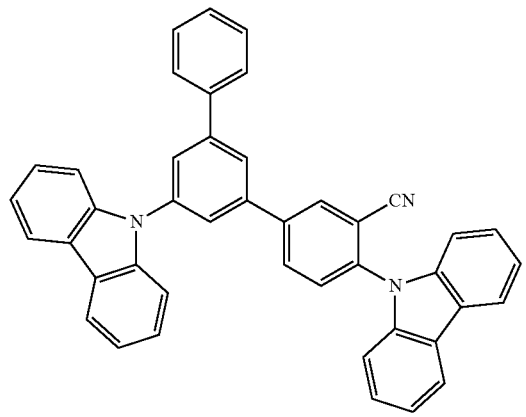
160
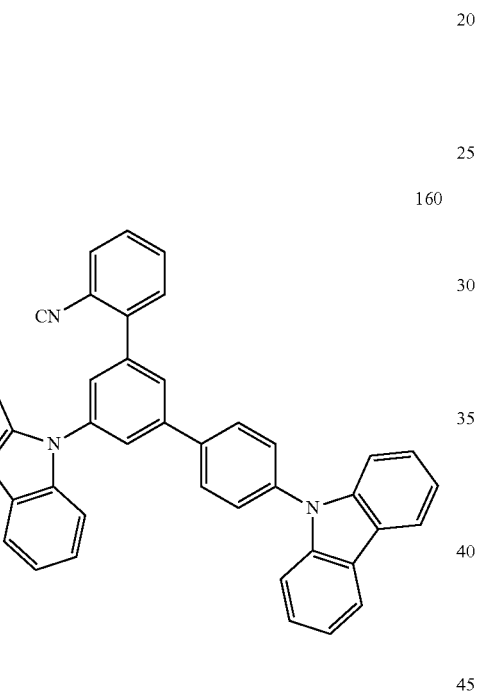
161
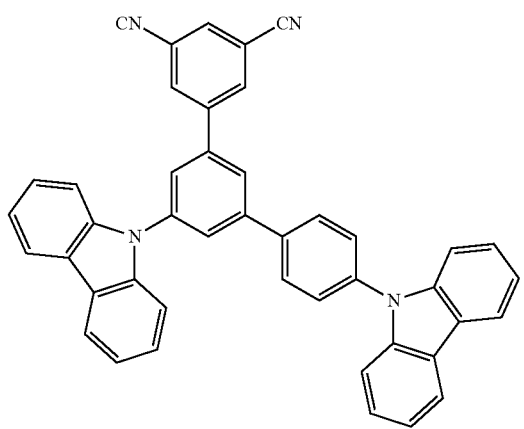
162
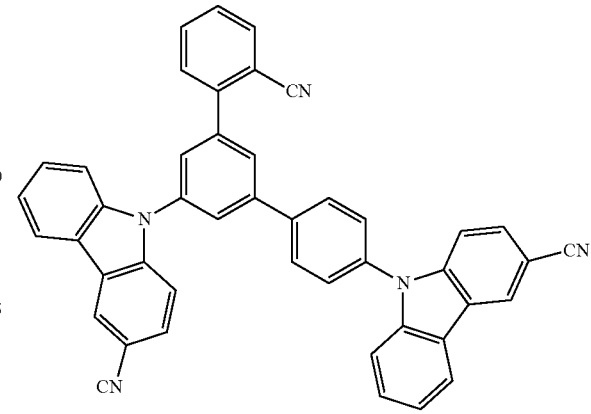
163
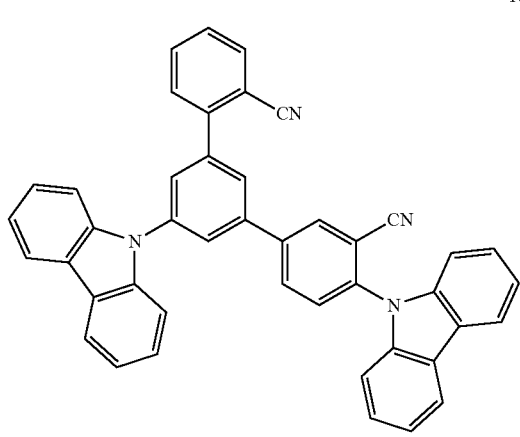
164
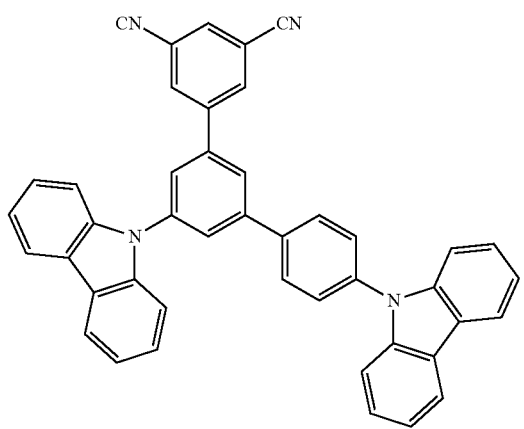

165
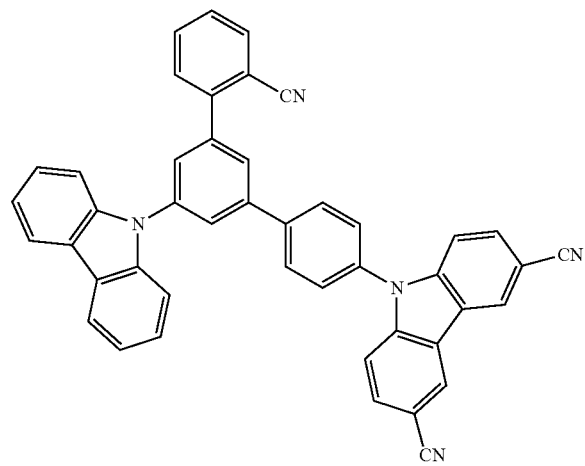
166
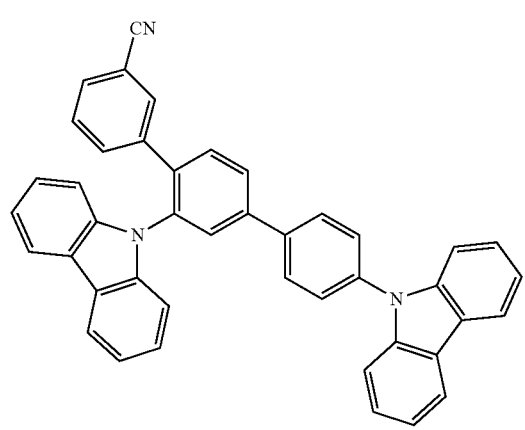
167
168
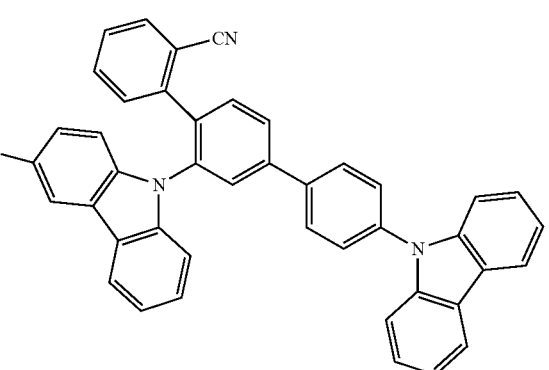
169
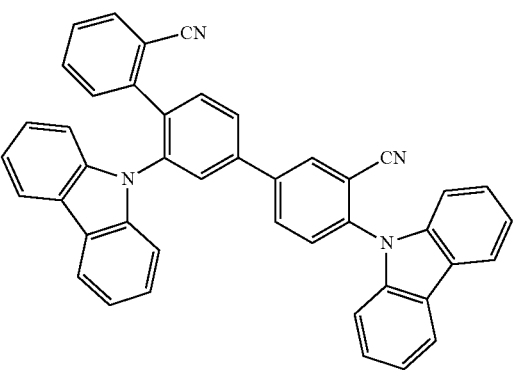
170
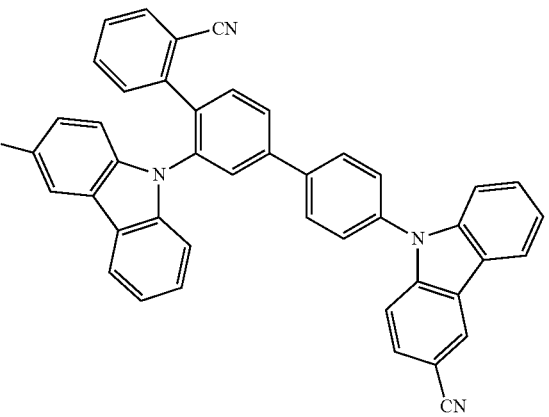
171
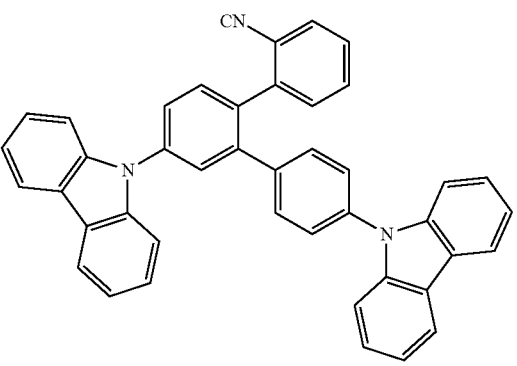

172
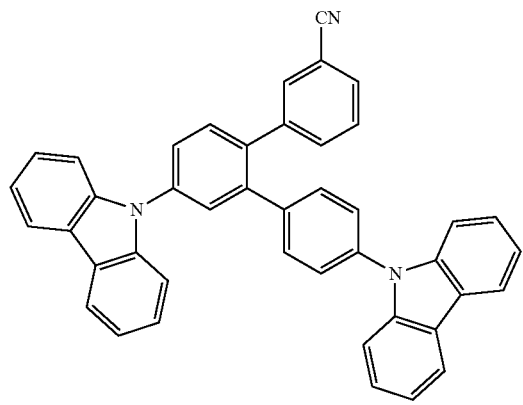
173
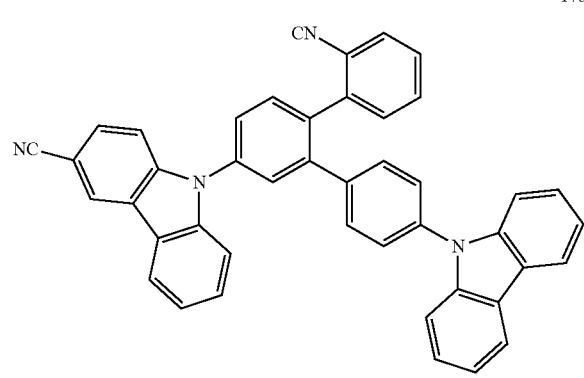
174
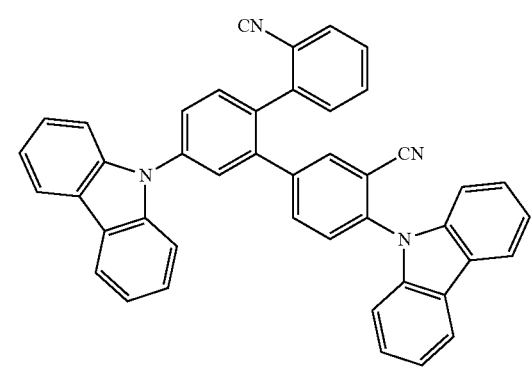
175
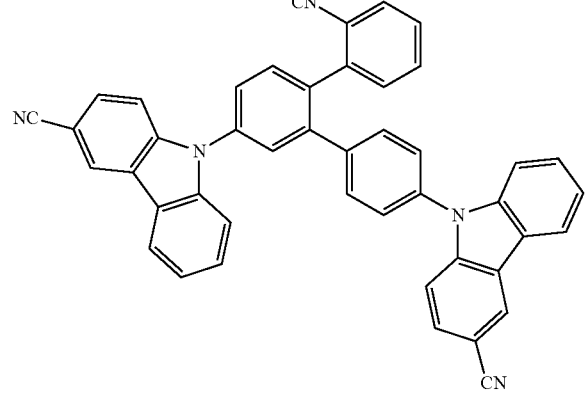
176
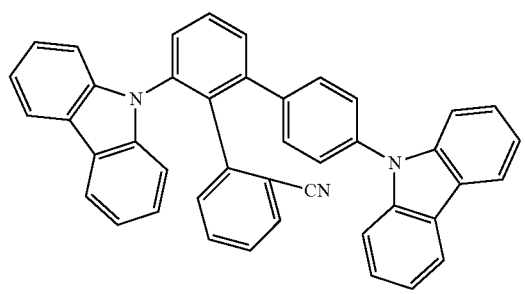
177
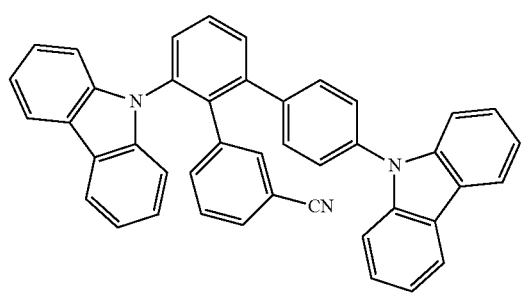
178
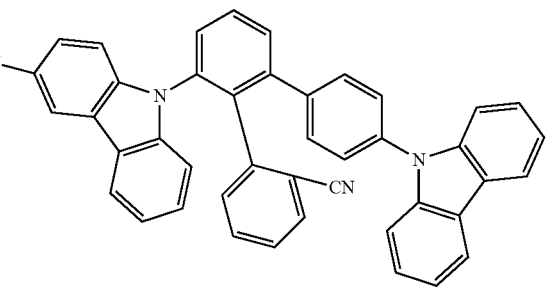
179
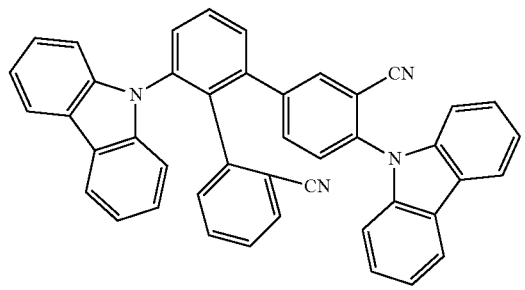
180
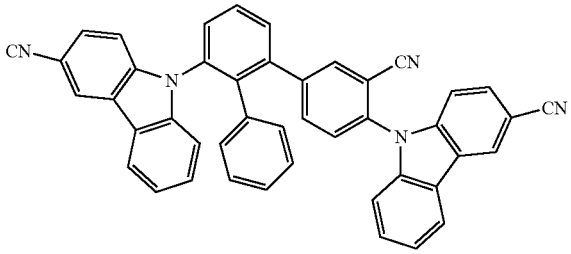

767
-continued
181
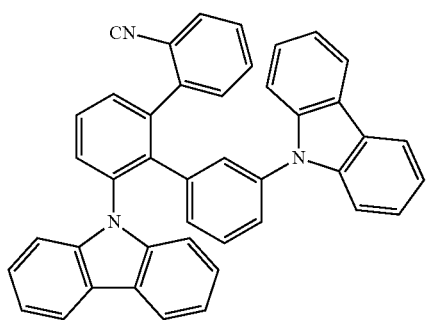
182
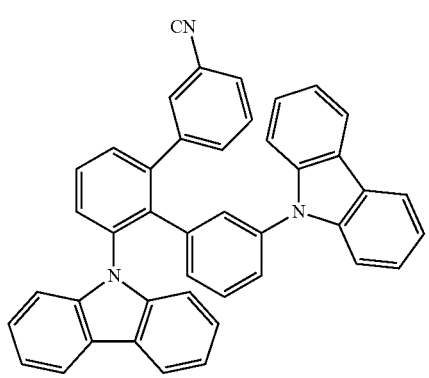
183
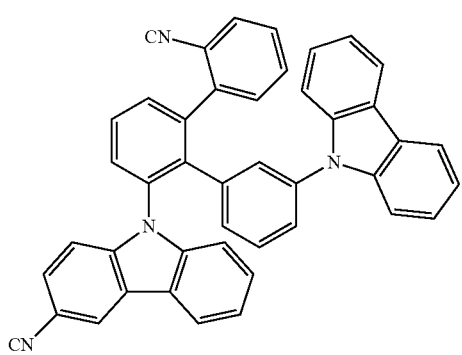
184
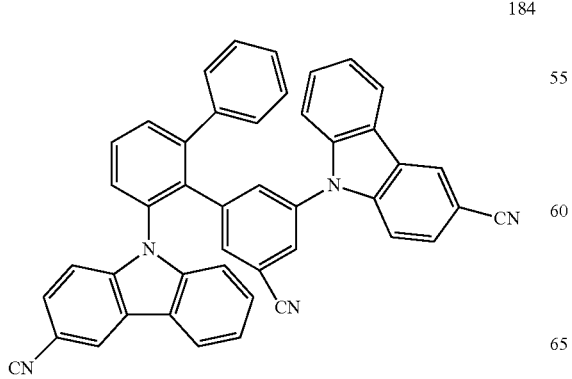
768
-continued
185
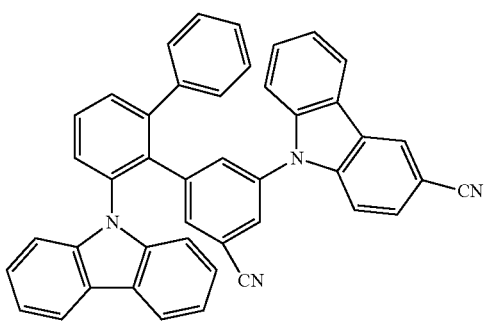
186
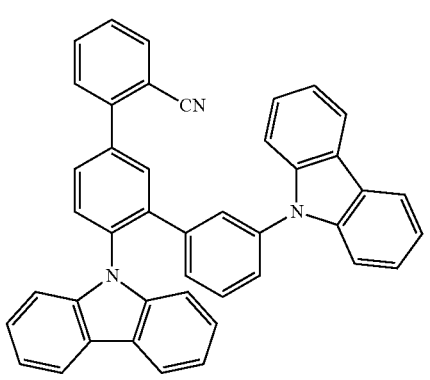
187
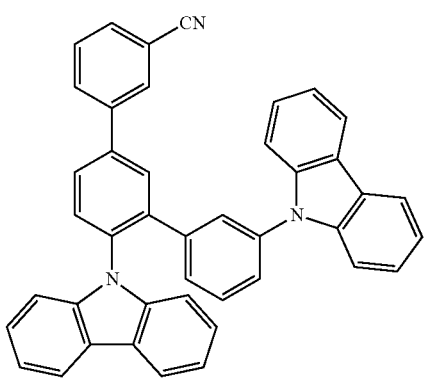
188
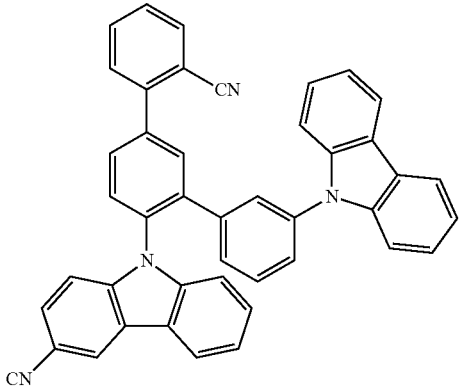

769
-continued
189
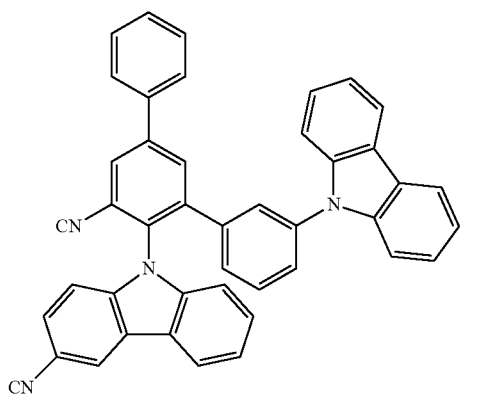
190
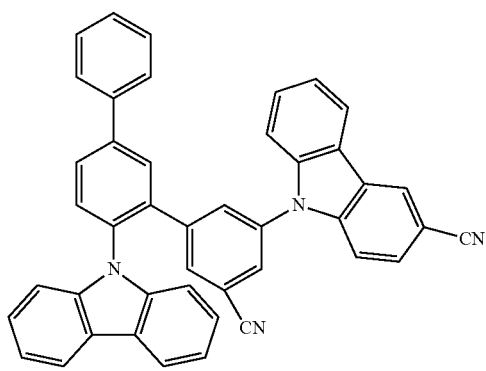
191
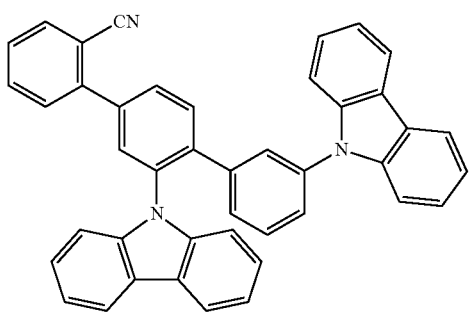
192
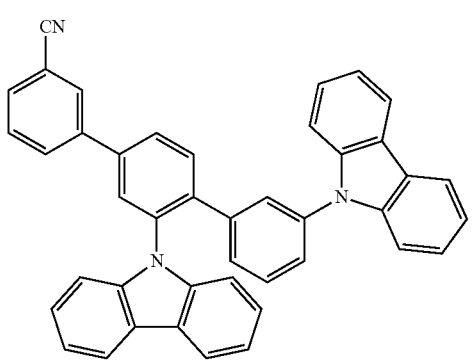
770
-continued
193
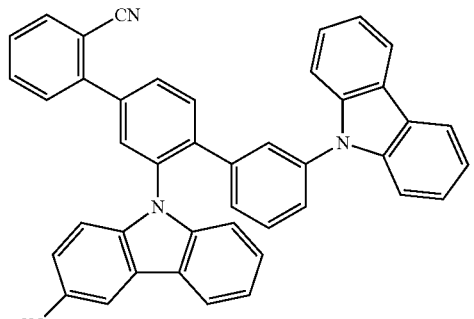
194
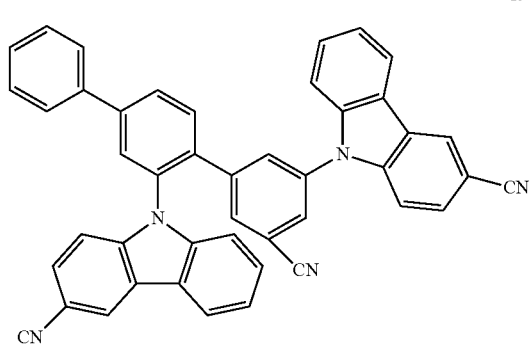
195
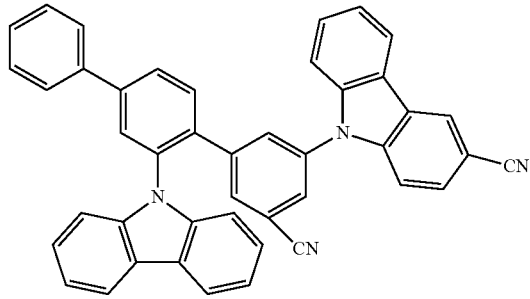
196
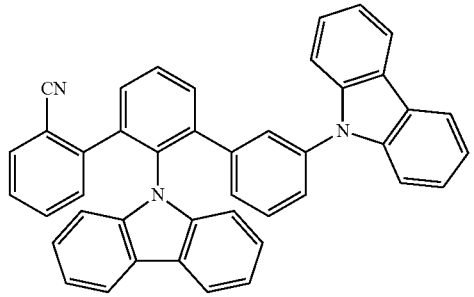
197
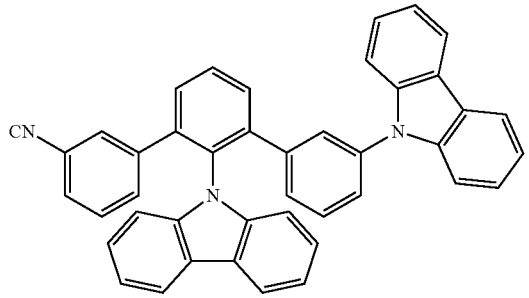

198
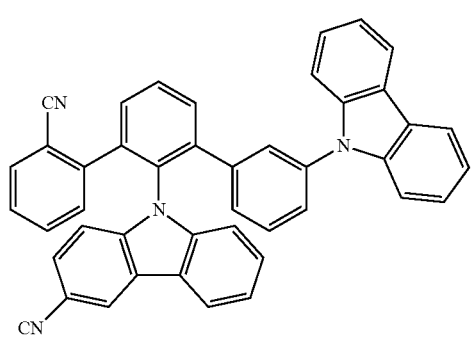
199
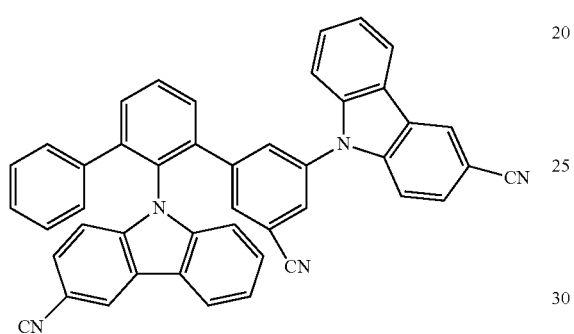
200
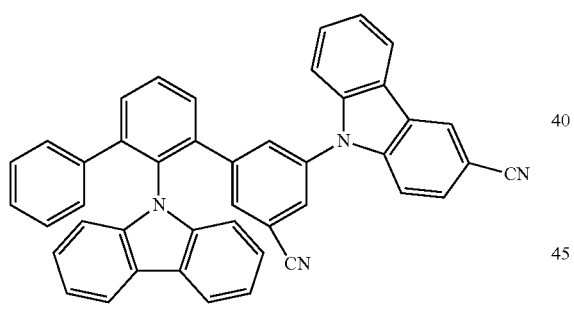
201
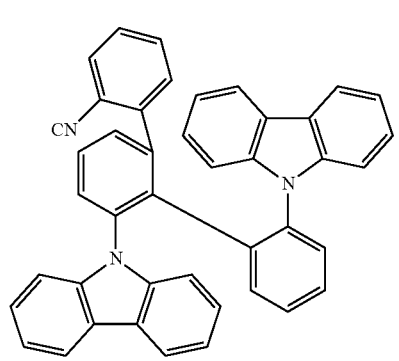
202
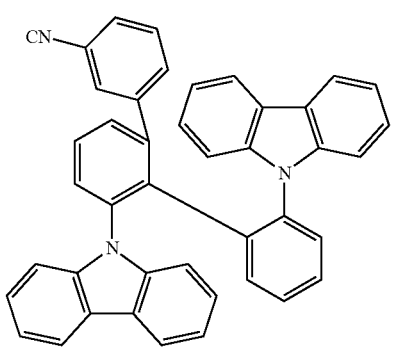
203
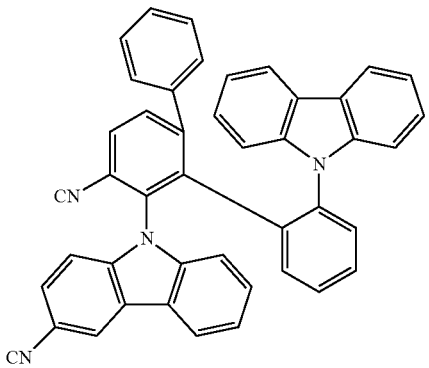
204
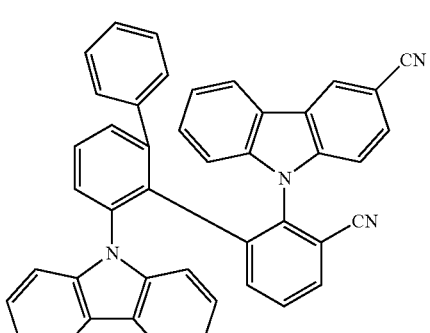
205
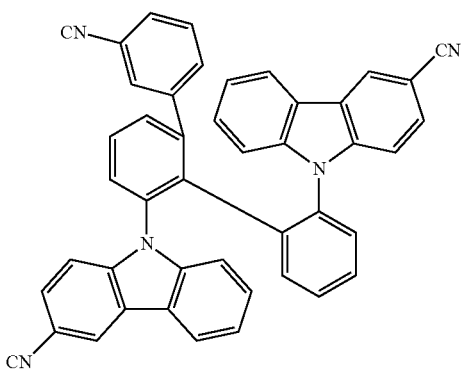

206
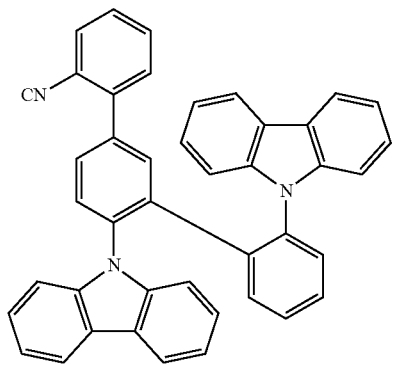
207
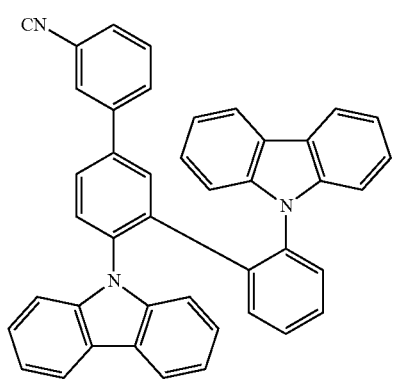
208
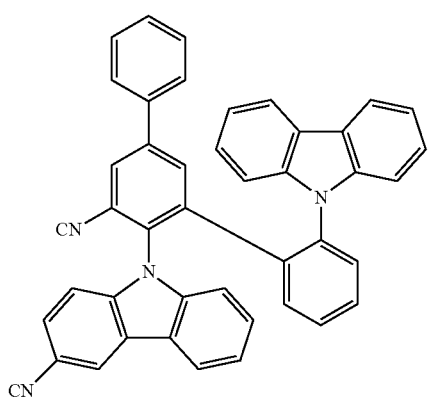
209
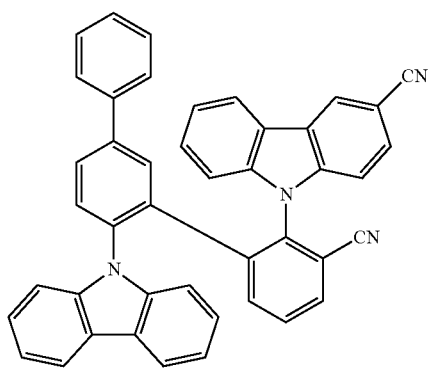
210
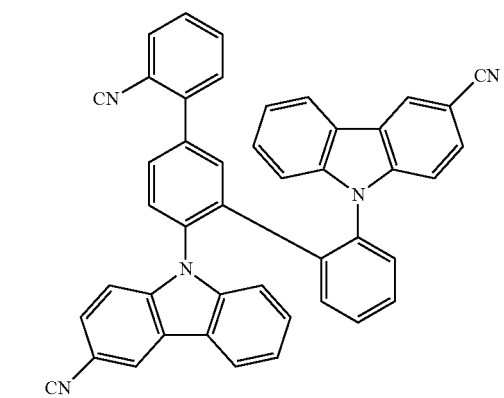
211
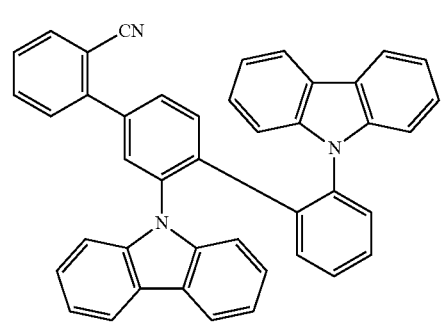
212
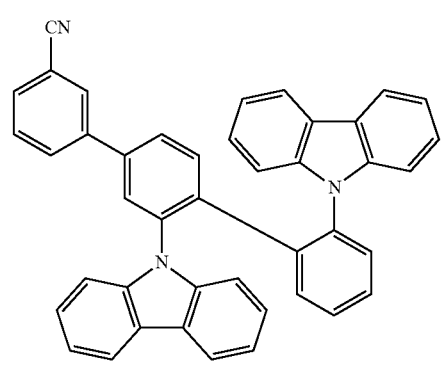
213
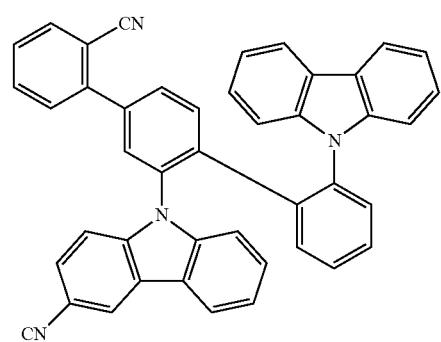

| 214 | 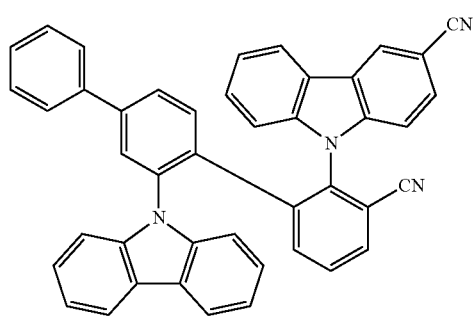 | 219 | 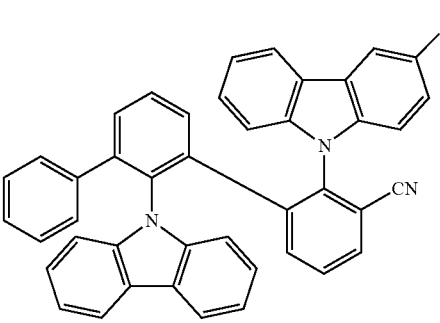 |
| 215 | 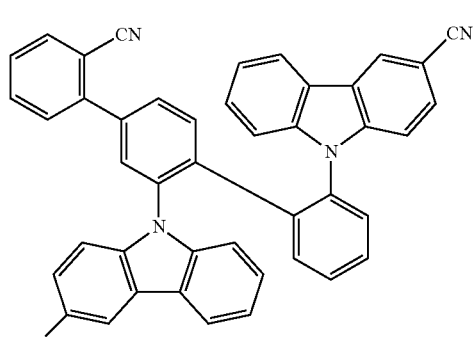 | 220 | 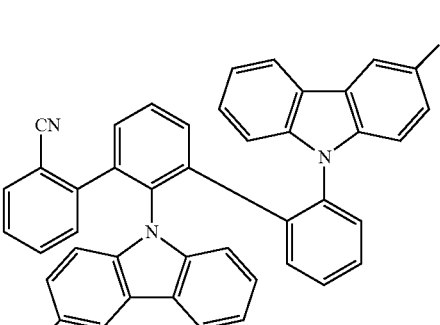 |
| 216 | 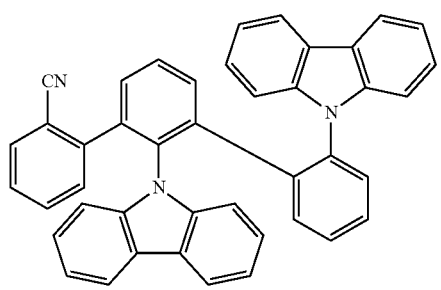 | 221 | 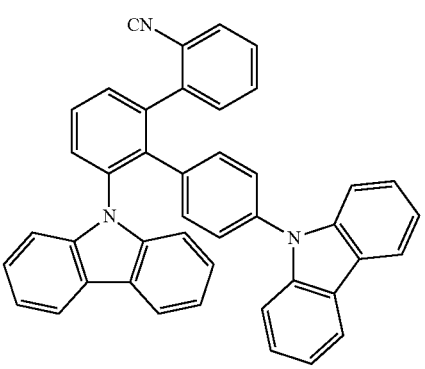 |
| 217 | 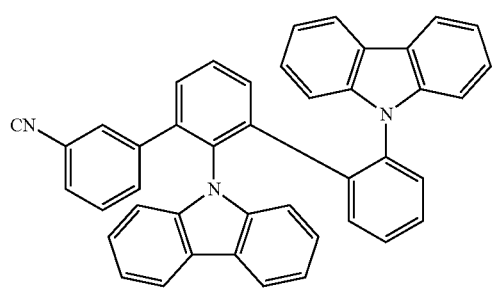 | 222 | 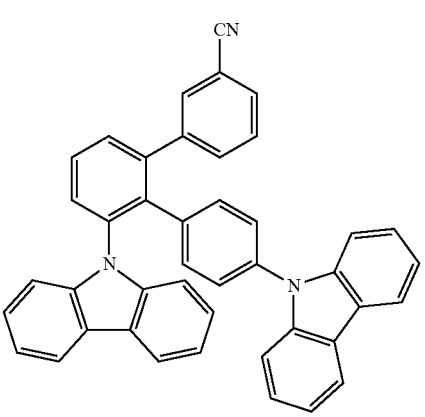 |
| 218 | | | |

-continued
223
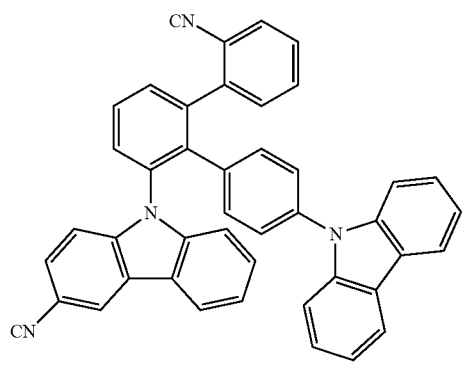
224
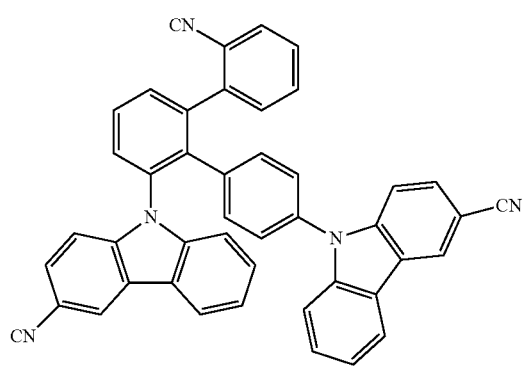
225
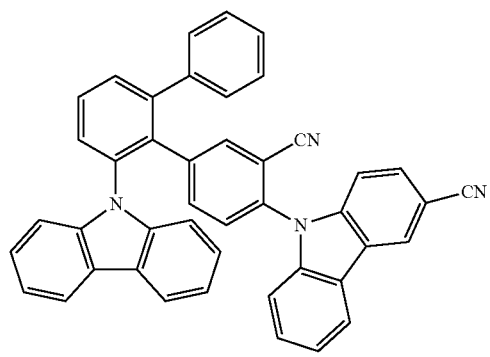
226
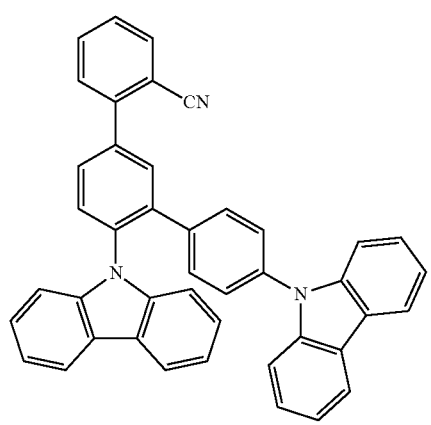
-continued
227
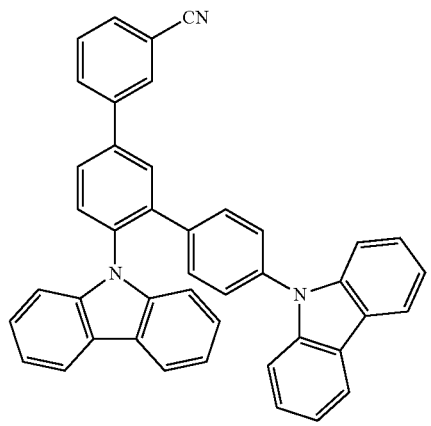
228
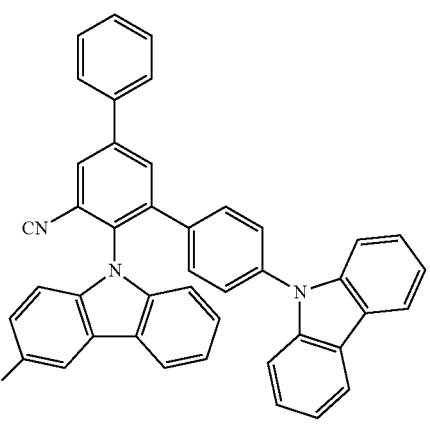
229
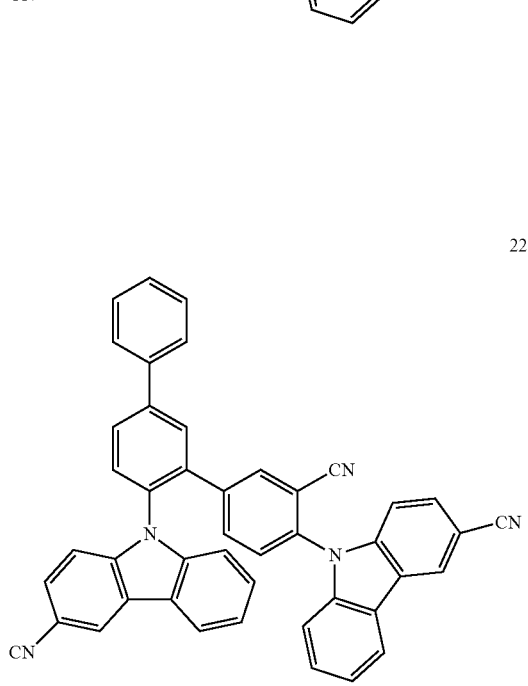

230
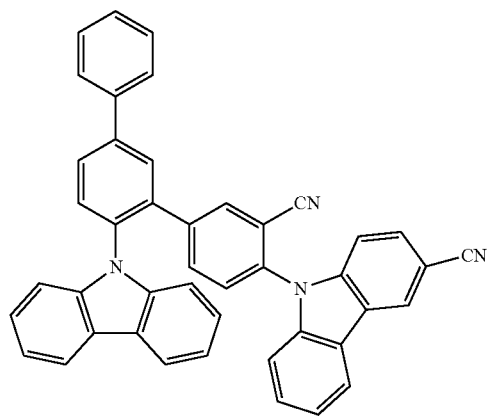
231
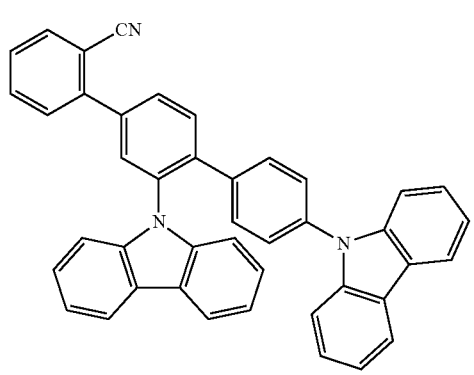
232
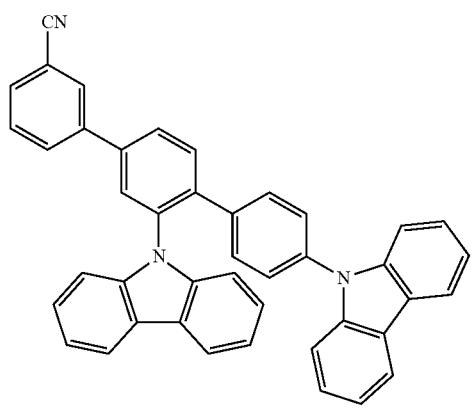
233
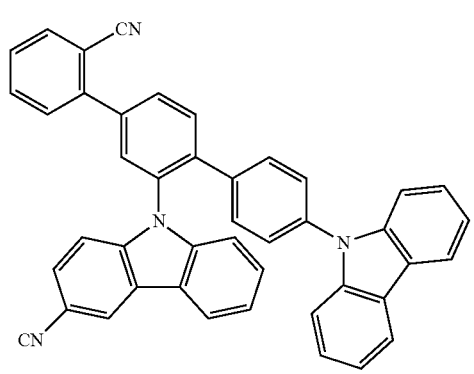
234
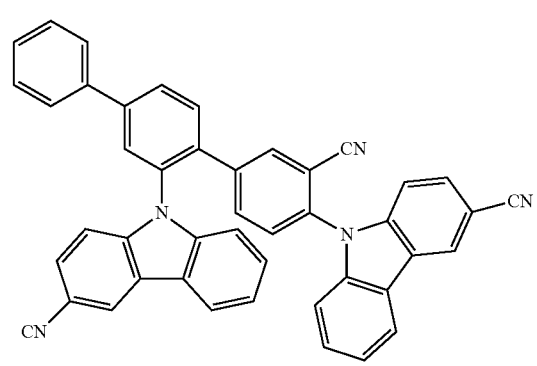
235
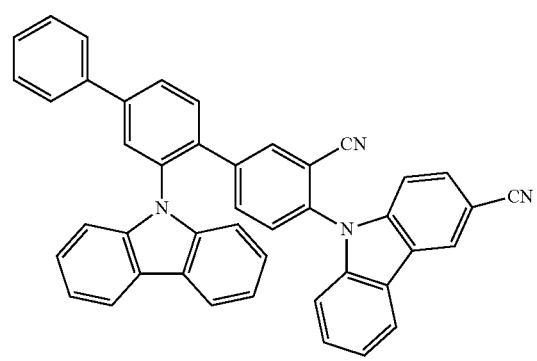
236
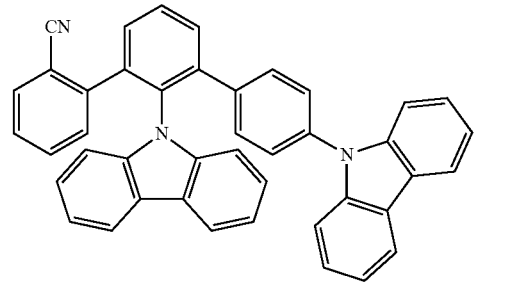
237
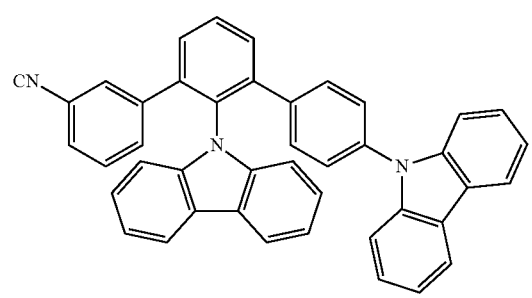
238
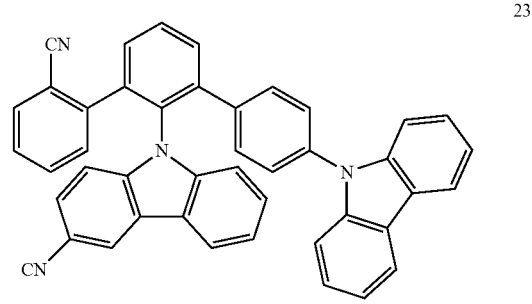

-continued
239
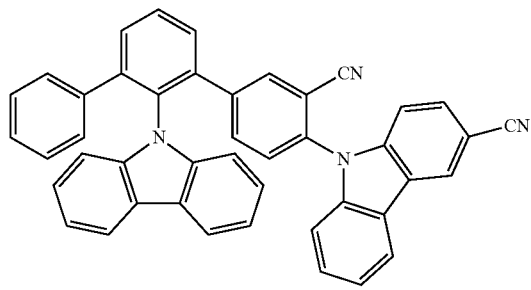
240
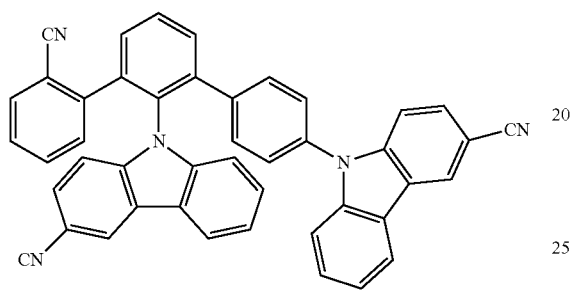
241
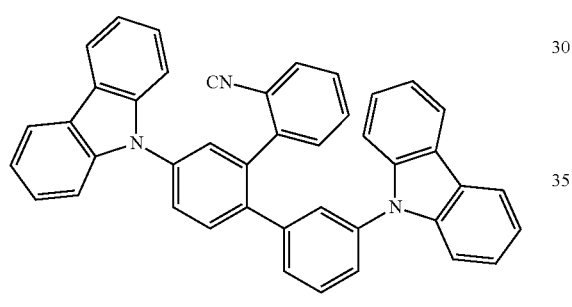
242
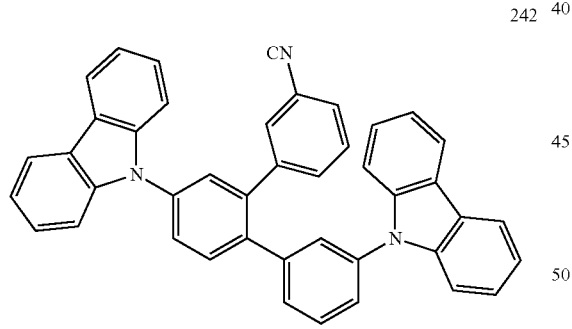
243
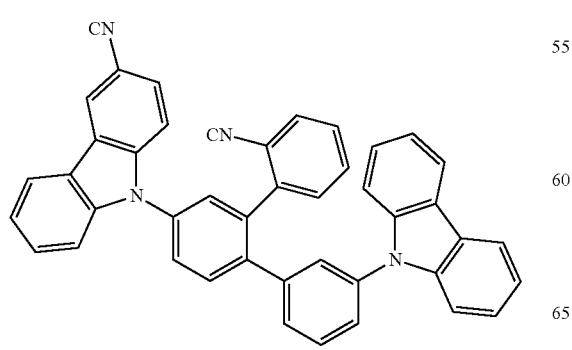
-continued
244
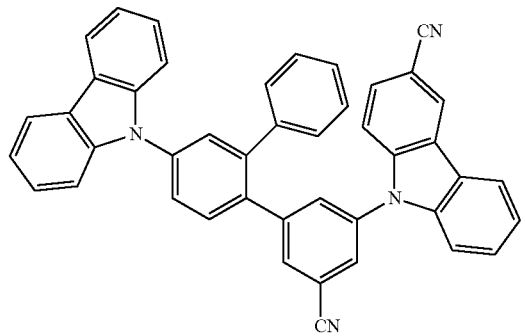
245
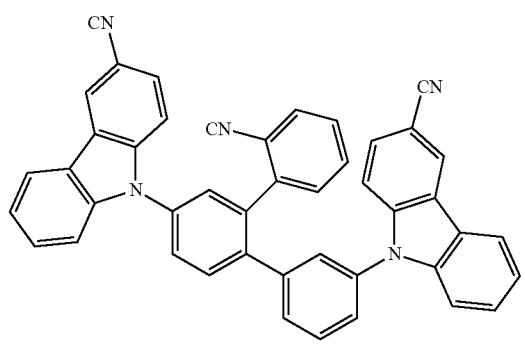
246
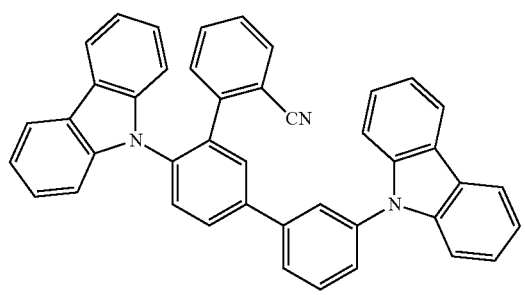
247
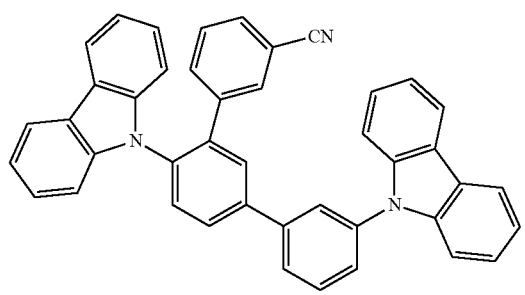

248
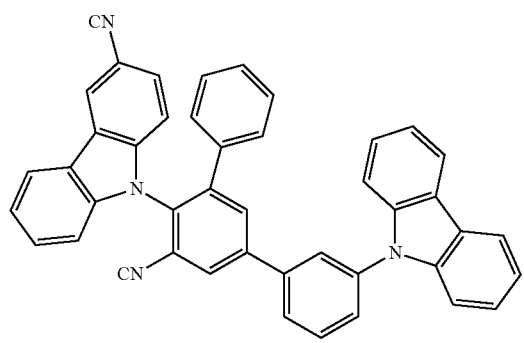
249
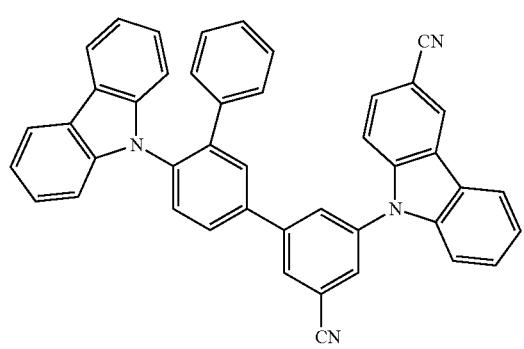
250
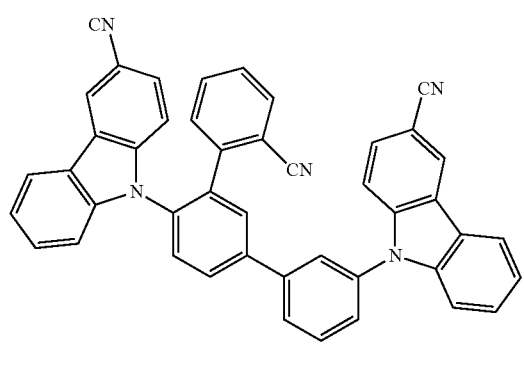
251
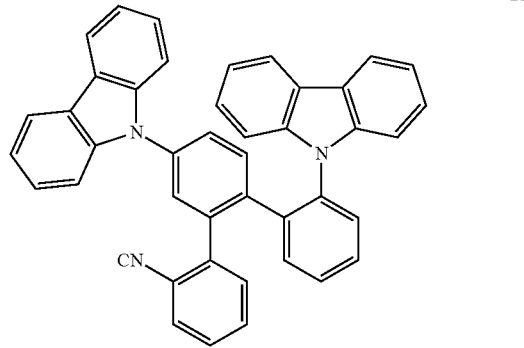
252
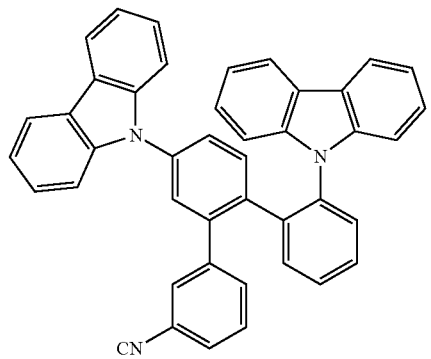
253
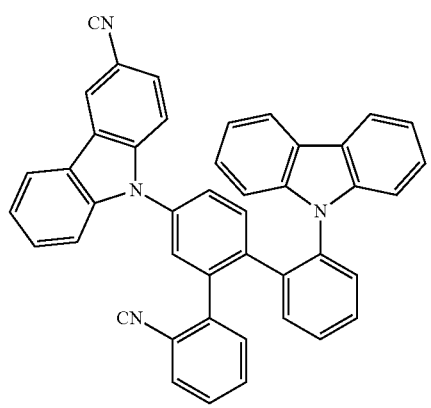
254
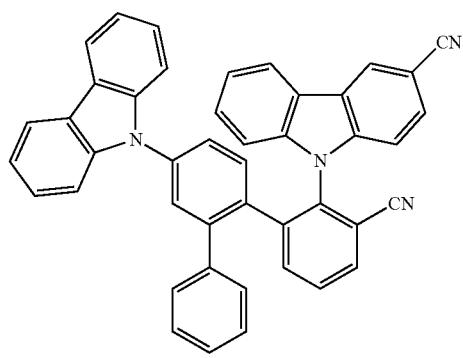
255
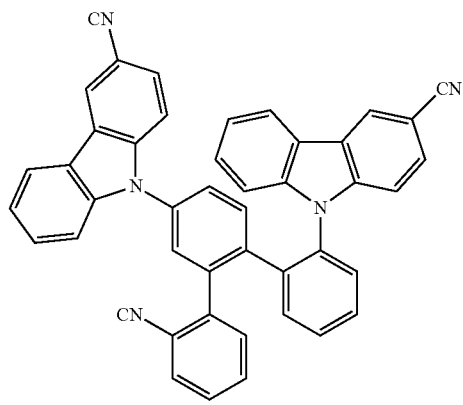

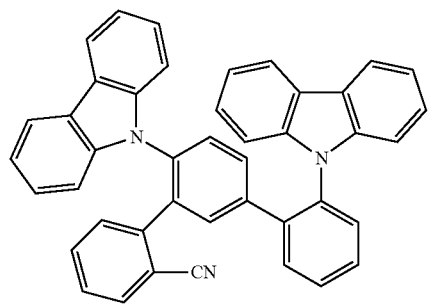
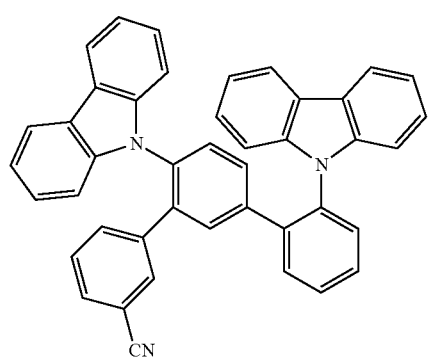
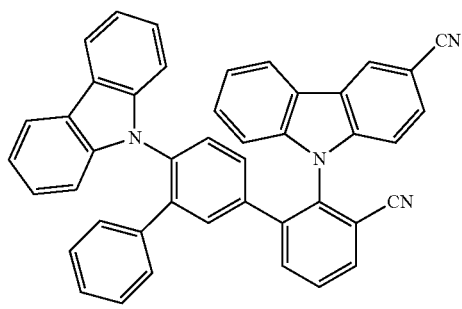
In some embodiments, the hole transporting host may include at least one of Compounds H-H1 to H-H103:
H-H1
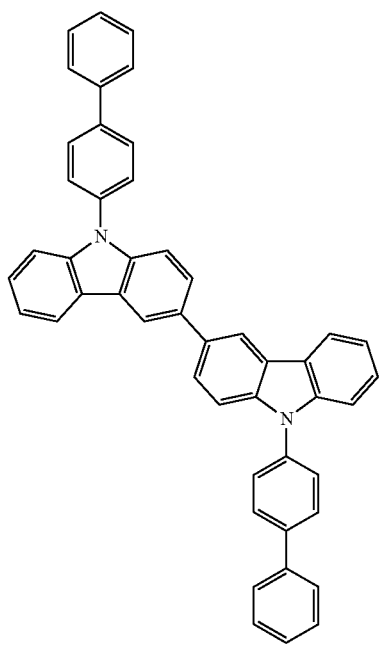

787
-continued
H-H2
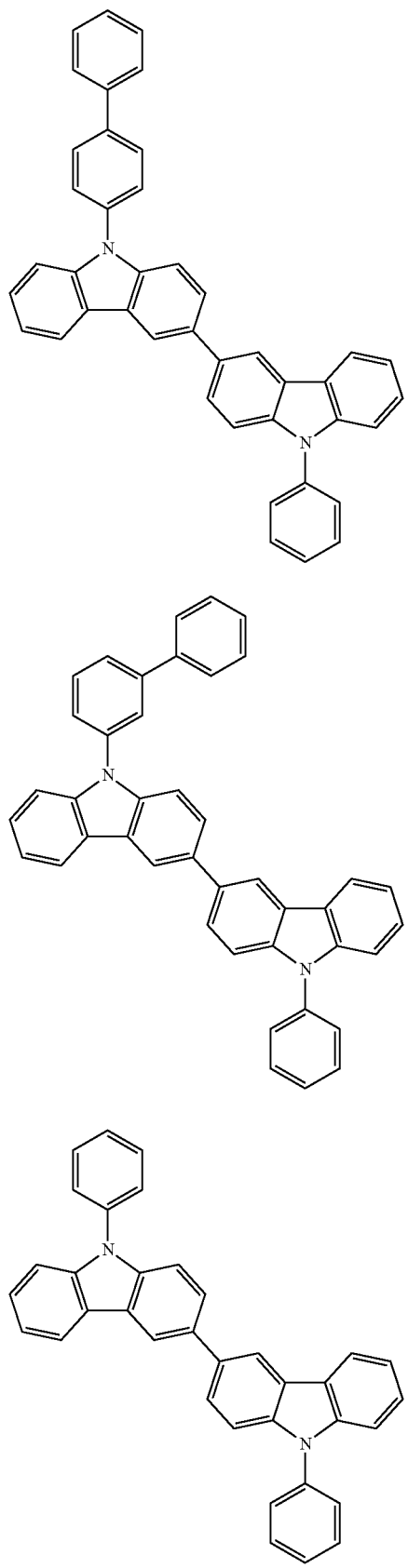
H-H3
H-H4
788
-continued
H-H5
H-H6

789
-continued
790
-continued
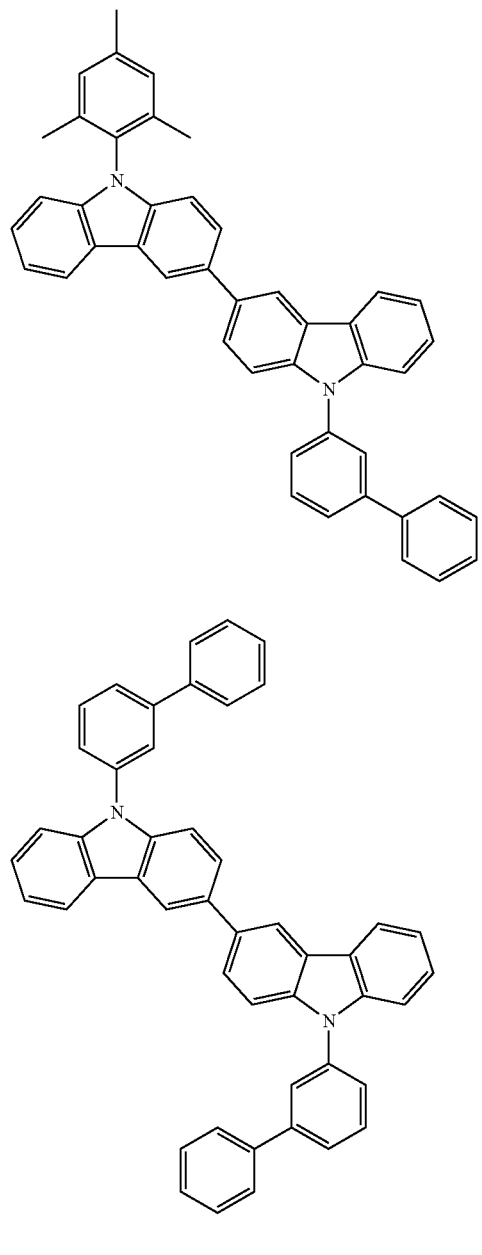
H-H7
H-H8
H-H9
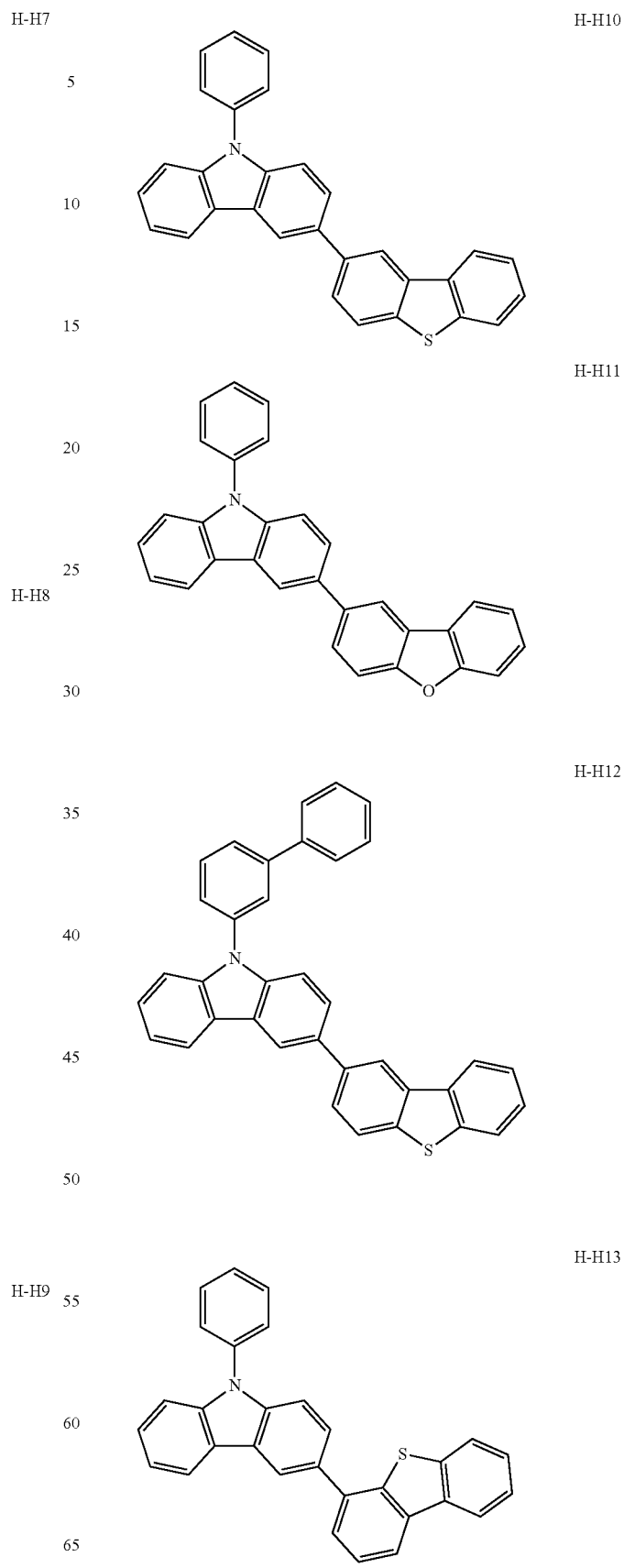
H-H10
H-H11
H-H12
H-H13

H-H14
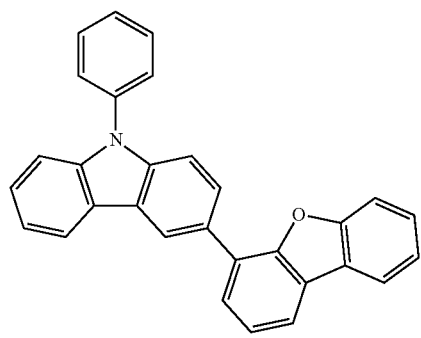
H-H15
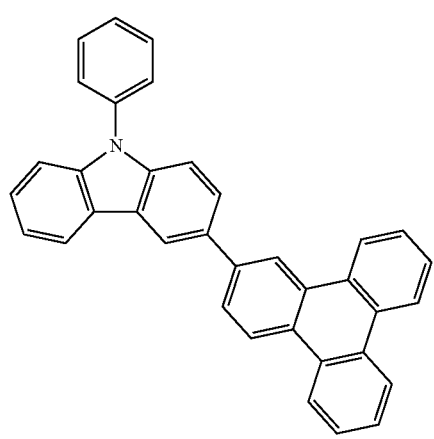
H-H16
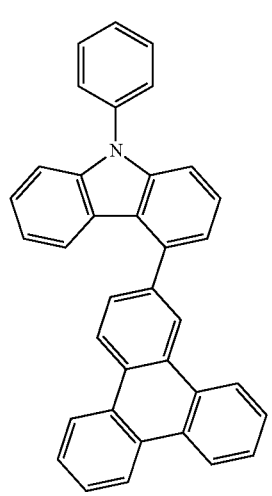
H-H17
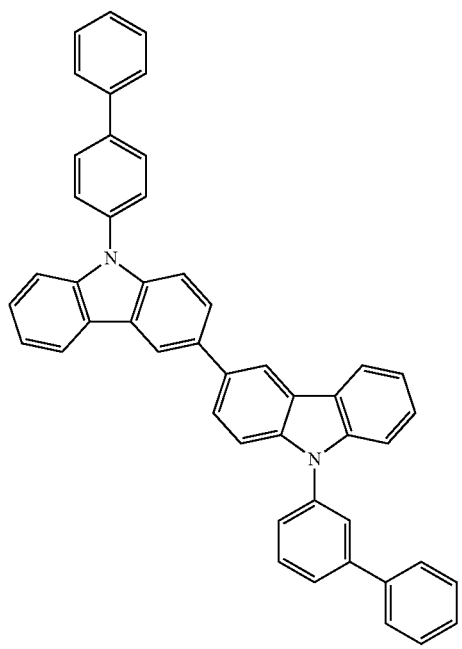
H-H18
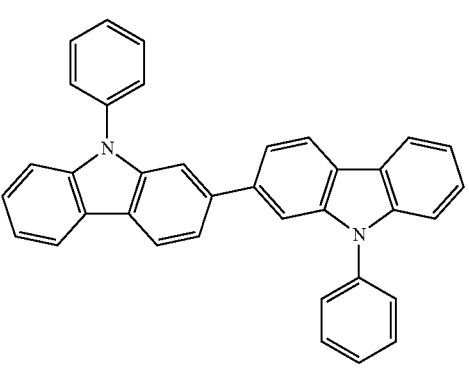
H-H19
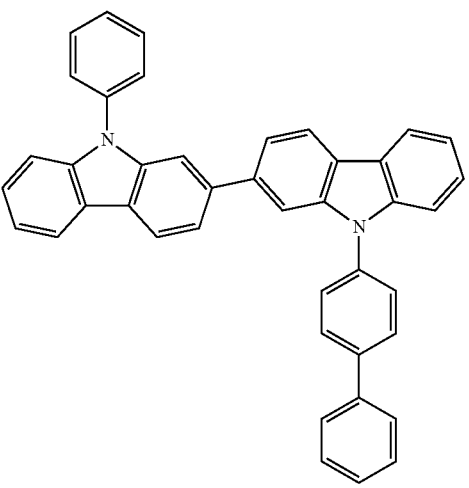

H-H20
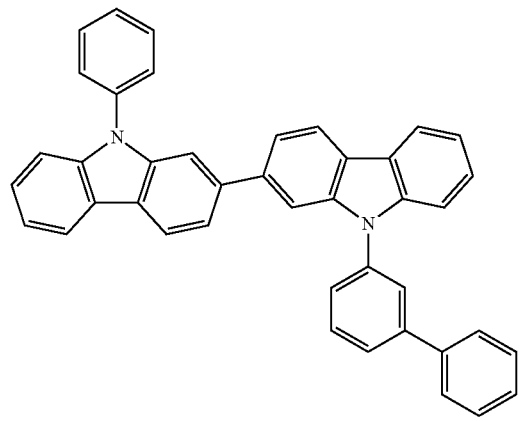
H-H21
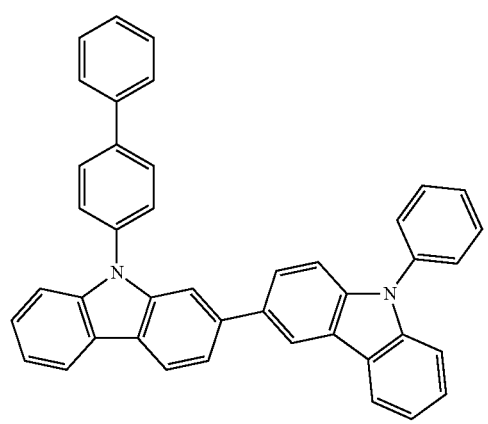
H-H22
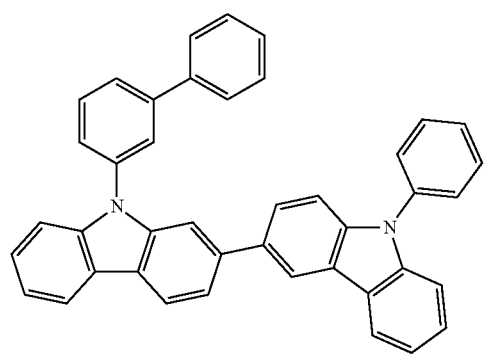
H-H23
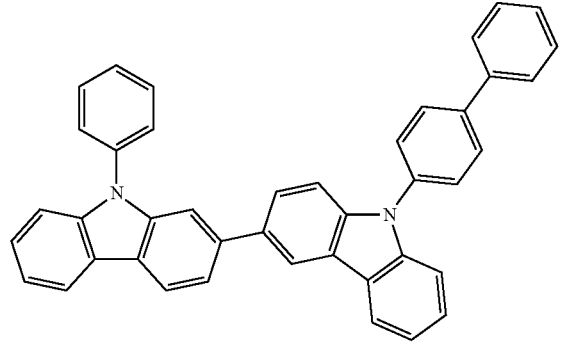
H-H24
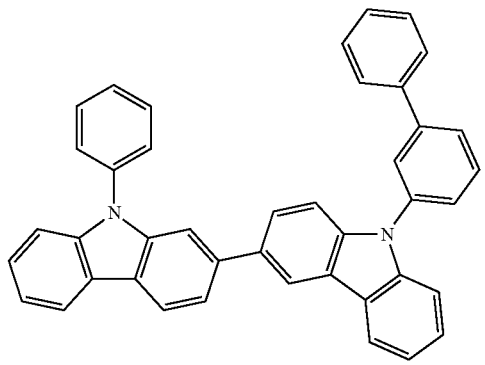
H-H25
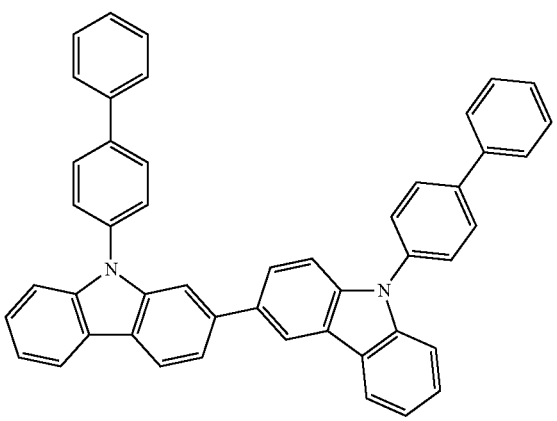
H-H26
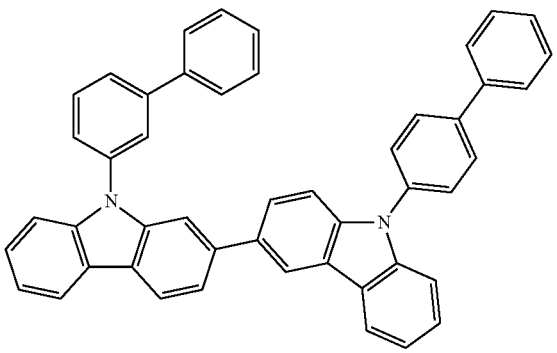
H-H27
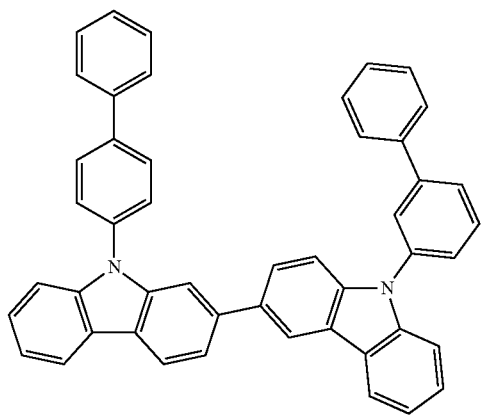

H-H28
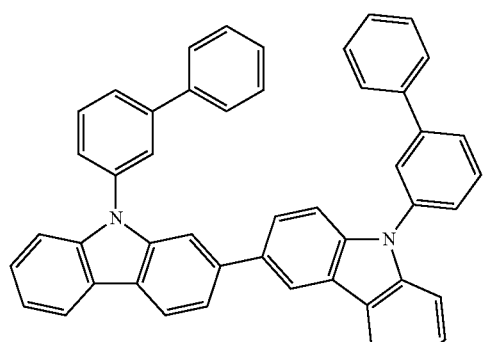
H-H29
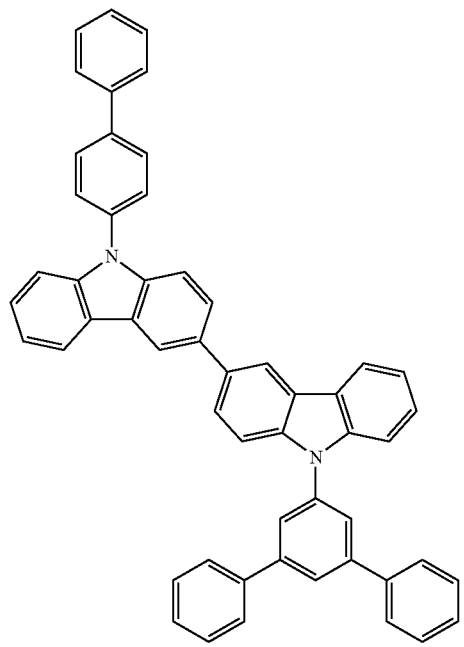
H-H30
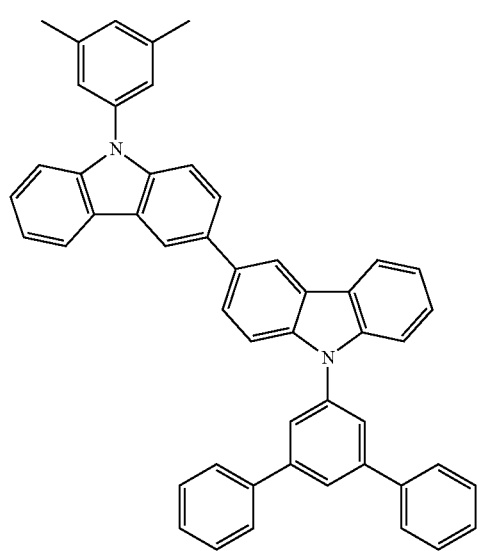
H-H31
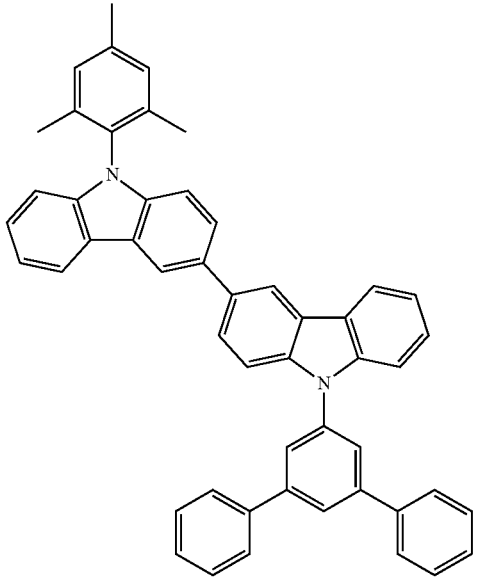
H-H32
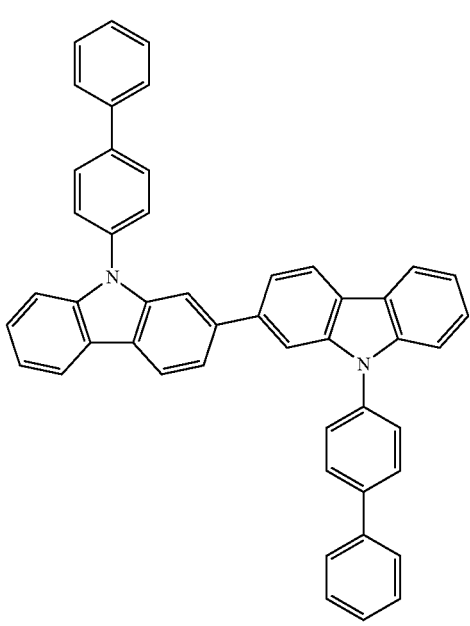

H-H33
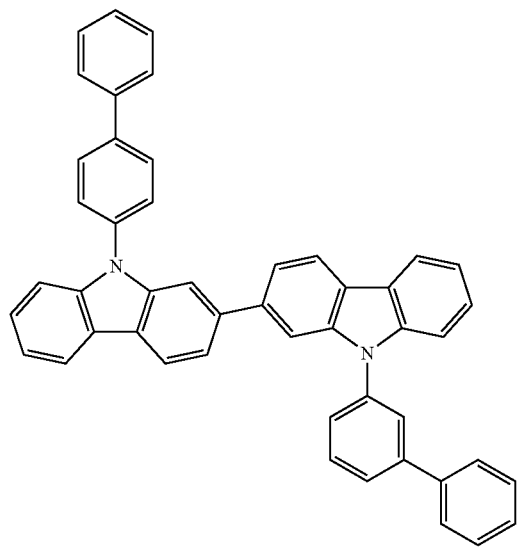
H-H34
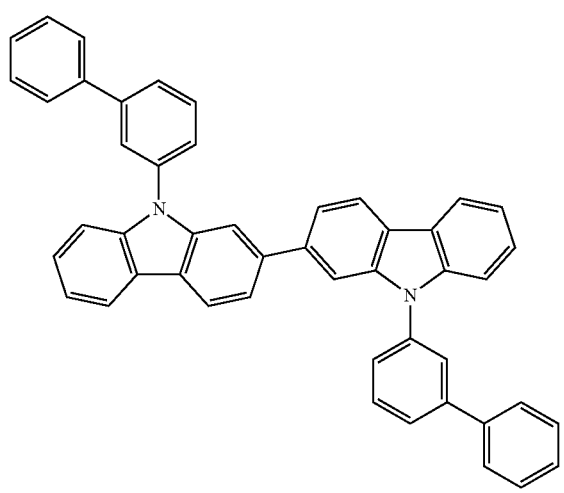
H-H35
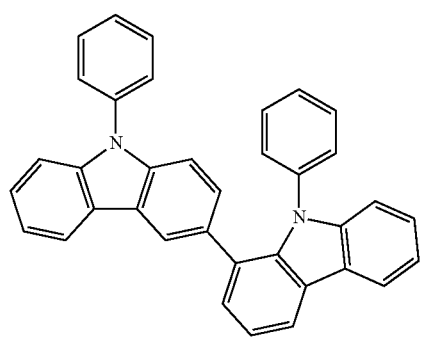
H-H36
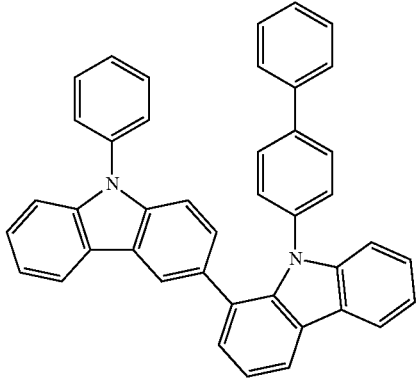
H-H37
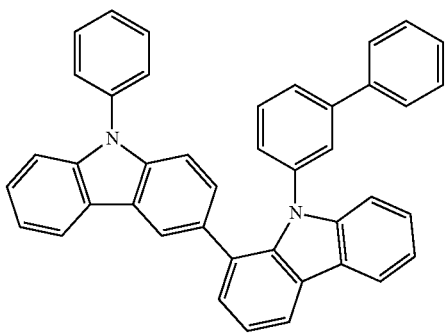
H-H38
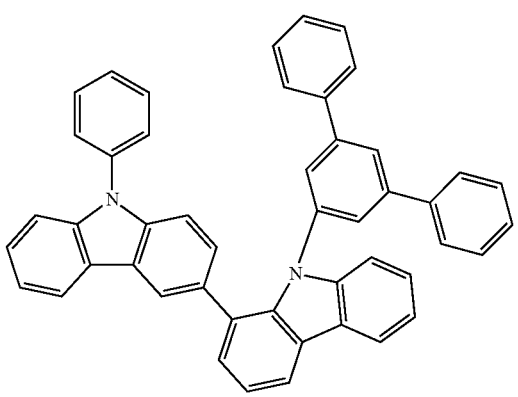
H-H39
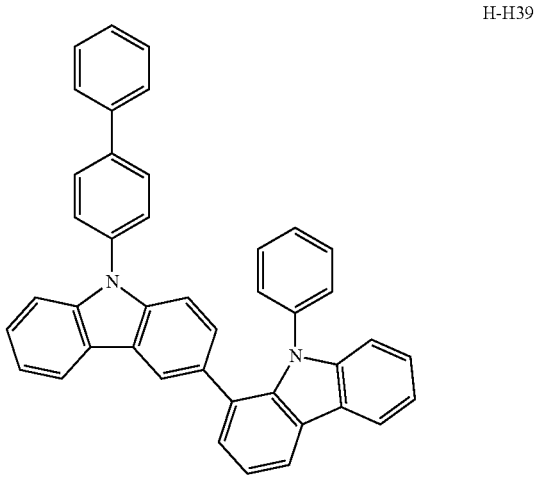

H-H40
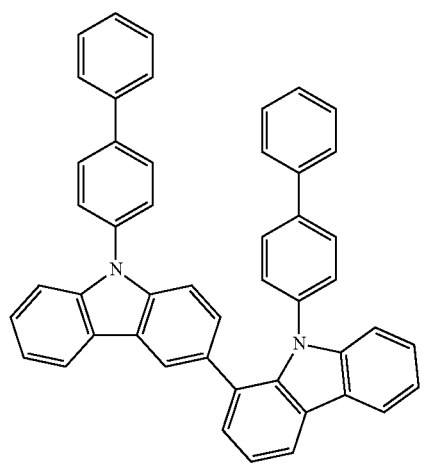
H-H41
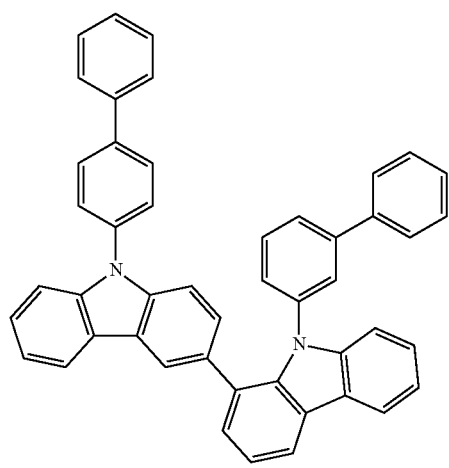
H-H42
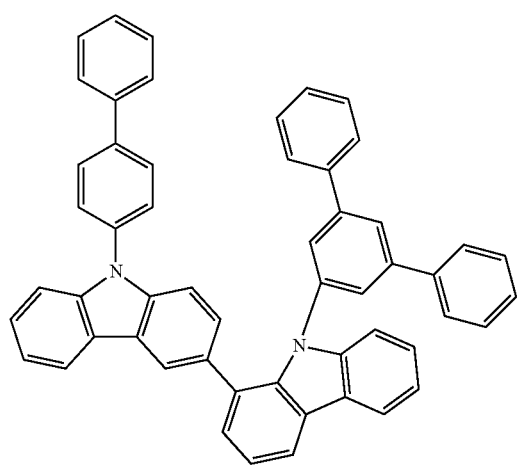
H-H43
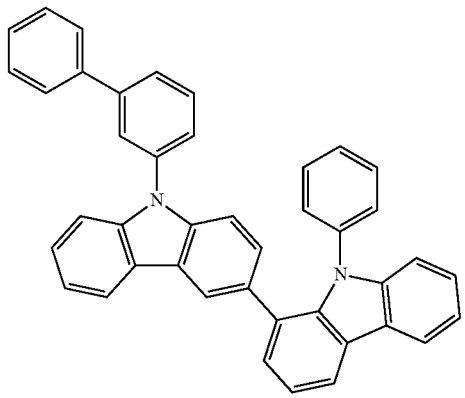
H-H44
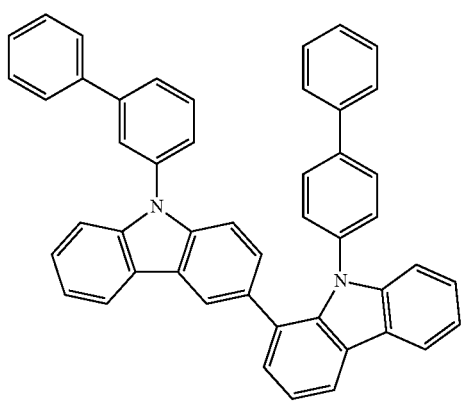
H-H45
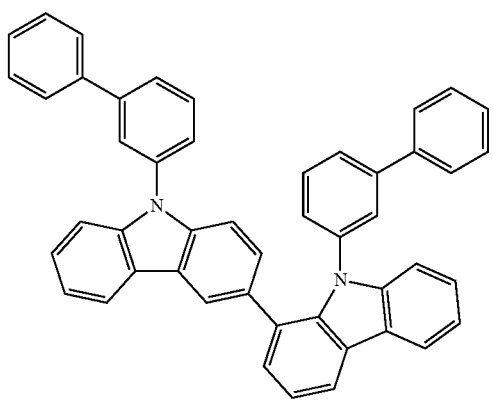
H-H46
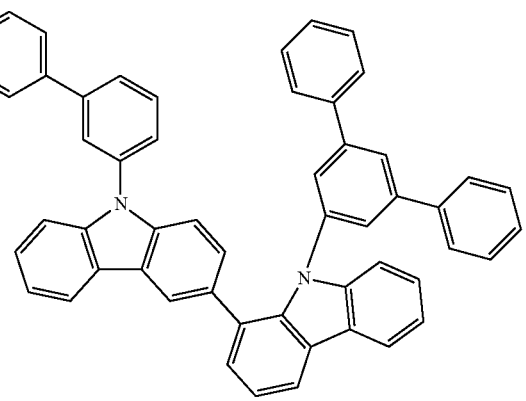

-continued
H-H47
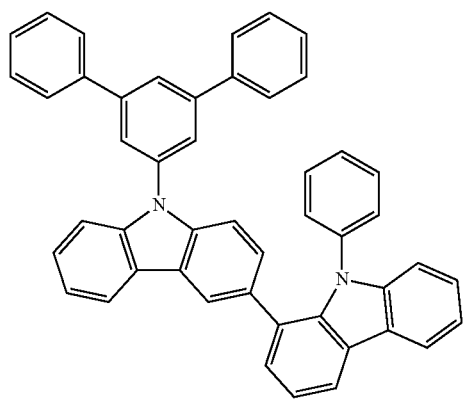
H-H48
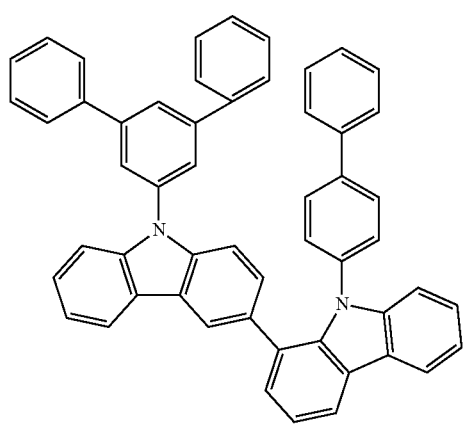
H-H49
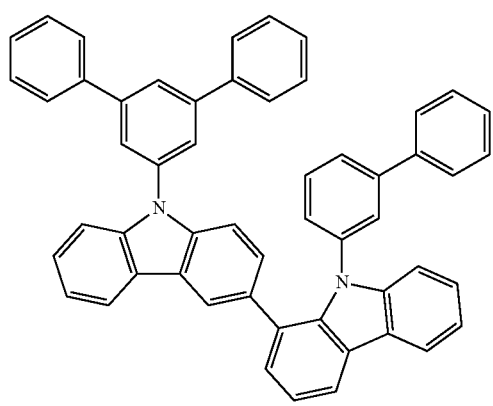
-continued
H-H50
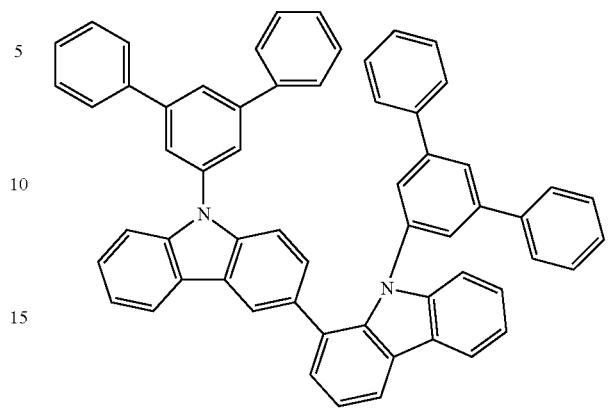
H-H51
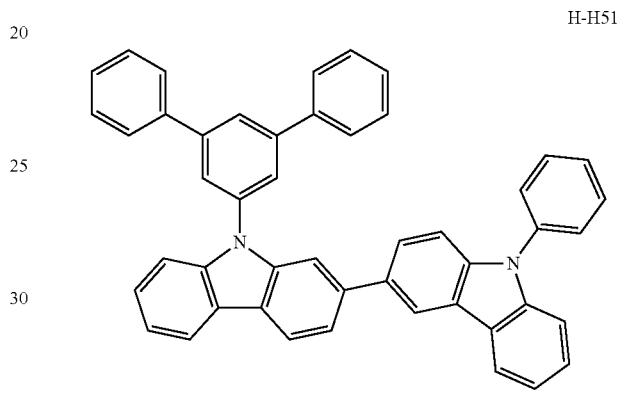
H-H52
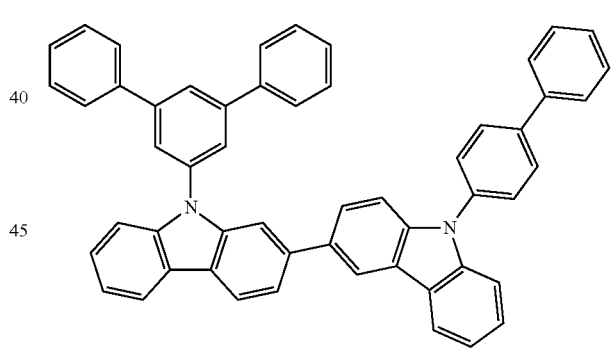
H-H53
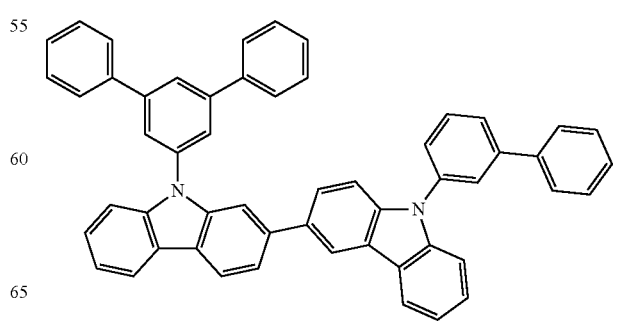

H-H54
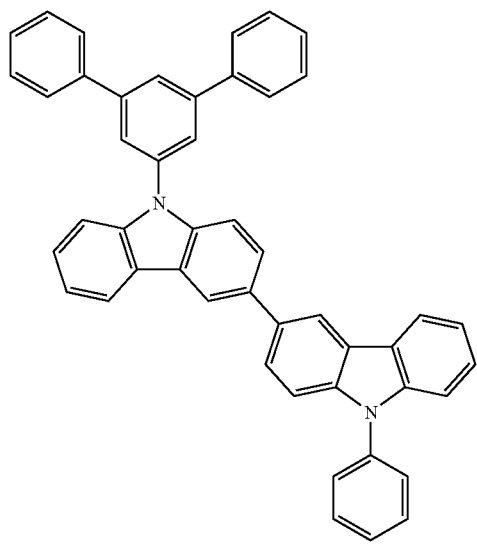
H-H55
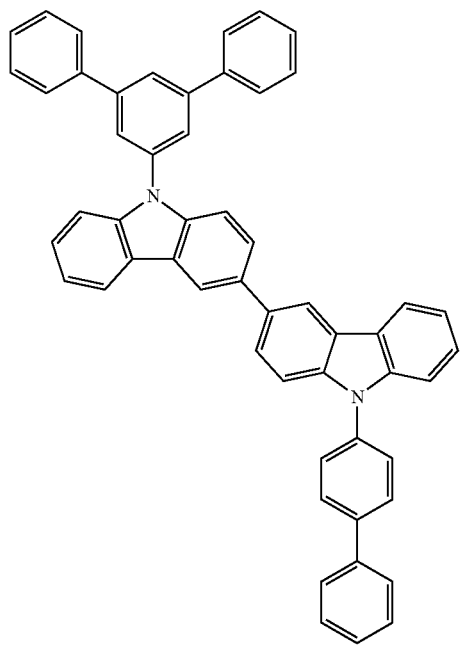
H-H56
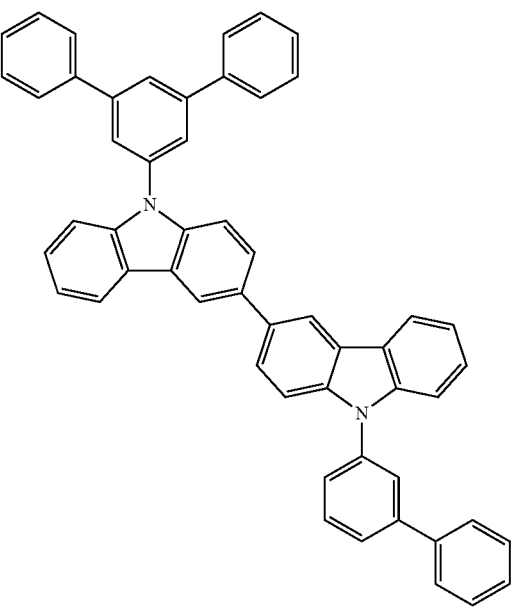
H-H57
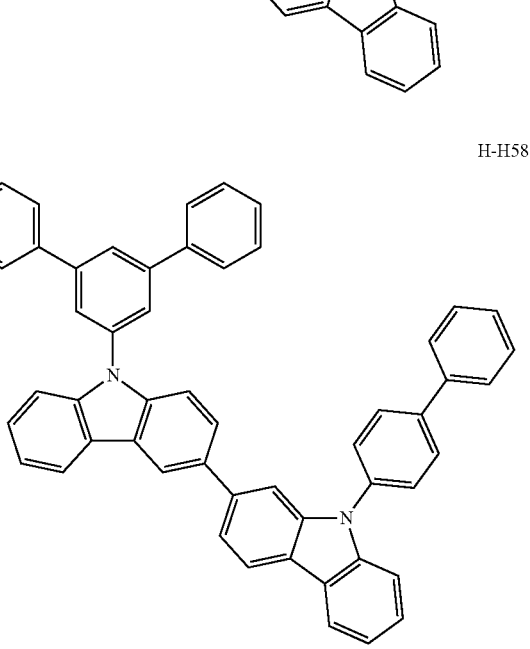
H-H58

H-H59
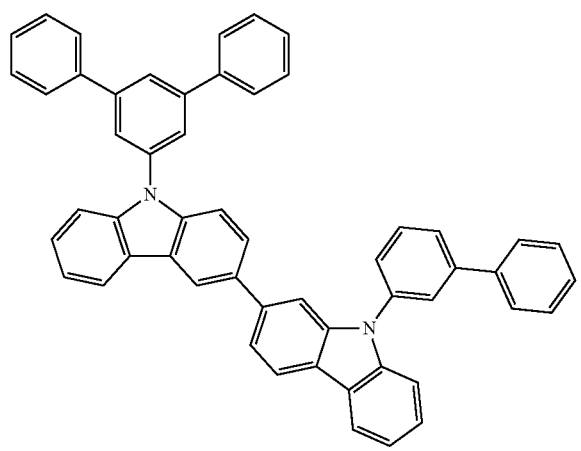
H-H60
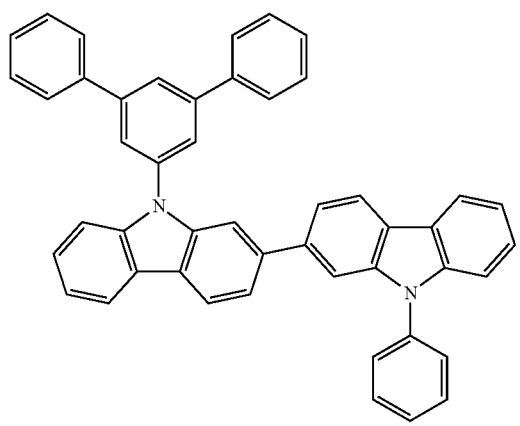
H-H61
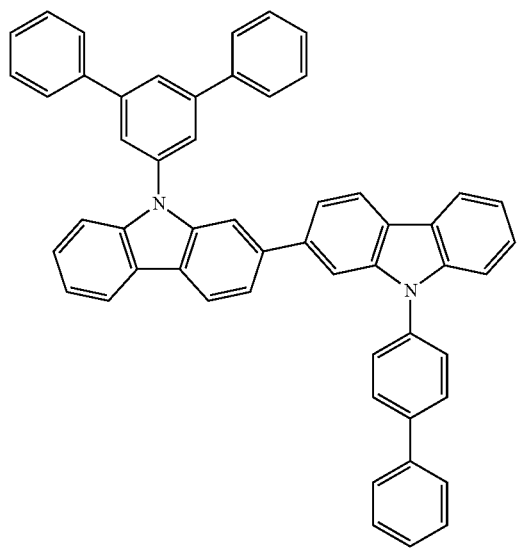
H-H62
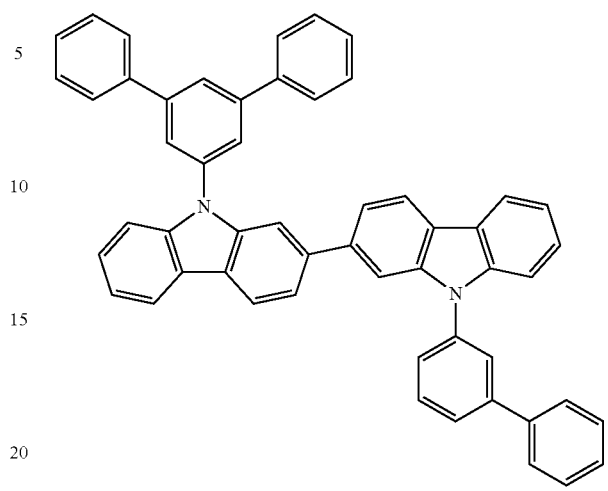
H-H63
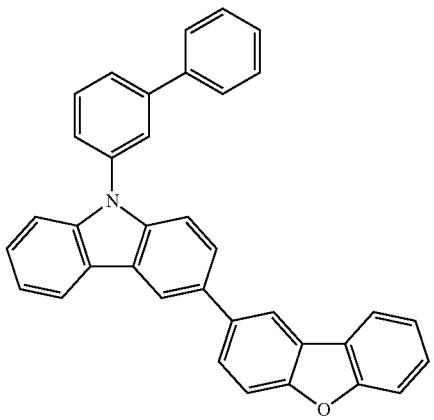
H-H64
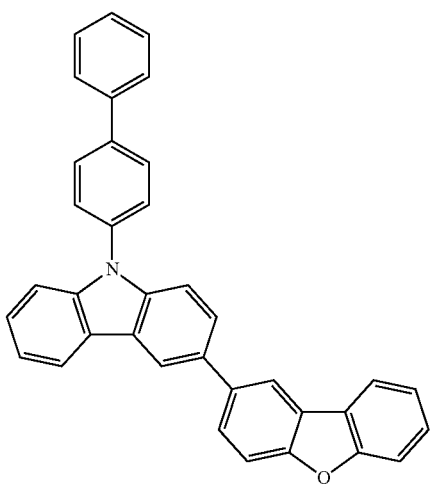

H-H65
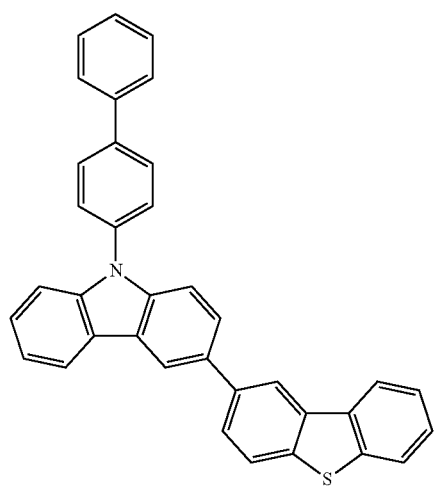
H-H66
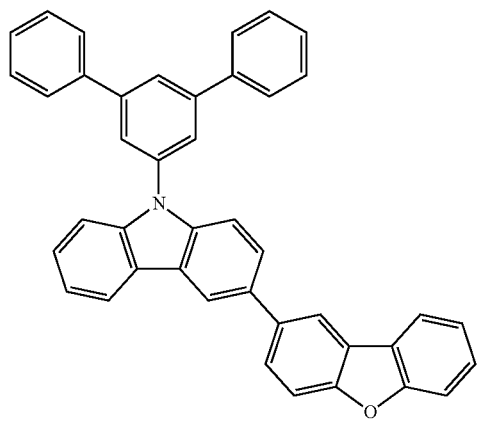
H-H67
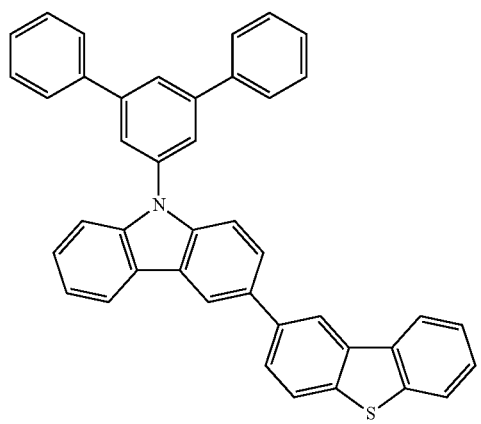
H-H68
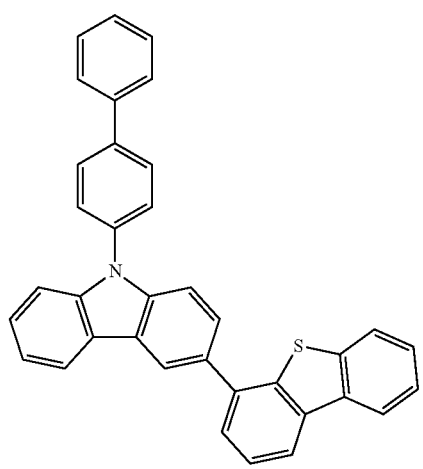
H-H69
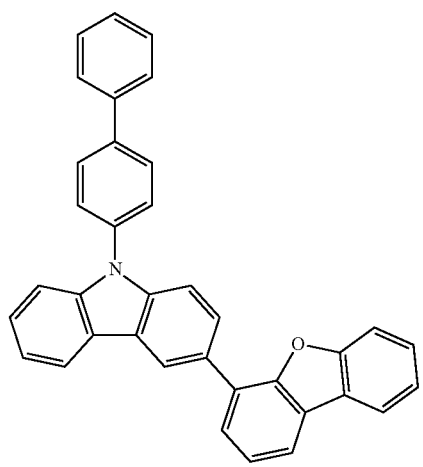
H-H70
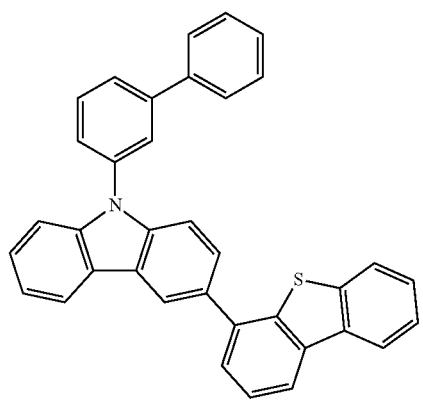

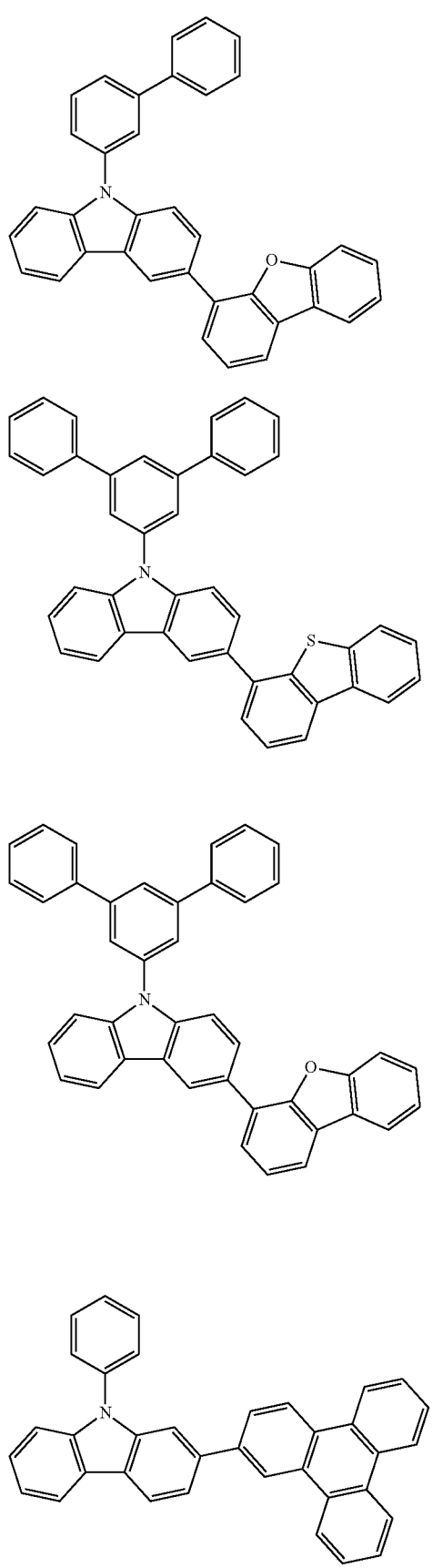
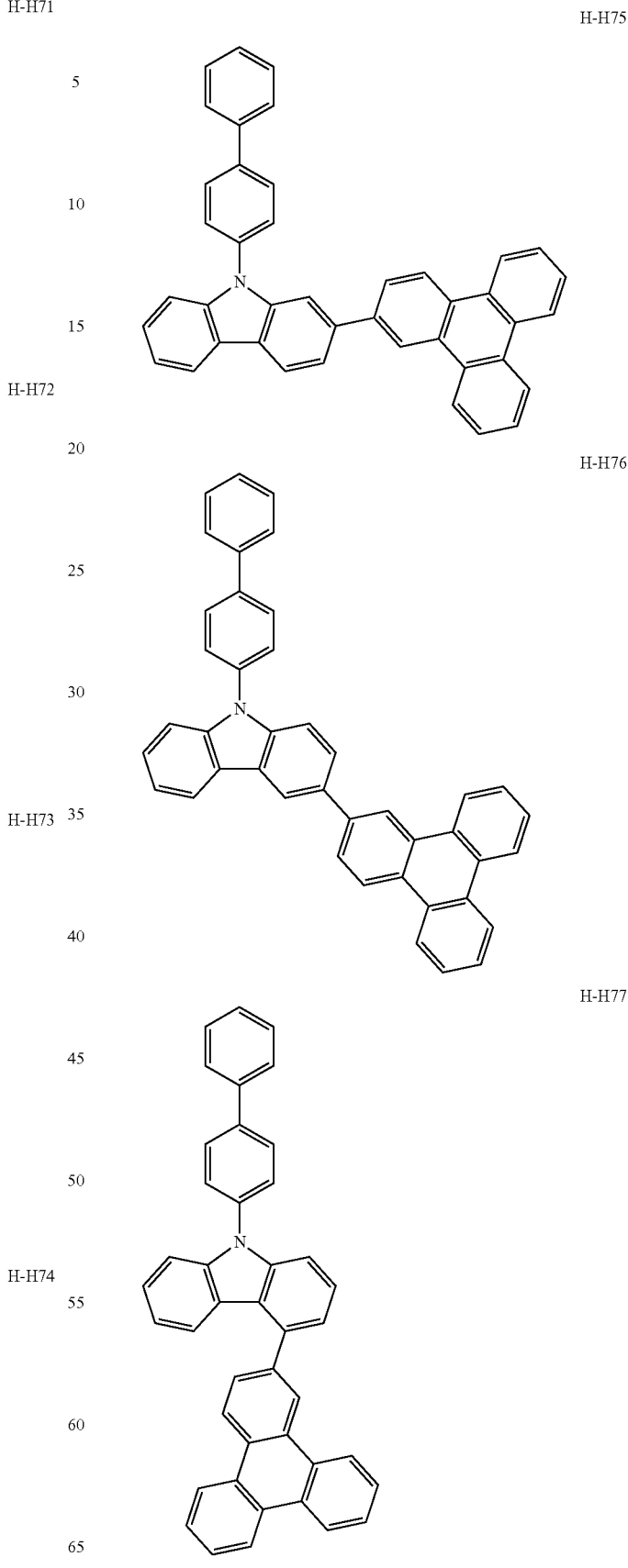

H-H78
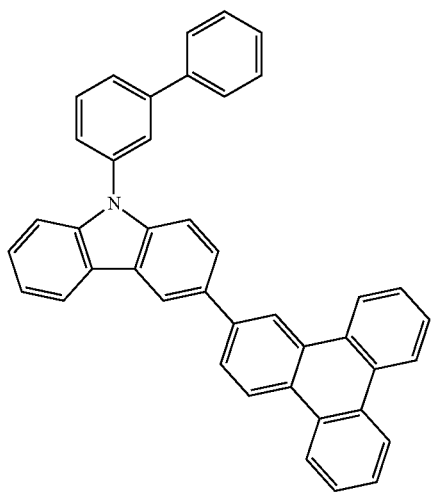
H-H79
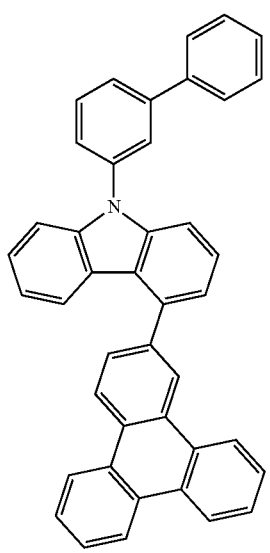
H-H80
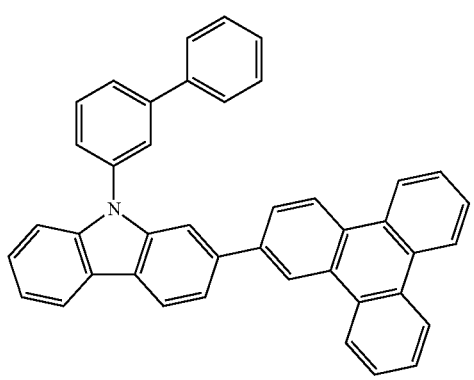
H-H81
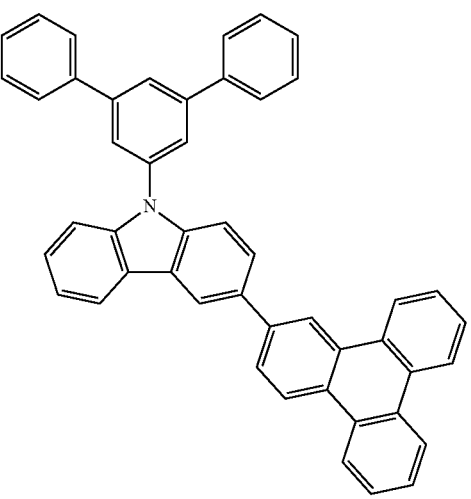
H-H82
H-H83
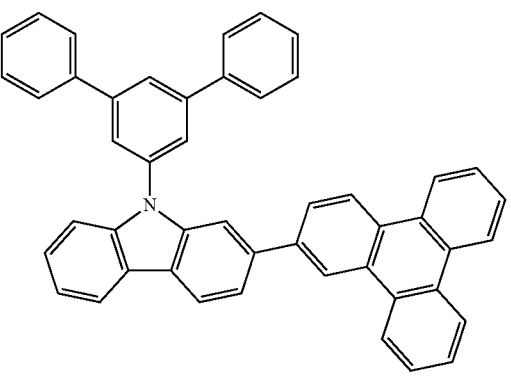

813
-continued
H-H84
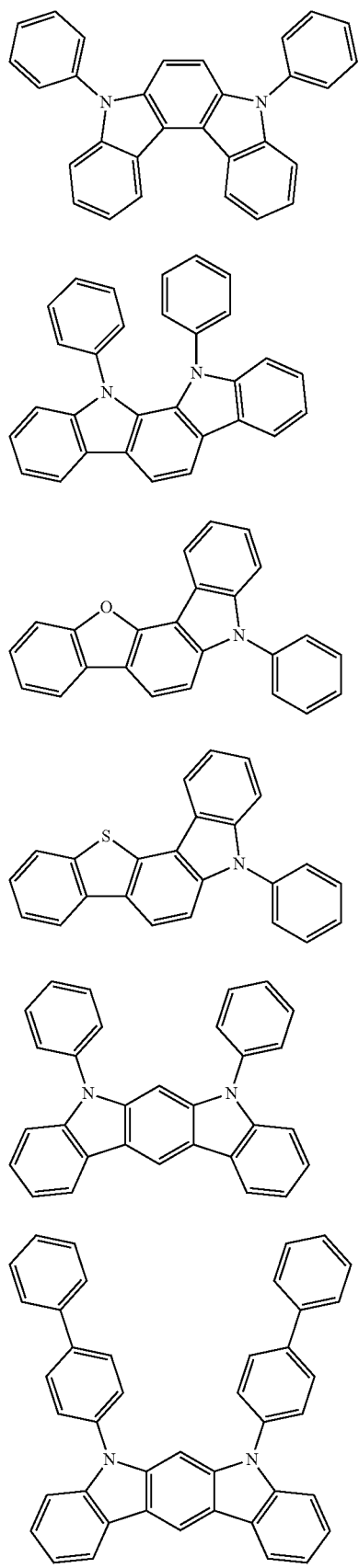
H-H85
H-H86
H-H87
H-H88
H-H89
814
-continued
H-H90
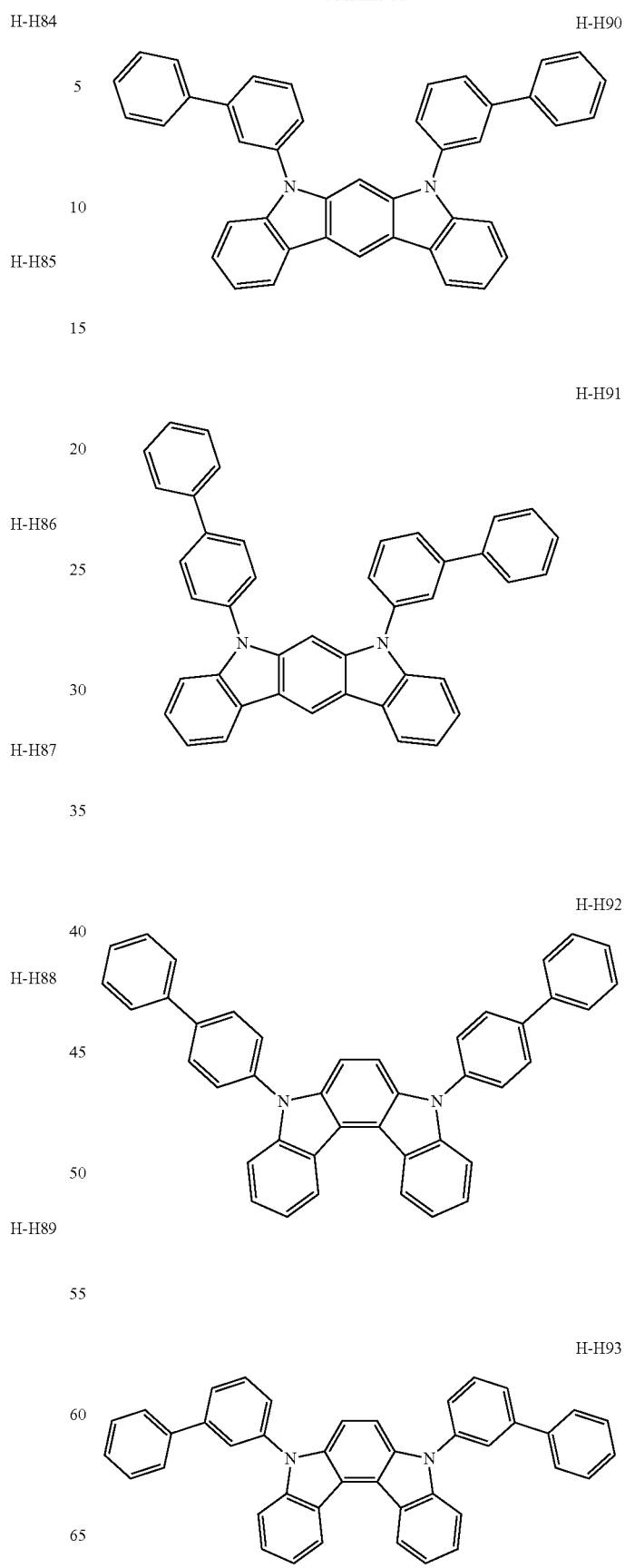
H-H91
H-H92
H-H93

H-H94
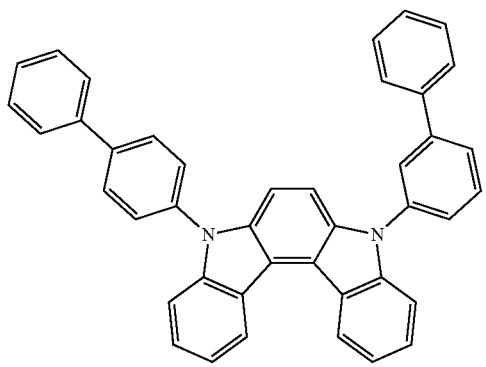
H-H95
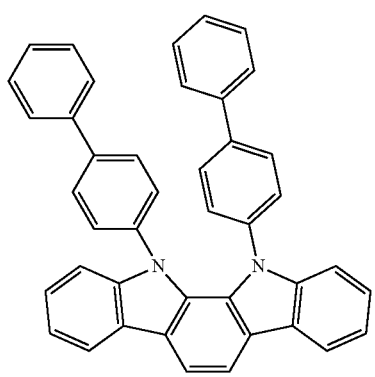
H-H96
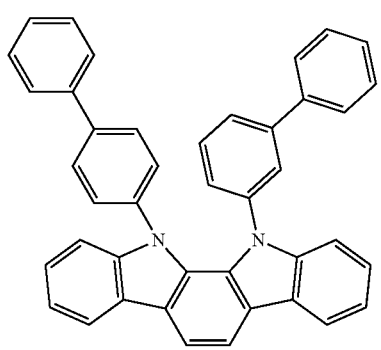
H-H97
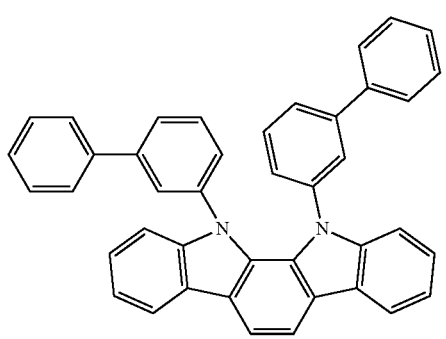
H-H98
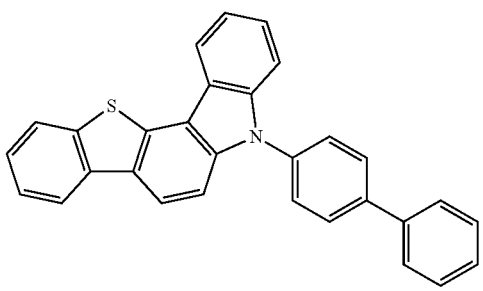
H-H99
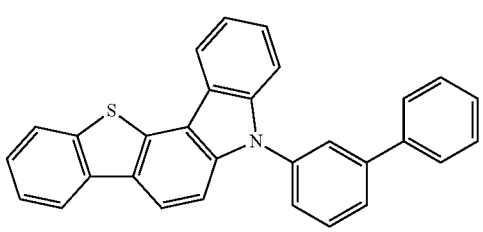
H-H100
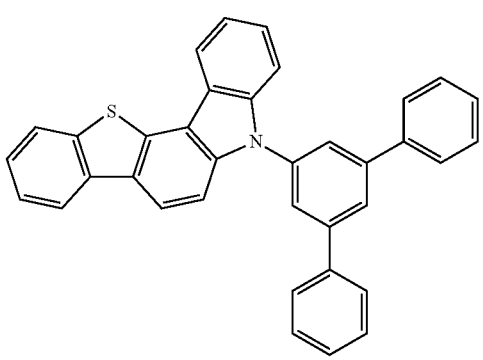
H-H101
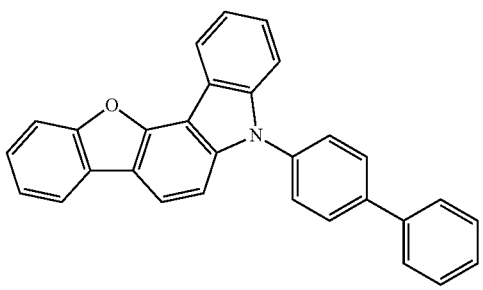
H-H102

H-H103
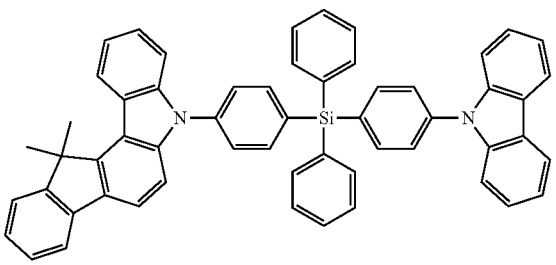
In some embodiments, the bipolar host may include a compound of Group HEH1:
Group HEH1
1
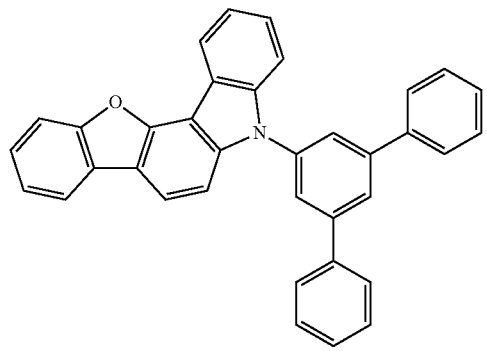
2
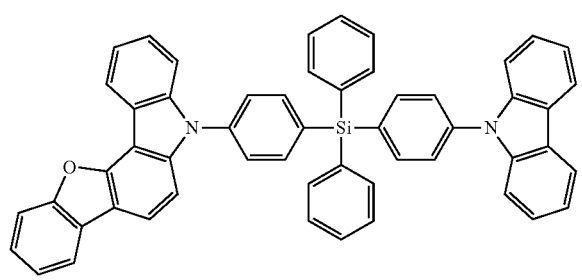
3
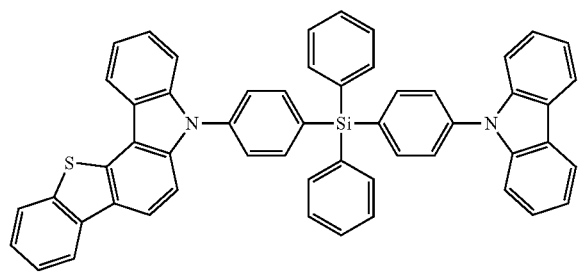
4
5
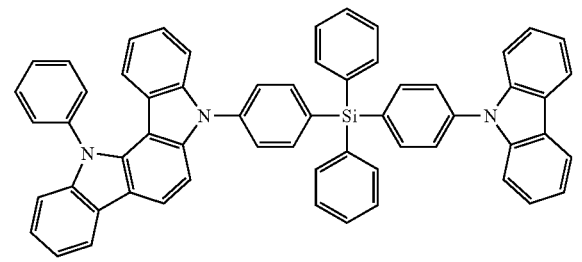
6
7
8
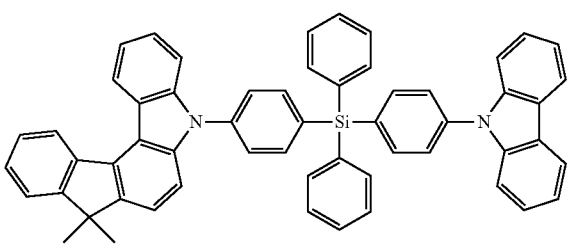

-continued
9
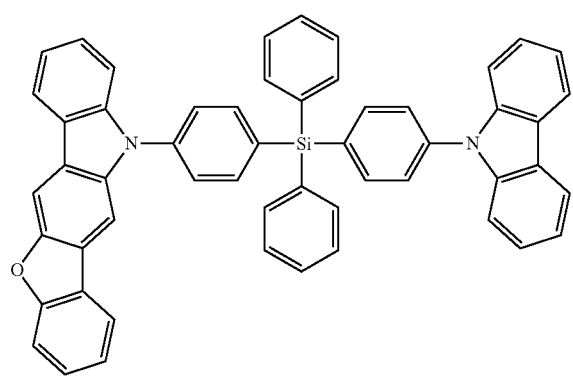
10
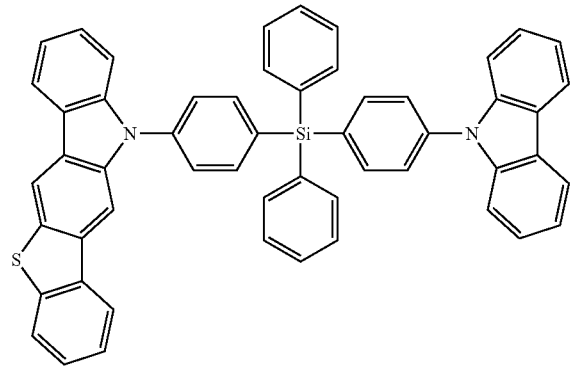
11
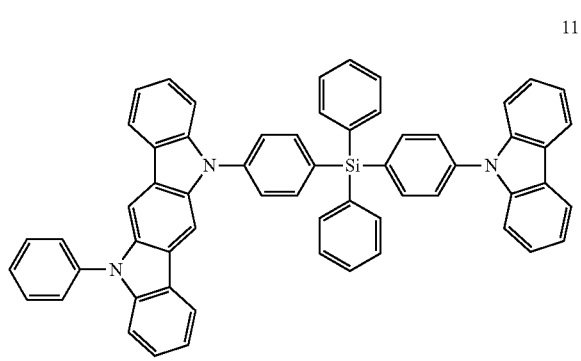
12
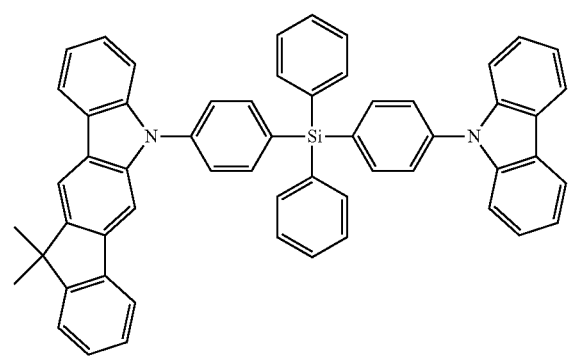
-continued
13
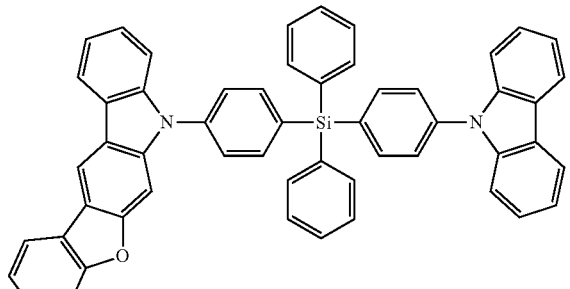
14
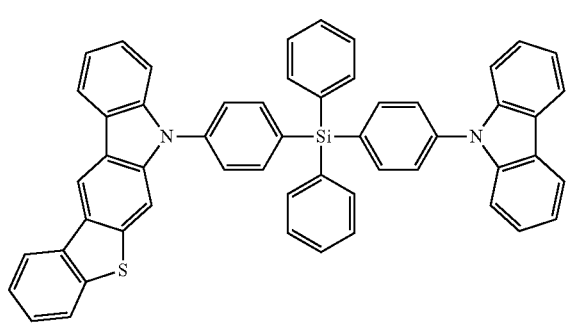
15
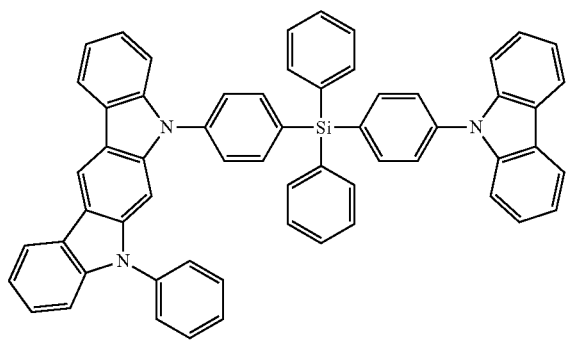
16
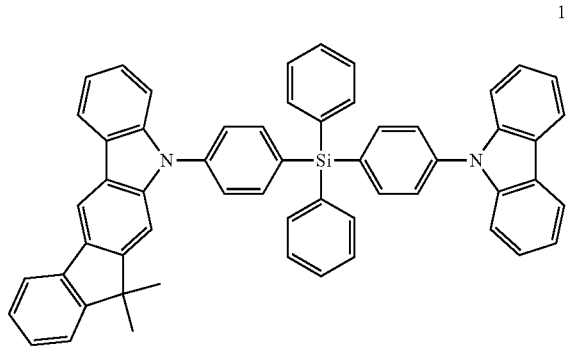

17
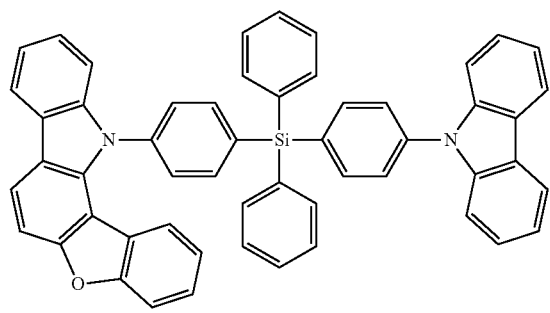
18
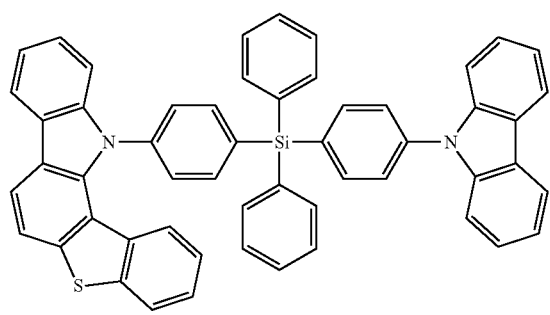
19
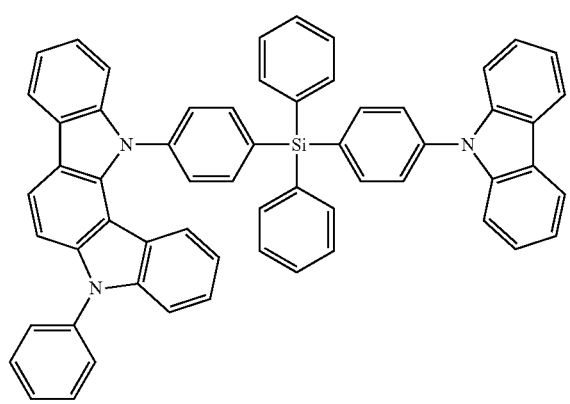
20
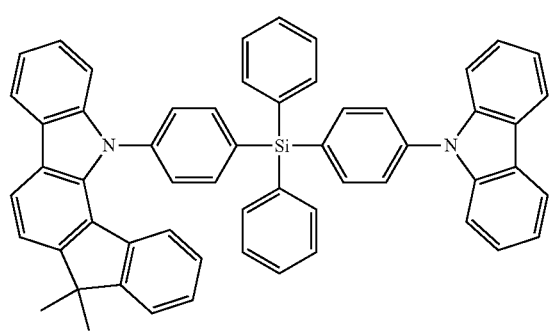
21
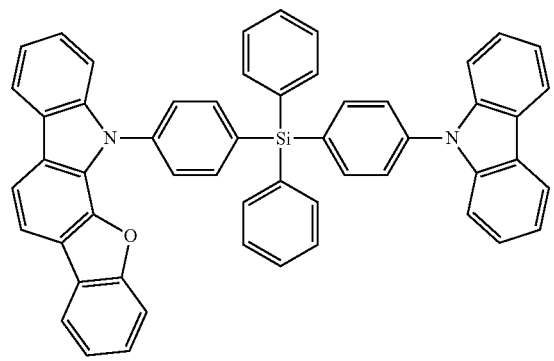
22
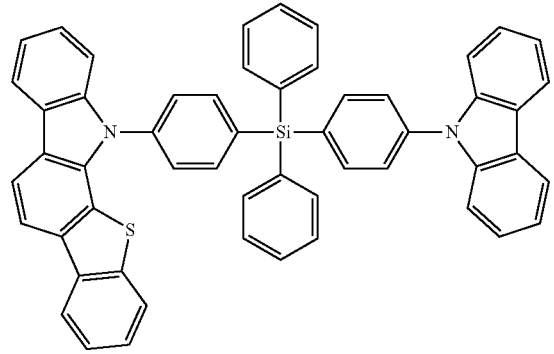
23
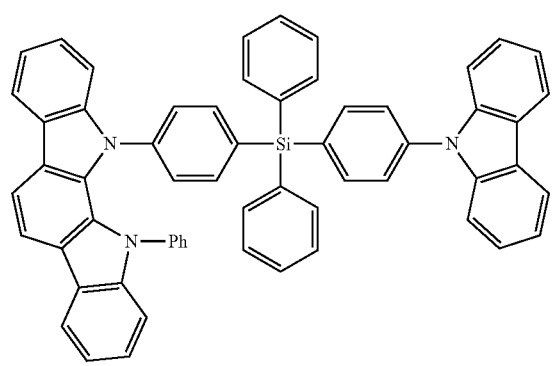
24
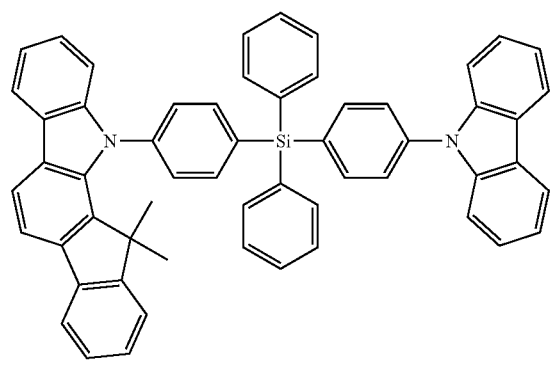

25
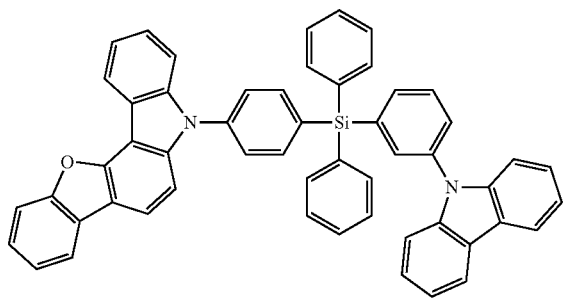
26
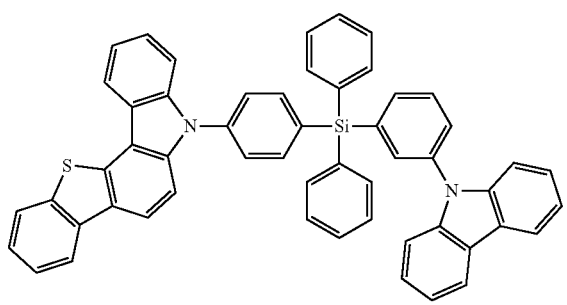
27
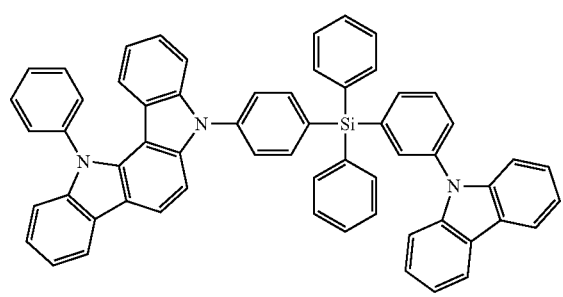
28
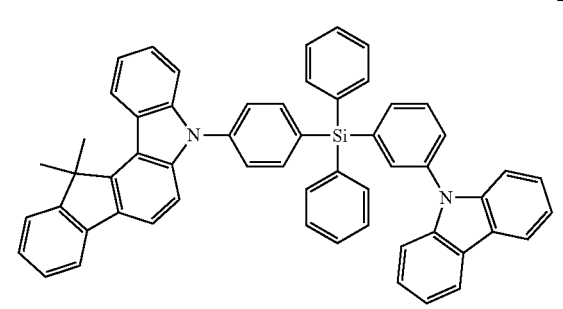
29
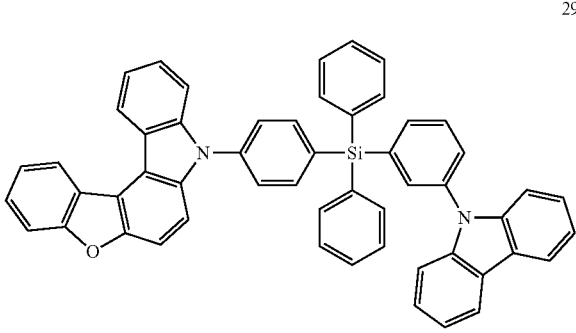
30
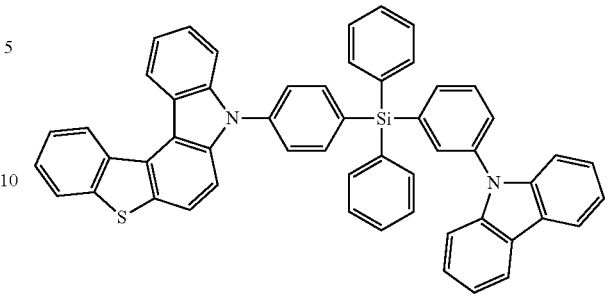
31
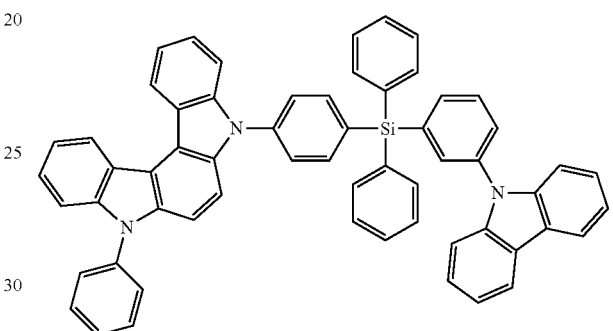
32
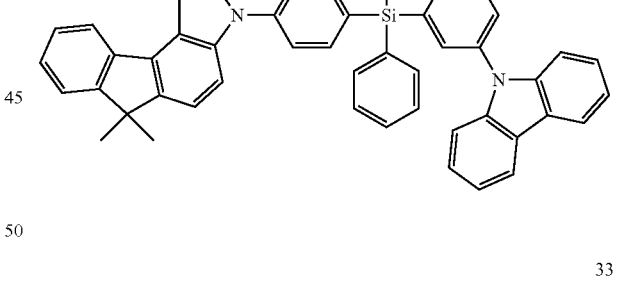
33
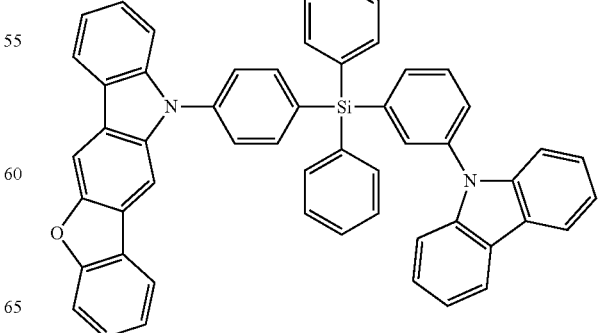

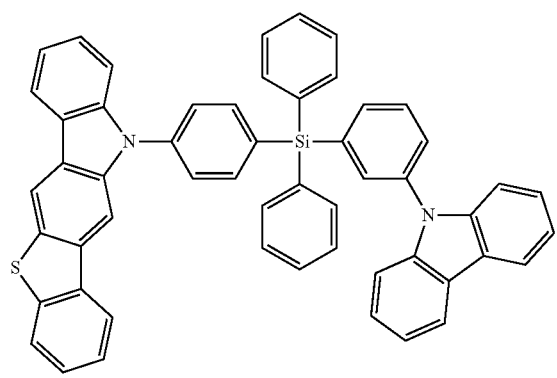
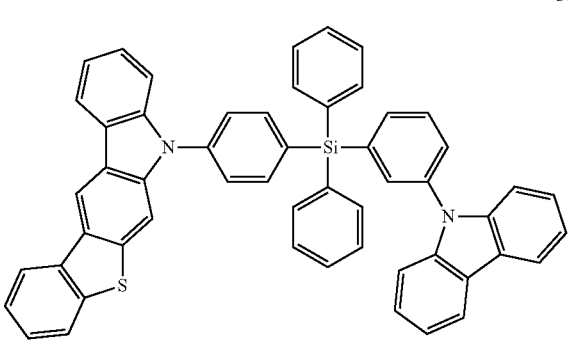

| 827 -continued | 828 -continued |
|---|---|
| 42 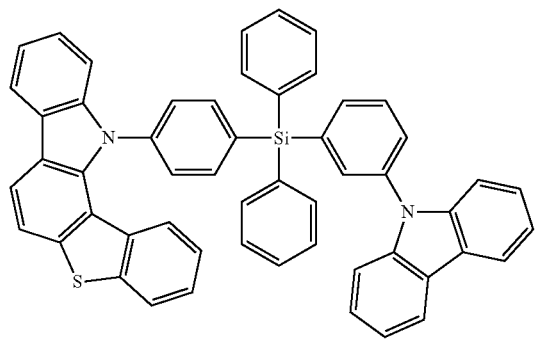 | 46 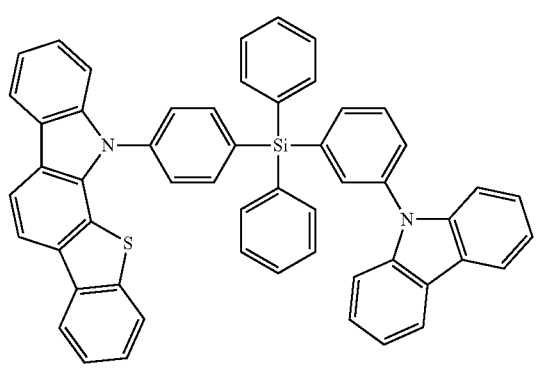 |
| 43 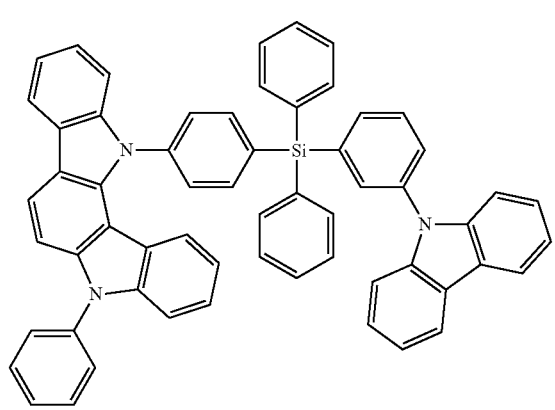 | 47 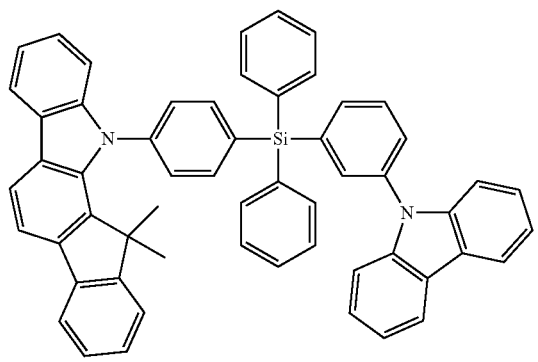 |
| 44 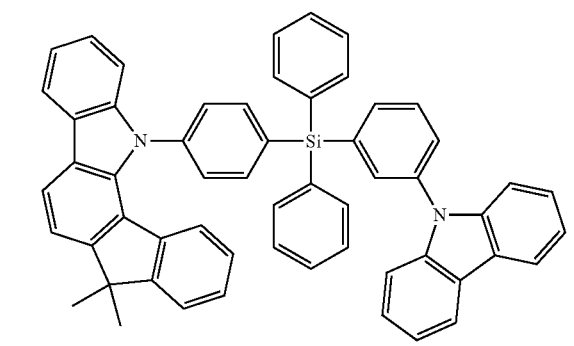 | 48 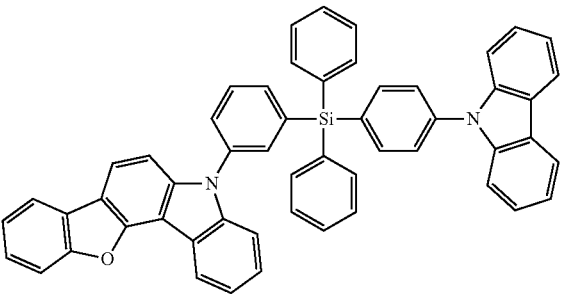 |
| 45 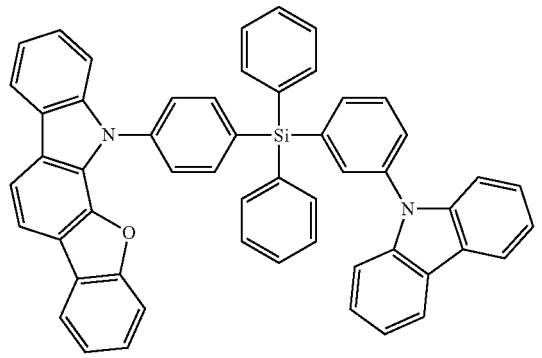 | 49 |

829
-continued
50
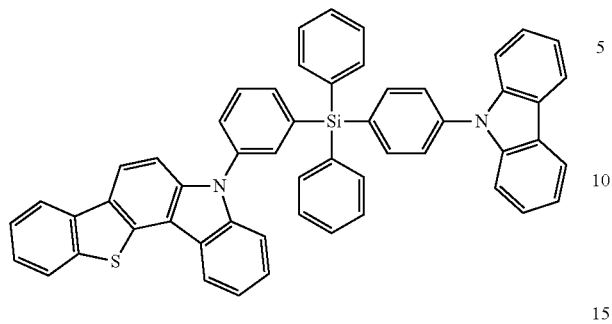
51
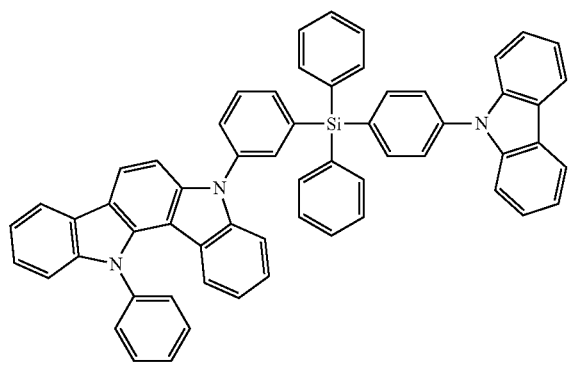
52
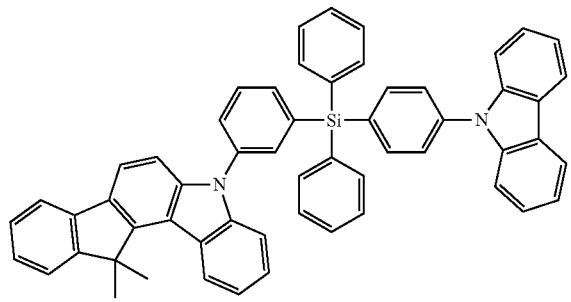
53
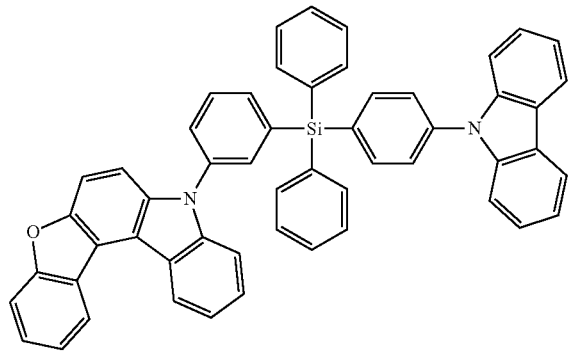
830
-continued
54
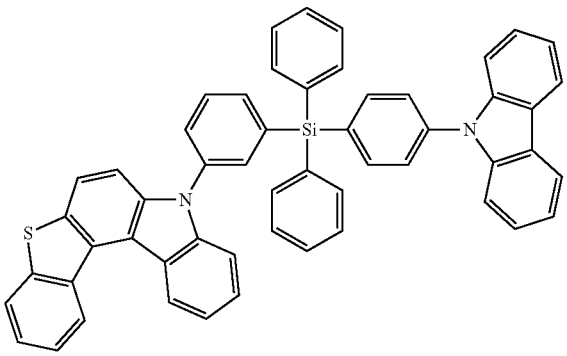
55
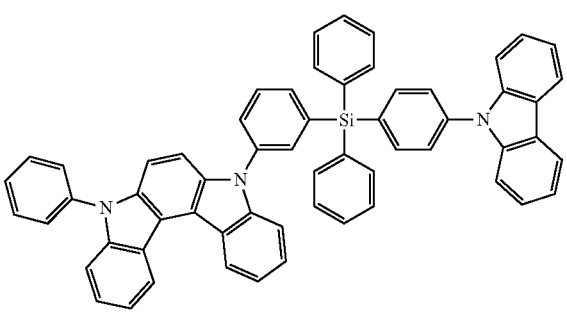
56
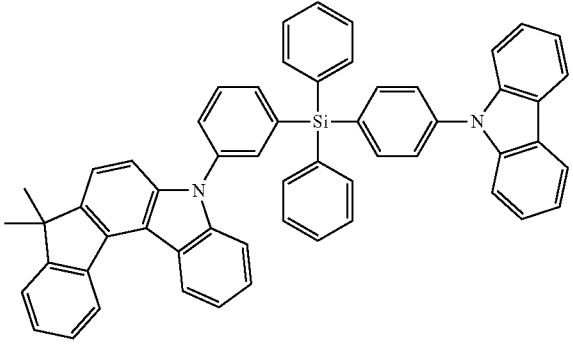
57
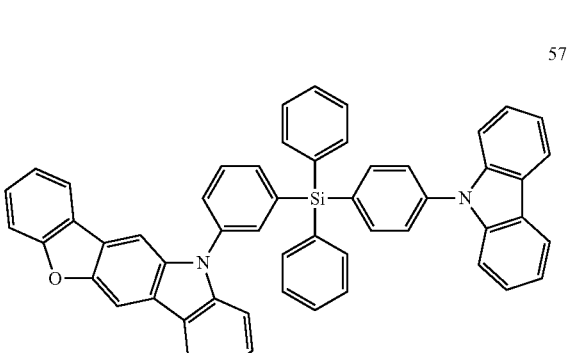

58
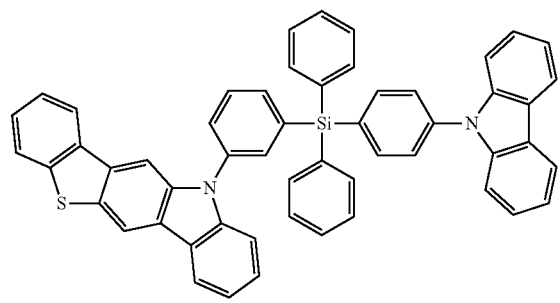
59
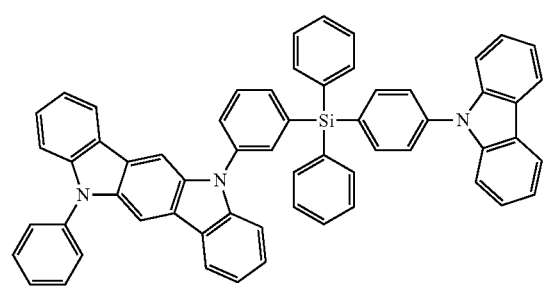
60
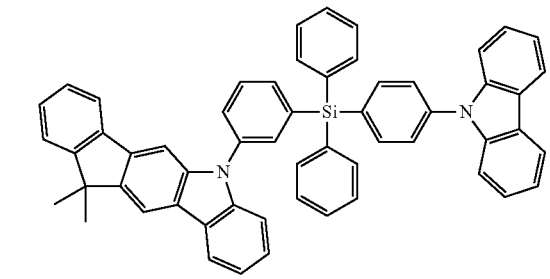
61
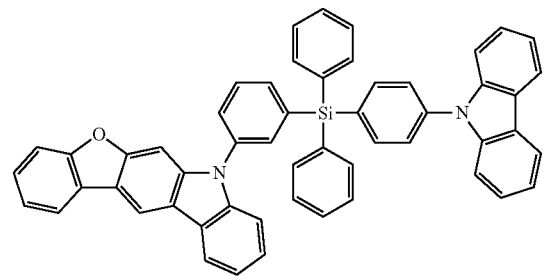
62
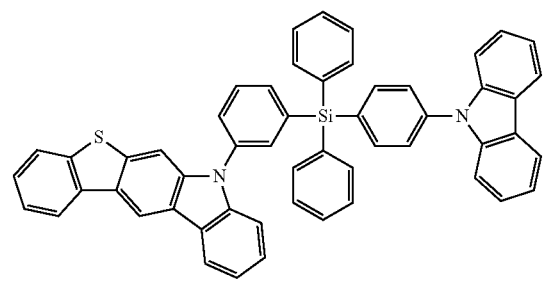
63
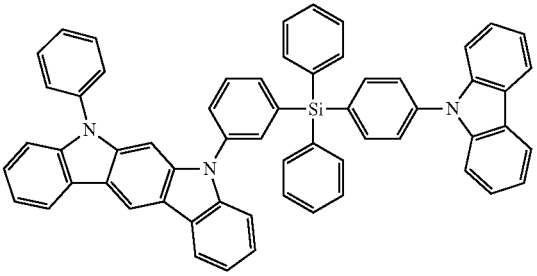
64
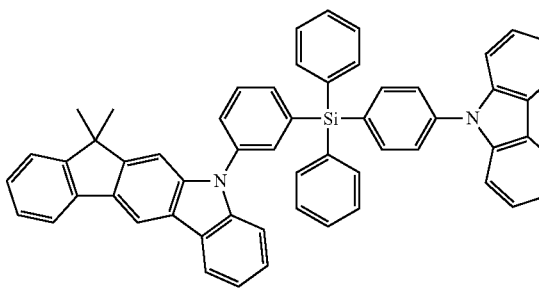
65
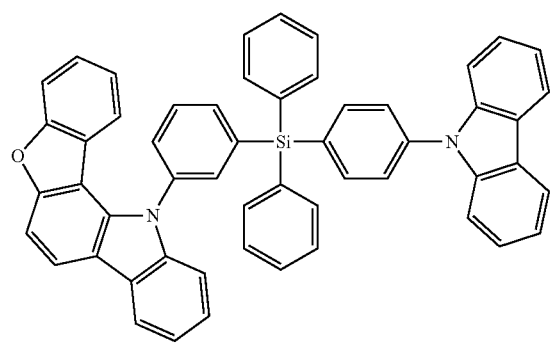
66
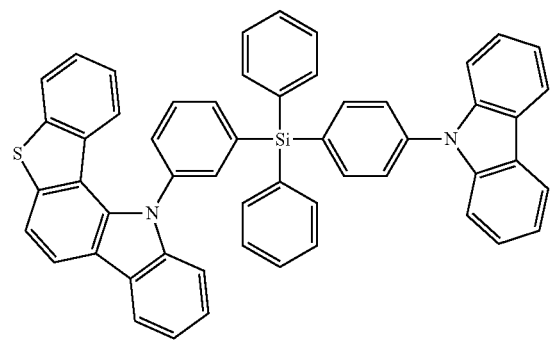
67
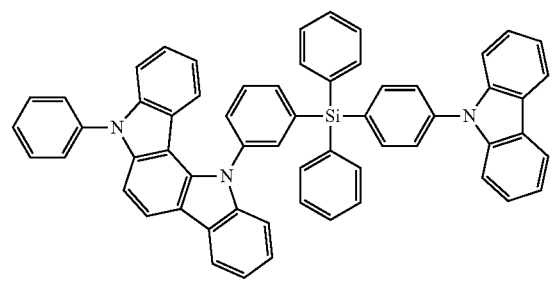

68
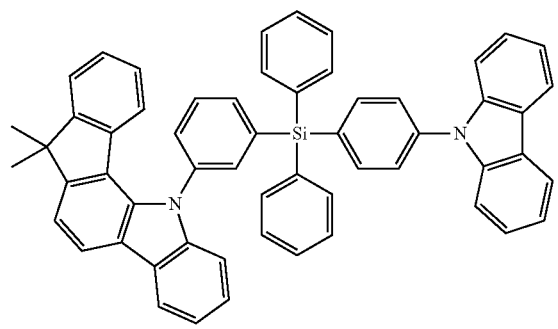
72
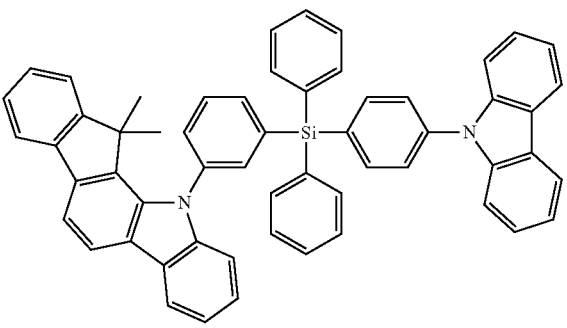
69
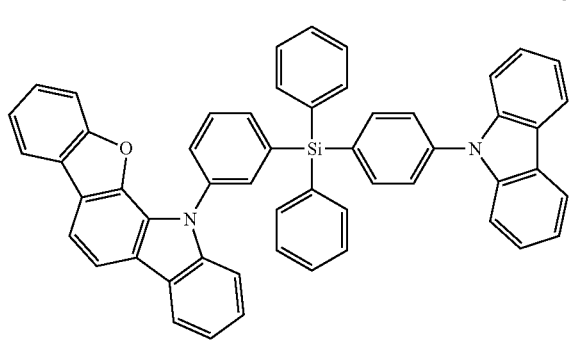
73
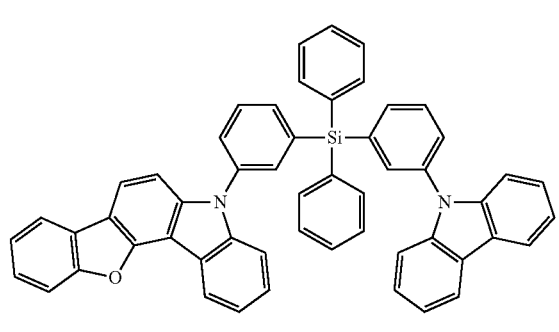
70
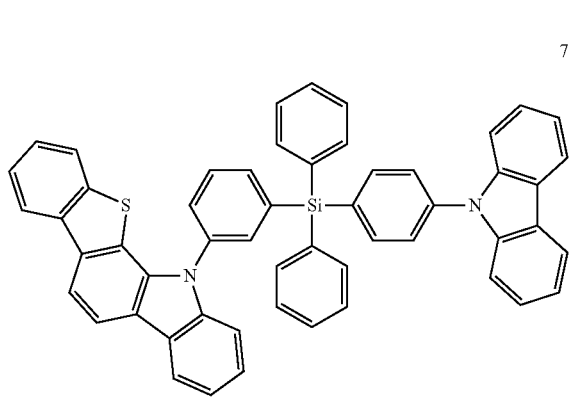
74
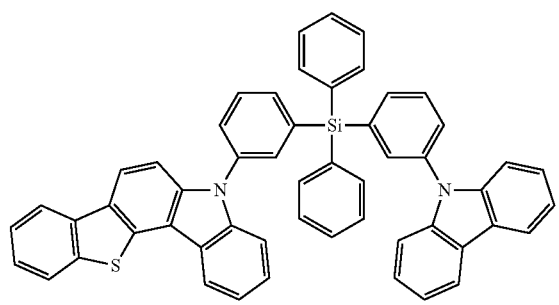
71
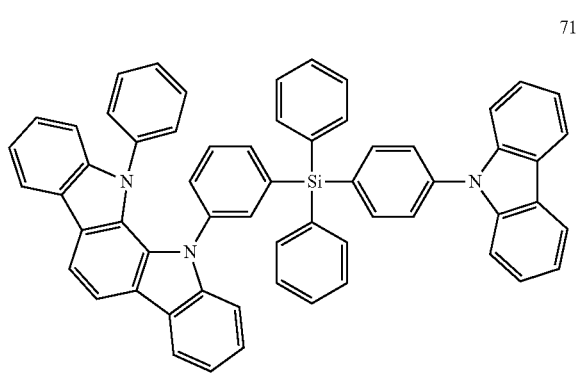
75
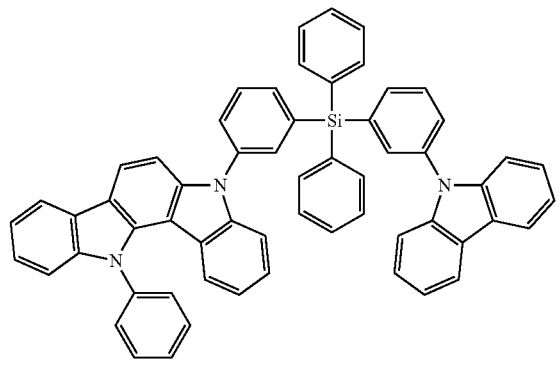

76
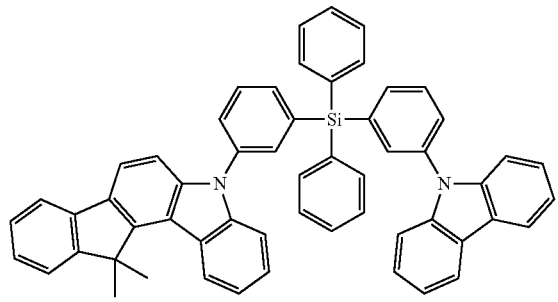
77
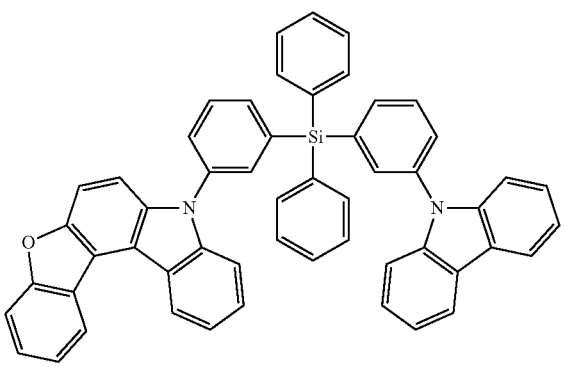
78
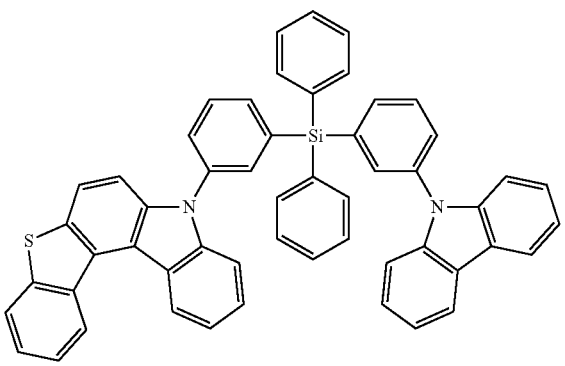
79
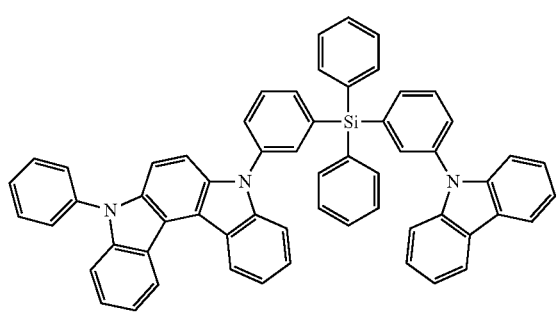
80
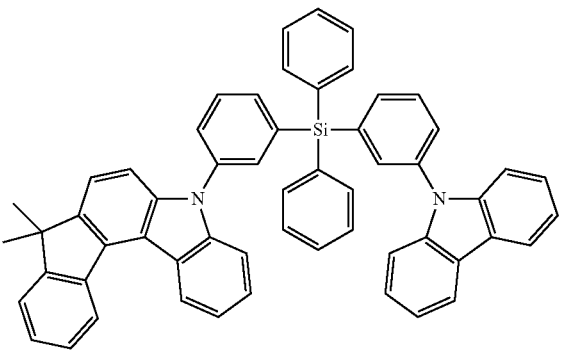
81
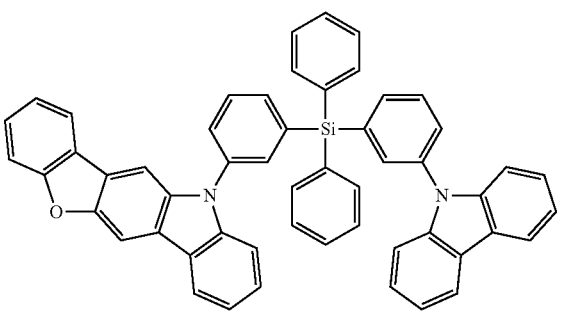
82
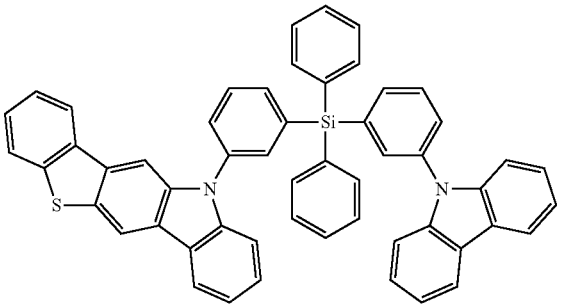
83
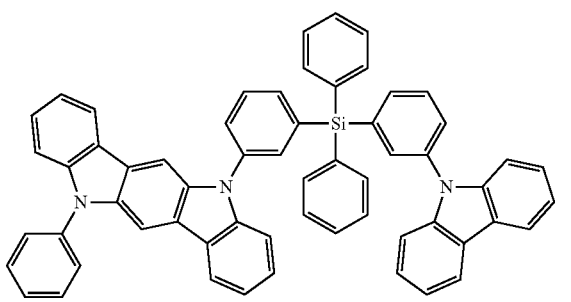

84
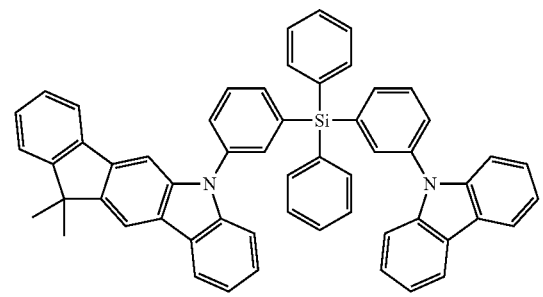
85
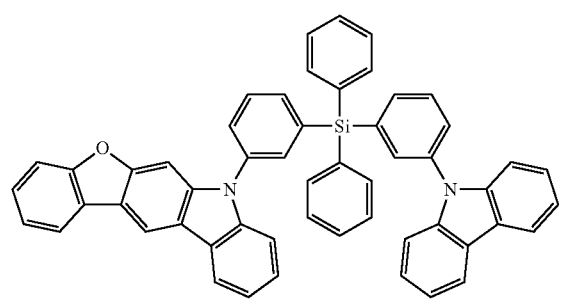
86
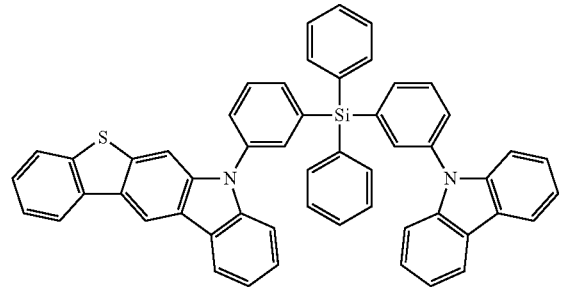
87
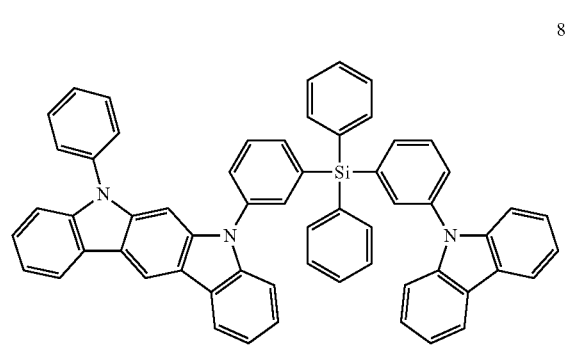
88
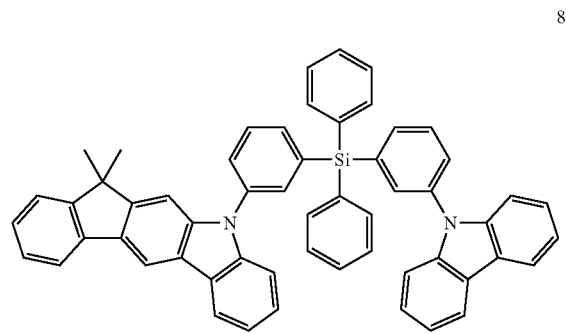
89
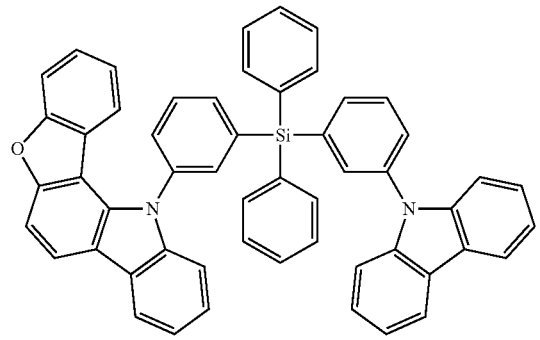
90
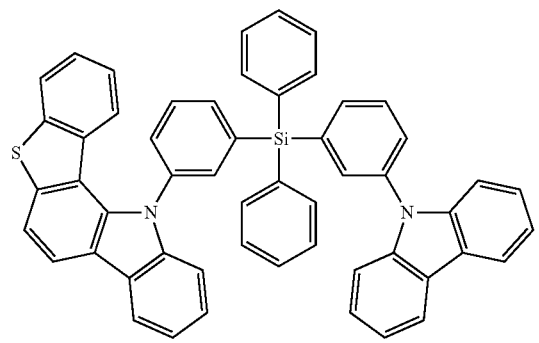
91
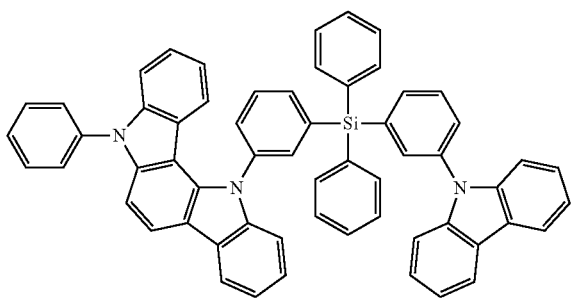
92
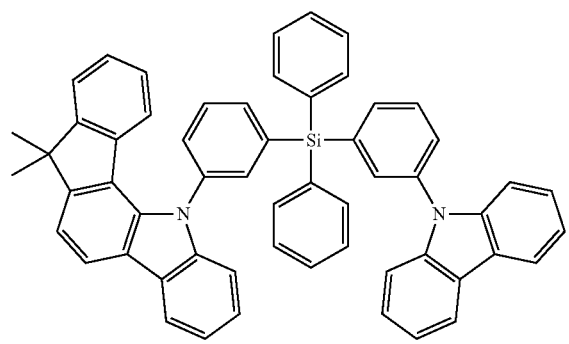

93
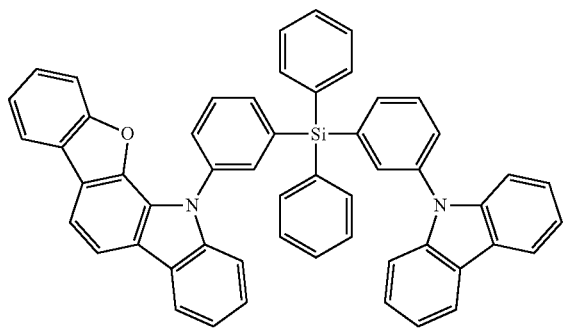
94
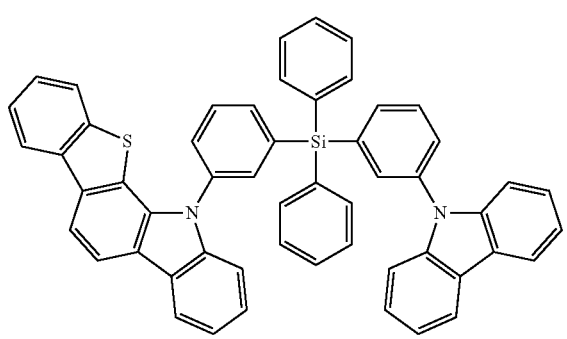
95
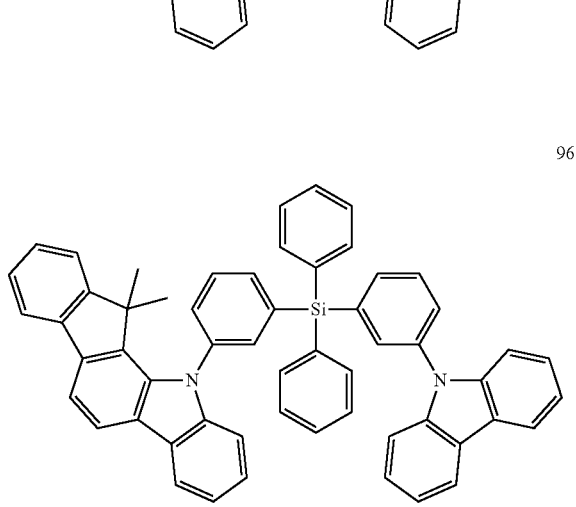
96
97
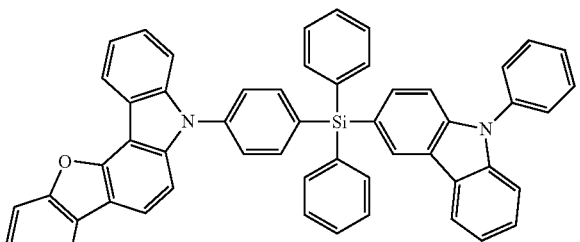
98
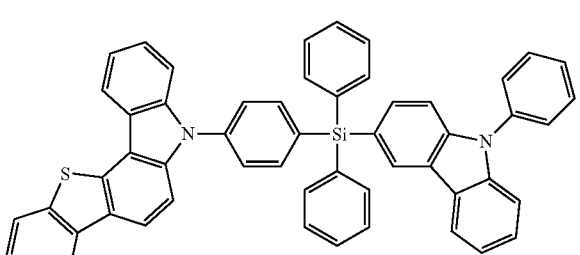
99
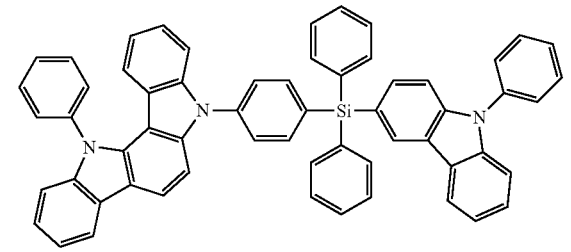
100
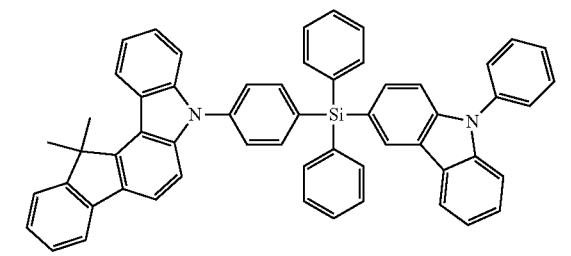
101
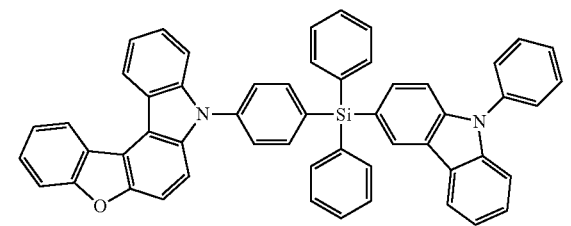

-continued
102
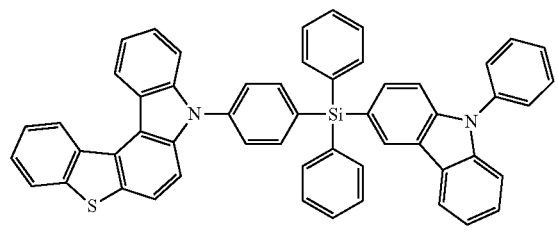
103
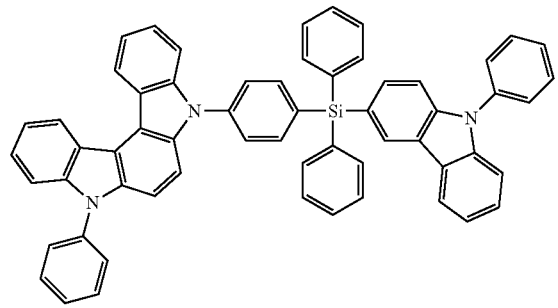
104
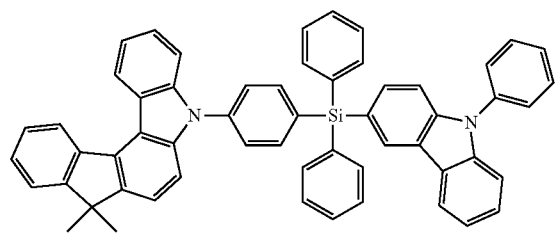
105
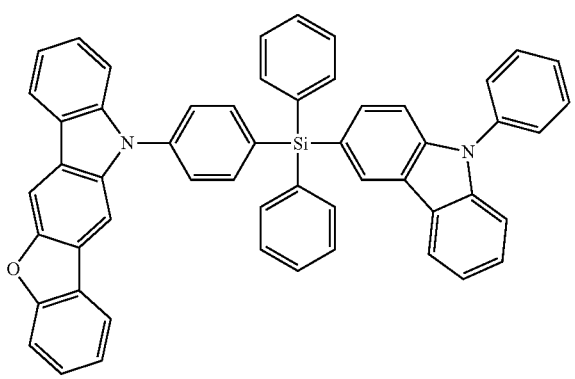
106
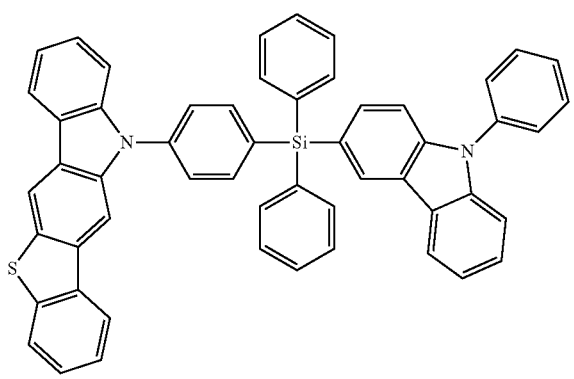
-continued
107
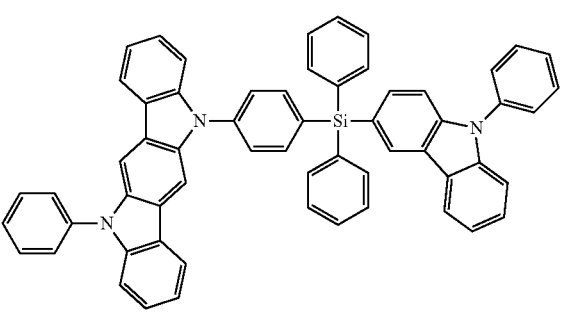
108
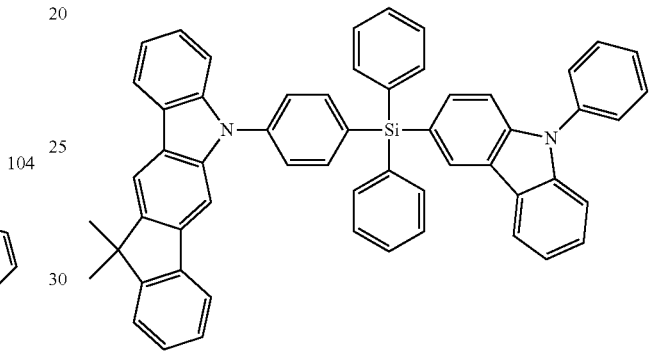
109
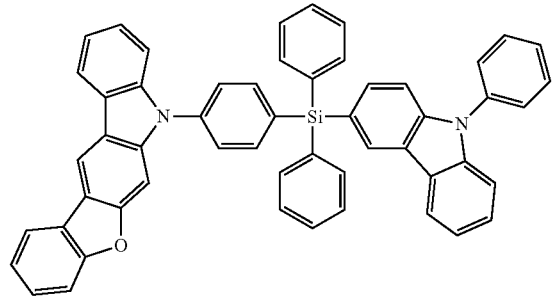
110
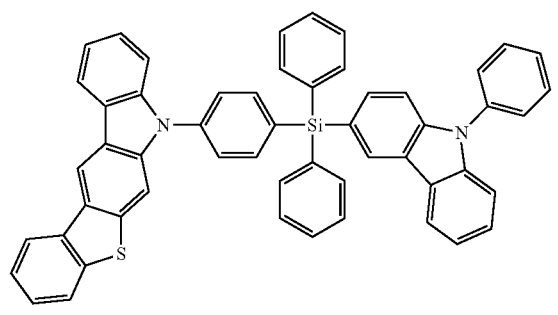

111 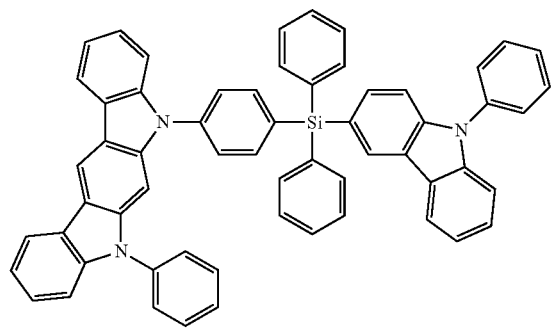
112 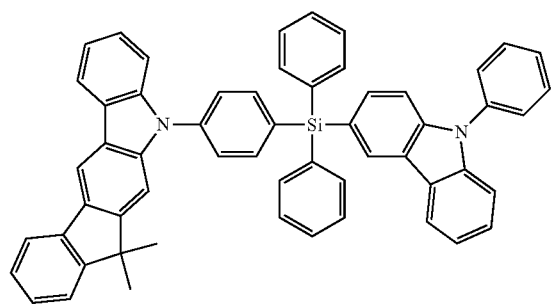
113 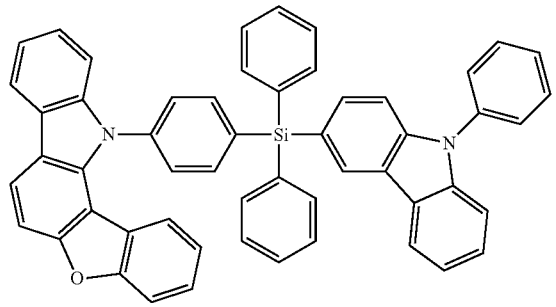
114 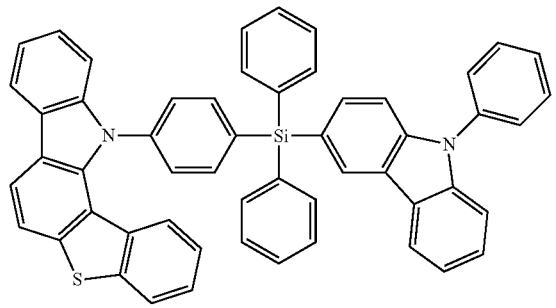
115 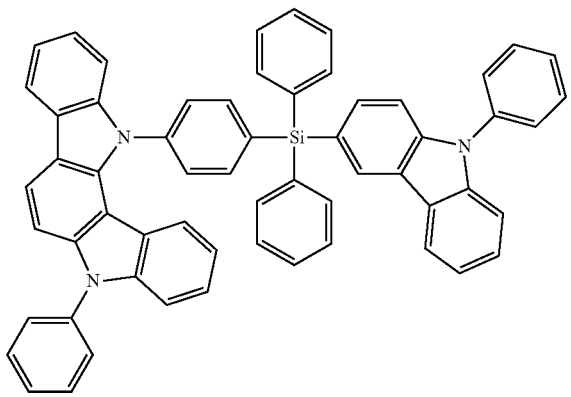
116 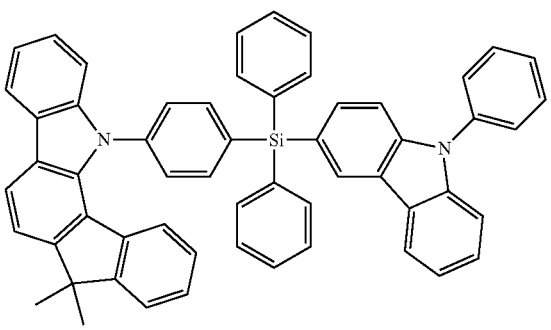
117 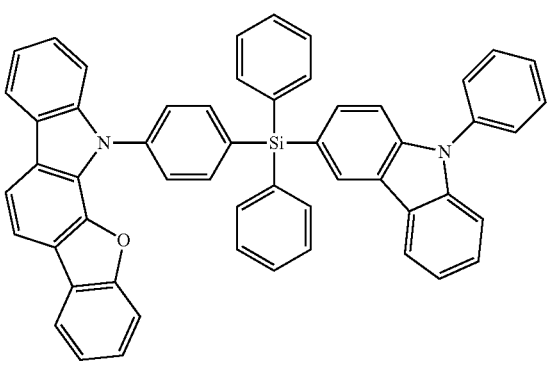
118 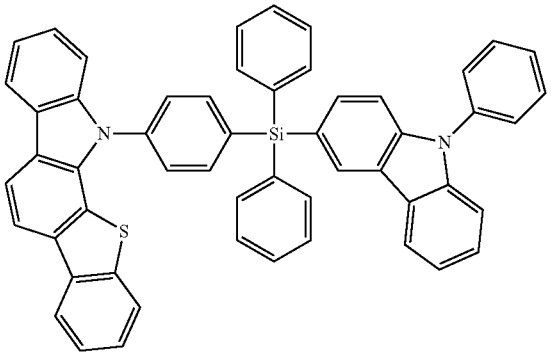

119
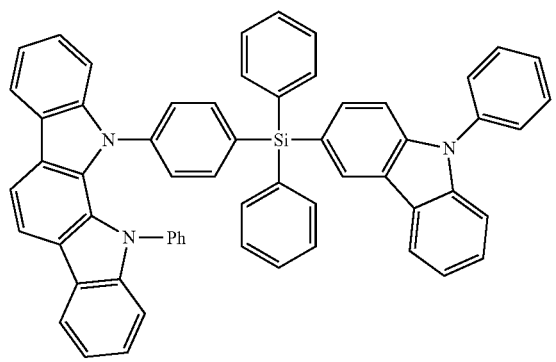
120
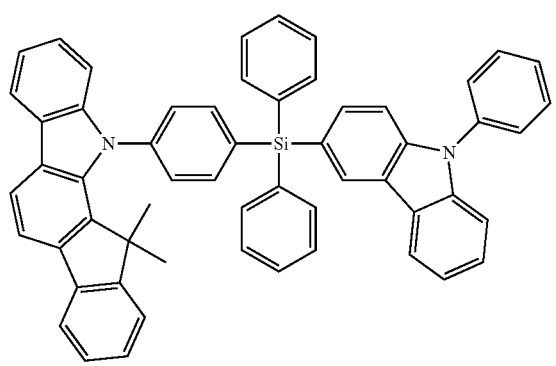
121
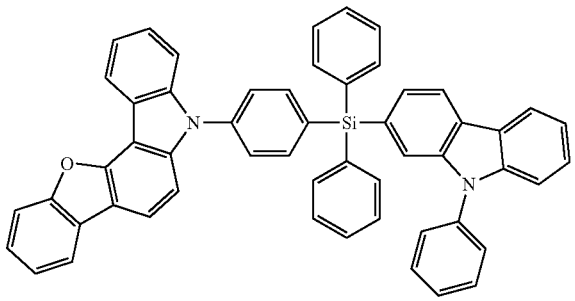
122
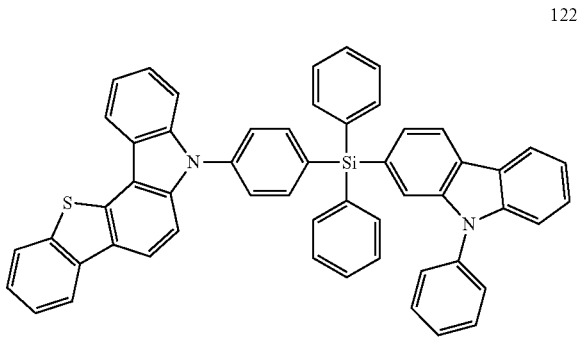
123
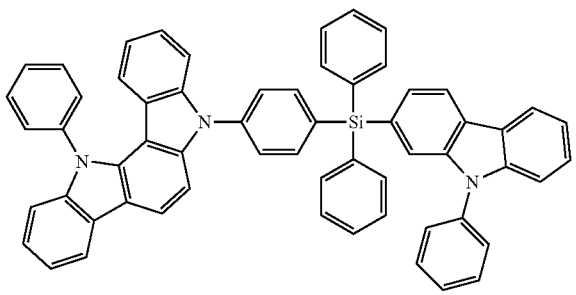
124
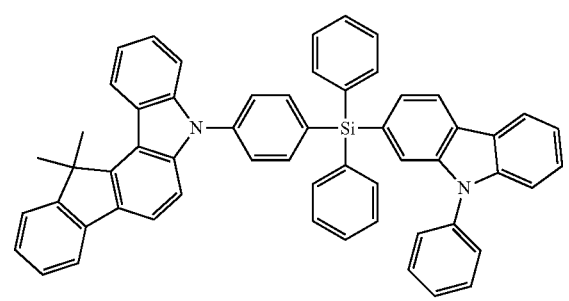
125
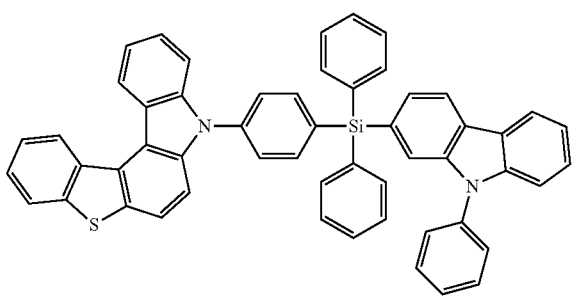
126
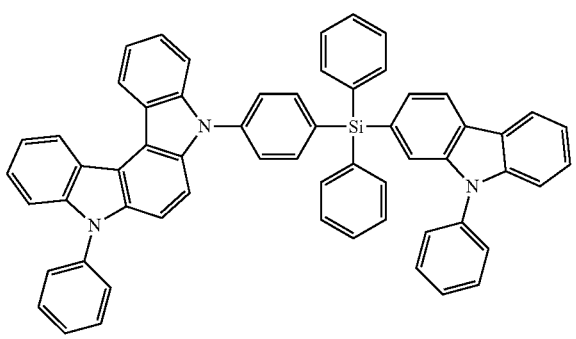
127

128
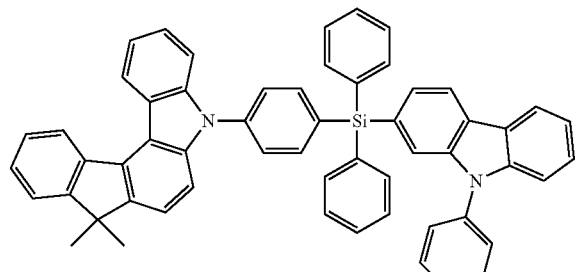
129
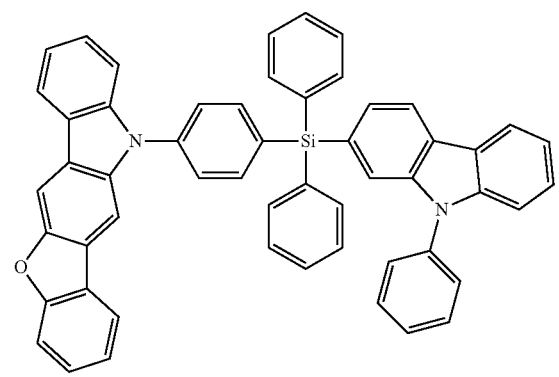
130
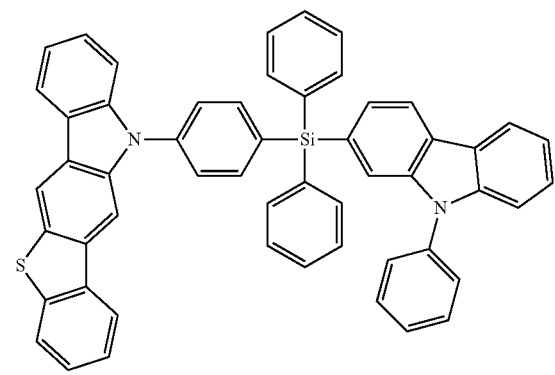
131
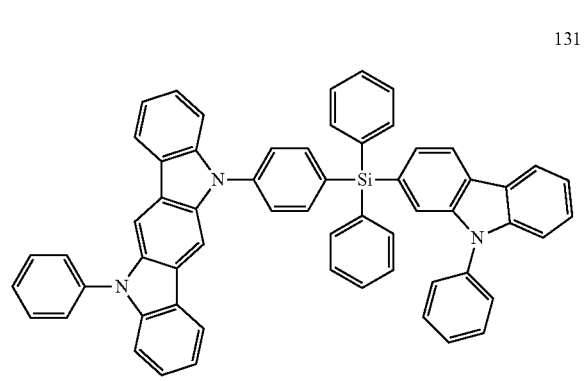
132
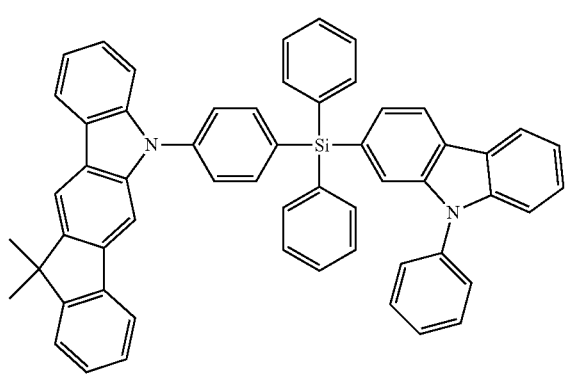
133
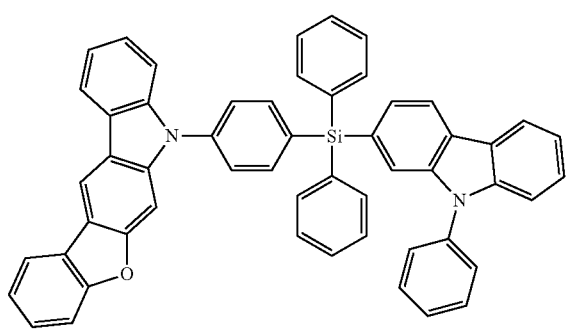
134
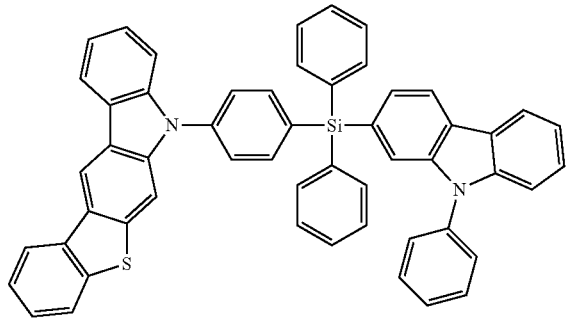
135
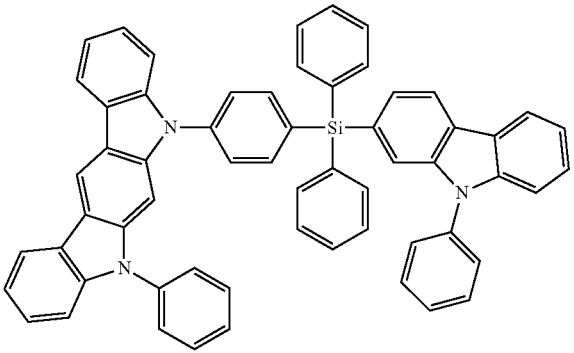

849
-continued
136
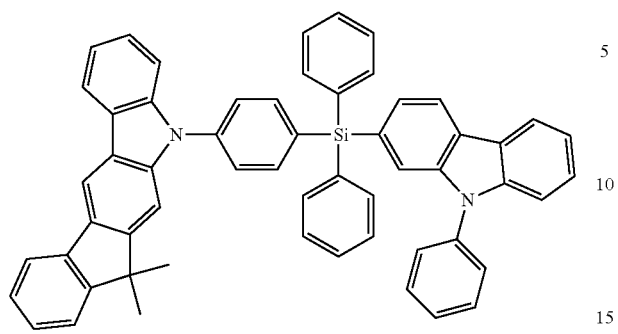
137
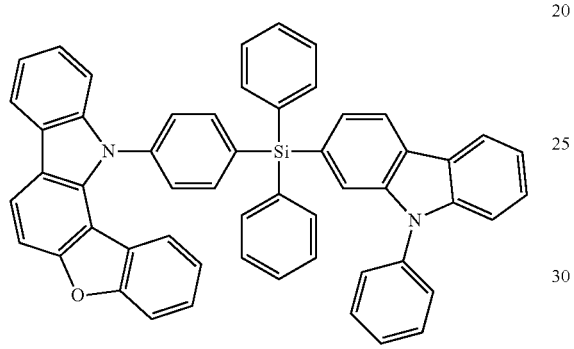
138
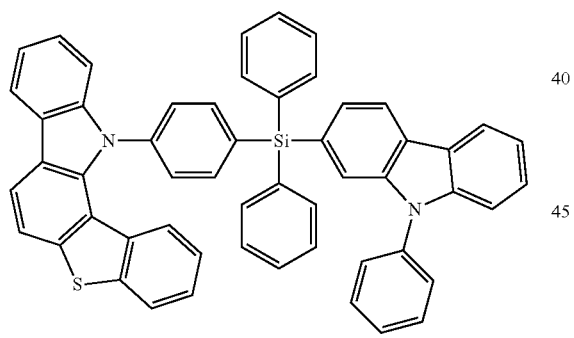
139
850
-continued
140
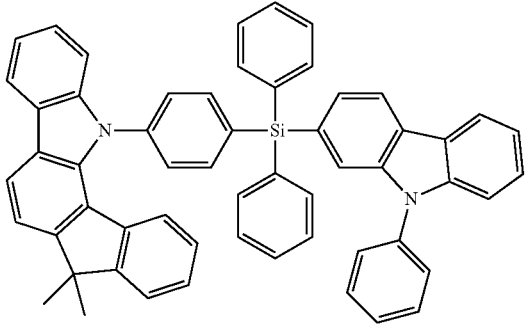
141
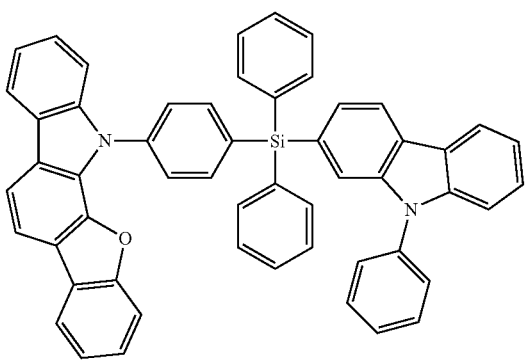
142
143
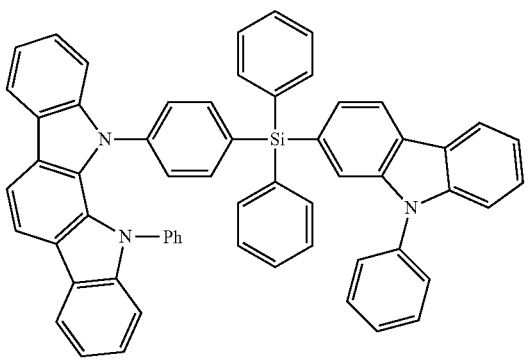

-continued
144
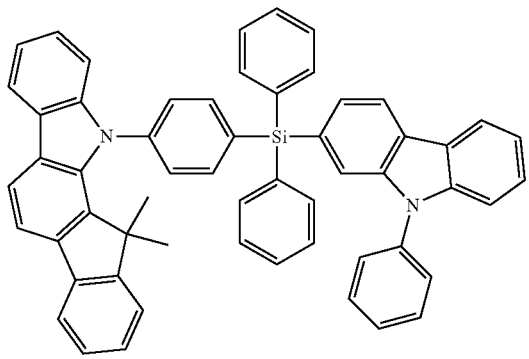
145
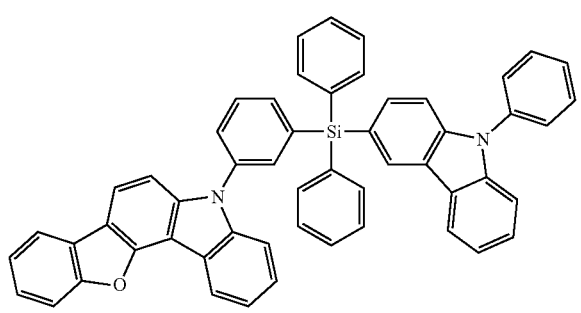
146
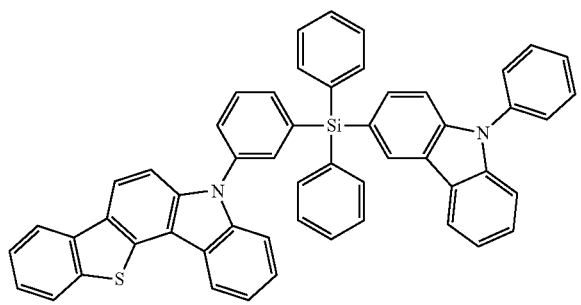
147
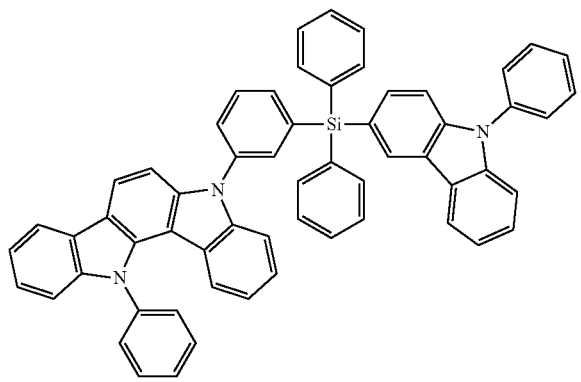
-continued
148
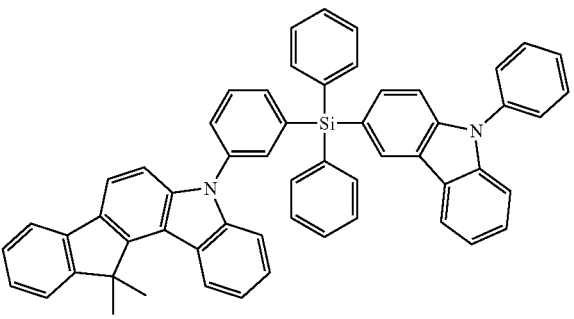
149
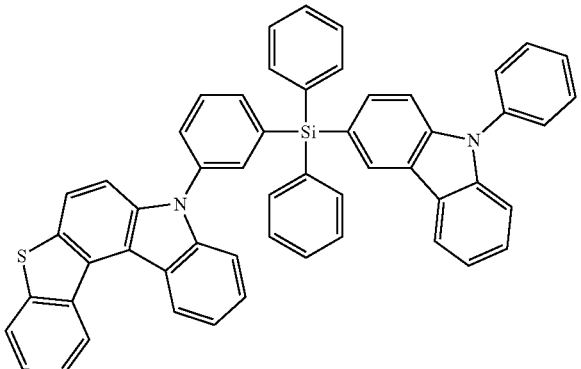
150
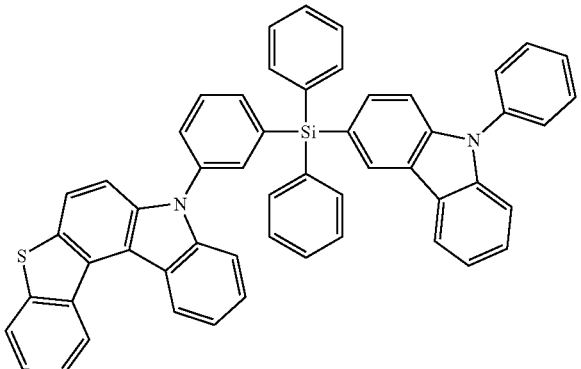
151
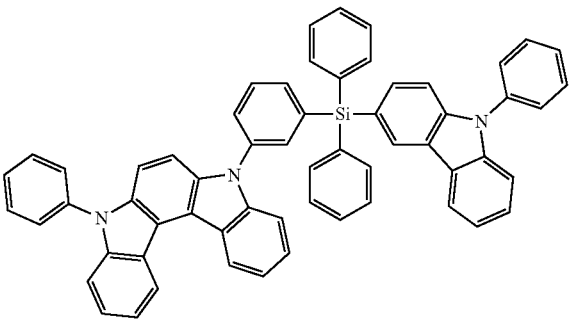

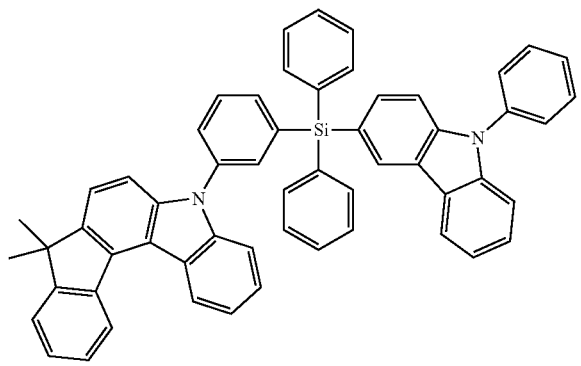
152
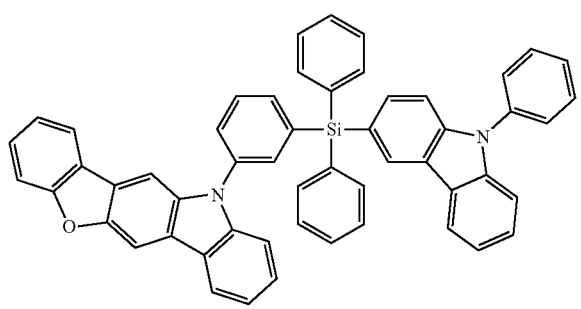
153
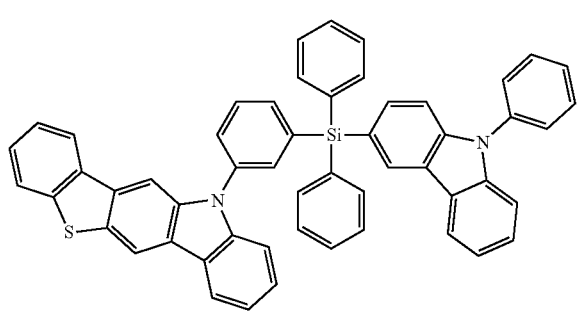
154
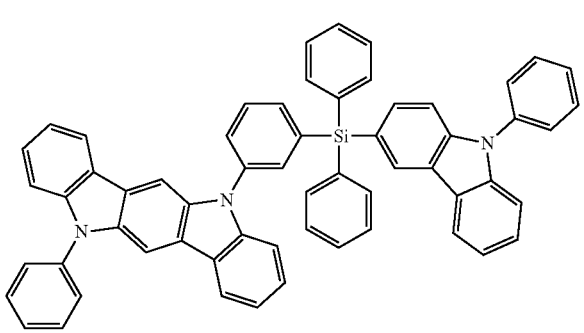
155
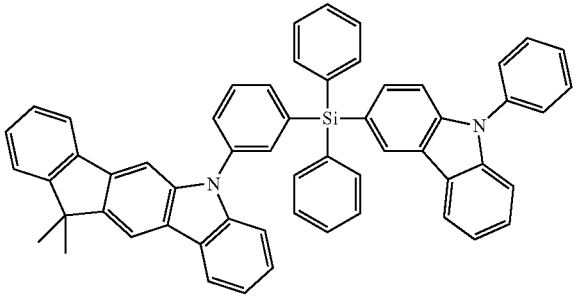
156
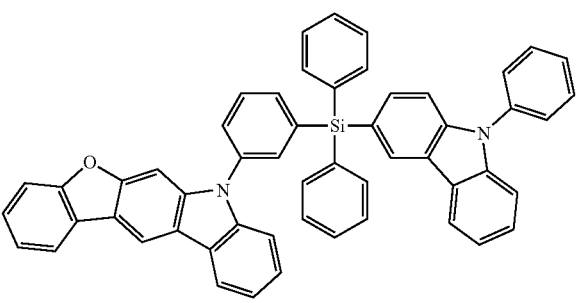
157
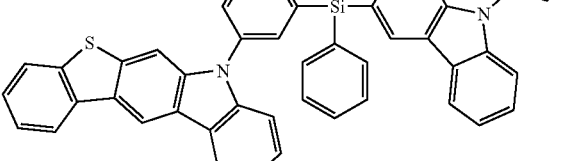
158
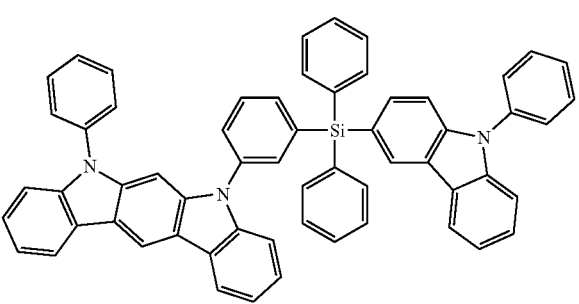
159
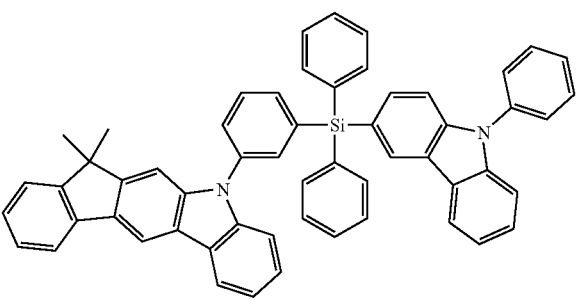
160

855
-continued
856
-continued
161
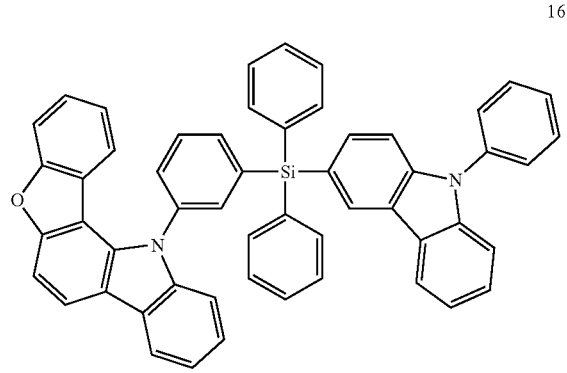
165
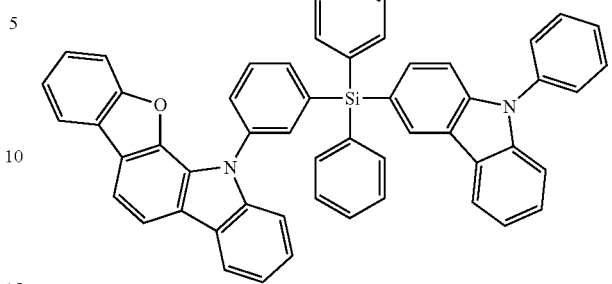
162
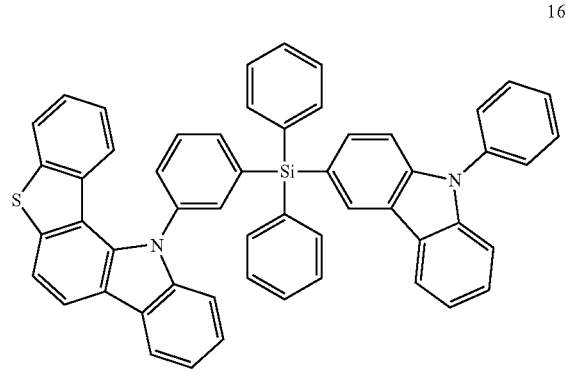
166
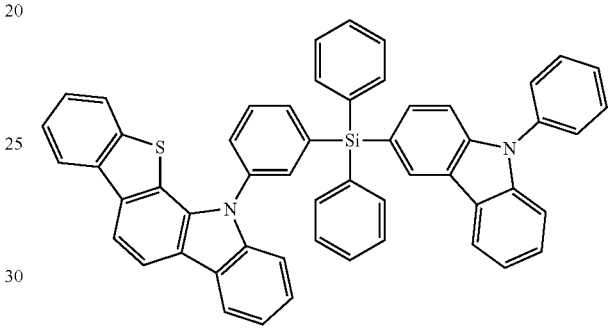
163
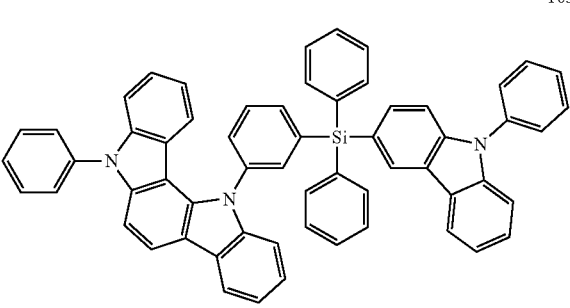
167
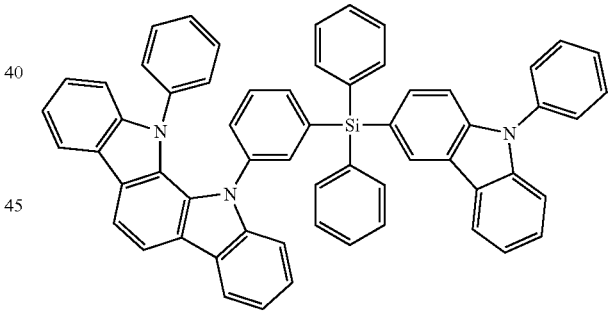
164
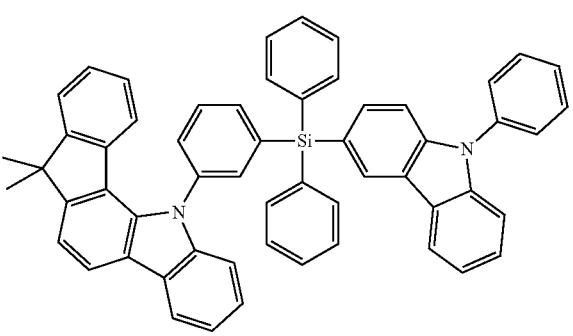
168
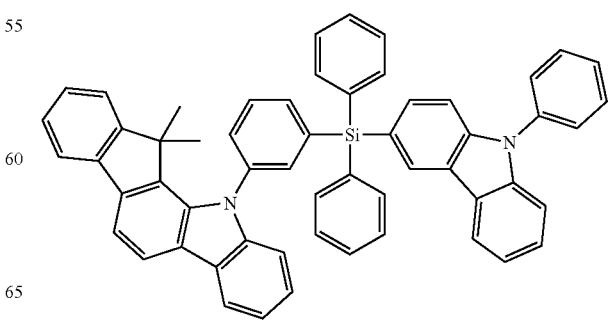

857
-continued
169
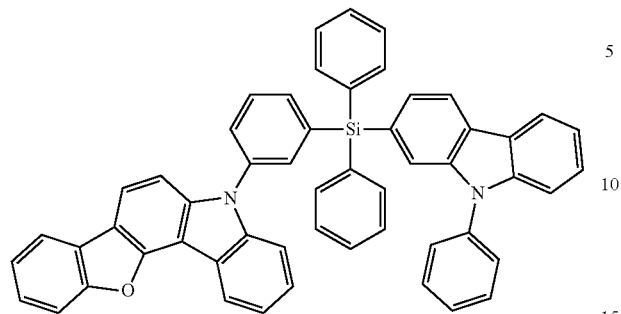
170
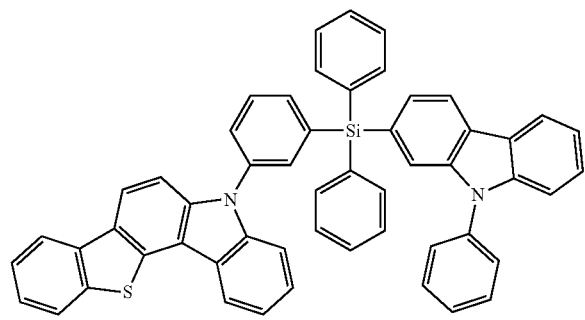
171
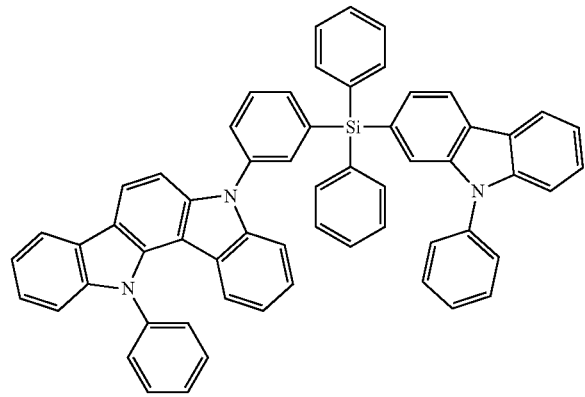
172
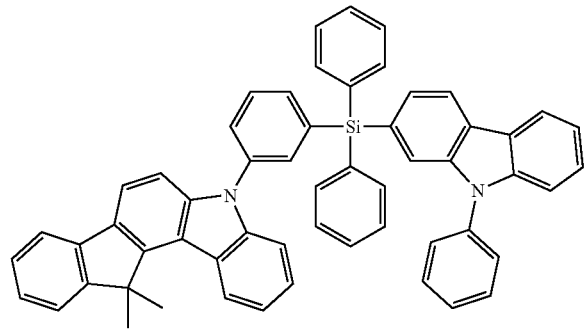
858
-continued
173
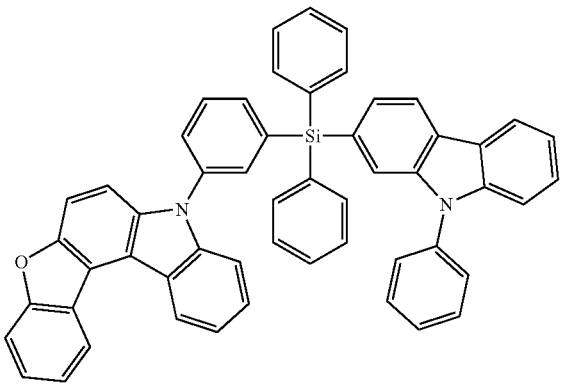
174
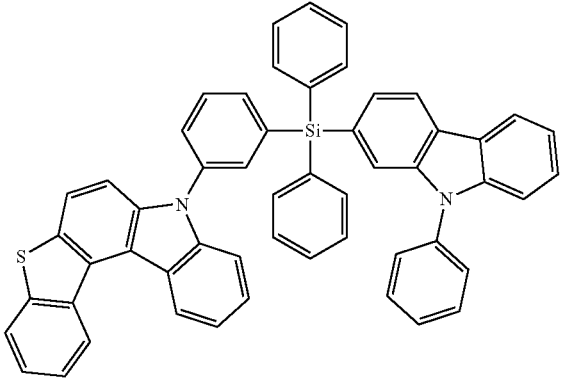
175
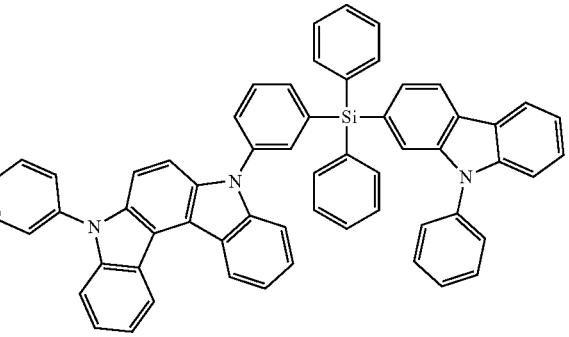
176
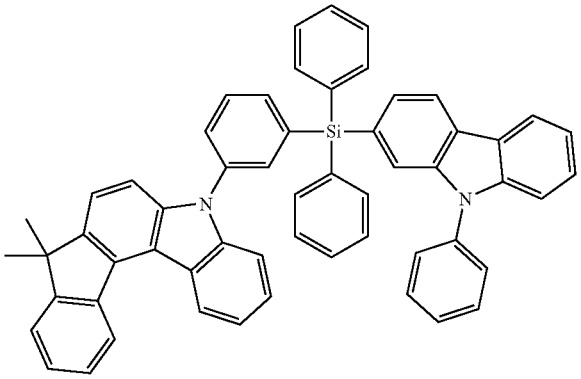

177

178

179

180

181

182

183

184

185 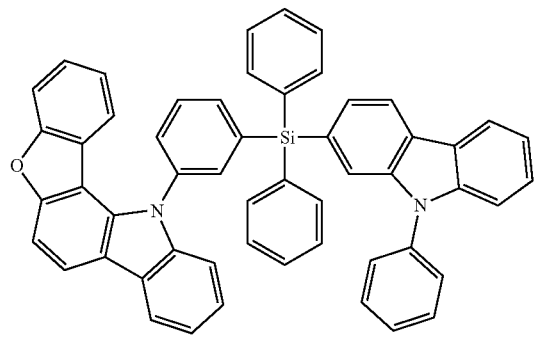
189 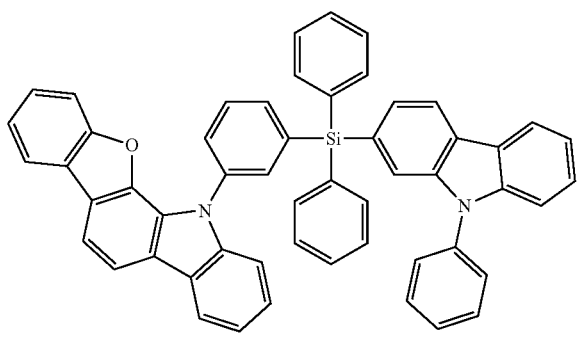
186 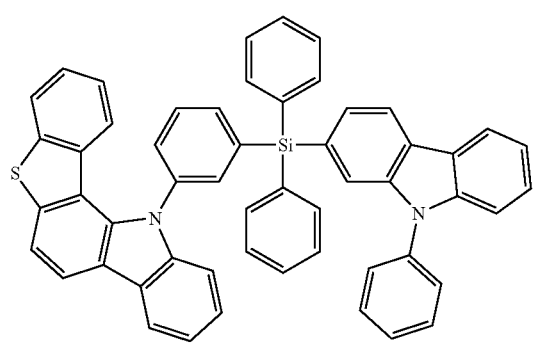
190 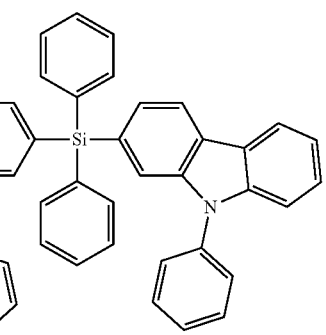
187 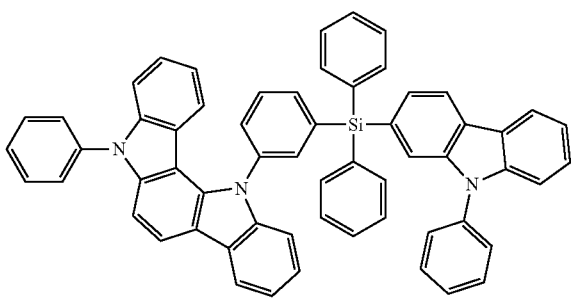
191 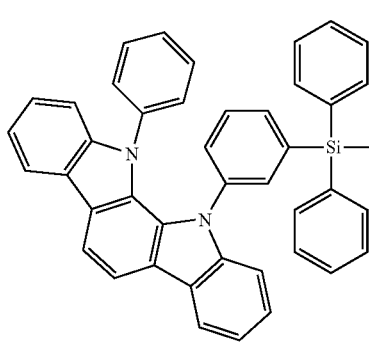
188 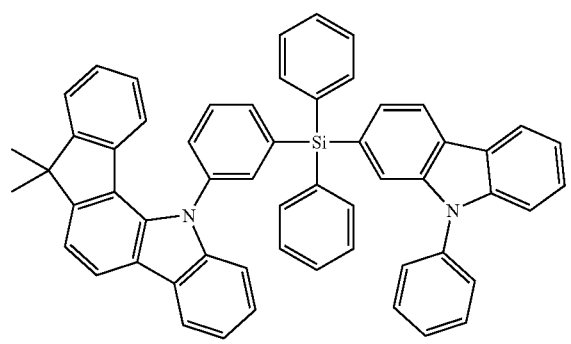
192 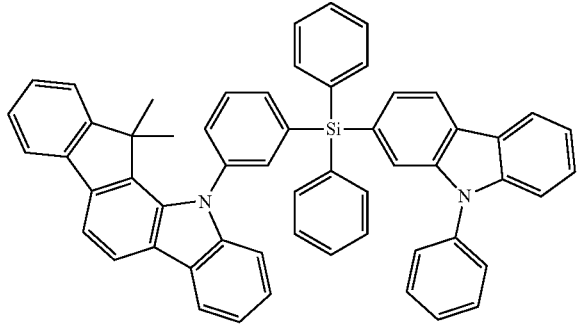

193
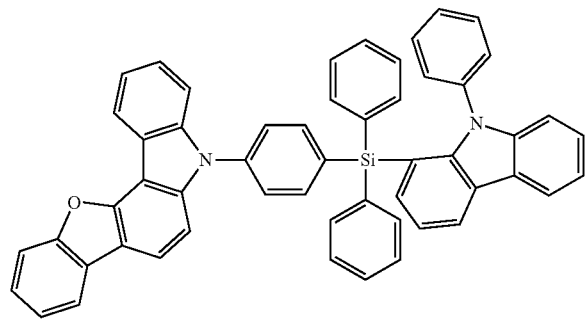
194
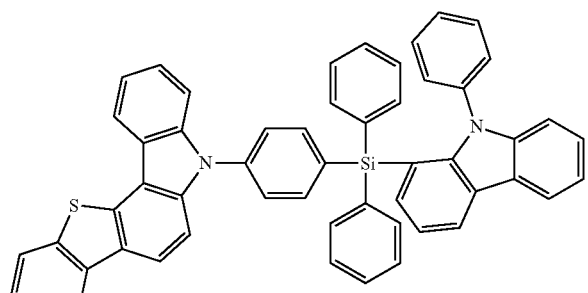
195
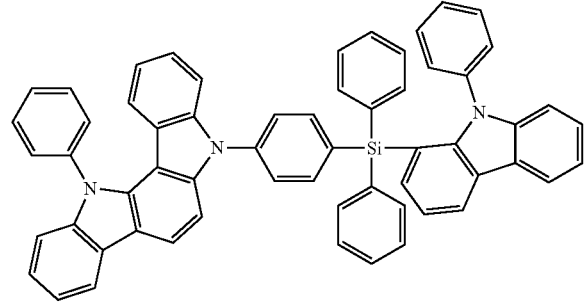
196
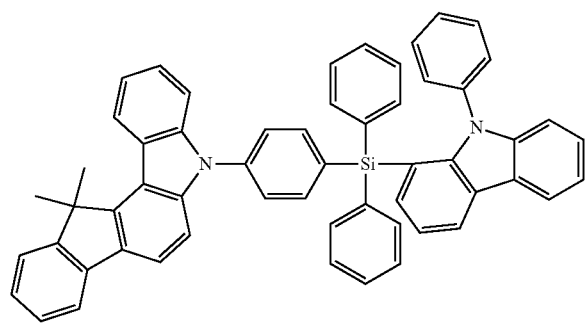
197
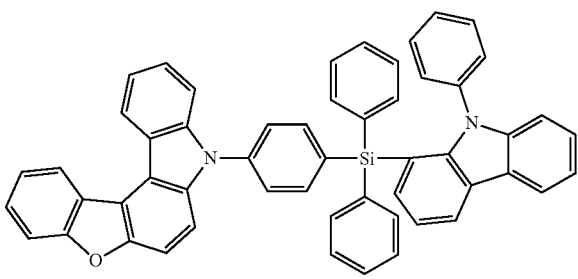
198
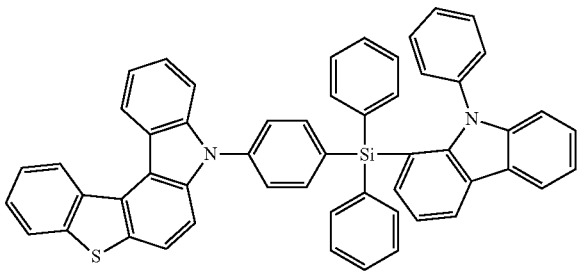
199
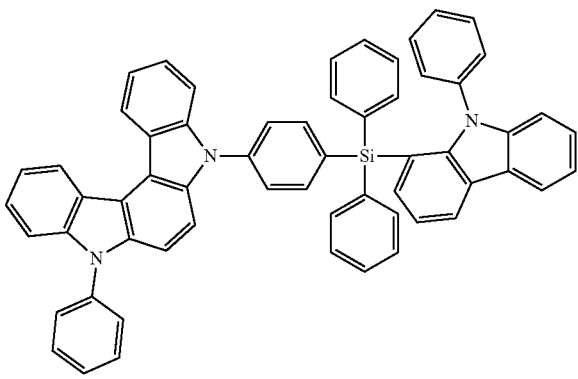
200
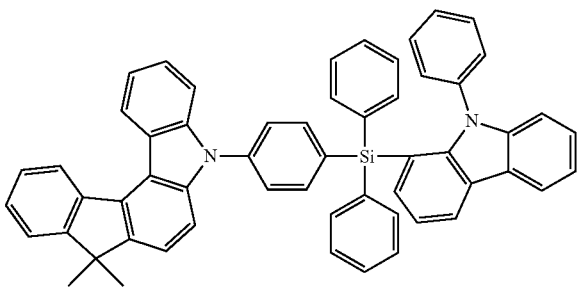

-continued
201
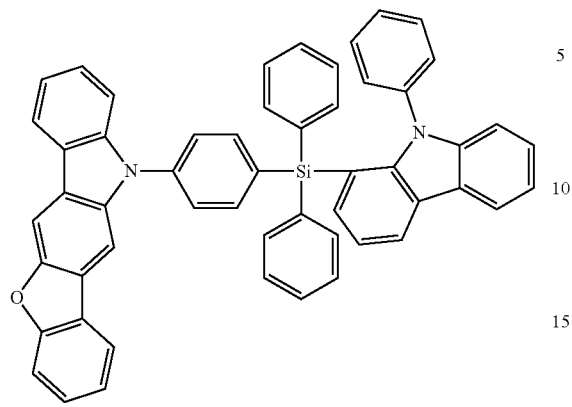
202
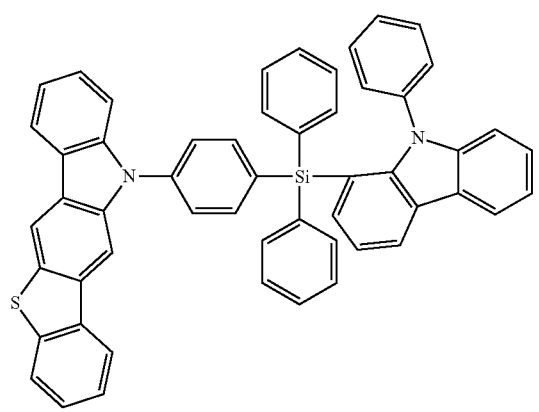
203
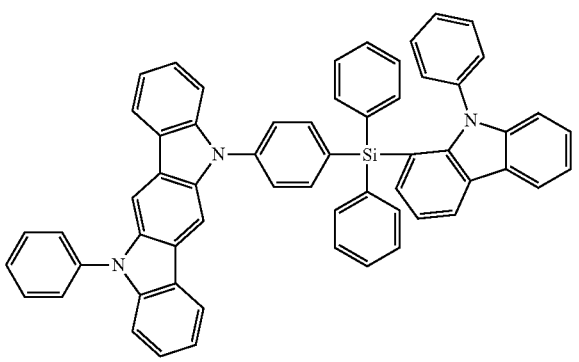
204
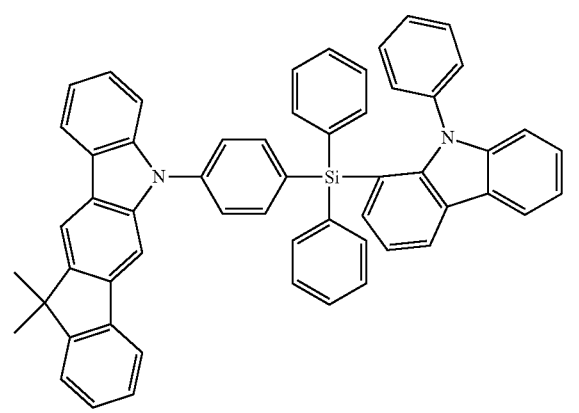
-continued
205
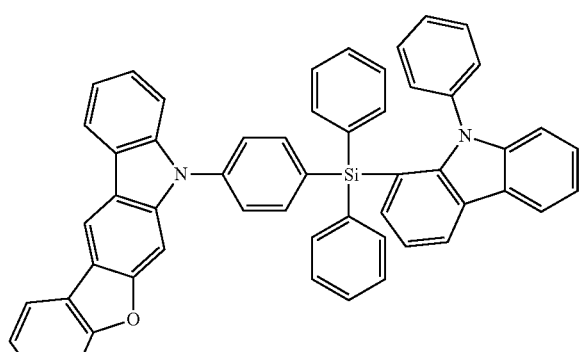
206
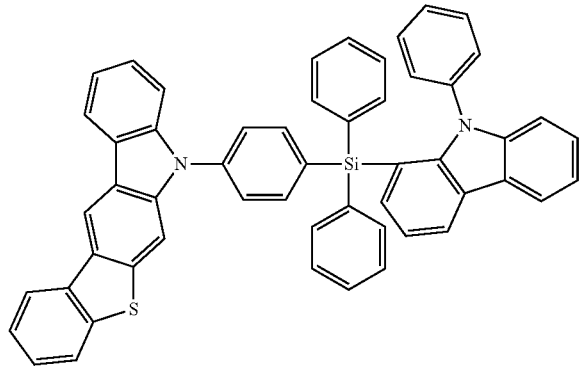
207
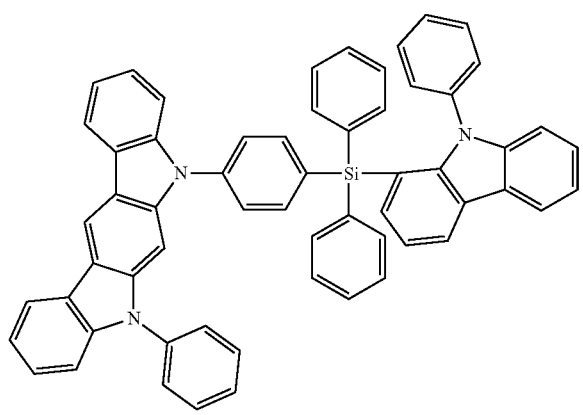
208
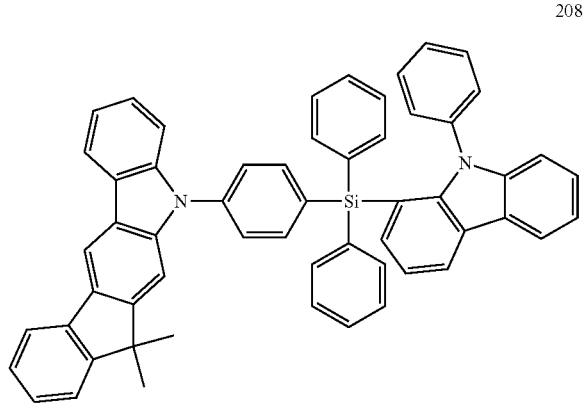

209
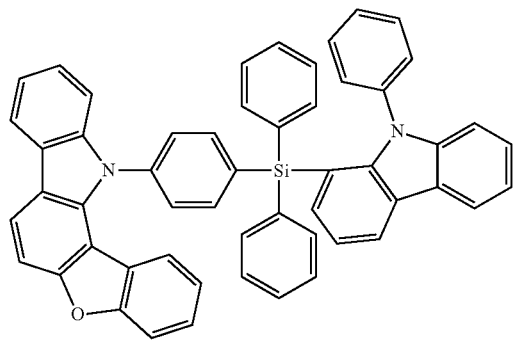
210
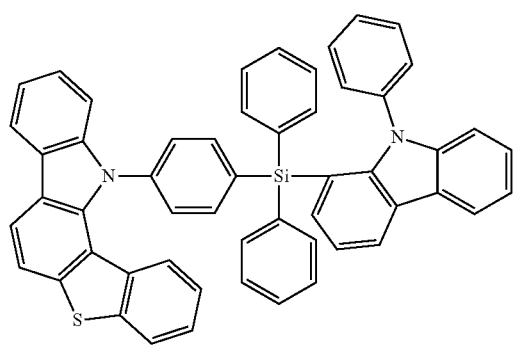
211
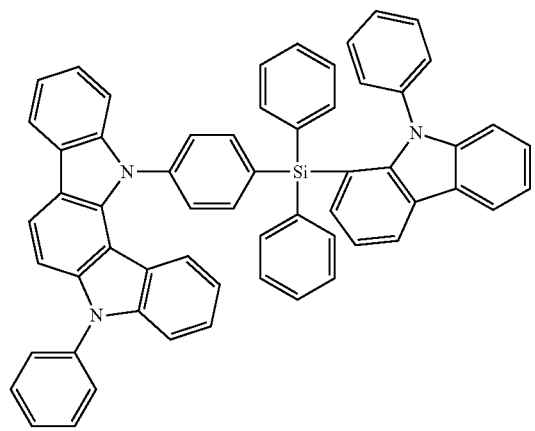
212
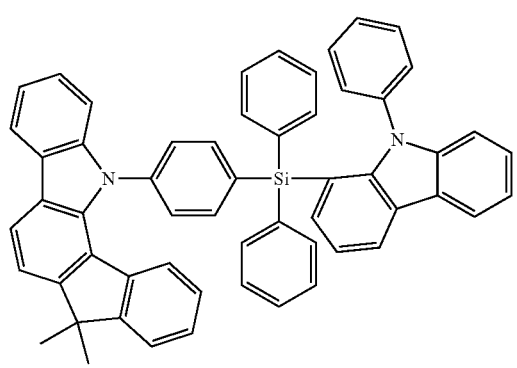
213
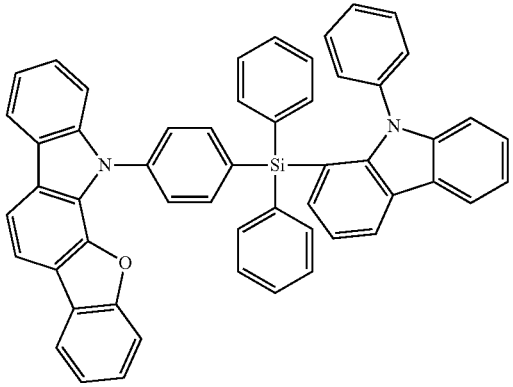
214
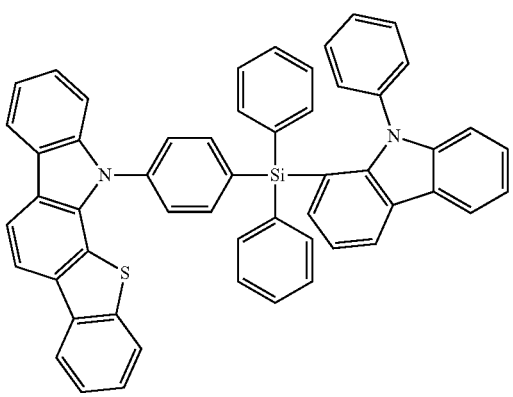
215
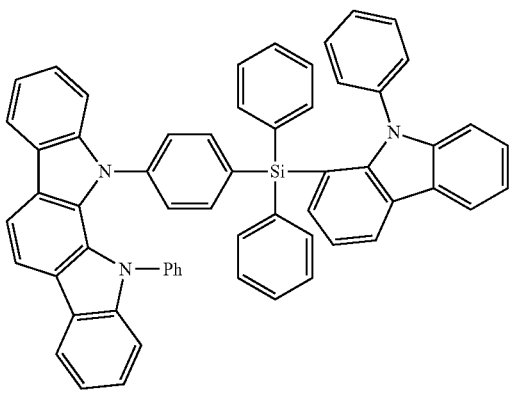
216
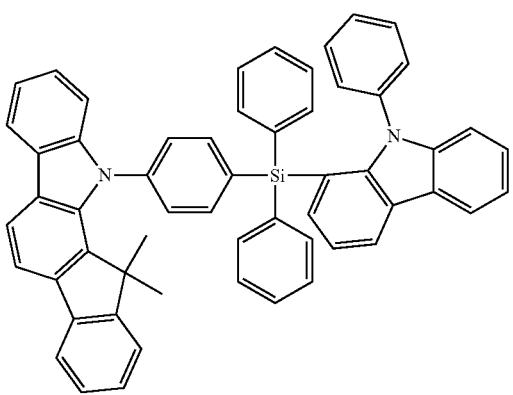

217
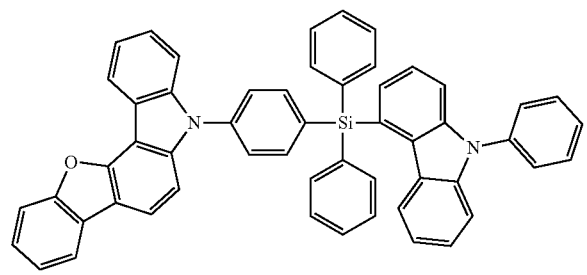
218
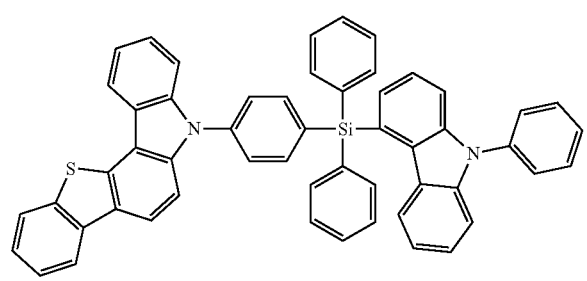
219
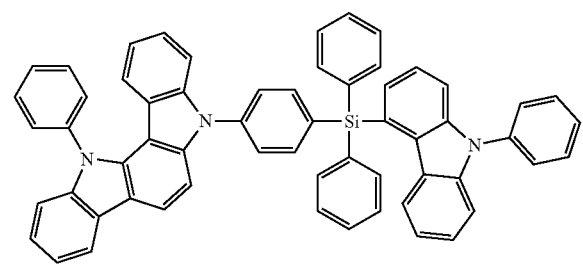
220
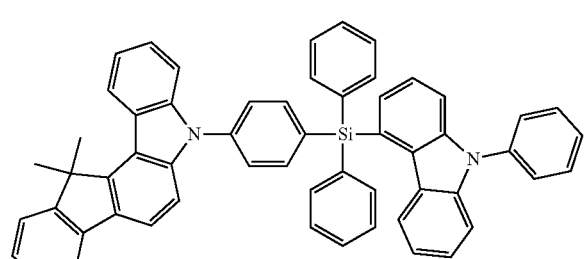
221
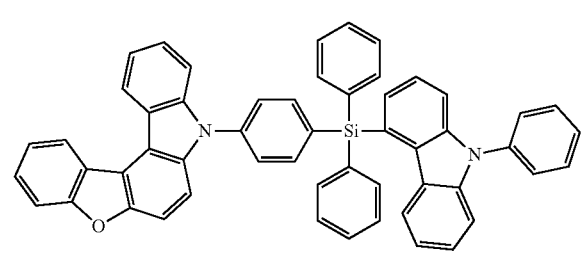
222
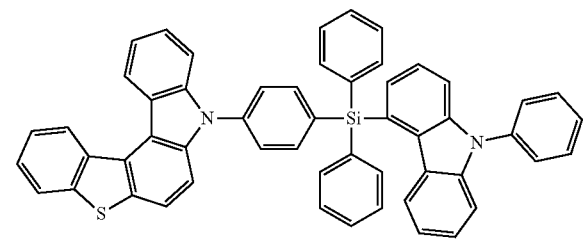
223
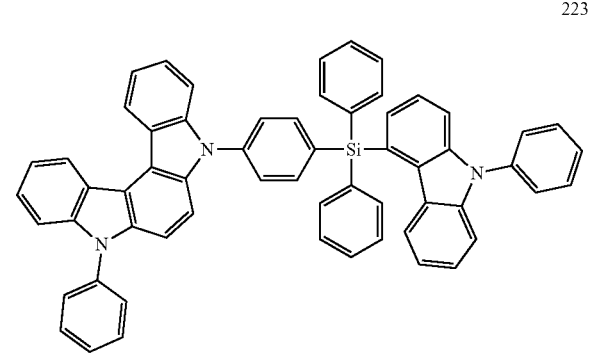
224
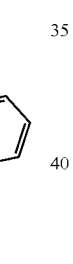
225
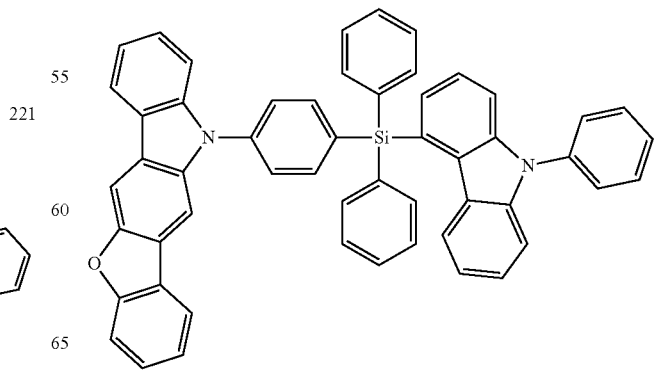

226
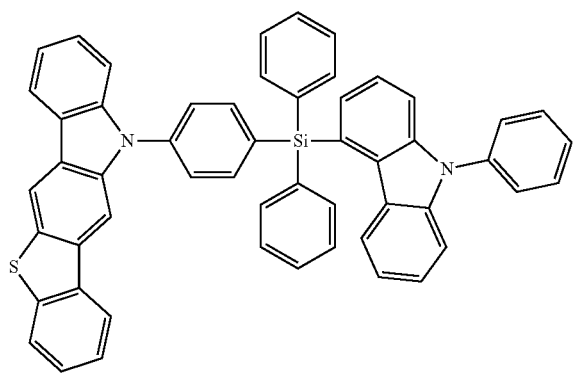
227
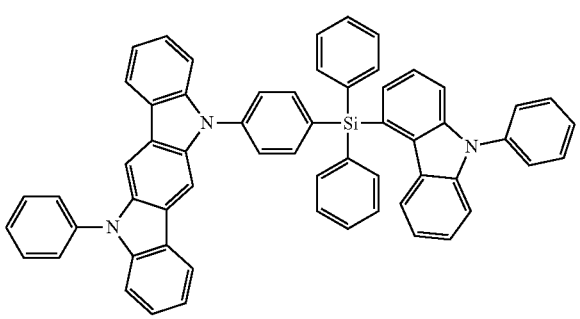
228
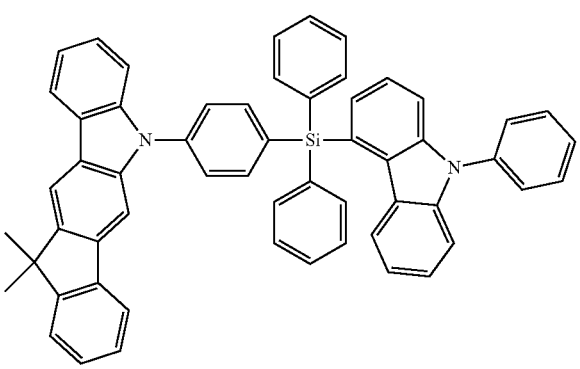
229
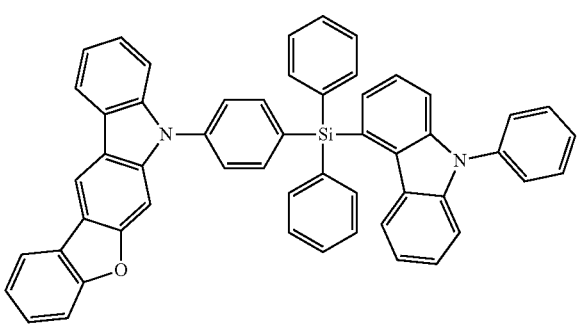
230
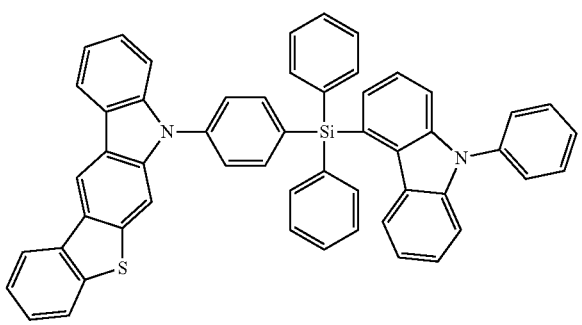
231
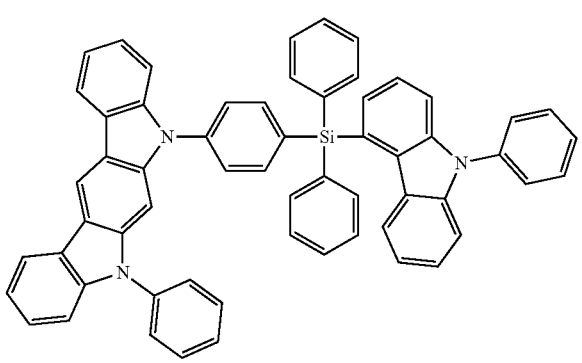
232
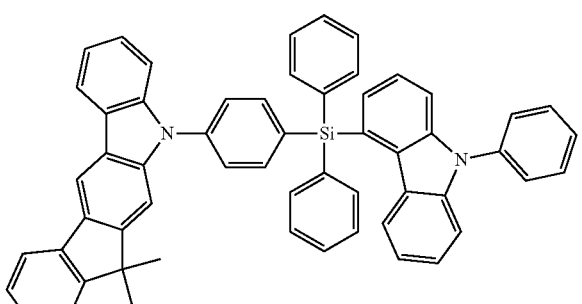
233
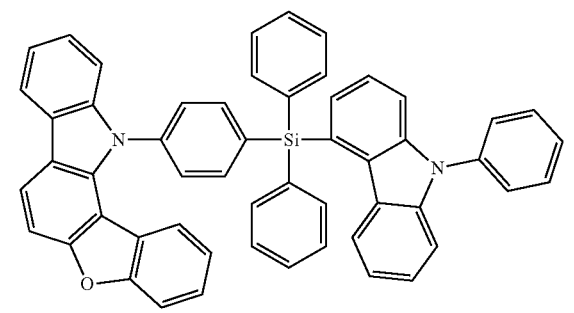

873
-continued
234
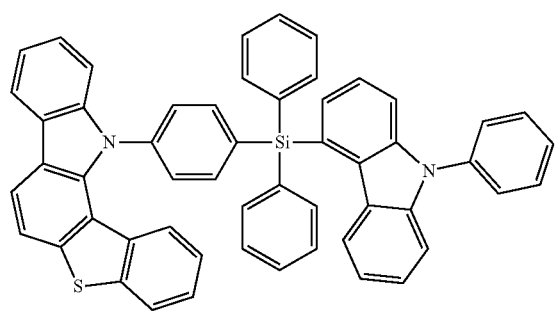
235
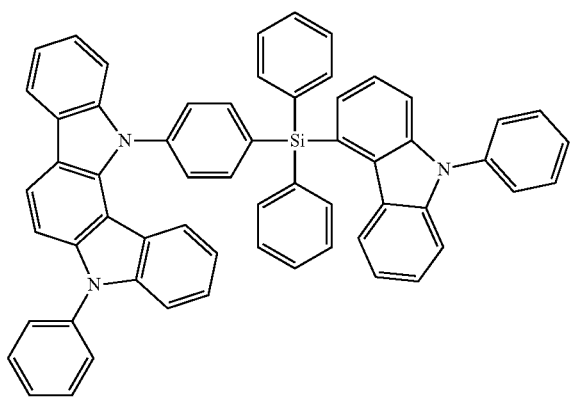
236
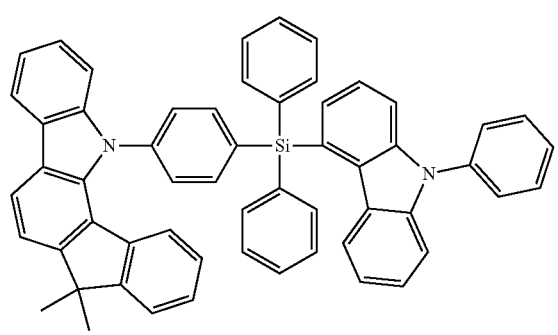
237
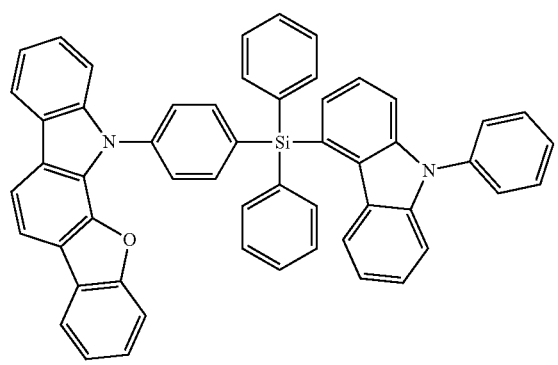
874
-continued
238
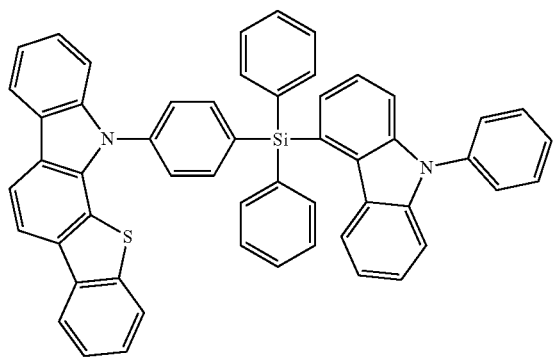
239
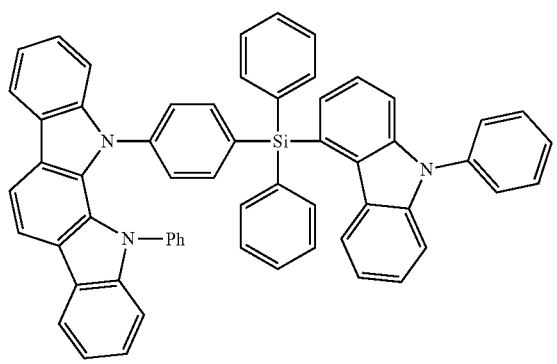
240
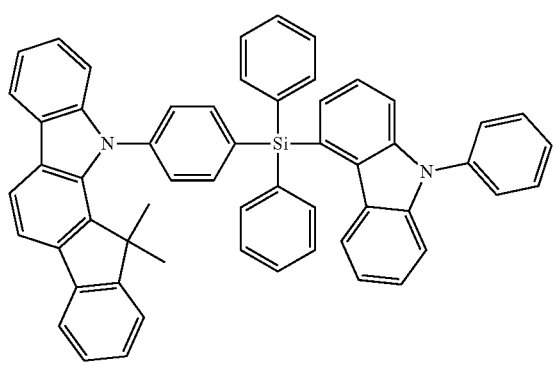
241
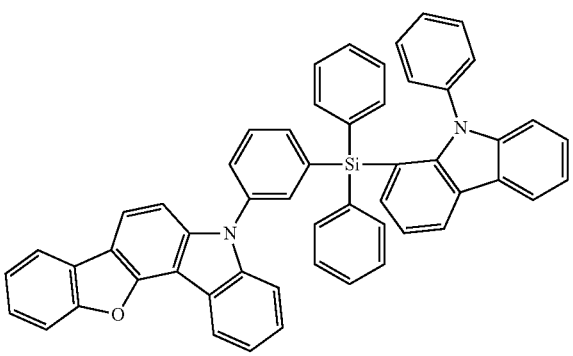

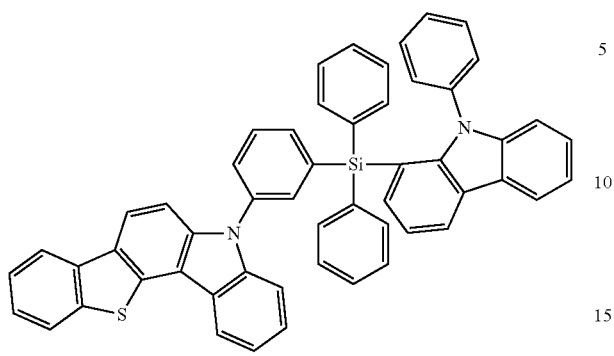
242
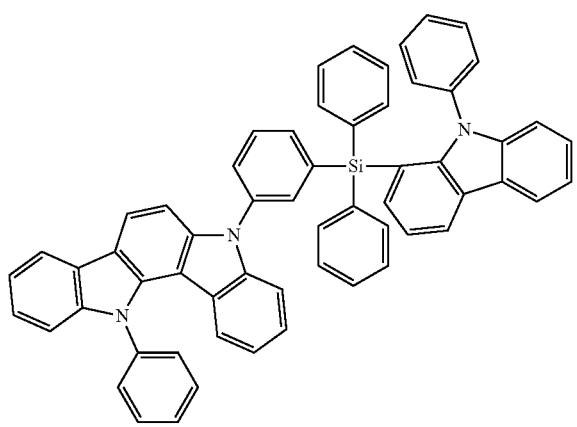
243
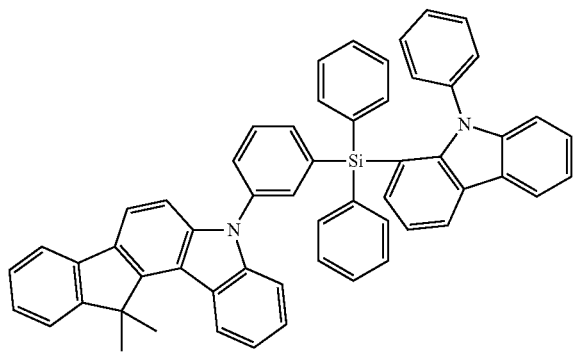
244
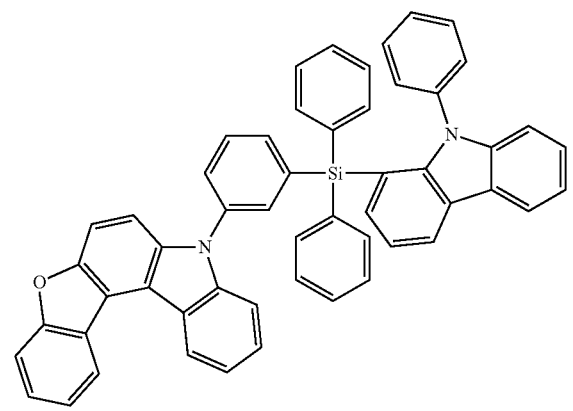
245
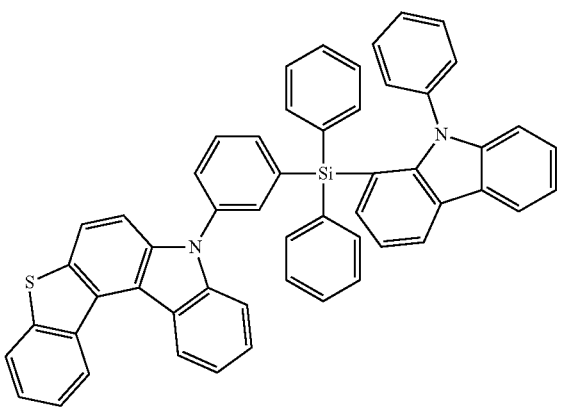
246
247
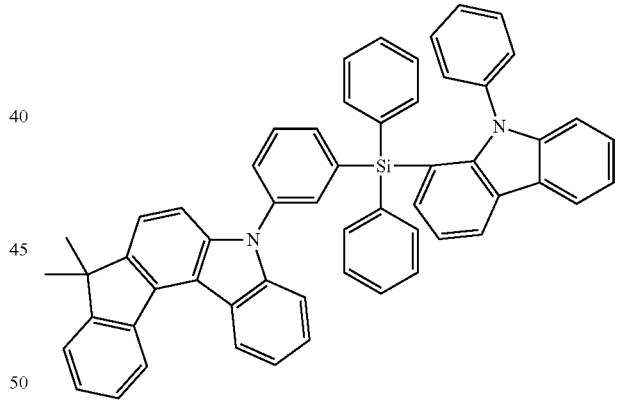
248
249

250
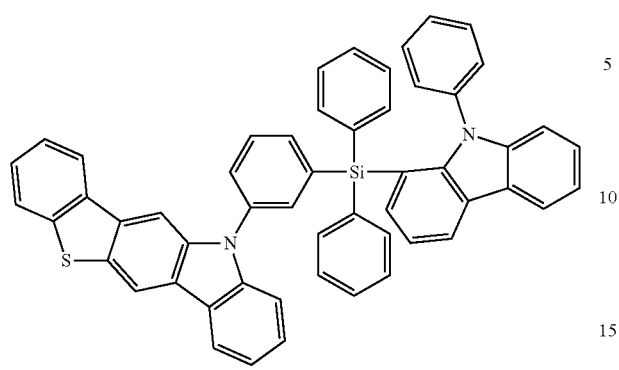
251
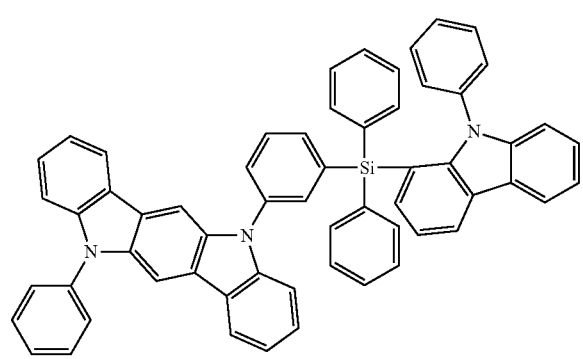
252
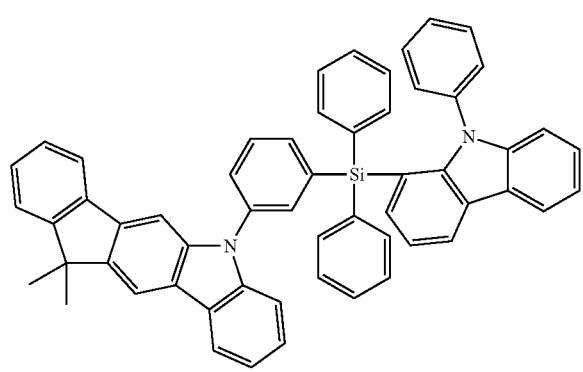
253
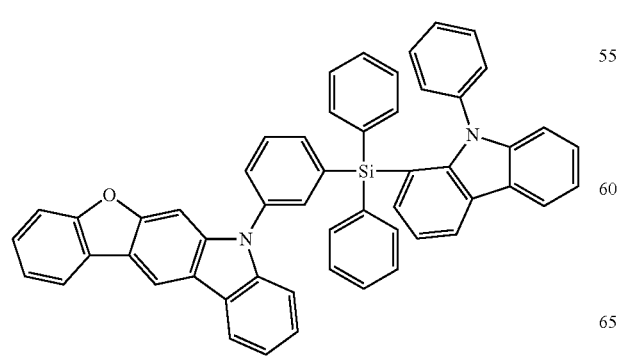
254
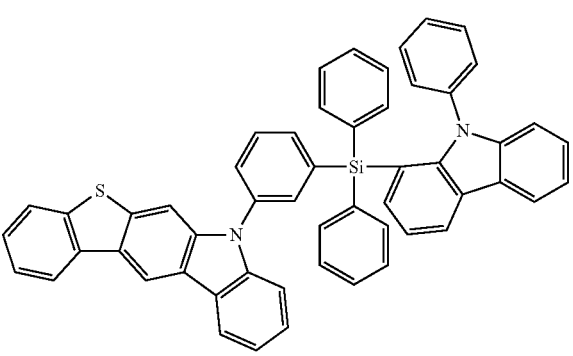
255
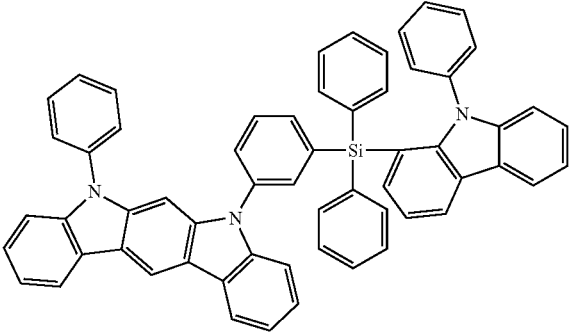
256
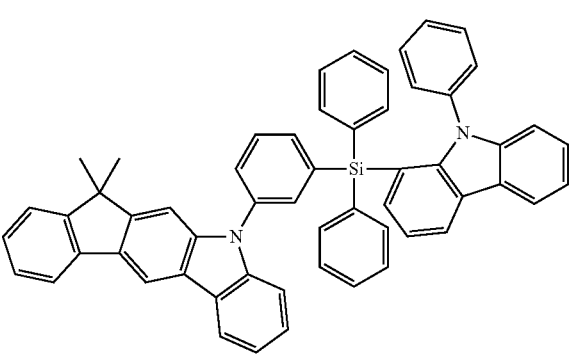
257
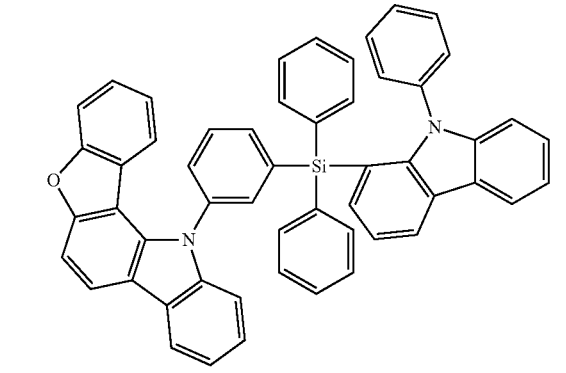

-continued
258
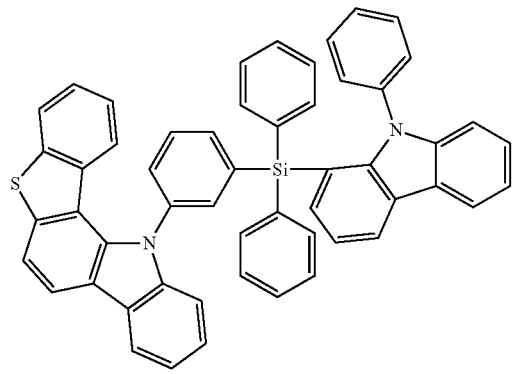
259
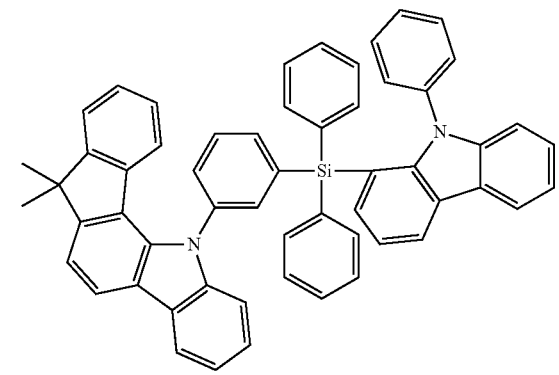
260
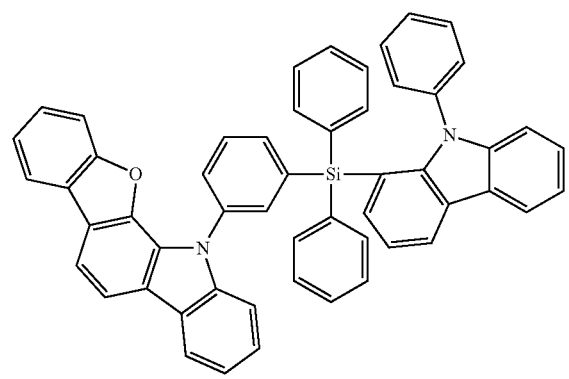
261
-continued
262
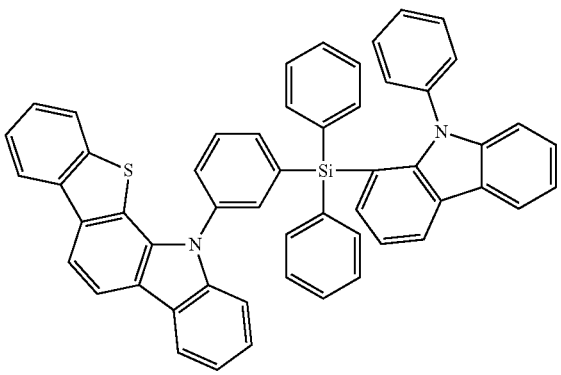

-continued
266
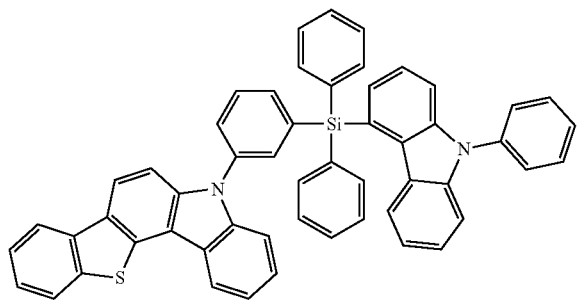
267
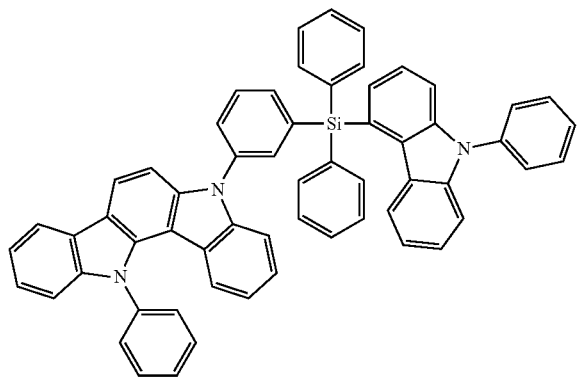
268
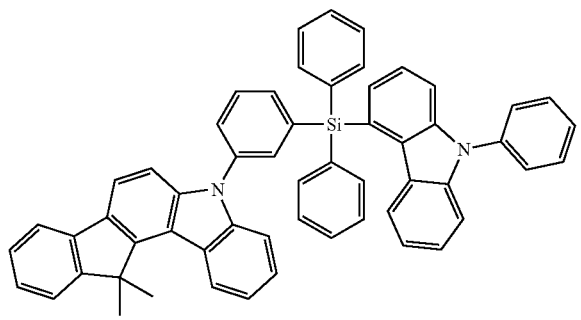
269
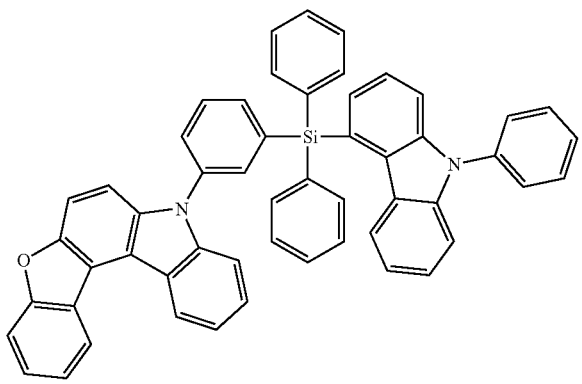
-continued
270
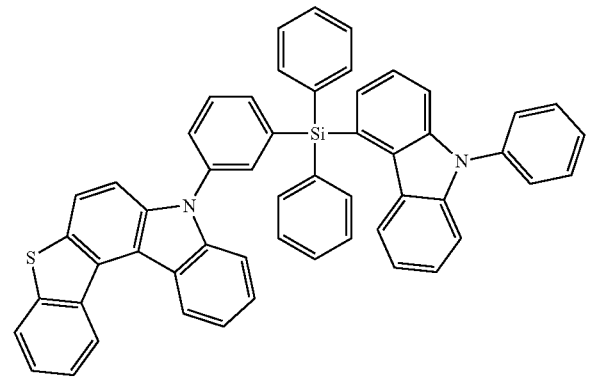
271
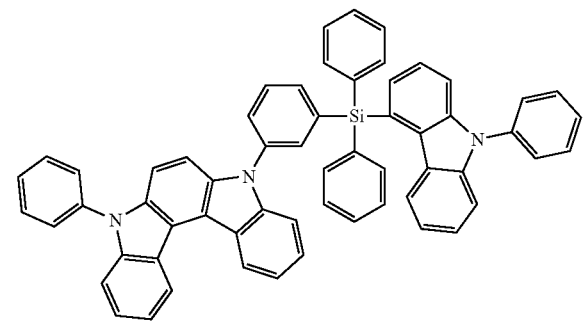
272
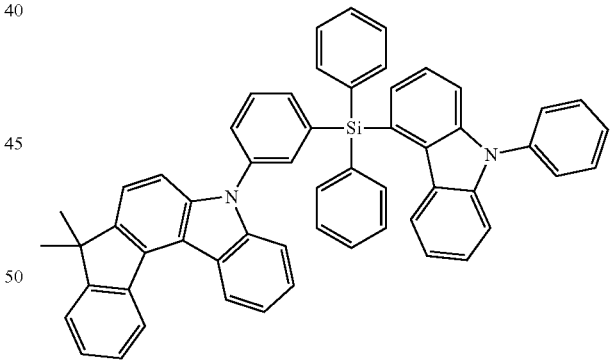
273
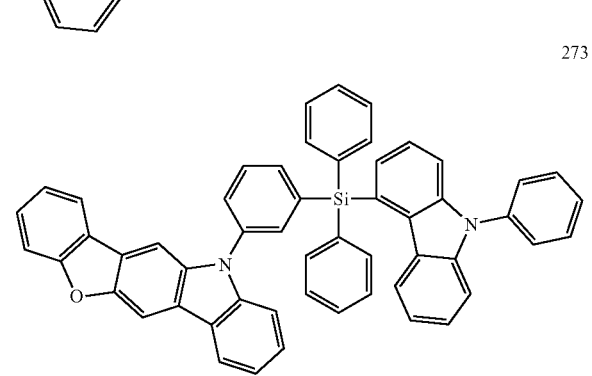

274
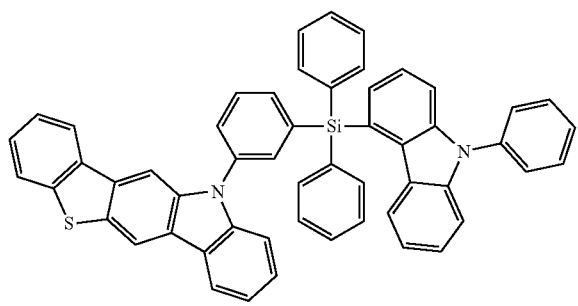
275
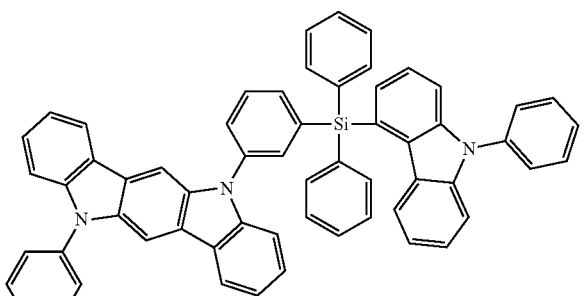
276
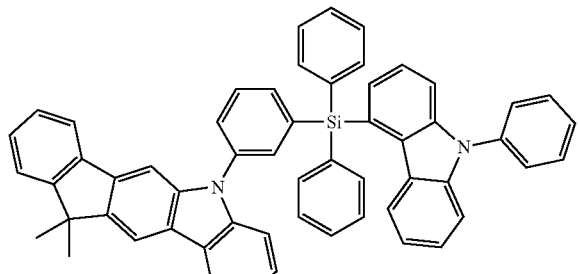
277
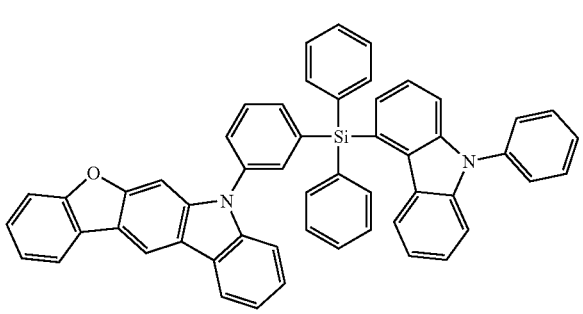
278
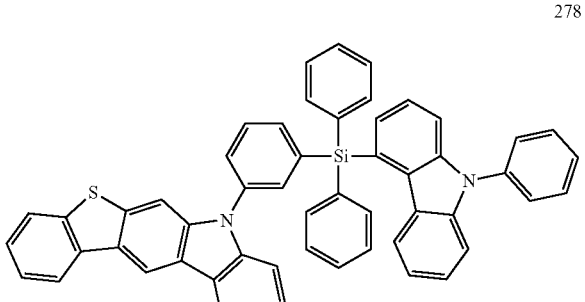
279
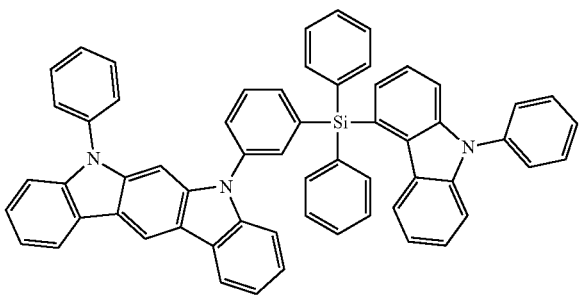
280
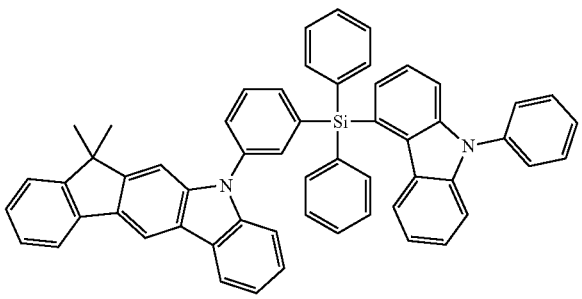
281
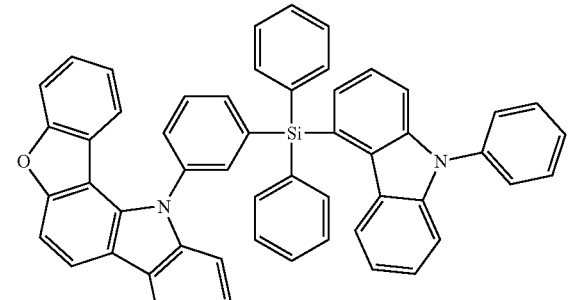
282
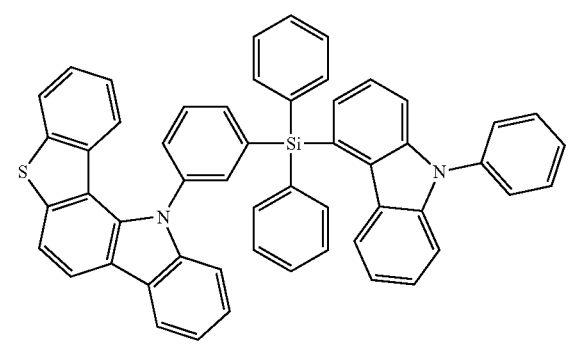

283
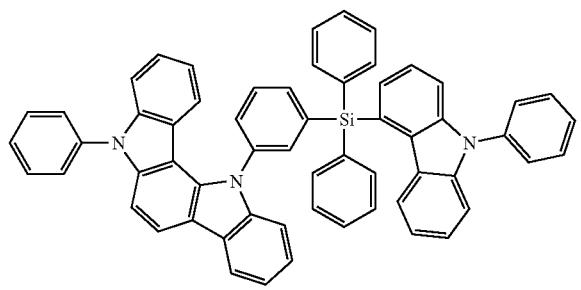
284
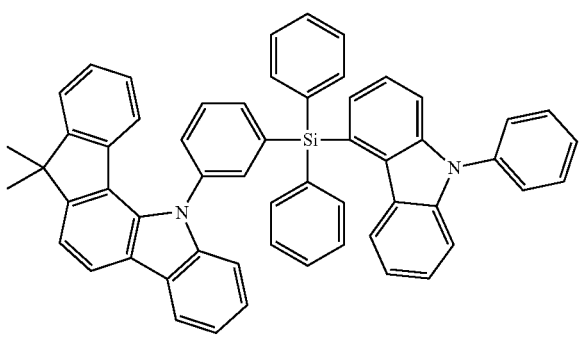
285
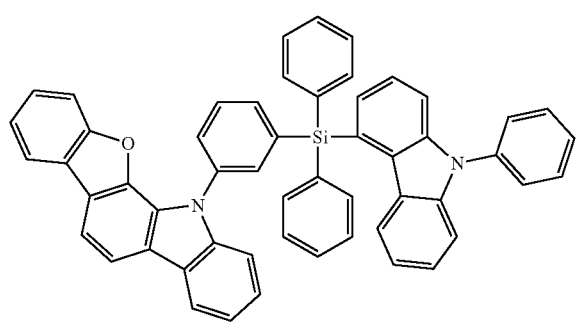
286
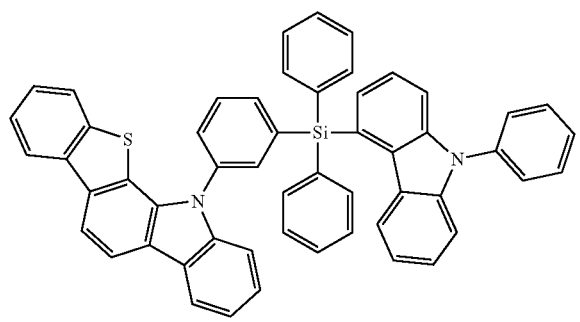
287
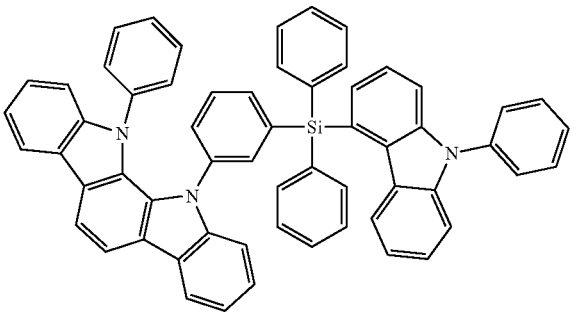
288
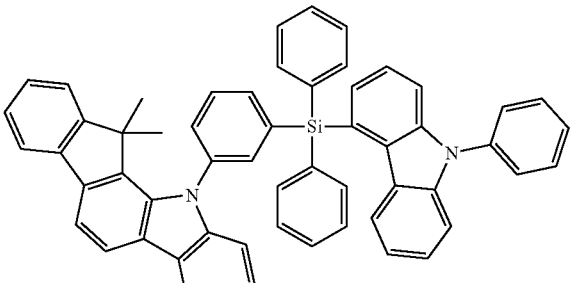
289
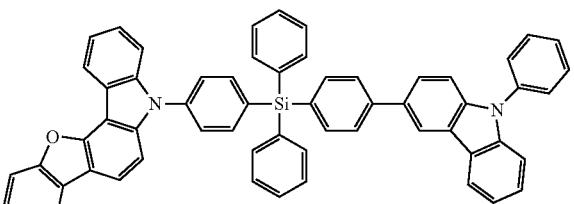
290
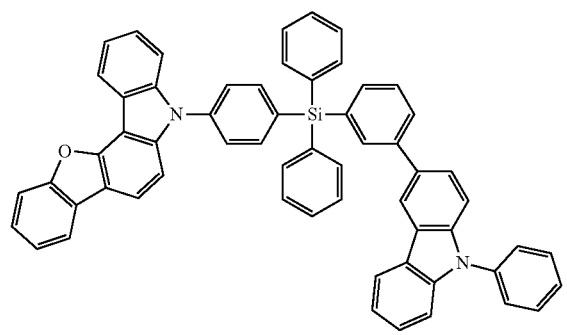
291
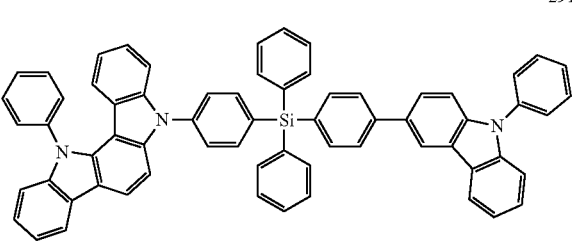

292
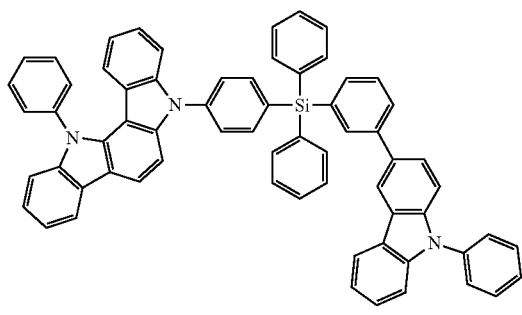
293
297
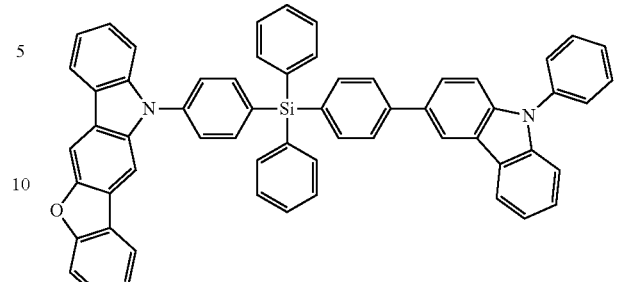
294
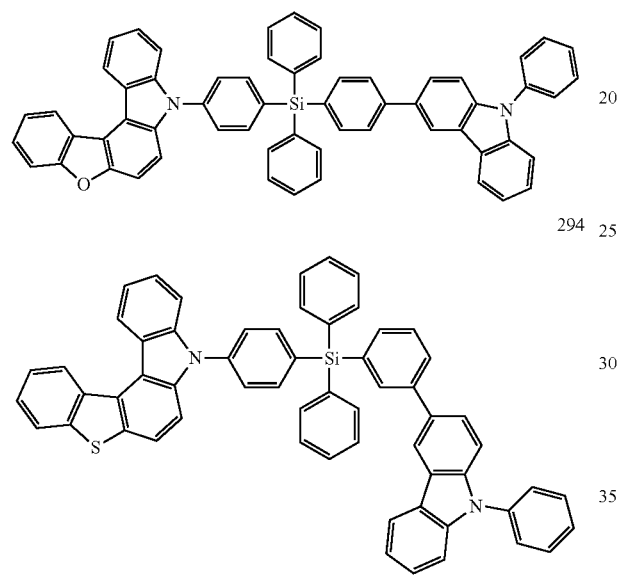
295
298
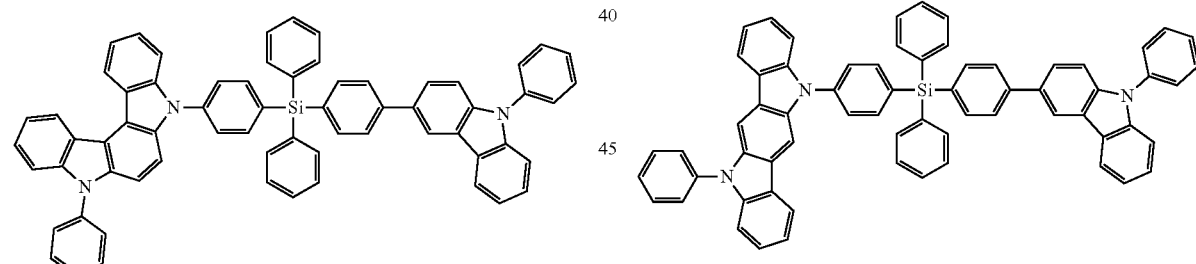
296
299
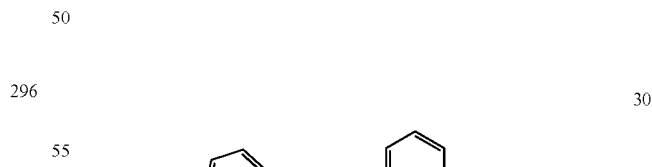
300
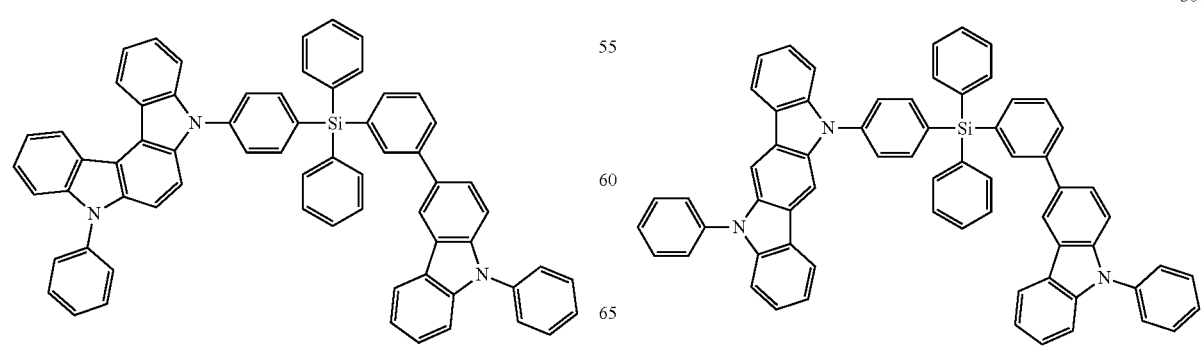

301
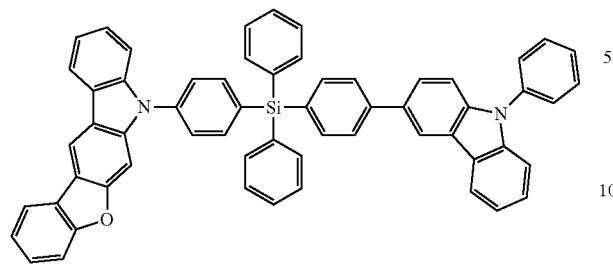
302
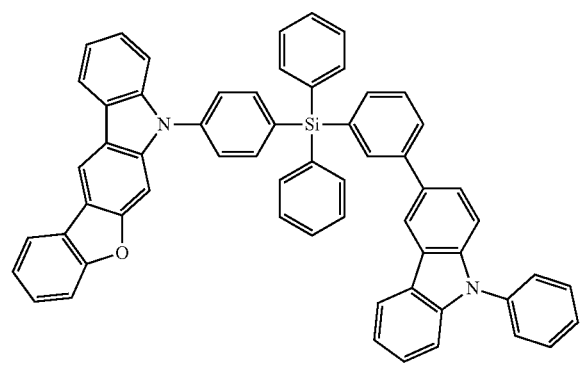
303
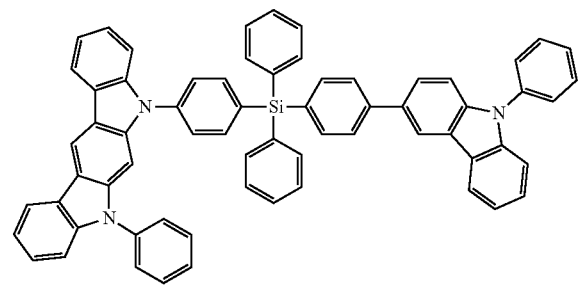
304
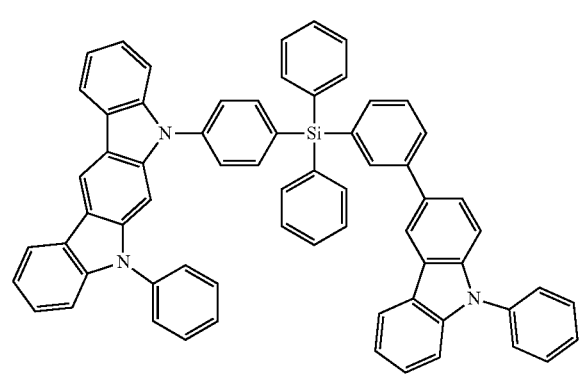
305
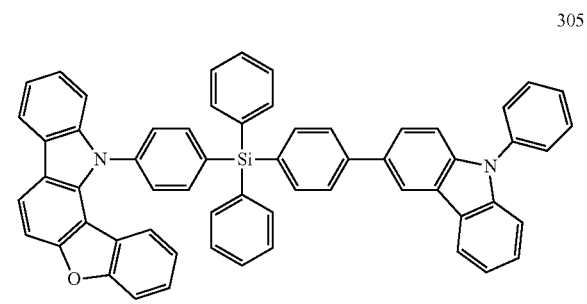
306
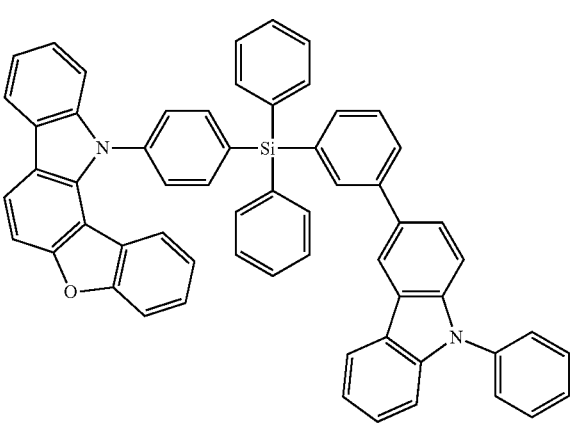
307
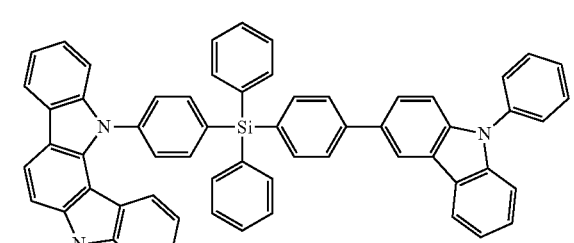
308
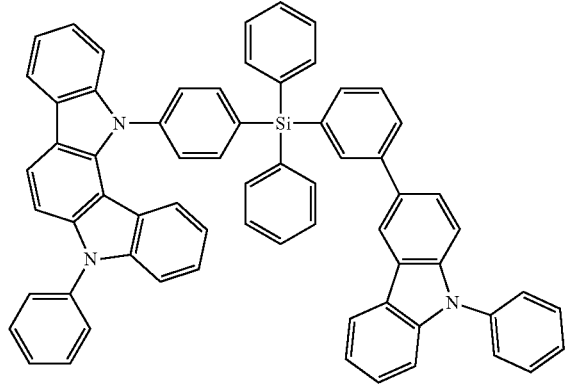
309
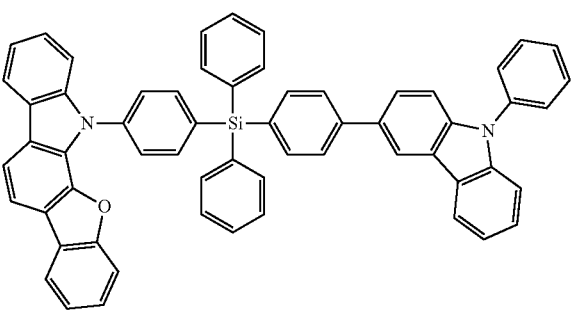

-continued
310
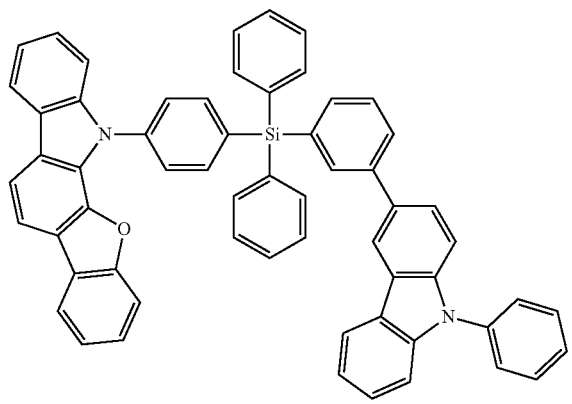
311
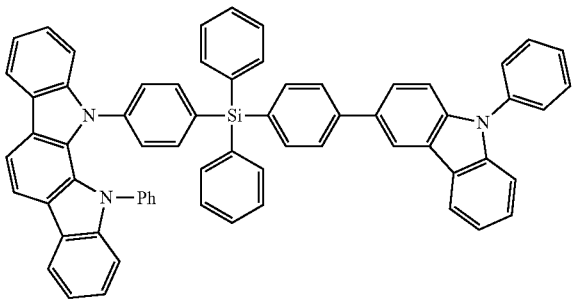
312
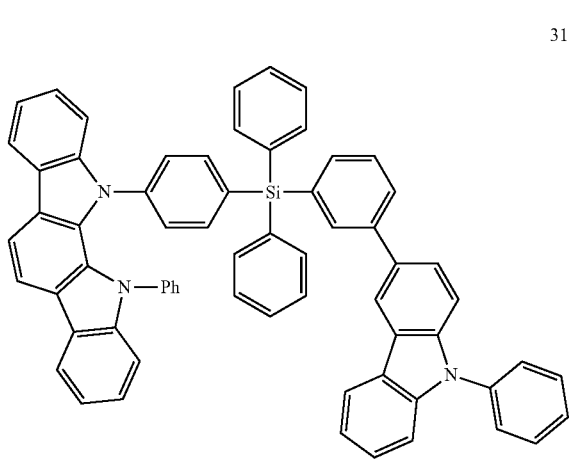
313
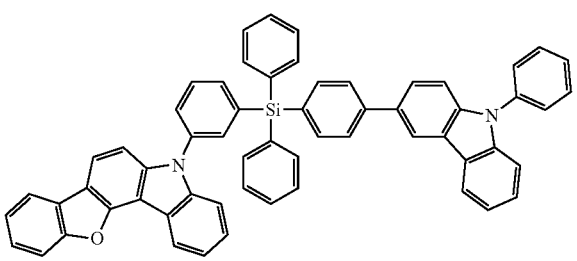
-continued
314
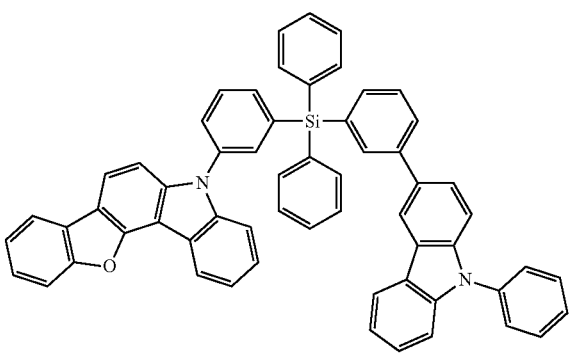
315
316
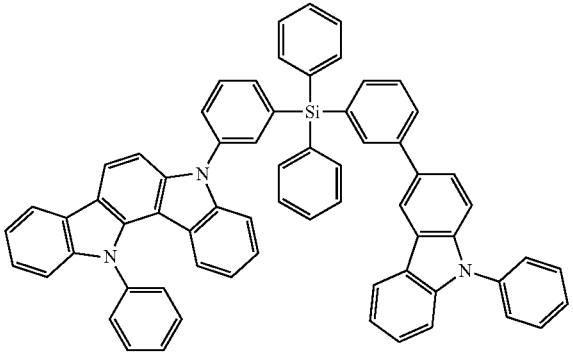
317
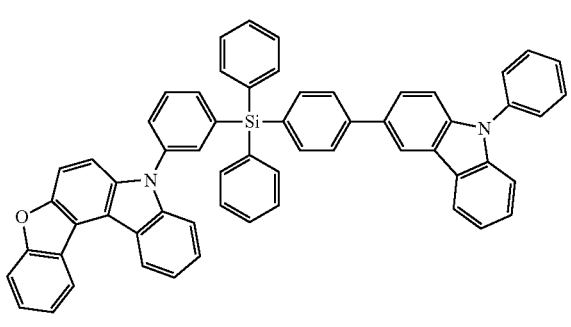

-continued
318
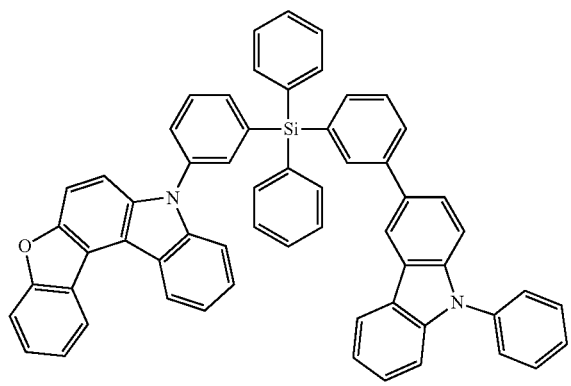
319
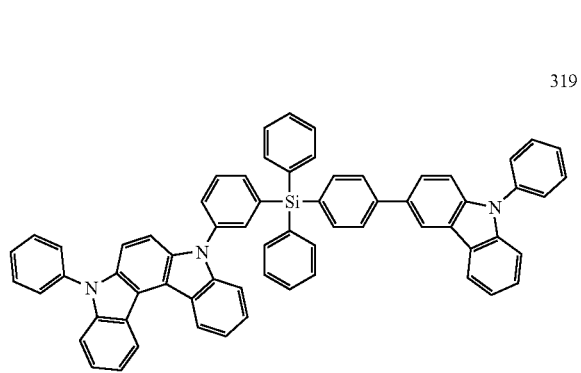
320
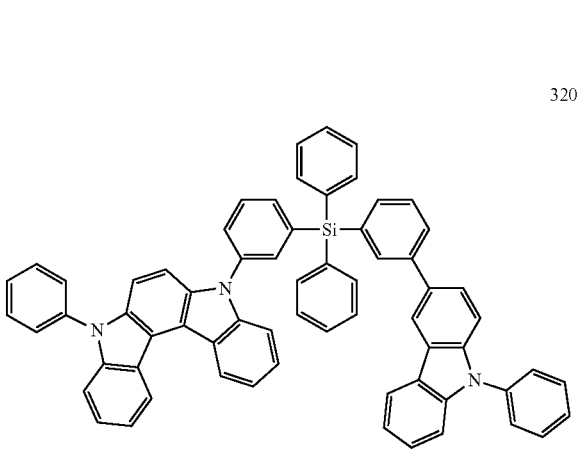
321
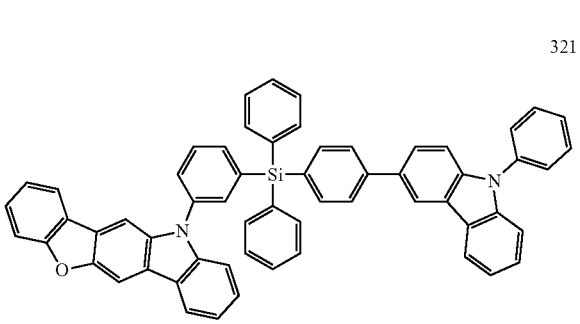
-continued
322
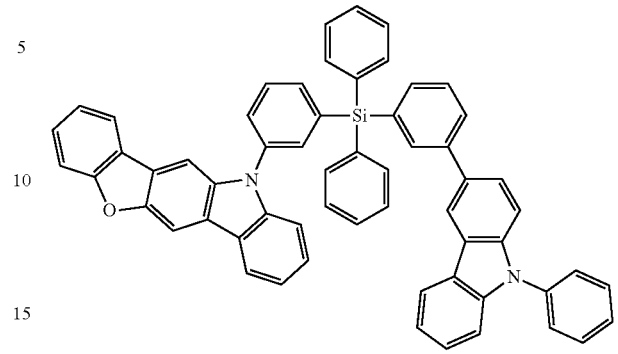
323
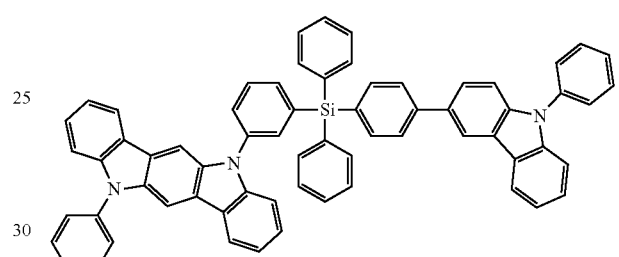
324
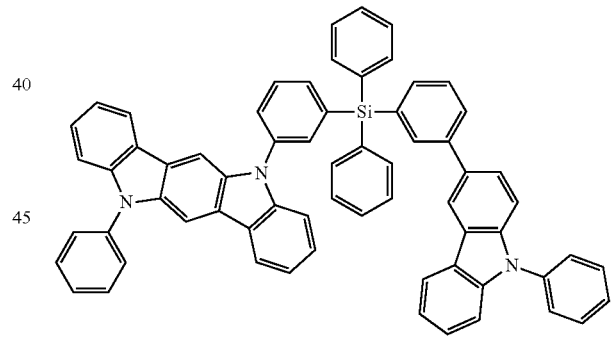
325
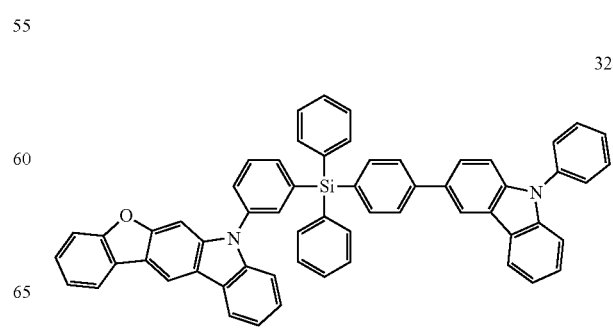

-continued
326
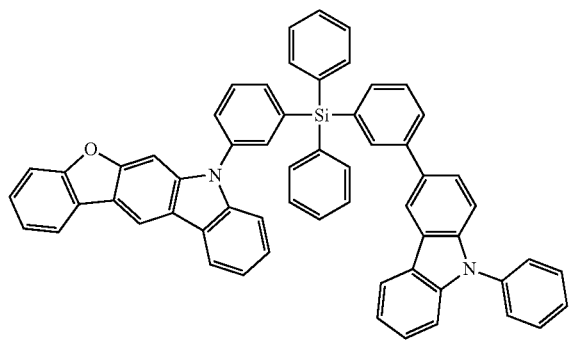
327
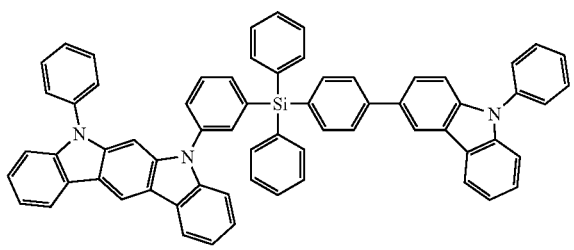
328
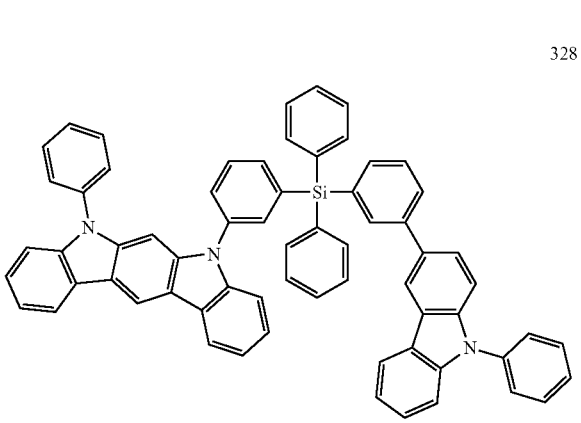
329
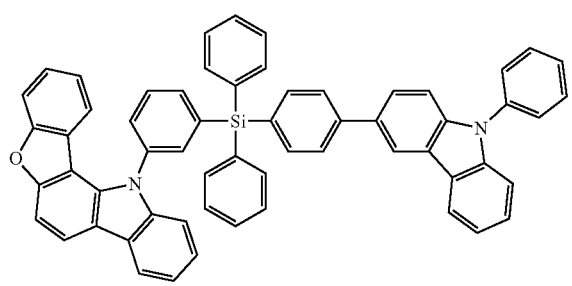
-continued
330
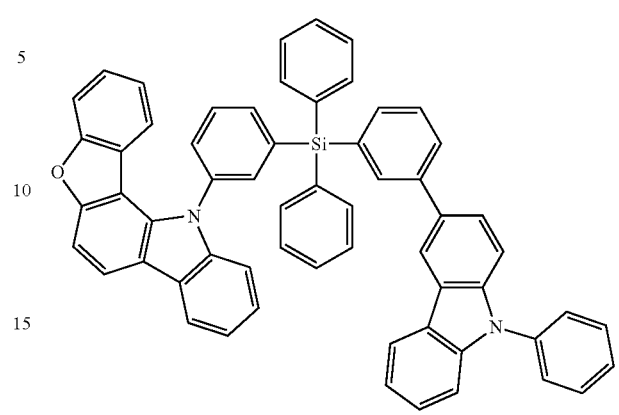
331
332
333
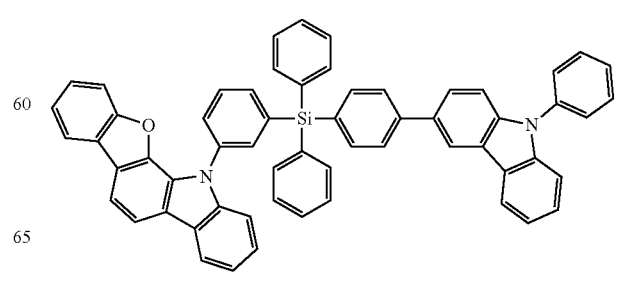

334
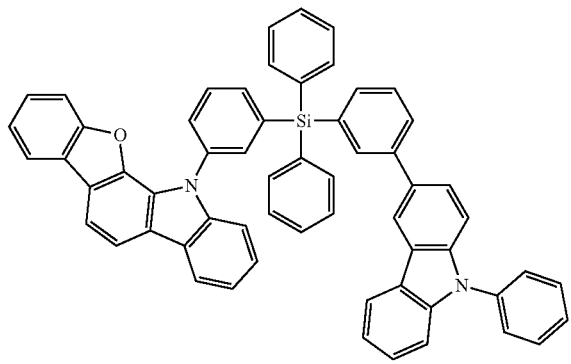
335
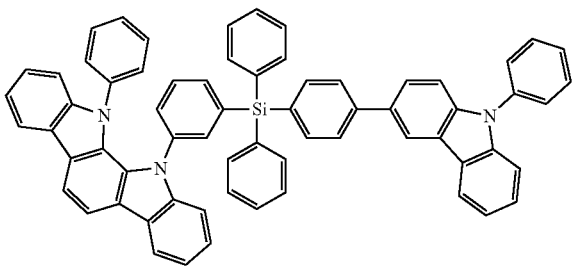
336
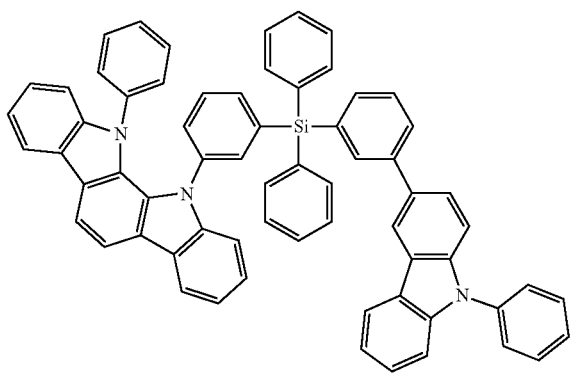
337
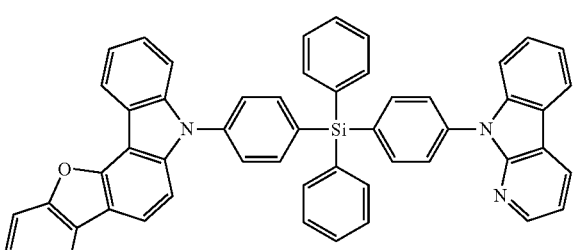
338
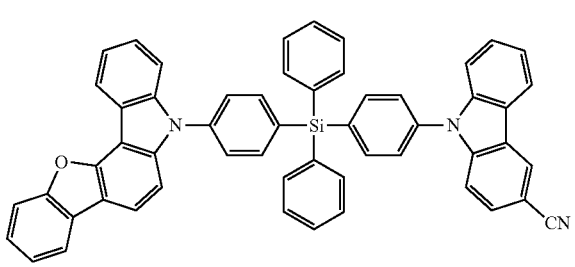
339
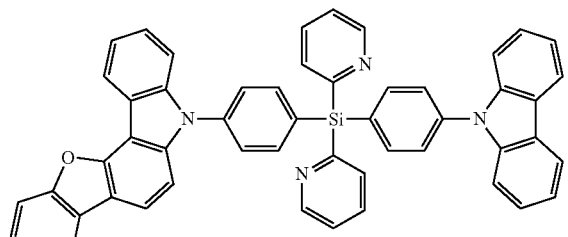
340
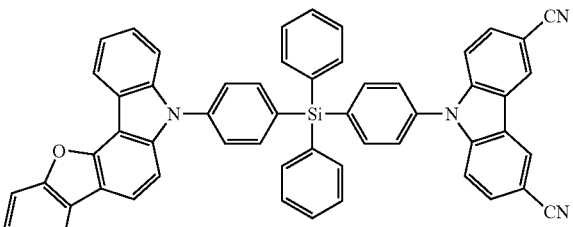
341
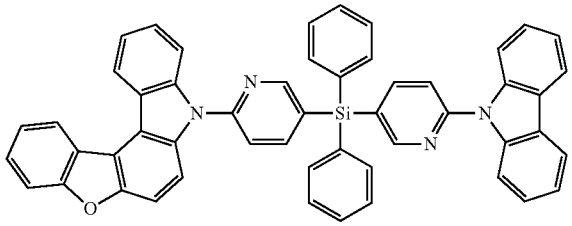
342
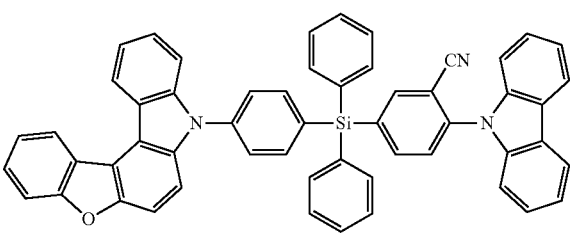
343
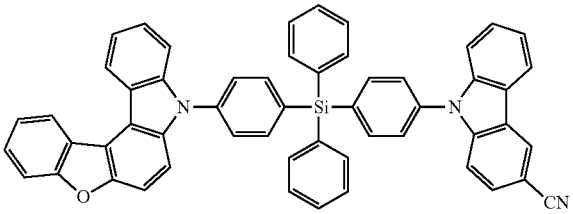
344
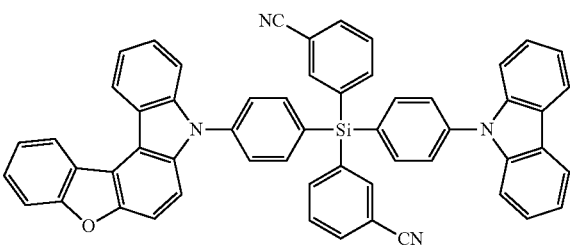

899
-continued
345
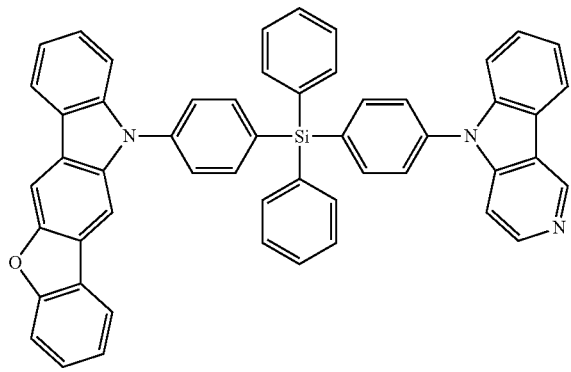
346
347
348
900
-continued
349
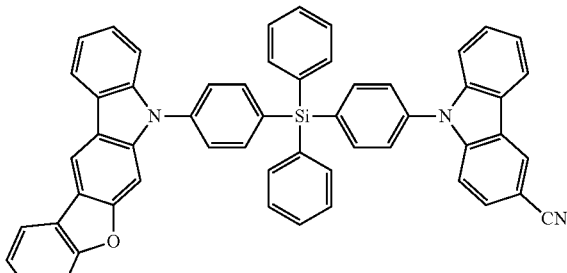
350
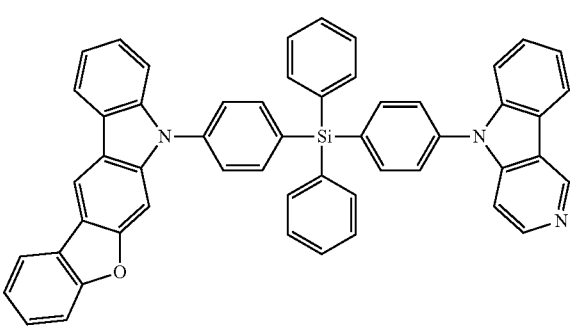
351
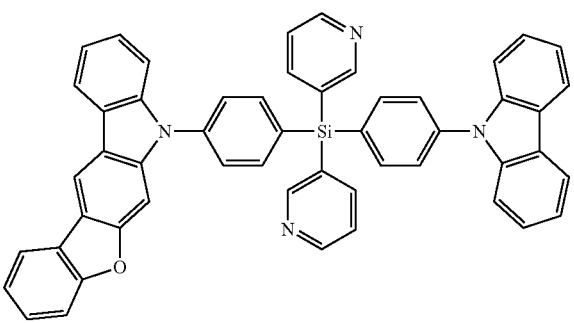
352
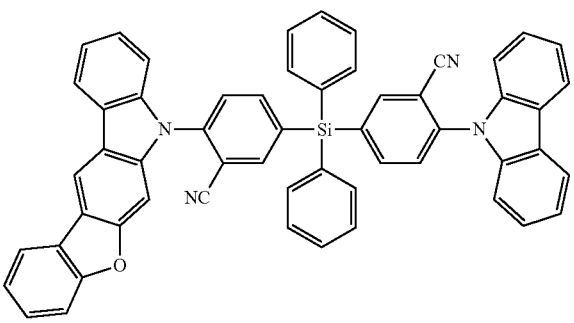

901
-continued
353
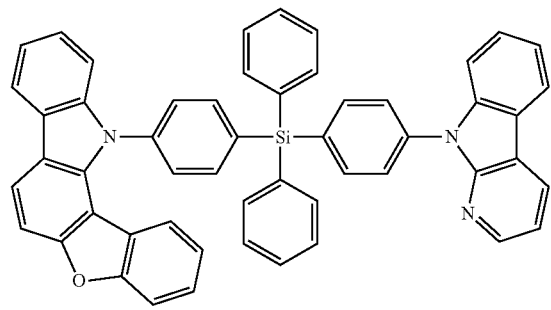
354
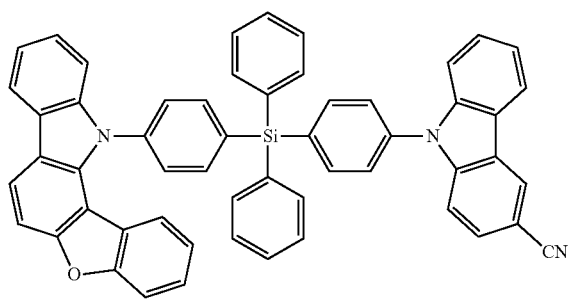
355
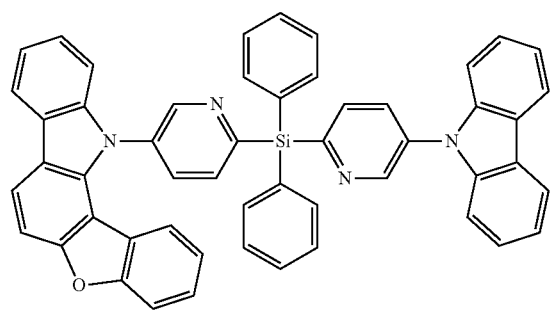
356
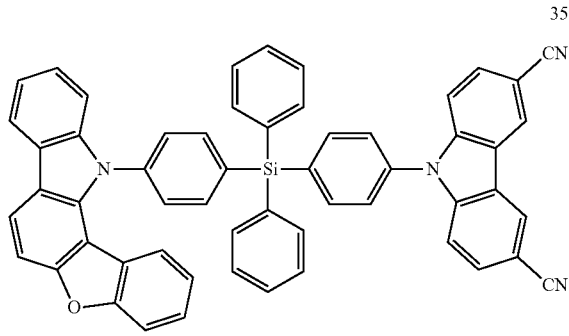
902
-continued
357
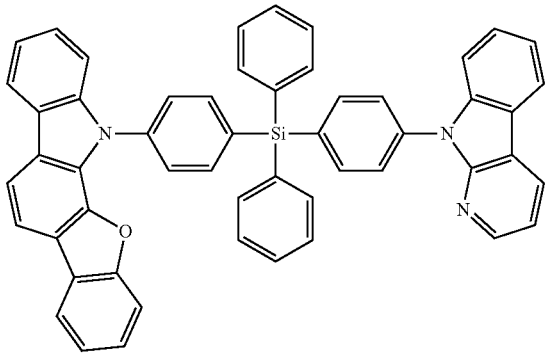
358
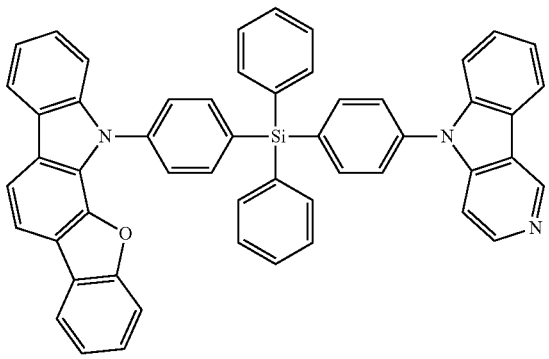
359
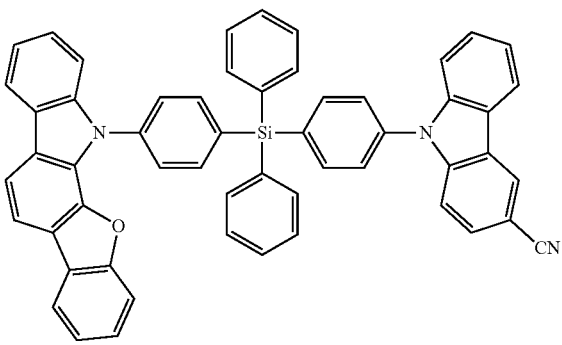
360
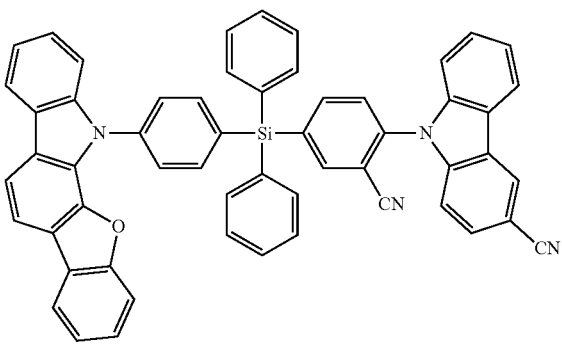

903
-continued
361
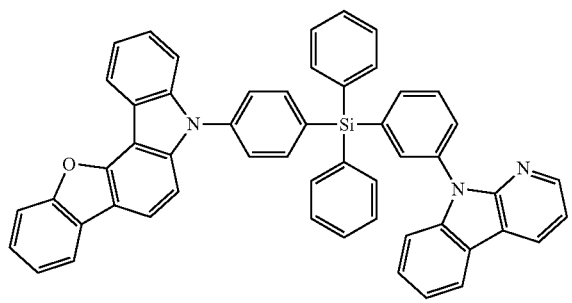
362
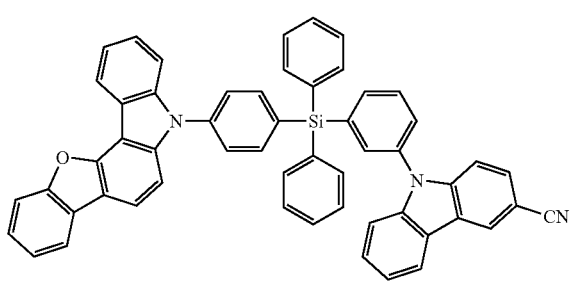
363
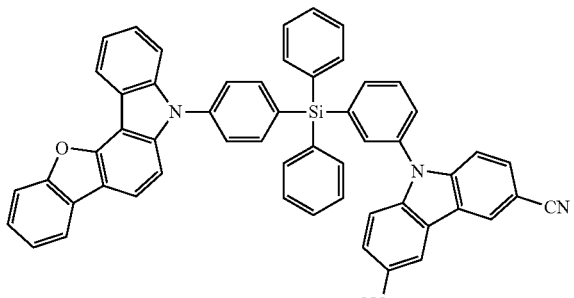
364
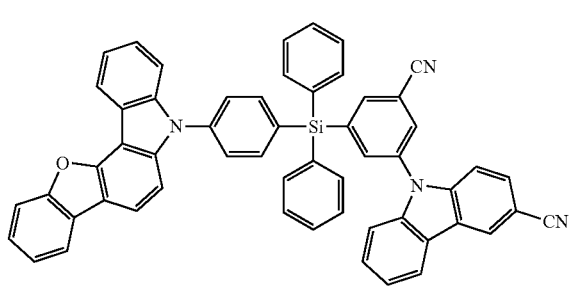
365
904
-continued
366
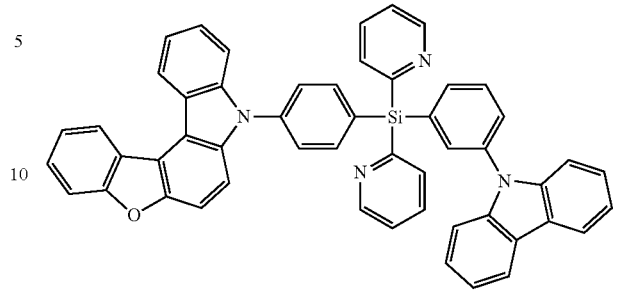
367
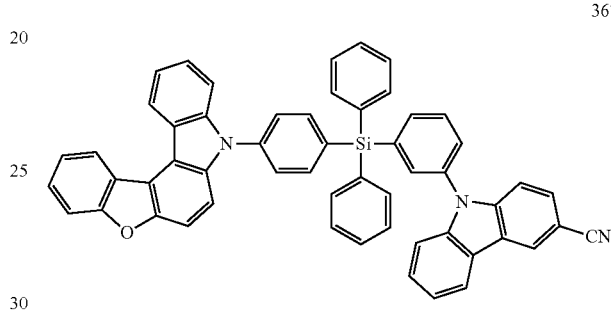
368
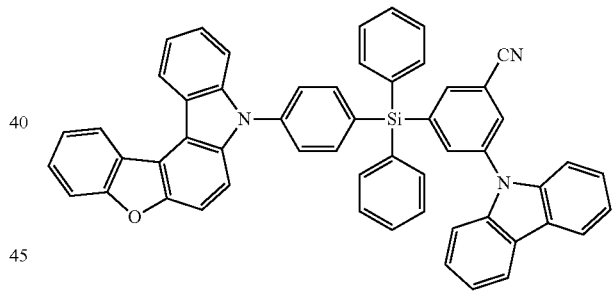
369
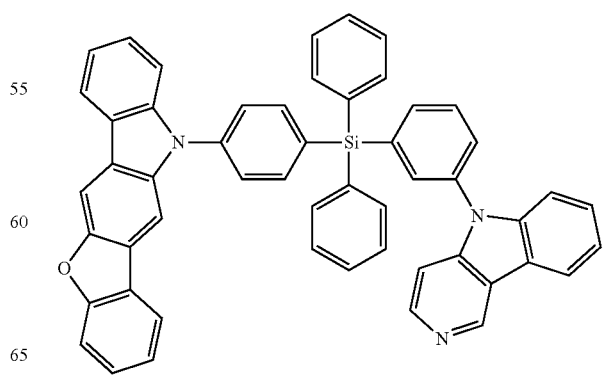

| 905 -continued | 906 -continued |
|---|---|
| 370 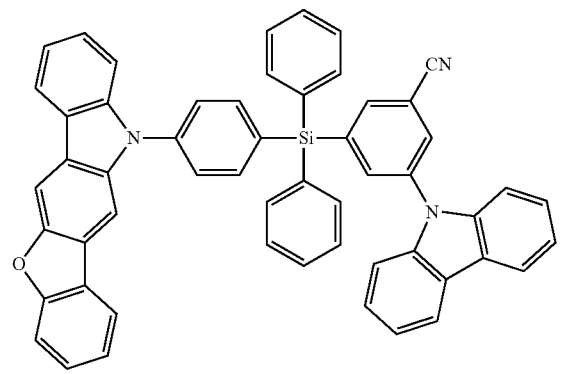 | 374 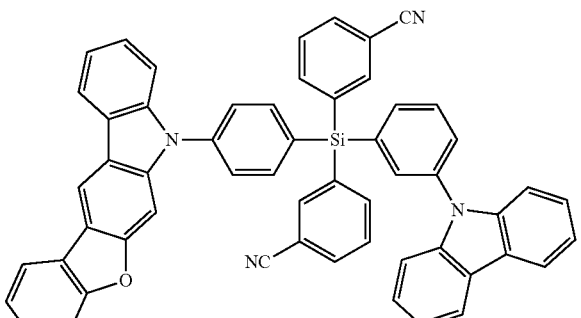 |
| 371 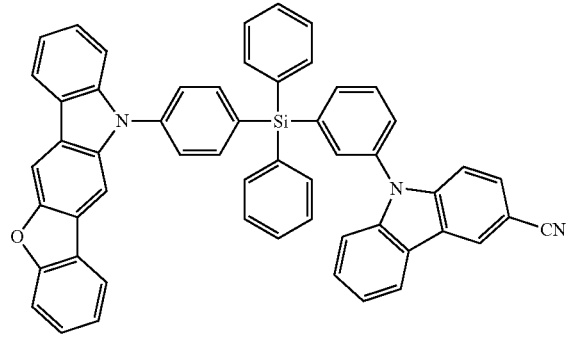 | 375 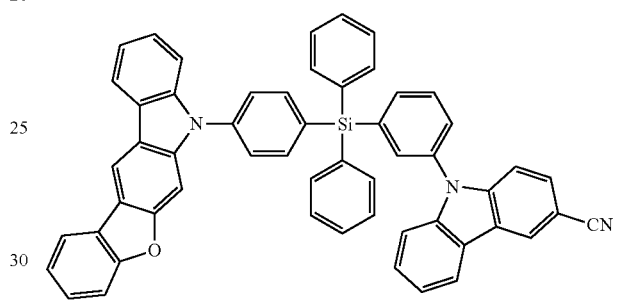 |
| 372 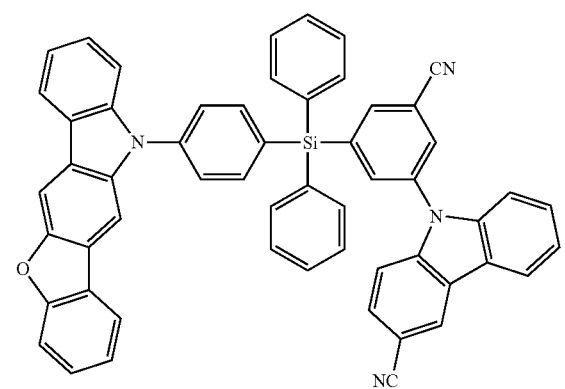 | 376 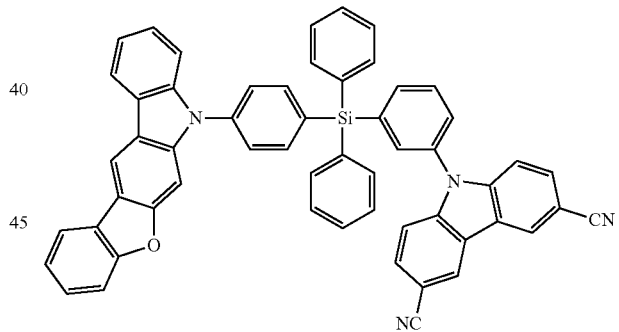 |
| 373 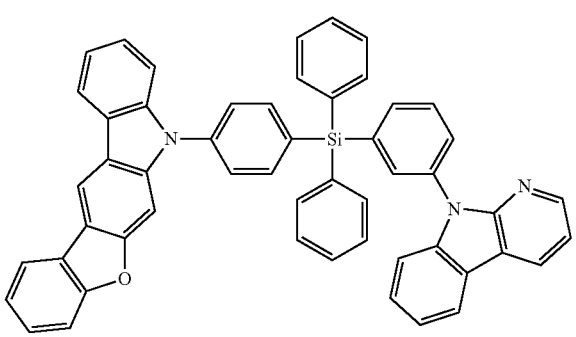 | 377 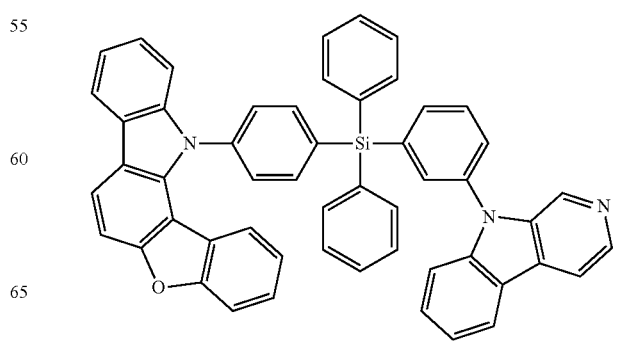 |

-continued
378
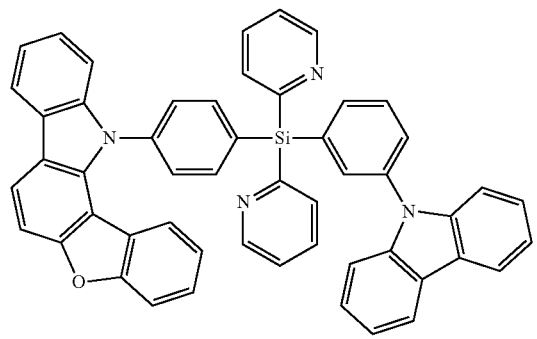
379
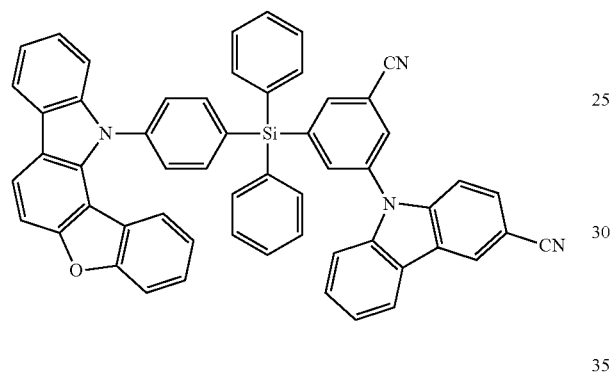
380
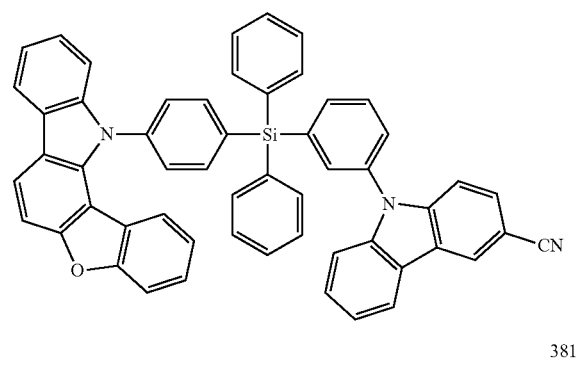
381
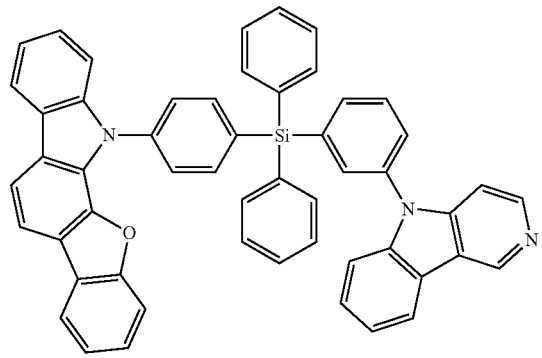
-continued
382
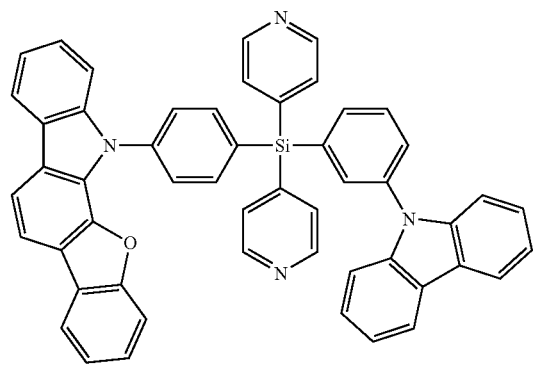
383
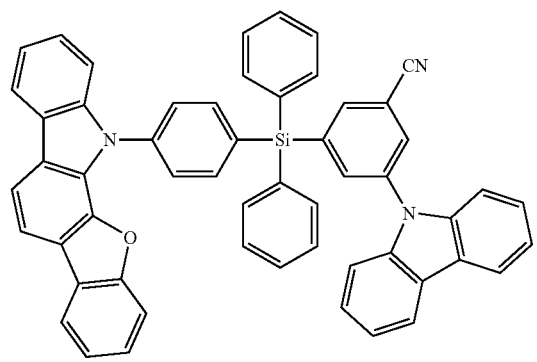
384
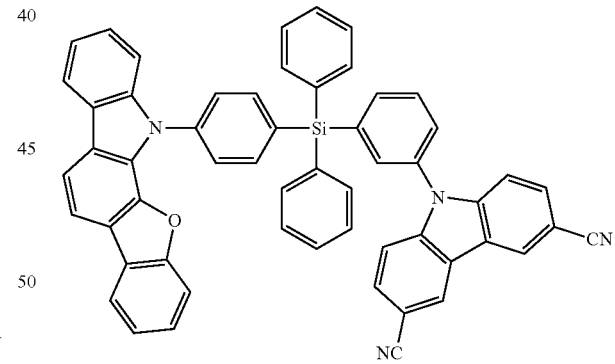
385
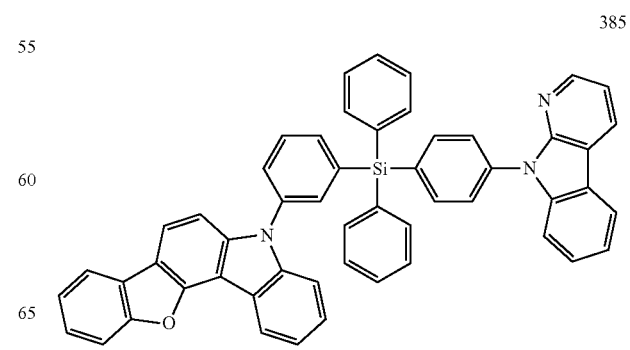

386
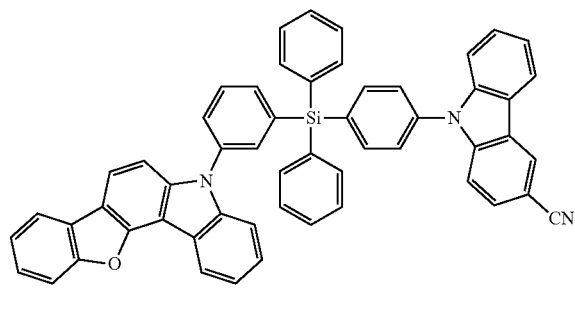
387
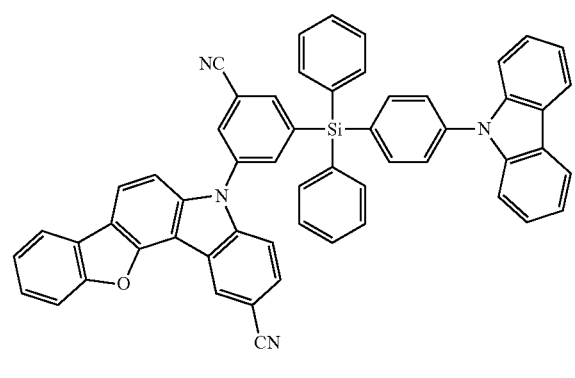
388
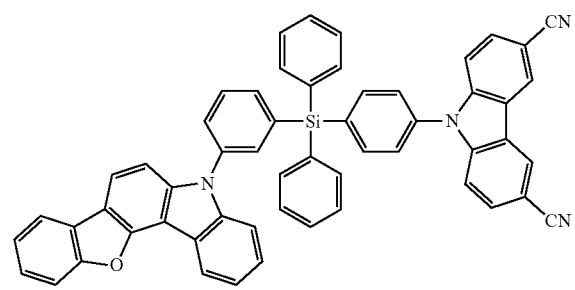
389
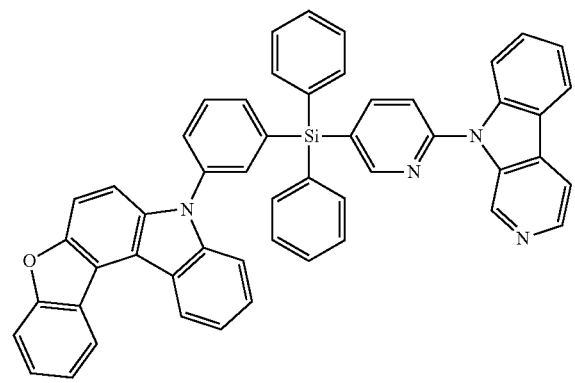
390
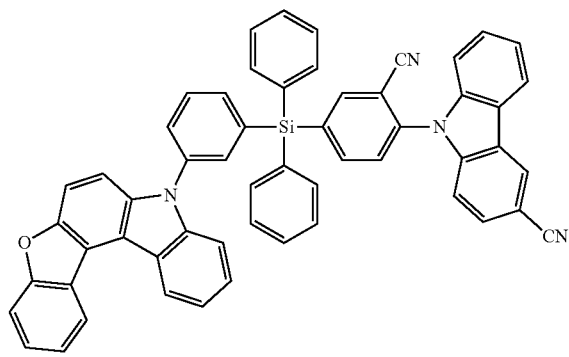
391
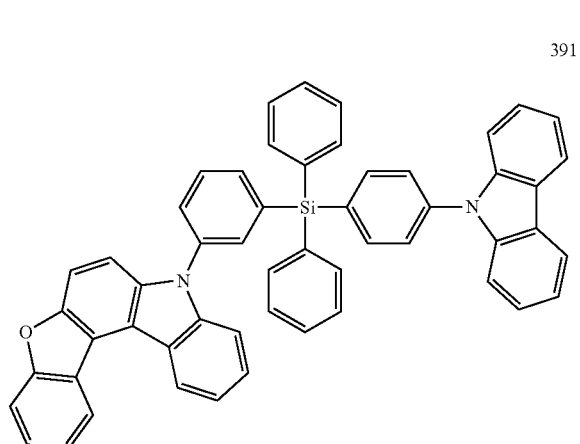
392
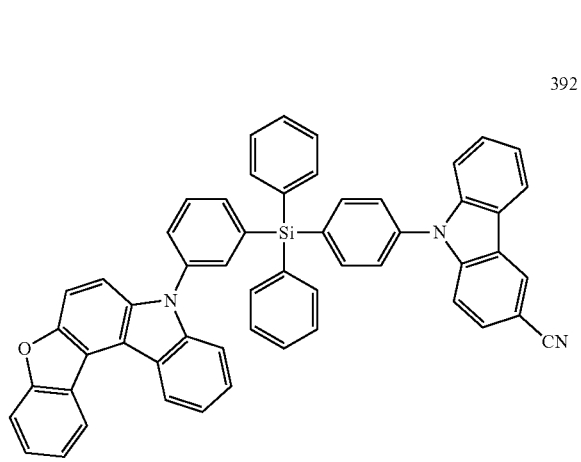
393
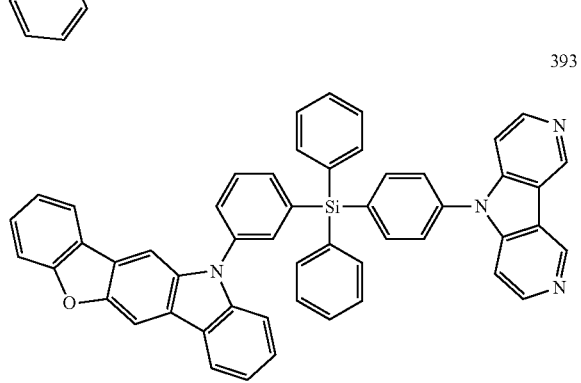

911
-continued
394
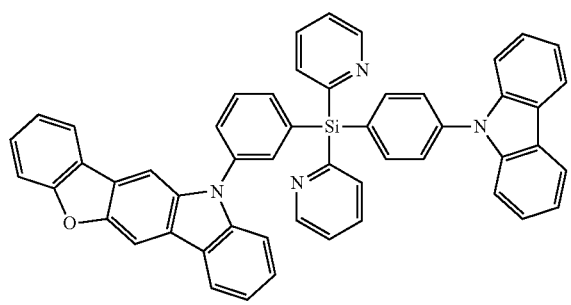
395
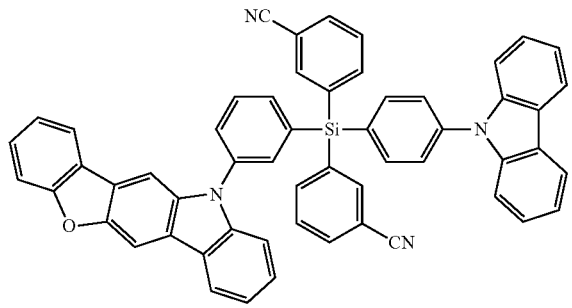
396
397
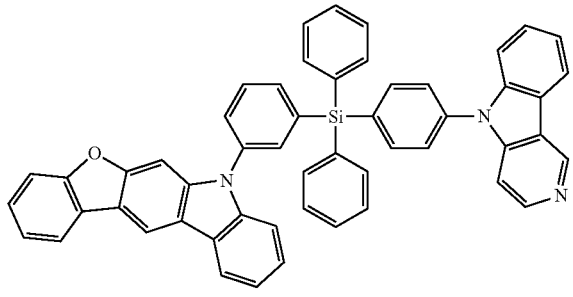
398
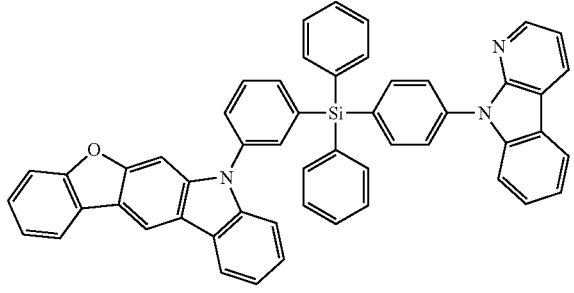
912
-continued
399
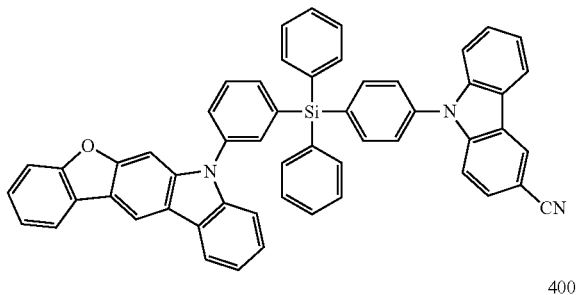
400
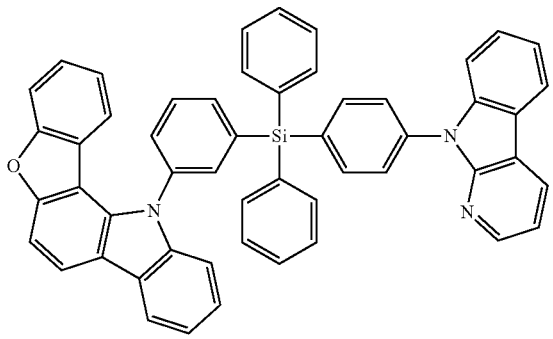
401
402
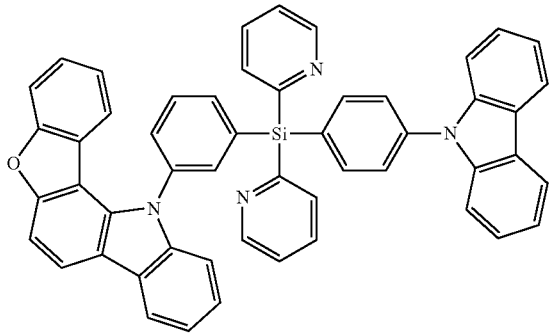
403
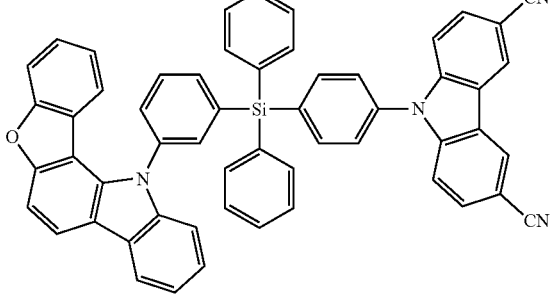

913
-continued
404
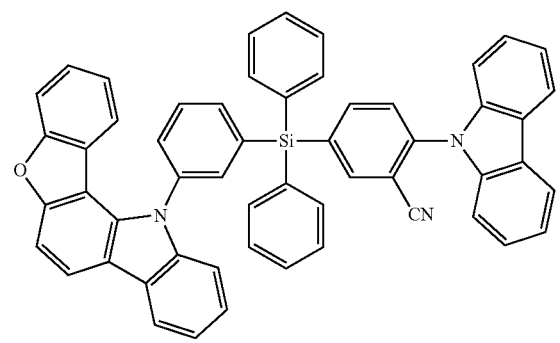
405
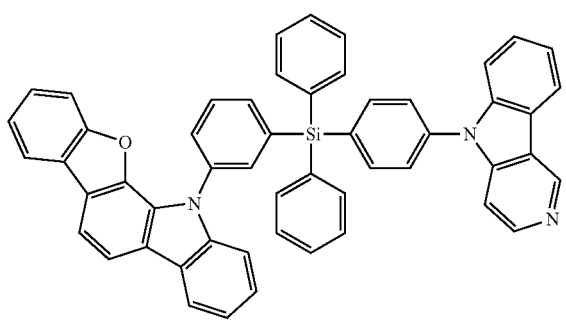
406
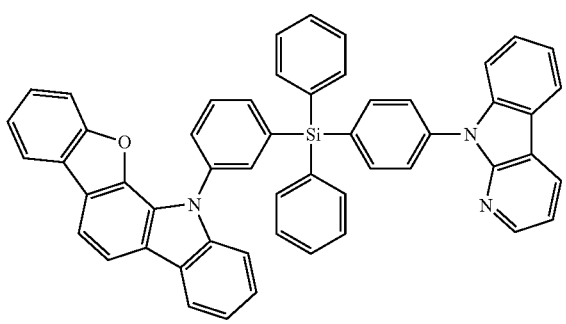
407
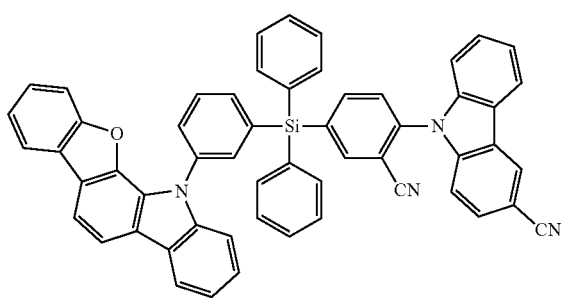
914
-continued
408
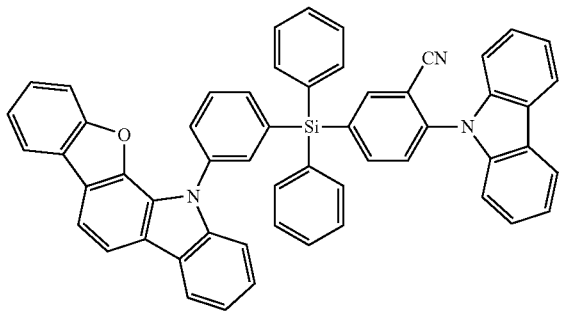
409
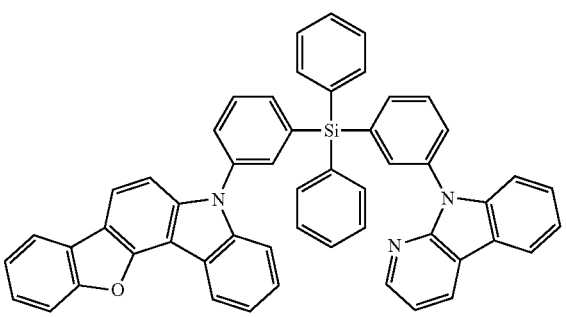
410
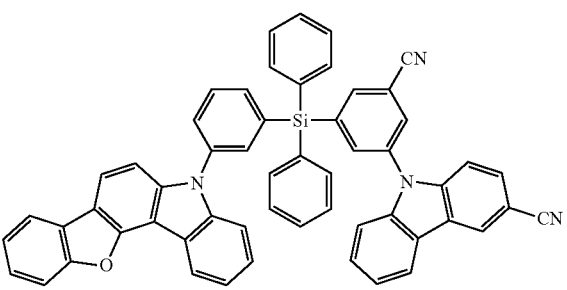
411
412
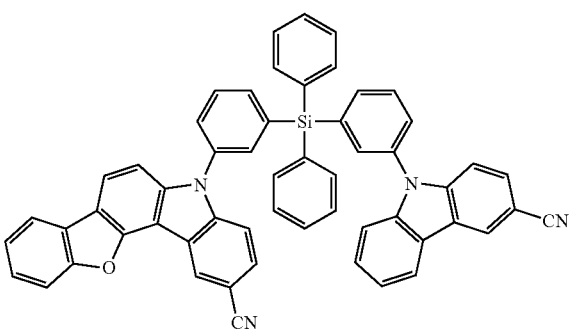

-continued
413
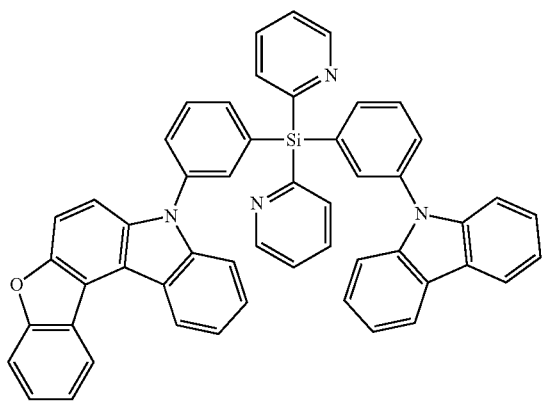
414
415
416
-continued
417
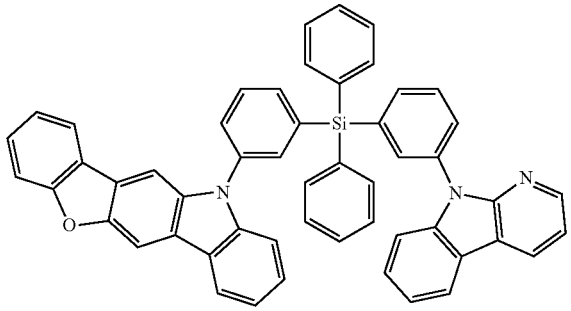
418
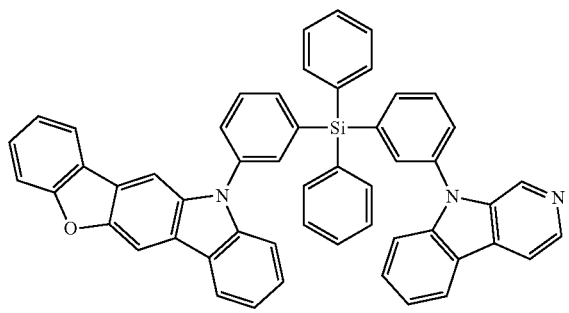
419
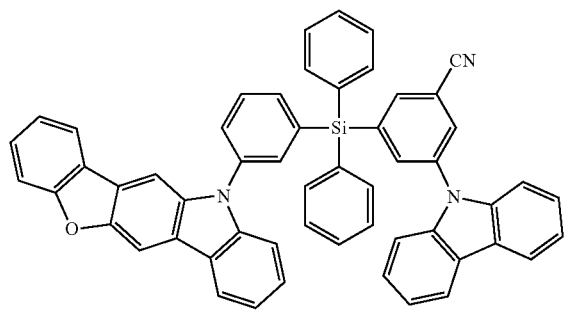
420
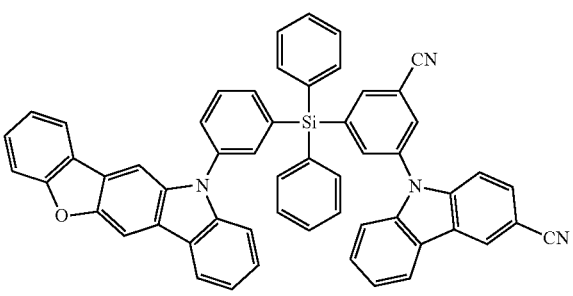
421
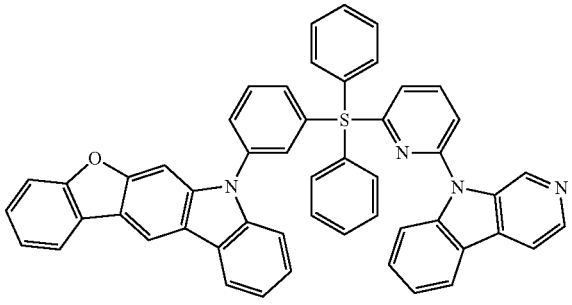

422
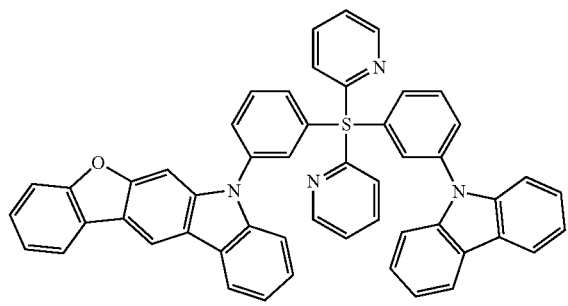
423
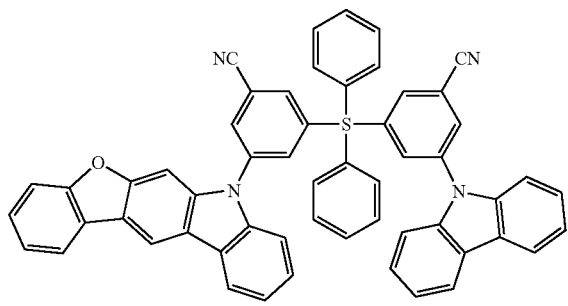
424
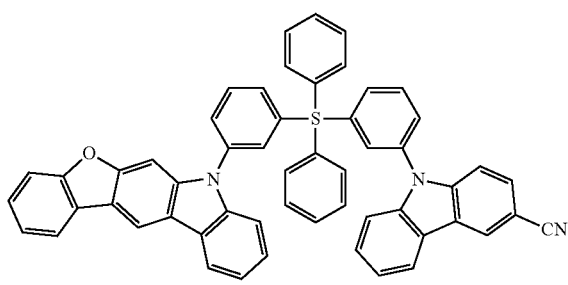
425
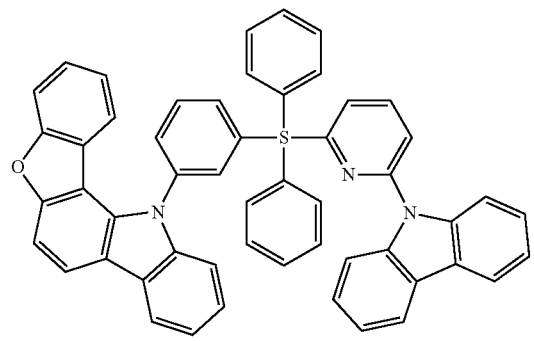
426
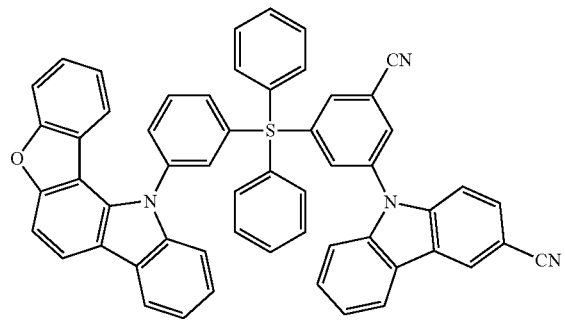
427
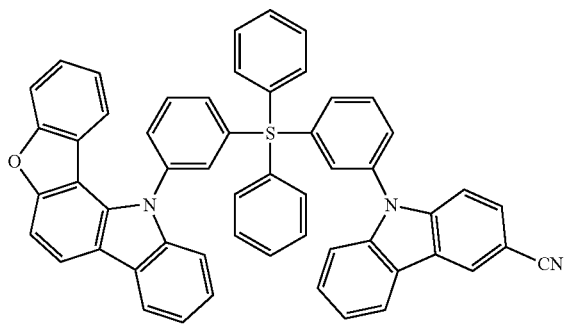
428
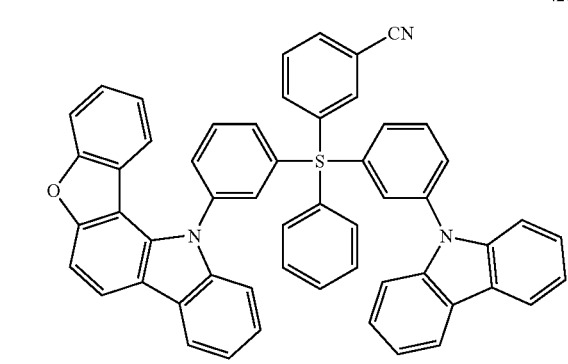
429
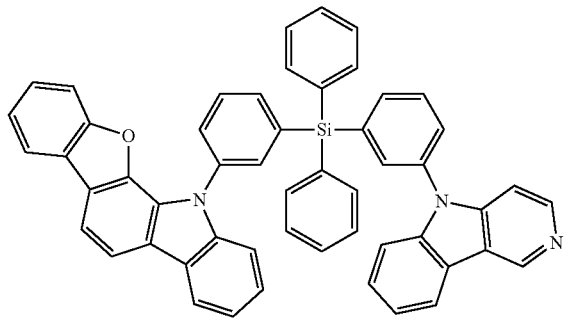

-continued

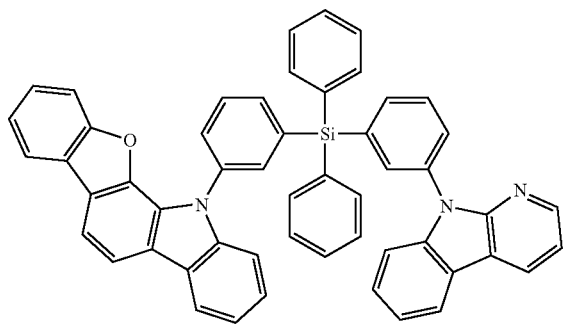
430

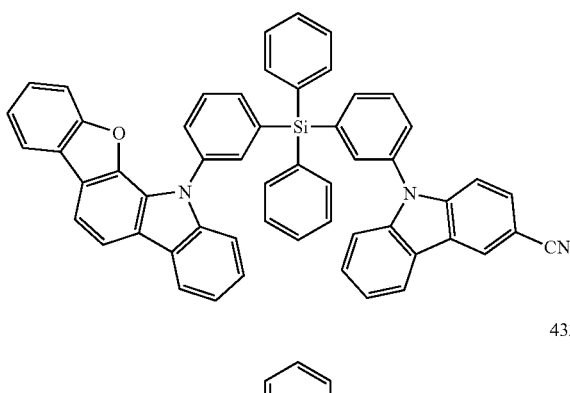
431

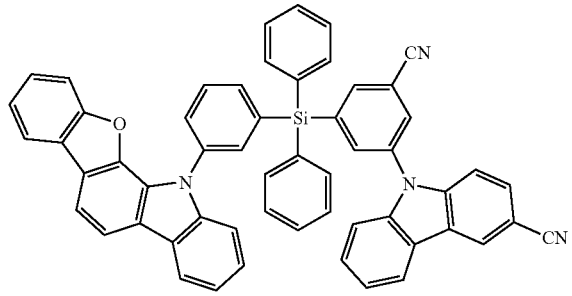
432 wherein, in Group HEH1, "Ph" represents a phenyl group.

In some embodiments, Compound H1 may be used as the hole transporting host. In one or more embodiments, Compound H2 or H4 may be used as the electron transporting host:

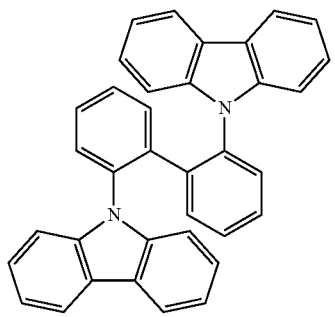
H1

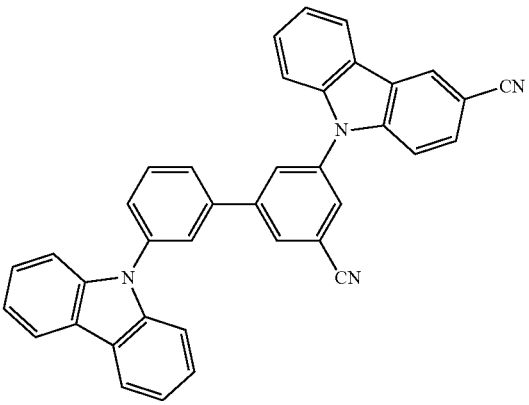
H2

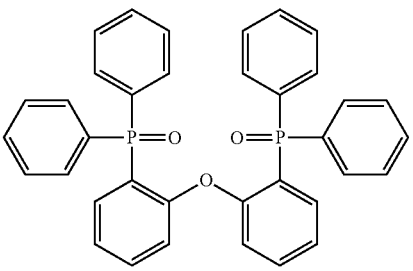
H4

When the host is a mixture of an electron transporting host and a hole transporting host, a weight ratio of the electron transporting host to the hole transporting host may be in a range of about 1:9 to about 9:1, for example, about 2:8 to about 8:2, for example, about 4:6 to about 6:4, or for example, about 5:5. When a weight ratio of the electron transporting host to the hole transporting host is within any of these ranges, holes and electrons transport balance into the emission layer 15 may be achieved.

Emitter in Emission Layer 15

The emitter may be a phosphorescence emitter or a fluorescence emitter.

The phosphorescence emitter may include a transition metal.

In some embodiments, the emitter may be a fluorescence emitter. In some embodiments, the fluorescence emitter may be a prompt fluorescence emitter, not a delayed fluorescence emitter. When the emitter is a prompt emitter, the emission layer according to the Third Embodiment may be a prompt fluorescence emission layer. The prompt fluorescence emission layer is different from a delayed fluorescence emission layer that may include a delayed fluorescence emitter and have a ratio of delayed fluorescence components emitted from the delayed fluorescence emitter in a range of about 70% to about 100%, based on the total emission components.

An absolute value of a difference between the HOMO energy level of the fluorescence emitter and the HOMO energy level of the sensitizer may be 0.5 eV or lower, 0.45 eV or lower, 0.4 eV or lower, 0.35 eV or lower, 0.3 eV or lower, 0.25 eV or lower, 0.2 eV or lower, or 0.15 eV or lower. For example, an absolute value of a difference between the HOMO energy level of the fluorescence emitter and the HOMO energy level of the sensitizer may be in a range of about 0 eV to about 0.5 eV, about 0 eV to about 0.45 eV, about 0 eV to about 0.4 eV, about 0 eV to about 0.35 eV, about 0 eV to about 0.3 eV, about 0 eV to about 0.25 eV, about 0 eV to about 0.2 eV, or about 0 eV to about 0.15 eV. In this embodiment, the HOMO energy level of the fluorescence emitter and the HOMO energy level of the sensitizer may each be, for example, evaluated using Gaussian 09 program according to the DFT method. In some embodiments, the DFT method was according to 6-31G(d,p) basis set.

The fluorescence emitter may be any compound that emits fluorescence.

The maximum emission wavelength of an emission spectrum of the fluorescence emitter may be about 400 nm or greater and about 550 nm or lower. In some embodiments, the maximum emission wavelength of an emission spectrum of the fluorescence emitter may be about 400 nm or greater and about 495 nm or lower or about 450 nm or greater and about 495 nm or lower. That is, the fluorescence emitter may emit blue light. The "maximum emission wavelength" as used herein refers to a wavelength of which the emission intensity is greatest. In other words, the "maximum emission wavelength" may be referred to as "peak emission wavelength".

In some embodiments, the fluorescence emitter may not include a metal atom.

In one or more embodiments, the fluorescence emitter may not include a transition metal.

In some embodiments, the fluorescence emitter may be a condensed polycyclic compound, a styryl-based compound, or any combination thereof.

In an embodiment, the fluorescence emitter may include a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group (a tetracene group), a picene group, a perylene group, a pentaphene group, an indenoanthracene group, a group represented by one of Formulae 501-1 to 501-18, or any combination thereof:

501-1
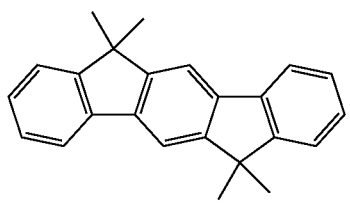

501-2
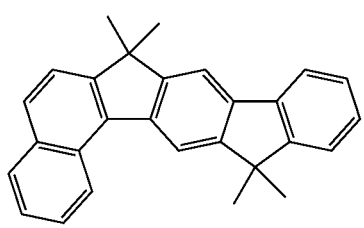

501-3
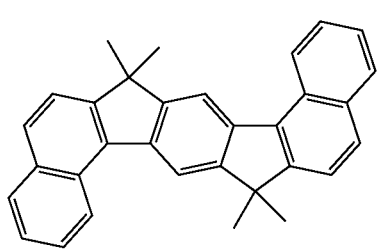

501-4
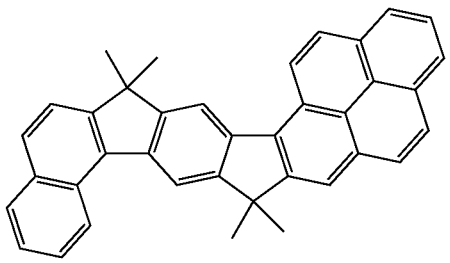

501-5
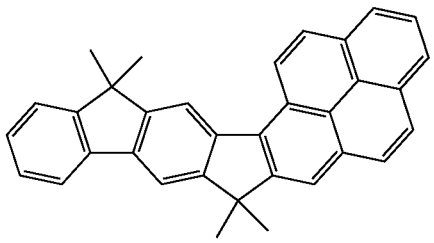

501-6
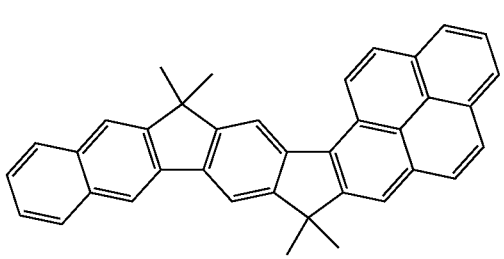

501-7
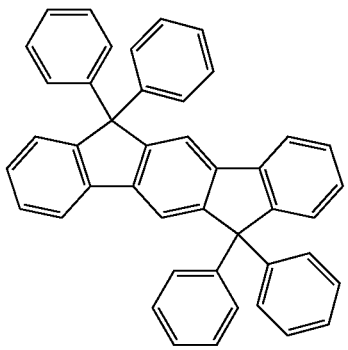

501-8
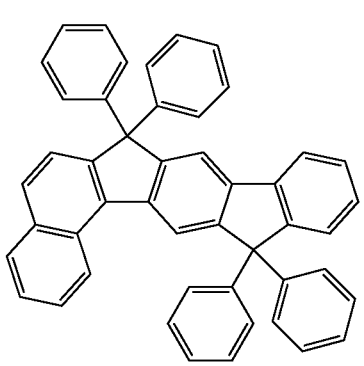

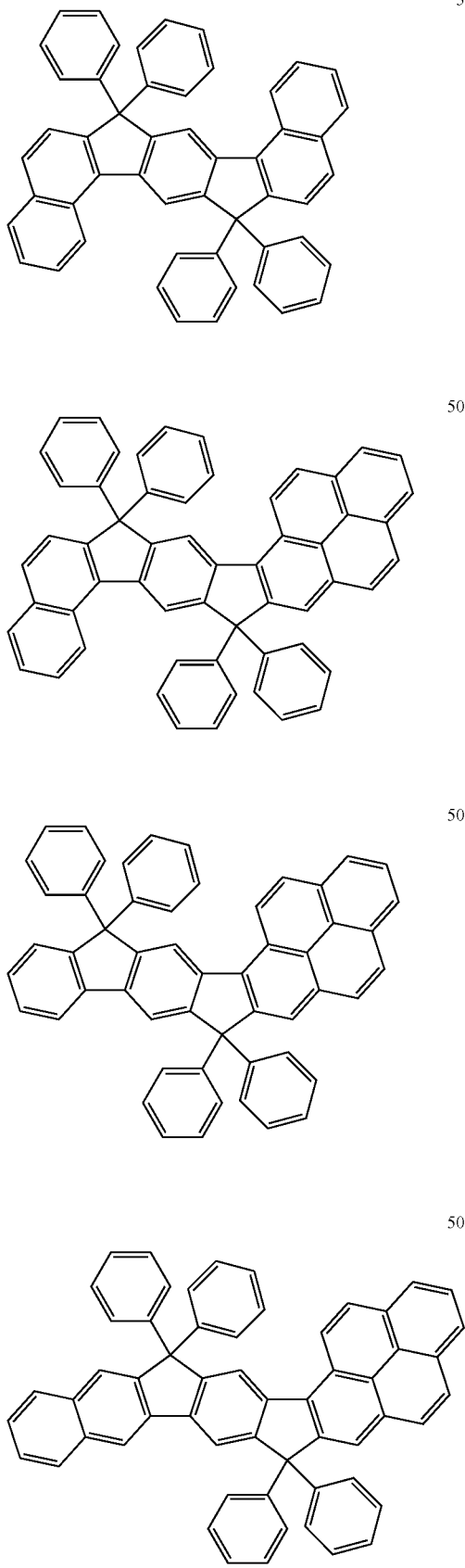
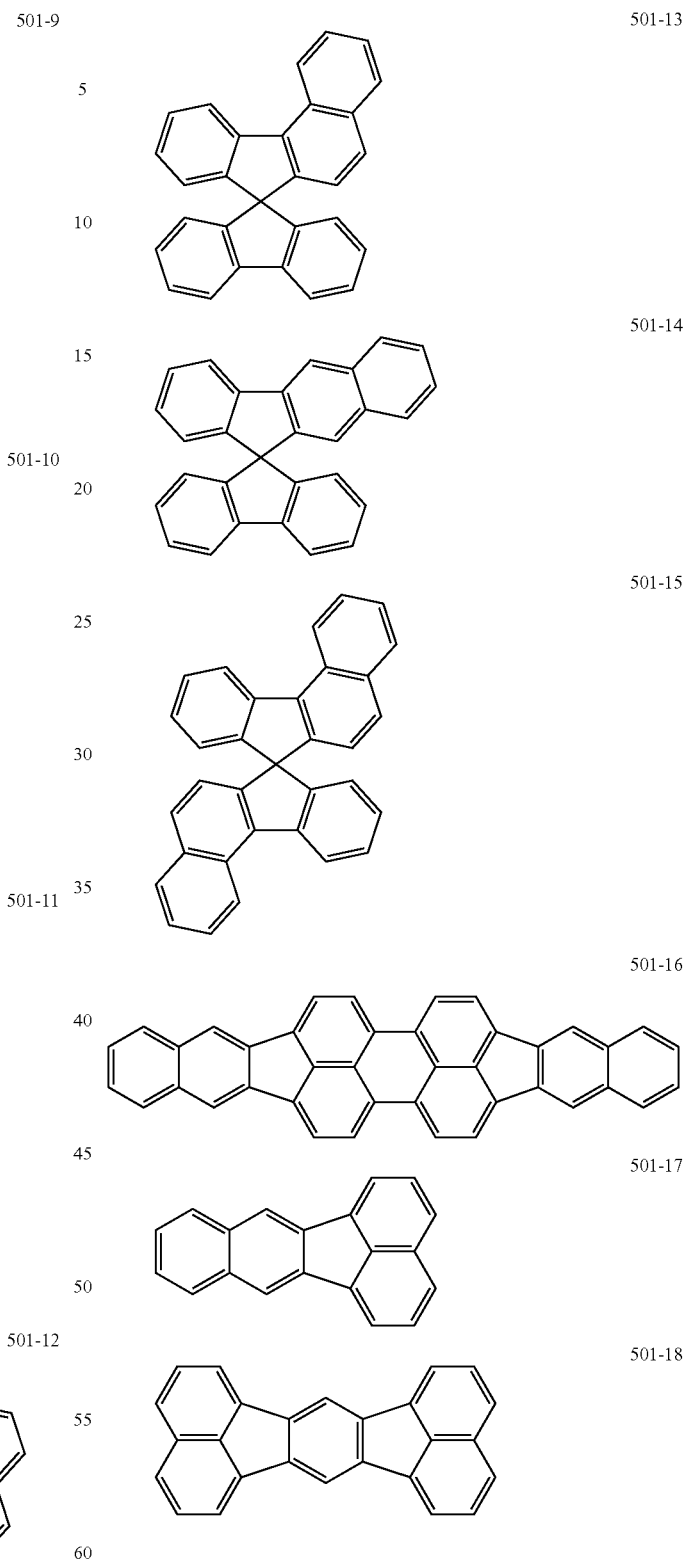
In one or more embodiments, the fluorescence emitter may include at least one of an amine-containing compound and a carbazole-containing compound.
In some embodiments, the fluorescence emitter may include a styryl-amine-based compound, a styryl-carbazole-based compound, or any combination thereof.

In some embodiments, the fluorescence emitter may include a compound represented by Formula 501 or Formula 502:

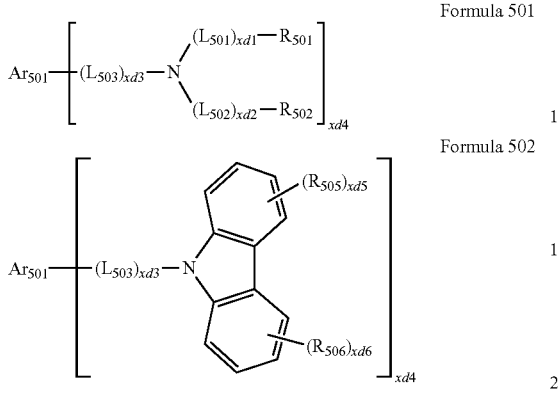

Formula 501

Formula 502 wherein, in Formulae 501 and 502, $Ar_{501}$ may be a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, or a group represented by one of Formulae 501-1 to 501-18, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{501}$)($Q_{502}$)($Q_{503}$), or any combination thereof, $L_{501}$ to $L_{503}$ may each independently be:

a single bond; or a $C_5$-$C_{60}$ carbocyclic group or a $C_1$-$C_{60}$ heterocyclic group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{501}$)($Q_{502}$)($Q_{503}$), or any combination thereof, xd1 to xd3 may each independently be an integer from 1 to 10, $R_{501}$ and $R_{502}$ may each independently be a $C_5$-$C_{60}$ carbocyclic group or a $C_1$-$C_{60}$ heterocyclic group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{501}$)($Q_{502}$)($Q_{503}$), or any combination thereof, $R_{505}$ and $R_{506}$ may be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or —Si($Q_{501}$)($Q_{502}$)($Q_{503}$), xd5 and xd6 may each independently be an integer from 1 to 4, and xd4 may be an integer from 1 to 6, wherein $Q_{501}$ to $Q_{503}$ may each independently be hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

In some embodiments, $R_{501}$ and $R_{502}$ may each independently be a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, or any combination thereof.

In some embodiments, xd4 may be an integer from 2 to 6 (or, 2, 3, or 4).

or, the fluorescence emitter may include a compound represented by one of Formulae 502-1 to 502-5:

Formula 502-1
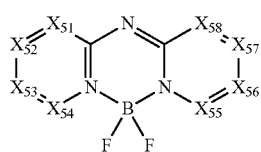

Formula 502-2
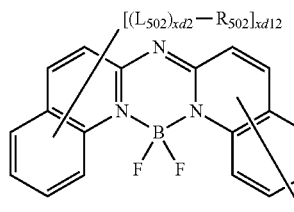

Formula 502-3
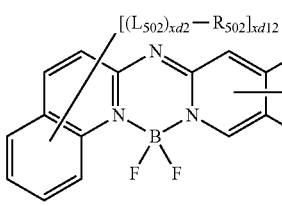

Formula 502-4
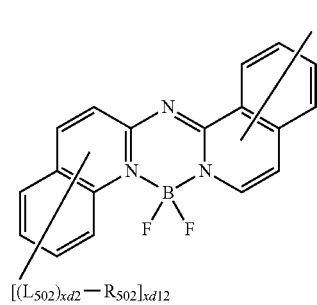

Formula 502-5
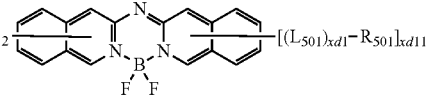

wherein, in Formulae 502-1 to 502-5, $X_{51}$ may be N or C-[$(L_{501})_{xd1}$-$R_{501}$], $X_{52}$ may be N or C-[$(L_{502})_{xd2}$-$R_{502}$], $X_{53}$ may be N or C-[$(L_{503})_{xd3}$-$R_{503}$], $X_{54}$ may be N or C-[$(L_{504})_{xd4}$-$R_{504}$], $X_{55}$ may be N or C-[$(L_{505})_{xd5}$-$R_{505}$], $X_{56}$ may be N or C-[$(L_{506})_{xd6}$-$R_{506}$], $X_{57}$ may be N or C-[$(L_{507})_{xd7}$-$R_{507}$], $X_{58}$ may be N or C-[$(L_{507})_{xd7}$-$R_{507}$], $L_{501}$ to $L_{508}$ may each be understood by referring to the description of $L_{501}$ in Formula 501, xd1 to xd8 may each be understood by referring to the description of xd1 in Formula 501, $R_{501}$ to $R_{508}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group; or a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, or any combination thereof, xd11 and xd12 may each independently be an integer from 0 to 5, two of $R_{501}$ to $R_{504}$ may optionally be bound to form a saturated or unsaturated ring, and two of $R_{505}$ to $R_{508}$ may optionally be bound to form a saturated or unsaturated ring.

The fluorescence emitter may include, e.g., one of Compounds FD(1) to FD(16), one of Compounds FD1 to FD19, or any combination thereof:

FD(1)
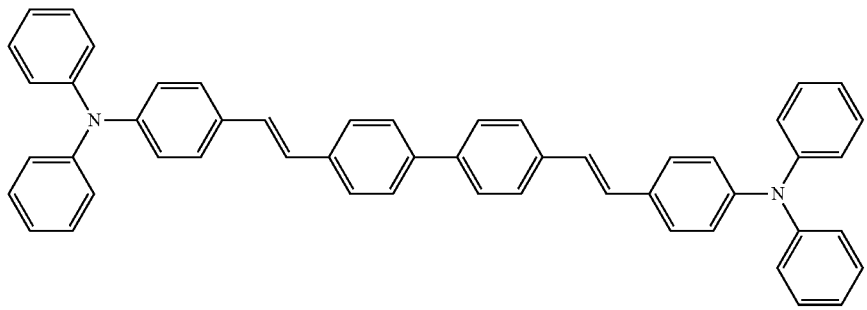
FD(2)
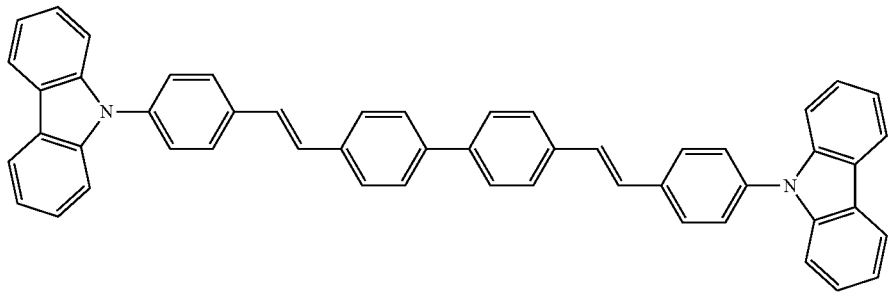
FD(3)
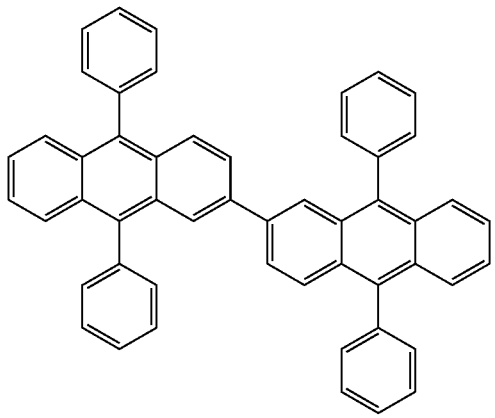
FD(4)
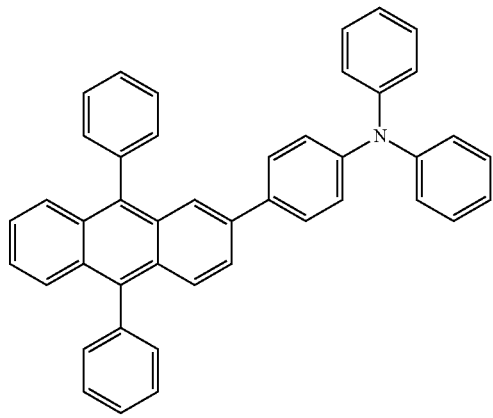
FD(5)
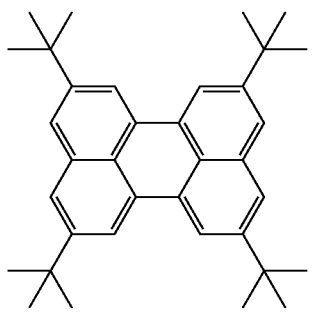
FD(6)
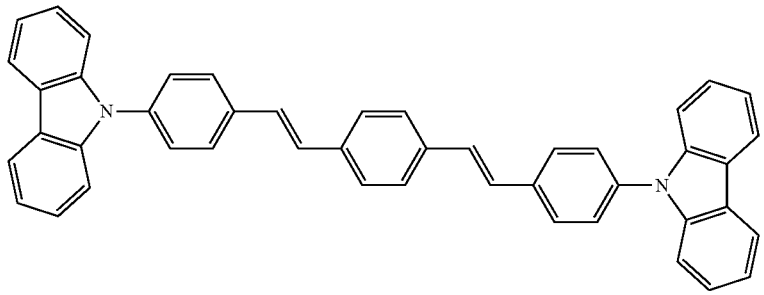

-continued
FD(7)
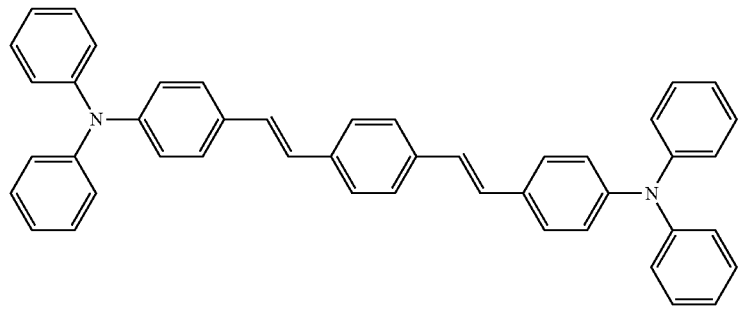
FD(8)
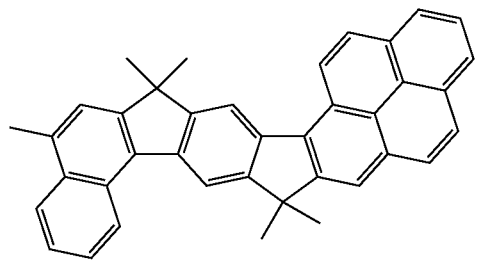
FD(9)
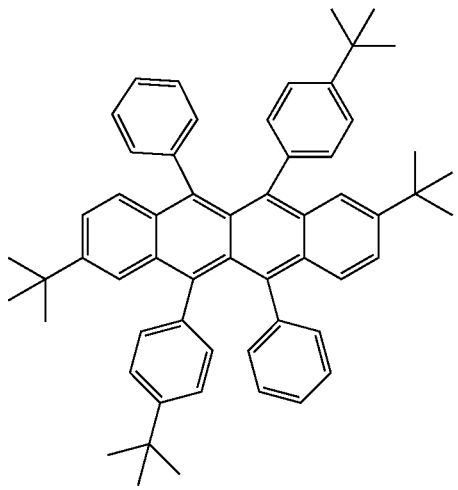
FD(10)
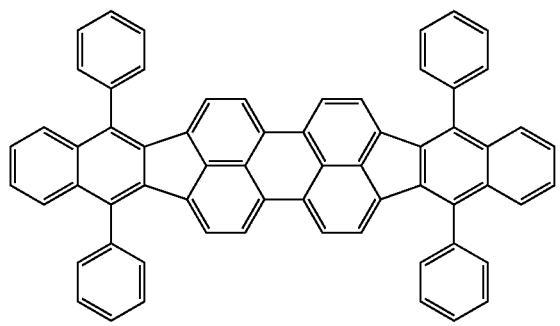
FD(11)
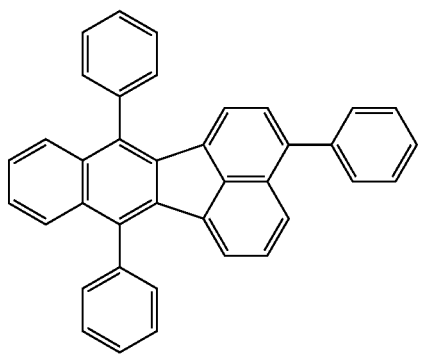
FD(12)
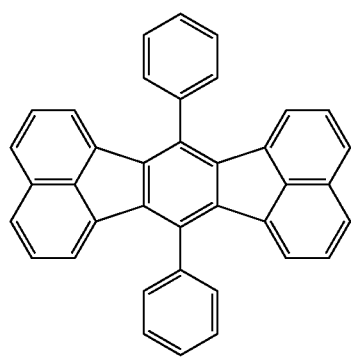
FD(13)
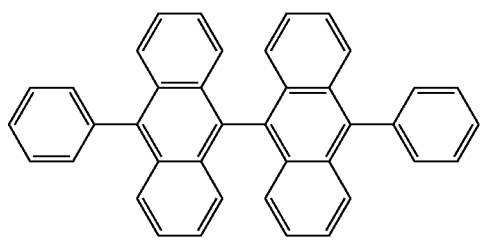

933                                     934
-continued
FD(14)
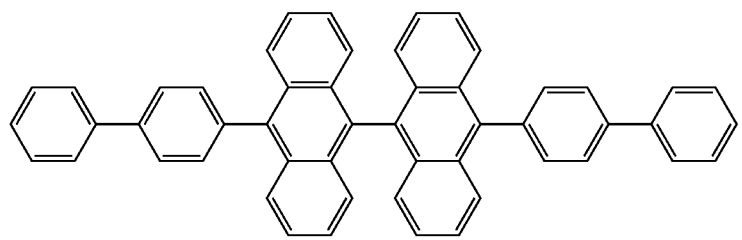
FD(15)                                  FD(16)
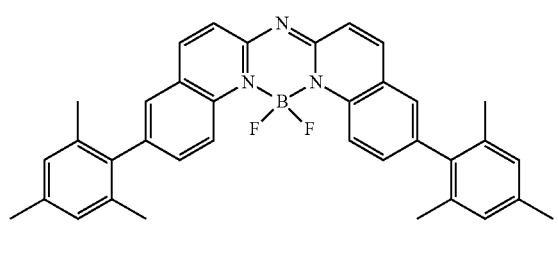    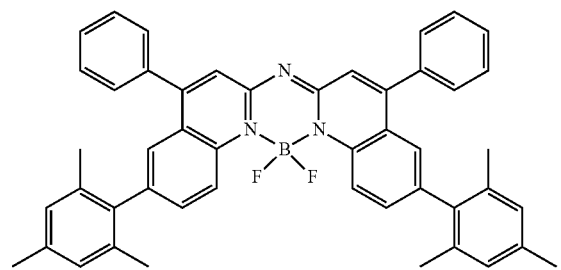
FD1                                     FD2
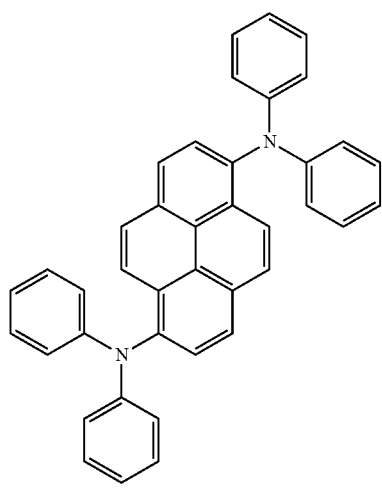    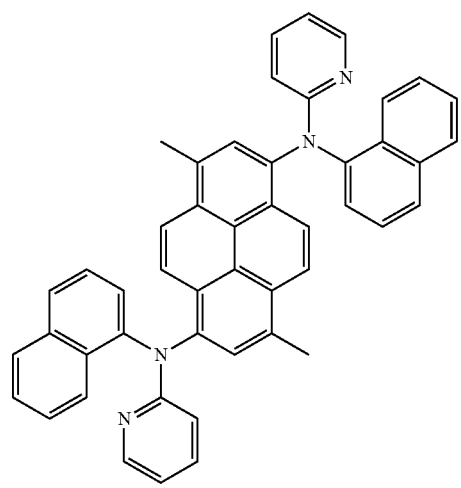

-continued
935
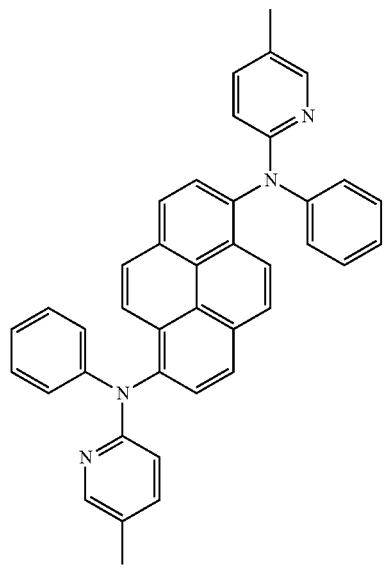
FD3
936
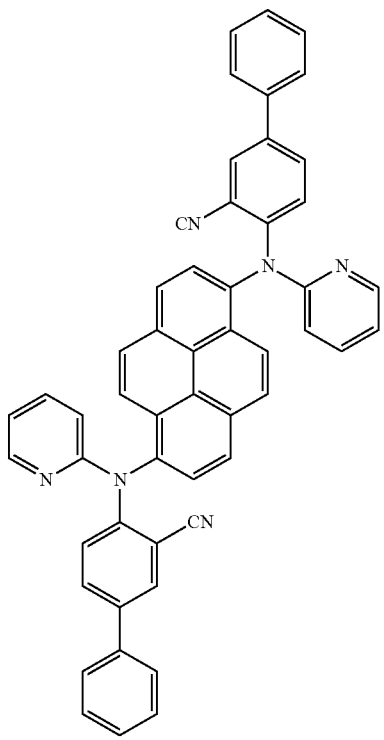
FD4
FD5
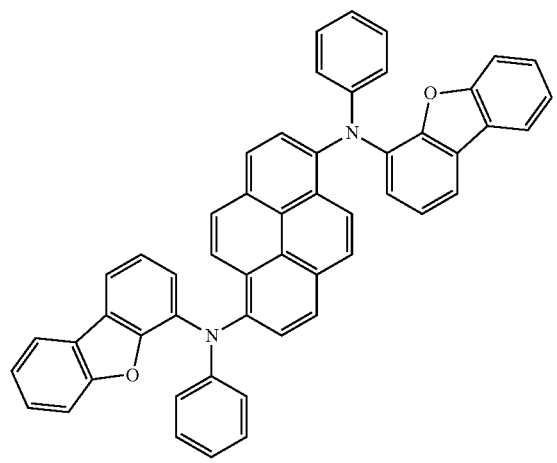
FD6
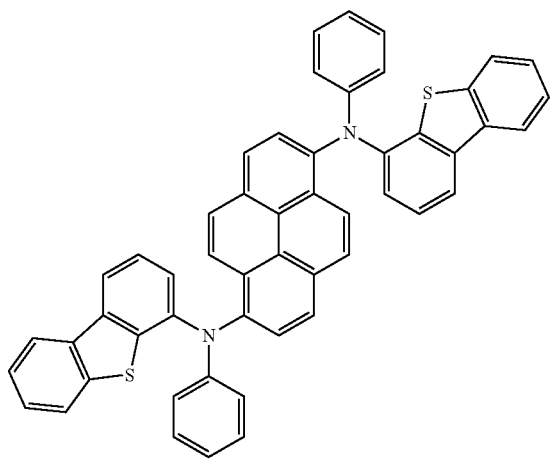
FD7
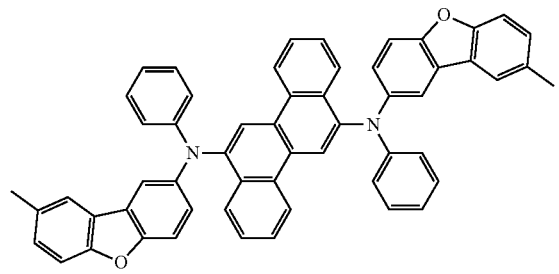
FD8
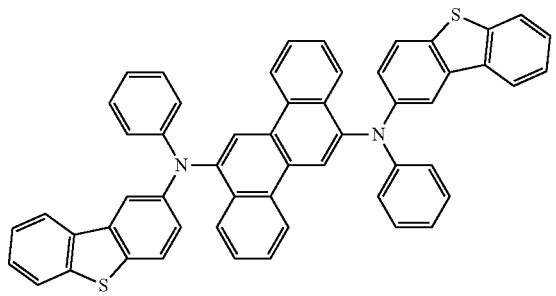

-continued
FD9
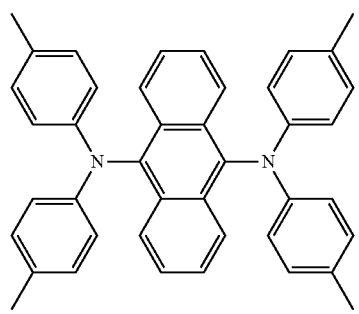
FD10
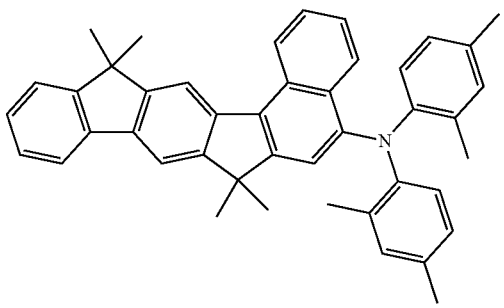
FD11
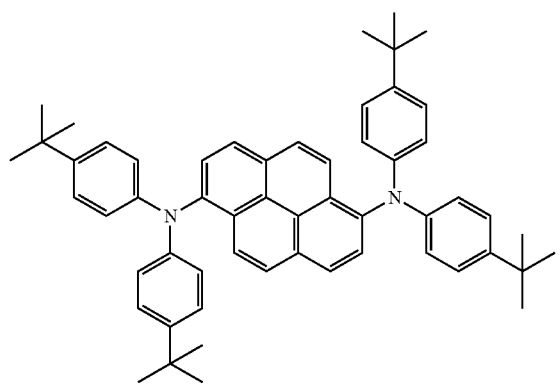
FD12
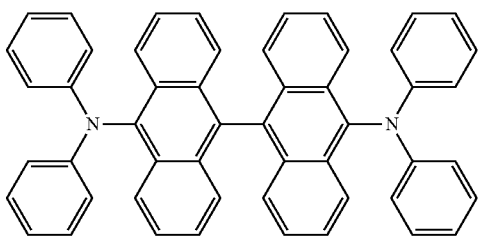
FD13
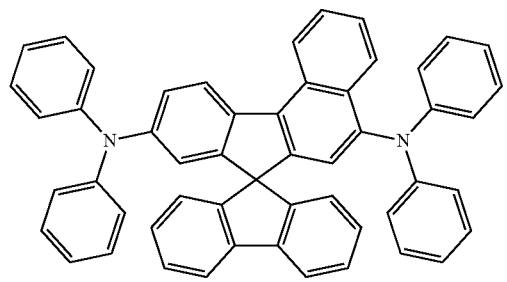
FD14
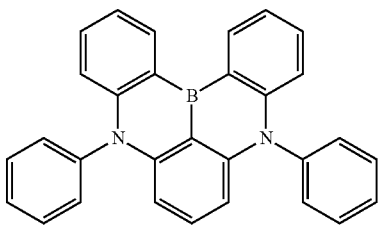
FD15
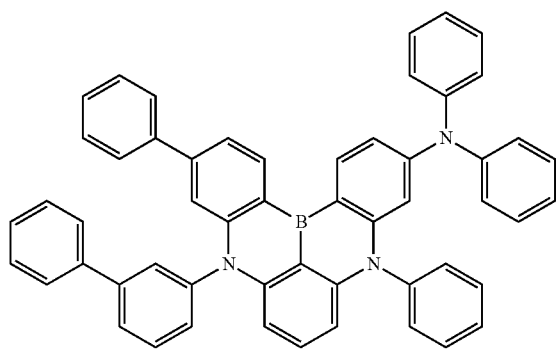
FD16
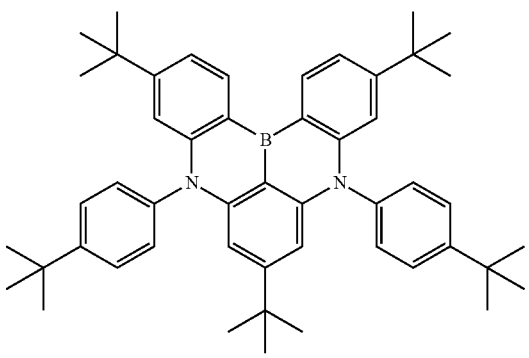

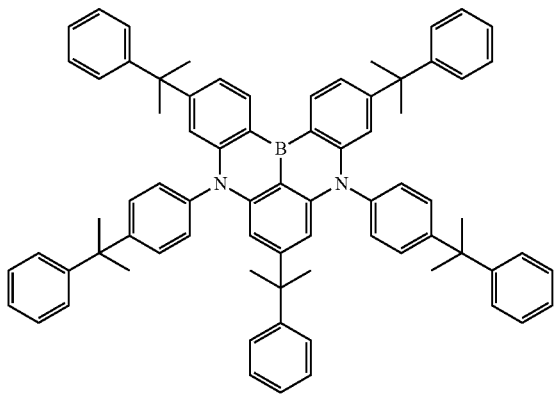

FD17

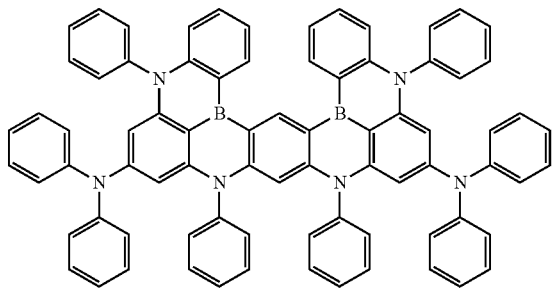

FD18

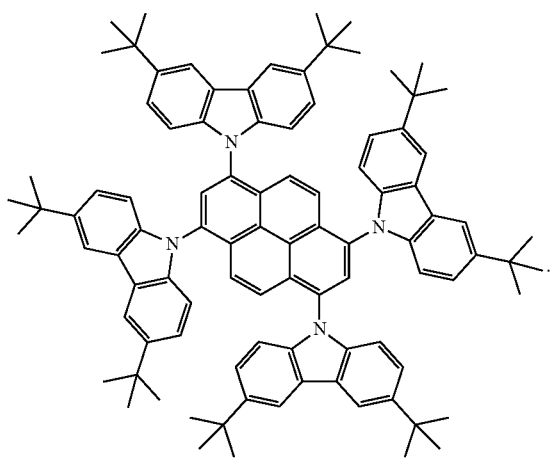

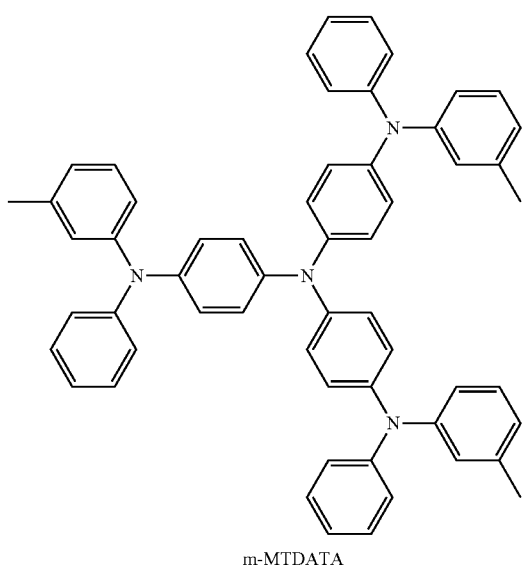

FD19

Hole Transport Region 12

In the organic light-emitting device 10, the hole transport region 12 may be between the first electrode 11 and the emission layer 15.

The hole transport region 12 may have a single-layered structure or a multi-layered structure.

For example, the hole transport region 12 may have a structure of hole injection layer, a structure of hole transport layer, a structure of hole injection layer/hole transport layer, a structure of hole injection layer/first hole transport layer/second hole transport layer, a structure of hole injection layer/first hole transport layer/second hole transport layer/electron blocking layer, a structure of hole transport layer/intermediate layer, a structure of hole injection layer/hole transport layer/intermediate layer, a structure of hole transport layer/electron blocking layer, or a structure of hole injection layer/hole transport layer/electron blocking layer.

The hole transport region 12 may include a compound having hole transport characteristics.

For example, the hole transport region 12 may include an amine-based compound.

In some embodiments, the hole transport region 12 may include m-MTDATA, TDATA, 2-TNATA, NPB, β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor-sulfonic acid (PANI/CSA), polyaniline/poly(4-styrene sulfonate) (PANI/PSS), a compound represented by one of Formulae 201 to 205, or any combination thereof:

m-MTDATA

-continued
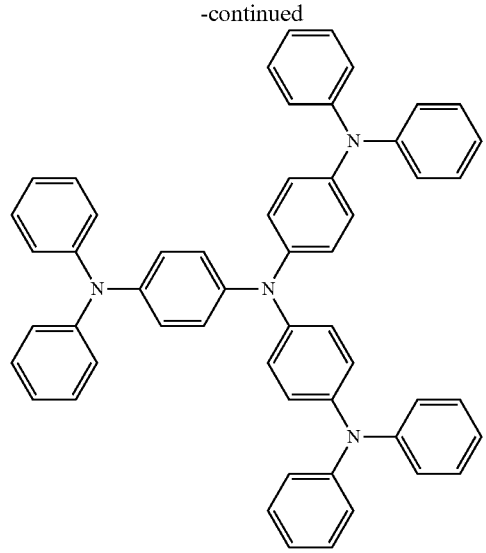
TDATA
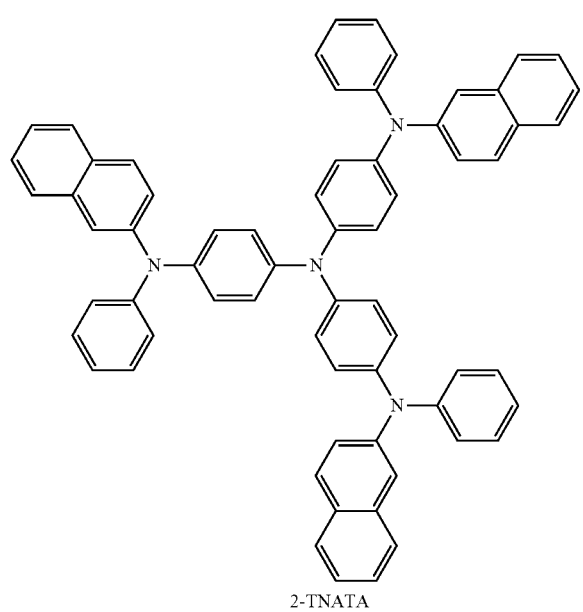
2-TNATA
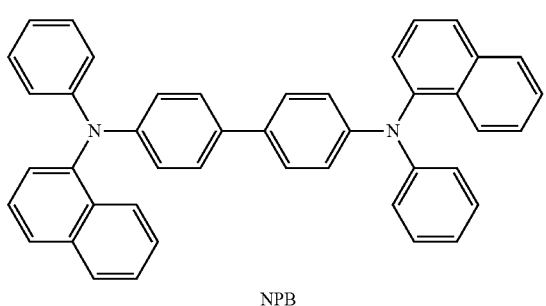
NPB
-continued
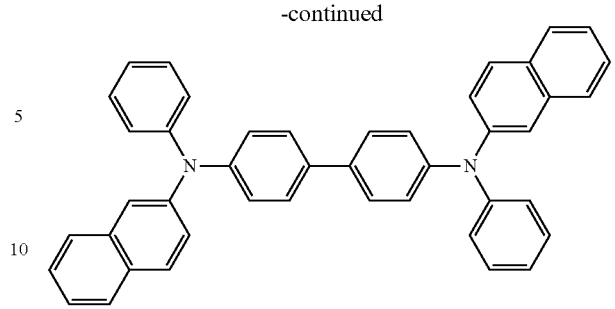
β-NPB
TPD
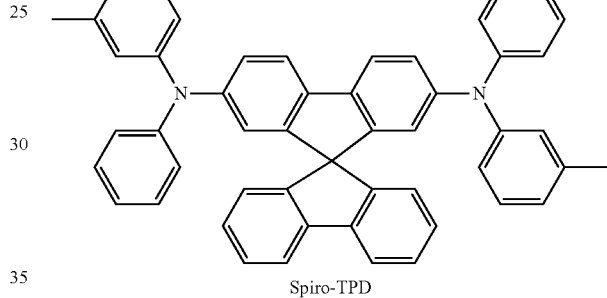
Spiro-TPD
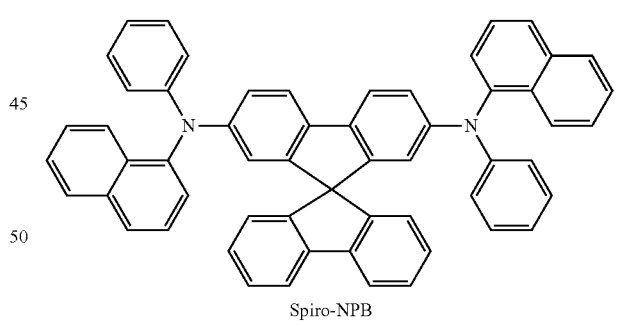
Spiro-NPB
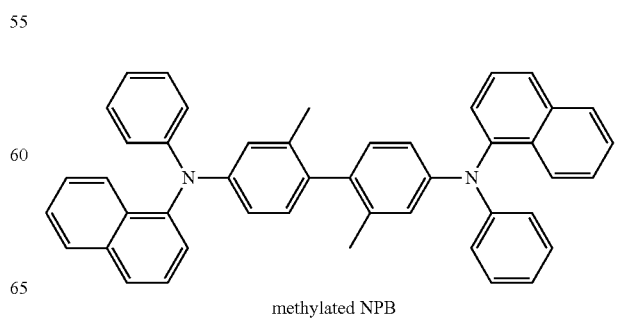
methylated NPB -continued

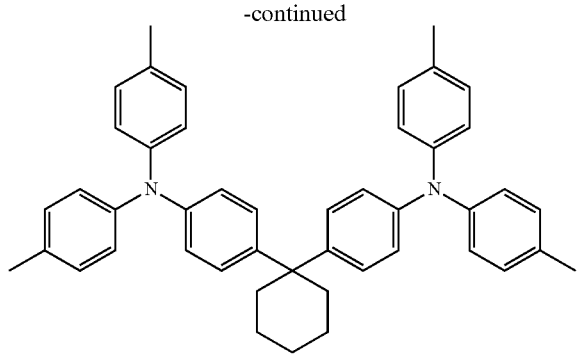

TAPC

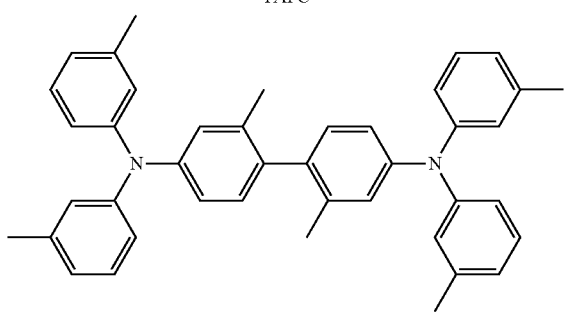

HMTPD

Formula 201

R$_{201}$—(L$_{201}$)$_{xa1}$—N$\begin{array}{c}\text{(L}_{202}\text{)}_{xa2}\text{—R}_{202}\\ \text{(L}_{203}\text{)}_{xa3}\text{—R}_{203}\end{array}$ Formula 202

R$_{201}$—(L$_{201}$)$_{xa1}$\
N—(L$_{205}$)$_{xa5}$—N
R$_{202}$—(L$_{202}$)$_{xa2}$/ \\(L$_{203}$)$_{xa3}$—R$_{203}$
(L$_{204}$)$_{xa4}$—R$_{204}$

Formula 203

R$_{201}$—(L$_{201}$)$_{xa1}$\ (L$_{205}$)$_{xa5}$—R$_{205}$
N—L$_{206}$ L$_{207}$—N (L$_{203}$)$_{xa3}$—R$_{203}$
R$_{202}$—(L$_{202}$)$_{xa2}$/ \\(L$_{204}$)$_{xa4}$—R$_{204}$

Formula 204

R$_{201}$-(L$_{201}$)$_{xa1}$\ (L$_{204}$)$_{xa4}$-R$_{204}$
R$_{201}$-(L$_{202}$)$_{xa2}$-N—(L$_{207}$)$_{xa7}$-N (L$_{205}$)$_{xa5}$-R$_{205}$
R$_{203}$-(L$_{203}$)$_{xa3}$/ (L$_{208}$)$_{xa8}$-N
-(L$_{209}$)$_{xa9}$ (L$_{206}$)$_{xa6}$-R$_{206}$

Formula 205

R$_{206}$—(L$_{206}$)$_{xa6}$\ /(L$_{205}$)$_{xa5}$—R$_{205}$
N
(L$_{207}$)$_{xa7}$
R$_{201}$—(L$_{201}$)$_{xa1}$\ (L$_{203}$)$_{xa3}$—R$_{203}$
N—L$_{208}$ L$_{209}$—N
R$_{202}$—(L$_{202}$)$_{xa2}$/ \\(L$_{204}$)$_{xa4}$—R$_{204}$ wherein, in Formulae 201 to 205, L$_{201}$ to L$_{209}$ may each independently be *—O—*', *—S—*', a substituted or unsubstituted C$_5$-C$_{60}$ carbocyclic group or a substituted or unsubstituted C$_1$-C$_{60}$ heterocyclic group, xa1 to xa9 may each independently be an integer from 0 to 5, R$_{201}$ to R$_{206}$ may each independently be a substituted or unsubstituted C$_3$-C$_{60}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$—C$_{60}$ arylthio group, a substituted or unsubstituted C$_1$-C$_{60}$ heteroaryl group, a substituted or unsubstituted monovalent non-aromatic condensed polycyclic group, or a substituted or unsubstituted monovalent non-aromatic condensed heteropolycyclic group, and adjacent two groups of R$_{201}$ to R$_{206}$ may optionally be bound to each other via a single bond, a dimethyl-methylene group or a diphenyl-methylene group.

In some embodiments,

L$_{201}$ to L$_{209}$ may be a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a coronene group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, or a triindolobenzene group, each unsubstituted or substituted with deuterium, a C$_1$-C$_{10}$ alkyl group, a C$_1$-C$_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, —Si(Q$_{11}$)(Q$_{12}$)(Q$_{13}$), or any combination thereof, xa1 to xa9 may each independently be 0, 1, or 2, and R$_{201}$ to R$_{206}$ may each independently be a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an indenocarbazolyl group, an indolocarbazolyl group, a benzofurocarbazolyl group, or a benzothienocarbazolyl group, each unsubstituted or substituted with deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si$(Q_{31})(Q_{32})(Q_{33})$, —N$(Q_{31})(Q_{32})$, or any combination thereof, wherein $Q_{11}$ to $Q_{13}$ and $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group.

According to an embodiment, the hole transport region 12 may include a carbazole-containing amine-based compound.

In one or more embodiments, the hole transport region 12 may include a carbazole-containing amine-based compound and a carbazole-free amine-based compound.

The carbazole-containing amine-based compound may include, for example, a compound represented by Formula 201 including a carbazole group and further including at least one of a dibenzofuran group, a dibenzothiophene group, a fluorene group, a spirofluorene group, an indenocarbazole group, an indolocarbazole group, a benzofurocarbazole group, a benzothienocarbazole group, or any combination thereof.

The carbazole-free amine-based compound may include, for example, a compound represented by Formula 201 not including a carbazole group and including at least one of a dibenzofuran group, a dibenzothiophene group, a fluorene group, a spirofluorene group, an indenocarbazole group, an indolocarbazole group, a benzofurocarbazole group, a benzothienocarbazole group, or any combination thereof.

In one or more embodiments, the hole transport region 12 may include a compound represented by Formula 201, a compound represented by Formula 202, or any combination thereof.

In some embodiments, the hole transport region 12 may include a compound represented by Formula 201-1, 202-1, 201-2 or any combination thereof:

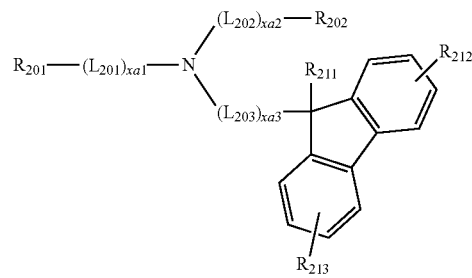

Formula 201-1

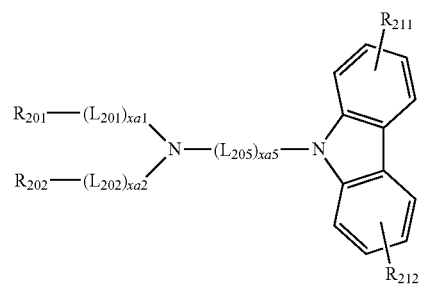

Formula 202-1

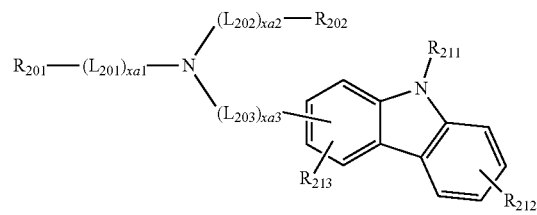

Formula 201-2 wherein in Formulae 201-1, 202-1, and 201-2, $L_{201}$ to $L_{203}$, $L_{205}$, xa1 to xa3, xa5, $R_{201}$, and $R_{202}$ may respectively be understood by referring to the descriptions of $L_{201}$ to $L_{203}$, $L_{205}$, xa1 to xa3, xa5, $R_{201}$, and $R_{202}$ provided herein, and $R_{211}$ to $R_{213}$ may each independently be hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a dimethylfluorenyl group, a diphenylfluorenyl group, a triphenylenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, or a pyridinyl group.

In some embodiments, the hole transport region 12 may include one of Compounds HT1 to HT39 or any combination thereof:

HT1

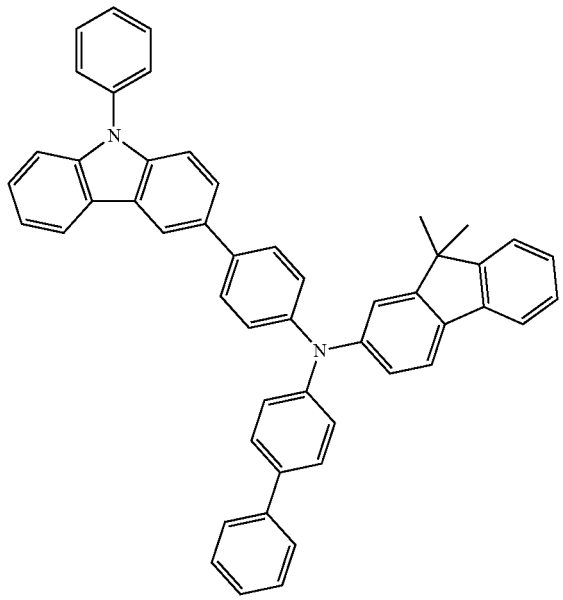

HT2

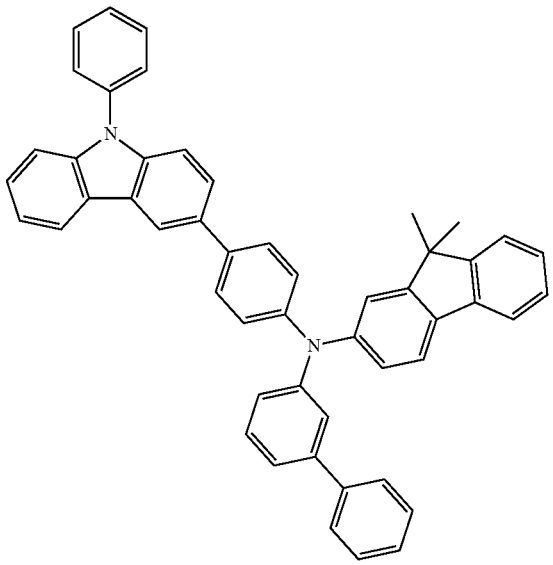

HT3

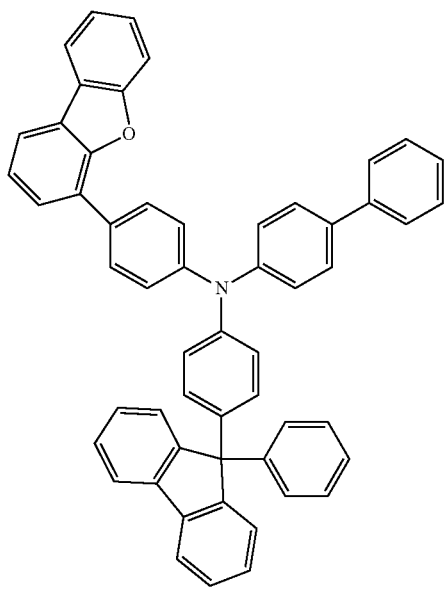

HT4

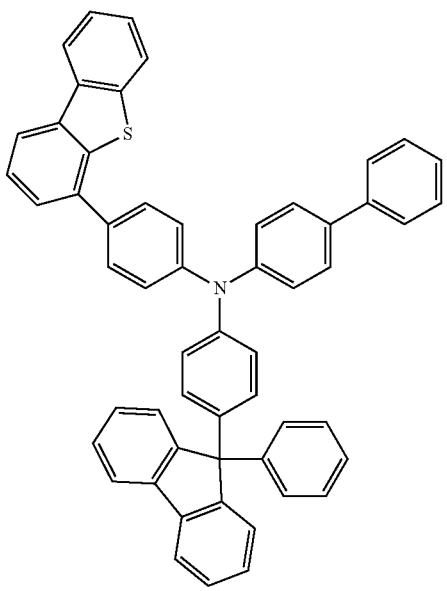

-continued
HT5
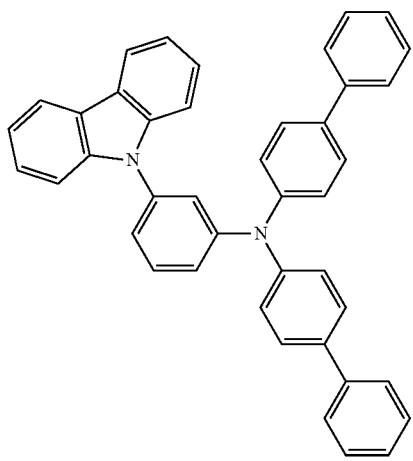
HT6
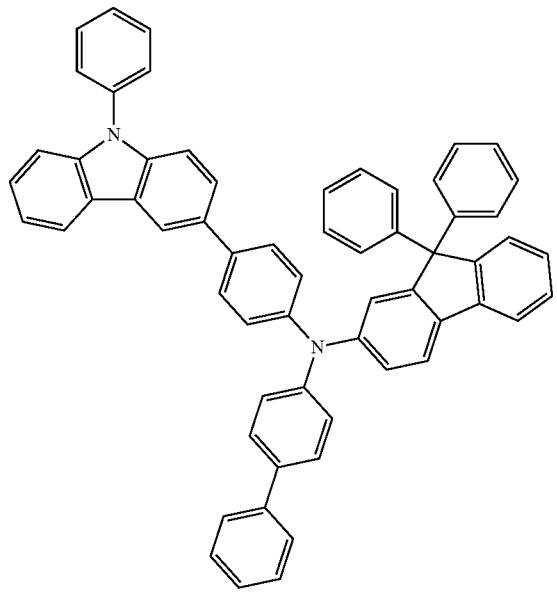
HT7
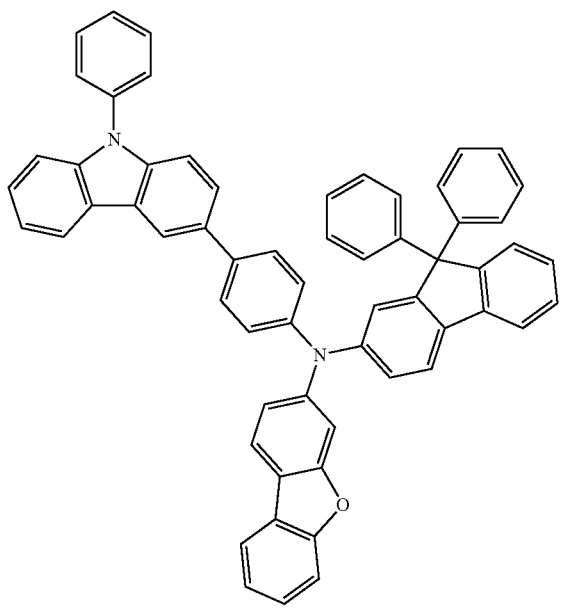
HT8
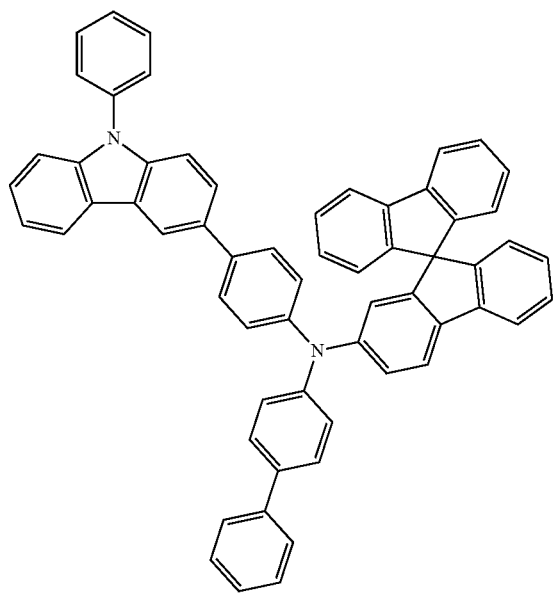

-continued
951
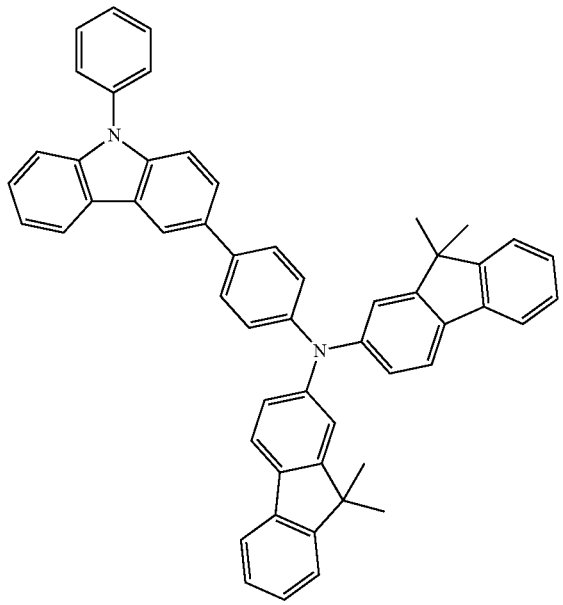
HT9
952
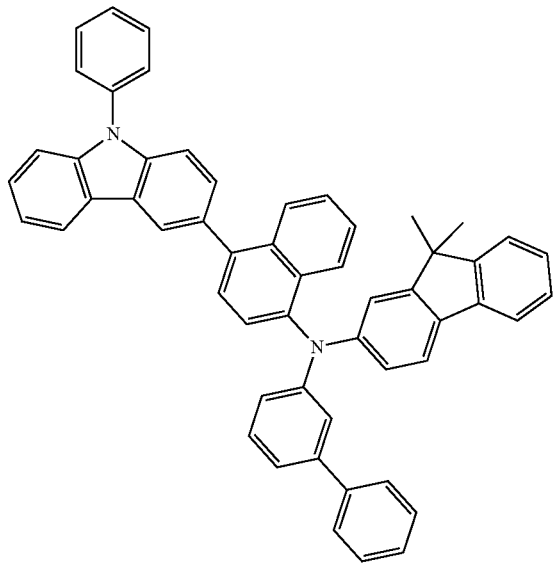
HT10
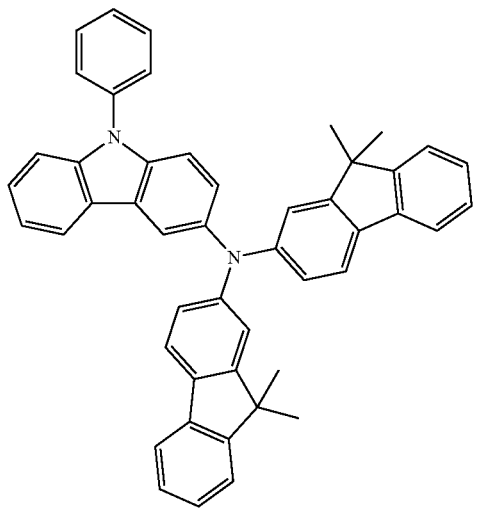
HT11
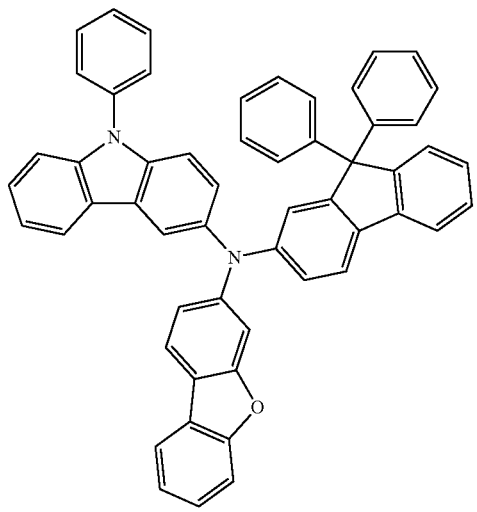
HT12

-continued
HT13
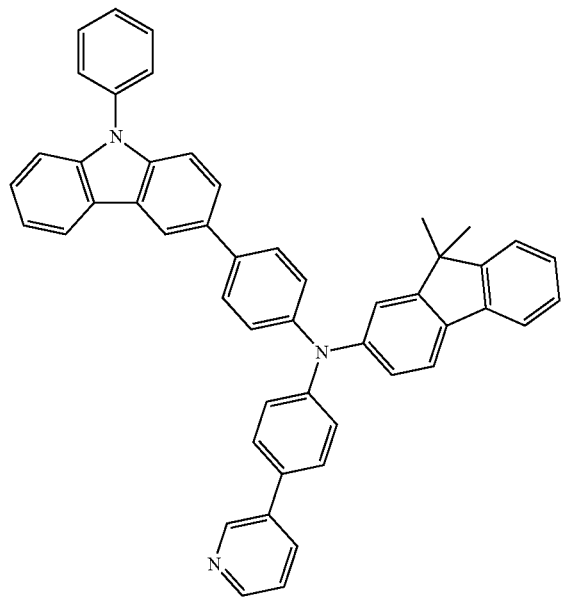
HT14
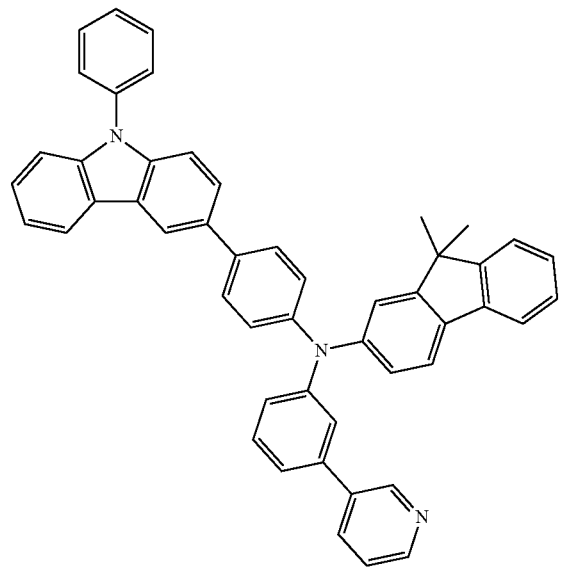
HT15
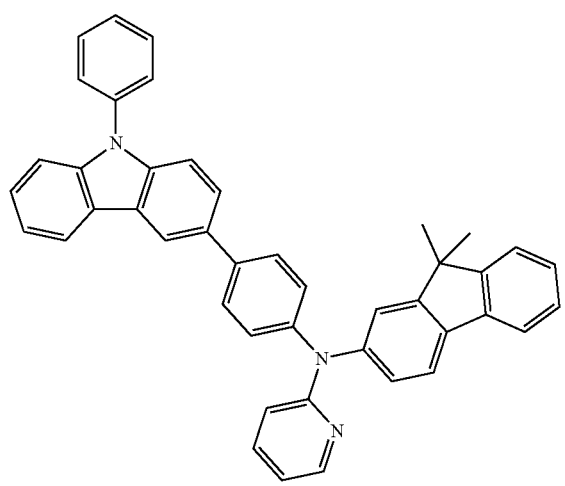
HT16
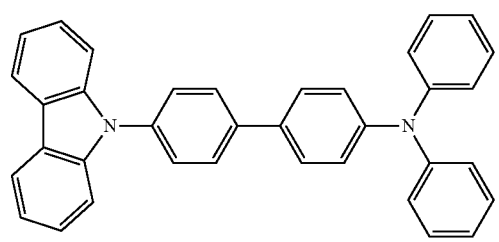
HT17
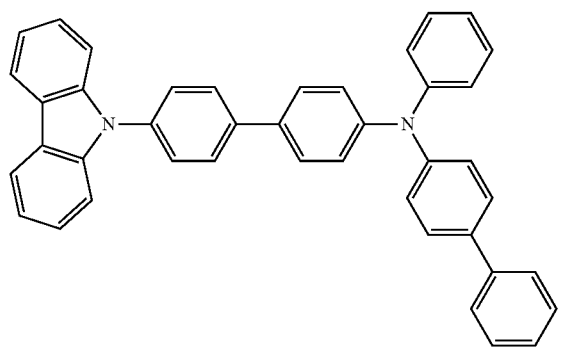
HT18
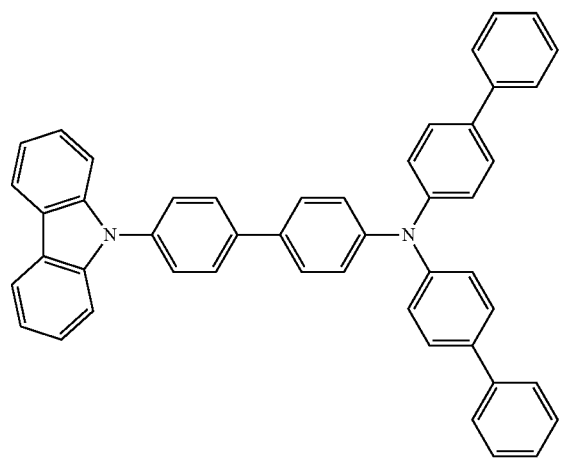

955 956
-continued
HT19
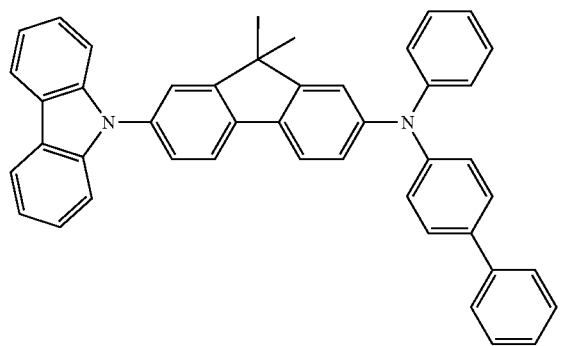
HT20
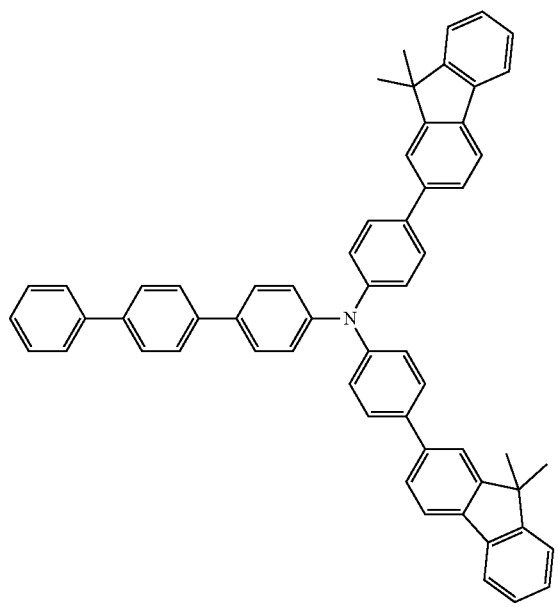
HT21
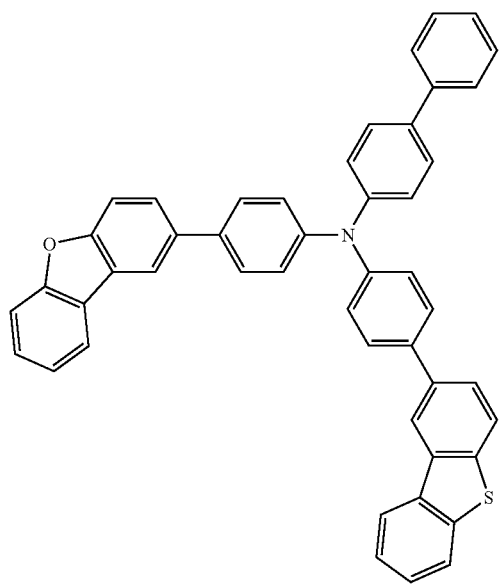
HT22
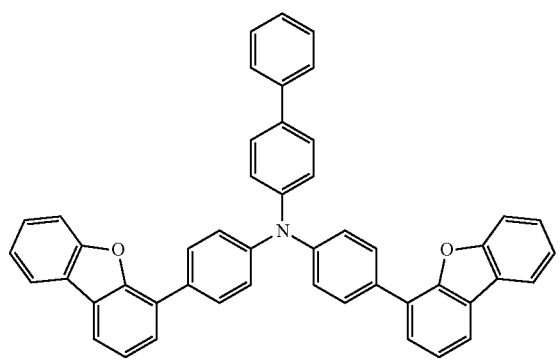

-continued
HT23
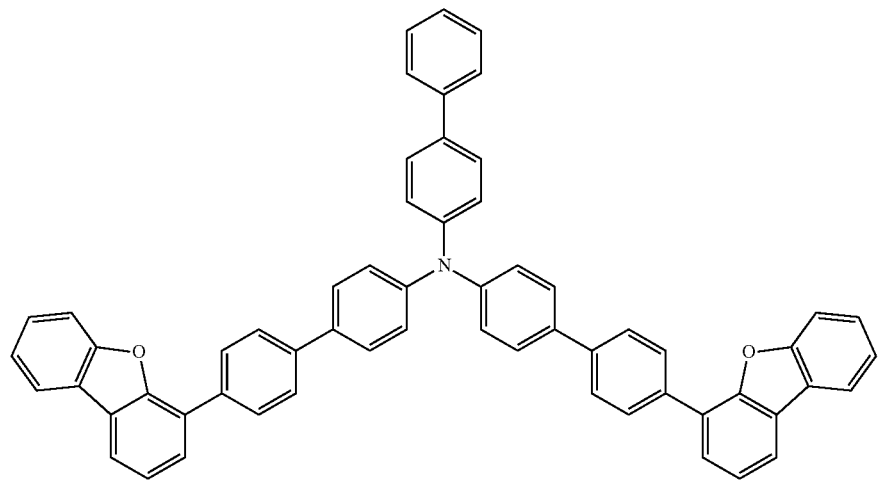
HT24
HT25
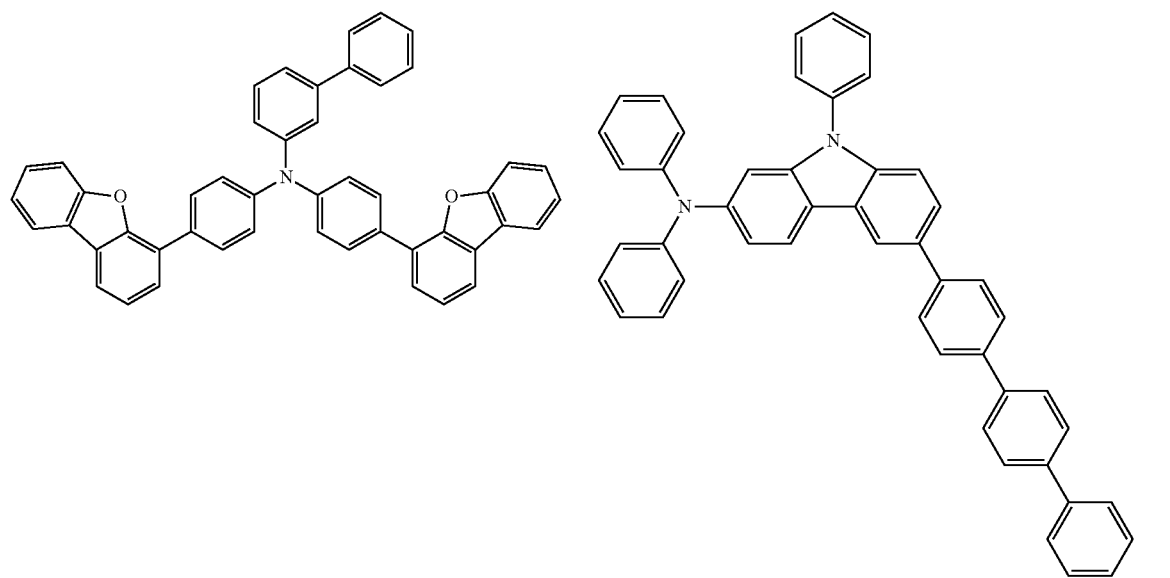
HT26
HT27
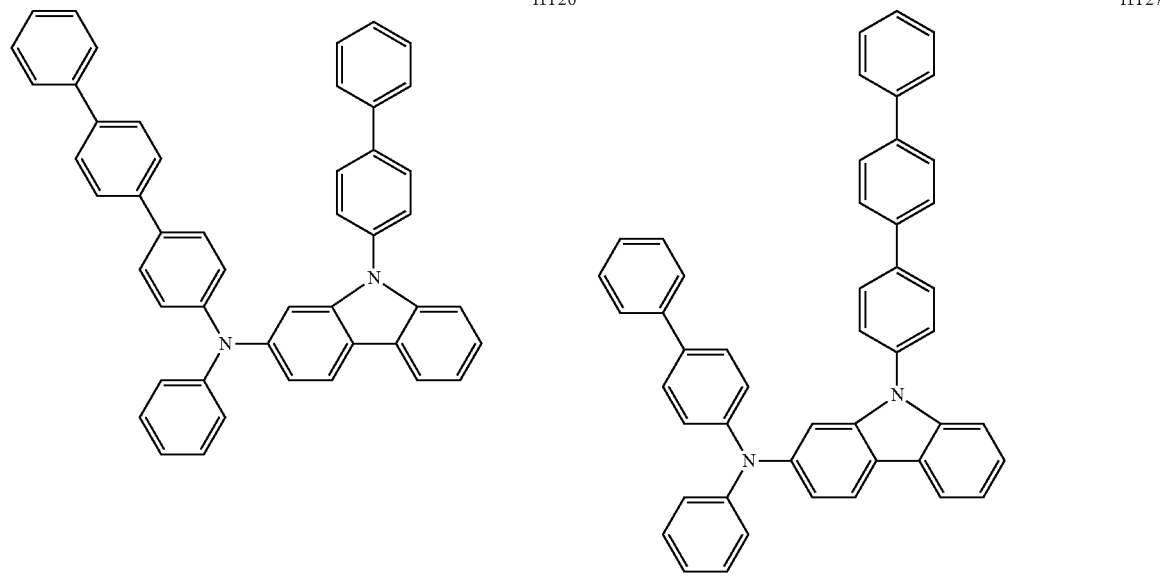

-continued
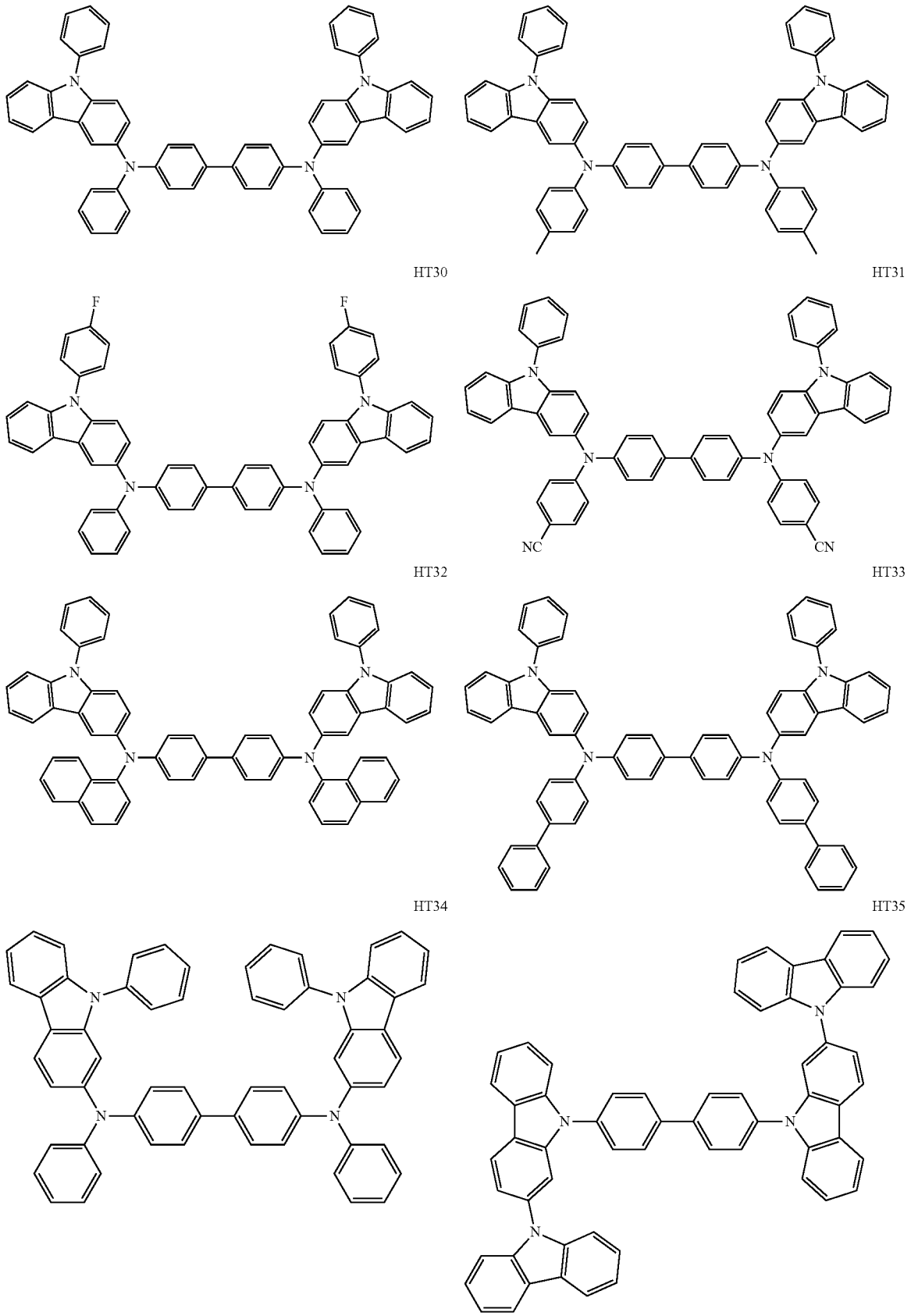

-continued

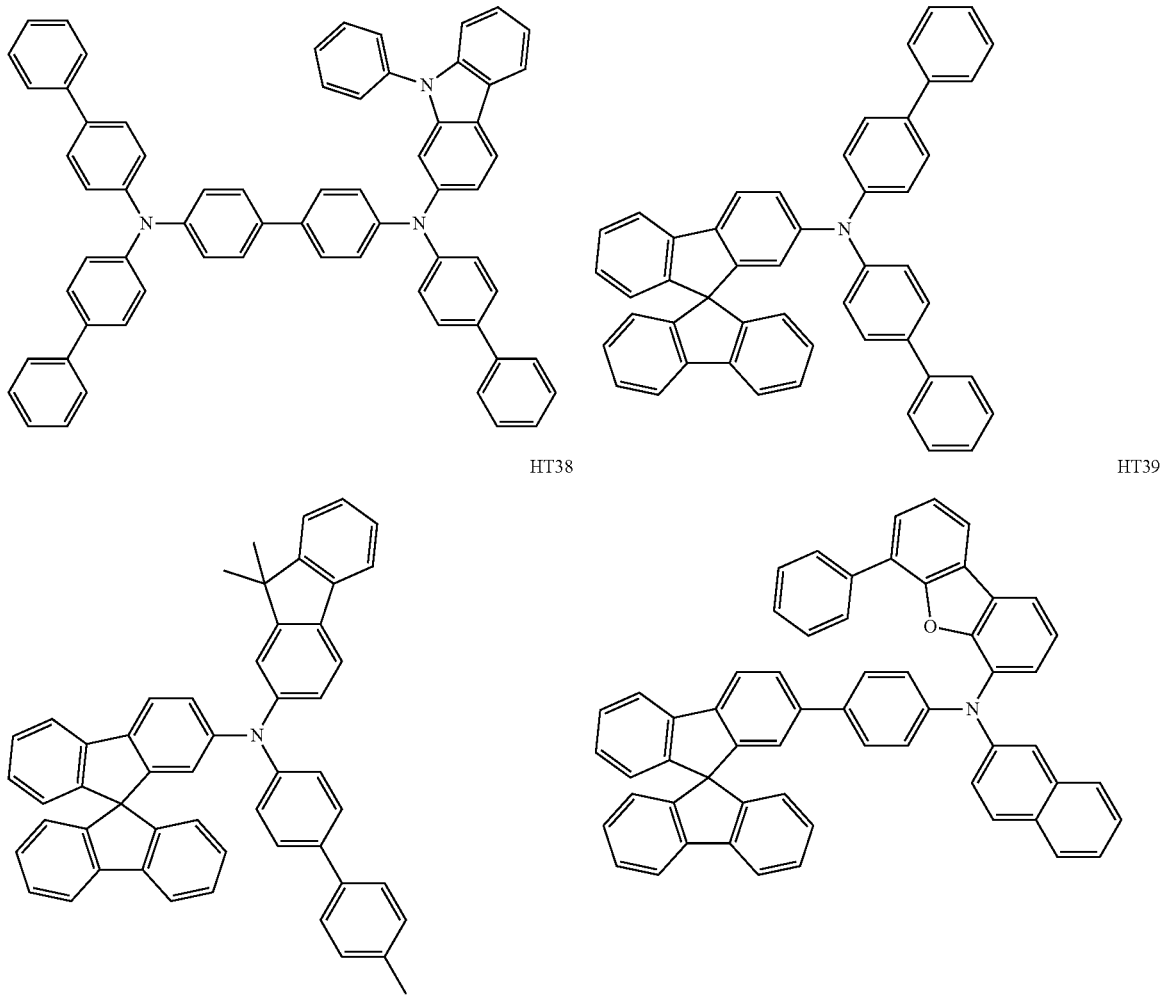

The hole transport region 12 of the organic light-emitting device 10 may further include a p-dopant. When the hole transport region 12 further includes a p-dopant, the hole transport region 12 may have a structure including a matrix (for example, at least one compound represented by Formulae 201 to 205) and a p-dopant included in the matrix. The p-dopant may be homogeneously or non-homogeneously doped in the hole transport region 12.

In some embodiments, a LUMO energy level of the p-dopant may be −3.5 eV or less.

The p-dopant may include a quinone derivative, a metal oxide, a compound containing a cyano group, or any combination thereof.

In some embodiments, the p-dopant may include:

- a quinone derivative such as tetracyanoquinodimethane (TCNQ), F4-TCNQ2,3,5,6-tetrafluoro-7,7,8,8-tetracyanoquinodimethane (F4-TCNQ), or F6-TCNNQ;
- a metal oxide such as tungsten oxide or molybdenum oxide;
- 1,4,5,8,9,12-hexaazatriphenylene-hexacarbonitrile (HAT-CN);
- a compound represented by Formula 221, or any combination thereof:

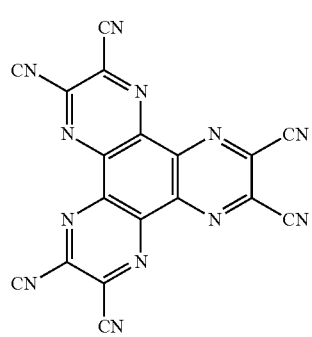

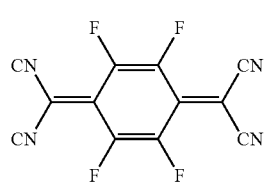

-continued

F6-TCNNQ

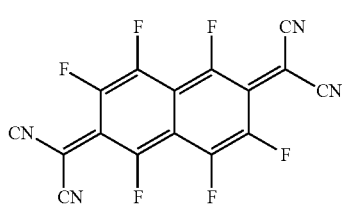

Formula 221

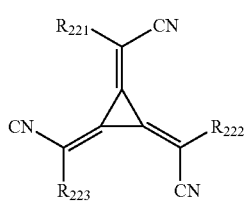

wherein, in Formula 221, $R_{221}$ to $R_{223}$ may each independently be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, wherein at least one substituent of $R_{221}$ to $R_{223}$ may be: a cyano group; —F; —Cl; —Br; —I; a $C_1$-$C_{20}$ alkyl group substituted with —F; a $C_1$-$C_{20}$ alkyl group substituted with —Cl; a $C_1$-$C_{20}$ alkyl group substituted with —Br; a $C_1$-$C_{20}$ alkyl group substituted with —I; or any combination thereof.

The compound represented by Formula 221 may include, for example, Compound HT-D2:

HT-D2

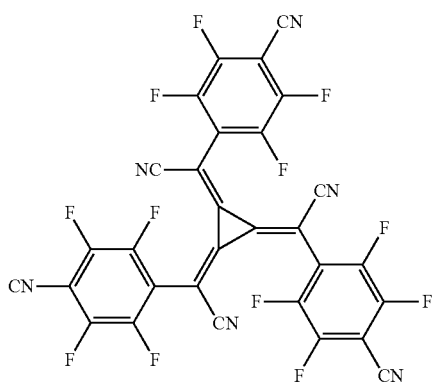

A thickness of the hole transport region 12 may be in a range of about 100 Å to about 10,000 Å, e.g., about 400 Å to about 2,000 Å, and a thickness of the emission layer 15 may be in a range of about 100 Å to about 3,000 Å, e.g., about 300 Å to about 1,000 Å. When the thicknesses of the hole transport region 12 and the emission layer 15 are within any of these ranges, satisfactory hole transporting characteristics and/or luminescence characteristics may be obtained without a substantial increase in driving voltage.

The hole transport region 12 may further include a buffer layer.

The buffer layer may compensate for an optical resonance distance depending on a wavelength of light emitted from the emission layer to improve the emission efficiency of an organic light-emitting device.

The hole transport region 12 may further include an electron blocking layer. The electron blocking layer may include a known material, e.g., mCP or DBFPO:

mCP

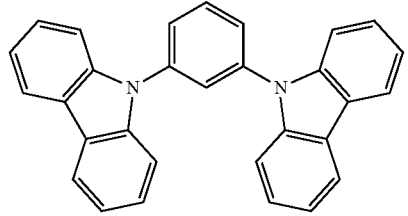

DBFPO

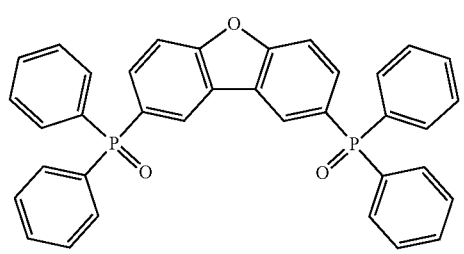

Electron Transport Region 17

In the organic light-emitting device 10, the electron transport region 17 may be between the emission layer 15 and the second electrode 19.

The electron transport region 17 may have a single-layered structure or a multi-layered structure.

For example, the electron transport region 17 may have a structure of an electron transport layer, a structure of electron transport layer/electron injection layer, a structure of buffer layer/electron transport layer, a structure of hole blocking layer/electron transport layer, a structure of buffer layer/electron transport layer/electron injection layer, or a structure of hole blocking layer/electron transport layer/electron injection layer. The electron transport region 17 may include an electron control layer.

The electron transport region 17 may include a known electron transport material.

The electron transport region 17 (for example, a buffer layer, a hole blocking layer, an electron control layer, or an electron transport layer in the electron transport region) may include a metal-free compound including at least one π electron-depleted nitrogen-containing $C_1$-$C_{60}$ cyclic group.

The π electron-depleted nitrogen-containing $C_1$-$C_{60}$ cyclic group may be understood by referring to the description of the π electron-depleted nitrogen-containing $C_1$-$C_{60}$ cyclic group provided herein.

In some embodiments, the electron transport region 17 may include a compound represented by Formula 601:

$$[Ar_{601}]_{xe11}\text{-}[(L_{601})_{xe1}\text{-}R_{601}]_{xe21}$$

Formula 601 wherein, in Formula 601, $Ar_{601}$ and $L_{601}$ may each independently be a $C_5$-$C_{60}$ carbocyclic group unsubstituted or substituted with at least one $R_{601a}$ or a $C_1$-$C_{60}$ heterocyclic group unsubstituted or substituted with at least one $R_{601a}$, xe11 may be 1, 2, or 3, xe1 may be an integer from 0 to 5, $R_{601a}$ and $R_{601}$ may each independently be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_{601})(Q_{602})(Q_{603})$, $-C(=O)(Q_{601})$, $-S(=O)_2(Q_{601})$, or $-P(=O)(Q_{601})(Q_{602})$, wherein $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In some embodiments, at least one of $Ar_{601}(s)$ in the number of xe11 and $R_{601}(s)$ in the number of xe21 may include a π electron-depleted nitrogen-containing $C_1$-$C_{60}$ cyclic group.

In some embodiments, in Formula 601, ring $Ar_{601}$ and $L_{601}$ may each independently be a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with deuterium, $-F$, $-Cl$, $-Br$, $-I$, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, $-Si(Q_{31})(Q_{32})(Q_{33})$, $-S(=O)_2(Q_{31})$, $-P(=O)(Q_{31})(Q_{32})$, or any combination thereof, wherein $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group.

When xe11 in Formula 601 is 2 or greater, at least two $Ar_{601}(s)$ may be bound via a single bond.

In one or more embodiments, $Ar_{601}$ in Formula 601 may be an anthracene group.

In some embodiments, the compound represented by Formula 601 may be represented by Formula 601-1:

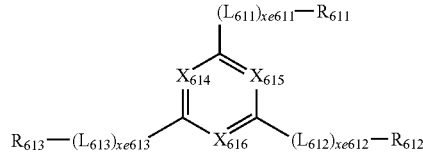

Formula 601-1 wherein, in Formula 601-1, $X_{614}$ may be N or $C(R_{614})$, $X_{615}$ may be N or $C(R_{615})$, $X_{616}$ may be N or $C(R_{616})$, at least one selected from $X_{614}$ to $X_{616}$ may be N, $L_{611}$ to $L_{613}$ may each independently be understood by referring to the description of $L_{601}$ provided herein, xe611 to xe613 may each independently be understood by referring to the description of xe1 provided herein, $R_{611}$ to $R_{613}$ may each independently be understood by referring to the description of $R_{601}$ provided herein, and $R_{614}$ to $R_{616}$ may each independently be hydrogen, deuterium, $-F$, $-Cl$, $-Br$, $-I$, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, or a naphthyl group.

In one or more embodiments, in Formulae 601 and 601-1, xe1 and xe611 to xe613 may each independently be 0, 1, or 2.

In one or more embodiments, in Formulae 601 and 601-1, $R_{601}$ and $R_{611}$ to $R_{613}$ may each independently be a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, or an azacarbazolyl group, each unsubstituted or substituted with deuterium, $-F$, $-Cl$, $-Br$, $-I$, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, or any combination thereof; or —S(=O)$_2$(Q$_{601}$) or —P(=O)(Q$_{601}$)(Q$_{602}$), wherein Q$_{601}$ and Q$_{602}$ may respectively be understood by referring to the descriptions of Q$_{601}$ and Q$_{602}$ provided herein.

The electron transport region 17 may include one of Compounds ET1 to ET36 or any combination thereof:

ET1

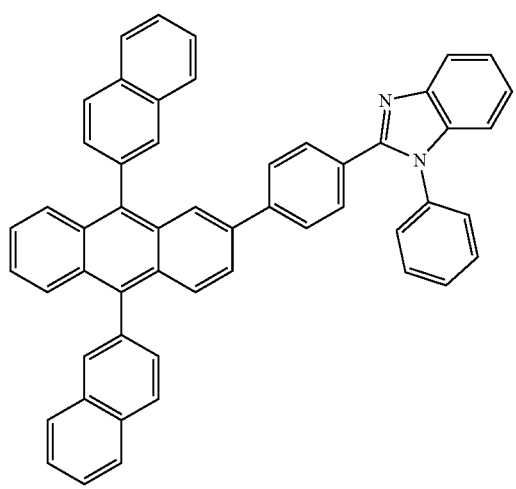

ET2

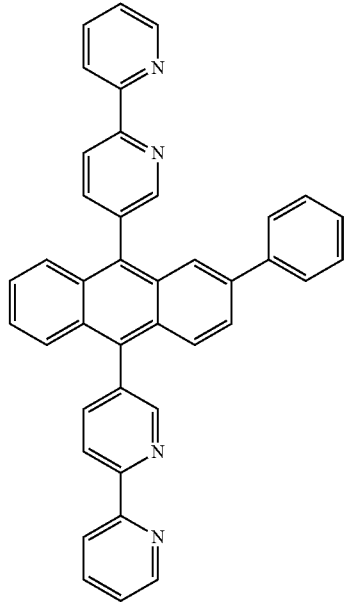

ET3

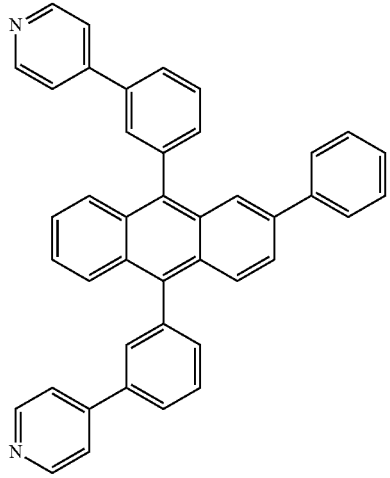

ET4

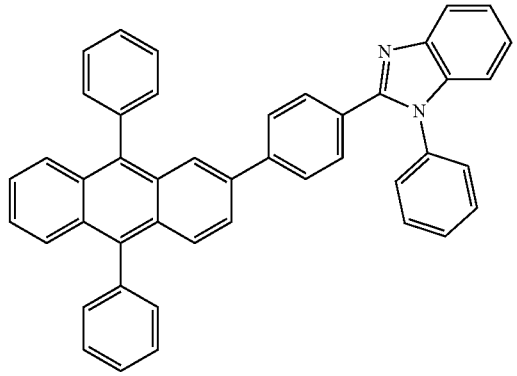

ET5
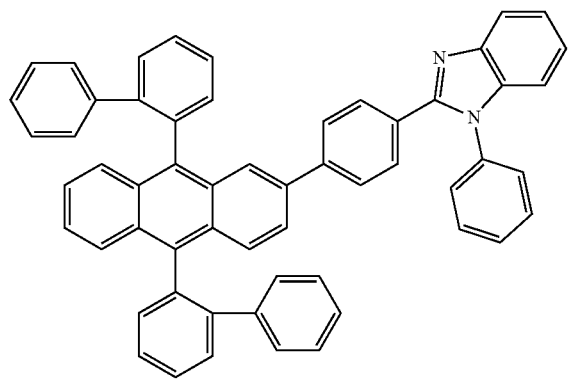
ET6
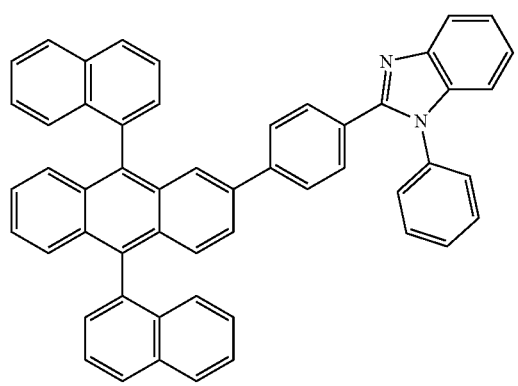
ET7
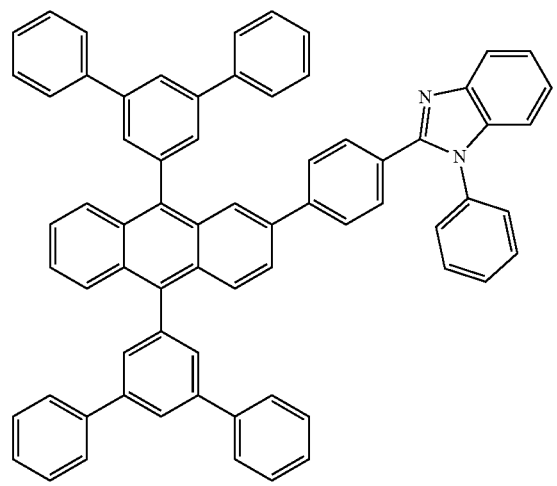
ET8
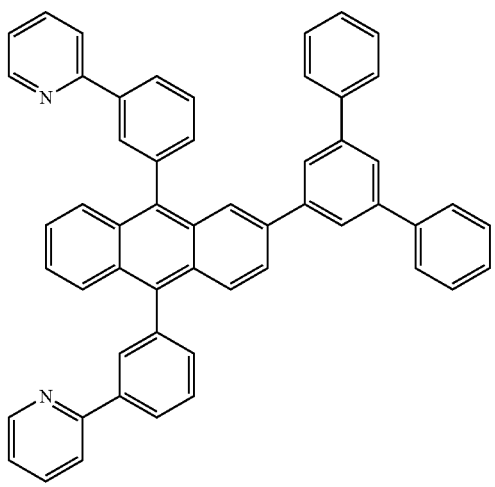
ET9
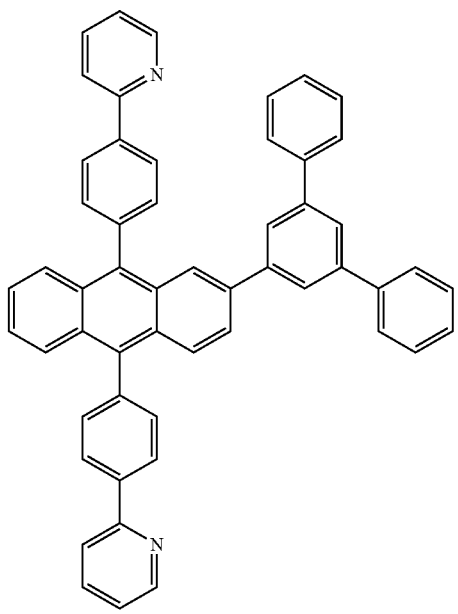

ET10
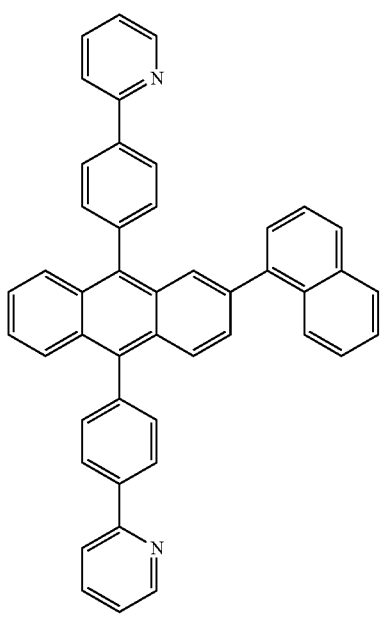
ET11
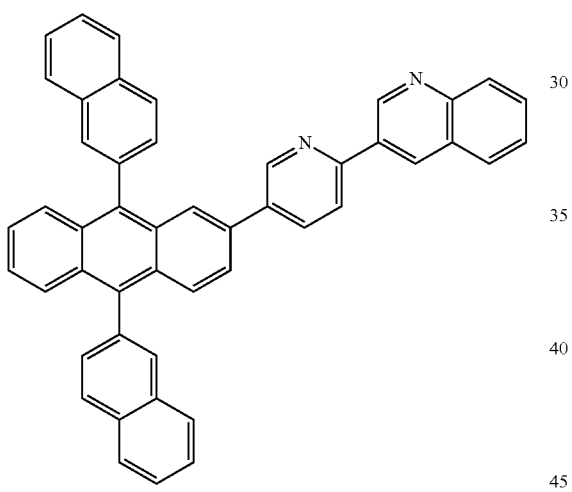
ET12
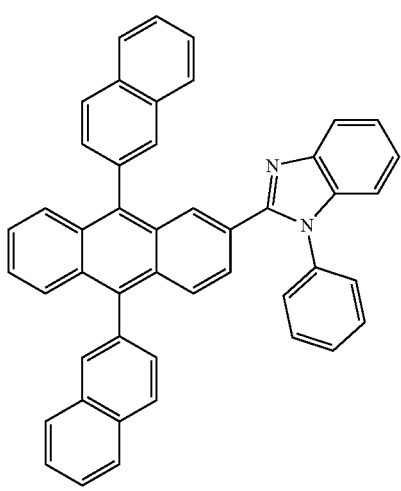
ET13
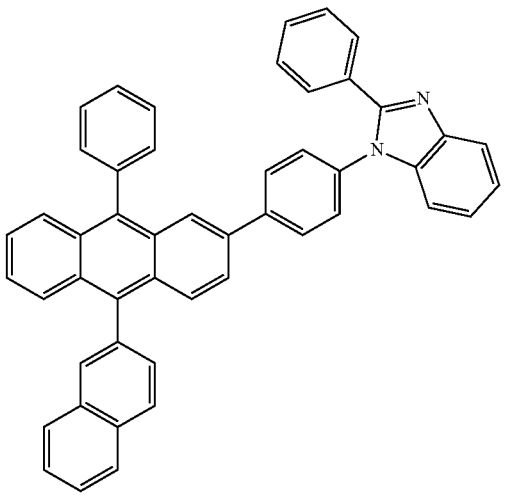
ET14
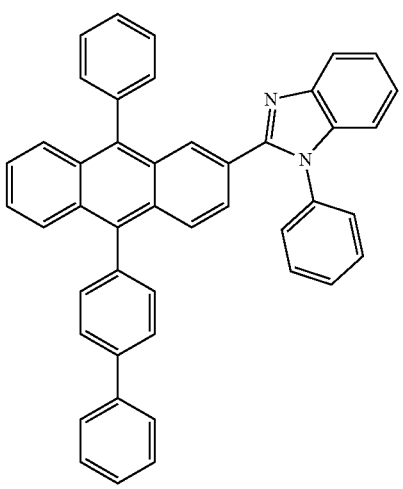
ET15
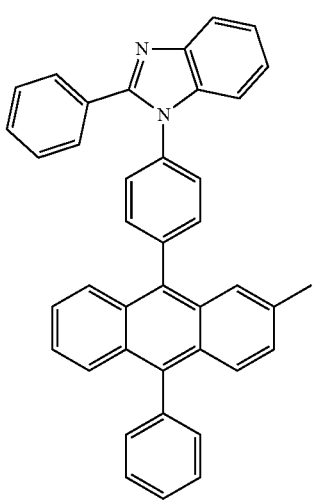

ET16
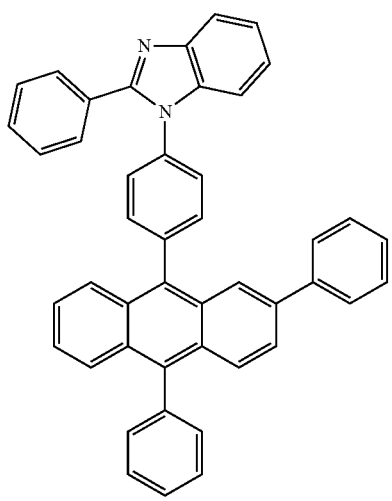
ET17
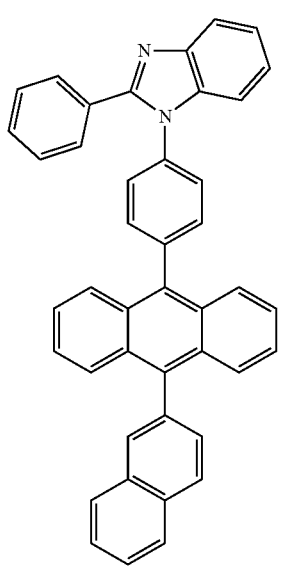
ET18
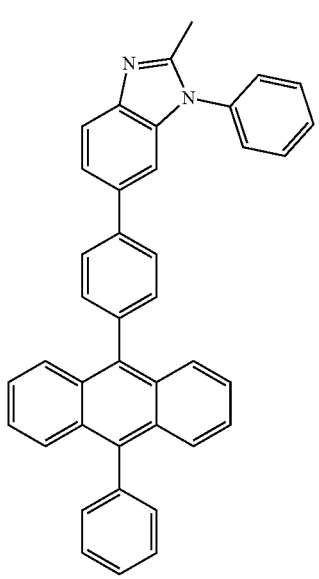
ET19
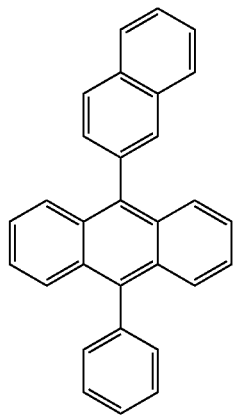
ET20
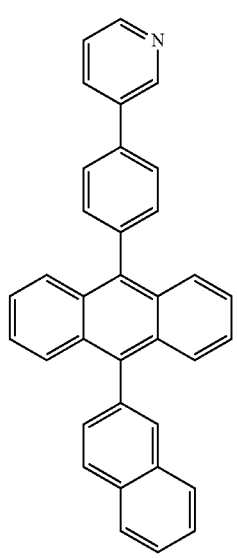
ET21
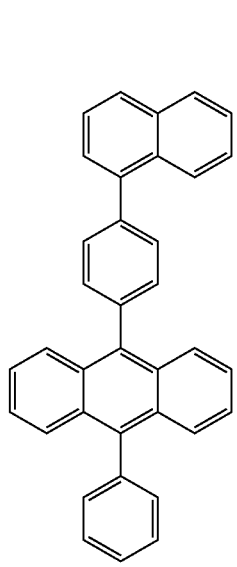

ET22
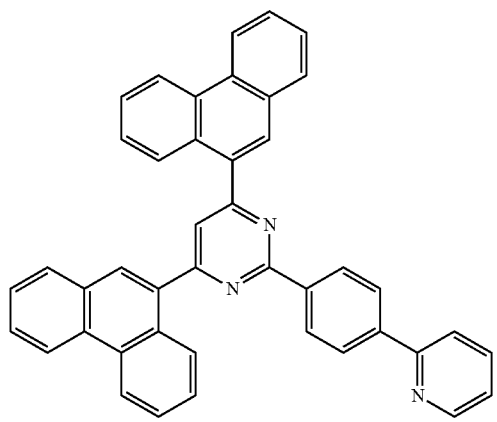
ET25
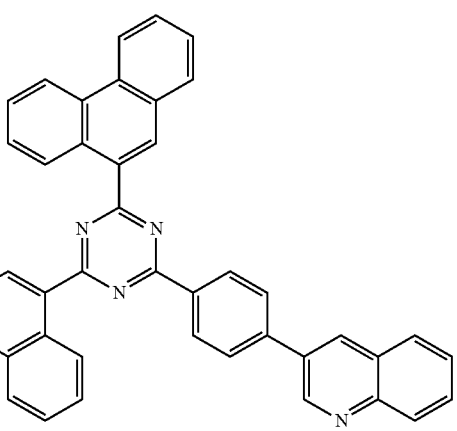
ET23
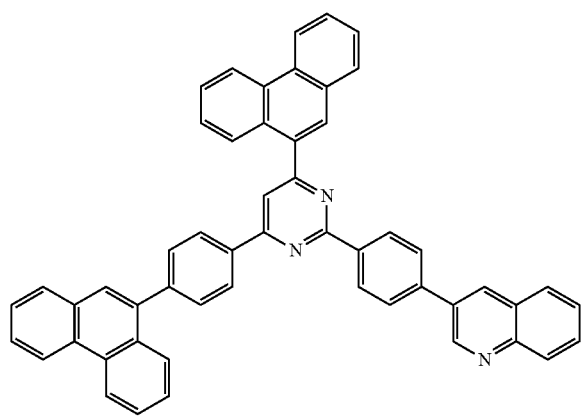
ET26
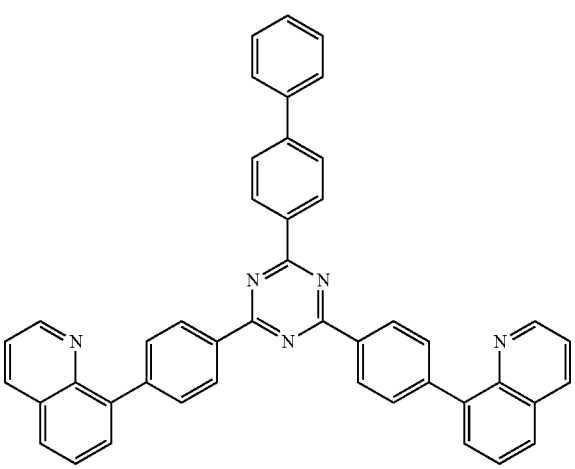
ET24
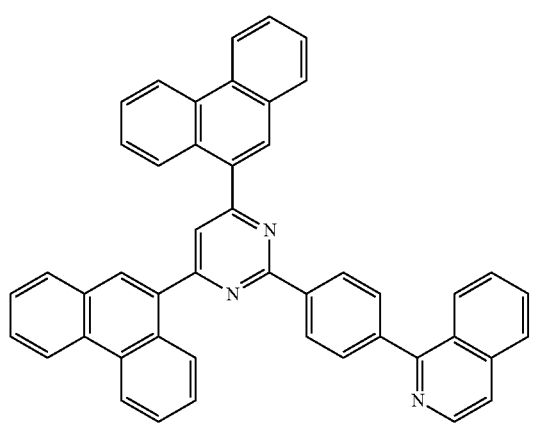
ET27
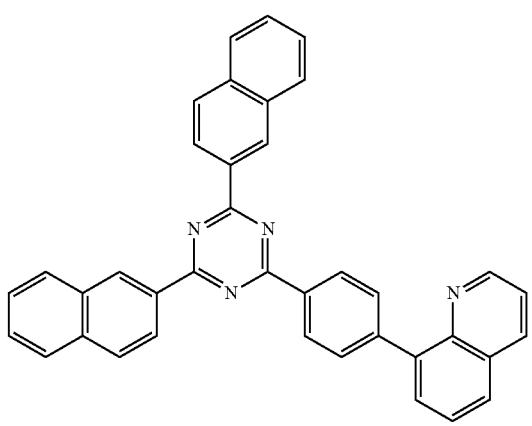

ET28
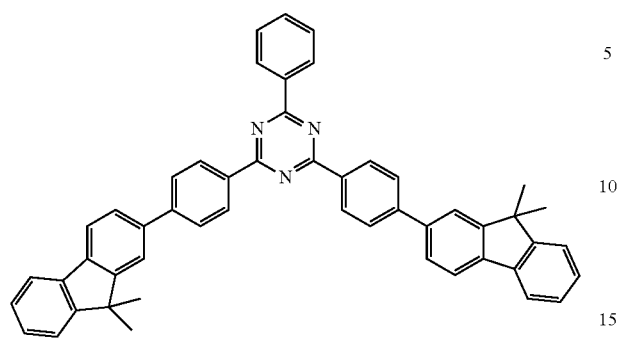
ET29
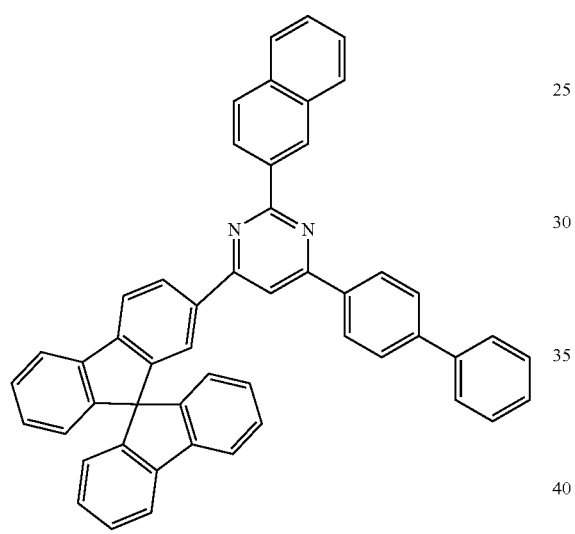
ET30
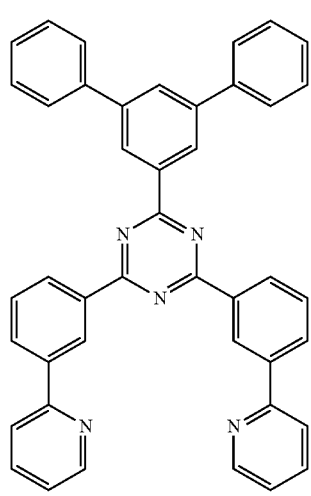
ET31
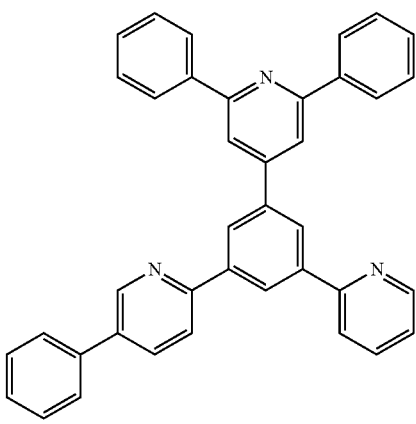
ET32
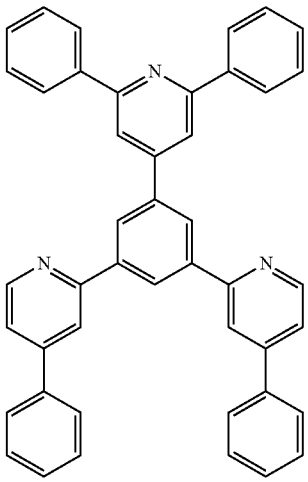
ET33
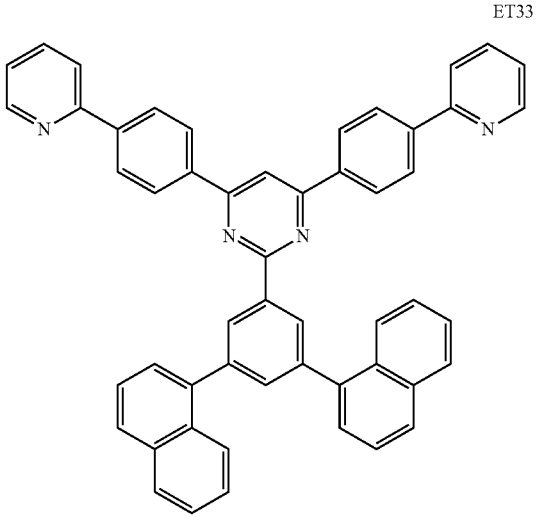

ET34

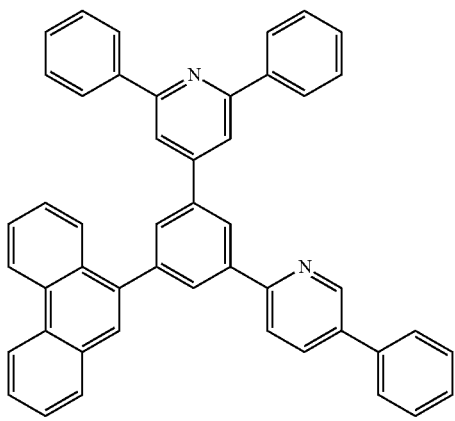

BCP

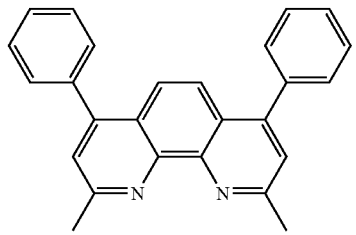

Bphen

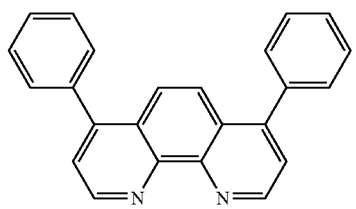

Alq₃

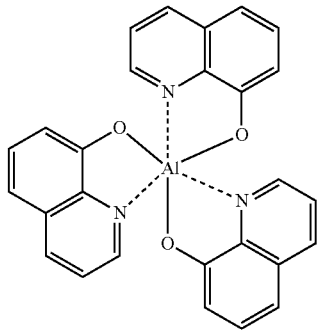

ET35

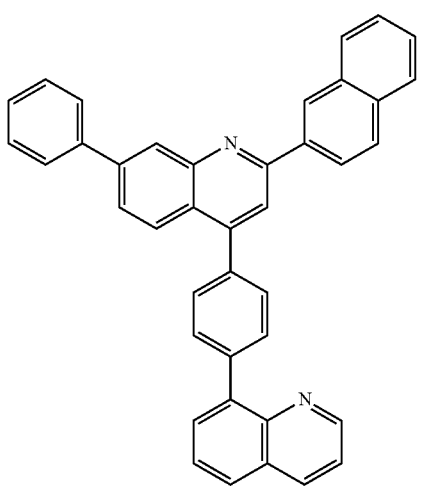

BAlq

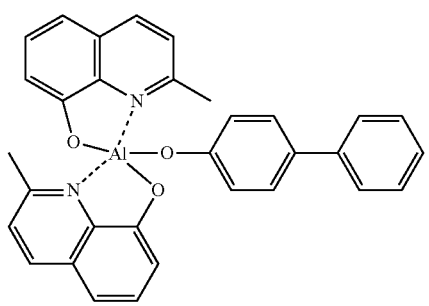

TAZ

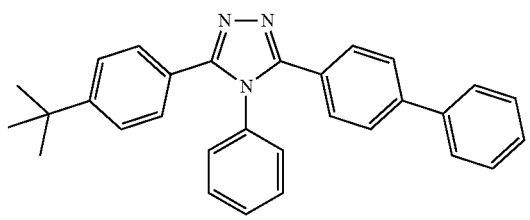

ET36

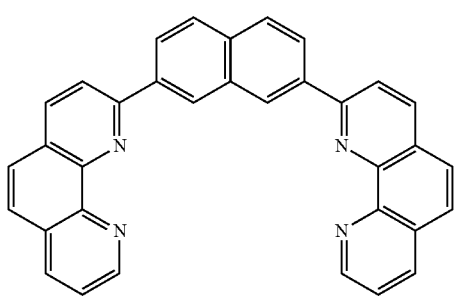

NTAZ

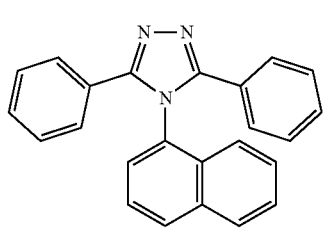

In some embodiments, the electron transport region 17 may include 2,9-dimethyl-4,7-diphenyl-1,10-phenanthroline (BCP), 4,7-diphenyl-1,10-phenanthroline (Bphen), Alq₃, BAlq, 3-(biphenyl-4-yl)-5-(4-tert-butylphenyl)-4-phenyl-4H-1,2,4-triazole (TAZ), NTAZ, DBFPO, or any combination thereof. In some embodiments, when the electron transport region 17 includes a hole blocking layer, the hole blocking layer may include BCP or Bphen:

The thicknesses of the buffer layer, the hole blocking layer, or the electron control layer may each independently be in a range of about 20 Å to about 1,000 Å, and in some embodiments, about 30 Å to about 300 Å. When the thicknesses of the buffer layer, the hole blocking layer or the electron control layer are within any of these ranges, excellent hole blocking characteristics or excellent electron controlling characteristics may be obtained without a substantial increase in driving voltage.

The thickness of the electron transport layer may be in a range of about 100 Å to about 1,000 Å, and in some embodiments, about 150 Å to about 500 Å. When the thickness of the electron transport layer is within any of these ranges, excellent electron transport characteristics may be obtained without a substantial increase in driving voltage.

The electron transport region 17 (e.g., the electron transport layer in the electron transport region 17) may further include, in addition to the materials described above, a material including metal.

The metal-containing material may include an alkali metal complex, an alkaline earth metal complex, or any combination thereof. A metal ion of the alkali metal complex may be a lithium (Li) ion, a sodium (Na) ion, a potassium (K) ion, a rubidium (Rb) ion, a cesium (Cs) ion, or any combination thereof. A metal ion of the alkaline earth metal complex may be a beryllium (Be) ion, a magnesium (Mg) ion, a calcium (Ca) ion, a strontium (Sr) ion, a barium (Ba) ion, or any combination thereof. Each ligand coordinated with the metal ion of the alkali metal complex and the alkaline earth metal complex may independently be hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, cyclopentadiene, or any combination thereof.

For example, the metal-containing material may include a Li complex. The Li complex may include, e.g., Compound ET-D1 (LiQ) or Compound ET-D2:

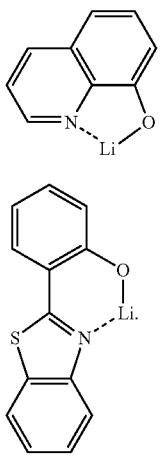

ET-D1

ET-D2

The electron transport region 17 may include an electron injection layer that facilitates injection of electrons from the second electrode 19. The electron injection layer may be in direct contact with the second electrode 19.

The electron injection layer may have i) a single-layered structure consisting of a single layer consisting of a single material, ii) a single-layered structure consisting of a single layer including a plurality of different materials, or iii) a multi-layered structure having a plurality of layers, each including a plurality of different materials.

The electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof.

The alkali metal may be Li, Na, K, Rb, Cs or any combination thereof. In some embodiments, the alkali metal may be Li, Na, or Cs. In an embodiment, the alkali metal may be Li or Cs.

The alkaline earth metal may be Mg, Ca, Sr, Ba, or any combination thereof.

The rare earth metal may be Sc, Y, Ce, Tb, Yb, Gd, or any combination thereof.

The alkali metal compound, the alkaline earth metal compound, and the rare earth metal compound may respectively be oxides, halides (e.g., fluorides, chlorides, bromides, or iodides), or any combination thereof of each of the alkali metal, the alkaline earth metal, and the rare earth metal.

The alkali metal compound may be one of alkali metal oxides such as $Li_2O$, $Cs_2O$, or $K_2O$, one of alkali metal halides such as LiF, NaF, CsF, KF, LiI, NaI, CsI, or KI, or any combination thereof. In some embodiments, the alkali metal compound may include LiF, $Li_2O$, NaF, LiI, NaI, CsI, KI, or any combination thereof.

The alkaline earth-metal compound may include one of alkaline earth-metal compounds, such as BaO, SrO, CaO, $Ba_xSr_{1-x}O$ (wherein 0<x<1), or $Ba_xCa_{1-x}O$ (wherein 0<x<1), or any combination thereof. In some embodiments, the alkaline earth metal compound may include BaO, SrO, CaO, or any combination thereof.

The rare earth metal compound may include $YbF_3$, $SCF_3$, $SCO_3$, $Y_2O_3$, $Ce_2O_3$, $GdF_3$, $TbF_3$, or any combination thereof. In some embodiments, the rare earth metal compound may include $YbF_3$, $SCF_3$, $TbF_3$, $YbI_3$, $ScI_3$, $TbI_3$, or any combination thereof.

The alkali metal complex, the alkaline earth metal complex, and the rare earth metal complex may each include ions of the above-described alkali metal, alkaline earth metal, and rare earth metal. Each ligand coordinated with the metal ion of the alkali metal complex, the alkaline earth metal complex, and the rare earth metal complex may independently include hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, cyclopentadiene, or any combination thereof.

The electron injection layer may consist of an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof, as described above. In some embodiments, the electron injection layer may further include an organic material. When the electron injection layer further includes an organic material, the alkali metal, the alkaline earth metal, the rare earth metal, the alkali metal compound, the alkaline earth metal compound, the rare earth metal compound, the alkali metal complex, the alkaline earth metal complex, the rare earth metal complex, or a combination thereof may be homogeneously or non-homogeneously dispersed in a matrix including the organic material.

The thickness of the electron injection layer may be in a range of about 1 Å to about 100 Å, and in some embodiments, about 3 Å to about 90 Å. When the thickness of the electron injection layer is within any of these ranges, excellent electron injection characteristics may be obtained without a substantial increase in driving voltage.

Second Electrode 19

The second electrode 19 may be on the organic layer 10A. In an embodiment, the second electrode 19 may be a cathode that is an electron injection electrode. In this embodiment, a material for forming the second electrode 19 may be a material having a low work function, for example, a metal, an alloy, an electrically conductive compound, or a combination thereof.

The second electrode 19 may include lithium (Li), silver (Ag), magnesium (Mg), aluminum (Al), aluminum-lithium (Al—Li), calcium (Ca), magnesium-indium (Mg-ln), magnesium-silver (Mg—Ag), ITO, IZO, or any combination thereof. The second electrode 19 may be a transmissive electrode, a semi-transmissive electrode, or a reflective electrode.

The second electrode 19 may have a single-layered structure, or a multi-layered structure including two or more layers.

General Definitions of Terms

The term "$C_1$-$C_{60}$ alkyl group" as used herein refers to a linear or branched saturated aliphatic hydrocarbon monovalent group having 1 to 60 carbon atoms, and the term "$C_1$-$C_{60}$ alkylene group" as used herein refers to a divalent group having the same structure as the $C_1$-$C_{60}$ alkyl group.

Examples of the $C_1$-$C_{60}$ alkyl group, the $C_1$-$C_{20}$ alkyl group, and/or the $C_1$-$C_{10}$ alkyl group may include a methyl group, an ethyl group, an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, or a tert-decyl group, each unsubstituted or substituted with a methyl group, an ethyl group, an n-propyl group, an iso-propyl group, an n-butyl group, a sec-butyl group, an isobutyl group, a tert-butyl group, an n-pentyl group, a tert-pentyl group, neopentyl group, an isopentyl group, a sec-pentyl group, a 3-pentyl group, a sec-isopentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, or any combination thereof.

The term "$C_1$-$C_{60}$ alkoxy group" as used herein refers to a monovalent group represented by —$OA_{101}$ (wherein $A_{101}$ is a $C_1$-$C_1$ alkyl group). Examples thereof include a methoxy group, an ethoxy group, a propoxy group, a butoxy group, and a pentoxy group.

The term "$C_2$-$C_{60}$ alkenyl group" as used herein refers to a group formed by placing at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alk-enylene group" as used herein refers to a divalent group having the same structure as the $C_2$-$C_{60}$ alkenyl group.

The term "$C_2$-$C_{60}$ alkynyl group" as used herein refers to a group formed by placing at least one carbon-carbon triple bond in the middle or at the terminus of the $C_2$-$C_{60}$ alkyl group. Examples thereof include an ethenyl group and a propenyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms. The term "$C_3$-$C_{10}$ cycloalkylene group" as used herein refers to a divalent group having the same structure as the $C_3$-$C_{10}$ cycloalkyl group.

Examples of the $C_3$-$C_{10}$ cycloalkyl group as used herein include a cyclopropyl group, a cyclobutyl group, a cyclopentyl group, a cyclohexyl group, a cycloheptyl group, a cyclooctyl group, an adamantanyl group, a norbornanyl (bicyclo[2.2.1]heptyl) group, a bicyclo[1.1.1]pentyl group, a bicyclo[2.1.1]hexyl group, and a bicyclo[2.2.2]octyl group.

The term "$C_1$-$C_{10}$ heterocycloalkyl group" as used herein refers to a monovalent monocyclic group having 1 to 10 carbon atoms and at least one heteroatom of N, O, P, Si, S, Se, Ge, B, or any combination thereof as ring-forming atoms. The term "$C_1$-$C_{10}$ heterocycloalkylene group" as used herein refers to a divalent group having the same structure as the $C_1$-$C_{10}$ heterocycloalkyl group.

Examples of the $C_1$-$C_{10}$ heterocycloalkyl group as used herein may include a silolanyl group, a silinanyl group, a tetrahydrofuranyl group, a tetrahydro-2H-pyranyl group, or a tetrahydrothiophenyl group.

The term "$C_3$-$C_{10}$ cycloalkenyl group" as used herein refers to a monovalent monocyclic group that has 3 to 10 carbon atoms and at least one carbon-carbon double bond in its ring, wherein the molecular structure as a whole is non-aromatic. Examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monocyclic group including at least one heteroatom of N, O, P, Si, S, Se, Ge, B, or any combination thereof as ring-forming atoms, 1 to 10 carbon atoms, and at least one double bond in its ring. Examples of the $C_1$-$C_{10}$ heterocycloalkenyl group include a 2,3-dihydrofuranyl group and a 2,3-dihydrothiophenyl group. The term "$C_1$-$C_{10}$ heterocycloalkylene group" as used herein refers to a divalent group having the same structure as the $C_1$-$C_{10}$ heterocycloalkyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include a plurality of rings, the plurality of rings may be fused to each other.

The term "$C_1$-$C_{60}$ heteroaryl group" as used herein refers to a monovalent group having a heterocyclic aromatic system having at least one heteroatom of N, O, P, Si, S, Se, Ge, B, or any combination thereof as ring-forming atoms and 1 to 60 carbon atoms. The term "$C_1$-$C_{60}$ heteroarylene group" as used herein refers to a divalent group having a heterocyclic aromatic system having at least one heteroatom of N, O, P, Si, S, Se, Ge and B as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the plurality of rings may be fused to each other.

The term "$C_6$-$C_{60}$ aryloxy group" as used herein is represented by —$OA_{102}$ (wherein $A_{102}$ is the $C_6$-$C_{60}$ aryl group). The term "$C_6$-$C_{60}$ arylthio group" as used herein is represented by —$SA_{103}$ (wherein $A_{103}$ is the $C_6$-$C_{60}$ aryl group).

The term "monovalent non-aromatic condensed polycyclic group" as used herein refers to a monovalent group having two or more rings condensed and only carbon atoms (for example, the number of carbon atoms may be in a range of 8 to 60) as ring-forming atoms, wherein the molecular structure as a whole is non-aromatic. Examples of the non-aromatic condensed polycyclic group include a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group having at least two rings condensed and a heteroatom selected from N, O, P, Si, S, Se, Ge, and B as well as carbon atoms (for example, the number of carbon atoms may be in a range of 1 to 60) as ring-forming atoms, wherein the molecular structure as a whole is non-aromatic. Examples of the monovalent non-aromatic condensed heteropolycyclic group include a carbazolyl group. The term "divalent non-aromatic condensed heteropolycyclic group" as used herein refers to a divalent group having substantially the same structure as the monovalent non-aromatic condensed heteropolycyclic group.

The term "π electron-depleted nitrogen-containing $C_1$-$C_{60}$ cyclic group" as used herein refers to a cyclic group having 1 to 60 carbon atoms and including at least one *—N=*' (wherein * and *' each indicate a binding site to an adjacent atom) as a ring-forming moiety. For example, the π electron-depleted nitrogen-containing $C_1$-$C_{60}$ cyclic group may be a) a first ring, b) a condensed ring in which at least two first rings are condensed, or c) a condensed ring in which at least one first ring and at least one second ring are condensed.

The term "π electron-rich $C_3$-$C_{60}$ cyclic group" as used herein refers to a cyclic group having 3 to 60 carbon atoms and not including at least one *—N=*' (wherein * and *' each indicate a binding site to an adjacent atom) as a ring-forming moiety. For example, the π electron-rich $C_3$-$C_{60}$ cyclic group may be a) a second ring or b) a condensed ring in which at least two second rings are condensed.

The "$C_5$-$C_{60}$ cyclic group" as used herein refers to a monocyclic or polycyclic group having 5 to 60 carbon atoms, e.g., a) a third ring or b) a condensed ring in which at least two third rings are condensed.

The "$C_1$-$C_{60}$ heterocyclic group" as used herein refers to a monocyclic or polycyclic group including at least one heteroatom and 1 to 60 carbon atoms, e.g., a) a fourth ring, b) a condensed ring in which at least two fourth rings are condensed, or c) a condensed ring in which at least one third ring is condensed with at least one fourth ring.

The "first ring" as used herein may be an imidazole group, a pyrazole group, a thiazole group, an isothiazole group, an oxazole group, an isoxazole group, a pyridine group, a pyrazine group, a pyridazine group, a pyrimidine group, a triazole group, a tetrazole group, an oxadiazole group, a triazine group, or a thiadiazole group.

The "second ring" as used herein may be a benzene group, a cyclopentadiene group, a pyrrole group, a furan group, a thiophene group, or a silole group.

The "third ring" as used herein may be a cyclopentane group, a cyclopentadiene group, an indene group, an adamantane group, a norbornene group, a bicyclo[1.1.1]pentane group, a bicyclo[2.1.1]hexane group, a bicyclo[2.2.1]heptane group (a norbornane group), a bicyclo[2.2.2]octane group, a cyclohexane group, a cyclohexene group, or a benzene group.

The "fourth ring" as used herein may be a furan group, a thiophene group, a pyrrole group, a silole group, an oxazole group, an isoxazole group, an oxadiazole group, an isooxadiazole group, oxatriazole group, an isooxatriazole group, a thiazole group, an isothiazole group, a thiadiazole group, an isothiadiazole group, a thiatriazole group, an isotriazole group, a pyrazole group, an imidazole group, a triazole group, a tetrazole group, an azasilole group, a diazasilole group, a trazasilole group, a pyridine group, a pyrimidine group, a pyrazine group, a pyridazine group, or a triazine group.

In some embodiments, the π electron-depleted nitrogen-containing $C_1$-$C_{60}$ cyclic group may be an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, an azadibenzofuran group, an azadibenzothiophene group, an azadibenzosilole group, an acridine group, or a pyridopyrazine group:

In one or more embodiments, the π electron-rich $C_3$-$C_{60}$ cyclic group may be a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, an indene group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, atriindolobenzene group, a pyrrolophenanthrene group, a furanophenanthrene group, a thienophenanthrene group, a benzonaphthofuran group, a benzonapthothiophene group, an (indolo)phenanthrene group, a (benzofurano) phenanthrene group, or a (benzothieno)phenanthrene group.

For example, the $C_5$-$C_{60}$ carbocyclic group may be a cyclopentane group, a cyclohexane group, a cyclohexene group, a benzene group, a naphthalene group, an anthracene group, a phenanthrene group, a triphenylene group, a pyrene group, a chrysene group, a 1,2,3,4-tetrahydronaphthalene group, a cyclopentadiene group, an indene group, a fluorene group, a 5,6,7,8-tetrahydroisoquinoline group, a 5,6,7,8-tetrahydroquinoline group, an adamantane group, a norbornane group, or a norbornene group.

For example, the $C_1$-$C_{60}$ heterocyclic group may be a thiophene group, a furan group, a pyrrole group, a cyclopentadiene group, a silole group, a borole group, a phosphole group, a selenophene group, a germole group, a benzothiophene group, a benzofuran group, an indole group, an indene group, a benzosilole group, a benzoborole group, a benzophosphole group, a benzoselenophene group, a benzogermole group, a dibenzothiophene group, a dibenzofuran group, a carbazole group, a dibenzosilole group, a dibenzoborole group, a dibenzophosphole group, a dibenzoselenophene group, a dibenzogermole group, a dibenzothiophene 5-oxide group, a 9H-fluorene-9-one group, a dibenzothiophene 5,5-dioxide group, an azabenzothiophene group, an azabenzofuran group, an azaindole group, an azaindene group, an azabenzosilole group, an azabenzoborole group, an azabenzophosphole group, an azabenzoselenophene group, an azabenzogermole group, an azadibenzothiophene group, an azadibenzofuran group, an azacarbazole group, an azafluorene group, an azadibenzosilole group, an azadibenzoborole group, an azadibenzophosphole group, an azadibenzoselenophene group, an azadibenzogermole group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, or a benzothiadiazole group.

The π electron-depleted nitrogen-containing $C_1$-$C_{60}$ cyclic group, a the π electron-rich $C_3$-$C_{60}$ cyclic group, the $C_5$-$C_{60}$ cyclic group, and the $C_1$-$C_{60}$ heterocyclic group may each be a part of a condensed ring or a monovalent, divalent, trivalent, quadvalent, pentavalent, or hexavalent, group, depending on the structure of the formula.

A substituent of the substituted π electron-depleted nitrogen-containing $C_1$-$C_{60}$ cyclic group, the substituted π electron-rich $C_3$-$C_{60}$ cyclic group, the substituted $C_5$-$C_{60}$ cyclic group, the substituted $C_1$-$C_{60}$ heterocyclic group, the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may each independently be:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkylheteroaryl group, a monovalent non-aromatic condensed polycyclic group, a monovalent non-aromatic condensed heteropolycyclic group, —N(Q$_{11}$)(Q$_{12}$), —Si(Q$_{13}$)(Q$_{14}$)(Q$_{15}$), —Ge(Q$_{13}$)(Q$_{14}$)(Q$_{15}$), —B(Q$_{16}$)(Q$_{17}$), —P(=O)(Q$_{18}$)(Q$_{19}$), —P(Q$_{18}$)(Q$_{19}$), or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a monovalent non-aromatic condensed polycyclic group, or a monovalent non-aromatic condensed heteropolycyclic group, each unsubstituted or substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a monovalent non-aromatic condensed polycyclic group, a monovalent non-aromatic condensed heteropolycyclic group, —N(Q$_{21}$)(Q$_{22}$), —Si(Q$_{23}$)(Q$_{24}$)(Q$_{25}$), —Ge(Q$_{23}$)(Q$_{24}$)(Q$_{25}$), —B(Q$_{26}$)(Q$_{27}$), —P(=O)(Q$_{28}$)(Q$_{29}$), —P(Q$_{28}$)(Q$_{29}$), or any combination thereof;

—N(Q$_{31}$)(Q$_{32}$), —Si(Q$_{33}$)(Q$_{34}$)(Q$_{35}$), —Ge(Q$_{33}$)(Q$_{34}$)(Q$_{35}$), —B(Q$_{36}$)(Q$_{37}$), —P(=O)(Q$_{38}$)(Q$_{39}$), or —P(Q$_{38}$)(Q$_{39}$); or any combination thereof.

$Q_1$ to $Q_9$, $Q_{11}$ to $Q_{19}$, $Q_{21}$ to $Q_{29}$, and $Q_{31}$ to $Q_{39}$ may each independently be: hydrogen; deuterium; —F; —Cl; —Br; —I; a hydroxyl group; a cyano group; a nitro group; an amidino group; a hydrazine group; a hydrazone group; a carboxylic acid group or a salt thereof; a sulfonic acid group or a salt thereof; a phosphoric acid group or a salt thereof; a $C_1$-$C_{60}$ alkyl group unsubstituted or substituted with deuterium, a $C_1$-$C_{60}$ alkyl group, a $C_6$-$C_{60}$ aryl group, or any combination thereof; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group unsubstituted or substituted with deuterium, a $C_1$-$C_{60}$ alkyl group, a $C_6$-$C_{60}$ aryl group, or any combination thereof; a $C_6$-$C_{60}$ aryloxy group; a $C_6$-$C_{60}$ arylthio group; a $C_1$-$C_{60}$ heteroaryl group; a monovalent non-aromatic condensed polycyclic group; or a monovalent non-aromatic condensed heteropolycyclic group.

For example, $Q_1$ to $Q_9$, $Q_{11}$ to $Q_{19}$, to $Q_{29}$, and to $Q_{39}$ may each independently be:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, or —$CD_2CDH_2$;

an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, a $C_1$-$C_{10}$ alkyl group, a phenyl group, or any combination thereof.

The term "room temperature" as used herein refers to a temperature of about 25° C.

The terms "a biphenyl group, a terphenyl group, and a tetraphenyl group" as used herein each refer to a monovalent group having two, three, and four phenyl groups linked via a single bond, respectively.

The terms "a cyano group-containing phenyl group, a cyano group-containing biphenyl group, a cyano group-containing terphenyl group, and a cyano group-containing tetraphenyl group" as used herein each refer to a phenyl group, a biphenyl group, a terphenyl group, and a tetraphenyl group, each substituted with at least one cyano group. In "the cyano group-containing phenyl group, the cyano group-containing biphenyl group, the cyano group-containing terphenyl group, and the cyano group-containing tetraphenyl group", a cyano group may be substituted at any position, and "the cyano group-containing phenyl group, the cyano group-containing biphenyl group, the cyano group-containing terphenyl group, and the cyano group-containing tetraphenyl group" may further include a substituent in addition to a cyano group. For example, 'a phenyl group substituted with a cyano group' and 'a phenyl group substituted with a methyl group' all belong to "a cyano group-containing phenyl group".

Hereinafter, a compound and an organic light-emitting device according to an embodiment will be described in detail with reference to Synthesis Examples and Embodiments, however, the present disclosure is not limited thereto. The wording "B was used instead of A" used in describing Synthesis Examples means that an identical molar equivalent of B was used in place of A.

EXAMPLES

Synthesis Example 1 (Compound 18)

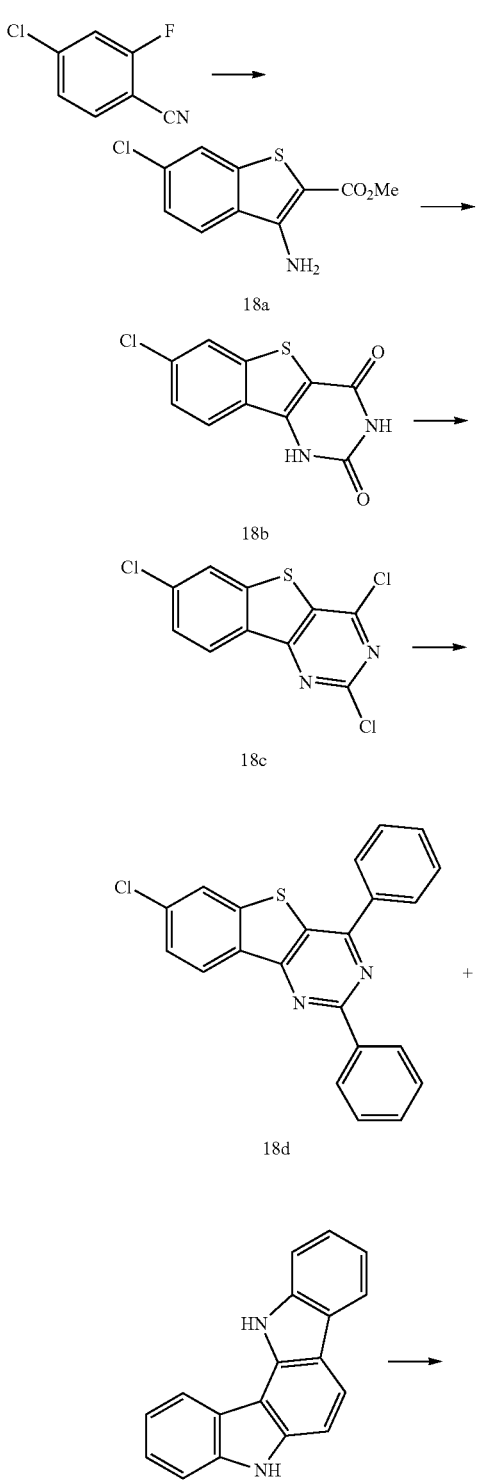

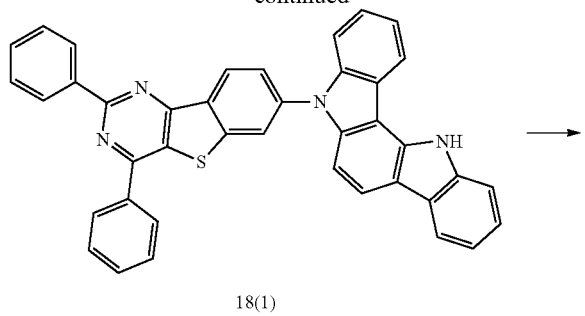

18(1)

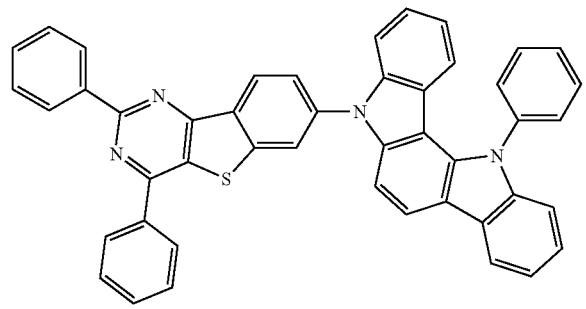

18

Synthesis of Intermediate 18a 25 grams (g) of 4-chloro-2-fluorobenzonitrile (160.71 mmol) and dimethyl formamide (DMF) were added to a reaction vessel, and the temperature was lowered to 0° C. by using an ice bath. Subsequently, 29.16 g of methyl 2-mercaptoacetate (321.42 mmol) was slowly added dropwise thereto, and 33.98 g of sodium tert-butoxide (353.56 mmol) was slowly added dropwise thereto. The resulting reaction product was stirred at a temperature of 10° C. for 1 hour. Once the reaction was complete, distilled water was added thereto for precipitation. The precipitate was filtered to obtain 34.18 g of Intermediate 18a (yield: 88%).

LC-Mass (calculated value: 241.69 g/mol, found value: $M^{+1}$=242 g/mol)

Synthesis of Intermediate 18b 34 g of Intermediate 18a (140.68 mmol) and dichloromethane ($CH_2Cl_2$) were added to a reaction vessel, and the temperature of the reaction vessel was lowered to −78° C. by using dry ice. Then, 18.21 g of chlorosulfonyl isocyanate (211.01 mmol) was slowly added dropwise thereto, followed by heating up to room temperature and stirring for 1 hour. Once the reaction was complete, the resulting solid was filtered, and the obtained solid was stirred at a temperature of 100° C. for 2 hours in 1N HCl aqueous solution, followed by cooling to room temperature. Then, the resulting solid product was filtered, the filtrate neutralized by using $K_2CO_3$ aqueous solution, followed by filtration and drying. The crude product resulting therefrom was heated in NaOH aqueous solution at a temperature of 100° C. for 2 hours. The reaction product resulting therefrom was cooled to room temperature, and HCl was used to adjust the pH to 4 to 5. The resulting solid was filtered to obtain a solid product. The obtained solid product was recrystallized using acetone to thereby obtain 21.33 g of Intermediate 18b (yield: 60%).

LC-Mass (calculated value: 252.67 g/mol, found value: $M^{+1}$=253 g/mol)

Synthesis of Intermediate 18c 20 g of Intermediate 18b (79.15 mmol) and $POCl_3$ 7 eq. were added to a reaction vessel, and N,N-dimethyl acetamide (DMA) was added thereto, followed by stirring at a temperature of 110° C. for 12 hours while heating. Once the reaction was complete, the reaction product was slowly added dropwise to an ice bath to form a precipitate, followed by filtration of the resulting solid. After washing with acetone and drying, 18.11 g of Intermediate 18c was obtained (yield: 79%).

LC-Mass (calculated value: 289.56 g/mol, found value: $M^{+1}$=290 g/mol)

Synthesis of Intermediate 18d 11.9 g of 1-bromo-4-chlorobenzene (62.16 mmol) and 80 mL of tetrahydrofuran (THF) were mixed, and the mixed solution was heated with 1.3 g of magnesium (Mg) at a temperature of 50° C. and stirred under reflux. The resulting reaction product was cooled to room temperature, and 15 g of Intermediate 18c (51.8 mmol) was added thereto, followed by heating at a temperature of 50° C. and stirring under reflux. Once the reaction was complete, the reaction mixture was cooled to room temperature, and water and HCl aqueous solution were added thereto. Then, the aqueous solution layer was removed by extraction, and the organic layer was filtered under reduced pressure through silica gel. The resulting filtrate was concentrated under reduced pressure. The resulting product was washed using dichloromethane ($CH_2Cl_2$), ethyl acetate (AcOEt), and ethanol (EtOH) and dried to thereby obtain 12.5 g of Intermediate 18d (yield: 65%).

LC-Mass (calculated value: 372.87 g/mol, found value: $M^{+1}$=373 g/mol)

Synthesis of Intermediate 18(1)

4.0 g of Intermediate 18d (10.73 mmol), 2.5 g of 5-phenyl-5,12-dihydroindolo[3,2-a]carbazole (9.75 mmol), 0.357 g of tris(dibenzylideneacetone)dipalladium (0) ($Pd_2(dba)_3$) (0.39 mmol), and 1.88 g of sodium-tert-butoxide (19.51 mmol) were added to 100 mL of toluene, followed by mixing. Then, 0.229 milliliters (mL) of tris-tert butylphosphine (50 percent by weight (wt %) in toluene) was slowly added dropwise thereto and stirred under reflux. Once the reaction was complete, the resulting mixture was cooled to room temperature, the aqueous solution layer was removed by extraction, and the organic layer was filtered through silica gel under reduced pressure. The obtained filtrate was concentrated under reduced pressure, and the resulting product was separated and purified through silica gel column chromatography. The resulting product was recrystallized using dichloromethane (DCM)/hexane (n-hexane) to thereby obtain 2.32 g of Intermediate 18(1) (yield: 40%).

LC-Mass (calculated value: 592.72 g/mol, found value: $M^{+1}$=593 g/mol)

Synthesis of Compound 18

1.42 g of Compound 18 (yield: 55%) was obtained in substantially the same manner as in Synthesis of Intermediate 18(1), except that 0.67 g of bromobenzene (4.27 mmol) was used instead of Intermediate 18d.

LC-Mass (calculated value: 668.82 g/mol, found value: $M^{+1}$=669 g/mol)

Synthesis Example 2 (Compound 28)
Synthesis Example 3 (Compound 14)
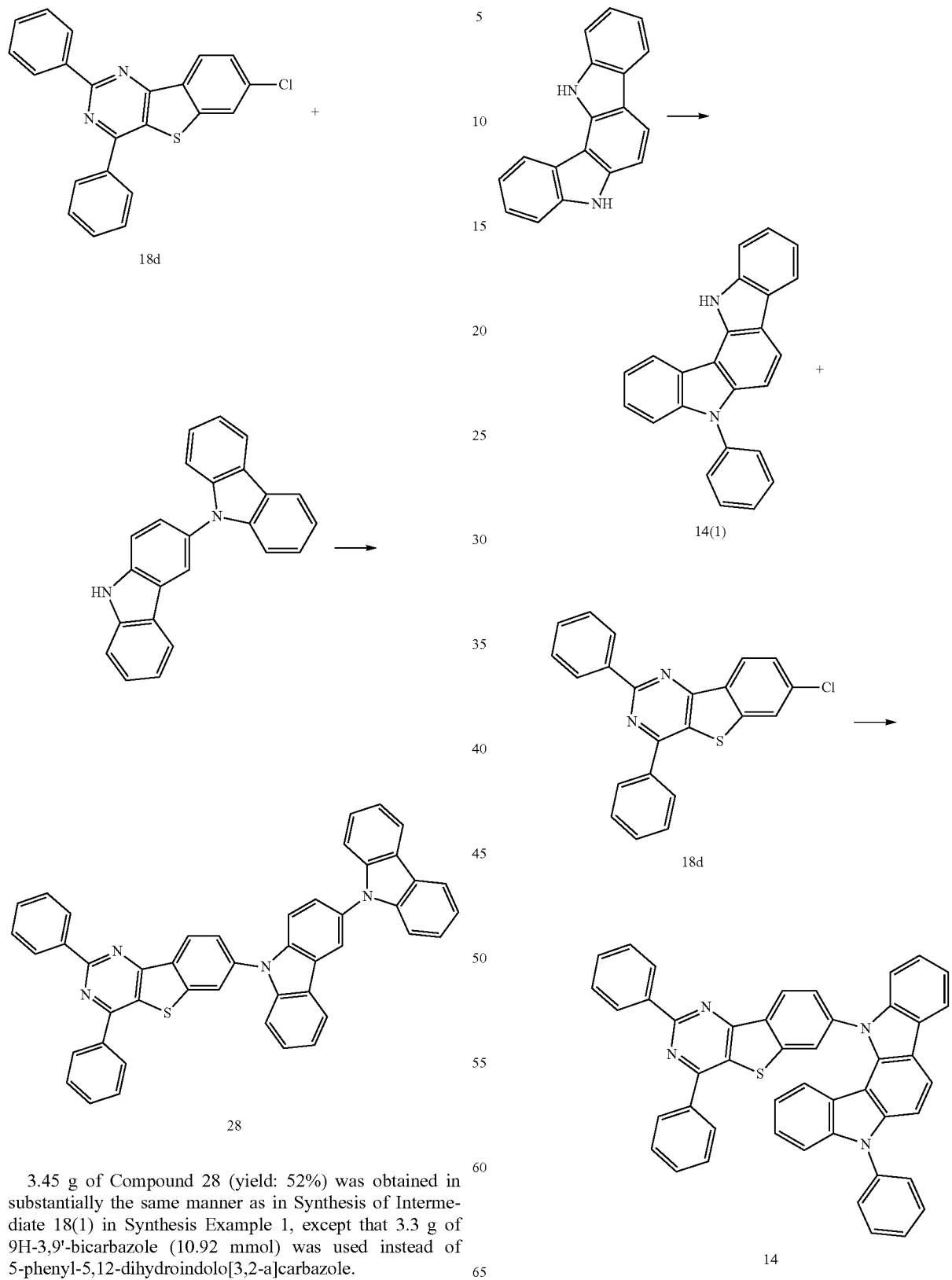
3.45 g of Compound 28 (yield: 52%) was obtained in substantially the same manner as in Synthesis of Intermediate 18(1) in Synthesis Example 1, except that 3.3 g of 9H-3,9'-bicarbazole (10.92 mmol) was used instead of 5-phenyl-5,12-dihydroindolo[3,2-a]carbazole.
LC-Mass (calculated value: 668.82 g/mol, found value: $M^{+1}$=669 g/mol)

Synthesis of Intermediate 14(1)

4.3 g of Intermediate 14(1) (yield: 66%) was obtained in substantially the same manner as in Synthesis of Intermediate 18(1) in Synthesis Example 1, except that 3.36 g of bromobenzene (21.46 mmol) was used instead of Intermediate 18d.

LC-Mass (calculated value: 332.41 g/mol, found value: $M^{+1}$=333 g/mol)

Synthesis of Compound 14

3.2 g of Compound 14 (yield: 50%) was obtained in substantially the same manner as in Synthesis of Intermediate 18(1) in Synthesis Example 1, except that Intermediate 14(1) was used instead of 5-phenyl-5,12-dihydroindolo[3,2-a]carbazole.

LC-Mass (calculated value: 668.82 g/mol, found value: $M^{+1}$=669 g/mol)

Evaluation Example 1: Evaluation on HOMO, LUMO, $T_1$, and $S_1$ Energy Levels

The HOMO, LUMO, $T_1$ and $S_1$ energy levels of the compounds shown in Table 2 were measured according to the method described in Table 1. The results thereof are shown in Table 2:

TABLE 1

| | |
|---|---|
| HOMO energy level evaluation method | A potential (Volts, V) versus current (Amperes, A) graph of each compound was obtained by using cyclic voltammetry (CV) (electrolyte: 0.1 molar (M) $Bu_4NPF_6$/solvent: $CH_2Cl_2$/electrode: 3-electrode system (working electrode: glassy carbon, reference electrode: Ag/AgCl, auxiliary electrode: Pt)). Subsequently, from oxidation onset of the graph, a HOMO energy level of the compound was calculated. |
| LUMO energy level evaluation method | Each compound was diluted at a concentration of $1 \times 10^{-5}$ M in Toluene, and an UV absorption spectrum thereof was measured at room temperature by using a Shimadzu UV-350 spectrometer. A LUMO energy level thereof was calculated by using an optical band gap (Eg) from an edge of the absorption spectrum and a HOMO energy level. |
| $T_1$ energy level evaluation method | A mixture (each compound was dissolved in 3 mL of toluene such that the concentration of each compound was $1 \times 10^{-4}$ M) of toluene and each compound was loaded into a quartz cell. Subsequently, the resultant quartz cell was loaded into liquid nitrogen (77 Kelvins (K)), a photoluminescence spectrum thereof was measured by using a device for measuring photoluminescence. The obtained spectrum was compared with a photoluminescence spectrum measured at room temperature, and peaks observed only at a low temperature were analyzed to calculate onset $T_1$ energy levels. |
| $S_1$ energy level evaluation method | A photoluminescence spectrum of a mixture of each compound, diluted with toluene at a concentration of about $1 \times 10^{-4}$ M, was measured by using a device for measuring photoluminescence at room temperature. The observed peaks were analyzed to calculate onset $S_1$ energy levels. |

TABLE 2

| Compound No. | HOMO (eV) | LUMO (eV) | $T_1$ (eV) | $S_1$ (eV) | $\Delta E_{ST}$ (eV) |
|---|---|---|---|---|---|
| 18 | −5.95 | −2.904 | 2.701 | 2.818 | 0.117 |
| 28 | −5.75 | −2.704 | 2.695 | 2.661 | 0.034 |
| 14 | −5.67 | −2.711 | 2.695 | 2.725 | 0.03 |

18

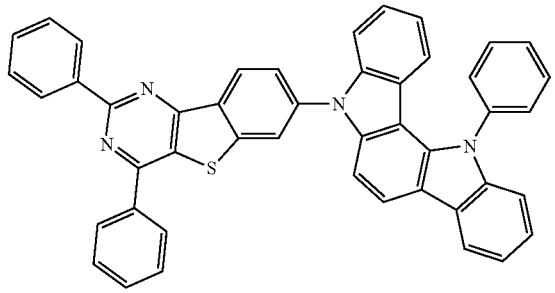

28

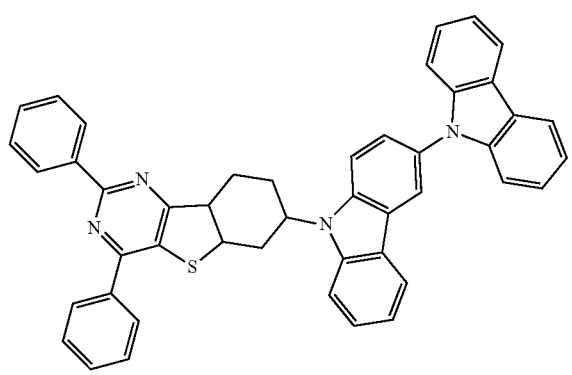

14

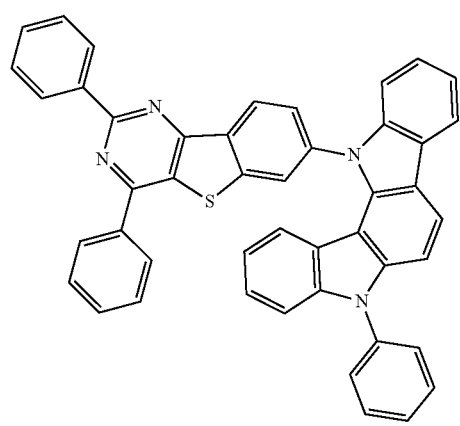

Referring to the results of Table 2, the compounds shown in Table 2 are found to have excellent electrical characteristics.

Evaluation Example 2: Evaluation of Full Width at Half Maximum (FWHM)

As the method described in Table 3, photoluminescence spectra of the compounds shown in Table 4 were measured, and the FWHM of each compound was evaluated. The results thereof are shown in Table 4.

TABLE 3

| Measurement of photoluminescence (PL) spectrum | Each compound was dissolved at a concentration of $10^{-4}$ M, and then a F7000 spectrofluorometer (available from Hitachi) in which a Xenon lamp was mounted was used to measure a PL spectrum (@ 298 K) of each compound. |
|---|---|

TABLE 4

| Compound No. | FWHM(nm) |
|---|---|
| 18 | 69 |
| 28 | 82 |
| 14 | 70 |

Referring to the results of Table 4, the compounds shown in Table 4 are found to have excellent emission characteristics.

Evaluation Example 3: Evaluation of Photoluminescent Quantum Yield (PLQY) and Decay Time (1) Preparation of Thin Film A quartz substrate was prepared by washing with chloroform and distilled water. Then, the compounds shown in Table 5 were each co-deposited with Compound H3 (Compound 3 in Group HE4) at a weight ratio of 5:5 at a vacuum pressure of $10^{-7}$ torr to prepare a thin film having a thickness of 50 nm. A quartz substrate was prepared as described above. Then, the compounds shown in Table 5 were each co-deposited with Compound H4 at a weight ratio of 5:5 at a vacuum pressure of $10^{-7}$ torr to prepare a thin film having a thickness of 50 nm.

(2) Evaluation of Photoluminescent Quantum Yield

The photoluminescent quantum yield in the thin film was evaluated by using Hamamatsu Photonics absolute PL quantum yield measurement system employing PLQY measurement software (Hamamatsu Photonics, Ltd., Shizuoka, Japan), in which a xenon light source, a monochromator, a photonic multichannel analyzer, and an integrating sphere are mounted. Thus, PLQY in film of the compounds shown in Table 5 were measured accordingly.

(3) Decay Time Evaluation

The PL spectrum of each thin film was evaluated at room temperature by using a time-resolved photoluminescence (TRPL) measurement system, FluoTime 300 (available from PicoQuant), and a pumping source, PLS340 (available from PicoQuant, excitation wavelength=340 nm, spectral width=20 nm). Then, a wavelength of the main peak in the PL spectrum was determined, and upon photon pulses (pulse width=500 picoseconds, ps) applied to the thin film by PLS340, the number of photons emitted at the wavelength of the main peak for each thin film was repeatedly measured over time by time-correlated single photon counting (TCSPC), thereby obtaining TRPL curves available for the sufficient fitting. $T_{decay}(Ex)$ (decay time) of the thin film was obtained by fitting at least two exponential decay functions to the results thereof. The functions used for the fitting are as described in Equation 1, and a decay time $T_{decay}$ having the largest value among values for each of the exponential decay functions used for the fitting was taken as $T_{decay}(Ex)$, i.e., a decay time. The results thereof are shown in Table 5. The remaining decay time $T_{decay}$ values were used to determine the lifetime of typical fluorescence to be decayed. Here, during the same measurement time as the measurement time for obtaining TRPL curves, the same measurement was repeated once more in a dark state (i.e., a state where a pumping signal incident on each of the films was blocked), thereby obtaining a baseline or a background signal curve available as a baseline for the fitting:

$$f(t) = \sum_{i=1}^{n} A_i \exp(-t/T_{decay,i})$$ Equation 1

TABLE 5

| Compound No. | Co-deposited material: H3 | | Co-deposited material: H4 | |
|---|---|---|---|---|
| | PLQY | $T_{decay}$(Ex) (μs) (decay time) | PLQY | $T_{decay}$(Ex) (μs) (decay time) |
| 18 | 32 | 32.32 | 68 | 48.28 |
| 28 | 44 | 15.8 | 82 | 14.98 |
| 14 | 71 | 13.47 | 81 | 10.86 |

Referring to the results of Table 5, the compounds shown in Table 5 are found to have excellent PLQY (in film) and decay time characteristics.

Example 1

A glass substrate having an indium tin oxide (ITO) electrode a first electrode, an anode) deposited thereon at a thickness of 1,500 Å was washed with distilled water in the presence of ultrasound waves. Once the washing with distilled water was complete, ultrasound wave washing was performed on the substrate using solvents, such as isopropyl alcohol, acetone, and methanol. Subsequently, the substrate was dried, transferred to a plasma washer, washed for 5 minutes using oxygen plasma, and mounted in a vacuum depositor.

Compound HT1 and Compound HT-D2 were co-deposited on the ITO electrode of the glass substrate to form a hole injection layer having a thickness of 100 Å. Subsequently, Compound HT1 was deposited on the hole injection layer to form a hole transport layer having a thickness of 1,350 Å. mCP was next deposited on the hole transport layer to form an electron blocking layer having a thickness of 100 Å, thereby forming a hole transport region.

A host (Compound H3) and an emitter (Compound 18) were co-deposited on the hole transport region at a volumetric ratio of 85:15 to form an emission layer having a thickness of 300 Å.

BCP was vacuum deposited on the emission layer to form a hole blocking layer having a thickness of about 100 Å. Compound ET27 and Liq were then co-deposited on the hole blocking layer to form an electron transport layer having a thickness of about 300 Å. Next, Liq was deposited on the electron transport layer to form an electron injection layer having a thickness of about 10 Å, and then, aluminum (Al) second electrode (a cathode) having a thickness of 1,000 Å was formed on the electron injection layer, thereby completing the manufacture of an organic light-emitting device.

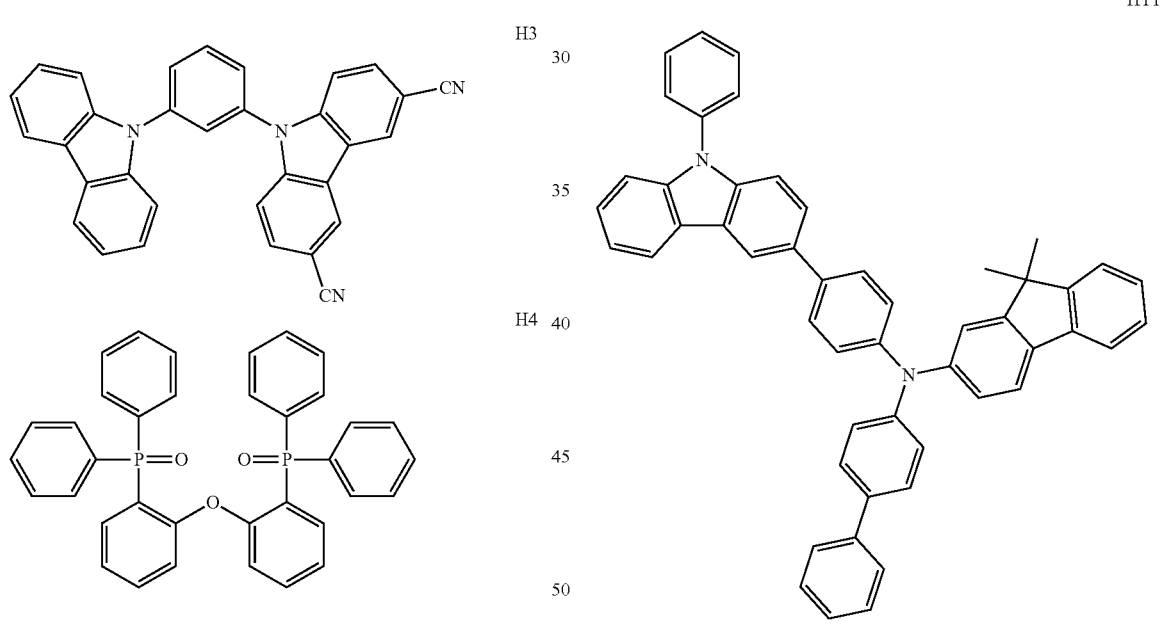

mCP

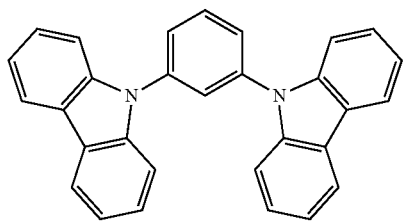

H3

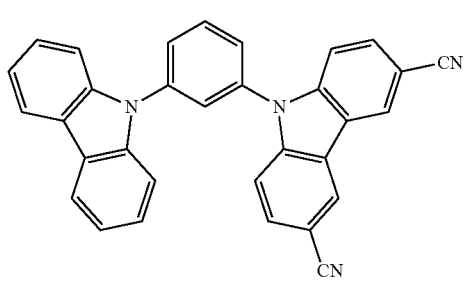

BCP

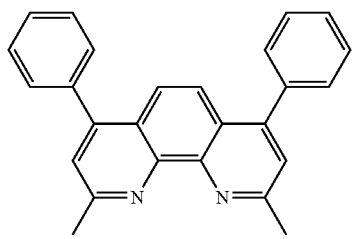

ET27

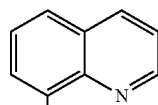

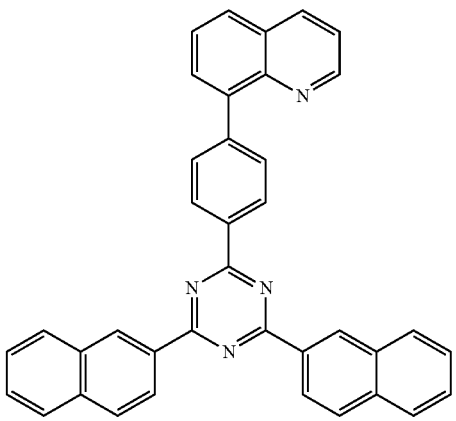

Examples 2 to 6 and Comparative Examples A1, A2, B1, B2, B3, C, D, and E

Organic light-emitting devices were manufactured in substantially the same manner as in Example 1, except that hosts and/or emitters shown in Table 6 were used in the formation of emission layer.

Evaluation Example 4: Device Data Evaluation

The driving voltage, emission efficiency, lifespan ($T_{95}$) of the organic light-emitting devices manufactured in Examples 1 to 6 and Comparative Examples A1, A2, B1, B2, B3, C, D, and E were measured by using a current voltmeter (Keithley 2400) and a luminance meter (Minolta Cs-1000A). The evaluation results are shown in Table 6. In Table 6, $T_{95}$ is lifespan data evaluating a period (hours) taken for the luminance (at 1000 candelas per square meter ($cd/m^2$)) to reach 95% with respect to 100% of the initial luminance. The emission efficiency and lifespan are shown in relative values based on the emission efficiency and lifespan of the organic light-emitting device prepared in Comparative Example A.

TABLE 6

| | Host | Emitter No. | Emission efficiency (relative value, %) | Driving voltage (V) | Lifespan ($T_{95}$) (relative value, %) | Emission color |
|---|---|---|---|---|---|---|
| Example 1 | H3 | 18 | 100 | 6.61 | 12 | Blue |
| Example 2 | H3 | 28 | 197 | 5.69 | 99 | Blue |
| Example 3 | H3 | 14 | 273 | 5.36 | 213 | Blue |
| Example 4 | H4 | 18 | 204 | 7.14 | Not measured | Blue |
| Example 5 | H4 | 28 | 206 | 7.57 | Not measured | Blue |
| Example 6 | H4 | 14 | 298 | 9.29 | Not measured | Blue |
| Comparative Example A1 | H3 | A1 | 205 | 3.68 | Not measured | Green |
| Comparative Example A2 | H4 | A2 | TADF characteristic not existed (less than 5% of low fluorescence emission efficiency) | | | |
| Comparative Example B1 | H3 | B1 | 25 | 6.34 | <0.1 | Blue |
| Comparative Example B2 | H3 | B2 | 71 | 4.48 | 3.74 | Blue |
| Comparative Example B3 | H3 | B3 | 124 | 7.89 | 0.21 | Blue |

TABLE 6-continued

| | Host | Emitter No. | Emission efficiency (relative value, %) | Driving voltage (V) | Lifespan (T95) (relative value, %) | Emission color |
|---|---|---|---|---|---|---|
| Comparative Example C | H4 | C | \multicolumn{4}{l}{TADF characteristic not existed (less than 5% of low fluorescence emission efficiency)} |
| Comparative Example D | H4 | D | \multicolumn{4}{l}{TADF characteristic not existed (less than 5% of low fluorescence emission efficiency)} |
| Comparative Example E | H4 | E | \multicolumn{4}{l}{TADF characteristic not existed (less than 5 % of low fluorescence emission efficiency)} |

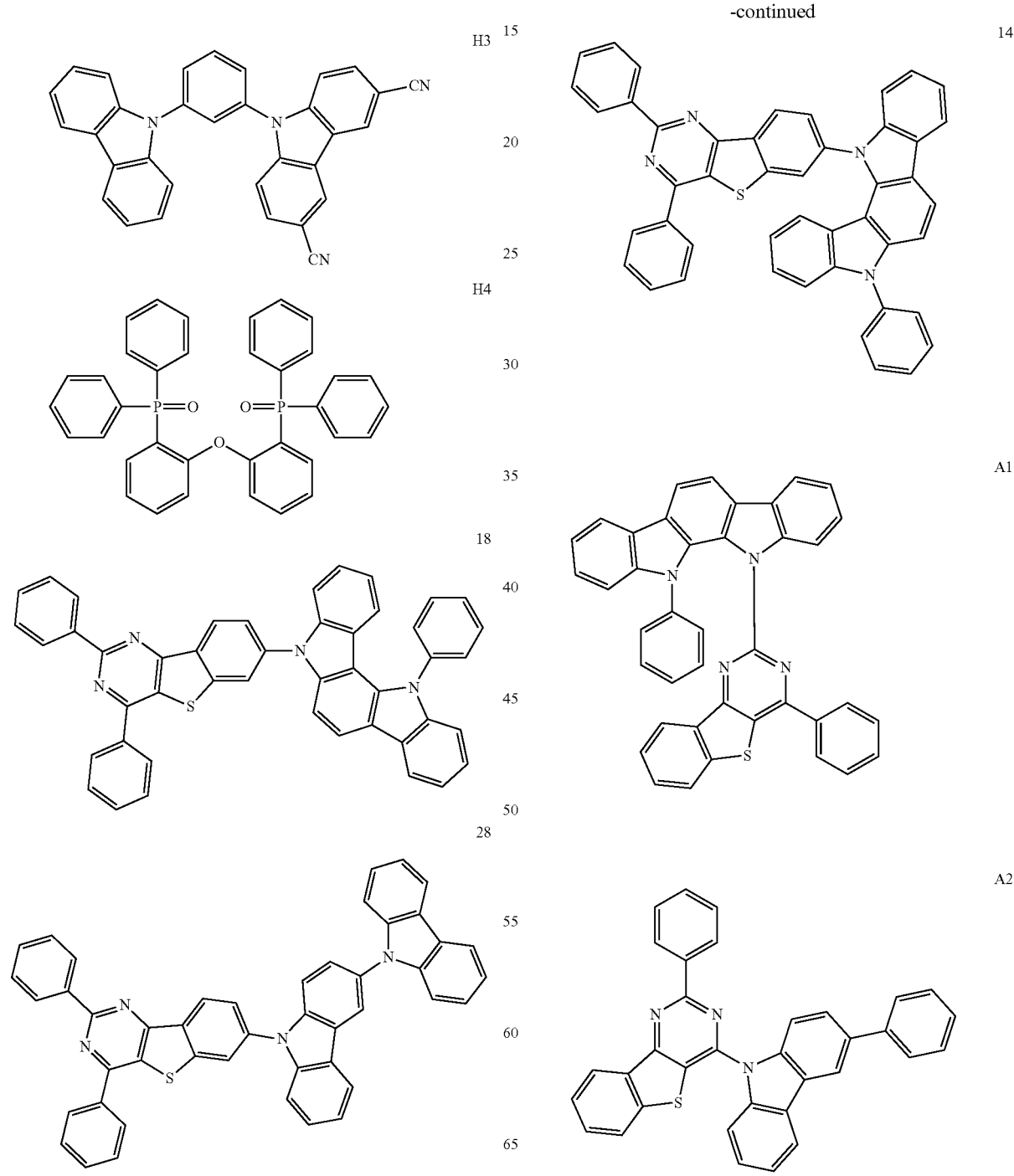

B1

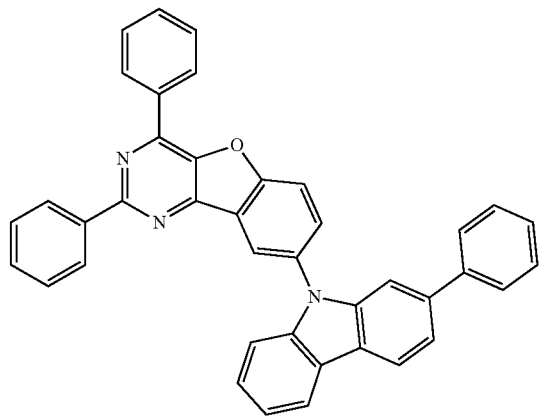

B2

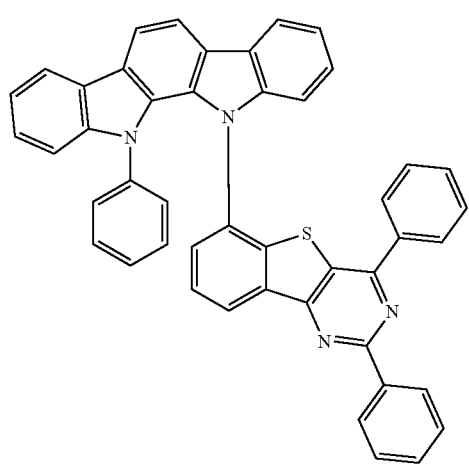

B3

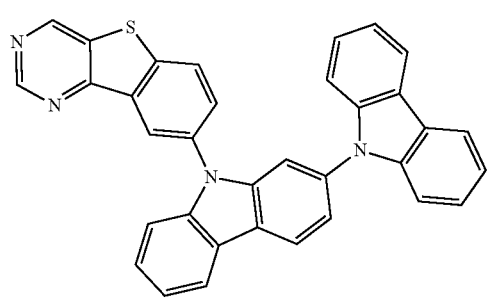

C

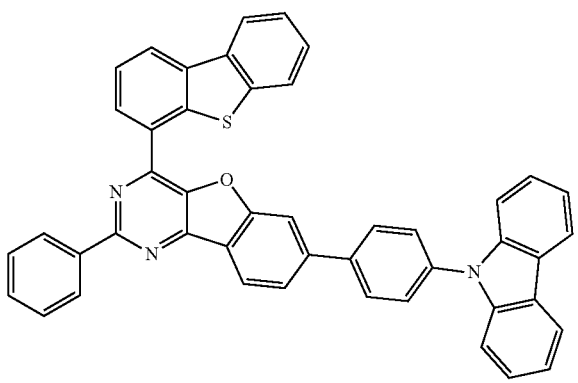

D

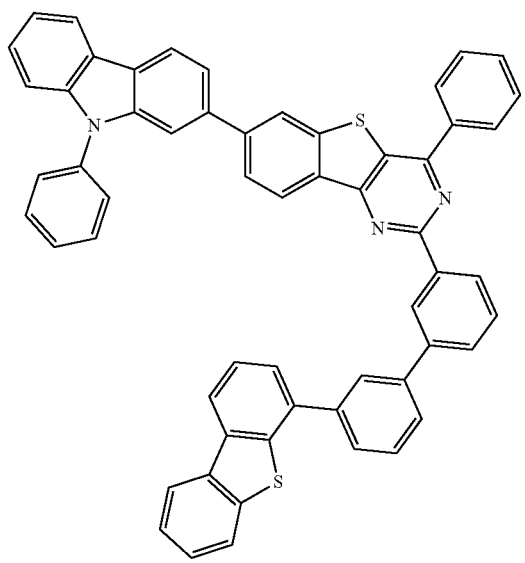

E

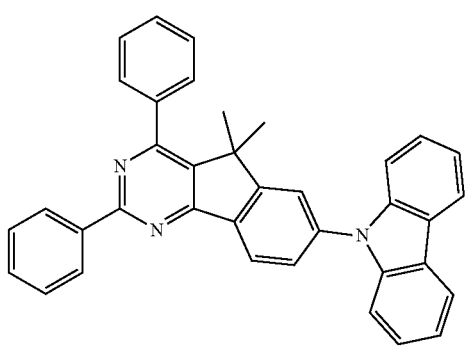

Referring to the results of Table 6, the organic light-emitting devices prepared in Examples 1 to 6 were found to have improved emission efficiency and lifespan, as compared with the organic light-emitting devices prepared in Comparative Examples A1, A2, B1, B2, B3, C, D, and E.

Example 11

A glass substrate, on which an ITO electrode was formed, was cut to a size of 50 millimeters (mm)×50 mm×0.5 mm. Then the glass substrate was sonicated in acetone isopropyl alcohol and pure water for about 15 minutes in each solvent and cleaned by exposure to ultraviolet rays with ozone for 30 minutes.

Subsequently, HAT-CN was deposited on the ITO electrode (anode) of the glass substrate to form a hole injection layer having a thickness of 100 Å, NPB was deposited on the hole injection layer to form a first hole transport layer having a thickness of 500 Å, TCTA was deposited on the first hole transport layer to form a second hole transport layer having a thickness of 50 Å, and mCP was deposited on the second hole transport layer to form an electron blocking layer having a thickness of 50 Å.

A first host (H1), a second host (H2), a sensitizer (Compound 18), and a fluorescence emitter (FD11) were co-deposited on the electron blocking layer to form an emission layer having a thickness of 400 Å. Here, a weight ratio of the first host to the second host to the sensitizer was 60:40:10, and the content of the fluorescence emitter was controlled to be 1.5 wt %, based on the total weight of the first host, the second host, the sensitizer, and the fluorescence emitter.

DBFPO was deposited on the emission layer to form a hole blocking layer having a thickness of 100 Å. DBFPO and LiQ were co-deposited on the hole blocking layer at a weight ratio of 5:5 to form an electron transport layer having a thickness of 300 Å. LiQ was deposited on the electron transport layer to form an electron injection layer having a thickness of 10 Å. Aluminum (Al) was deposited on the electron injection layer to form cathode having a thickness of 1000 Å, thereby completing the manufacture of an organic light-emitting device.

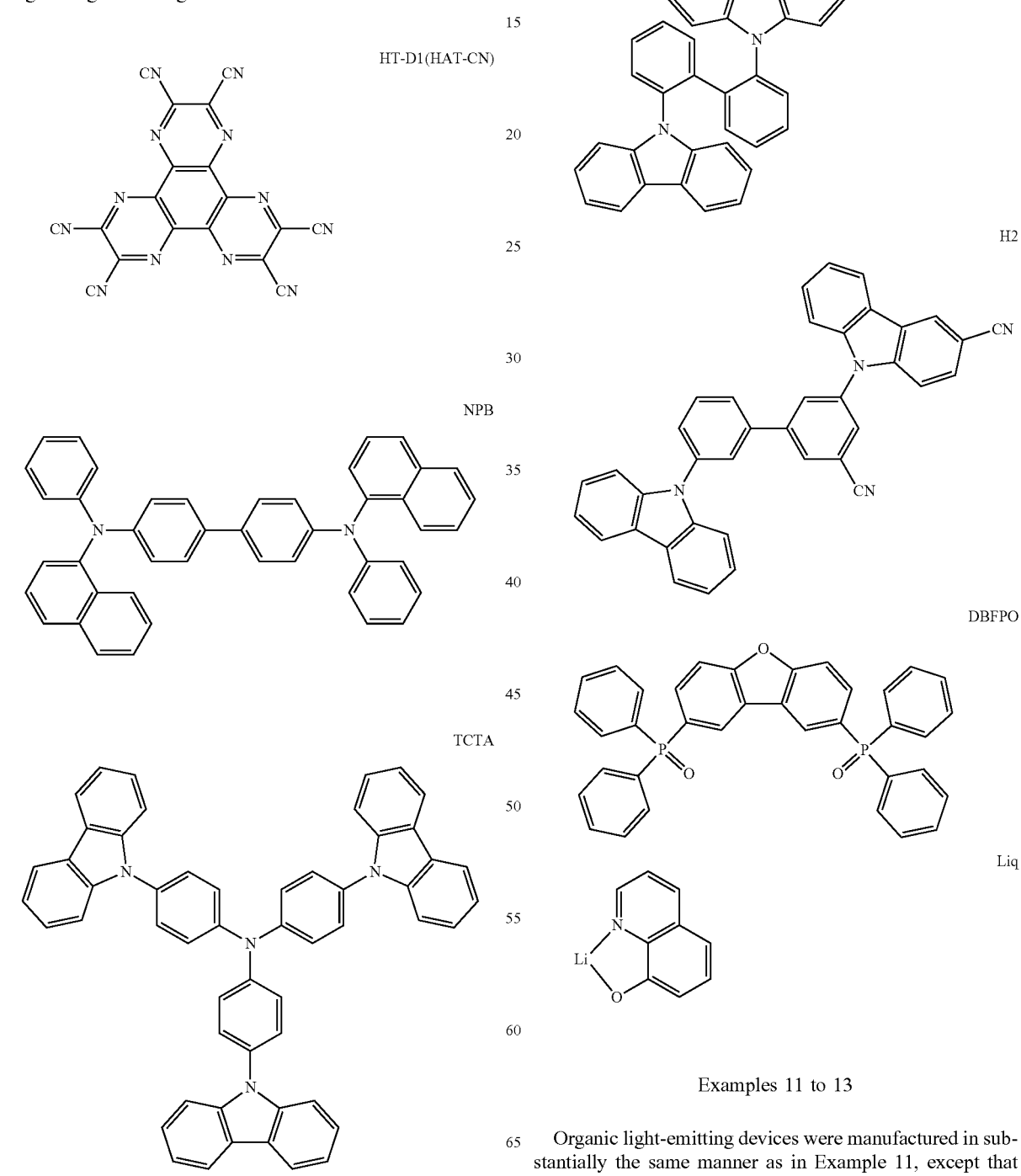

Examples 11 to 13

Organic light-emitting devices were manufactured in substantially the same manner as in Example 11, except that sensitizers shown in Table 7 were used in the emission layer.

Evaluation Example 5: Device Data Evaluation

The driving voltage, emission efficiency, lifespan ($T_{95}$) of the organic light-emitting devices manufactured in Examples 11 to 13 were measured in the same manner as in Evaluation Example 4 by using a current voltmeter (Keithley 2400) and a luminance meter (Minolta Cs-1000A). The evaluation results are shown in Table 7. The emission efficiency and lifespan in Table 7 are shown in relative values based on the emission efficiency and lifespan of the organic light-emitting device prepared in Comparative Example A.

TABLE 7

| | Sensitizer No. | Emitter No. | Driving voltage (V) | Emission efficiency (relative value, %) | Lifespan ($T_{95}$) (relative value, %) |
|---|---|---|---|---|---|
| Example 11 | 18 | FD11 | 7.41 | 100 | 100 |
| Example 12 | 28 | FD11 | 7.06 | 135 | 224 |
| Example 13 | 14 | FD11 | 6.61 | 166 | 343 |

FD11

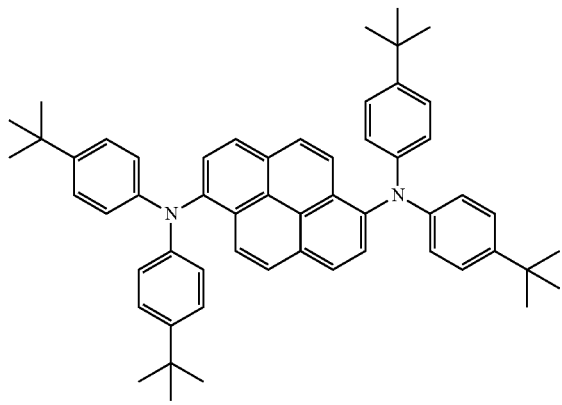

18

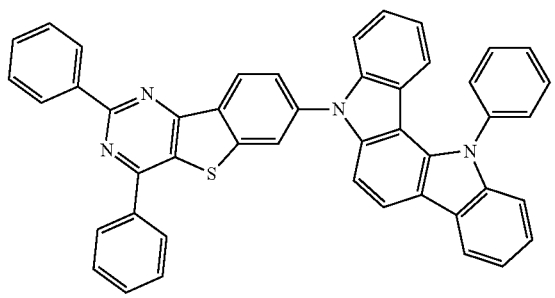

28

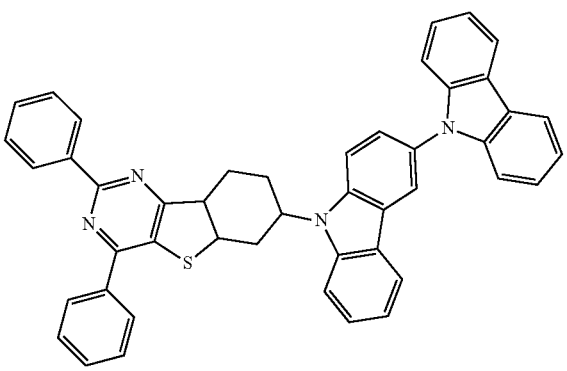

14

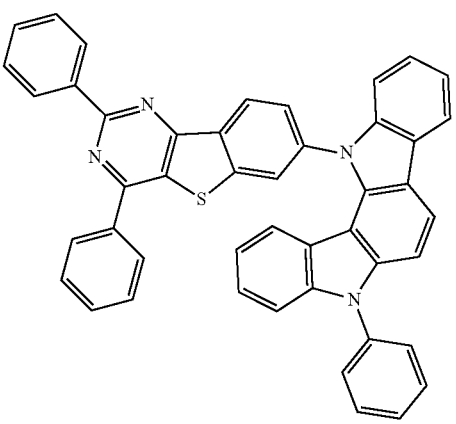

Referring to the results of Table 7, the organic light-emitting devices prepared in Examples 11 to 13 were found to have improved emission efficiency and lifespan simultaneously.

As apparent from the foregoing description, when the heterocyclic compound represented by Formula 1 is used, an organic light-emitting device having high emission efficiency and long lifespan characteristics and an electronic apparatus including the organic light-emitting device may be provided.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A heterocyclic compound represented by Formula 1:

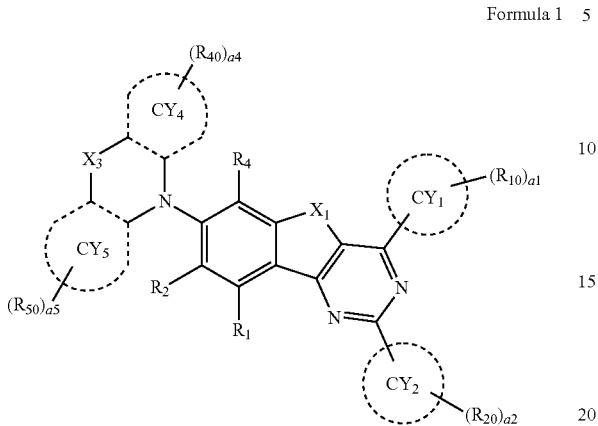

Formula 1 wherein, in Formula 1, ring $CY_1$, ring $CY_2$, ring $CY_4$, and ring $CY_5$ are each independently a π electron-rich $C_3$-$C_{60}$ cyclic group, wherein ring $CY_1$, ring $CY_2$, ring $CY_4$, and ring $CY_5$ are each independently a benzene group, a naphthalene group, a phenanthrene group, a furan group, a thiophene group, a pyrrole group, a cyclopentene group, a silole group, a germole group, a benzofuran group, a benzothiophene group, an indole group, an indene group, a benzosilole group, a benzogermole group, a dibenzofuran group, a dibenzothiophene group, a carbazole group, a fluorene group, a dibenzosilole group, a dibenzogermole group, an indolodibenzofuran group, an indolodibenzothiophene group, an undolocarbazole group, an indolofluorene group, an indolodibenzosilole group, an indolodibenzogermole group, or a 9,10-dihydroacridine group, $X_1$ is O, S, $Si(R_5)(R_6)$, $Ge(R_5)(R_6)$, or $P(=O)(R_5)$, $X_3$ is a single bond, O, S, $N(R_{31})$, $C(R_{31})(R_{32})$, $Si(R_{31})(R_{32})$, or $Ge(R_{31})(R_{32})$, $R_1$, $R_2$, $R_4$ to $R_6$, $R_{10}$, and $R_{20}$ are each independently hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$Ge(Q_3)(Q_4)(Q_5)$, —$B(Q_6)(Q_7)$, —$P(=O)(Q_8)(Q_9)$, or —$P(Q_8)(Q_9)$, $R_{31}$, $R_{32}$, $R_{40}$, and $R_{50}$ are each independently:

hydrogen, deuterium, —F, or a cyano group; or a $C_1$-$C_{60}$ alkyl group, a $C_1$-$C_{60}$ alkoxy group, a π electron-rich $C_3$-$C_{60}$ cyclic group, or a pyridinyl group, each unsubstituted or substituted with deuterium, —F, a cyano group, a $C_1$-$C_{60}$ alkyl group, a $C_1$-$C_{60}$ alkoxy group, a π electron-rich $C_3$-$C_{60}$ cyclic group, a pyridinyl group, a biphenyl group, a terphenyl group, or any combination thereof, wherein the π electron-rich $C_3$-$C_{60}$ cyclic group is a cyclic group having 3 to 60 carbon atoms and not including at least one *—N=*' as a ring-forming moiety, wherein * and *' each indicated a binding site to an adjacent atom, a1, a2, a4, and a5 are each independently an integer from 0 to 20, and a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —$C_1$, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-Coo aryl group, a $C_6$-Coo aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$Ge(Q_{13})(Q_{14})(Q_{15})$, —$B(Q_{16})(Q_{17})$, —$P(=O)(Q_{18})(Q_{19})$, —$P(Q_{18})(Q_{19})$, or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-Coo arylthio group, a $C_1$-$C_{60}$ heteroaryl group, a monovalent non-aromatic condensed polycyclic group, or a monovalent non-aromatic condensed heteropolycyclic group, each unsubstituted or substituted with deuterium, —F, —$C_1$, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{00}$ arylthio group, a $C_1$-$C_{60}$ heteroaryl group, a monovalent non-aromatic condensed polycyclic group, a monovalent non-aromatic condensed heteropolycyclic group, $-N(Q_{21})(Q_{22})$, $-Si(Q_{23})(Q_{24})(Q_{25})$, $-Ge(Q_{23})(Q_{24})(Q_{25})$, $-B(Q_{26})(Q_{27})$, $-P(=O)(Q_{28})(Q_{29})$, $-P(Q_{28})(Q_{29})$, or any combination thereof;

$-N(Q_{31})(Q_{32})$, $-Si(Q_{33})(Q_{34})(Q_{35})$, $-Ge(Q_{33})(Q_{34})(Q_{35})$, $-B(Q_{36})(Q_{37})$, $-P(=O)(Q_{38})(Q_{39})$, or $-P(Q_{38})(Q_{39})$; or any combination thereof, wherein $Q_1$ to $Q_9$, $Q_{11}$ to $Q_{19}$, $Q_{21}$ to $Q_{29}$, and $Q_{31}$ to $Q_{39}$ are each independently: hydrogen; deuterium; —F; —Cl; —Br; —I; a hydroxyl group; a cyano group; a nitro group; an amidino group; a hydrazine group; a hydrazone group; a carboxylic acid group or a salt thereof; a sulfonic acid group or a salt thereof; a phosphoric acid group or a salt thereof; a $C_1$-$C_{60}$ alkyl group unsubstituted or substituted with deuterium, a $C_1$-$C_{60}$ alkyl group, a $C_6$-$C_{60}$ aryl group, or any combination thereof; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group unsubstituted or substituted with deuterium, a $C_1$-$C_{60}$ alkyl group, a $C_6$-$C_{60}$ aryl group, or any combination thereof; a $C_6$-$C_{60}$ aryloxy group; a $C_6$-$C_{60}$ arylthio group; a $C_1$-$C_{60}$ heteroaryl group; a monovalent non-aromatic condensed polycyclic group; or a monovalent non-aromatic condensed heteropolycyclic group.

2. The heterocyclic compound of claim 1, wherein $X_1$ is O or S.

3. The heterocyclic compound of claim 1, wherein $X_3$ is a single bond.

4. The heterocyclic compound of claim 1, wherein $R_1$, $R_2$, $R_4$ to $R_6$, $R_{10}$, and $R_{20}$ are each independently:

hydrogen, deuterium, —F, or a cyano group; or a $C_1$-$C_{60}$ alkyl group, a $C_1$-$C_{60}$ alkoxy group, a π electron-rich $C_3$-$C_{60}$ cyclic group, or a pyridinyl group, each unsubstituted or substituted with deuterium, —F, a cyano group, a $C_1$-$C_{60}$ alkyl group, a $C_1$-$C_{60}$ alkoxy group, a π electron-rich $C_3$-$C_{60}$ cyclic group, a pyridinyl group, a biphenyl group, a terphenyl group, or any combination thereof, wherein the π electron-rich $C_3$-$C_{60}$ cyclic group is a cyclic group having 3 to 60 carbon atoms and not including at least one *—N=*' as a ring-forming moiety, wherein * and *' each indicate a binding site to an adjacent atom.

5. The heterocyclic compound of claim 1, wherein $R_1$, $R_2$, $R_4$ to $R_6$, $R_{10}$, $R_{20}$, $R_{31}$, $R_{32}$, $R_{40}$, and $R_{50}$ are each independently:

hydrogen, deuterium, —F, or a cyano group; or a $C_1$-$C_{20}$ alkyl group, a phenyl group, a naphthyl group, a phenanthrenyl group, a furanyl group, a thiophenyl group, a pyrrolyl group, a cyclopentenyl group, a silolyl group, a germolyl group, a benzofuranyl group, a benzothiophenyl group, an indolyl group, an indenyl group, a benzosilolyl group, a benzogermolyl group, a dibenzofuranyl group, a dibenzothiophenyl group, a carbazolyl group, a fluorenyl group, a dibenzosilolyl group, a dibenzogermolyl group, a benzonaphthofuranyl group, a benzonaphthothiophenyl group, a benzocarbazolyl group, a benzofluorenyl group, a benzonaphthosilolyl group, a benzonaphthogermolyl group, a dinaphthofuranyl group, a dinaphthothiophenyl group, a dibenzocarbazolyl group, a dibenzofluorenyl group, a dinaphthosilolyl group, a dinaphthogermolyl group, a pyridinyl group, a biphenyl group, or a terphenyl group, each unsubstituted or substituted with deuterium, —F, a cyano group, a $C_1$-$C_{20}$ alkyl group, a phenyl group, a naphthyl group, a phenanthrenyl group, a furanyl group, a thiophenyl group, a pyrrolyl group, a cyclopentenyl group, a silolyl group, a germolyl group, a benzofuranyl group, a benzothiophenyl group, an indolyl group, an indenyl group, a benzosilolyl group, a benzogermolyl group, a dibenzofuranyl group, a dibenzothiophenyl group, a carbazolyl group, a fluorenyl group, a dibenzosilolyl group, a dibenzogermolyl group, a benzonaphthofuranyl group, a benzonaphthothiophenyl group, a benzocarbazolyl group, a benzofluorenyl group, a benzonaphthosilolyl group, a benzonaphthogermolyl group, a dinaphthofuranyl group, a dinaphthothiophenyl group, a dibenzocarbazolyl group, a dibenzofluorenyl group, a dinaphthosilolyl group, a dinaphthogermolyl group, a pyridinyl group, a biphenyl group, a terphenyl group, or any combination thereof.

6. The heterocyclic compound of claim 1, wherein a group represented by

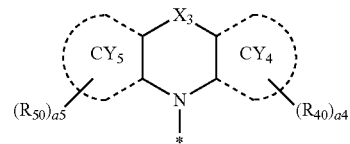

in Formula 1 is represented by one of Formulae 3-1 to 3-7:

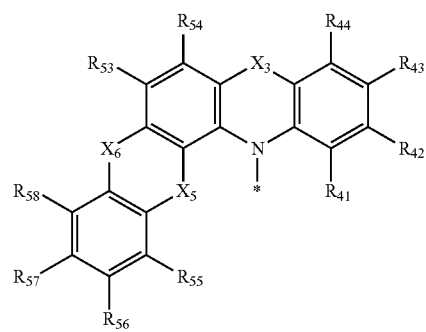

3-1

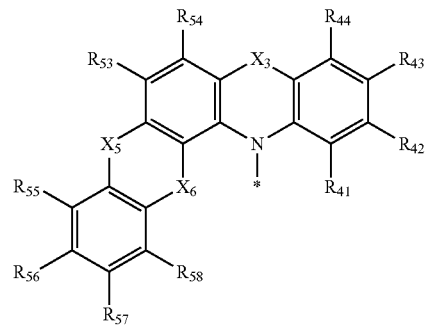

3-2

-continued

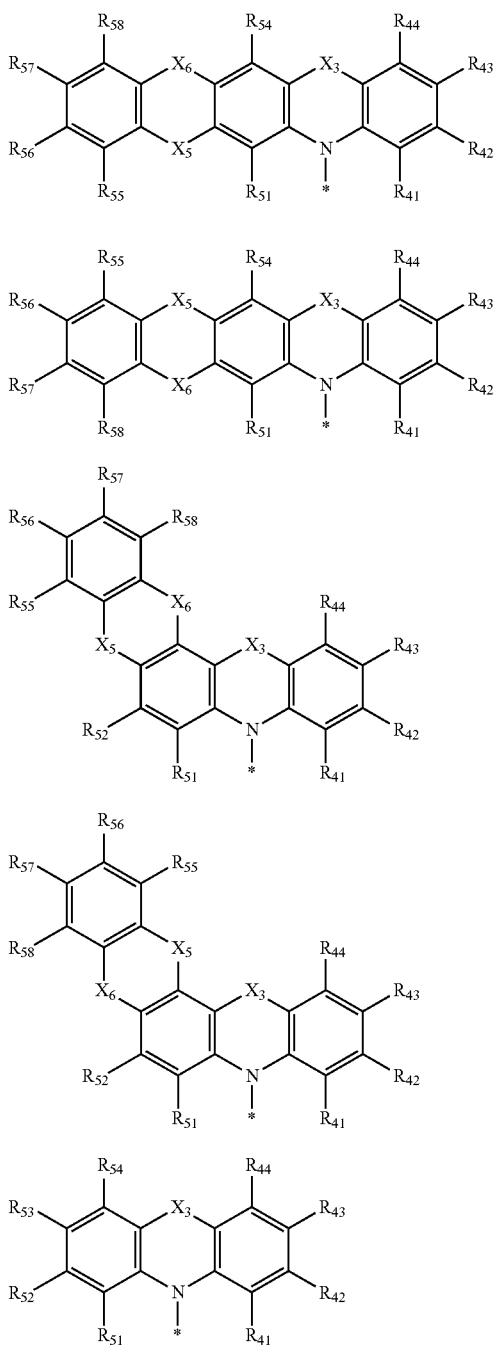

wherein, in Formulae 3-1 to 3-7,
$X_3$ is understood by referring to the description of $X_3$ in claim 1,
$X_5$ is O, S, N($R_{59}$), C($R_{59a}$)($R_{59b}$), Si($R_{59a}$)($R_{59b}$), or Ge($R_{59a}$)($R_{59b}$), $X_6$ is a single bond, O, S, N($R_{59c}$), C($R_{59d}$)($R_{59e}$), Si($R_{59d}$)($R_{59e}$), or Ge($R_{59d}$)($R_{59e}$),
$R_{41}$ to $R_{44}$ are each understood by referring to the description of $R_{40}$ in claim 1,
$R_{51}$ to $R_{59}$, and $R_{59a}$ to $R_{59e}$ are each understood by referring to the description of $R_{50}$ in claim 1, and
\* indicates a binding site to an adjacent atom.

7. The heterocyclic compound of claim 1, wherein a group represented by

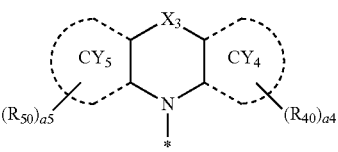

in Formula 1 is represented by Formula 3-7, and at least one of $R_{43}$ and $R_{53}$ in Formula 3-7 is not hydrogen.

8. The heterocyclic compound of claim 1, wherein the heterocyclic compound emits delayed fluorescence.

9. The heterocyclic compound of claim 1, wherein the heterocyclic compound emits blue light.

10. An organic light-emitting device comprising:
a first electrode;
a second electrode; and
an organic layer located between the first electrode and the second electrode and comprising an emission layer,
wherein the organic layer comprises the heterocyclic compound of claim 1.

11. The organic light-emitting device of claim 10, wherein the heterocyclic compound is included in the emission layer.

12. The organic light-emitting device of claim 11, wherein the emission layer comprises a host and an emitter, the host is different from the emitter, and the heterocyclic compound is included in the emitter.

13. The organic light-emitting device of claim 12, wherein a ratio of emission components emitted from the heterocyclic compound is in a range of about 70% to about 100%, based on total emission components emitted from the emission layer.

14. The organic light-emitting device of claim 12, wherein the emission layer emits blue light.

15. The organic light-emitting device of claim 11, wherein the emission layer comprises a host, an emitter, and a sensitizer, the host, the emitter, and the sensitizer are different from each other, and the heterocyclic compound is included in the sensitizer.

16. The organic light-emitting device of claim 15, wherein a ratio of emission components emitted from the emitter is in a range of about 70% to about 100%, based on total emission components emitted from the emission layer.

17. The organic light-emitting device of claim 12, wherein the host does not comprise a transition metal.

18. The organic light-emitting device of claim 15, wherein the emitter is a fluorescence emitter.

19. An electronic apparatus comprising the organic light-emitting device of claim 10.

\* \* \* \* \*